United States Patent
Dürrenberger et al.

(10) Patent No.: US 10,738,041 B2
(45) Date of Patent: *Aug. 11, 2020

(54) FERROPORTIN INHIBITORS

(71) Applicant: Vifor (International) AG, St. Gallen (CH)

(72) Inventors: Franz Dürrenberger, Dornach (CH); Wilm Buhr, Constance (DE); Susanna Burckhardt, Zürich (CH); Michael Burgert, Friedrichshafen (DE); Aris Kalogerakis, Winterthur (CH); Stefan Reim, St. Gallen (CH); Vania Manolova, Zollikon (CH); Susan Boyce, Quickborn (DE); Christopher John Yarnold, Didcot Oxon (GB); Paula Pena, Witney (GB); Jon Shepherd, Abingdon (GB); Cristina Lecci, Abingdon (GB); Richard Jarjes-Pike, Newbury (GB); John Scott, Abingdon (GB)

(73) Assignee: Vifor (International) AG, St. Gallen (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/768,025

(22) PCT Filed: Oct. 21, 2016

(86) PCT No.: PCT/EP2016/075305
§ 371 (c)(1),
(2) Date: Apr. 13, 2018

(87) PCT Pub. No.: WO2017/068089
PCT Pub. Date: Apr. 27, 2017

(65) Prior Publication Data
US 2018/0297991 A1 Oct. 18, 2018

(30) Foreign Application Priority Data

Oct. 23, 2015 (EP) ..................... 15191176
Oct. 23, 2015 (EP) ..................... 15191179

(51) Int. Cl.
*C07D 413/14* (2006.01)
*A61K 31/427* (2006.01)
(Continued)

(52) U.S. Cl.
CPC ........ *C07D 413/14* (2013.01); *A61K 31/4184* (2013.01); *A61K 31/426* (2013.01); *A61K 31/427* (2013.01); *A61K 31/435* (2013.01); *A61K 31/437* (2013.01); *A61K 31/4355* (2013.01); *A61K 31/4375* (2013.01); *A61K 31/444* (2013.01); *A61K 31/4439* (2013.01); *A61K 31/4709* (2013.01); *A61K 31/4725* (2013.01); *A61K 31/497* (2013.01); *A61K 31/4985* (2013.01); *A61K 31/501* (2013.01); *A61K 31/506* (2013.01); *A61K 31/5377* (2013.01); *A61K 31/55* (2013.01); *A61K 45/06* (2013.01); *A61P 3/12* (2018.01);
(Continued)

(58) Field of Classification Search
CPC .. C07D 413/14; C07D 277/56; C07D 401/14; C07D 403/14; C07D 417/12; C07D 417/14; C07D 471/04; C07D 487/04; A61P 7/06; A61P 25/28; A61P 25/16; A61P 3/12; A61K 31/4184; A61K 31/426; A61K 31/427; A61K 31/435; A61K 31/4355; A61K 31/437; A61K 31/4375; A61K 31/4439; A61K 31/444; A61K 31/4725; A61K 31/497; A61K 31/4985; A61K 31/501; A61K 31/506; A61K 31/5377; A61K 31/55; A61K 45/06
USPC .................................................. 514/210.21
See application file for complete search history.

(56) References Cited

U.S. PATENT DOCUMENTS 5,922,761 A 7/1999 Lai
6,723,742 B2 4/2004 Lattmann et al.
(Continued)

FOREIGN PATENT DOCUMENTS

CN 103508957 A 1/2014
EP 1072265 A1 1/2001
(Continued)

OTHER PUBLICATIONS

Machine translation of WO 2011/029832 (Year: 2011).*
(Continued)

*Primary Examiner* — Yevgeny Valenrod
(74) *Attorney, Agent, or Firm* — Rankin, Hill & Clark LLP; Christopher Jan Korff

(57) ABSTRACT

The invention relates to novel ferroportin inhibitors of the general formula (I) pharmaceutical compositions comprising them and the use thereof as medicaments, in particular for the prophylaxis and/or treatment of diseases caused by a lack of hepcidin or iron metabolism disorders, such as particularly iron overload states such as in particular thalassemia and hemochromatosis.

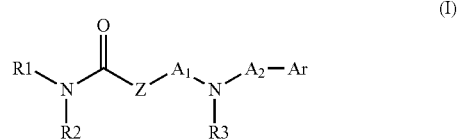

(I)

18 Claims, 3 Drawing Sheets

(51) Int. Cl.

| | | |
|---|---|---|
| *A61K 31/437* | (2006.01) | |
| *A61K 31/444* | (2006.01) | |
| *A61K 31/501* | (2006.01) | |
| *A61K 31/506* | (2006.01) | |
| *A61K 31/55* | (2006.01) | |
| *C07D 417/12* | (2006.01) | |
| *C07D 471/04* | (2006.01) | |
| *C07D 401/14* | (2006.01) | |
| *A61K 31/426* | (2006.01) | |
| *A61K 31/435* | (2006.01) | |
| *A61K 31/497* | (2006.01) | |
| *A61K 45/06* | (2006.01) | |
| *C07D 277/56* | (2006.01) | |
| *C07D 403/14* | (2006.01) | |
| *C07D 413/04* | (2006.01) | |
| *C07D 487/04* | (2006.01) | |
| *A61K 31/4184* | (2006.01) | |
| *A61K 31/4355* | (2006.01) | |
| *A61K 31/4375* | (2006.01) | |
| *A61K 31/4439* | (2006.01) | |
| *A61K 31/4985* | (2006.01) | |
| *A61K 31/5377* | (2006.01) | |
| *C07D 417/14* | (2006.01) | |
| *A61K 31/4709* | (2006.01) | |
| *A61K 31/4725* | (2006.01) | |
| *A61P 7/06* | (2006.01) | |
| *A61P 25/28* | (2006.01) | |
| *A61P 25/16* | (2006.01) | |
| *A61P 3/12* | (2006.01) | |
| *A61K 31/16* | (2006.01) | |
| *A61K 31/4422* | (2006.01) | |
| *A61K 36/9066* | (2006.01) | |

(52) U.S. Cl.
CPC ............... *A61P 7/06* (2018.01); *A61P 25/16* (2018.01); *A61P 25/28* (2018.01); *C07D 277/56* (2013.01); *C07D 401/14* (2013.01); *C07D 403/14* (2013.01); *C07D 413/04* (2013.01); *C07D 417/12* (2013.01); *C07D 417/14* (2013.01); *C07D 471/04* (2013.01); *C07D 487/04* (2013.01); *A61K 31/16* (2013.01); *A61K 31/4422* (2013.01); *A61K 36/9066* (2013.01); *A61K 2300/00* (2013.01); *Y02A 50/411* (2018.01)

(56) References Cited

U.S. PATENT DOCUMENTS

| | | | |
|---|---|---|---|
| 7,365,225 B2 | 4/2008 | Thomas et al. | |
| 8,278,337 B2 | 10/2012 | Belanger et al. | |
| 8,324,265 B2 | 12/2012 | Kurose et al. | |
| 8,338,610 B2 | 12/2012 | Kuzmich et al. | |
| 8,623,859 B2 | 1/2014 | Madden et al. | |
| 9,040,091 B2 | 5/2015 | Talton | |
| 9,586,914 B2 | 3/2017 | Fairlie et al. | |
| 9,896,481 B2 | 2/2018 | Ganz et al. | |
| 10,010,535 B2 | 7/2018 | Bergeron, Jr. | |
| 10,364,239 B2 * | 7/2019 | Durrenberger | A61K 31/435 |
| 2003/0109548 A1 | 6/2003 | Royt et al. | |
| 2004/0138268 A1 | 7/2004 | Boy et al. | |
| 2006/0100196 A1 | 5/2006 | Gailunas et al. | |
| 2006/0161007 A1 | 7/2006 | Martin et al. | |
| 2006/0252807 A1 | 11/2006 | Severance et al. | |
| 2008/0234327 A1 | 9/2008 | Cadieux et al. | |
| 2008/0234384 A1 | 9/2008 | Chafeev et al. | |
| 2009/0069408 A1 | 3/2009 | Chafeev et al. | |
| 2009/0118200 A1 | 5/2009 | Bergman et al. | |
| 2010/0093724 A1 | 4/2010 | Cook et al. | |
| 2010/0093871 A1 | 4/2010 | Kagehara et al. | |
| 2010/0240713 A1 | 9/2010 | Cadieux et al. | |
| 2011/0224136 A1 | 9/2011 | Ting et al. | |
| 2012/0040951 A1 | 2/2012 | Chuaqui et al. | |
| 2012/0094974 A1 | 4/2012 | Chen et al. | |
| 2013/0303508 A1 | 11/2013 | Clark et al. | |
| 2016/0235870 A1 | 8/2016 | Chong | |
| 2016/0243201 A1 | 8/2016 | Ginzburg | |
| 2019/0345151 A1 * | 11/2019 | Durrenberger | C07D 403/14 |

FOREIGN PATENT DOCUMENTS

| | | |
|---|---|---|
| EP | 1074254 A3 | 9/2002 |
| EP | 1889842 A1 | 2/2008 |
| GB | 937878 | 9/1963 |
| WO | 98/25887 A2 | 6/1998 |
| WO | 98/27108 A2 | 6/1998 |
| WO | 2005/014576 A1 | 2/2005 |
| WO | 2005/051411 A1 | 6/2005 |
| WO | 2006/040646 A1 | 4/2006 |
| WO | 2006/062224 A1 | 6/2006 |
| WO | 2011/023722 A1 | 3/2011 |
| WO | 2011/029832 A1 | 3/2011 |
| WO | 2017/068089 A2 | 4/2017 |

OTHER PUBLICATIONS

Espacenet bibliographic data for CN103508957 published Jan. 15, 2014, one page.
Espacenet bibliographic data for WO9827108 published Jun. 25, 1998, two pages.
Espacenet bibliographic data for WO2011023722 published Mar. 3, 2011, two pages.
Espacenet bibliographic data for WO2011029832 published Mar. 17, 2011, two pages.
International Search Report for corresponding PCT/EP2016/075305, seven pages.
Zou et al. "Discovery of pyrazole as C-terminus of selective BACE1 inhibitors," European Journal of Medicinal Chemistry 68 (2013) pp. 270-283.
Tussing-Humphreys, PhD, RD et al. "Rethinking Iron Regulation and Assessment in Iron Deficiency, Anemia of Chronic Disease, and Obesity: Introducing Hepcidin," Journal of the Academy of Nutrition and Dietetics, vol. 112, No. 3, Mar. 2012, pp. 391-400.
Riordan et al. "Bleomycin Analogs, Synthesis and Proton NMR Spectral Assignments of Thiazole Amides Related to Bleomycin A2(1)," J. Heterocyclic Chem., vol. 18, Oct. 1981, pp. 1213-1221.
Sasaki "Synthesis of a Novel Bis(2,4'-Bithiazole) Derivative as a Co(II)—Activated DNA Cleaving Agent," Chem. Pharm. Bull. vol. 42, No. 8, (1994), pp. 1685-1687.
Ballell et al. "Fueling Open-Source Drug Discovery: 177 Small-Molecule Leads against Tuberculosis," ChemMedChem 2013, 8, pp. 313-321.
English translation of Japanese Notice of Rejection dated Mar. 9, 2020, four pages.
Pathak et al., "Solution-Phase Parallel Synthesis of Acyclic Nucleoside Libraries of Purine, Pyrimidine, and Triazole Acetamides," ACS Combinatorial Science, 2014, vol. 16, pp. 485-493.
Database Registry Online 9 Chemical Abstracts service, Columbus, Ohio, US; Jul. 8, 2015, retrieved from STN Database Accession No. 1797310-72-5, one page.

* cited by examiner

A

B

FERROPORTIN INHIBITORS

The invention relates to novel ferroportin inhibitors of the general formula (I), pharmaceutical compositions comprising them and the use thereof as medicaments, in particular for the prophylaxis and/or treatment of diseases caused by a lack of hepcidin or iron metabolism disorders, such as particularly iron overload states such as in particular thalassemia and hemochromatosis.

BACKGROUND AND PRIOR ART

Iron is an essential trace element for almost all organisms and is relevant in particular with respect to growth and the formation of blood. The balance of the iron metabolism is in this case primarily regulated on the level of iron recovery from haemoglobin of ageing erythrocytes and the duodenal absorption of dietary iron. The released iron is taken up via the intestine, in particular via specific transport systems (DMT-1, ferroportin), transferred into the blood circulation and thereby conveyed to the appropriate tissues and organs (transferrin, transferrin receptors).

In the human body, the element iron is of great importance, inter alia for oxygen transport, oxygen uptake, cell functions such as mitochondrial electron transport, cognitive functions, etc. and ultimately for the entire energy metabolism.

On average, the human body contains 4 to 5 g iron, with it being present in enzymes, in haemoglobin and myoglobin, as well as depot or reserve iron in the form of ferritin and hemosiderin. Approximately half of this iron, about 2 g, is present as heme iron, bound in the haemoglobin of the erythrocytes. Since these erythrocytes have only a limited lifespan (75-150 days), new ones have to be formed continuously and old ones degraded (over 2 million erythrocytes are being formed per second). This high regeneration capacity is achieved by macrophages phagocytizing the ageing erythrocytes, lysing them and thus recycling the iron thus obtained for the iron metabolism. The majority of the iron required for erythropoiesis, about 25 mg per day, is provided in this way.

The daily iron requirement of a human adult is between 0.5 to 1.5 mg per day, infants and women during pregnancy require 2 to 5 mg of iron per day. The daily iron loss, e.g. by desquamation of skin and epithelial cells, is low. Increased iron loss occurs, for example, during menstrual hemorrhage in women. Generally, blood loss can significantly reduce the iron level since about 1 mg iron is lost per 2 ml blood. In a healthy human adult, the normal daily loss of iron of about 1 mg is usually replaced via the daily food intake thus rebalancing the daily iron requirement to the adequate level The iron level is regulated by absorption, with the absorption rate of the iron present in food being between 6 and 12%, and up to 25% in the case of iron deficiency. The absorption rate is regulated by the organism depending on the iron requirement and the size of the iron store. In the process, the human organism utilizes both divalent as well as trivalent iron ions. Usually, iron(III) compounds are dissolved in the stomach at a sufficiently acid pH value and thus made available for absorption. The absorption of the iron is carried out in the upper small intestine by mucosal cells. In the process, trivalent non-heme iron is first reduced in the intestinal cell membrane to Fe(II) for absorption, for example by ferric reductase (membrane-bound duodenal cytochrome b), so that it can then be transported into the intestinal cells by means of the transport protein DMT1 (divalent metal transporter 1). In contrast, heme iron enters the enterocytes through the cell membrane without any change. In the enterocytes, iron is either stored in ferritin as depot iron, or released into the blood by the transport protein ferroportin. Hepcidin plays a central role in this process because it is the essential regulating factor of iron absorption. The divalent iron transported into the blood by ferroportin is converted into trivalent iron by oxidases (ceruloplasmin, hephaestin), the trivalent iron then being transported to the relevant places in the organism by transferrin (see for example "Balancing acts: molecular control of mammalian iron metabolism". M. W. Hentze, Cell 117, 2004, 285-297).

Mammalian organisms are unable to actively discharge iron. The iron metabolism is substantially controlled by hepcidin via the cellular release of iron from macrophages, hepatocytes and enterocytes.

Hepcidin is a peptide hormone produced in the liver. The predominant active form has 25 amino acids (see for example: "Hepcidin, a key regulator of iron metabolism and mediator of anaemia of inflammation". T. Ganz, Blood, 102, 2003, 783-8), although two forms which are shortened at the amino end, hepcidin-22 and hepcidin-20, have been found. Hepcidin acts on the absorption of iron via the intestine and via the placenta and on the release of iron from the reticuloendothelial system. In the body, hepcidin is synthesized in the liver from what is known as pro-hepcidin, pro-hepcidin being coded by the gene known as the HAMP gene. The formation of hepcidin is regulated in direct correlation to the organisms iron level, i.e. if the organism is supplied with sufficient iron and oxygen, more hepcidin is formed, if iron and oxygen levels are low, or in case of increased erythropoiesis less hepcidin is formed. In the small intestinal mucosal cells and in the macrophages hepcidin binds with the transport protein ferroportin, which conventionally transports the phagocytotically recycled iron from the interior of the cell into the blood.

The transport protein ferroportin is a transmembrane protein consisting of 571 amino acids which is formed in the liver, spleen, kidneys, heart, intestine and placenta. In particular, ferroportin is localized in the basolateral membrane of intestinal epithelial cells. Ferroportin bound in this way thus acts to export the iron into the blood. In this case, it is most probable that ferroportin transports iron as $Fe^{2+}$. If hepcidin binds to ferroportin, ferroportin is transported into the interior of the cell, where its breakdown takes place so that the release of the phagocytotically recycled iron from the cells is then almost completely blocked. If the ferroportin is inactivated, for example by hepcidin, so that it is unable to export the iron which is stored in the mucosal cells, the stored iron is lost with the natural shedding of cells via the stools. The absorption of iron in the intestine is therefore reduced, when ferroportin is inactivated or inhibited, for example by hepcidin. In addition, ferroportin is markedly localized in the reticuloendothelial system (RES), to which the macrophages also belong. Hepcidin plays an important part here when iron metabolism is impaired by chronic inflammation. In case of inflammation in particular interleukin-6 is increased, triggering an increase in hepcidin levels. As a result, more hepcidin is bound to the ferroportin of the macrophages, thus blocking the release of stored iron, which ultimately leads to anemia of inflammation (ACD or AI).

On the other hand, if the serum iron level decreases, hepcidin production in the hepatocytes of the liver is reduced so that less hepcidin is released and accordingly less ferroportin is inactivated, allowing a larger amount of stored iron to be transported into the serum.

Therefrom it becomes apparent that the hepcidin-ferroportin system directly regulates the iron metabolism and that a disorder of the hepcidin regulation mechanism therefore has a direct effect on iron metabolism in the organism. In principle the hepcidin-ferroportin regulation mechanism acts via the two following opposite principles:

On the one hand, an increase of hepcidin leads to inactivation of ferroportin, thus blocking the release of stored iron from the cells into the serum, thus decreasing the serum iron level. In pathological cases a decreased serum iron level leads to a reduced hemoglobin level, reduced erythrocyte production and thus to iron deficiency anemia.

On the other hand, a decrease of hepcidin results in an increase of active ferroportin, thus allowing an enhanced release of stored iron and an enhanced iron uptake e.g. from the food, thus increasing the serum iron level. In pathological cases an increased iron level leads to iron overload.

Iron overload states and diseases are characterized by excess iron levels. Therein, the problems arise from excess serum iron level which lead to non-transferrin bound iron (NTBI). The NTBI is rapidly taken up unspecifically by the organs, leading to an accumulation of iron in tissue and organs. Iron overload causes many diseases and undesired medical conditions, including cardiac, liver and endocrine damage. Further, iron accumulation in brain has been observed in patients suffering from neurodegenerative diseases such as for example Alzheimer's disease and Parkinson's disease. As a particular detrimental aspect of excess free iron the undesired formation of radicals must be mentioned. In particular iron(II) ions catalyze the formation (inter alia via Fenton reaction) of reactive oxygen species (ROS). These ROS cause damage to DNA, lipids, proteins and carbohydrates which has far-reaching effects in cells, tissue and organs. The formation of ROS is well known and described in the literature to cause the so-called oxidative stress.

A well-established hitherto existing method for treating iron overload is based on the concept to reduce the amount of iron in the serum by increased removal of the iron from the body. The eldest known and still routine treatment method in an otherwise-healthy person consists of regularly scheduled phlebotomies (bloodletting). When first diagnosed, the phlebotomies are usually scheduled fairly frequent, e.g. once a week, until iron levels are brought to within normal range, followed by phlebotomies which are then scheduled once a month or every three months depending upon the patient's rate of iron loading.

For patients unable to tolerate routine blood draws, there are chelating agents available for use. For example, deferoxamine (also known as desferrioxamine B, N'-{5-[acetyl (hydroxy)amino]pentyl}-N-[5-({4-[(5-aminopentyl)(hydroxy)amino]-4-oxobutanoyl} amino)pentyl]-N-hydroxysuccinamide or Desferal®), which is a bacterial siderophore, is an established drug used in chelation therapy. Deferoxamine binds iron in the bloodstream as an chelator and enhances its elimination via urine and faeces. Typical treatment of chronic iron overload requires subcutaneous injection over a period of 8-12 hours daily. Parenterally injectable compositions of desferrioxamine-B salts are described for example in WO 1998/25887.

Two newer drugs, licensed for use in patients receiving regular blood transfusions to treat thalassemia, resulting in the development of iron overload, are deferasirox and deferiprone.

Deferasirox (Exjade®, 4-(3,5-bis(2-hydroxyphenyl)-1H-1,2,4-triazol-1-yl)benzoic acid), being described for example in WO 1997/49395 and deferiprone (Ferriprox®, 3-hydroxy-1,2-dimethylpyridin-4(1H)-one) are similarly acting as an iron chelating agent, thus being suitable as a drug for iron chelation therapy.

Further compounds acting as iron chelator for use in the treatment of iron overload have been described. For example WO 2013/142258 relates to encapsulated particles of diethylenetriaminepentaacetate (DTPA) and a zinc salt. WO 2003/041709 relates to 4-hydroxy-2-alkylquniolines such as 4-hydroxy-2-nonylqunioline as an iron chelator. WO 1998/09626 relates to chelating agents for treating iron overload states on the basis of dithiocarbamate-containing compositions.

WO 2015/077655 relates to desferrithiocin derivatives of the formula (A) or (J)

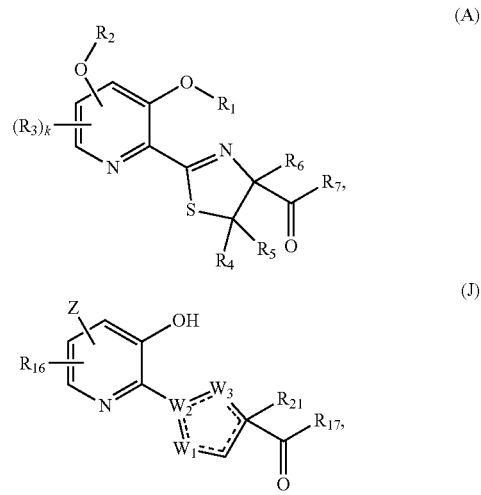

for the use in the treatment of iron overload diseases. According to WO 2015/077655 said desferrithiocin derivatives have been found to act as iron chelating agents.

WO 2005/051411 relates to novel antibiotics or antimycotics on the basis of oxachelin and derivatives thereof according to formula

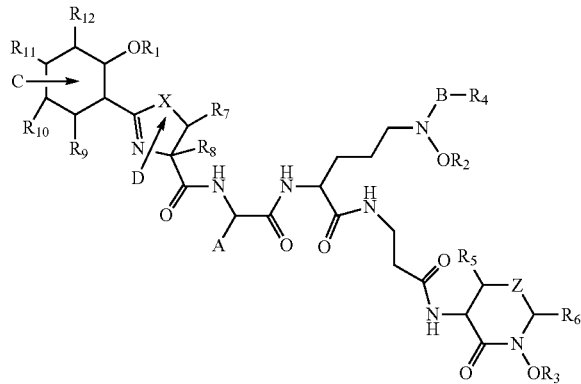

which are described to act as an iron chelator and to be used in the treatment of iron overload diseases.

The disadvantage in the treatment of iron overload by chelation therapy is the removal of the chelated iron from the body when the iron overload has already occurred instead of preventing the occurrence of the disorder. Further, the established drugs for iron chelation therapy are known to exhibit a toxic potential.

Modern approaches can be expected to supersede this method increasingly, in particular with increasing knowledge about the underlying mechanisms and development of appropriate treating methods on the basis of such knowledge. Hepcidin agonists or compounds which have an inhibiting or supporting effect on the biochemical regulatory pathways in the iron metabolism are basically known from the prior art.

Iron overload may occur, for example, if hepcidin expression is prevented, for example due to a genetic defect, such as in the known iron overload disease haemochromatosis. Hemochromatosis is a disease of iron overload caused by mutations in genes that control hepcidin synthesis or in the hepcidin gene itself. Low or absent levels of hepcidin in these patients result in enhanced amounts of active ferroportin, allowing increased absorption of dietary iron, leading to severe iron overload, which causes cardiac, liver and endocrine damages. Hepcidin mimetic peptides, i.e. peptides which similarly bind and inactivate ferroportin, have been shown to effectively reverse the accumulation of tissue iron in the hepcidin knockout mouse, a model of Type 2 (juvenile) hemochromatosis. (Ramos et al, Blood 2012).

In the known iron overload disease beta-thalassemia a mutation in the beta globin gene causes a reduction in hemoglobin production and ineffective erythropoiesis, the inability to produce adequate numbers of red cells because of damage to and death of developing red cells in the bone marrow. This causes upregulation of the rate of erythropoiesis and a reduction in hepcidin level to make more iron available for increased erythropoietic activity. This maladaptive response results in iron overload due to the reduced hepcidin levels, which lead to enhanced amounts of active ferroportin, allowing increased absorption of dietary iron, as described above. Red cells in thalassemia have a shortened half-life because of the toxicity of an imbalanced ratio of alpha- and beta-hemoglobin-subunits. Also in the treatment of beta-thalassemia the use of hepcidin mimetic peptides has been described, the therapeutic rationale being based on the increase of hepcidin activity leading to iron restriction and reduction of iron mediated damage in red cells. Administration of hepcidin mimetic peptides to the th3/+ mouse, a model of non-transfusion dependent beta-thalassemia resulted in relief of ineffective erythropoiesis, increased red cell survival time and improvement of anemia. In this model the prevention of iron overload due to reduction in the absorption of dietary iron turned out as an additional benefit of the hepcidin mimetic therapy (Gardenghi et al, 2010; Casu et al 2013).

The described therapeutic approaches are based on a direct involvement into the disturbed iron metabolism pathway by directly acting via the primary regulator hepcidin by providing a hepcidin mimetic or a hepcidin agonist, i.e. acting in the sense of a kind of hepcidin substitute or supply. The approach is based on the therapeutic rationale to treat iron overload, i.e. excess serum iron level, by inhibiting ferroportin, via the hepcidin-inactivation mechanism, thus blocking excessive iron absorption.

Further known iron overload related diseases are diseases associated with ineffective erythropoiesis such as the myelodysplastic syndromes (also known as MDS or myelodysplasia), polycythemia vera, etc.

Further, mutations in genes involved in sensing the systemic iron stores, such as hepcidin (Hamp1), hemochromatosis protein (HFE), hemojuvelin (HJV) and transferrin receptor 2 (TFR2) cause iron overload in mice and men. Accordingly, diseases related to HFE and gene mutations, chronic hemolysis associated diseases, sickle cell diseases, red cell membrane disorders, as well as Glucose-6-phosphate dehydrogenase deficiency (G6PD deficiency), erythropoietic *porphyria* and Friedrich's Ataxia can be mentioned. Further, subgroups of iron overload comprise transfusional iron overload, iron intoxication, pulmonary hemosiderosis, osteopenia, insulin resistance, African iron overload, Hallervordan Spatz disease, hyperferritinemia, ceruloplasmin deficiency, neonatal hemochromatosis and red blood cell disorders comprising thalassemia, alpha thalassemia, thalassemia *intermedia*, sickle cell disease and myelodysplastic syndrome are included.

Further disease and/or disorders and/or diseased conditions associated with elevated iron levels include, but are not limited to, diseases with elevated iron level, comprising ataxia, Friedrich's ataxia, age-related macular degeneration, age-related cataract, age-related retinal diseases and neurodegenrative disease, whereby such neurodegenrative disease comprises Alzheimer's disease, Parkinson's disease, pantothenate kinase-associated neurodegeneration, restless leg syndrom and Huntington's disease, Hepcidin is a host defense peptide, representing a component of the innate immune system that responds to invading organisms. It has been described that many bacteria are highly dependent on a supply of iron from the host (so-called siderophilic organisms) and have evolved mechanisms to capture iron from the local tissues. The ability to limit the amount of iron available to such organisms by ferroportin-inhibitors may represent effective adjunctive therapy. One such siderophilic organism is *Vibrio vulnificus*, which causes rare but extremely severe infections in coastal communities, often in subjects with undiagnosed iron overload. Studies in animals that have been inoculated with a lethal dose of *Vibrio vulnificus* have demonstrated nearly 100% survival in response to treatment with hepcidin mimetic peptides, inactivating ferroportin, regardless of whether treatment is started before or after the infection is initiated (Arezes et al 2015).

As known hepcidin mimetics the so-called minihepcidins can be mentioned, described for example in WO 2013/086143. Minihepcidins are small-sized synthetic peptide analogues of the hepcidin N-terminus which is crucial for hepcidin interaction with ferroportin. Minihepcidins have been developed on the basis that the first 9 amino acids of hepcidin (DTHFPICIF) have been found to be sufficient for in vitro activity (measured as ferroportin-GFP degradation). Minihepcidins have a modified hepcidin-9 amino acid sequence to exhibit improved resistance to proteolysis and enhanced biophysical interaction with ferroportin. Minihepcidins are described to be useful for the treatment of human iron overload conditions caused by hepcidin deficiency.

WO 2015/069660 describes methods for increasing hepcidin expression for treating iron overload disorders by decreasing non-transferrin bound iron (NTBI) by administering a modified iron binding/releasing transferrin.

All the described compounds which act as hepcidin agonists, hepcidin mimetics or ferroportin inhibitor etc. are relatively high molecular weight compounds, in particular those which are obtainable predominantly by genetic engineering. Various further approaches on the basis of biomolecular interactions and biomolecules have been described. The disadvantage is the complex preparation and high sensitivity of such biomolecular compounds. In particular methods on the basis of ferroportin antibodies are not sufficiently efficient as the antibody-inhibited ferroportin is permanently reproduced by the organism and the inhibition is thus not sufficiently long-lasting to achieve the desired therapeutic effect.

Low molecular weight compounds which play a part in iron metabolism and can have an inhibiting or promoting effect are also known.

For example WO 2008/151288, WO 2008/118790, WO 2008/115999, and WO 2008/109840 describe compounds acting as divalent metal transporter-1 (DMT1) inhibitors and their use for the treatment of iron disorders such as thalassemia or hemochromatosis.

WO 2008/123093 relates to an agent for prevention or treatment of iron overload disorders, comprising 22 beta-methoxyolean-12-ene-3 beta,24(4 beta)-diol.

EP 1074254 and EP1072265 relate to the use of catechic- and flavonoid-structure plant polyphenols for treating iron overload.

WO 2011/029832 relates to thiazol and oxazol compounds, which act as hepcidin antagonists and are thus described to be suitable in the use for the treatment of iron deficiency diseases. Therein, hepcidin antagonistic activity is described to inhibit the inhibition of ferroportin by hepcidin, which is the opposite effect as has been found by the inventors of the present invention for the compounds as described herein.

Chemical compounds based on the structures of the general formulae of the present invention have hitherto not been disclosed in connection with their activity as ferroportin inhibitors or for the use in the prophylaxis and treatment of iron metabolism disorders which are associated with increased iron levels such as iron overload.

US 2004/0138268 A1, US 2011/0224136 A1, CN 103508957, WO 2006/062224 A1, WO 2015/051362 A1, EP 1953145 A1, WO 2009/154739 A2, GB 937878 A, WO 2011/023722 A1, WO 2010/020556 A1, WO 2005/011685 A1, WO 00/56724 A1, WO 2010/036632 A1, WO 2005/014576 A1, WO 2013/067578 A1, WO 2005/116355 A1 or in Zou Yiquan et al. "Discovery of pyrazole as C-terminus of selective BACE1 inhibitors"; Eur. J. of Medicinal Chemistry 68 (2013) 270-283, Tussing-Humphreys et al. "Rethinking Iron Regulation and Assessment in Iron Deficiency, Anemia of Chronic Disease, and Obesity: Introducing Hepcidin" J. Academy of Nutrition and Dietetics (2012), Vol. 122, No. 3, 391-400, Riordan et al. "Bleomycin analogs. Synthesis and proton NMR spectral assignments of thiazole amides related to bleomycin A2 (1)"; J. Heterocyclic Chem. 18, 1213 (1981), Hideaki Sasaki "Synthesis of a novel bis(2,4'-bithiazole) derivative as a Co(II)-activated DNA cleaving agent"; Chem. Pharm. Bull. 42(8) 1685-1687 (1994), and Ballell et al. "Fueling open-source drug discovery. 177 small-molecule leads against tuberculosis"; Chem Med Chem 2013, 8, 313-321 describe compounds for different medical uses and mechanisms of action.

OBJECT

The object of the present invention was to provide, in particular, new therapeutically effective compounds that can be used for an effective therapy for the prophylaxis and treatment of iron metabolism disorders which are associated with increased iron levels, such as in particular iron overload. In a further object, the new compounds should exhibit few side effects and have a very low toxicity and good bioavailability and compatibility. Moreover, these new compounds, in contrast to the known iron chelating compounds, should be suitable to prevent the occurrence of increased iron levels and thus the related disorders, instead of removing excess iron from the body when the iron overload has already occurred. In a further object the new compounds should have a defined structure (stoichiometry) and should be preparable by simple synthesis processes, exhibit less sensitivity and improved long-lasting efficiency as compared to the known biomolecular compounds, such as antibodies.

This goal was achieved by the development of the novel compounds according to the formulae as defined herein, such as in particular formula (I), which have been found to act as ferroportin inhibitors, thus being suitable for the use in the inhibition of iron transport, and thus being effective in the prophylaxis and treatment of iron metabolism disorders which are associated with increased iron levels, such as in particular iron overload, as well as in in the prophylaxis and treatment of diseases caused by a lack of hepcidin, diseases related to or caused by increased iron levels or iron overload and diseases associated with ineffective erythropoiesis.

BRIEF DESCRIPTION OF THE DRAWINGS

FIG. 3 shows serum iron reduction induced by hepcidin and ferroportin inhibitor according to Example Compound 94 (Example Compound No. 94).

DESCRIPTION OF THE INVENTION

Figure 1:
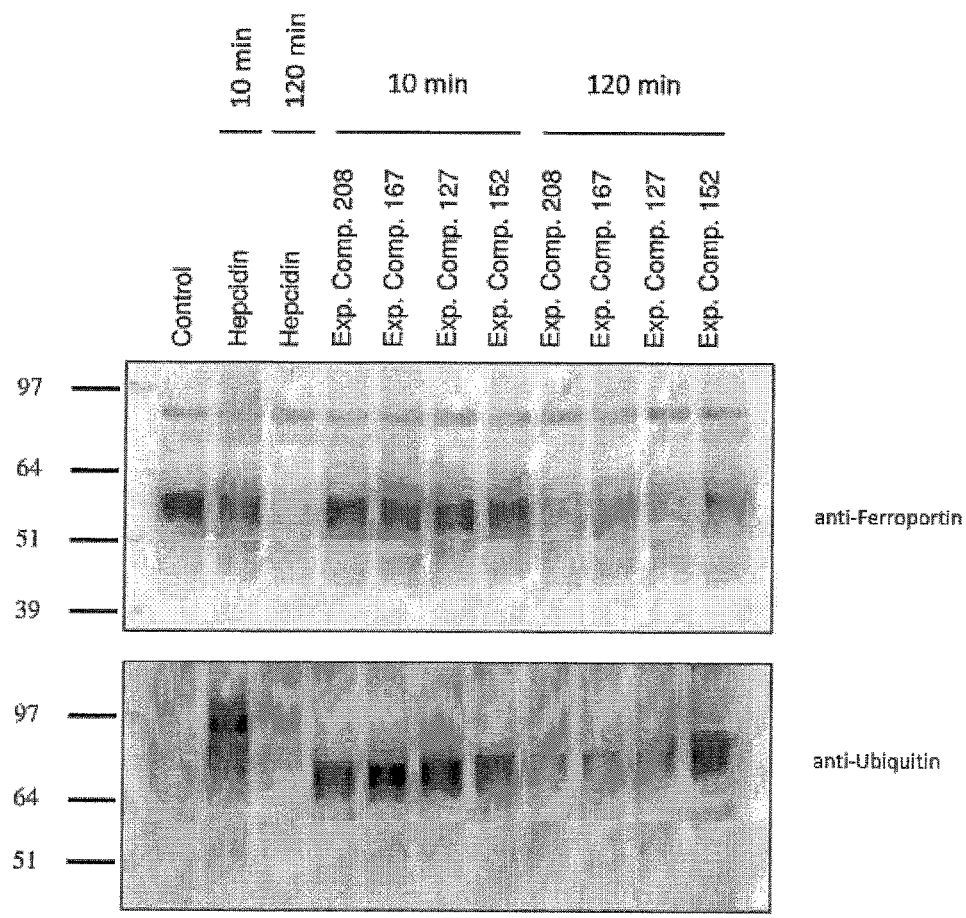
FIG. 1 shows Fpn inhibitor trigger ubiquitination and degradation of Fpn expressed in a mouse macrophage cell line.

The inventors have surprisingly found that specific compounds having the general structural formula (I) as defined herein, act as ferroportin inhibitors, thus effectively inhibiting iron transport and accordingly being particularly suitable for the use as medicaments, in particular for the use in the treatment and/or prophylaxis of diseases caused by a lack of hepcidin, diseases associated with ineffective erythropoiesis or iron metabolism disorders leading to increased iron levels, such as particularly iron overload states such as in particular thalassemia and hemochromatosis. Very particularly the new compounds turned out to be suitable for treating thalassemia and hemochromatosis. The new compounds are also suitable for the treatment of diseases caused by pathologically low hepcidin levels and for the use in the inhibition of iron transport.

Accordingly, the invention relates to compounds of general formula (I)

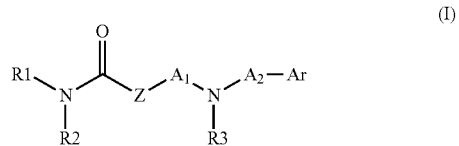

or pharmaceutically acceptable salts thereof, for the use as ferroportin inhibitors, wherein $R^1$ and $R^2$ are the same or different and are independently selected from the group consisting of
hydrogen,
optionally substituted alkyl,
optionally substituted aryl,
optionally substituted heteroaryl,
optionally substituted heterocyclyl, or
$R^1$ and $R^2$ together with the nitrogen atom to which they are bonded form an optionally substituted 3- to 6-membered ring, which may optionally contain further heteroatoms, or
one of $R^1$ and $R^2$ is an alkanoyl-group, which together with Z being an amino group (—NH—) forms a 5- or 6-membered heterocyclic diketone containing two nitrogen atoms;

Z is a cyclic group or a linear group and is selected from
optionally substituted 5- or 6-membered heteroaryl
optionally substituted aryl,
optionally substituted 5- or 6-membered heterocyclyl,
amino (—NH—),
an alkylaminocarbonyl group [—(CH$_2$)$_n$—NH—(C═O)—], preferably with n=1, or
an alkylcarbonylamino group [—(CH$_2$)$_n$—(C═O)—NH—], preferably with n=1;

$A^1$ is optionally substituted alkanediyl;
$A^2$ is
optionally substituted alkanediyl,
a direct bond, or
a sulfonyl group (—SO$_2$—);
$R^3$ is
hydrogen, or
optionally substituted alkyl; or
$A^1$ and $R^3$ together with the nitrogen atom to which they are bonded form an optionally substituted 4 to 6-membered mono- or bicyclic ring; or
$R^3$ and $A^2$ together with the nitrogen atom to which they are bonded form an optionally substituted 4- to 7-membered ring; and
Ar is
optionally substituted aryl,
optionally substituted monocyclic heteroaryl, or
optionally substituted bicyclic heteroaryl, which may be fused with a ring formed by
$R^3$ and $A^2$ together with the nitrogen atom to which they are bonded.

Therein and throughout the invention, the above-mentioned substituent groups are defined as follows:

Optionally substituted alkyl preferably includes:
linear or branched alkyl preferably containing 1 to 8, more preferably 1 to 6, more preferably 1 to 4, even more preferred 1 to 3 (C$_1$-C$_3$-alkyl) or 1, 2 or 3 carbon atoms.

Optionally substituted alkyl further includes cycloalkyl containing preferably 3 to 8, more preferably 5 or 6 carbon atoms.

Examples of alkyl residues containing 1 to 8 carbon atoms include: a methyl group, an ethyl group, an n-propyl group, an i-propyl group, an n-butyl group, an i-butyl group, a sec-butyl group, a t-butyl group, an n-pentyl group, an i-pentyl group, a sec-pentyl group, a t-pentyl group, a 2-methylbutyl group, an n-hexyl group, a 1-methylpentyl group, a 2-methylpentyl group, a 3-methylpentyl group, a 4-methylpentyl group, a 1-ethylbutyl group, a 2-ethylbutyl group, a 3-ethylbutyl group, a 1,1-dimethylbutyl group, a 2,2-dimethylbutyl group, a 3,3-dimethylbutyl group, a 1-ethyl-1-methylpropyl group, an n-heptyl group, a 1-methylhexyl group, a 2-methylhexyl group, a 3-methylhexyl group, a 4-methylhexyl group, a 5-methylhexyl group, a 1-ethylpentyl group, a 2-ethylpentyl group, a 3-ethylpentyl group, a 4-ethylpentyl group, a 1,1-dimethylpentyl group, a 2,2-dimethylpentyl group, a 3,3-dimethylpentyl group, a 4,4-dimethylpentyl group, a 1-propylbutyl group, an n-octyl group, a 1-methylheptyl group, a 2-methylheptyl group, a 3-methylheptyl group, a 4-methylheptyl group, a 5-methylheptyl group, a 6-methylheptyl group, a 1-ethylhexyl group, a 2-ethylhexyl group, a 3-ethylhexyl group, a 4-ethylhexyl group, a 5-ethylhexyl group, a 1,1-dimethylhexyl group, a 2,2-dimethylhexyl group, a 3,3-dimethylhexyl group, a 4,4-dimethylhexyl group, a 5,5-dimethylhexyl group, a 1-propylpentyl group, a 2-propylpentyl group, etc. Those containing 1 to 6, preferably 1 to 4 carbon atoms, such as in particular methyl, ethyl, n-propyl, i-propyl, n-butyl, i-butyl, sec-butyl, and t-butyl are preferred. C$_1$-C$_3$ alkyl, in particular, methyl, ethyl and i-propyl are more preferred. Most preferred are C$_1$ and C$_2$ alkyl, such as methyl and ethyl.

Cycloalkyl residues containing 3 to 8 carbon atoms preferably include: a cyclopropyl group, a cyclobutyl group, a cyclopentyl group, a cyclohexyl group, a cycloheptyl group and a cyclooctyl group. A cyclopropyl group, a cyclobutyl group, a cyclopentyl group and a cyclohexyl group are preferred. A cyclopentyl group and a cyclohexyl group are particularly preferred.

Substituents of the above-defined optionally substituted alkyl preferably include 1 to 3 of the same or different substituents, more preferably 1 or 2 of the same or different substituents, selected, for example, from the group consisting of: optionally substituted cycloalkyl, as defined above, hydroxy, an oxo-group (═O), carboxy, halogen, as defined below, cyano, alkoxy, as defined below, optionally substituted acyl, as defined below, optionally substituted acyloxy, as defined below, optionally substituted aryl, as defined below, optionally substituted heteroaryl, as defined below, optionally substituted heterocyclyl, as defined below, optionally substituted amino, as defined below, optionally substituted alkyl, aryl or heterocyclylsulfonyl (R—SO$_2$—), as defined below as well as an alkylene group such as in particular a methylene-group, forming for example a methylene-substituted ethyl-group (—CH$_3$—(C═CH$_2$)— or *>═, wherein * indicates the binding site). Preferably the 1 to 3 substituents of alkyl are selected from optionally substituted cycloalkyl, hydroxy, oxo (═O), carboxy, optionally substituted acyloxy, halogen, optionally substituted aryl, optionally substituted heteroaryl, optionally substituted heterocyclyl, optionally substituted amino, optionally substituted alkyl, aryl or heterocyclylsulfonyl (R—SO$_2$—) and an alkylene group such as in particular a methylene-group. More preferred are 1 to 3 substituents of alkyl, selected from optionally substituted aryl, optionally substituted heteroaryl, and optionally substituted heterocyclyl and an alkylene group such as in particular a methylene-group. More preferred is one substituent of alkyl. Most preferred is one substituent of alkyl, which is optionally substituted aryl or optionally substituted heteroaryl as defined below.

Within the meaning of the present invention, halogen includes fluorine, chlorine, bromine and iodine, preferably fluorine or chlorine, most preferred is fluorine.

Examples of a linear or branched alkyl residue substituted by halogen and containing 1 to 8 carbon atoms include:
a fluoromethyl group, a difluoromethyl group, a trifluoromethyl group, a chloromethyl group, a dichloromethyl group, a trichloromethyl group, a bromomethyl group, a dibromomethyl group, a tribromomethyl group, a 1-fluoroethyl group, a 1-chloroethyl group, a 1-bromoethyl group, a 2-fluoroethyl group, a 2-chloroethyl group, a 2-bromoethyl group, a difluoroethyl group such as a 1,2-difluoroethyl group, a 1,2-dichloroethyl group, a 1,2-dibromoethyl group, a 2,2-difluoroethyl group, a 2,2-dichloroethyl group, a 2,2-dibromoethyl group a 2,2,2-trifluoroethyl group, a heptafluoroethyl group, a 1-fluoropropyl group, a 1-chloropropyl group, a 1-bromopropyl group, a 2-fluoropropyl group, a 2-chloropropyl group, a 2-bromopropyl group, a 3-fluoropropyl group, a 3-chloropropyl group, a 3-bromopropyl group, a 1,2-difluoropropyl group, a 1,2-dichloropropyl group, a 1,2-dibromopropyl group, a 2,3-difluoropropyl group, a 2,3-dichloropropyl group, a 2,3-dibromopropyl group, a 3,3,3-trifluoropropyl group, a 2,2,3,3,3-pentafluoropropyl group, a 2-fluorobutyl group, a 2-chlorobutyl group, a 2-bromobutyl group, a 4-fluorobutyl group, a 4-chlorobutyl group, a 4-bromobutyl group, a 4,4,4-trifluorobutyl group, a 2,2,3,3,4,4,4-heptafluorobutyl group, a perfluorobutyl group, a 2-fluoropentyl group, a 2-chloropentyl group, a 2-bromopentyl group, a 5-fluoropentyl group, a 5-chloropentyl group, a 5-bromopentyl group, a perfluoropentyl group, a 2-fluorohexyl group, a 2-chlorohexyl group, a 2-bromohexyl group, a 6-fluorohexyl group, a 6-chlorohexyl group, a 6-bromohexyl group, a perfluorohexyl group, a 2-fluoroheptyl group, a 2-chloroheptyl group, a 2-bromoheptoyl group, a 7-fluoroheptyl group, a 7-chloroheptyl group, a 7-bromoheptyl group, a perfluoroheptyl group, etc. Fluoroalkyl, difluoroalkyl and trifluoroalkyl are mentioned in particular, and trifluoromethyl and mono- and di-fluoroethyl is preferred. Particularly preferred is trifluoromethyl and 2,2-difluoroethyl.

Examples of a cycloalkyl residue substituted by halogen and containing 3 to 8 carbon atoms include: a 2-fluorocyclopentyl group, a 2-chlorocyclopentyl group, a 2-bromocyclopentyl group, a 3-fluorocyclopentyl group, a 3-chlorocyclopentyl group, a 3-bromocyclopentyl group, a 2-fluorocyclohexyl group, a 2-chlorocyclohexyl group, a 2-bromocyclohexyl group, a 3-fluorocyclohexyl group, a 3-chlorocyclohexyl group, a 3-bromocyclohexyl group, a 4-fluorocyclohexyl group, a 4-chlorocyclohexyl group, a 4-bromocyclohexyl group, a di-fluorocyclopentyl group, a di-chlorocyclopentyl group, a di-bromocyclopentyl group, a di-fluorocyclohexyl group, a di-chlorocyclohexyl group, a di-bromocyclohexyl group, a tri-fluorocyclohexyl group, a tri-chlorocyclohexyl group, a tri-bromocyclohexyl group, etc.

Examples of a hydroxy-substituted alkyl residue include the above-mentioned alkyl residues which contain 1 to 3 hydroxyl residues such as, for example, hydroxymethyl, 2-hydroxyethyl, 3-hydroxypropyl, etc. Hydroxymethyl being preferred.

Examples of an oxo-substituted alkyl residue includes the above-mentioned alkyl residues, wherein at least one carbon atom is substituted by an oxo-group forming a carbonyl group [—(C═O)—] in the alkyl chain or an alkanoyl-group [alkyl-(C═O)—)], such as $C_1$ to $C_6$ alkanoyl, such as formyl, acetyl, propionyl, butyryl, isobutyryl, valeryl, isovaleryl, pivaloyl, hexanoyl, etc. Preferred is an oxo-substitution of the alkyl residue in the form of a carbonyl-group [—(C═O)—] or an acetyl-group like [—(C═O)—CH$_3$] or [—(C═O)—CH$_2$—].

Examples of an alkoxy-substituted alkyl residue include the above-mentioned alkyl residues which contain 1 to 3 alkoxy residues as defined below such as, for example, methoxymethyl, ethoxymethyl, 2-methoxyethylene, etc.

Examples of an acyl-substituted alkyl residue include the above-mentioned alkyl residues which contain 1 to 3 acyl residues as defined below.

Examples of an acyloxy-substituted alkyl residue include the above-mentioned alkyl residues which contain 1 to 3, preferably 1 acyloxy residues [—O—(C═O)—].

Examples of a cycloalkyl-substituted alkyl group include the above-mentioned alkyl residues containing 1 to 3, preferably 1 (optionally substituted) cycloalkyl group such as, for example: cyclopropylmethyl, cyclobutylmethyl, cyclopentylmethyl cyclohexylmethyl, 2-cyclopropylethyl, 2-cyclobutylethyl, 2-cyclopentylethyl 2-cyclohexylethyl, 2- or 3-cyclopropylpropyl, 2- or 3-cyclobutylpropyl, 2- or 3-cyclopentylpropyl, 2- or 3-cyclohexylpropyl, etc. Preferred are cyclopropylmethyl and cyclohexylmethyl.

Examples of an aryl-substituted alkyl group include the above-mentioned alkyl residues containing 1 to 3, preferably 1 (optionally substituted) aryl group, as defined below, such as, for example, phenylmethyl, 1- or 2-phenylethyl, 2- or 3-phenylpropyl, etc., phenylmethyl, 1-phenylethyl, 2-phenylethyl, and 2-phenylpropyl being preferred. Also particularly preferred are alkyl groups, as defined above, which are substituted by substituted aryl, as defined below, in particular by phenyl being substituted with 1 to 3, preferably 1 or 2 of the same of different substituents, preferably selected from halogen, such as preferably F and Cl, cyano, optionally substituted alkyl, such as preferably methyl, ethyl, halogen-substituted alkyl such as trifluoromethyl, optionally substituted alkoxy, such as methoxy, ethoxy, halogen-substituted alkoxy such as difluoromethoxy, trifluoromethoxy, an optionally substituted amino group such as amino (NH$_2$—) or mono- or di-alkylamino such as preferably dimethylamino, an optionally substituted heterocyclyl group, such as pyrrolidinyl, alkyl-substituted piperazinyl, or morpholinyl, or an optionally substituted heterocyclylsulfonyl group, such as N-morpholinyl-sulfonyl, forming in particular alkyl-groups, which are substituted with substituted aryl according to the formulas

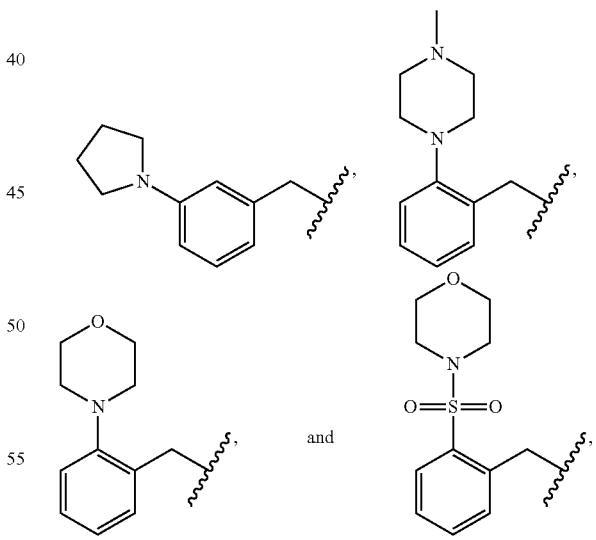

which are particularly preferred for $R^1$ and/or $R^2$.

Examples of a heterocyclyl-substituted alkyl group include the above-mentioned alkyl residues containing 1 to 3, preferably 1 (optionally substituted) heterocyclyl group, as defined below, which may be substituted with 1 to 3, preferably with 1 substituent. Preferably the heterocyclyl group as a substituent of alkyl is for example a morpholinyl group, a piperazinyl group, a piperidinyl group etc. As defined above, the heterocylcyl group may be substituted and a preferred substituent is an optionally substituted alkyl group, preferably a methyl or ethyl group or a trifluoromethyl group. Particularly preferred is a a piperidinyl group and a methyl-substituted morpholinyl group.

Examples of a heteroaryl-substituted alkyl group include the above-mentioned alkyl residues containing 1 to 3, preferably 1 (optionally substituted) heteroaryl group, as defined below, such as, for example a pyridinyl, a pyridazinyl, a pyrimidinyl, a pyrazinyl, a pyrazolyl, an imidazolyl, a benzimidazolyl, a thiophenyl, or an oxazolyl group, such as pyridine-2-yl-methyl, pyridine-3-yl-methyl, pyridine-4-yl-methyl, 2-pyridine-2-yl-ethyl, 2-pyridine-1-yl-ethyl, 2-pyridine-3-yl-ethyl, pyridazine-3-yl-methyl, pyridazine-3-yl-ethyl pyrimidine-2-yl-methyl, pyrimidine-4-yl-methyl, pyrazine-2-yl-methyl, pyrazol-3-yl-methyl, pyrazol-4-yl-methyl, pyrazol-5-yl-methyl, imidazole-2-yl-methyl, imidazole-5-yl-methyl, benzimidazol-2-yl-methyl, thiophen-2-yl-methyl, thiophen-3-yl-methyl, 1,3-oxazole-2-yl-methyl.

Preferred is an alkyl group which is substituted with optionally substituted pyridazinyl, such as in particular pyridazin-3-yl-methyl and pyridazin-3-yl-ethyl, optionally substituted pyridinyl, such as in particular optionally substituted pyridine-2-yl-methyl, pyridine-3-yl-methyl, pyridine-4-yl-methyl, 2-pyridine-2-yl-ethyl, 2-pyridine-1-yl-ethyl, 2-pyridine-3-yl-ethyl, very particularly optionally substituted pyridine-2-yl-methyl and 2-pyridin-2-yl-ethyl, optionally substituted pyrazol-3-yl-methyl, pyrazol-4-yl-methyl, pyrazol-5-yl-methyl, pyrazol-3-yl-ethyl, pyrazol-4-yl-ethyl, pyrazol-5-yl-ethyl. Particularly preferred is substituted pyridinyl-alkyl, such as substituted pyridinyl-methyl or substituted pyridinyl-ethyl, wherein the 1, 2 or 3 substituents are selected from halogen, such as fluorine, $C_1$-$C_3$-alkyl, such as methyl, and trifluoromethyl. Particularly preferred is fluorine substituted pyridinyl-alkyl, such as fluorine substituted pyridinyl-methyl or fluorine substituted pyridinyl-ethyl. Most preferred is fluorine substituted pyridinyl-methyl according to formula

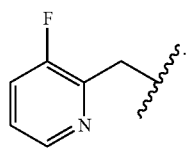

Examples of a heteroaryl-substituted alkyl group includes further in particular a cyclo-alkyl residue as defined above, which is bound to the heteroaryl-substituent by forming a fused ring with the heteroaryl-substituent as defined above, preferably the fused cyclo-alkyl-residue is cyclopentyl or cyclohexyl. Further, preferably the fused heteroaryl-subsituten is pyridinyl, forming for example fused rings such as cyclopenta-pyridinyl and cyclohexa-pyridinyl, according to the formulas

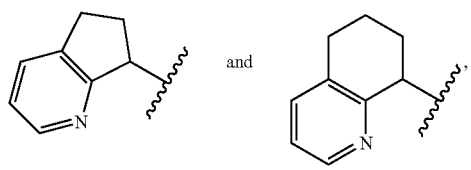 [SMILES: *C1CCc2cccnc21 ; *C1CCCc2cccnc21]

which are particularly preferred for $R^1$ and/or $R^2$ or a group Cycl-[CQ]$_n$, wherein Q is $C_1$-$C_4$-alkyl, which forms a fused 5- or 6-membered ring with Cycl.

In each case the heterocyclyl-substituent of an alkyl-residue as defined herein may be substituted with 1 to 3, preferably 1 or 2 of the same or different substituents, which are preferably selected from halogen, such as preferably F and Cl, cyano, optionally substituted alkyl, such as preferably methyl, ethyl, halogen-substituted alkyl such as trifluoromethyl and hydroxy-substituted alkyl such as hydroxymethyl, optionally substituted alkoxy, such as preferably methoxy and ethoxy, an oxo-group (=O), a heterocyclyl group as defined below, such as an N-morpholinyl group, an aminocarbonyl group, an optionally substituted amino group, such as preferably amino ($NH_2$—) or mono- or di-alkylamino such as preferably dimethylamino.

Examples of an amino-substituted alkyl residue include the above-mentioned alkyl residues containing 1 to 3, preferably 1 (optionally substituted) amino group, as defined below, such as, for example, aminoalkyl ($NH_2$-alkyl) or mono- or dialkylamino-alkyl, such as aminomethyl, 2-aminoethyl, 2- or 3-aminopropyl, methylaminomethyl, methylaminoethyl, methylaminopropyl, 2-ethylaminomethyl, 3-ethylaminomethyl, 2-ethylaminoethyl, 3-ethylaminoethyl, etc. or an alkyl group, which may be substituted with an optionally substituted alkyloxycarbonylamino group such as a group according to formula

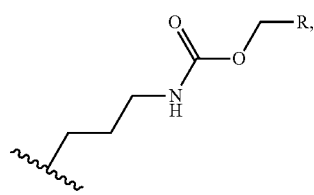

wherein R defines a substituent of alkyl as defined above, preferably a phenyl group, such group being particularly preferred for $R^3$.

Throughout the invention, optionally substituted aryl preferably includes:

aromatic hydrocarbon residues containing 6 to 14 carbon atoms (excluding the carbon atoms of the possible substituents), which may be monocyclic or bicyclic, including, for example: phenyl, naphthyl, phenanthrenyl and anthracenyl, which may optionally be substituted preferably by 1 to 3 of the same or different substituents selected from hydroxy, halogen, as defined above, cyano, optionally substituted amino, as defined below, optionally substituted alkyl, as defined above, optionally substituted acyl, as defined below, and optionally substituted alkoxy, as defined below, optionally substituted aryloxy, as defined below, optionally substituted heterocyclyloxy, as defined below, optionally substituted aryl, as defined herein, optionally substituted heterocyclylyl, as defined below. Optionally substituted phenyl is preferred, such as unsubstituted phenyl and phenyl which is substituted with 1 to 3, more preferably with 1 or 2 substituents, which may be the same or different. The 1 to 3 phenyl substituents are in particular selected from the group consisting of heterocyclyl as defined below, halogen as defined above such as in particular F, optionally substituted amino as defined below such as in particular (—$NH_2$) or mono- or dialkylamino with dimethylamino being preferred, cyano, optionally substituted alkoxy as defined below such as in particular di-fluoromethoxy and trifluoromethoxy, and an optionally substituted sulfonyl-group which may form in particular a group

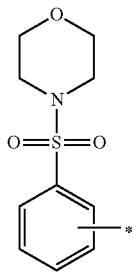

with * indicating the binding site of the substituted phenyl substituent. Most preferred is halogen-substituted phenyl, alkoxy substituted phenyl and hydroxyl-substituted phenyl. The aforementioned substituents of phenyl are particularly preferred for the group "Cycl" in the formulae as defined herein with the meaning of a substituted aryl group being substituted phenyl. Further preferred is unsubstituted phenyl.

Examples of an alkyl-substituted aryl group preferably include: aryl, as described above which is substituted by straight-chain or branched alkyl containing 1 to 8, preferably 1 to 4 carbon atoms, as described above. Toluoyl is the preferred alkylaryl.

Examples of a hydroxy-substituted aryl group preferably include: aryl, as described above, which is substituted by 1 to 3 hydroxyl residues such as, for example 2-hydroxyphenyl, 3-hydroxyphenyl, 4-hydroxyphenyl, 2,4-di-hydroxyphenyl, 2,5-di-hydroxyphenyl, 2,6-di-hydroxyphenyl, 3,5-di-hydroxyphenyl, 3,6-di-hydroxyphenyl, 2,4,6-tri-hydroxyphenyl, etc.

Examples of a halogen-substituted aryl group preferably include: aryl, as described above, which is substituted by 1 to 3 halogen atoms such as, for example 2-chloro- or fluorophenyl, 3-chloro- or fluorophenyl, 4-chloro- or fluorophenyl, 2,4-di-(chloro- and/or fluoro)phenyl, 2,5-di-(chloro- and/or fluoro)phenyl, 2,6-di-(chloro- and/or fluoro) phenyl, 3,5-di-(chloro- and/or fluoro)phenyl, 3,6-di-(chloro- and/or fluoro)phenyl, 2,4,6-tri-(chloro- and/or fluoro)phenyl, etc.

Examples of an alkoxy-substituted aryl group preferably include: aryl, as described above, which is substituted by 1 to 3 alkoxy residues, as described below, such as preferably 2-methoxyphenyl, 3-methoxyphenyl, 4-methoxyphenyl, 2-ethoxyphenyl, 3-ethoxyphenyl, 4-ethoxyphenyl, 2,4-di-methoxyphenyl, etc., as well as di-fluoromethoxyphenyl and trifluoromethoxyphenyl.

Throughout the invention, optionally substituted heterocyclyl preferably includes:

Saturated or unsaturated mono- or bicyclic 4- to 8-membered heterocyclic residues containing 1 to 3, preferably 1 to 2 same or different hetero atoms, selected from N, O and S and which may optionally be substituted preferably by 1 to 3 substituents, wherein reference may be made to the definition of possible substituents for optionally substituted heterocyclyl. 4-, 5- and 6-membered saturated or unsaturated, mono- or bicyclic optionally substituted heterocyclic residues are preferred, and examples comprise azetidinyl, pyrrolidinyl, tetrahydrofuranyl, tetrahydrothiophenyl, piperidinyl, piperazinyl, tetrahydropyranyl, tetrahydrothiopyranyl, morpholinyl, etc., such as azetidin-1-yl, azetidin-2-yl, azetidin-3-yl, tetrahydrofuran-2-yl, tetrahydrofuran-3-yl, tetrahydro-thiophen-2-yl, tetrahydro-thiophen-3-yl, pyrrolidin-1-yl, pyrrolidin-2-yl, pyrrolidin-3-yl, morpholin-1-yl, morpholin-2-yl, morpholin-3-yl, piperidin-1-yl, piperidin-2-yl, piperidin-3-yl, piperidin-4-yl, piperazin-1-yl, piperazin-2-yl, tetrahydropyran-2-yl, tetrahydropyran-3-yl, tetrahydropyran-4-yl, etc., which may optionally be condensed with aromatic rings. Particularly preferred are azetidinyl, pyrrolidinyl, piperidinyl, and morpholinyl residues. Particularly preferred are the following heterocyclic residues, which may be substituted as defined above:

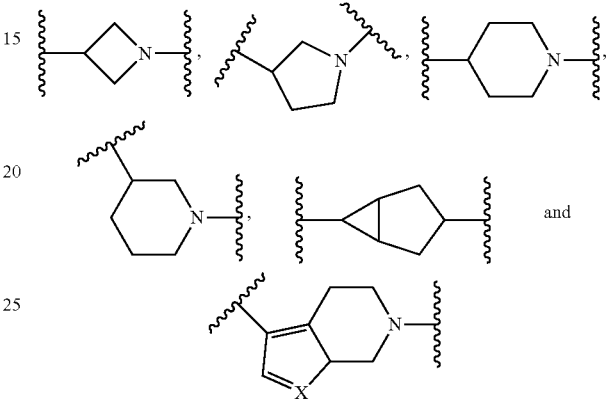

(with X being N, O or S, preferably S), which are particularly preferred for $A^1$, and

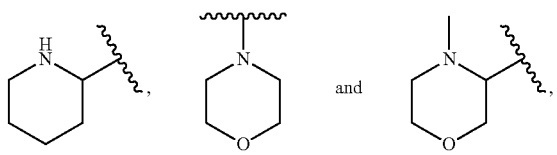

being particularly preferred for $R^1$ and/or $R^2$, and

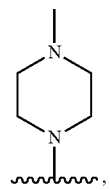

which is particularly preferred as a substituent for an aryl group.

Preferred substituents of heterocyclyl-residues comprise an alkyl-group such as preferably methyl and ethyl, a hydroxyl-group, and an oxo-group (=O).

Throughout the invention, optionally substituted heteroaryl includes:

heteroaromatic hydrocarbon residues containing 4 to 9 ring carbon atoms, which additionally preferably contain 1 to 3 of the same or different heteroatoms from the series S, O, N in the ring and therefore preferably form 5- to 12-membered heteroaromatic residues which may preferably be monocyclic but also bicyclic. Preferred aromatic heterocyclic residues include: pyridyl (pyridinyl), pyridyl-N-oxide, pyridazinyl, pyrimidyl, pyrazinyl, thienyl (thiophenyl), furyl, pyrrolyl, pyrazolyl, imidazolyl, triazolyl, thiazolyl, oxazolyl or isoxazolyl, indolizinyl, indolyl, benzo[b]thienyl, benzo[b]furyl, indazolyl, quinolyl, isoquinolyl, naphthyridinyl, quinazolinyl, quinoxalinyl. 5- or 6-membered aromatic heterocycles are preferred, such as from the group of 5-membered heteroaryl, for example thiazolyl such as thiazol-2-yl, 2-thiazol-2-yl, 2-thiazol-4-yl, thienyl (thiophenyl) such as thien-3-yl, pyrazolyl such as 1-pyrazol-4-yl, 3-pyrazol-5-yl, imidazolyl such as imidazole-2-yl, 2-imidazol-4-yl, 1-imidazol-4-yl, triazolyl such as 1-triazol-3-yl, 1-triazol-4-yl, such as 1,2,4-triazol-3-yl or 1,2,3-triazol-4-yl, oxazolyl such as 2-oxazol-4-yl, 2-oxazol-5-yl, oxadiazolyl such as 1,2,4-oxadiazol-3-yl and from the group of 6-membered heteroaryl, for example pyridyl (pyridinyl) such as pyrid-1-yl, pyrid-2-yl, pyrid-3-yl, pyrid-4-yl, 2-pyrid-4-yl, 2-pyrid-6-yl, 3-pyrid-5-yl (pyridin-1-yl, pyridin-2-yl, pyridin-3-yl, pyridin-4-yl, 2-pyridin-4-yl, 2-pyridin-6-yl, 3-pyridin-5-yl), pyrimidin-2-yl, pyrimidin-4-yl, pyrimidin-5-yl, and from the group of bicyclic heteroaromatic residues in particular benzimidazolyl such as benzimidazol-2-yl, benzimidazol-4-yl, benzimidazol-5-yl, as well as benzimidazolpyridinyl according to formula

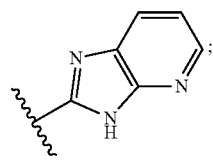 [SMILES: *c1nc2cccnc2[nH]1]

or benzoxazol-2-yl according to formula

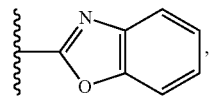

or benzimidazol forming a fused ring with a heterocyclyl residue, as defined above.

The aforementioned heteroaryl-groups may have one or more, preferably 1 to 3, more preferably 1 or 2 same or different substituents, which are in particular selected from halogen, such as preferably F and Cl, cyano, optionally substituted alkyl as defined above, such as preferably methyl, ethyl, n-propyl, i-propyl, halogen-substituted alkyl such as difluoromethyl or trifluoromethyl, hydroxy-substituted alkyl such as hydroxymethyl, aminocarbonyl-substituted alkyl such as aminocarbonylmethyl, carboxyl-substituted alkyl such as carboxylmethyl, an alkenyl group such as propenyl, optionally substituted alkoxy, such as preferably methoxy and ethoxy, a hydroxyl group (—OH), an oxo-group (=O), a carboxyl group [—(C=O)—OH], a heterocyclyl group as defined above, such as a N-morpholinyl group, an aminocarbonyl group, such as $NH_2$—(C=O)—, an optionally substituted amino group, such as preferably amino ($NH_2$—) or mono- or di-alkylamino such as preferably dimethylamino.

In particular, examples of an alkyl-substituted heteroaryl group preferably include: heteroaryl, as described above, which is substituted by linear or branched, optionally substituted alkyl containing 1 to 8, preferably 1 to 4 carbon atoms, as described above, such as in particular methylimidazolyl such as in particular N-methylimidazolyl, methylbenzimidazolyl such as in particular N-methylbenzimidazolyl, 5-methylbenzimidazolyl, 4-trifluoromethylbenzimidazolyl, 5-trifluoromethylbenzimidazolyl, N-aminocarbonylmethylbenzimidazolyl, N-carboxylmethylaminocarbonyl, N-methylpyrazolyl, 1(N),5-dimethylpyrazolyl, methylpyridinyl such as 2-methylpyridin-3-yl, 2-methylpyridin-4-yl, 3-methylpyridin-2-yl, 3-methylpyridin-3-yl, 3-methylpyridin-4-yl, 4-methylpyridin-2-yl, 5-methylpyridin-2-yl, 6-methylpyridin-2-yl etc., dimethylpyridinyl such as 3,5-dimethylpyridin-2-yl, 4,6-dimethylpyridin-3-yl, trifluoromethylpyridinyl, in particular 3- or 4-trifluoromethylpyridin-2-yl, 6-trifluoromethylpyridin-3-yl, 3-hydroxymethylpyridin-2-yl, 5-methylpyrimidin-2-yl, etc.

Examples of a halogen-substituted heteroaryl group preferably include: heteroaryl, as described above, which is substituted by 1 to 3, preferably 1 or 2 halogen atoms such as preferably by F and/or Cl, including in particular fluoropyridinyl such as 3-fluoro-pyridin-2-yl, 4-fluoro-pyridin-2-yl, 5-fluoro-pyridin-2-yl, 6-fluoro-pyridin-2-yl, 3-chloro-pyridin-2-yl, 4-chloro-pyridin-2-yl, 5-chloro-pyridin-2-yl, 6-chloro-pyridin-2-yl, 2-fluoro-pyridin-3-yl, 4-fluoro-pyridin-3-yl, 5-fluoro-pyridin-3-yl, 6-fluoro-pyridin-3-yl, 2-chloro-pyridin-3-yl, 4-chloro-pyridin-3-yl, 5-chloro-pyridin-3-yl, 6-chloro-pyridin-3-yl, 2-fluoro-pyridin-4-yl, 3-fluoro-pyridin-4-yl, 5-fluoro-pyridin-4-yl, 6-fluoro-pyridin-4-yl, 2-chloro-pyridin-4-yl, 3-chloro-pyridin-4-yl, 5-chloro-pyridin-4-yl, 6-chloro-pyridin-4-yl, etc., di-fluoropyridinyl such as 3,5-di-fluoropyridin-2-yl, fluoro-chloropyridinyl such as 3-chloro-5-fluoro-pyridin-2-yl, etc.

Examples of a halogen- and alkyl-substituted heteroaryl group preferably include: heteroaryl, as described above, which is substituted by 1 to 3 halogen atoms such as preferably by F and/or Cl, and 1 to 3 linear or branched, optionally substituted alkyl-residues as described above, such as in particular 3-fluoro-6-methylpyridin-2-yl, 3-chloro-5-trifluoromethylpyridin-2-yl.

Further preferred examples of substituted heteroaryl-groups include:
methoxypyridinyl such as 3-, 4-, 5- or 6-methoxypyridin-2-yl, 2-, 4-, 5- or 6-methoxypyridin-3-yl, 2-, 3-, 5- or 6-methoxypyridin-4-yl, etc., hydroxypyridinyl such as 3-, 4-, 5- or 6-hydroxypyridin-2-yl, 2-, 4-, 5- or 6-hydroxypyridin-3-yl, 2-, 3-, 5- or 6-hydroxypyridin-4-yl, etc., oxopyridinyl such as 6-oxo-1,6-dihydropyridin-2-yl, 2-oxo-1,2-dihydropyridin-3-yl etc., aminopyridinyl such as 6-dimethylaminopyridin-3-yl, aminocarbonylpyridinyl such as 6-aminocarbonylpyridin-3-yl, cyanopyridinyl such as 3-, 4-, 5- or 6-cyanopyridin-2-yl, 2-, 4-, 5- or 6-cyanopyridin-3-yl, 2-, 3-, 5- or 6-cyanopyridin-4-yl, etc., as well as 2-morpholin-4-yl-pyridin-4-yl.

With respect to 1 to 3, preferably 1 or 2 same or different optional substituents of a bicyclic heteroaryl group Ar or Het-2 according to any of the formulae as defined herein said heteroaryl-substituents are preferably selected from halogen, such as preferably F and Cl, cyano, optionally substituted alkyl as defined above, such as preferably methyl, ethyl, n-propyl, i-propyl, halogen-substituted alkyl such as difluoromethyl or trifluoromethyl, aminocarbonyl-substituted alkyl such as aminocarbonylmethyl, carboxyl-substituted alkyl such as carboxylmethyl, optionally substituted alkoxy, such as preferably methoxy and ethoxy and a carboxyl group [—(C=O)—OH]. It is most preferred, that such a substituted Ar or Het-2 group comprises 1 or 2 same or different substituents selected from F, Cl, cyano, optionally substituted alkyl such as methyl and trifluoromethyl, aminocarbonyl-substituted alkyl such as aminocarbonylmethyl, carboxyl-substituted alkyl such as carboxylmethyl, optionally substituted alkoxy, such as methoxy and a carboxyl group [—(C═O)—OH].

With respect to 1 to 4, preferably 1 to 3, more preferably 1 or 2 same or different substituents of a heteroaryl group Cycl according to any of the formulae as defined herein said heteroaryl-substituents are preferably selected from halogen, such as preferably F and Cl, cyano, optionally substituted alkyl as defined above, such as preferably methyl, ethyl, n-propyl, i-propyl, halogen-substituted alkyl such as difluoromethyl or trifluoromethyl, hydroxy-substituted alkyl such as hydroxymethyl, optionally substituted alkoxy, such as preferably methoxy and ethoxy, an oxo-group (═O), a heterocyclyl group as defined above, such as a N-morpholinyl group, an aminocarbonyl group such as $NH_2$—(C═O)—, an optionally substituted amino group, such as preferably amino ($NH_2$—) or mono- or di-alkylamino such as preferably dimethylamino. It is most preferred, that such a substituted heteroaryl group Cycl comprises 1 or 2 same or different substituents selected from F, Cl, cyano, optionally substituted alkyl such as methyl, trifluoromethyl, and hydroxymethyl, optionally substituted alkoxy, such as methoxy, an oxo-group (═O), forming for example an oxo-substituted heteroaryl of the formula

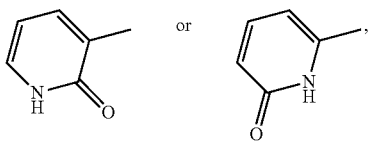

a heterocyclyl group such as a N-morpholinyl group, an aminocarbonyl group such as $NH_2$—(C═O)—, an optionally substituted amino group, such as di-alkylamino such as dimethylamino Optionally substituted acyl here and hereinafter includes: formyl (—CH(═O)), optionally substituted aliphatic acyl (alkanoyl=alkyl-CO, wherein reference may be made to the foregoing definition of optionally substituted alkyl with respect to the alkyl group), optionally substituted aromatic acyl (aroyl=aryl-CO—, wherein reference may be made to the foregoing definition of optionally substituted aryl with respect to the aryl group), optionally substituted heteroaromatic acyl (heteroaroyl=heteroaryl-CO—, wherein reference may be made to the foregoing definition of optionally substituted heteroaryl with respect to the heteroaryl group), or heterocyclic acyl (heterocycloyl=heterocyclyl-CO—, wherein reference may be made to the foregoing definition of optionally substituted heterocyclyl with respect to the heterocyclyl group). Aliphatic acyl=alkanoyl=alkyl-CO— is preferred.

Optionally substituted amino according to the invention preferably includes: amino (—$NH_2$), optionally substituted mono- or dialkylamino (alkyl-NH—, (alkyl)$_2$N—), wherein with respect to "alkyl" reference can be made to the definition of optionally substituted alkyl above. Further included are optionally substituted mono- or diarylamino, mono- or diheteroarylamino and mono- or diheterocyclylamino radicals or mixed optionally substituted alkylarylamino, alkylheteroarylamino and alkylheterocyclylamino radicals, wherein reference can be made to the above definitions of optionally substituted alkyl, aryl, heteroaryl and heterocyclyl. According to the present invention an amino group further includes a group —NH—, such as in particular in the definition of the substituent Z, wherein the amino group —NH— is bound to the $R^1R^2N$—(C═O)— group and to the $A^1$ substituent as shown for example in the general formula (I).

Optionally substituted amino is preferably optionally substituted mono- or dialkylamino (alkyl-NH—, (alkyl)$_2$N—), in particular with 1 to 8, preferably 1 to 6, more preferably 1 to 3 carbon atoms, as previously mentioned. Most preferred optionally substituted amino is mono- or dimethylamino and mono- or diethylamino. Most preferred is an amino group (—$NH_2$) or (—NH—) and a dimethylamino group.

As a further substituted amino group of the present invention an alkylcarbonylamino group [—(CH$_2$)$_n$—(C═O)—NH-] or alkylaminocarbonyl group [—(CH$_2$)$_n$—NH—(C═O)—] may be mentioned, which are both included in and preferred for the definition of the substituent Z of the present invention. Therein n is an integer of 1 to 6, preferably 1 to 3, more preferably 1 or 2. Most preferred is an alkylcarbonylamino group or alkylaminocarbonyl group Z with the meaning [—(CH$_2$)—(C═O)—NH-] or [—(CH$_2$)—NH—(C═O)—], respectively.

It is further possible that an amino group (—NH—) forms a 5- or 6-membered heterocyclic ring together with an optionally substituted alkyl-group (such as an oxo-substituted alkyl group) or alkanoyl-group, such as preferably with an alkanoyl group. It is accordingly possible that, for example, one of the substituents $R^1$ and $R^2$ is an oxo-substituted alkyl group or alkanoyl-group (alkyl-(C═O)—), as defined above, which together with Z being an amino group (—NH—) forms a 5- or 6-membered heterocyclic diketone containing two nitrogen atoms, for example according to the following formula

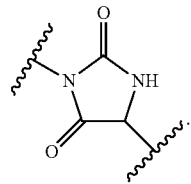 [SMILES: *C1NC(=O)N(*)C1=O]

Throughout the invention, optionally substituted alkanediyl is preferably a divalent straight-chained or branched alkanediyl radical having from 1 to 7, preferably from 1 to 6, more preferably from 1 to 4, carbon atoms, which can optionally carry from 1 to 3, preferably 1 or 2 substituents selected from the group consisting of halogen, hydroxy, an oxo group (forming a carbonyl or acyl group) and an amino group as defined above. The following may be mentioned as preferred examples: methylene, ethane-1,2-diyl, ethane-1,1-diyl, propane-1,3-diyl, propane-1,1-diyl, propane-1,2-diyl, propane-2,2-diyl, butane-1,4-diyl, butane-1,2-diyl, butane-1,3-diyl, butane-2,3-diyl, butane-1,1-diyl, butane-2,2-diyl, butane-3,3-diyl, pentane-1,5-diyl, etc. Particularly preferred is methylene, ethane-1,2-diyl, ethane-1,1-diyl, propane-1,3-diyl, propane-2,2-diyl, and butane-2,2-diyl. Most preferred are methylene and ethane-1,2-diyl.

A preferred substituted alkanediyl radical is a hydroxy-substituted alkanediyl such as a hydroxyl-substituted ethanediyl, an oxo-substituted alkanediyl such as an oxo-substituted methylene or ethanediyl radical, forming a carbonyl or an acyl (acetyl) group, a halogen substituted alkanediyl group such as an alkanediyl group being substituted with one or two halogen atoms selected from F and Cl, preferably 2,2-di-fluoro-ethanediyl, or an alkanediyl group which is substituted with an oxo and an amino group, forming an aminocarbonyl group such as preferably a group [—(C=O)—NH—].

According to the present invention the substituents $R^1$ and $R^2$ or a respective group —[CQ]$_n$-, wherein Q is $C_1$-$C_4$-alkyl, may together with the nitrogen atom to which they are bonded form an optionally substituted 3- to 6-membered ring, which may optionally contain further heteroatoms. Therein, $R^1$ and $R^2$ (or the group —[CQ]$_n$-, wherein Q is $C_1$-$C_4$-alkyl) may preferably together with the nitrogen atom to which they are bonded form a 5- or 6-membered ring, which may contain further heteroatoms, preferably one further heteroatom selected from N and O. Therein it is most preferred that $R^1$ and $R^2$ (or the group —[CQ]$_n$-, wherein Q is $C_1$-$C_4$-alkyl) together with the nitrogen atom to which they are bonded form a 6-membered ring, which contains no further heteroatom, forming an N-piperidinyl ring or a 6-membered ring, which contains one further heteroatom O, forming an N-morpholinyl ring. In particular such N-piperidinyl ring may be substituted with aryl or heteroaryl as defined above, preferably with phenyl or piperidinyl, forming a biciclyc ring according to the formula

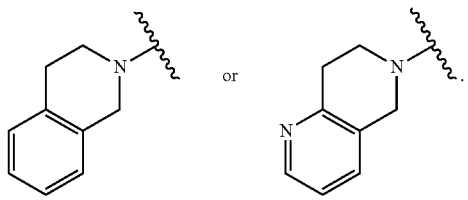 [SMILES: *N1CCc2ccccc2C1 ; *N1CCc2ncccc2C1]

As explained above in context with the definition of amino it is further possible that one of $R^1$ and $R^2$ is an optionally substituted alkyl-group (preferably an oxo-substituted alkyl group) or alkanoyl-group (alkyl-(C=O)—), each as defined above, which together with Z being an amino group (—NH—) forms a 5- or 6-membered heterocyclic diketone containing two nitrogen atoms, as shown above.

According to the present invention it is further possible that $A^1$, having the meaning of a linear or branched alkanediyl group as defined above, and $R^3$, having the meaning of an optionally substituted alkyl group as defined above, together with the nitrogen atom to which they are bonded form an optionally substituted 4- to 6-membered mono- or bicyclic ring, which may be fused with Z, being a heteroaryl group, and which may be substituted with 1 to 3 substituents as defined above, such as for example according to the following formulas

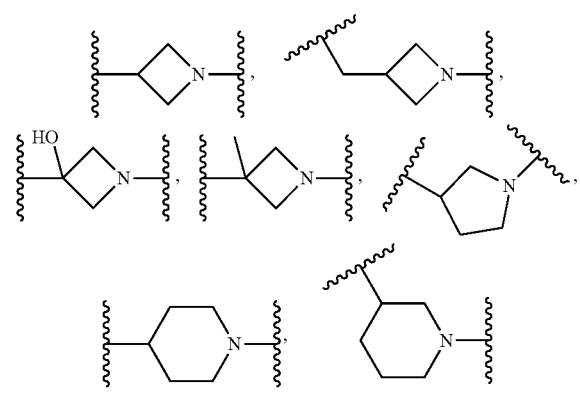

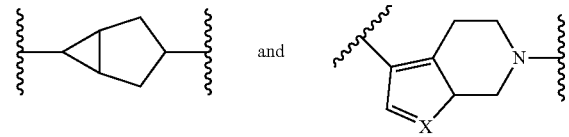

(with X being N, O or S, preferably S), wherein

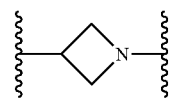 [SMILES: *C1CN(*)C1]

is preferred.

In the context of the present invention it is further possible that $R^3$ and $A^2$ together with the nitrogen atom to which they are bonded form an optionally substituted 4- to 7-membered ring, wherein optional substituents are preferably selected from heteroaryl as defined above and an oxo group. A heteroaryl substituent may then also form a fused ring with the 4- to 7-membered ring formed by $R^3$ and $A^2$ together with the nitrogen atom to which they are bonded. Examples include residues according to the following formulas:

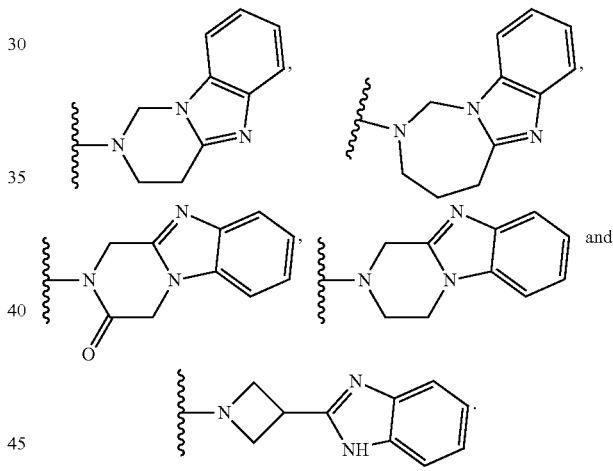

It is particularly preferred that the substitutents in the formula (I) above have the meaning as follows:

$R^1$ and $R^2$ are the same or different and are independently selected from the group consisting of
  hydrogen,
  optionally substituted alkyl, or
  $R^1$ and $R^2$ (or a respective group —[CQ]$_n$-, wherein Q is $C_1$-$C_4$-alkyl) together with the nitrogen atom to which they are bonded form an optionally substituted 3- to 6-membered ring, which may optionally contain further heteroatoms;

Z is a cyclic group or a linear group and is selected from
  optionally substituted 5- or 6-membered heteroaryl
  optionally substituted aryl,
  optionally substituted 5- or 6-membered heterocyclyl,
  amino (—NH—),
  an alkylaminocarbonyl group [—(CH$_2$)—NH—(C=O)—], or an alkylcarbonylamino group [—(CH$_2$)—(C=O)—NH—];
A$^1$ is optionally substituted alkanediyl;
A$^2$ is
  optionally substituted alkanediyl, or
  a direct bond;
R$^3$ is
  hydrogen, or
  C$_1$-C$_3$-alkyl; such as preferably methyl or ethyl, more preferably methyl; or
A$^1$ and R$^3$ together with the nitrogen atom to which they are bonded form an optionally substituted 4-membered monocyclic ring; or
R$^3$ and A$^2$ together with the nitrogen atom to which they are bonded form an optionally substituted 4- to 7-membered ring; and
Ar is optionally substituted bicyclic heteroaryl.

Further Preferred Embodiment 2

A further preferred embodiment of the present invention relates to compounds according to formula (I) as defined above, wherein Z is an optionally substituted cyclic group Z-Cycl, forming compounds according to formula (II):

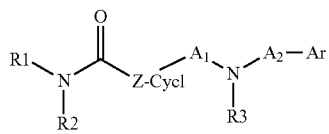

(II)

wherein Z-Cycl is selected from
  an optionally substituted 5- or 6-membered heteroaryl, as defined above,
  an optionally substituted aryl, as defined above, and
  an optionally substituted 5- or 6-membered heterocyclyl, as defined above; and
wherein R$^1$, R$^2$, R$^3$, A$^1$, A$^2$ and Ar have the meaning as defined above.

Preferred are compounds, wherein Z-Cycl is selected from an optionally substituted aromatic group, preferably comprising an optionally substituted 5- or 6-membered heteroaryl, as defined above, and an optionally substituted aryl, as defined above.

Also preferred are compounds, wherein Z-Cycl is selected from an optionally substituted 5- or 6-membered heterocyclic group, preferably comprising an aromatic heteroaryl and a heterocyclyl, each as defined above.

Preferably Z-Cycl is selected from
  a phenyl group as defined above,
  an optionally substituted 5-membered heteroaryl, as defined above,
  an optionally substituted 6-membered heteroaryl, as defined above, preferably a pyridinyl group as defined above, or
  a 5- or 6-membered heterocyclyl selected from a pyrrolidinyl and a piperidinyl group.

More preferably Z-Cycl is selected from an optionally substituted 5-membered heteroaryl as defined above. In particular said 5-membered heteroaryl for Z is selected from
  an oxazolyl group,
  a thiazolyl group,
  a triazolyl group,
  an oxadiazolyl group,
  a pyrazolyl group,
  an imidazolyl group, and
  a thiophenyl (thienyl) group; each as defined above.

More preferred is
  an oxazolyl group,
  a thiazolyl group,
  a triazolyl group, and
  an oxadiazolyl group,
  a pyrazolyl group; each as defined above.
Even more preferred is
  an oxazolyl group,
  a thiazolyl group, and
  a triazolyl group; each as defined above.
Even more preferred is
  an oxazolyl group, and
  a thiazolyl group; each as defined above.
Most preferred is
  an oxazolyl group, as defined above.

Embodiment 2a

A particularly preferred embodiment (2a) relates to compounds, wherein Z is a cyclic group Z-Cycl, which is selected from an optionally substituted 5-membered heteroaryl, forming a compound of the formula (IIa)

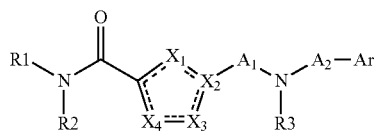

(IIa)

wherein 1 to 3 heteroatoms X (X$^1$, X$^2$, X$^3$ and/or X$^4$) are present, wherein X$^1$ to X$^4$ may be the same or different and are independently selected from the group consisting of C, N, S and O. Preferably in formula (IIa) 1 to 3 heteroatoms X are present, wherein
  X$^1$ is C, N, S or O;
  X$^2$ is C or N;
  X$^3$ is C, N, S or O; and
  X$^4$ is C, N, S or O, preferably X$^4$ is C, N or S,
and wherein X$^1$, X$^3$ and X$^4$ with the meaning of C or N may carry hydrogen or a further substituent, such as preferably a substituent as defined above for substituted heteroaryl.

Embodiment 2b

Another particularly preferred embodiment (2b) relates to compounds, wherein Z is a cyclic group Z-Cycl, which is selected from an optionally substituted 6-membered heteroaryl, forming a compound of the formula (IIb)

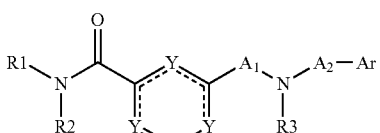

(IIb)

wherein Y is N or C, with the proviso that at least one Y is N.
Preferably only one Y is N and the remaining Y are C.
Therein, any Y with the meaning of C may carry hydrogen and/or a further substituent, preferably substituents as defined above for optionally substituted heteroaryl.

In formula (IIa) and/or (IIb) $R^1$, $R^2$, $R^3$, $A^1$, $A^2$ and Ar have the meaning as defined in any one of the above or the following embodiments described herein.

Embodiment 2a-a

Another particularly preferred embodiment (2a-a) relates to compounds, wherein Z is a cyclic group Z-Cycl, which is selected from an optionally substituted 5-membered heteroaryl, as defined above and according to formula (IIa) above, wherein $X^1$ is N, forming a compound of the formula (IIa-a)

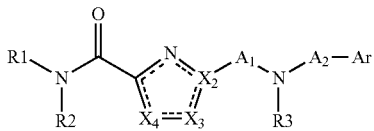
(II-a)

wherein one or two further heteroatoms X ($X^2$, $X^3$, $X^4$) are present, and wherein $X^2$ is C or N;

$X^3$ is C, N, S or O; and $X^4$ is C or N;

with the proviso that in case of two further heteroatoms both are selected to be N or one is N and one (except $X^2$) is O; and wherein $X^3$ and $X^4$ with the meaning of C or N may carry a further substituent such as preferably hydrogen or a substituent as defined above for substituted heteroaryl.

Embodiment 2a-b

Another particularly preferred embodiment (2a-b) relates to compounds, wherein Z is a cyclic group Z-Cycl, which is selected from an optionally substituted 5-membered heteroaryl, as defined above and according to formula (IIa) above, wherein $X^2$ and $X^3$ are both N, forming a compound of the formula (IIa-b)

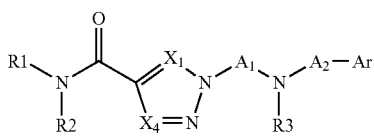
(IIa-b)

with $X^1$ and $X^4$ being C; and wherein $X^1$ and/or $X^4$ may carry hydrogen or a further substituent, such as preferably a substituent as defined above for substituted heteroaryl.

Embodiment 2a-c

Another particularly preferred embodiment (2a-c) relates to compounds, wherein Z is a cyclic group Z-Cycl, which is selected from an optionally substituted 5-membered heteroaryl, as defined above and according to formula (IIa) or (IIa-a) above, wherein $X^1$ is N, $X^2$ is C and $X^3$ is S, forming a compound of the formula (IIa-c)

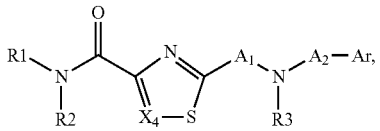
(IIa-c)

wherein $X^4$ is C or N, preferably C, which may carry a further substituent, such as preferably hydrogen or a substituent as defined above for substituted heteroaryl.

Embodiment 2a-d

Another particularly preferred embodiment (2a-d) relates to compounds, wherein Z is a cyclic group Z-Cycl, which is selected from an optionally substituted 5-membered heteroaryl, as defined above and according to formula (IIa) or (IIa-a) above, wherein $X^1$ is N, $X^2$ is C and $X^3$ is O, forming a compound of the formula (IIa-d)

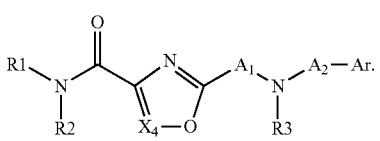
(IIa-d)

wherein $X^4$ is C or N, and which may carry a further substituent, such as preferably hydrogen or a substituent as defined above for substituted heteroaryl forming compounds according to formula (IIa-d-1)

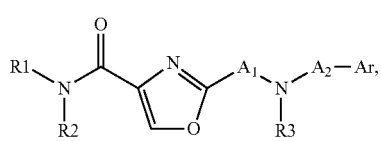
(IIa-d-1)

wherein $X^4$ being C may carry a hydrogen or a further substituent, and which is preferred; or forming compounds according to formula (IIa-d-2)

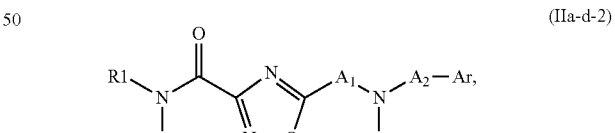
(IIa-d-2)

wherein $X^4$ being N may carry a further substituent.

Embodiment 2a-e

Another particularly preferred embodiment (2a-e) relates to compounds, wherein Z is a cyclic group Z-Cycl, which is selected from an optionally substituted 5-membered heteroaryl, as defined above and according to formula (IIa) above, wherein $X^2$, $X^3$ and $X^4$ are N, forming a compound of the formula (IIa-e)

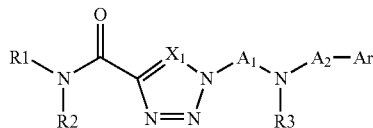

(IIa-e)

with X¹ being C, which may carry a further substituent.

Embodiment 2b-a

Another particularly preferred embodiment (2b-a) relates to compounds, wherein Z is a cyclic group Z-Cycl, which is selected from an optionally substituted 6-membered heteroaryl, as defined above and according to formula (IIb) above, containing one heteroatom N, being selected from compounds according to formula (IIb-a)

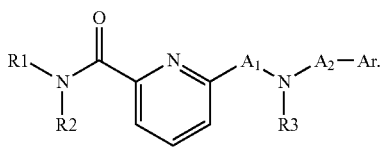

(IIb-a)

Embodiment 2b-b

Another particularly preferred embodiment (2b-b) relates to compounds, wherein Z is a cyclic group Z-Cycl, which is selected from an optionally substituted 6-membered heteroaryl, as defined above and according to formula (IIb) above, containing one heteroatom N, being selected from compounds according to formula (IIb-b)

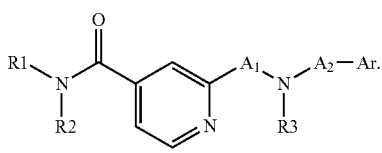

(IIb-b)

Embodiment 2b-c

Another particularly preferred embodiment (2b-c) relates to compounds, wherein Z is a cyclic group Z-Cycl, which is selected from an optionally substituted 6-membered heteroaryl, as defined above and according to formula (IIb) above, containing one heteroatom N, being selected from compounds according to formula (IIb-c)

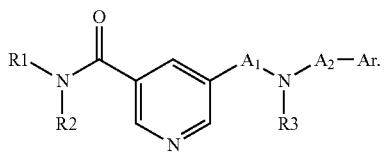

(IIb-c)

Embodiment 2b-d

Another particularly preferred embodiment (2b-d) relates to compounds, wherein Z is a cyclic group Z-Cycl, which is selected from an optionally substituted 6-membered heteroaryl, as defined above and according to formula (IIb) above, containing one heteroatom N, being selected from compounds according to formula (IIb-d)

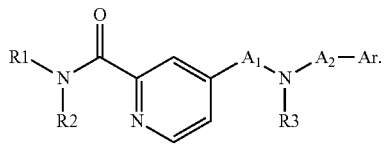

(IIb-d)

Among the embodiments 2b-a to 2b-d the embodiment 2b-c, referring to compounds according to formula (IIb-c), is most preferred.

In the embodiments 2b-a to 2b-d it is further possible that the pyridinyl-ring (Z-Cycl) may carry further substituents as defined above for substituted heteroaryl.

Embodiment 2c

Another particularly preferred embodiment (2c) relates to compounds, wherein Z is a cyclic group Z-Cycl, which is selected from an optionally substituted 6-membered aryl, as defined above, such as preferably an optionally substituted phenyl group. Very particularly Z-Cycl is a phenyl group, forming a compound of the formula (IIc)

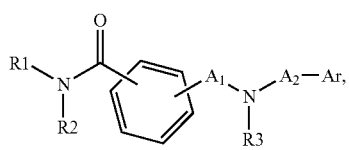

(IIc)

wherein the phenyl-ring may be substituted with 1 to 3, preferably 1 or 2, preferably 1 substituents as defined above.

Embodiment 2c-a

Another particularly preferred embodiment (2c-a) relates to compounds, wherein Z is a cyclic group Z-Cycl, which is selected from the group of optionally substituted 6-membered aryl and has the meaning of phenyl, according to formula (IIc) above, and is further selected from compounds according to formula (IIc-a)

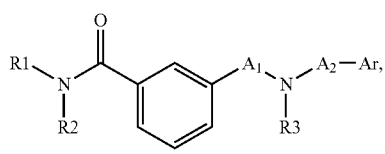

(IIc-a)

wherein the phenyl-ring (Z-Cycl) may optionally be substituted with 1 to 3, preferably 1 or 2, preferably 1 substituents as defined above.

Embodiment 2c-b

Another particularly preferred embodiment (2c-b) relates to compounds, wherein Z-Cycl is selected from the group of optionally substituted 6-membered aryl and has the meaning of phenyl, according to formula (IIc) above, and is further selected from compounds according to formula (IIc-b)

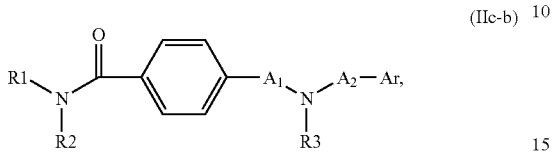

(IIc-b)

wherein the phenyl-ring (Z-Cycl) may optionally be substituted with 1 to 3, preferably 1 or 2, preferably 1 substituents as defined above.

Embodiment 2d

Another particularly preferred embodiment (2d) relates to compounds, wherein Z is an optionally substituted 5- or 6-membered heterocyclic group N-Cycl, forming compounds according to formula (IId):

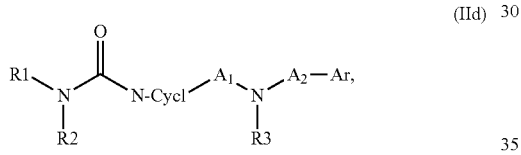

(IId)

wherein N-Cycl is a 5- or 6-membered heterocyclyl group as defined above, which contains at least one N atom. For reasons of clarification it is noted that the abbreviation "N-Cycl" used in formula (IId) is not limited to indicate a specific binding position of N in "N-Cycl", in particular the abbreviation "N-Cycl" is not limited to nitrogen containing heterocycles, wherein the binding to the $R^1R^2N$—(C=O)-group takes place via the cyclic nitrogen atom.

Embodiment 2d-a

Another particularly preferred embodiment (2d-a) relates to compounds according to formula (IId) above, wherein Z is a nitrogen containing 6-membered heterocyclic group N-Cycl as defined above, which is preferably a piperidinyl group, preferably forming compounds according to formula (IId-a)

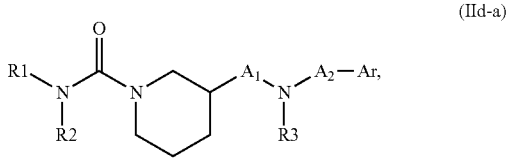

(IId-a)

wherein the piperidinyl-ring may optionally be substituted with 1 to 3, preferably 1 or 2, preferably 1 substituents as defined above for substituted heterocyclyl.

Embodiment 2d-b

Another particularly preferred embodiment (2d-b) relates to compounds according to formula (IId) above, wherein Z is a nitrogen containing 5-membered heterocyclic group N-Cycl as defined above, which is preferably a pyrrolidinyl-group, preferably forming compounds according to formula (IId-b)

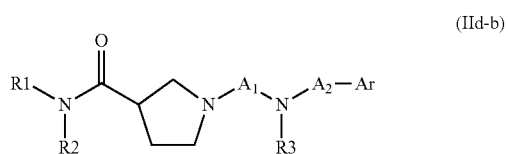

(IId-b)

wherein the pyrrolidinyl-ring may optionally be substituted with 1 to 3, preferably 1 or 2, preferably 1 substituents as defined above for substituted heterocycyl.

Embodiment 2e and 2f

Another embodiment of the present invention relates to compounds, wherein Z is a linear group of the formula

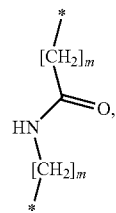

wherein, * indicates the possible binding sites to A1 in formula (I) above, and wherein
m is 0 or 1, with the proviso that m is 1 on the binding site *, which binds to the [$NR^1R^2$—(C=O)—] group in formula (I) above. Examples include compounds of formula (I) above, wherein Z is an alkylaminocarbonyl group [—(CH$_2$)—NH—(C=O)—] according to embodiment 2e and as shown in the following formula (IIe)

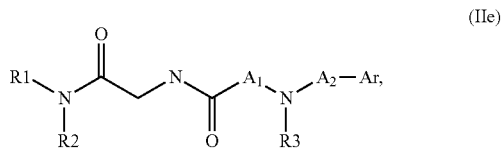

(IIe)

and compounds of formula (I) above, wherein Z is an acetamide-group [—(CH$_2$)—(C=O)—NH-] according to embodiment 2f and as shown in the following formula (IIf)

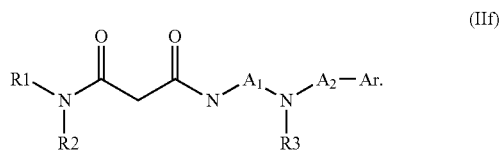

(IIf)

In each of the above mentioned embodiments 2a, 2a-a, 2a-b, 2a-c and 2a-d, 2a-d-1 and 2a-d-2, as well as 2b, 2b-a, 2b-b, 2b-c and 2b-d, as well as 2c, 2c-a and 2c-b, as well as 2d, 2d-a and 2d-b, as well as 2e and 2f the substituents $R^1$, $R^2$, $R^3$, $A^1$, $A^2$ and Ar have the meaning as defined in context with any one of the embodiments described herein, in particular as defined for formula (I) and as defined in context with embodiments 3, 3a, 3b, 3b-a, 3b-b, 3b-c, 3b-d, 3b-e, 4, 4a, 4b, 4c and 4d below.

Further Preferred Embodiment 3

A further preferred embodiment of the present invention relates to any one of the compounds as defined above, wherein at least one of $R^1$ and $R^2$ is a linear or branched alkyl group —[CQ]$_n$- with Q=H or $C_1$-$C_4$-alkyl, which is substituted with a cyclic group "Cycl", designated as $R^{2*}$, wherein Cycl is selected from
  optionally substituted aryl, and
  optionally substituted heteroaryl,
and wherein n is an integer of 1 to 3;
the remaining of $R^1$ or $R^2$, designated as $R^{1*}$, is selected from
  hydrogen, and
  optionally substituted alkyl; and
Z, $R^3$, $A^1$, $A^2$ and Ar have the meaning as defined in any one of the preceding embodiments.
In particular when one of $R^1$ and $R^2$ is a branched alkyl group —[CQ]$_n$- with Q=$C_1$-$C_4$-alkyl, it is possible and preferred that the alkyl-group of Q forms a fused ring with the cyclic group "Cycl".
A further preferred embodiment of the present invention relates to any one of the compounds as defined above, wherein at least one of $R^1$ and $R^2$ is a linear, branched or cyclic alkyl group (a cyclic alkyl group meaning in particular a cycloalkyl fused with the group Cycl), as defined above, which is substituted with a cyclic group "Cycl", designated as $R^{2*}$; forming compounds according to formula (A-III):

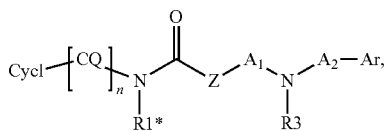

(A-III)

wherein in the group —[CQ]$_n$-Q=H or $C_1$-$C_4$-alkyl, preferably Q=H resulting in formula (III)

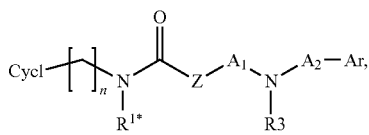

(III)

wherein "Cycl" is selected from
  optionally substituted aryl, as defined above,
  optionally substituted heteroaryl, as defined above, and
  optionally substituted heterocyclyl, as defined above;
  preferably optionally substituted aryl or heteroaryl, as defined above,
n is an integer of 1 to 8, preferably 1 to 4, preferably 1 to 3, such as 1, 2 or 3, more preferred 1 (in particular in embodiments with Q=$C_1$-$C_4$-alkyl); and the remaining of $R^1$ or $R^2$ (designated as $R^{1*}$) is selected from
  hydrogen,
  optionally substituted alkyl, as defined above, and
  an alkanoyl group, such as preferably an acetyl-group, which together with Z, being an amino group (—NH—), forms a 5- or 6-membered, preferably a 5-membered heterocyclic diketone containing two nitrogen atoms, as defined above;
  preferably hydrogen and optionally substituted alkyl, as defined above; and
Z, $R^3$, $A^1$, $A^2$ and Ar have the meaning as defined in context with any one of the embodiments described herein.

Embodiment 3a

Another particularly preferred embodiment (3a) of the present invention relates to compounds as defined herein and in particular to compounds according to formula (III) above, wherein at least one of $R^1$ and $R^2$ is a linear, branched or cyclic alkyl group, as defined above, which is substituted with a cyclic group "Cycl", designated as $R^{2*}$; which is selected from optionally substituted aryl, as defined above, such as in particular an optionally substituted phenyl group forming compounds according to formula (A-IIIa)

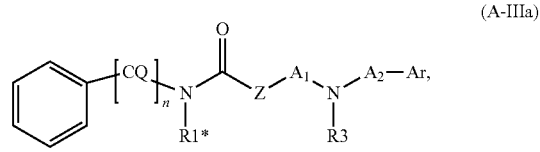

(A-IIIa)

wherein in the group —[CQ]$_n$-Q=H or $C_1$-$C_4$-alkyl, preferably Q=H resulting in formula (IIIa)

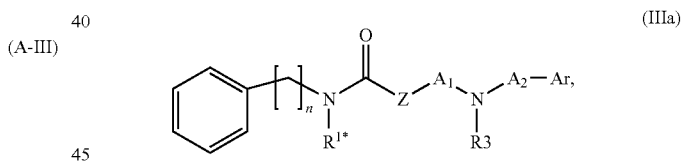

(IIIa)

wherein n is an integer of 1 to 8, preferably 1 to 4, preferably 1 to 3 such as 1, 2 or 3, more preferred 1 (in particular in embodiments with Q=$C_1$-$C_4$-alkyl); and the phenyl-ring may optionally be substituted with 1 to 3, preferably 1 or 2, preferably 1 substituents as defined above preferably the substituents of the phenyl ring are selected from halogen and hydroxy; and
the remaining of $R^1$ or $R^2$ (designated as $R^{1*}$) has the meaning as defined above, particularly as defined for formula (I) and as defined in context with embodiment 3 above and
Z, $R^3$, $A^1$, $A^2$ and Ar have the meaning as defined in context with any one of the embodiments described herein.

Embodiment 3b

Another preferred embodiment (3b) of the present invention relates to compounds as defined herein and in particular to compounds according to formula (III) above, wherein at least one of $R^1$ and $R^2$ is a linear, branched or cyclic alkyl group, as defined above, which is substituted with a cyclic group "Cycl" being an optionally substituted heterocyclic group as defined above, "Het-1", forming compounds according to formula (A-IIIb)

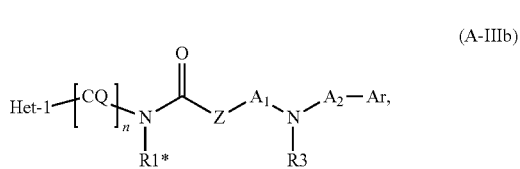
(A-IIIb)

wherein in the group —[CQ]$_n$-Q=H or C$_1$-C$_4$-alkyl, preferably Q=H resulting in formula (IIIb)

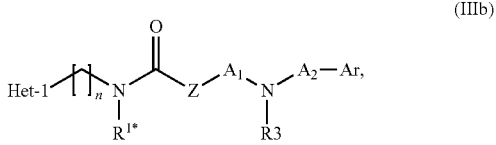
(IIIb)

with Het-1 being selected from
  an optionally substituted, optionally fused 5- to 6-membered heteroaryl, as defined above, or
  an optionally substituted 5- or 6-membered aliphatic heterocyclyl, preferably a 6-membered aliphatic heterocyclyl, each as defined above
wherein the Het-1 group contains 1 or 2 identical or different heteroatoms selected from N, O and S, preferably selected from N and O, more preferably N; and
the Het-1 group may carry 1 to 3, preferably 1 or 2, preferably 1 substituents as defined above, preferably selected from halogen, cyano, optionally substituted alkyl as defined above, optionally substituted alkoxy, a hydroxyl group (—OH), an oxo-group (=O), a carboxyl group [—(C=O)—OH], a heterocyclyl group as defined above, an aminocarbonyl group, an optionally substituted amino group;
n is an integer of 1 to 8, preferably 1 to 4, preferably 1 to 3 such as 1, 2 or 3, more preferred 1 (in particular in embodiments with Q=C$_1$-C$_4$-alkyl); and
the remaining of R$^1$ or R$^2$ (designated as R$^{1*}$) has the meaning as defined above, particularly as defined for formula (I) and as defined in context with embodiment 3 above; and
Z, R$^3$, A$^1$, A$^2$ and Ar have the meaning as defined in context with any one of the embodiments described herein.

Embodiment 3b-a

Another preferred embodiment (3b-a) of the present invention relates to compounds according to formula (IIIb) above, wherein Het-1 is selected from an optionally substituted 5-membered heteroaryl, as defined above, preferably an optionally substituted pyrazolyl, forming for example compounds according to formula (A-IIIb-a)

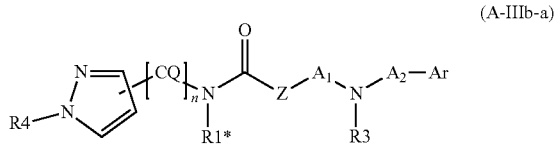
(A-IIIb-a)

wherein in the group —[CQ]$_n$-Q=H or C$_1$-C$_4$-alkyl, preferably Q=H resulting in formula (IIIb-a)

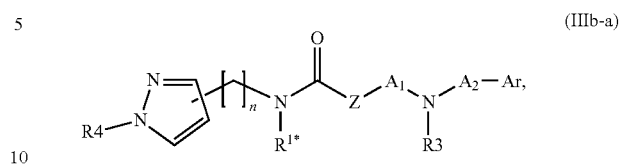
(IIIb-a)

wherein R$^4$ is hydrogen or alkyl as defined above, preferably C$_1$-C$_3$-alkyl,
n is an integer of 1 to 8, preferably 1 to 4, preferably 1 to 3, such as 1, 2 or 3, more preferred 1 (in particular in embodiments with Q=C$_1$-C$_4$-alkyl); and
the remaining of R$^1$ or R$^2$ (designated as R$^{1*}$) has the meaning as defined above, particularly as defined for formula (I) and as defined in context with embodiment 3 and 3b above, and wherein the pyrazolyl ring may carry 1 or 2 further substituents as defined above; and
Z, R$^3$, A$^1$, A$^2$ and Ar have the meaning as defined in context with any one of the embodiments described herein.

Embodiment 3b-b

Another preferred embodiment (3b-b) of the present invention relates to compounds according to formula (IIIb) above, wherein Het-1 is selected from an optionally substituted 5-membered heteroaryl, as defined above, preferably an optionally substituted imidazolyl, forming for example compounds according to formula (A-IIIb-b)

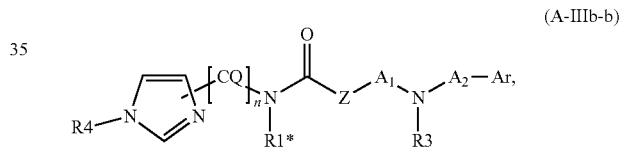
(A-IIIb-b)

wherein in the group —[CQ]$_n$-Q=H or C$_1$-C$_4$-alkyl, preferably Q=H resulting in formula (IIIb-b)

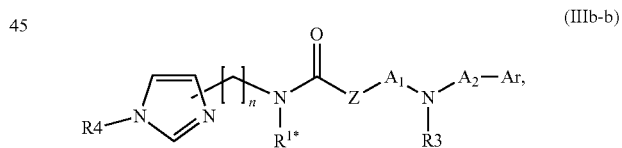
(IIIb-b)

wherein R$^4$ is hydrogen or alkyl as defined above, preferably C$_1$-C$_3$-alkyl,
n is an integer of 1 to 8, preferably 1 to 4, preferably 1 to 3 such as 1, 2 or 3 more preferred 1 (in particular in embodiments with Q=C$_1$-C$_4$-alkyl); and
the remaining of R$^1$ or R$^2$ (designated as R$^{1*}$) has the meaning as defined above, particularly as defined for formula (I) and as defined in context with embodiment 3 and 3b above, and wherein the imidazolyl ring may carry 1 or 2 further substituents as defined above and
Z, R$^3$, A$^1$, A$^2$ and Ar have the meaning as defined in context with any one of the embodiments described herein.

Embodiment 3b-c

Another preferred embodiment (3b-c) of the present invention relates to compounds according to formula (IIIb)

above, wherein Het-1 is selected from an optionally substituted 6-membered heteroaryl, as defined above, preferably an optionally substituted pyrimidinyl, forming for example compounds according to formula (A-IIIb-c)

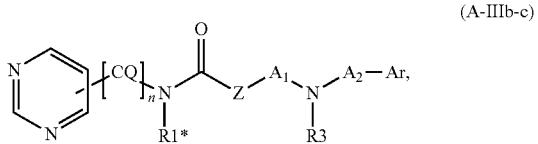

(A-IIIb-c)

wherein in the group —[CQ]$_n$-Q=H or $C_1$-$C_4$-alkyl, preferably Q=H resulting in formula (IIIb-c)

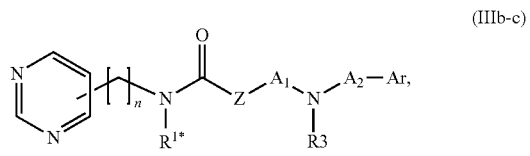

(IIIb-c)

wherein n is an integer of 1 to 8, preferably 1 to 4, preferably 1 to 3 such as 1, 2 or 3, more preferred 1 (in particular in embodiments with Q=$C_1$-$C_4$-alkyl); and the remaining of $R^1$ or $R^2$ (designated as $R^{1*}$) has the meaning as defined above, particularly as defined for formula (I) and as defined in context with embodiment 3 and 3b above, and wherein the pyrimidinyl ring may carry 1 to 3, preferably 1 or 2 further substituents as defined above; and
Z, $R^3$, $A^1$, $A^2$ and Ar have the meaning as defined in context with any one of the embodiments described herein.

Embodiment 3b-d

Another preferred embodiment (3b-d) of the present invention relates to compounds according to formula (IIIb) above, wherein Het-1 is selected from an optionally substituted 6-membered heteroaryl, as defined above, preferably an optionally substituted pyridazinyl, forming for example compounds according to formula (A-IIIb-d)

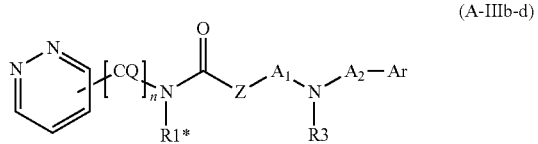

(A-IIIb-d)

wherein in the group —[CQ]$_n$-Q=H or $C_1$-$C_4$-alkyl, preferably Q=H resulting in formula (IIIb-d)

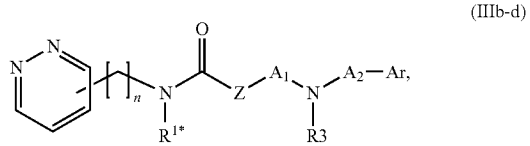

(IIIb-d)

wherein n is an integer of 1 to 8, preferably 1 to 4, preferably 1 to 3 such as 1, 2 or 3, more preferred 1 (in particular in embodiments with Q=$C_1$-$C_4$-alkyl); and the remaining of $R^1$ or $R^2$ (designated as $R^{1*}$) has the meaning as defined above, particularly as defined for formula (I) and as defined in context with embodiment 3 and 3b above, and wherein the pyridazinyl ring may carry 1 to 3, preferably 1 or 2 further substituents as defined above; and
Z, $R^3$, $A^1$, $A^2$ and Ar have the meaning as defined in context with any one of the embodiments described herein.

Embodiment 3b-e

Another particularly preferred embodiment (3b-e) of the present invention relates to compounds according to formula (IIIb) above, wherein Het-1 is selected from an optionally substituted 6-membered heteroaryl, as defined above, preferably an optionally substituted pyridinyl, forming for example compounds according to formula (A-IIIb-e)

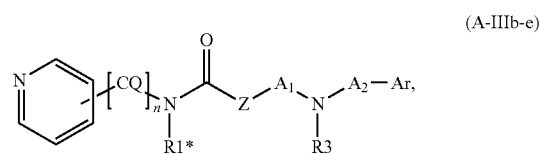

(A-IIIb-e)

wherein in the group —[CQ]$_n$-Q=H or $C_1$-$C_4$-alkyl, preferably Q=H resulting in formula (IIIb-e)

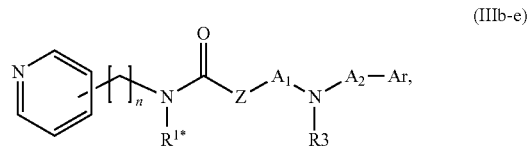

(IIIb-e)

wherein n is an integer of 1 to 8, preferably 1 to 4, preferably 1 to 3 such as 1, 2 or 3, more preferred 1 (in particular in embodiments with Q=$C_1$-$C_4$-alkyl); and the remaining of $R^1$ or $R^2$ (designated as $R^{1*}$) has the meaning as defined above, particularly as defined for formula (I) and as defined in context with embodiment 3 and 3b above, and wherein the pyridinyl ring may carry 1 to 3, preferably 1 or 2 further substituents as defined above, and
Z, $R^3$, $A^1$, $A^2$ and Ar have the meaning as defined in context with any one of the embodiments described herein.

Embodiment 3b-f

Another particularly preferred embodiment (3b-f) of the present invention relates to compounds according to formula (IIIb) above, wherein Het-1 is selected from a substituted pyridinyl, forming compounds according to formula (A-IIIb-f)

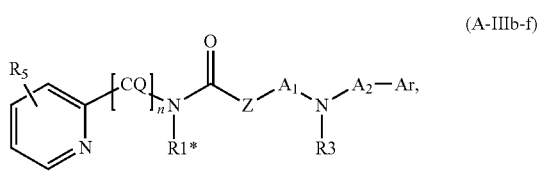

(A-IIIb-f)

wherein in the group —[CQ]$_n$-Q=H or $C_1$-$C_4$-alkyl, preferably Q=H resulting in formula (IIIb-f)

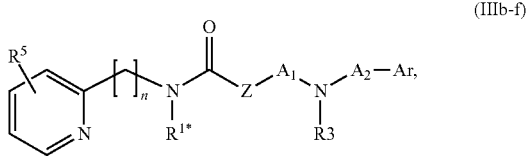

(IIIb-f)

wherein n is an integer of 1 to 8, preferably 1 to 4, preferably 1 to 3 such as 1, 2 or 3, more preferred 1 (in particular in embodiments with Q=$C_1$-$C_4$-alkyl); and the remaining $R^1$ or $R^2$ (designated as $R^{1*}$) has the meaning as defined above, particularly as defined for formula (I) and as defined in context with embodiment 3 and 3b above, and wherein $R^5$ indicates 1 to 4, preferably 1 to 3, preferably 1 or 2, more preferably 1 optional substituents, which may independently be selected from halogen, preferably Cl or F, more preferably F,
optionally substituted alkyl, preferably $C_1$-$C_3$-alkyl, such as preferably methyl, or trifluoromethyl
hydroxy,
alkoxy, preferably methoxy;

preferably $R^5$ is selected from halogen, preferably Cl or F, more preferably F, and
$C_1$-$C_3$-alkyl, such as preferably methyl, or trifluoromethyl; and Z, $R^3$, $A^1$, $A^2$ and Ar have the meaning as defined in context with any one of the embodiments described herein.

Embodiment 3b-g

Another very particularly preferred embodiment (3b-g) of the present invention relates to compounds according to formula (IIIb) above, wherein Het-1 is selected from a substituted pyridinyl, forming compounds according to formula (A-IIIb-g)

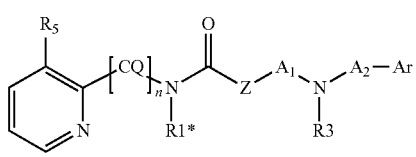

(A-IIIb-g)

wherein in the group —[CQ]$_n$-Q=H or $C_1$-$C_4$-alkyl, preferably Q=H resulting in formula (IIIb-g)

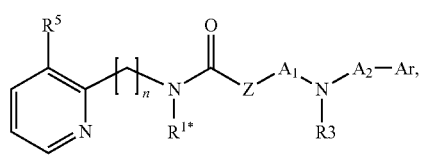

(IIIb-g)

wherein n and the remaining of $R^1$ or $R^2$ (designated as $R^{1*}$) has the meaning as defined for embodiment 3b-f, and wherein $R^5$ is selected from halogen, preferably Cl or F, more preferably F,
optionally substituted alkyl, preferably $C_1$-$C_3$-alkyl, such as preferably methyl, or trifluoromethyl
hydroxy,
alkoxy, preferably methoxy;

more preferably $R^5$ is selected from halogen, preferably Cl or F, more preferably F, and
$C_1$-$C_3$-alkyl, such as preferably methyl, or trifluoromethyl; and Z, $R^3$, $A^1$, $A^2$ and Ar have the meaning as defined in context with any one of the embodiments described herein.

It is further very particularly preferred that in the compounds as defined in embodiments 3, 3a, 3b, 3b-a, 3b-b, 3b-c, 3b-d, 3b-e, 3b-f and 3b-g the at least one of $R^1$ and $R^2$ being a linear, branched or cyclic alkyl group substituted with a cyclic group "Cycl". Such linear, branched or cyclic alkyl group means a linear or branched alkyl group —[CQ]$_n$- with Q=H or $C_1$-$C_4$-alkyl, which is substituted with said cyclic group "Cycl". In particular when one of $R^1$ and $R^2$ is a branched alkyl group —[CQ]$_n$- with Q=$C_1$-$C_4$-alkyl, it is possible and preferred that the alkyl-group of Q forms a forms a cyclic alkyl residue in the form of a fused ring with the cyclic group "Cycl". Accordingly said "linear, branched or cyclic alkyl residue (which is substituted with a cyclic group "Cycl") is selected from an optionally substituted linear or branched alkanediyl group, as defined above, which is preferably selected from
methylene,
ethane-1,2-diyl,
ethane-1,1-diyl,
propane-1,3-diyl,
propane-1,1-diyl,
propane-1,2-diyl, and
propane-2,2-diyl; or
(in particular with Q being a $C_1$-$C_4$-alkyl forming) an optionally substituted cycloalkyl group, as defined above, which is preferably selected from
cyclopropane and
cyclohexane;
which in a further preferred embodiment may preferably form a fused bicyclic ring with Cycl being a Het-1 group selected from a 6-membered heteroaryl as defined above.

More preferred is an optionally substituted linear or branched alkanediyl residue, as defined above. Even more preferably such optionally substituted alkanediyl residue is selected from the group consisting of methylene, ethane-1,2-diyl, ethane-1,1-diyl and propane-2,2-diyl; more preferably methylene or ethane-1,2-diyl; most preferred is methylene.

In each of the above mentioned embodiments 3, 3a, 3b, 3b-a, 3b-b, 3b-c, 3b-d, 3b-e, 3b-f and 3b-g the remaining of $R^1$ or $R^2$, designated as $R^{1*}$, Z, $R^3$, $A^1$, $A^2$ and Ar may have the meaning as defined for formula (I) and as defined in context with any one of the embodiments described herein, in particular as defined in context with embodiments 2a, 2a-a, 2a-b, 2a-c and 2a-d, as well as 2b, 2b-a, 2b-b, 2b-c and 2b-d, as well as 2c, 2c-a and 2c-b, as well as 2d, 2d-a and 2d-b, as well as 2e and 2f above and 4, 4a, 4b, 4c and 4d below.

Further Preferred Embodiment 4

A further preferred embodiment of the present invention relates to any one of the compounds as defined above, wherein Ar is an optionally substituted mono- or bicyclic heteroaryl, as defined above, "Het-2", forming compounds according to formula (IV)

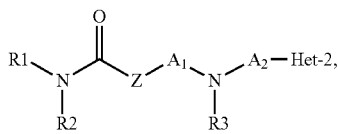

(IV)

with Het-2 being selected from
- an optionally substituted 5- or 6-membered monocyclic heteroaryl, as defined above, and
- an optionally substituted bicyclic heteroaryl, as defined above, which may be fused with a ring formed by $R^3$ and $A^2$ together with the nitrogen atom to which they are bonded.

Embodiment 4a

Another preferred embodiment (4a) relates to compounds as defined herein and in particular to compounds according to formula (IV) above, wherein Ar being an optionally substituted mono- or bicyclic heteroaryl "Het-2" is selected from an optionally substituted 5-membered monocyclic heteroaryl, as defined above, forming for example compounds according to formula (IVa)

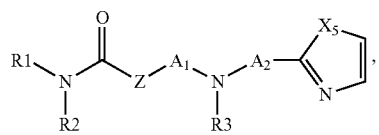

(IVa)

wherein $X^5$ is S or N—$R^4$ with $R^4$ having the meaning as defined above, in particular in context with embodiments 3b-a and 3b-b, and wherein the 5-membered heteroaryl ring of Het-2 may carry 1 to 3 further substituents, preferably 1 or 2 further substituents, more preferably 1 further substituent, as defined above.

Embodiment 4b

Another preferred embodiment (4b) relates to compounds as defined herein and in particular to compounds according to formula (IV) above, wherein Ar being an optionally substituted mono- or bicyclic heteroaryl "Het-2" is selected from an optionally substituted 6-membered monocyclic heteroaryl, as defined above, forming for example compounds according to formula (IVb)

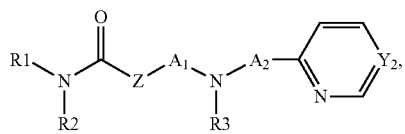

(IVb)

wherein $Y^2$ is C or N, and wherein the 6-membered heteroaryl ring of Het-2 may carry 1 to 3 substituents, preferably 1 or 2 substituents, more preferably 1 substituent, as defined above.

Embodiment 4c

Another particularly preferred embodiment (4c) relates to compounds as defined herein and in particular to compounds according to formula (IV) above, wherein Ar being an optionally substituted mono or bicyclic heteroaryl "Het-2" is selected from an optionally substituted bicyclic heteroaryl, as defined above, forming for example compounds according to formula (IVc)

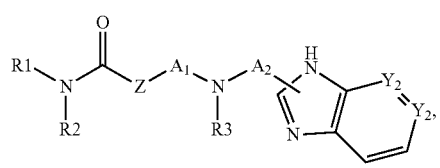

(IVc)

with
- both $Y^2$ being C or
- one $Y^2$ being N and one $Y^2$ being C, and wherein the bicyclic heteroaryl ring of Het-2 may carry 1 to 3 substituents, preferably 1 or 2 substituents, more preferably 1 substituent, as defined above, and wherein the optionally substituted bicyclic heteroaryl ring of Het-2 may be fused with a ring formed by $R^3$ and $A^2$ together with the nitrogen atom to which they are bonded.

Embodiment 4d

Another very particularly preferred embodiment (4d) relates to compounds as defined herein and in particular to compounds according to formula (IV) and (IVc) above, wherein Ar being an optionally substituted mono- or bicyclic heteroaryl "Het-2" is selected from an optionally substituted bicyclic heteroaryl, which is selected from benzimidazolyl, as defined above, forming compounds according to formula (IVd)

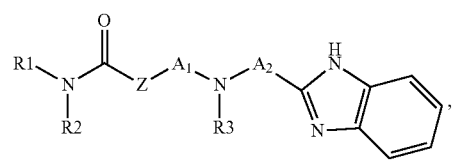

(IVd)

wherein the benzimidazolyl ring of Het-2 may carry 1 to 3 substituents, preferably 1 or 2 substituents, more preferably 1 substituent, as defined above, and
wherein the benzimidazolyl ring of Het-2 may be fused with a ring formed by $R^3$ and $A^2$ together with the nitrogen atom to which they are bonded.

Further Preferred Embodiment 5

A further particularly preferred embodiment of the present invention relates to any one of the compounds as defined above, wherein Ar is an optionally substituted bicyclic heteroaryl, as defined above in embodiment 4c and 4d and wherein Het-1 is selected from an optionally substituted 6-membered heteroaryl, as defined above in embodiments 3b-e, 3b-f and 3b-g, forming for example compounds according to formula (Va-1), (Vb-1) or (Vc-1) or (Va-2), (Vb-2) or (Vc-2):

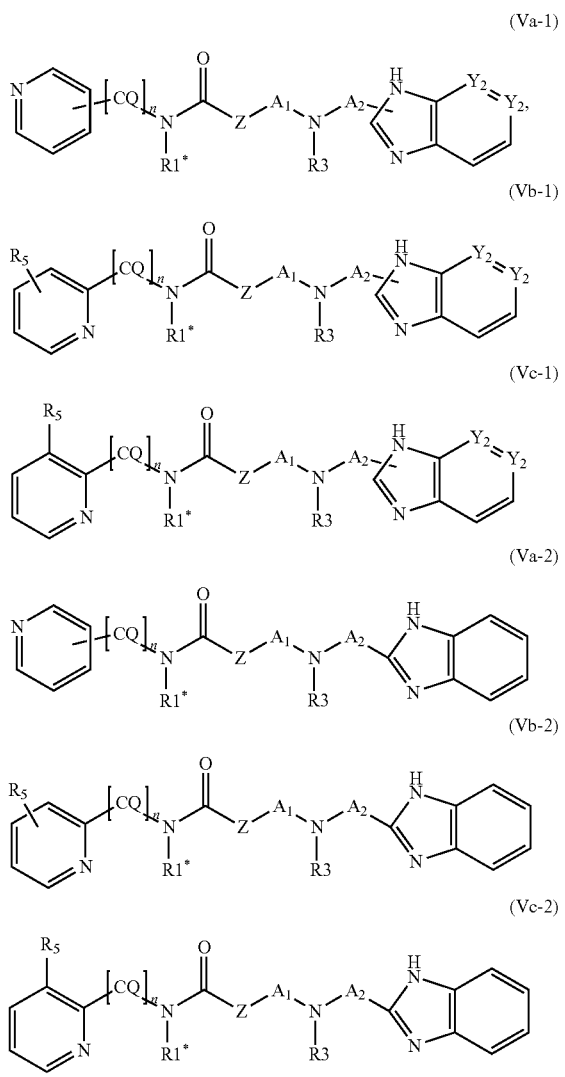

wherein Q, n, $R^5$, $Y^2$, as well as R1*, Z, $R^3$, $A^1$ and $A^2$ have the meaning as defined in context with any one of the embodiments described herein and wherein the pyridinyl ring may carry 1 to 3, preferably 1 or 2 further substituents as defined above and wherein the benzimidazolyl ring of Het-2 may carry 1 to 3 substituents, preferably 1 or 2 substituents, more preferably 1 substituent, as defined above, and wherein the benzimidazolyl ring of Het-2 may be fused with a ring formed by $R^3$ and $A^2$ together with the nitrogen atom to which they are bonded; in each case as defined in particular as in embodiments 4c and 4d and embodiments 3b-e, 3b-f and 3b-g.

Preferably, $R^5$ indicates at least one substituent, which is selected from fluorine.

In each of the above mentioned embodiments 4, 4a, 4b, 4c and 4d and 5 the remaining substituents $R^1$, $R^2$, Z, $R^3$, $A^1$ and $A^2$ may have the meaning as defined for formula (I) and as defined in context with any one of the embodiments described herein, in particular as defined in context with embodiments 2a, 2a-a, 2a-b, 2a-c and 2a-d, as well as 2b, 2b-a, 2b-b, 2b-c and 2b-d, as well as 2c, 2c-a and 2c-b, as well as 2d, 2d-a and 2d-b, as well as 2e and 2f above, and 3, 3a, 3b, 3b-a, 3b-b, 3b-c, 3b-d, 3b-e, 3b-f and 3b-g above.

It is further very particularly preferred that in the compounds according to the present invention, such as in particular in the compounds as defined in formula (I) and in embodiments 2a, 2a-a, 2a-b, 2a-c and 2a-d, as well as 2b, 2b-a, 2b-b, 2b-c and 2b-d, as well as 2c, 2c-a and 2c-b, as well as 2d, 2d-a and 2d-b, as well as 2e and 2f and 3, 3a, 3b, 3b-a, 3b-b, 3b-c, 3b-d, 3b-e, 3b-f and, 3b-g, as well as 4, 4a, 4b, 4c and 4d above, as well as 5, $A^1$ and $A^2$ each are optionally substituted alkanediyl, as defined above, and are the same or different and are independently selected from optionally substituted
  methylene and
  ethane-1,2-diyl, or
  $A^1$ and $R^3$ together with the nitrogen atom to which they are bonded form an optionally substituted 4- to 6-membered mono- or bicyclic ring, preferably a 4- or 6-membered mono- or bicyclic ring, more preferably a 4-membered ring, as defined above. Therein, more preferably
  $A^1$ and $A^2$ are identical and are methylene,
  $A^1$ and $A^2$ are identical and are ethane-1,2-diyl,
  $A^1$ is methylene and $A^2$ is ethane-1,2-diyl,
  $A^1$ is ethane-1,2-diyl and $A^2$ is methylene,
  $A^1$ and $R^3$ together with the nitrogen atom to which they are bonded form an optionally substituted 4- to 6-membered mono- or bicyclic ring, preferably a 4-membered ring, and $A^2$ is methylene, or
  $A^1$ and $R^3$ together with the nitrogen atom to which they are bonded form an optionally substituted 4- to 6-membered mono- or bicyclic ring, preferably a 4-membered ring, and $A^2$ is ethane-1,2-diyl; more preferably
  $A^1$ and $A^2$ are identical and are ethane-1,2-diyl,
  $A^1$ is ethane-1,2-diyl and $A^2$ is methylene or
  $A^1$ and $R^3$ together with the nitrogen atom to which they are bonded form an optionally substituted 4-membered monocyclic ring, and $A^2$ is ethane-1,2-diyl; even more preferably
  $A^1$ and $A^2$ are identical and are ethane-1,2-diyl, or
  $A^1$ is ethane-1,2-diyl and $A^2$ is methylene.

In further preferred embodiments of compounds according to the general formulae (I), (II), (III), (IV) and the substructures thereof as defined above, as well as according to the formulae (Va-1), (Vb-1), (Vc-1), (Va-2), (Vb-2) and (Vc-2), the individual substituents have the following definitions in each case:

1. One of $R^1$ and $R^2$ is designated as $R^1$ and is hydrogen and one of $R^1$ or $R^2$ is designated as $R^{2*}$ and is selected from hydrogen, and optionally substituted alkyl, as defined above, preferably aryl-substituted alkyl and heteroaryl-substituted alkyl, wherein the aryl and heteroaryl substituent each may carry 1 to 3 substituents, as defined above, preferably selected from halogen and hydroxy. Particularly preferred is that the at least one of $R^1$ or $R^2$ which is designated as $R^{2*}$ is optionally substituted aryl-methyl or heteroaryl-methyl, most preferred is optionally substituted heteroaryl-methyl.

2. Z is a cyclic group, selected from
  optionally substituted 5- or 6-membered heteroaryl, preferably 5-membered heteroaryl,
  optionally substituted aryl, preferably phenyl, and
  optionally substituted 5- or 6-membered heterocyclyl. Particularly preferred is the meaning of thiazolyl, oxazolyl, triazolyl, oxadiazolyl and pyrazolyl, as defined above.

3. $A^1$ and $A^2$ are optionally substituted alkanediyl and are the same or different and are independently selected from
  $A^1$ and $A^2$ are identical and are methylene,
  $A^1$ and $A^2$ are identical and are ethane-1,2-diyl, $A^1$ is methylene and $A^2$ is ethane-1,2-diyl,
$A^1$ is ethane-1,2-diyl and $A^2$ is methylene,
$A^1$ and $R^3$ together with the nitrogen atom to which they are bonded form an optionally substituted 4-membered monocyclic ring, and $A^2$ is methylene, or
$A^1$ and $R^3$ together with the nitrogen atom to which they are bonded form an optionally substituted 4-membered monocyclic ring, and $A^2$ is ethane-1,2-diyl.

Particularly preferred is that $A^1$ is methylene or ethane-1,2-diyl and $A^2$ is ethane-1,2-diyl, or that $A^1$ and $R^3$ together with the nitrogen atom to which they are bonded form an optionally substituted 4-membered monocyclic ring and $A^2$ is ethane-1,2-diyl.

4. $R^3$ is hydrogen or optionally substituted alkyl, as defined above, or $A^1$ and $R^3$ together with the nitrogen atom to which they are bonded form an optionally substituted 4- to 6-membered mono- or bicycyclic ring, preferably hydrogen.

5. Ar is Het-1 as defined above, preferably optionally substituted mono- or bicyclic heteroaryl, as defined above, preferably optionally substituted benzimidazolyl as defined above.

In particular with respect to compounds of formula (I) and according to embodiments 2a, 2a-a, 2a-b, 2a-c and 2a-d it is particularly preferred that $R^1$ and $R^2$ are different, with one being hydrogen and the other one being an optionally substituted alkyl. More preferably, one of $R^1$ and $R^2$ is hydrogen and the other one is an alkyl residue, which is substituted with
an optionally substituted aryl group as defined above, preferably with an optionally substituted phenyl group as defined above, or
with an optionally substituted heteroaryl group as defined above, preferably with
an optionally substituted pyridinyl group,
an optionally substituted pyridazinyl group,
an optionally substituted pyrimidinyl group,
an optionally substituted pyrazolyl group,
an optionally substituted imidazolyl group.

Even more preferably, one of $R^1$ and $R^2$ is hydrogen and the other one is an alkyl residue, which is substituted with
an optionally substituted phenyl group,
an optionally substituted pyridinyl group,
an optionally substituted pyridazinyl group,
an optionally substituted pyrimidinyl group, Still more preferably, one of $R^1$ and $R^2$ is hydrogen and the other one is an alkyl residue, which is substituted with
an optionally substituted phenyl group, or
an optionally substituted pyridinyl group,
wherein the optionally substituted pyridinyl group as a substituent of an alkyl residue for one of $R^1$ and $R^2$ is most preferred. More preferably a halogen substituted pyridinyl group such as in particular a pyridinyl group substituted with one fluorine substituent is selected, such as in particular a group according to formula

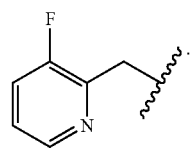 [SMILES: *Cc1ncccc1F]

It is further preferred that herein and in particular for compounds of formula (I) and as defined in any one of the above defined embodiments 2a, 2a-a, 2a-b, 2a-c and 2a-d Ar has the meaning of a bicyclic heteroaryl, such as in particular benzimidazol, particularly benzimidazo-2-yl according to formula

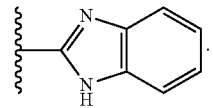

It is further preferred that herein $A^1$ and $A^2$ each are optionally substituted alkanediyl, as defined above, such as very preferably with $A^1$ and $A^2$ being identical and methylene, or $A^1$ and $A^2$ being identical and ethane-1,2-diyl, or $A^1$ being methylene and $A^2$ being ethane-1,2-diyl, or $A^1$ being ethane-1,2-diyl and $A^2$ being methylene, more preferably with A and $A^2$ being identical and ethane-1,2-diyl, or with $A^1$ being ethane-1,2-diyl and $A^2$ being methylene.

In particular with respect to compounds of formula (I) and according to embodiments 2b, 2b-a, 2b-b, 2b-c and 2b-d it is particularly preferred that $R^1$ and $R^2$ are different, with one being hydrogen and the other one being an optionally substituted alkyl. More preferably, one of $R^1$ and $R^2$ is hydrogen and the other one is an alkyl residue, which is substituted with an optionally substituted heteroaryl group as defined above, preferably with an optionally substituted pyridinyl group as defined above, more preferably with a halogen substituted pyridinyl group such as in particular a pyridinyl group substituted with one fluorine substituent.

It is further preferred that herein and in particular in compounds of formula (I) and as defined in any one of the above defined embodiments 2b, 2b-a, 2b-b, 2b-c and 2b-d Ar has the meaning of a bicyclic heteroaryl, such as in particular benzimidazol, particularly benzimidazo-2-yl as defined above.

It is further preferred that herein $A^1$ and $A^2$ each are optionally substituted alkanediyl, as defined above, such as very preferably with $A^1$ and $A^2$ being identical and methylene, or $A^1$ and $A^2$ being identical and ethane-1,2-diyl, or $A^1$ being methylene and $A^2$ being ethane-1,2-diyl, or $A^1$ being ethane-1,2-diyl and $A^2$ being methylene, more preferably with $A^1$ and $A^2$ being identical and ethane-1,2-diyl, or with $A^1$ being ethane-1,2-diyl and $A^2$ being methylene, or wherein $A^1$ and $R^3$ together with the nitrogen atom to which they are bonded form an optionally substituted 4-membered monocyclic ring, and $A^2$ is ethane-1,2-diyl.

In particular with respect to compounds of formula (I) and according to embodiments 2c, 2c-a and 2c-b it is particularly preferred that $R^1$ and $R^2$ are different, with one being hydrogen and the other one being an optionally substituted alkyl. More preferably, one of $R^1$ and $R^2$ is hydrogen and the other one is an alkyl residue, which is substituted with an optionally substituted aryl group as defined above, preferably with an optionally substituted phenyl group as defined above, or with an optionally substituted heteroaryl group as defined above, preferably with an optionally substituted pyridinyl group as defined above, more preferably with a halogen substituted pyridinyl group such as in particular a pyridinyl group substituted with 1 F.

It is further preferred that herein and in compounds of formula (I) and according to any one of the above defined embodiments 2c, 2c-a and 2c-b Ar has the meaning of a bicyclic heteroaryl, such as in particular benzimidazol, particularly benzimidazol-2-yl as defined above.

It is further preferred that herein $A^1$ and $A^2$ each are optionally substituted alkanediyl, as defined above, such as very preferably with $A^1$ and $A^2$ being identical and methylene, or $A^1$ and $A^2$ being identical and ethane-1,2-diyl, or $A^1$ being methylene and $A^2$ being ethane-1,2-diyl, or $A^1$ being ethane-1,2-diyl and $A^2$ being methylene, more preferably with $A^1$ and $A^2$ being identical and ethane-1,2-diyl, or with $A^1$ being ethane-1,2-diyl and $A^2$ being methylene.

In particular with respect to compounds of formula (I) and according to embodiments 2d, 2d-a and 2d-b it is particularly preferred that $R^1$ and $R^2$ are different, with one being hydrogen and the other one being an optionally substituted alkyl. More preferably, one of $R^1$ and $R^2$ is hydrogen and the other one is an alkyl residue, which is substituted with an optionally substituted heteroaryl group as defined above, preferably with an optionally substituted pyridinyl group as defined above, more preferably with a halogen substituted pyridinyl group such as in particular a pyridinyl group substituted with 1 F.

It is further preferred that herein and in compounds of formula (I) and according to any one of the above defined embodiments 2d, 2d-a and 2d-b Ar has the meaning of a bicyclic heteroaryl, such as in particular benzimidazol, particularly benzimidazol-2-yl as defined above.

It is further preferred that herein $A^1$ and $A^2$ each are optionally substituted alkanediyl, as defined above, such as very preferably with $A^1$ and $A^2$ being identical and methylene, or $A^1$ and $A^2$ being identical and ethane-1,2-diyl, or $A^1$ being methylene and $A^2$ being ethane-1,2-diyl, or $A^1$ being ethane-1,2-diyl and $A^2$ being methylene, more preferably with $A^1$ and $A^2$ being identical and ethane-1,2-diyl, or with $A^1$ being ethane-1,2-diyl and $A^2$ being methylene.

Particularly preferably the compounds according to the present invention are selected from the compounds:

| Exp No. | Compound |
|---|---|
| 1 | |
| 2 | |
| 3 | |

-continued
| Exp No. | Compound |
|---|---|
| 4 | 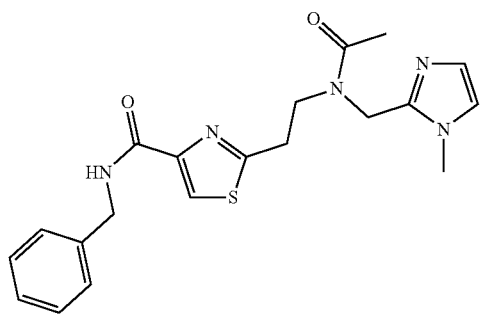 [SMILES: CC(=O)N(CCc1nc(C(=O)NCc2ccccc2)cs1)Cc1nccn1C] |
| 5 | 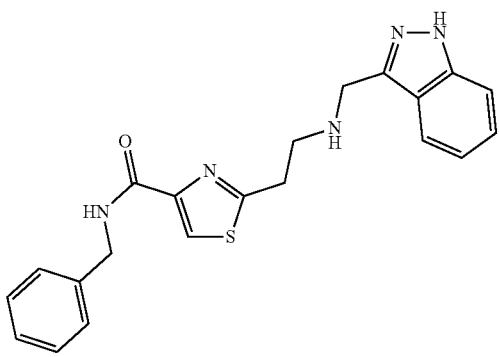 [SMILES: O=C(NCc1ccccc1)c1csc(CCNCc2n[nH]c3ccccc23)n1] |
| 6 | 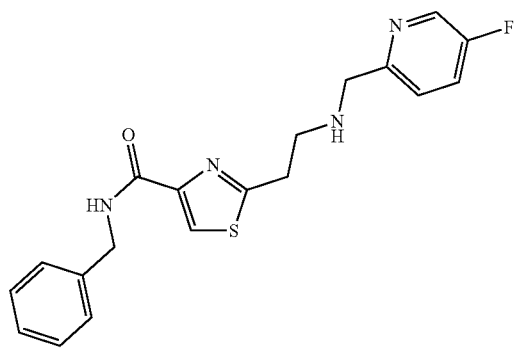 [SMILES: O=C(NCc1ccccc1)c1csc(CCNCc2ccc(F)cn2)n1] |
| 7 | 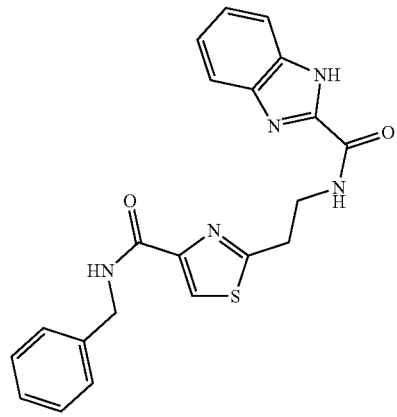 [SMILES: O=C(NCc1ccccc1)c1csc(CCNC(=O)c2nc3ccccc3[nH]2)n1] |

-continued
| Exp No. | Compound |
|---|---|
| 8 | 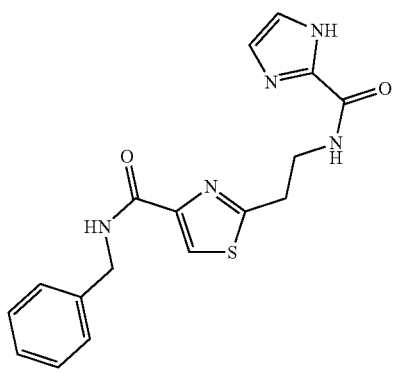 [SMILES: O=C(NCc1ccccc1)c1csc(CCNC(=O)c2ncc[nH]2)n1] |
| 9 | 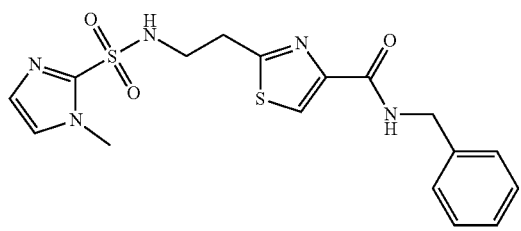 [SMILES: Cn1ccnc1S(=O)(=O)NCCc1nc(C(=O)NCc2ccccc2)cs1] |
| 10 | 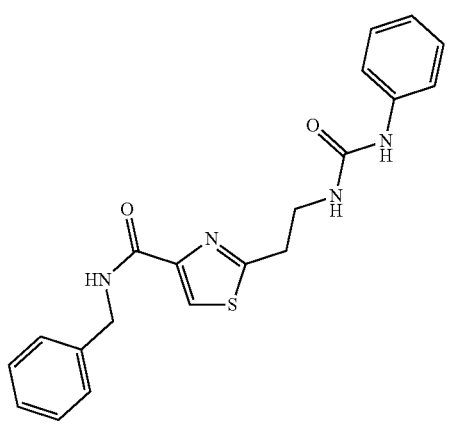 [SMILES: O=C(NCCc1nc(C(=O)NCc2ccccc2)cs1)Nc1ccccc1] |
| 11 | 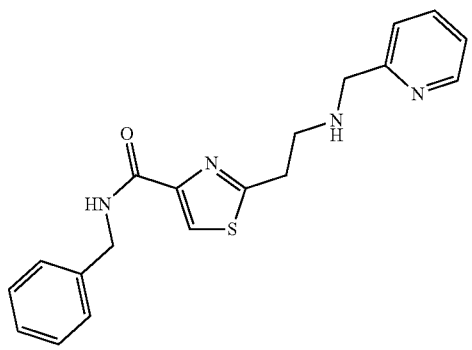 [SMILES: O=C(NCc1ccccc1)c1csc(CCNCc2ccccn2)n1] |

| Exp No. | Compound |
|---|---|
| 12 | |
| 13 | |
| 14 | |
| 15 | |
| 16 | |
| 17 | |

-continued
| Exp No. | Compound |
|---|---|
| 18 | 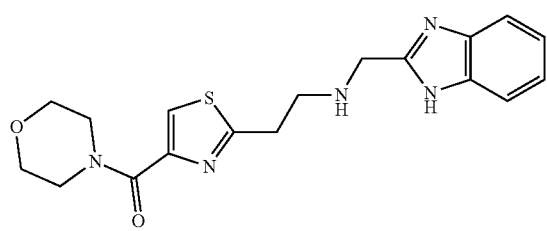 [SMILES: O=C(c1csc(CCNCc2nc3ccccc3[nH]2)n1)N1CCOCC1] |
| 19 | 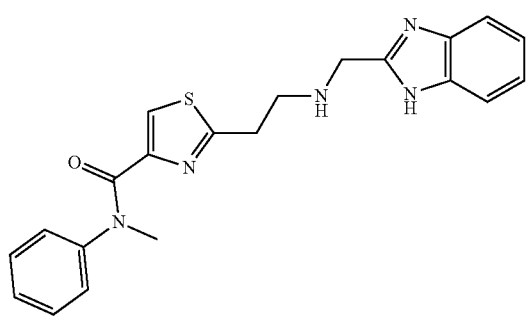 [SMILES: CN(C(=O)c1csc(CCNCc2nc3ccccc3[nH]2)n1)c1ccccc1] |
| 20 | 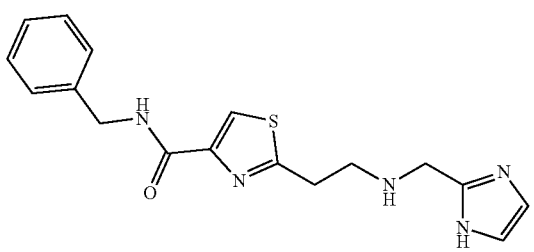 [SMILES: O=C(NCc1ccccc1)c1csc(CCNCc2ncc[nH]2)n1] |
| 21 | 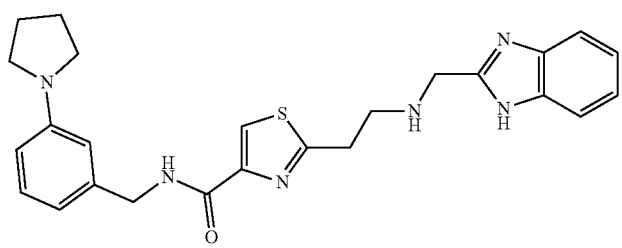 [SMILES: O=C(NCc1cccc(N2CCCC2)c1)c1csc(CCNCc2nc3ccccc3[nH]2)n1] |
| 22 | 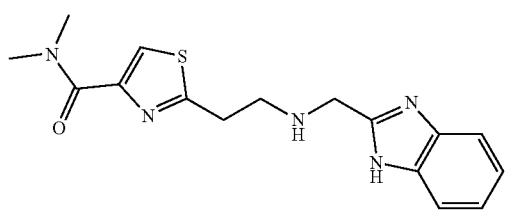 [SMILES: CN(C)C(=O)c1csc(CCNCc2nc3ccccc3[nH]2)n1] |
| 23 | 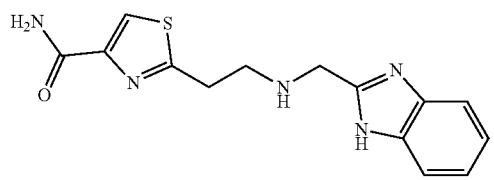 [SMILES: NC(=O)c1csc(CCNCc2nc3ccccc3[nH]2)n1] |

| Exp No. | Compound |
|---|---|
| 24 | 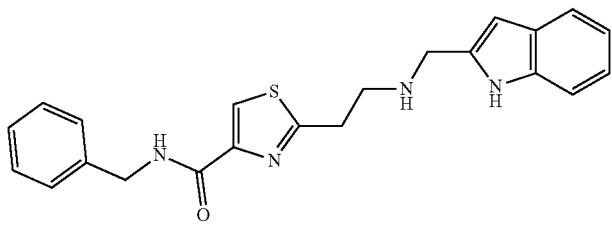 [SMILES: O=C(NCc1ccccc1)c1csc(CCNCc2cc3ccccc3[nH]2)n1] |
| 25 | 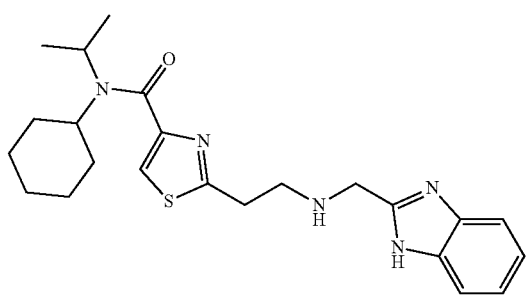 [SMILES: CC(C)N(C(=O)c1csc(CCNCc2nc3ccccc3[nH]2)n1)C1CCCCC1] |
| 26 | 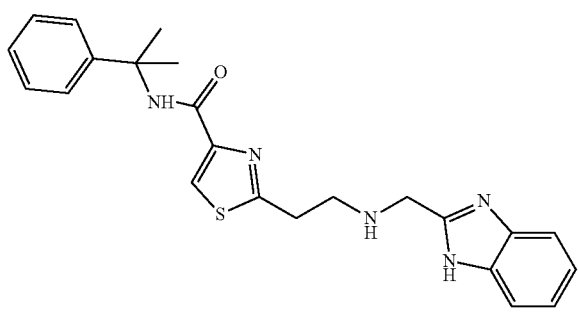 [SMILES: CC(C)(NC(=O)c1csc(CCNCc2nc3ccccc3[nH]2)n1)c1ccccc1] |
| 27 | 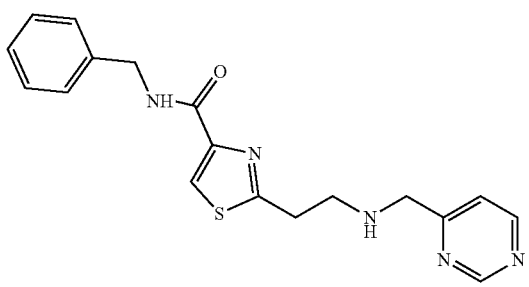 [SMILES: O=C(NCc1ccccc1)c1csc(CCNCc2ccncn2)n1] |
| 28 | 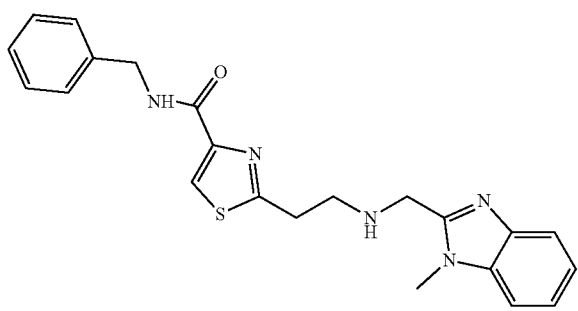 [SMILES: Cn1c(CNCCc2nc(C(=O)NCc3ccccc3)cs2)nc2ccccc21] |

| Exp No. | Compound |
|---|---|
| 29 | 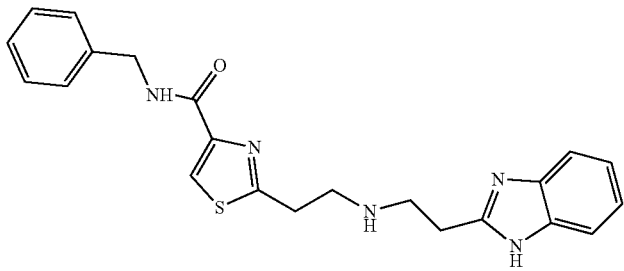 [SMILES: O=C(NCc1ccccc1)c1csc(CCNCCc2nc3ccccc3[nH]2)n1] |
| 30 | 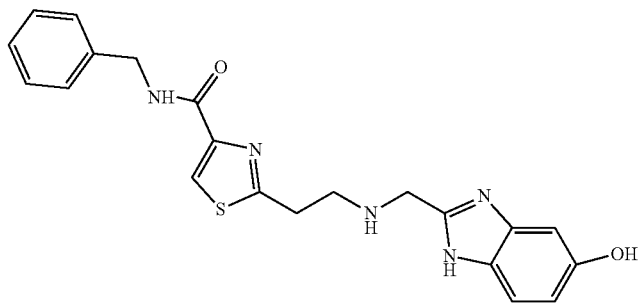 [SMILES: O=C(NCc1ccccc1)c1csc(CCNCc2nc3cc(O)ccc3[nH]2)n1] |
| 31 | 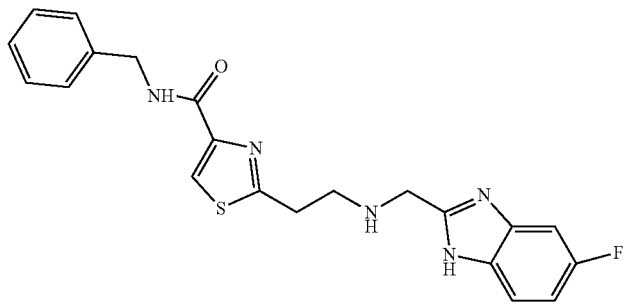 [SMILES: O=C(NCc1ccccc1)c1csc(CCNCc2nc3cc(F)ccc3[nH]2)n1] |
| 32 | 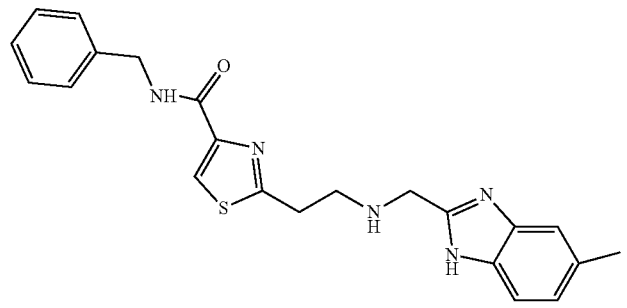 [SMILES: Cc1ccc2[nH]c(CNCCc3nc(C(=O)NCc4ccccc4)cs3)nc2c1] |
| 33 | 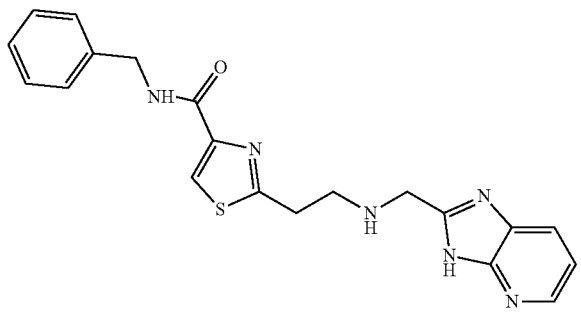 [SMILES: O=C(NCc1ccccc1)c1csc(CCNCc2nc3cccnc3[nH]2)n1] |

-continued
| Exp No. | Compound |
|---|---|
| 34 | 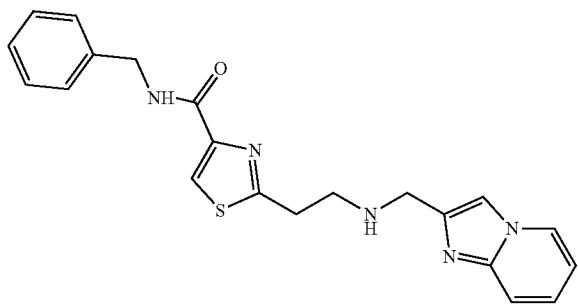 [SMILES: O=C(NCc1ccccc1)c1csc(CCNCc2cn3ccccc3n2)n1] |
| 35 | 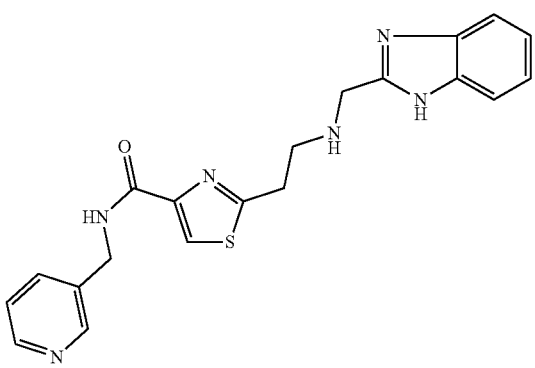 [SMILES: O=C(NCc1cccnc1)c1csc(CCNCc2nc3ccccc3[nH]2)n1] |
| 36 | 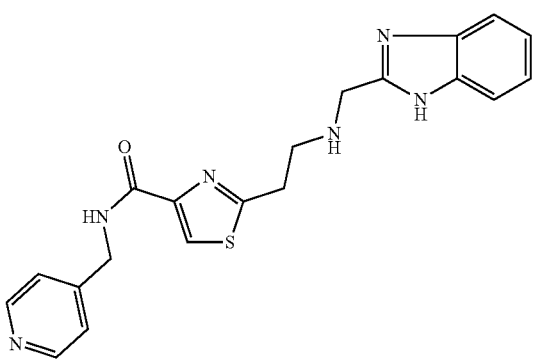 [SMILES: O=C(NCc1ccncc1)c1csc(CCNCc2nc3ccccc3[nH]2)n1] |
| 37 | 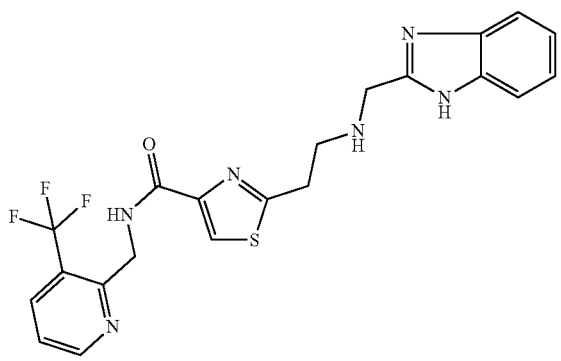 [SMILES: O=C(NCc1ncccc1C(F)(F)F)c1csc(CCNCc2nc3ccccc3[nH]2)n1] |

| Exp No. | Compound |
|---|---|
| 38 | 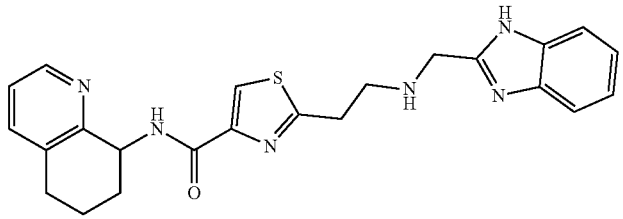 [SMILES: O=C(NC1CCCc2cccnc21)c1csc(CCNCc2nc3ccccc3[nH]2)n1] |
| 39 | 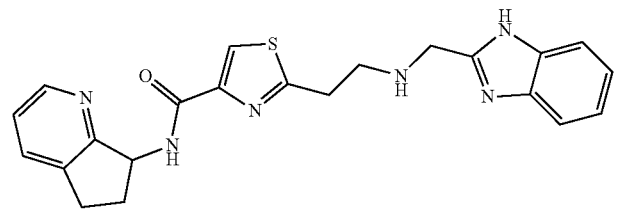 [SMILES: O=C(NC1CCc2cccnc21)c1csc(CCNCc2nc3ccccc3[nH]2)n1] |
| 40 | 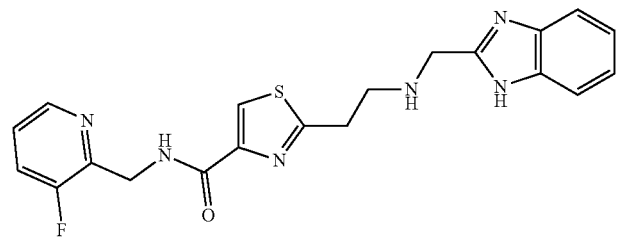 [SMILES: O=C(NCc1ncccc1F)c1csc(CCNCc2nc3ccccc3[nH]2)n1] |
| 41 | 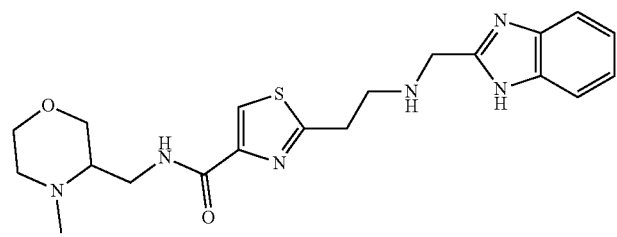 [SMILES: CN1CCOCC1CNC(=O)c1csc(CCNCc2nc3ccccc3[nH]2)n1] |
| 42 | 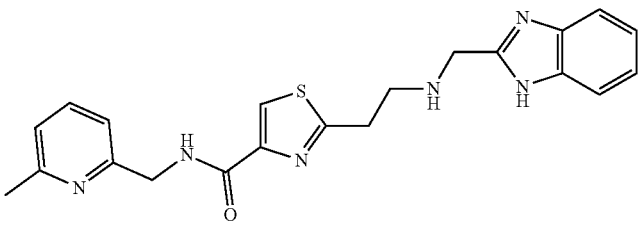 [SMILES: Cc1cccc(CNC(=O)c2csc(CCNCc3nc4ccccc4[nH]3)n2)n1] |
| 43 | 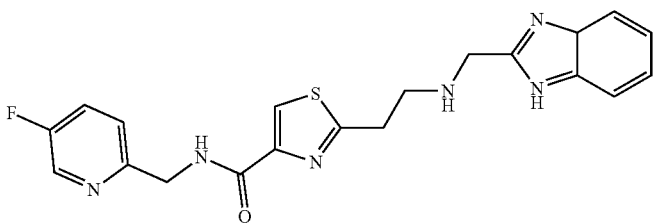 [SMILES: O=C(NCc1ccc(F)cn1)c1csc(CCNCC2=NC3C=CC=CC3=N2)n1] |

| Exp No. | Compound |
|---|---|
| 44 | 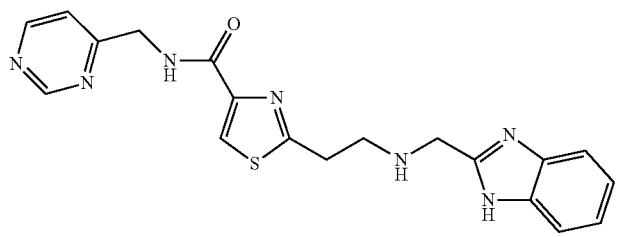 [SMILES: O=C(NCc1ccncn1)c1csc(CCNCc2nc3ccccc3[nH]2)n1] |
| 45 | 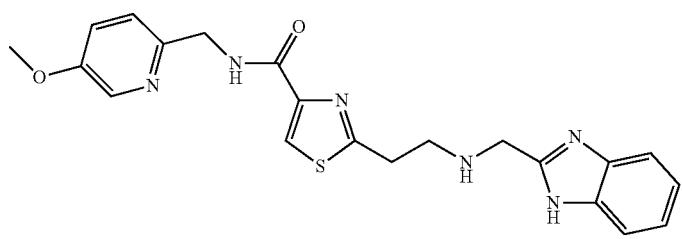 [SMILES: COc1ccc(CNC(=O)c2csc(CCNCc3nc4ccccc4[nH]3)n2)nc1] |
| 46 | 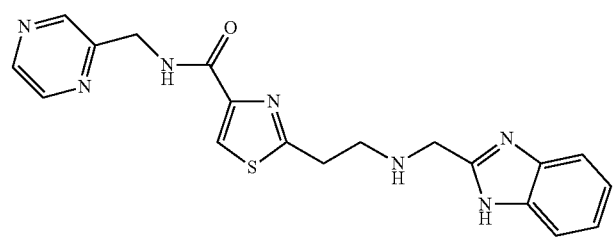 [SMILES: O=C(NCc1cnccn1)c1csc(CCNCc2nc3ccccc3[nH]2)n1] |
| 47 | 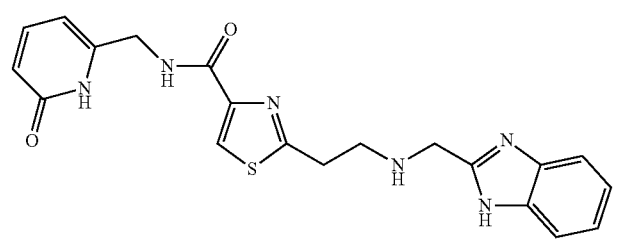 [SMILES: O=C(NCc1cccc(=O)[nH]1)c1csc(CCNCc2nc3ccccc3[nH]2)n1] |
| 48 | 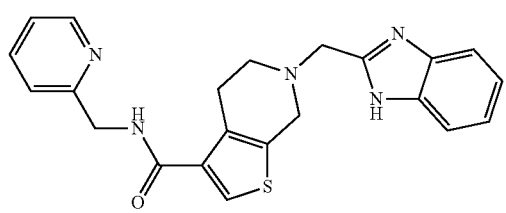 [SMILES: O=C(NCc1ccccn1)c1csc2c1CCN(Cc1nc3ccccc3[nH]1)C2] |
| 49 | 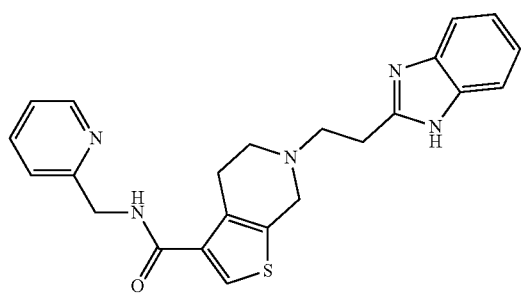 [SMILES: O=C(NCc1ccccn1)c1csc2c1CCN(CCc1nc3ccccc3[nH]1)C2] |

| Exp No. | Compound |
|---|---|
| 50 | 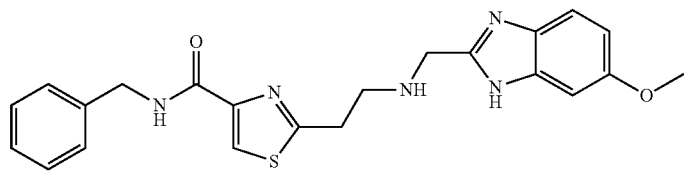 [SMILES: COc1ccc2nc(CNCCc3nc(C(=O)NCc4ccccc4)cs3)[nH]c2c1] |
| 51 | 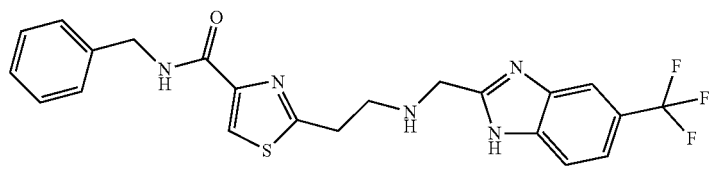 [SMILES: O=C(NCc1ccccc1)c1csc(CCNCc2nc3cc(C(F)(F)F)ccc3[nH]2)n1] |
| 52 | 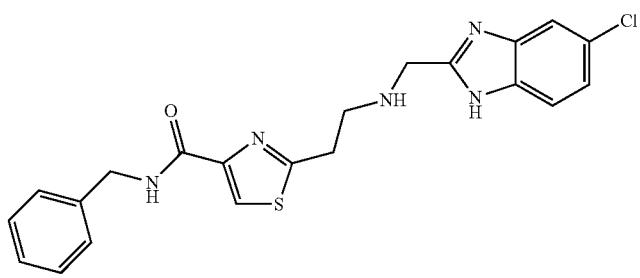 [SMILES: O=C(NCc1ccccc1)c1csc(CCNCc2nc3cc(Cl)ccc3[nH]2)n1] |
| 54 | 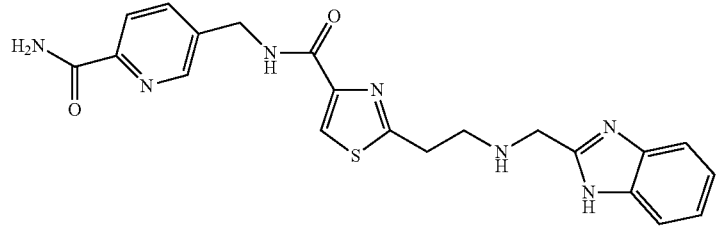 [SMILES: NC(=O)c1ccc(CNC(=O)c2csc(CCNCc3nc4ccccc4[nH]3)n2)cn1] |
| 55 | 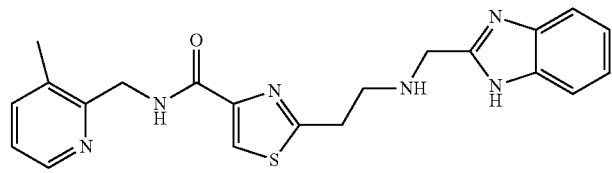 [SMILES: Cc1cccnc1CNC(=O)c1csc(CCNCc2nc3ccccc3[nH]2)n1] |
| 56 | 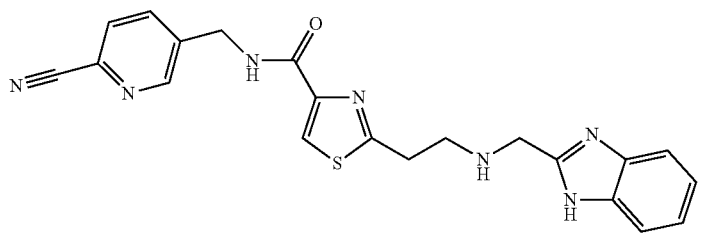 [SMILES: N#Cc1ccc(CNC(=O)c2csc(CCNCc3nc4ccccc4[nH]3)n2)cn1] |
| 57 | 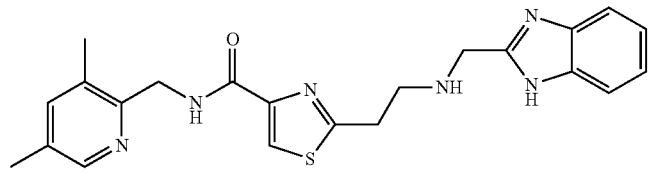 [SMILES: Cc1cnc(CNC(=O)c2csc(CCNCc3nc4ccccc4[nH]3)n2)c(C)c1] |

-continued
| Exp No. | Compound |
|---|---|
| 58 | 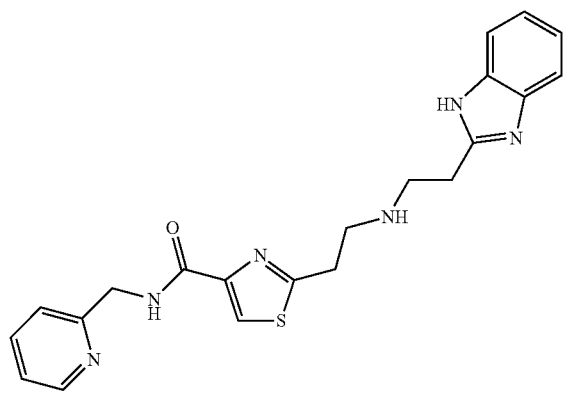 [SMILES: O=C(NCc1ccccn1)c1csc(CCNCCc2nc3ccccc3[nH]2)n1] |
| 59 | 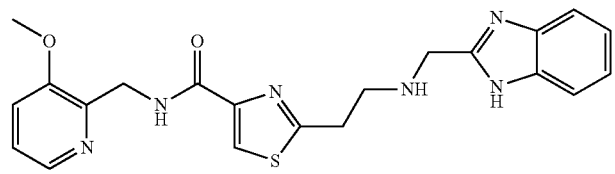 [SMILES: COc1cccnc1CNC(=O)c1csc(CCNCc2nc3ccccc3[nH]2)n1] |
| 60 | 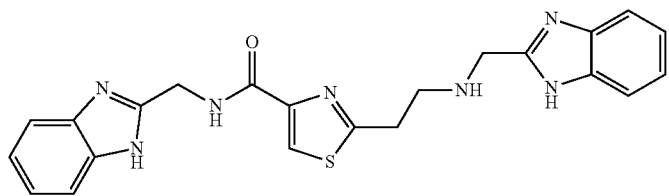 [SMILES: O=C(NCc1nc2ccccc2[nH]1)c1csc(CCNCc2nc3ccccc3[nH]2)n1] |
| 61 | 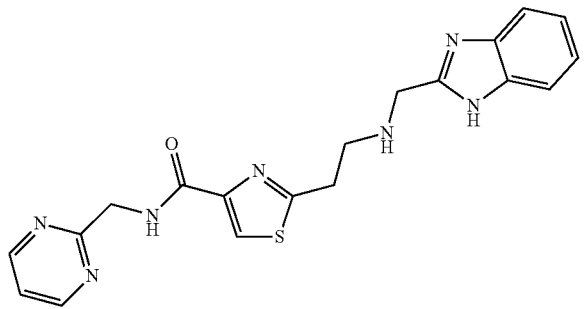 [SMILES: O=C(NCc1ncccn1)c1csc(CCNCc2nc3ccccc3[nH]2)n1] |
| 62 | 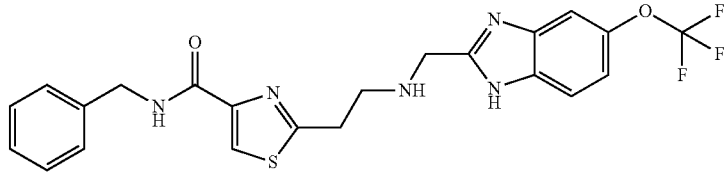 [SMILES: O=C(NCc1ccccc1)c1csc(CCNCc2nc3cc(OC(F)(F)F)ccc3[nH]2)n1] |
| 63 | 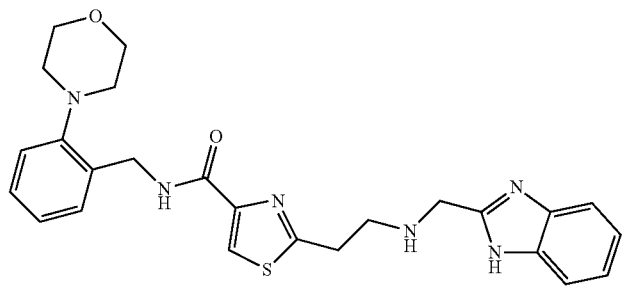 [SMILES: O=C(NCc1ccccc1N1CCOCC1)c1csc(CCNCc2nc3ccccc3[nH]2)n1] |

-continued
| Exp No. | Compound |
|---|---|
| 64 | 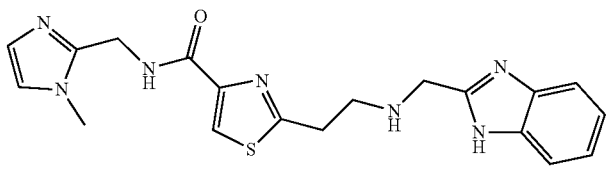 [SMILES: Cn1ccnc1CNC(=O)c1csc(CCNCc2nc3ccccc3[nH]2)n1] |
| 65 | 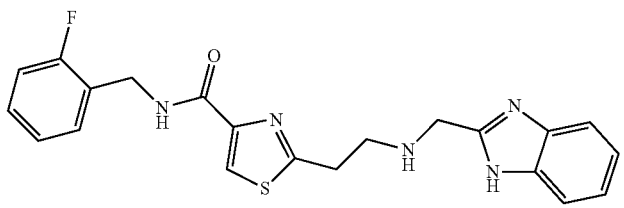 [SMILES: O=C(NCc1ccccc1F)c1csc(CCNCc2nc3ccccc3[nH]2)n1] |
| 66 | 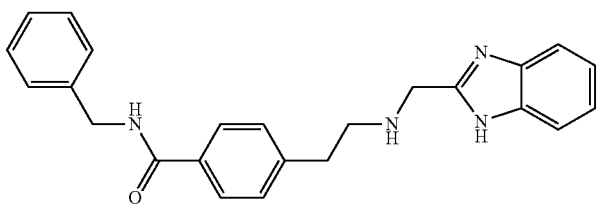 [SMILES: O=C(NCc1ccccc1)c1ccc(CCNCc2nc3ccccc3[nH]2)cc1] |
| 67 | 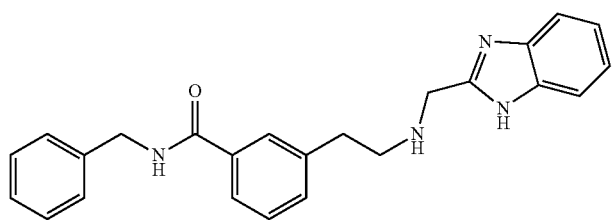 [SMILES: O=C(NCc1ccccc1)c1cccc(CCNCc2nc3ccccc3[nH]2)c1] |
| 68 | 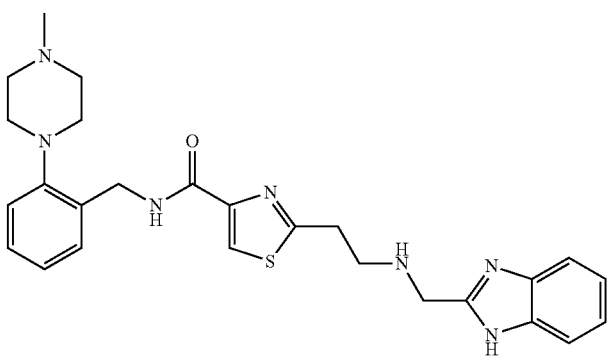 [SMILES: CN1CCN(c2ccccc2CNC(=O)c2csc(CCNCc3nc4ccccc4[nH]3)n2)CC1] |
| 69 | 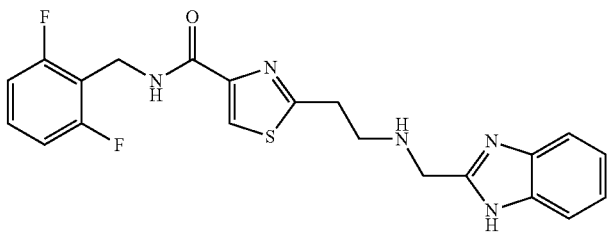 [SMILES: O=C(NCc1c(F)cccc1F)c1csc(CCNCc2nc3ccccc3[nH]2)n1] |

| Exp No. | Compound |
|---|---|
| 70 | 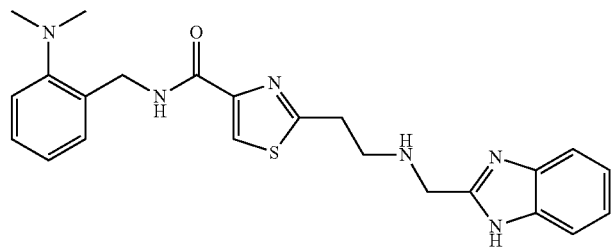 [SMILES: CN(C)c1ccccc1CNC(=O)c1csc(CCNCc2nc3ccccc3[nH]2)n1] |
| 71 | 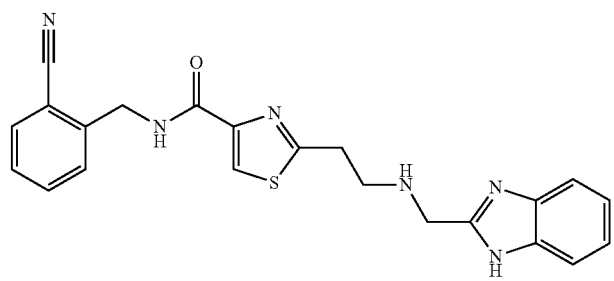 [SMILES: N#Cc1ccccc1CNC(=O)c1csc(CCNCc2nc3ccccc3[nH]2)n1] |
| 72 | 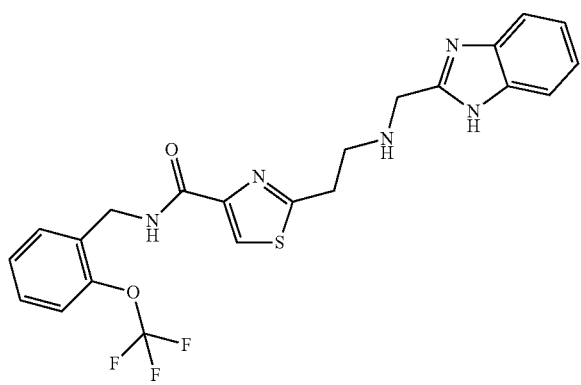 [SMILES: O=C(NCc1ccccc1OC(F)(F)F)c1csc(CCNCc2nc3ccccc3[nH]2)n1] |
| 73 | 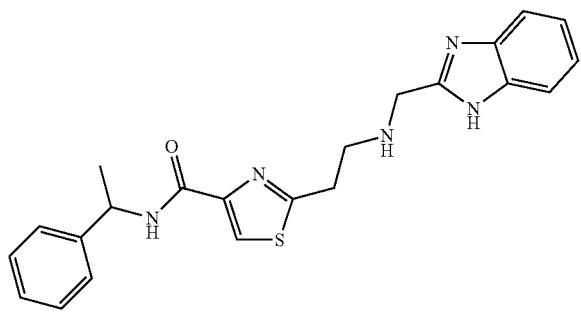 [SMILES: CC(NC(=O)c1csc(CCNCc2nc3ccccc3[nH]2)n1)c1ccccc1] |
| 74 | 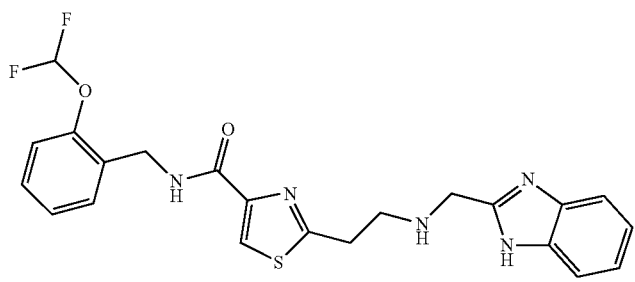 [SMILES: O=C(NCc1ccccc1OC(F)F)c1csc(CCNCc2nc3ccccc3[nH]2)n1] |

| Exp No. | Compound |
|---|---|
| 75 | 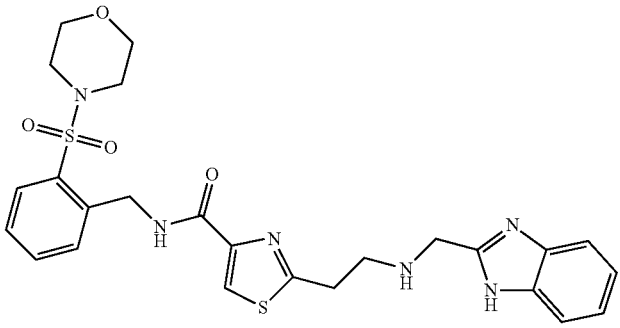 [SMILES: O=C(NCc1ccccc1S(=O)(=O)N1CCOCC1)c1csc(CCNCc2nc3ccccc3[nH]2)n1] |
| 76 | 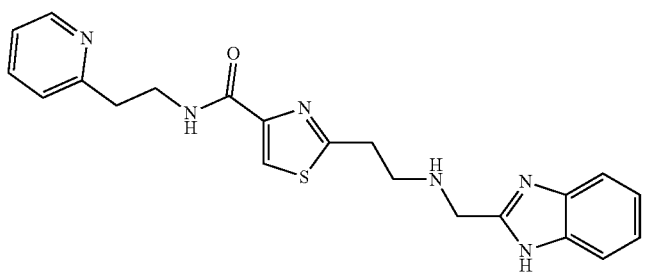 [SMILES: O=C(NCCc1ccccn1)c1csc(CCNCc2nc3ccccc3[nH]2)n1] |
| 77 | 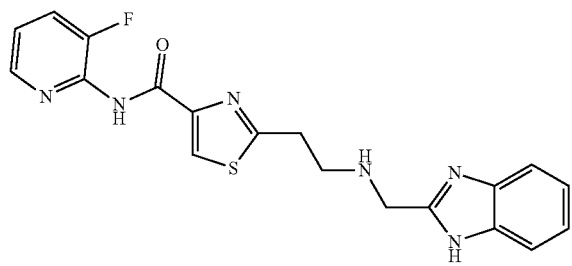 [SMILES: O=C(Nc1ncccc1F)c1csc(CCNCc2nc3ccccc3[nH]2)n1] |
| 78 | 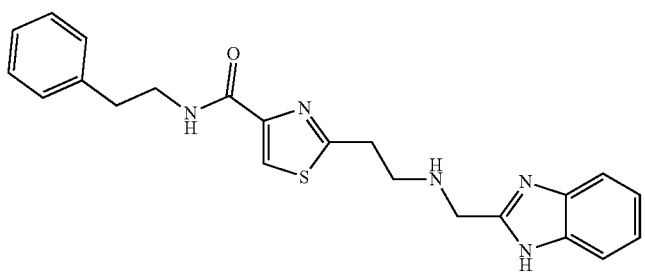 [SMILES: O=C(NCCc1ccccc1)c1csc(CCNCc2nc3ccccc3[nH]2)n1] |
| 79 | 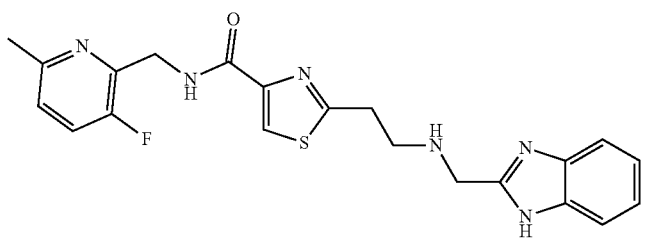 [SMILES: Cc1ccc(F)c(CNC(=O)c2csc(CCNCc3nc4ccccc4[nH]3)n2)n1] |

| Exp No. | Compound |
|---|---|
| 80 | 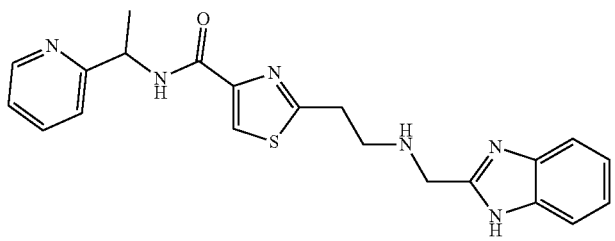 [SMILES: CC(NC(=O)c1csc(CCNCc2nc3ccccc3[nH]2)n1)c1ccccn1] |
| 81 | 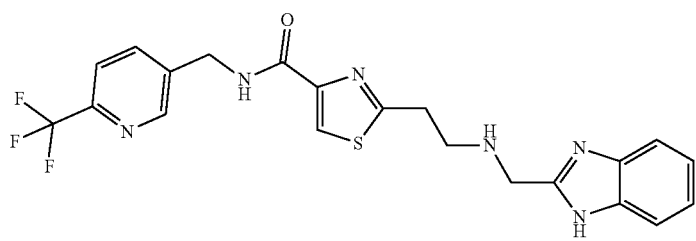 [SMILES: O=C(NCc1ccc(C(F)(F)F)nc1)c1csc(CCNCc2nc3ccccc3[nH]2)n1] |
| 82 | 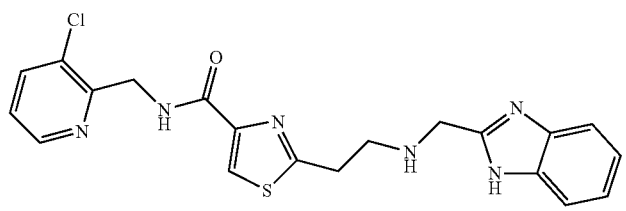 [SMILES: O=C(NCc1ncccc1Cl)c1csc(CCNCc2nc3ccccc3[nH]2)n1] |
| 83 | 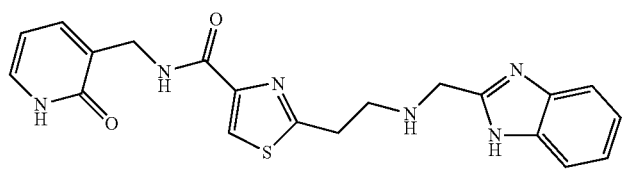 [SMILES: O=C(NCc1ccc[nH]c1=O)c1csc(CCNCc2nc3ccccc3[nH]2)n1] |
| 84 | 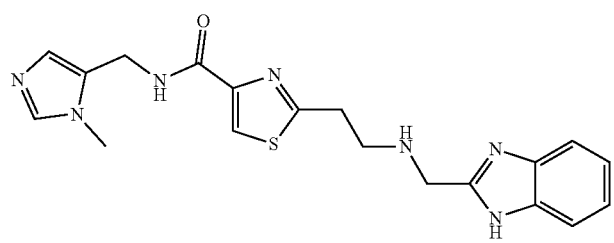 [SMILES: Cn1cncc1CNC(=O)c1csc(CCNCc2nc3ccccc3[nH]2)n1] |
| 85 | 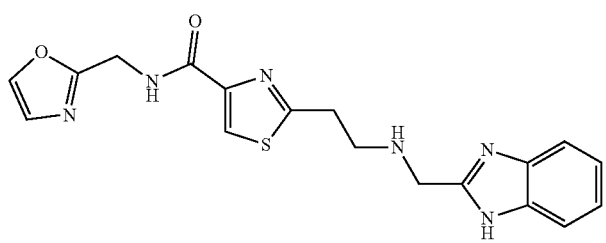 [SMILES: O=C(NCc1ncco1)c1csc(CCNCc2nc3ccccc3[nH]2)n1] |

| Exp No. | Compound |
|---|---|
| 86 | |
| 87 | |
| 88 | |
| 89 | |
| 90 | |
| 91 | |
| 92 | |

-continued
| Exp No. | Compound |
|---|---|
| 93 | 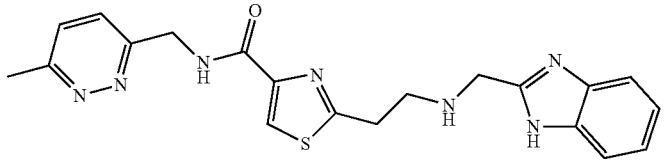 [SMILES: Cc1ccc(CNC(=O)c2csc(CCNCc3nc4ccccc4[nH]3)n2)nn1] |
| 94 | 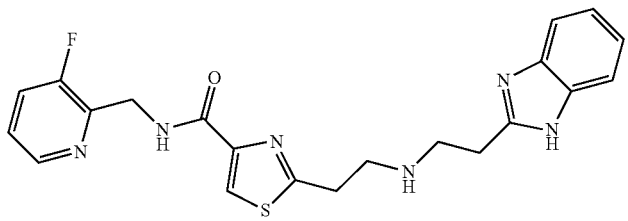 [SMILES: O=C(NCc1ncccc1F)c1csc(CCNCCc2nc3ccccc3[nH]2)n1] |
| 95 | 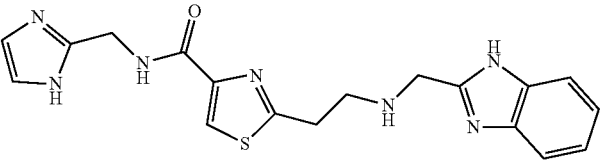 [SMILES: O=C(NCc1ncc[nH]1)c1csc(CCNCc2nc3ccccc3[nH]2)n1] |
| 96 | 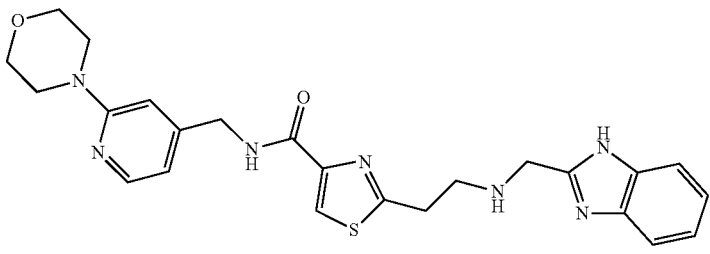 [SMILES: O=C(NCc1ccnc(N2CCOCC2)c1)c1csc(CCNCc2nc3ccccc3[nH]2)n1] |
| 97 | 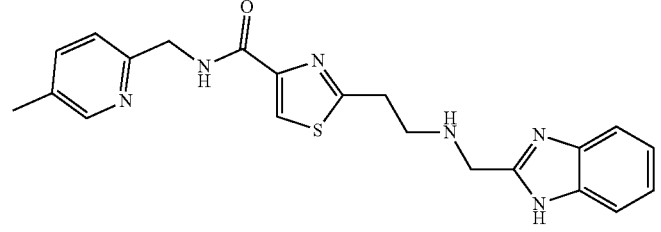 [SMILES: Cc1ccc(CNC(=O)c2csc(CCNCc3nc4ccccc4[nH]3)n2)nc1] |
| 98 | 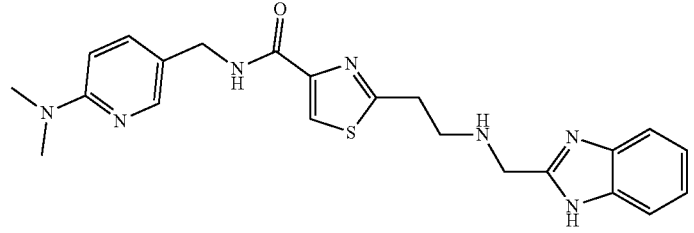 [SMILES: CN(C)c1ccc(CNC(=O)c2csc(CCNCc3nc4ccccc4[nH]3)n2)cn1] |
| 99 | 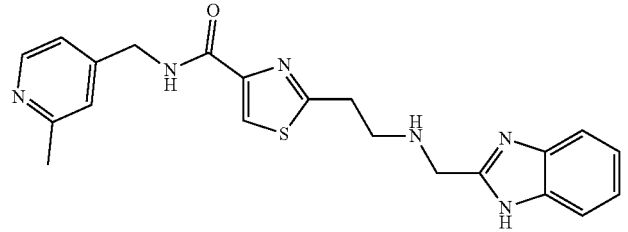 [SMILES: Cc1cc(CNC(=O)c2csc(CCNCc3nc4ccccc4[nH]3)n2)ccn1] |

-continued
| Exp No. | Compound |
|---|---|
| 100 | 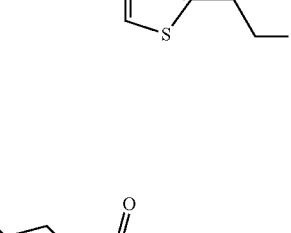 |
| 101 | 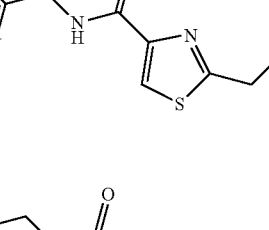 |
| 102 | 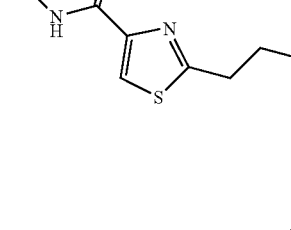 |
| 103 | 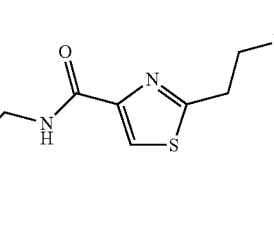 |
| 104 | 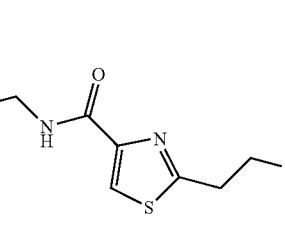 |
| 105 | 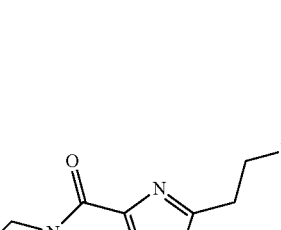 |

-continued

| Exp No. | Compound |
|---|---|
| 106 | |
| 107 | |
| 108 | |
| 109 | |
| 110 | |

-continued
| Exp No. | Compound |
|---|---|
| 111 | 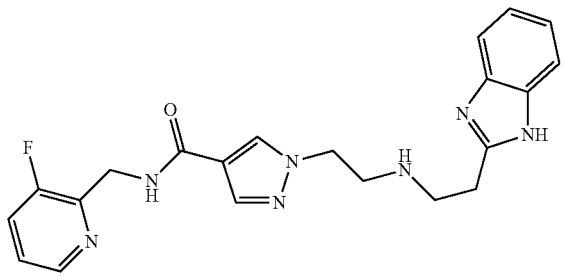 [SMILES: O=C(NCc1ncccc1F)c1cnn(CCNCCc2nc3ccccc3[nH]2)c1] |
| 112 | 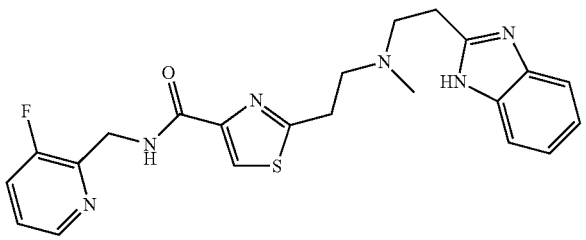 [SMILES: CN(CCc1nc2ccccc2[nH]1)CCc1nc(C(=O)NCc2ncccc2F)cs1] |
| 113 | 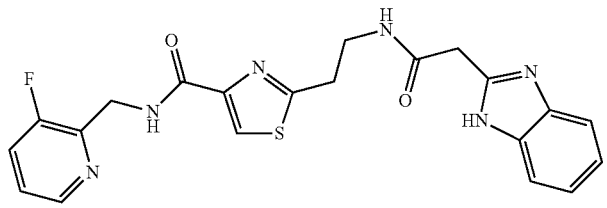 [SMILES: O=C(Cc1nc2ccccc2[nH]1)NCCc1nc(C(=O)NCc2ncccc2F)cs1] |
| 114 | 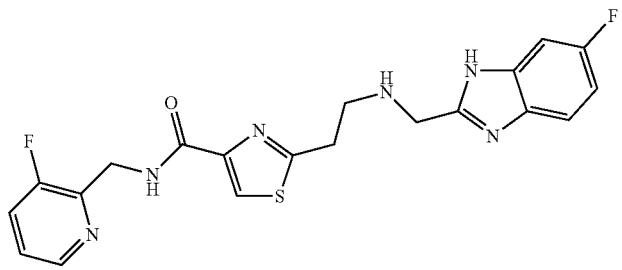 [SMILES: O=C(NCc1ncccc1F)c1csc(CCNCc2nc3ccc(F)cc3[nH]2)n1] |
| 115 | 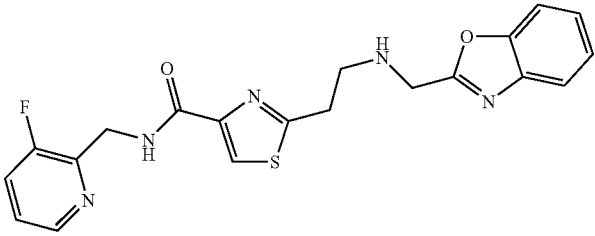 [SMILES: O=C(NCc1ncccc1F)c1csc(CCNCc2nc3ccccc3o2)n1] |
| 116 | 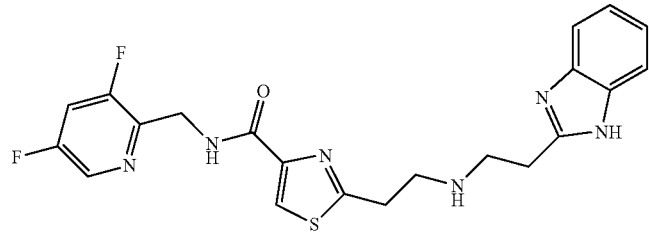 [SMILES: O=C(NCc1ncc(F)cc1F)c1csc(CCNCCc2nc3ccccc3[nH]2)n1] |

-continued

| Exp No. | Compound |
|---|---|
| 117 | |
| 118 | |
| 119 | |
| 120 | |
| 121 | |
| 122 | |

-continued

| Exp No. | Compound |
|---|---|
| 123 | |
| 124 | |
| 125 | |
| 126 | |
| 127 | |

| Exp No. | Compound |
|---|---|
| 128 | 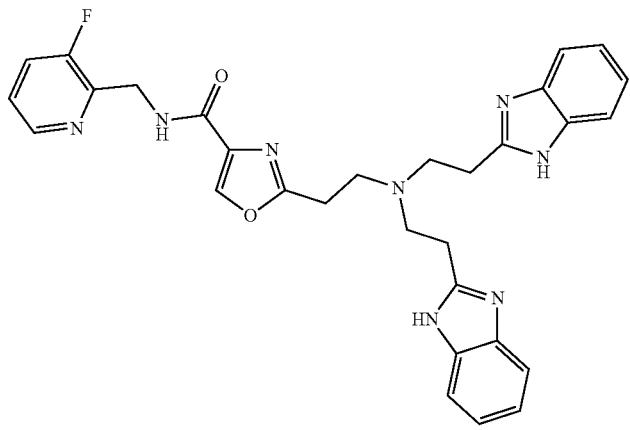 [SMILES: O=C(NCc1ncccc1F)c1coc(CCN(CCc2nc3ccccc3[nH]2)CCc2nc3ccccc3[nH]2)n1] |
| 129 | 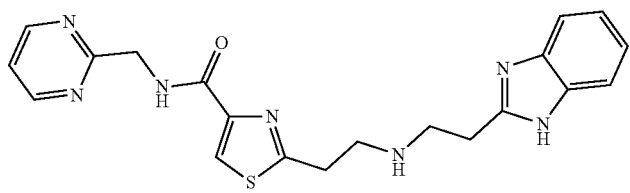 [SMILES: O=C(NCc1ncccn1)c1csc(CCNCCc2nc3ccccc3[nH]2)n1] |
| 131 | 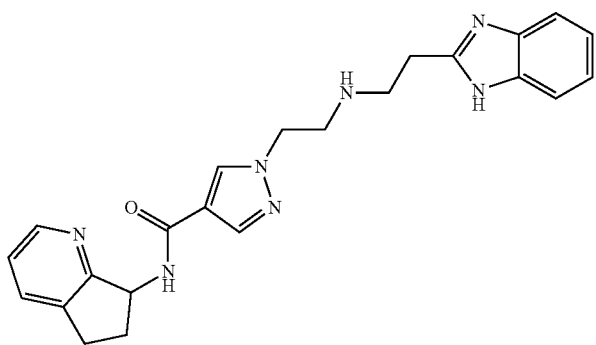 [SMILES: O=C(NC1CCc2cccnc21)c1cnn(CCNCCc2nc3ccccc3[nH]2)c1] |
| 132 | 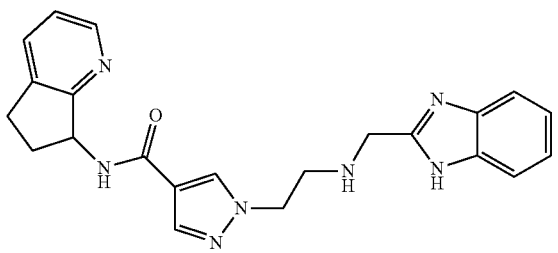 [SMILES: O=C(NC1CCc2cccnc21)c1cnn(CCNCc2nc3ccccc3[nH]2)c1] |
| 133 | 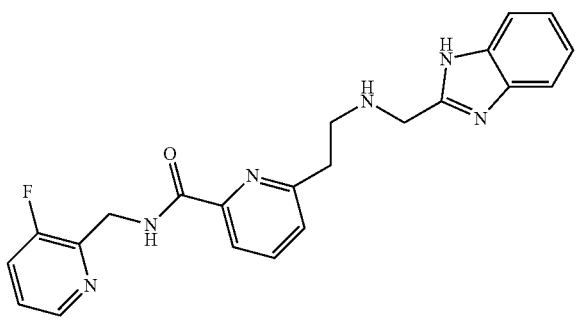 [SMILES: O=C(NCc1ncccc1F)c1cccc(CCNCc2nc3ccccc3[nH]2)n1] |

| Exp No. | Compound |
|---|---|
| 134 | 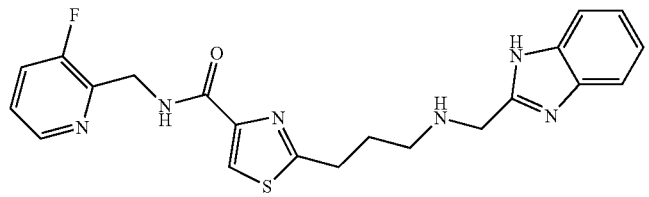 [SMILES: O=C(NCc1ncccc1F)c1csc(CCCNCc2nc3ccccc3[nH]2)n1] |
| 135 | 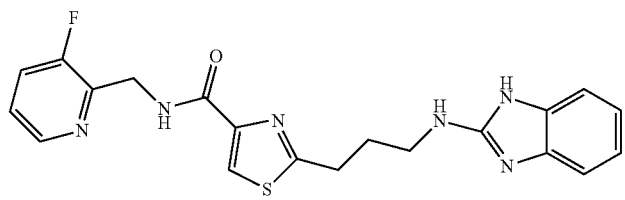 [SMILES: O=C(NCc1ncccc1F)c1csc(CCCNc2nc3ccccc3[nH]2)n1] |
| 136 | 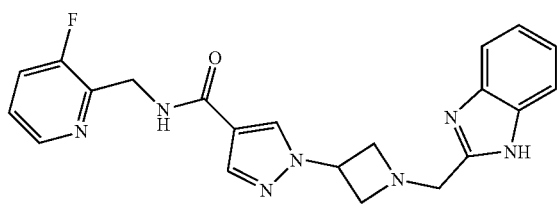 [SMILES: O=C(NCc1ncccc1F)c1cnn(C2CN(Cc3nc4ccccc4[nH]3)C2)c1] |
| 137 | 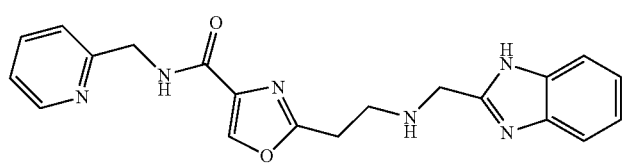 [SMILES: O=C(NCc1ccccn1)c1coc(CCNCc2nc3ccccc3[nH]2)n1] |
| 138 | 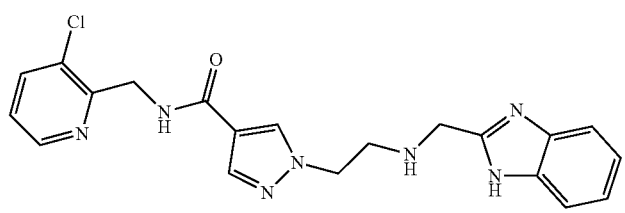 [SMILES: O=C(NCc1ncccc1Cl)c1cnn(CCNCc2nc3ccccc3[nH]2)c1] |
| 139 | 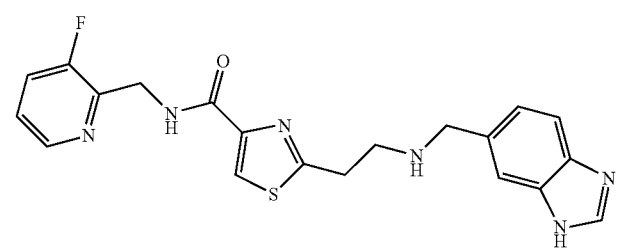 [SMILES: O=C(NCc1ncccc1F)c1csc(CCNCc2ccc3nc[nH]c3c2)n1] |
| 140 | 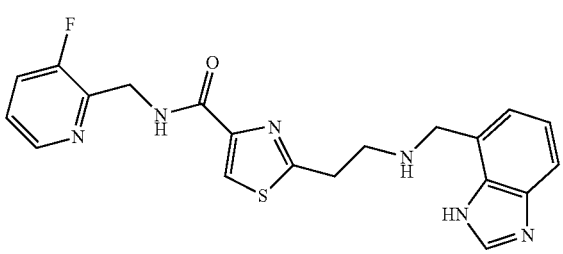 [SMILES: O=C(NCc1ncccc1F)c1csc(CCNCc2cccc3nc[nH]c23)n1] |

-continued
| Exp No. | Compound |
|---|---|
| 141 | 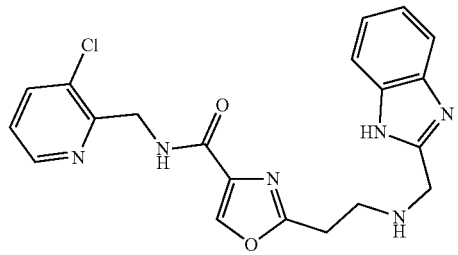 [SMILES: O=C(NCc1ncccc1Cl)c1coc(CCNCc2nc3ccccc3[nH]2)n1] |
| 142 | 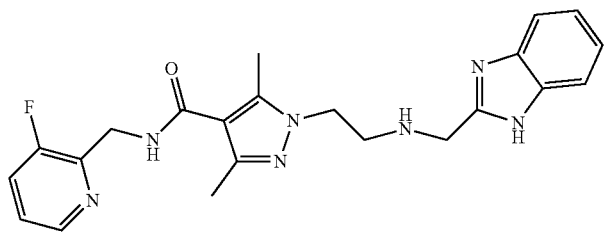 [SMILES: Cc1nn(CCNCc2nc3ccccc3[nH]2)c(C)c1C(=O)NCc1ncccc1F] |
| 144 | 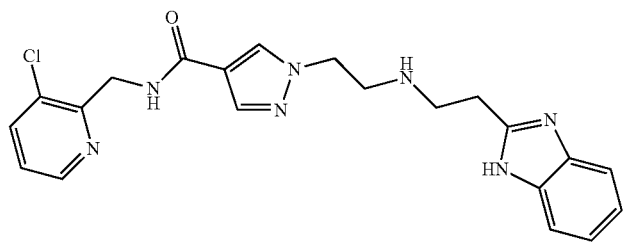 [SMILES: O=C(NCc1ncccc1Cl)c1cnn(CCNCCc2nc3ccccc3[nH]2)c1] |
| 145 | 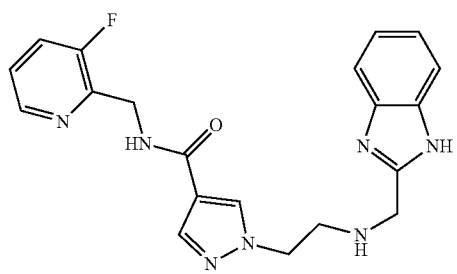 [SMILES: O=C(NCc1ncccc1F)c1cnn(CCNCc2nc3ccccc3[nH]2)c1] |
| 146 | 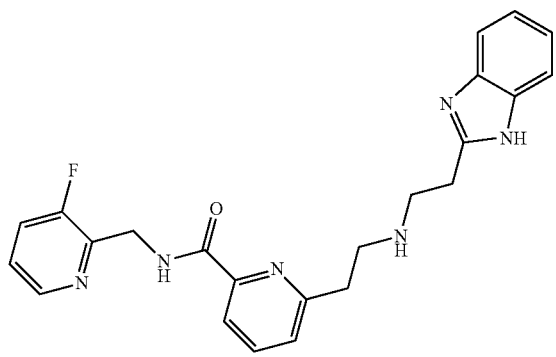 [SMILES: O=C(NCc1ncccc1F)c1cccc(CCNCCc2nc3ccccc3[nH]2)n1] |

-continued
| Exp No. | Compound |
|---|---|
| 147 | 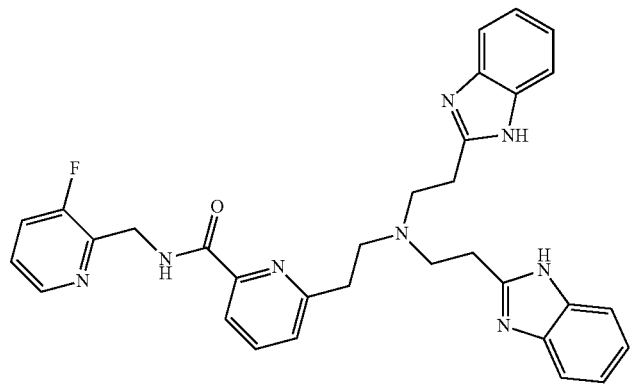 [SMILES: O=C(NCc1ncccc1F)c1cccc(CCN(CCc2nc3ccccc3[nH]2)CCc2nc3ccccc3[nH]2)n1] |
| 148 | 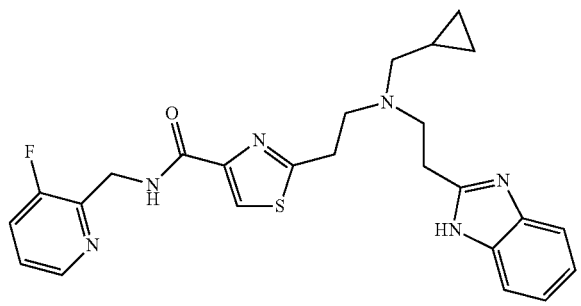 [SMILES: O=C(NCc1ncccc1F)c1csc(CCN(CCc2nc3ccccc3[nH]2)CC2CC2)n1] |
| 149 | 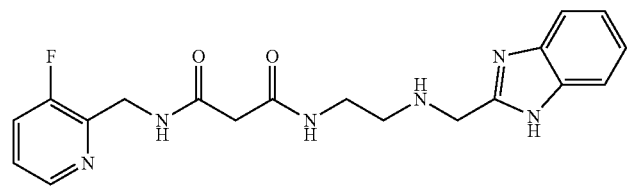 [SMILES: O=C(CC(=O)NCc1ncccc1F)NCCNCc1nc2ccccc2[nH]1] |
| 150 | 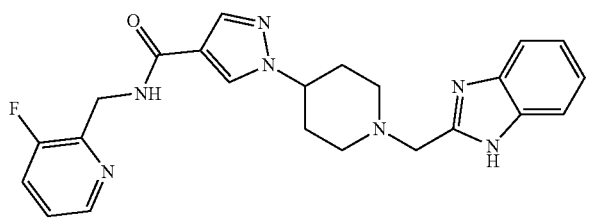 [SMILES: O=C(NCc1ncccc1F)c1cnn(C2CCN(Cc3nc4ccccc4[nH]3)CC2)c1] |
| 151 | 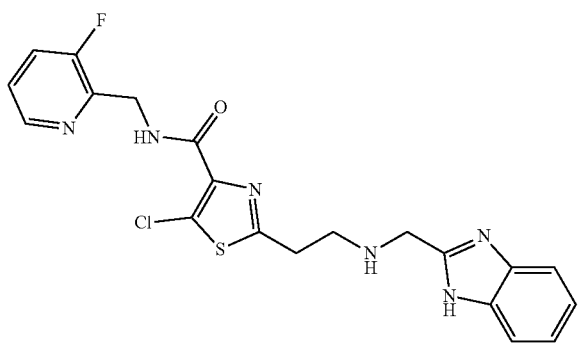 [SMILES: O=C(NCc1ncccc1F)c1nc(CCNCc2nc3ccccc3[nH]2)sc1Cl] |

-continued
| Exp No. | Compound |
|---|---|
| 152 | 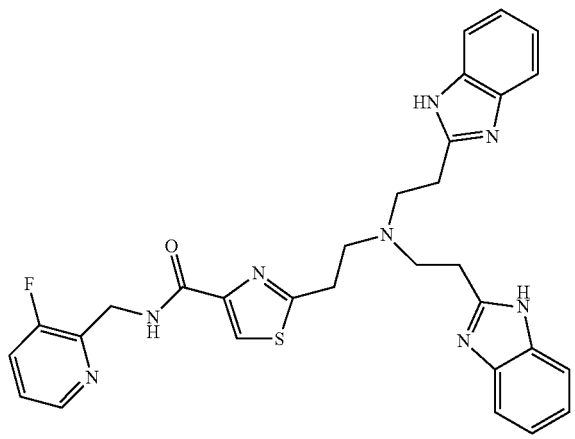 [SMILES: O=C(NCc1ncccc1F)c1csc(CCN(CCc2nc3ccccc3[nH]2)CCc2nc3ccccc3[nH]2)n1] |
| 153 | 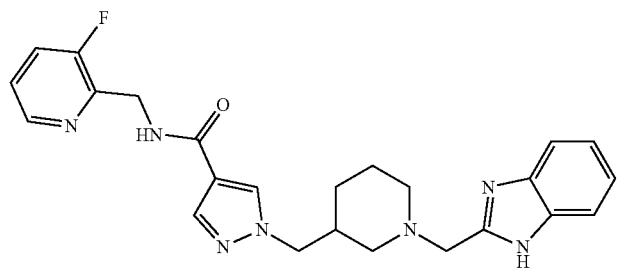 [SMILES: O=C(NCc1ncccc1F)c1cnn(CC2CCCN(Cc3nc4ccccc4[nH]3)C2)c1] |
| 154 | 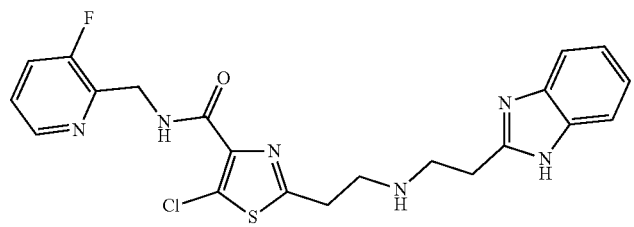 [SMILES: O=C(NCc1ncccc1F)c1nc(CCNCCc2nc3ccccc3[nH]2)sc1Cl] |
| 155 | 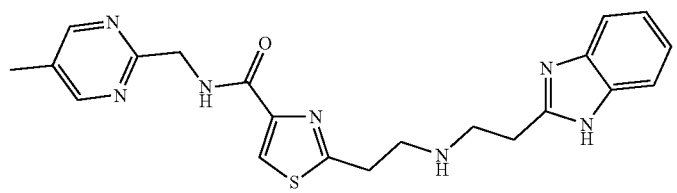 [SMILES: Cc1cnc(CNC(=O)c2csc(CCNCCc3nc4ccccc4[nH]3)n2)nc1] |
| 156 | 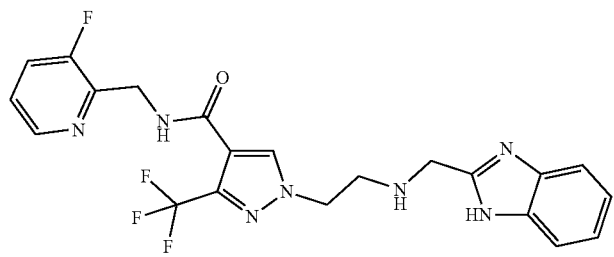 [SMILES: O=C(NCc1ncccc1F)c1cn(CCNCc2nc3ccccc3[nH]2)nc1C(F)(F)F] |

-continued
| Exp No. | Compound |
|---|---|
| 157 | 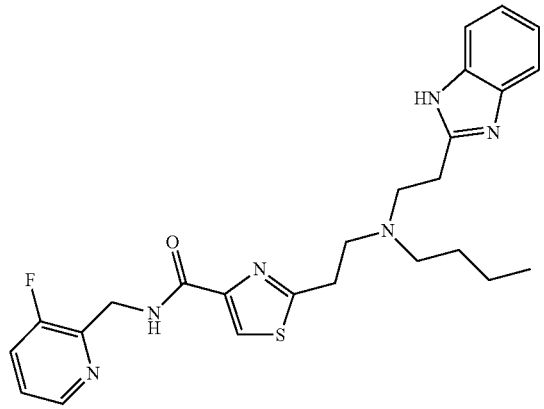 [SMILES: CCCCN(CCc1nc2ccccc2[nH]1)CCc1nc(C(=O)NCc2ncccc2F)cs1] |
| 158 | 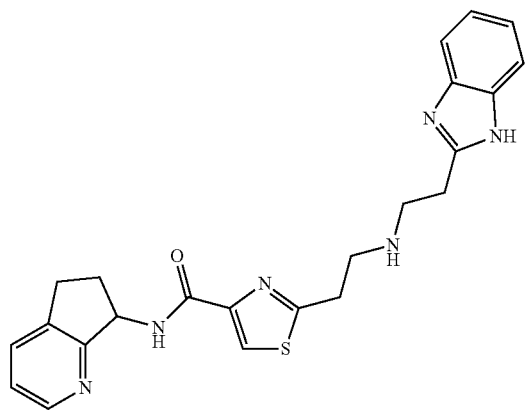 [SMILES: O=C(NC1CCc2cccnc21)c1csc(CCNCCc2nc3ccccc3[nH]2)n1] |
| 159 | 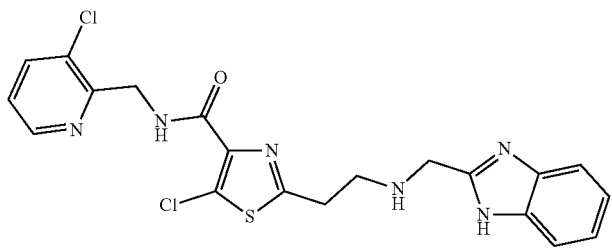 [SMILES: O=C(NCc1ncccc1Cl)c1nc(CCNCc2nc3ccccc3[nH]2)sc1Cl] |
| 160 | 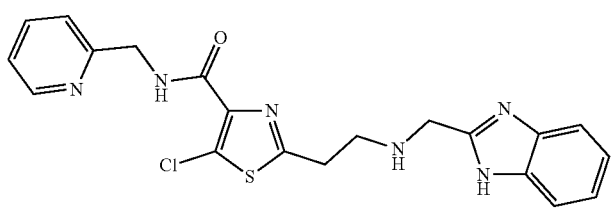 [SMILES: O=C(NCc1ccccn1)c1nc(CCNCc2nc3ccccc3[nH]2)sc1Cl] |
| 161 | 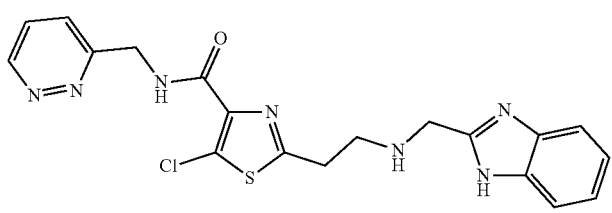 [SMILES: O=C(NCc1cccnn1)c1nc(CCNCc2nc3ccccc3[nH]2)sc1Cl] |

| Exp No. | Compound |
|---|---|
| 162 | 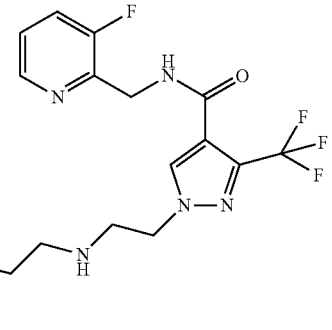 |
| 163 | 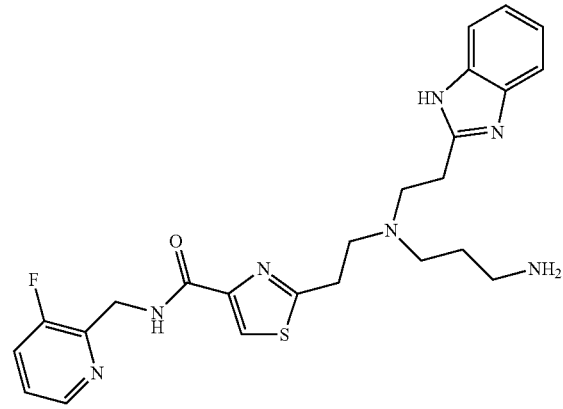 [SMILES: NCCCN(CCc1nc2ccccc2[nH]1)CCc1nc(C(=O)NCc2ncccc2F)cs1] |
| 164 | 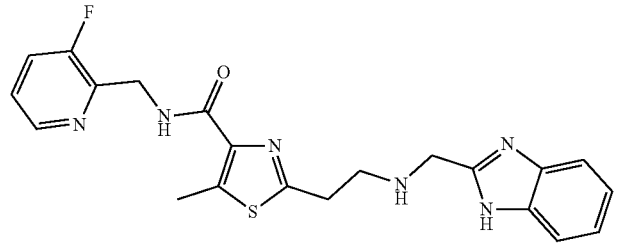 [SMILES: Cc1sc(CCNCc2nc3ccccc3[nH]2)nc1C(=O)NCc1ncccc1F] |
| 165 | 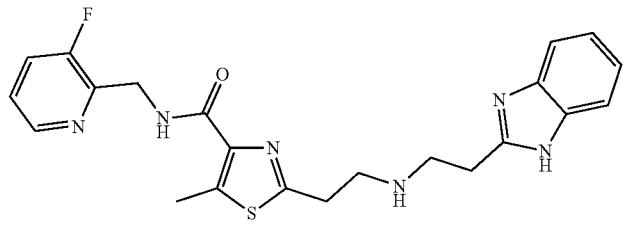 [SMILES: Cc1sc(CCNCCc2nc3ccccc3[nH]2)nc1C(=O)NCc1ncccc1F] |
| 166 | 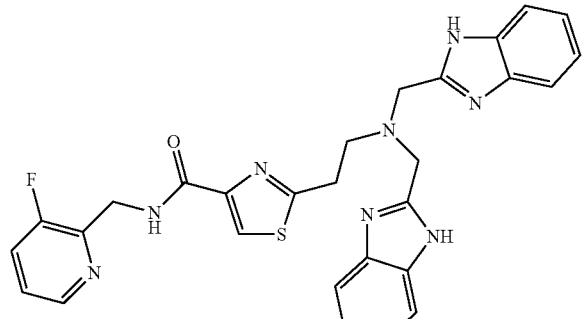 |

| Exp No. | Compound |
|---|---|
| 167 | 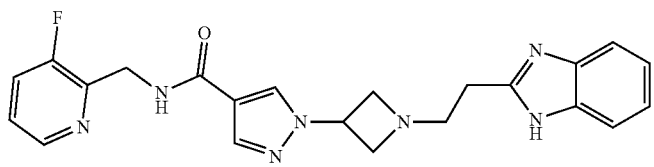 [SMILES: O=C(NCc1ncccc1F)c1cnn(C2CN(CCc3nc4ccccc4[nH]3)C2)c1] |
| 168 | 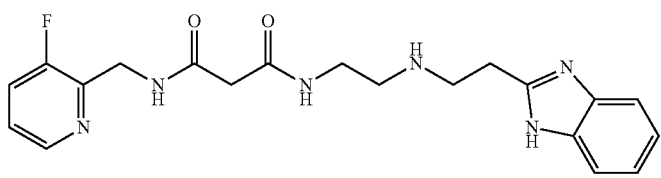 [SMILES: O=C(CC(=O)NCc1ncccc1F)NCCNCCc1nc2ccccc2[nH]1] |
| 169 | 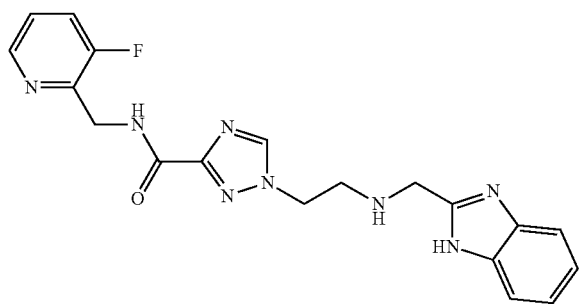 [SMILES: O=C(NCc1ncccc1F)c1ncn(CCNCc2nc3ccccc3[nH]2)n1] |
| 170 | 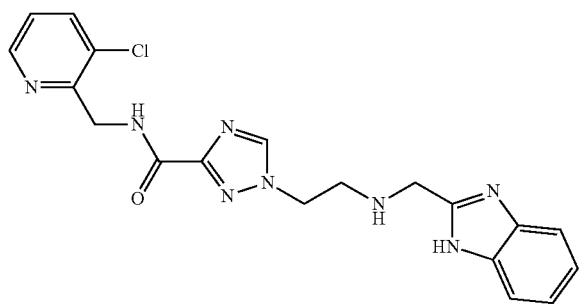 [SMILES: O=C(NCc1ncccc1Cl)c1ncn(CCNCc2nc3ccccc3[nH]2)n1] |
| 171 | 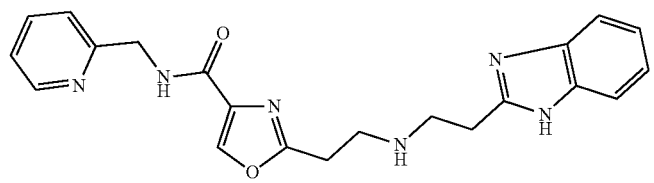 [SMILES: O=C(NCc1ccccn1)c1coc(CCNCCc2nc3ccccc3[nH]2)n1] |
| 172 | 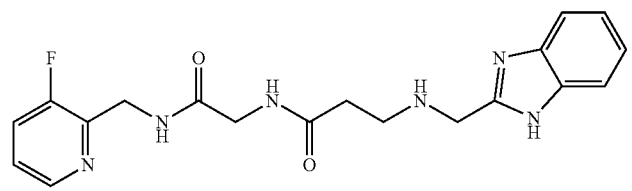 [SMILES: O=C(CCNCc1nc2ccccc2[nH]1)NCC(=O)NCc1ncccc1F] |

| Exp No. | Compound |
|---|---|
| 173 | 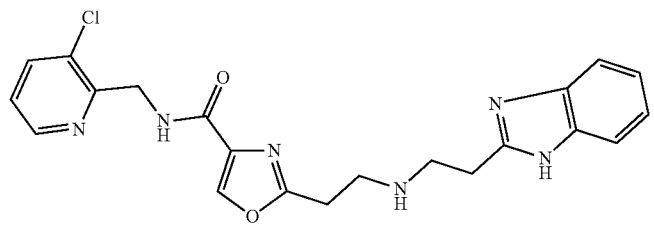 [SMILES: O=C(NCc1ncccc1Cl)c1coc(CCNCCc2nc3ccccc3[nH]2)n1] |
| 174 | 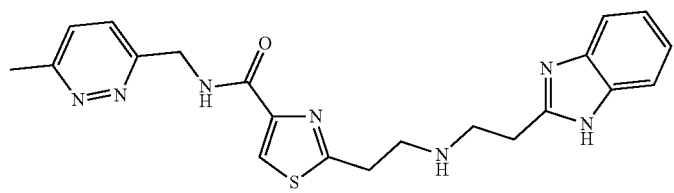 [SMILES: Cc1ccc(CNC(=O)c2csc(CCNCCc3nc4ccccc4[nH]3)n2)nn1] |
| 175 | 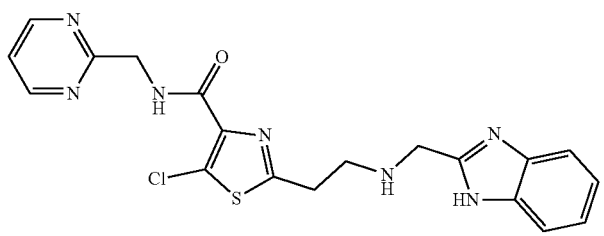 [SMILES: O=C(NCc1ncccn1)c1nc(CCNCc2nc3ccccc3[nH]2)sc1Cl] |
| 176 | 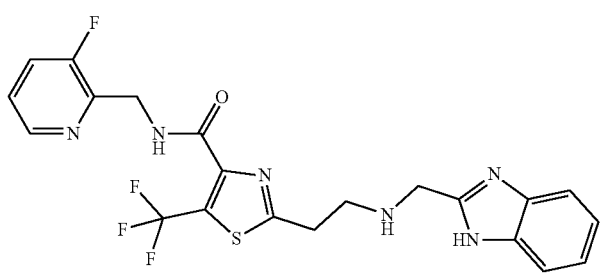 [SMILES: O=C(NCc1ncccc1F)c1nc(CCNCc2nc3ccccc3[nH]2)sc1C(F)(F)F] |
| 177 | 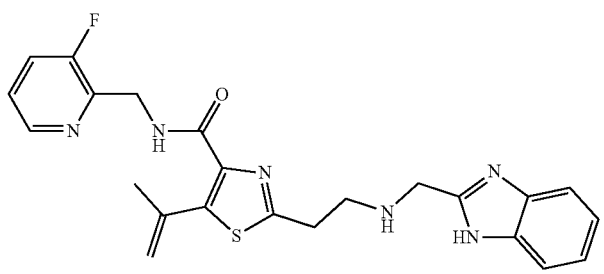 [SMILES: C=C(C)c1sc(CCNCc2nc3ccccc3[nH]2)nc1C(=O)NCc1ncccc1F] |
| 178 | 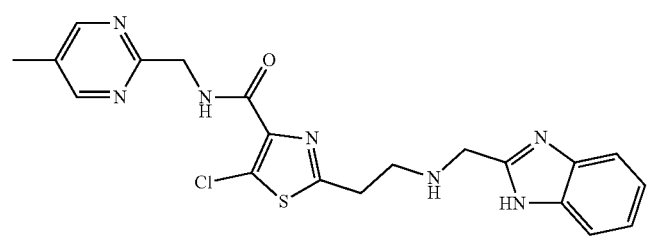 [SMILES: Cc1cnc(CNC(=O)c2nc(CCNCc3nc4ccccc4[nH]3)sc2Cl)nc1] |

| Exp No. | Compound |
|---|---|
| 179 | (structure) |
| 180 | (structure) |
| 181 | (structure) |
| 182 | (structure) |
| 183 | (structure) |

-continued

| Exp No. | Compound |
|---|---|
| 184 | |
| 185 | |
| 186 | |
| 187 | |
| 188 | |

-continued
| Exp No. | Compound |
|---|---|
| 189 | 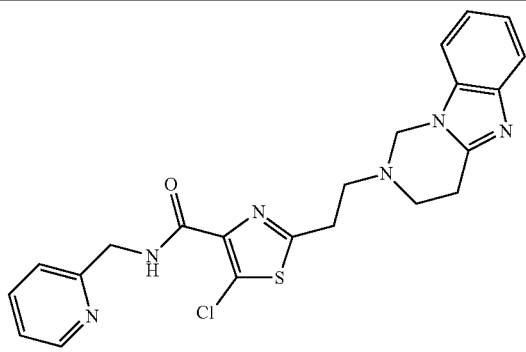 |
| 190 | 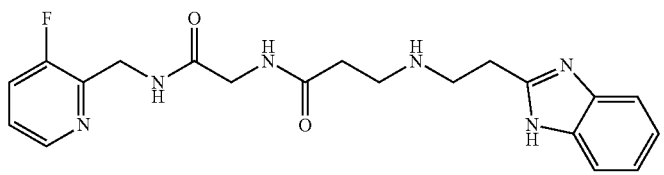 [SMILES: O=C(CCNCCc1nc2ccccc2[nH]1)NCC(=O)NCc1ncccc1F] |
| 191 | 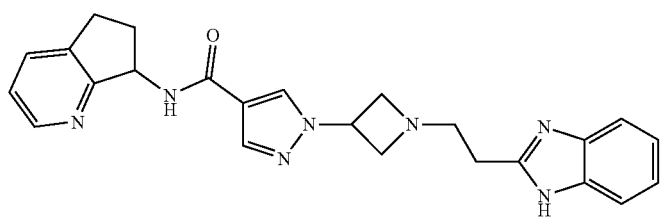 [SMILES: O=C(NC1CCc2cccnc21)c1cnn(C2CN(CCc3nc4ccccc4[nH]3)C2)c1] |
| 192 | 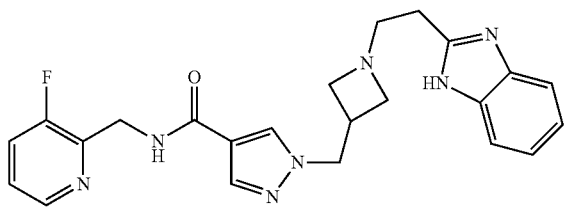 [SMILES: O=C(NCc1ncccc1F)c1cnn(CC2CN(CCc3nc4ccccc4[nH]3)C2)c1] |
| 193 | 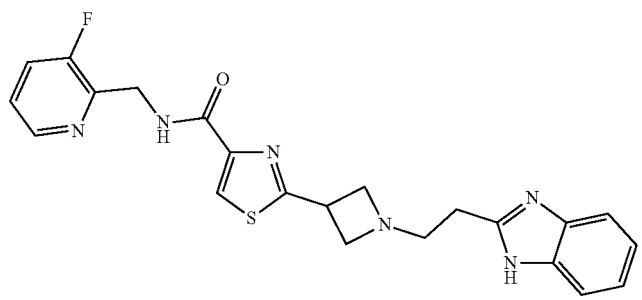 [SMILES: O=C(NCc1ncccc1F)c1csc(C2CN(CCc3nc4ccccc4[nH]3)C2)n1] |
| 194 | 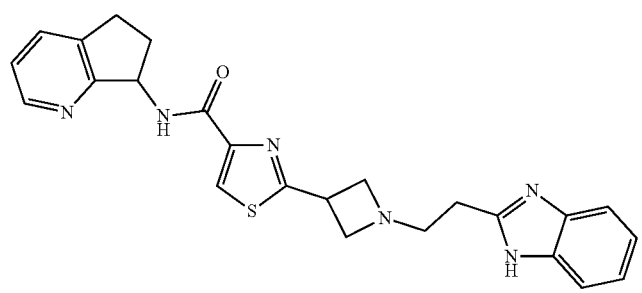 [SMILES: O=C(NC1CCc2cccnc21)c1csc(C2CN(CCc3nc4ccccc4[nH]3)C2)n1] |

| Exp No. | Compound |
|---|---|
| 195 | 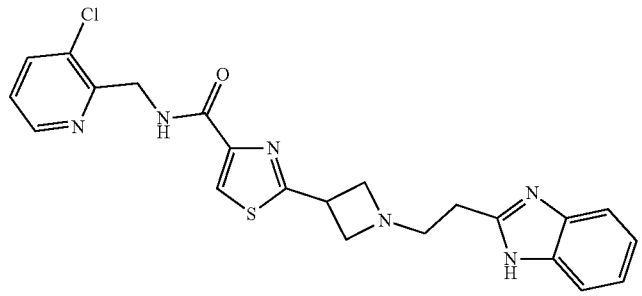 |
| 196 | 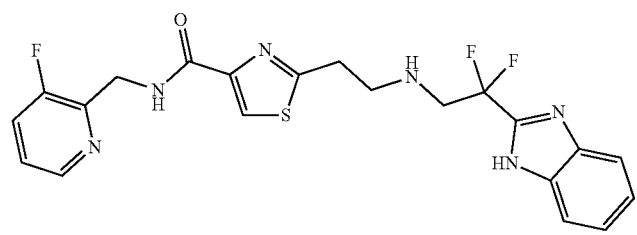 [SMILES: O=C(NCc1ncccc1F)c1csc(CCNCC(F)(F)c2nc3ccccc3[nH]2)n1] |
| 197 | 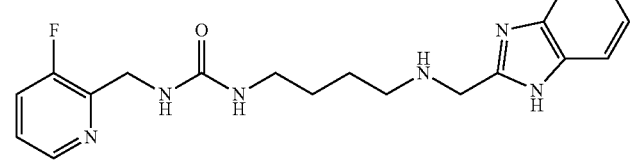 |
| 198 | 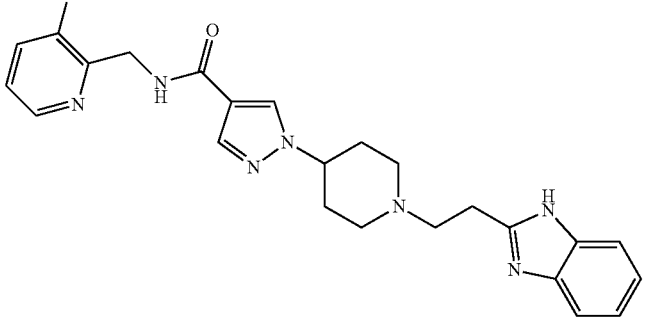 |
| 199 | 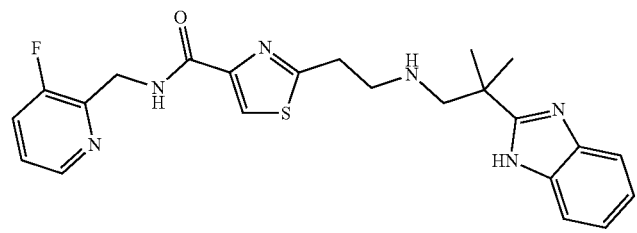 [SMILES: CC(C)(CNCCc1nc(C(=O)NCc2ncccc2F)cs1)c1nc2ccccc2[nH]1] |
| 200 | 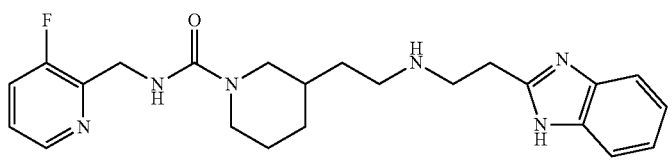 [SMILES: O=C(NCc1ncccc1F)N1CCCC(CCNCCc2nc3ccccc3[nH]2)C1] |

-continued
| Exp No. | Compound |
|---|---|
| 201 | 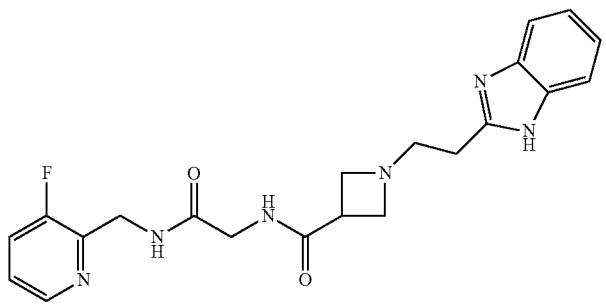 [SMILES: O=C(CNC(=O)C1CN(CCc2nc3ccccc3[nH]2)C1)NCc1ncccc1F] |
| 202 | 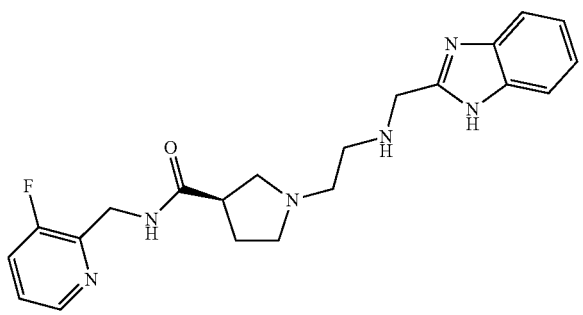 [SMILES: O=C(NCc1ncccc1F)[C@@H]1CCN(CCNCc2nc3ccccc3[nH]2)C1] |
| 204 | 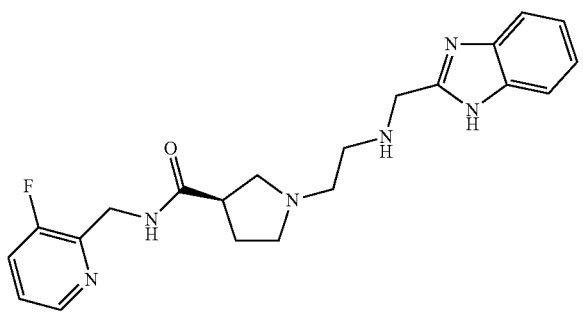 [SMILES: O=C(NCc1ncccc1F)[C@@H]1CCN(CCNCc2nc3ccccc3[nH]2)C1] |
| 205 | 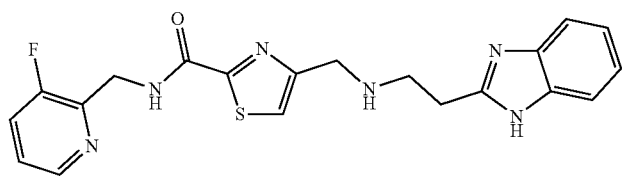 [SMILES: O=C(NCc1ncccc1F)c1nc(CNCCc2nc3ccccc3[nH]2)cs1] |
| 206 | 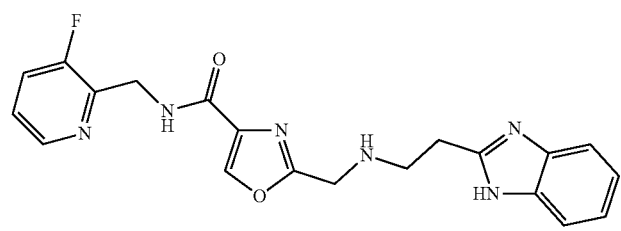 [SMILES: O=C(NCc1ncccc1F)c1coc(CNCCc2nc3ccccc3[nH]2)n1] |
| 207 | 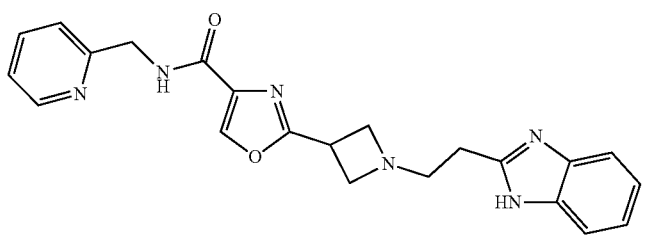 [SMILES: O=C(NCc1ccccn1)c1coc(C2CN(CCc3nc4ccccc4[nH]3)C2)n1] |

| Exp No. | Compound |
|---|---|
| 208 | 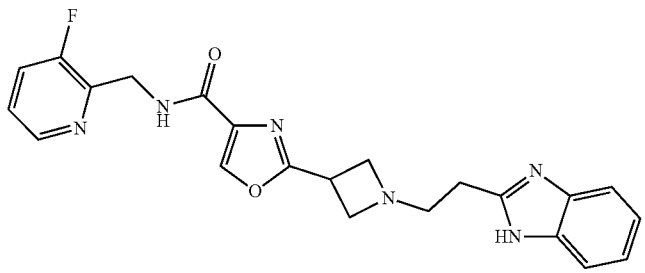 [SMILES: O=C(NCc1ncccc1F)c1coc(C2CN(CCc3nc4ccccc4[nH]3)C2)n1] |
| 209 | 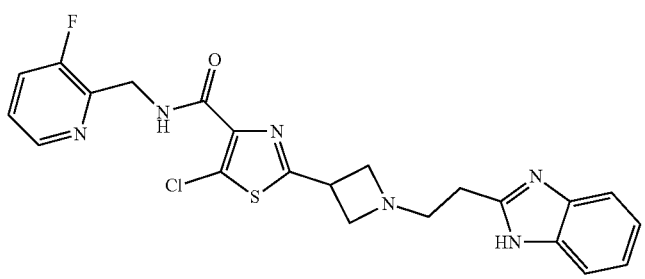 [SMILES: O=C(NCc1ncccc1F)c1nc(C2CN(CCc3nc4ccccc4[nH]3)C2)sc1Cl] |
| 210 | 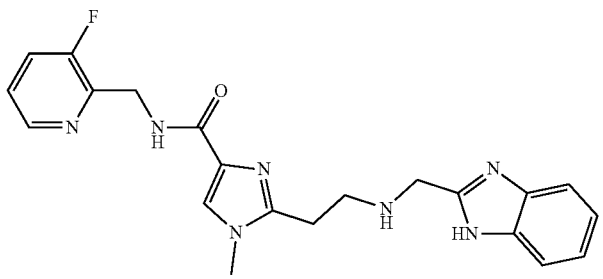 [SMILES: Cn1cc(C(=O)NCc2ncccc2F)nc1CCNCc1nc2ccccc2[nH]1] |
| 211 | 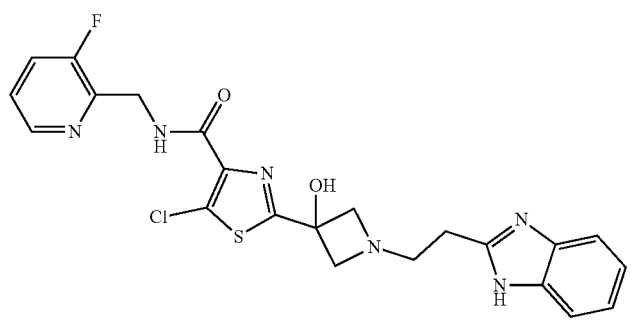 [SMILES: O=C(NCc1ncccc1F)c1nc(C2(O)CN(CCc3nc4ccccc4[nH]3)C2)sc1Cl] |
| 212 | 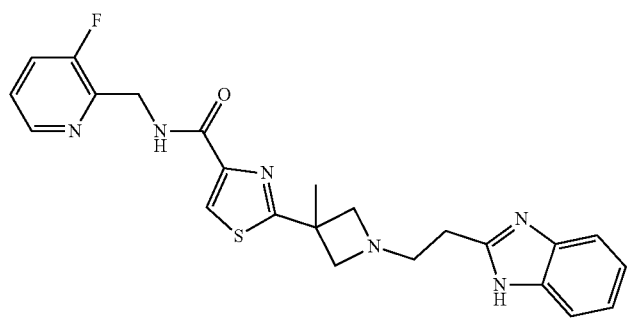 [SMILES: CC1(c2nc(C(=O)NCc3ncccc3F)cs2)CN(CCc2nc3ccccc3[nH]2)C1] |

-continued
| Exp No. | Compound |
|---|---|
| 213 | 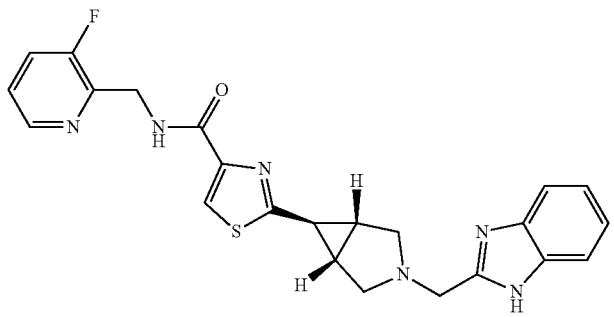 [SMILES: O=C(NCc1ncccc1F)c1csc([C@H]2[C@@H]3CN(Cc4nc5ccccc5[nH]4)C[C@@H]32)n1] |
| 214 | 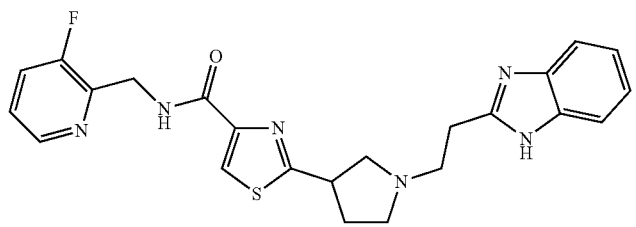 [SMILES: O=C(NCc1ncccc1F)c1csc(C2CCN(CCc3nc4ccccc4[nH]3)C2)n1] |
| 215 | 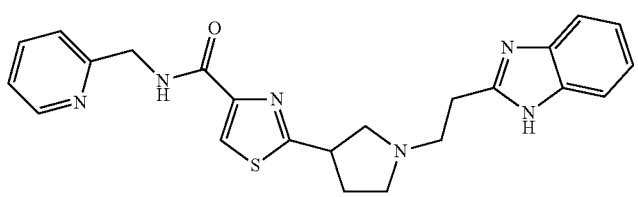 [SMILES: O=C(NCc1ccccn1)c1csc(C2CCN(CCc3nc4ccccc4[nH]3)C2)n1] |
| 218 | 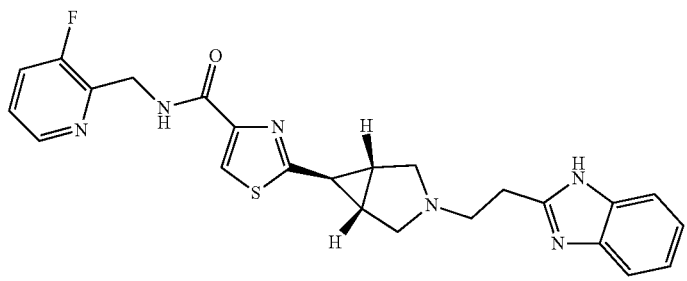 [SMILES: O=C(NCc1ncccc1F)c1csc([C@H]2[C@@H]3CN(CCc4nc5ccccc5[nH]4)C[C@@H]32)n1] |
| 219 | 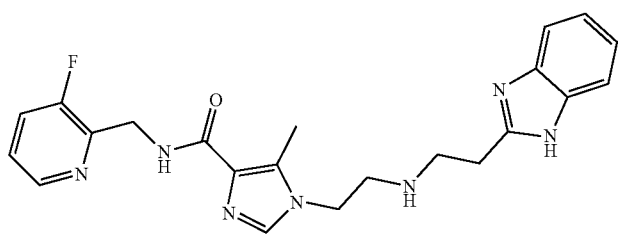 [SMILES: Cc1c(C(=O)NCc2ncccc2F)ncn1CCNCCc1nc2ccccc2[nH]1] |
| 220 | 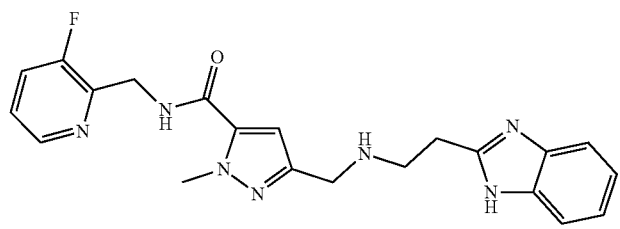 [SMILES: Cn1nc(CNCCc2nc3ccccc3[nH]2)cc1C(=O)NCc1ncccc1F] |

-continued
| Exp No. | Compound |
|---|---|
| 221 | 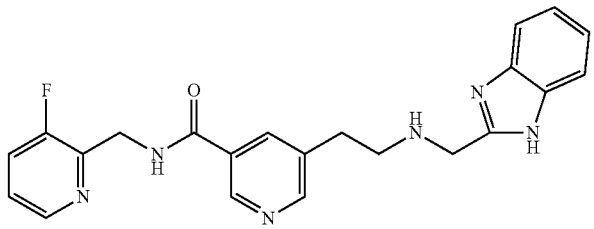 [SMILES: O=C(NCc1ncccc1F)c1cncc(CCNCc2nc3ccccc3[nH]2)c1] |
| 222 | 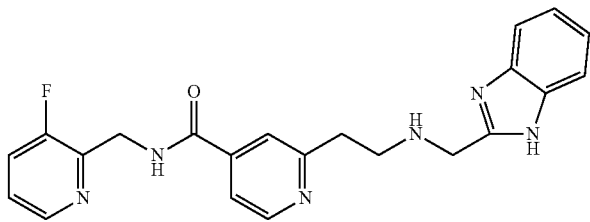 [SMILES: O=C(NCc1ncccc1F)c1ccnc(CCNCc2nc3ccccc3[nH]2)c1] |
| 223 | 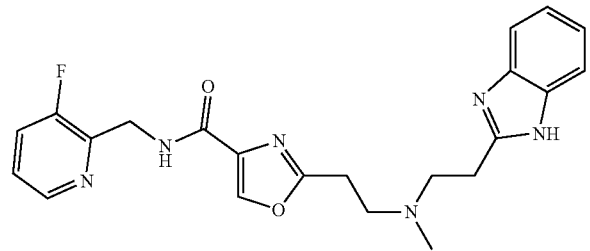 [SMILES: CN(CCc1nc2ccccc2[nH]1)CCc1nc(C(=O)NCc2ncccc2F)co1] |
| 224 | 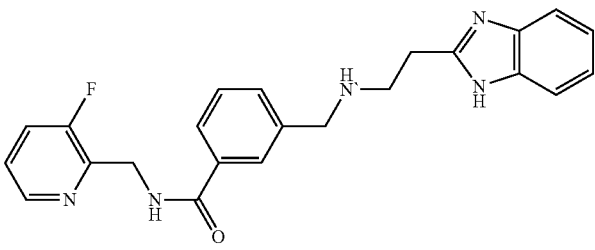 |
| 226 | 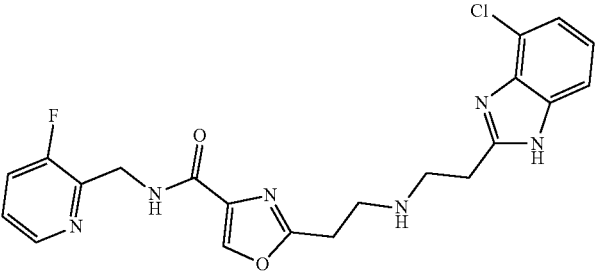 [SMILES: O=C(NCc1ncccc1F)c1coc(CCNCCc2nc3c(Cl)cccc3[nH]2)n1] |
| 227 | 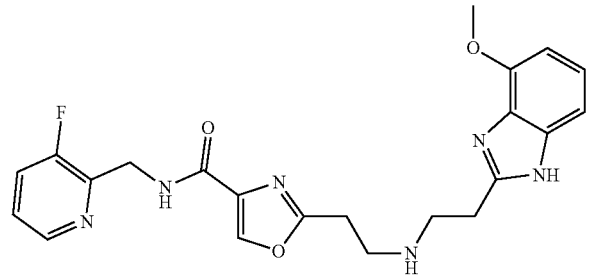 [SMILES: COc1cccc2[nH]c(CCNCCc3nc(C(=O)NCc4ncccc4F)co3)nc12] |

| Exp No. | Compound |
|---|---|
| 228 | 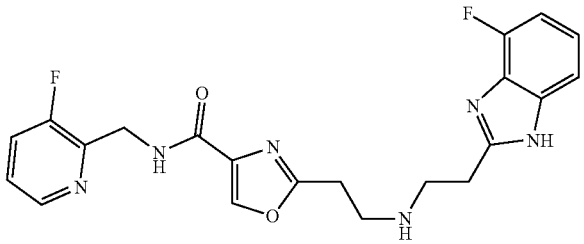 [SMILES: O=C(NCc1ncccc1F)c1coc(CCNCCc2nc3c(F)cccc3[nH]2)n1] |
| 229 | 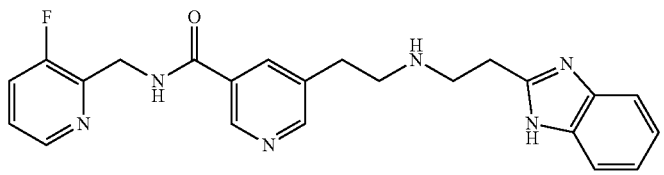 [SMILES: O=C(NCc1ncccc1F)c1cncc(CCNCCc2nc3ccccc3[nH]2)c1] |
| 230 | 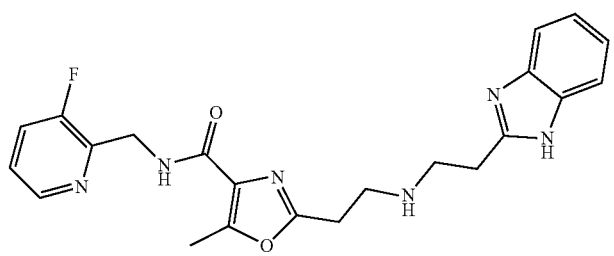 [SMILES: Cc1oc(CCNCCc2nc3ccccc3[nH]2)nc1C(=O)NCc1ncccc1F] |
| 231 | 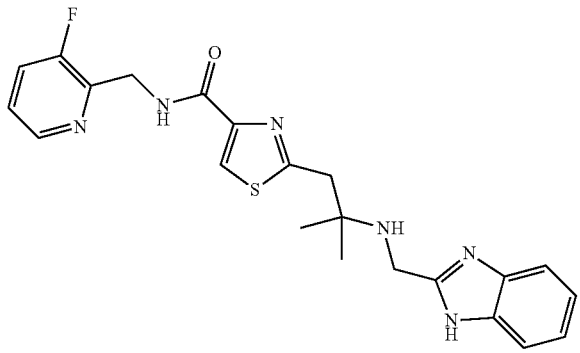 [SMILES: CC(C)(Cc1nc(C(=O)NCc2ncccc2F)cs1)NCc1nc2ccccc2[nH]1] |
| 232 | 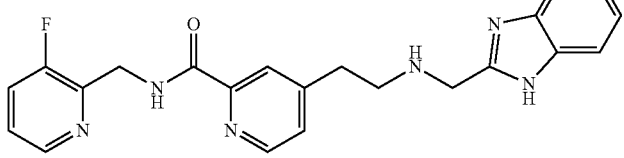 |
| 233 | 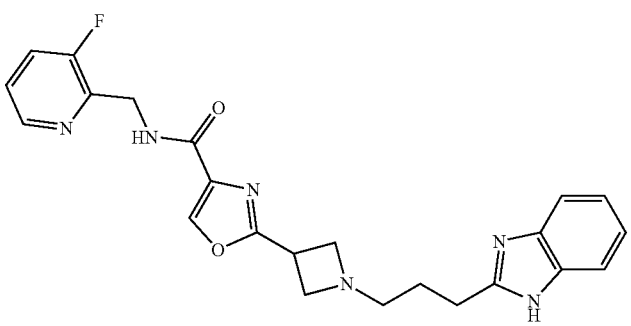 [SMILES: O=C(NCc1ncccc1F)c1coc(C2CN(CCCc3nc4ccccc4[nH]3)C2)n1] |

-continued
| Exp No. | Compound |
|---|---|
| 235 | 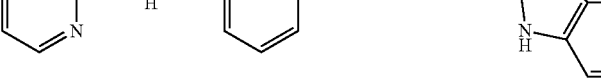 |
| 236 | 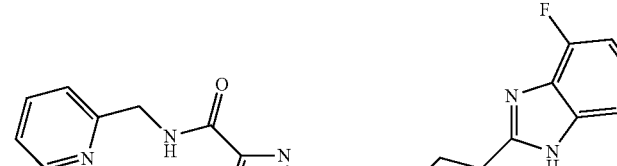 |
| 237 | 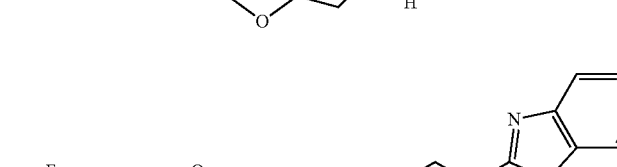 |
| 239 | 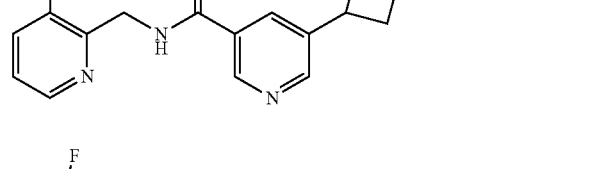 |
| 240 | 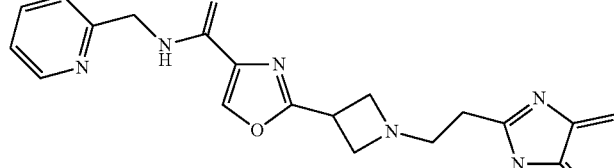 |
| 241 | 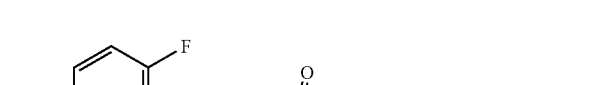 |

-continued
| Exp No. | Compound |
|---|---|
| 242 | 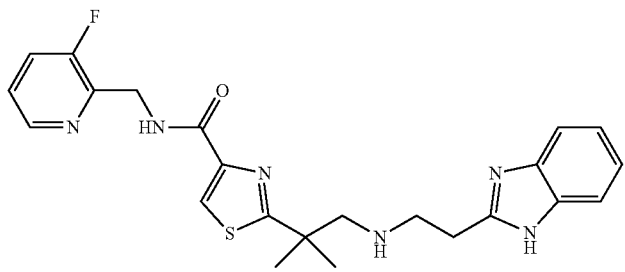 [SMILES: CC(C)(CNCCc1nc2ccccc2[nH]1)c1nc(C(=O)NCc2ncccc2F)cs1] |
| 243 | 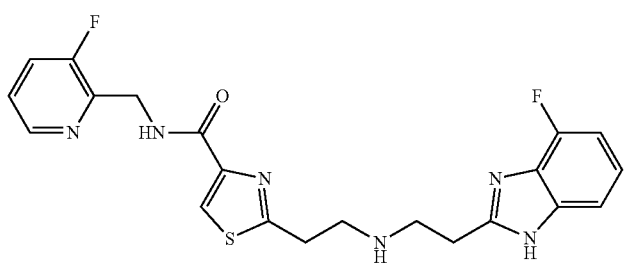 [SMILES: O=C(NCc1ncccc1F)c1csc(CCNCCc2nc3c(F)cccc3[nH]2)n1] |
| 244 | 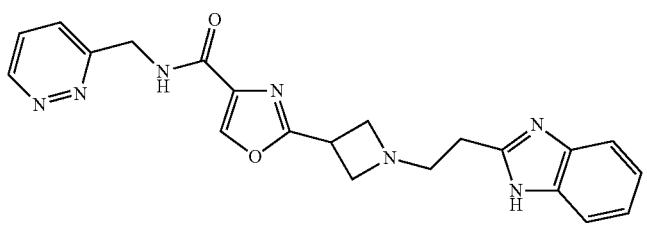 [SMILES: O=C(NCc1cccnn1)c1coc(C2CN(CCc3nc4ccccc4[nH]3)C2)n1] |
| 245 | 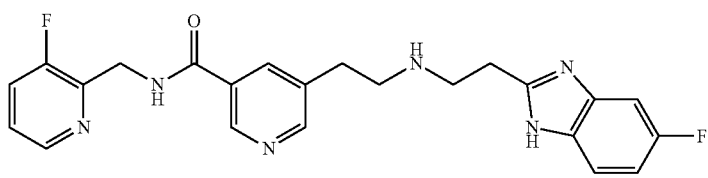 [SMILES: O=C(NCc1ncccc1F)c1cncc(CCNCCc2nc3cc(F)ccc3[nH]2)c1] |
| 246 | 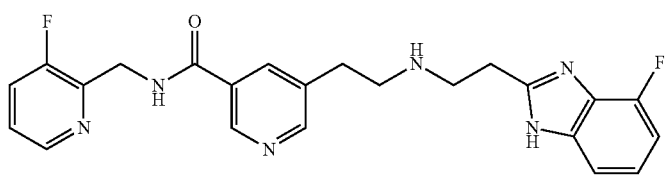 [SMILES: O=C(NCc1ncccc1F)c1cncc(CCNCCc2nc3c(F)cccc3[nH]2)c1] |
| 247 | 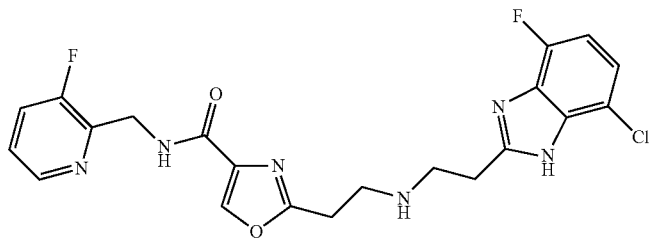 [SMILES: O=C(NCc1ncccc1F)c1coc(CCNCCc2nc3c(F)ccc(Cl)c3[nH]2)n1] |

| Exp No. | Compound |
|---|---|
| 248 | 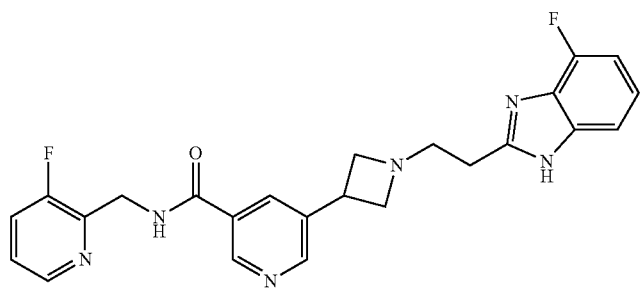 [SMILES: O=C(NCc1ncccc1F)c1cncc(C2CN(CCc3nc4c(F)cccc4[nH]3)C2)c1] |
| 249 | 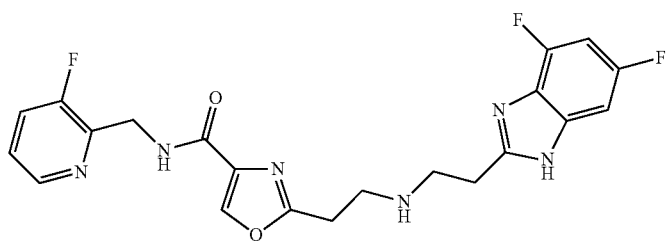 [SMILES: O=C(NCc1ncccc1F)c1coc(CCNCCc2nc3c(F)cc(F)cc3[nH]2)n1] |
| 250 | 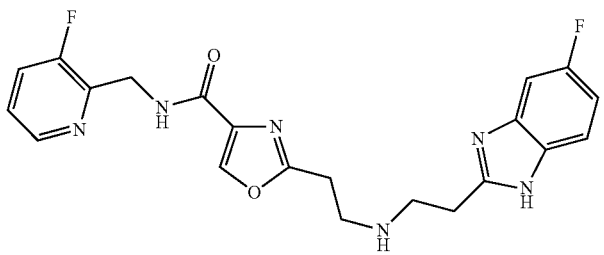 [SMILES: O=C(NCc1ncccc1F)c1coc(CCNCCc2nc3cc(F)ccc3[nH]2)n1] |
| 251 | 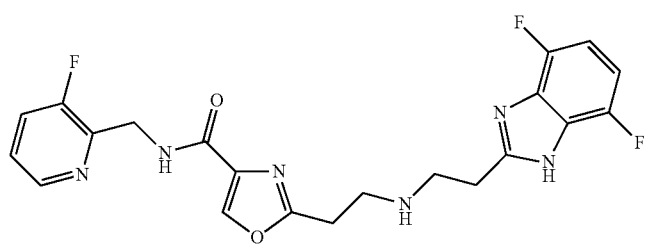 [SMILES: O=C(NCc1ncccc1F)c1coc(CCNCCc2nc3c(F)ccc(F)c3[nH]2)n1] |
| 252 | 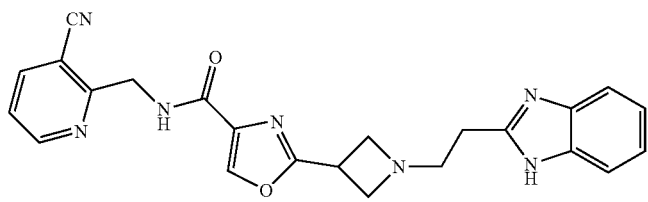 [SMILES: N#Cc1cccnc1CNC(=O)c1coc(C2CN(CCc3nc4ccccc4[nH]3)C2)n1] |
| 253 | 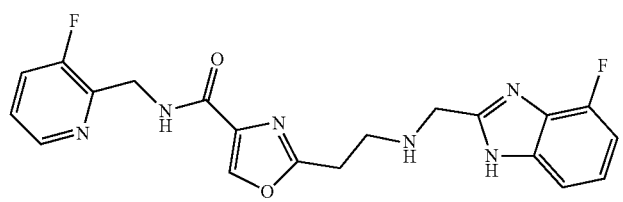 [SMILES: O=C(NCc1ncccc1F)c1coc(CCNCc2nc3c(F)cccc3[nH]2)n1] |

| Exp No. | Compound |
|---|---|
| 255 | 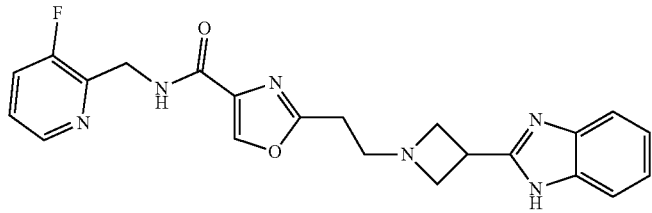 [SMILES: O=C(NCc1ncccc1F)c1coc(CCN2CC(c3nc4ccccc4[nH]3)C2)n1] |
| 256 | 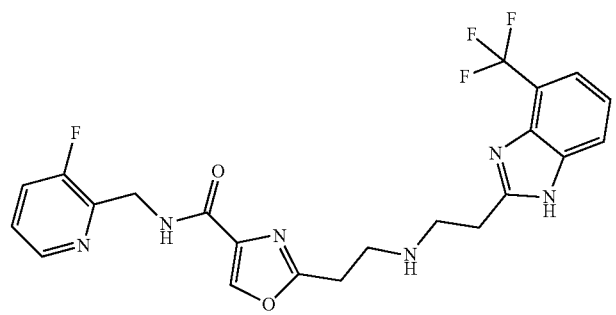 [SMILES: O=C(NCc1ncccc1F)c1coc(CCNCCc2nc3c(C(F)(F)F)cccc3[nH]2)n1] |
| 257 | 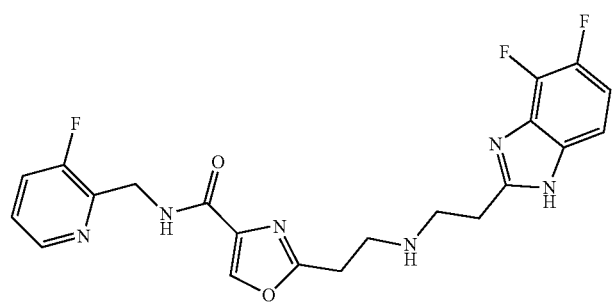 [SMILES: O=C(NCc1ncccc1F)c1coc(CCNCCc2nc3c(F)c(F)ccc3[nH]2)n1] |
| 258 | 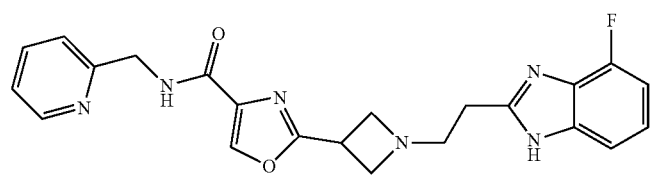 [SMILES: O=C(NCc1ccccn1)c1coc(C2CN(CCc3nc4c(F)cccc4[nH]3)C2)n1] |
| 261 | 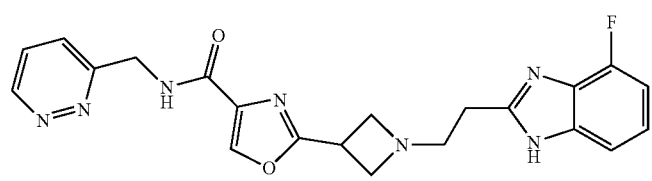 [SMILES: O=C(NCc1cccnn1)c1coc(C2CN(CCc3nc4c(F)cccc4[nH]3)C2)n1] |
| 262 | 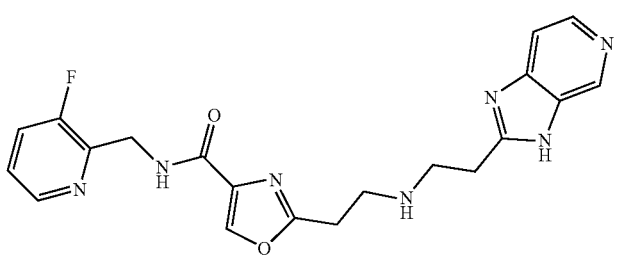 [SMILES: O=C(NCc1ncccc1F)c1coc(CCNCCc2nc3ccncc3[nH]2)n1] |

| Exp No. | Compound |
|---|---|
| 263 | 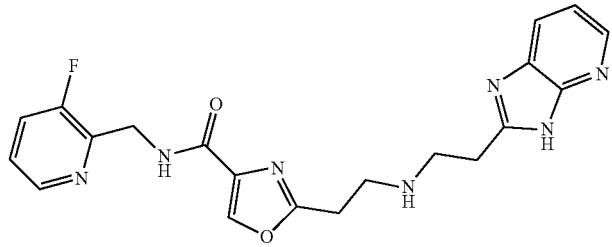 [SMILES: O=C(NCc1ncccc1F)c1coc(CCNCCc2nc3cccnc3[nH]2)n1] |
| 264 | 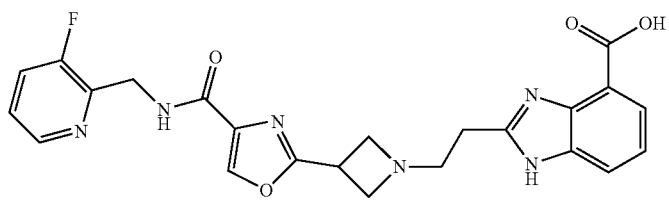 [SMILES: O=C(NCc1ncccc1F)c1coc(C2CN(CCc3nc4c(C(=O)O)cccc4[nH]3)C2)n1] |
| 265 | 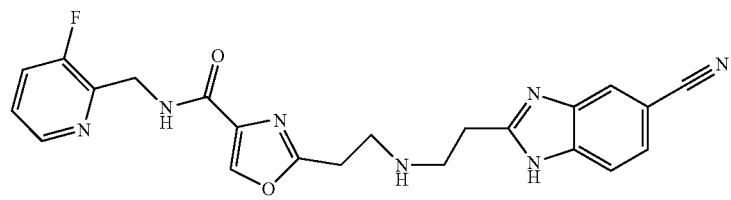 [SMILES: N#Cc1ccc2[nH]c(CCNCCc3nc(C(=O)NCc4ncccc4F)co3)nc2c1] |
| 266 | 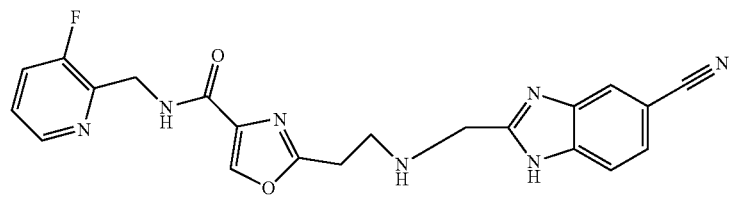 [SMILES: N#Cc1ccc2[nH]c(CNCCc3nc(C(=O)NCc4ncccc4F)co3)nc2c1] |
| 267 | 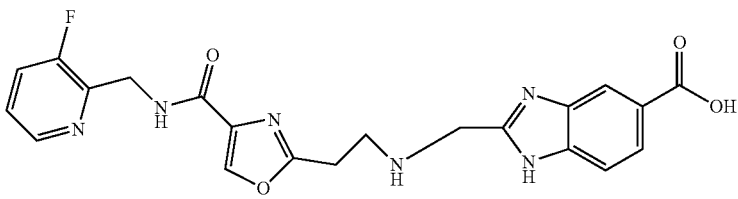 [SMILES: O=C(O)c1ccc2[nH]c(CNCCc3nc(C(=O)NCc4ncccc4F)co3)nc2c1] |
| 268 | 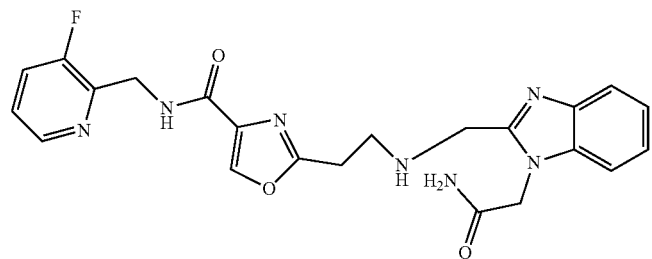 [SMILES: NC(=O)Cn1c(CNCCc2nc(C(=O)NCc3ncccc3F)co2)nc2ccccc21] |

-continued
| Exp No. | Compound |
|---|---|
| 269 | 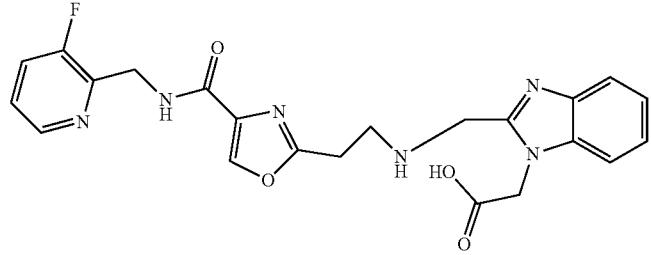 [SMILES: O=C(O)Cn1c(CNCCc2nc(C(=O)NCc3ncccc3F)co2)nc2ccccc21] |
| 270 | 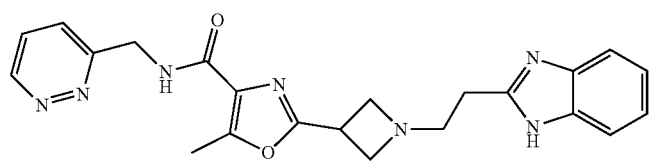 [SMILES: Cc1oc(C2CN(CCc3nc4ccccc4[nH]3)C2)nc1C(=O)NCc1cccnn1] |
| 271 | 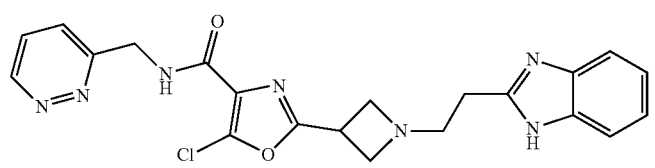 [SMILES: O=C(NCc1cccnn1)c1nc(C2CN(CCc3nc4ccccc4[nH]3)C2)oc1Cl] |
| 272 | 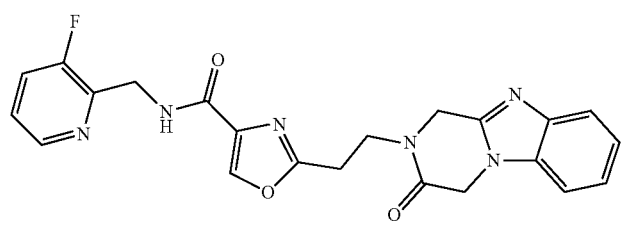 [SMILES: O=C(NCc1ncccc1F)c1coc(CCN2Cc3nc4ccccc4n3CC2=O)n1] |
| 273 | 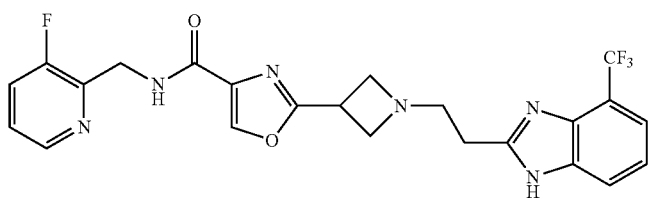 [SMILES: O=C(NCc1ncccc1F)c1coc(C2CN(CCc3nc4c(C(F)(F)F)cccc4[nH]3)C2)n1] |
| 274 | 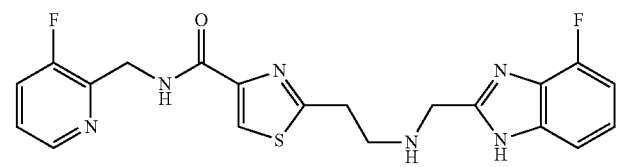 [SMILES: O=C(NCc1ncccc1F)c1csc(CCNCc2nc3c(F)cccc3[nH]2)n1] |
| 275 | 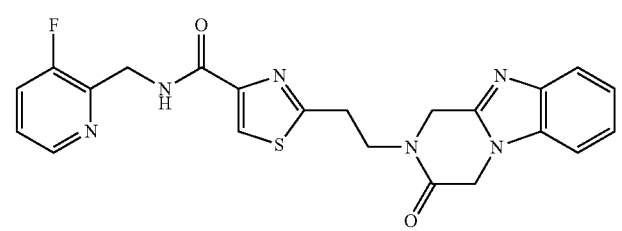 [SMILES: O=C(NCc1ncccc1F)c1csc(CCN2Cc3nc4ccccc4n3CC2=O)n1] |

| Exp No. | Compound |
|---|---|
| 276 | 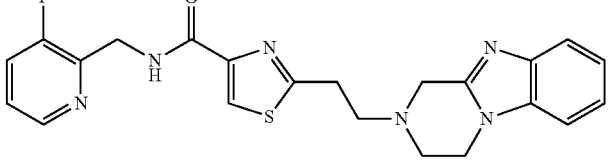 |
| 277 | 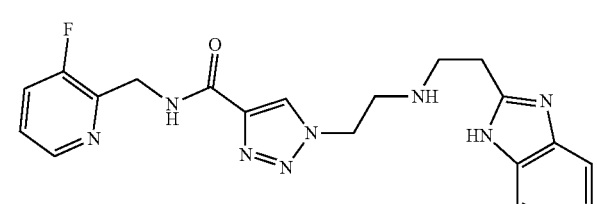 |
| 278 | 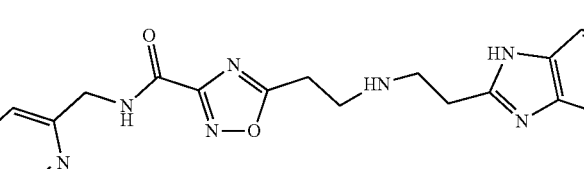 |
| 279 | 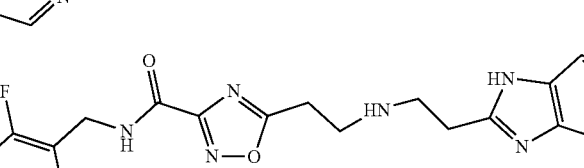 | or pharmaceutically acceptable salts thereof.

More preferred are the compounds according to formula (I), wherein Ar is an optionally substituted, optionally fused bicyclic heteroaryl, such as Examples Nos.:
1, 5, 7, 12, 13, 14, 15, 16, 17, 18, 19, 21, 22, 23, 24, 25, 26, 28, 29, 30, 31, 32, 33, 34, 35, 36, 37, 38, 39, 40, 41, 42, 43, 44, 45, 46, 47, 48, 49, 50, 51, 52, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 131, 132, 133, 134, 135, 136, 137, 138, 139, 140, 141, 142, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 204, 205, 206, 207, 208, 209, 210, 211, 212, 213, 214, 215, 218, 219, 220, 221, 222, 223, 224, 226, 227, 228, 229, 230, 231, 232, 233, 235, 236, 237, 239, 240, 241, 242, 243, 244, 245, 246, 247, 248, 249, 250, 251, 252, 253, 255, 256, 257, 258, 261, 262, 263, 264, 265, 266, 267, 268, 269, 270, 271, 272, 273, 274, 275, 276, 277, 278 and 279.

More preferred are the compounds according to formula (I), wherein Ar is an optionally substituted, optionally fused bicyclic heteroaryl and one of $R^1/R^2$ is heteroaryl or an alkyl substituted with an optionally substituted heteroaryl or a heterocyclyl group, such as Examples Nos.:
12, 16, 35, 36, 37, 38, 39, 40, 41, 42, 43, 44, 45, 46, 47, 48, 49, 54, 55, 56, 57, 58, 59, 60, 61, 64, 76, 79, 80, 81, 82, 83, 84, 85, 86, 87, 88, 89, 90, 91, 92, 93, 94, 95, 96, 97, 98, 99, 100, 101, 102, 103, 104, 105, 106, 108, 109, 110, 111, 112, 113, 114, 115, 116, 117, 118, 119, 120, 121, 122, 123, 124, 125, 126, 127, 128, 129, 131, 132, 133, 134, 135, 136, 137, 138, 139, 140, 141, 142, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 204, 205, 206, 207, 208, 209, 210, 211, 212, 213, 214, 215, 218, 219, 220, 221, 222, 223, 224, 226, 227, 228, 229, 230, 231, 232, 233, 235, 236, 237, 239, 240, 241, 242, 243, 244, 245, 246, 247, 248, 249, 250, 251, 252, 253, 255, 256, 257, 258, 261, 262, 263, 264, 265, 266, 267, 268, 269, 270, 271, 272, 273, 274, 275, 276, 277, 278 and 279.

More preferred are the compounds according to formula (I), wherein Ar is an optionally substituted, optionally fused bicyclic heteroaryl and one of $R^1/R^2$ is alkyl substituted with a 6-membered optionally substituted heteroaryl group, such as Examples Nos.:
12, 35, 36, 37, 38, 39, 40, 42, 43, 44, 45, 46, 47, 48, 49, 54, 55, 56, 57, 58, 59, 61, 76, 79, 80, 81, 82, 83, 87, 89, 90, 92, 93, 94, 96, 97, 98, 99, 101, 102, 103, 104, 105, 106, 108, 109, 110, 111, 112, 113, 114, 115, 116, 117, 118, 119, 120, 121, 122, 123, 124, 125, 126, 127, 128, 129, 131, 132, 133, 134, 135, 136, 137, 138, 139, 140, 141, 142, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 186, 187, 188, 189, 190, 191, 192, 193, 194, 195, 196, 197, 198, 199, 200, 201, 202, 204, 205, 206, 207, 208, 209, 210, 211, 212, 213, 214, 215, 218, 219, 220, 221, 222, 223, 224, 226, 227, 228, 229, 230, 231, 232, 233, 235, 236, 237, 239, 240, 241, 242, 243, 244, 245, 246, 247, 248, 249, 250, 251, 252, 253, 255, 256, 257, 258, 261, 262, 263, 264, 265, 266, 267, 268, 269, 270, 271, 272, 273, 274, 275, 276, 277, 278 and 279.

More preferred are the compounds according to formula (I), wherein Ar is an optionally substituted, optionally fused bicyclic heteroaryl and one of $R^1/R^2$ is alkyl substituted with an optionally substituted pyridinyl-group, such as Examples Nos.:
12, 35, 36, 37, 38, 39, 40, 42, 43, 45, 47, 48, 49, 54, 55, 56, 57, 58, 59, 76, 79, 80, 81, 82, 83, 89, 90, 92, 94, 96, 97, 98, 99, 101, 102, 103, 104, 105, 106, 108, 109, 110, 111, 112, 113, 114, 115, 116, 117, 118, 119, 120, 121, 123, 124, 125, 126, 127, 128, 131, 132, 133, 134, 135, 136, 137, 138, 139, 140, 141, 142, 144, 145, 146, 147, 148, 149, 150, 151, 152, 153, 154, 156, 157, 158, 159, 160, 162, 163, 164, 165, 166, 167, 168, 169, 170, 171, 172, 173, 176, 177, 179, 180, 181, 184, 186, 187, 189, 190, 191, 192, 193, 194, 195, 196, 197, 198, 199, 200, 201, 202, 204, 205, 206, 207, 208, 209, 210, 211, 212, 213, 214, 215, 218, 219, 220, 221, 222, 223, 224, 226, 227, 228, 229, 230, 231, 232, 233, 235, 236, 237, 239, 240, 241, 242, 243, 245, 246, 247, 248, 249, 250, 251, 252, 253, 255, 256, 257, 258, 262, 263, 264, 265, 266, 267, 268, 269, 272, 273, 274, 275, 276, 277, 278 and 279.

More preferred are the compounds according to formula (I), wherein Ar is an optionally substituted, optionally fused bicyclic heteroaryl and one of $R^1/R^2$ is alkyl substituted with an optionally substituted pyridinyl-group and Z is an optionally substituted, optionally fused 5-membered heteroaryl group, such as Examples Nos.:
12, 35, 36, 37, 38, 39, 40, 42, 43, 45, 47, 48, 49, 54, 55, 56, 57, 58, 59, 76, 79, 80, 81, 82, 83, 89, 90, 92, 94, 96, 97, 98, 99, 110, 102, 103, 104, 105, 106, 108, 109, 110, 111, 112, 113, 114, 115, 116, 117, 118, 119, 120, 121, 123, 124 125, 126, 127, 128, 131, 132, 134, 135, 136, 137, 138, 139, 140, 141, 142, 144, 145, 148, 150, 151, 152, 153, 154, 156, 157, 158, 159, 160, 162, 163, 164, 165, 166, 167, 169, 170, 171, 173, 176, 177, 179, 180, 181, 184, 186, 187, 189, 191, 192, 193, 194, 195, 196, 198, 199, 205, 206, 207, 208, 209, 210, 211, 212, 213, 214, 215, 218, 219, 220, 223, 226, 227, 228, 230, 231, 233, 236, 239, 242, 243, 247, 249, 250, 251, 252, 253, 255, 256, 257, 258, 262, 263, 264, 265, 266, 267, 268, 269, 272, 273, 274, 275, 276, 277, 278 and 279.

More preferred are the compounds according to formula (I), wherein Ar is an optionally substituted, optionally fused bicyclic heteroaryl and one of $R^1/R^2$ is alkyl substituted with an optionally substituted pyridinyl-group and Z is an optionally substituted, optionally fused 5-membered heteroaryl group, selected from an oxazolyl-group such as Examples Nos.:
126, 127, 128, 137, 141, 171, 173, 206, 207, 208, 223, 226, 227, 228, 230, 233, 239, 247, 249, 250, 251, 252, 253, 255, 256, 257, 258, 262, 263, 264, 265, 266, 267, 268, 269, 272, 273;

and/or selected from a thiazolyl-group such as Examples Nos.:
12, 35, 36, 37, 38, 39, 40, 42, 43, 45, 47, 54, 55, 56, 57, 58, 59, 76, 79, 80, 81, 82, 83, 89, 90, 94, 96, 97, 98, 99, 101, 102, 103, 104, 105, 106, 108, 110, 112, 113, 114, 115, 116, 118, 119, 120, 121, 123, 124, 125, 134, 135, 139, 140, 148, 151, 152, 154, 157, 158, 159, 160, 163, 164, 165, 166, 176, 177, 179, 180, 184, 186, 189, 193, 194, 195, 196, 199, 209, 211, 212, 213, 214, 215, 218, 231, 236, 242, 243, 274, 275, 276;

and/or selected from a triazolyl-group such as Examples Nos.:
169, 170, 181, 277.

Further, compounds with one of $R^1/R^2$ being a fluorine-substituted pyridinyl-group are preferred, such as as Examples Nos.:
40, 77, 94, 112, 113, 114, 115, 118, 119, 120, 121, 125, 126, 127, 128, 134, 135, 139, 140, 148, 151, 152, 154, 157, 163, 164, 165, 166, 169, 176, 177, 179, 180, 181, 186, 193, 196, 199, 206, 208, 209, 211, 212, 213, 214, 218, 223, 226, 227, 228, 230, 231, 233, 239, 242, 243, 247, 249, 250, 251, 253, 255, 256, 257, 262, 263, 264, 265, 266, 267, 268, 269, 272, 273, 274, 275, 276, 277 and 279.

Pharmaceutically acceptable salts of the compounds according to the invention include, for example, salts with suitable anions, such as carboxylates, sulfonates, sulfates, chlorides, bromides, iodides, phosphates, tartrates, methane sulfonates, hydroxyethane sulfonates, glycinates, maleates, propionates, fumarates, toluene sulfonates, benzene sulfonates, trifluoroacetates, naphthalenedisulfonates-1,5, salicylates, benzoates, lactates, salts of malic acid, salts of 3-hydroxy-2-naphthoic acid-2, citrates and acetates.

Pharmaceutically acceptable salts of the compounds according to the invention further include, for example, salts with suitable pharmaceutically acceptable bases, such as, for example, salts with alkaline or alkaline-earth hydroxides, such as NaOH, KOH, $Ca(OH)_2$, $Mg(OH)_2$ etc., amine compounds such as ethylamine, diethylamine, triethylamine, ethyldiisopropylamine, ethanolamine, diethanolamine, triethanolamine, methylglucamine, dicyclohexylamine, dimethylaminoethanol, procaine, dibenzylamine, N-methylmorpholine, arginine, lysine, ethylenediamine, N-methylpiperidin, 2-amino-2-methyl-propanol-(1), 2-amino-2-methyl-propandiol-(1,3), 2-amino-2-hydroxyl-methyl-propandiol-(1,3) (TRIS) etc.

Depending on their structure, the compounds according to the invention may exist in stereoisomeric forms (enantiomers, diastereomers) in the presence of asymmetric carbon atoms. The invention therefore includes the use of the enantiomers or diastereomers and the respective mixtures thereof. The pure-enantiomer forms may optionally be obtained by conventional processes of optical resolution, such as by fractional crystallisation of diastereomers thereof by reaction with optically active compounds. Since the compounds according to the invention may occur in tautomeric forms, the present invention covers the use of all tautomeric forms.

The compounds provided according to the invention may be present as mixtures of various possible isomeric forms, in particular of stereoisomers such as, for example, E- and Z-, syn and anti, as well as optical isomers. The E-isomers and also the Z-isomers as well as the optical isomers and any mixtures of these isomers are claimed.

The novel compounds of the present invention can be present in an amorphous, crystalline or partially crystalline form or they may also be present exist as hydrates.

The compounds according to formula (I) and its further embodiments, as defined above, have surprisingly been found to act as ferroportin inhibitors and are thus suitable for the use as ferroportin inhibitors.

As already explained above, ferroportin is the iron transport protein, which is responsible for the uptake of the released iron via the intestine and its transfer into the blood circulation, thereby conveying the iron to the appropriate tissues and organs. Inactivation or inhibition of the ferroportin disables the export of the iron, thereby reducing the absorption of iron in the intestine. Ferroportin inhibition in the sense of the present invention therefore includes the inhibition of iron transport from the cells into the blood circulation and the inhibition of iron absorption in the intestine. Therein, the inhibition of iron transport and/or iron reflux may be effected by different ways of mechanism, comprising for example inhibition of iron transport activity of ferroportin and thus inhibition of iron reflux, triggering internalization, degradation and/or reduction of ferroportin, administering hepcidin agonists, i.e. compounds which compete with hepcidin or by compounds, which inhibit the binding of hepcidin to ferroportin. Ferroportin inhibition may be determined by measuring the inhibition of ferroportin mediated iron transport activity in an iron response assay (BLAzer-Assay), as described in more detail in the Examples below. Further, ferroportin inhibition may be determined by measuring ferroportin internalization and/or degradation in the Ferroportin Internalization and Degradation Assay (FACS) or by examining the Ferroportin Ubiquitination and Degradation, each as described in more detail in the Examples below. Further, ferroportin inhibition may be determined by measuring the activity as an hepcidin agonist, for example by determining the Hepcidin binding capacity to ferroportin in the Hepcidin Internalization Assay (J774), as described in more detail in the Examples below. Further, ferroportin inhibition may be determined by confirming the inhibition of hepcidin binding to ferroportin, for example in the Biophysical Ferroportin-Hepcidin Binding Assay (Hep Bind FP), as described in more detail in the Examples below.

Further, ferroportin inhibition may be determined by determining the activity of a compound regarding its ability to block iron export via ferroportin, for example with a test for measuring inhibition of iron efflux, as described in more detail in the Examples below.

Ferroportin inhibition in the sense of the present invention can thus in particular be defined by exhibiting a ferroportin inhibiting activity in at least one of the aforementioned test methods, shown in particular by:

Inhibition of ferroportin mediated iron transport activity in an iron response assay (Blazer Assay): $IC_{50}$ value [µm] of not more than 100 (≤100), preferably not more than 50 (≤50), more preferably below 50 (<50).

Ferroportin Internalization and Degradation Assay (FACS): $EC_{50}$ value [µm] of not more than 100 (≤100), preferably not more than 50 (≤50), more preferably below 50 (<50).

Ferroportin Ubiquitination and Degradation: visually inspected effect in Western blots of "+ comparable to hepcidin", "+/− intermediate effect" and "+/+/− stronger intermediate effect", preferred is an effect "+" or "+/+/−", most preferred is an effect "+".

Hepcidin Internalization Assay (J774): $IC_{50}$ value of not more than 100 (≤100), preferably not more than 50 (≤50), more preferably below 50 (<50).

Biophysical Ferroportin-Hepcidin Binding Assay: $IC_{50}$ value of not more than 100 (≤100), preferably not more than 50 (≤50), more preferably below 50 (<50).

Inhibition of Iron Efflux: $IC_{50}$ value of not more than 100 (≤100), preferably not more than 50 (≤50), more preferably below 50 (<50).

Ferroportin inhibition may further be determined inin vivo models, as described in more detail in the Examples below. Suitable in vivo models may comprise, for example, examination of hypoferremia in naïve mice via measurement of serum iron reduction; examination of prevention of iron absorption in anemic rats via measurement of serum iron inhibition; examination of correction of hyperferremia in beta2-microglobulin deficient mice via measurement of serum iron reduction; examination of prevention of iron overload in beta2-microglobulin deficient mice via measurement of total iron in spleen or liver; examination of improvement of anemia, ineffective erythropoiesis and iron overload in a mouse model of β-thalassemia *intermedia*.

The activity of the compounds of the present invention as ferroportin inhibitors can in particular be determined by the methods as described in the Examples below.

As further already explained above, ferroportin inhibition may for example be effected by hepcidin, which is thus an essential regulating factor of iron absorption, inhibiting ferroportin and thus blocking iron transport from the cells into the blood circulation and iron absorption. It has further surprisingly been found that several of the compounds as defined herein act as hepcidin mimetics or hepcidin agonists, which is also included by ferroportin inhibition in the sense of the present invention.

Accordingly, the compounds as defined in the present invention are also suitable for use in the inhibition of iron transport from the cells into the blood circulation and the inhibition of iron absorption in the intestine, as well as for the use as hepcidin mimetics or hepcidin agonists.

Due to the activity of the compounds as defined herein as ferroportin inhibitors, the compounds of the present invention are further particularly suitable for the use in the inhibition of iron transport mediated by ferroportin and thereby for the use in the prophylaxis and/or treatment of iron metabolism disorders leading to increased iron levels, of diseases related to or caused by increased iron levels, increased iron absorption or iron overload, such as in particular of tissue iron overload, of diseases associated with ineffective erythropoiesis, or of diseases caused by reduced levels of hepcidin. Further, the compounds of the present invention are suitable for the use in an adjunctive therapy by limiting the amount of iron available to pathogenic microorganisms, such as the bacterium *Vibrio vulnificus*, thereby preventing or treating infections caused by said pathogenic microorganisms.

Therein, diseases being associated with, being related to, being caused by or leading to increased iron levels, increased iron absorption, iron overload (e.g. tissue iron overload) or ineffective erythropoiesis comprise thalassemia, hemoglobinopathy, such as hemoglobin E disease (HbE), hemoglobin H disease (HbH), haemochromatosis, hemolytic anemia, such as sickle cell anemia (sickle cell disease) and congenital dyserythropoietic anemia.

Diseases being associated with, being related to, being caused by or leading to increased iron levels, increased iron absorption, iron overload (e.g. tissue iron overload) further comprise neurodegenerative diseases, such as for example Alzheimer's disease and Parkinson's disease, wherein the compounds are considered to be effective by limiting the deposition or increase of iron in tissue or cells.

The compounds of the present invention are further suitable for the use in the prophylaxis and/or treatment of formation of radicals, reactive oxygen species (ROS) and oxidative stress caused by excess iron or iron overload as well as in the prophylaxis and/or treatment of cardiac, liver and endocrine damage caused by excess iron or iron overload, and further in the prophylaxis and/or treatment of inflammation triggered by excess iron or iron overload.

Diseases associated with ineffective erythropoiesis comprise in particular myelodysplastic syndromes (MDS, myelodysplasia) and polycythemia vera as well as congenital dyserythropoietic anemia.

Further diseases, disorders and/or diseased conditions comprise iron overload caused by mutations in genes involved in sensing the systemic iron stores, such as hepcidin (Hamp1), hemochromatosis protein (HFE), hemojuvelin (HJV) and transferrin receptor 2 (TFR2), such as in particular diseases related to HFE and HJV gene mutations, chronic hemolysis associated diseases, sickle cell diseases, red cell membrane disorders, Glucose-6-phosphate dehydrogenase deficiency (G6PD deficiency), erythropoietic *porphyria*, Friedrich's Ataxia, as well as subgroups of iron overload such as transfusional iron overload, iron intoxication, pulmonary hemosiderosis, osteopenia, insulin resistense, African iron overload, Hallervordan Spatz disease, hyperferritinemia, ceruloplasmin deficiency, neonatal hemochromatosis and red blood cell disorders comprising thalassemia, including alpha thalassemia, beta thalassemia and delta thalassemia, thalassemia *intermedia*, sickle cell disease and myelodyplastic syndrome.

Further disease and/or disorders and/or diseased conditions associated with elevated iron levels include, but are not limited to, diseases with elevated iron level, comprising ataxia, Friedrich's ataxia, age-related macular degeneration, age-related cataract, age-related retinal diseases and neurodegenrative disease, such as pantothenate kinase-associated neurodegeneration, restless leg syndrom and Huntington's disease.

The compounds of the present invention my further be suitable for the use in the prophylaxis and treatment of diseases caused by a lack of hepcidin.

In view thereof a further object of the present invention relates to a medicament containing one or more of the compounds as defined above, such as in particular a medicament for the prophylaxis and treatment in any of the indications, states, disorders or diseases as defined above.

A further object of the present invention relates to pharmaceutical compositions and medicaments comprising one or more of the compounds according to the invention as defined above as well as optionally one or more pharmacologically acceptable carriers and/or auxiliary substances and/or solvents. A further object of the present invention relates to pharmaceutical compositions and medicaments comprising one or more of the compounds according to the invention as defined above as well as optionally one or more further pharmaceutically effective compounds. The said pharmaceutical compositions contain, for example up to 99 weight-% or up to 90 weight-% or up to 80 weight-% or or up to 70 weight-% of the compounds of the invention, the remainder being each formed by pharmacologically acceptable carriers and/or auxiliaries and/or solvents and/or optionally further pharmaceutically active compounds.

Therein, the pharmaceutically acceptable carriers, auxiliary substances or solvents are common pharmaceutical carriers, auxiliary substances or solvents, including various organic or inorganic carrier and/or auxiliary materials as they are customarily used for pharmaceutical purposes, in particular for solid medicament formulations. Examples include excipients, such as saccharose, starch, mannitol, sorbitol, lactose, glucose, cellulose, talcum, calcium phosphate, calcium carbonate; binding agents, such as cellulose, methylcellulose, hydroxypropylcellulose, polypropyl pyrrolidone, gelatine, gum arabic, polyethylene glycol, saccharose, starch; disintegrating agents, such as starch, hydrolyzed starch, carboxymethylcellulose, calcium salt of carboxymethylcellulose, hydroxypropyl starch, sodium glycol starch, sodium bicarbonate, calcium phosphate, calcium citrate; lubricants, such as magnesium stearate, talcum, sodium laurylsulfate; flavorants, such as citric acid, menthol, glycin, orange powder; preserving agents, such as sodium benzoate, sodium bisulfite, paraben (for example methylparaben, ethylparaben, propylparaben, butylparaben); stabilizers, such as citric acid, sodium citrate, acetic acid and multicarboxylic acids from the titriplex series, such as, for example, diethylenetriaminepentaacetic acid (DTPA); suspending agents, such as methycellulose, polyvinyl pyrrolidone, aluminum stearate; dispersing agents; diluting agents, such as water, organic solvents; waxes, fats and oils, such as beeswax, cocoa butter; polyethylene glycol; white petrolatum; etc.

Liquid medicament formulations, such as solutions, suspensions and gels usually contain liquid carrier, such as water and/or pharmaceutically acceptable organic solvents. Furthermore, such liquid formulations can also contain pH-adjusting agents, emulsifiers or dispersing agents, buffering agents, preserving agents, wetting agents, gelatinizing agents (for example methylcellulose), dyes and/or flavouring agents, for example as defined above. The compositions may be isotonic, that is, they can have the same osmotic pressure as blood. The isotonicity of the composition can be adjusted by using sodium chloride and other pharmaceutically acceptable agents, such as, for example, dextrose, maltose, boric acid, sodium tartrate, propylene glycol and other inorganic or organic soluble substances. The viscosity of the liquid compositions can be adjusted by means of a pharmaceutically acceptable thickening agent, such as methylcellulose. Other suitable thickening agents include, for example, xanthan gum, carboxymethylcellulose, hydroxypropylcellulose, carbomer and the like. The preferred concentration of the thickening agent will depend on the agent selected.

Pharmaceutically acceptable preserving agents can be used in order to increase the storage life of the liquid composition. Benzyl alcohol can be suitable, even though a plurality of preserving agents including, for example, paraben, thimerosal, chlorobutanol and benzalkonium chloride can also be used.

The above-mentioned pharmaceutical compositions are suitable, for example, for intravenous, intraperitoneal, intramuscular, intravaginal, intrabuccal, percutaneous, subcutaneous, mucocutaneous, oral, rectal, transdermal, topical, intradermal, intragasteral or intracutaneous application and are provided, for example, in the form of pills, tablets, enteric-coated tablets, film tablets, layer tablets, sustained release formulations for oral, subcutaneous or cutaneous administration (in particular as a plaster), depot formulations, dragees, suppositories, gels, salves, syrup, granulates, suppositories, emulsions, dispersions, microcapsules, microformulations, nanoformulations, liposomal formulations, capsules, enteric-coated capsules, powders, inhalation powders, microcrystalline formulations, inhalation sprays, epipastics, drops, nose drops, nose sprays, aerosols, ampoules, solutions, juices, suspensions, infusion solutions or injection solutions etc.

A further object of the present invention relates to medicaments or combined preparations containing one or more of the compounds as defined above and at least one further pharmaceutically active compound, such as in particular a compound for the prophylaxis and treatment of iron overload and the associated symptoms, preferably an iron-chelating compound, or a compound for the prophylaxis and treatment of any of the states, disorders or diseases as defined above, such as in particular a pharmaceutically active compound for the prophylaxis and treatment of thalassemia, haemochromatosis, neurodegenerative diseases (such as Alzheimer's disease or Parkinson's disease) and the associated symptoms.

A further object of the present invention relates to the use of the compounds as defined above per se, as in particular compounds according to formula (IIa-b), (IIb), (IIb-a), (IIb-b), (IIb-c), (IIb-d), (IIc), (IIc-a), (IIc-b), (IId), (IId-a), (IId-b), (IIe), and (II f), as well as (Va-1), (Va-2), (Vb-1), (Vb-2), (Vc-1) and (Vc-2), as defined above, in a combination therapy (fixed dose or free dose combinations for sequential use) with one or two other active ingredients (drugs). Such combination therapy comprises co-administration of the compounds of the present invention with the at least one additional pharmaceutically active compound (drug). Combination therapy in a fixed dose combination therapy comprises co-administration of the compounds of the present invention with the at least one additional pharmaceutically active compound in a fixed-dose formulation. Combination therapy in a free dose combination therapy comprises co-administration of the compounds of the present invention and the at least one additional pharmaceutically active compound in free doses of the respective compounds, either by simultaneous administration of the individual compounds or by sequential use of the individual compounds distributed over a time period. The at least one additional pharmaceutically active compound (drug) comprises in particular drugs for reducing iron overload (e.g. Tmprss6-ASO) or iron chelators, in particular curcumin, SSP-004184, Deferitrin, deferasirox, deferoxamine and/or deferiprone, or antioxidants such as n-acetyl cysteine, anti-diabetics such as GLP-1 receptor agonists, antibiotics such as vancomycin (Van) or tobramycin, drugs for the treatment of malaria, anticancer agents, antifungal drugs, drugs for the treatment of neurodegenerative diseases such as Alzheimer's disease and Parkinson's disease (e.g. dopamine agonists such as Levodopa), anti-viral drugs such as interferon-$\alpha$ or ribavirin, or immunosuppressents (cyclosporine A or cyclosporine A derivatives), iron supplements, vitamin supplements, red cell production stimulators, anti-inflammatory biologies, anti-thrombolytics, statins, vasopressors and inotropic compounds.

A further object of the present invention relates to the use of the above combinations for the prophylaxis and/or treatment of diseases caused by a lack of hepcidin or iron metabolism disorders, such as particularly iron overload states such as in particular thalassemia and hemochromatosis and other disorders as described in the present application.

A further object of the present invention relates to the use of the compounds as defined herein per se, as in particular compounds according to formula (IIa-b), (IIb), (IIb-a), (IIb-b), (IIb-c), (IIb-d), (IIc), (IIc-a), (IIc-b), (IId), (IId-a), (IId-b), (IIe), and (II f), as well as (Va-1), (Va-2), (Vb-1), (Vb-2), (Vc-1) and (Vc-2), as defined above, or the hereinabove described combination therapies, in combination with Blood transfusion.

The compounds, medicaments and or combined preparations according to the present invention may be administered orally, parentally, as well as intravenously.

For this purpose, the compounds according to the invention are preferably provided in medicaments or pharmaceutical compositions in the form of pills, tablets, such as enteric-coated tablets, film tablets and layer tablets, sustained release formulations for oral administration, depot formulations, dragees, granulates, emulsions, dispersions, microcapsules, microformulations, nanoformulations, liposomal formulations, capsules, such as enteric-coated capsules, powders, microcrystalline formulations, epipastics, drops, ampoules, solutions, suspensions, infusion solutions or injection solutions or in the form of a preparation suitable for inhalation.

In a preferred embodiment of the invention the compounds are administered in the form of a tablet or capsule, as defined above. These may be present, for example, as acid resistant forms or with pH dependent coatings.

The compounds of the present invention as the active substance can be administered, for example, with a unit dose of 0.001 mg/kg to 500 mg/kg body weight, for example 1 to 4 times a day. However, the dose can be increased or reduced depending on the age, weight, condition of the patient, severity of the disease or type of administration.

Accordingly, a further object of the present invention relates to compounds, medicaments, compositions and combined preparations as defined above for the preparation of a medicament, particularly for the prophylaxis and treatment of any indication, state, disorder or disease as defined above, in particular for oral or parenteral administration.

A further object of the present invention relates to a method for the prophylaxis and treatment as defined above, such as in particular for the prophylaxis and/or treatment of iron metabolism disorders being associated with or leading to increased iron levels and in particular iron overload, diseases related to or caused by increased iron levels or iron overload, iron storage diseases being associated with or leading to increased iron levels, and diseases being associated with ineffective erythropoiesis, the method comprising administering, to a patient (human or animal) in need thereof, a compound, a medicament, a composition or a combined preparation as defined above.

Therein, diseases being associated with, being related to, being caused by or leading to increased iron levels or iron overload are as defined above.

A further object of the present invention relates to the use of the compounds as defined above for the preparation of a medicament, particularly for the prophylaxis and treatment and of any indication, state, disorder or disease as defined above.

A further object of the present invention relates to the compounds as defined above per se, as well as to the use of the compounds as a medicament (in general), such as in particular compounds according to formula (IIa-b), (IIb), (IIb-a), (IIb-b), (IIb-c), (IIb-d), (IIc), (IIc-a), (IIc-b), (IId), (IId-a), (IId-b), (IIe), and (II f), as well as (Va-1), (Va-2), (Vb-1), (Vb-2), (Vc-1) and (Vc-2), as defined above. The invention further very particularly relates to the novel compounds per se, which are selected from the table above, as well as to the use thereof as a medicament (in general), with the exception of Example Compound No. 1.

The compounds according to the invention of general structural formula (I) may basically be obtained by the processes described below and as shown in the general procedures (General Schemes). Accordingly, a further object of the invention is a process for the production of the compounds of general formula (I) as described herein, which includes:

a) reacting compounds of formula (a)

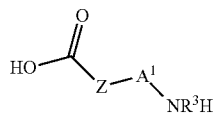
(a)

with compounds of formula (b) NH—R$^1$R$^2$,
to obtain compounds of formula (c)

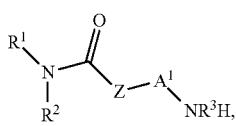
(c)

and
b) further reacting said compounds (c) with compounds of formula (d)

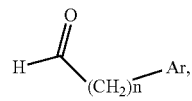
(d)

(d), with n=0 to 7, preferably 0 to 5, preferably 0 to 1 or 2, to obtain compounds of formula (I);

wherein R$^1$, R$^2$, Z, A$^1$, R$^3$ and Ar have the meaning as defined herein. In principle the order of reaction steps is optional. It is further possible to start with the reaction of compounds (a) with compounds (d), followed by reaction with compound (b) to obtain compounds of formula (I). Further several intermediate steps are possible and several intermediate compounds are obtained as shown in the following Examples in detail. Several of the intermediate compounds are also novel compounds, which shall be covered from the present invention.

General Scheme 1

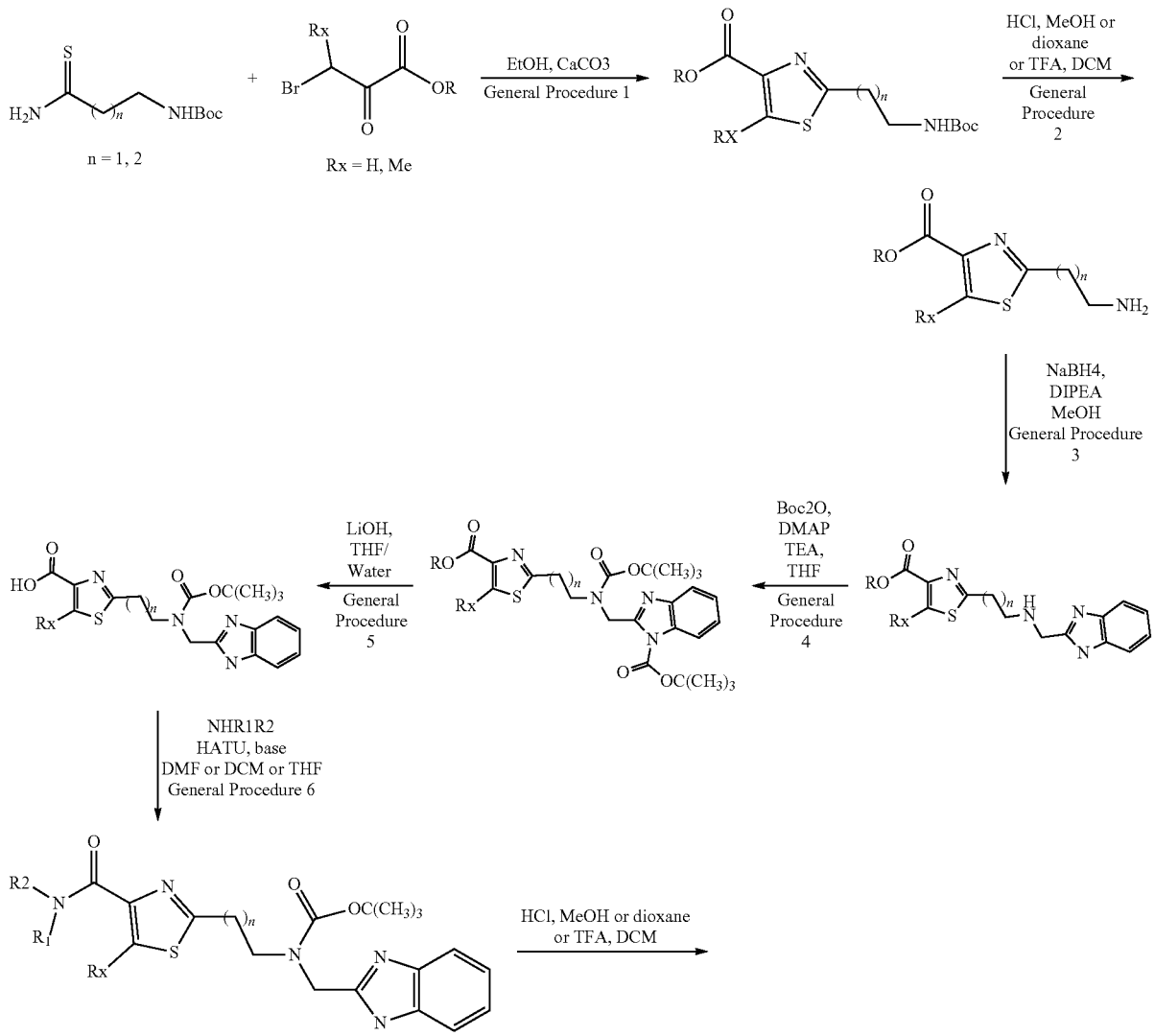

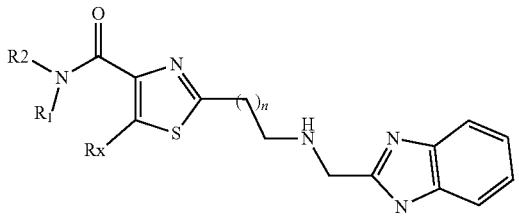
therein Rx indicates an optional substituent to the thiazolyl-heterocycle
n indicates an integer as defined in context with A¹
R in the RO—(C═O)— indicates ...
General Scheme 2
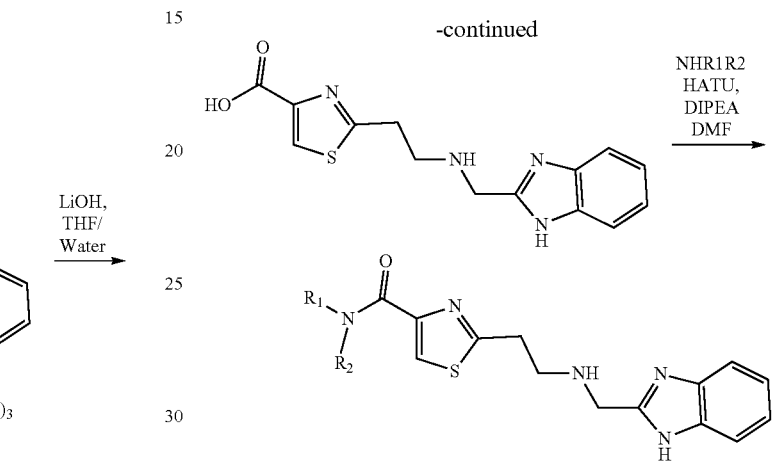
General Scheme 4
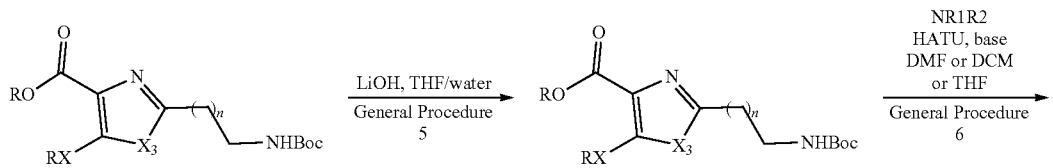
n = 1, 2;
Rx = optional substituent of Z as defined herein
X₃ = S, O
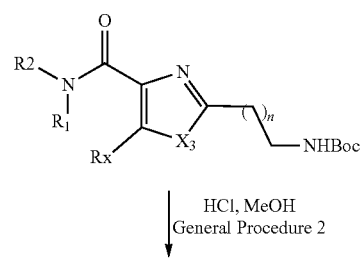
HCl, MeOH
General Procedure 2

153
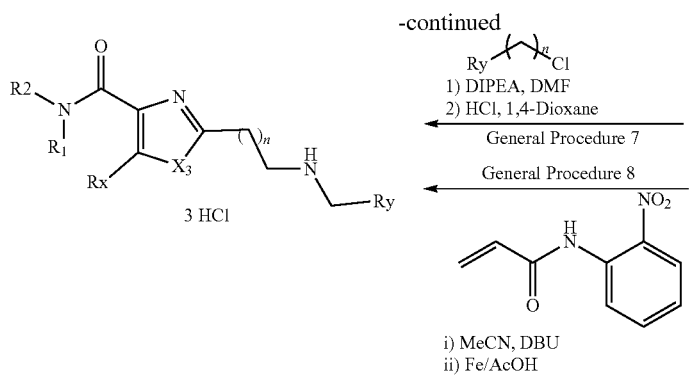
Ry = Ar is defined herein
154
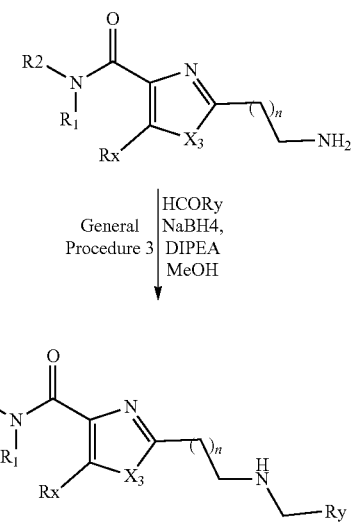
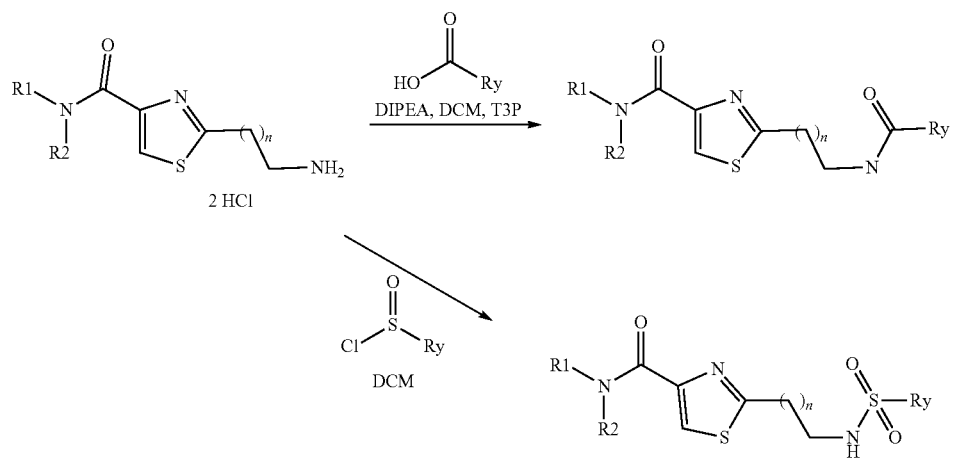
Ry = Ar is defined herein
General Scheme 6
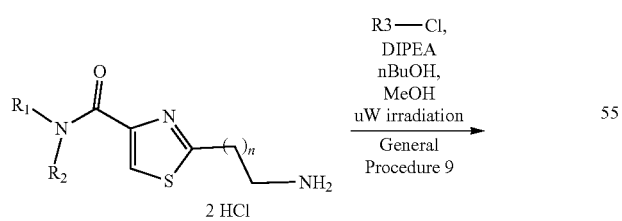
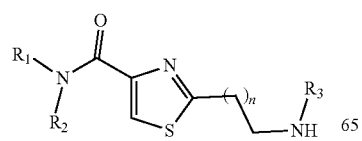

General Scheme 7
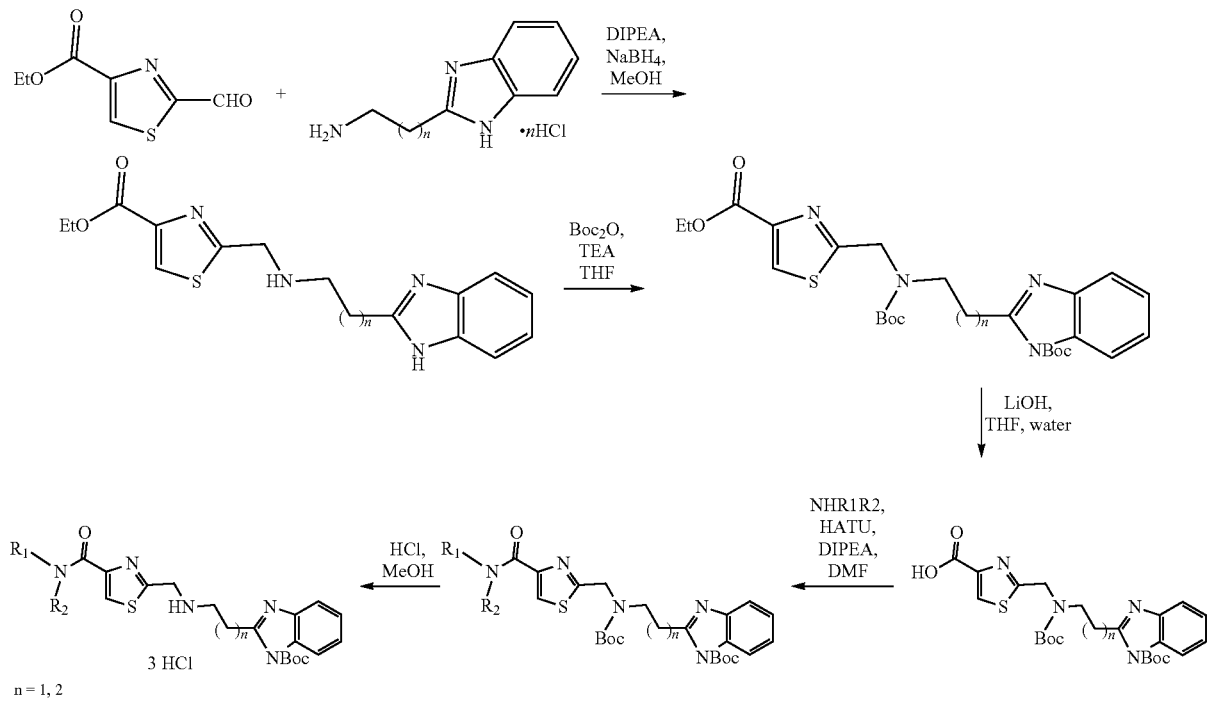
n = 1, 2
General Scheme 8
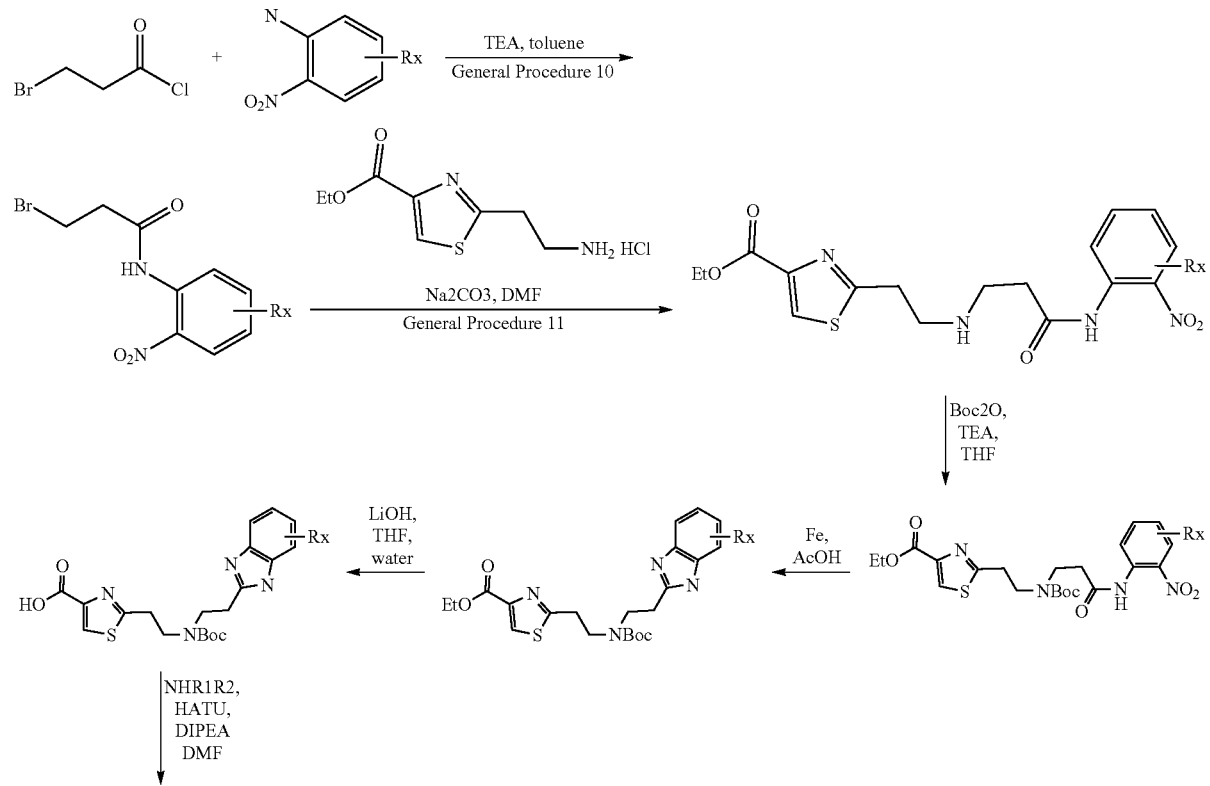

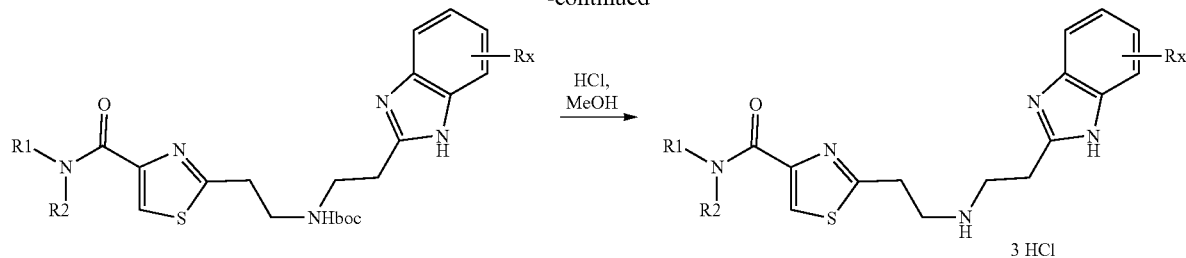
Rx = substituent as defined herein
General Scheme 9
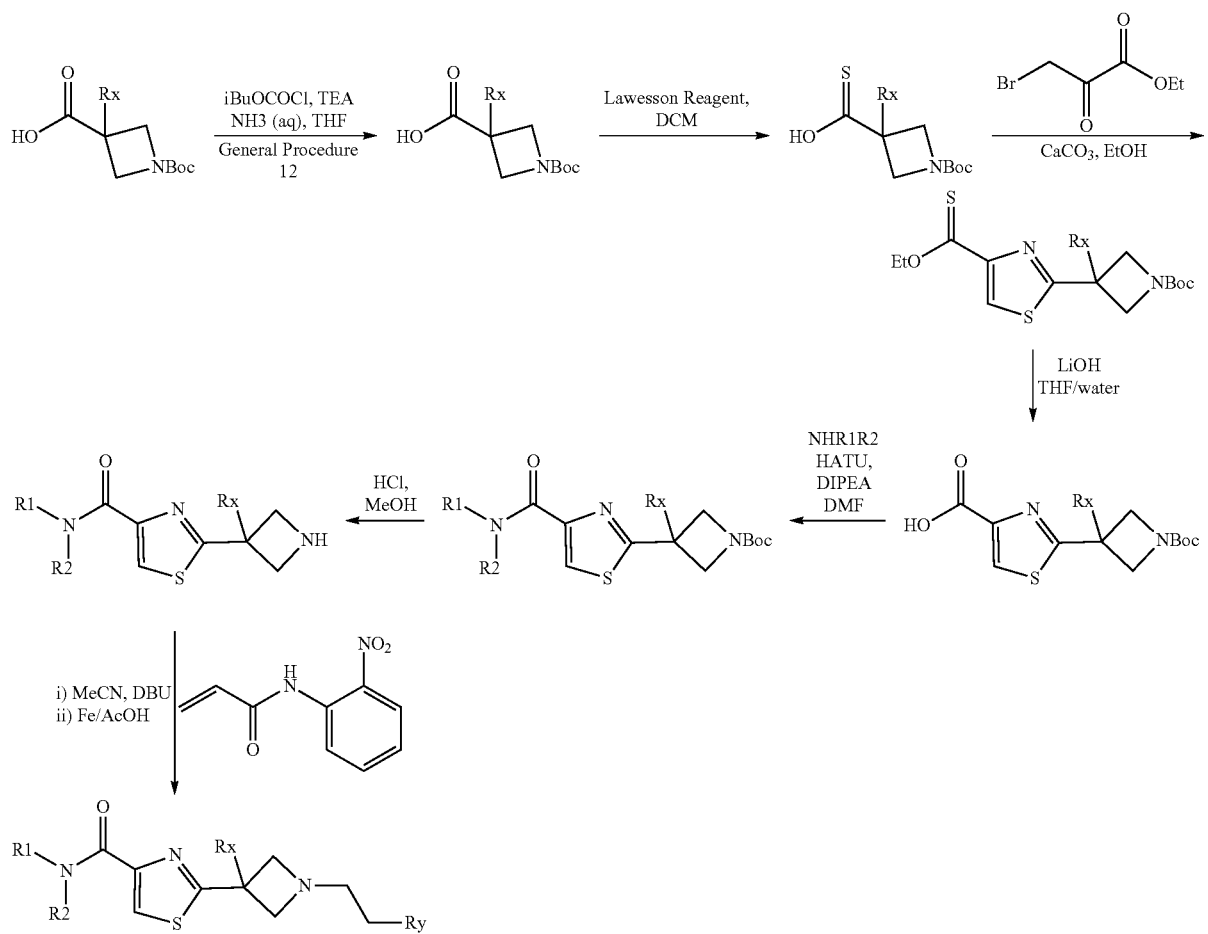
Rx = H, Me
Ry = Ar as defined herein

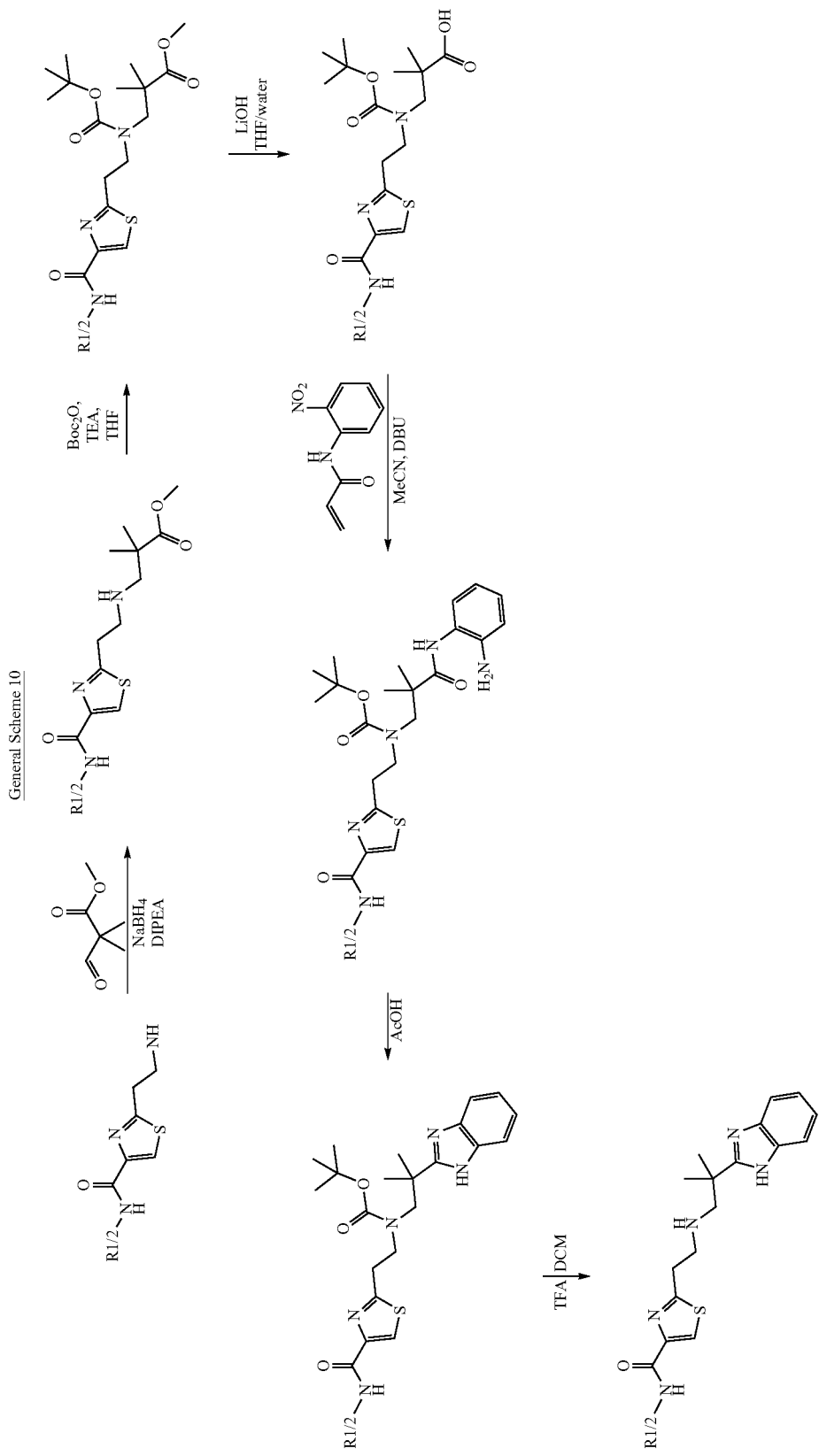

General Scheme 11
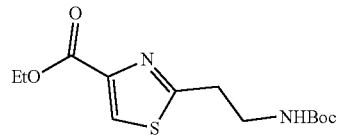
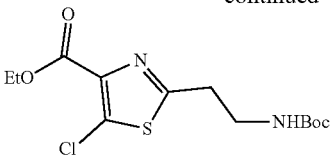
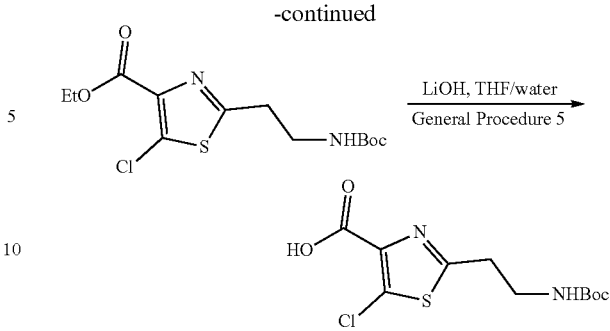
General Scheme 12
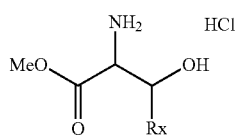
+
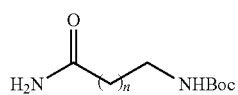
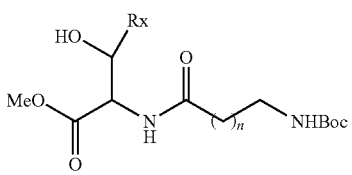
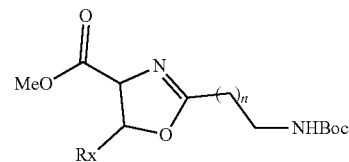
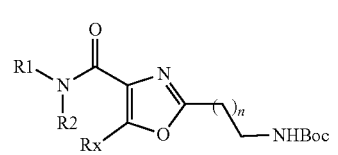
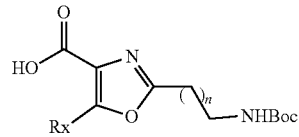
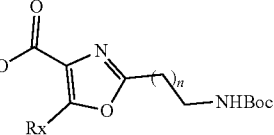
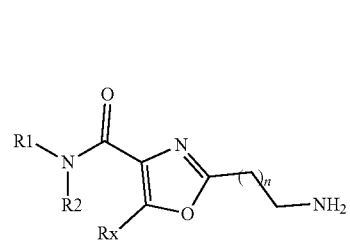
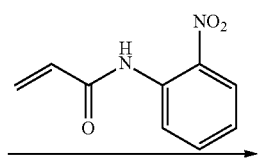
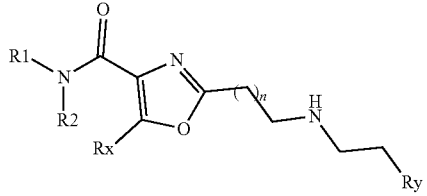
n = 1, 2
Rx = X, Me
Ry = Ar as defined herein General Scheme 13
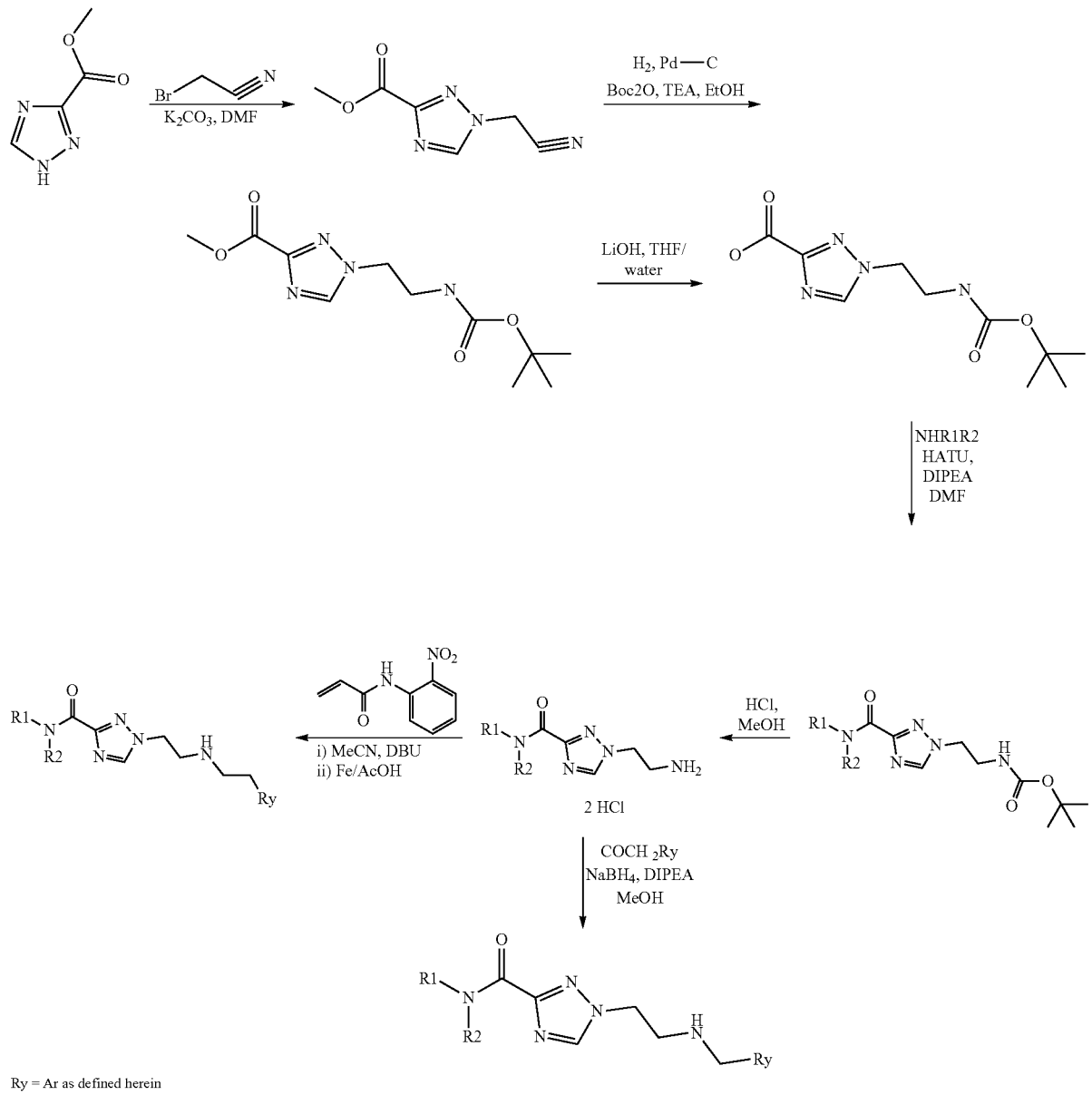
Ry = Ar as defined herein
General Scheme 14
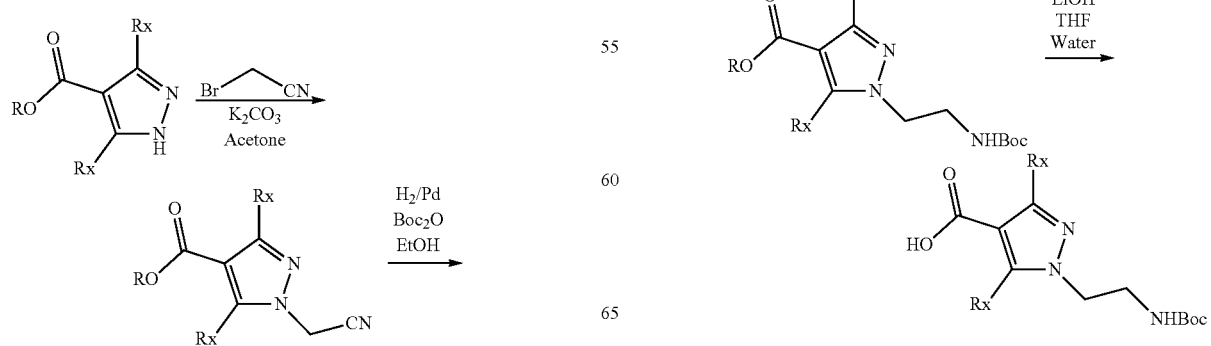

General Scheme 15
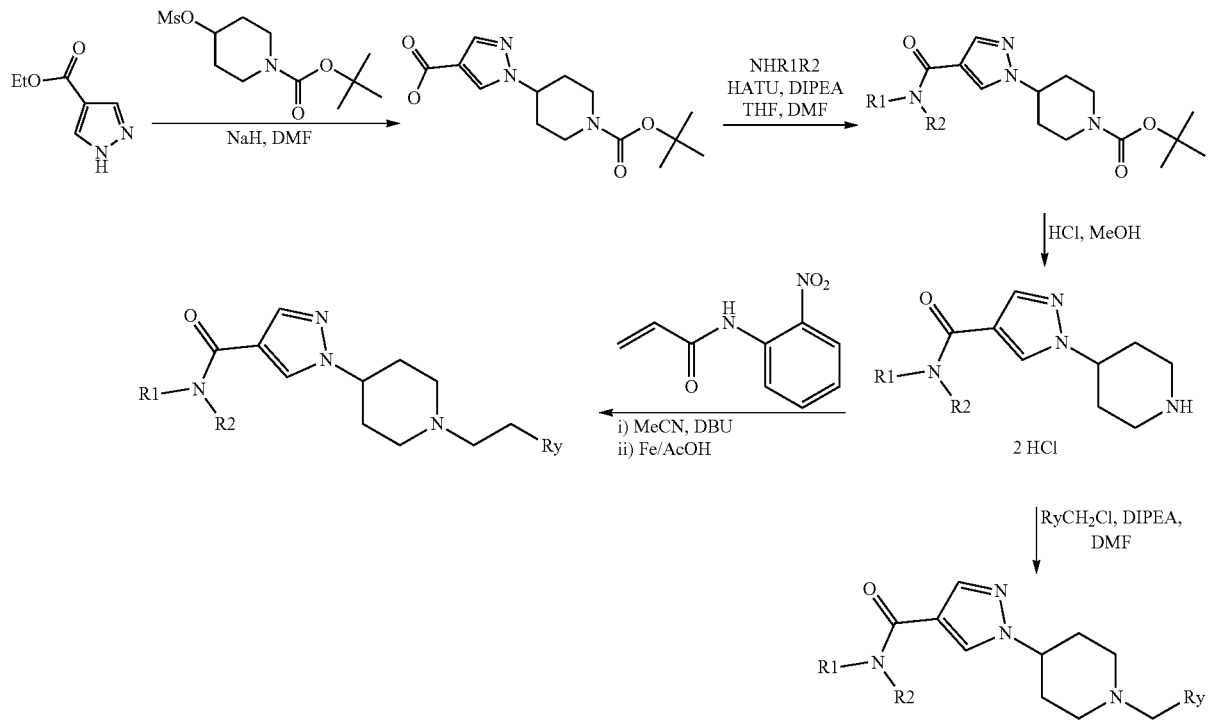
Ry = Ar as defined herein
General Scheme 16
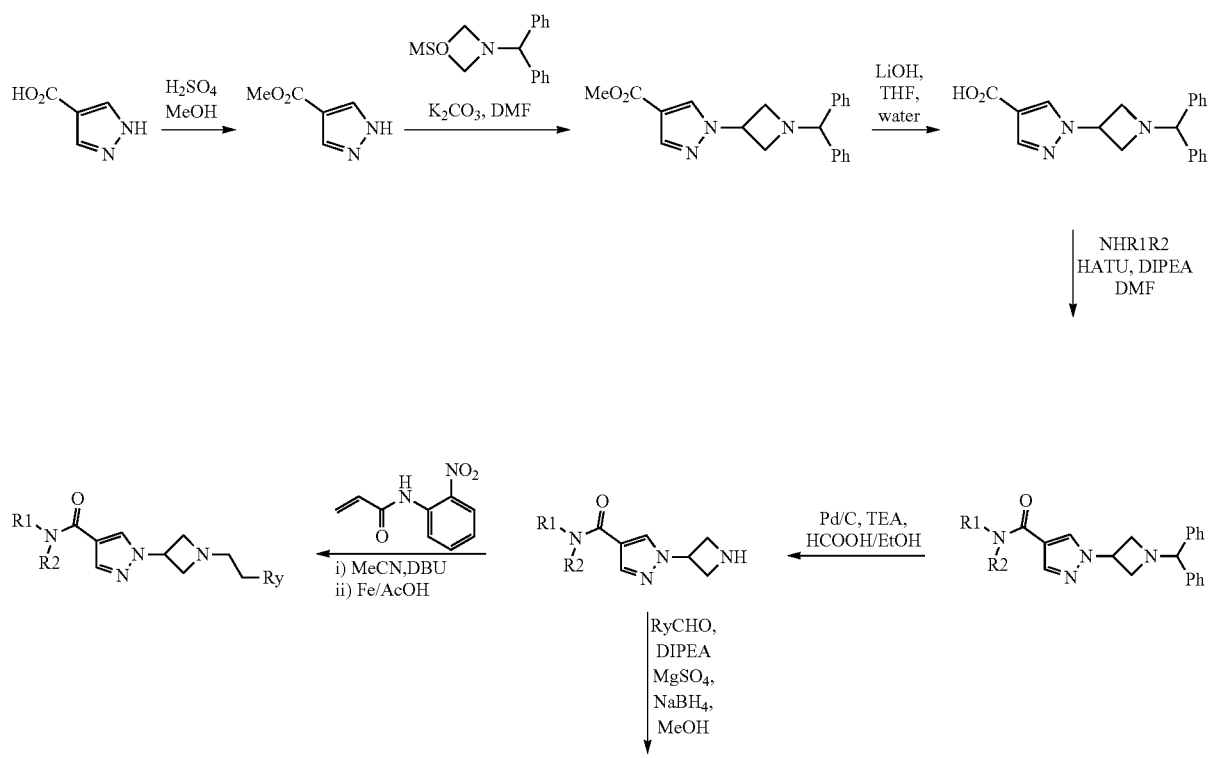

-continued
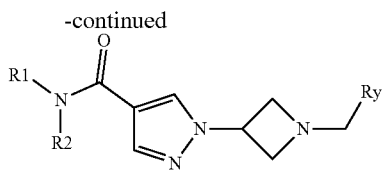
Ry = Ar as defined herein
General Scheme 18
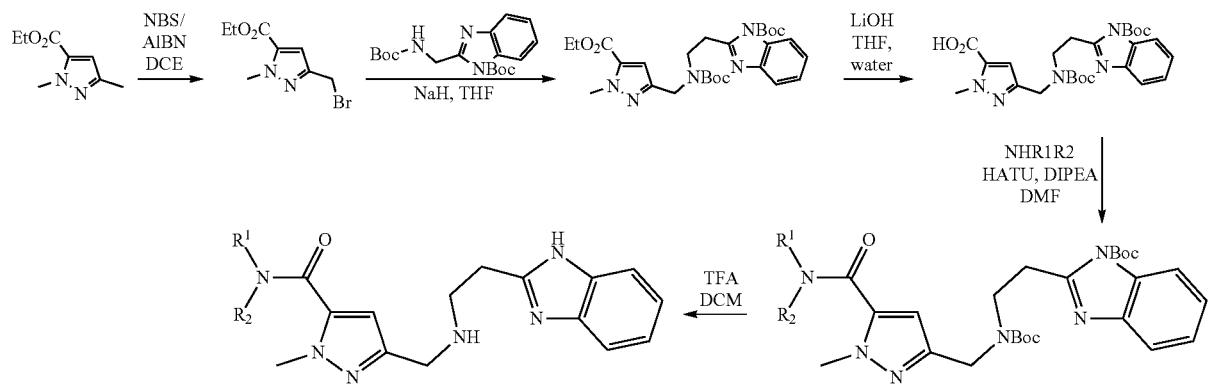
General Scheme 19
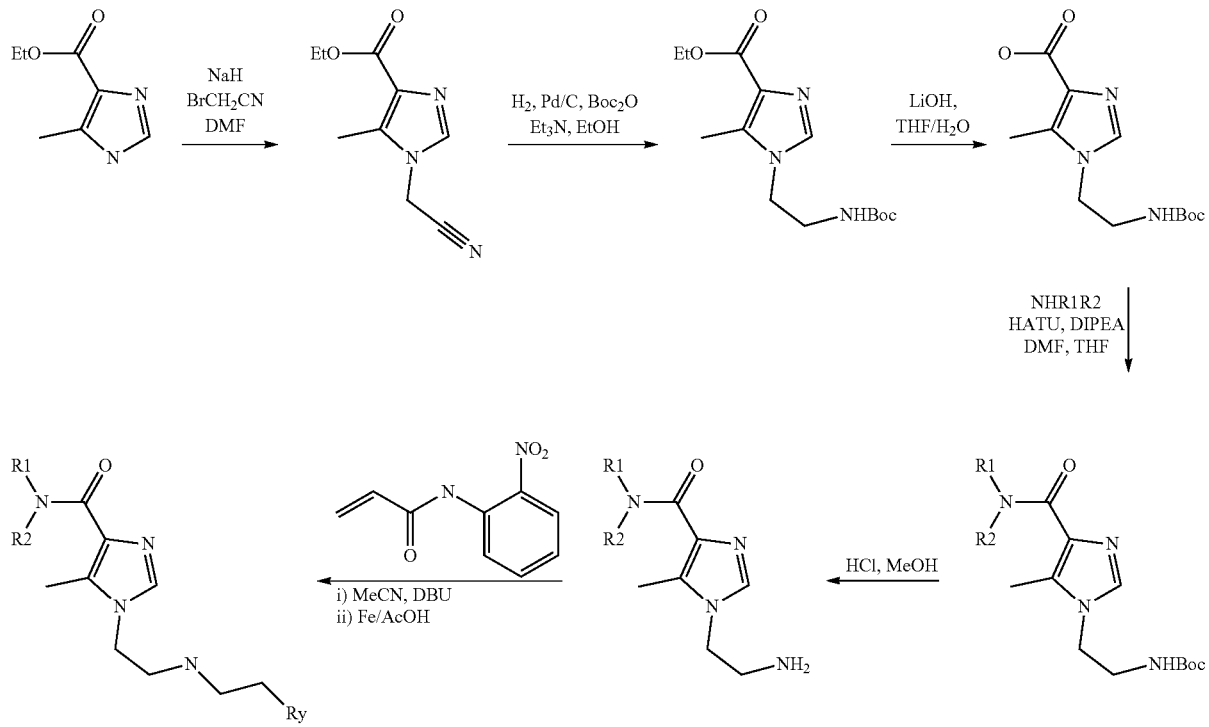
Ry = Ar as defined herein General Scheme 20
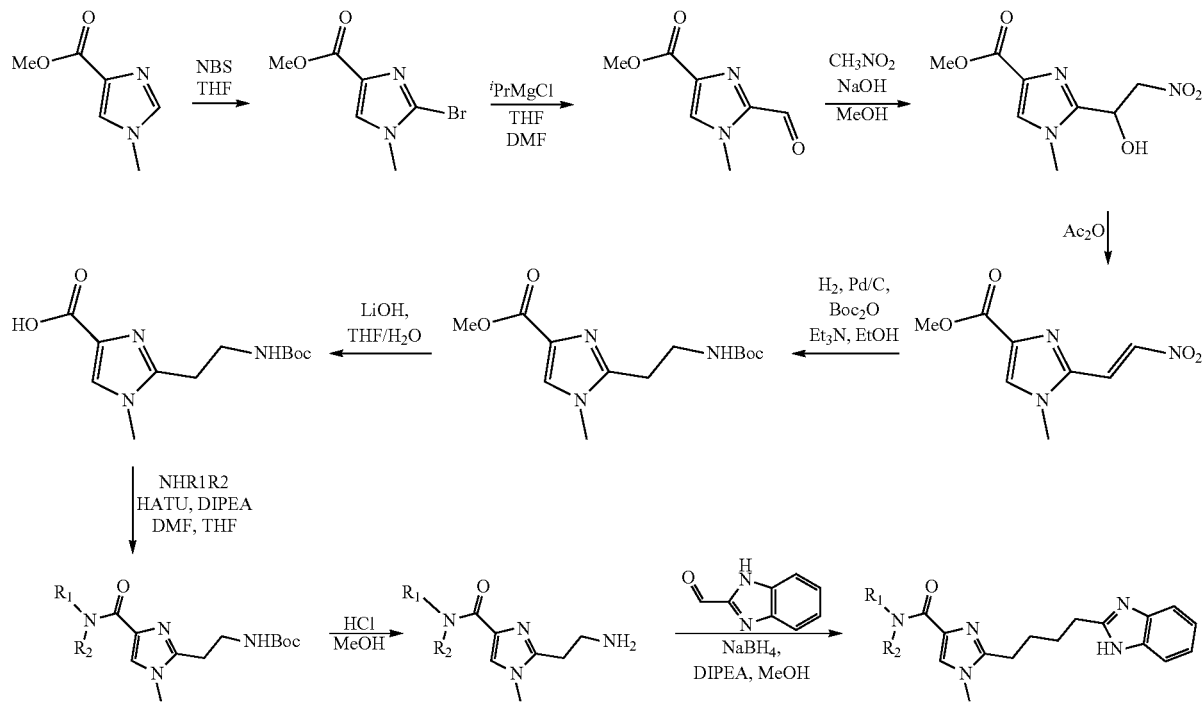
General Scheme 21
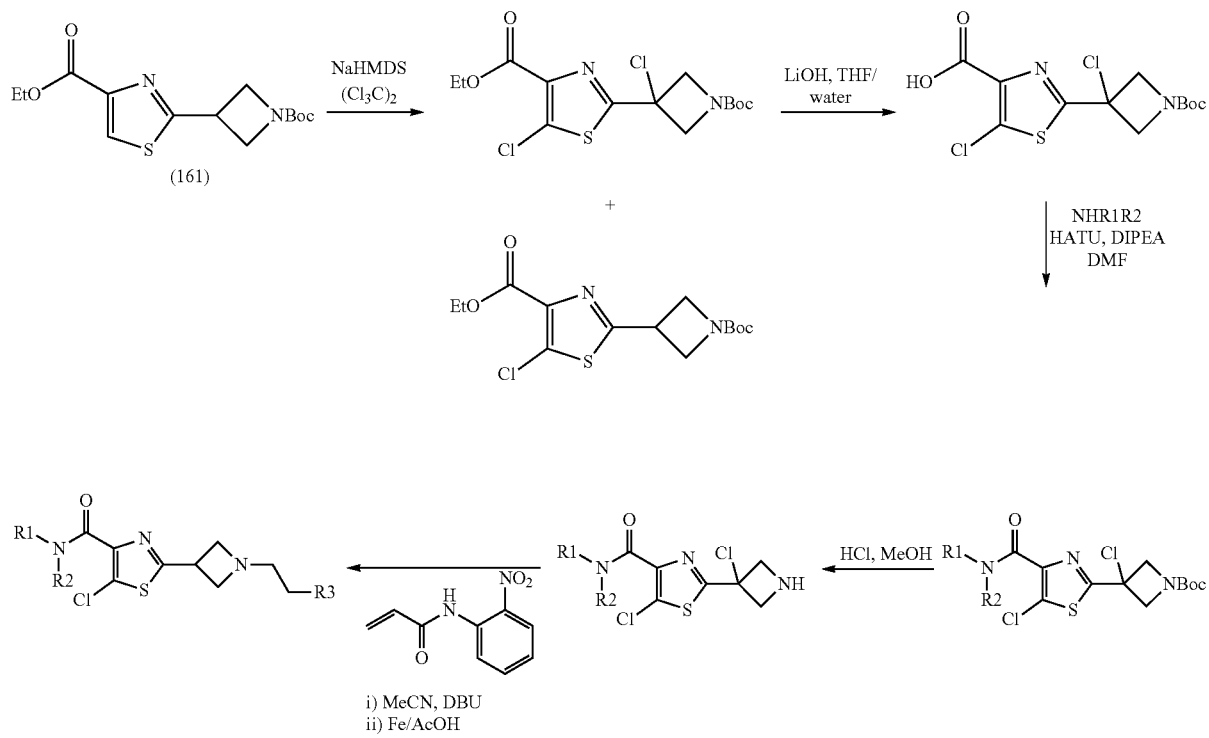
Ry = Ar as defined herein

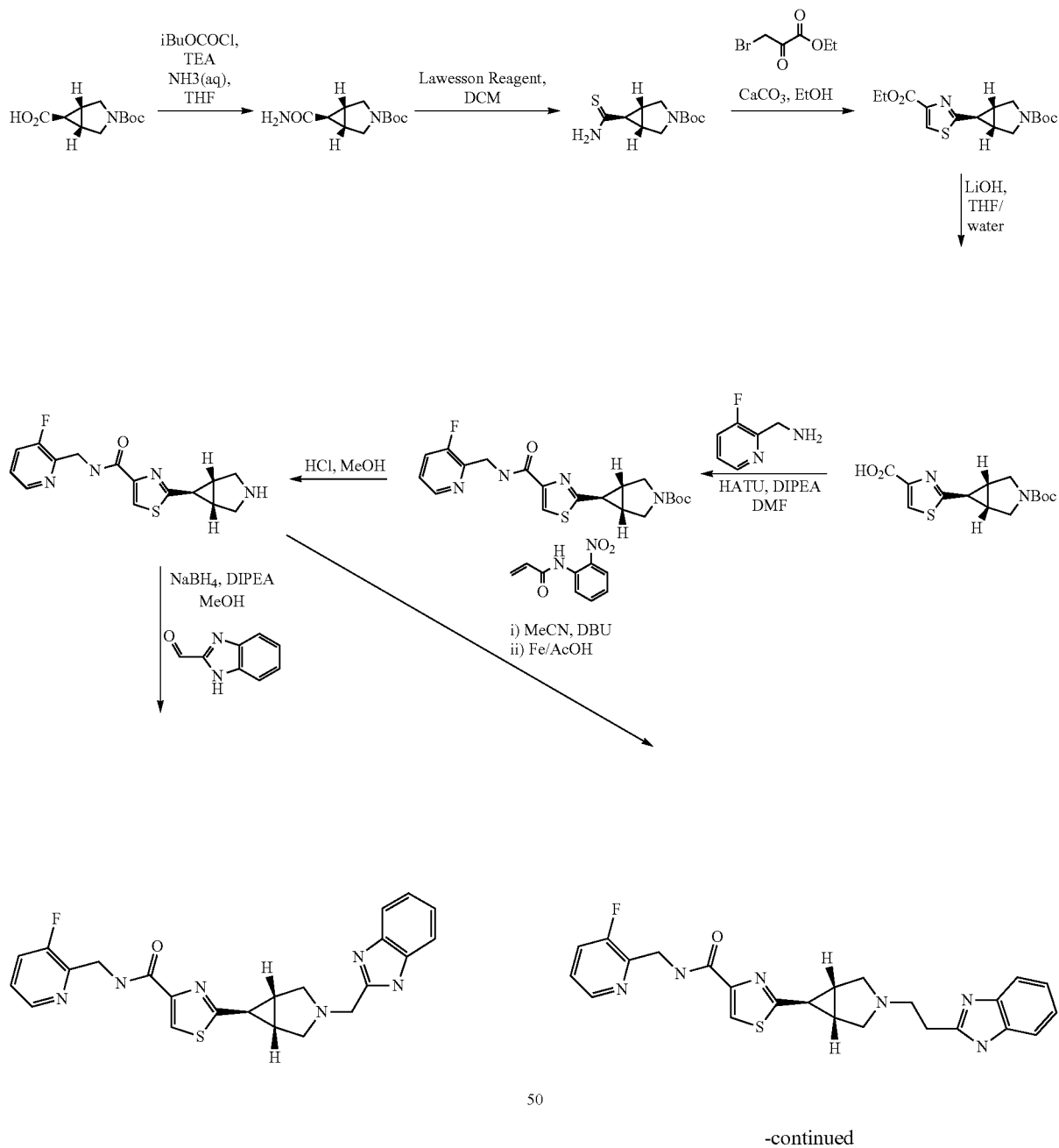
General Scheme 22
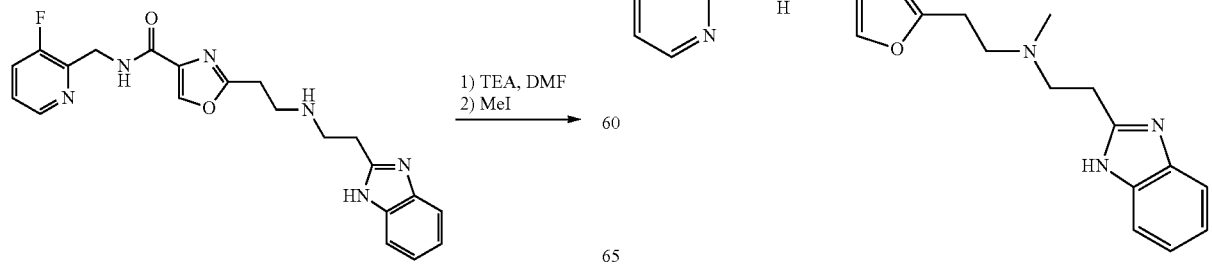
General Scheme 23

General Scheme 25
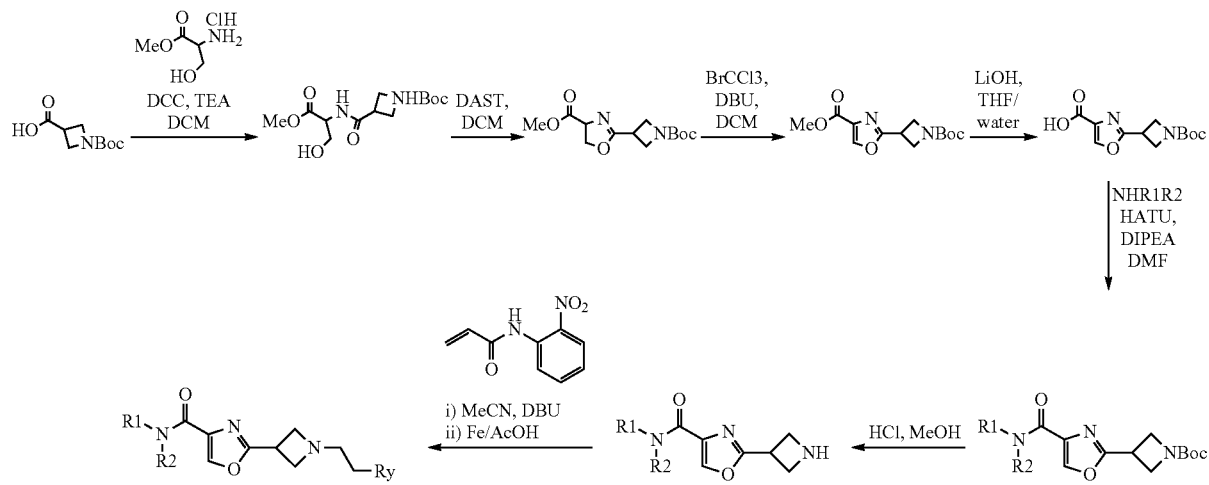
General Scheme 26
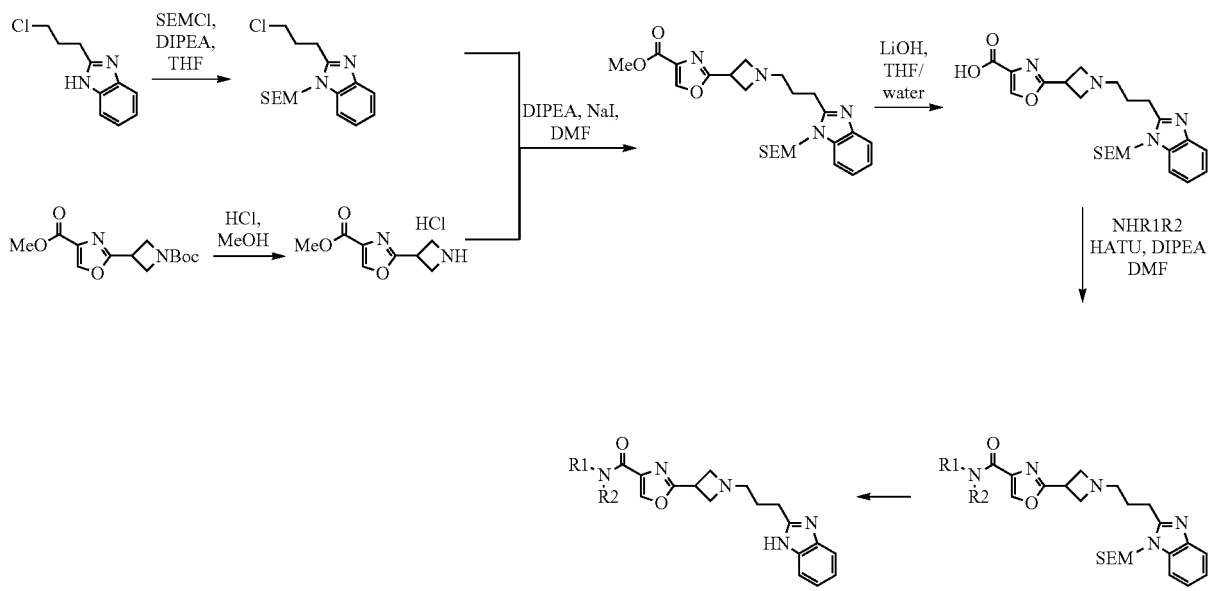
General Scheme 28
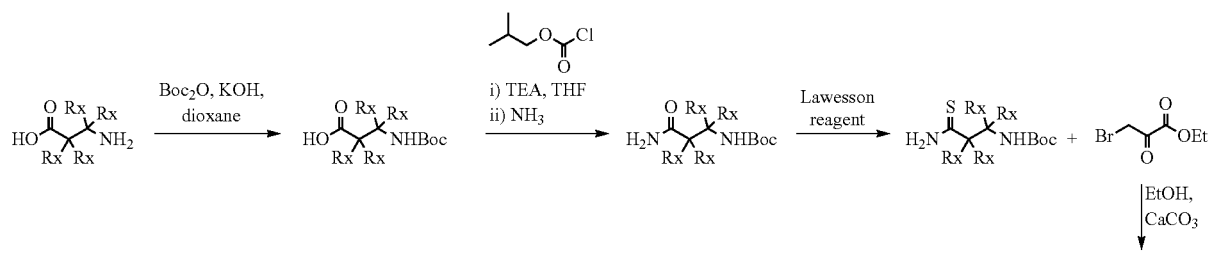

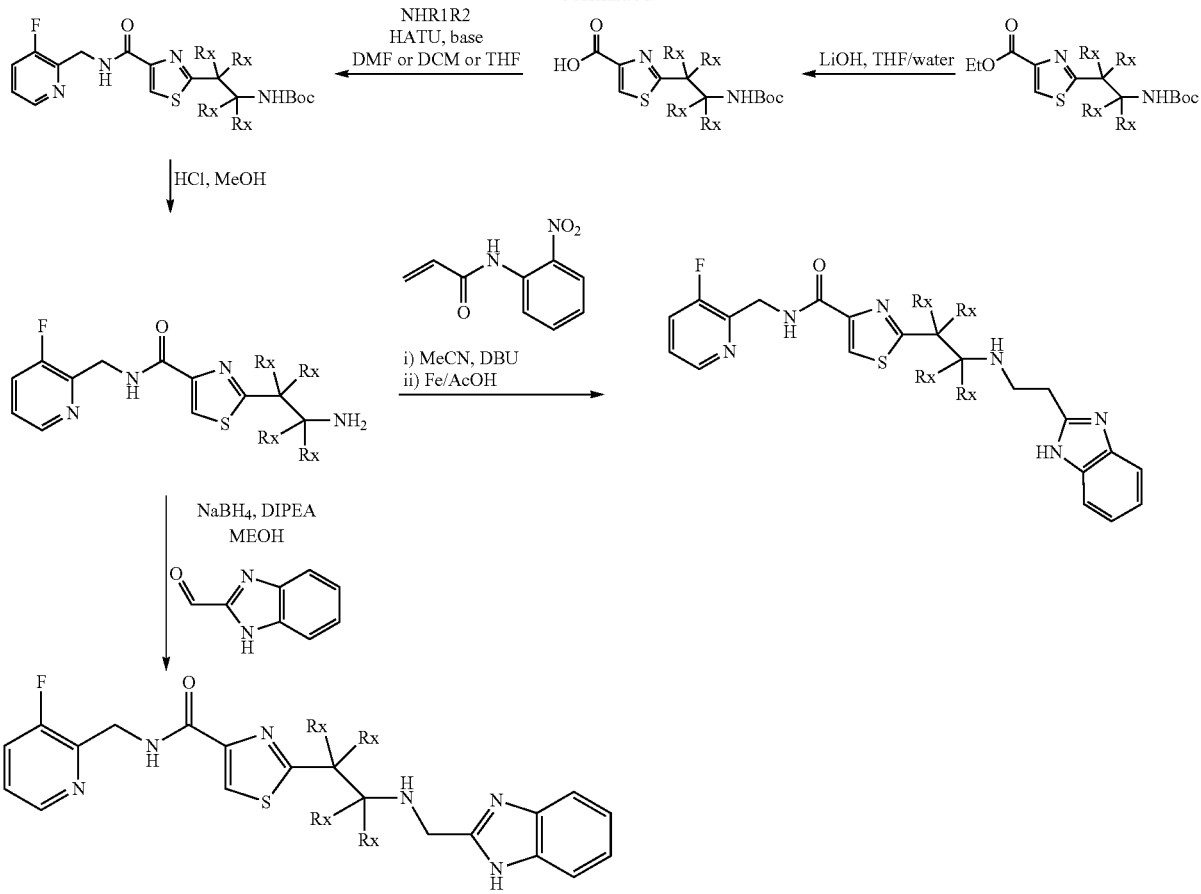
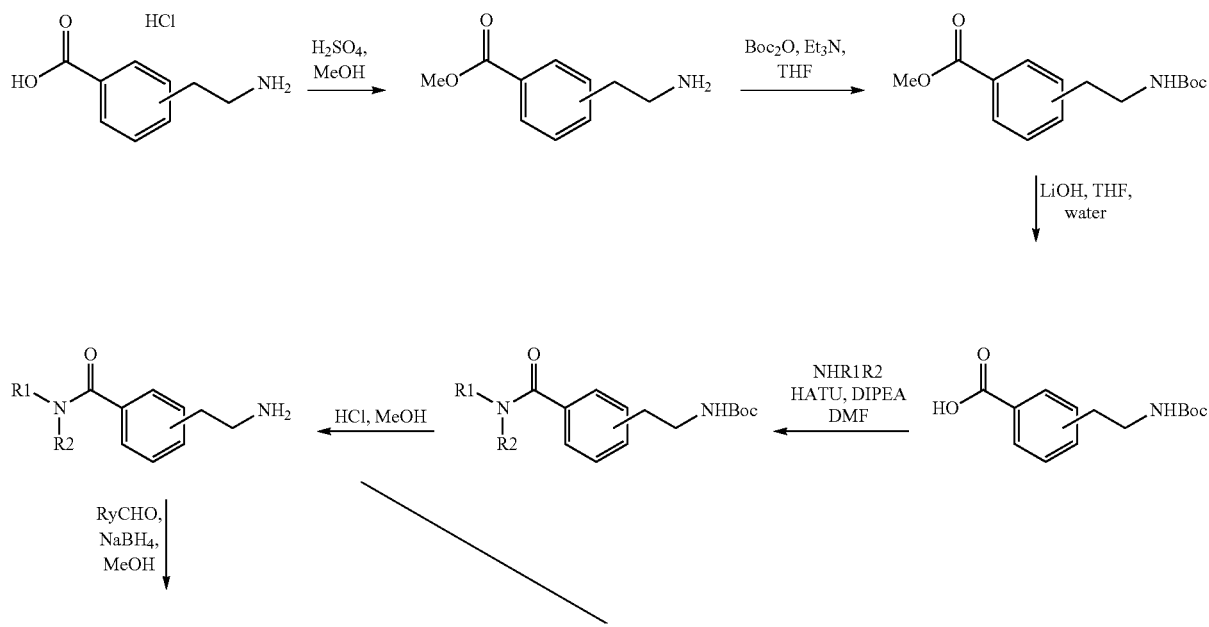
General Scheme 29
Rx = substituents as defined herein 177 178
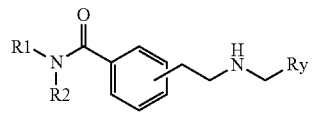
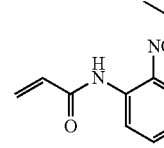
i) MeCN, DBU
ii) Fe/AcOH
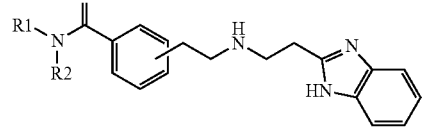
Ry = Ar as defined herein
General Scheme 30
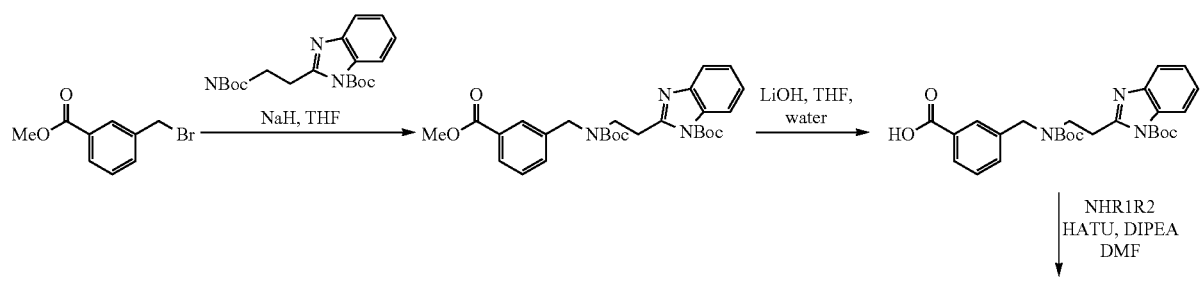
General Scheme 31
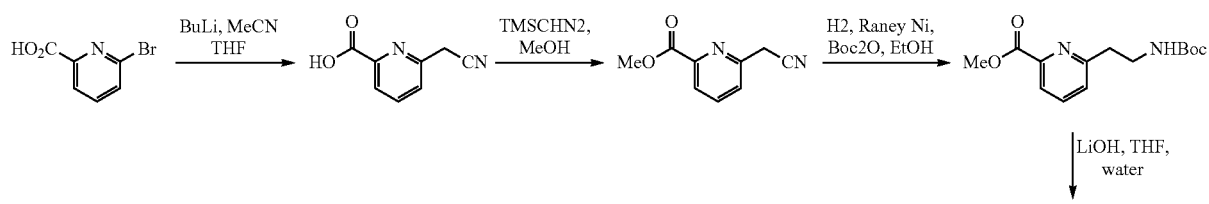

179 180
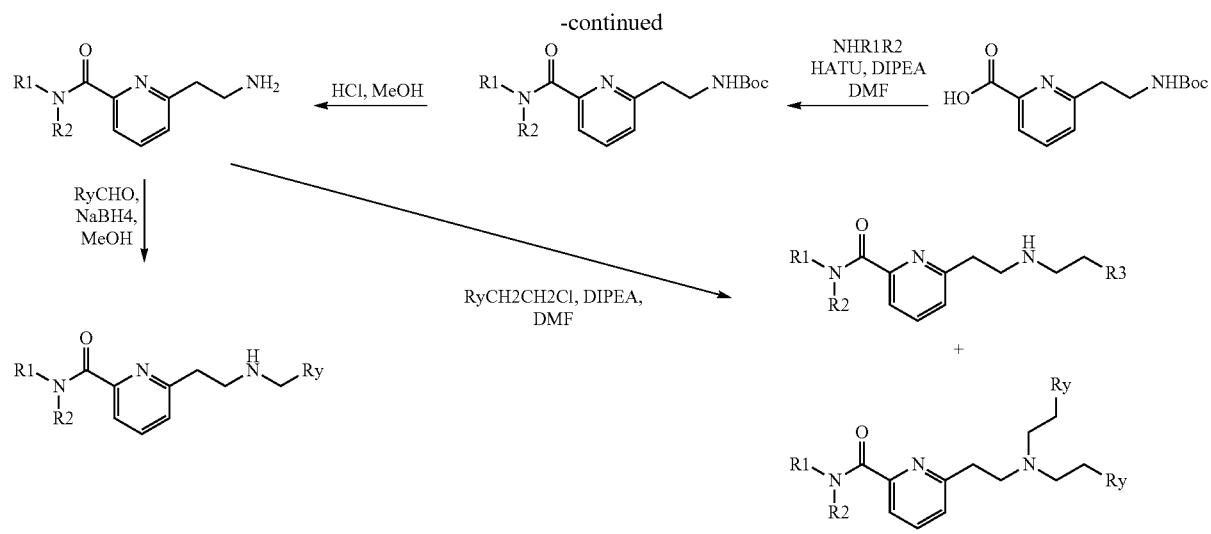
Ry = Ar as defined herein

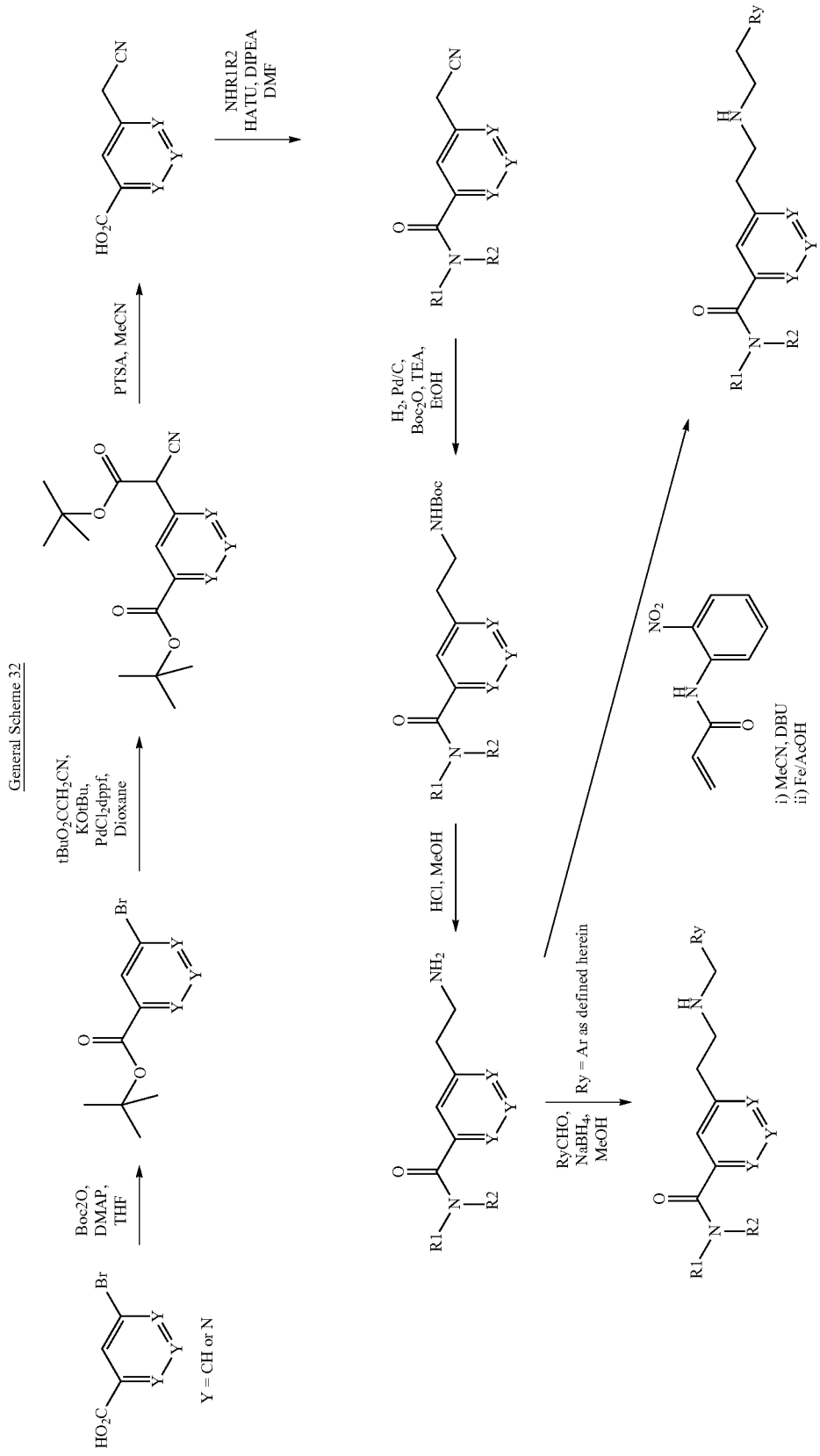
General Scheme 32

General Scheme 33
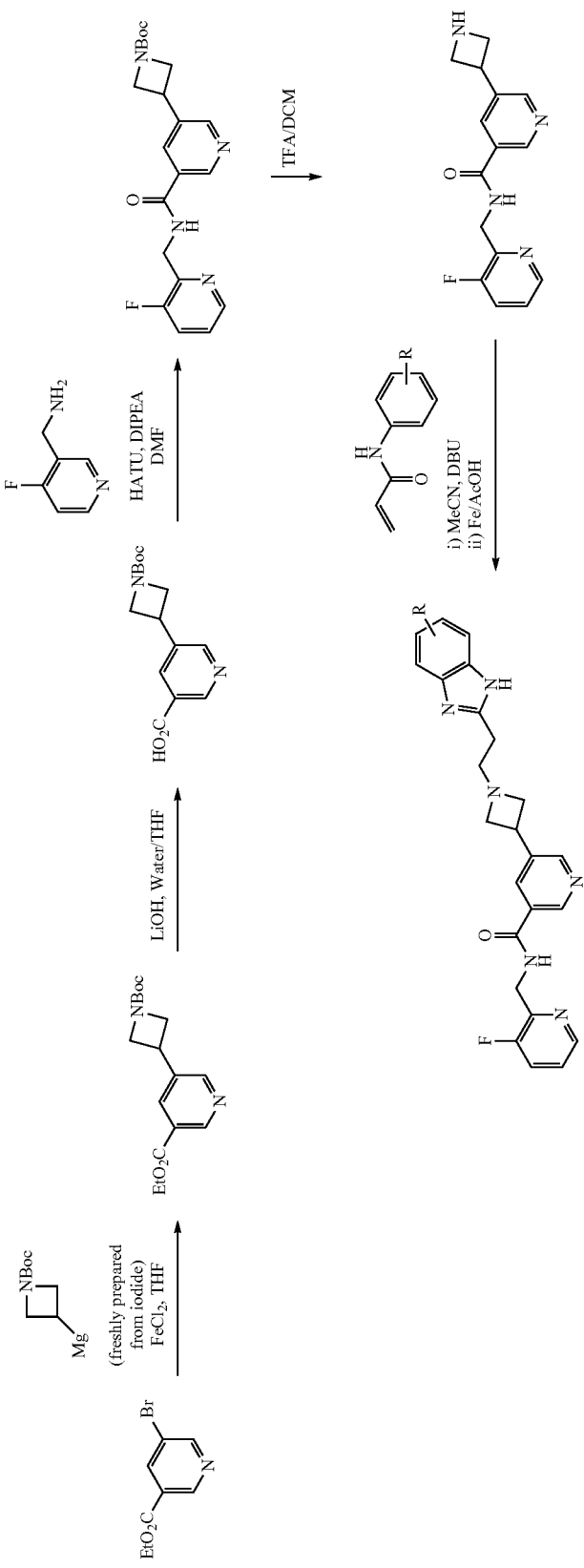
R = substituent of Ar as defined herein

General Scheme 34
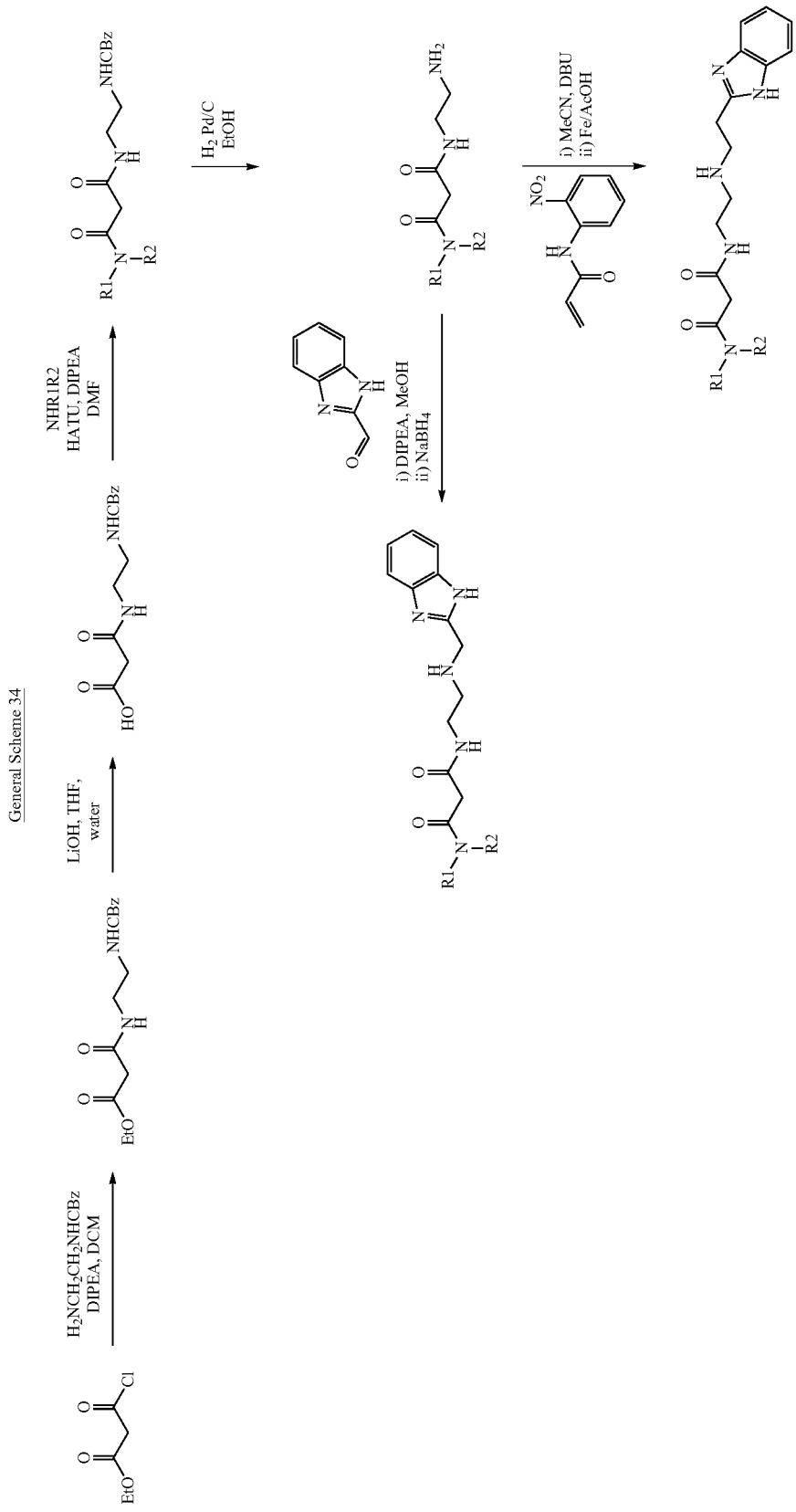

General Scheme 35
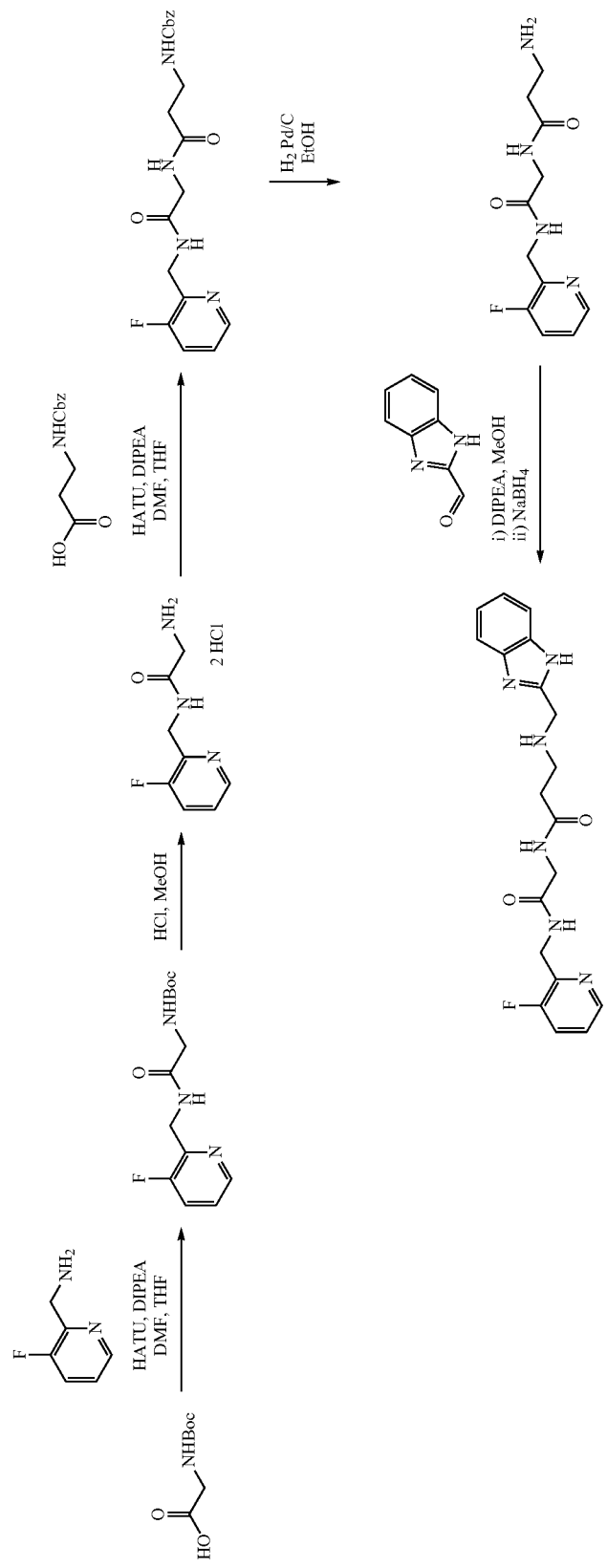

General Scheme 36
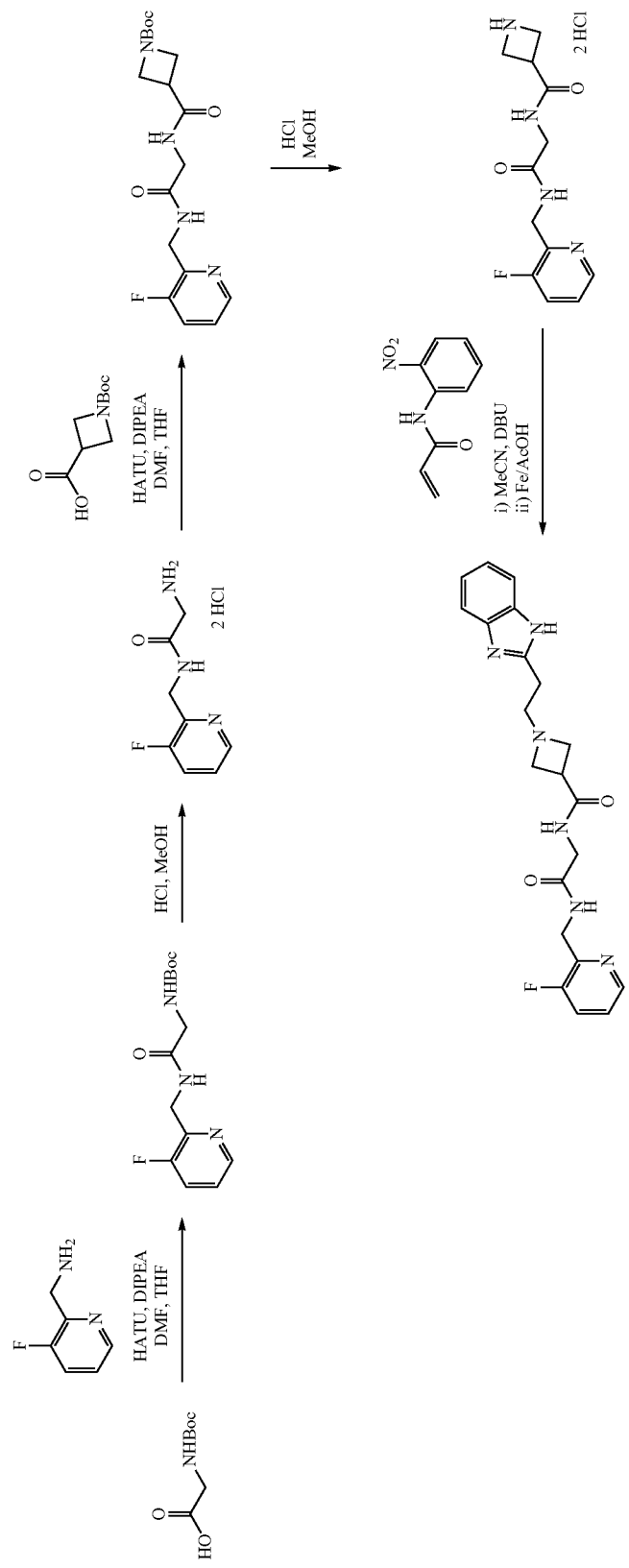

General Scheme 37
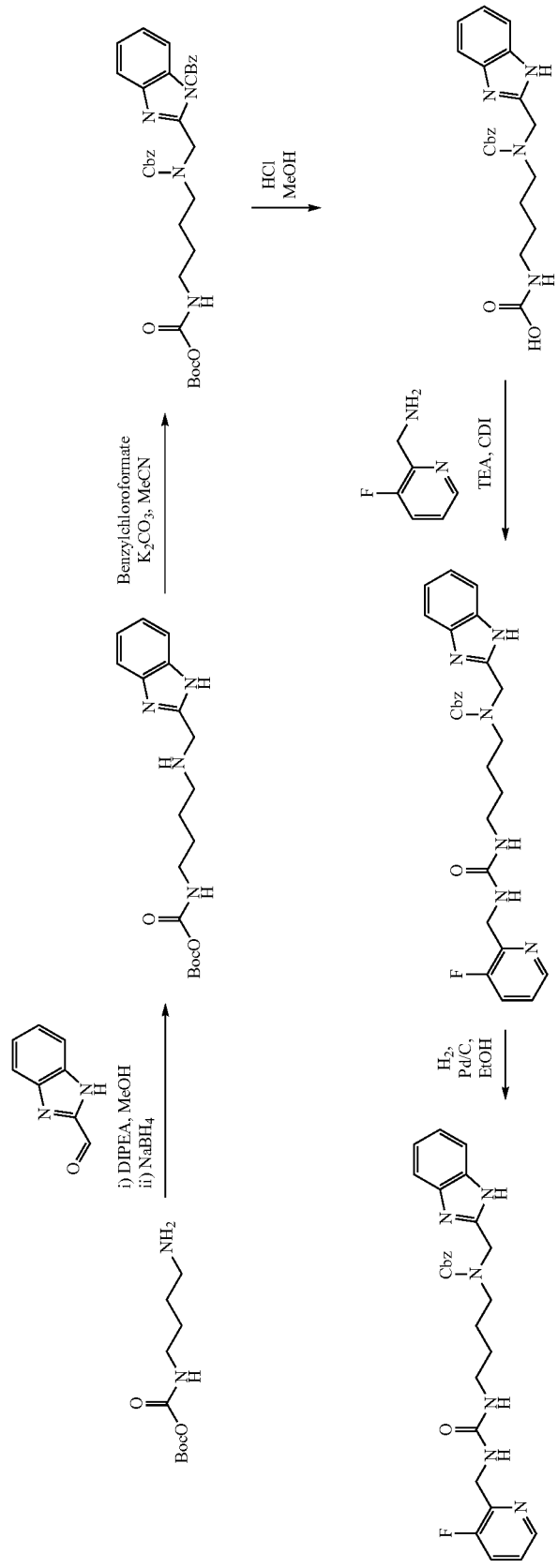

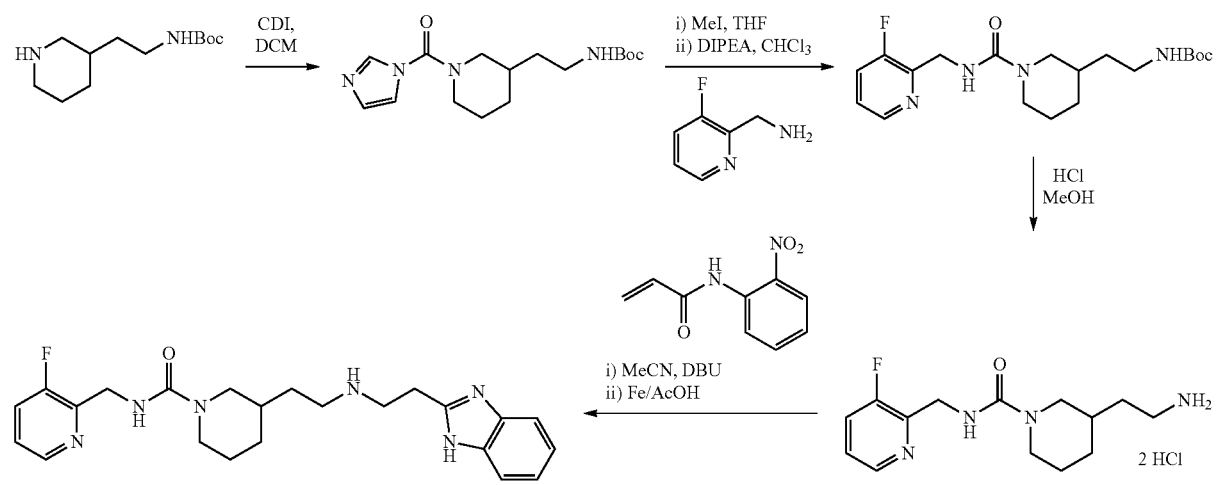
General Scheme 38

General Scheme 39
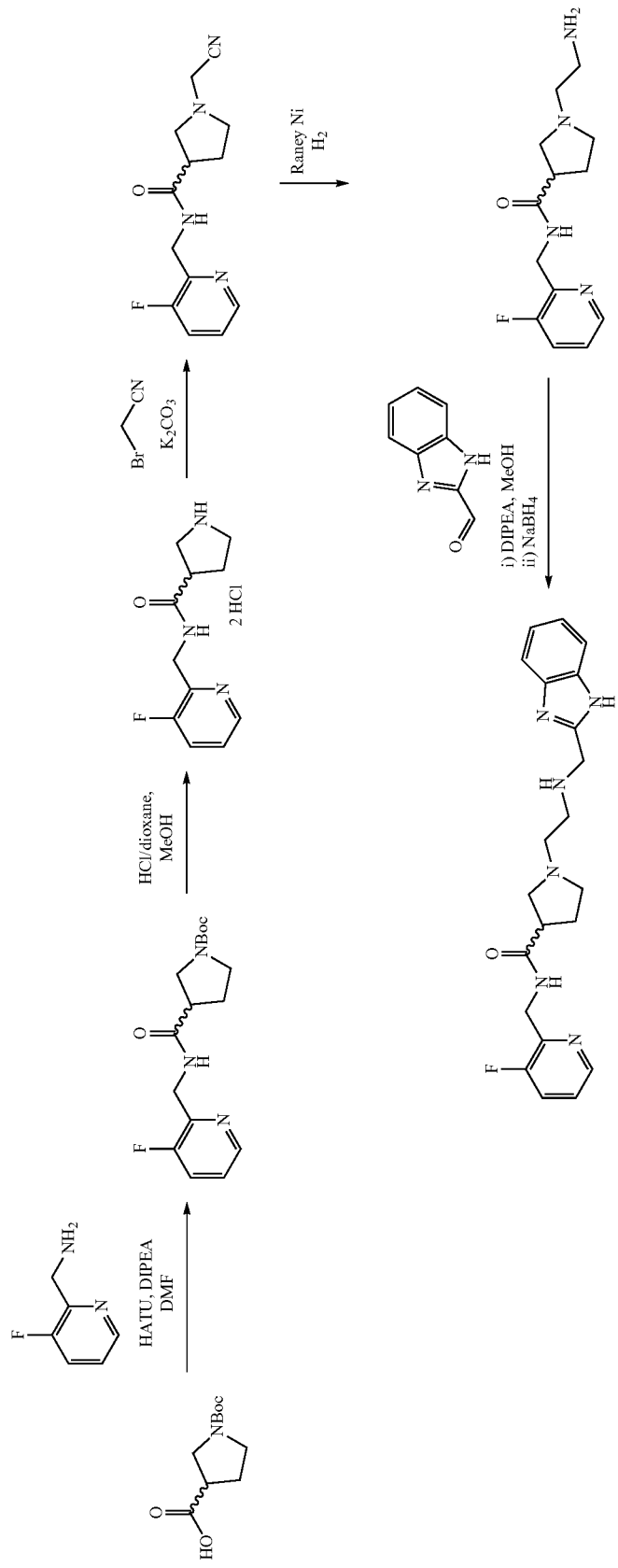

General Scheme 41
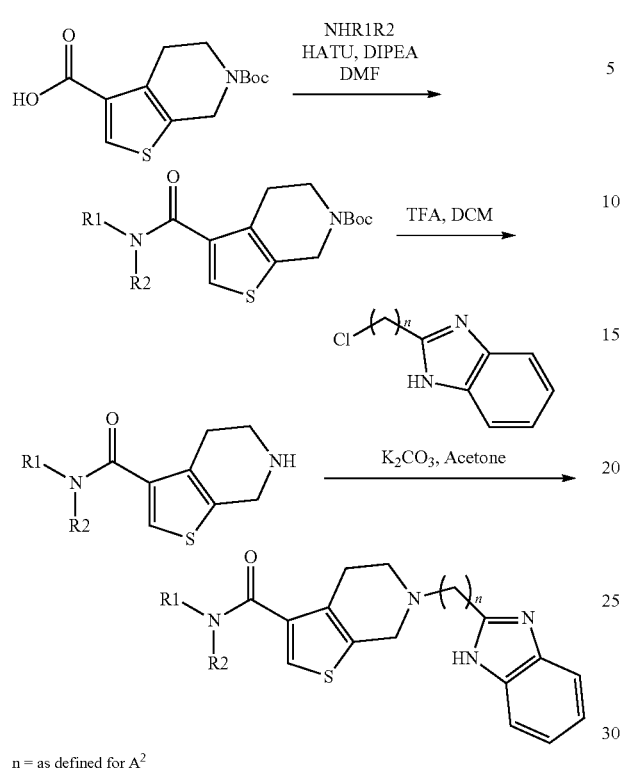
n = as defined for $A^2$
-continued
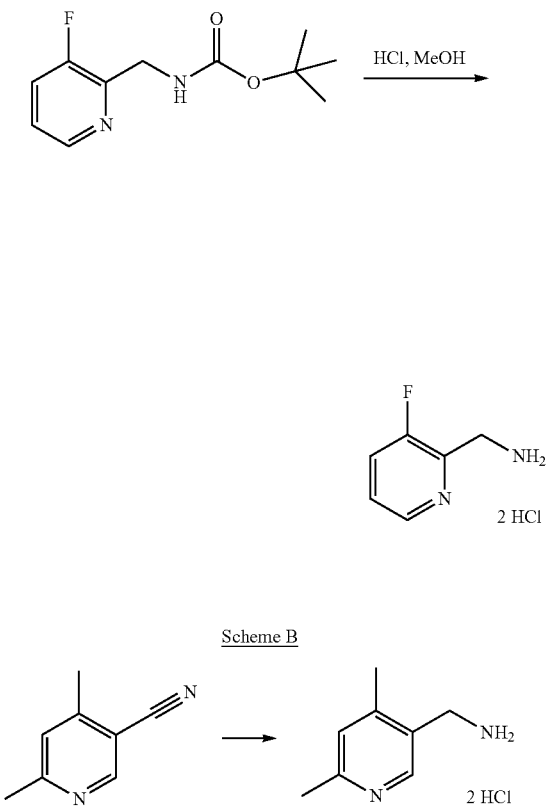
Scheme B
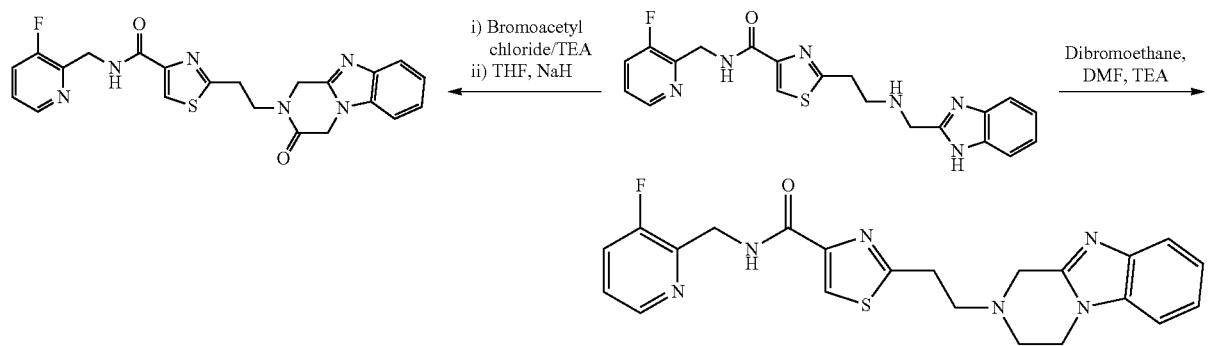
General Scheme 42
Intermediates:
Scheme A
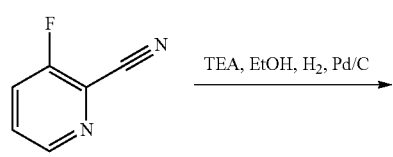
Scheme C
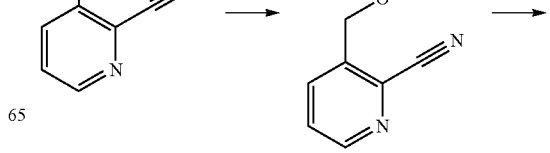

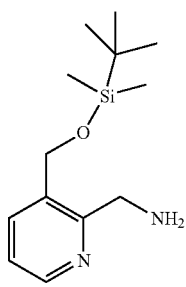

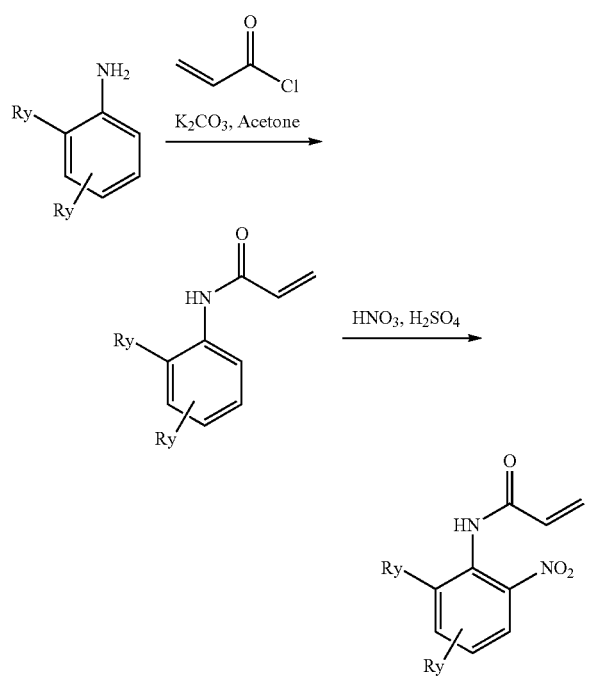

Ry = substituent of Ar as defined above

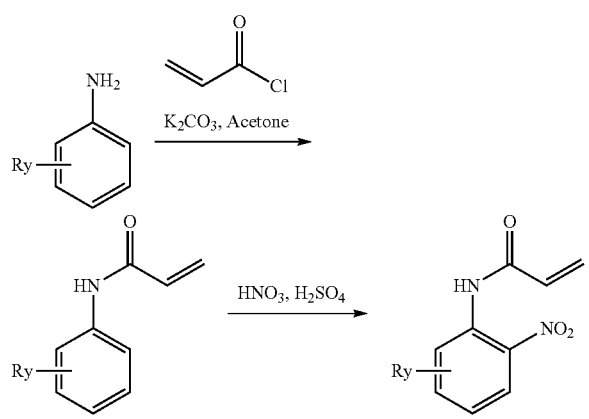

Ry = substituent of phenyl as defined herein

EXAMPLES

The invention is illustrated in more detail by the following examples. The examples are merely explanatory, and the person skilled in the art can extend the specific examples to further claimed compounds.

Pharmacological Assays

1. Hepcidin Internalization Assay (J774)

This cellular assay allows quantification of the binding of hepcidin to ferroportin (Fpn) through microscopic detection of internalization of a fluorescently labeled hepcidin into J774 cells. J774 is a mouse macrophage cell line which was shown to express Fpn endogenously upon incubation with iron (Knutson et al, 2005). Binding of hepcidin to Fpn triggers internalization and degradation of both hepcidin and Fpn. However, the TMR (6-carboxytetramethylrhodamine) fluorophore attached to hepcidin remains associated with the cell after degradation of the hepcidin peptide backbone. Therefore, microscopic detection of ceH associated TMR fluorescence is a measure of hepcidin binding to Fpn and internalization of hepcidin and Fpn. If TMR-hepcidin is prevented from binding to Fpn, cellular TMR fluorescence remains low (Dürrenberger et al, 2013). The effect of small molecular weight Fpn inhibitor compounds in this assay was evaluated in vitro as described below.

J774 cells, harvested from ca. 80% confluent cultures, were plated at $8 \times 10^5$ cells/ml in complete medium (DMEM, 10% FBS, 1% Penicillin-Streptomycin) containing 200 μM Fe(III)NTA (nitrilotriacetic acid), 100 μl per well of 96 well MicroClear plates (Greiner; Cat. 655090) and grown at 37° C. with 5% $CO_2$. After overnight incubation, cells were washed 3 times with pre-warmed DMEM w/o phenol red, 30 μl/well of DMEM w/o phenol red was added after the final wash and 10 μl/well of dilution series of test compounds were added in triplicates. J774 cells were pre-incubated with test compounds at 37° C. with 5% $CO_2$ for 15 min. before TMR-hepcidin was added at 25 nM final concentration. Cells were incubated in a total volume of 50 μl at 37° C. with 5% $CO_2$ for 2 hours, then Hoechst 33342 dye was added to a final concentration of 0.5 μg/ml to stain nuclei and further incubated for 10 min. at 37° C. with 5% $CO_2$. Cells were washed 3 times with PBS and fixed in 100 μl of 4% paraformaldehyde in PBS for 15 min. at room temperature. After removal of the paraformaldehyde solution, cells were washed 3 times with PBS leaving 100 μl per well and the plates were sealed with foil plate seal. TMR (530-550 nm excitation/575-625 nm emission/400 ms exposure time) and Hoechst 33342 (360-370 nm excitation/420-460 nm emission/10 ms exposure time) fluorescence images were acquired using a ScanR plate imager (Olympus) with a 20× high NA objective. Four pictures were acquired per well and fluorescence channel covering ca. 1500 cells per well. The acquired image data was analysed with the ScanR image analysis software. Image analysis included detection of nuclei (Hoechst 33342 fluorescence), identification of cell-associated regions, application of a virtual channel and thresholding for rolling-ball-type background reduction, followed by application of the Sum(Mean) algorithm to measure the TMR fluorescence associated with cells as a quantitative measure for internalized TMR-hepcidin. $IC_{50}$ values were calculated with the Sum(Mean) raw data using "log (inhibitor) vs. response" curve fitting of Prism 5 software (GraphPad Software Inc., version 5.02). For each data set the fit of the "log(inhibitor) vs. response (three parameters)" model was compared to the fit of the "log(inhibitor) vs. response–Variable slope (four parameters)" model and the $IC_{50}$ data of the preferred model was used. $IC_{50}$ data of the Fpn inhibitors that were tested in the hepcidin internalization assay are listed in Table 1. The IC$_{50}$ of unlabeled hepcidin in this assay is 0.015±0.011 μM.

TABLE 1

Average (AVE) IC$_{50}$ data of Fpn inhibitors tested in the hepcidin internalization assay is shown for multiple measurements

| Exp. Comp. No. | J774 IC50 (uM) |
|---|---|
| 1 | 0.5 |
| 2 | 6.3 |
| 3 | 16.6 |
| 4 | 15.4 |
| 5 | 10.4 |
| 6 | 12.7 |
| 7 | 14.2 |
| 8 | 42.9 |
| 11 | 20.9 |
| 12 | 0.08 |
| 13 | 1.7 |
| 14 | 4.9 |
| 15 | 1.6 |
| 16 | 0.90 |
| 17 | 6.4 |
| 18 | 8.7 |
| 19 | 10.0 |
| 20 | 9.4 |
| 21 | 6.7 |
| 22 | 17.2 |
| 23 | 15.8 |
| 24 | 2.8 |
| 25 | 2.2 |
| 26 | 0.7 |
| 27 | 38.4 |
| 28 | 0.18 |
| 29 | 0.51 |
| 30 | 12.9 |
| 31 | 1.1 |
| 32 | 2.6 |
| 33 | 3.62 |
| 34 | 0.36 |
| 35 | 0.19 |
| 36 | 0.25 |
| 37 | 0.81 |
| 38 | 0.03 |
| 39 | 0.07 |
| 40 | 0.049 |
| 41 | 3.98 |
| 42 | 0.60 |
| 43 | 0.25 |
| 44 | 1.33 |
| 45 | 0.44 |
| 46 | 0.59 |
| 47 | 0.72 |
| 49 | 30.58 |
| 50 | 0.41 |
| 51 | 0.36 |
| 52 | 0.34 |
| 54 | 0.46 |
| 55 | 0.015 |
| 56 | 0.41 |
| 57 | 0.10 |
| 58 | 0.01 |
| 59 | 0.05 |
| 60 | 2.39 |
| 61 | 0.56 |
| 62 | 0.93 |
| 63 | 0.61 |
| 64 | 0.13 |
| 65 | 0.85 |
| 66 | 0.41 |
| 67 | 0.53 |
| 68 | 2.5 |
| 69 | 0.26 |
| 70 | 0.53 |
| 71 | 0.24 |
| 72 | 1.36 |
| 73 | 0.37 |
| 74 | 0.21 |
| 75 | 0.53 |
| 76 | 0.34 |
| 77 | 0.35 |
| 78 | 0.41 |
| 79 | 0.037 |
| 80 | 0.345 |
| 81 | 0.42 |
| 82 | 0.006 |
| 83 | 0.096 |
| 84 | 0.40 |
| 85 | 0.029 |
| 86 | 0.48 |
| 87 | 0.19 |
| 88 | 0.78 |
| 89 | 0.089 |
| 90 | 0.025 |
| 91 | 2.07 |
| 92 | 0.83 |
| 93 | 0.53 |
| 94 | 0.012 |
| 95 | 7.23 |
| 96 | 2.97 |
| 97 | 0.27 |
| 98 | 1.85 |
| 99 | 2.99 |
| 100 | 0.46 |
| 101 | 0.28 |
| 102 | 0.058 |
| 103 | 2.37 |
| 104 | 0.90 |
| 105 | 0.077 |
| 106 | 1.52 |
| 107 | 1.32 |
| 108 | 0.13 |
| 109 | 0.076 |
| 110 | 1.699 |
| 111 | 0.035 |
| 112 | 0.378 |
| 113 | >25.0 (<50) |
| 114 | 0.118 |
| 115 | >25.0 (<50) |
| 116 | 1.000 |
| 117 | 9.695 |
| 118 | 0.103 |
| 119 | 0.164 |
| 120 | 0.034 |
| 121 | 0.473 |
| 122 | 0.026 |
| 123 | 0.17 |
| 124 | 6.332 |
| 125 | 1.660 |
| 126 | 0.096 |
| 127 | 0.009 |
| 128 | 0.005 |
| 129 | 0.353 |
| 131 | 0.090 |
| 132 | 0.580 |
| 133 | 4.560 |
| 134 | 0.377 |
| 135 | 3.407 |
| 136 | >10.49 (<50) |
| 137 | 0.514 |
| 138 | 0.179 |
| 139 | 4.794 |
| 140 | 3.727 |
| 141 | 0.167 |
| 142 | 21.606 |
| 144 | 0.012 |
| 145 | 0.385 |
| 146 | 3.107 |

TABLE 1-continued

Average (AVE) IC$_{50}$ data of Fpn inhibitors tested in the hepcidin internalization assay is shown for multiple measurements

| Exp. Comp. No. | J774 IC50 (uM) |
|---|---|
| 147 | 0.533 |
| 148 | 2.085 |
| 149 | 6.249 |
| 151 | 0.111 |
| 152 | 0.004 |
| 154 | 0.0083 |
| 155 | 0.347 |
| 156 | 2.462 |
| 157 | 0.717 |
| 158 | 0.047 |
| 159 | 0.091 |
| 160 | 0.256 |
| 161 | 0.361 |
| 162 | 0.297 |
| 163 | 0.828 |
| 164 | 0.343 |
| 165 | 0.100 |
| 166 | 1.118 |
| 167 | 0.145 |
| 168 | 0.884 |
| 169 | 0.750 |
| 170 | 0.482 |
| 171 | 0.026 |
| 172 | 3.928 |
| 173 | 0.006 |
| 174 | 0.141 |
| 175 | 1.025 |
| 176 | 0.957 |
| 177 | 4.203 |
| 178 | 3.637 |
| 179 | 0.216 |
| 180 | 30.855 |
| 181 | 0.135 |
| 182 | 0.989 |
| 183 | 0.131 |
| 184 | 0.063 |
| 185 | 2.232 |
| 186 | 0.30 |
| 187 | 87 |
| 188 | 1.16 |
| 189 | 0.060 |
| 190 | 0.74 |
| 191 | 0.33 |
| 192 | 13.56 |
| 193 | 0.287 |
| 194 | 0.72 |
| 195 | 0.21 |
| 196 | 1.13 |
| 197 | 0.61 |
| 198 | 27.05 |
| 199 | 0.78 |
| 200 | 3.14 |
| 201 | 1.93 |
| 202 | 5.00 |
| 204 | 3.3 |
| 205 | 0.37 |
| 206 | 0.18 |
| 207 | 0.183 |
| 208 | 0.012 |
| 209 | 0.379 |
| 210 | 4.913 |
| 211 | 0.747 |
| 212 | 8.514 |
| 214 | 14.1 |
| 215 | 27.7 |
| 218 | 4.5 |
| 219 | 2.43 |
| 220 | 0.29 |
| 221 | 0.36 |
| 222 | 3.4 |
| 223 | 1.9 |
| 224 | 0.14 |
| 226 | 0.049 |
| 227 | 0.130 |
| 228 | 0.046 |
| 229 | 0.056 |
| 230 | 0.14 |
| 231 | 5.2 |
| 232 | 1.9 |
| 233 | 16 |
| 235 | 0.91 |
| 236 | 0.15 |
| 237 | 0.081 |
| 239 | 0.036 |
| 240 | 2.45 |
| 241 | 2.1 |
| 242 | 8.92 |
| 243 | 0.032 |
| 244 | 0.090 |
| 245 | 0.188 |
| 246 | 0.276 |
| 247 | 0.082 |
| 248 | 0.363 |
| 249 | 0.040 |
| 250 | 0.014 |
| 251 | 0.062 |
| 253 | 0.226 |
| 256 | 0.081 |
| 257 | 0.035 |
| 258 | 0.152 |
| 261 | 0.554 |
| 265 | 0.070 |
| 273 | 0.228 |
| 274 | 0.145 |
| 275 | 26.035 |
| 276 | 27.160 |
| 277 | 0.011 |
| 278 | 0.476 |
| 279 | 2.009 |

2. Biophysical Ferroportin-Hepcidin Binding Assay

This biophysical assay was developed to confirm inhibition of hepcidin binding to ferroportin (Fpn) more directly. Incubation of TMR-hepcidin with purified human Fpn isolated from *Pichia pastoris* yeast cells expressing human Fpn with a C-terminal FLAG affinity tag (Bonaccorsi di Patti, 2014) leads to increased fluorescence polarization (FP) of the TMR-hepcidin ligand. Small molecular weight Fpn inhibitors were tested for inhibition of binding of TMR-hepcidin to Fpn, as detected by dose-dependent decrease of the TMR FP signal, as described in detail below.

A mixture of 1.3 µM human Fpn and 30 nM TMR-hepcidin in FP assay buffer containing 50 mM Tris-HCl pH 7.3, 200 mM NaCl, 0.02% DDM, 0.1% BSA was plated into a 384 well black low volume round bottom plate (Corning, Cat. 3677) at 16 µl per well. 8 µl of serial dilutions of test compounds were added in duplicates to reach final Fpn and TMR-hepcidin concentrations of 1 µM and 20 nM, respectively. Plates were incubated for 90 minutes at room temperature and parallel (S) and perpendicular (P) fluorescence was measured in a Synergy H1 fluorescence reader (BioTek). FP values were calculated in mP according to the following formula.

$$mP = \frac{F_{parallel} - F_{perpendicular}}{F_{parallel} + F_{perpendicular}} \times 1000$$

IC$_{50}$ values were determined with the calculated mP values as described for the hepcidin internalization assay and are listed in Table 2. The IC$_{50}$ of unlabeled hepcidin in this assay is 0.37±0.067 μM.

TABLE 2

Average (AVE) IC$_{50}$ data of Fpn inhibitors tested in the biophysical hepcidin-ferroportin binding assay is shown for multiple measurements.

| Exp. Comp. No. | FP IC50 (uM) |
|---|---|
| 1 | 0.49 |
| 2 | 10.58 |
| 6 | 48.56 |
| 11 | 7.83 |
| 12 | 0.86 |
| 13 | 0.53 |
| 14 | 14.94 |
| 15 | 1.47 |
| 16 | 1.72 |
| 17 | 3.53 |
| 19 | 10.22 |
| 20 | 9.61 |
| 21 | 1.43 |
| 22 | 14.24 |
| 25 | 3.93 |
| 26 | 1.12 |
| 28 | 1.22 |
| 29 | 0.136 |
| 30 | 2.33 |
| 31 | 0.94 |
| 32 | 1.21 |
| 33 | 17.18 |
| 34 | 4.29 |
| 35 | 2.16 |
| 36 | 3.65 |
| 37 | 1.90 |
| 38 | 0.233 |
| 39 | 1.34 |
| 40 | 0.068 |
| 41 | 11.96 |
| 42 | 2.17 |
| 43 | 1.52 |
| 44 | 5.34 |
| 45 | 2.1 |
| 46 | 4.34 |
| 47 | 3.42 |
| 49 | 23.97 |
| 50 | 1.48 |
| 51 | 0.53 |
| 52 | 1.36 |
| 54 | 11.37 |
| 55 | 0.087 |
| 56 | 0.566 |
| 57 | 0.43 |
| 58 | 0.076 |
| 59 | 0.270 |
| 60 | 0.974 |
| 61 | 1.690 |
| 62 | 0.436 |
| 63 | 0.846 |
| 64 | 1.237 |
| 65 | 0.95 |
| 66 | 53.8 |
| 67 | 3.401 |
| 68 | 4.056 |
| 69 | 1.513 |
| 70 | 1.065 |
| 71 | 0.508 |
| 72 | 0.931 |
| 73 | 1.003 |
| 74 | 0.451 |
| 75 | 1.830 |
| 76 | 5.083 |
| 77 | 2.813 |
| 78 | 4.146 |
| 79 | 0.820 |
| 80 | 2.276 |
| 81 | 2.974 |
| 82 | 0.374 |
| 83 | 1.046 |
| 84 | 2.412 |
| 85 | 1.866 |
| 86 | 4.957 |
| 87 | 2.249 |
| 88 | 6.757 |
| 89 | 0.922 |
| 90 | 0.418 |
| 91 | 12.060 |
| 92 | 1.268 |
| 93 | 1.03 |
| 94 | 0.044 |
| 95 | 13.040 |
| 96 | 7.286 |
| 97 | 2.132 |
| 98 | 5.713 |
| 99 | 4.327 |
| 100 | 1.419 |
| 101 | 0.315 |
| 102 | 0.258 |
| 103 | 2.525 |
| 104 | 1.756 |
| 105 | 0.420 |
| 106 | 4.457 |
| 107 | 5.742 |
| 108 | 0.478 |
| 109 | 0.172 |
| 110 | 3.422 |
| 111 | 0.051 |
| 112 | 1.035 |
| 113 | 71.2 |
| 114 | 0.23 |
| 115 | 109 |
| 116 | 0.058 |
| 117 | 9.0 |
| 118 | 0.25 |
| 119 | 5.3 |
| 120 | 0.071 |
| 121 | 5.1 |
| 122 | 0.214 |
| 123 | 0.112 |
| 124 | 3.5 |
| 125 | 3.7 |
| 126 | 0.12 |
| 127 | 0.023 |
| 128 | 0.036 |
| 129 | 1.078 |
| 131 | 0.133 |
| 132 | 0.57 |
| 133 | 2.5 |
| 134 | 0.97 |
| 135 | 36.90 |
| 136 | 6.85 |
| 137 | 1.04 |
| 138 | 0.16 |
| 139 | 63.1 |
| 140 | 6.9 |
| 141 | 0.049 |
| 142 | 10.5 |
| 144 | 0.073 |
| 145 | 0.35 |
| 146 | 1.3 |
| 147 | 0.56 |
| 148 | 7.3 |
| 149 | 17 |
| 150 | 73 |
| 151 | 0.089 |
| 152 | 0.023 |
| 153 | 57.77 |
| 154 | 0.030 |
| 155 | 0.46 |

TABLE 2-continued

Average (AVE) IC$_{50}$ data of Fpn inhibitors tested in the biophysical hepcidin-ferroportin binding assay is shown for multiple measurements.

| Exp. Comp. No. | FP IC50 (uM) |
|---|---|
| 156 | 0.71 |
| 157 | 4.27 |
| 158 | 0.041 |
| 159 | 0.035 |
| 160 | 0.097 |
| 161 | 0.26 |
| 162 | 0.14 |
| 163 | 2.97 |
| 164 | 0.14 |
| 165 | 0.061 |
| 166 | 0.37 |
| 167 | 0.104 |
| 168 | 1.36 |
| 169 | 0.54 |
| 170 | 0.28 |
| 171 | 0.066 |
| 172 | 3.40 |
| 173 | 0.031 |
| 174 | 0.32 |
| 175 | 0.95 |
| 176 | 1.16 |
| 177 | 15.44 |
| 178 | 1.92 |
| 179 | 0.42 |
| 180 | 22.40 |
| 181 | 0.089 |
| 182 | 0.33 |
| 183 | 0.19 |
| 184 | 0.10 |
| 185 | 2.90 |
| 186 | 0.14 |
| 187 | 35.48 |
| 188 | 0.63 |
| 189 | 0.047 |
| 190 | 0.66 |
| 191 | 0.52 |
| 192 | 49.26 |
| 193 | 0.074 |
| 194 | 0.73 |
| 195 | 0.077 |
| 196 | 0.87 |
| 197 | 0.55 |
| 199 | 0.45 |
| 200 | 5.65 |
| 201 | 0.79 |
| 202 | 1.32 |
| 204 | 1.63 |
| 205 | 0.29 |
| 206 | 0.036 |
| 207 | 0.047 |
| 208 | 0.019 |
| 209 | 0.038 |
| 210 | 1.877 |
| 211 | 0.154 |
| 212 | 3.758 |
| 214 | 3.188 |
| 215 | 15.610 |
| 218 | 2.2 |
| 219 | 1.1 |
| 220 | 0.093 |
| 221 | 0.147 |
| 222 | 0.808 |
| 223 | 2.680 |
| 224 | 0.201 |
| 226 | 0.026 |
| 227 | 0.096 |
| 228 | 0.021 |
| 229 | 0.043 |
| 230 | 0.058 |
| 231 | 1.658 |
| 232 | 0.267 |
| 233 | 6.776 |
| 235 | 0.295 |
| 236 | 0.123 |
| 237 | 0.066 |
| 239 | 0.038 |
| 240 | 2.671 |
| 241 | 1.648 |
| 242 | 27.810 |
| 243 | 0.034 |
| 244 | 0.182 |
| 245 | 0.295 |
| 246 | 0.263 |
| 247 | 0.178 |
| 248 | 0.306 |
| 249 | 0.044 |
| 250 | 0.019 |
| 251 | 0.071 |
| 253 | 0.1481 |
| 256 | 0.046 |
| 257 | 0.038 |
| 258 | 0.194 |
| 261 | 0.4396 |

3. Inhibition of Ferroportin Mediated Iron Export Activity in an Iron Response Assay Intracellular iron levels are indirectly measured in this assay by monitoring the activity of a beta-lactamase (BLA) reporter gene fused to the human ferritin promoter and the associated iron regulatory element (IRE) contained within the 5' untranslated region of the ferritin mRNA. Expression of ferroportin (Fpn) in such a cell line leads to iron efflux and lower iron levels as reflected by lower activity of the reporter gene. On the other hand, inhibition of Fpn-mediated iron efflux results in elevated cellular iron levels which is detected as increased reporter gene activity. Small molecular weight Fpn inhibitor compounds were tested for dose-dependent effects in this in vitro iron response assay as described below.

The HEK-293 cell line #354 was generated by stable integration of (i) a human Fpn-GFP fusion construct inserted in a derivative of the doxycycline-inducible pTRE-Tight-BI plasmid (Clontech, Cat. 631068) and (ii) a human ferritin promoter-BLA reporter gene into a derivative of the HEK-293 Tet-ON Advanced cell line (Clontech). To generate the ferritin-BLA reporter gene construct, a 1.4 kb fragment of the human ferritin H promoter was amplified by PCR from human genomic DNA (forward primer 5'-CAGGTTTGT-GAGCATCCTGAA-3'; reverse primer 5'-GGCGGC-GACTAAGGAGAGG-3') and inserted in front of the BLA gene present in the pcDNA™6.2/cGeneBLAzer™-DEST plasmid (Invitrogen, Cat. 12578-043) thereby replacing the original CMV promoter and placing the IRE that regulates translation of the ferritin gene ca. 170 bp upstream of the start codon of the reporter gene. #354 cells were harvested from ca. 80% confluent cultures, seeded at $1.8 \times 10^5$ cells/ml in DMEM/F12 GlutaMAX™ medium (Invitrogen, Cat. 31331-028) containing 10% FBS (Clontech, Cat. 631106), 1% Penicillin-Streptomycin, 200 µg/ml Hygromycin B (Invitrogen, Cat. 10687-010), Blasticidin 5 µg/ml, (Invitrogen, Cat. R210-01), 4 µg/ml doxycycline (Clontech, Cat. 631311), 50 µl per well of 384 well PDL-coated plates and grown at 37° C. with 5% $CO_2$. After overnight incubation, 10 µl/well of dilution series of the test compounds were added in quadruplicates and plates were further incubated overnight at 37° C. with 5% CQ. Cells were washed 3 times with HBSS leaving 25 μl per well. BLA activity was detected by adding 5 μl/well of the GeneBlazer reagent CCF4-AM (Invitrogen, Cat. K1085) to the cells. After incubation of the plates in the dark at 18° C. for 60 min., blue and green fluorescence signals were measured in a Safre2 fluorescence plate reader (Tecan) with excitation at 410 nm and emissions at 458 nm (blue) and 522 nm (green). The ratio of blue/green fluorescence as a measure for BLA activity was calculated and $EC_{50}$ values were determined with the calculated blue/green fluorescence ratios as described for the hepcidin internalization assay. The $EC_{50}$ data of the tested Fpn inhibitors is listed in Table 3. The $EC_0$ of hepcidin in this assay is 0.096±0.063 μM (n=37).

TABLE 3

Average (AVE) $EC_{50}$ data of Fpn inhibitors tested in the iron response assay is shown for multiple measurements.

| Exp. Comp. No. | BLAzer EC50 (uM) |
|---|---|
| 2 | 1.64 |
| 12 | 8.27 |
| 13 | 27.02 |
| 15 | 2.22 |
| 24 | 12.84 |
| 29 | 2.53 |
| 32 | 1.87 |
| 37 | 7.92 |
| 38 | 2.98 |
| 39 | 2.90 |
| 40 | 1.45 |
| 42 | 36.26 |
| 43 | 30.95 |
| 44 | 18.31 |
| 46 | 38.67 |
| 51 | 4.47 |
| 52 | 2.08 |
| 55 | 1.23 |
| 56 | 10.38 |
| 57 | 2.11 |
| 58 | 1.72 |
| 59 | 1.38 |
| 61 | 37.46 |
| 64 | 4.53 |
| 65 | 32.33 |
| 67 | 33.46 |
| 68 | 10.40 |
| 71 | 1.79 |
| 75 | 6.00 |
| 79 | 0.84 |
| 82 | 0.76 |
| 84 | 13.15 |
| 85 | 18.69 |
| 86 | 22.34 |
| 87 | 16.56 |
| 88 | 13.08 |
| 89 | 5.05 |
| 90 | 4.03 |
| 92 | 17.78 |
| 93 | 20.55 |
| 94 | 0.53 |
| 97 | 1.81 |
| 99 | 22.80 |
| 100 | 6.56 |
| 101 | 2.92 |
| 102 | 1.85 |
| 105 | 2.63 |
| 107 | 20.98 |
| 108 | 4.12 |
| 109 | 2.62 |
| 111 | 0.62 |
| 112 | 13.47 |
| 114 | 4.45 |
| 116 | 2.79 |
| 118 | 2.69 |
| 120 | 1.60 |
| 122 | 4.33 |
| 123 | 3.04 |
| 126 | 1.26 |
| 127 | 0.42 |
| 128 | 0.097 |
| 129 | 10.56 |
| 131 | 0.75 |
| 132 | 13.94 |
| 133 | >20.0 <50 |
| 134 | 4.09 |
| 135 | >20.00 <50 |
| 136 | >20.00 <50 |
| 137 | 5.75 |
| 138 | 1.72 |
| 139 | >20.00 <50 |
| 140 | >20.00 <50 |
| 141 | 1.11 |
| 144 | 0.47 |
| 145 | 4.7 |
| 151 | 0.72 |
| 152 | 0.17 |
| 154 | 0.74 |
| 155 | 8.17 |
| 156 | 16.13 |
| 158 | 0.62 |
| 159 | 1.16 |
| 160 | 1.91 |
| 161 | 17.18 |
| 162 | 4.37 |
| 164 | 2.11 |
| 165 | 2.59 |
| 167 | 2.84 |
| 169 | 8.23 |
| 170 | 3.96 |
| 171 | 1.23 |
| 173 | 0.10 |
| 174 | 7.73 |
| 179 | 25.94 |
| 181 | 3.72 |
| 182 | 6.84 |
| 183 | 3.58 |
| 184 | 1.60 |
| 186 | 4.94 |
| 188 | >39.07 <50 |
| 189 | 3.10 |
| 190 | 27.30 |
| 191 | 8.38 |
| 193 | 3.64 |
| 194 | >3.22 <50 |
| 195 | 3.55 |
| 196 | 12.72 |
| 197 | 18.10 |
| 199 | 5.70 |
| 200 | 45.14 |
| 201 | 39.40 |
| 205 | 3.83 |
| 206 | 3.26 |
| 207 | 2.76 |
| 208 | 0.50 |
| 209 | 3.38 |
| 211 | 6.1 |
| 220 | 17.0 |
| 221 | 16.9 |
| 224 | 8.2 |
| 226 | 2.34 |

TABLE 3-continued

Average (AVE) $EC_{50}$ data of Fpn inhibitors tested in the iron response assay is shown for multiple measurements.

| Exp. Comp. No. | BLAzer EC50 (uM) |
|---|---|
| 227 | 24.90 |
| 228 | 2.12 |
| 229 | 4.06 |
| 230 | 6.38 |
| 232 | 12.05 |
| 236 | 12.72 |
| 237 | 2.46 |
| 239 | 0.88 |
| 243 | 1.40 |
| 244 | 3.86 |
| 245 | 6.14 |
| 246 | 12.91 |
| 247 | 3.15 |
| 248 | 6.34 |
| 249 | 1.55 |
| 250 | 0.46 |
| 251 | 2.27 |
| 253 | 3.176 |
| 256 | 0.628 |
| 257 | 0.636 |
| 258 | 2.525 |
| 265 | 1.998 |
| 273 | 3.604 |
| 274 | 1.122 |
| 277 | 0.17 |

4. Ferroportin Internalization and Degradation Assay

HEK-293 cell line #354 (described in example 3) was used to measure the capacity of the compounds to induce internalization and degradation of ferroportin (Fpn) by fluorescence activated cell sorting (FACS). Growing HEK-293 #354 cells in doxycycline containing media induced expression of human Fpn-GFP fusion protein on the cell surface. Data from 10 independent experiments showed that cultivation of HEK #354 cells for 48 h in the presence of 4 μg/ml doxycycline induced in average 42.6%±6.4% Fpn-GFP-positive cells. Small molecular weight Fpn inhibitor compounds were tested for dose-dependent effects on the Fpn-GFP mean fluorescence intensity (MFI) on HEK-293 cell line #354, as described below. HEK #354 cells were harvested from ca. 80% confluent cultures, seeded at $0.6 \times 10^6$ (cells/ml in DMEM/F12 GlutaMAX™ medium (Invitrogen, Cat. 31331-028) containing 10% FBS (Clontech, Cat. 631106), 1% Penicillin-Streptomycin (Invitrogen, Cat. 15140-122), 200 μg/ml Hygromycin B (Invitrogen, Cat. 10687-010), Blasticidin 5 μg/ml, (Invitrogen, Cat. R210-01), 4 μg/ml doxycycline (Clontech, Cat. 631311), 50 μl per well of 384 well plates (Greiner; Cat. 781091) and grown at 37° C. with 5% $CO_2$. After overnight incubation, 10 μl/well of dilution series of the test compounds were added in quadruplicates and plates were further incubated overnight at 37° C. with 5% $CO_2$. Cells were washed once with FACS buffer (PBS containing 1% FBS, 2 mM EDTA and 0.05% $NaN_3$), harvested in FACS buffer with 0.5 μg/ml propidium iodide (Sigma, Cat. P4864) and analyzed in a flow cytometer (CANTO™ II, BD Biosciences) equipped with high throughput sampler. Live HEK #354 cells were gated as propidium iodide negative population and analyzed for expression of Fpn-GFP. MFI of Fpn-GFP of >2000 live cells for each compound dilution was calculated using FlowJo (Tree Star's, Oregon) and the potency of the Fpn-inhibitors to induce internalization and degradation of Fpn-GFP was calculated as described for the hepcidin internalization assay. $EC_{50}$ data of the Fpn inhibitors that were tested in the ferroportin internalization and degradation assay by FACS are listed in Table 4. The average $EC_{50}$ value of hepcidin in this assay is 0.004±0.002 μM.

TABLE 4

Average (AVE) $EC_{50}$ data of Fpn inhibitors tested in the ferroportin internalization and degradation assay is shown for multiple measurements.

| Exp. Comp. No. | EC50 (μM) |
|---|---|
| 1 | 4.66 |
| 40 | 0.81 |
| 55 | 1.029 |
| 58 | 0.387 |
| 82 | 0.689 |
| 94 | 0.22 |
| 109 | 0.885 |
| 111 | 0.075 |
| 112 | 3.775 |
| 113 | 41.330 |
| 114 | 2.956 |
| 115 | 38.250 |
| 116 | 0.590 |
| 117 | >25.0 <50 |
| 118 | 4.908 |
| 120 | 0.530 |
| 122 | 3.015 |
| 123 | 4.507 |
| 126 | 0.757 |
| 127 | 0.081 |
| 128 | 0.006 |
| 129 | 4.464 |
| 131 | 0.194 |
| 132 | 2.148 |
| 133 | 20.721 |
| 134 | 5.194 |
| 135 | 21.210 |
| 136 | 17.860 |
| 137 | 11.073 |
| 138 | 0.678 |
| 139 | >20.0 <50 |
| 140 | >20.0 <50 |
| 141 | 0.290 |
| 142 | 39.745 |
| 144 | 0.043 |
| 145 | 1.245 |
| 146 | 25.319 |
| 147 | 0.813 |
| 148 | 1.050 |
| 149 | 26.318 |
| 151 | 0.523 |
| 152 | 0.071 |
| 154 | 0.130 |
| 155 | 3.954 |
| 156 | 12.110 |
| 157 | 7.862 |
| 158 | 0.325 |
| 159 | 0.757 |
| 160 | 1.287 |
| 161 | 5.300 |
| 162 | 1.412 |
| 163 | 7.411 |
| 164 | 3.207 |
| 165 | 0.587 |
| 166 | >20.0 <50 |
| 167 | 1.462 |
| 168 | 52.150 |
| 169 | 4.121 |
| 171 | 0.571 |
| 171-B | 0.319 |
| 173 | 0.071 |
| 174 | 3.960 |
| 175 | 12.452 |
| 176 | 16.985 |

TABLE 4-continued

Average (AVE) EC$_{50}$ data of Fpn inhibitors tested in the ferroportin internalization and degradation assay is shown for multiple measurements.

| Exp. Comp. No. | EC50 (µM) |
|---|---|
| 179 | 1.207 |
| 181 | 0.930 |
| 182 | 23.692 |
| 183 | 1.850 |
| 184 | 1.188 |
| 185 | 14.361 |
| 186 | 5.059 |
| 188 | 35.985 |
| 189 | 0.679 |
| 190 | 8.522 |
| 191 | 2.512 |
| 193 | 3.946 |
| 193-B | 1.391 |
| 194 | 8.050 |
| 195 | 1.459 |
| 196 | 24.845 |
| 199 | 2.966 |
| 197 | 25.020 |
| 205 | 11.115 |
| 206 | 2.072 |
| 207 | 1.608 |
| 208 | 0.15 |
| 209 | 2.440 |
| 211 | 4.43 |
| 213 × 3 HCl | 4.14 |
| 220 | 3.82 |
| 221 | 2.36 |
| 224 | 1.83 |
| 226 | 0.49 |
| 227 | 1.58 |
| 228 | 0.46 |
| 228-B | 0.22 |
| 229 | 1.15 |
| 230 | 0.95 |
| 231 | 8.33 |
| 236 | 2.16 |
| 237 | 0.94 |
| 239 | 0.32 |
| 243 | 0.51 |
| 244 | 1.69 |
| 245 | 2.20 |
| 246 | 4.57 |
| 247 | 2.18 |
| 248 | 3.06 |
| 249 | 0.95 |
| 250 | 0.60 |
| 251 | 1.42 |
| 253 | 1.828 |
| 256 | 0.736 |
| 257 | 0.518 |
| 258 | 1.231 |
| 265 | 1.196 |
| 273 | 1.721 |
| 274 | 0.582 |
| 277 | 0.069 |

5. Ferroportin Ubiquitination and Degradation

Exposure of cells expressing ferroportin (Fpn) to hepcidin is known to trigger ubiquitination aid subsequent internalization and degradation of Fpn (Qiao, 2012). The potential of Fpn inhibitors to induce Fpn ubiquitination and degradation was investigated with an immunoprecipitation assay using the J774 mouse macrophage cell line which expresses Fpn upon treatment with iron.

J774 cells (DSMZ, Cat. ACC170) were seeded at 0.8×10$^6$ cells/ml in 15 ml of medium (DMEM Gibco Cat. 11971-025, 10% heat inactivated FBS Gibco Cat. 10500-064, 1% Penicillin-Streptomycin Gibco Cat. 15140-122) containing 200 µM Fe(III)-NTA into 10 cm tissue culture dishes (Greiner Cat. 664160) and grown overnight at 37° C. with 5% CO$_2$. Cells were incubated with synthetic human hepcidin (Bachem, Cat. H-5926) or Fpn inhibitor compounds for 10 min or 120 min. Cells were washed and lysed witi ice-cold lysis buffer (Pierce, Life Technoligies, Cat. 87787) including 1× HALT protease inhibitor cocktail (Life technologies, Cat. 78429) and 10 mM iodoacetamide (Sigma, Cat. 16125) to stabilize ubiquitinated proteins. Immunoprecipitation was done using the Pierce Classic IP Kit (Life Technologies, Cat. 26146) following the manufacturer's protocol. Briefly, 2 mg protein in 1.25 ml IP lysis buffer was incubated by mixing for 1 h at 4° C. with control agarose beads to pre-clear the lysate and reduce nonspecific signal. Unbound lysate was then incubated overnight with 12 µg per reaction of the affinity purified anti-Fpn antibody F308 that was raised against a GST fusion protein of mouse Fpn amino acids 224308. Immune complexes were captured by pipetting 14 µl settled Pierce Protein A/G Plus Agarose beads (Life Technologies, Cat. 20423) per reaction and the slurry was incubated for 1.5 h at 4° C. with gentle end-over-end mixing. The beads were washed and immune complexes were eluted directly with 75 µl SDS NuPAGE LDS sample buffer (Life Technologies, Cat. NP0007) containing DTT (Life Technologies, Cat. NP0009). After immunoprecipitation samples were analyzed by Western blotting using a rabbit anti-mouse MTP1 antiserum (Alpha Diagnostic International, Cat. MTP11-A) and a mouse anti-mono- and polyubiquitinylated conjugates monoclonal antibody (Enzo Lifesciences, Cat. BML-PW8810) for detection of ferroportin and ubiquitin, respectively. Mouse monoclonal anti-rabbit IgG light chain (Abcam, Cat. ab99697) and anti-mouse IgG H&L (Abcam, Cat. ab6789) HRP conjugates were used as secondary antibodies.

A selection of eleven Fpn inhibitors were tested in this assay and compared to hepcidin. As shown in FIG. 1 and Table 5, treatment of cells with Fpn inhibitors lead to rapid ubiquitination within 10 minutes (FIG. 1 upper panel) and degradation after 2 hours of Fpn (FIG. 1 lower panel). The degree of Fpn degradation by the Fpn inhibitors was comparable to the effect of hepcidin. However, hepcidin treatment resulted in ubiquitinated Fpn with higher molecular weight compared to Fpn inhibitor treatment, suggesting poly ubiquitination versus mono-ubiquitination by hepcidin versus Fpn inhibitors, respectively.

TABLE 5

Summary of Fpn inhibitors tested in the Fpn ubiquitination and degradation assay. The effects of treatment with Fpn inhibitors on Fpn degradation and Fpn ubiquitination were scored by visual inspection of Western blots (+ comparable to hepcidin; − no effect; +/− intermediate effect).

| Exp. Comp. No. | Concentration (uM) | Fpn Ubiquitination (10 min.) | Fpn Degradation (120 min.) |
|---|---|---|---|
| 40 | 1.9 | + | + |
| 94 | 0.3 | + | + |
| 111 | 0.3 | + | + |
| 126 | 0.8 | +/− | + |
| 127 | 0.1 | + | + |
| 128 | 0.05 | + | + |
| 152 | 0.04 | + | +/− |
| 167 | 1.5 | + | + |
| 208 | 0.2 | + | + |
| 226 | 0.5 | + | + |
| hepcidin | 0.15 | + | + |

FIG. 1 Fpn inhibitor trigger ubiquitination and degradation of Fpn expressed in a mouse macrophage cell line. J774 cells were incubated overnight with Fe(III)-NTA to induce expression of Fpn. Cells were then treated with ca. 10-fold $IC_{50}$ concentrations, as determined in the hepcidin internalization assay (see Table 1), of hepcidin (Hepcidin, 150 nM) or Fpn inhibitors Example Compound No. 208 (210 nM), Example Compound No. 167 (1.5 µM), Example Compound No. 127 (120 nM), Example Compound No. 152 (40 nM) for 10 or 120 min before harvesting and immunoprecipitation with the anti-Fpn antibody F308. Mock treated cells were harvested after 120 min (Control).

Immunoblotting of immunoprecipitates with the anti-Fpn antibody MTP1 revealed disappearance of ferroportin 120 min after treatment with the Fpn inhibitors, to a similar extent as in the sample treated with hepcidin (upper panel). Rapid ubiquitination of Fpn was observed 10 min after treatment of cells with Fpn inhibitors and hepcidin. Protein molecular weight standards are indicated on the left in kD.

6. Inhibition of Iron Efflux by Ferroportin Inhibitors

The activity of hepcidin and ferroportin inhibitor compounds regarding their ability to block iron export via ferroportin was tested on T47D cells (ECACC, Cat. 85102201) as described below.

Cells were plated in 24-well plates (Greiner, Cat. 662160) containing 350,000 cells/well and incubated overnight with 100 µM $^{58}Fe$ ($^{58}Fe(II)$-Sulfate, Vifor Pharma Batch No. ROR 3085) in 500 µM L-Ascorbic Acid (Sigma Aldrich, Cat. 795437) containing growth medium. Cells were washed once with 500 µl iron uptake buffer (IUB; PIPES 40 mM, Cat. P1851, Glucose Monohydrate 10 mM, Cat. 49158, Sodium Chloride 260 mM, Cat. 71379, Potassium Chloride 20 mM, Cat. P9541, Magnesium Sulfate 2 mM, Cat. 63138, Sigma Aldrich), then once with removal buffer (2 min incubation, BPDS 100 µM, Cat. 11890 and $Na_2S^2O_4$ 500 µM, Cat. 157953, Sigma Aldrich, in IUB) and again twice with IUB. A serial dilution of hepdicin (Bachem) or ferroportin inhibitors (4 µM-0.0064 µM, 5 fold dilution) was added in a total volume of 0.6 ml per well. Cells were incubated at 37° C. with 5% CO2 for 20 h. Supernatants were collected and $^{58}Fe$ was measured using inductively coupled plasma mass spectrometry (ICP-MS, Thermo Scientific, Element 2). Pellets were harvested for protein concentration measurements. Results are plotted as $ng^{58}Fe$ in supernatant per mg protein in cell lysates. Example Compound No. 127 inhibited iron efflux with similar potency as the endogenous Fpn ligand hepcidin (FIG. 2).

Figure 2:
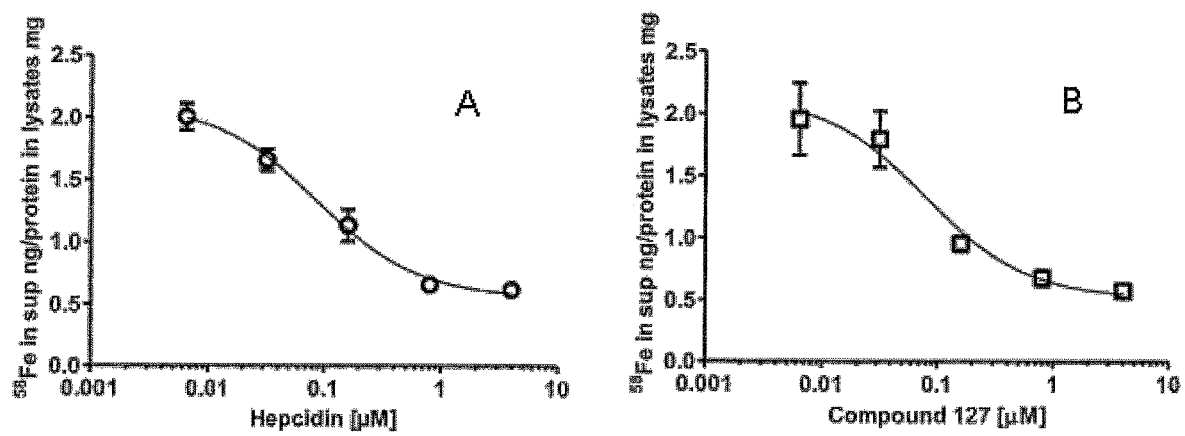
FIG. 2 shows representative iron efflux inhibition of Hepcidin ($IC_{50}$: 0.086 μM) and Example Compound No. 127 ($IC_{50}$: 0.080 μM).

FIG. 2 Representative iron efflux inhibition of Hepcidin ($IC_{50}$: 0.086 µM) and Example Compound No. 127 ($IC_{50}$: 0.080 µM).

7. Hypoferremia in Naïve Mice

Figure 3A:
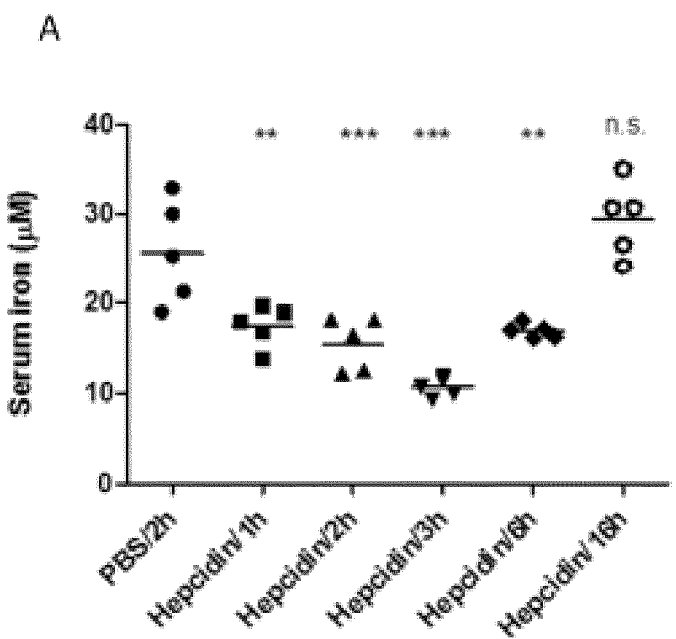
FIG. 3(A) shows kinetic of serum iron in naïve C57BL/6 mice injected with synthetic hepcidin (5 mg/kg) intraperitoneally (i.p.) for the indicated time. * - ***- indicate statistically significant serum iron reduction compared to PBS-treated mice.
Figure 3B:
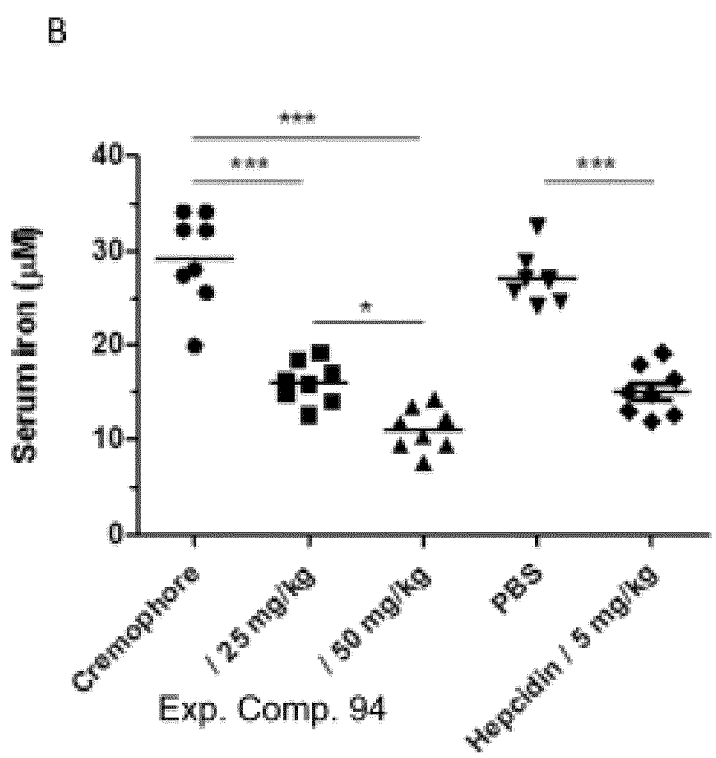
FIG. 3(B) shows serum iron levels in naïve C57BL/6 mice treated with the indicated amounts of either hepcidin (i.p.) or Example Compound 94 (Example Compound No. 94). (p.o.) for 3h.

Injection of synthetic hepcidin in wild-type (WT) naïve mice resulted in a reduction of serum iron levels (40-50% from the vehicle control) with a maximal effect at 3-4 hours post treatment (Rivera, 2005; FIG. 3A). This data suggested that the injected hepcidin binds to and triggers the internalization of ferroportin (Fpn) on duodenal enterocytes and splenocytes, causing a rapid drop in serum iron. Similarly, orally administered small molecular weight Fpn inhibitors decreased the levels of serum iron of WT C57BL/6 mice in a dose-dependent manner (FIG. 3B) with an efficacy comparable to hepcidin. This data validated the use of WT mice as a simple and reliable model for testing the acute efficacy of Fpn inhibitors in vivo. Female C57BL/6 mice (Janvier, France) at age of 9 weeks were fed a standard diet (Harlan Provimi Kliba 3436) and treated per os (p.o.) with compounds or the corresponding amount of vehicle at a volume of 10 ml/kg body weight. Fpn inhibitors were formulated in 0.5% methylcellulose/water or 20% cremophor EL/water and dosed p.o. in mice at 10, 30 or 100 mg/kg body weight. Three hours later, mice were pre terminally anesthetized in isoflurane chambers and blood was collected by retro-orbital bleeding. Mice were sacrificed by cervical dislocation and spleens, livers and duodena were harvested and used for biomarker analysis. All experiments have been conducted in compliance with the license approved by the responsible veterinarian authorities. Serum was isolated by centrifugation of blood into gel-containing microtainers and serum iron was determined by the MULTIGENT Iron assay (Abbott Diagnostics, 6K95). Eight mice per group were used and one-way ANOVA with Bonferroni's multiple comparison test was performed to analyze the statistical differences between the experimental groups. The efficacy of selected Fpn inhibitors in WT C57BL/6 mice is shown in Table 6.

FIG. 3 Serum iron reduction induced by hepcidin and ferroportin inhibitor according to Example Compound 94 (Example Compound No. 94).

A Kinetic of serum iron in naïve C57BL/6 mice injected with synthetic hepcidin (5 mg/kg) intraperitoneally (i.p.) for the indicated time. \*-\*\*\*- indicate statistically significant serum iron reduction compared to PBS-treated mice.

B Serum iron levels in naïve C57BL/6 mice treated with the indicated amounts of either hepcidin (i.p.) or Example Compound 94 (Example Compound No. 94). (p.o.) for 3 h.

TABLE 6

Table 6 Efficacy of Fpn inhibitors tested in the naïve mouse hypoferremia model.
Serum iron reduction induced by selected ferroportin inhibitors dosed p.o. in naïve WT C57BL/6 mice at 10, 30 and 100 mg/kg. Relative serum iron reduction at 3 h after dosing was calculated by subtracting the average of serum iron values of animals dosed with the Fpn inhibitor from that of vehicle treated animals. The difference in average serum iron values between vehicle and compound treated groups was then divided by the average of serum iron of the vehble control group and listed as percentage.

| | Serum Iron Reduction at 3 h (%) | | |
|---|---|---|---|
| Exp. Comp. No. | Dose 10 mg/kg | Dose 30 mg/kg | Dose 100 mg/kg |
| 12 | 15 | 20 | 45 |
| 27 | 20 | 30 | 45 |
| 39 | 10 | 20 | 35 |
| 40 | 10 | 30 | 50 |
| 55 | 0 | 20 | 55 |
| 58 | 20 | 30 | 40 |
| 90 | 0 | 0 | 40 |
| 94 | 30 | 50 | 80 |
| 118 | 8 | 24 | 49 |
| 126 | 7 | 23 | 62 |
| 127 | 17 | 47 | 54 |
| 137 | −2 | 14 | 25 |
| 154 | 13 | 35 | 56 |
| 159 | 4 | 26 | 60 |
| 167 | 19 | 17 | 34 |
| 171 | 10 | 42 | 61 |
| 193 | 13 | 11 | 31 |
| 208 | 50 | 65 | 73 |
| 228 | 13 | 26 | 55 |
| 237 | 0 | 15 | 27 |
| 239 | 12 | 20 | 51 |
| 250 | 5 | 18 | 40 |
| 277 | 6 | 21 | 54 |

8. Prevention of Iron Absorption in Anemic Rats

Figure 4:
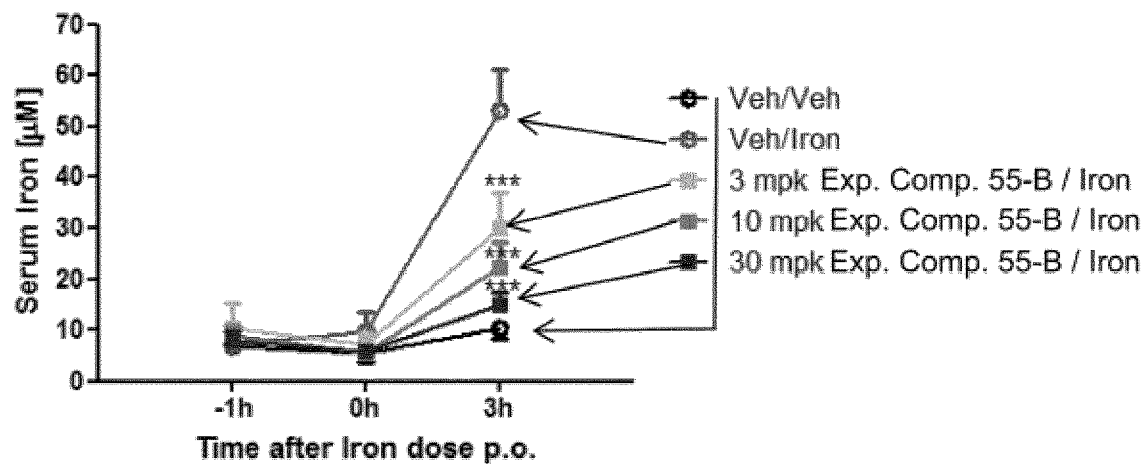
FIG. 4 shows dose-dependent block of iron absorption in anemic rats by Fpn inhibitor Example Compound No. 55.

To assess the in vivo efficacy of ferroportin (Fpn) inhibitors to block iron absorption, a series of Fpn inhibitors were tested in an anemic rat model for iron absorption. Wistar rats (34 weeks old, n=5, Janvier Labs) were fed a low iron diet (Provimi-Kliba, Cat. 2039) until their hemoglobin (Hb)

values reached 7-8 g/dl one day before dosing of the Fpn inhibitor compounds. One hour before oral application of 0.5 mg/kg of ferrous sulfate, test compounds formulated in methyl cellulose or Cremophor were dosed orally. Blood samples were taken by tail vein puncture one hour before administration of iron (−1 h), immediately after dosing of the Fpn inhibitors (0 h) and one hour (1 h), three hours (3 h) and occasionally up to 6 hours (6 h) after dosing of the test compounds. Serum iron levels were measured (Abbott Diagnostics, Cat. 6K95) and inhibition of the rise of serum iron three hours after dosing of the test compound was calculated as a measure for efficacy of the Fpn inhibitors in blocking iron absorption (Table 7). As shown in FIG. 4, oral administration of the Fpn inhibitor Example Compound No. 55 at 3 mg/kg, 10 mg/kg or 30 mg/kg reduced serum iron levels by 54%, 72% and 89%, respectively, three hours after iron dosing when compared to serum iron levels of vehicle-control animals before iron dosing and corrected for the baseline serum iron levels in vehicle-treated animals that did not receive a dose of iron.

FIG. 4 Dose-dependent block of iron absorption in anemic rats by Fpn inhibitor Example Compound No. 55. One hour before oral administration of a dose of ferrous sulfate (0.5 mg/kg), Example Compound No. 55 was orally administered either at 3 mg/kg (light blue line), 10 mg/kg (green line) or 30 mg/kg (dark blue line). Dosing of Example Compound No. 55 led to statistically significant (p<0.001) and dose-dependent inhibition of the increase in serum iron observed 3 hours after iron dosing in animals treated with vehicle (red line). Baseline serum iron levels in the vehicle-treated group that did not receive a dose of iron are also shown (black line). Averages with standard deviations are plotted for each treatment group and time point.

TABLE 7

Table 7 Fpn inhibitors tested in the anemic rat model for inhibition of iron absorption. Relative inhibition values (%) of serum iron levels are shown, corrected for average baseline serum iron levels of the control group which did not receive a dose of oral iron, compared to control groups treated with vehicle before iron dosing. Average values of groups (n = 5) treated with the indicated doses of Fpn inhibitor are shown. Statistically significant (2-way ANOVA with Bonferroni post test) differences observed between compound - treated and vehicle-treated groups are indicated (*p < 0.001; p < 0.01, *p < 0.05).

| Exp. Comp. No. | Serum Iron Inhibition (%) at 3 h | | | | |
|---|---|---|---|---|---|
| | Dose 1 mg/kg | Dose 3 mg/kg | Dose 10 mg/kg | Dose 30 mg/kg | Dose 100 mg/kg |
| 40 | nd | nd | 32** | 53*** | 97*** |
| 55 | nd | 54*** | 72*** | 91*** | 109*** |
| 58 | nd | nd | nd | 64*** | 95*** |
| 94 | 59*** | 0 | 70*** | nd | nd |
| 127 | nd | −8 | 47*** | 79*** | nd |
| 154 | nd | 22* | 16 | 58*** | nd |
| 159 | nd | 21** | 32*** | 71*** | nd |
| 167 | nd | −39*** | −34*** | 47*** | nd |
| 171 | nd | −3 | 16** | 34*** | nd |
| 208 | nd | 59*** | 86*** | 109*** | nd |

9. Correction of Hyperferremia in Beta2-Microglobulin Deficient Mice

Mutations in genes involved in sensing the systemic iron stores, such as hepcidin (Hamp1), hemochromatosis protein (HFE), hemojuvelin (HJV) and transferrin receptor 2 (TFR2) cause iron overload in mice and men. HFE, HJV and TFR2 molecules on hepatocytes are necessary for signaling of appropriate hepcidin production and their deficiency results in pathophysiologically low hepcidin levels and excessive iron absorption. HFE mutations is the most frequent cause of hereditary hemochromatosis (HH) in Caucasian adults. HFE is a MHC class I-like membrane molecule that associates with beta 2-microglobulin and participates in hepcidin transcriptional regulation through the bone morphogenetic protein receptor (BMPR) pathway. HFE−/− mice have decreased hepcidin levels, develop hyperferremia and high hepatic iron levels, which makes them a suitable animal model for studying iron overload in humans (Zhou, 1998). Mice deficient in beta 2-microglobulin (b2m−/−) develop hyperferremia and hemochromatosis similarly to HFE−/− animals, as beta 2-microglobulin is necessary for the cell-surface expression and function of HFE (Rothenberg and Voland, 1996). Due to the unavailability of HFE−/− mice, b2m−/− mice were used as a model of iron overload. A pilot study confirmed that HFE−/− and b2m−/− mice have similar iron metabolism-related parameters.

Female and male homozygous b2m−/− mice were supplied from Jackson Laboratories (B6.129P2-B2mtm1Unc/J, Stock Number: 002087) at age of 6 to 7 weeks and fed standard diet (Harlan Provimi Kliba 3436) ad libitum. Age and gender matched WT C57BL/6 mice were supplied by Charles River. To study the acute effects of ferroportin (Fpn) inhibitors in iron overload b2m−/− mice were treated with compounds or the corresponding amount of vehicle at a volume of 10 ml/kg body weight. Fpn inhibitor compounds were formulated in 0.5% methylcellulose/water or 20% cremophor EL/water and dosed p.o. in mice at 50 mg/kg body weight. WT controls received only vehicle. Three hours later, mice were pre-terminally anesthetized in isoflurane chambers and blood was collected by retro-orbital bleeding. Mice were sacrificed by cervical dislocation and spleens, livers and duodena were harvested and used for biomarker analysis. All experiments have been performed in compliance with license approved by the responsible veterinarian authorities. Serum was isolated by centrifugation of blood into gel-containing microtainers (BD Biosciences) and serum iron was determined by the MULTIGENT Iron assay (Abbott Diagnostics, Cat. 6K95). Four to nine mice per group were used and one-way ANOVA with Bonferroni's multiple comparison test was applied to analyze the statistical differences between the experimental groups.

To investigate the effects of Fpn inhibitors Example Compound No. 40 and Example Compound No. 94 in conditions of iron overload b2m−/− mice or WT controls were dosed with Fpn inhibitors or vehicle for 3 h. Due to their genetic deficiency, b2m−/− mice treated with vehicle showed significantly higher serum iron levels compared to WT mice (FIG. 5, group average of 60 µM in A and 56 µM in B). Treatment of b2m−/− mice with Example Compound No. 40 or Example Compound No. 94 at 50 mg/kg for 3 h corrected the elevated serum iron to the levels observed in WT controls (FIG. 4). These data demonstrated the acute efficacy of small molecular weight ferroportin inhibitors in a disease relevant model. Serum iron correction was observed in further studies as summarized in Table 8.

Figure 5:
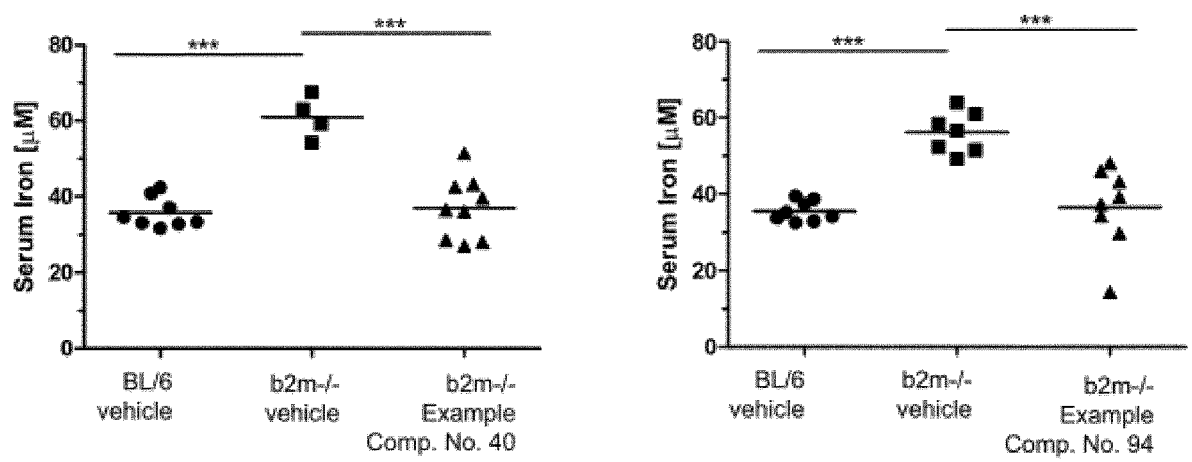
FIG. 5 shows complete correction of the elevated serum iron levels in b2m-/- mice by treatment with the ferroportin inhibitors Example Compound No. 40/ methylcellulose and Example Compound No. 94/ cremophor EL for 3h.

FIG. 5 Complete correction of the elevated serum iron levels in b2m−/− mice by treatment with the ferroportin inhibitors Example Compound No. 40/methylcellulose (A.) and Example Compound No. 94/cremophor EL (B.) for 3 h.

TABLE 8

Table 8 Fpn inhibitors tested in the beta2-microglobulin deficient mouse model for lowering elevated serum iron levels
Blood was collected 1 (#) or 3 (##) hours after oral administration of the indicated doses of Fpn inhibitors to beta2-microglobulin deficient mice and serum iron concentrations were measured. Relative reduction (%) of serum iron levels are shown, which were calculated by subtracting the average of serum iron values of animals dosed with the Fpn inhibitor from that of vehicle-treated animals. The difference in average serum iron values between vehicle and compound treated groups was then divided by the average of serum iron of the vehicle control group and listed as percentage. Values are listed separately for female (♀) and male (♂) animals, because a marked sex-dependent difference in efficacy was noted. Statistically significant (2-way ANOVA with Bonferroni post test) differences observed between compound-treated and vehicle-treated groups are indicated (*p < 0.001; p < 0.01, *p < 0.05).

| Exp. Comp. No. | | Serum Iron Reduction (%) Dose 20 mg/kg | Dose 60 mg/kg |
|---|---|---|---|
| 40# | ♀ | 0 | 13 |
|     | ♂ | 35** | 32** |
| 40# | ♀ | nd | 10 |
|     | ♂ | nd | 58** |
|     | ♀ | nd | 47 |
|     | ♂ | nd | 67 |
| 127 | ♀ | 47*** | 74*** |
|     | ♂ | 21 | 83** |
| 208## | ♀ | 9 | 49*** |
|     | ♂ | 44 | 67** |

10. Prevention of Iron Overload in Beta2-Microglobulin Deficient Mice

As a result of decreased hepcidin levels and increased iron absorption in the gut beta2-microglobulin deficient (b2m−/−) mice on a standard diet accumulate excessive amounts of iron in liver, heart and pancreas. A pilot study showed that liver iron loading in b2m−/− starts at age of 3-4 weeks and that liver iron levels reached up to 4 fold the liver iron content of wild-type (WT) mice at age of 6 weeks. In addition, feeding 3 week old b2m−/− mice a diet with low iron content (LID) immediately after weaning prevented liver iron loading by age of 6-7 weeks. The efficacy of the Fpn inhibitors to prevent liver iron accumulation in b2m−/− mice was investigated. Three weeks old b2−/− mice fed LID were dosed with either Fpn inhibitor or vehicle (methylcellulose; 10 ml/kg). Mice had access to drinking water supplemented with 1 mM $^{58}$Fe(II)-sulfate and 10 mM ascorbic acid. Dosing of Fpn inhibitor or vehicle followed by exposure to iron-containing water was repeated for 14 days. Mice were euthanized and the liver and spleen iron contents were analyzed by ICP-OES (all iron isotopes) and liver tissue was also analyzed for $^{58}$Fe concentration (ICP-MS). The data summarized in Table 9 illustrates that oral dosing of Fpn inhibitors for two weeks prevented liver iron loading in b2m−/− mice and increased spleen iron concentrations, indicating inhibition of ferroportin both in the intestine and in the spleen.

These data demonstrated the efficacy of a small molecular weight ferroportin inhibitor to prevent liver iron loading in b2−/− mice, which provides a proof of concept in a disease-relevant model.

TABLE 9

Fpn inhibitors tested in the beta2-microglobulin deficient mouse model for inhibition of liver iron overload.
Livers and spleens were collected after 14 day treatment (p.o.; b.i.d) of beta2-microglobulin deficient mice with the indicated doses of Fpn inhibitors. Total liver and spleen tissue iron concentrations were measured using ICP-OES and $^{58}$Fe liver concentrations were determined with ICRMS. Relative changes (%) of tissue iron levels are shown, which were calculated by normalizing the difference between the averages of tissue iron values of animals dosed with the Fpn inhibitors and those of vehicle-treated animals with the average of vehicle controls. Values are listed separately for female (♀) and male (♂) animals, because a marked sex-dependent difference in efficacy was noted. Statistically significant (2-way ANOVA with Bonferroni post test) differences observed between compound-treated and vehicle-treated groups are indicated (*p < 0.001; p < 0.01, *p < 0.05).

| Exp. Comp. No. | | Total Spleen Iron Increase (%) | | Total Liver Iron Reduction (%) | | $^{58}$Fe Liver Iron Reduction (%) | |
|---|---|---|---|---|---|---|---|
| | | Dose (mg/kg) | | | | | |
| | | 20 | 60 | 20 | 60 | 20 | 60 |
| 40 | ♀ | 50* | 85*** | 32 | 67* | 44 | 80* |
|    | ♂ | 25 | 24 | 31 | 69*** | 53* | 81*** |
| 40 | ♀ | nd | 9 | nd | 66 | nd | 67 |
|    | ♂ | nd | 36 | nd | 85** | nd | 95** |
| 94 | ♀ | nd | 65 | nd | 57 | nd | na |
|    | ♂ | nd | 41 | nd | 79 | nd | na |
| 127 | ♀ | 71* | 51 | −38 | 2 | 34 | 63*** |
|     | ♂ | −7 | −16 | 50** | 65*** | 71*** | 73*** |
| 208 | ♀ | 56** | 150*** | 15 | 8 | 71* | 87** |
|     | ♂ | 21 | 43 | 41 | 84 | 58 | 94 | nd, not determined;
na, not available.

11. Improvement of Anemia, Ineffective Erythropoiesis and Iron Overload in a Mouse Model of β-Thalassemia Intermedia β-thalassemia is inherited anemia caused by mutations in the β-globin gene of hemoglobin resulting in abnormal red blood cells with decreased life span. The most severe form, thalassemia major, requires blood transfusions which result in secondary iron overload. Patients with thalassemia intermedia have a moderate transfusion-independent anemia but still develop iron overload due to inefficient erythropoiesis and chronic repression of hepcidin production.

As shown in the previous examples, oral ferroportin (Fpn) inhibitors similarly to hepcidin blocked ferroportin mediated export of iron from cells in vitro and upon dosing in wild-type mice transiently reduced serum iron. Based on these findings and published studies (Schmidt P J, et al, Blood 2013, Guo S, et al, JCI, 2013 and Casu C. et al, Blood, 2016) Fpn inhibitors were examined with respect to its capacity to prevent iron loading and improve erythropoiesis in thalassemia intermedia by restricting iron absorption and reutilization from senescent erythrocytes. The efficacy of Fpn inhibitors was investigated using a mouse model of transfusion-independent β-thalassemia. Mice with heterozygous deletion of β1 and β2 globin genes (called Hbb th3/+ mice) develop transfusion-independent anemia, ineffective erythropoiesis, splenomegaly and secondary iron overload in spleen, liver and kidneys. Heterozygous Hbb th3/+ mice were supplied from Jackson Laboratories (B6;129P-Hbb-b1tm1Unc Hbb-b2tm1Unc/J, Stock Number: 002683) at age of 8-18 weeks and during experiments fed a low iron diet (Harlan Provimi Kliba 2039, 13.4 ppm Fe) ad libitum. Hbb th3/+ mice were dosed twice daily with either compound at 20 or 60 mg/kg or with methylcellulose (10 ml/kg, Sigma, Cat. 274429) as a vehicle. Between both doses mice had access to drinking water supplemented with 1 mM $^{58}$Fe(II)- sulfate (Vifor Pharma, Batch No. ROR 3096) and 10 mM ascorbic acid (Sigma, Cat. 795437) for 6 h. The concentration of Fe(II)-Sulfate supplied in the drinking water has been adjusted to substitute for intake of standard rodent diet with iron content of 250 ppm. Water without $^{58}$Fe(II)-Sulfate and ascorbic acid was provided during the remaining 18 h. Dosing of Fpn inhibitors or vehicle followed by exposure to iron-containing water was repeated for 20 to 46 days in individual experiments.

As previously shown in wild-type and b2m−/− mice, Fpn inhibitors dosed for 3 h in Hbb th3/+ mice reduced efficiently serum iron levels also in this mouse strain (Table 10), demonstrating the ability of these small molecules to cause iron restriction.

Hbb th3/+ mice are anemic with hemoglobin levels in the range of 70-80 g/L. Oral administration of Fpn inhibitors in Hbb th3/+ mice for two weeks increased significantly hemoglobin levels compared to vehicle treated mice (Table 10). The change of hemoglobin levels in compound-dosed compared to vehicle-treated group reached 19-22 g/L by the study end. Additional hematologic parameters were measured in terminal blood using automated blood cell analyzer. Treating Hbb th3/+ mice with Fpn inhibitors increased red blood cell counts, hematocrit and decreased reticulocyte concentration and red cell distribution width (RDW), indicating improved erythropoiesis. In addition, Hbb th3/+ mice receiving Fpn inhibitors had significantly lower leucocyte counts in blood compared to the vehicle group, further demonstrating the beneficial effect of Fpn inhibitors in correcting pathologically altered parameters in the disease model. Therefore, Fpn inhibitors improved significantly anemia and corrected blood composition in the mouse model of thalassemia *intermedia*.

The inefficient erythropoiesis of Hbb th3/+ mice causes excessive proliferation of erythroid precursors in spleen, leading to splenomegaly. Treatment of Hbb th3/+ mice with Fpn inhibitors resulted in significant reduction in spleen weight, therefore highlighting the potential of Fpn inhibitors to revert splenomegaly (Table 10).

The effect of Fpn inhibitors on erythropoiesis was studied by analyzing the percentage of differentiating erythroid precursors in bone marrow and spleen using flow cytometry and Ter119 (eBioscience, Cat. 17-5921) and CD44 (BioLegend, Cat. 103028) markers. Bone marrow or spleen cells isolated from Hbb th3/+ mice treated with Fpn inhibitors contained significantly reduced percentage of the early erythroid precursors proerythroblasts, basophilic, and polychromatic erythroblast and increased percentage of mature erythrocytes compared to vehicle-treated Hbb th3/+ mice (Table 10). These data demonstrated that Fpn inhibitors ameliorated the inefficient erythropoiesis in Hbb th3/+ mice and are in agreement with the improved hematological parameters in blood.

Serum erythropoietin levels in Hbb th3/+ mice and patients with thalassemia are upregulated due to a feedback response to anemia, hypoxia and inefficient erythropoiesis (Guo et al. JCI, 2013). Hbb th3/+ mice treated with Fpn inhibitors produced significantly less serum erythropoietin (DuoSet ELISA R&D Systems, Cat. DY959) compared to the vehicle group, most likely as a consequence of partially corrected anemia and improved erythropoiesis (Table 10).

Elevated erythropoietin levels in Hbb th3/+ mice hduced overexpression of erythroferrone, an erythroid regulator hormone known to suppress hepcidin (Kautz L. et al, Nat. Genet., 2014). In agreement with reduced serum erythropoietin, erythroferrone mRNA expression was significantly reduced in spleens of Fpn inhibitor-treated Hbb th3/+ mice compared to those administered with vehicle alone (Table 10). Erythroferrone is produced by erythrocyte precursors proliferating massively in spleens of Hbb th3/+ mice as a consequence of extramedullar erythropoiesis. Therefore, the effect of Fpn inhibitors on erythroferrone expression in spleen is mediated by the improved erythropoiesis.

Increased iron demand due to inefficient erythropoiesis and chronically low hepcidin levels in patients with thalassemia causes organ iron loading and associated morbidities, such as hepatocellular carcinoma and heart failure (Rivella S. Haematologica, 2015). Hbb th3/+ mice absorb excessive amounts of iron as a consequence of inadequately low hepcidin levels relative to the high iron content in liver, spleen and kidney and increased ferroportin expression in duodenum (Gardenghi S., Blood, 2007). Total liver iron and $^{58}$Fe content in organs of Hbb th3/+ mice treated with either vehicle or Fpn inhibitors were analyzed by inductively coupled plasma optical emission spectrometry (ICP-OES) and inductively coupled plasma mass spectrometry (ICP-MS), respectively. $^{58}$Fe concentrations in livers and spleens of Hbb th3/+ mice dosed with Fpn inhibitors were significantly lower compared to those of vehicle treated mice, indicating that Fpn inhibitors prevent organ iron accumulation (Table 10).

As Fpn inhibitors are systemically available, they are able to block iron export in all ferroportin expressing tissues, including duodenum, spleen and liver. Accordingly, Fpn inhibitors are expected to prevent iron absorption from duodenum, however, they could not remove pre-existing iron in liver and spleen. Indeed, total liver iron in mice treated with Fpn inhibitor or vehicle remained unchanged (not shown). Importantly, Fpn inhibitors reduced significantly $^{58}$Fe concentration in spleens and livers of Hbb th3/+ mice, demonstrating the ability of these small molecules to prevent iron loading.

Additionally, reactive oxygen species (ROS) were detected in bone marrow cells using a fluorescent indicator, CM-H$_2$DCFDA (Thermo Fisher Scientific, Cat. C6827). Flow cytometric analysis showed that Fpn inhibitors decreased significantly ROS in mature erythroid cells compared to vehicle treated Hbb th3/+ mice (Table 10).

These data demonstrated the disease-modifying capacity of orally administered small molecular weight ferroportin inhibitors in improving anemia and ineffective erythropoiesis, as well in reducing splenomegaly and preventing further liver and spleen iron loading in a disease model of β-thalassemia *intermedia*.

Table 10. Efficacy of Ferroportin inhibitors in a mouse model of thalassemia intermedia (Hbb th3/+ mice). The indicated Fpn inhibitors were dosed twice daily for 27 days (Example Compound 127) or 46 days (Example Compound 40). Data are expressed as difference to the vehicle control group for hemoglobin and as % change to the vehicle control group for all other parameter shown

| Parameter | Exp. Comp. No. 40 | Exp. Comp. No. 127 |
|---|---|---|
| Decrease in serum iron by 20/60 mg/kg compound | 28/58% | 68/81% |
| Correction of anemia at day 20-48 by 20/60 mg/kg | 6/13 g/L | 12/20 g/L |
| Increase in blood erythrocyte counts by 20/60 mg/kg compound | 2/22% | 0/36% |
| Decrease in blood reticulocyte counts by 20/60 mg/kg compound | 19/43% | 16/61% |

Table 10. Efficacy of Ferroportin inhibitors in a mouse model of thalassemia intermedia (Hbb th3/+ mice). The indicated Fpn inhibitors were dosed twice daily for 27 days (Example Compound 127) or 46 days (Example Compound 40). Data are expressed as difference to the vehicle control group for hemoglobin and as % change to the vehicle control group for all other parameter shown

| Parameter | Exp. Comp. No. 40 | Exp. Comp. No. 127 |
|---|---|---|
| Increase in hematocrit by 20/60 mg/kg compound | 0/1% | 3/20% |
| Decrease in RDW by 20/60 mg/kg compound | NA/NA | 19/25% |
| Decrease in leukocyte counts by 20/60 mg/kg compound | 0/36% | 46/66% |
| Decreased in ROS in bone marrow erythrocytes | NA/NA | NA/75% |
| Decrease in relative spleen weight by 20/60 mg/kg | 23/48% | 40/61% |
| Decrease in $^{58}$Fe spleen iron content by 20/60 mg/kg compound | 19/51% | 43/68% |
| Prevention of liver $^{58}$Fe loading by 20/60 mg/kg | 20/48% | 39/59% |
| Decrease in serum erythropoietin by 20/60 mg/kg compound | 6/37% | 32/33% |
| Decrease in spleen erythroferrone mRNA by 20/60 mg/kg compound | NA/NA | 1012/3030% |

Preparation of Example Compounds

General Experimental Details

Commercially available reagents and solvents (HPLC grade) were used without further purification. 1H NMR spectra were recorded on a Bruker DRX 500 MHz spectrometer, a Bruker DPX 250 MHz spectrometer or a Bruker Avance spectrometer 400 MHz in deuterated solvents. Chemical shifts (δ) are in parts per million.

Compounds were purified by flash column chromatography on normal phase silica on Biotage Isolera systems using the appropriate SNAP cartridge and gradient. Alternatively compounds were purified on reverse phase using Biotage Isolera systems with the appropriate C18 SNAP cartridge and reverse-phase eluent or by preparative HPLC (if stated otherwise).

Analytical HPLC-MS

Method A (MET/CR/1673)

| Column | Supelco Ascentis Express (Part No. 53802-U) 2.1 × 30 mm, 2.7 μm |
|---|---|
| Column Temp | 40° C. |
| Mobile Phase | A, Water + 0.1% Formic acid |
| | B, Acetonitrile + 0.1% Formic acid |

| Gradient | Time (mins) | % organic |
|---|---|---|
| | 0 | 5 |
| | 1.5 | 100 |
| | 1.6 | 100 |
| | 1.61 | 5 |

| Flow rate | 1 ml/min |
|---|---|
| Injection Vol | 3 μl |
| Detection | |
| Signal | UV 215 |
| PDA Spectrum | Range: 210-420 nm step: 1 nm |
| MSD Signal settings | Scan Pos (Shimadzu): 100-1000 |
| | Scan Pos (MS14): 130-850 |

Method B (MET/CR/1600)

| Column | Phenomenex Gemini-NX C18 (Part No. 00D-4453-B0) 2.0 × 100 mm, 3 μm column |
|---|---|
| Column Temp | 40° C. |
| Mobile Phase | A, 2 mM amm. bicarbonate, buffered to pH 10 |
| | B, Acetonitrile |

| Gradient | Time (mins) | % organic |
|---|---|---|
| | 0.00 | 5 |
| | 5.50 | 100 |
| | 5.90 | 100 |
| | 5.92 | 5 |

| Flow rate | 0.5 ml/min |
|---|---|
| Injection Vol | 3 μl |
| Detection | |
| Signal | UV 215 |
| PDA Spectrum | Range: 210-420 nm step: 1 nm |
| MSD Signal settings | Scan Pos: 100-1000 |

Method C (MET/CR/1416)

| Column | Waters Atlantis dC18 (Part No. 186001295) 2.1 × 100 mm, 3 μm |
|---|---|
| Column Temp | 40° C. |
| Mobile Phase | A, Water + 0.1% Formic acid |
| | B, Acetonitrile + 0.1% Formic acid |

| Gradient | Time (mins) | % organic |
|---|---|---|
| | 0.00 | 5 |
| | 5.00 | 100 |
| | 5.40 | 100 |
| | 5.42 | 5 |

| Flow rate | 0.6 ml/min |
|---|---|
| Injection Vol | 3 μl |
| Detection | |
| Signal | UV 215 |
| PDA Spectrum | Range: 210-420 nm step: 1 nm |
| MSD Signal settings | Scan Pos: 100-1000 |

Method D—(MET/uPLC/AB101)

| Column | Phenomenex Kinetix-XB C18 (Part No.00D-4498-AN) 2.1 × 100 mm, 1.7 μm |
|---|---|
| Column Temp | 40° C. |
| Mobile Phase | A, Water + 0.1% Formic acid |
| | B, Acetonitrile + 0.1% Formic acid |

| Gradient | Time (mins) | % organic |
|---|---|---|
| | 0.00 | 5 |
| | 5.30 | 100 |
| | 5.80 | 100 |
| | 5.82 | 5 |

| Flow rate | 0.6 ml/min |
|---|---|
| Injection Vol | 1 μl |
| Detection | |
| Signal | UV 215 |
| PDA Spectrum | Range: 200-400 nm step: 1 nm |
| MSD Signal settings | Scan Pos: 150-850 |

Method E—(MET/CR/1278)

| Column | Waters Atlantis dC18 (Part No. 186001291) 2.1 × 50 mm, 3 µm |
|---|---|
| Column Temp | 40° C. |
| Mobile Phase | A, Water + 0.1% Formic acid B, Acetonitrile + 0.1% Formic acid |

| Gradient | Time (mins) | % organic |
|---|---|---|
| | 0.00 | 5 |
| | 2.50 | 100 |
| | 2.70 | 100 |
| | 2.71 | 5 |
| | 3.50 | 5 |

| Flow rate | 1 ml/min |
|---|---|
| Injection Vol | 3 µl |
| Detection Signal | UV 215 |
| PDA Spectrum | Range: 210-420 nm step: 1 nm |
| MSD Signal settings | Scan Pos (Shimadzu): 100-1000 Scan Pos (M514): 130-850 |

Method F—MET/CR/0990

| Column | Phenomenex Gemini-NX C18 (00B-4453-B0) 2.0 × 50 mm, 3 um |
|---|---|
| Column Temp | 40° C. |
| Mobile Phase | A, 2 mM Ammonium bicarbonate, buffered to pH 10 B, Acetonitrile |

| Gradient | Time (mins) | % organic |
|---|---|---|
| | 0.00 | 1 |
| | 1.80 | 100 |
| | 2.10 | 100 |
| | 2.30 | 1 |
| | 3.50 | 1 |

| Flow rate | 1 ml/min |
|---|---|
| Injection Vol | 3 µl |
| Detection Signal | UV 215 |
| PDA Spectrum | Range: 210-420 nm step: 1 nm |
| MSD Signal settings | Scan Pos: 150-850 |

Method G—MET/CR/2044

| Column | Thermofisher Hypercarb ™ Porous Graphitic Carbon 2.1 mm × 50 mm, 3 µm |
|---|---|
| Column Temp | 40° C. |
| Mobile Phase | A, 25 mM Ammonium acetate in HPLC grade water pH-5 B, 25 mM Ammonium acetate in HPLC grade acetonitrile |

| Gradient | Time (mins) | % organic |
|---|---|---|
| | 0.00 | 2 |
| | 4 | 100 |
| | 5 | 100 |
| | 6 | 2 |
| | 6.5 | 2 |

| Flow rate | 0.5 ml/min |
|---|---|
| Injection Vol | 3 µl |
| Detection Signal | UV 215 |
| PDA Spectrum | Range: 210-420 nm step: 1 nm |
| MSD Signal settings | Scan Pos: 150-850 |

Method H—METUPLCMS-A-004

| Column | Acquity UPLC BEH C18 2.1 mm × 50 mm, 1.7 µM |
|---|---|
| Column Temp | Ambient |
| Mobile Phase | A, Water/acetonitrile, 9:1 + 0.1% formic acid B, Acetonitrile/water, 9:1 + 0.1% formic acid |

| Gradient | Time (mins) | % organic |
|---|---|---|
| | 0.00 | 5 |
| | 1.5 | 100 |
| | 1.7 | 100 |
| | 1.8 | 5 |
| | 2.0 | 5 |

| Flow rate | 0.7 ml/min |
|---|---|
| Injection Vol | 4 µl |
| Detection Signal | UV 215 |
| PDA Spectrum | Range: 210-420 nm |
| MSD Signal settings | Scan Pos: 150-800 |

Method I—METUPLCMS-A-006

| Column | Acquity UPLC HSS T3 2.1 mm × 100 mm, 1.8 µm |
|---|---|
| Column Temp | 40° C. |
| Mobile Phase | A, Water/acetonitrile, 9:1 + 0.1% formic acid B, Acetonitrile/water, 9 1 + 0.1% formic acid |

| Gradient | Time (mins) | % organic |
|---|---|---|
| | 0.00 | 5 |
| | 5.30 | 100 |
| | 5.80 | 100 |
| | 5.82 | 5 |
| | 6.00 | 5 |

| Flow rate | 0.7 ml/min |
|---|---|
| Injection Vol | 4 µl |
| Detection Signal | UV 215 |
| PDA Spectrum | Range: 210-420 nm |
| MSD Signal settings | Scan Pos: 150-800 |

Method J—METUPLCMS-A-007

| Column | Acquity UPLC BEH C18 2.1 × 100 mm, 1.7 µm |
|---|---|
| Column Temp | 40° C. |
| Mobile Phase | A, 2 mM Ammonium Bicarbonate B, Acetonitrile: 2 mM Ammonium Bicarbonate (95:5) |

| Gradient | Time (mins) | % organic |
|---|---|---|
| | 0.00 | 5 |
| | 5.30 | 100 |
| | 5.80 | 100 |
| | 5.82 | 5 |
| | 6.00 | 5 |

| Flow rate | 0.6 ml/min |
|---|---|
| Injection Vol | 4 µl |
| Detection Signal | UV 215 |
| PDA Spectrum | Range: 210-420 nm |
| MSD Signal settings | Scan Pos: 150-800 |

Method K—MET/UPLCMS-A/013

| | |
|---|---|
| Column | Acquity UPLC HSS T3 |
| | 2.1 × 100 mm, 1.8 μm |
| Column Temp | 40° C. |
| Mobile Phase | A, Water + 0.1% formic acid, acetonitrile + 0.1% formic acid (90:10) |
| | B, Acetonitrile + 0.1% formic acid, water + 0.1% formic acid (90:10) |

| Gradient | Time (mins) | % organic |
|---|---|---|
| | 0.00 | 30 |
| | 5.30 | 100 |
| | 5.80 | 100 |
| | 5.82 | 30 |
| | 6.00 | 30 |

| | |
|---|---|
| Flow rate | 0.6 ml/min |
| Detection Signal | UV 215 |
| PDA Spectrum | Range: 210-420 nm |
| MSD Signal settings | Scan Pos: 150-800 |

Method L—MET-THERMOMS-B-015

| | |
|---|---|
| Column | X-bridge C-18 |
| | 250 × 4.6 mm, 5 μm |
| Column Temp | NA |
| Injection Vol. | 10 μl |
| Mobile Phase | A, 2 mM Ammonium Bicarbonate (pH-10)/pH 10 adjusted using liq. NH$_3$ |
| | B, Acetonitrile |

| Gradient | Time (mins) | % organic |
|---|---|---|
| | 0.0 | 5 |
| | 10.0 | 100 |
| | 10.5 | 100 |
| | 11.0 | 5 |
| | 12.0 | 5 |

| | |
|---|---|
| Detection Signal | UV 215 |
| MSD Signal settings | Scan Pos: 50-1000 |

Method M—MET/CR/1410

| | |
|---|---|
| Column | Phenomenex Kinetex Core-Shell C18 |
| | (Part No. 00D-4601-AN) |
| | 2.1 × 50 mm, 5 μm |
| Column Temp | 40° C. |
| Mobile Phase | A, Water + 0.1% Formic acid |
| | B, Acetonitrile + 0.1% Formic acid |

| Gradient | Time (mins) | % organic (B) |
|---|---|---|
| | 0.00 | 5 |
| | 1.20 | 100 |
| | 1.30 | 100 |
| | 1.31 | 5 |

| | |
|---|---|
| Flow rate | 1.2 ml/min |
| Injection Vol | 3 μl |

Preparative HPLC—Neutral pH Method

| | |
|---|---|
| Column | Waters Sunfire C18 (Part no.186003971) |
| | 30 × 100 mm, 10 um |
| Column Temp | Room temperature |
| Mobile Phase | A, Water |
| | B, Acetonitrile |

| Gradient | Time (mins) | % organic |
|---|---|---|
| | 0 | 10 |
| | 2 | 10 |
| | 2.5 | 15 |
| | 14.5 | 100 |
| | 15.5 | 100 |
| | 16 | 10 |
| | 17 | 10 |

| | |
|---|---|
| Flow rate | 40 ml/min |
| Injection Vol | 1500 μl |
| Detection Signal | UV 215 |

Preparative HPLC—Low pH Prep Method (Acid)

| | |
|---|---|
| Column | Waters Sunfire C18 (Part no.186003971) |
| | 30 × 100 mm, 10 μm |
| Column Temp | Room temperature |
| Mobile Phase | A, Water + 0.1% Formic acid |
| | B, Acetonitrile + 0.1% Formic acid |

| Gradient | Time (mins) | % organic |
|---|---|---|
| | 0 | 5 |
| | 2 | 5 |
| | 2.5 | 10 |
| | 14.5 | 100 |
| | 15.5 | 100 |
| | 16 | 5 |
| | 17 | 5 |

| | |
|---|---|
| Flow rate | 40 ml/min |
| Injection Vol | 1500 μl |
| Detection Signal | UV 215 |

Preparative HPLC—High pH Prep Method (Basic)

| | |
|---|---|
| Column | Waters Xbridge C18 (Part no.186003930) |
| | 30 × 100 mm, 10 μm |
| Column Temp | Room temperature |
| Mobile Phase | A, Water + 0.2% Ammonium hydroxide |
| | B, Acetonitrile + 0.2% Ammonium hydroxide |

| Gradient | Time (mins) | % organic |
|---|---|---|
| | 0 | 5 |
| | 2.5 | 5 |
| | 16.05 | 95 |
| | 18.2 | 95 |
| | 19.1 | 5 |
| | 20 | 5 |

| | |
|---|---|
| Flow rate | 40 ml/min |
| Injection Vol | 1500 μl |
| Detection Signal | UV 215 |

Abbreviations

AcOH Acetic acid
AIBN 2,2'-Azobis(2-methylpropionitrile)
BH$_3$ Borane
Boc$_2$O Di-tert-butyl dicarbonate
CaCO$_3$ Calcium carbonate
CBz Benzyloxy carbamate
CDI 1,1'-Carbonyldiimidazole
CHCl$_3$ Chloroform d Day(s)
DAST N-ethyl-N-(trifluoro-lambda-4-sulfanyl)ethanamine
DBU 1,8-Diazabicycloundec-7-ene
DCC N,N'-dicyclohexylcarbodiimide
DCE 1,2-Dichloroethane
DCM Dichloromethane
DIAD Diisopropyl azodicarboxylate
DIPEA N,N-diisoproylethylamine
DMAP N,N-dimethylpyridin-4-amine
DMF N,N-dimethylformamide
$Et_2O$ Diethyl ether
EtOAc Ethyl acetate
EtOH Ethanol
h Hour(s)
HATU 1-[Bis(dimethylamino)methylene]-1H-1,2,3-triazolo[4,5-b]pyridinium-3-Oxide Hexafluorophosphate
HCl Hydrochloric acid
HPLC High Performance Liquid Chromatography
IPA Isopropyl alcohol
$K_2CO_3$ Potassium carbonate
KO$^t$Bu Potassium tert-butoxide
KHMDS Potassium 1,1,1,3,3,3-hexamethyldisilazan-2-ide
$KHSO_4$ Potassium bisulfate
$LiAlH_4$ Lithium Aluminium Hydride
LiCl Lithium chloride
LiOH Lithium hydroxide
MeCN Acetonitrile
MeI Methyl iodide
MeOH Methanol
min Minute(s)
MW Molecular weight
$NaBH_4$ Sodium borohydride
$NaHCO_3$ Sodium hydrogen carbonate
NaH Sodium Hydride (60% in mineral oil)
NaOH Sodium hydroxide
NBS N-bromosuccinimide
NCS N-chlorosuccinimide
$NH_4Cl$ Ammonium chloride
Pd/C Palladium on carbon
$PdCl_2$(dppf) Dichloro[1,1'-bis(diphenylphosphino)ferrocene]palladium(II)
$Pd_2dba_3$ Tris(dibenzylideneacetone)dipalladium(0)
$PPh_3$ Triphenylphosphine
PTSA p-Toluenesulfonic acid
TBME tert-butyl methyl ether
TBSCl tert-Butyldimethylsilyl chloride
TEA Triethylamine
TFA Trifluoroacetic acid
TMOF Trimethyl orthoformate
Xantphos 4,5-Bis(diphenylphosphino)-9,9-dimethylxanthene Example Compound No 1

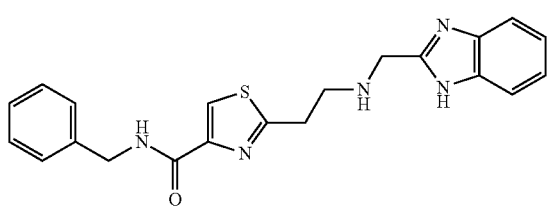 [SMILES: O=C(NCc1ccccc1)c1csc(CCNCc2nc3ccccc3[nH]2)n1]

Example compound No. 1 can be prepared as described in WO 2011/029832.
Intermediates
Scheme A Above:

Tert-butyl N-[(3-fluoroyridin-2-yl)methyl]carbamate (A1)

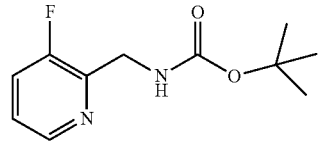 [SMILES: CC(C)(C)OC(=O)NCc1ncccc1F]

A suspension of 3-fluoropyridine-2-carbonitrile (8.0 g, 6.55 mmol), di-tert-butyl dicarbonate (15.7 g, 72.07 mmol), TEA (10.05 ml, 72.07 mmol) in EtOH (300 ml) was purged with $N_2$. Pd/C (10% wt., 0.7 g, 6.55 mmol) was added and the reaction mixture was stirred under an atmosphere of hydrogen for 16 h. The reaction mixture was filtered through celite, rinsed with MeOH (100 ml) and the filtrates were removed under vacuum to afford the crude product. Purification by flash column chromatography (gradient elution 0-70% EtOAc/heptane) afforded the title compound (11.3 g, 72%) as an off-white solid.

1H-NMR (DMSO-d6, 250 MHz): d[ppm]=8.41-8.31 (m, 1H), 7.65 (ddd, J=10.1, 8.3, 1.3 Hz, 1H), 7.38 (dt, J=8.5, 4.4 Hz, 1H), 7.18 (s, 1H), 4.30 (d, J=5.4 Hz, 2H), 1.37 (s, 9H)

HPLCMS (Method A): [m/z]: 226.9 $[M+H]^+$ (3-Fluoropyridin-2-yl)methanamine Dihydrochloride (A2)

In a similar fashion to general procedure 2, tert-butyl N-[(3-fluoropyridin-2-yl)methyl]carbamate (A1) (11.3 g, 47.45 mmol) and 12M HCl (59.3 ml, 711.72 mmol) in MeOH (150 ml) at 40° C. for 2 h, gave the title compound (9.7 g, 100%) as an off-white solid.

1H-NMR (Methanol-d4, 500 MHz): d[ppm]=8.48 (dt, J=4.7, 1.3 Hz, 1H), 7.69 (ddd, J=9.7, 8.5, 1.2 Hz, 1H), 7.50 (dt, J=8.8, 4.5 Hz, 1H), 4.37 (s, 2H)

HPLCMS (Method A): [m/z]: 126.9 $[M+H]^+$

Scheme B Above:

(4, 6-Dimethylpyridin-3-yl)methanamine Hydrochloride (B1)

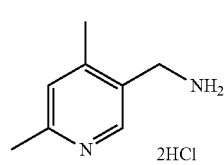

4,6-dimethylpyridine-3-carbonitrile (0.15 g, 1.135 mmol) in MeOH (150 ml) was subjected to the H-Cube with 10% palladium on carbon at a flow rate of 1 ml/min using $H_2$ at 50 bar and room temperature into a solution of 1M HCl (1 ml). The solvent was evaporated in vacuo to give the title compound (190 mg, 64%) as a white solid. Used without purification.

1H-NMR (DMSO-d6, 500 MHz): d[ppm]=8.74-8.66 (m, 1H), 8.62-8.42 (m, 3H), 7.76-7.64 (m, 1H), 4.23-4.13 (m, 2H), 2.66-2.63 (m, 3H), 2.58-2.54 (m, 3H)

HPLCMS (Method E): [m/z]: 136.9 [M+H]$^+$

Scheme C Above:

2-(Hydroxymethyl)benzonitrile (C1)

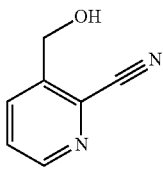

1M $BH_3$ in THF (1.51 ml) was added to an ice-cooled (0° C.) solution of 3-formylpyridine-2-carbonitrile (200 mg, 1.51 mmol) in THF (5 ml). The reaction was allowed to warm to room temperature and stirred for 15 h. The reaction was poured onto ice/water (25 ml). The aqueous layer extracted with EtOAc (3×20 ml). The combined organic layers were dried ($Na_2SO_4$), filtered and the solvent evaporated to give a brown oil. Purification by flash column chromatography (eluting with a gradient 20-100% EtOAc/heptane) gave the titled compound (45.5 mg, 22.4%) as a yellow solid.

1H-NMR (CDCl$_3$, 500 MHz): d[ppm]=8.55 (dd, J=4.7, 1.4 Hz, 1H), 8.01-7.95 (m, 1H), 7.49 (dd, J=8.0, 4.7 Hz, 1H), 4.89 (s, 2H)

HPLCMS (Method A): [m/z]: 134.85 [M+H]$^+$

2-{[(Tert-butyldimethylsilyl)oxy]methyl}benzonitrile (C2)

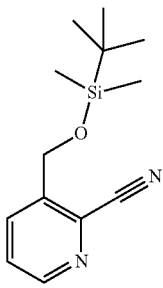 [SMILES: CC(C)(C)[Si](C)(C)OCc1cccnc1C#N]

1M TBSCI in DCM (0.369 ml, 0.369 mmol) was added dropwise to a solution of 3-(hydroxymethyl)pyridine-2-carbonitrile (C1) (45 mg, 0.335 mmol) and imidazole (46 mg, 0.671 mmol) in DMF (2 ml). The reaction was stirred at room temperature for 15 h. The solvent was evaporated and the crude product purified by flash column chromatography (eluting with a gradient of 0-50% EtOAc-heptane) to give the titled compound (44 mg, 52.8%) as a yellow oil.

1H-NMR (CDCl$_3$, 500 MHz): d[ppm]=8.60-8.58 (m, 1H), 8.10-7.96 (m, 1H), 7.53 (dd, J=8.0, 4.7 Hz, 1H), 4.94 (s, 2H), 0.95 (s, 9H), 0.15 (s, 6H)

HPLCMS (Method A): [m/z]: 249.00 [M+H]$^+$ (3-{[(Tert-butyldimethylsilyl)oxy]methyl}pyridin-2-yl)methanamine (C3)

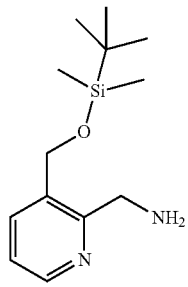 [SMILES: CC(C)(C)[Si](C)(C)OCc1cccnc1CN]

2M LiAlH$_4$ in THF (0.09 ml) was added dropwise to an ice-cooled solution (0° C.) of 3-{[(tert-butyldimethylsilyl)oxy]methyl}pyridine-2-carbonitrile (C2) (44 mg, 0.18 mmol) in THF (3 ml). The reaction was allowed to warm to room temperature and stirred for 2 h. Diethyl ether (5 ml) was added followed by $H_2O$ (1 ml), then 20% w/w NaOH (1 ml) and water (3 ml). The layers separated. The aqueous layer was extracted with EtOAc (3×10 ml). The combined organic layers were dried ($Na_2SO_4$), filtered and the solvent evaporated. The crude product was purified by flash column chromatography (eluting with a gradient of 0-100% EtOAc/heptane) to give the title compound (10 mg, 22.4%) as a yellow oil.

HPLCMS (Method A): [m/z]: 252.95 [M+H]$^+$

N-(2-Nitrophenyl)prop-2-enamide (D)

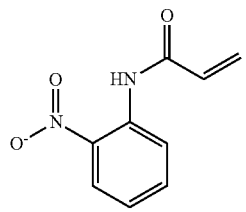

To a stirring suspension of 2-nitroaniline (5.0 g, 36.2 mmol) and $K_2CO_3$ (15.01 g, 108.6 mmol) in acetone (100 ml) at room temperature was added acryloyl chloride (11.8 ml, 145 mmol) and the mixture stirred for 16 h. The reaction mixture was filtered and concentrated in vacuo to give the crude product. Purification by flash column chromatography (gradient elution 10-15% EtOAc/heptane) afforded the title compound (6.95 g, 78%) as a yellow solid.

1H-NMR (CDCl$_3$, 250 MHz): d[ppm]=10.59 (s, 1H), 8.90 (dd, J=8.6, 1.3 Hz, 1H), 8.25 (dd, J=8.5, 1.6 Hz, 1H), 7.68 (ddd, J=8.5, 7.3, 1.4 Hz, 1H), 7.21 (ddd, J=8.6, 7.3, 1.4 Hz, 1H), 6.54-6.28 (m, 2H), 5.89 (dd, J=9.9, 1.3 Hz, 1H)

HPLCMS (Method A): [m/z]: 192.9 [M+H]$^+$

2-(Chloromethyl)-5-(trifluoromethyl)-1H-1,3-benzodiazole (E)

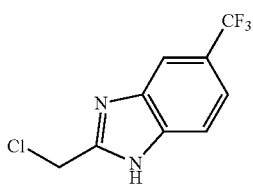 [SMILES: FC(F)(F)c1ccc2[nH]c(CCl)nc2c1]

12 M HCl (1 ml, 12 mmol) was added to a mixture of 4-(trifluoromethyl)benzene-1,2-diamine (1 g, 5.68 mmol) and chloroacetic acid (0.590 g, 6.25 mmol) in water (20 ml) and the mixture was heated at 100° C. for 2 h. Further 12 M HCl (4 ml, 48 mmol) was added and the reaction mixture heated at 120° C. for 3 h. The mixture was then cooled to room temperature and quenched by addition of 7 M ammonia in MeOH until basic, extracted with EtOAc (3×20 ml) and the combined organic layers were washed with brine (20 ml), dried (MgSO$_4$), filtered and evaporated in vacuo. Flash column chromatography (eluting with a gradient 5-50% EtOAc/heptane) afforded the crude title compound as a purple solid (0.571 g, 24%, 56% purity) which was used without further purification.

HPLCMS (Method E): [m/z]: 234.85 [M+H]$^+$

Tert-Butyl 2-(chloromethyl) methyl-1H-1,3-benzodiazole-1-carboxylate (F)

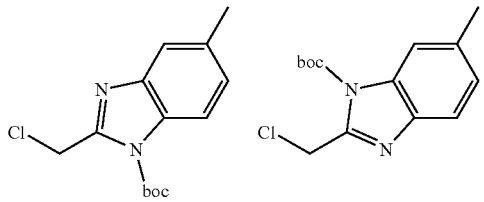

To the solution 2-(chloromethyl)-6-methyl-1H-1,3-benzodiazole (1 g, 6 mmol) in DMF (20 ml) was added DIPEA (1.4 g, 11 mmol) followed by addition of Boc anhydride (1.8 g, 8 mmol). The reaction was stirred for 18 h. Water was added to the reaction and extracted with ethyl acetate. The organic phase was dried, Na$_2$SO$_4$, concentrated in vacuo to the crude product which was purified by flash column chromatography using n-hexane to ethyl acetate/n-hexane (5:95) to hexane to give the required product as a yellow oil (0.7 g, 22%). The required product was obtained as a mixture which was not separable and used in the next step.

1H-NMR (CDCl$_3$, 400 MHz): d[ppm]=7.84 (d, J=8.7 Hz, 2H), 7.62 (d, J=8.2 Hz, 1H), 7.53 (s, 1H), 7.20 (dd, J=13.0, 4.6 Hz, 2H), 5.05 (s, 2H), 5.04 (s, 2H), 2.50 (s, 3H), 2.47 (s, 3H), 1.74 (s, 9H), 1.73 (s, 9H)

N-(3-fluoro-2-nitrophenyl)prop-2-enamide (G)

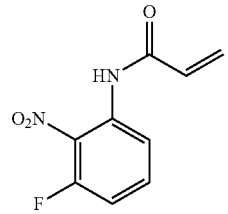

To an N$_2$ purged suspension of 3-fluoro-2-nitroaniline (500 mg, 3.20 mmol) and K$_2$CO$_3$ (1.33 g, 9.61 mmol) in acetone (10 ml) was added prop-2-enoyl chloride dropwise (1.0 ml, 12.8 mmol). The reaction mixture was left stirring at room temperature for 16 h. The reaction was filtered, concentrated in vacuo and purified by flash column chromatography (eluting with a gradient of 0-70% EtOAc/heptane) to afford the title compound (604 mg, 87%) as a yellow solid.

1H-NMR (DMSO-d6, 250 MHz): d[ppm]=10.58 (s, 1H), 7.69 (m, 1H), 7.46-7.33 (m, 2H), 6.43 (dd, J=17.0, 9.8 Hz, 1H), 6.27 (dd, J=17.0, 2.1 Hz, 1H), 5.85 (dd, J=9.8, 2.1 Hz, 1H)

HPLCMS (Method A): [m/z]: 210.95 [M+H]$^+$

N-(3-chloro-2-nitrophenyl)prop-2-enamide (H)

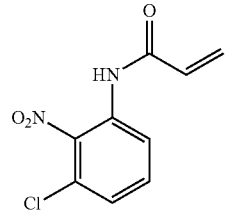

Acryloyl chloride (1.03 ml, 12.67 mmol) was slowly added to a suspension of 3-chloro-2-nitroaniline (0.729 g, 4.22 mmol) and K$_2$CO$_3$ (2.34 g, 16.9 mmol) in acetone (20 ml). The reaction mixture was stirred at room temperature for 4 h, filtered and the residue was rinsed with acetone. The combined filtrates were evaporated in vacuo. Purification by flash column chromatography (eluting with a gradient of 0-60% EtOAc/heptane) afforded the title compound (0.52 g, 47%) as a yellow solid.

1H-NMR (CDCl$_3$, 500 MHz): d[ppm]=8.36 (dd, J=8.3, 1.1 Hz, 1H), 8.28 (s, 1H), 7.49 (dd, J=8.3, 8.3 Hz, 1H), 7.32 (dd, J=8.3, 1.1 Hz, 1H), 6.47 (dd, J=16.9, 0.8 Hz, 1H), 6.25 (dd, J=16.9, 10.3 Hz, 1H), 5.90 (dd, J=10.3, 0.8 Hz, 1H)

HPLCMS (Method M): [m/z]: 227.00 [M+H]$^+$

N-(2-methoxy-6-nitrophenyl)prop-2-enamide (I)

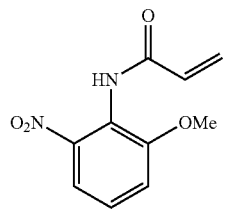 [SMILES: C=CC(=O)Nc1c(OC)cccc1[N+](=O)[O-]]

To an N$_2$ purged stirring suspension of 2-methoxy-6-nitroaniline (0.52 g, 3.09 mmol) and K$_2$CO$_3$ (1.71 g, 12.4 mmol) in acetone (30 ml) was added acryloyl chloride (0.754 ml, 9.28 mmol) dropwise. The reaction mixture was left stirring at room temperature for 16 h. The mixture was filtered, concentrated, diluted with EtOAc, washed with water, dried (MgSO$_4$), filtered and concentrated to give the crude product. Purification by flash column chromatography (eluting with a gradient of 0-100% EtOAc/heptane followed by 0-2% MeOH/EtOAc) afforded the title compound (0.674 g, 96%) as an orange solid.

1H-NMR (CDCl$_3$, 250 MHz): d[ppm]=7.82 (s, 1H), 7.57 (dd, J=8.2, 1.3 Hz, 1H), 7.31 (t, J=8.3 Hz, 1H), 7.19 (dd, J=8.3, 1.3 Hz, 1H), 6.47 (dd, J=17.0, 1.7 Hz, 1H), 6.33 (dd, J=17.0, 9.8 Hz, 1H), 5.85 (dd, J=9.8, 1.7 Hz, 1H), 3.97 (s, 3H)

HPLCMS (Method M): [m/z]: 223.05 [M+H]$^+$

N-(5-fluoro-2-nitrophenyl)prop-2-enamide (J)

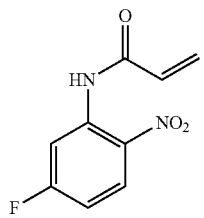

Acryloyl chloride (3.8 ml, 46.5 mmol) was added slowly to a suspension of 5-fluoro-2-nitroaniline (2.4 g, 15.5 mmol) and K$_2$CO$_3$ (8.57 g, 62 mmol) in acetone (100 ml) and the mixture was stirred at room temperature for 3 d and at reflux for 6 h. Further acryloyl chloride (3.8 ml, 46.5 mmol) and DMAP (0.95 g, 7.75 mmol) were added and the mixture heated at reflux for a further 2 h. The reaction mixture was cooled to room temperature and filtered. The residue was rinsed with acetone and the combined filtrates evaporated under vacuum. The resultant residue was re-dissolved in Et$_2$O (350 ml) and saturated NaHCO$_3$ (aq) (200 ml). The mixture was stirred vigorously for 15 min. The phases were separated and the organic phase washed with a further portion of saturated NaHCO$_3$(aq) (100 ml) and brine (100 ml), dried (sodium sulphate) and evaporated under vacuum. Purification by flushing through a plug of silica (eluting with a gradient of 0-4% Et$_2$O/heptane) afforded the title compound (1.04 g, 32%) as a pale yellow solid.

1H-NMR (CDCl$_3$, 250 MHz): d[ppm]=10.83 (s, 1H), 8.79 (dd, J=11.2, 2.5 Hz, 1H), 8.34 (dd, J=9.2, 5.7 Hz, 1H), 6.99-6.82 (m, 1H), 6.53 (d, J=16.9 Hz, 1H), 6.35 (dd, J=17.1, 9.9 Hz, 1H), 5.95 (d, J=10.1 Hz, 1H)

HPLCMS (Method M): [m/z]: 211.15 [M+H]$^+$

General Scheme K-I Above:

N-(2-chloro-5-fluorophenyl)prop-2-enamide (K1)

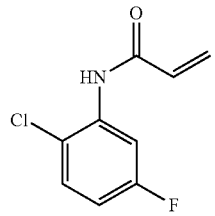

To an N$_2$ purged suspension of 2-chloro-5-fluoroaniline (3.0 g, 20.6 mmol) and K$_2$CO$_3$ (11.4 g, 82.4 mmol) in acetone (80 ml) at room temperature was added dropwise prep-2-enoyl chloride (5.0 ml, 61.8 mmol) and stirred for 16 h. The reaction mixture was filtered, concentrated in vacuo and purified by flash column chromatography (eluting with a gradient of 0-35% EtOAc/heptane) to afford the title compound (3.99 g, 84%) as a white solid.

1H-NMR (CDCl$_3$, 250 MHz): d[ppm]=8.40 (dd, J=10.9, 3.0 Hz, 1H), 7.79 (s, 1H), 7.35 (dd, J=8.9, 5.6 Hz, 1H), 6.81 (ddd, J=8.9, 7.6, 3.0 Hz, 1H), 6.50 (dd, J=16.9, 1.2 Hz, 1H), 6.32 (dd, J=16.9, 10.0 Hz, 1H), 5.88 (dd, J=10.0, 1.2 Hz, 1H)

HPLCMS (Method A): [m/z]: 200.10 [M+H]$^+$

N-(6-chloro-3-fluoro-2-nitrophenyl)prop-2-enamide (K2)

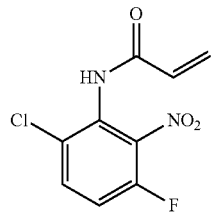 [SMILES: C=CC(=O)Nc1c(Cl)ccc(F)c1[N+](=O)[O-]]

To an N$_2$ purged solution of N-(2-chloro-5-fluorophenyl)prop-2-enamide (K1) (3.99 g, 17.4 mmol), concentrated H$_2$SO$_4$ (15 ml) and AcOH (6 ml) at 00° C. was added red fuming HNO$_3$ (1.8 ml, 38.3 mmol) dropwise and the reaction was left stirring for 2 h. The reaction mixture was poured onto ice water and extracted using DCM (4×40 ml). The combined organic extracts were dried (MgSO$_4$), filtered, concentrated in vacuo and purified by flash column chromatography (eluting with a gradient of 0-70% EtOAc/heptane) to give the title compound (1.08 g, 20%) as a white solid.

1H-NMR (CDCl$_3$, 250 MHz): d[ppm]=7.64 (dd, J=9.1, 5.0 Hz, 1H), 7.51 (s, 1H), 7.19 (m, 1H), 652 (dd, J=16.9, 1.1 Hz, 1H), 6.32 (dd, J=16.9, 10.2 Hz, 1H), 5.94 (dd, J=10.1, 1.1 Hz, 1H)

HPLCMS (Method A): [m/z]: 244.95 [M+H]+

N-(2,4-difluorophenyl)prop-2-enamide (K3)

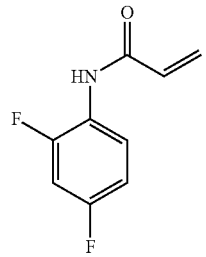

To an N₂ purged suspension of 2,4-difluoroaniline (2 g, 1.49 mmol) and K₂CO₃ (8.56 g, 61.7 mmol) in acetone (60 ml) at room temperature was added prop-2-enoyl chloride (3.7 ml, 46.5 mmol) dropwise. The reaction mixture was left stirring for 16 h. The reaction was filtered, concentrated, purified by flash column chromatography (eluting with a gradient of 0-30% EtOAc/heptane) and triturated with heptane to give the title compound (2.9 g, 100%) as a white solid.

1H-NMR (CDCl₃, 250 MHz): d[ppm]=8.49-8.29 (m, 1H), 7.33 (s, 1H), 6.99-6.84 (m, 2H), 6.48 (dd, J=16.9, 1.4 Hz, 1H), 6.29 (dd, J=16.8, 10.1 Hz, 1H), 5.85 (dd, J=10.1, 1.4 Hz, 1H)

HPLCMS (Method A): [m/z]: 183.95 [M+H]⁺

N-(2,4-difluoro-6-nitrophenyl)prop-2-enamide (K4)

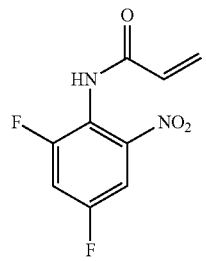 [SMILES: C=CC(=O)Nc1c(F)cc(F)cc1[N+](=O)[O-]]

To an N₂ purged solution of N-(2,4-difluorophenyl)prop-2-enamide (K3) (2.9 g, 15.4 mmol), AcOH (5 ml) and concentrated H₂SO₄ (13 ml) at 0° C. was added red fuming nitric acid (1.6 ml) dropwise. The reaction mixture was left stirring for 2 h. The reaction was poured onto ice water and the resulting solution extracted using DCM (4×40 ml). The combined organic extracts were washed with brine, dried (MgSO₄), filtered, concentrated in vacuo and triturated with heptane to give the crude product as a beige solid (3.23 g). Purification by flash column chromatography (eluting with a gradient of 0-40% EtOAc/heptane) gave the title compound (1.25 g, 35.5%) as a white solid.

1H-NMR (CDCl₃, 250 MHz): d[ppm]=8.17 (s, 1H), 7.67 (dt, J=7.9, 2.4 Hz, 1H), 7.34-7.28 (m, 1H), 6.51 (dd, J=17.0, 1.4 Hz, 1H), 6.35 (dd, J=17.0, 9.9 Hz, 1H), 5.92 (dd, J=9.9, 1.3 Hz, 1H)

HPLCMS (Method A): [m/z]: 229.05 [M+H]+

N-(2,5-difluorophenyl)prop-2-enamide (K5)

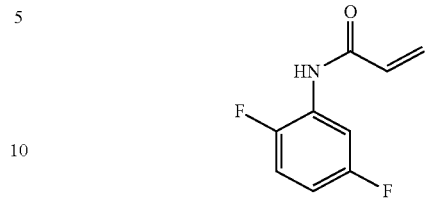

To an N₂ purged stirring solution of 2,5-difluoroaniline (1.5 ml, 15.5 mmol) and K₂CO₃ (6.42 g, 46.5 mmol) in acetone (60 ml) at room temperature was added prop-2-enoyl chloride (5.0 ml, 61.96 mmol) dropwise. The reaction mixture was left stirring at room temperature for 2 h. The reaction was filtered and the filtrate concentrated to give a white solid, which was triturated with heptane to give the title compound (2.91 g, quantitative) as a white solid.

1H-NMR (CDCl₃, 250 MHz): d[ppm]=8.30 (m, 1H), 7.50 (s, 1H), 7.07 (m, 1H), 6.85-6.70 (m, 1H), 6.50 (dd, J=16.8, 1.2 Hz, 1H), 6.30 (dd, J=16.9, 10.1 Hz, 1H), 5.87 (dd, J=10.1, 1.2 Hz, 1H)

HPLCMS (Method A): [m/z]: 183.95 [M+H]⁺

N-(3,6-difluoro-2-nitrophenyl)prop-2-enamide (K6)

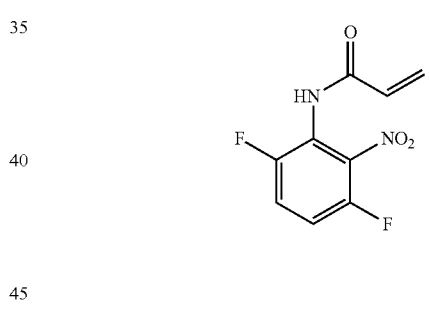

To an N₂ purged stirring solution of N-(2,5-difluorophenyl)prop-2-enamide (K5) (2.91 g, 15.9 mmol), AcOH (5 ml) and conconcentrated H₂SO₄ (13 ml) at 00° C. was added red fuming HNO₃ (1.6 ml, 34.0 mmol) dropwise. The reaction mixture was left stirring for 2 h. The reaction was poured onto ice water and the resulting solution was extracted using DCM (4×40 ml). The combined organic extracts were washed with brine, dried (MgSO₄), filtered and concentrated in vacuo. Purification by flash column chromatography (eluting with a gradient of 0-60% EtOAc/heptane), followed by flash column chromatography (eluting with a gradient of 20% EtOAc/heptane) gave the title compound (0.316 g, 8%) as a whete solid.

1H-NMR (CDCl₃, 500 MHz): d[ppm]=7.64 (s, 1H), 7.39 (m, 1H), 7.19 (m, 1H), 6.51 (dd, J=17.0, 0.7 Hz, 1H), 6.32 (dd, J=17.0, 10.4 Hz, 1H), 5.93 (dd, J=10.4, 0.7 Hz, 1H)

HPLCMS (Method A): [m/z]: 228.95 [M+H]⁺

N-[2-(trifluoromethyl)phenyl]prop-2-enamide (K7)

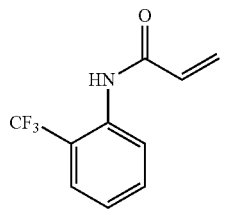

To an N$_2$ purged suspension solution of 2-(trifluoromethyl)aniline (3.1 ml, 24.83 mmol) and K$_2$CO$_3$ (10.3 g, 74.48 mmol) in acetone (90 ml) was added prop-2-enoyl chloride (8.0 ml, 99.30 mmol) dropwise. The reaction mixture was left stirring at room temperature for 3 h. The reaction was filtered, concentrated in vacuo and triturated with heptane to afford the title compound (4.74 g, 86%) as a white solid.

1H-NMR (CDCl$_3$, 250 MHz): d[ppm]=8.34 (d, J=8.2 Hz, 1H), 7.70-7.45 (m, 3H), 7.28-7.22 (m, 1H), 6.46 (dd, J=16.9, 1.3 Hz, 1H), 6.29 (dd, J=16.9, 10.0 Hz, 1H), 5.86 (dd, J=10.0, 1.3 Hz, 1H)

HPLCMS (Method A): [m/z]: 215.90 [M+H]$^+$

N-[2-nitro-6-trifluoromethyl)phenyl]prop-2-enamide (K8)

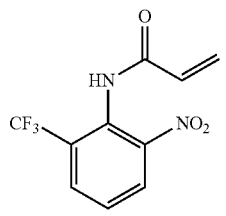 [SMILES: C=CC(=O)Nc1c([N+](=O)[O-])cccc1C(F)(F)F]

To an N$_2$ purged solution of N-[2-(trifluoromethyl)phenyl]prop-2-enamide (K7) (4.64 g, 20.91 mmol), AcOH (5 ml) and concentrated H$_2$SO$_4$ (13 ml) at 00° C. was added red fuming HNO$_3$ (1.6 ml, 34.05 mmol) dropwise. The reaction mixture was left stirring at room temperature for 16 h. The reaction was poured onto ice water and then extracted using DCM (4×40 ml). The combined organic extracts were dried (MgSO$_4$), filtered and concentrated in vacuo. Purification by flash column chromatography (eluting with a gradient of 0-20% EtOAc/heptane) gave the title compound (0.829 g, 12%) as a beige solid.

HPLCMS (Method A): [m/z]: 260.95 [M+H]$^+$

N-(2,3-Difluorophenyl)prop-2-enamide (K9)

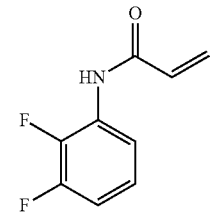

To an N$_2$ purged solution of 2,3-difluoroaniline (3 ml, 31 mmol) and K$_2$CO$_3$ (12.9 g, 92.9 mmol) in acetone (120 ml) at room temperature was added dropwise prop-2-enoyl chloride (10 ml, 124 mmol). The reaction mixture was left stirring for 16 h. The reaction was filtered and the filtrate concentrated to give a white solid which was triturated from heptane to give the title compound (4.97 g, 87%) as a white solid.

1H-NMR (CDCl$_3$, 250 MHz): d[ppm]=8.29-8.12 (m, 1H), 7.46 (s, 1H), 7.18-7.04 (m, 1H), 7.02-6.85 (m, 1H), 6.50 (dd, J=16.8, 1.3 Hz, 1H), 6.31 (dd, J=16.9, 10.1 Hz, 1H), 5.87 (dd, J=10.1, 1.3 Hz, 1H)

HPLCMS (Method A): [m/z]: 184.2 [M+H]$^+$

N-(2,3-Difluoro-6-nitrophenyl)prop-2-enamide (K10)

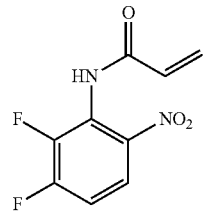 [SMILES: C=CC(=O)Nc1c([N+](=O)[O-])ccc(F)c1F]

To an N$_2$ purged solution of N-(2,3-difluorophenyl)prop-2-enamide (K9) (4.9 g, 26.8 mmol), AcOH (5 ml) and concentrated H$_2$SO$_4$ (13 ml) at 00° C. was added nitric acid (1.6 ml) dropwise. The reaction mixture was left stirring for 2 h. The reaction was poured onto ice/water and the solution extracted using DCM (5×30 ml). The combined organic extracts were washed with brine (50 ml), dried over MgSO$_4$, filtered and concentrated to give the crude product. This was triturated with heptane (100 ml). The suspension was filtered and the residue collected to give a mixture of both para/ortho nitrated regioisomers as a beige solid (6 g). Purification by acidic prep-HPLC gave the title compound (42 g) as a white solid.

HPLCMS (Method A): [m/z]: 228.95 [M+H]$^+$

General Scheme K-II Above:

N-(4-Cyanophenyl)prop-2-enamide (K11)

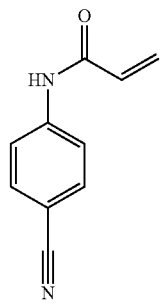

Acryloyl chloride (0.69 ml, 8.46 mmol) was added to an ice-cold suspension of 4-aminobenzonitrile (250 mg, 2.12 mmol) and K$_2$CO$_3$ (880 mg, 6.35 mmol) in acetone (5 ml). The mixture was stirred for 18 h whilst warming to room temperature. The reaction mixture was filtered and the residue rinsed with acetone (5 ml). The combined filtrates were evaporated in vacuo and the crude purification by flash column chromatography using an elution gradient 0-80% EtOAc/heptane to afford the title compound (353 mg, 96%) as a white solid.

1H-NMR (CDCl$_3$, 250 MHz): d[ppm]=7.73 (d, J=8.8 Hz, 2H), 7.68-7.58 (m, 2H), 7.37 (s, 1H), 6.49 (dd, J=16.8, 1.0 Hz, 1H), 6.25 (dd, J=16.8, 10.2 Hz, 1H), 5.86 (dd, J=10.2, 1.0 Hz, 1H)

HPLCMS (Method M): [m/z]: 173.45 [M+H]$^+$

N-(4-Cyano-2-nitrophenyl)prop-2-enamide (K12)

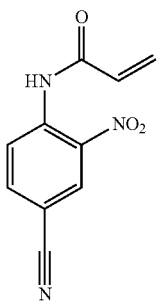 [SMILES: C=CC(=O)Nc1ccc(C#N)cc1[N+](=O)[O-]]

Nitric acid (0.6 ml) was added dropwise to an ice-cold solution of N-(4-cyanophenyl)prop-2-enamide (K11) (1.03 g, 5.75 mmol) in acetic acid (2 ml) and sulfuric acid (4.75 ml). The reaction mixture was stirred for 3 h, then poured into ice-cold water and the mixture extracted with DCM (4×20 ml). The combined organic extracts were dried (MgSO$_4$) and evaporated in vacuo. Purification by flash column chromatography using an elution gradient 0-90% EtOAc/heptane afforded the title compound (1.2 g, 93%) as a yellow solid.

1H-NMR (CDCl$_3$, 250 MHz): d[ppm]=10.77 (s, 1H), 9.14 (d, J=8.9 Hz, 1H), 8.58 (d, J=2.0 Hz, 1H), 7.90 (dd, J=8.9, 1.7 Hz, 1H), 6.54 (dd, J=17.0, 0.9 Hz, 1H), 6.35 (dd, J=17.0, 10.1 Hz, 1H), 5.98 (dd, J=10.1, 0.9 Hz, 1H)

Tert-butyl 2-(chloromethyl)-1H-1,3-benzodiazole-1-carboxylate (L)

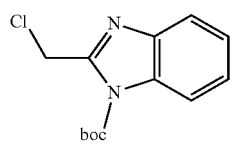

A mixture of 2-(chloromethyl)-1H-1,3-benzodiazole (10 g, 0.06 mol), BOC$_2$O (18 ml, 0.06 mol) and TEA (6.07 g, 0.06 mol) in DCM (304 ml) was cooled to 0° C. A catalytic amount of DMAP (0.73 g, 0.006 mol) was added and the reaction mixture was stirred at room temperature for 2 h. The mixture was diluted with EtOAc (150 ml), washed with saturated NaHCO$_3$ (150 ml), brine (150 ml), dried (Na$_2$SO$_4$), filtered and concentrated to give the crude product. Purification by flash column chromatography (eluting with a gradient of 5-10% EtOAc/heptane) gave the title compound (7 g, 44%) as an off white oil.

HPLCMS (Method H): [m/z]: 167.2 [M-Boc+H]$^+$

General Scheme 1 Above:

General Procedure 1: ethyl 2-(2-{[(tert-butoxy)carbonyl]amino}ethyl)-1,3-thiazole-4-carboxylate (1)

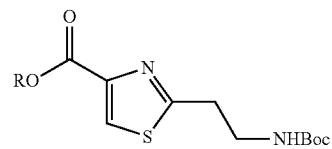

To a suspension of ethyl 3-bromo-2-oxopropanoate (12.35 ml, 107.69 mmol) and tert-butyl (3-amino-3-thioxopropyl) carbamate (20 g, 97.9 mmol) in EtOH (200 ml) was added CaCO$_3$ (5.3 g, 52.87 mmol) portion wise and the reaction mixture stirred at room temperature for 12 h. The mixture was concentrated in vacuo and the residue partitioned between EtOAc (200 ml) and sat. NaHCO$_3$ (100 ml). The organic layer was separated and washed with water (100 ml), brine (100 ml), dried (MgSO$_4$), filtered and concentrated in vacuo to give the required product. Purification by flash column chromatography (isocratic elution 20% EtOAc/heptane) afforded the title compound (22 g, 69.6%) as a yellow solid.

1H-NMR (Methanol-d4, 250 MHz): d[ppm]=8.29 (s, 1H), 4.39 (q, J=7.1 Hz, 2H), 3.47 (t, J=6.5 Hz, 2H), 3.22 (t, J=6.5 Hz, 2H), 1.41 (d, J=6.2 Hz, 14H)

HPLCMS (Method A): [m/z]: 301.0 [M+H]$^+$

Methyl 2-(2-{[(tert-butoxy)carbonyl]amino}ethyl)-1,3-thiazole-4-carboxylate (2)

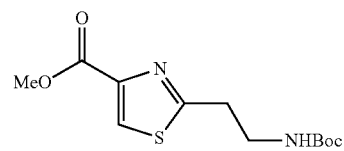

In a similar fashion to general procedure 1, tert-Butyl (3-amino-3-thioxopropyl)carbamate (10 g, 48.95 mmol), methyl 3-bromo-2-oxopropanoate (5.73 ml, 53.85 mmol) and CaCO$_3$ (0.9 ml, 26.43 mmol) in EtOH (120 ml) afforded the title compound (10.2 g, 60%, 83% purity) as a yellow solid after purification by flash chromatography (eluting with a gradient of 20-80% EtOAc/heptane).

HPLCMS (Method A): [m/z]: 286.9 [M+H]$^+$

Methyl 2-(2-{[(tert-butoxy)carbonyl]amino}ethyl-1,3-thiazole-4-carboxylate (3)

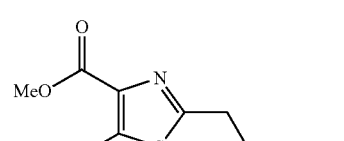

In a similar fashion to general procedure 1, tert-butyl N-(2-carbamothioylethyl)carbamate (0.89 g, 4.35 mmol), methyl 3-bromo-2-oxobutanoate (0.93 g, 4.78 mmol) and CaCO$_3$ (0.23 g, 2 mmol) in EtOH (15 ml) afforded the title compound (0.769 g, 58%) as a yellow oil after purification by flash column chromatography (eluting with a gradient of 10-60% EtOAc/heptane).

1H-NMR (CDCl3, 250 MHz): d[ppm]=4.88 (s, 1H), 3.95 (s, 3H), 3.55 (q, J=6.5 Hz, 2H), 3.17 (t, J=6.5 Hz, 2H), 2.76 (s, 3H), 1.46 (s, 9H)

HPLCMS (Method A): [m/z]: 301.05 [M+H]$^+$

Ethyl 2-(3-{[(tert-butoxy)carbonyl]amino}propyl)-1,3-thiazole-4-carboxylate (4)

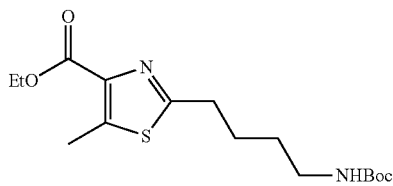 [SMILES: CCOC(=O)c1nc(CCCCNC(=O)OC(C)(C)C)sc1C]

In a similar fashion to general procedure 1, tert-butyl N-(3-carbamothioylpropyl)carbamate (535 mg, 2.45 mmol), ethyl 3-bromo-2-oxopropanoate (0.31 ml, 2.7 mmol) and CaCO$_3$ (132 mg, 1.32 mmol) in EtOH (10 ml) afforded the title compound (726 mg, 93%) as a yellow oil after purification by flash column chromatography (eluting with a gradient of 0-50% EtOAc/heptane).

1H-NMR (DMSO-d6, 500 MHz): d[ppm]=8.38 (s, 1H), 6.90 (s, 1H), 4.29 (q, J=7.1 Hz, 2H), 3.15-2.90 (m, 4H), 1.83 (m, 2H), 1.38 (s, 9H), 1.30 (t, J=7.1 Hz, 3H)

HPLCMS (Method A): [m/z]: 315 [M+H]$^+$

General Procedure 2: Methyl 2-(2-aminoethyl)-1,3-thiazole-4-carboxylate (5)

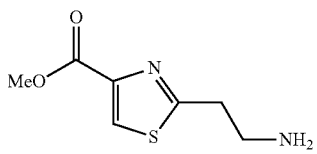 [SMILES: COC(=O)c1csc(CCN)n1]

4M HCl in dioxane (44 ml, 176 mmol) was added to a solution of methyl 2-(2-{[(tert-butoxy)carbonyl]amino}ethyl)-1,3-thiazole-4-carboxylate (2) (10.2 g, 35.62 mmol) in dioxane and the mixture was stirred at room temperature for 12 h, then at 40° C. for 24 h. The mixture was cooled b room temperature and evaporated in vacuo. The residue was dissolved in DCM (20 ml) and washed with saturated NaHCO$_3$ (3×10 ml). The combined aqueous phases were re-extracted with diethyl ether (3×100 ml) and the combined organic phases were dried (MgSO$_4$), filtered and evaporated in vacuo to afford the title compound (1.96 g, 30%) as a brown solid.

HPLCMS (Method A): [m/z]: 186.9 [M+H]$^+$

General Procedure 3: Methyl 2-{2-[(1H-1,3-benzodiazol-2-ylmethyl)amino]ethyl}-1,3-thiazole-4-carboxylate (6)

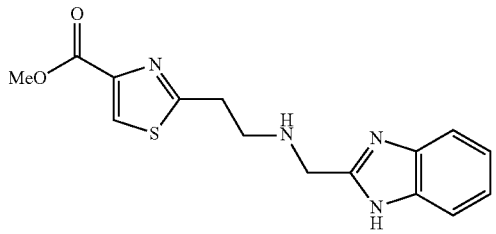 [SMILES: COC(=O)c1csc(CCNCc2nc3ccccc3[nH]2)n1]

A suspension of methyl 2-(2-aminoethyl)-1,3-thiazole-4-carboxylate (5) (1.96 g, 10.52 mmol), 1H-benzimidazole-2-carbaldehyde (2.31 g, 15.79 mmol) and DIPEA (1.83 ml, 10.52 mmol) in MeOH (100 ml) was stirred at room temperature for 12 h. The reaction mixture was cooled to 0° C., NaBH$_4$ (0.597 g, 15.79 mmol) was added and the mixture stirred at room temperature for 2 h. The reaction mixture was concentrated in vacuo and the residue dissolved in EtOAc (100 ml) and washed with saturated Na$_2$CO$_3$ (2×50 ml). The combined aqueous layers were extracted with EtOAc (3×50 ml) and the combined organic layers dried (MgSO$_4$), filtered and evaporated in vacuo. Purification by flash column chromatography (KP—NH, eluting with a gradient of 0-10% MeOH/DCM) afforded the title compound (1.4 g, 38%, 90% purity) as a tan solid.

1H-NMR (Methanol-d4, 250 MHz): d[ppm]=8.27 (s, 1H), 7.60-7.49 (m, 2H), 7.29-7.17 (m, 2H), 4.09 (s, 2H), 3.92 (s, 3H), 3.26 (t, J=6.3 Hz, 2H), 3.10 (t, J=6.8 Hz, 2H)

HPLCMS (Method A): [m/z]: 317 [M+H]$^+$

General Procedure 4: Tert-butyl 2-({[(tert-butoxy)carbonyl]({2-[4-(methoxycarbonyl)-1,3-thiazol-2-yl]ethyl})amino}methyl)-1H-1,3-benzodiazole-1-carboxylate (7)

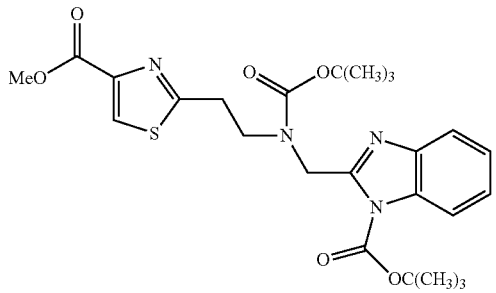

To a solution of methyl 2-{2-[(1H-1,3-benzodiazol-2-ylmethyl)amino]ethyl}-1,3-thiazole-4-carboxylate (6) (74%, 2.94 g, 6.88 mmol), Boc$_2$O (3.75 g, 17.19 mmol) and TEA (2.38 ml, 17.19 mmol) in THF (60 ml) was added DMAP (168 mg, 1.38 mmol) and the reaction was stirred at room temperature for 16 h. The reaction was evaporated to dryness, diluted with EtOAc (100 ml) and washed with water (3×50 ml). The organic was dried over MgSO$_4$, filtered and evaporated to dryness. The crude residue was purified by FCC eluting with 0-100% EtOAc in heptane to give 3.8 g of desired product.

General Procedure 5: 2-(2-{[(Tert-butoxy)carbonyl]({1-[(tert-butoxy)carbonyl]-1H-1,3-benzodiazol-2-yl}methyl)amino}ethyl)-1,3-thiazole-4-carboxylic Acid (8)

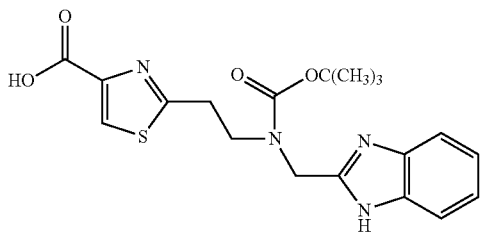

Lithium hydroxide (0.48 mg, 20.08 mmol) was added to a solution of tert-butyl 2-({[(tert-butoxy)carbonyl]({2-[4-(methoxycarbonyl)-1,3-thiazol-2-yl]ethyl})amino}methyl)-1H-1,3-benzodiazole-1-carboxylate (7) (3.8 g, 6.69 mmol) in THF/water (40 ml/10 ml) at 0° C. The reaction mixture was stirred at room temperature for 48 h. The mixture was concentrated in vacuo and acidified to pH ~3-4 using AcOH. The reaction mixture was extracted with THF/EtOAc (3:1, 3×50 ml). The combined organic extracts were washed with brine (100 ml), dried (MgSO₄), filtered, reduced in vacuo and azeotroped with heptane (3×50 ml) to give the title compound (2.4 g, 84.6%) as a yellow foam.

1H-NMR (Methanol-d4, 250 MHz): d[ppm]=8.15 (d, J=17.0 Hz, 1H), 7.69 (s, 2H), 7.27 (dd, J=6.1, 3.2 Hz, 2H), 4.79 (s, 2H), 3.87-3.74 (m, 2H), 3.40-3.33 (m, 3H), 1.38-1.01 (m, 10H)

HPLCMS (Method A): [m/z]: 403 [M+H]⁺

General Procedure 6: Tert-butyl N-(1H-1,3-benzodiazol-2-ylmethyl)-N-(2-{4-[(pyridin-2-ylmethyl)carbamoyl]-1,3-thiazol-2-yl}ethyl)carbamate (9)

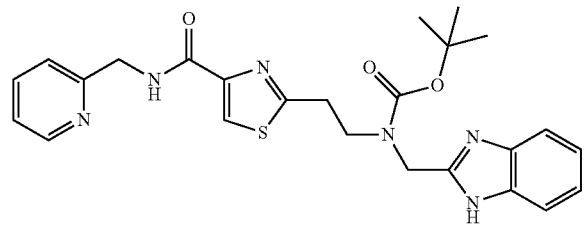 [SMILES: CC(C)(C)OC(=O)N(CCc1nc(C(=O)NCc2ccccn2)cs1)Cc1nc2ccccc2[nH]1]

To a stirring solution of 2-{2-[(1H-1,3-benzodiazol-2-ylmethyl)[(tert-butoxy)carbonyl]amino]ethyl}-1,3-thiazole-4-carboxylic acid (8) (3 g, 7.08 mmol), 1-(pyridin-2-yl)methanamine (1.1 ml, 10.62 mmol), DIPEA (3.7 ml, 21.24 mmol) and DMF (50 ml) at room temperature was added HATU (5.39 g, 14.16 mmol). The reaction mixture was allowed to stir at room temperature for 16 h.

The reaction was diluted with EtOAc (100 ml) and washed with sat. NaHCO₃ (3×50 ml) and brine (3×50 ml). The organic layer was separated, dried (MgSO4), filtered and evaporated to dryness. The crude residue was purified by flash column chromatography (kp-NH, eluting with a gradient of 20-100% EtOAc in heptane) and then azeotroped with heptane to give the title compound (2.2 g, 62%) as a yellow foam.

1H-NMR (MeOD, 500 MHz): d[ppm]=8.49 (d, J=4.4 Hz, 1H), 8.10 (s, 1H), 7.80 (td, J=7.8, 1.7 Hz, 1H), 7.54 (s, 2H), 7.42 (d, J=7.9 Hz, 1H), 7.31 (dd, J=7.1, 5.2 Hz, 1H), 7.26-7.20 (m, 2H), 4.75 (d, J=12.3 Hz, 2H), 4.70 (s, 2H), 3.92-3.79 (m, 2H), 3.36 (d, J=8.1 Hz, 1H), 1.43-1.25 (m, 10H)

HPLCMS (Method D): [m/z]: 493.1 [M+H]⁺

Tert-butyl N-(1H-1,3-benzodiazol-2-ylmethyl)-N-(2-{4-[(cyclohexylmethyl)carbamoyl]-1,3-thiazol-2-yl}ethyl)carbamate (10)

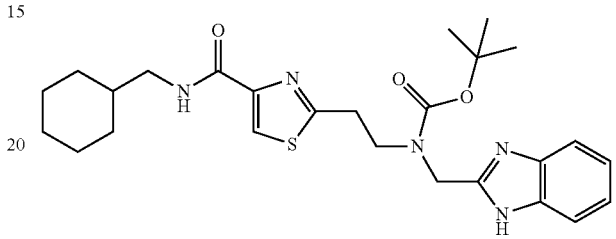

In a similar fashion to general procedure 6, 2-{2-[(1H-1,3-benzodiazol-2-ylmethyl)[(tert-butoxy)carbonyl]amino]ethyl}-1,3-thiazole-4-carboxylic acid (8) (99.8 mg, 0.248 mmol), cyclohexylmethanamine (33.69 mg, 0.298 mmol), DIPEA (96.16 mg, 0.744 mmol) and HATU (113.16 mg, 0.298 mmol) in DMF (4 ml) at room temperature for 1 h afforded the title compound (116 mg, 47% purity) as an off white oil after purification by flash column chromatography (eluting with a gradient of (10% MeOH/DCM). The title compound was used in the next step without further purification.

HPLCMS (Method H): [m/z]: 498.7 [M+H]⁺

Tert-butyl N-(1H-1,3-benzodiazol-2-ylmethyl)-N-{2-[4-(1,2,3,4-tetrahydroisoquinoline-2-carbonyl)-1,3-thiazol-2-yl]ethyl}carbamate (11)

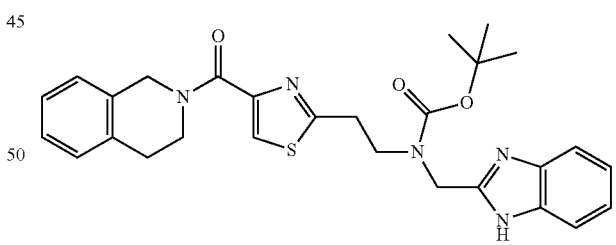

In a similar fashion to general procedure 6, 2-{2-[(1H-1,3-benzodiazol-2-ylmethyl)[(tert-butoxy)carbonyl]amino]ethyl}-1,3-thiazole-4-carboxylic acid (8) (99.8 mg, 0.248 mmol), 1,2,3,4-tetrahydroisoquinoline (39.64 mg, 0.298 mmol), DIPEA (96.16 mg, 0.744 mmol) and HATU (113.16 mg, 0.298 mmol) in DMF (4 ml) at room temperature for 1 h afforded the title compound (124 mg, 59% purity) as an off white oil after purification by flash column chromatography (eluting with a gradient of 0-10% MeOH/DCM). The title compound was used in the next step without further purification.

HPLCMS (Method H): [m/z]: 518.7 [M+H]⁺

247

Tert-butyl N-(1H-1,3-benzodiazol-2-ylmethyl)-N-(2-{4-[(thiophen-2-ylmethyl)carbamoyl]-1,3-thiazol-2-yl}ethyl)carbamate (12)

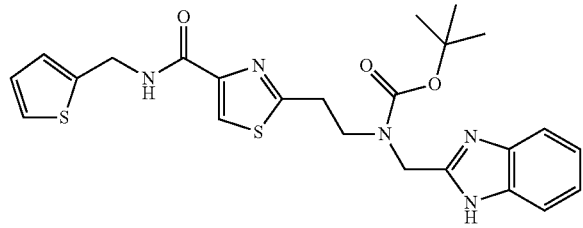 [SMILES: CC(C)(C)OC(=O)N(CCc1nc(C(=O)NCc2cccs2)cs1)Cc1nc2ccccc2[nH]1]

To a solution of 2-{2-[(1H-1,3-benzodiazol-2-ylmethyl)[(tert-butoxy)carbonyl]amino]ethyl}-1,3-thiazole-4-carboxylic acid (8) (150 mg, 0.373 mmol) in DMF (10 ml) was added 1H-1,2,3-benzotriazol-1-ol (50 mg, 0.373 mmol) and EDC:HCl (71 mg, 0.373 mmol) at (PC. The reaction mixture was allowed to stir for 15 min before TEA (38 mg, 0.373 mmol) was added followed by thiophen-2-ylmethanamine (42 mg, 0.373 mmol). The reaction mixture was allowed to warm up to room temperature and stir overnight. The title compound (185 mg, 16% purity) was obtained after work up following general procedure 6. This was used in the next step without purification.

HPLCMS (Method H): [m/z]: 498.6 [M+H]$^+$

Tert-butyl N-(1H-1,3-benzodiazol-2-ylmethyl)-N-(2-{4-[benzyl(methyl)carbamoyl]-1,3-thiazol-2-yl}ethyl)carbamate (13)

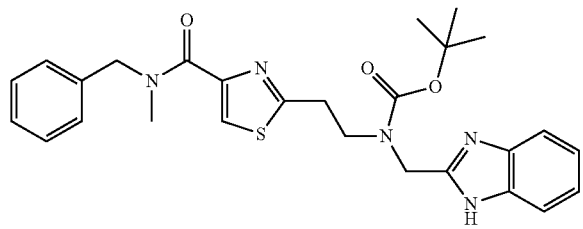 [SMILES: CN(Cc1ccccc1)C(=O)c1csc(CCN(Cc2nc3ccccc3[nH]2)C(=O)OC(C)(C)C)n1]

In a similar fashion to general procedure 6, 2-{2-[(1H-1,3-benzodiazol-2-ylmethyl)[(tert-butoxy)carbonyl]amino]ethyl}-1,3-thiazole-4-carboxylic acid (8) (99.8 mg, 0.248 mmol), benzyl(methyl)amine (36.06 mg, 0.298 mmol), DIPEA (96.16 mg, 0.744 mmol) and HATU (113.16 mg, 0.298 mmol) in DMF (4 ml) at room temperature for 1 h afforded the title compound (118 mg, 55% purity) as an off white oil after purification by flash column chromatography (eluting with a gradient of 0-10% MeOH/DCM). The title compound was used in the next step without further purification.

HPLCMS (Method H): [m/z]: 506.7 [M+H]$^+$

248

Tert-butyl N-(1H-1,3-benzodiazol-2-ylmethyl)-N-{2-[4-(morpholine-4-carbonyl)-1,3-thiazol-2-yl]ethyl}carbamate (14)

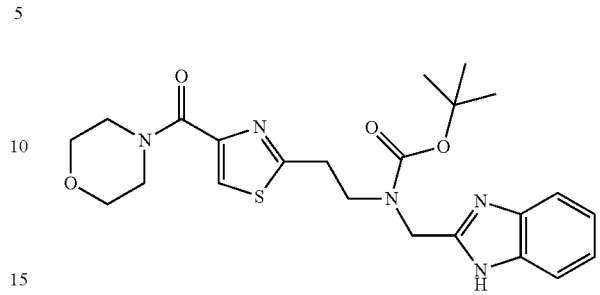

In a similar fashion to general procedure 6, 2-{2-[(1H-1,3-benzodiazol-2-ylmethyl)[(tert-butoxy)carbonyl]amino]ethyl}-1,3-thiazole-4-carboxylic acid (8) (99.8 mg, 0.248 mmol), morpholine (25.93 mg, 0.298 mmol), DIPEA (96.16 mg, 0.744 mmol) and HATU (113.16 mg, 0.298 mmol) in DMF (4 ml) at room temperature for 1 h afforded the title compound (110 mg) as an off white oil after purification by flash column chromatography (eluting with a gradient of 0-10% MeOH/DCM). The title compound was used in the next step without further purification.

Tert-butyl N-(1H-1,3-benzodiazol-2-ylmethyl)-N-(2-{4-[methyl(phenyl)carbamoyl]-1,3-thiazol-2-yl}ethyl)carbamate (15)

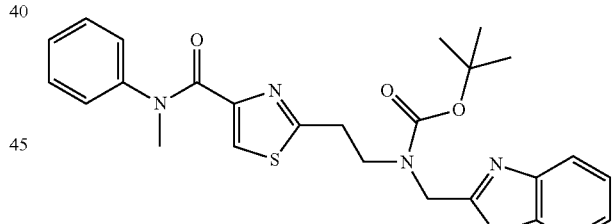

In a similar fashion to general procedure 6, 2-{2-[(1H-1,3-benzodiazol-2-ylmethyl)[(tert-butoxy)carbonyl]amino]ethyl}-1,3-thiazole-4-carboxylic acid (8) (99.8 mg, 0.248 mmol), N-methylaniline (31.89 mg, 0.298 mmol), DIPEA (96.16 mg, 0.744 mmol) and HATU (113.16 mg, 0.298 mmol) in DMF (4 ml) at room temperature for 1 h afforded the title compound (118 mg, 59% purity) as an off white oil after purification by flash column chromatography (eluting with a gradient of 0-10% MeOH/DCM). The title compound was used in the next step without further purification.

HPLCMS (Method H): [m/z]: 492.7 [M+H]$^+$

249

Tert-butyl N-(1H-1,3-benzodiazol-2-ylmethyl)-N-{2-[4-({[2-(pyrrolidin-1-yl)phenyl]methyl}carbamoyl)-1,3-thiazol-2-yl]ethyl}carbamate (16)

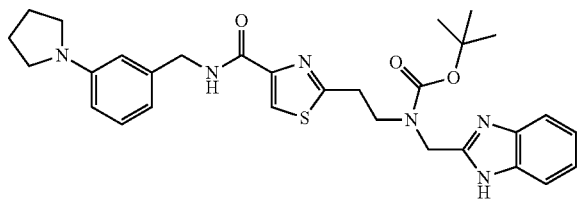 [SMILES: CC(C)(C)OC(=O)N(CCc1nc(C(=O)NCc2cccc(N3CCCC3)c2)cs1)Cc1nc2ccccc2[nH]1]

In a similar fashion to general procedure 6, 2-{2-[(1H-1,3-benzodiazol-2-ylmethyl)[(tert-butoxy)carbonyl]amino]ethyl}-1,3-thiazole-4-carboxylic acid (8) (200 mg, 0.497 mmol), [3-(pyrrolidin-1-yl)phenyl]methanamine (105 mg, 0.596 mmol), DIPEA (193 mg, 1.491 mmol) and HATU (227 mg, 0.596 mmol) in DMF (5 ml) at room temperature for 1 h afforded the title compound (100 mg, 30%, 84% purity) as an off white oil after purification by flash column chromatography (eluting with a gradient of 0-10% MeOH/DCM).

HPLCMS (Method H): [m/z]: 561.7 [M+H]$^+$

Tert-butyl N-(1H-1,3-benzodiazol-2-ylmethyl)-N-{2-[4-(dimethylcarbamoyl)-1,3-thiazol-2-yl]ethyl}carbamate (17)

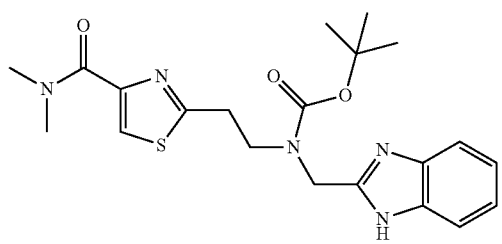 [SMILES: CN(C)C(=O)c1csc(CCN(Cc2nc3ccccc3[nH]2)C(=O)OC(C)(C)C)n1]

In a similar fashion to general procedure 6, 2-{2-[(1H-1,3-benzodiazol-2-ylmethyl)[(tert-butoxy)carbonyl]amino]ethyl}-1,3-thiazole-4-carboxylic acid (8) (100 mg, 0.248 mmol), dimethylamine (2 M solution in THF) (13 mg, 0.298 mmol), DIPEA (96 mg, 0.745 mmol) and HATU (113 mg, 0.298 mmol) in DMF (10 ml) at room temperature for 1 h afforded the title compound (90 mg, 67%, 80% purity) as a white solid after purification by flash column chromatography (eluting with a gradient of 0-10% MeOH/DCM).

HPLCMS (Method H): [m/z]: 430.6 [M+H]$^+$

250

Tert-butyl N-(1H-1,3-benzodiazol-2-ylmethyl)-N-(2-{4-[cyclohexyl(propan-2-yl)carbamoyl]-1,3-thiazol-2-yl}ethyl)carbamate (18)

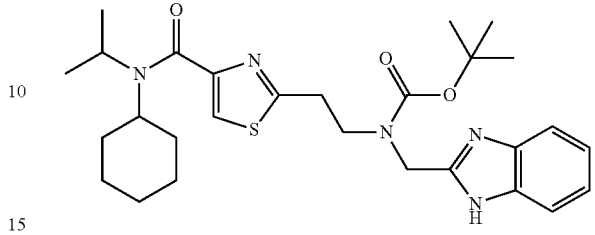

In a similar fashion to general procedure 6, 2-{2-[(1H-1,3-benzodiazol-2-ylmethyl)[(tert-butoxy)carbonyl]amino]ethyl}-1,3-thiazole-4-carboxylic acid (8) (99.8 mg, 0.248 mmol), N-(propan-2-yl)cyclohexanamine (42.04 mg, 0.298 mmol), DIPEA (96.16 mg, 0.744 mmol) and HATU (113.16 mg, 0.298 mmol) in DMF (4 ml) at room temperature for 1 h afforded the title compound (124 mg, 17% purity) as an off white oil after purification by flash column chromatography (eluting with a gradient of 0-10% MeOH/DCM). The title compound was used in the next step without further purification.

HPLCMS (Method H): [m/z]: 526.8 [M+H]$^+$

Tert-butyl N-(1H-1,3-benzodiazol-2-ylmethyl)-N-(2-{4-[(2-phenylpropan-2-yl)carbamoyl]-1,3-thiazol-2-yl}ethyl)carbamate (19)

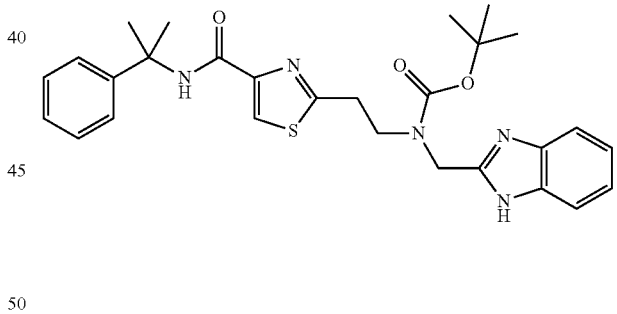

In a similar fashion to general procedure 6, 2-{2-[(1H-1,3-benzodiazol-2-ylmethyl)[(tert-butoxy)carbonyl]amino]ethyl}-1,3-thiazole-4-carboxylic acid (8) (99.8 mg, 0.248 mmol), 2-phenylpropan-2-amine (40.24 mg, 0.298 mmol), DIPEA (96.16 mg, 0.744 mmol) and HATU (113.16 mg, 0.298 mmol) in DMF (4 ml) at room temperature for 1 h afforded the title compound (120 mg, 51% purity) as an off white oil after purification by flash column chromatography (eluting with a gradient of 0-10% MeOH/DCM). The title compound was used in the next step without further purification.

HPLCMS (Method H): [m/z]: 520.7 [M+H]$^+$

251

Tert-butyl N-(1H-1,3-benzodiazol-2-ylmethyl)-N-{2-[4-(benzylcarbamoyl)-1,3-thiazol-2-yl]ethyl}carbamate (20)

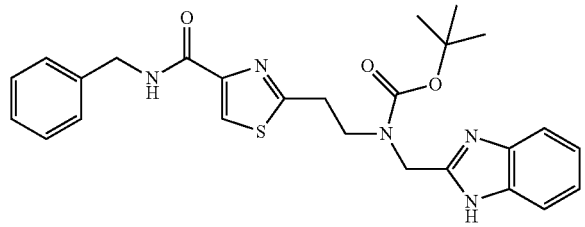 [SMILES: CC(C)(C)OC(=O)N(CCc1nc(C(=O)NCc2ccccc2)cs1)Cc1nc2ccccc2[nH]1]

In a similar fashion to general procedure 6, 2-{2-[(1H-1,3-benzodiazol-2-ylmethyl)[(tert-butoxy)carbonyl]amino]ethyl}-1,3-thiazole-4-carboxylic acid (8) (350 mg, 0.87 mmol), phenylmethanamine (103 mg, 0.957 mmol), DIPEA (337 mg, 2.61 mmol) and HATU (397 mg, 1.04 mmol) in DMF (10 ml) afforded the title compound (390 mg, 89% purity) as a white solid after purification by flash column chromatography (eluting with a gradient of 0-10% MeOH/DCM).

HPLCMS (Method H): [m/z]: 492.6 [M+H]$^+$

Tert-butyl N-{2-[4-(benzylcarbamoyl)-1,3-thiazol-2-yl]ethyl}-N-[(1-methyl-1H-1,3-benzodiazol-2-yl)methyl]carbamate (21)

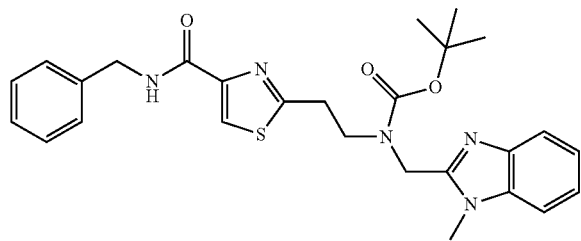 [SMILES: Cn1c(CN(CCc2nc(C(=O)NCc3ccccc3)cs2)C(=O)OC(C)(C)C)nc2ccccc21]

To a stirred solution of tert-butyl N-(1H-1,3-benzodiazol-2-ylmethyl)-N-{2-[4-(benzylcarbamoyl)-1,3-thiazol-2-yl]ethyl} carbamate (20) (380 mg, 0.773 mmol) and TEA (78 mg, 0.773 mmol) in DCM (15 ml) was added MeI (165 mg, 1.159 mmol) under argon atmosphere. The reaction mixture was stirred at room temperature overnight. The reaction mixture was evaporated under vacuum to dryness to afford the title compound (280 mg, 72% purity) as an off white solid. The crude product was used in the next step without purification.

HPLCMS (Method H): [m/z]: 506.6 [M+H]$^+$

252

Tert-butyl N-(1H-1,3-benzodiazol-2-ylmethyl)-N-(2-{4-[(pyridin-3-ylmethyl)carbamoyl]-1,3-thiazol-2-yl}ethyl)carbamate (22)

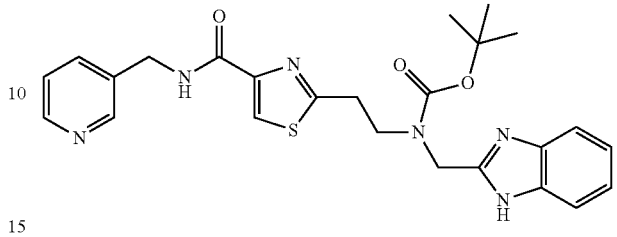

In a similar fashion to general procedure 6, 2-{2-[(1H-1,3-benzodiazol-2-ylmethyl)[(tert-butoxy)carbonyl]amino]ethyl}-1,3-thiazole-4-carboxylic acid (8) (199.6 mg, 0.496 mmol), pyridin-3-ylmethanamine (59 mg, 0.546 mmol), DIPEA (192.3 mg, 1.488 mmol) and HATU (226 mg, 0.595 mmol) in DMF (8 ml) afforded the title compound (184 mg, 75%) as a white solid after purification by flash column chromatography (eluting with a gradient of 0-10% MeOH/DCM).

1H-NMR (CDCl$_3$, 400 MHz): d[ppm]=8.61 (d, J=1.6 Hz, 1H), 8.52 (d, J=3.6 Hz, 1H), 7.96 (s, 1H), 7.81 (s, 1H), 7.73-7.67 (m, 1H), 7.55 (dd, J=6.0, 3.2 Hz, 2H), 7.28 (s, 1H), 7.25 (dd, J=6.1, 3.2 Hz, 2H), 4.63 (d, J=6.6 Hz, 4H), 3.77 (t, J=6.5 Hz, 2H), 3.22 (t, J=6.3 Hz, 2H), 1.37 (s, 9H)

HPLCMS (Method H): [m/z]: 493.4 [M+H]$^+$

Tert-butyl N-(1H-1,3-benzodiazol-2-ylmethyl)-N-(2-{4-[(pyridin-4-ylmethyl)carbamoyl]-1,3-thiazol-2-yl}ethyl)carbamate (23)


In a similar fashion to general procedure 6, 2-{2-[(1H-1,3-benzodiazol-2-ylmethyl)[(tert-butoxy)carbonyl]amino]ethyl}-1,3-thiazole-4-carboxylic acid (8) (199.6 mg, 0.496 mmol), pyridin-4-ylmethanamine (59 mg, 0.546 mmol), DIPEA (192.3 mg, 1.488 mmol) and HATU (226 mg, 0.595 mmol) in DMF (8 ml) afforded the title compound (140 mg, 57%) as a white solid after purification by flash column chromatography (eluting with a gradient of 0-10% MeOH/DCM).

1H-NMR (CDCl$_3$, 400 MHz): d[ppm]=8.56 (d, J=5.9 Hz, 2H), 7.98 (s, 1H), 7.82 (s, 1H), 7.59-7.48 (m, 2H), 7.24 (dd, J=6.0, 3.2 Hz, 4H), 4.62 (d, J=6.6 Hz, 4H), 3.78 (t, J=6.5 Hz, 2H), 3.25 (t, J=6.4 Hz, 2H), 1.41 (d, J=13.9 Hz, 9H)

HPLCMS (Method H): [m/z]: 493.4 [M+H]$^+$

253

Tert-butyl N-(1H-1,3-benzodiazol-2-ylmethyl)-N-{2-[4-({[3-(trifluoromethyl)pyridin-2-yl]methyl}carbamoyl)-1,3-thiazol-2-yl]ethyl}carbamate (24)

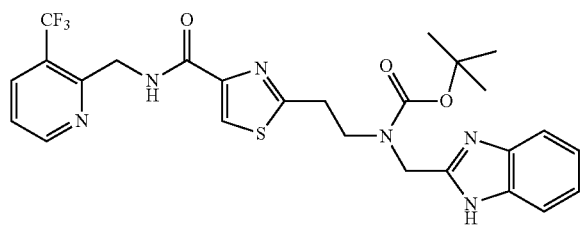 [SMILES: CC(C)(C)OC(=O)N(CCc1nc(C(=O)NCc2ncccc2C(F)(F)F)cs1)Cc1nc2ccccc2[nH]1]

In a similar fashion to general procedure 6, 2-{2-[(1H-1,3-benzodiazol-2-ylmethyl)[(tert-butoxy)carbonyl]amino]ethyl}-1,3-thiazole-4-carboxylic acid (8) (80.09 mg, 0.199 mmol), [3-(trifluoromethyl)pyridin-2-yl]methanamine hydrochloride (46.54 mg, 0.219 mmol), DIPEA (102.9 mg, 0.796 mmol) and HATU (90.8 mg, 0.239 mmol) in DNF (2.5 ml) afforded the title compound (85 mg, 76%, 98% purity) as a white solid after purification by flash column chromatography (eluting with a gradient of 0-10% MeOH/DCM).

HPLCMS (Method H): [m/z]: 561.5 [M+H]$^+$

Tert-butyl N-(1H-1,3-benzodiazol-2-ylmethyl)-N-(2-{4-[(5,6,7,8-tetrahydroquinolin-8-yl)carbamoyl]-1,3-thiazol-2-yl}ethyl)carbamate (25)

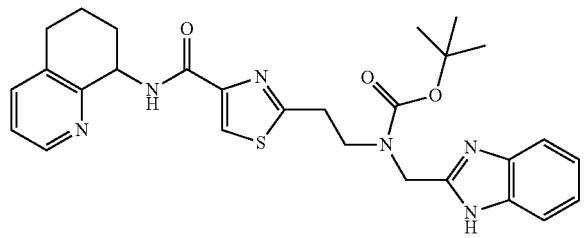 [SMILES: CC(C)(C)OC(=O)N(CCc1nc(C(=O)NC2CCCc3cccnc32)cs1)Cc1nc2ccccc2[nH]1]

In a similar fashion to general procedure 6, 2-{2-[(1H-1,3-benzodiazol-2-ylmethyl)[(tert-butoxy)carbonyl]amino]ethyl}-1,3-thiazole-4-carboxylic acid (8) (80.09 mg, 0.199 mmol), N-methyl-5,6,7,8-tetrahydroquinolin-8-amine dihydrochloride (48.4 mg, 0.219 mmol), DIPEA (102.9 mg, 0.796 mmol) and HATU (90.8 mg, 0.239 mmol) in DMF (2.5 ml) afforded the title compound (92 mg, 87%) as a white solid after purification by flash column chromatography (eluting with a gradient of 0-10% MeOH/DCM).

HPLCMS (Method H): [m/z]: 533.5 [M+H]$^+$

254

Tert-butyl N-(1H-1,3-benzodiazol-2-ylmethyl)-N-{2-[4-({5H,6H,7H-cyclopenta[b]pyridin-7-yl}carbamoyl)-1,3-thiazol-2-yl]ethyl}carbamate (26)

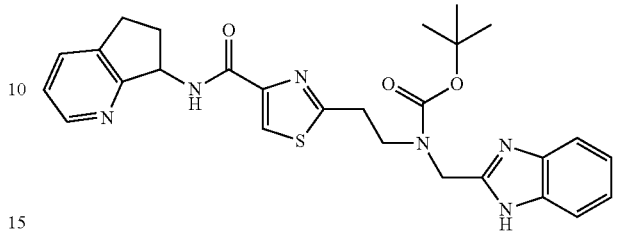

In a similar fashion to general procedure 6, 2-{2-[(1H-1,3-benzodiazol-2-ylmethyl)[(tert-butoxy)carbonyl]amino]ethyl}-1,3-thiazole-4-carboxylic acid (8) (80.9 mg, 0.199 mmol), N-methyl-5H,6H,7H-cyclopenta[b]pyridin-7-amine hydrochloride (37.35 mg, 0.219 mmol), DIPEA (102.9 mg, 0.796 mmol) and HATU (90.8 mg, 0.239 mmol) in DMF (2.5 ml) afforded the title compound (90 mg, 87%) as a white solid after purification by flash column chromatography (eluting with a gradient of 0-10% MeOH/DCM).

HPLCMS (Method H): [m/z]: 519.5 [M+H]$^+$

Tert-butyl N-(1H-1,3-benzodiazol-2-ylmethyl)-N-[2-(4-{[(4-methylmorpholin-2-yl)methyl]carbamoyl}-1,3-thiazol-2-yl)ethyl]carbamate (27)

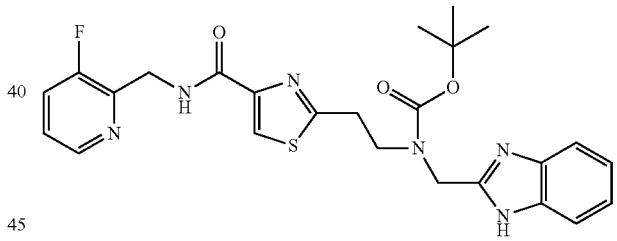

In a similar fashion to general procedure 6, 2-{2-[(1H-1,3-benzodiazol-2-ylmethyl)[(tert-butoxy)carbonyl]amino]ethyl}-1,3-thiazole-4-carboxylic acid (8) (3 g, 7.545 mmol), (3-fluoropyridin-2-yl)methanamine dihydrochloride (A2) (2.26 g, 11.18 mmol), DIPEA (12.98 ml, 74.54 mmol) and HATU (4.251 g, 11.18 mmol) in DMF (60 ml) afforded the title compound (4.13 mg, 89%) as a yellow oil after purification by flash column chromatography (kp-NH, eluting with a gradient of 20-100% EtOAc/heptane followed by 0-20% MeOH/EtOAc).

1H-NMR (DMSO-d6, 500 MHz): d[ppm]=12.29 (s, 1H), 8.69 (s, 1H), 8.36 (s, 1H), 8.17 (s, 1H), 7.70 (t, J=9.5 Hz, 1H), 7.48 (s, 2H), 7.40 (dt, J=8.6, 4.4 Hz, 1H), 7.14 (s, 2H), 4.66 (d, J=8.8 Hz, 4H), 3.73 (s, 2H), 2.52 (s, 2H), 1.99 (s, 4H), 1.26 (d, J=44.9 Hz, 9H)

HPLCMS (Method A): [m/z]: 511.15 [M+H]$^+$

Tert-butyl N-(1H-1,3-benzodiazol-2-ylmethyl)-N-[2-(4-{[(4-methylmorpholin-2-yl)methyl]carbamoyl}-1,3-thiazol-2-yl)ethyl]carbamate (28)

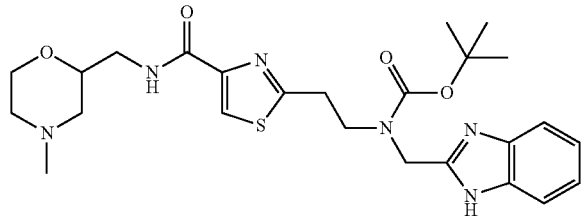 [SMILES: CN1CCOC(CNC(=O)c2csc(CCN(Cc3nc4ccccc4[nH]3)C(=O)OC(C)(C)C)n2)C1]

In a similar fashion to general procedure 6, 2-{2-[(1H-1,3-benzodiazol-2-ylmethyl)[(tert-butoxy)carbonyl]amino]ethyl}-1,3-thiazole-4-carboxylic acid (8) (99.8 mg, 0.248 mmol), (4-methylmorpholin-3-yl)methanamine (35.5 mg, 0.273 mmol), DIPEA (96.16 mg, 0.744 mmol) and T3P (189.4 mg, 0.298 mmol) in DMF (4 ml) afforded the title compound (90 mg, 70%) as a white solid after purification by flash column chromatography (eluting with a gradient of 0-10% MeOH/DCM).

1H-NMR (CDCl$_3$, 400 MHz): d[ppm]=7.90 (s, 1H), 7.59 (s, 3H), 7.28 (t, J=3.6 Hz, 1H), 4.64 (s, 2H), 3.79 (td, J=12.0, 4.7 Hz, 5H), 3.70-3.59 (m, 2H), 3.47 (ddd, J=14.7, 10.3, 6.6 Hz, 4H), 3.22 (t, J=6.4 Hz, 2H), 2.74 (d, J=11.4 Hz, 1H), 2.49-2.32 (m, 6H), 1.40 (s, 9H)

Tert-butyl N-(1H-1,3-benzodiazol-2-ylmethyl)-N-[2-(4-{[(6-methylpyridin-2-yl)methyl]carbamoyl}-1,3-thiazol-2-yl)ethyl]carbamate (29)

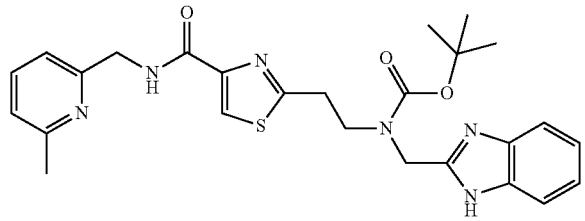 [SMILES: Cc1cccc(CNC(=O)c2csc(CCN(Cc3nc4ccccc4[nH]3)C(=O)OC(C)(C)C)n2)n1]

In a similar fashion to general procedure 6, 2-{2-[(1H-1,3-benzodiazol-2-ylmethyl)[(tert-butoxy)carbonyl]amino]ethyl}-1,3-thiazole-4-carboxylic acid 6 (99.8 mg, 0.248 mmol), (6-methylpyridin-2-yl)methanamine (33.33 mg, 0.273 mmol), DIPEA (96.16 mg, 0.744 mmol) and T3P (189.4 mg, 0.298 mmol) in DMF (4 ml) afforded the title compound (95 mg, 75%) as a white solid after purification by flash column chromatography (eluting with a gradient of 0-10% MeOH/DCM).

1H-NMR (CDCl$_3$, 400 MHz): d[ppm]=8.14 (s, 1H), 7.90 (s, 1H), 7.55 (dd, J=14.1, 6.6 Hz, 3H), 7.23 (dd, J=6.0, 3.2 Hz, 2H), 7.14 (d, J=7.7 Hz, 1H), 7.06 (d, J=7.7 Hz, 1H), 4.71 (d, J=5.5 Hz, 2H), 4.66 (s, 2H), 3.80 (t, J=6.3 Hz, 2H), 3.22 (t, J=6.4 Hz, 2H), 2.55 (s, 3H), 1.34 (s, 9H)

Tert-butyl N-(1H-1,3-benzodiazol-2-ylmethyl)-N-[2-(4-{[(5-fluoropyridin-2-yl)methyl]carbamoyl}-1,3-thiazol-2-yl)ethyl]carbamate (30)

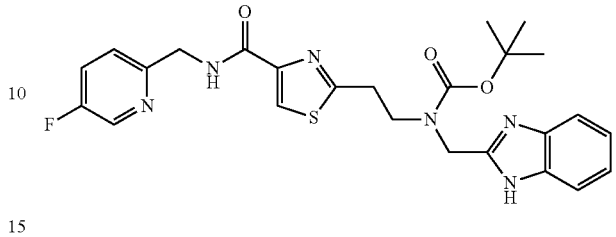

In a similar fashion to general procedure 6, 2-{2-[(1H-1,3-benzodiazol-2-ylmethyl)[(tert-butoxy)carbonyl]amino]ethyl}-1,3-thiazole-4-carboxylic acid (8) (99.8 mg, 0.248 mmol), (5-fluoropyridin-2-yl)methanamine (34.41 mg, 0.273 mmol), DIPEA (96.16 mg, 0.744 mmol) and T3P (189.4 mg, 0.298 mmol) in DMF (4 ml) afforded the title compound (89 mg, 70%) as a white solid after purification by flash column chromatography (eluting with a gradient of 0-10% MeOH/DCM).

1H-NMR (CDCl$_3$, 400 MHz): d[ppm]=8.44 (s, 1H), 8.12 (s, 1H), 7.92 (s, 1H), 7.56 (s, 2H), 7.44-7.30 (m, 2H), 7.25 (dd, J=6.1, 3.2 Hz, 2H), 4.73 (d, J=5.6 Hz, 2H), 4.66 (s, 2H), 3.79 (t, J=6.3 Hz, 2H), 3.23 (t, J=6.3 Hz, 2H), 3.04 (s, 1H), 1.34 (s, 9H)

Tert-butyl N-(1H-1,3-benzodiazol-2-ylmethyl)-N-(2-{4-[(pyrimidin-4-ylmethyl)carbamoyl]-1,3-thiazol-2-yl}ethyl)carbamate (31)

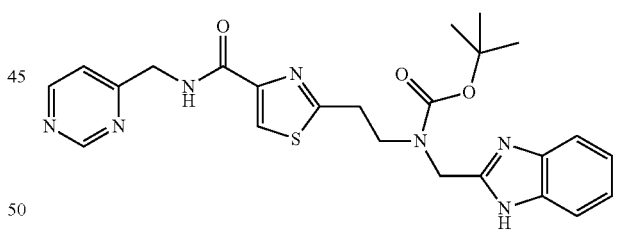

In a similar fashion to general procedure 6, 2-{2-[(1H-1,3-benzodiazol-2-ylmethyl)[(tert-butoxy)carbonyl]amino]ethyl}-1,3-thiazole-4-carboxylic acid (8) (150 mg, 0.373 mmo), pyrimidin-4-ylmethanamine (48.8 mg, 0.447 mmol), DIPEA (48.1 mg, 0.373 mmol) and HATU (141.7 mg, 0.373 mmol) in DMF (2 ml) at room temperature overnight gave the title compound (80 mg, 60% purity) as an yellow oil after purification by flash column chromatography (eluting with a gradient of 10% MeOH in DCM).

HPLCMS (Method H): [m/z]: 494.6 [M+H]$^+$

Tert-butyl N-(1H-1,3-benzodiazol-2-ylmethyl)-N-[2-(4-{[(5-methoxypyridin-2-yl)methyl]carbamoyl}-1,3-thiazol-2-yl)ethyl]carbamate (32)

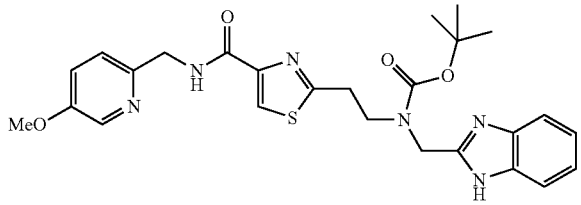 [SMILES: COc1ccc(CNC(=O)c2csc(CCN(Cc3nc4ccccc4[nH]3)C(=O)OC(C)(C)C)n2)nc1]

In a similar fashion to general procedure 6, 2-{2-[(1H-1,3-benzodiazol-2-ylmethyl)[(tert-butoxy)carbonyl]amino]ethyl}-1,3-thiazole-4-carboxylic acid (8) (150 mg, 0.373 mmo), (5-methoxypyridin-2-yl)methanamine (48.17 mg, 0.447 mmol), DIPEA (48.1 mg, 0.373 mmol) and HATU (141.7 mg, 0.373 mmol) in DMF (2 ml) at room temperature overnight gave the title compound (80 mg, 41%) as brown solid after purification by flash column chromatography (eluting with a gradient of 10% MeOH in DCM).
HPLCMS (Method H): [m/z]: 523.6 [M+H]$^+$ Tert-butyl N-(1H-1,3-benzodiazol-2-ylmethyl)-N-(2-{4-[(pyrazin-2-ylmethyl)carbamoyl]-1,3-thiazol-2-yl}ethyl)carbamate (33)

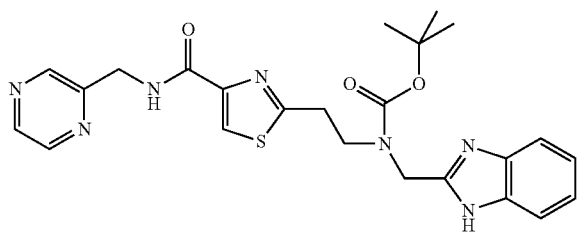 [SMILES: CC(C)(C)OC(=O)N(CCc1nc(C(=O)NCc2cnccn2)cs1)Cc1nc2ccccc2[nH]1]

In a similar fashion to general procedure 6, 2-{2-[(1H-1,3-benzodiazol-2-ylmethyl)[(tert-butoxy)carbonyl]amino]ethyl}-1,3-thiazole-4-carboxylic acid (8) (150 mg, 0.373 mmol), pyrazin-2-ylmethanamine (48.8 mg, 0.447 mmol), DIPEA (192.68 mg, 1.491 mmol) and HATU (141.7 mg, 0.373 mmol) in DMF (2 ml) at room temperature overnight gave the title compound (95 mg, 52%) as yellow solid after purification by flash column chromatography (eluting with a gradient of 10% MeOH in DCM).
HPLCMS (Method H): [m/z]: 394.5 [M+H-Boc]$^+$ Tert-butyl N-(1H-1,3-benzodiazol-2-ylmethyl)-N-[2-(4-{[(6-oxo-1,6-dihydropyridin-2-yl)methyl]carbamoyl}-1,3-thiazol-2-yl)ethyl]carbamate (34)

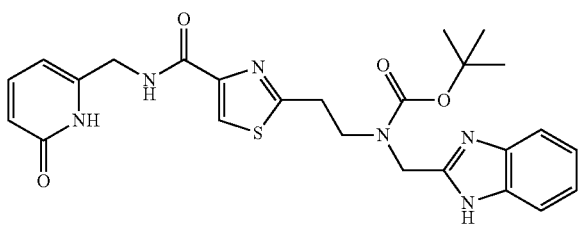 [SMILES: CC(C)(C)OC(=O)N(CCc1nc(C(=O)NCc2cccc(=O)[nH]2)cs1)Cc1nc2ccccc2[nH]1]

In a similar fashion to general procedure 6, 2-{2-[(1H-1,3-benzodiazol-2-ylmethyl)[(tert-butoxy)carbonyl]amino]ethyl}-1,3-thiazole-4-carboxylic acid (8) (150 mg, 0.373 mmol), 6-(aminomethyl)-1,2-dihydropyridin-2-one (55.52 mg, 0.447 mmol), DIPEA (48.17 mg, 0.373 mmol) and HATU (141.7 mg, 0.373 mmol) in DMF (2 ml) at room temperature overnight gave the title compound (90 mg, 47%) as yellow solid after purification by flash column chromatography (eluting with a gradient of 10% MeOH/DCM).
HPLCMS (Method H): [m/z]: 509.6 [M+H]$^+$ Tert-butyl N-(1H-1,3-benzodiazol-2-ylmethyl)-N-[2-(4-{[(6-carbamoylpyridin-3-yl)methyl]carbamoyl}-1,3-thiazol-2-yl)ethyl]carbamate (35) and Tert-butyl N-(1H-1,3-benzodiazol-2-ylmethyl)-N-[2-(4-{[(6-cyanopyridin-3-yl)methyl]carbamoyl}-1,3-thiazol-2-yl)ethyl]carbamate (36)

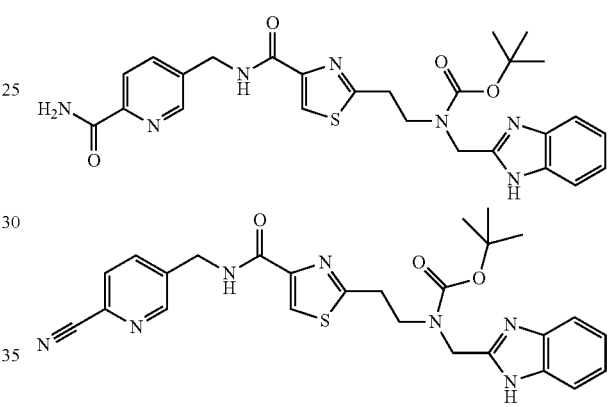

In a similar fashion to general procedure 6, 2-{2-[(1H-1,3-benzodiazol-2-ylmethyl)[(tert-butoxy)carbonyl]amino]ethyl}-1,3-thiazole-4-carboxylic acid (8) (100 mg, 0.248 mmol), 5-(aminomethyl)pyridine-2-carbonitrile (33 mg, 0.248 mmol), HATU (189 mg, 0.497 mmol) and DIPEA (96 mg, 0.745 mmol) in DMF (1 ml) at room temperature for 18 h, gave a 2:1 ratio of boc amide and boc nitrile (80 mg) after purification by flash column chromatography (DCM:MeOH, 9:1). The mixture was used in the next step without separation.
HPLCMS (Method H): [m/z]: 418.5 [M+H-boc]$^+$ and 436.3 [M+H-boc]$^+$ Tert-butyl N-(1H-1,3-benzodiazol-2-ylmethyl)-N-[2-(4-{[(3,5-dimethylpyridin-2-yl)methyl]carbamoyl}-1,3-thiazol-2-yl)ethyl]carbamate (37)

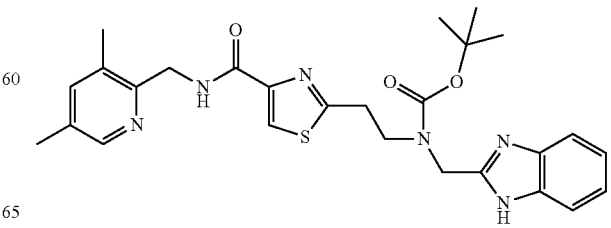

In a similar fashion to general procedure 6, 2-{2-[(1H-1,3-benzodiazol-2-ylmethyl)[(tert-butoxy)carbonyl]amino]ethyl}-1,3-thiazole-4-carboxylic acid (8) (0.3 g, 0.708 mmol), (3,5-dimethylpyridin-2-yl)methanamine hydrochloride (0.183 g, 1.062 mmol), DIPEA (0.555 ml, 3.187 mmol) and HATU (0.404 g, 1.062 mmol) in DMF (6 ml) at room temperature for 4 h, gave the title compound (0.198 g, 51%) as a yellow oil after purification by flash column chromatography (kp-NH, eluting with a gradient of EtOAc (30%)/heptane (70%) followed by 100% EtOAc).

1H-NMR (DMSO-d6, 500 MHz): d[ppm]=12.29 (s, 1H), 8.75 (s, 1H), 8.19 (s, 2H), 7.56 (d, J=7.6 Hz, 1H), 7.48-7.40 (m, 2H), 7.14 (p, J=7.0 Hz, 2H), 4.66 (s, 2H), 4.53 (d, J=4.8 Hz, 2H), 3.73 (s, 2H), 2.27 (s, 3H), 2.23 (s, 3H), 1.31 (s, 9H)

HPLCMS (Method A): [m/z]: 521.15 [M+H]$^+$

Tert-butyl N-(1H-1,3-benzodiazol-2-ylmethyl)-N-(2-{4-[(pyrimidin-2-ylmethyl)carbamoyl]-1,3-thiazol-2-yl}ethyl)carbamate (38)

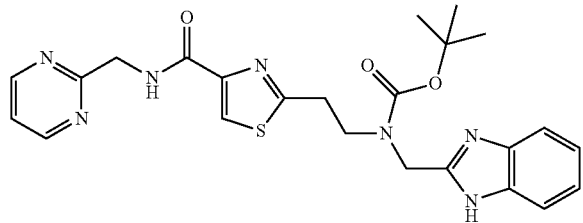 [SMILES: CC(C)(C)OC(=O)N(CCc1nc(C(=O)NCc2ncccn2)cs1)Cc1nc2ccccc2[nH]1]

In a similar fashion to general procedure 6, 2-{2-[(1H-1,3-benzodiazol-2-ylmethyl)[(tert-butoxy)carbonyl]amino]ethyl}-1,3-thiazole-4-carboxylic acid (8) (100 mg, 0.20 mmol), 1-(pyrimidin-2-yl)methanamine (22 mg, 0.20 mmol), DIPEA (0.1 ml, 0.60 mmol) and HATU (113 mg, 0.30 mmol) in DCM (5 ml) afforded the title compound (86 mg, 73%) as a brown residue after purification by flash column chromatography (eluting with a gradient of 0-20% MeOH/EtOAc).

HPLCMS (Method A): [m/z]: 494.1 [M+H]$^+$

Tert-butyl N-(1H-1,3-benzodiazol-2-ylmethyl)-N-{2-[4-({[2-(4-methylpiperazin-1-yl)phenyl]methyl}carbamoyl)-1,3-thiazol-2-yl]ethyl}carbamate (39)

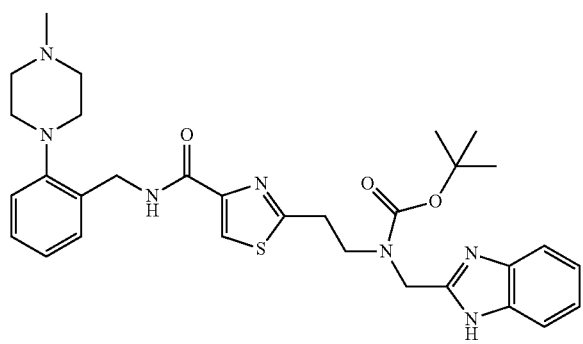 [SMILES: CN1CCN(c2ccccc2CNC(=O)c2csc(CCN(Cc3nc4ccccc4[nH]3)C(=O)OC(C)(C)C)n2)CC1]

In a similar fashion to general procedure 6, 2-{2-[(1H-1,3-benzodiazol-2-ylmethyl)[(tert-butoxy)carbonyl]amino]ethyl}-1,3-thiazole-4-carboxylic acid (8) (130 mg, 0.24 mmol, 75% purity), 1-[2-(4-methylpiperazin-1-yl)phenyl]methanamine (75 mg, 0.36 mmol), DIPEA (127 µl, 0.73 mmol) and HATU (138 mg, 0.36 mmol) in DMF (2 ml) afforded the title compound (13 mg, 9%) as a white solid following purification by basic prep-HPLC.

HPLCMS (Method D): [m/z]: 590.3 [M+H]$^+$

Tert-butyl N-(1H-1,3-benzodiazol-2-ylmethyl)-N-[2-(4-{[(2,6-difluorophenyl)methyl]carbamoyl}-1,3-thiazol-2-yl)ethyl]carbamate (40)

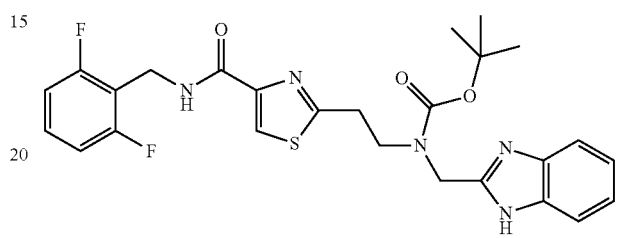

In a similar fashion to general procedure 6, 2-{2-[(1H-1,3-benzodiazol-2-ylmethyl)[(tert-butoxy)carbonyl]amino]ethyl}-1,3-thiazole-4-carboxylic acid (8) (110 mg, 0.25 mmol, 90% purity), 1-(2,6-difluorophenyl)methanamine (53 mg, 0.37 mmol), DIPEA (0.13 ml, 0.74 mmol) and HATU (140 mg, 0.37 mmol) in DMF (2 ml) afforded the title compound (90 mg, 68%) as a yellow oil after purification by flash column chromatography (kp-NH, eluting with a gradient of 2-100% EtOAc/heptane).

HPLCMS (Method E): [m/z]: 528.3 [M+H]$^+$

Tert-butyl N-(1H-1,3-benzodiazol-2-ylmethyl)-N-{2-[4-({[2-(dimethylamino)phenyl]methyl}carbamoyl)-1,3-thiazol-2-yl]ethyl}carbamate (41)

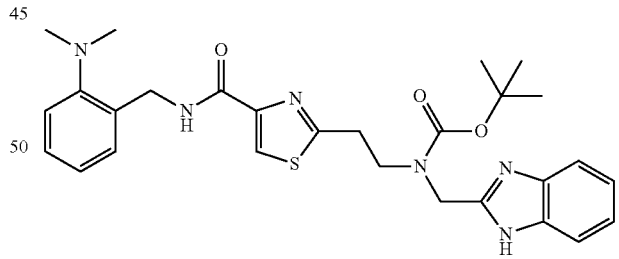

In a similar fashion to general procedure 6, 2-{2-[(1H-1,3-benzodiazol-2-ylmethyl)[(tert-butoxy)carbonyl]amino]ethyl}-1,3-thiazole-4-carboxylic acid (8) (109 mg, 0.22 mmol, 80% purity), 2-(aminomethyl)-N,N-dimethylaniline (66 mg, 0.44 mmol), DIPEA (226 µl, 1.30 mmol) and HATU (240 mg, 0.64 mmol) in DMF (2 ml) at 50° C. afforded the title compound (73 mg, 61%) as an orange oil after purification by flash column chromatography (kp-NH, eluting with a gradient of 5-100% EtOAc/heptane).

HPLCMS (Method D): [m/z]: 535.2 [M+H]$^+$

261

Tert-butyl N-(1H-1,3-benzodiazol-2-ylmethyl)-N-[2-(4-{[(2-cyanophenyl)methyl]carbamoyl}-1,3-thiazol-2-yl)ethyl]carbamate (42)

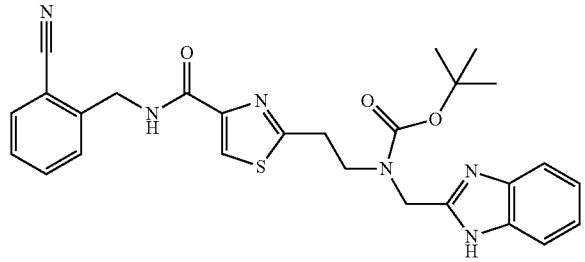 [SMILES: CC(C)(C)OC(=O)N(CCc1nc(C(=O)NCc2ccccc2C#N)cs1)Cc1nc2ccccc2[nH]1]

In a similar fashion to general procedure 6, 2-{2-[(1H-1,3-benzodiazol-2-ylmethyl)[(tert-butoxy)carbonyl]amino]ethyl}-1,3-thiazole-4-carboxylic acid (8) (109 mg, 0.22 mmol, 80% purity), 2-(aminomethyl)benzonitrile hydrochloride (74 mg, 0.44 mmol), DIPEA (226 µl, 1.30 mmol) and HATU (240 mg, 0.64 mmol) in DMF (2 ml) at 50° C. afforded the crude title compound (54 mg, 30%, 63% purity) as an orange oil after purification by flash column chromatography (kp-NH, eluting with a gradient of 5-100% EtOAc/heptane).

HPLCMS (Method D): [m/z]: 517.2 [M+H]$^+$

Tert-butyl N-(1H-1,3-benzodiazol-2-ylmethyl)-N-{2-[4-({[2-(trifluoromethoxy)phenyl]methyl}carbamoyl)-1,3-thiazol-2-yl]ethyl}carbamate (43)

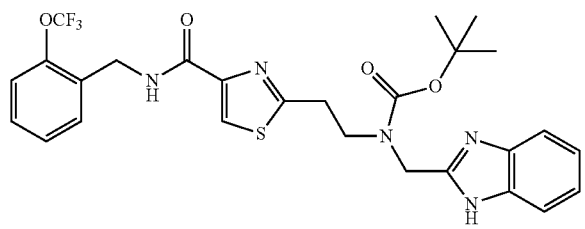 [SMILES: CC(C)(C)OC(=O)N(CCc1nc(C(=O)NCc2ccccc2OC(F)(F)F)cs1)Cc1nc2ccccc2[nH]1]

In a similar fashion to general procedure 6, 2 2-{2-[(1H-1,3-benzodiazol-2-ylmethyl)[(tert-butoxy)carbonyl]amino]ethyl}-1,3-thiazole-4-carboxylic acid (8) (109 mg, 0.22 mmol, 80% purity), 1-[2-(trifluoromethoxy)phenyl]methanamine (103 mg, 0.54 mmol), DIPEA (283 µl, 1.63 mmol) and HATU (248 mg, 0.65 mmol) in DMF (2 ml) at 50° C. afforded the crude title compound (110 mg, 78%, 88% purity) as a yellow oil after purification by flash column chromatography (kp-NH, eluting with a gradient of 8-100% EtOAc/heptane).

HPLCMS (Method E): [m/z]: 576.2 [M+H]$^+$

262

Tert-butyl N-(1H-1,3-benzodiazol-2-ylmethyl)-N-(2-{4-[(1-phenylethyl)carbamoyl]-1,3-thiazol-2-yl}ethyl)carbamate (44)

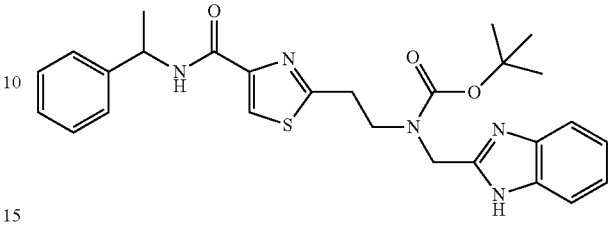

In a similar fashion to general procedure 6, 2-{2-[(1H-1,3-benzodiazol-2-ylmethyl)[(tert-butoxy)carbonyl]amino]ethyl}-1,3-thiazole-4-carboxylic acid (8) (0.11 g, 0.22 mmol, 80% purity), 1-phenylethanamine (0.07 ml, 0.54 mmol), DIPEA (0.303 ml, 1.63 mmol) and HATU (0.25 g, 0.64 mmol) in DMF (2 ml) afforded the crude title compound (110 mg, 77%, 77% purity) as a yellow oil after purification by flash column chromatography (KP—NH, eluting with a gradient of 8-100% EtOAc/heptane).

HPLCMS (Method E): [m/z]: 506.2 [M+H]$^+$

Tert-butyl N-(1H-1,3-benzodiazol-2-ylmethyl)-N-{2-[4-({[2-(difluoromethoxy)phenyl]methyl}carbamoyl)-1,3-thiazol-2-yl]ethyl}carbamate (45)

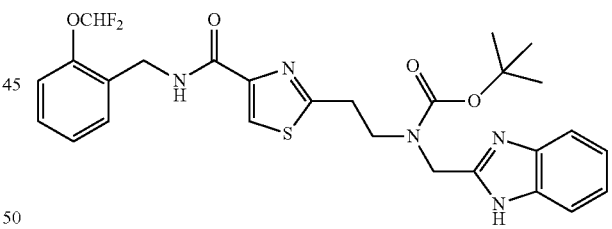

In a similar fashion to general procedure 6, 2-{2-[(1H-1,3-benzodiazol-2-ylmethyl)[(tert-butoxy)carbonyl]amino]ethyl}-1,3-thiazole-4-carboxylic acid (8) (109 mg, 0.22 mmol, 80% purity), 1-[2-(difluoromethoxy)phenyl]methanamine (83 mg, 0.48 mmol), DIPEA (0.23 ml, 1.3 mmol) and HATU (250 mg, 0.65 mmol) in DMF (2 ml) afforded the crude title compound (470 mg) as an orange oil which was used in the next step without purification.

HPLCMS (Method A): [m/z]: 558.25 [M+H]$^+$

263

Tert-butyl N-(1H-1,3-benzodiazol-2-ylmethyl)-N-{2-[4-({[2-(morpholine-4-sulfonyl)phenyl]methyl}carbamoyl)-1,3-thiazol-2-yl]ethyl}carbamate (46)

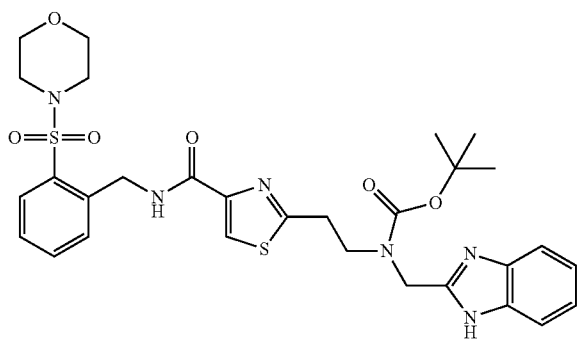 [SMILES: CC(C)(C)OC(=O)N(CCc1nc(C(=O)NCc2ccccc2S(=O)(=O)N2CCOCC2)cs1)Cc1nc2ccccc2[nH]1]

In a similar fashion to general procedure 6, 2-{2-[(1H-1,3-benzodiazol-2-ylmethyl)[(tert-butoxy)carbonyl]amino]ethyl}-1,3-thiazole-4-carboxylic acid (8) (109 mg, 0.217 mmol, 80% purity), 1-[2-(morpholin-4-ylsulfonyl)phenyl]methanamine hydrochloride (140 mg, 0.48 mmol), DIPEA (0.23 ml, 1.3 mmol) and HATU (247 mg, 0.65 mmol) in DMF (2 ml) afforded the crude title compound (440 mg) as an orange oil after direct evaporation of the reaction mixture in vacuo. The material was used without purification.

HPLCMS (Method A): [m/z]: 641.35 [M+H]$^+$

Tert-butyl N-(1H-1,3-benzodiazol-2-ylmethyl)-N-[2-(4-{[2-(pyridin-2-yl)ethyl]carbamoyl}-1,3-thiazol-2-yl)ethyl]carbamate (47)

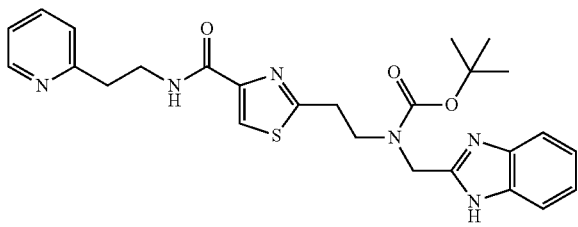 [SMILES: CC(C)(C)OC(=O)N(CCc1nc(C(=O)NCCc2ccccn2)cs1)Cc1nc2ccccc2[nH]1]

In a similar fashion to general procedure 6, 2-{2-[(1H-1,3-benzodiazol-2-ylmethyl)[(tert-butoxy)carbonyl]amino]ethyl}-1,3-thiazole-4-carboxylic acid (8) (100 mg, 0.2 mmol, 80% purity), 2-(pyridin-2-yl)ethanamine (49 mg, 0.4 mmol), DIPEA (104 µl, 0.6 mmol) and HATU (151 mg, 0.4 mmol) in DMF (2 ml) afforded the title compound (52 mg, 52%) as a cream solid after purification by flash column chromatography KP—NH, eluting with a gradient of 5-100% EtOAc/heptane).

HPLCMS (Method A): [m/z]: 507.15 [M+H]$^+$

264

Tert-butyl N-(1H-1,3-benzodiazol-2-ylmethyl)-N-(2-{4-[(3-fluoropyridin-2-yl)carbamoyl]-1,3-thiazol-2-yl}ethyl)carbamate (48)

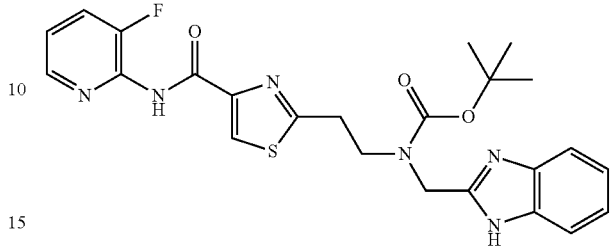

In a similar fashion to general procedure 6, a solution of 2-{2-[(1H-1,3-benzodiazol-2-ylmethyl)[(tert-butoxy)carbonyl]amino]ethyl}-1,3-thiazole-4-carboxylic acid (8) (80%, 150 mg, 0.3 mmol), 3-fluoropyridin-2-amine (100 mg, 0.89 mmol), DIPEA (312 µl, 1.78 mmol) and HATU (340 mg, 0.87 mmol) in DMF (2 ml) was heated at 100° C. for 16 h. The reaction mixture was concentrated in vacuo to give the crude title compound (705 mg) as a brown oil which was used in the next step without purification.

HPLCMS (Method A): [m/z]: 497.10 [M+H]$^+$

Tert-butyl N-(1H-1,3-benzodiazol-2-ylmethyl)-N-(2-{4-[(2-phenylethyl)carbamoyl]-1,3-thiazol-2-yl}ethyl)carbamate (49)

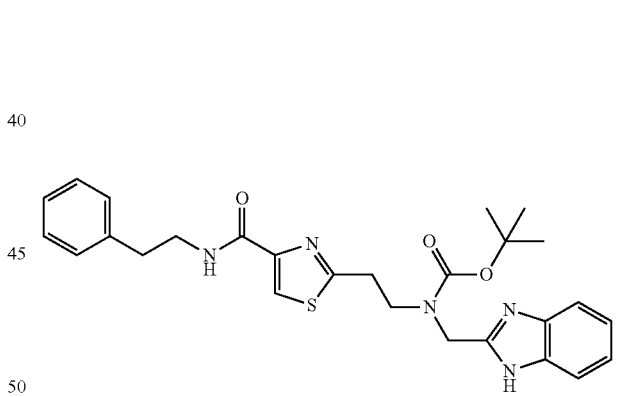

In a similar fashion to general procedure 6, 2-{2-[(1H-1,3-benzodiazol-2-ylmethyl)[(tert-butoxy)carbonyl]amino]ethyl}-1,3-thiazole-4-carboxylic acid (8) (0.1 g, 0.25 mmol), 2-phenylethanamine (0.03 ml, 0.25 mmol), DIPEA (0.13 ml, 0.75 mmol) and HATU (0.14 g, 0.37 mmol) in DMF (2 ml) afforded the title compound (71 mg, 56%) as a yellow oil after purification by flash column chromatography (eluting with a gradient of 2-100% EtOAc/heptane).

HPLCMS (Method A): [m/z]: 506.2 [M+H]$^+$

Tert-butyl N-(1H-1,3-benzodiazol-2-ylmethyl)-N-[2-(4-{[(3-fluoro-6-methylpyridin-2-yl)methyl]carbamoyl}-1,3-thiazol-2-yl)ethyl]carbamate (50)

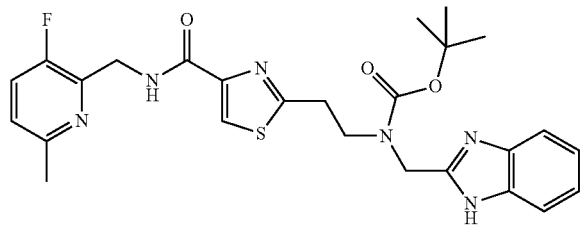 [SMILES: Cc1ccc(F)c(CNC(=O)c2csc(CCN(Cc3nc4ccccc4[nH]3)C(=O)OC(C)(C)C)n2)n1]

In a similar fashion to general procedure 6, 2-{2-[(1H-1,3-benzodiazol-2-ylmethyl)[(tert-butoxy)carbonyl]amino]ethyl}-1,3-thiazole-4-carboxylic acid (8) (150 mg, 0.298 mmol, 80% purity), (3-fluoro-6-methylpyridin-2-yl)methanamine hydrochloride (79 mg, 0.447 mmol), DIPEA (156 µl, 0.894 mmol) and HATU (230 mg, 0.596 mmol) in DMF (3 ml) afforded the title compound (76 mg, 48%) as a pale yellow oil after purification by flash column chromatography (kp-NH, eluting with a gradient of 0-100% EtOAc/heptane).

HPLCMS (Method A): [m/z]: 525.40 [M+H]$^+$

Tert-butyl N-(1H-1,3-benzodiazol-2-ylmethyl)-N-[2-(4-{[1-(pyridin-2-yl)ethyl]carbamoyl}-1,3-thiazol-2-yl)ethyl]carbamate (51)

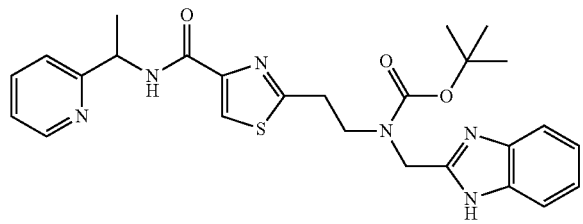 [SMILES: CC(NC(=O)c1csc(CCN(Cc2nc3ccccc3[nH]2)C(=O)OC(C)(C)C)n1)c1ccccn1]

In a similar manner to general procedure 6, 2-{2-[(1H-1,3-benzodiazol-2-ylmethyl)[(tert-butoxy)carbonyl]amino]ethyl}-1,3-thiazole-4-carboxylic acid (8) (150 mg, 0.298 mmol, 80% purity), 1-(pyridin-2-yl)ethanamine (55 mg, 0.447 mmol), DIPEA (156 µl, 0.894 mmol) and HATU (227 mg, 0.596 mmol) in DMF (3 ml) afforded the title compound (78 mg, 50%) as a colourless oil after purification by flash column chromatography (kp-NH, eluting with a gradient of 0-100% EtOAc/heptane).

HPLCMS (Method A): [m/z]: 507.20 [M+H]$^+$

Tert-butyl N-(1H-1,3-benzodiazol-2-ylmethyl)-N-{2-[4-({[6-(trifluoromethyl)pyridin-3-yl]methyl}carbamoyl)-1,3-thiazol-2-yl]ethyl}carbamate (52)

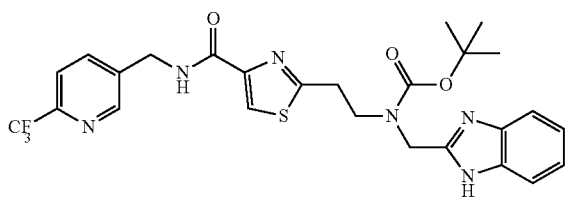 [SMILES: CC(C)(C)OC(=O)N(CCc1nc(C(=O)NCc2ccc(C(F)(F)F)nc2)cs1)Cc1nc2ccccc2[nH]1]

In a similar manner to general procedure 6, 2-{2-[(1H-1,3-benzodiazol-2-ylmethyl)[(tert-butoxy)carbonyl]amino]ethyl}-1,3-thiazole-4-carboxylic acid (8) (150 mg, 0.298 mmol, 80% purity), 1-[6-(trifluoromethyl)pyridin-3-yl]methanamine (79 mg, 0.447 mmol), DIPEA (156 µl, 0.894 mmol) and HATU (227 mg, 0.596 mmol) in DMF (3 ml) afforded the title compound (92 mg, 46%) as a colourless oil after purification by flash column chromatography (kp-NH, eluting with a gradient of 0-100% EtOAc/heptane).

HPLCMS (Method A): [m/z]: 561.35 [M+H]$^+$

Tert-butyl N-(1H-1,3-benzodiazol-2-ylmethyl)-N-[2-(4-{[(3-chloropyridin-2-yl)methyl]carbamoyl}-1,3-thiazol-2-yl)ethyl]carbamate (53)

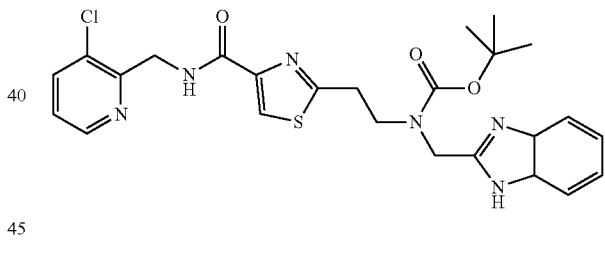

In a similar fashion to general procedure 6, 2-{2-[(1H-1,3-benzodiazol-2-ylmethyl)[(tert-butoxy)carbonyl]amino]ethyl}-1,3-thiazole-4-carboxylic acid (8) (150 mg, 0.34 mmol, 92% purity), 1-(3-chloropyridin-2-yl)methanamine dihydrochloride (111 mg, 0.51 mmol), DIPEA (299 µl, 1.71 mmol) and HATU (196 mg, 0.51 mmol) in DMF (2 ml) afforded the title compound (161 mg, 73% purity, 63%) as a yellow oil after purification by flash column chromatography (kp-NH, eluting with a gradient of 20-100% EtOAc/heptane).

1H-NMR (CDCl$_3$, 500 MHz): d[ppm]=10.47 (s, 1H), 8.59 (s, 1H), 8.52-8.42 (m, 1H), 7.92 (s, 1H), 7.71 (d, J=8.2 Hz, 2H), 7.32 (s, 1H), 7.25-7.16 (m, 3H), 4.85 (d, J=4.8 Hz, 2H), 4.69 (s, 2H), 3.81 (s, 2H), 3.23 (t, J=6.5 Hz, 2H), 1.35 (s, 9H)

HPLCMS (Method A): [m/z]: 527.35 [M+H]$^+$

267

Tert-butyl N-(1H-1,3-benzodiazol-2-ylmethyl)-N-{2-[4-({[2-(tert-butoxy)pyridin-3-yl]methyl}carbamoyl)-1,3-thiazol-2-yl]ethyl}carbamate (54)

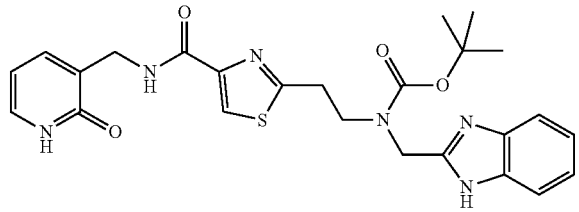

In a similar fashion to general procedure 6, 2-{2-[(1H-1,3-benzodiazol-2-ylmethyl)[(tert-butoxy)carbonyl]amino]ethyl}-1,3-thiazole-4-carboxylic acid (8) (150 mg, 0.34 mmol, 92% purity), 1-(2-tert-butoxypyridin-3-yl)methanamine (93 mg, 0.514 mmol), DIPEA (179 µl, 1.03 mmol) and HATU (196 mg, 0.51 mmol) in DMF (2 ml) afforded the title compound (205 mg, 61%, 58% purity) as a yellow oil after purification by flash column chromatography (kp-NH, eluting with a gradient of 20-100% EtOAc/heptane).

1H-NMR (CDCl₃, 500 MHz): d[ppm]=10.09 (s, 1H), 7.89 (d, J=15.7 Hz, 2H), 7.71 (s, 1H), 7.54-7.45 (m, 2H), 7.40 (d, J=4.9 Hz, 1H), 7.24 (s, 1H), 6.77 (td, J=7.3, 5.0 Hz, 2H), 4.60 (s, 2H), 4.49 (d, J=6.5 Hz, 2H), 3.77 (t, J=6.5 Hz, 2H), 3.22 (s, 2H), 1.63 (s, 9H), 1.33 (s, 9H)

HPLCMS (Method A): [m/z]: 565.15 [M+H]⁺

Tert-butyl N-(1H-1,3-benzodiazol-2-ylmethyl)-N-[2-(4-{[(1-methyl-1H-imidazol-5-yl)methyl]carbamoyl}-1,3-thiazol-2-yl)ethyl]carbamate (55)

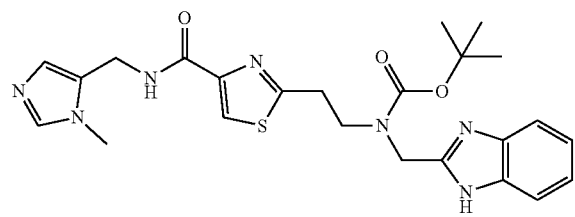 [SMILES: Cn1cncc1CNC(=O)c1csc(CCN(Cc2nc3ccccc3[nH]2)C(=O)OC(C)(C)C)n1]

In a similar fashion to general procedure 6, 2-{2-[(1H-1,3-benzodiazol-2-ylmethyl)[(tert-butoxy)carbonyl]amino]ethyl}-1,3-thiazole-4-carboxylic acid (8) (150 mg, 0.37 mmol), (1-methyl-1H-imidazol-5-yl)methanamine (62 mg, 0.56 mmol), DIPEA (185 µl, 1.12 mmol) and HATU (213 mg, 0.56 mmol) in DMF (2 ml) afforded the title compound (175 mg, 95%) as a yellow oil after purification by flash column chromatography (eluting with a gradient of 0-3% MeOH/DCM).

1H-NMR (Methanol-d4, 500 MHz): d[ppm]=8.08 (s, 1H), 7.58-7.52 (m, 3H), 7.26-7.20 (m, 2H), 6.96 (s, 1H), 4.69 (d, J=12.4 Hz, 2H), 4.60 (s, 2H), 3.95-3.75 (m, 2H), 3.70 (s, 3H), 3.39-3.24 (m, 2H), 1.44-1.26 (m, 9H)

HPLCMS (Method A): [m/z]: 496.05 [M+H]⁺

268

Tert-butyl N-(1H-1,3-benzodiazol-2-ylmethyl)-N-(2-{4-[(1,3-oxazol-2-ylmethyl)carbamoyl]-1,3-thiazol-2-yl}ethyl)carbamate (56)

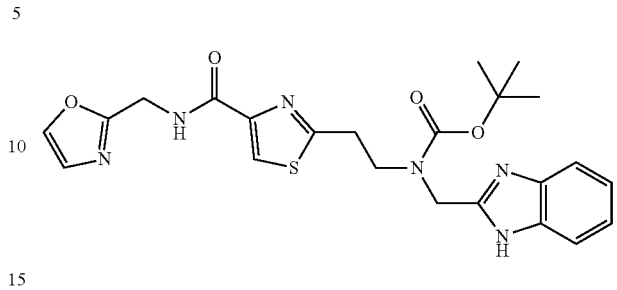

In a similar fashion to general procedure 6, 2-{2-[(1H-1,3-benzodiazol-2-ylmethyl)[(tert-butoxy)carbonyl]amino]ethyl}-1,3-thiazole-4-carboxylic acid (8) (150 mg, 0.298 mmol, 80% purity), 1,3-oxazol-2-ylmethanamine dihydrochloride (102 mg, 0.596 mmol), DIPEA (312 µl, 1.79 mmol) and HATU (227 mg, 0.596 mmol) in DMF (3 ml) afforded the title compound (94 mg, 63%) as a tan oil after purification by flash column chromatography (kp-NH, eluting with a gradient of 0-100% EtOAc/heptane).

HPLCMS (Method A): [m/z]: 483.05 [M+H]⁺

Tert-butyl N-(1H-1,3-benzodiazol-2-ylmethyl)-N-[2-(4-{[(1-methyl-1H-pyrazol-3-yl)methyl]carbamoyl}-1,3-thiazol-2-yl)ethyl]carbamate (57)

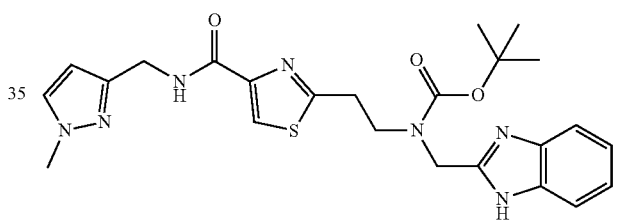

In a similar fashion to general procedure 6, 2-{2-[(1H-1,3-benzodiazol-2-ylmethyl)[(tert-butoxy)carbonyl]amino]ethyl}-1,3-thiazole-4-carboxylic acid (8) (150 mg, 0.298 mmol, 80% purity), 1-(1-methyl-1H-pyrazol-3-yl)methanamine (50 mg, 0.45 mmol), DIPEA (156 µl, 0.894 mmol) and HATU (227 mg, 0.596 mmol) in DMF (3 ml) afforded the title compound (53 mg, 34%) as a tan oil after purification by flash column chromatography (kp-NH, eluting with a gradient of 0-100% EtOAc/heptane).

HPLCMS (Method A): [m/z]: 496.45 [M+H]⁺

Tert-butyl N-(1H-1,3-benzodiazol-2-ylmethyl)-N-(2-{4-[(pyridazin-3-ylmethyl)carbamoyl]-1,3-thiazol-2-yl}ethyl)carbamate (58)

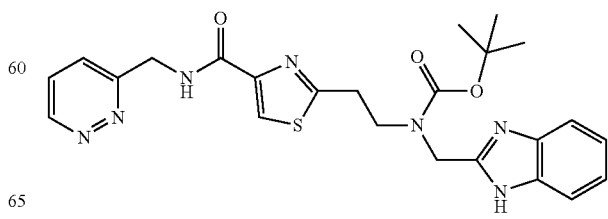

In a similar fashion to general procedure 6, 2-{2-[(1H-1,3-benzodiazol-2-ylmethyl)[(tert-butoxy)carbonyl]amino]ethyl}-1,3-thiazole-4-carboxylic acid (8) (100 mg, 0.23 mmol, 92% purity), 1-(pyridazin-3-yl)methanamine (37 mg, 0.34 mmol), DIPEA (119 µl, 0.69 mmol) and HATU (130 mg, 0.34 mmol) in DMF (2 ml) afforded the title compound (101 mg, 88%) as a pale yellow oil after purification by flash column chromatography (kp-NH, eluting with a gradient of 50-100% EtOAc/heptane followed by 0-15% MeOH/EtOAc).

HPLCMS (Method A): [m/z]: 494.1 [M+H]$^+$

Tert-butyl N-(1H-1,3-benzodiazol-2-ylmethyl)-N-[2-(4-{[(1-methyl-1H-pyrazol-5-yl)methyl]carbamoyl}-1,3-thiazol-2-yl)ethyl]carbamate (59)

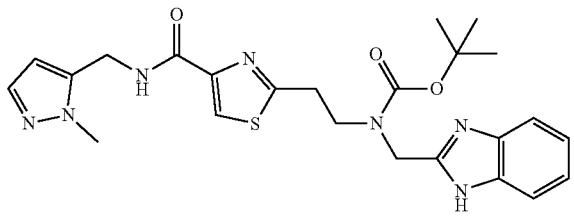 [SMILES: Cn1nccc1CNC(=O)c1csc(CCN(Cc2nc3ccccc3[nH]2)C(=O)OC(C)(C)C)n1]

In a similar fashion to general procedure 6, 2-{2-[(1H-1,3-benzodiazol-2-ylmethyl)[(tert-butoxy)carbonyl]amino]ethyl}-1,3-thiazole-4-carboxylic acid (8) (100 mg, 0.23 mmol, 92% purity), 1-(1-methyl-1H-pyrazol-5-yl)methanamine (38 mg, 0.34 mmol), DIPEA (119 µl, 0.69 mmol) and HATU (130 mg, 0.34 mmol) in DMF (2 ml) afforded the title compound (51 mg, 45%) as a pale yellow oil after purification by flash column chromatography (kp-NH, eluting with a gradient of 50-100% EtOAc/heptane followed by 0-20% MeOH/EtOAc).

HPLCMS (Method A): [m/z]: 496.3 [M+H]$^+$

Tert-butyl N-(1H-1,3-benzodiazol-2-ylmethyl)-N-[2-(4-{[(3-fluoropyridin-4-yl)methyl]carbamoyl}-1,3-thiazol-2-yl)ethyl]carbamate (60)

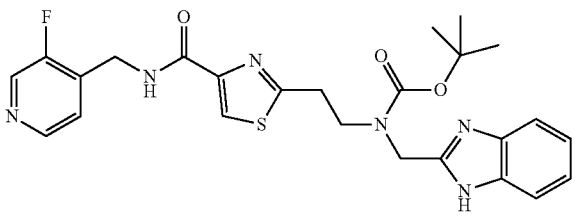 [SMILES: CC(C)(C)OC(=O)N(CCc1nc(C(=O)NCc2ccncc2F)cs1)Cc1nc2ccccc2[nH]1]

In a similar fashion to general procedure 6, 2-{2-[(1H-1,3-benzodiazol-2-ylmethyl)[(tert-butoxy)carbonyl]amino]ethyl}-1,3-thiazole-4-carboxylic acid (8) (100 mg, 0.23 mmol, 92% purity), 1-(3-fluoropyridin-4-yl)methanamine (43 mg, 0.34 mmol), DIPEA (119 µl, 0.69 mmol) and HATU (130 mg, 0.34 mmol) in DMF (3 ml) afforded the title compound (137 mg, 83%, 71% purity) as a yellow oil after flash column chromatography (kp-NH, eluting with a gradient of 50-100% EtOAc/heptane).

1H-NMR (CDCl$_3$, 500 MHz): d[ppm]=10.10 (s, 1H), 8.43 (d, J=6.0 Hz, 1H), 8.37 (dd, J=9.8, 4.9 Hz, 2H), 7.96 (s, 1H), 7.81-7.68 (m, 2H), 7.40 (d, J=8.6 Hz, 1H), 7.35-7.27 (m, 1H), 7.25-7.22 (m, 1H), 4.68 (d, J=6.0 Hz, 2H), 4.62 (s, 2H), 3.78 (t, J=6.5 Hz, 2H), 3.27-3.23 (m, 2H), 1.37 (s, 9H)

HPLCMS (Method A): [m/z]: 511.15 [M+H]$^+$

Tert-butyl N-(1H-1,3-benzodiazol-2-ylmethyl)-N-[2-(4-{[(3-methylpyridin-4-yl)methyl]carbamoyl}-1,3-thiazol-2-yl)ethyl]carbamate (61)

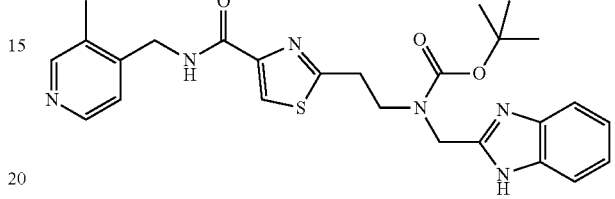

In a similar fashion to general procedure 6, 2-{2-[(1H-1,3-benzodiazol-2-ylmethyl)[(tert-butoxy)carbonyl]amino]ethyl}-1,3-thiazole-4-carboxylic acid (8) (700 mg, 1.65 mmol, 95% purity), (3-methylpyridin-4-yl)methanamine dihydrochloride (387 mg, 1.98 mmol), DIPEA (863 µl, 4.9 mmol) and HATU (1260 mg, 3.3 mmol) in DMF (10 ml) afforded the title compound (363 mg, 43%) as a yellow oil after purification by flash chromatography (kp-NH, using an elution gradient 20-100% EtOAc/heptane).

HPLCMS (Method A): [m/z]: 507.1 [M+H]$^+$

Tert-butyl N-(1H-1,3-benzodiazol-2-ylmethyl)-N-[2-(4-{[(1-methyl-1H-pyrazol-4-yl)methyl]carbamoyl}-1,3-thiazol-2-yl)ethyl]carbamate (62)

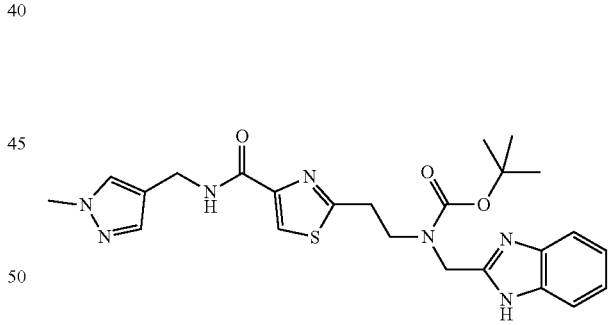

In a similar fashion to general procedure 6, 2-{2-[(1H-1,3-benzodiazol-2-ylmethyl)[(tert-butoxy)carbonyl]amino]ethyl}-1,3-thiazole-4-carboxylic acid (8) (100 mg, 0.25 mmol), (1-methyl-1H-pyrazol-4-yl)methanamine (41 mg, 0.37 mmol), DIPEA (130 µl, 0.75 mmol) and HATU (142 mg, 0.37 mmol) in DMF (2 ml) afforded the title compound (125 mg, quant.) as a yellow oil after purification by flash column chromatography (eluting with a gradient of 0-20% MeOH/EtOAc).

HPLCMS (Method A): [m/z]: 496.1 [M+H]$^+$

Tert-butyl N-(1H-1,3-benzodiazol-2-ylmethyl)-N-[2-(4-{[(6-methyl pyridazin-3-yl)methyl]carbamoyl}-1,3-thiazol-2-yl)ethyl]carbamate (63)

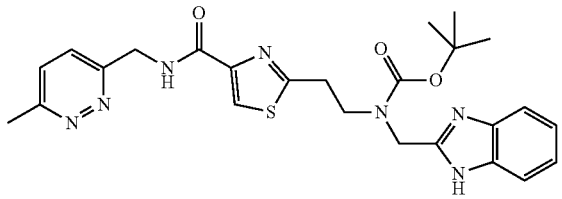 [SMILES: Cc1ccc(CNC(=O)c2csc(CCN(Cc3nc4ccccc4[nH]3)C(=O)OC(C)(C)C)n2)nn1]

In a similar fashion to general procedure 6, 2-{2-[(1H-1,3-benzodiazol-2-ylmethyl)[(tert-butoxy)carbonyl]amino]ethyl}-1,3-thiazole-4-carboxylic acid (8) (100 mg, 0.23 mmol, 92% purity), (6-methylpyridazin-3-yl)methanamine (42 mg, 0.34 mmol), DIPEA (119 μl, 0.69 mmol) and HATU (130 ng, 0.34 mmol) in DMF (3 ml) afforded the crude title compound (99 mg, 67%, 79% purity) after flash column chromatography (kp-NH, eluting with a gradient of 70-100% EtOAc/heptane).

1H-NMR (CDCl₃, 500 MHz): d[ppm]=10.50 (s, 1H), 8.28 (s, 1H), 7.92 (s, 1H) 7.72 (s, 1H), 7.40-7.29 (m, 3H), 7.23 (dd, J=6.4, 2.8 Hz, 2H), 4.68 (s, 2H), 3.82 (s, 2H), 3.24 (s, 2H), 2.73 (s, 2H), 2.71 (s, 3H), 1.36 (s, 9H)

HPLCMS (Method A): [m/z]: 508.10 [M+H]$^+$

Tert-butyl N-(1H-1,3-benzodiazol-2-ylmethyl)-N-(2-{4-[(1H-imidazol-2-ylmethyl)carbamoyl]-1,3-thiazol-2-yl}ethyl)carbamate (64)

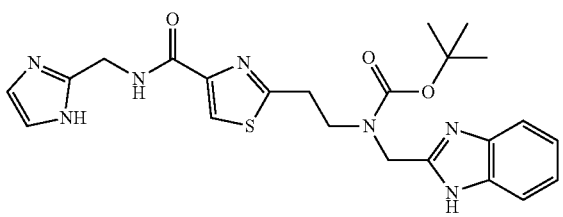 [SMILES: CC(C)(C)OC(=O)N(CCc1nc(C(=O)NCc2ncc[nH]2)cs1)Cc1nc2ccccc2[nH]1]

In a similar fashion to general procedure 6, 2-{2-[(1H-1,3-benzodiazol-2-ylmethyl)[(tert-butoxy)carbonyl]amino]ethyl}-1,3-thiazole-4-carboxylic acid (8) (100 mg, 0.25 mmol), 1-(1H-imidazol-2-yl)methanamine (42 mg, 0.25 mmol), DIPEA (164 μl, 0.99 mmol) and HATU (188 mg, 0.50 mmol) in DMF (2 ml) afforded the title compound (65 mg, 54%) as a yellow oil after purification by flash column chromatography (kp-NH, eluting with a gradient 0-5% MeOH/DCM).

HPLCMS (Method A): [m/z]: 482.25 [M+H]$^+$

Tert-butyl N-(1H-1,3-benzodiazol-2-ylmethyl)-N-{2-[4-({[2-(morpholin-4-yl)pyridin-4-yl]methyl}carbamoyl)-1,3-thiazol-2-yl]ethyl}carbamate (65)

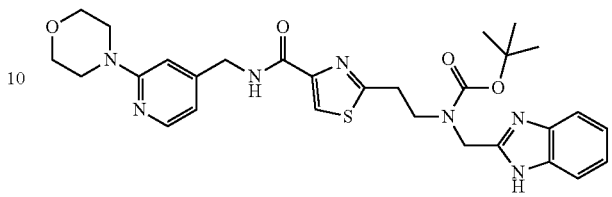

In a similar fashion to general procedure 6, 2-{2-[(1H-1,3-benzodiazol-2-ylmethyl)[(tert-butoxy)carbonyl]amino]ethyl}-1,3-thiazole-4-carboxylic acid (8) (100 mg, 0.25 mmol), [3-(morpholin-4-yl)pyridin-4-yl]methanamine (48 mg, 0.25 mmol), DIPEA (164 μl, 0.99 mmol) and HATU (189 mg, 0.50 mmol) in DMF (2 ml) afforded the title compound (112 mg, 78%) as a yellow solid after purification by flash column chromatography (kp-NH, eluting with a gradient of 50-100% EtOAc/heptane).

HPLCMS (Method A): [m/z]: 578.10 [M+H]$^+$

Tert-butyl N-(1H-1,3-benzodiazol-2-ylmethyl)-N-[2-(4-{[(5-methylpyridin-2-yl)methyl]carbamoyl}-1,3-thiazol-2-yl)ethyl]carbamate (66)

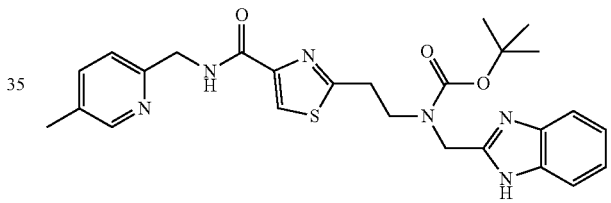

In a similar fashion to general procedure 6, 2-{2-[(1H-1,3-benzodiazol-2-ylmethyl)[(tert-butoxy)carbonyl]amino]ethyl}-1,3-thiazole-4-carboxylic acid (8) (100 mg, 0.20 mmol, 80% purity), 1-(5-methylpyridin-2-yl)methanamine (29 mg, 0.24 mmol), DIPEA (104 μl, 0.60 mmol) and HATU (15 1 mg, 0.40 mmol) in DMF (2 ml) afforded the title compound (48 mg, 47%) as a colourless oil after purification by flash column chromatography (kp-NH, eluting with a gradient of 0-100% EtOAc/heptane).

HPLCMS (Method A): [m/z]: 507.1 [M+H]$^+$

Tert-butyl N-(1H-1,3-benzodiazol-2-ylmethyl)-N-{2-[4-({[6-(dimethylamino)pyridin-3-yl]methyl}carbamoyl)-1,3-thiazol-2-yl]ethyl}carbamate (67)

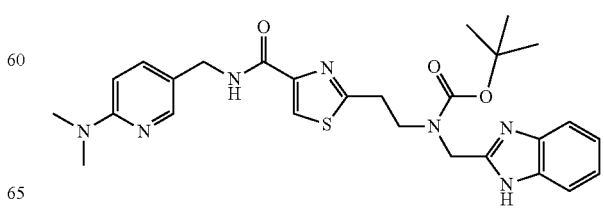

In a similar fashion to general procedure 6, 2-{2-[(1H-1,3-benzodiazol-2-ylmethyl)[(tert-butoxy)carbonyl]amino]ethyl}-1,3-thiazole-4-carboxylic acid (8) (100 mg, 0.20 mmol, 80% purity), 5-(aminomethyl)-N,N-dimethylpyridin-2-amine (30 mg, 0.20 mmol), DIPEA (104 µl, 0.60 mmol) and HATU (151 mg, 0.40 mmol) in DMF (2 ml) afforded the title compound (36 mg, 34%) as a colourless oil after purification by flash column chromatography (kp-NH, eluting with a gradient of 0-100% EtOAc/heptane).

HPLCMS (Method A): [m/z]: 536.35 [M+H]⁺

Tert-butyl N-(1H-1,3-benzodiazol-2-ylmethyl)-N-[2-(4-{[(2-methylpyridin-4-yl)methyl]carbamoyl}-1,3-thiazol-2-yl)ethyl]carbamate (68)

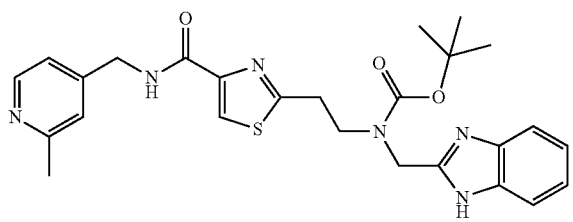 [SMILES: Cc1cc(CNC(=O)c2csc(CCN(Cc3nc4ccccc4[nH]3)C(=O)OC(C)(C)C)n2)ccn1]

In a similar fashion to general procedure 6, 2-{2-[(1H-1,3-benzodiazol-2-ylmethyl)[(tert-butoxy)carbonyl]amino]ethyl}-1,3-thiazole-4-carboxylic acid (8) (100 mg, 0.20 mmol, 80% purity), 1-(2-methylpyridin-4-yl)methanamine (36 mg, 0.30 mmol), DIPEA (104 µl, 0.60 mmol) and HATU (151 mg, 0.40 mmol) in DMF (2 ml) afforded the title compound (36 mg, 36%) as a colourless oil after purification by flash column chromatography (kp-NH, eluting with a gradient of 0-100% EtOAc/heptane).

HPLCMS (Method A): [m/z]: 507.3 [M+H]⁺

Tert-butyl N-(1H-1,3-benzodiazol-2-ylmethyl)-N-[2-(4-{[(1,5-dimethyl-1H-pyrazol-4-yl)methyl]carbamoyl}-1,3-thiazol-2-yl)ethyl]carbamate (69)

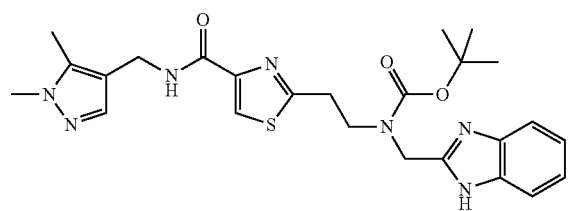 [SMILES: Cc1c(CNC(=O)c2csc(CCN(Cc3nc4ccccc4[nH]3)C(=O)OC(C)(C)C)n2)cnn1C]

In a similar fashion to general procedure 6, 2-{2-[(1H-1,3-benzodiazol-2-ylmethyl)[(tert-butoxy)carbonyl]amino]ethyl}-1,3-thiazole-4-carboxylic acid (8) (100 mg, 0.20 mmol, 80% purity), 1-(1,5-dimethyl-1H-pyrazol-4-yl)methanamine (37 mg, 0.30 mmol), DIPEA (104 µl, 0.60 mmol) and HATU (151 mg, 0.40 mmol) in DMF (2 ml) afforded the title compound (74 mg, 73%) as a colourless oil after purification by flash column chromatography (kp-NH, eluting with a gradient of 0-100% EtOAc/heptane).

HPLCMS (Method A): [m/z]: 510.15 [M+H]⁺

Tert-butyl N-(1H-1,3-benzodiazol-2-ylmethyl)-N-{2-[4-({[3-chloro-5-(trifluoromethyl)pyridin-2-yl]methyl}carbamoyl)-1,3-thiazol-2-yl]ethyl}carbamate (70)

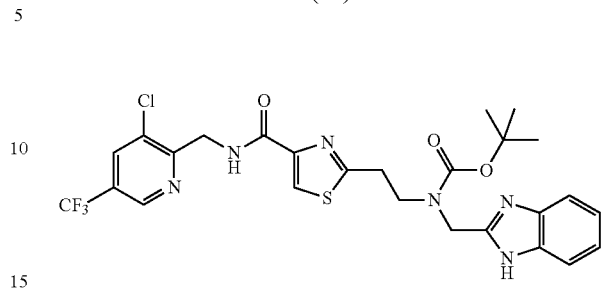

In a similar fashion to general procedure 6, 2-{2-[(1H-1,3-benzodiazol-2-ylmethyl)[(tert-butoxy)carbonyl]amino]ethyl}-1,3-thiazole-4-carboxylic acid (8) (100 mg, 0.236 mmol), 1-[3-chloro-5-(trifluoromethyl)pyridin-2-yl]methanamine hydrochloride (87 mg, 0.354 mmol), DIPEA (0.21 ml, 1.18 mmol), and HATU (135 mg, 0.354 mmol) in DMF (3 ml) afforded the title compound (216 mg, 69%, 45% purity) as a yellow oil after flash column chromatography (KP—NH, eluting with a gradient of 20-100% EtOAc/heptane). The title compound was used in the next step without further purification.

HPLCMS (Method A): [m/z]: 595.1 [M+H]⁺

Tert-butyl N-(1H-1,3-benzodiazol-2-ylmethyl)-N-[2-(4-{[(3-chloro-5-fluoropyridin-2-yl)methyl]carbamoyl}-1,3-thiazol-2-yl)ethyl]carbamate (71)

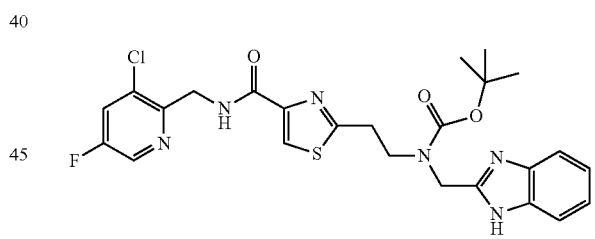

In a similar fashion to general procedure 6, 2-{2-[(1H-1,3-benzodiazol-2-ylmethyl)[(tert-butoxy)carbonyl]amino]ethyl}-1,3-thiazole-4-carboxylic acid (8) (100 mg, 0.236 mmol), (3-chloro-5-fluoropyridin-2-yl)methanamine hydrochloride (70 mg, 0.354 mmol), DIPEA (0.21 ml, 1.18 mmol), and HATU (135 mg, 0.354 mmol) in DMF (3 ml) afforded the title compound (157 mg, 76%, 62% purity) as a yellow oil after flash column chromatography (KP—NH, eluting with a gradient of 20-100% EtOAc/heptane). The title compound was used in the next step without further purification.

HPLCMS (Method A): [m/z]: 545.15 [M+H]⁺

Tert-butyl N-(1H-1,3-benzodiazol-2-ylmethyl)-N-[2-(4-{[(2-fluoropyridin-3-yl)methyl]carbamoyl}-1,3-thiazol-2-yl)ethyl]carbamate (72)

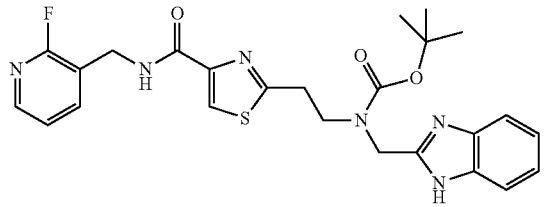 [SMILES: CC(C)(C)OC(=O)N(CCc1nc(C(=O)NCc2cccnc2F)cs1)Cc1nc2ccccc2[nH]1]

In a similar fashion to general procedure 6, 2-{2-[(1H-1,3-benzodiazol-2-ylmethyl)[(tert-butoxy)carbonyl]amino]ethyl}-1,3-thiazole-4-carboxylic acid (8) (100 mg, 0.236 mmol, 95% purity), 1-(2-fluoropyridin-3-yl)methanamine (47.01 mg, 0.373 mmol), DIPEA (0.13 ml, 0.745 mmol) and HATU (141.7 mg, 0.373 mmol) in DMF (2 ml) afforded the title compound (0.359 g, quant.) as a brown solid after evaporation of the solvent. The title compound was used in the next step without further purification.

HPLCMS (Method A): [m/z]: 511.10 [M+H]$^+$

Tert-butyl N-(1H-1,3-benzodiazol-2-ylmethyl)-N-[2-(4-{[(2-methoxypyridin-4-yl)methyl]carbamoyl}-1,3-thiazol-2-yl)ethyl]carbamate (73)

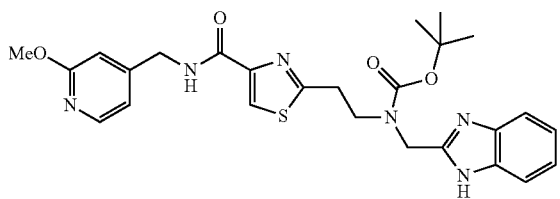 [SMILES: COc1cc(CNC(=O)c2csc(CCN(Cc3nc4ccccc4[nH]3)C(=O)OC(C)(C)C)n2)ccn1]

In a similar fashion to general procedure 6, 2-{2-[(1H-1,3-benzodiazol-2-ylmethyl)[(tert-butoxy)carbonyl]amino]ethyl}-1,3-thiazole-4-carboxylic acid (8) (100 mg, 0.236 mmol, 95% purity), 1-(2-methoxypyridin-4-yl)methanamine (49 mg, 0.354 mmol), DIPEA (0.12 ml, 0.708 mmol) and HATU (135 mg, 0.354 mmol) in DMF (3 ml) afforded the title compound (104 mg, 81%, 96% purity) as a white solid after purification by flash column chromatography (eluting with a gradient of 30-100% EtOAc/heptane).

1H-NMR (CDCl$_3$, 500 MHz): d[ppm]=10.07 (s, 1H), 8.10 (d, J=5.3 Hz, 1H), 7.96 (s, 1H), 7.73-7.66 (m, 2H), 7.41-7.37 (m, 1H), 7.25-7.22 (m, 2H), 6.85-6.82 (m, 1H), 6.69 (s, 1H), 4.62 (s, 2H), 4.56 (d, J=6.3 Hz, 2H), 3.91 (s, 3H), 3.78 (t, J=6.6 Hz, 2H), 3.24 (t, J=6.2 Hz, 2H), 1.39 (s, 9H)

HPLCMS (Method A): [m/z]: 523.3 [M+H]$^+$

Tert-butyl N-(1H-1,3-benzodiazol-2-ylmethyl)-N-[2-(4-{[(4,6-dimethylpyridin-3-yl)methyl]carbamoyl}-1,3-thiazol-2-yl)ethyl]carbamate (74)

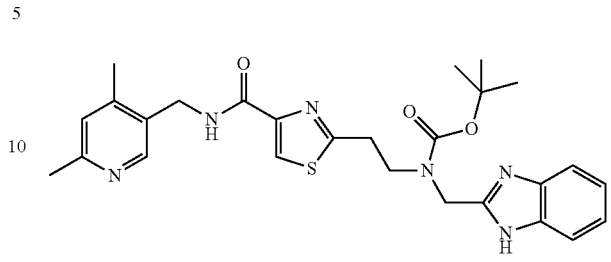

In a similar fashion to general procedure 6, 2-{2-[(1H-1,3-benzodiazol-2-ylmethyl)[(tert-butoxy)carbonyl]amino]ethyl}-1,3-thiazole-4-carboxylic acid (8) (100 mg, 0.236 mmol, 95% purity), (4,6-dimethylpyridin-3-yl)methanamine dihydrochloride (B1) (93 mg, 0.354 mmol, 80% purity), DIPEA (0.206 ml, 1.18 mmol) and HATU (135 mg, 0.354 mmol) in DMF (3 ml) afforded the title compound (77 mg, 63%) as a yellow oil after purification by flash column chromatography (eluting with a gradient of 0-15% MeOH/EtOAc).

HPLCMS (Method A): [m/z]: 521.05 [M+H]$^+$

Tert-butyl N-(1H-1,3-benzodiazol-2-ylmethyl)-N-[2-(4-{[(4-methylpyridin-2-yl)methyl]carbamoyl}1,3-thiazol-2-yl)ethyl]carbamate (75)

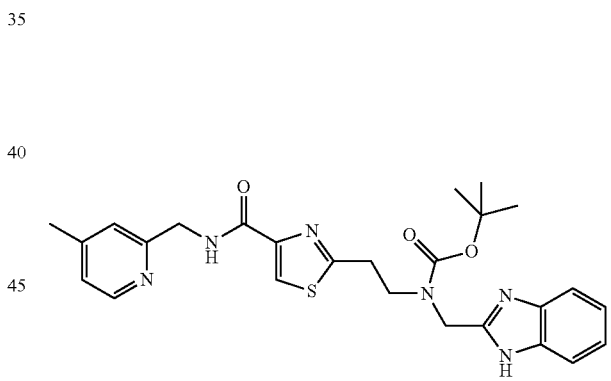

In a similar fashion to general procedure 6, 2-{2-[(1H-1,3-benzodiazol-2-ylmethyl)[(tert-butoxy)carbonyl]amino]ethyl}-1,3-thiazole-4-carboxylic acid (8) (100 mg, 0.236 mmol, 95% purity), (4,6-dimethylpyridin-3-yl)methanamine dihydrochloride (93 mg, 0.354 mmol), DIPEA (0.123 ml, 0.708 mmol) and HATU (135 mg, 0.354 mmol) in DMF (2 ml) afforded the title compound (90 mg, 72%) as a yellow oil after purification by flash column chromatography (KP—NH, eluting with a gradient of 20-100% EtOAc/heptane followed by 0-20% MeOH/EtOAc).

HPLCMS (Method A): [m/z]: 507.10 [M+H]$^+$

Tert-butyl N-(1H-1,3-benzodiazol-2-ylmethyl)-N-{2-[4-(5,6,7,8-tetrahydro-1,6-naphthyridine-6-carbonyl)-1,3-thiazol-2-yl]ethyl}carbamate (76)

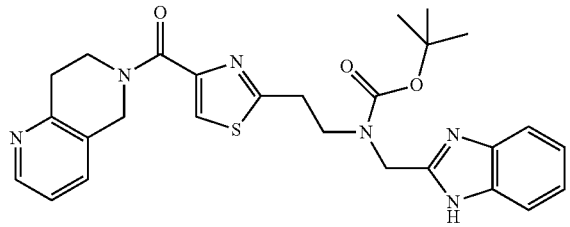 [SMILES: CC(C)(C)OC(=O)N(CCc1nc(C(=O)N2CCc3ncccc3C2)cs1)Cc1nc2ccccc2[nH]1]

In a similar fashion to general procedure 6, 2-{2-[(1H-1,3-benzodiazol-2-ylmethyl)[(tert-butoxy)carbonyl]amino]ethyl}-1,3-thiazole-4-carboxylic acid (8) (100 mg, 0.236 mmol, 95% purity), 5,6,7,8-tetrahydro-1,6-naphthyridine dihydrochloride (62 mg, 0.298 mmol), DIPEA (0.173 ml, 0.994 mmol) and HATU (151 mg, 0.398 mmol) in DMF (2 ml) afforded the title compound (90 mg, 72%) as a colourless oil after purification by flash column chromatography (kp-NH, eluting with a gradient of 0-100% EtOAc/heptane).

HPLCMS (Method A): [m/z]: 519.15 [M+H]⁺

Tert-butyl N-(1H-1,3-benzodiazol-2-ylmethyl)-N-[2-(4-{[(3,5-difluoropyridin-2-yl)methyl] carbamoyl}-1,3-thiazol-2-yl)ethyl]carbamate (77)

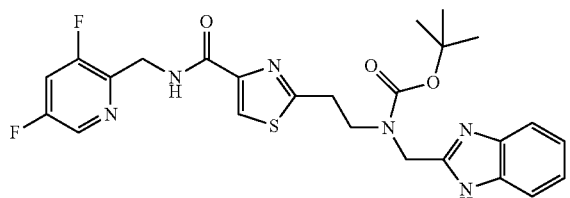

In a similar fashion to general procedure 6, 2-{2-[(1H-1,3-benzodiazol-2-ylmethyl)[(tert-butoxy)carbonyl]amino]ethyl}-1,3-thiazole-4-carboxylic acid (8) (100 mg, 0.236 mmol, 95% purity), (3,5-difluoropyridin-2-yl)methanamine dihydrochloride (65 mg, 0.298 mmol), DIPEA (0.173 ml, 0.994 mmol) and HATU (151 mg, 0.398 mmol) in DMF (3 ml) afforded the title compound (112 mg, quant.) as a colourless oil after purification by flash column chromatography (kp-NH, eluting with a gradient of 0-100% EtOAc/heptane).

HPLCMS (Method A): [m/z]: 529.10 [M+H]⁺

Tert-butyl N-(1H-1,3-benzodiazol-2-ylmethyl)-N-[2-(4-{[(3-{[(tert-butyldimethylsilyl)oxy]methyl}pyridin-2-yl) methyl]carbamoyl}-1,3-thiazol-2-yl)ethyl]carbamate (78)

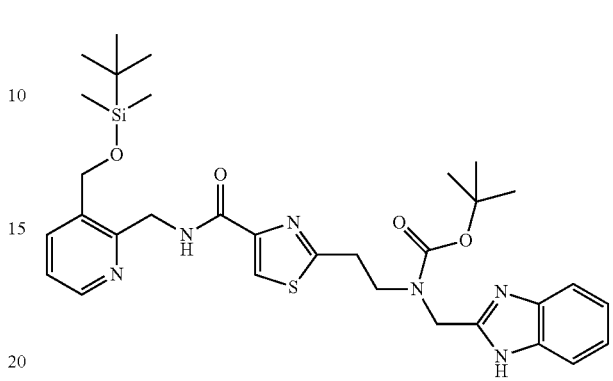

In a similar fashion to general procedure 6, 2-{2-[(1H-1,3-benzodiazol-2-ylmethyl)[(tert-butoxy)carbonyl]amino]ethyl}-1,3-thiazole-4-carboxylic acid (8) (15.94 mg, 0.04 mmol), (3-{[(tert-butyldimethylsilyl)oxy]methyl}pyridin-2-yl)methanamine (C3) (10 mg, 0.04 mmol), DIPEA (0.03 ml, 0.16 mmol) and HATU (30.13 mg, 0.08 mmol) in DMF (2 ml) afforded the title compound (17.5 mg, 34%, 30% purity) as an orange oil after purification by flash column chromatography (eluting with a gradient of 0-100% EtOAc/heptane).

HPLCMS (Method A): [m/z]: 637.15 [M+H]⁺

Tert-butyl 2-{[(2-{2-[(1H-1,3-benzodiazol-2-ylmethyl)[(tert-butoxy)carbonyl]amino]ethyl}-1,3-thiazol-4-yl)formamido]methyl}piperidine-1-carboxylate (79)

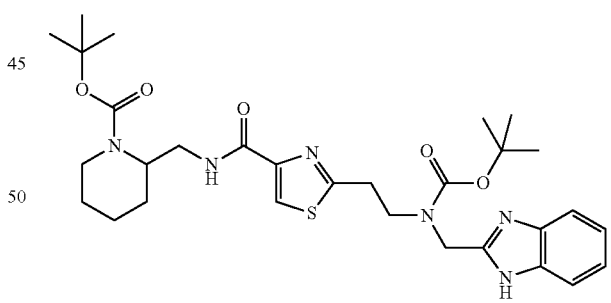

In a similar fashion to general procedure 6, 2-{2-[(1H-1,3-benzodiazol-2-ylmethyl)[(tert-butoxy)carbonyl]amino]ethyl}-1,3-thiazole-4-carboxylic acid (8) (200 mg, 0.5 mmol), tert-butyl 2-(aminomethyl)piperidine-1-carboxylate (149 mg, 0.7 mmol), TEA (66.16 µl, 0.5 mmol) and HATU (280 mg, 0.75 mmol) in DMF (5 ml) at room temperature for 2 h, afforded the title compound (50 mg, 17%) as an orange oil after purification by flash column chromatography (eluting with a gradient of 0-100% EtOAc/heptane) followed by basic prep-HPLC.

HPLCMS (Method A): [m/z]: 599.4 [M+H]⁺

2-{2-[(1H-1,3-Benzodiazol-2-ylmethyl)amino]ethyl}-N-(pyridin-2-ylmethyl)-1,3-thiazole-4-carboxamide Trihydrochloride (Example Compound No. 12)

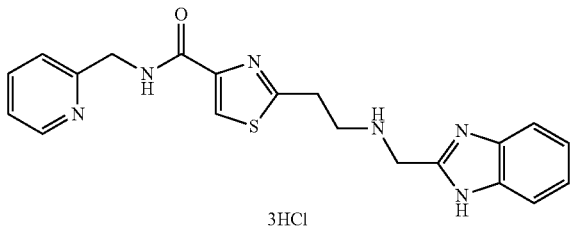 [SMILES: O=C(NCc1ccccn1)c1csc(CCNCc2nc3ccccc3[nH]2)n1]

In a similar fashion to general procedure 2, 4M HCl in dioxane (11 ml) and tert-butyl N-(1H-1,3-benzodiazol-2-ylmethyl)-N-(2-{4-[(pyridin-2-ylmethyl)carbamoyl]-1,3-thiazol-2-yl}ethyl)carbamate (9) (2.2 g, 4.47 mmol) in dioxane (30 ml) at room temperature for 16 h, gave the title compound (HCl salt) (1.7 g, 76%) as a yellow solid after trituration from $Et_2O$ (2×30 ml) followed by DCM (2×20 ml) and $Et_2O$ (2×30 ml).

1H-NMR (DMSO-d6, 500 MHz): d[ppm]=10.39 (s, 1H), 9.68 (t, J=6.0 Hz, 1H), 8.86-8.75 (m, 1H), 8.44 (td, J=7.9, 1.5 Hz, 1H), 8.30 (s, 1H), 7.96-7.84 (m, 2H), 7.76 (dt, J=6.5, 3.3 Hz, 2H), 7.44 (dq, J=6.5, 3.4 Hz, 2H), 4.86 (d, J=6.0 Hz, 2H), 4.76 (s, 2H), 3.66 (dt, J=38.8, 7.1 Hz, 4H)

HPLCMS (Method C): [m/z]: 493.4 $[M+H]^+$

2-{2-[(1H-1,3-Benzodiazol-2-ylmethyl)amino]ethyl}-N-(cyclohexylmethyl)-1,3-thiazole-4-carboxamide (Example Compound No. 13)

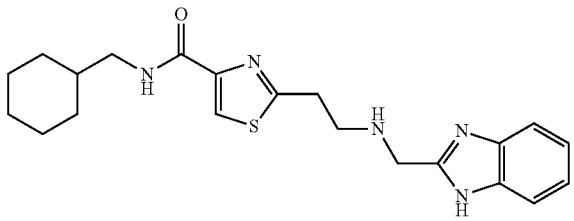 [SMILES: O=C(NCC1CCCCC1)c1csc(CCNCc2nc3ccccc3[nH]2)n1]

In a similar fashion to general procedure 2, tert-butyl N-(1H-1,3-benzodiazol-2-ylmethyl)-N-(2-{4-[(cyclohexylmethyl)carbamoyl]-1,3-thiazol-2-yl}ethyl)carbamate (10) (111.5 mg, 0.224 mmol) and 50% TFA in DCM (10 ml) at room temperature overnight gave the title compound (30 mg, 34%, 98% purity) as a white oil after purification by flash column chromatography (eluting with a gradient of 0-10% MeOH in DCM).

1H-NMR (CDCl3, 400 MHz): d[ppm]=7.96 (s, 1H), 7.56-7.53 (m, 2H), 7.41 (s, 1H), 7.25-7.17 (m, 2H), 4.16 (s, 2H), 3.25 (t, J=6.9 Hz, 2H), 3.17-3.13 (m, 4H), 1.79-1.60 (m, 5H), 1.60-1.46 (m, 1H), 1.29-1.06 (m, 4H), 0.95 (m, 2H)

HPLCMS (Method J): [m/z]: 498.5 $[M+H]^+$

(1H-1,3-Benzodiazol-2-ylmethyl)({2-[4-(1,2,3,4-tetrahydroisoquinoline-2-carbonyl)-1,3-thiazol-2-yl]ethyl})amine (Example Compound No. 15)

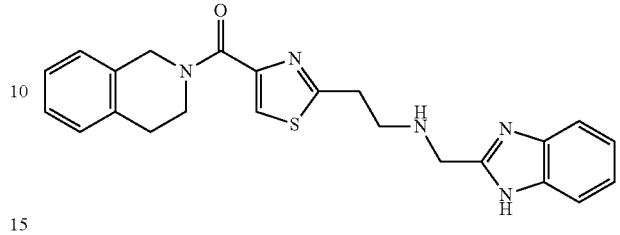

In a similar fashion to general procedure 2, tert-butyl N-(1H-1,3-benzodiazol-2-ylmethyl)-N-{2-[4-(1,2,3,4-tetrahydroisoquinoline-2-carbonyl)-1,3-thiazol-2-yl]ethyl}carbamate (11) (115.95 mg, 0.224 mmol) and 50% TFA in DCM (10 ml) at room temperature overnight gave the title compound (25 mg, 27%, 99% purity) as a white oil after purification by flash column chromatography (eluting with a gradient of 0-10% MeOH in DCM).

1H-NMR (CDCl3, 400 MHz): d[ppm]=7.70 (s, 1H), 7.55 (m, 2H), 7.14-6.94 (m, 6H), 4.89 (s, 2H), 4.14 (s, 2H), 3.95 (m, 2H), 3.22 (m, 2H), 3.13 (m, 2H), 2.96-2.85 (m, 2H)

HPLCMS (Method J): [m/z]: 416.5 $[M+H]^+$

2-{2-[(1H-1,3-Benzodiazol-2-ylmethyl)amino]ethyl}-N-(thiophen-2-ylmethyl)-1,3-thiazole-4-carboxamide (Example Compound No. 16)

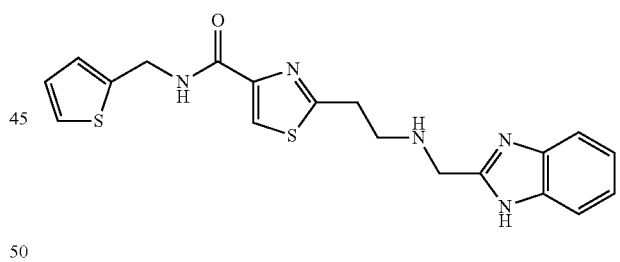

In a similar fashion to general procedure 7, tert-butyl N-(1H-1,3-benzodiazol-2-ylmethyl)-N-(2-{4-[(thiophen-2-ylmethyl)carbamoyl]-1,3-thiazol-2-yl}ethyl)carbamate (12) (180 mg, 0.362 mmol) and 50% TFA in DCM (10 ml) at room temperature overnight gave the title compound (51 mg, 34%, 98% purity) as a white oil after purification by prep-HPLC.

1H-NMR (CDCl3, 400 MHz): d[ppm]=8.05 (s, 1H), 7.59 (m, 3H), 7.24 (m, 2H), 7.21-7.19 (dd, J=5.1, 1.2 Hz, 1H), 7.01 (m, 1H), 6.94 (m, 1H), 4.78 (d, J=6.0, 2H), 4.15 (s, 2H), 3.27-3.07 (m, 4H)

HPLCMS (Method J): [m/z]: 398.5 $[M+H]^+$

281

2-{2-[(1H-1,3-Benzodiazol-2-ylmethyl)amino]ethyl}-N-benzyl-N-methyl-1,3-thiazole-4-carboxamide (Example Compound No. 17)

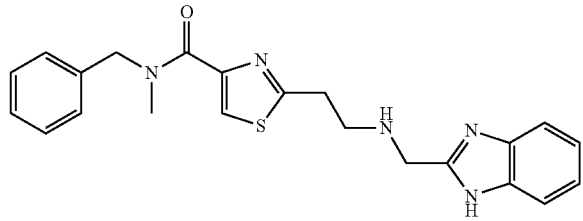 [SMILES: CN(Cc1ccccc1)C(=O)c1csc(CCNCc2nc3ccccc3[nH]2)n1]

In a similar fashion using general procedure 2, tert-butyl N-(1H-1,3-benzodiazol-2-ylmethyl)-N-(2-{4-[benzyl(methyl)carbamoyl]-1,3-thiazol-2-yl}ethyl)carbamate (13) (113.26 mg, 0.224 mmol) and 50% TFA in DCM (10 ml) at room temperature overnight gave the title compound (40 mg, 44%, 99% purity) as a white oil after purification by flash column chromatography (eluting with a gradient of (10% MeOH in DCM).

1H-NMR (CDCl$_3$, 400 MHz): d[ppm]=7.64 (bs, 1H), 7.56 (bs, 2H), 7.39-7.27 (m, 4H), 7.19 (m, 3H), 4.78 (bs, 2H), 4.25-3.93 (m, 2H), 3.17-3.12 (m, 4H), 3.06 (bs, 3H)

HPLCMS (Method J): [m/z]: 406.5 [M+H]$^+$ (1H-1,3-Benzodiazol-2-ylmethyl)({2-[4-(morpholine-4-carbonyl)-1,3-thiazol-2-yl]ethyl})amine (Example Compound No. 18)

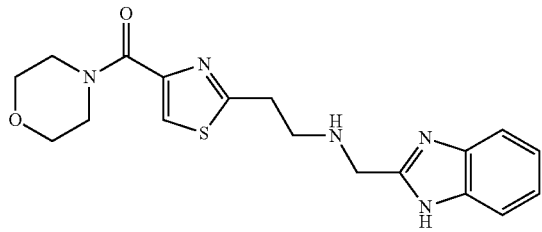 [SMILES: O=C(c1csc(CCNCc2nc3ccccc3[nH]2)n1)N1CCOCC1]

In a similar fashion using general procedure 2, tert-butyl N-(1H-1,3-benzodiazol-2-ylmethyl)-N-{2-[4-(morpholine-4-carbonyl)-1,3-thiazol-2-yl]ethyl}carbamate (14) (105.6 mg, 0.224 mmol) and 50% TFA in DCM (10 ml) at room temperature overnight gave the title compound (20 mg, 24%, 95% purity) as a white oil after purification by flash column chromatography (eluting with a gradient of (10% MeOH in DCM).

1H-NMR (CDCl$_3$, 400 MHz): d[ppm]=7.68 (s, 1H), 7.58-7.56 (m, 2H), 7.23 (m, 2H), 4.17 (s, 2H), 3.79-3.78 (m, 4H), 3.69 (bs, 4H), 3.22 (m, 2H), 3.14 (s, 2H)

HPLCMS (Method J): [m/z]: 372.5 [M+H]$^+$

282

2-{2-[(1H-1,3-Benzodiazol-2-ylmethyl)amino]ethyl}-N-methyl-N-phenyl-1,3-thiazole-4-carboxamide (Example Compound No. 19)

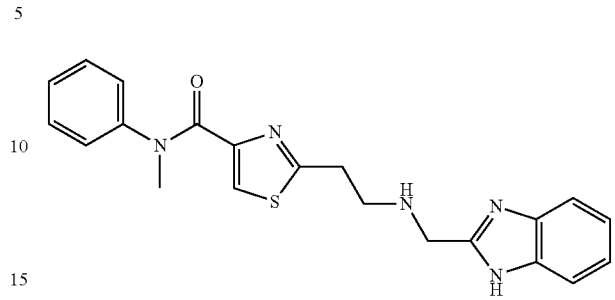

In a similar fashion to general procedure 2, tert-butyl N-(1H-1,3-benzodiazol-2-ylmethyl)-N-(2-{4-[methyl(phenyl)carbamoyl]-1,3-thiazol-2-yl}ethyl)carbamate (15) (110.12 mg, 0.224 mmol) and 50% TFA in DCM (10 ml) at room temperature overnight gave the title compound (40 mg, 45%, 85% purity) as a white oil after purification by flash column chromatography (eluting with a gradient of (10% MeOH in DCM).

1H-NMR (CDCl$_3$, 400 MHz): d[ppm]=7.69 (bs, 2H), 7.29-7.21 (m, 5H), 7.10 (s, 2H), 4.28 (s, 2H), 3.60-3.43 (m, 3H), 3.18 (bs, 2H), 3.05 (bs, 2H)

HPLCMS (Method J): [m/z]: 392.5 [M+H]$^+$

2-{2-[(1H-1,3-Benzodiazol-2-ylmethyl)amino]ethyl}-N-{[2-(pyrrolidin-1-yl)phenyl]methyl}-1,3-thiazole-4-carboxamide (Example Compound No. 21)

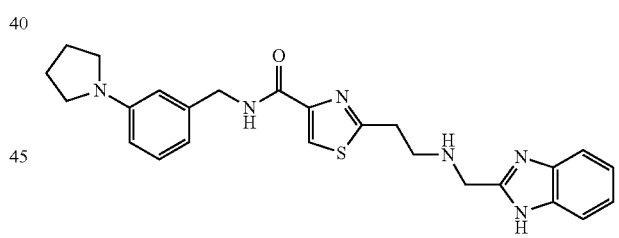

In a similar fashion to general procedure 2, tert-butyl N-(1H-1,3-benzodiazol-2-ylmethyl)-N-{2-[4-({[2-(pyrrolidin-1-yl)phenyl]methyl}carbamoyl)-1,3-thiazol-2-yl]ethyl}carbamate (16) (100 mg, 0.178 mmol) and 50% TFA in DCM (8 ml) at room temperature overnight gave the title compound (70 mg, 69%, 82% purity) as a white oil after purification by flash column chromatography (eluting with a gradient of 57% MeOH in DCM).

1H-NMR (CDCl$_3$, 400 MHz): d[ppm]=7.94 (s, 1H), 7.85 (t, J=5.6 Hz, 1H), 7.53-7.47 (m, 2H), 7.24-7.16 (m, 2H), 7.12 (t, J=7.8 Hz, 1H), 6.59 (d, J=7.5 Hz, 1H), 6.48 (s, 1H), 6.43 (d, J=8.1 Hz, 1H), 4.53 (d, J=5.9 Hz, 2H), 4.14 (s, 2H), 3.21 (m, 4H), 3.12-3.05 (m, 4H), 2.00-1.90 (m, 4H)

HPLCMS (Method J): [m/z]: 461.6 [M+H]$^+$

2-{2-[(1H-1,3-Benzodiazol-2-ylmethyl)amino]ethyl}-N,N-dimethyl-1,3-thiazole-4-carboxamide (Example Compound No. 22)

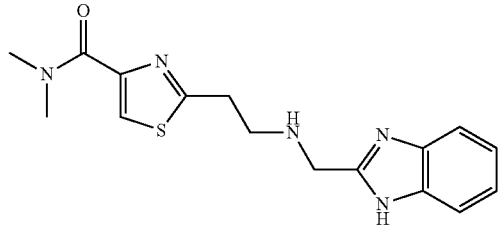 [SMILES: CN(C)C(=O)c1csc(CCNCc2nc3ccccc3[nH]2)n1]

In a similar fashion to general procedure 2, tert-butyl N-(1H-1,3-benzodiazol-2-ylmethyl)-N-{2-[4-(dimethylcarbamoyl)-1,3-thiazol-2-yl]ethyl}carbamate (17) (90 mg, 0.209 mmol) and 50% TFA in DCM (5 ml) at room temperature overnight gave the title compound (18 mg, 25%) as a white oil after purification by flash column chromatography (eluting with a gradient of 5-7% MeOH in DCM).

1H-NMR (CDCl$_3$, 400 MHz): d[ppm]=7.63 (s, 1H), 7.56 (dd, J=5.8, 3.1 Hz, 2H), 7.26-7.14 (m, 2H), 4.73 (s, 2H), 3.29-3.01 (m, 10H)

HPLCMS (Method I): [m/z]: 330.4 [M+H]$^+$

2-{2-[(1H-1,3-Benzodiazol-2-ylmethyl)amino]ethyl}-N-(2-phenylpropan-2-yl)-1,3-thiazole-4-carboxamide (Example Compound No. 26)

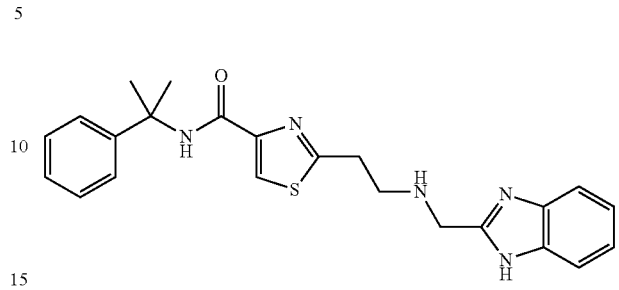

In a similar fashion to general procedure 2, tert-butyl N-(1H-1,3-benzodiazol-2-ylmethyl)-N-(2-{4-[(2-phenylpropan-2-yl)carbamoyl]-1,3-thiazol-2-yl}ethyl)carbamate (19) (305 mg, 0.587 mmol) and 4M HCl in dioxane (20 ml) at room temperature overnight gave the title compound (80 mg, 32%) as an off white oil after purification by flash column chromatography (eluting with a gradient of 10-15% MeOH in DCM).

1H-NMR (CDCl$_3$, 400 MHz): d[ppm]=7.82 (s, 1H), 7.75 (s, 1H), 7.49 (dd, J=5.9, 3.1 Hz, 2H), 7.47-7.39 (m, 2H), 7.26 (t, J=7.7 Hz, 2H), 7.20-7.14 (m, 2H), 4.05 (s, 2H), 3.09 (d, J=5.6 Hz, 2H), 3.05 (d, J=5.7 Hz, 2H), 1.78 (s, 6H)

HPLCMS (Method J): [m/z]: 420.4 [M+H]$^+$

2-{2-[(1H-1,3-Benzodiazol-2-ylmethyl)amino]ethyl}-N-cyclohexyl-N-(propan-2-yl)-1,3-thiazole-4-carboxamide (Example Compound No. 25)

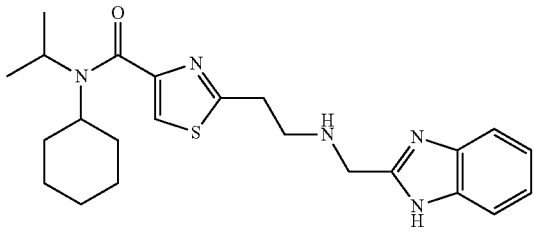 [SMILES: CC(C)N(C(=O)c1csc(CCNCc2nc3ccccc3[nH]2)n1)C1CCCCC1]

In a similar fashion to general procedure 2, tert-butyl N-(1H-1,3-benzodiazol-2-ylmethyl)-N-(2-{4-[cyclohexyl(propan-2-yl)carbamoyl]-1,3-thiazol-2-yl}ethyl)carbamate (18) (275 mg, 0.523 mmol) and 4M HCl in dioxane (20 ml) at room temperature overnight gave the title compound (70 mg, 29%) as an off white oil after purification by flash column chromatography (eluting with a gradient of 10-15% MeOH in DCM).

1H-NMR (CDCl$_3$, 400 MHz): d[ppm]=7.56 (dt, J=6.5, 3.3 Hz, 2H), 7.37 (s, 1H), 7.20-7.15 (m, 2H), 4.09 (s, 2H), 3.60 (br s, 1H), 3.43 (dd, J=12.4, 5.9 Hz, 1H), 3.18 (t, J=6.2 Hz, 2H), 3.06 (m, 3H), 2.16-2.08 (m, 1H), 1.80 (m, 4H), 1.64-1.54 (m, 3H), 1.40 (d, J=6.5 Hz, 3H), 1.21 (m, 4H)

HPLCMS (Method K): [m/z]: 426.2 [M+H]$^+$

N-Benzyl-2-(2-{[(1-methyl-1H-1,3-benzodiazol-2-yl)methyl]amino}ethyl)-1,3-thiazole-4-carboxamide (Example Compound No. 28)

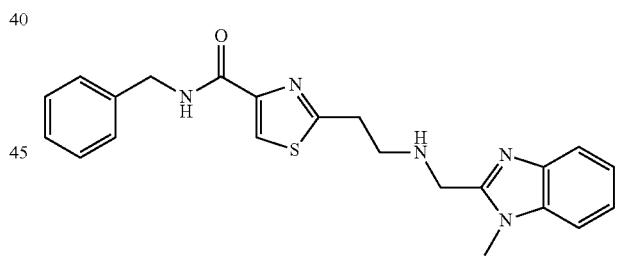

In a similar fashion to general procedure 2, tert-butyl N-{2-[4-(benzylcarbamoyl)-1,3-thiazol-2-yl]ethyl}-N-[(1-methyl-1H-1,3-benzodiazol-2-yl)methyl]carbamate (21) (280 mg, 0.554 mmol) and 20% TFA in DCM (20 ml) at room temperature overnight gave the title compound (50 mg, 21%) as a white solid after purification by flash column chromatography (eluting with a gradient of 10-15% MeOH in DCM).

1H-NMR (CDCl$_3$, 400 MHz): d[ppm]=8.22 (s, 1H), 7.58 (dd, J=12.6, 8.1 Hz, 2H), 7.38 (d, J=1.0 Hz, 1H), 7.33-7.18 (m, 6H), 4.69 (s, 2H), 4.58 (s, 2H), 3.85 (s, 3H), 3.73 (t, J=6.4 Hz, 2H), 3.57 (t, J=6.4 Hz, 2H)

HPLCMS (Method J): [m/z]: 406.07 [M+H]$^+$

2-{2-[(1H-1,3-Benzodiazol-2-ylmethyl)amino]ethyl}-N-(pyridin-3-ylmethyl)-1,3-thiazole-4-carboxamide Trihydrochloride (Example Compound No. 35)

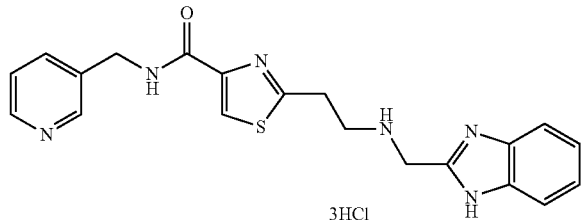 [SMILES: O=C(NCc1cccnc1)c1csc(CCNCc2nc3ccccc3[nH]2)n1]

In a similar fashion to general procedure 2, tert-butyl N-(1H-1,3-benzodiazol-2-ylmethyl)-N-(2-{4-[(pyridin-3-ylmethyl)carbamoyl]-1,3-thiazol-2-yl}ethyl)carbamate (22) (184 mg, 0.374 mmol) and 4M HCl in dioxane (15 ml) at room temperature for 18 h gave the title compound (80 mg, 53%) as the tri HCl salt as a white solid after precipitation with Et$_2$O.

1H-NMR (DMSO-d6, 400 MHz): d[ppm]=10.28 (bs, 3H), 9.64 (t, J=6.2 Hz, 1H), 8.90 (s, 1H), 8.81 (d, J=5.4 Hz, 1H), 8.55 (d, J=8.1 Hz, 1H), 8.25 (s, 1H), 8.00 (dd, J=8.0, 5.7 Hz, 1H), 7.73 (m, 2H), 7.48-7.34 (m, 2H), 4.71 (s, 2H), 4.65 (d, J=6.2 Hz, 2H), 3.66 (t, J=6.6 Hz, 2H), 3.57 (t, J=6.3 Hz, 2H)

HPLCMS (Method J): [m/z]: 493.3 [M+H]$^+$

2-{2-[(1H-1,3-Benzodiazol-2-ylmethyl)amino]ethyl}-N-(pyridin-4-ylmethyl)-1,3-thiazole-4-carboxamide Trihydrochloride (Example Compound No. 36)

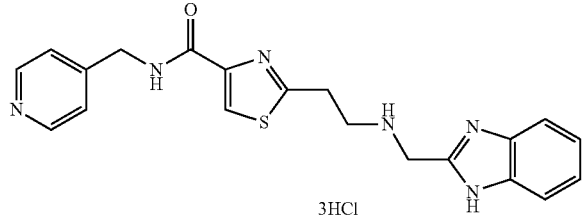 [SMILES: O=C(NCc1ccncc1)c1csc(CCNCc2nc3ccccc3[nH]2)n1]

In a similar fashion to general procedure 2, tert-butyl N-(1H-1,3-benzodiazol-2-ylmethyl)-N-(2-{4-[(pyridin-4-ylmethyl)carbamoyl]-1,3-thiazol-2-yl}ethyl)carbamate (23) (145.8 mg, 0.296 mmol) and 4M HCl in dioxane (15 ml) at room temperature for 18 h gave the title compound (70 mg, 47%) as the tri HCl salt as a white solid after precipitation with Et$_2$O.

1H-NMR (DMSO, 400 MHz): d[ppm]=10.40 (bs, 3H), 9.69 (t, J=6.2 Hz, 1H), 8.83 (d, J=6.7 Hz, 2H), 8.28 (s, 1H), 7.98 (d, J=6.6 Hz, 2H), 7.81-7.69 (m, 2H), 7.49-7.37 (m, 2H), 4.73 (d, J=5.1 Hz, 4H), 3.68 (t, J=6.5 Hz, 2H), 3.60 (t, J=6.4 Hz, 2H)

HPLCMS (Method J): [m/z]: 493.3 [M+H]$^+$

2-{2-[(1H-1,3-Benzodiazol-2-ylmethyl)amino]ethyl}-N-{[3-(trifluoromethyl)pyridin-2-yl]methyl}-1,3-thiazole-4-carboxamide (Example Compound No. 37)

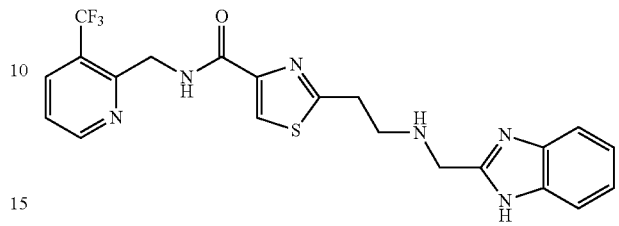

In a similar fashion to general procedure 2, tert-butyl N-(1H-1,3-benzodiazol-2-ylmethyl)-N-{2-[4-({[3-(trifluoromethyl)pyridin-2-yl]methyl}carbamoyl)-1,3-thiazol-2-yl]ethyl}carbamate (24) (86.33 mg, 0.154 mmol) and 4M HCl in dioxane (10 ml) at room temperature for 18 h gave the title compound (25 mg, 35%) as a yellow oil after purification by flash column chromatography (eluting with a gradient of 10-15% MeOH in DCM).

1H-NMR (MeOD, 400 MHz): d[ppm]=8.62 (d, J=4.8 Hz, 1H), 8.13-8.09 (m, 1H), 8.08 (s, 1H), 7.52-7.47 (m, 2H), 7.47-7.41 (m, 1H), 7.22-7.14 (m, 2H), 4.86 (s, 2H), 4.09 (s, 2H), 3.27 (t, J=6.6 Hz, 2H), 3.13 (t, J=6.6 Hz, 2H)

HPLCMS (Method J): [m/z]: 461.6 [M+H]$^+$

2-{2-[(1H-1,3-Benzodiazol-2-ylmethyl)amino]ethyl}-N-(5,6,7,8-tetrahydroquinolin-8-ylmethyl)-1,3-thiazole-4-carboxamide (Example Compound No. 38)

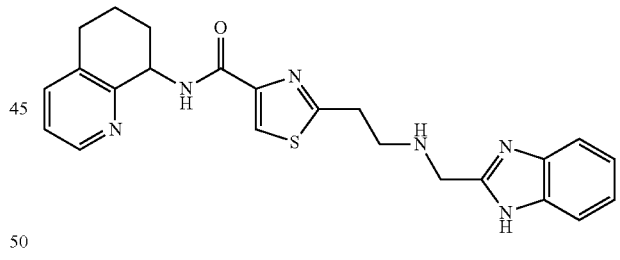

In a similar fashion to general procedure 2, tert-butyl N-(1H-1,3-benzodiazol-2-ylmethyl)-N-(2-{4-[(5,6,7,8-tetrahydroquinolin-8-ylmethyl)carbamoyl]-1,3-thiazol-2-yl}ethyl)carbamate (25) (82.03 mg, 0.154 mmol) and 4M HCl in dioxane (10 ml) at room temperature for 18 h gave the title compound (35 mg, 52%) as a yellow oil after purification by flash column chromatography (eluting with a gradient of 10-15% MeOH in DCM).

1H-NMR (MeOD, 400 MHz): d[ppm]=8.27 (d, J=3.6 Hz, 1H), 8.08 (s, 1H), 7.58 (d, J=7.6 Hz, 1H), 7.49 (m, 2H), 7.27-7.15 (m, 3H), 5.22-5.12 (m, 1H), 4.05 (s, 2H), 3.21 (t, J=6.7 Hz, 2H), 3.05 (t, J=6.4 Hz, 2H), 2.96-2.77 (m, 2H), 2.34-2.20 (m, 1H), 2.05-1.79 (m, 3H)

HPLCMS (Method J): [m/z]: 433.6 [M+H]$^+$

2-{2-[(1H-1,3-Benzodiazol-2-ylmethyl)amino]ethyl}-N-{5H,6H,7H-cyclopenta[b]pyridin-7-yl}-1,3-thiazole-4-carboxamide Trihydrochloride (Example Compound No. 39)

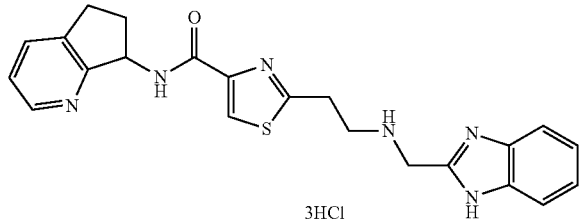 [SMILES: O=C(NC1CCc2cccnc21)c1csc(CCNCc2nc3ccccc3[nH]2)n1]

In a similar fashion to general procedure 2, 4M HCl in dioxane (6.36 ml) was added to tertbutyl N-(1H-1,3-benzodiazol-2-ylmethyl)-N-{2-[4-({5H,6H,7H-cyclopenta[b]pyridin-7-yl}carbamoyl)-1,3-thiazol 2-yl]ethyl}carbamate (26) (1.32 g, 2.55 mmol) in dioxane (30 ml) and stirred at room temperature for 48 h to give the title compound (1.03 g, 76%) after crystalisation from DCM/MeOH.

1H-NMR (MeOD, 500 MHz): d[ppm]=8.56 (d, J=5.8 Hz, 1H), 8.52-8.48 (m, 1H), 8.31 (s, 1H), 7.92 (dd, J=7.7, 6.0 Hz, 1H), 7.86 (dt, J=6.7, 3.3 Hz, 2H), 7.66 (dt, J=6.3, 3.3 Hz, 2H), 5.95 (t, J=8.8 Hz, 1H), 5.01 (s, 2H), 3.87 (t, J=6.2 Hz, 2H), 3.71-3.63 (m, 2H), 3.42-3.35 (m, 1H), 3.21 (dt, J=17.1, 8.7 Hz, 1H), 2.86-2.77 (m, 1H), 2.51 (dq, J=12.9, 9.2 Hz, 1H)

HPLCMS (Method C): [m/z]: 419.05 [M+H]$^+$

2-{2-[(1H-1,3-Benzodiazol-2-ylmethyl)amino]ethyl}-N-[(3-fluoropyridin-2-)methyl)]-1,3-thiazole-4-carboxamide Trihydrochloride (Example Compound No. 40)

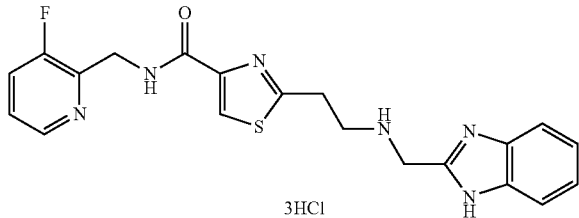 [SMILES: O=C(NCc1ncccc1F)c1csc(CCNCc2nc3ccccc3[nH]2)n1]

In a similar fashion to general procedure 2, 4M HCl in dioxane (16.57 ml, 66.26 mmol) was added to tert-butyl N-(1H-1,3-benzodiazol-2-ylmethyl)-N-[2-(4-{[(3-fluoropyridin-2-yl)methyl]carbamoyl}-1,3-thiazol-2-yl)ethyl]carbamate (27) (4.13 g, 6.63 mmol) in dioxane (40 ml) and stirred at room temperature for 16 h to give the title compound (3.04 g, 88%) as a white solid after precipitation from Et$_2$O (100 ml).

1H-NMR (MeOD, 500 MHz): d[ppm]=8.47 (d, J=5.1 Hz, 1H), 8.28 (s, 1H), 8.11 (s, 1H), 7.84 (dd, J=6.1, 3.1 Hz, 2H), 7.76 (s, 1H), 7.62 (dd, J=6.1, 3.0 Hz, 2H), 4.99 (s, 2H), 4.95 (s, 2H), 3.84 (t, J=6.2 Hz, 2H), 3.65 (t, J=6.2 Hz, 2H)

HPLCMS (Method D): [m/z]: 411.1 [M+H]$^+$

2-{2-[(1H-1,3-Benzodiazol-2-ylmethyl)amino]ethyl}-N-[(4-methylmorpholin-2-yl)methyl]-1,3-thiazole-4-carboxamide (Example Compound No. 41)

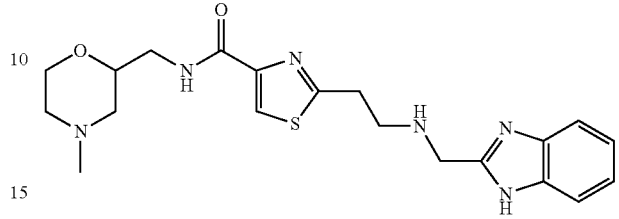

In a similar fashion to general procedure 2, tert-butyl N-(1H-1,3-benzodiazol-2-ylmethyl)-N-[2-(4-{[(4-methylmorpholin-2-yl)methyl]carbamoyl}-1,3-thiazol-2-yl)ethyl]carbamate (28) (80.8 mg, 0.157 mmol) and 4M HCl in dioxane (15 ml) at room temperature overnight gave the title compound (31 mg, 47%) as a pale yellow oil after purification by flash column chromatography (eluting with a gradient of 10-15% MeOH in DCM).

1H-NMR (MeOD, 400 MHz): d[ppm]=8.05 (s, 1H), 7.53 (m, 2H), 7.26-7.17 (m, 2H), 4.08 (s, 2H), 3.82-3.69 (m, 2H), 3.65-3.49 (m, 2H), 3.40-3.33 (m, 2H), 3.25 (t, J=6.6 Hz, 2H), 3.10 (t, J=6.6 Hz, 2H), 2.69 (m, 1H), 2.37 (s, 3H), 2.36-2.28 (m, 2H)

HPLCMS (Method J): [m/z]: 415.6 [M+H]$^+$

2-{2-[(1H-1,3-Benzodiazol-2-ylmethyl)amino]ethyl}-N-[(6-methylpyridin-2-yl)methyl]-1,3-thiazole-4-carboxamide (Example Compound No. 42)

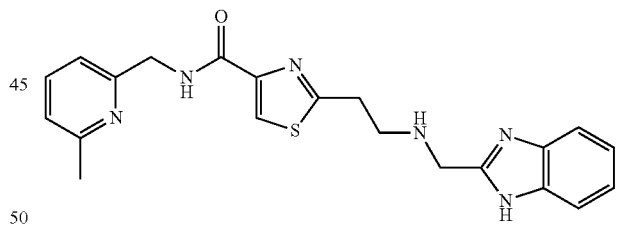

In a similar fashion to general procedure 2, tert-butyl N-(1H-1,3-benzodiazol-2-ylmethyl)-N-[2-(4-{[(6-methylpyridin-2-yl)methyl]carbamoyl}-1,3-thiazol-2-yl)ethyl]carbamate (29) (79.5 mg, 0.157 mmol) and 4M HCl in dioxane (15 ml) at room temperature overnight gave the title compound (25.5 mg, 36%) as a pale yellow oil after purification by flash column chromatography (eluting with a gradient of 10-15% MeOH in DCM).

1H-NMR (MeOD, 400 MHz): d[ppm]=8.09 (s, 1H), 7.63 (t, J=7.7 Hz, 1H), 7.50 (m, 2H), 7.23-7.17 (m, 3H), 7.15 (m, 2H), 4.63 (s, 2H), 4.08 (s, 2H), 3.26 (t, J=6.7 Hz, 2H), 3.11 (t, J=6.6 Hz, 2H), 2.50 (s, 3H)

HPLCMS (Method J): [m/z]: 405.5 [M+H]$^+$

2-{2-[(1H-1,3-Benzodiazol-2-ylmethyl)amino]ethyl}-N-[(5-fluoropyridin-2-)methyl)]-1,3-thiazole-4-carboxamide (Example Compound No. 43)

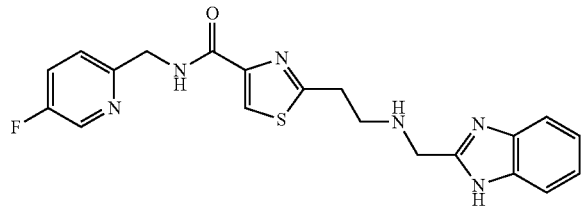 [SMILES: O=C(NCc1ccc(F)cn1)c1csc(CCNCc2nc3ccccc3[nH]2)n1]

In a similar fashion to general procedure 2, tert-butyl N-(1H-1,3-benzodiazol-2-ylmethyl)-N-[2-(4-{[(5-fluoropyridin-2-yl)methyl]carbamoyl}-1,3-thiazol-2-yl)ethyl]carbamate (30) (80.2 mg, 0.157 mmol) and 4M HCl in dioxane (15 ml) at room temperature overnight gave the title compound (12.5 mg, 17%) as a pale yellow oil after purification by flash column chromatography (eluting with a gradient of 10-15% MeOH in DCM).

1H-NMR (MeOD, 400 MHz): d[ppm]=8.36 (d, J=2.6 Hz, 1H), 8.08 (s, 1H), 7.59-7.46 (m, 3H), 7.42 (m, 1H), 7.20 (m, 2H), 4.66 (s, 2H), 4.08 (s, 2H), 3.26 (t, J=6.5 Hz, 2H), 3.11 (t, J=6.5 Hz, 2H)

HPLCMS (Method J): [m/z]: 411.5 [M+H]$^+$

2-{2-[(1H-1,3-Benzodiazol-2-ylmethyl)amino]ethyl}-N-(pyrimidin-4-ylmethyl)-1,3-thiazole-4-carboxamide (Example Compound No. 44)

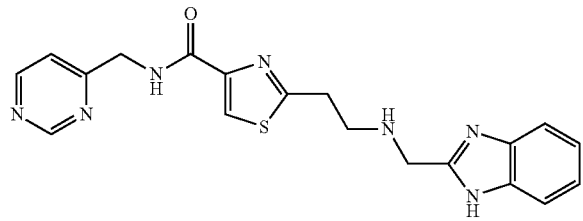 [SMILES: O=C(NCc1ccncn1)c1csc(CCNCc2nc3ccccc3[nH]2)n1]

In a similar fashion to general procedure 2, tert-butyl N-(1H-1,3-benzodiazol-2-ylmethyl)-N-(2-{4-[(pyrimidin-4-ylmethyl)carbamoyl]-1,3-thiazol-2-yl}ethyl)carbamate (31) (75 mg, 0.152 mmol) and 4M HCl in dioxane (2 ml) at room temperature for 4 h gave the title compound (22 mg, 37%) as a yellow solid after purification by flash column chromatography (eluting with a gradient of 8% MeOH in DCM).

1H-NMR (MeOD, 400 MHz): d[ppm]=9.05 (d, J=1.1 Hz, 1H), 8.67 (d, J=5.3 Hz, 1H), 8.12 (s, 1H), 7.51 (dd, J=6.0, 3.2 Hz, 2H), 7.46 (d, J=5.3 Hz, 1H), 7.26-7.18 (m, 2H), 4.68 (s, 2H), 4.10 (s, 2H), 3.28 (t, J=6.5 Hz, 2H), 3.14 (t, J=6.6 Hz, 2H)

HPLCMS (Method J): [m/z]: 394.4 [M+H]$^+$

2-{2-[(1H-1,3-Benzodiazol-2-ylmethyl)amino]ethyl}-N-[(5-methoxypyridin-2-yl)methyl]-1,3-thiazole-4-carboxamide (Example Compound No. 45)

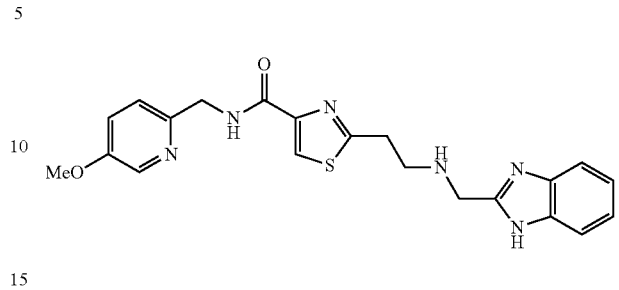

In a similar fashion to general procedure 2, tert-butyl N-(1H-1,3-benzodiazol-2-ylmethyl)-N-[2-(4-{[(5-methoxypyridin-2-yl)methyl]carbamoyl}-1,3-thiazol-2-yl)ethyl]carbamate (32) (80 mg, 0.153 mmol) and 4M HCl in dioxane (2 ml) at room temperature for 4 h gave the title compound (53 mg, 82%) as a yellow solid after purification by flash column chromatography (eluting with a gradient of 8% MeOH in DCM).

1H-NMR (MeOD, 400 MHz): d[ppm]=8.17-8.13 (m, 1H), 8.08 (s, 1H), 7.54-7.47 (m, 2H), 7.35-7.31 (m, 2H), 7.25-7.18 (m, 2H), 4.61 (s, 2H), 4.07 (d, J=8.0 Hz, 2H), 3.84 (s, 3H), 3.26 (t, J=6.6 Hz, 2H), 3.11 (t, J=6.6 Hz, 2H)

HPLCMS (Method J): [m/z]: 423.4 [M+H]$^+$

2-{2-[(1H-1,3-Benzodiazol-2-ylmethyl)amino]ethyl}-N-(pyrazin-2-ylmethyl)-1,3-thiazole-4-carboxamide (Example Compound No. 46)

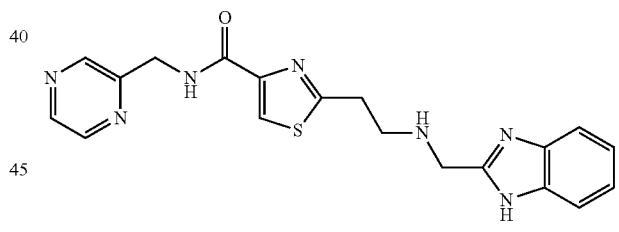

In a similar fashion to general procedure 2, tert-butyl N-(1H-1,3-benzodiazol-2-ylmethyl)-N-(2-{4-[(pyrazin-2-ylmethyl)carbamoyl]-1,3-thiazol-2-yl}ethyl)carbamate (33) (70 mg, 0.142 mmol) and 4M HCl in dioxane (2 ml) at room temperature for 4 h gave the title compound (30 mg, 53.7%) as a brown solid after purification by flash column chromatography (eluting with a gradient of 8% MeOH in DCM).

1H-NMR (MeOD, 400 MHz): d[ppm]=8.63 (s, 1H), 8.56-8.51 (m, 1H), 8.48 (d, J=2.6 Hz, 1H), 8.12 (s, 1H), 7.52 (dd, J=6.0, 3.2 Hz, 2H), 7.22 (dd, J=6.1, 3.1 Hz, 2H), 4.74 (s, 2H), 4.13 (s, 2H), 3.28 (t, J=6.5 Hz, 2H), 3.17 (t, J=6.5 Hz, 2H)

HPLCMS (Method I): [m/z]: 394.4 [M+H]$^+$

2-{2-[(1H-1,3-Benzodiazol-2-ylmethyl)amino]ethyl}-N-[(6-oxo-1,6-dihydropyridin-2-yl)methyl]-1,3-thiazole-4-carboxamide (Example Compound No. 47)

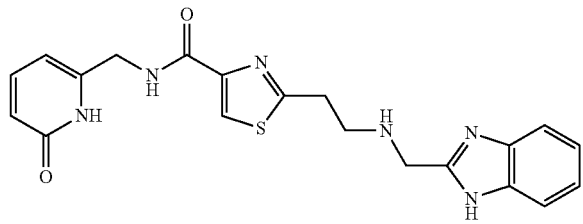 [SMILES: O=C(NCc1cccc(=O)[nH]1)c1csc(CCNCc2nc3ccccc3[nH]2)n1]

In a similar fashion to general procedure 2, tert-butyl N-(1H-1,3-benzodiazol-2-ylmethyl)-N-[2-(4-{[(6-oxo-1,6-dihydropyridin-2-yl)methyl]carbamoyl}-1,3-thiazol-2-yl)ethyl]carbamate (34) (70 mg, 0.138 mmol) and 4M HCl in dioxane HCl (2 ml) at room temperature for 4 h gave the title compound (30 mg, 53%) as a yellow solid after purification by flash column chromatography (eluting with a gradient of 8% MeOH in DCM).

1H-NMR (MeOD, 400 MHz): d[ppm]=8.12 (s, 1H), 7.51 (m, 3H), 7.22 (dd, J=6.0, 3.2 Hz, 2H), 6.42 (d, J=9.1 Hz, 1H), 6.30 (d, J=6.9 Hz, 1H), 4.44 (s, 2H), 4.09 (s, 2H), 3.27 (t, J=6.7 Hz, 2H), 3.12 (t, J=6.7 Hz, 2H)

HPLCMS (Method J): [m/z]: 409.4 [M+H]$^+$

2-{2-[(1H-1,3-Benzodiazol-2-ylmethyl)amino]ethyl}-N-[(6-cyanopyridin-3-yl)methyl]-1,3-thiazole-4-carboxamide (Example Compound No. 56) and 5-{[(2-{2-[(1H-1,3-Benzodiazol-2-ylmethyl)amino]ethyl}-1,3-thiazol-4-yl)formamido]methyl}pyridine-2-carboxamide (Example Compound No. 54)

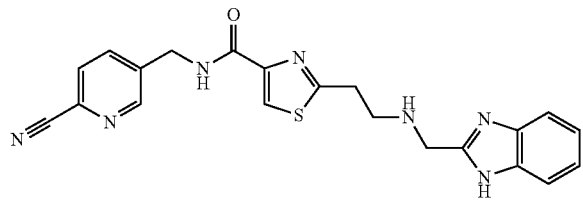

In a similar fashion to general procedure 2, a mixture of tert-butyl N-(1H-1,3-benzodiazol-2-ylmethyl)-N-[2-(4-{[(6-carbamoylpyridin-3-yl)methyl]carbamoyl}-1,3-thiazol-2-yl)ethyl]carbamate (35) and tert-butyl N-(1H-1,3-benzodiazol-2-ylmethyl)-N-[2-(4-{[(6-cyanopyridin-3-yl)methyl]carbamoyl}-1,3-thiazol-2-yl)ethyl]carbamate (36) (80 mg, 0.155 mmol) and 4 M HCl in dioxane (3 ml) at room temperature for 18 h gave two products. Formamide (Example Compound No. 54) (16 mg, 23%) was isolated following flash column chromatography (eluting with a gradient of DCM/MeOH, 9:1). Crude nitrile (Example Compound No. 56) was also isolated and was further purified by basic prep-HPLC to give the required product as a brown solid (24 mg, 37%).

Formamide: 1H-NMR (Methanol-d4, 400 MHz): d[ppm]=8.49 (t, J=10.2 Hz, 1H), 7.99 (s, 1H), 7.94 (t, J=10.0 Hz, 1H), 7.78 (dt, J=8.1, 4.0 Hz, 1H), 7.46-7.34 (m, 2H), 7.11 (dd, J=6.0, 3.1 Hz, 2H), 4.56 (d, J=14.2 Hz, 2H), 4.02 (d, J=8.0 Hz, 2H), 3.19 (m, 4H), 3.06 (t, J=6.5 Hz, 2H)

HPLCMS (Method I): [m/z]: 436.5 [M+H]$^+$

Nitrile: 1H-NMR (DMSO-d6, 500 MHz): d[ppm]=12.18 (s, 1H), 9.08 (t, J=6.2 Hz, 1H), 8.70 (s, 1H), 8.14 (s, 1H), 7.97 (d, J=8.0 Hz, 1H), 7.92 (dd, J=8.1, 2.0 Hz, 1H), 7.48 (d, J=294 Hz, 2H), 7.12 (d, J=4.7 Hz, 2H), 4.54 (d, J=6.2 Hz, 2H), 4.10 (d, J=5.2 Hz, 1H), 3.96 (s, 2H), 3.18-3.15 (m, 2H), 2.98 (d, J=6.6 Hz, 2H)

HPLCMS (Method I): [m/z]: 418.2 [M+H]$^+$

2-{2-[(1H-1,3-Benzodiazol-2-ylmethyl)amino]ethyl}-N-[(3,5-dimethylpyridin-2-yl)methyl]-1,3-thiazole-4-carboxamide (Example Compound No. 57)

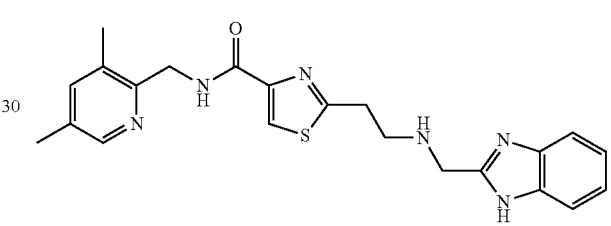

In a similar fashion to general procedure 2, tert-butyl N-(1H-1,3-benzodiazol-2-ylmethyl)-N-[2-(4-{[(3,5-dimethylpyridin-2-yl)methyl]carbamoyl}-1,3-thiazol-2-yl)ethyl]carbamate (37) (198 mg, 0.36 mmol) and 12 M HCl (0.307 ml, 8.42 mmol) in MeOH (10 ml) at 40° C. for 21 h gave the title compound (90 mg, 59%) as a yellow solid after purification by neutral prep-HPLC.

1H-NMR (DMSO-d6, 500 MHz): d[ppm]=12.17 (s, 1H), 8.71 (t, J=4.8 Hz 1H), 8.16 (s, 1H), 8.14 (s, 1H), 7.51 (s, 1H), 7.42 (s, 2H), 7.12 (d, J=4.9 Hz, 2H), 4.52 (d, J=4.9 Hz, 2H), 3.97 (s, 2H), 3.17 (d, J=4.9 Hz, 2H), 2.98 (t, J=6.8 Hz, 2H), 2.27 (s, 3H), 2.24 (s, 3H)

HPLCMS (Method B): [m/z]: 421.2 [M+H]$^+$

2-{2-[(1H-1,3-Benzodiazol-2-ylmethyl)amino]ethyl}-N-(pyrimidin-2-ylmethyl)-1,3-thiazole-4-carboxamide (Example Compound No. 61)

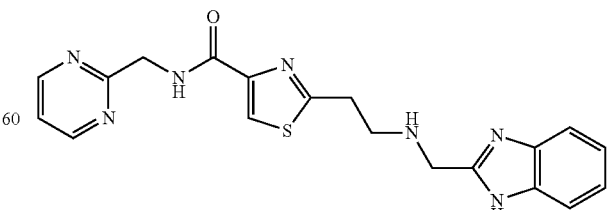

In a similar fashion to general procedure 2, tert-butyl 2-({[(tert-butoxy)carbonyl](2-{4-[(pyrimidin-2-ylmethyl)

carbamoyl]-1,3-thiazol-2-yl}ethyl)amino}methyl)-1H-1,3-benzodiazole-1-carboxylate (38) (86 mg, 0.145 mmol) and 12 M HCl (0.282 ml, 3.378 mmol) in MeOH (2 ml) at 40'C for 24 h gave the title compound (24 mg, 42%) as a brown solid after purification by flash column chromatography (eluting with a gradient 100% DCM, 90% DCM:10% MeOH and 90% DCM:10% methanolic ammonia) followed by basic prep-HPLC.

1H-NMR (DMSO-d6, 500 MHz): d[ppm]=12.18 (s, 1H), 8.75 (dd, J=10.2, 5.4 Hz, 3H), 8.13 (s, 1H), 7.48 (d, J=36.0 Hz, 2H), 7.39 (t, J=4.9 Hz, 1H), 7.19-7.03 (m, 2H), 4.66 (d, J=5.8 Hz, 2H), 3.97 (s, 2H), 3.20 (t, J=6.8 Hz, 2H), 2.99 (t, J=6.8 Hz, 2H), 2.66 (s, 1H)

HPLCMS (Method B): [m/z]: 394.2 [M+H]+

2-{2-[(1H-1,3-Benzodiazol-2-ylmethyl)amino]ethyl}-N-{[2-(4-methylpiperazin-1-yl)phenyl]methyl}-1,3-thiazole-4-carboxamide (Example Compound No. 68)

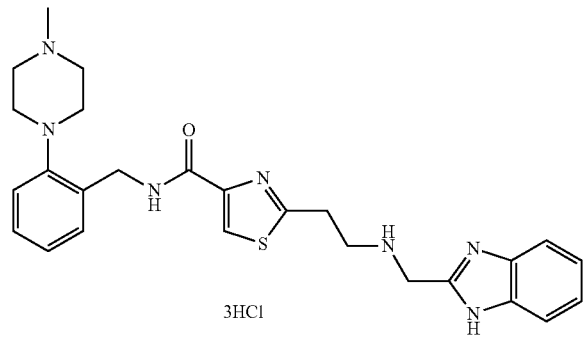 [SMILES: CN1CCN(c2ccccc2CNC(=O)c2csc(CCNCc3nc4ccccc4[nH]3)n2)CC1]

In a similar fashion to general procedure 2, tert-butyl N-(1H-1,3-benzodiazol-2-ylmethyl)-N-{2-[4-({[2-(4-methylpiperazin-1-yl)phenyl]methyl}carbamoyl)-1,3-thiazol-2-yl]ethyl}carbamate (39) (13.4 mg, 0.02 mmol) in dioxane (0.5 ml) and 4M HCl in dioxane (55.1 µl) at 50'C for 16 h gave the title compound (11.5 mg, 85%) as a white solid after trituration with DCM.

1H-NMR (Methanol-d4, 500 MHz): d[ppm]=8.28 (s, 1H), 7.88 (dt, J=6.6, 3.3 Hz, 2H), 7.69 (dt, J=6.3, 3.3 Hz, 2H), 7.45 (t, J=7.6 Hz, 1H), 7.33 (d, J=6.7 Hz, 2H), 7.20-7.14 (m, 1H), 5.06 (s, 2H), 4.78 (s, 2H), 3.87 (t, J=6.2 Hz, 2H), 3.72-3.59 (m, 4H), 3.49 (t, J=10.5 Hz, 2H), 3.37 (s, 2H), 3.27 (d, J=11.0 Hz, 2H), 3.02 (s, 3H)

HPLCMS (Method D): [m/z]: 490.3 [M+H]+

2-{2-[(1H-1,3-Benzodiazol-2-ylmethyl)amino]ethyl}-N-[(2,6-difluorophenyl)methyl]-1,3-thiazole-4-carboxamide (Example Compound No. 69)

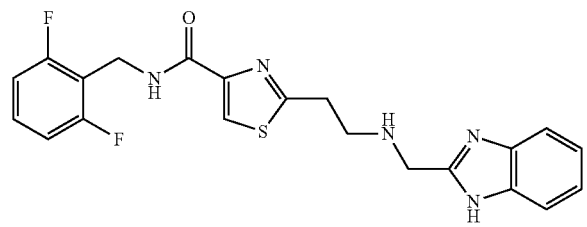 [SMILES: O=C(NCc1c(F)cccc1F)c1csc(CCNCc2nc3ccccc3[nH]2)n1]

In a similar fashion to general procedure 2, tert-butyl N-(1H-1,3-benzodiazol-2-ylmethyl)-N-[2-(4-{[(2,6-difluorophenyl)methyl]carbamoyl}-1,3-thiazol-2-yl)ethyl]carbamate (40) (90 mg, 0.17 mmol) in dioxane (2 ml) and 4M HCl in dioxane (427 µl) at room temperature for 16 h gave the title compound (15 mg, 20.6%) as a off white solid after purification by prep-HPLC.

1H-NMR (Methanol-d4, 500 MHz): d[ppm]=8.06 (s, 1H), 7.53 (dd, J=5.8, 3.2 Hz, 2H), 7.34 (tt, J=8.4, 6.5 Hz, 1H), 7.29-7.16 (m, 2H), 7.03-6.88 (m, 2H), 4.68 (s, 2H), 4.07 (s, 2H), 3.23 (t, J=6.6 Hz, 2H), 3.09 (t, J=6.6 Hz, 2H)

HPLCMS (Method A): [m/z]: 428.1 [M+H]+

2-{2-[(1H-1,3-Benzodiazol-2-ylmethyl)amino]ethyl}-N-{[2-(dimethylamino)phenyl]methyl}-1,3-thiazole-4-carboxamide (Example Compound No. 70)

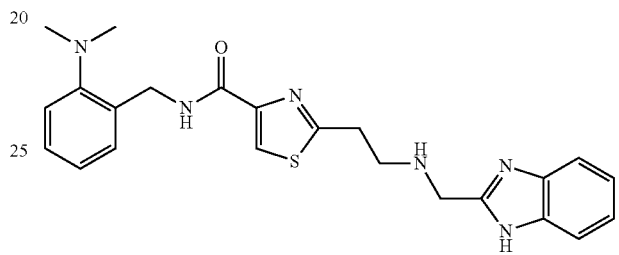

In a similar fashion to general procedure 2, tert-butyl N-(1H-1,3-benzodiazol-2-ylmethyl)-N-{2-[4-({[2-(dimethylamino)phenyl]methyl}carbamoyl)-1,3-thiazol-2-yl]ethyl}carbamate (41) (73 mg, 0.14 mmol) in dioxane (2 ml) and 4M HCl in dioxane (341 µl) at 50° C. for 16 h gave title compound (8.7 mg, 14%) following purification by prep-HPLC.

1H-NMR (Methanol-d4, 500 MHz): d[ppm]=8.08 (s, 1H), 7.53 (dd, J=5.9, 3.2 Hz, 2H), 7.29-7.14 (m, 5H), 7.02 (td, J=7.4, 1.1 Hz, 1H), 4.68 (s, 2H), 4.08 (s, 2H), 3.25 (t, J=6.7 Hz, 2H), 3.11 (t, J=6.8 Hz, 2H), 2.67 (s, 6H)

HPLCMS (Method D): [m/z]: 435.3 [M+H]+

2-{2-[(1H-1,3-Benzodiazol-2-ylmethyl)amino]ethyl}-N-[(2-cyanophenyl)methyl]-1,3-thiazole-4-carboxamide (Example Compound No. 71)

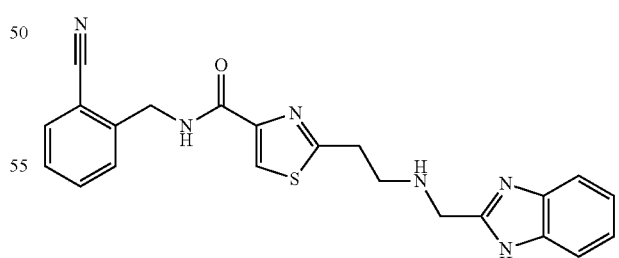

In a similar fashion to general procedure 2, tert-butyl N-(1H-1,3-benzodiazol-2-ylmethyl)-N-[2-(4-{[(2-cyanophenyl)methyl]carbamoyl}-1,3-thiazol-2-yl)ethyl]carbamate (42) (54 mg, 0.1 mmol) in dioxane (2 ml) and 4M HCl in dioxane (261 µl) at 500° C. for 12 h gave the title compound (8 mg, 18%) as a yellow solid after purification by prep-HPLC.

1H-NMR (Methanol-d4, 500 MHz): d[ppm]=8.11 (s, 1H), 7.74-7.69 (m, 1H), 7.60 (td, J=7.8, 1.2 Hz, 1H), 7.56-7.50 (m, 3H), 7.43 (t, J=7.6 Hz, 1H), 7.25-7.19 (m, 2H), 4.78 (s, 2H), 4.09 (s, 2H), 3.27 (t, J=6.6 Hz, 2H), 3.13 (t, J=6.6 Hz, 2H)

2-{2-[(1H-1,3-Benzodiazol-2-ylmethyl)amino]ethyl}-N-{[2-(trifluoromethoxy)phenyl]methyl}-1,3-thiazole-4-carboxamide (Example Compound No. 72)

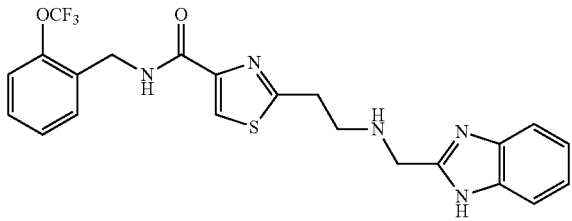 [SMILES: O=C(NCc1ccccc1OC(F)(F)F)c1csc(CCNCc2nc3ccccc3[nH]2)n1]

In a similar fashion to general procedure 2, tert-butyl N-(1H-1,3-benzodiazol-2-ylmethyl)-N-{2-[4-({[2-(trifluoromethoxy)phenyl]methyl}carbamoyl)-1,3-thiazol-2-yl]ethyl}carbamate (43) (110 mg, 0.191 mmol), 12M HCl (0.317 ml, 4.458 mmol) in MeOH (2 ml) at room temperature for 16 h, gave the title compound (41 mg, 45%) as a white solid after purification by basic prep-HPLC.

1H-NMR (DMSO-d6, 500 MHz): d[ppm]=12.19 (s, 1H), 8.88 (t, J=6.2 Hz, 1H), 8.15 (s, 1H), 7.48 (d, J=31.2 Hz, 2H), 7.42-7.30 (m, 4H), 7.13 (d, J=4.9 Hz, 2H), 4.53 (d, J=6.3 Hz, 2H), 3.97 (s, 2H), 3.19 (t, J=6.8 Hz, 2H), 2.99 (t, J=6.8 Hz, 2H)

HPLCMS (Method A): [m/z]: 476.2 [M+H]$^+$

2-{2-[(1H-1,3-Benzodiazol-2-ylmethyl)amino]ethyl}-N-(1-phenylethyl)-1,3-thiazole-4-carboxamide (Example Compound No. 73)

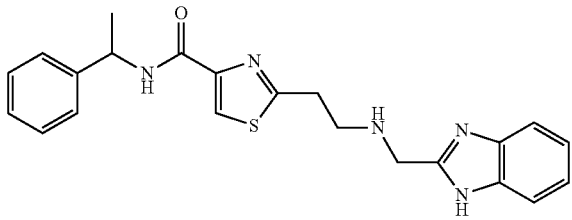 [SMILES: CC(NC(=O)c1csc(CCNCc2nc3ccccc3[nH]2)n1)c1ccccc1]

In a similar fashion to general procedure 2, tert-butyl N-(1H-1,3-benzodiazol-2-ylmethyl)-N-(2-{4-[(1-phenylethyl)carbamoyl]-1,3-thiazol-2-yl}ethyl)carbamate (44) (110 mg, 0.218 mmol), 12M HCl (0.423 ml, 5.07 mmol) in MeOH (2 ml) at room temperature for 16 h, afforded the title compound (13 mg, 15%) as a white solid after purification by basic prep-HPLC.

1H-NMR (DMSO-d6, 500 MHz): d[ppm]=12.17 (s, 1H), 8.51 (d, J=8.5 Hz, 1H), 8.09 (s, 1H), 7.46 (s, 2H), 7.39 (d, J=7.4 Hz, 2H), 7.30 (t, J=7.6 Hz, 2H), 7.22 (t, J=7.3 Hz, 1H), 7.13 (s, 2H), 5.20-5.02 (m, 1H), 3.96 (s, 2H), 3.17 (d, J=6.7 Hz, 2H), 2.97 (t, J=6.9 Hz, 2H), 1.49 (d, J=7.1 Hz, 3H)

HPLCMS (Method B): [m/z]: 406.2 [M+H]$^+$

2-{2-[(1H-1,3-Benzodiazol-2-ylmethyl)amino]ethyl}-N-{[2-(difluoromethoxy)phenyl]methyl}-1,3-thiazole-4-carboxamide (Example Compound No. 74)

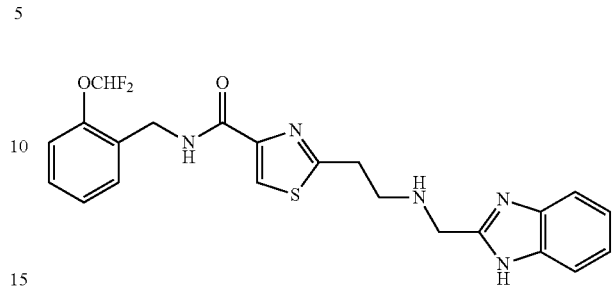

In a similar fashion to general procedure 2, crude tert-butyl N-(1H-1,3-benzodiazol-2-ylmethyl)-N-{2-[4-({[2-(difluoromethoxy)phenyl]methyl}carbamoyl)-1,3-thiazol-2-yl]ethyl}carbamate (45) (470 mg), 12 M HCl (5 ml) in MeOH (5 ml) at 50° C. for 2 h, afforded the title compound (56 mg, 35%) as a pale yellow solid after purification by flash column chromatography (KP—NH, eluting with a gradient of 0-15% MeOH/DCM) followed by prep-HPLC.

1H-NMR (DMSO-d6, 500 MHz): d[ppm]=12.18 (s, 1H), 8.79 (t, J=6.2 Hz, 1H), 8.13 (s, 1H), 7.47 (s, 2H), 7.35-7.28 (m, 2H), 7.25-7.06 (m, 5H), 4.48 (d, J=6.2 Hz, 2H), 3.96 (s, 2H), 3.22-3.17 (m, 2H), 2.98 (t, J=6.8 Hz, 2H)

HPLCMS (Method D): [m/z]: 458.2 [M+H]$^+$

2-{2-[(1H-1,3-Benzodiazol-2-ylmethyl)amino]ethyl}-N-{[2-(morpholine-4-sulfonyl)phenyl]methyl}-1,3-thiazole-4-carboxamide (Example Compound No. 75)

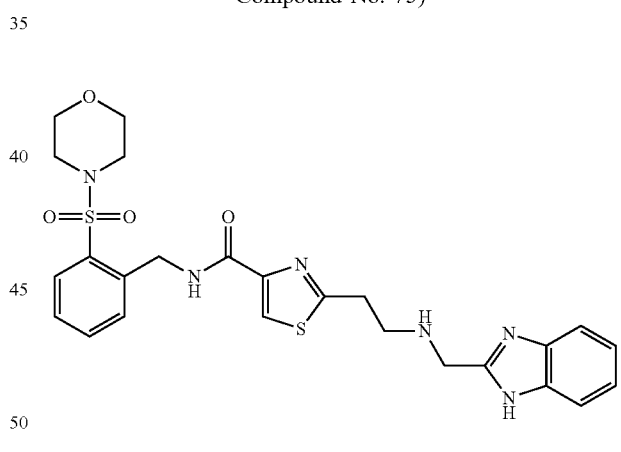

In a similar fashion to general procedure 2, crude tert-butyl N-(1H-1,3-benzodiazol-2-ylmethyl)-N-{2-[4-({[2-(morpholine-4-sulfonyl)phenyl]methyl}carbamoyl)-1,3-thiazol-2-yl]ethyl}carbamate (46) (440 mg), 12M HCl (5 ml) in MeOH (5 ml) at 50° C. for 2 h, afforded the title compound (67 mg, 42%) as a pale yellow solid after purification by flash column chromatography (KP—NH, eluting with a gradient of 0-15% MeOH/DCM) followed by prep-HPLC.

1H-NMR (DMSO-d6, 500 MHz): d[ppm]=12.19 (s, 1H), 8.88 (t, J=6.3 Hz, 1H), 8.17 (s, 1H), 7.84 (d, J=7.9 Hz, 1H), 7.66 (t, J=7.6 Hz, 1H), 7.50 (dd, J=11.8, 7.7 Hz, 4H), 7.17-7.06 (m, 2H), 4.81 (d, J=6.2 Hz, 2H), 3.97 (s, 2H), 3.70-3.61 (m, 4H), 3.20 (t, J=6.8 Hz, 2H), 3.10-3.04 (m, 4H), 2.99 (t, J=6.7 Hz, 2H)

HPLCMS (Method D): [m/z]: 541.2 [M+H]$^+$

2-{2-[(1H-1,3-Benzodiazol-2-ylmethyl)amino]ethyl}-N-[2-(pyridin-2-yl)ethyl]-1,3-thiazole-4-carboxamide (Example Compound No. 76)

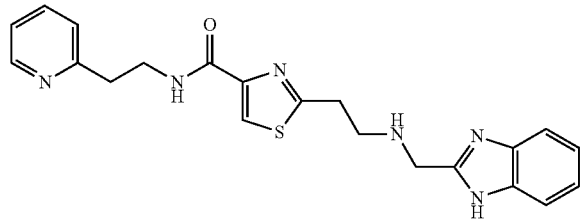 [SMILES: O=C(NCCc1ccccn1)c1csc(CCNCc2nc3ccccc3[nH]2)n1]

In a similar fashion to general procedure 2, dioxane (2 ml) was added to tertbutyl N-(1H-1,3-benzodiazol-2-ylmethyl)-N-[2-(4-{[2-(pyridin-2-yl)ethyl]carbamoyl}-1,3-thiazol-2-yl)ethyl]carbamate (47) (52 mg, 0.103 mmol) and 4 M HCl in dioxane (257 µl, 1.03 mmol). The reaction mixture was stirred at room temperature for 16 h to afford the title compound (11 mg, 26%) as a tan solid after purification by neutral prep-HPLC.

1H-NMR (Methanol-d4, 500 MHz): d[ppm]=8.44 (ddd, J=5.0, 1.7, 0.8 Hz, 1H), 8.03 (s, 1H), 7.72 (td, J=7.7, 1.8 Hz, 1H), 7.55 (dd, J=5.8, 3.2 Hz, 2H), 7.33 (d, J=7.8 Hz, 1H), 7.29-7.19 (m, 3H), 4.09 (s, 2H), 3.74 (t, J=7.1 Hz, 2H), 3.25 (t, J=6.7 Hz, 2H), 3.13-3.05 (m, 4H)

HPLCMS (Method B): [m/z]: 407.1 [M+H]$^+$

2-{2-[(1H-1,3-Benzodiazol-2-ylmethyl)amino]ethyl}-N-(3-fluoropyridin-2-yl)-1,3-thiazole-4-carboxamide (Example Compound No. 77)

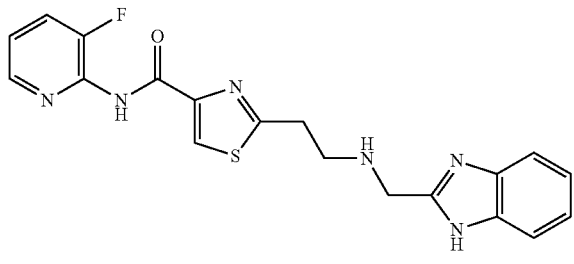 [SMILES: O=C(Nc1ncccc1F)c1csc(CCNCc2nc3ccccc3[nH]2)n1]

In a similar fashion to general procedure 2, dioxane (4 ml) was added to crude tertbutyl N-(1H-1,3-benzodiazol-2-ylmethyl)-N-(2-{4-[(3-fluoropyridin-2-yl)carbamoyl]-1,3-thiazol-2-yl}ethyl)carbamate (48) (705 mg) and 4M HCl in dioxane (1.56 ml, 6.24 mmol). The reaction mixture was stirred at room temperature for 16 h to afford the title compound (10 mg, 3.9%) as a tan solid after purification by neutral prep-HPLC.

1H-NMR (Methanol-d4, 500 MHz): d[ppm]=8.37 (s, 1H), 8.29 (dd, J=4.7, 1.0 Hz, 1H), 7.75 (ddd, J=9.8, 8.4, 1.4 Hz, 1H), 7.52 (dd, J=6.1, 3.2 Hz, 2H), 7.41 (ddd, J=8.4, 4.7, 3.8 Hz, 1H), 7.24 (dd, J=6.1, 3.2 Hz, 2H), 4.44 (s, 2H), 3.56-3.46 (m, 4H)

HPLCMS (Method D): [m/z]: 397.1 [M+H]$^+$

2-{2-[(1H-1,3-Benzodiazol-2-ylmethyl)amino]ethyl}-N-(2-phenylethyl)-1,3-thiazole-4-carboxamide (Example Compound No. 78)

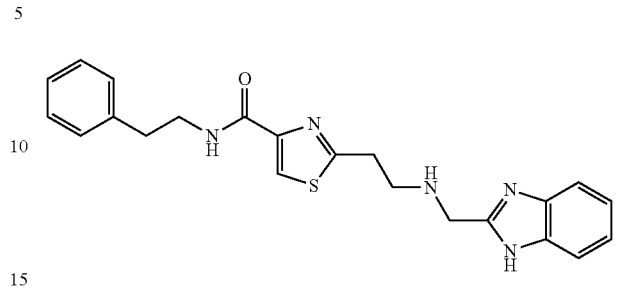

In a similar fashion to general procedure 2, tert-butyl N-(1H-1,3-benzodiazol-2-ylmethyl)-N-(2-{4-[(2-phenylethyl)carbamoyl]-1,3-thiazol-2-yl}ethyl)carbamate (49) (75 mg, 0.148 mmol), 12M HCl (0.288 ml, 3.495 mmol) in MeOH (5 ml) at room temperature for 18 h, following further addition of 12M HCl (0.288 ml, 3.495 mmol) and the mixture stirred at 40° C. for 3 h, afforded the title compound (15 mg, 25%) as a brown solid after purification by basic prep-HPLC.

1H-NMR (DMSO-d6, 500 MHz): d[ppm]=12.20 (s, 1H), 8.36 (t, J=6.0 Hz, 1H), 8.08 (s, 1H), 7.53 (d, J=7.7 Hz, 1H), 7.44 (d, J=7.0 Hz, 1H), 7.33-7.04 (m, 6H), 3.96 (s, 2H), 3.52-3.43 (m, 2H), 3.16 (t, J=6.1 Hz, 2H), 2.95 (t, J=6.8 Hz, 2H), 2.87-2.74 (m, 2H)

HPLCMS (Method D): [m/z]: 406.2 [M+H]$^+$

2-{2-[(1H-1,3-Benzodiazol-2-ylmethyl)amino]ethyl}-N-[(3-fluoro-6-methylpyridin-2-yl)methyl]-1,3-thiazole-4-carboxamide (Example Compound No. 79)

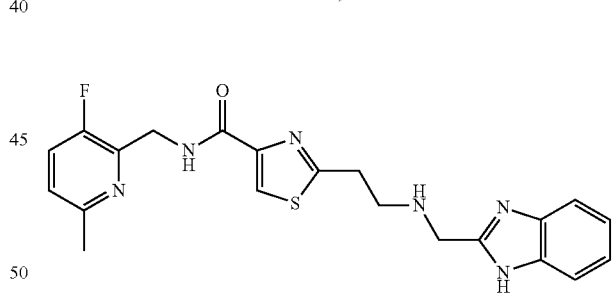

In a similar fashion to general procedure 2, 4M HCl in dioxane (0.36 ml) was added to a solution of tert butyl N-(1H-1,3-benzodiazol-2-ylmethyl)-N-[2-(4-{[(3-fluoro-6-methylpyridin-2-yl)methyl]carbamoyl}-1,3-thiazol-2-yl)ethyl]carbamate (50) (76 mg, 0.14 mmol) in dioxane (2 ml) and the mixture was stirred at room temperature for 16 h, to give the title compound (24 mg, 39%) as a colourless oil after purification by basic prep-HPLC.

1H-NMR (Methanol-d4, 500 MHz): d[ppm]=8.09 (s, 1H), 7.55-7.42 (m, 3H), 7.29-7.14 (m, 3H), 4.71 (d, J=1.7 Hz, 2H), 4.09 (s, 2H), 3.27 (t, J=6.7 Hz, 2H), 3.14 (t, J=6.7 Hz, 2H), 2.45 (s, 3H)

HPLCMS (Method D): [m/z]: 425.2 [M+H]$^+$

2-{2-[(1H-1,3-Benzodiazol-2-ylmethyl)amino]ethyl}-N-[1-(pyridin-2-yl)ethyl]-1,3-thiazole-4-carboxamide (Example Compound No. 80)

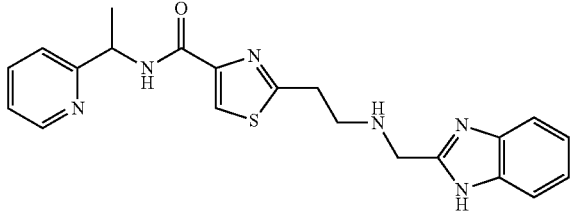

In a similar fashion to general procedure 2, 4M HCl in dioxane (0.39 ml, 1.56 mmol) was added to a solution of tert-butyl N-(1H-1,3-benzodiazol-2-ylmethyl)-N-[2-(4-{[1-(pyridin-2-yl)ethyl]carbamoyl}-1,3-thiazol-2-yl)ethyl]carbamate (51) (78 mg, 0.15 mmol) in dioxane (2 ml) and the mixture was stirred at room temperature for 16 h, to give the title compound (15 mg, 23%) as a colourless oil after purification by basic prep-HPLC.

1H-NMR (Methanol-d4, 500 MHz): d[ppm]=8.48 (ddd, J=4.9, 1.7, 0.9 Hz, 1H), 8.08 (s, 1H), 7.79 (td, J=7.8, 1.7 Hz, 1H), 7.54 (dd, J=5.7, 3.2 Hz, 2H), 7.45 (d, J=7.8 Hz, 1H), 7.29 (ddd, J=7.5, 49, 1.1 Hz, 1H), 7.26-7.18 (m, 2H), 5.25 (d, J=7.0 Hz, 1H), 4.11 (s, 2H), 3.29 (t, J=6.7 Hz, 2H), 3.16-3.12 (m, 2H), 1.57 (d, J=7.0 Hz, 3H)

HPLCMS (Method D): [m/z]: 407.2 [M+H]$^+$

2-{2-[(1H-1,3-Benzodiazol-2-ylmethyl)amino]ethyl}-N-{[6-(trifluoromethyl)pyridin-3-yl]methyl}-1,3-thiazole-4-carboxamide (Example Compound No. 81)

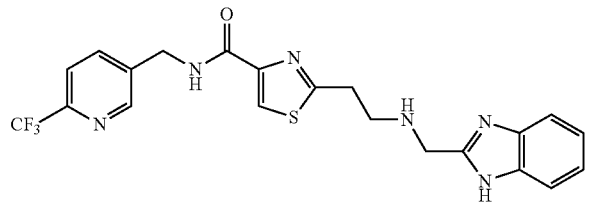 [SMILES: O=C(NCc1ccc(C(F)(F)F)nc1)c1csc(CCNCc2nc3ccccc3[nH]2)n1]

In a similar fashion to general procedure 2, 4M HCl in dioxane (0.41 ml, 1.64 mmol) was added to a solution of tert-butyl N-(1H-1,3-benzodiazol-2-ylmethyl)-N-{2-[4-({[6-(trifluoromethyl)pyridin-3-yl]methyl}carbamoyl)-1,3-thiazol-2-yl]ethyl}carbamate (52) (92 mg, 0.16 mmol) in dioxane (2 ml) and the mixture was stirred at room temperature for 16 h, to afford the title compound (21 mg, 27%) as a colourless oil after purification by basic prep-HPLC.

1H-NMR (Methanol-d4, 500 MHz): d[ppm]=8.71 (d, J=1.5 Hz, 1H), 8.11 (s, 1H), 8.00 (dd, J=8.1, 1.5 Hz, 1H), 7.77 (d, J=8.1 Hz, 1H), 7.53 (dd, J=5.8, 3.2 Hz, 2H), 7.28-7.14 (m, 2H), 4.68 (s, 2H), 4.09 (s, 2H), 3.27 (t, J=6.7 Hz, 2H), 3.12 (t, J=6.7 Hz, 2H)

HPLCMS (Method D): [m/z]: 461.1 [M+H]$^+$

2-{2-[(1H-1,3-Benzodiazol-2-ylmethyl)amino]ethyl}-N-[(3-chloropyridin-2-yl)methyl]-1,3-thiazole-4-carboxamide (Example Compound No. 82)

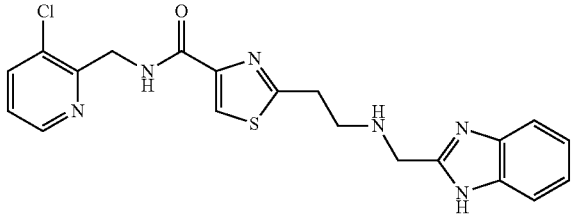 [SMILES: O=C(NCc1ncccc1Cl)c1csc(CCNCc2nc3ccccc3[nH]2)n1]

In a similar fashion to general procedure 2, tert-butyl N-(1H-1,3-benzodiazol-2-ylmethyl)-N-[2-(4-{[(3-chloropyridin-2-yl)methyl]carbamoyl}-1,3-thiazol-2-yl)ethyl]carbamate (53) (161 mg, 0.363 mmol) and 12M HCl (1.6 ml, 19.2 mmol) in MeOH (1.6 ml) at 50° C. for 4 h, afforded the title compound (72 mg, 54%) as a white solid after purification by basic prep-HPLC.

1H-NMR (DMSO-d6, 500 MHz): d[ppm]=12.22 (s, 1H), 8.71 (t, J=5.5 Hz, 1H), 8.47 (dd, J=4.7, 1.3 Hz, 1H), 8.15 (s, 1H), 7.95 (dd, J=8.1, 1.3 Hz, 1H), 7.51 (s, 1H), 7.45 (s, 1H), 7.37 (dd, J=8.1, 4.7 Hz, 1H), 7.12 (d, J=4.8 Hz, 2H), 4.67 (d, J=5.5 Hz, 2H), 3.97 (s, 2H), 3.20 (t, J=6.8 Hz, 2H), 2.98 (t, J=6.8 Hz, 2H)

HPLCMS (Method D): [m/z]: 427.1 [M+H]$^+$

2-{2-[(1H-1,3-Benzodiazol-2-ylmethyl)amino]ethyl}-N-[(2-oxo-1,2-dihydropyridin-3-yl)methyl]-1,3-thiazole-4-carboxamide (Example Compound No. 83)

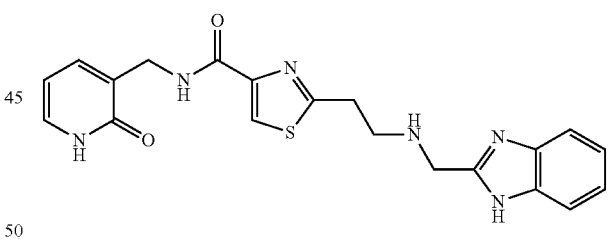

In a similar fashion to general procedure 2, crude tert-butyl N-(1H-1,3-benzodiazol-2-ylmethyl)-N-{2-[4-({[2-(tert-butoxy)pyridin-3-yl]methyl}carbamoyl)-1,3-thiazol-2-yl]ethyl}carbamate (54) (205 mg, 0.36 mmol) and 12M HCl (2 ml) in MeOH (2 ml) at 50° C. for 4 h, afforded the title compound (66 mg, 44%) as a pale yellow solid after purification by basic prep-HPLC.

1H-NMR (DMSO-d6, 500 MHz): d[ppm]=12.17 (br s, 1H), 11.65 (br s, 1H), 8.59 (t, J=6.0 Hz, 1H), 8.11 (s, 1H), 7.48 (s, 2H), 7.32-7.26 (m, 1H), 7.24 (d, J=6.7 Hz, 1H), 7.12 (dd, J=6.0, 3.1 Hz, 2H), 6.15 (t, J=6.6 Hz, 1H), 4.22 (d, J=6.0 Hz, 2H), 3.96 (s, 2H), 3.21-3.14 (m, 2H), 2.97 (t, J=6.8 Hz, 2H)

HPLCMS (Method D): [m/z]: 409.2 [M+H]$^+$

301

2-{2-[(1H-1,3-Benzodiazol-2-ylmethyl)amino]ethyl}-N-[(1-methyl-1H-imidazol-5-yl)methyl]-1,3-thiazole-4-carboxamide (Example Compound No. 84)

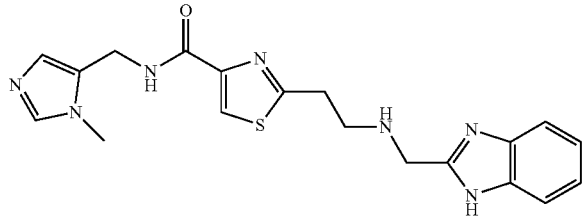 [SMILES: Cn1cncc1CNC(=O)c1csc(CCNCc2nc3ccccc3[nH]2)n1]

In a similar fashion to general procedure 2, tert-butyl N-(1H-1,3-benzodiazol-2-ylmethyl)-N-[2-(4-{[(1-methyl-1H-imidazol-5-yl)methyl]carbamoyl}-1,3-thiazol-2-yl)ethyl]carbamate (55) (148 mg, 0.3 mmol) and 4M HCl in dioxane (7 ml) at room temperature for 2 h, afforded title compound (58 mg, 49%) as a colourless glass after purification by basic prep-HPLC.

1H-NMR (DMSO-d6, 500 MHz): d[ppm]=8.66 (t, J=6.0 Hz, 1H), 8.13 (s, 1H), 7.60-7.31 (m, 3H), 7.28-6.97 (m, 2H), 6.79 (s, 1H), 4.41 (d, J=6.0 Hz, 2H), 3.96 (s, 2H), 3.60 (s, 3H), 3.16 (t, J=6.8 Hz, 2H), 2.97 (t, J=6.8 Hz, 2H)

HPLCMS (Method B): [m/z]: 396.2 [M+H]$^+$

2-{2-[(1H-1,3-Benzodiazol-2-ylmethyl)amino]ethyl}-N-(1,3-oxazol-2-ylmethyl)-1,3-thiazole-4-carboxamide (Example Compound No. 85)

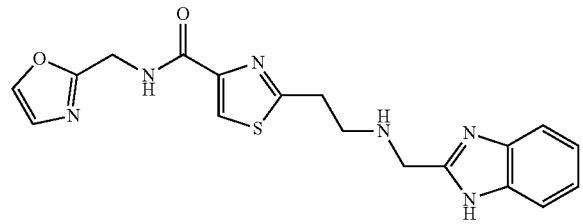 [SMILES: O=C(NCc1ncco1)c1csc(CCNCc2nc3ccccc3[nH]2)n1]

In a similar fashion to general procedure 2, 4M HCl in dioxane (0.49 ml, 1.96 mmol) was added to a solution of tert-butyl N-(1H-1,3-benzodiazol-2-ylmethyl)-N-(2-{4-[(1,3-oxazol-2-ylmethyl)carbamoyl]-1,3-thiazol-2-yl}ethyl)carbamate (56) (95 mg, 0.196 mmol) in dioxane (2 ml) and the mixture was stirred at room temperature for 3 h, to give the title compound (13 mg, 17%) as a pale yellow oil after purification by neutral prep-HPLC.

1H-NMR (Methanol-d4, 500 MHz): d[ppm]=8.11 (s, 1H), 7.87 (d, J=0.8 Hz, 1H), 7.54 (dd, J=5.9, 3.2 Hz, 2H), 7.27-7.18 (m, 2H), 7.13 (d, J=0.8 Hz, 1H), 4.70 (s, 2H), 4.10 (s, 2H), 3.27 (t, J=6.6 Hz, 2H), 3.13 (t, J=6.6 Hz, 2H)

HPLCMS (Method D): [m/z]: 383.1 [M+H]$^+$

302

2-{2-[(1H-1,3-Benzodiazol-2-ylmethyl)amino]ethyl}-N-[(1-methyl-1H-pyrazol-3-yl)methyl]-1,3-thiazole-4-carboxamide (Example Compound No. 86)

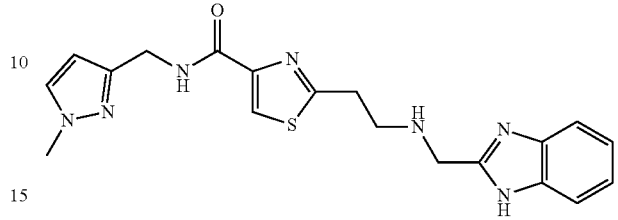

In a similar fashion to general procedure 2, 4M HCl in dioxane (0.27 ml, 1.08 mmol) was added to a solution of tert-butyl N-(1H-1,3-benzodiazol-2-ylmethyl)-N-[2-(4-{[(1-methyl-1H-pyrazol-3-yl)methyl]carbamoyl}-1,3-thiazol-2-yl)ethyl]carbamate (57) (53 mg, 0.11 mmol) in dioxane (2 ml) at room temperature for 3 h, to give the title compound (16 mg, 38%) as a transparent oil after purification by neutral prep-HPLC.

1H-NMR (Methanol-d4, 500 MHz): d[ppm]=8.08 (s, 1H), 7.57-7.46 (m, 3H), 7.28-7.15 (m, 2H), 6.22 (d, J=2.2 Hz, 1H), 4.55 (s, 2H), 4.08 (s, 2H), 3.84 (s, 3H), 3.25 (t, J=6.7 Hz, 2H), 3.10 (t, J=6.7 Hz, 2H)

HPLCMS (Method D): [m/z]: 396.2 [M+H]$^+$

2-{2-[(1H-1,3-Benzodiazol-2-ylmethyl)amino]ethyl}-N-(pyridazin-3-ylmethyl)-1,3-thiazole-4-carboxamide (Example Compound No. 87)

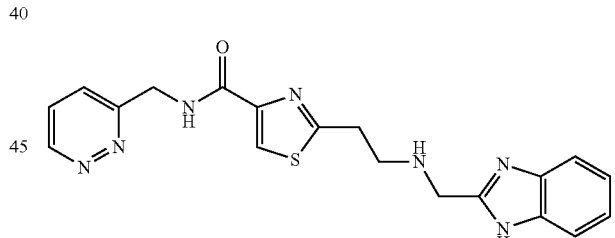

In a similar fashion to general procedure 2, 4M HCl in dioxane (0.51 ml, 2.04 mmol) was added to a solution of tert-butyl N-(1H-1,3-benzodiazol-2-ylmethyl)-N-(2-{4-[(pyridazin-3-ylmethyl)carbamoyl]-1,3-thiazol-2-yl}ethyl)carbamate (58) (101 mg, 0.2 mmol) in dioxane (2 ml) at 50° C. for 1 h, to give the title compound (15 mg, 19%) as a tan solid after purification by neutral prep-HPLC.

1H-NMR (Methanol-d4, 500 MHz): d[ppm]=9.10 (dd, J=4.8, 1.7 Hz, 1H), 8.12 (s, 1H), 7.76-7.64 (m, 2H), 7.53 (dd, J=6.0, 3.2 Hz, 2H), 7.22 (dd, J=6.0, 3.2 Hz, 2H), 4.89 (s, 2H), 4.10 (s, 2H), 3.28 (t, J=6.6 Hz, 2H), 3.13 (t, J=6.6 Hz, 2H)

HPLCMS (Method D): [m/z]: 394.1 [M+H]$^+$

2-{2-[(1H-1,3-Benzodiazol-2-ylmethyl)amino]ethyl}-N-[(1-methyl-1H-pyrazol-5-yl)methyl]-1,3-thiazole-4-carboxamide (Example Compound No. 88)

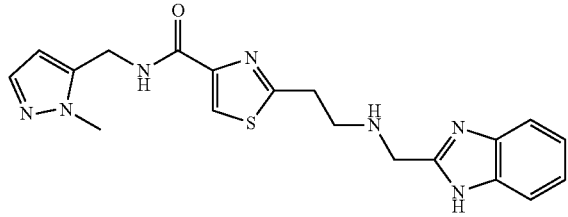 [SMILES: Cn1nccc1CNC(=O)c1csc(CCNCc2nc3ccccc3[nH]2)n1]

In a similar fashion to general procedure 2, 4M HCl in dioxane (0.26 ml, 1.04 mmol) was added to a solution of tert-butyl N-(1H-1,3-benzodiazol-2-ylmethyl)-N-[2-(4-{[(1-methyl-1H-pyrazol-5-yl)methyl]carbamoyl}-1,3-thiazol-2-yl)ethyl]carbamate (59) (51 mg, 0.103 mmol) in dioxane (2 ml) at 50° C. for 1 h, to give the title compound (12 mg, 30%) as an orange oil after purification by neutral prep-HPLC.

1H-NMR (Methanol-d4, 500 MHz): d[ppm]=8.10 (s, 1H), 7.53 (dd, J=6.0, 3.2 Hz, 2H), 7.36 (d, J=1.9 Hz, 1H), 7.23 (dd, J=6.0, 3.2 Hz, 2H), 6.25 (d, J=1.9 Hz, 1H), 4.63 (s, 2H), 4.08 (s, 2H), 3.89 (s, 3H), 3.26 (t, J=6.7 Hz, 2H), 3.11 (t, J=6.7 Hz, 2H)

HPLCMS (Method D): [m/z]: 396.2 [M+H]$^+$

2-{2-[(1H-1,3-Benzodiazol-2-ylmethyl)amino]ethyl}-N-[(3-fluoropyridin-4-)methyl)]-1,3-thiazole-4-carboxamide (Example Compound No. 89)

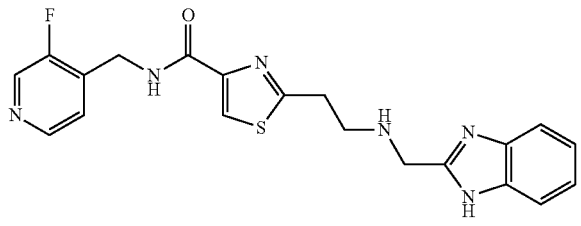 [SMILES: O=C(NCc1ccncc1F)c1csc(CCNCc2nc3ccccc3[nH]2)n1]

In a similar fashion to general procedure 2, tert-butyl N-(1H-1,3-benzodiazol-2-ylmethyl)-N-[2-(4-{[(3-fluoropyridin-4-yl)methyl]carbamoyl}-1,3-thiazol-2-yl)ethyl]carbamate (60) (137 mg, 0.191 mmol, 71% purity) and 12M HCl (1.4 ml, 16.8 mmol) in MeOH (1.4 ml) at 50° C. for 2 h afforded the title compound (46 mg, 59%) as a pale yellow solid after purification by neutral prep-HPLC.

1H-NMR (DMSO-d6, 500 MHz): d[ppm]=12.18 (s, 1H), 8.99 (t, J=6.1 Hz, 1H), 8.49 (d, J=1.6 Hz, 1H), 8.35 (d, J=4.8 Hz, 1H), 8.15 (s, 1H), 7.48 (br s, 2H), 7.35-7.26 (m, 1H), 7.12 (d, J=3.5 Hz, 2H), 4.52 (d, J=6.1 Hz, 2H), 3.97 (s, 2H), 3.19 (t, J=6.8 Hz, 2H), 2.98 (t, J=6.8 Hz, 2H)

HPLCMS (Method B): [m/z]: 411.1 [M+H]$^+$

2-{2-[(1H-1,3-Benzodiazol-2-ylmethyl)amino]ethyl}-N-[(3-methylpyridin-4-yl)methyl]-1,3-thiazole-4-carboxamide Trihydrochloride (Example Compound No. 90)

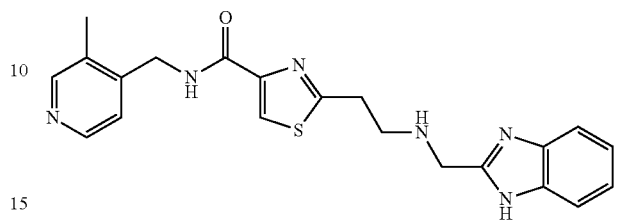

In a similar fashion to general procedure 2, 4M HCl in dioxane (1.8 ml) was added to a solution of tert-butyl N-(1H-1,3-benzodiazol-2-ylmethyl)-N-[2-(4-{[(3-methylpyridin-4-yl)methyl]carbamoyl}-1,3-thiazol-2-yl)ethyl]carbamate (61) (363 mg, 0.72 mmol) in dioxane (5 ml) at room temperature for 16 h to afford the title compound (203 mg, 55%) as a white solid. The solid was obtained from precipitation from DCM/MeOH on addition of heptane, followed by a wash with Et$_2$O.

1H-NMR (Methanol-d4, 500 MHz): d[ppm]=8.69 (s, 1H), 8.60 (d, J=6.1 Hz, 1H), 8.30 (s, 1H), 8.00 (d, J=6.1 Hz, 1H), 7.83 (dt, J=6.5, 3.3 Hz, 2H), 7.61 (dt, J=6.5, 3.3 Hz, 2H), 5.00 (s, 2H), 3.89 (t, J=6.3 Hz, 2H), 3.69 (t, J=6.3 Hz, 2H), 2.63 (s, 3H) (a CH$_2$ signal obscured by solvent)

HPLCMS (Method B): [m/z]: 407.2 [M+H]$^+$

2-{2-[(1H-1,3-Benzodiazol-2-ylmethyl)amino]ethyl}-N-[(1-methyl-1H-pyrazol-4-yl)methyl]-1,3-thiazole-4-carboxamide (Example Compound No. 91)

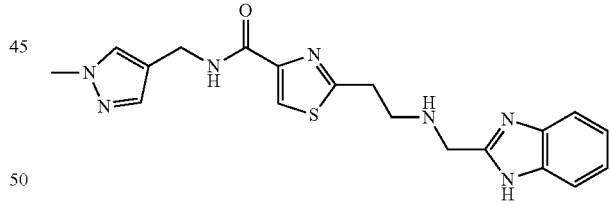

In a similar fashion to general procedure 2, tert-butyl N-(1H-1,3-benzodiazol-2-ylmethyl)-N-[2-(4-{[(1-methyl-1H-pyrazol-4-yl)methyl]carbamoyl}-1,3-thiazol-2-yl)ethyl]carbamate (62) (125 mg, 0.25 mmol) and 12M HCl (0.49 ml, 5.88 mmol) in MeOH (5 ml) at 50° C. for 2 h, gave the title compound (42 mg, 42%) as a yellow/brown solid after purification by basic prep-HPLC.

1H-NMR (DMSO-d6, 500 MHz): d[ppm]=12.16 (s, 1H), 8.55 (t, J=6.0 Hz, 1H), 8.08 (s, 1H), 7.55 (s, 1H), 7.48 (d, J=38.4 Hz, 2H), 7.32 (s, 1H), 7.20-7.03 (m, 2H), 4.25 (d, J=6.0 Hz, 2H), 3.95 (s, 2H), 3.76 (s, 3H), 3.15 (t, J=6.8 Hz, 2H), 2.95 (t, J=6.8 Hz, 2H)

HPLCMS (Method D): [m/z]: 396.2 [M+H]$^+$

2-{2-[(1H-1,3-Benzodiazol-2-ylmethyl)amino]ethyl}-N-[(6-methylpyridazin-3-yl)methyl]-1,3-thiazole-4-carboxamide (Example Compound No. 93)

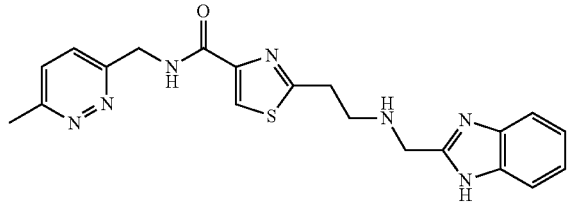 [SMILES: Cc1ccc(CNC(=O)c2csc(CCNCc3nc4ccccc4[nH]3)n2)nn1]

In a similar fashion to general procedure 2, crude tert-butyl N-(1H-1,3-benzodiazol-2-ylmethyl)-N-[2-(4-{[(6-methylpyridazin-3-yl)methyl]carbamoyl}-1,3-thiazol-2-yl)ethyl]carbamate (63) (99 mg, 0.154 mmol, 79% purity) and 12M HCl (1 ml) in MeOH (1 ml) at 50° C. for 2 h gave the title compound (32 mg, 51%) as a light-brown solid after purification by neutral prep-HPLC.

1H-NMR (DMSO-d6, 500 MHz): d[ppm]=12.18 (s, 1H), 9.01 (t, J=6.1 Hz, 1H), 8.14 (s, 1H), 7.57-7.39 (m, 4H), 7.13 (s, 2H), 4.70 (d, J=6.1 Hz, 2H), 3.96 (s, 2H), 3.19 (t, J=6.8 Hz, 2H), 2.98 (t, J=6.8 Hz, 2H), 2.58 (s, 3H)

HPLCMS (Method B): [m/z]: 408.2 [M+H]$^+$

2-{2-[(1H-1,3-Benzodiazol-2-ylmethyl)amino]ethyl}-N-(1H-imidazol-2-ylmethyl)-1,3-thiazole-4-carboxamide (Example Compound No. 95)

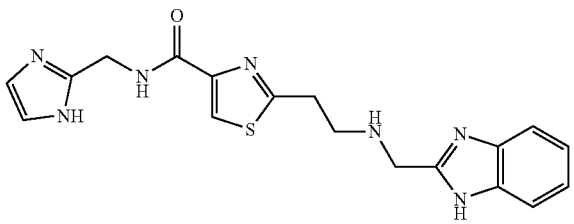 [SMILES: O=C(NCc1ncc[nH]1)c1csc(CCNCc2nc3ccccc3[nH]2)n1]

In a similar fashion to general procedure 2, 4M HCl in dioxane (1 ml, 4 mmol) was added to a solution of tert-butyl N-(1H-1,3-benzodiazol-2-ylmethyl)-N-(2-{4-[(1H-imidazol-2-ylmethyl)carbamoyl]-1,3-thiazol-2-yl}ethyl)carbamate (64) (61 mg, 0.13 mmol) in dioxane (4 ml) at room temperature for 18 h, to afford the title compound (23 mg, 48%) as a yellow solid after purification by basic prep-HPLC.

1H-NMR (DMSO-d6, 500 MHz): d[ppm]=12.19 (s, 1H), 11.77 (s, 1H), 8.61 (t, J=5.9 Hz, 1H), 8.14 (s, 1H), 7.49 (br s, 2H), 7.13 (dd, J=5.9, 2.8 Hz, 2H), 7.00 (br s, 1H), 6.81 (br s, 1H), 4.48 (d, J=5.9 Hz, 2H), 3.97 (s, 2H), 3.17 (d, J=6.2 Hz, 2H), 2.98 (t, J=6.8 Hz, 2H)

HPLCMS (Method B): [m/z]: 382.1 [M+H]$^+$

2-{2-[(1H-1,3-Benzodiazol-2-ylmethyl)amino]ethyl}-N-{[2-(morpholin-4-yl)pyridin-4-yl]methyl}-1,3-thiazole-4-carboxamide (Example Compound No. 96)

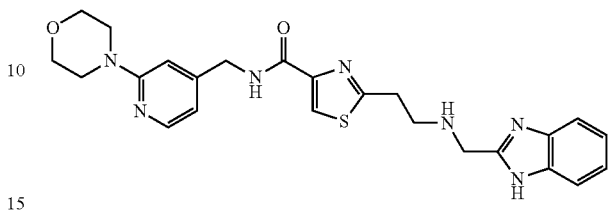

In a similar fashion to general procedure 2, 4M HCl in dioxane (1 ml) was added to a solution of tert-butyl N-(1H-1,3-benzodiazol-2-ylmethyl)-N-{2-[4-({[2-(morpholin-4-yl)pyridin-4-yl]methyl} carbamoyl)-1,3-thiazol-2-yl]ethyl}carbamate (65) (108 mg, 0.19 mmol) in dioxane (4 ml) at room temperature for 15 h, to afford the title compound (46 mg, 51%) as an orange solid after purification by neutral prep-HPLC.

1H-NMR (DMSO-d6, 500 MHz): d[ppm]=8.90 (t, J=6.3 Hz, 1H), 8.15 (s, 1H), 8.03 (d, J=5.1 Hz, 1H), 7.50 (dd, J=5.7, 3.3 Hz, 2H), 7.14 (dq, J=7.1, 3.9 Hz, 2H), 6.73 (s, 1H), 6.61 (d, J=5.1 Hz, 1H), 4.38 (d, J=6.3 Hz, 2H), 4.15 (d, J=29.7 Hz, 1H), 4.05 (s, 2H), 3.72-3.62 (m, 4H), 3.23 (t, J=6.8 Hz, 2H), 3.18 (s, 2H) 3.07 (t, J=6.8 Hz, 2H)

HPLCMS (Method B): [m/z]: 478.2 [M+H]$^+$

2-{2-[(1H-1,3-Benzodiazol-2-ylmethyl)amino]ethyl}-N-[(5-methylpyridin-2-yl)methyl]-1,3-thiazole-4-carboxamide (Example Compound No. 97)

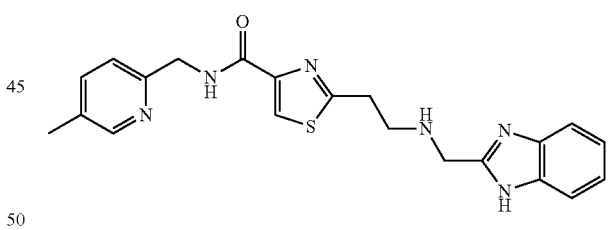

In a similar fashion to general procedure 2, 4M HCl in dioxane (0.24 ml, 0.96 mmol) was added to a solution of tert-butyl N-(1H-1,3-benzodiazol-2-ylmethyl)-N-[2-(4-{[(5-methylpyridin-2-yl)methyl]carbamoyl}-1,3-thiazol-2-yl)ethyl]carbamate (66) (48 mg, 0.095 mmol) in dioxane (2 ml) at room temperature for 12 h to afford the title compound (10 mg, 26%) as a colourless oil after purification by neutral prep-HPLC.

1H-NMR (Methanol-d4, 500 MHz): d[ppm]=8.31 (s, 1H), 8.10 (s, 1H), 7.60 (dd, J=8.0, 1.8 HZ 1H), 7.52 (dd, J=6.0, 3.1 Hz, 2H), 7.29 (d, J=8.0 Hz, 1H), 7.22 (dd, J=6.0, 3.1 Hz, 2H), 4.65 (s, 2H), 4.10 (s, 2H), 3.28 (t, J=6.6 Hz, 2H), 3.13 (t, J=6.6 Hz, 2H), 2.33 (s, 3H)

HPLCMS (Method D): [m/z]: 407.1 [M+H]$^+$

2-{2-[(1H-1,3-Benzodiazol-2-ylmethyl)amino]ethyl}-N-{[6-(dimethylamino)pyridin-3-yl]methyl}-1,3-thiazole-4-carboxamide (Example Compound No. 98)

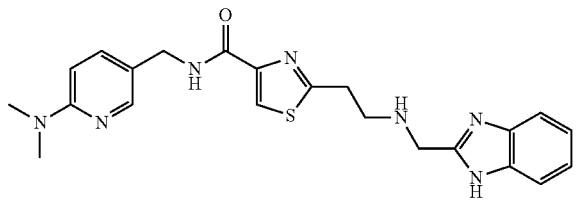 [SMILES: CN(C)c1ccc(CNC(=O)c2csc(CCNCc3nc4ccccc4[nH]3)n2)cn1]

In a similar fashion to general procedure 2, 4M HCl in dioxane (0.17 ml, 0.68 mmol) was added to a solution of tert-butyl N-(1H-1,3-benzodiazol-2-ylmethyl)-N-{2-[4-({[6-(dimethylamino)pyridin-3-yl]methyl}carbamoyl)-1,3-thiazol-2-yl]ethyl}carbamate (67) (36 mg, 0.07 mmol) in dioxane (2 ml) at room temperature for 12 h to afford the title compound (8 mg, 27%) as a colourless oil after purification by neutral prep-HPLC.

1H-NMR (Methanol-d4, 500 MHz): d[ppm]=8.07 (s, 1H), 8.05 (d, J=2.1 Hz, 1H), 7.57-7.50 (m, 3H), 7.26-7.20 (m, 2H), 6.61 (d, J=8.8 Hz, 1H), 4.43 (s, 2H), 4.07 (s, 2H), 3.24 (t, J=6.6 Hz, 2H), 3.10 (t, J=6.6 Hz, 2H), 3.06 (s, 6H)

HPLCMS (Method B): [m/z]: 436.3 [M+H]$^+$

2-{2-[(1H-1,3-Benzodiazol-2-ylmethyl)amino]ethyl}-N-[(2-methylpyridin-4-yl)methyl]-1,3-thiazole-4-carboxamide (Example Compound No. 99)

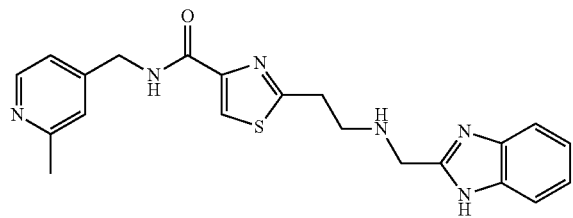 [SMILES: Cc1cc(CNC(=O)c2csc(CCNCc3nc4ccccc4[nH]3)n2)ccn1]

In a similar fashion to general procedure 2, 4M HCl in dioxane (0.18 ml, 0.72 mmol) was added to a solution of tert-butyl N-(1H-1,3-benzodiazol-2-ylmethyl)-N-[2-(4-{[(2-methylpyridin-4-yl)methyl]carbamoyl}-1,3-thiazol-2-yl)ethyl]carbamate (68) (36 mg, 0.07 mmol) in dioxane (2 ml) at room temperature for 12 h to afford the title compound (20 mg, 69%) as a colourless oil after purification by neutral prep-HPLC.

1H-NMR (Methanol-d4, 500 MHz): d[ppm]=8.31 (d, J=5.3 Hz, 1H), 8.11 (s, 1H), 7.52 (dd, J=5.9, 3.2 Hz, 2H), 7.30-7.13 (m, 4H), 4.58 (s, 2H), 4.09 (s, 2H), 3.28 (t, J=6.6 Hz, 2H), 3.13 (t, J=6.6 Hz, 2H), 2.49 (s, 3H)

HPLCMS (Method B): [m/z]: 407.2 [M+H]$^+$

2-{2-[(1H-1,3-Benzodiazol-2-ylmethyl)amino]ethyl}-N-[(1,5-dimethyl-1H-pyrazol-4-yl)methyl]-1,3-thiazole-4-carboxamide (Example Compound No. 100)

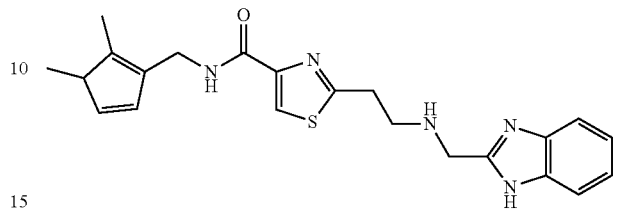

In a similar fashion to general procedure 2, 4M HCl in dioxane (0.36 ml, 1.44 mmol) was added to a solution of tert-butyl N-(1H-1,3-benzodiazol-2-ylmethyl)-N-[2-(4-{[(1,5-dimethyl-1H-pyrazol-4-yl)methyl]carbamoyl}-1,3-thiazol-2-yl)ethyl]carbamate (69) (74 mg, 0.15 mmol) in dioxane (2 ml) at room temperature for 12 h, to afford the title compound (19 mg, 33%) as a colourless oil after purification by neutral prep-HPLC.

1H-NMR (Methanol-d4, 500 MHz): d[ppm]=8.05 (s, 1H), 7.53 (dd, J=5.8, 3.2 Hz, 2H), 7.38 (s, 1H), 7.30-7.17 (m, 2H), 4.38 (s, 2H), 4.07 (s, 2H), 3.74 (s, 3H), 3.23 (t, J=6.7 Hz, 2H), 3.09 (t, J=6.7 Hz, 2H), 2.29 (s, 3H)

HPLCMS (Method D): [m/z]: 410.2 [M+H]$^+$

2-{2-[(1H-1,3-Benzodiazol-2-ylmethyl)amino]ethyl}-N-{[3-chloro-5-(trifluoromethyl)pyridin-2-yl]methyl}-1,3-thiazole-4-carboxamide (Example Compound No. 101)

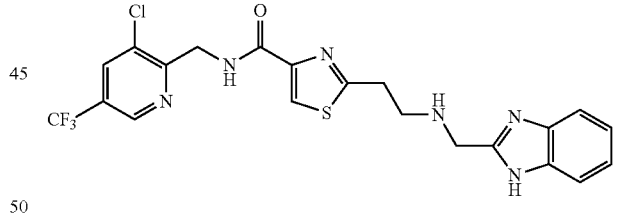

In a similar fashion to general procedure 2, tert-butyl N-(1H-1,3-benzodiazol-2-ylmethyl)-N-{2-[4-({[3-chloro-5-(trifluoromethyl)pyridin-2-yl]methyl}carbamoyl)-1,3-thiazol-2-yl]ethyl}carbamate (70) (216 mg, 0.163 mmol, 45% purity) and 12M HCl (2.1 ml) in MeOH (2.1 ml) at 50° C. for 2 h gave the title compound (67 mg, 80%) as a white solid after purification by basic prep-HPLC.

1H-NMR (DMSO-d6, 500 MHz): d[ppm]=12.18 (s, 1H), 8.91-8.86 (m, 1H), 8.77 (t, J=5.6 Hz, 1H), 8.45 (d, J=1.5 Hz, 1H), 8.14 (s, 1H), 7.59-7.35 (m, 2H), 7.19-7.05 (m, 2H), 4.75 (d, J=5.6 Hz, 2H), 3.97 (s, 2H), 3.20 (t, J=6.8 Hz, 2H), 2.99 (t, J=6.8 Hz, 2H)

HPLCMS (Method D): [m/z]: 495.0 [M+H]$^+$

2-{2-[(1H-1,3-Benzodiazol-2-ylmethyl)amino]ethyl}-N-[(3-chloro-5-fluoropyridin-2-yl)methyl]-1,3-thiazole-4-carboxamide (Example Compound No. 102)

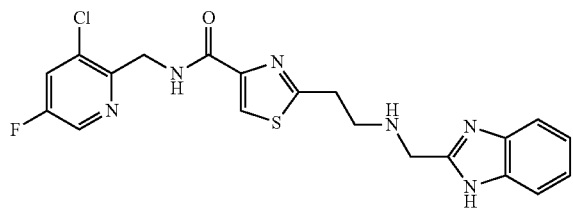

In a similar fashion to general procedure 2, tert-butyl N-(1H-1,3-benzodiazol-2-ylmethyl)-N-[2-(4-{[(3-chloro-5-fluoropyridin-2-yl)methyl]carbamoyl}-1,3-thiazol-2-yl)ethyl]carbamate (71) (157 mg, 76%, 62% purity) and 12 M HCl (1.6 ml) in MeOH (1.6 ml) at 50° C. for 2 h gave the title compound (50 mg, 62%) as a white solid after purification by basic prep-HPLC.

1H-NMR (DMSO-d6, 500 MHz): d[ppm]=12.17 (s, 1H), 8.67 (t, J=5.6 Hz, 1H), 8.54 (d, J=2.5 Hz, 1H), 8.14 (s, 1H), 8.11 (dd, J=8.5, 2.5 Hz, 1H), 7.60-7.36 (m, 2H), 7.12 (d, J=4.7 Hz, 2H), 4.64 (d, J=5.1 Hz, 2H), 3.97 (s, 2H), 3.19 (t, J=6.8 Hz, 2H), 298 (t, J=6.8 Hz, 2H)

HPLCMS (Method D): [m/z]: 445.1 [M+H]$^+$

2-{2-[(1H-1,3-Benzodiazol-2-ylmethyl)amino]ethyl}-N-[(2-fluoropyridin-3-yl)methyl]-1,3-thiazole-4-carboxamide (Example Compound No. 103)

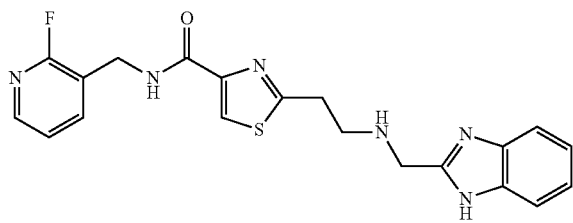

In a similar fashion to general procedure 2, tert-butyl N-(1H-1,3-benzodiazol-2-ylmethyl)-N-[2-(4-{[(2-fluoropyridin-3-yl)methyl]carbamoyl}-1,3-thiazol-2-yl)ethyl]carbamate (72) (127 mg, 0.249 mmol) and 4M HCl in dioxane (0.622 ml, 2.487 mmol) in dioxane (4.4 ml) at room temperature for 5 h gave the title compound (26 mg, 25%) as a yellow solid after purification by basic prep-HPLC.

1H-NMR (DMSO-d6, 500 MHz): d[ppm]=8.94 (t, J=6.2 Hz, 1H), 8.17 (s, 1H), 8.13-8.09 (m, 1H), 7.85-7.79 (m, 1H), 7.55-7.46 (m, 2H), 7.32-7.28 (m, 1H), 7.18-7.12 (m, 2H), 4.47 (d, J=6.1 Hz, 2H), 4.11-4.08 (m, 2H), 3.27-3.23 (m, 2H), 3.15-3.08 (br m, 2H)

HPLCMS (Method F): [m/z]: 411.2 [M+H]$^+$

2-{2-[(1H-1,3-Benzodiazol-2-ylmethyl)amino]ethyl}-N-[(2-methoxypyridin-4-yl)methyl]-1,3-thiazole-4-carboxamide (Example Compound No. 104)

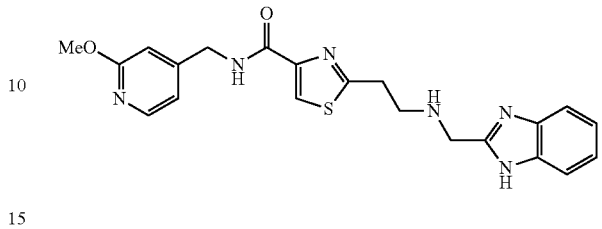

In a similar fashion to general procedure 2, tert-butyl N-(1H-1,3-benzodiazol-2-ylmethyl)-N-[2-(4-{[(2-methoxypyridin-4-yl)methyl]carbamoyl}-1,3-thiazol-2-yl)ethyl]carbamate (73) (104 mg, 0.199 mmol, 96% purity) and 12M HCl (1 ml) in MeOH (1 ml) at 50° C. for 2 h gave the title compound (35 mg, 42%) as a pale yellow solid after purification by basic prep-HPLC.

1H-NMR (DMSO-d6, 500 MHz): d[ppm]=12.17 (s, 1H), 8.95 (t, J=6.3 Hz, 1H), 8.13 (s, 1H), 8.06 (d, J=5.3 Hz, 1H), 7.58-7.38 (m, 2H), 7.17-7.07 (m, 2H), 6.89 (dd, J=5.3, 1.1 Hz, 1H), 6.65 (s, 1H), 4.40 (d, J=6.3 Hz, 2H), 3.96 (s, 2H), 3.81 (s, 3H), 3.19 (t, J=6.8 Hz, 2H), 2.98 (t, J=6.8 Hz, 2H)

HPLCMS (Method B): [m/z]: 423.1 [M+H]$^+$

2-{2-[(1H-1,3-Benzodiazol-2-ylmethyl)amino]ethyl}-N-[(4,6-dimethylpyridin-3-yl)methyl]-1,3-thiazole-4-carboxamide (Example Compound No. 105)

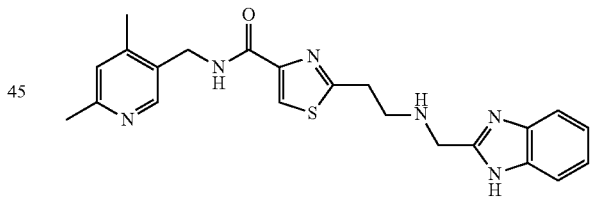

In a similar fashion to general procedure 2, tert-butyl N-(1H-1,3-benzodiazol-2-ylmethyl)-N-[2-(4-{[(4,6-dimethylpyridin-3-yl)methyl]carbamoyl}-1,3-thiazol-2-yl)ethyl]carbamate (74) (0.077 g, 0.148 mmol) and 12M HCl (0.287 ml, 3.449 mmol) in MeOH (5 ml) at 45° C. for 20 h gave the title compound (25 mg, 40%) as a yellow solid after purification by neutral prep-HPLC.

1H-NMR (DMSO-d6, 500 MHz): d[ppm]=8.73 (t, J=6.1 Hz, 1H), 8.25 (s, 1H), 8.11 (s, 1H), 7.56-7.37 (br m, 2H), 7.16-7.09 (m, 2H), 7.02 (s, 1H), 4.42 (d, J=6.0 Hz, 2H), 3.95 (s, 2H), 3.16 (t, J=6.5 Hz, 5H), 2.96 (t, J=6.8 Hz, 2H), 2.37 (s, 3H), 2.28 (s, 3H)

HPLCMS (Method G): [m/z]: 421.2 [M+H]$^+$

2-{2-[(1H-1,3-Benzodiazol-2-ylmethyl)amino]ethyl}-N-[(4-methylpyridin-2-yl)methyl]-1,3-thiazole-4-carboxamide (Example Compound No. 106)

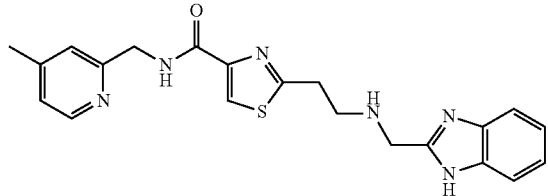 [SMILES: Cc1ccnc(CNC(=O)c2csc(CCNCc3nc4ccccc4[nH]3)n2)c1]

In a similar fashion to general procedure 2, tert-butyl N-(1H-1,3-benzodiazol-2-ylmethyl)-N-[2-(4-{[(4-methylpyridin-2-yl)methyl]carbamoyl}-1,3-thiazol-2-yl)ethyl]carbamate (75) (90 mg, 0.178 mmol) and 12M HCl (0.345 ml, 4.143 mmol) in MeOH (5 ml) at 45° C. for 20 h gave the title compound (21 mg, 29%) as a yellow solid after purification by neutral prep-HPLC.

1H-NMR (DMSO-d6, 500 MHz): d[ppm]=8.82 (t, J=6.0 Hz, 1H), 8.34 (d, J=5.0 Hz, 1H), 8.14 (s, 1H), 7.57-7.39 (m, 2H), 7.14-7.10 (m, 3H), 7.09 (d, J=5.1 Hz, 1H), 4.52 (d, J=6.0 Hz, 2H), 3.97 (s, 2H), 3.19 (t, J=6.8 Hz, 3H), 3.01-2.96 (m, 2H), 2.27 (s, 3H)

HPLCMS (Method G): [m/z]: 407.2 [M+H]+

(1H-1,3-Benzodiazol-2-ylmethyl)({2-[4-(1,2,3,4-tetrahydro-2,6-naphthyridine-2-carbonyl)-1,3-thiazol-2-yl]ethyl})amine (Example Compound No. 107)

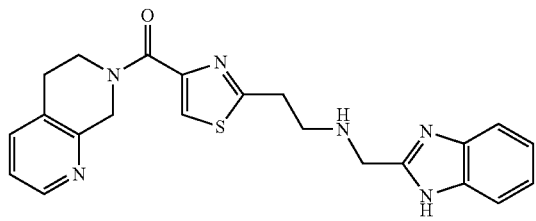 [SMILES: O=C(c1csc(CCNCc2nc3ccccc3[nH]2)n1)N1CCc2cccnc2C1]

In a similar fashion to general procedure 2, tert-butyl N-(1H-1,3-benzodiazol-2-ylmethyl)-N-{2-[4-(5,6,7,8-tetrahydro-1,6-naphthyridine-6-carbonyl)-1,3-thiazol-2-yl]ethyl}carbamate (76) (94.2 mg, 0.18 mmol) and 4M HCl in dioxane (0.454 ml, 1.816 mmol) in dioxane (2 ml) at room temperature for 12 h gave the title compound (27 mg, 35%) as a colourless oil after purification by neutral prep-HPLC.

1H-NMR (Methanol-d4, 500 MHz): d[ppm]=8.41-8.22 (br m, 1H), 7.95 (s, 1H), 7.78-7.63 (br m, 1H), 7.53-7.48 (m, 2H), 7.38-7.22 (br m, 1H), 7.19 (br s, 2H), 5.00-4.87 (br m, 2H), 4.11 (s, 2H), 4.06-4.00 (m, 2H), 3.28 (t, J=6.7 Hz, 2H), 3.13 (t, J=6.6 Hz, 2H), 3.08-3.00 (m, 2H)

HPLCMS (Method B): [m/z]: 419.2 [M+H]+

2-{2-[(1H-1,3-Benzodiazol-2-ylmethyl)amino]ethyl}-N-[(3,5-difluoropyridin-2-yl)methyl]-1,3-thiazole-4-carboxamide (Example Compound No. 108)

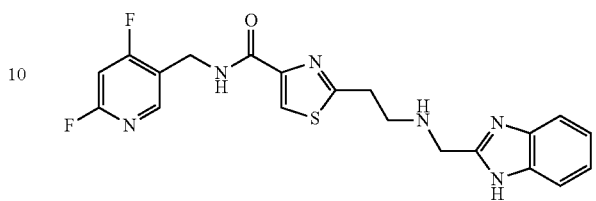

In a similar fashion to general procedure 2, tert-butyl N-(1H-1,3-benzodiazol-2-ylmethyl)-N-[2-(4-{[(3,5-difluoropyridin-2-yl)methyl]carbamoyl}-1,3-thiazol-2-yl)ethyl]carbamate (77) (112 mg, 0.21 mmol) and 4M HCl in dioxane (0.53 ml, 2.119 mmol) in dioxane (2 ml) at room temperature for 16 h gave the title compound (36.7 mg, 40%) as a colourless oil after purification by neutral prep-HPLC.

1H-NMR (Methanol-d4, 500 MHz): d[ppm]=8.27 (d, J=2.3 Hz, 1H), 8.09 (s, 1H), 7.61-7.55 (m, 1H), 7.54-7.49 (m, 2H), 7.25-7.16 (m, 2H), 4.74 (s, 2H), 4.10 (s, 2H), 3.28 (t, J=6.6 Hz, 2H), 3.14 (t, J=6.6 Hz, 2H)

HPLCMS (Method B): [m/z]: 429.2 [M+H]+

2-{2-[(1H-1,3-Benzodiazol-2-ylmethyl)amino]ethyl}-N-{[3-(hydroxymethyl)pyridin-2-yl]methyl}-1,3-thiazole-4-carboxamide (Example Compound No. 110)

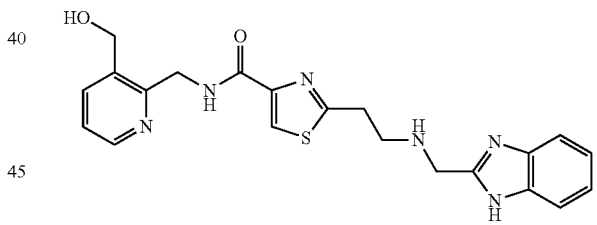

In a similar fashion to general procedure 2, 4M HCl in dioxane (3.28 ml, 13.13 mmol) was added to a solution of tert-butyl N-(1H-1,3-benzodiazol-2-ylmethyl)-N-[2-(4-{[(3-{[(tert-butyldimethylsilyl)oxy]methyl}pyridin-2-yl)methyl]carbamoyl}-1,3-thiazol-2-yl)ethyl]carbamate (78) (191.5 mg, 0.09 mmol, 30% purity) in dioxane (2 ml) at room temperature for 15 h to give the title compound (8.9 mg, 23.5%) as a yellow oil after purification by basic prep-HPLC.

1H-NMR (DMSO-d6, 500 MHz): d[ppm]=12.21 (s, 1H), 8.75 (t, J=5.0 Hz, 1H), 8.40 (dd, J=4.8, 1.4 Hz, 1H), 8.14 (s, 1H), 7.81-7.77 (m, 1H), 7.57-7.40 (br m, 2H), 7.31 (dd, J=7.6, 4.8 Hz, 1H), 7.14-7.10 (m, 2H), 5.41 (br s, 1H), 4.63-4.59 (m, 4H), 3.97 (s, 2H), 3.20 (t, J=6.8 Hz, 2H), 2.98 (t, J=6.8 Hz, 2H)

HPLCMS (Method B): [m/z]: 422.2 [M+H]+

2-{2-[(1H-1,3-Benzodiazol-2-ylmethyl)amino]ethyl}-N-(piperidin-2-ylmethyl)-1,3-thiazole-4-carboxamide (Example Compound No. 185)

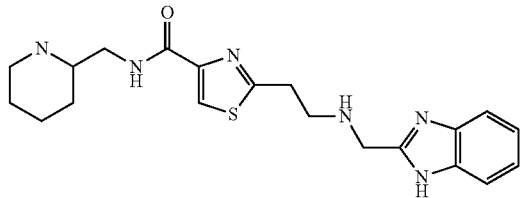 [SMILES: O=C(NCC1CCCCN1)c1csc(CCNCc2nc3ccccc3[nH]2)n1]

In a similar fashion to general procedure 2, tert-butyl 2-{[(2-{2-[(1H-1,3-benzodiazol-2-ylmethyl)][(tert-butoxy)carbonyl]amino]ethyl}-1,3-thiazol-4-yl)formamido]methyl}piperidine-1-carboxylate (79) (50 mg, 0.084 mmol) and 12M HCl (0.21 ml, 2.52 mmol) in MeOH (5 ml) afforded the title compound freebase (10 mg, 30%) as a white solid after purification by basic prep-HPLC.

1H-NMR (Methanol-d4, 500 MHz): d[ppm]=8.06 (s, 1H), 7.57-7.52 (m, 2H), 7.25-7.21 (m, 2H), 4.09 (s, 2H), 3.37 (d, J=6.2 Hz, 2H), 3.26 (t, J=6.7 Hz, 2H), 3.12 (t, J=6.7 Hz, 2H), 3.04 (dt, J=14.0, 3.9 Hz, 1H), 2.81-2.72 (m, 1H), 2.60 (td, J=12.0, 2.9 Hz, 1H), 1.85-1.77 (m, 1H), 1.76-1.69 (m, 1H), 1.65-1.58 (m, 1H), 1.50-1.33 (m, 2H), 1.25-1.13 (m, 1H)

HPLCMS (Method C): [m/z]: 399.2 [M+H]$^+$

General Scheme 2 Above:

2-{2-[(1H-1,3-Benzodiazol-2-ylmethyl)amino]ethyl}-1,3-thiazole-4-carboxylic Acid (80)

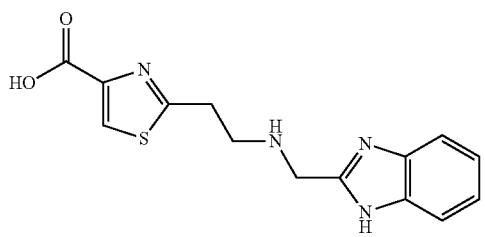 [SMILES: O=C(O)c1csc(CCNCc2nc3ccccc3[nH]2)n1]

In a similar fashion to general procedure 5, LiOH (0.142 g, 5.92 mmol) and tert-butyl 2-({[(tert-butoxy)carbonyl]({2-[4-(methoxycarbonyl)-1,3-thiazol-2-yl]ethyl})amino}methyl)-1H-1,3-benzodiazole-1-carboxylate (7) (1.12 g) in THF/Water (50 ml/10 ml) was stirred at room temperature for 16 h. The reaction mixture was acidified to pH ~1-2 using saturated KHSO$_4$ solution and then concentrated in vacuo. The crude residue was triturated with DCM/IPA followed by MeOH/EtOAc to give the title compound (1.2 g, 50% purity) as a cream solid.

1H-NMR (Methanol-d4, 500 MHz): d[ppm]=8.39 (s, 1H), 7.96-7.91 (m, 2H), 7.71-7.76 (m, 2H), 5.07 (s, 2H), 3.84 (t, J=6.3 Hz, 2H), 3.64 (t, J=6.3 Hz, 2H)

HPLCMS (Method A): [m/z]: 303.2 [M+H]$^+$

2-{2-[(1H-1,3-Benzodiazol-2-ylmethyl)amino]ethyl}-N-{[2-(morpholin-4-yl)phenyl]methyl}-1,3-thiazole-4-carboxamide (Example Compound No. 63)

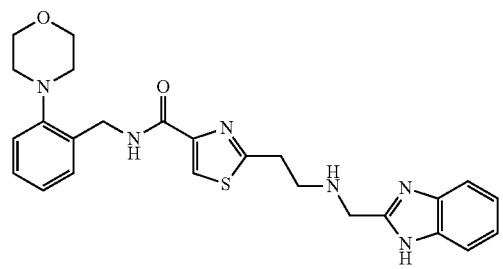 [SMILES: O=C(NCc1ccccc1N1CCOCC1)c1csc(CCNCc2nc3ccccc3[nH]2)n1]

In a similar fashion to general procedure 6, 2-{2-[(1H-1,3-benzodiazol-2-ylmethyl)amino]ethyl}-1,3-thiazole-4-carboxylic acid (80) (200 mg, 0.66 mmol, 50% purity), 1-[2-(morpholin-4-yl)phenyl]methanamine (127 mg, 0.66 mmol), DIPEA (0.35 ml, 1.98 mmol) and HATU (377 mg, 0.99 mmol) in DMF (5 ml) afforded the title compound (37 mg, 12%) as a yellow solid after purification by basic prep-HPLC.

1H-NMR (Methanol-d4, 500 MHz): d[ppm]=8.06 (s, 1H), 7.50 (dd, J=5.9, 3.2 Hz, 2H), 7.27 (t, J=8.0 Hz, 2H), 7.24-7.18 (m, 2H), 7.16 (d, J=7.6 Hz, 1H), 7.06 (t, J=7.6 Hz, 1H), 4.67 (s, 2H), 4.05 (s, 2H), 3.88-3.80 (m, 4H), 3.23 (t, J=6.8 Hz, 2H), 3.07 (t, J=6.8 Hz, 2H), 2.90-2.84 (m, 4H)

HPLCMS (Method B): [m/z]: 477.2 [M+H]$^+$

2-{2-[(1H-1,3-Benzodiazol-2-ylmethyl)amino]ethyl}-N-[(1-methyl-1H-imidazol-2-yl)methyl]-1,3-thiazole-4-carboxamide (Example Compound No. 64)

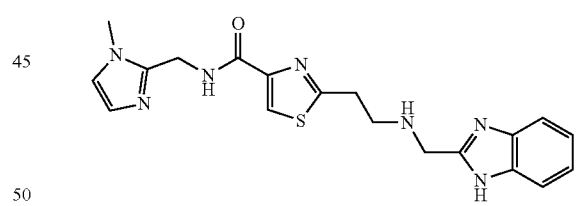

In a similar fashion to general procedure 6, 2-{2-[(1H-1,3-benzodiazol-2-ylmethyl)amino]ethyl}-1,3-thiazole-4-carboxylic acid (80) (200 mg, 0.33 mmol, 50% purity), 1-(1-methyl-1H-imidazol-2-yl)methanamine (36 mg, 0.33 mmol), DIPEA (230 µl, 1.32 mmol) and HATU (189 mg, 0.496 mmol) in DCM (5 ml) and DMF (1 ml) afforded the title compound (15 mg, 12%) after purification by basc prep-HPLC.

1H-NMR (Methanol-d4, 500 MHz): d[ppm]=8.09 (s, 1H), 7.53 (dd, J=5.9, 3.2 Hz, 2H), 7.26-7.20 (m, 2H), 7.03 (d, J=1.1 Hz, 1H), 6.89 (d, J=1.2 Hz, 1H), 4.66 (s, 2H), 4.08 (s, 2H), 3.73 (s, 3H), 3.25 (t, J=6.7 Hz, 2H), 3.11 (t, J=6.7 Hz, 2H)

HPLCMS (Method B): [m/z]: 396.2 [M+H]$^+$

2-{2-[(1H-1,3-Benzodiazol-2-ylmethyl)amino]ethyl}-N-[(2-fluorophenyl)methyl]-1,3-thiazole-4-carboxamide (Example Compound No. 65)

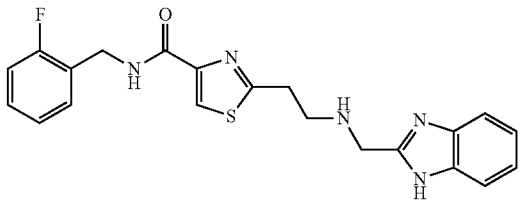 [SMILES: O=C(NCc1ccccc1F)c1csc(CCNCc2nc3ccccc3[nH]2)n1]

In a similar fashion to general procedure 6, 2-{2-[(1H-1,3-benzodiazol-2-ylmethyl)amino]ethyl}-1,3-thiazole-4-carboxylic acid (80) (200 mg, 0.53 mmol, 50% purity), 1-(2-fluorophenyl)methanamine (66 mg, 0.53 mmol), DIPEA (369 µl, 2.12 mmol) and HATU (302 mg, 0.79 mmol) in DMF (2 ml) afforded the title compound (13 mg, 6%) as a white solid after purification by basic prep-HPLC.

1H-NMR (Methanol-d4, 500 MHz): d[ppm]=8.09 (s, 1H), 7.53 (dd, J=5.9, 3.2 Hz, 2H), 7.40-7.35 (m, 1H), 7.32-7.26 (m, 1H), 7.25-7.19 (m, 2H), 7.15-7.05 (m, 2H), 4.64 (s, 2H), 4.08 (s, 2H), 3.26 (t, J=6.7 Hz, 2H), 3.11 (t, J=6.7 Hz, 2H)

HPLCMS (Method D): [m/z]: 410.2 [M+H]$^+$

General Scheme 4 Above:

2-(2-{[(Tert-butoxy)carbonyl]amino}ethyl)-1,3-thiazole-4-carboxylic Acid (87)

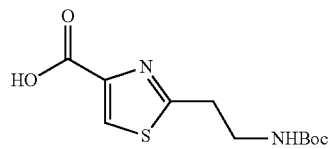

In a similar fashion to general procedure 5, ethyl 2-(2-{[(tert-butoxy)carbonyl]amino}ethyl)-1,3-thiazole-4-carboxylate (1) (8 g, 26.63 mmol) and LiOH (1.91 g, 79.90 mmol) in THF/water (200 ml/70 ml) at room temperature for 20 h, gave the title compound (10.16 g, 99.7%) as a yellow oil.

1H-NMR (DMSO-d6, 500 MHz): d[ppm]=8.32 (s, 1H), 6.99 (s, 1H), 3.28 (t, J=6.9 Hz, 2H overlapping with solvent), 3.10 (t, J=6.9 Hz, 2H), 1.36 (s, 9H)

1H-NMR (Methanol-d4, 500 MHz): d[ppm]=8.24 (s, 1H), 3.46 (t, J=6.6 Hz, 2H), 3.19 (t, J=6.6 Hz, 2H), 1.41 (s, 9H)

HPLCMS (Method A): [m/z]: 294.9 [M+H]$^+$

2-(2-{[(Tert-butoxy)carbonyl]amino}ethyl)-5-methyl-1,3-thiazole-4-carboxylic Acid (88)

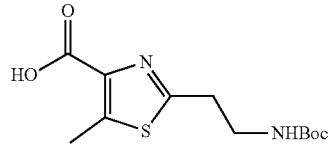 [SMILES: Cc1sc(CCNC(=O)OC(C)(C)C)nc1C(=O)O]

In a similar fashion to general procedure 5, methyl 2-(2-{[(tert-butoxy)carbonyl]amino}ethyl)-5-methyl-1,3-thiazole-4-carboxylate (3) (769 mg, 2.56 mmol) and LiOH (310 mg, 13 mmol) in THF/water (20 ml/20 ml) afforded the title compound (681 mg, 88%) as a yellow oil.

1H-NMR (DMSO-d6, 250 MHz): d[ppm]=12.76 (s, 1H), 6.99 (t, J=5.6 Hz, 1H), 3.30-3.19 (m, 2H), 3.01 (t, J=6.9 Hz, 2H), 2.65 (s, 3H), 1.37 (s, 9H)

HPLCMS (Method A): [m/z]: 301.05 [M+H]$^+$

2-(3-{[(Tert-butoxy)carbonyl]amino}propyl)-1,3-thiazole-4-carboxylic Acid (89)

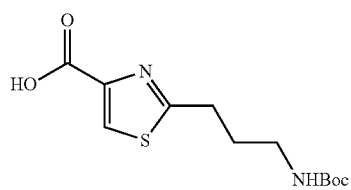 [SMILES: CC(C)(C)OC(=O)NCCCc1nc(C(=O)O)cs1]

In a similar fashion to general procedure 5, ethyl 2-(3-{[(tert-butoxy)carbonyl]amino}propyl)-1,3-thiazole-4-carboxylate (4) (726 mg, 2.31 mmol) and LiOH (166 mg, 6.93 mmol) in THF (12 ml) and water (4 ml) afforded the crude title compound (791 mg) as a yellow oil.

1H-NMR (DMSO-d6, 500 MHz): d[ppm]=8.13 (s, 1H), 6.91 (t, J=5.0 Hz, 1H), 3.05-2.93 (m, 4H), 1.83 (p, J=7.2 Hz, 2H), 1.38 (s, 9H)

HPLCMS (Method A): [m/z]: 285 [M+H]$^+$

Tert-butyl N-[2-(4-{[(3-fluoropyridin-2-yl)methyl]carbamoyl}-1,3-thiazol-2-yl)ethyl]carbamate (90)

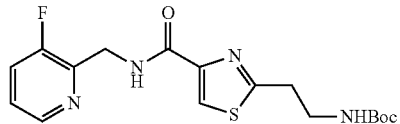 [SMILES: CC(C)(C)OC(=O)NCCc1nc(C(=O)NCc2ncccc2F)cs1]

In a similar fashion to general procedure 6, (3-fluoropyridin-2-yl)methanamine dihydrochloride (A2) (8.03 g, 40.35 mmol), 2-(2-{[(tert-butoxy)carbonyl]amino}ethyl)-1,3-thiazole-4-carboxylic acid (87) (10.2 g, 26.9 mmol), DIPEA (28.1 ml, 161.4 mmol) and HATU (12.3 g, 32.3 mmol) in THF (300 ml) at room temperature for 2 h, gave the title compound (13.27 g) as an orange oil after purification by flash column chromatography (eluting with a gradient of 20-100% EtOAc/heptane).

1H-NMR (DMSO-d6, 500 MHz): d[ppm]=8.70 (t, J=5.6 Hz, 1H), 8.39 (d, J=4.6 Hz, 1H), 8.15 (s, 1H), 7.73-7.67 (m, 1H), 7.40 (dt, J=8.5, 4.4 Hz, 1H), 7.04 (s, 1H), 4.65 (d, J=5.6 Hz, 2H), 3.31 (t, J=6.8 Hz, 2H, overlapping with NMR solvent), 3.13 (t, J=6.8 Hz, 2H), 1.36 (s, 9H)

HPLCMS (Method A): [m/z]: 381 [M+H]$^+$

Tert-butyl N-{2-[4-(benzylcarbamoyl)-1,3-thiazol-2-yl]ethyl}carbamate (91)

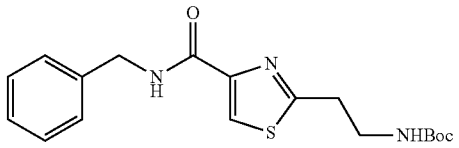 [SMILES: CC(C)(C)OC(=O)NCCc1nc(C(=O)NCc2ccccc2)cs1]

In a similar fashion to general procedure 6, 2-(2-{[(tert-butoxy)carbonyl]amino}ethyl)-1,3-thiazole-4-carboxylic acid (87) (4.09 g, 15.0 mmol), benzylamine (1.8 ml, 16.5 mmol), DIPEA (7.9 ml, 45.1 mmol) and HATU (8.570 g, 22.5 mmol) in DCM (205 ml) afforded the title compound (3.38 g, 56%, 90% purity) as a yellow oil after purification by flash column chromatography (eluting with a gradient of 21-100% EtOAc/heptane).

1H-NMR (CDCl$_3$, 500 MHz): d[ppm]=8.03 (s, 1H), 7.61 (s, 1H), 7.39-7.32 (m, 4H), 7.31-7.27 (m, 1H), 4.64 (d, J=6.1 Hz, 2H), 3.54 (d, J=6.4 Hz, 2H), 3.17 (t, J=6.4 Hz, 2H), 1.42 (s, 9H)

HPLCMS (Method E): [m/z]: 384 [M+Na]$^+$

Tert-butyl N-(2-{4-[(pyridin-2-ylmethyl)carbamoyl]-1,3-thiazol-2-yl}ethyl)carbamate (92)

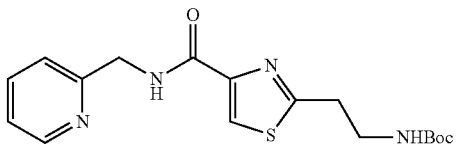

In a similar fashion to general procedure 6, 2-(2-{[(tert-butoxy)carbonyl]amino}ethyl)-1,3-thiazole-4-carboxylic acid (87) (0.500 g, 1.836 mmol), 1-(pyridin-2-yl)methanamine (0.199 g, 1.836 mmol), HATU (1.047 g, 2.754 mmol) and DIPEA (0.959 ml, 5.508 mmol) in DCM (25 ml) gave the title compound (0.905 g, quant.) as a yellow oil after purification by flash chromatography (using a gradient of 20% heptane:80% ethyl acetate to 100% ethyl acetate).

HPLCMS (Method A): [m/z]: 363.05 [M+H]$^+$

Tert-butyl N-(2-{4-[(pyridazin-3-ylmethyl)carbamoyl]-1,3-thiazol-2-yl}ethyl)carbamate (93)

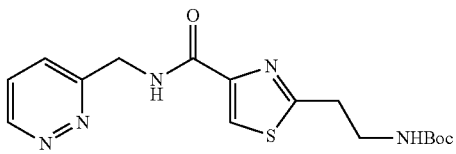 [SMILES: CC(C)(C)OC(=O)NCCc1nc(C(=O)NCc2cccnn2)cs1]

In a similar fashion to general procedure 6, 2-(2-{[(tert-butoxy)carbonyl]amino}ethyl)-1,3-thiazole-4-carboxylic acid (87) (0.7 g, 2.57 mmol), pyridazin-3-ylmethanamine (0.42 g, 3.86 mmol), DIPEA (2.24 ml, 12.85 mmol) and HATU (1.47 g, 3.86 mmol) in DMF (15 ml) afforded the title compound (0.919 g, 98%) as a brown oil after purification by flash column chromatography (eluting with a gradient of 0-5% MeOH-DCM).

1H-NMR (CDCl$_3$, 500 MHz): d[ppm]=9.21 (d, J=4.0 Hz, 1H), 8.41-8.32 (br m, 1H), 8.03 (s, 1H), 7.91-7.85 (br m, 1H), 7.77-7.69 (br m, 1H), 5.01 (d, J=5.7 Hz, 2H), 4.96 (br s, 1H), 3.65-3.46 (m, 2H), 3.20 (t, J=6.2 Hz, 2H), 1.42 (s, 9H)

HPLCMS (Method A): [m/z]: 364.05 [M+H]$^+$

Tert-butyl N-[2-(4-{[(6-methylpyridazin-3-yl)methyl]carbamoyl}-1,3-thiazol-2-yl)ethyl]carbamate (94)

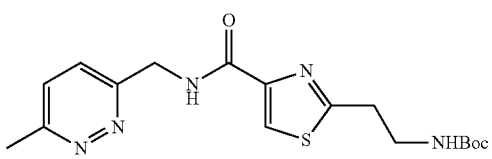 [SMILES: Cc1ccc(CNC(=O)c2csc(CCNC(=O)OC(C)(C)C)n2)nn1]

In a similar fashion using general procedure 6, 2-(2-{[(tert-butoxy)carbonyl]amino}ethyl)-1,3-thiazole-4-carboxylic acid (87) (1.3 g, 4.15 mmol), (6-methylpyridazin-3-yl)methanamine hydrochloride (0.8 g, 5.01 mmol), DIPEA (2.89 ml, 16.61 mmol) and HATU (1.90 g, 5.01 mmol) in THF (35 ml) and DMF (5 ml) gave the title compound (0.878 g, 45%) as a colourless oil after purification by flash column chromatography (kp-NH, eluting with a gradient of 0-15% MeOH/EtOAc) followed by a second flash column chromatography (kp-NH, eluting with a gradient of 70-100% EtOAc/heptane).

1H-NMR (DMSO-d6, 500 MHz): d[ppm]=9.04 (t, J=6.0 Hz, 1H), 8.17 (s, 1H), 7.50 (q, J=8.6 Hz, 2H), 7.05 (s, 1H), 4.71 (d, J=6.1 Hz, 2H), 3.13 (t, J=6.8 Hz, 2H), 2.59 (s, 3H), 1.36 (s, 9H)

HPLCMS (Method A): [m/z]: 378.05 [M+H]$^+$

Tert-butyl N-(2-{4-[(pyrimidin-2-ylmethyl)carbamoyl]-1,3-thiazol-2-yl}ethyl)carbamate (95)

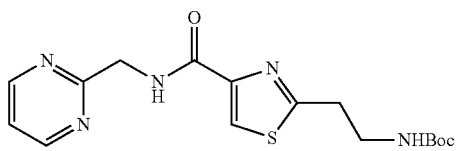 [SMILES: CC(C)(C)OC(=O)NCCc1nc(C(=O)NCc2ncccn2)cs1]

In a similar fashion to general procedure 6, 2-(2-{[(tert-butoxy)carbonyl]amino}ethyl)-1,3-thiazole-4-carboxylic acid (87) (0.7 g, 2.57 mmol), pyrimidin-2-ylmethanamine (0.42 g, 3.86 mmol), DIPEA (2.24 ml, 12.85 mmol) and HATU (1.47 g, 3.86 mmol) in DMF (15 ml) afforded the title compound (0.545 g, 58%) as a pale yellow solid after purification by flash column chromatography (eluting with a gradient of 05% MeOH/DCM).

1H-NMR (CDCl$_3$, 250 MHz): d[ppm]=8.83 (s, 1H), 8.81 (s, 1H), 8.46 (br s, 1H), 8.06 (s 1H), 7.32 (app t, J=4.8 Hz, 1H), 5.01 (br s, 1H), 4.97 (d, J=5.3 Hz, 2H), 3.67-3.56 (m, 2H), 3.26 (t, J=6.4 Hz, 2H), 1.47 (s, 9H)

HPLCMS (Method A): [m/z]: 364.05 [M+H]$^+$

Tert-butyl N-[2-(4-{[(5-methylpyrimidin-2-yl)methyl]carbamoyl}-1,3-thiazol-2-yl)ethyl]carbamate (96)

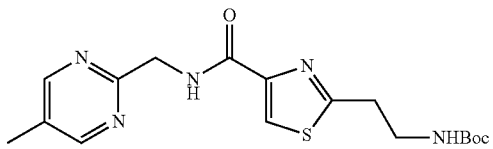 [SMILES: Cc1cnc(CNC(=O)c2csc(CCNC(=O)OC(C)(C)C)n2)nc1]

In a similar fashion to general procedure 6, 2-(2-{[(tert-butoxy)carbonyl]amino}ethyl)-1,3-thiazole-4-carboxylic acid (87) (500 mg, 1.6 mmol, 87% purity), (5-methylpyrimidin-2-yl)methanamine (295 mg, 2.4 mmol), DIPEA (1.39 ml, 7.99 mmol) and HATU (911 mg, 2.4 mmol) in THF (15 ml) and DMF (3 ml) afforded the crude title compound (600 mg, 85%, 85% purity) as a yellow oil after flash chromatography (eluting with a gradient of 0-80% EtOAc/heptane).

HPLCMS (Method A): [m/z]: 378.10 [M+H]$^+$

Tert-butyl N-{2-[4-({5H,6H,7H-cyclopenta[b]pyridine-7-yl}carbamoyl)-1,3-thiazol-2-yl]ethyl}carbamate (97)

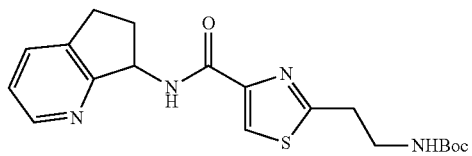 [SMILES: CC(C)(C)OC(=O)NCCc1nc(C(=O)NC2CCc3cccnc32)cs1]

In a similar fashion to general procedure 6, 2-(2-{[(tert-butoxy)carbonyl]amino}ethyl)-1,3-thiazole-4-carboxylic acid (87) (1.2 g, 4.41 mmol), 5H,6H,7H-cyclopenta[b]pyridin-7-amine hydrochloride (1.13 g, 6.61 mmol), DIPEA (2.3 ml, 13.22 mmol) and HATU (2.51 g, 6.61 mmol) in DMF (24 ml) afforded the title compound (1.53 g, 85%) as a pale pink powder after purification by flash column chromatography (eluting with a gradient of 0-5% MeOH/DCM).

HPLCMS (Method A): [m/z]: 389.15 [M+H]$^+$

Tert-butyl N-[2-(4-{[(3-methoxypyridin-2-yl)methyl]carbamoyl}-1,3-thiazol-2-yl)ethyl]carbamate (98)

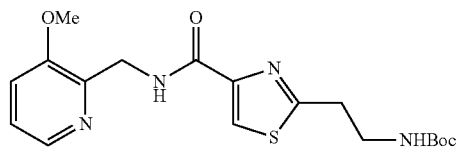 [SMILES: COc1cccnc1CNC(=O)c1csc(CCNC(=O)OC(C)(C)C)n1]

In a similar fashion to general procedure 6, 2-(2-{[(tert-butoxy)carbonyl]amino}ethyl)-1,3-thiazole-4-carboxylic acid (87) (250 mg, 0.918 mmol), (3-methoxypyridin-2-yl)methanamine dihydrochloride (213 mg, 1.01 mmol), DIPEA (0.80 ml, 4.59 mmol) and HATU (524 mg, 1.38 mmol) in DCM (15 ml) afforded the crude title compound (417 mg) as a yellow oil after flash column chromatography (eluting with a gradient of 30-100% EtOAc/heptane).

1H-NMR (CDCl$_3$, 500 MHz): d[ppm]=8.68 (s, 1H), 8.21 (d, J=4.7 Hz, 1H), 8.02 (s, 1H), 7.21 (dd, J=8.2, 4.7 Hz, 1H), 7.16 (d, J=8.3 Hz, 1H), 5.02 (s, 1H), 4.76 (d, J=4.7 Hz, 2H), 3.89 (s, 3H), 3.63 (d, J=6.0 Hz, 2H), 3.23 (t, J=6.0 Hz, 2H), 1.44 (s, 9H)

HPLCMS (Method A): [m/z]: 393.40 [M+H]$^+$

Tert-butyl N-[2-(4-{[(3-methoxypyridin-2-yl)methyl]carbamoyl}-1,3-thiazol-2-yl)ethyl]carbamate (99)

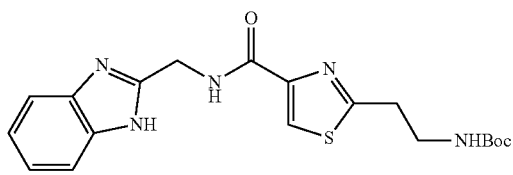 [SMILES: CC(C)(C)OC(=O)NCCc1nc(C(=O)NCc2nc3ccccc3[nH]2)cs1]

In a similar fashion to general procedure 6, 2-(2-{[(tert-butoxy)carbonyl]amino}ethyl)-1,3-thiazole-4-carboxylic acid (87) (250 mg, 0.918 mmol), 1-(1H-benzimidazol-2-yl)methanamine (149 mg, 1.01 mmol), DIPEA (0.48 ml, 2.75 mmol) and HATU (524 mg, 1.38 mmol) in DCM (15 ml) afforded the crude title compound (0.709 mg, quantitative, 81% purity) as a yellow oil after purification by flash column chromatography (eluting with a gradient of 0-10% MeOH/DCM).

HPLCMS (Method A): [m/z]: 402 [M+H]$^+$

Tert-butyl N-[2-(4-{[(3-fluoropyridin-2-yl)methyl]carbamoyl}-5-methyl-1,3-thiazol-2-yl)ethyl]carbamate (100)

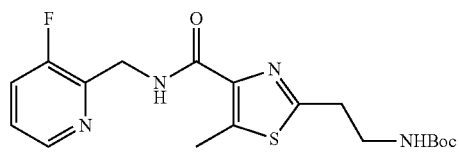

In a similar fashion to general procedure 6, 2-(2-{[(tert-butoxy)carbonyl]amino}ethyl)-5-methyl-1,3-thiazole-4-carboxylic acid (88) (680 mg, 2.37 mmol), (3-fluoropyridin-2-yl)methanamine dihydrochloride (A2) (615 mg, 3.09 mmol), TEA (1.16 ml, 8.0 mmol) and HATU (1350 mg, 3.56 mmol) in DCM (30 ml) afforded the title compound (824 mg, 85%) as a yellow oil.

1H-NMR (CDCl$_3$, 500 MHz): d[ppm]=8.45 (m, 2H), 7.42 (ddd, J=9.4, 8.3, 1.2 Hz, 1H), 7.30-7.24 (m, 1H), 4.99 (s, 1H), 4.83 (dd, J=5.2, 1.5 Hz, 2H), 3.59 (d, J=6.0 Hz, 2H), 3.13 (t, J=6.0 Hz, 2H), 2.83 (s, 3H), 1.46 (s, 9H)

HPLCMS (Method A): [m/z]: 395.15 [M+H]$^+$

Tert-butyl N-(2-{5-methyl-4-[(pyrimidin-2-ylmethyl)carbamoyl]-1,3-thiazol-2-yl}ethyl)carbamate (101)

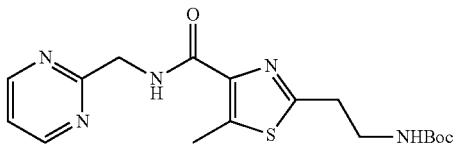 [SMILES: Cc1sc(CCNC(=O)OC(C)(C)C)nc1C(=O)NCc1ncccn1]

In a similar fashion to general procedure 6, 2-(2-{[(tert-butoxy)carbonyl]amino}ethyl)-5-methyl-1,3-thiazole-4-carboxylic acid (88) (0.315 g, 0.912 mmol), 1-(pyrimidin-2-yl)methanamine (0.119 g, 1.094 mmol), THF (7 ml), DMF (1 ml), DIPEA (0.318 ml, 1.824 mmol) and HATU (0.416 g, 1.094 mmol) gave the title compound (0.134 g, 27%) as a colourless oil after purification by flash column chromatography (with a gradient of 30-100% EtOAc in heptane).
HPLCMS (Method A): [m/z]: 378.10 [M+H]$^+$

Tert-butyl N-[3-(4-{[(3-fluoropyridin-2-yl)methyl]carbamoyl}-1,3-thiazol-2-yl)propyl]carbamate (102)

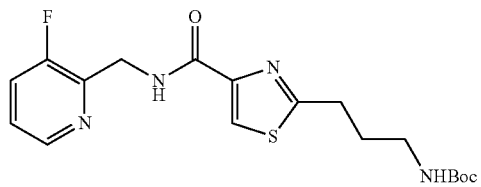 [SMILES: CC(C)(C)OC(=O)NCCCc1nc(C(=O)NCc2ncccc2F)cs1]

In a similar fashion to general procedure 6, 2-(3-{[(tert-butoxy)carbonyl]amino}propyl)-1,3-thiazole-4-carboxylic acid (89) (661 mg, 2.31 mmol), (3-fluoropyridin-2-yl)methanamine dihydrochloride (A2) (689 mg, 3.46 mmol), DIPEA (2.41 ml, 13.85 mmol) and HATU (1053 mg, 2.77 mmol) in DMF (4 ml) and THF (4 ml) afforded the title compound (914 mg, 93%, 93% purity) as a yellow oil after purification by flash chromatography (eluting with a gradient of 20-100% EtOAc/heptane).
HPLCMS (Method A): [m/z]: 395.05 [M+H]$^+$

2-(2-Aminoethyl)-N-[(3-fluoropyridin-2-yl)methyl]-1,3-thiazole-4-carboxamide dihydrochloride (103)

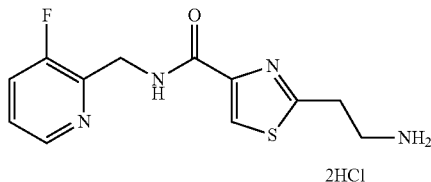 [SMILES: NCCc1nc(C(=O)NCc2ncccc2F)cs1]

In a similar fashion to general procedure 2, 12M HCl (35.3 ml) and tertbutyl N-[2-(4-{[(3-fluoropyridin-2-yl)methyl]carbamoyl}-1,3-thiazol-2-yl)ethyl]carbamate (90) (13.3 g, 28.25 mmol) in MeOH (250 ml) were stirred at 50° C. for 3 h. The mixture was concentrated in vacuo to give the title compound (12.8 g) as an off-white solid.

1H-NMR (DMSO-d6, 500 MHz): d[ppm]=8.98 (s, 1H), 8.39 (d, J=4.7 Hz, 1H), 8.21 (s, 1H), 8.17 (s, 3H), 7.72 (t, J=9.3 Hz, 1H), 7.42 (dt, J=8.5, 4.4 Hz, 1H), 4.67 (d, J=5.8 Hz, 2H), 3.38 (t, J=6.5 Hz, 2H), 3.30-3.25 (m, 2H)
HPLCMS (Method A): [m/z]: 280.9 [M+H]$^+$

2-(2-Aminoethyl)-N-benzyl-1,3-thiazole-4-carboxamide hydrochloride (104)

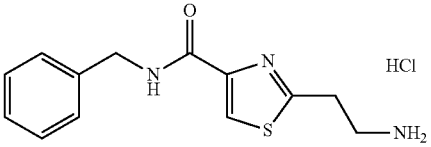 [SMILES: NCCc1nc(C(=O)NCc2ccccc2)cs1 ; Cl]

In a similar fashion to general procedure 2, 12M HCl (2.5 ml) and tertbutyl N-{2-[4-(benzylcarbamoyl)-1,3-thiazol-2-yl]ethyl}carbamate (91) (456 mg, 1.29 mmol) in MeOH (4.5 ml) at room temperature for 4 h gave the title compound (336 mg, 100%) as a beige solid. The product was used in subsequent reactions without purification.
HPLCMS (Method E): [m/z]: 261.95 [M+H]$^+$

2-(2-Aminoethyl)-N-(pyridin-2-ylmethyl)-1,3-thiazole-4-carboxamide Dihydrochloride (105)

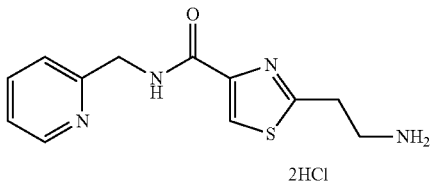 [SMILES: NCCc1nc(C(=O)NCc2ccccn2)cs1]

In a similar fashion to general procedure 2, tert-butyl N-(2-{4-[(pyridin-2-ylmethyl)carbamoyl]-1,3-thiazol-2-yl}ethyl)carbamate (92) (0.905 g, 2.50 mmol), 12M HCl (4.852 ml, 58.23 mmol) in MeOH (9 ml) gave the title compound (0.840 g, quant.) as a white solid.
HPLCMS (Method A): [m/z]: 262.95 [M+H]$^+$

2-(2-Aminoethyl)-N-(pyridazin-3-ylmethyl)-1,3-thiazole-4-carboxamide Dihydrochloride (106)

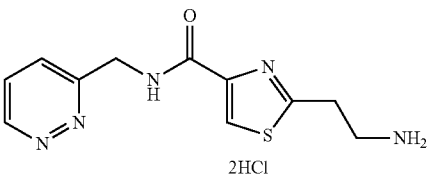 [SMILES: NCCc1nc(C(=O)NCc2cccnn2)cs1]

In a similar fashion to general procedure 2, tert-butyl N-(2-{4-[(pyridazin-3-ylmethyl)carbamoyl]-1,3-thiazol-2-yl}ethyl)carbamate (93) (0.919 g, 2.53 mmol) and 12M HCl (4.22 ml) in MeOH (15 ml) at room temperature for 16 h gave the title compound (0.840 g, 97%) as a brown residue.
1H-NMR (Deuterium Oxide, 500 MHz): d[ppm]=9.17 (dd, J=4.9, 1.5 Hz, 1H), 8.12 (s, 1H), 8.03 (dd, J=8.6, 1.5 Hz, 1H), 7.99 (dd, J=8.6, 4.9 Hz, 1H), 4.86 (s, 2H), 3.45-3.39 (m, 2H), 3.48-3.43 (m, 2H)
HPLCMS (Method A): [m/z]: 263.95 [M+H]$^+$

2-(2-Aminoethyl)-N-[(6-methyl pyridazin-3-yl)methyl]-1,3-thiazole-4-carboxamide Dihydrochloride (107)

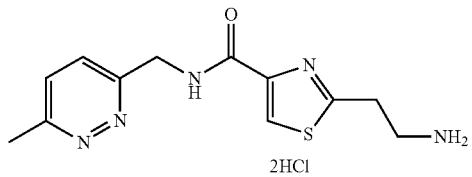 [SMILES: Cc1ccc(CNC(=O)c2csc(CCN)n2)nn1]

In a similar fashion to general procedure 2, tert-butyl N-[2-(4-{[(6-methylpyridazin-3-yl)methyl]carbamoyl}-1,3-thiazol-2-yl)ethyl]carbamate (94) (878 mg, 1.86 mmol) and 12M HCl (3.10 ml) in MeOH (15 ml) at room temperature for 24 h, gave the title compound (764 mg, quant.) as an off-white solid. The product was used in subsequent reactions without purification.

1H-NMR (MeOD, 500 MHz): d[ppm]=8.49 (d, J=8.9 Hz, 1H), 8.41 (d, J=8.9 Hz, 1H), 8.26 (s, 1H), 4.97 (s, 2H), 3.53-3.47 (m, 4H), 2.91 (s, 3H)

HPLCMS (Method A): [m/z]: 277.95 [M+H]$^+$

2-(2-Aminoethyl)-N-(pyrimidin-2-ylmethyl)-1,3-thiazole-4-carboxamide Dihydrochloride (108)

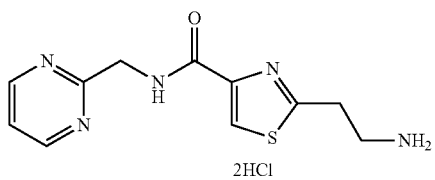 [SMILES: NCCc1nc(C(=O)NCc2ncccn2)cs1]

In a similar fashion to general procedure 2, tert-butyl N-(2-{4-[(pyrimidin-2-ylmethyl)carbamoyl]-1,3-thiazol-2-yl}ethyl)carbamate (95) (0.545 g, 1.499 mmol) and 12M HCl (4.22 ml) in MeOH (15 ml) at room temperature for 16 h gave the title compound (0.530 g, quant.) as a pale yellow foam.

1H-NMR (Deuterium Oxide, 500 MHz): d[ppm]=8.73 (d, J=5.1 Hz, 2H), 8.16 (s, 1H), 7.47 (app t, J=5.1 Hz, 1H), 4.80 (s, 2H), 3.51-3.46 (m, 2H), 3.45-3.41 (m, 2H)

HPLCMS (ESI+): [m/z]: 263.95 [M+H]$^+$ as the freebase (METCR1673 Generic 2 min)

2-(2-Aminoethyl)-N-[(5-methylpyrimidin-2-yl)methyl]-1,3-thiazole-4-carboxamide (109)

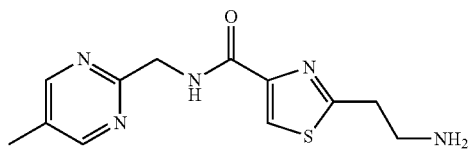 [SMILES: Cc1cnc(CNC(=O)c2csc(CCN)n2)nc1]

In a similar fashion to general procedure 2, tert-butyl N-[2-(4-{[(5-methylpyrimidin-2-yl)methyl]carbamoyl}-1,3-thiazol-2-yl)ethyl]carbamate (96) (600 mg, 1.59 mmol) and 12 M HCl (2.65 ml) in MeOH (10 ml) afforded the title compound freebase (283 mg, 44%) as a white solid after purification by flash chromatography (eluting with a gradient of 0-10% 7 M ammonia in MeOH/DCM).

1H-NMR (DMSO-d6, 500 MHz): d[ppm]=8.77-8.70 (m, 1H), 8.62 (s, 2H), 8.14 (s, 1H), 4.64 (d, J=4.0 Hz, 2H), 3.13 (t, J=6.6 Hz, 2H), 3.02 (t, J=6.6 Hz, 2H), 2.26 (s, 3H)

HPLCMS (Method A): [m/z]: 278.2 [M+H]$^+$

2-(2-Aminoethyl)-N-{5H,6H,7H-cyclopenta[b]pyridine-7-yl}-1,3-thiazole-4-carboxamide Dihydrochloride (110)

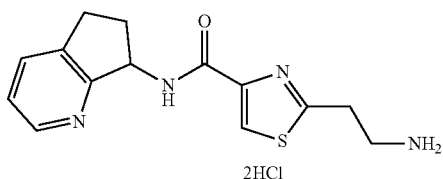 [SMILES: NCCc1nc(C(=O)NC2CCc3cccnc32)cs1]

In a similar fashion to general procedure 2, 4M HCl in dioxane (14.45 ml, 57.8 mmol) was added to an ice cold solution of tert-butyl N-{2-[4-({5H, 6H, 7H-cyclopenta[b]pyridin-7-yl}carbamoyl)-1,3-thiazol-2-yl]ethyl}carbamate (97) (1.53 g, 3.94 mmol) in MeOH (5 ml). The mixture was stirred at room temperature for 2 h. The title compound (1.32 g, 93%) was isolated by filtration after precipitation from Et$_2$O (5 ml).

HPLCMS (Method A): [m/z]: 289.05 [M+H]$^+$

2-(2-Aminoethyl)-N-[(3-methoxypyridin-2-yl)methyl]-1,3-thiazole-4-carboxamide (111)

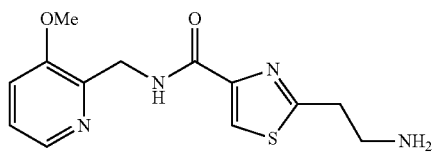 [SMILES: COc1cccnc1CNC(=O)c1csc(CCN)n1]

In a similar fashion to general procedure 2, 12M HCl (2.5 ml) and crude tertbutyl N-[2-(4-{[(3-methoxypyridin-2-yl)methyl]carbamoyl}-1,3-thiazol-2-yl)ethyl]carbamate (98) (417 mg) in MeOH (5 ml) at room temperature for 2 h, gave the title compound (125 mg) as a white solid after purification by flash column chromatography (kp-NH, eluting with a gradient of 0-10% MeOH/DCM).

1H-NMR (DMSO-d6, 500 MHz): d[ppm]=8.59 (s, 1H), 8.15-8.11 (m, 2H), 7.44 (d, J=8.3 Hz, 1H), 7.33 (dd, J=8.3, 4.7 Hz, 1H), 4.57 (d, J=5.2 Hz, 2H), 3.88 (s, 3H), 3.08 (t, J=6.6 Hz, 2H), 2.94 (t, J=6.6 Hz, 2H), 2.69 (s, 2H)

HPLCMS (Method A): [m/z]: 292.95 [M+H]$^+$

2-(2-Aminoethyl)-N-(1H-1,3-benzodiazol-2-ylmethyl)-1,3-thiazole-4-carboxamide (112)

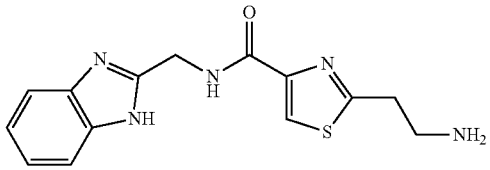 [SMILES: NCCc1nc(C(=O)NCc2nc3ccccc3[nH]2)cs1]

In a similar fashion to general procedure 2, 12M HCl (2.5 ml) and crude tertbutyl N-(2-{4-[(1H-1,3-benzodiazol-2-ylmethyl)carbamoyl]-1,3-thiazol-2-yl}ethyl)carbamate (99) (709 mg, 1.43 mmol, 81% purity) in MeOH (5 ml) at room temperature for 2 h, gave the title compound (111 mg, 25%) as a brown solid after purification by flash column chromatography (kp-NH, eluting with a gradient of 0-10% MeOH/DCM).

1H-NMR (DMSO-d6, 500 MHz): d[ppm]=8.88 (s, 1H), 8.17 (s, 1H), 7.49 (s, 2H), 7.13 (dd, J=6.0, 3.1 Hz, 2H), 4.68 (d, J=6.0 Hz, 2H), 3.08 (t, J=6.6 Hz, 2H), 2.95 (t, J=6.6 Hz, 2H)

HPLCMS (Method A): [m/z]: 301.95 [M+H]+

2-(2-Aminoethyl)-N-[(3-fluoropyridin-2-yl)methyl]-5-methyl-1,3-thiazole-4-carboxamide Dihydrochloride (113)

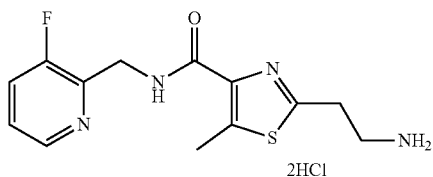 [SMILES: Cc1sc(CCN)nc1C(=O)NCc1ncccc1F]

In a similar fashion to general procedure 2, tert-butyl N-[2-(4-{[(3-fluoropyridin-2-yl)methyl]carbamoyl}-5-methyl-1,3-thiazol-2-yl)ethyl]carbamate (100) (823 mg, 2.09 mmol) and 12M HCl (3 ml) in MeOH (30 ml) afforded the title compound (794 mg, quant.) as a tan solid.

1H-NMR (DMSO-d6, 250 MHz): d[ppm]=8.87 (t, J=5.9 Hz, 1H), 8.40 (dt, J=4.4, 1.3 Hz, 1H), 8.13 (s, 3H), 7.73 (ddd, J=9.9, 8.3, 1.2 Hz, 1H), 7.43 (dt, J=8.5, 4.5 Hz, 1H), 4.69-4.60 (m, 2H), 3.32-3.19 (m, 4H), 2.71 (s, 3H)

HPLCMS (Method A): [m/z]: 295.05 [M+H]+

2-(2-Aminoethyl)-5-methyl-N-(pyrimidin-2-ylmethyl)-1,3-thiazole-4-carboxamide Dihydrochloride (114)

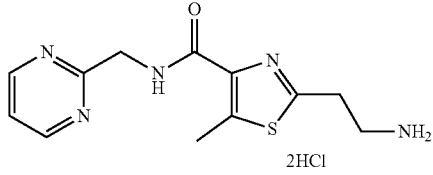 [SMILES: Cc1sc(CCN)nc1C(=O)NCc1ncccn1]

In a similar fashion to general procedure 2, tert-butyl N-(2-{5-methyl-4-[(pyrimidin-2-ylmethyl)carbamoyl]-1,3-thiazol-2-yl}ethyl)carbamate (101) (0.482 g, 0.795 mmol), MeOH (6 ml) and 12M HCl (1.325 ml, 15.90 mmol) give the title compound (0.420 g, 99%) as a yellow solid HPLCMS (Method A): [m/z]: 277.95 [M+H]+

2-(3-Aminopropyl)-N-[(3-fluoropyridin-2-yl)methyl]-1,3-thiazole-4-carboxamide Dihydrochloride (115)

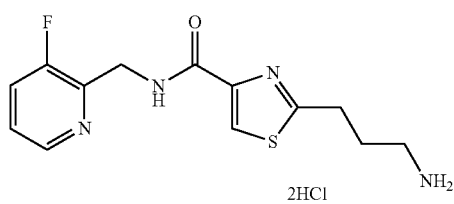 [SMILES: NCCCc1nc(C(=O)NCc2ncccc2F)cs1]

In a similar fashion to general procedure 2, 4M HCl in dioxane (2.89 ml, 11.55 mol) and tertbutyl N-[3-(4-{[(3-fluoropyridin-2-yl)methyl]carbamoyl}-1,3-thiazol-2-yl)propyl]carbamate (102) (0.91 g, 2.31 mmol) in dioxane (6 ml) and MeOH (2 ml) afforded the title compound (1.13 g, 85%, 64% purity) as a pale orange oil. Compound was used on the next step without purification.

HPLCMS (Method A): [m/z]: 295.00 [M+H]+

N-Benzyl-2-(2-{[(1-methyl-1H-imidazol-2-yl)methyl]amino}ethyl)-1,3-thiazole-4-carboxamide (Example Compound No. 2)

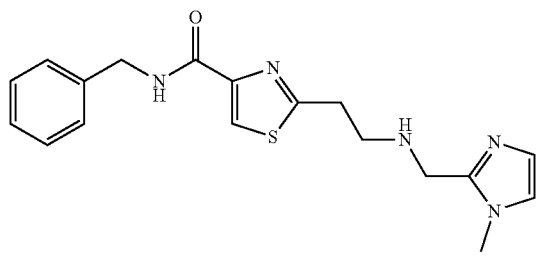 [SMILES: Cn1ccnc1CNCCc1nc(C(=O)NCc2ccccc2)cs1]

In a similar fashion to general procedure 3, 2-(2-aminoethyl)-N-benzyl-1,3-thiazole-4-carboxamide (104) (100 mg, 0.383 mmol), 1-methyl-1H-imidazole-2-carbaldehyde (33.7 mg, 0.306 mmol) in MeOH (6 ml) at room temperature for 1 h, followed by addition of NaBH4 (11.6 mg, 0.383 mmol) gave the title compound (60 mg, 43%) as an orange solid after purification by flash column chromatography (eluting with a gradient of 95:5, DCM/MeOH).

1H-NMR (CDCl3, 400 MHz): d[ppm]=8.00 (m, 2H), 7.38-7.27 (m, 5H), 6.85 (d, J=1.1 Hz, 1H), 6.77 (d, J=1.0 Hz, 1H), 4.64 (d, J=6.2 Hz, 2H), 3.88 (s, 2H), 3.59 (s, 3H), 3.16-3.13 (m, 2H), 3.09-3.06 (m, 2H), 2.81 (s, 1H)

HPLCMS (Method J): [m/z]: 356.2 [M+H]+

327

N-Benzyl-2-{2-[(1,3-thiazol-2-ylmethyl)amino]ethyl}-1,3-thiazole-4-carboxamide (Example Compound No. 3)

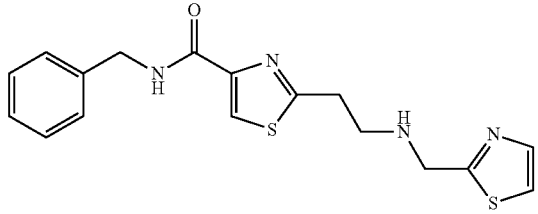 [SMILES: O=C(NCc1ccccc1)c1csc(CCNCc2nccs2)n1]

In a similar fashion using general procedure 3, 2-(2-aminoethyl)-N-benzyl-1,3-thiazole-4-carboxamide (104) (50 mg, 0.172 mmol), 1,3-thiazole-2-carbaldehyde (19.48 mg, 0.17 mmol), AcOH (10.3 mg, 0.172 mmol) in MeOH (5 ml) at room temperature for 1.5 h, followed by addition of NaBH$_4$ (6.51 mg, 0.17 mmol) gave the title compound (45 mg, 72%) as an colourless oil after purification by flash column chromatography (eluting with a gradient of 95:5, DCM/MeOH).

1H-NMR (CDCl$_3$, 400 MHz): d[ppm]=8.03 (s, 1H), 7.71 (m, 1H), 7.65 (d, J=3.3 Hz, 1H), 7.40-7.28 (m, 5H), 7.21 (d, J=3.3 Hz, 1H), 4.65 (d, J=6.1 Hz, 2H), 4.17 (s, 2H), 3.21-3.16 (m, 2H), 3.16-3.10 (m, 2H)

HPLCMS (Method J): [m/z]: 359.2 [M+H]$^+$

N-Benzyl-2-(2-{N-[(1-methyl-1H-imidazol-2-yl)methyl]acetamido}ethyl)-1,3-thiazole-4-carboxamide (Example Compound No. 4)

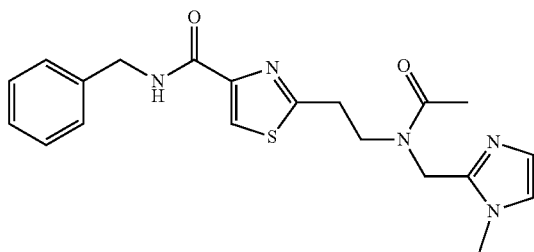 [SMILES: CC(=O)N(CCc1nc(C(=O)NCc2ccccc2)cs1)Cc1nccn1C]

To the solution of N-benzyl-2-(2-{[(1-methyl-1H-imidazol-2-yl)methyl]amino}ethyl)-1,3-thiazole-4-carboxamide (Example Compound No. 2) (30 mg, 0.08 mmol) in DCM (5 ml) was added acetyl chloride (6.63 mg, 0.08 mmol) at 00° C. under argon atmosphere. The reaction was stirred until completion, the solvent evaporated in vacuo to afford the required product (30 mg, 85%) as a white solid which required no further purification.

1H-NMR (Methanol-d4, 400 MHz): d[ppm]=8.21 (s, 1H), 7.48-7.46 (dd, J=5.1, 2.0 Hz, 2H), 7.40-7.34 (m, 5H), 7.31-7.29 (m, 1H), 4.88 (s, 2H), 4.62 (s, 2H), 4.09-4.01 (m, 2H), 3.85 (s, 3H), 3.48 (t, J=6.5 Hz, 2H), 1.99 (s, 3H)

HPLCMS (Method J): [m/z]: 398.3 [M+H]$^+$

328

N-Benzyl-2-{2-[(1H-indazol-3-ylmethyl)amino]ethyl}-1,3-thiazole-4-carboxamide (Example Compound No. 5)

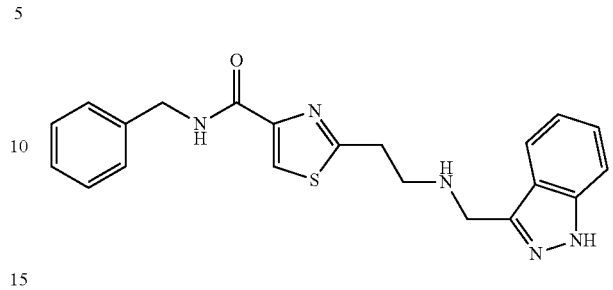

In a similar fashion using general procedure 3, 2-(2-aminoethyl)-N-benzyl-1,3-thiazole-4-carboxamide (104) (65 mg, 0.249 mmol), 1H-indazole-3-carbaldehyde (29.1 mg, 0.199 mmol) in MeOH (3 ml) at room temperature for 1 h, followed by addition of NaBH$_4$ (7.5 mg, 0.199 mmol) gave the title compound (21 mg, 21.5%) as an orange solid after purification by flash column chromatography (eluting with a gradient of 95:5, DCM/MeOH).

1H-NMR (DMSO-d6, 400 MHz): d[ppm]=13.36 (s, 1H), 9.29 (s, 2H), 8.90 (d, J=6.5 Hz, 1H), 8.16 (s, 1H), 7.87 (d, J=8.2 Hz, 1H), 7.52 (d, J=8.5 Hz, 1H), 7.38-7.32 (m, 1H), 7.25 (d, J=4.4 Hz, 3H), 7.17 (dd, J=8.7, 4.6 Hz, 1H), 7.15-7.09 (m, 1H), 4.59 (t, J=5.5 Hz, 2H), 4.42 (d, J=6.4 Hz, 2H), 3.48 (s, 4H)

HPLCMS (Method J): [m/z]: 392.2 [M+H]$^+$

N-Benzyl-2-(2-{[(5-fluoropyridin-2-yl)methyl]amino}ethyl)-1,3-thiazole-4-carboxamide (Example Compound No. 6)

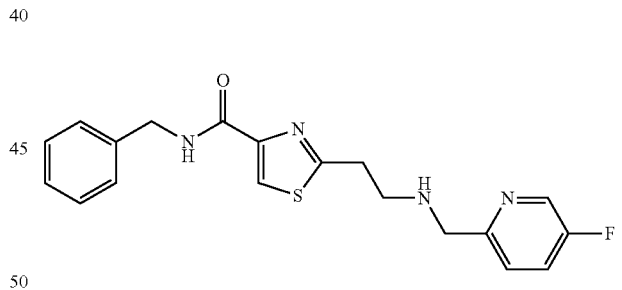

In a similar fashion using general procedure 3, 2-(2-aminoethyl)-N-benzyl-1,3-thiazole-4-carboxamide (104) (65 mg, 0.249 mmol), 5-fluoropyridine-2-carbaldehyde (24.9 mg, 0.199 mmol) in MeOH (3 ml) at room temperature for 1 h, followed by addition of NaBH$_4$ (7.5 mg, 0.199 mmol) gave the title compound (21 mg, 23%) as an orange solid after purification by flash column chromatography (eluting with a gradient of 95:5, DCM/MeOH).

1H-NMR (CDCl$_3$, 400 MHz): d[ppm]=8.22 (d, J=2.7 Hz, 1H), 7.96 (s, 1H), 7.62 (s, 1H), 7.32-7.20 (m, 6H), 4.58 (d, J=6.4 Hz, 2H), 3.86 (s, 2H), 3.12 (t, J=6.2 Hz, 2H), 3.00 (t, J=6.2 Hz, 2H)

HPLCMS (Method J): [m/z]: 371.2 [M+H]$^+$

N-Benzyl-2-{2-[(pyridin-2-ylmethyl)amino]ethyl}-1,3-thiazole-4-carboxamide (Example Compound No. 11)

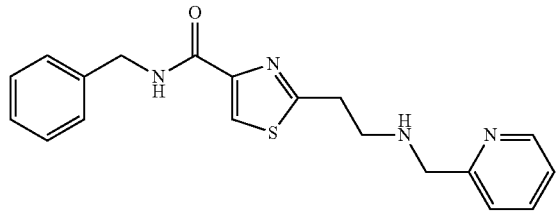 [SMILES: O=C(NCc1ccccc1)c1csc(CCNCc2ccccn2)n1]

In a similar fashion to general procedure 3, 2-(2-aminoethyl)-N-benzyl-1,3-thiazole-4-carboxamide (104) (65 mg, 0.249 mmol), pyridine-2-carbaldehyde (21.3 mg, 0.199 mmol) in MeOH (3 ml) at room temperature for 1 h, followed by addition of NaBH$_4$ (7.5 mg, 0.199 mmol) gave the title compound (30 mg, 34%) as an orange solid after purification by flash column chromatography (eluting with a gradient of 95:5, DCM/MeOH).

1H-NMR (CDCl$_3$, 400 MHz): d[ppm]=8.41 (d, J=4.2 Hz, 1H), 8.03 (s, 1H), 7.85 (s, 1H), 7.61-7.59 (td, J=7.7, 1.8 Hz, 1H), 7.40-7.24 (m, 6H), 7.17-7.09 (m, 1H), 4.65 (d, J=6.2 Hz, 2H), 4.00 (s, 2H), 3.25-3.22 (m, 2H), 3.14-3.11 (m, 2H), 3.07-2.84 (m, 1H)

HPLCMS (Method J): [m/z]: 353.2 [M+H]$^+$

N-Benzyl-2-{2-[(1H-indol-2-ylmethyl)amino]ethyl}-1,3-thiazole-4-carboxamide (Example Compound No. 24)

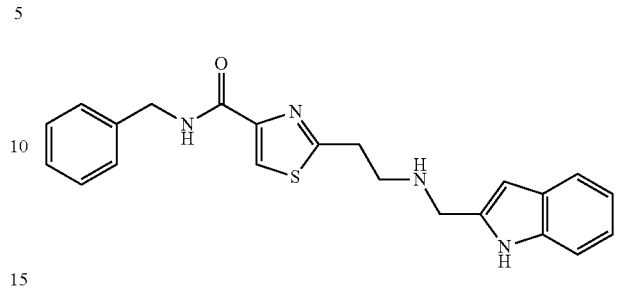

In a similar fashion to general procedure 3, 2-(2-aminoethyl)-N-benzyl-1,3-thiazole-4-carboxamide (104) (100 mg, 0.383 mmol), 1H-indole-2-carbaldehyde (44.5 mg, 0.306 mmol), AcOH (23 mg, 0.383 mmol) in MeOH (15 ml) at room temperature for 3 h, followed by addition of NaBH$_4$ (29 mg, 0.766 mmol) gave the title compound (40 mg, 27%) as an yellow oil after purification by flash column chromatography (eluting with a gradient of 3% MeOH in DCM).

1H-NMR (CDCl$_3$, 400 MHz): d[ppm]=8.71 (s, 1H), 8.02 (s, 1H), 7.68 (m, 1H), 7.54 (d, J=7.8 Hz, 1H), 7.33 (d, J=6.6 Hz, 3H), 7.30 (d, J=7.8 Hz, 2H)), 7.17-7.12 (m, 1H), 7.10-7.05 (m, 1H), 6.34 (s, 1H), 4.62 (d, J=6.1 Hz, 2H), 4.02 (s, 2H), 3.14 (t, J=6.0 Hz, 2H), 3.06 (t, J=6.0 Hz, 2H), HPLCMS (Method J): [m/z]: 391.5 [M+H]$^+$

N-Benzyl-2-{2-[(1H-imidazol-2-ylmethyl)amino]ethyl}-1,3-thiazole-4-carboxamide (Example Compound No. 20)

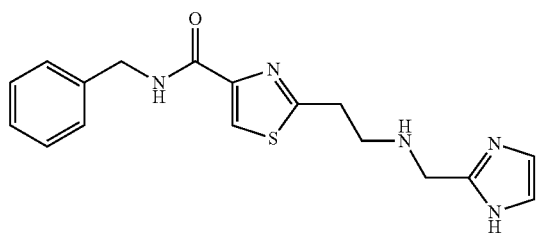 [SMILES: O=C(NCc1ccccc1)c1csc(CCNCc2ncc[nH]2)n1]

In a similar fashion to general procedure 3, 2-(2-aminoethyl)-N-benzyl-1,3-thiazole-4-carboxamide (104) (490 mg, 1.87 mmol), 1H-imidazole-2-carbaldehyde (150 mg, 1.56 mmol), AcOH (94 mg, 1.56 mmol) in MeOH (4 ml) at room temperature for 6 h, followed by addition of NaBH (59 mg, 1.56 mmol) gave the title compound (25 mg, 4.4%) as an white oil after purification by flash column chromatography (eluting with a gradient of 3% MeOH in DCM).

1H-NMR (CDCl$_3$, 400 MHz): d[ppm]=8.05 (s, 1H), 8.00 (s, 1H), 7.40-7.30 (m, 4H), 7.30-7.25 (m, 1H), 6.90 (s, 2H), 4.67 (bs, 2H), 4.64 (d, J=6.1 Hz, 2H), 4.02 (s, 2H), 3.16 (t, J=5.7 Hz, 2H), 3.09 (t, J=5.7 Hz, 2H)

HPLCMS (Method J): [m/z]: 342.4 [M+H]$^+$

N-Benzyl-2-{2-[(pyrimidin-4-ylmethyl)amino]ethyl}-1,3-thiazole-4-carboxamide (Example Compound No. 27)


In a similar fashion to general procedure 3, 2-(2-aminoethyl)-N-benzyl-1,3-thiazole-4-carboxamide (104) (150 mg, 0.574 mmol), pyrimidine-4-carbaldehyde (61 mg, 0.564 mmol), TEA (0.79 ml, 6 mmol) in MeOH (2 ml) at room temperature for 6 h, followed by addition of NaBH$_4$ (32 mg, 0.846 mmol) gave the title compound (150 mg, 75%) as an brown oil after purification by flash column chromatography (eluting with a gradient of 5% MeOH in DCM).

1H-NMR (CDCl$_3$, 400 MHz): d[ppm]=9.05 (d, J=1.3 Hz, 1H), 8.63 (d, J=5.2 Hz, 1H), 8.04 (s, 1H), 7.69 (s, 1H), 7.39-7.27 (m, 6H), 4.66 (d, J=6.1 Hz, 2H), 3.94 (s, 2H), 3.20 (t, J=6.3 Hz, 2H), 3.09 (t, J=6.6 Hz, 2H), HPLCMS (Method L): [m/z]: 354.0 [M+H]$^+$

331

N-Benzyl-2-[2-({imidazo[1,2-a]pyridin-2-ylmethyl}amino)ethyl]-1,3-thiazole-4-carboxamide
(Example Compound No. 34)

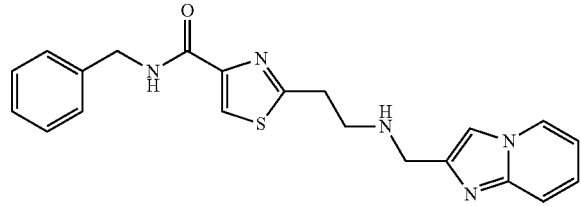 [SMILES: O=C(NCc1ccccc1)c1csc(CCNCc2cn3ccccc3n2)n1]

In a similar fashion to general procedure 3, 2-(2-aminoethyl)-N-benzyl-1,3-thiazole-4-carboxamide (104) (100 mg, 0.383 mmol), imidazo[1,2-a]pyridine-2-carbaldehyde (55.9 mg, 0.383 mmol), TEA (193.6 mg, 1.91 mmol) in MeOH (2 ml) at room temperature for 6 h, followed by addition of NaBH$_4$ (21.7 mg, 0.574 mmol) gave the title compound (35 mg, 21%) as an brown oil after purification by flash column chromatography (eluting with a gradient of 5% MeOH in DCM).

1H-NMR (CDCl$_3$, 400 MHz): d[ppm]=8.09-7.97 (m, 2H), 7.79 (s, 1H), 7.55-7.42 (m, 2H), 7.40-7.23 (m, 5H), 7.13 (ddd, J=10.1, 6.1, 2.7 Hz, 1H), 6.81-6.70 (m, 1H), 4.64 (d, J=6.1 Hz, 2H), 3.99 (d, J=4.9 Hz, 2H), 3.19 (dd, J=10.0, 3.6 Hz, 2H), 3.11 (t, J=6.2 Hz, 2H), HPLCMS (Method L): [m/z]: 392.1 [M+H]$^+$ N-Benzyl-2-(2-{[(6-methoxy-1H-1,3-benzodiazol-2-yl)methyl]amino}ethyl)-1,3-thiazole-4-carboxamide
(Example Compound No. 50)

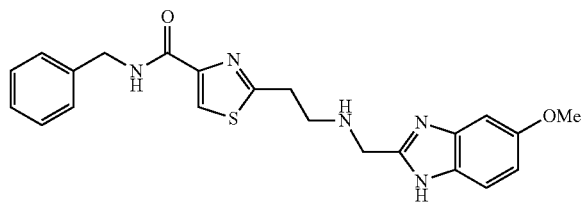 [SMILES: COc1ccc2[nH]c(CNCCc3nc(C(=O)NCc4ccccc4)cs3)nc2c1]

In a similar fashion to general procedure 3, 2-(2-aminoethyl)-N-benzyl-1,3-thiazole-4-carboxamide hydrochloride (104) (100 mg, 336 mmol), 6-methoxy-1H-1,3-benzodiazole-2-carbaldehyde (59 mg, 336 mmol) in DCE (2 ml) at room temperature for 2 h, followed by addition of NaBH(OAc)$_3$ (100 mg, 470 mmol) gave the title compound (24 mg, 16%) as an orange solid after purification by basic prep-HPLC.

1H-NMR (DMSO-d6, 500 MHz): d[ppm]=12.00 (s, 1H), 8.85 (t, J=6.3 Hz, 1H), 8.12 (s, 1H), 7.43-7.27 (m, 5H), 7.22 (dt, J=8.7, 4.2 Hz, 1H), 6.99 (d, J=55.2 Hz, 1H), 6.74 (s, 1H), 4.44 (d, J=6.4 Hz, 2H), 3.91 (s, 2H), 3.75 (s, 3H), 3.31 (s, 1H), 3.16 (t, J=6.8 Hz, 2H), 2.95 (t, J=6.7 Hz, 2H)

HPLCMS (Method B): [m/z]: 422.3 [M+H]$^+$

332

2-{2-[(1H-1,3-Benzodiazol-2-ylmethyl)amino]ethyl}-N-[(3-methoxypyridin-2-yl)methyl]-1,3-thiazole-4-carboxamide (Example Compound No. 59)

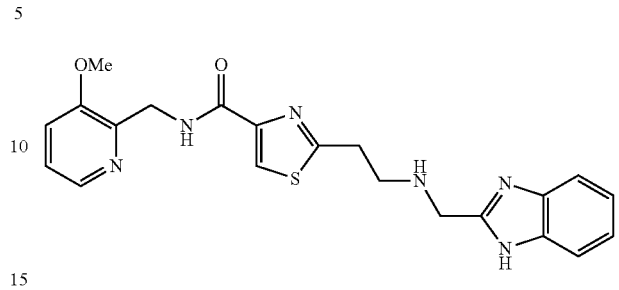

In a similar fashion using general procedure 3, 2-(2-aminoethyl)-N-[(3-methoxypyridin-2-yl)methyl]-1,3-thiazole-4-carboxamide (111) (90 mg, 0.308 mmol) and 1H-benzimidazole-2-carbaldehyde (49 mg, 0.339 mmol) in DCE (9 ml) at room temperature for 2 h, followed by the addition of NaBH(OAc)$_3$ (91 mg, 0.431 mmol) gave the title compound (50 mg, 38%) as a yellow solid after purification by basic prep-HPLC.

1H-NMR (DMSO-d6, 500 MHz): d[ppm]=12.18 (s, 1H), 8.58 (t, J=5.2 Hz, 1H), 8.14 (s, 1H), 8.09-8.06 (m, 1H), 7.59-7.40 (m, 3H), 7.31 (dd, J=8.3, 4.7 Hz, 1H), 7.12 (d, J=3.5 Hz, 2H), 4.56 (d, J=5.2 Hz, 2H), 3.97 (s, 2H), 3.87 (s, 3H), 3.20 (t, J=6.8 Hz, 2H), 2.98 (t, J=6.8 Hz, 2H)

HPLCMS (Method B): [m/z]: 423.2 [M+H]$^+$

N-(1H-1,3-Benzodiazol-2-ylmethyl)-2-{2-[(1H-1,3-benzodiazol-2-ylmethyl)amino]ethyl}-1,3-thiazole-4-carboxamide (Example Compound No. 60)

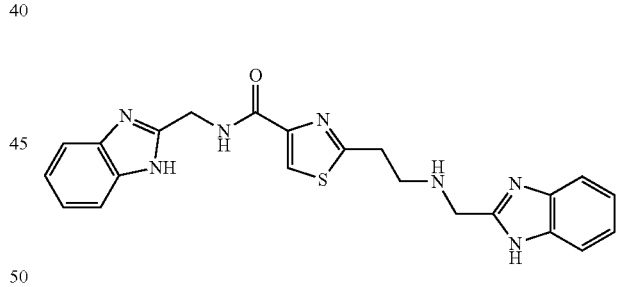

In a similar fashion using general procedure 3, 2-(2-aminoethyl)-N-(1H-1,3-benzodiazol-2-ylmethyl)-1,3-thiazole-4-carboxamide (112) (111 mg, 0.368 mmol) and 1H-benzimidazole-2-carbaldehyde (59 mg, 0.405 mmol) in DCE (12 ml) at room temperature for 2 h, followed by addition of NaBH(OAc)$_3$ (109 mg, 0.516 mmol) gave the title compound (15 mg, 9%) as a yellow solid after purification by basic prep-HPLC.

1H-NMR (DMSO-d6, 500 MHz): d[ppm]=12.23 (s, 2H), 8.89 (t, J=5.9 Hz, 1H), 8.18 (s, 1H), 7.49 (s, 4H), 7.13 (tt, J=7.0, 3.5 Hz, 4H), 4.69 (d, J=5.9 Hz, 2H), 3.98 (s, 2H), 3.21 (t, J=6.8 Hz, 2H), 3.00 (t, J=6.8 Hz, 2H)

HPLCMS (Method B): [m/z]: 430.3 [M−H]$^+$

N-Benzyl-2-[2-({[5-(trifluoromethoxy)-1H-1,3-benzodiazol-2-yl]methyl}amino)ethyl]-1,3-thiazole-4-carboxamide (Example Compound No. 62)

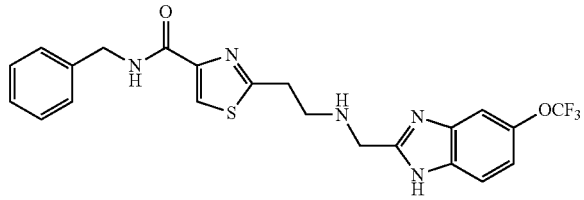 [SMILES: O=C(NCc1ccccc1)c1csc(CCNCc2nc3cc(OC(F)(F)F)ccc3[nH]2)n1]

In a similar fashion using general procedure 3, 2-(2-aminoethyl)-N-benzyl-1,3-thiazole-4-carboxamide (104) (150 mg, 0.494 mmol, 86% pure) and 6-(trifluoromethoxy)-1H-1,3-benzodiazole-2-carbaldehyde (125 mg, 0.543 mmol) in DCE (15 ml) at room temperature for 15 min, followed the addition of NaBH(OAc) (146 mg, 0.691 mmol) gave the title compound (77 mg, 33%) as a yellow solid after purification by basic prep-HPLC.

1H-NMR (DMSO-d6, 500 MHz): d[ppm]=12.45 (s, 1H), 8.84 (t, J=6.3 Hz, 1H), 8.12 (s, 1H), 7.57 (d, J=8.7 Hz, 1H), 7.48 (s, 1H), 7.30 (d, J=4.4 Hz, 4H), 7.23 (h, J=4.0 Hz, 1H), 7.13 (d, J=8.7 Hz, 1H), 4.45 (d, J=6.4 Hz, 2H), 3.98 (s, 2H), 3.22-3.13 (m, 2H), 2.98 (t, J=6.8 Hz, 2H), 2.70 (s, 1H)

HPLCMS (Method B): [m/z]: 476.1 [M+H]$^+$

2-(2-{[(6-Fluoro-1H-1,3-benzodiazol-2-yl)methyl]amino}ethyl)-N-[(3-fluoropyridin-2-yl)methyl]-1,3-thiazole-4-carboxamide trihydrochloride (Example Compound No. 114)

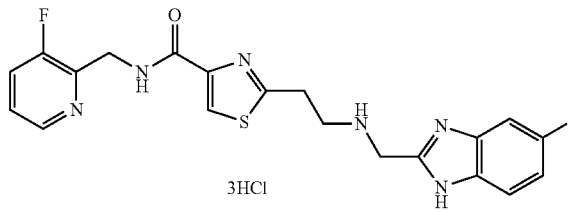

In a similar fashion to general procedure 3, 2-(2-aminoethyl)-N-[(3-fluoropyridin-2-yl)methyl]-1,3-thiazole-4-carboxamide dihydrochloride (103) (200 mg, 0.49 mmol), 6-fluoro-1H-benzimidazole-2-carbaldehyde (89 mg, 0.539 mmol) and DIPEA (0.342 ml, 1.961 mmol) in MeOH (10 ml) at room temperature for 24 h, followed by addition of NaBH$_4$ (28 mg, 0.735 mmol) gave the title compound (83 mg, free base) as a brown solid after purification by basic basic prep-HPLC. The freebase and 12M HCl (1 ml) in MeOH (4 ml) were stirred at room temperature to give the title compound (111 mg 42%) after solvent evaporation in vacuo.

1H-NMR (Methanol-d4, 500 MHz): d[ppm]=8.52 (s, 1H), 8.28 (s, 1H), 8.24 (s, 1H), 7.86 (s, 1H), 7.78 (s, 1H), 7.53 (s, 1H), 7.34 (s, 1H), 4.97 (s, 2H), 4.92 (s, 2H), 3.84 (s, 2H), 3.64 (t, J=6.1 Hz, 2H)

HPLCMS (Method D): [m/z]: 429.1 [M+H]$^+$

2-{2-[(1H-1,3-Benzodiazol-5-ylmethyl)amino]ethyl}-N-[(3-fluoropyridin-2-yl)methyl]-1,3-thiazole-4-carboxamide (Example Compound No. 139)

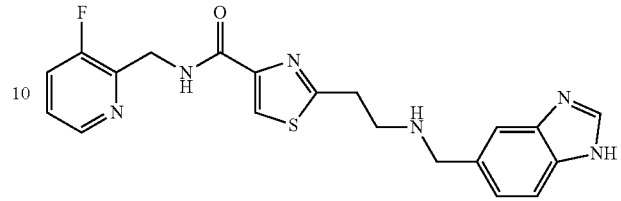

In a similar fashion to general procedure 3, 2-(2-aminoethyl)-N-[(3-fluoropyridin-2-yl)methyl]-1,3-thiazole-4-carboxamide dihydrochloride (103) (400 mg, 0.64 mmol, 56% purity), 1H-1,3-benzodiazole-5-carbaldehyde (112 mg, 0.77 mmol) and DIPEA (0.56 ml, 3.19 mmol) in MeOH (10 ml) at room temperature for 18 h, followed by by the addition of NaBH$_4$ (36 mg, 0.96 mmol) gave the title compound (207 mg, 75.9%) as a cream solid following purification by flash column chromatography (KP—NH, eluting with a gradient of 0-20% MeOH/DCM).

1H-NMR (Methanol-d4, 500 MHz): d[ppm]=8.31-8.29 (m, 1H), 8.14 (s, 1H), 8.10 (s, 1H), 7.64-7.53 (m, 3H), 7.37-7.33 (m, 1H), 7.29 (dd, J=8.3, 1.3 Hz, 1H), 4.79 (d, J=1.6 Hz, 2H), 3.96 (s, 2H), 3.28 (t, J=6.9 Hz, 2H), 3.09 (t, J=6.9 Hz, 2H)

HPLCMS (Method C): [m/z]: 411.2 [M+H]$^+$

2-{2-[(1H-1,3-Benzodiazol-4-ylmethyl)amino]ethyl}-N-[(3-fluoropyridin-2-)methyl)]-1,3-thiazole-4-carboxamide (Example Compound No. 140)

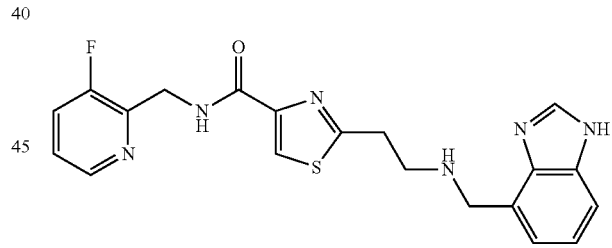

In a similar fashion using general procedure 3, 2-(2-aminoethyl)-N-[(3-fluoropyridin-2-yl)methyl]-1,3-thiazole-4-carboxamide dihydrochloride (103) (400 mg, 0.64 mmol, 56.3% purity), 1H-1,3-benzodiazole-4-carbaldehyde (112 mg, 0.77 mmol) and DIPEA (0.56 ml, 3.19 mmol) in MeOH (10 ml) at room temperature for 18 h, followed by by the addition of NaBH$_4$ (36 mg, 0.96 mmol) gave the title compound (255 mg, 96.4%) as an off-white solid after purification by flash column chromatography (KP—NH, eluting with a gradient of 0-10% MeOH/DCM).

1H-NMR (DMSO-d6, 500 MHz): d[ppm]=12.41 (s, 1H), 8.65 (t, J=5.5 Hz, 1H), 8.39-8.36 (m, 1H), 8.17 (br s, 1H), 8.12 (br s, 1H), 7.72-7.67 (m, 1H), 7.43-7.37 (m, 1H), 7.22-7.08 (m, 2H), 4.66 (dd, J=5.7, 1.4 Hz, 2H), 4.13 (s, 1H), 4.04 (s, 1H), 3.18 (t, J=6.5 Hz, 2H), 2.97-2.87 (m, 2H)

HPLCMS (Method C): [m/z]: 411.2 [M+H]$^+$

2-{3-[(1H-1,3-Benzodiazol-2-ylmethyl)amino]propyl}-N-[(3-fluoropyridin-2-yl)methyl]-1,3-thiazole-4-carboxamide Trihydrochloride (Example Compound No. 134)

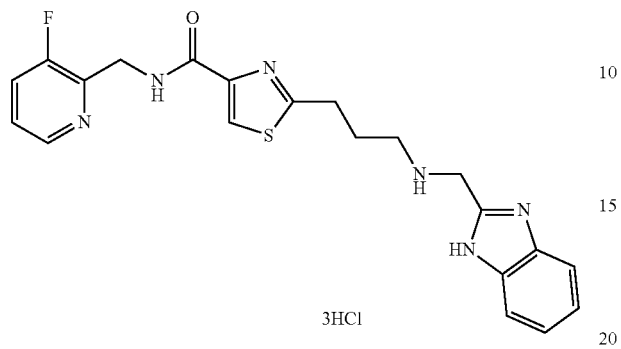

In a similar fashion to general procedure 3, 2-(3-aminopropyl)-N-[(3-fluoropyridin-2-yl)methyl]-1,3-thiazole-4-carboxamide dihydrochloride (115) (150 mg, 0.261 mmol, 64% purity), 1H-benzimidazole-2-carbaldehyde (46 mg, 0.314 mmol), DIPEA (0.18 ml, 1.05 mmol) in MeOH (2 ml) at room temperature for 16 h, followed by addition of NaBH₄ (15 mg, 0.39 mmol) afforded the freebase compound (53 mg, 48%) as a colourless oil after purification by basic prep-HPLC.

1H-NMR (DMSO-d6, 250 MHz): d[ppm]=12.16 (s, 1H), 8.66 (t, J=5.5 Hz, 1H), 8.38 (dt, J=4.7, 1.4 Hz, 1H), 8.13 (s, 1H), 7.70 (ddd, J=10.0, 8.4, 1.2 Hz, 1H), 7.61-7.27 (m, 2H), 7.11 (dd, J=6.0, 3.1 Hz, 2H), 4.65 (dd, J=5.5, 1.4 Hz, 2H), 3.91 (s, 2H), 3.09 (t, 2H), 2.64 (t, J=6.8 Hz, 2H), 1.92 (m, 2H)

HPLCMS (Method D): [m/z]: 425.2 [M+H]⁺

The freebase (35 mg, 0.082 mmol) and 12M HCl (20 μL, 0.247 mmol) were stirred in MeOH (2 ml) at room temperature to afford the title compound (44 mg, quant.) as a white solid after the solvent was removed in vacuo.

1H-NMR (D₂O, 500 MHz): d[ppm]=8.50 (dd, J=5.4, 1.2 Hz, 1H), 8.19-8.12 (m, 2H), 7.89-7.78 (m, 3H), 7.66 (dt, J=6.3, 3.3 Hz, 2H), 4.89 (s, 2H), 4.85 (d, J=1.3 Hz, 2H), 3.46-3.39 (m, 2H), 3.26 (t, J=7.2 Hz, 2H), 2.33 (m, 2H)

HPLCMS (Method D): [m/z]: 425.2 [M+H]⁺

2-{2-[(1H-1,3-Benzodiazol-2-ylmethyl)amino]ethyl}-N-[(3-fluoropyridin-2-yl)methyl]-5-methyl-1,3-thiazole-4-carboxamide (Example Compound No. 164)

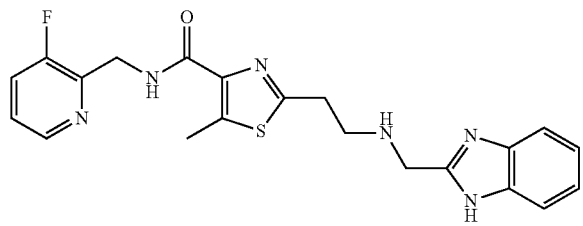 [SMILES: Cc1sc(CCNCc2nc3ccccc3[nH]2)nc1C(=O)NCc1ncccc1F]

In a similar fashion using general procedure 3, 2-(2-aminoethyl)-N-[(3-fluoropyridin-2-yl)methyl]-5-methyl-1,3-thiazole-4-carboxamide dihydrochloride (113) (274 mg, 0.75 mmol), 1H-1,3-benzodiazole-2-carbaldehyde (109 mg, 0.75 mmol), DIPEA (0.45 ml, 2.61 mmol) and anhydrous MgSO₄ (200 mg) in MeOH (10 ml) and DCM (10 ml) at room temperature for 20 h, followed by addition of NaBH₄ (60 mg, 1.48 mmol) afforded the title compound (140 mg, 44%) as a pale yellow solid after purification by prep-HPLC.

1H-NMR (DMSO-d6, 500 MHz): d[ppm]=12.17 (s, 1H), 8.59 (t, J=5.6 Hz, 1H), 8.36 (dt, J=4.7, 1.4 Hz, 1H), 7.70 (ddd, J=9.9, 8.4, 1.1 Hz, 1H), 7.53 (d, J=7.5 Hz, 1H), 7.44 (d, J=7.5 Hz, 1H), 7.40 (dt, J=8.5, 4.4 Hz, 1H), 7.13 (p, J=6.6 Hz, 2H), 4.65-4.59 (m, 2H), 3.96 (s, 2H), 3.10 (t, J=6.8 Hz, 2H), 2.94 (t, J=6.8 Hz, 2H), 2.68 (s, 3H)

HPLCMS (Method C): [m/z]: 425.2 [M+H]⁺

General Procedure 7: 2-(2-{[2-(1H-1,3-benzodiazol-2-yl)ethyl]amino}ethyl)-N-[(3-fluoropyridin-2-yl)methyl]-1,3-thiazole-4-carboxamide (Example Compound No. 94)

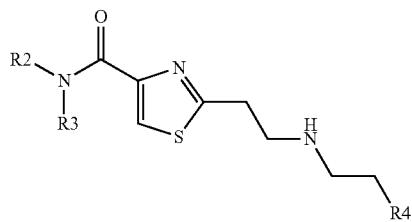

2-(2-Aminoethyl)-N-[(3-fluoropyridin-2-yl)methyl]-1,3-thiazole-4-carboxamide dihydrochloride (103) (2.0 g, 3.96 mmol) was added to a solution of 2-(2-chloroethyl)-1H-1,3-benzodiazole hydrochloride (1.12 g, 5.15 mmol) and DIPEA (10.6 ml, 59.45 mmol) in DMF (60 ml). The reaction mixture was allowed to stir at 30° C. for 6 d (reaction was monitored by LCMS). The mixture was concentrated in vacuo and the residue was neutralised using sat. NaHCO₃ (aq). The aqueous layer was extracted using 4:1 CHCl₃/IPA (4×100 ml) and the combined organic layers were dried (MgSO₄), filtered and evaporated in vacuo. The crude residue was purified by flash column chromatography (kp-NH, eluting with a gradient of 60-100% EtOAc/heptane followed by 0-20% MeOH/EtOAc) follow by neutral reverse-phase column chromatography (gradient elution 0-60% MeCN/water) to give the title compound (0.173 g, 10%) as a yellow oil.

1H-NMR (Methanol-d4, 500 MHz): d[ppm]=8.31 (d, J=4.6 Hz, 1H), 8.02 (s, 1H), 7.57 (t, J=9.1 Hz, 1H), 7.45-7.40 (m, 2H), 7.36 (dd, J=8.6, 4.3 Hz, 1H), 7.17 (dd, J=6.0, 3.2 Hz, 2H), 4.68 (s, 2H), 3.26 (d, J=6.8 Hz, 2H), 3.15-3.07 (m, 6H)

HPLCMS (Method D): [m/z]: 425.1 [M+H]⁺

2-(2-{[2-(1H-1,3-Benzodiazol-2-yl)ethyl]amino}ethyl)-N-[(3-fluoropyridin-2-yl)methyl]-1,3-thiazole-4-carboxamide Trihydrochloride (Example Compound No. 94—HCl Salt)

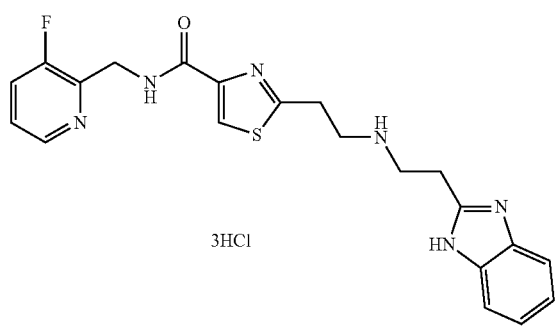 [SMILES: O=C(NCc1ncccc1F)c1csc(CCNCCc2nc3ccccc3[nH]2)n1]

4M HCl in 1,4-dioxane (2.38 ml, 9.82 mmol) was added to a solution of 2-(2-{[2-(1H-1,3-benzodiazol-2-yl)ethyl]amino}ethyl)-N-[(3-fluoropyridin-2-yl)methyl]-1,3-thiazole-4-carboxamide (Example Compound No. 94) (1.30 g, 2.98 mmol) in MeOH (15 ml) and the reaction mixture was stirred at room temperature for 2 h. The mixture was evaporated in vacuo to afford the title compound (1.16 g, 70%) as an off-white solid.

1H-NMR (Methanol-d4, 500 MHz): d[ppm]=8.48 (s, 1H), 8.25 (s, 1H), 8.07 (s, 1H), 7.79 (dt, J=6.9, 3.4 Hz, 2H), 7.73 (s, 1H), 7.61 (dd, J=6.2, 3.1 Hz, 2H), 4.91 (s, 2H), 3.82 (s, 4H), 3.75 (t, J=6.4 Hz, 2H), 3.61 (t, J=6.4 Hz, 2H)

HPLCMS (Method D): [m/z]: 425.1 [M+H]$^+$

N-Benzyl-2-[2-({3H-imidazo[4,5-b]pyridin-2-ylmethyl}amino)ethyl]-1,3-thiazole-4-carboxamide (Example Compound No. 33)

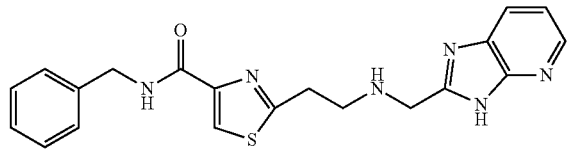 [SMILES: O=C(NCc1ccccc1)c1csc(CCNCc2nc3cccnc3[nH]2)n1]

In a similar fashion to general procedure 7, 2-(2-aminoethyl)-N-benzyl-1,3-thiazole-4-carboxamide (104) (130 mg, 0.49 mmol), 2-(chloromethyl)-3H-imidazo[4,5-b]pyridine hydrochloride (100 mg, 0.49 mmol) and DIPEA (0.168 ml, 0.98 mmol) in DMF (1 ml) at 90° C., gave the title compound (43 mg, 22%) as an yellow oil after purification by flash column chromatography, eluting with a gradient 100% DCM to DCM:MeOH:NH$_3$ (95:5:1).

1H-NMR (CDCl$_3$, 400 MHz): d[ppm]=8.24 (d, J=5.5 Hz, 2H), 8.08 (s, 1H), 7.93 (d, J=8.0 Hz, 1H), 7.38-7.22 (m, 5H), 7.18 (dd, J=8.0, 4.9 Hz, 1H), 4.69 (d, J=6.1 Hz, 2H), 4.22 (s, 2H), 3.19-3.14 (m, 4H)

HPLCMS (Method L): [m/z]: [m/z]: 393.13

Tert-butyl 2-[({2-[4-(benzylcarbamoyl)-1,3-thiazol-2-yl]ethyl}amino)methyl]-5-methyl-1H-1,3-benzodiazole-1-carboxylate (116)

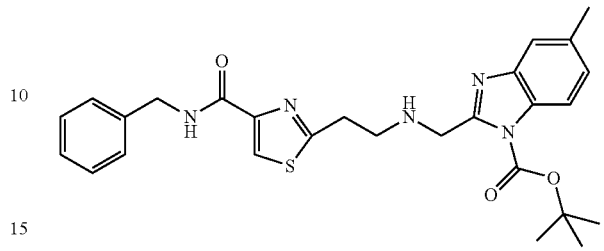

To a solution of 2-(2-aminoethyl)-N-benzyl-1,3-thiazole-4-carboxamide (104) (186 mg, 0.71 mmol) in DMF (5 ml) was added DIPEA (0.138 ml, 1 mmol), followed by addition of tert-butyl 2-(chloromethyl)-5-methyl-1H-1,3-benzodiazole-1-carboxylate (F) (200 mg, 0.71 mmol) and the reaction heated at 900° C. Upon completion (LCMS) the mixture was concentrated in vacuo. Residue was purified by flash column chromatography (eluting with DCM/MeOH, 95:5) as a yellow oil (85 mg, 24%).

1H-NMR (CDCl$_3$, 400 MHz): d[ppm]=7.95 (s, 1H), 7.61 (s, 1H), 7.31 (dd, J=24.4, 4.2 Hz, 6H), 7.07 (d, J=8.2 Hz, 1H), 4.61 (d, J=6.1 Hz, 2H), 4.58 (s, 2H), 3.74 (t, J=6.6 Hz, 2H), 3.20 (t, J=6.6 Hz, 2H), 2.46 (s, 3H), 1.36 (s, 9H), HPLCMS (Method I): [m/z]: 506.6 [M+H]$^+$

N-Benzyl-2-(2-{[(5-methyl-1H-1,3-benzodiazol-2-yl)methyl]amino}ethyl)-1,3-thiazole-4-carboxamide (Example Compound No. 32)

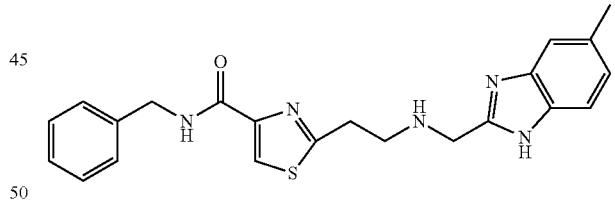

In a similar fashion using general procedure 2, tert-butyl 2-[({2-[4-(benzylcarbamoyl)-1,3-thiazol-2-yl]ethyl}amino)methyl]-5-methyl-1H-1,3-benzodiazole-1-carboxylate (116) (87 mg, 0.17 mmol) in 1,4-dioxane (10 ml) at 0° C. was added HCl (613 mg, 17 mmol) in dioxane (0.5 ml) under argon. The reaction was stirred for 18 h, the solvent removed in vacuo to provide a white solid, washed with Et$_2$O and n-pentane (45 mg, 60%).

1H-NMR (DMSO-d6, 400 MHz): d[ppm]=10.26 (s, 1H), 9.23 (s, 1H), 8.22 (s, 1H), 7.65 (d, J=8.4 Hz, 1H), 7.56 (s, 1H), 7.35-7.18 (m, 6H), 4.70 (s, 2H), 4.45 (d, J=6.4 Hz, 2H), 3.64 (t, J=6.8 Hz, 2H), 3.58-3.49 (m, 2H), 2.46 (s, 3H), HPLCMS (Method L): [m/z]: 406.7 [M+H]$^+$

339

N-Benzyl-2-(2-{[(5-fluoro-1H-1,3-benzodiazol-2-yl)methyl]amino}ethyl)-1,3-thiazole-4-carboxamide (Example Compound No. 31)

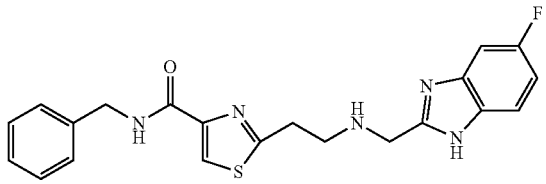 [SMILES: O=C(NCc1ccccc1)c1csc(CCNCc2nc3cc(F)ccc3[nH]2)n1]

In a similar fashion to general procedure 7, 2-(2-aminoethyl)-N-benzyl-1,3-thiazole-4-carboxamide (104) (99 mg, 0.38 mmol), 2-(chloromethyl)-5-fluoro-1H-1,3-benzodiazole (70 mg, 0.38 mmol) and DIPEA (0.065 ml, 0.38 mmol) in DMF (3 ml) at 90° C., gave the title compound (20 mg, 13%) as a brown oil after purification by flash column chromatography, eluting with a gradient of 100% DCM to DCM/MeOH (95:5).

1H-NMR (CDCl$_3$, 400 MHz): d[ppm]=8.01 (s, 1H), 7.71 (m, 1H), 7.42 (s, 1H), 7.34-7.27 (m, 4H), 7.25 (m, 1H), 7.19 (d, J=8.8 Hz, 1H), 7.00-6.91 (m, 1H), 4.61 (d, J=6.1 Hz, 2H), 4.08 (s, 2H), 3.17-3.05 (m, 4H)

HPLCMS (Method J): [m/z]: [m/z]: 410.5

Tert-butyl 2-[({2-[4-(benzylcarbamoyl)-1,3-thiazol-2-yl]ethyl}amino)methyl]-5-methoxy-1H-1,3-benzodiazole-1-carboxylate (117) and N-benzyl-2-(2-{[(5-methoxy-1H-1,3-benzodiazol-2-yl)methyl]amino}ethyl)-1,3-thiazole-4-carboxamide (118)

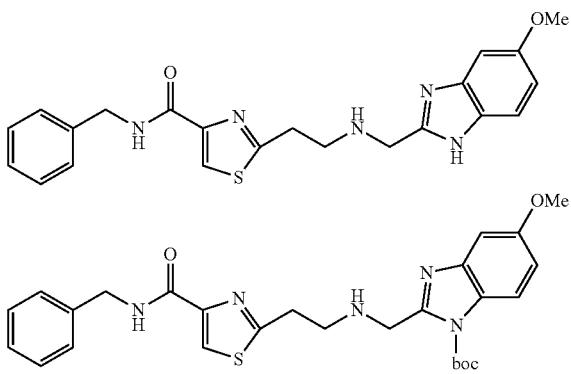

In a similar fashion to general procedure 7, 2-(2-aminoethyl)-N-benzyl-1,3-thiazole-4-carboxamide (104) (0.4 g, 2 mmol), tert-butyl 2-(chloromethyl)-5-methoxy-1H-1,3-benzodiazole-1-carboxylate (F) (0.45 g, 2 mmol), DIPEA (0.4 g, 3 mmol) and NaI (0.23 g, 2 mmol) in MeCN (30 ml) under argon at 90° C. for 18 h, gave a mixture of a red solid, (boc deprotected product, 350 mg, 27%) and the expected product as a white solid (133 mg, 21%) after purification by flash column chromatography (eluting with a gradient DCM/MeOH 5-7%).

HPLCMS (Method I): [m/z]: 522.6 [M+H]$^+$ and 422.6 [M+H]$^+$

340

N-Benzyl-2-(2-{[(5-hydroxy-1H-1,3-benzodiazol-2-yl)methyl]amino}ethyl)-1,3-thiazole-4-carboxamide (Example Compound No. 30)

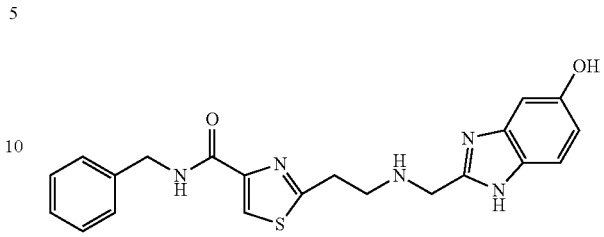

To a solution of N-benzyl-2-{[(5-methoxy-1H-1,3-benzodiazol-2-yl)methyl]amino}ethyl)-1,3-thiazole-4-carboxamide (118) (130 mg, 0.31 mmol, 53% purity) in DCM (15 ml), cooled to −78° C., was added BBr$_3$ (735 μl of a 1 M solution in DCM) dropwise under argon atmosphere. The reaction allowed to warm to room temperature and stirred for 18 h. Ammonia (aq) was added and the mixture concentrated under vacuum. The required product (3.2 mg, 4%) was isolated after fbsh column chromatography eluted with MeOH/DCM (9:1). The compound was purified further using prep-TLC using the same elution conditions.

1H-NMR (Methanol-d4, 400 MHz): d[ppm]=8.07 (s, 1H), 7.34-7.20 (m, 6H), 6.89 (d, J=2.1 Hz, 1H), 6.75 (dd, J=8.7, 2.3 Hz, 1H), 4.56 (s, 2H), 4.02 (s, 2H), 3.23 (t, J=6.6 Hz, 2H), 3.10 (t, J=6.6 Hz, 2H)

HPLCMS (Method H): [m/z]: 408.5 [M+H]$^+$

N-Benzyl-2-[2-({[5-(trifluoromethyl)-1H-1,3-benzodiazol-2-yl]methyl}amino)ethyl]-1,3-thiazole-4-carboxamide (Example Compound No. 51)

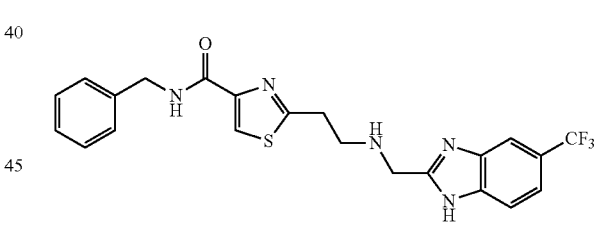

In a similar fashion to general procedure 7, 2-(2-aminoethyl)-N-benzyl-1,3-thiazole-4-carboxamide hydrochloride (104) (100 mg, 336 mmol), 2-(chloromethyl)-5-(trifluoromethyl)-1H-1,3-benzodiazole (E) (155 mg, 369 mmol), K$_2$CO$_3$ (232 mg, 1.68 mmol) and DMF (3 ml) at room temperature for 3 d, gave the title compound (10 mg, 6%) as a brown solid after purification by prep-HPLC (MeCN/Water, 2 mM NH$_4$HCO$_3$), followed by flash column chromatography (eluting with a gradient of MeOH/DCM, 1:9).

1H-NMR (DMSO-d6, 500 MHz): d[ppm]=8.85 (t, J=6.3 Hz, 1H), 8.12 (s, 1H), 7.84 (s, 1H), 7.67 (d, J=8.4 Hz, 1H), 7.45 (d, J=8.4 Hz, 1H), 7.30 (d, J=4.4 Hz, 4H), 7.22 (dt, J=8.6, 4.2 Hz, 1H), 4.44 (d, J=6.4 Hz, 2H), 4.02 (s, 2H), 3.21-3.16 (m, 2H), 2.98 (t, J=6.8 Hz, 2H)

HPLCMS (Method B): [m/z]: 460.1 [M+H]$^+$

N-Benzyl-2-(2-{[(5-chloro-1H-1,3-benzodiazol-2-yl)methyl]amino}ethyl)-1,3-thiazole-4-carboxamide (Example Compound No. 52)

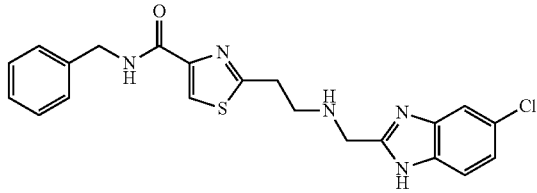 [SMILES: O=C(NCc1ccccc1)c1csc(CCNCc2nc3cc(Cl)ccc3[nH]2)n1]

In a similar fashion to general procedure 7, 2-(2-aminoethyl)-N-benzyl-1,3-thiazole-4-carboxamide (104) (110 mg, 0.37 mmol), 5-chloro-2-(chloromethyl)-1H-benzimidazole (84 mg, 0.41 mmol), K$_2$CO$_3$ (205 mg, 1.48 mmol) in acetone (5 ml) at room temperature for 3 d gave the title compound (5.7 mg, 3.6%) as a brown solid after purification by basic prep-HPLC.

1H-NMR (DMSO-d6, 500 MHz): d[ppm]=12.34 (s, 1H), 8.84 (t, J=6.3 Hz, 1H), 8.12 (s, 1H), 7.50 (s, 2H), 7.30 (d, J=4.3 Hz, 4H), 7.23 (q, J=4.3 Hz, 1H), 7.15 (d, J=8.7 Hz, 1H), 4.44 (d, J=6.4 Hz, 2H), 3.96 (s, 2H), 3.17 (t, J=6.8 Hz, 2H), 2.96 (t, J=6.7 Hz, 2H)

HPLCMS (Method E): [m/z]: 426.0 [M+H]$^+$

2-{2-[(1,3-Benzoxazol-2-ylmethyl)amino]ethyl}-N-[(3-fluoropyridin-2-yl)methyl]-1,3-thiazole-4-carboxamide (Example Compound No. 115)

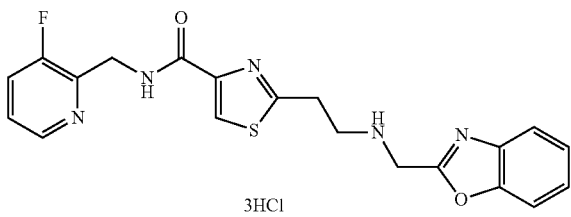 [SMILES: O=C(NCc1ncccc1F)c1csc(CCNCc2nc3ccccc3o2)n1]

In a similar fashion to general procedure 7, 2-(2-aminoethyl)-N-[(3-fluoropyridin-2-yl)methyl]-1,3-thiazole-4-carboxamide dihydrochloride (103) (300 mg, 0.735 mmol), 2-(chloromethyl)-1,3-benzoxazole (160 mg, 0.956 mmol), DIPEA (1.922 ml, 11.03 mmol) and DMF (15 ml) at 30° C. for 24 h, gave the title compound (102 mg, 34%) as a yellow oil after purification by basic prep-HPLC.

1H-NMR (Methanol-d4, 500 MHz): d[ppm]=8.30 (d, J=4.7 Hz, 1H), 8.08 (s, 1H), 7.66-7.62 (m, 1H), 7.60-7.54 (m, 2H), 7.39-7.32 (m, 3H), 4.77 (d, J=1.6 Hz, 2H), 4.14 (s, 2H), 3.27 (d, J=6.3 Hz, 2H), 3.18 (t, J=6.6 Hz, 2H)

HPLCMS (Method D): [m/z]: 412.1 [M+H]$^+$

2-(2-{[2-(1H-1,3-Benzodiazol-2-yl)ethyl]amino}ethyl)-N-benzyl-1,3-thiazole-4-carboxamide (Example Compound No. 29)

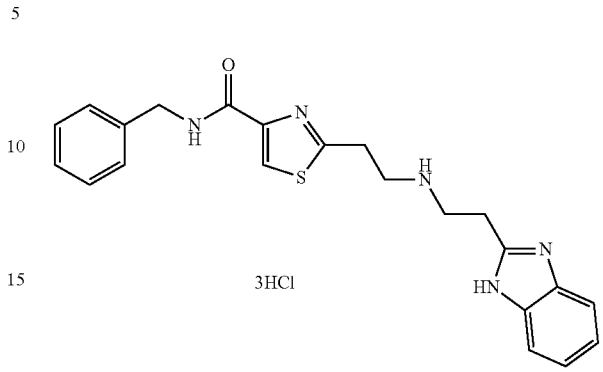

In a similar fashion to general procedure 7, 2-(2-aminoethyl)-N-benzyl-1,3-thiazole-4-carboxamide hydrochloride (104) (80%, 1 g, 2.69 mmol), 2-(2-chloroethyl)-1H-1,3-benzodiazole hydrochloride (0.7 g, 3.22 mmol) and DIPEA (7.19 ml, 40.29 mmol) in DMF (10 ml) at room temperature for 7 d gave the free base compound (230 mg) after purification by flash column chromatography (kp-NH, eluting with a gradient 60-100% EtOAc/heptane, followed by 0-20% MeOH/EtOAc).

The glassy solid was then dissolved in MeOH (2 ml) and 4M HCl in dioxane (0.5 rd) and stirred at room temperature for 2 h to give the title compound (310 mg, 23%) as the HCl salt.

1H-NMR (MeOD, 500 MHz): d[ppm]=8.23 (s, 1H), 7.79 (dt, J=6.7, 3.4 Hz, 2H), 7.63 (dt, J=6.2, 3.4 Hz, 2H), 7.38 (d, J=7.5 Hz, 2H), 7.32 (t, J=7.5 Hz, 2H), 7.24 (t, J=7.3 Hz, 1H), 4.60 (s, 2H), 3.77 (s, 4H), 3.72 (t, J=6.5 Hz, 2H), 3.59 (t, J=6.5 Hz, 2H).

HPLCMS (Method D): [m/z]: 406.2 [M+H]$^+$

2-(2-{[2-(1H-1,3-Benzodiazol-2-yl)ethyl]amino}ethyl)-N-(pyridin-2-ylmethyl)-1,3-thiazole-4-carboxamide (Example Compound No. 58)

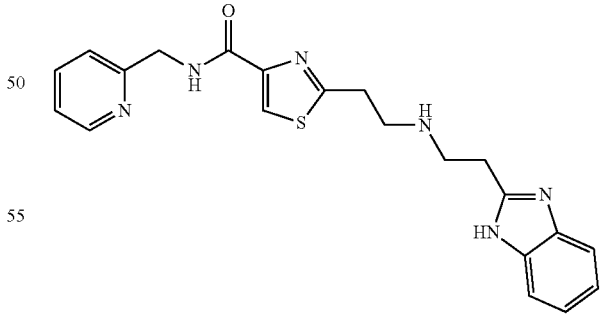

In a similar fashion to general procedure 7, 2-(2-aminoethyl)-N-(pyridin-2-ylmethyl)-1,3-thiazole-4-carboxamide dihydrochloride (105) (240 mg, 0.72 mmol), 2-(2-chloroethyl)-1H-1,3-benzodiazole (259 mg, 1.43 mmol) and DIPEA (2.17 ml, 12.53 mmol) in DMF (10 ml) afforded the title compound (64 mg, 22%) as a brown solid after purification by basic prep-HPLC followed by flash column chromatography (eluting with a gradient of 0-10% MeOH/DCM followed by 0.8 M ammonia in MeOH/DCM)

1H-NMR (DMSO-d6, 500 MHz): d[ppm]=8.87 (t, J=6.0 Hz, 1H), 8.50 (d, J=4.6 Hz, 1H), 8.10 (s, 1H), 7.74 (td, J=7.7, 1.7 Hz, 1H), 7.44 (s, 2H), 7.33-7.21 (m, 2H), 7.10 (dd, J=5.9, 3.2 Hz, 2H), 4.55 (d, J=6.0 Hz, 2H), 3.15 (t, J=6.7 Hz, 2H), 3.02 (t, J=6.7 Hz, 2H), 2.90-2.96 (m, 4H)

HPLCMS (Method G): [m/z]: 407.2 [M+H]+

2-(2-{[2-(1H-1,3-Benzodiazol-2-yl)ethyl](methyl)amino}ethyl)-N-[(3-fluoropyridin-2-yl)methyl]-1,3-thiazole-4-carboxamide Trihydrochloride (Example Compound No. 112)

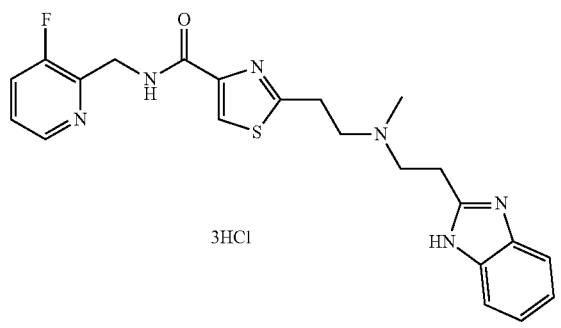 [SMILES: CN(CCc1nc2ccccc2[nH]1)CCc1nc(C(=O)NCc2ncccc2F)cs1]

2-(2-{[2-(1H-1,3-benzodiazol-2-yl)ethyl]amino}ethyl)-N-[(3-fluoropyridin-2-yl)methyl]-1,3-thiazole-4-carboxamide trihydrochloride (Example Compound No. 94) (114 mg, 0.205 mmol), Et3N (0.143 ml, 1.025 mmol) and DMF (1 ml) were stirred at room temperature for 1 h. MeI (0.059 ml, 0.949 mmol) was added and stirred at room temperature for 140 h. Water (10 ml) was added and the solvent reduced in vacuo. The crude product was purified by basic prep-HPLC to give the free base (18 mg). MeOH (2 ml) and 4 M HCl in dioxane (0.05 ml, 0.205 mmol) were added and stirred at room temperature for 2 h. The reaction was concentrated in vacuo to give the title compound (24 mg, 21%) as a yellow solid.

1H-NMR (Methanol-d4, 500 MHz): d[ppm]=8.48-8.39 (br m, 1H), 8.26 (s, 1H), 8.02-7.84 (br m, 1H), 7.82-7.76 (m, 2H), 7.67-7.54 (m, 3H), 4.84 (s, 2H, obscured by H2O peak), 3.99-3.84 (m, 6H), 3.71 (t, J=6.8 Hz, 2H), 3.16 (s, 3H)

HPLCMS (Method D): [m/z]: 439.1 [M+H]+

2-{2-[2-(1H-1, 3-Benzodiazol-2-yl)acetamido]ethyl}-N-[(3-fluoropyridin-2-yl)methyl]-1,3-thiazole-4-carboxamide Dihydrochloride (Example Compound No. 113)

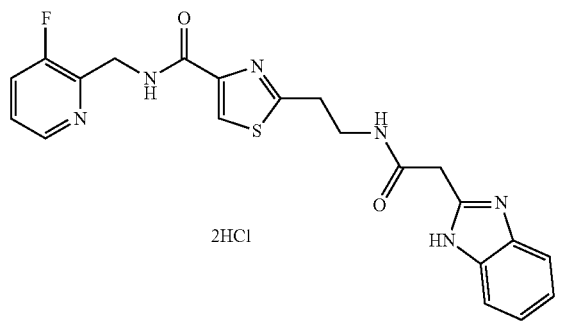 [SMILES: O=C(Cc1nc2ccccc2[nH]1)NCCc1nc(C(=O)NCc2ncccc2F)cs1]

In a similar fashion to general procedure 6, 2-(2-aminoethyl)-N-[(3-fluoropyridin-2-yl)methyl]-1,3-thiazole-4-carboxamide dihydrochloride (103) (150 mg, 0.368 mmol), 2-(1H-1,3-Benzodiazol-2-yl)acetic acid (114 mg, 0.552 mmol), DIPEA (0.384 ml, 2.206 mmol) and HATU (210 mg, 0.52 mmol) in THF (20 ml) at room temperature for 2 h, gave the freebase compound (73 mg) after purified by basic prep-HPLC. The freebase and 12M HCl (2 ml) in MeOH (6 ml) were stirred at room temperature for 2 h. The reaction was concentrated in vacuo to give the title compound (97 mg, 51%) as a brown solid.

1H NMR (Methanol-d4, 500 MHz): d[ppm]=8.60 (dd, J=5.5, 1.2 Hz, 1H), 8.32 (td, J=8.9, 1.1 Hz, 1H), 8.15 (s, 1H), 7.96-7.90 (m, 1H), 7.81-7.75 (m, 2H), 7.63-7.58 (m, 2H), 4.93 (d, J=1.1 Hz, 2H), 4.27 (s, 2H), 3.76 (t, J=6.7 Hz, 2H), 3.32 (t, J=6.6 Hz, 2H)

HPLCMS (Method D): [m/z]: 439.1 [M+H]+

2-{2-[(Cyclopropylmethyl)amino]ethyl}-N-[(3-fluoropyridin-2-yl)methyl]-1,3-thiazole-4 carboxamide (119)

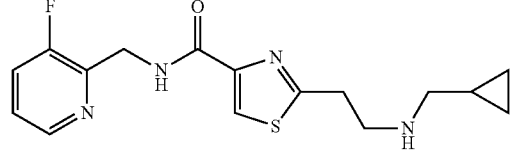 [SMILES: O=C(NCc1ncccc1F)c1csc(CCNCC2CC2)n1]

In a similar fashion to general procedure 3, 2-(2-aminoethyl)-N-[(3-fluoropyridin-2-yl)methyl]-1,3-thiazole-4-carboxamide dihydrochloride (103) (56% purity, 500 mg, 0.793 mmol), cyclopropanecarbaldehyde (67 mg, 0.951 mmol) and DIPEA (0.552 ml, 3.17 mmol) in MeOH (7 ml) at room temperature for 16 h, followed by the addition of NaBH4 (45 mg, 1.19 mmol) gave the title compound (149 mg, 51%) as a colourless oil after purification by flash column chromatography (kp-NH, eluting with a gradient 0-10% MeOH/DCM).

1H-NMR (DMSO-d6, 500 MHz): d[ppm]=8.65 (t, J=5.7 Hz, 1H), 8.39 (dt, J=4.5, 1.3 Hz, 1H), 8.12 (s, 1H), 7.71 (ddd, J=10.0, 8.3, 1.3 Hz, 1H), 7.41 (dt, J=8.6, 4.5 Hz, 1H), 4.66 (dd, J=5.7, 1.4 Hz, 2H), 3.13 (t, J=6.7 Hz, 2H), 2.92 (t, J=6.7 Hz, 2H), 2.43 (d, J=6.6 Hz, 2H), 1.92 (s, 1H), 0.93-0.81 (m, 1H), 0.43-0.35 (m, 2H), 0.13-0.06 (m, 2H)

HPLCMS (Method F): [m/z]: 335.8 [M+H]+

2-(2-{[2-(1H-1,3-Benzodiazol-2-yl)ethyl](cyclopropylmethyl)amino}ethyl)-N-[(3-fluoropyridin-2-yl)methyl]-1,3-thiazole-4-carboxamide (Example Compound No. 148)

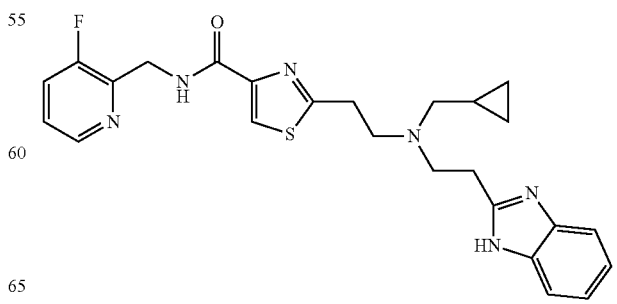

In a similar fashion to general procedure 7, 2-{2-[(cyclopropylmethyl)amino]ethyl}-N-[(3-fluoropyridin-2-yl)methyl]-1,3-thiazole-4-carboxamide (119) (149 mg, 0.45 mmol), 2-(2-chloroethyl)-1H-1,3-benzodiazole hydrochloride (116 mg, 0.53 mmol) and DIPEA (0.4 ml, 2.23 mmol) at 3° C. for 32 h afforded the title compound (5 mg, 2%) as a yellow oil after purification by basic prep-HPLC followed by flash column chromatography (eluting with a gradient of 0-10% MeOH in DCM then 0-10% 7 M ammonia in MeOH/DCM).

1H-NMR (Acetone-d6, 500 MHz): d[ppm]=8.48 (s, 1H), 8.39 (d, J=4.7 Hz, 1H), 7.98 (s, 1H), 7.66-7.54 (m, 1H), 7.49-7.33 (m, 3H), 7.10 (dd, J=6.0, 3.2 Hz, 2H), 4.75 (dd, J=5.3, 1.5 Hz, 2H), 3.33 (t, J=6.7 Hz, 2H), 3.30-3.11 (m, 6H), 2.67 (d, J=6.7 Hz, 2H), 1.10-0.94 (m, 1H), 0.60-0.43 (m, 2H), 0.26-0.22 (m, 2H)

HPLCMS (Method B): [m/z]: 479.2 [M+H]+

2-(2-{[2-(1H-1,3-Benzodiazol-2-yl)ethyl]amino}ethyl)-N-(pyridazin-3-ylmethyl)-1,3-thiazole-4-carboxamide Trihydrochloride (Example Compound No. 122)

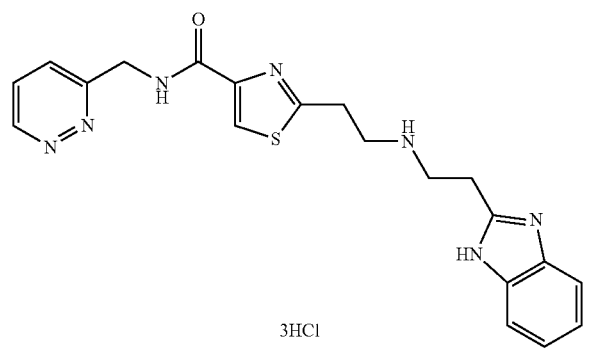 [SMILES: O=C(NCc1cccnn1)c1csc(CCNCCc2nc3ccccc3[nH]2)n1]

In a similar fashion using general procedure 7, 2-(2-aminoethyl)-N-(pyridazin-3-ylmethyl)-1,3-thiazole-4-carboxamide dihydrochloride (106) (409 mg, 1.22 mmol), 2-(2-chloroethyl)-1H-1,3-benzodiazole hydrochloride (316.9 mg, 1.46 mmol) and DIPEA (3.18 ml, 0.02 mol) in DMF (5 ml) at room temperature for 5 d gave the freebase product after purification by flash column chromatography using a gradient elution of 0-20% MeOH/DCM followed by further purification by basic prep-HPLC.

The freebase product was re-dissolved in MeOH (5 ml) and treated with 12 M HCl (1 ml) for 1 h to give the title compound (132 mg, 21%) as a pale yellow solid.

1H-NMR (Methanol-d4, 500 MHz): d[ppm]=9.52 (dd, J=5.2, 1.2 Hz, 1H), 8.59 (dd, J=8.7, 1.2 Hz, 1H), 8.46 (dd, J=8.7, 5.2 Hz, 1H), 8.28 (s, 1H), 7.83 (dd, J=6.2, 3.1 Hz, 2H), 7.65 (td, J=6.2, 5.5, 2.2 Hz, 2H), 5.04 (s, 2H), 3.90-3.82 (m, J=4.2 Hz, 4H), 3.79 (t, J=6.4 Hz, 2H), 3.64 (t, J=6.4 Hz, 2H)

HPLCMS (Method C): [m/z]: 408.2 [M+H]+

2-(2-{[2-(1H-1,3-Benzodiazol-2-yl)ethyl]amino}ethyl)-N-(pyrimidin-2-ylmethyl)-1,3-thiazole-4-carboxamide Trihydrochloride (Example Compound No. 129)

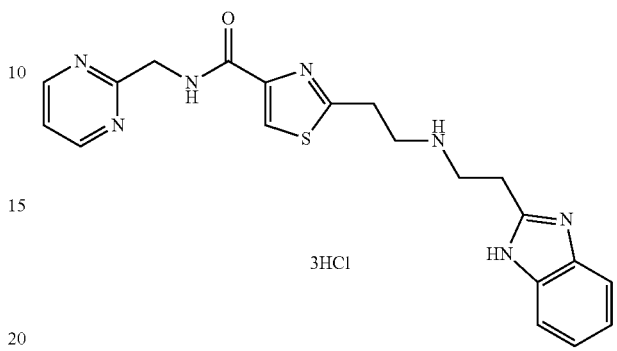

In a similar fashion to general procedure 7, 2-(2-aminoethyl)-N-(pyrimidin-2-ylmethyl)-1,3-thiazole-4-carboxamide dihydrochloride (108) (300 mg, 0.89 mmol), 2-(2-chloroethyl)-1H-1,3-benzodiazole hydrochloride (193.7 mg, 0.89 mmol) and DIPEA (3.11 ml, 17.8 mmol) in DMF (10 ml) at room temperature for 9 d gave the freebase product after purification by flash column chromatography (eluting with a gradient of 0-40% MeOH/DCM) followed by further purification by basic prep-HPLC.

The freebase product was re-dissolved in MeOH (5 ml) and treated with 12M HCl for 30 min to give the title compound (26 mg, 6%) as a pale yellow solid.

1H-NMR (D2O, 500 MHz): d[ppm]=8.66 (d, J=5.1 Hz, 2H), 8.15 (s, 1H), 7.67 (dt, J=6.7, 3.4 Hz, 2H), 7.53 (td, J=6.2, 5.5, 2.1 Hz, 2H), 7.40 (t, J=5.1 Hz, 1H), 4.60 (s, 2H), 3.76-3.65 (m, 6H), 3.54 (t, J=6.4 Hz, 2H)

HPLCMS (Method E): [m/z]: 408.1 [M+H]+

General Procedure 8: 2-(2-{[2-(1H-1,3-benzodiazol-2-yl)ethyl]amino}ethyl)-N-[(5-methylpyrimidin-2-yl)methyl]-1,3-thiazole-4-carboxamide (Example Compound No. 155)

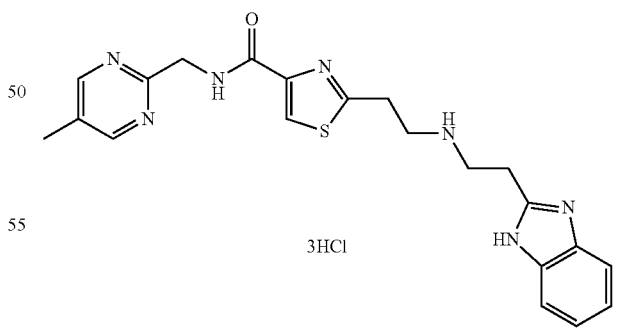

DBU (15.37 µl, 0.1 mmol) was added to a suspension of 2-(2-aminoethyl)-N-[(5-methylpyrimidin-2-yl)methyl]-1,3-thiazole-4-carboxamide dihydrochloride (109) (36 mg, 0.1 mmol) in MeCN (3 ml). N-(2-nitrophenyl)prop-2-enamide (D) (19 mg, 0.1 mmol) was added and the reaction mixture was stirred at room temperature overnight. The reaction was diluted with EtOAc (5 ml) and washed with 10% NaHCO3

(5 ml), water (5 ml), brine (5 ml), dried (MgSO4), filtered and evaporated to give a crude intermediate which was further reacted with iron powder (3 mg, 0.05 mmol) in AcOH (3 ml) at 80° C. for 3 h. The reaction mixture was diluted with water (5 ml), then made basic by slow addition of 10M NaOH (aq). The mixture was then further diluted with water (10 ml) and extracted with 4:1 chloroform/IPA (4×30 ml). The combined organic layers were separated, dried (MgSO$_4$) and evaporated under vacuum. The crude material was purified by basic prep-HPLC to give the title compound (8 mg, 67%) as a colourless film.

1H-NMR (Acetone-d6, 500 MHz): d[ppm]=8.58 (s, 2H), 8.44 (s, 1H), 8.03 (s, 1H), 7.45 (s, 2H), 7.14-7.05 (m, 2H), 4.72 (d, J=4.3 Hz, 2H), 3.24 (t, J=6.5 Hz, 2H), 3.13 (m, 4H), 3.07 (t, J=6.2 Hz, 2H), 2.29 (s, 3H)

HPLCMS (Method C): [m/z]: 422.0 [M+H]$^+$

N-{5H,6H,7H-Cyclopenta[b]pyridin-7-yl}-2-[2-({2-[(2-nitrophenyl)carbamoyl]ethyl}amino)ethyl]-1,3-thiazole-4-carboxamide (Example Compound No. 158)

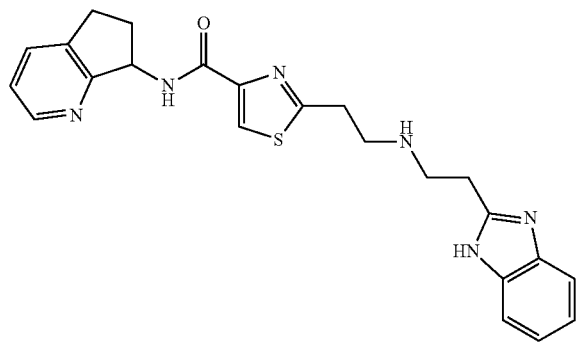 [SMILES: O=C(NC1CCc2cccnc21)c1csc(CCNCCc2nc3ccccc3[nH]2)n1]

In a similar fashion to general procedure 8, 2-(2-amino-ethyl)-N-{5H,6H,7H-cyclopenta[b]pyridin-7-yl}-1,3-thiazole-4-carboxamide dihydrochloride (110) (660 mg, 1.83 mmol), N-(2-nitrophenyl)prop-2-enamide (D) (344 mg, 1.79 mmol) and DBU (0.8 ml, 5.37 mmol) in MeCN (8 ml) gave a crude intermediate which was further reacted with iron powder (180 mg, 3.22 mmol) in AcOH (10 ml) to afford the title compound (176 mg, 25%) as a pale yellow foam after purification by flash column chromatography (eluting with a gradient of 5-10% 3 M ammonia in MeOH/DCM) followed by basic prep-HPLC.

1H-NMR (CDCl$_3$, 500 MHz): d[ppm]=8.27 (d, J=4.7 Hz, 1H), 8.17 (s, 1H), 8.07 (br s, 1H), 7.43 (br s, 2H), 7.37-7.32 (m, 1H), 7.19 (dt, J=8.5, 4.4 Hz, 1H), 7.15-7.11 (m, 2H), 4.73 (dd, J=5.0, 1.3 Hz, 2H), 3.18 (t, J=6.2 Hz, 2H), 3.17-3.08 (m, 4H), 3.04 (t, J=6.2 Hz, 2H)

HPLCMS (Method C): [m/z]: 433.2 [M+H]$^+$ 2-(2-{[2-(1H-1,3-Benzodiazol-2-yl)ethyl]amino}ethyl)-N-[(6-methylpyridazin-3-yl)methyl]-1,3-thiazole-4-carboxamide (Example Compound No. 174)

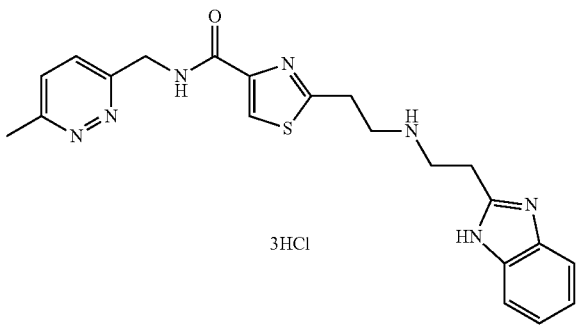 [SMILES: Cc1ccc(CNC(=O)c2csc(CCNCCc3nc4ccccc4[nH]3)n2)nn1]

In a similar fashion to general procedure 8, 2-(2-amino-ethyl)-N-[(6-methylpyridazin-3-yl)methyl]-1,3-thiazole-4-carboxamide dihydrochloride (107) (382 mg, 0.932 mmol), N-(2-nitrophenyl)prop-2-enamide (D) (161 mg, 0.839 mmol) and DBU (0.300 ml, 2.01 mmol) in MeCN (15 ml) at room temperature for 2 h gave the required Michael intermediate (163 mg, 31%) as a yellow oil after purification by flash column chromatography (0-3% MeOH/DCM) followed by a second purification using an isolute silica column with a gradient of 0-2% 7M NH$_3$/MeOH in DCM.

The Michael intermediate (163 mg, 0.288 mmol) was reacted with iron powder (32 mg) in AcOH (3 ml) at 80° C. for 1 h to give the title compound (15 mg, 12%) as a beige solid after purification by basic prep HPLC followed kp-NH silica column chromatography.

1H-NMR (DMSO-d6, 500 MHz): d[ppm]=9.00 (t, J=6.0 Hz, 1H), 8.10 (s, 1H), 7.52-7.42 (m, 4H), 7.13-7.09 (m, 2H), 4.70 (d, J=6.1 Hz, 2H), 3.15 (t, J=6.7 Hz, 2H), 3.04-3.00 (m, 2H), 3.00-2.94 (m, 4H), 2.59 (s, 3H)

HPLCMS (Method B): [m/z]: 422.2 [M+H]$^+$ 2-(2-{[2-(1H-1,3-Benzodiazol-2-yl)ethyl]amino}ethyl)-N-[(3-fluoropyridin-2-yl)methyl]-5-methyl-1,3-thiazole-4-carboxamide (Example Compound No. 165)

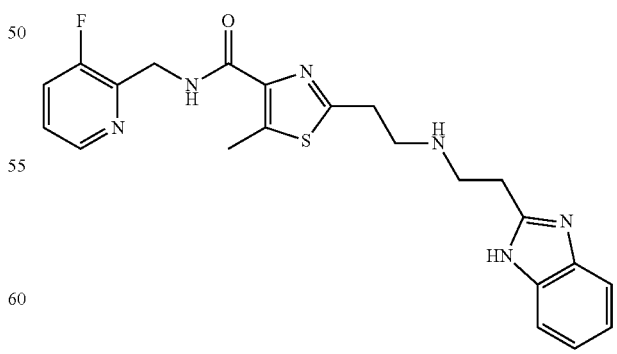

In a similar fashion to general procedure 8, 2-(2-amino-ethyl)-N-[(3-fluoropyridin-2-yl)methyl]-5-methyl-1,3-thiazole-4-carboxamide dihydrochloride (113) (528 mg, 1.44 mmol), N-(2-nitrophenyl)prop-2-enamide (D) (276 mg, 1.44 mmol) and DBU (0.64 ml, 0 mol) in MeCN (20 ml) at room temperature for 16 h gave the crude Michael intermediate (50%, 697 mg, 0.72 mmol) which was then reacted with iron powder (40 mg) in AcOH (4 ml) at 80° C. for 1.5 h to give the title compound (99 mg, 32%) as a pale yellow solid after purification by flash column chromatography eluting 2-40% MeOH in DCM followed by prep-HPLC.

1H-NMR (DMSO-d6, 500 MHz): d[ppm]=8.57 (t, J=5.6 Hz, 1H), 8.38 (dt, J=4.3, 1.3 Hz, 1H), 7.73-7.66 (m, 1H), 7.45 (dd, J=5.7, 3.2 Hz, 2H), 7.40 (dt, J=8.6, 4.4 Hz, 1H), 7.13-7.08 (m, 2H), 4.61 (d, J=5.5 Hz, 2H), 3.06 (q, J=6.3 Hz, 4H), 2.97 (q, J=6.7 Hz, 4H), 2.60 (s, 3H)

HPLCMS (Method C): [m/z]: 439.2 [M+H]+

2-(2-{[2-(1H-1,3-Benzodiazol-2-yl)ethyl]amino}ethyl)-5-methyl-N-(pyrimidin-2-ylmethyl)-1,3-thiazole-4-carboxamide (Example Compound No. 188)

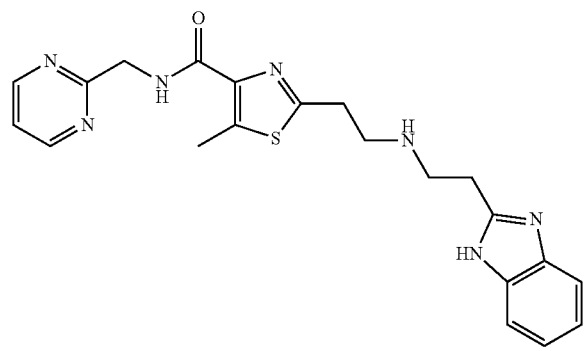 [SMILES: Cc1sc(CCNCCc2nc3ccccc3[nH]2)nc1C(=O)NCc1ncccn1]

In a similar fashion to general procedure 8, 2-(2-aminoethyl)-5-methyl-N-(pyrimidin-2-ylmethyl)-1,3-thiazole-4-carboxamide dihydrochloride (114) (315 mg, 0.594 mmol), N-(2-nitrophenyl)prop-2-enamide (D) (114 mg, 0.594 mmol) and DBU (0.266 ml, 1.781 mmol) in MeCN (12 ml) at room temperature for 3 h gave the required Michael intermediate (142 mg, 42%) as a yellow oil after purification using isolute silica column eluting with a gradient of 0-6% MeOH in DCM.

The Michael intermediate (142 mg, 0.248 mmol) was reacted with iron powder (42 mg) in AcOH (3 ml) at 80° C. for 1.5 h to give the title compound (7 mg, 7%) as a brown solid after purification by basic prep-HPLC followed by isolute silica column chromatography eluting with a gradient of 18% MeOH in DCM.

1H-NMR (Methanol-d4, 500 MHz): d[ppm]=8.72 (d, J=4.9 Hz, 2H), 7.43 (dt, J=6.6, 3.3 Hz, 2H), 7.35 (t, J=4.9 Hz, 1H), 7.19 (dt, J=6.0, 3.4 Hz, 2H), 4.65 (s, 2H), 3.24 (t, J=6.8 Hz, 2H), 3.22-3.17 (m, 4H), 3.15 (t, J=6.6 Hz, 2H), 2.68 (s, 3H)

HPLCMS (Method D): [m/z]: 422.2 [M+H]+

Benzyl N-(3-{[2-(1H-1,3-benzodiazol-2-yl)ethyl][2-(4-{[(3-fluoropyridin-2-yl)methyl]carbamoyl}-1,3-thiazol-2-yl)ethyl]amino}propyl)carbamate (Example Compound No. 179)

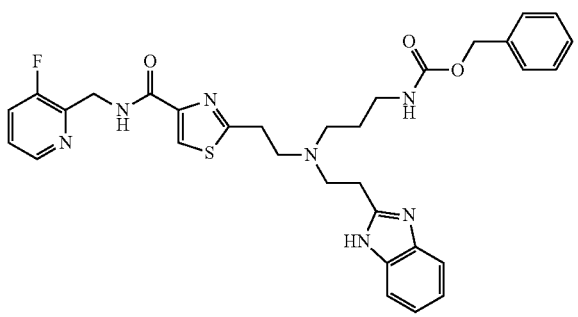 [SMILES: O=C(NCCCN(CCc1nc2ccccc2[nH]1)CCc1nc(C(=O)NCc2ncccc2F)cs1)OCc1ccccc1]

In a similar fashion to general procedure 3, 2-(2-{[2-(1H-1,3-benzodiazol-2-yl)ethyl]amino}ethyl)-N-[(3-fluoropyridin-2-yl)methyl]-1,3-thiazole-4-carboxamide (Example Compound No. 94—freebase) (166 mg, 0.391 mmol), benzyl (3-oxopropyl)carbamate (97 mg, 0.469 mmol) and DIPEA (0.12 ml, 0.587 mmol) in MeOH (1 ml) at room temperature for 1 h, followed by the addition of NaBH4 (22 mg, 0.587 mmol) afforded the title compound (94 mg, 39%) as a pale yellow oil after purification by flash chromatography (eluting with a gradient of 0-5% MeOH/DCM).

HPLCMS (Method F): [m/z]: 616.2 [M+H]+

2-{2-[(3-Aminopropyl)[2-(1H-1,3-benzodiazol-2-yl)ethyl]amino]ethyl}-N-[(3-fluoropyridin-2-yl)methyl]-1,3-thiazole-4-carboxamide (Example Compound No. 163)

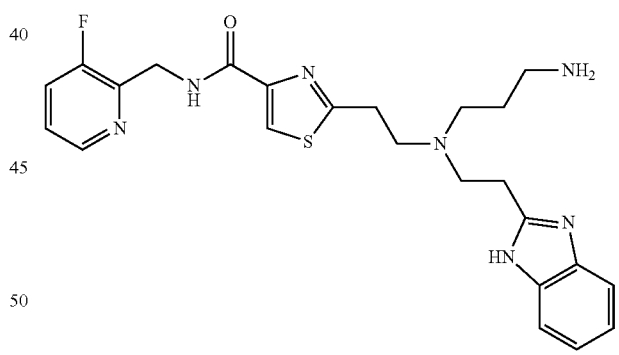

A solution of benzyl N-(3-{[2-(1H-1,3-benzodiazol-2-yl)ethyl][2-(4-{[(3-fluoropyridin-2-yl)methyl]carbamoyl}-1,3-thiazol-2-yl)ethyl]amino}propyl)carbamate (Example Compound No. 179) (45 mg, 0.073 mmol) in AcOH/HBr (1:1, 1 ml) was stirred at 50° C. for 2 h. The reaction mixture was evaporated in vacuo. Purification by basic prep-HPLC afforded the title compound (16 mg, 45%) as a colourless oil.

1H-NMR (Methanol-d4, 500 MHz): d[ppm]=8.32 (d, J=4.7 Hz, 1H), 7.90 (s, 1H), 7.63-7.52 (m, 1H), 7.44 (dt, J=6.6, 3.3 Hz, 2H), 7.35 (dt, J=8.6, 4.4 Hz, 1H), 7.17 (dt, J=6.0, 3.3 Hz, 2H), 4.75 (d, J=1.5 Hz, 2H), 3.20 (t, J=6.6 Hz, 2H), 3.04 (s, 4H), 2.98 (t, J=6.6 Hz, 2H), 2.65 (m, 4H), 1.67 (m, 2H)

HPLCMS (Method D): [m/z]: 482.2 [M+H]+

2-(2-{[2-(1H-1,3-Benzodiazol-2-yl)ethyl](butyl)amino}ethyl)-N-[(3-fluoropyridin-2-yl)methyl]-1,3-thiazole-4-carboxamide (Example Compound No. 157)

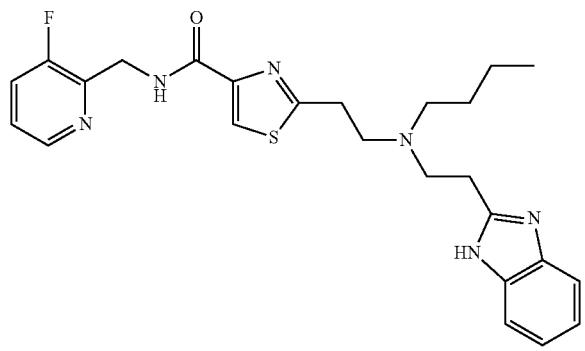 [SMILES: CCCCN(CCc1nc2ccccc2[nH]1)CCc1nc(C(=O)NCc2ncccc2F)cs1]

In a similar fashion to general procedure 3, 2-(2-{[2-(1H-1,3-benzodiazol-2-yl)ethyl]amino}ethyl)-N-[(3-fluoropyridin-2-yl)methyl]-1,3-thiazole-4-carboxamide (Example Compound No. 94—freebase) (60 mg, 0.141 mmol), butanal (12 mg, 0.174 mmol) and DIPEA (98 µl, 0.56 mmol) in MeOH (1 ml) at room temperature for 1 h followed by the addition of NaBH$_4$ (8 mg, 0.21 mmol) afforded the title compound (50 mg, 73%) as a yellow oil after purification by basic prep-HPLC.

1H-NMR (DMSO-d6, 500 MHz): d[ppm]=12.13 (s, 1H), 8.66 (t, J=5.6 Hz, 1H), 8.37 (d, J=4.7 Hz, 1H), 8.06 (s, 1H), 7.69 (ddd, J=9.9, 8.4, 1.2 Hz, 1H), 7.57-7.32 (m, 3H), 7.17-7.01 (m, 2H), 4.65 (d, J=4.6 Hz, 2H), 3.17 (t, J=6.7 Hz, 2H), 2.96 (m, 4H), 2.88 (t, J=6.7 Hz, 2H), 2.58-2.51 (m, 2H), 1.40 (m, 2H), 1.23 (m, 2H), 0.83 (t, J=7.4 Hz, 3H)

HPLCMS (Method D): [m/z]: 481.3 [M+H]$^+$ 2-(2-{bis[2-(1H-1,3-Benzodiazol-2-yl)ethyl]amino}ethyl)-N-[(3-fluoropyridin-2-yl)methyl]-1,3-thiazole-4-carboxamide (Example Compound No. 152)

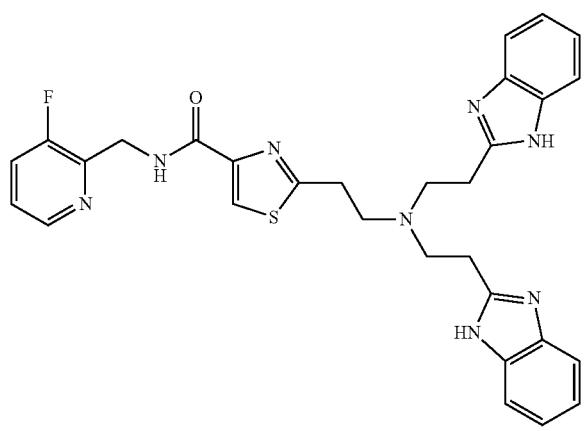 [SMILES: O=C(NCc1ncccc1F)c1csc(CCN(CCc2nc3ccccc3[nH]2)CCc2nc3ccccc3[nH]2)n1]

In a similar fashion to general procedure 7, 2-(2-{[2-(1H-1,3-benzodiazol-2-yl)ethyl]amino}ethyl)-N-[(3-fluoropyridin-2-yl)methyl]-1,3-thiazole-4-carboxamide (Example Compound No. 94—freebase) (400 mg, 1.13 mmol), 2-(2-chloroethyl)-1H-1,3-benzodiazole hydrochloride (492 mg, 2.27 mmol) and DIPEA (3.03 ml, 17 mol) in DMF (5 ml) at 30° C. for 3 d, afforded the title compound (10 mg, 1.5%) as an off-white solid after purification by basic prep-HPLC followed by flash column chromatography (eluting with a gradient of 0-10% MeOH/DCM followed by 0-10% 7N ammonia in MeOH/DCM) and a second basic prep-HPLC.

1H-NMR (DMSO-d6, 500 MHz): d[ppm]=12.28 (s, 1H), 8.66 (t, J=5.7 Hz, 1H), 8.37 (dt, J=4.6, 1.4 Hz, 1H), 8.06 (s, 1H), 7.69 (ddd, J=10.0, 8.3, 1.3 Hz, 1H), 7.61-7.46 (m, 3H), 7.39 (dq, J=8.6, 4.2 Hz, 2H), 7.23-7.04 (m, 4H), 4.77-4.52 (m, 4H), 3.27 (t, J=7.2 Hz, 2H), 3.15-3.04 (m, 2H), 3.02-2.90 (m, 4H), 2.87 (t, J=6.7 Hz, 2H)

HPLCMS (Method B): [m/z]: 569.3 [M+H]$^+$

2-{2-[bis(1H-1,3-Benzodiazol-2-ylmethyl)amino]ethyl}-N-[(3-fluoropyridin-2-yl)methyl]-1,3-thiazole-4-carboxamide (Example Compound No. 166)

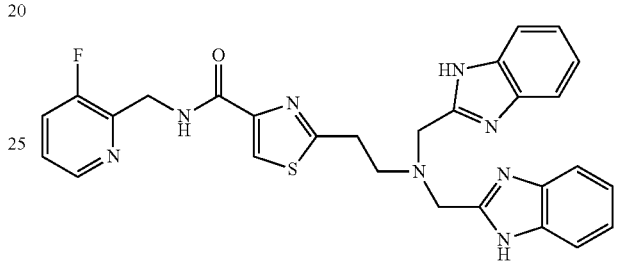

In a similar fashion to general procedure 7, 2-{2-[(1H-1,3-benzodiazol-2-ylmethyl)amino]ethyl}-N-[(3-fluoropyridin-2-yl)methyl]-1,3-thiazole-4-carboxamide (Example Compound No. 40) (110 mg, 0.268 mmol), 2-(chloromethyl)-1H-1,3-benzodiazole (45 mg, 0.268 mmol), DIPEA (0.467 ml, 2.68 mmol) in DMF (1 ml) at 45° C. for 3 h then at 55° C. for 1 h, afforded the title compound (10 mg, 7%) as a white solid after purification by basic prep-HPLC followed by flash column chromatography (eluting with a gradient of 0-10% MeOH/DCM followed by 0-10% 7N ammonia in MeOH/DCM).

1H-NMR (Acetone-d6, 500 MHz): d[ppm]=11.99 (s, 1H), 8.43 (s, 1H), 8.33 (d, J=4.7 Hz, 1H), 8.02 (s, 1H), 7.71-7.55 (m, 3H), 7.51 (s, 2H), 7.37 (dt, J=8.5, 4.4 Hz, 1H), 7.17 (d, J=5.7 Hz, 4H), 4.80-4.70 (m, 2H), 4.17 (s, 4H), 3.37 (t, J=6.9 Hz, 2H), 3.20 (t, J=6.9 Hz, 2H)

HPLCMS (Method B): [m/z]: 541.3 [M+H]$^+$ 2-(2-{[2-(4-Fluoro-1H-1,3-benzodiazol-2-yl)ethyl]amino}ethyl)-N-[(3-fluoropyridin-2-yl)methyl]-1,3-thiazole-4-carboxamide (Example Compound No. 243)

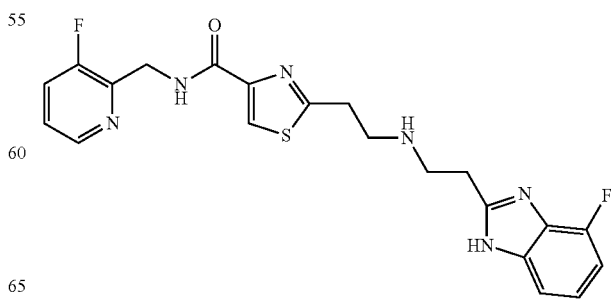

In a similar fashion to general procedure 8, 2-(2-amino-ethyl)-N-[(3-fluoropyridin-2-yl)methyl]-1,3-thiazole-4-carboxamide dihydrochloride (103) (662 mg, 1.87 mmol), N-(3-fluoro-2-nitrophenyl)prop-2-enamide (G) (394 mg, 1.87 mmol) and DBU (924 µl, 6.18 mmol) in MeCN (10 ml) gave a crude intermediate which was further reacted with iron powder (286 mg, 5.12 mmol) in AcOH (15 ml) to afford the title compound (203 mg, 34%) as a white solid after purification by basic prep-HPLC followed by flash column chromatography (eluting with a gradient of 0-20% MeOH/DCM).

1H-NMR (DMSO-d6, 500 MHz): d[ppm]=8.66 (t, J=5.6 Hz, 1H), 8.39 (dt, J=4.7, 1.3 Hz, 1H), 8.08 (s, 1H), 7.70 (ddd, J=10.0, 8.4, 1.1 Hz, 1H), 7.40 (dt, J=8.7, 4.4 Hz, 1H), 7.27 (d, J=8.0 Hz, 1H), 7.10 (td, J=8.0, 4.9 Hz, 1H), 6.92 (dd, J=11.1, 8.0 Hz, 1H), 4.68-4.62 (m, 2H), 3.16 (t, J=6.7 Hz, 2H), 3.05 (t, J=6.7 Hz, 2H), 2.99 (t, J=6.6 Hz, 4H)

HPLCMS (Method B): [m/z]: 443.2 [M+H]+

2-(2-{[(4-fluoro-1H-1,3-benzodiazol-2-yl)methyl]amino}ethyl)-N-[(3-fluoropyridin-2-yl)methyl]-1,3-oxazole-4-carboxamide (Example Compound No. 253)

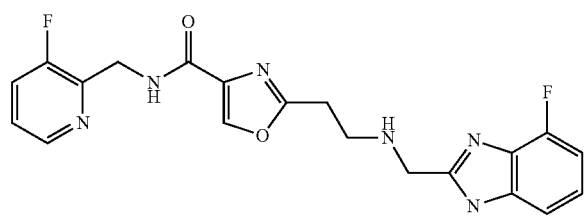 [SMILES: O=C(NCc1ncccc1F)c1coc(CCNCc2nc3c(F)cccc3[nH]2)n1]

In a similar fashion to general procedure 7, 2-(2-amino-ethyl)-N-[(3-fluoropyridin-2-yl)methyl]-1,3-oxazole-4-carboxamide dihydrochloride (235) (100 mg, 0.3 mmol), 2-(chloromethyl)-7-fluoro-1H-1,3-benzodiazole hydrochloride (66 mg, 0.3 mmol) and DIPEA (258 µl, 1.48 mmol) in DMF (2.5 ml) was stirred at 40° C. for 73 h, to afforded the title compound (23 mg, 18%) as a brown glassy solid after purification by reverse phase Biotage (A=water/0.1% NH3; B=MeCN/0.1% NH3; eluting with a gradient of 10% A/B for 2 column volumns, 10% to 30% A/B for 4 column volumns, 30% to 60% A/B for 10 column volumes and 60% to 100% for 5 column volumes).

1H-NMR (DMSO-d6, 500 MHz): d[ppm]=12.49 (br s, 1H), 8.54-8.47 (m, 2H), 8.39-8.34 (m, 1H), 7.73-7.65 (m, 1H), 7.42-7.37 (m, 1H), 7.34-7.24 (m, 1H), 7.15-7.06 (m, 1H), 6.92 (t, 1H), 4.63-4.57 (m, 2H), 3.99-3.91 (m, 2H), 3.02-2.94 (m, 4H), 2.63 (br s, 1H)

HPLCMS (Method D): [m/z]: 413.2 [M+H]+

2-(2-{[(4-fluoro-1H-1,3-benzodiazol-2-yl)methyl]amino}ethyl)-N-[(3-fluoropyridin-2-yl)methyl]-1,3-thiazole-4-carboxamide (Example Compound No. 274)

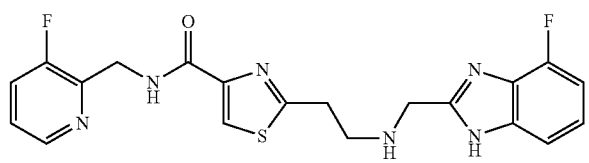 [SMILES: O=C(NCc1ncccc1F)c1csc(CCNCc2nc3c(F)cccc3[nH]2)n1]

In a similar fashion to general procedure 7, 2-(2-amino-ethyl)-N-[(3-fluoropyridin-2-yl)methyl]-1,3-thiazole-4-carboxamide dihydrochloride (103) (200 mg, 0.57 mmol), 2-(chloromethyl)-7-fluoro-1H-1,3-benzodiazole hydrochloride (125 mg, 0.57 mmol) and DIPEA (493 µl, 2.83 mmol) in DMF (5.5 ml) was heated at 40° C. for 18 h, stirred at room temperature for 2 d and then heated at 40° C. for 4 h to give the title compound (7 mg, 3%) as a glassy brown solid after purification by reverse phase chromatography [(eluting with a gradient of 10-100% (water+0.1% ammonia)/(MeCN+0.1% ammonia)].

1H-NMR (DMSO-d6, 500 MHz): d[ppm]=12.50 (s, 1H), 8.70-8.61 (m, 1H), 8.39-8.32 (m, 1H), 8.13 (s, 1H), 7.72-7.66 (m, 1H), 7.42-7.36 (m, 1H), 7.34-7.25 (m, 1H), 7.15-7.08 (m, 1H), 6.93 (m, 1H), 4.68- 4.62 (m, 2H), 4.00-3.94 (m, 2H), 3.22-3.15 (m, 2H), 3.01-2.93 (m, 2H), 2.71 (s, 1H)

HPLCMS (Method D): [m/z]: 429.1 [M+H]+

General Scheme 5 Above:

N-{2-[4-(Benzylcarbamoyl)-1,3-thiazol-2-yl]ethyl}-1H-1,3-benzodiazole-2-carboxamide (Example Compound No. 7)

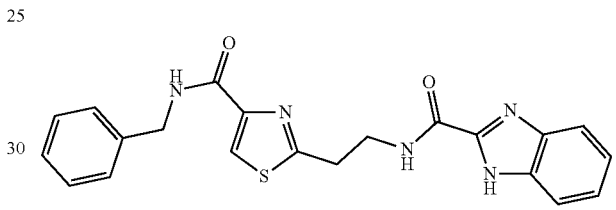

2-(2-Aminoethyl)-N-benzyl-1,3-thiazole-4-carboxamide (104) (70 mg, 0.27 mmol) and 1H-1,3-benzodiazole-2-carboxylic acid (43.43 mg, 0.27 mmol) were dissolved with DCM (5 ml). DIPEA (0.09 ml, 0.54 mmol) was added dropwise, the reaction cooled to 0° C. and T3P (0.12 ml, 0.4 mmol) added dropwise. The reaction was stirred for 1 h at room temperature and then quenched with water (25 ml), extracted with DCM (2×20 ml) and the combined organic layer, dried Na2SO4, filtered & concentrated to give a crude product which was purified by flash chromatography (EtOAc/hexane, 1:1) as a beige coloured solid (80 mg, 71%)

1H-NMR (DMSO-d6, 400 MHz): d[ppm]=13.23 (s, 1H), 9.19 (t, J=6.0 Hz, 1H), 8.87 (t, J=6.3 Hz, 1H), 8.13 (s, 1H), 7.69 (d, J=7.7 Hz, 1H), 7.51 (d, J=7.6 Hz, 1H), 7.33-7.19 (m, 7H), 4.42 (d, J=6.3 Hz, 2H), 3.72 (q, J=6.7 Hz, 2H), 3.33 (d, J=6.8 Hz, 2H)

HPLCMS (Method J): [m/z]: 406.2 [M+H]+

N-Benzyl-2-[2-(1H-imidazol-2-ylformamido)ethyl]-1,3-thiazole-4-carboxamide (Example Compound No. 8)

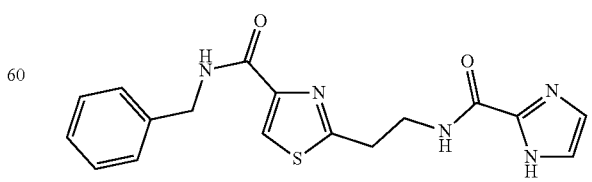

2-(2-Aminoethyl)-N-benzyl-1,3-thiazole-4-carboxamide (104) (70 mg, 0.27 mmol) and 1H-imidazole-2-carboxylic acid (42.89 mg, 0.38 mmol) were dissolved in DCM (5 ml). DIPEA (0.132 ml, 0.76 mmol) was added dropwise, the reaction cooled to 0° C. and T3P (0.17 ml, 0.57 mmol) added dropwise. The reaction was stirred for 1 h at room temperature and then quenched with water (25 ml), extracted with DCM (2×20 ml) and the combined organic layer, dried Na$_2$SO$_4$, filtered & concentrated to give a crude product which was purified by flash chromatography (ethyl acetate/hexane, 1:1) as a colourless solid (38 mg, 48%)

1H-NMR (DMSO-d6, 400 MHz): d[ppm]=12.98 (s, 1H), 8.89 (t, J=6.4 Hz, 1H), 8.69 (t, J=6.0 Hz, 1H), 8.13 (s, 1H), 7.29 (d, J=4.4 Hz, 4H), 7.21 (dd, J=9.1, 4.5 Hz, 2H), 6.98 (s, 1H), 4.44 (d, J=6.4 Hz, 2H), 3.64 (q, J=6.8 Hz, 2H), 3.26 (t, J=6.9 Hz, 2H)

HPLCMS (Method J): [m/z]: 354.4 [M+H]$^+$

N-Benzyl-2-[2-(1-methyl-1H-imidazole-2-sulfonamido)ethyl]-1,3-thiazole-4-carboxamide (Example Compound No. 9)

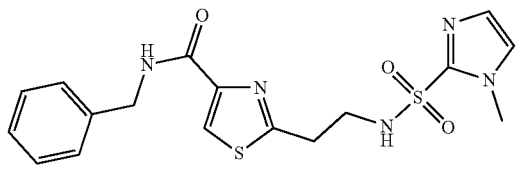 [SMILES: Cn1ccnc1S(=O)(=O)NCCc1nc(C(=O)NCc2ccccc2)cs1]

2-(2-Aminoethyl)-N-benzyl-1,3-thiazole-4-carboxamide (104) (80 mg, 0.31 mmol) and 1-methyl-1H-imidazole-2-sulfonyl chloride (66.35 mg, 0.37 mmol) were dissolved in DCM (5 ml) and the reaction stirred for 2 h. The reaction mixture was concentrated and sat. NaHCO$_3$ added. The aqueous layer was extracted with EtOAc (3×15 ml), combined, dried Na$_2$SO$_4$ was and the required product isolated by flash column chromatography, (ethyl acetate/hexane, 1:1) as a colourless solid (38 mg, 48%)

1H-NMR (CDCl$_3$, 400 MHz): d[ppm]=8.02 (m, 2H), 7.36-7.23 (m, 5H), 6.97 (t, J=4.02 Hz, 1H), 6.86 (d, J=0.9 Hz, 1H), 6.83 (d, J=1.0 Hz, 1H), 4.61 (d, J=6.2 Hz, 2H), 3.87 (s, 3H), 3.63 (q, J=6.2 Hz, 2H), 3.25 (t, J=6.3 Hz, 2H)

HPLCMS (Method J): [m/z]: 406.4 [M+H]$^+$

N-Benzyl-2-{2-[(phenylcarbamoyl)amino]ethyl}-1,3-thiazole-4-carboxamide (Example Compound No. 10)

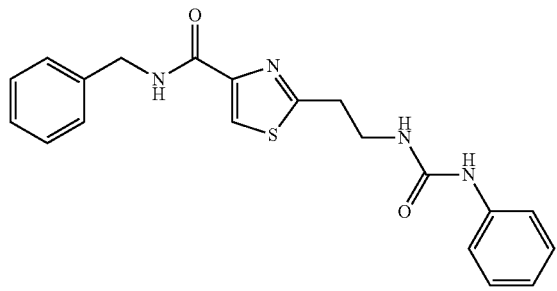 [SMILES: O=C(NCCc1nc(C(=O)NCc2ccccc2)cs1)Nc1ccccc1]

2-(2-Aminoethyl)-N-benzyl-1,3-thiazole-4-carboxamide (104) (50 mg, 0.19 mmol) and benzene isocyanate (30 mg, 0.23 mmol) were dissolved in DCM (5 ml) and the reaction stirred for 2 h. The reaction mixture was concentrated and the required product isolated by flash column chromatography, (ethyl acetate/hexane, 1:1) as a colourless solid (46 mg, 62%)

1H-NMR (CDCl$_3$, 400 MHz): d[ppm]=7.86 (d, J=2.3 Hz), 7.63 (s, 1H), 7.36-7.28 (m, 5H) 7.25-7.20 (m, 4H), 7.02 (m, 1H), 6.82 (s, 1H), 5.44 (s, 1H), 4.57 (d, J=6.0 Hz, 2H), 3.70 (q, J=6.2, 2H), 3.21 (t, J=6.1 Hz, 2H), 3.70 (q, J=6.2, 2H)

HPLCMS (Method J): [m/z]: 381.5 [M+H]$^+$

General Scheme 6 Above:

General Procedure 9: 2-{2-[(1H-1,3-Benzodiazol-2-yl)amino]ethyl}-N-[(3-fluoropyridin-2-yl)methyl]-1,3-thiazole-4-carboxamide dihydrochloride (Example Compound No. 121)

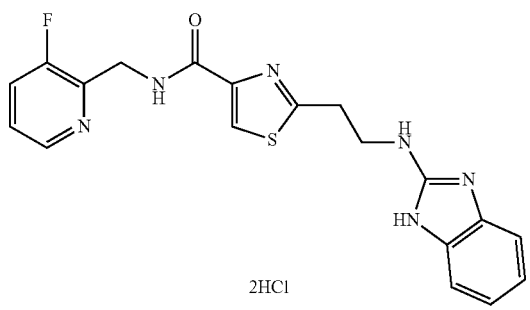 [SMILES: O=C(NCc1ncccc1F)c1csc(CCNc2nc3ccccc3[nH]2)n1]

A solution of 2-(2-aminoethyl)-N-[(3-fluoropyridin-2-yl)methyl]-1,3-thiazole-4-carboxamide dihydrochloride (103) (1.65 g, 2.62 mmol, 56% purity), 2-chloro-1H-benzimidazole (0.1 g, 0.66 mmol) and DIPEA (0.571 ml, 3.277 mmol) in n-butanol (3 ml) and MeOH (0.1 ml) was heated at 150° C. under microwave irradiation for 2.5 h. The reaction mixture was concentrated in vacuo. The residue was dissolved in saturated NaHCO$_3$ solution, diluted with water (20 ml) and extracted with 4:1 chloroform/IPA (4×20 ml). The combined organic extracts were dried (MgSO$_4$), filtered and evaporated in vacuo. The residue was purified by flash column chromatography (kp-NH, eluting with a gradient of 0-10% MeOH/EtOAc) followed by basic prep-HPLC. The residue obtained was dissolved in MeOH (4 ml) and treated with 12 M HCl (1 ml) for 2 h. Evaporation in vacuo afforded the title compound (0.131 g, 43%) as a white solid.

1H-NMR (Methanol-d4, 500 MHz): d[ppm]=8.60 (d, J=5.5 Hz, 1H), 8.31 (t, J=8.3 Hz, 1H), 8.19 (s, 1H), 7.93 (br, J=3.8 Hz, 1H), 7.38 (dt, J=7.1, 3.5 Hz, 2H), 7.28 (dd, J=5.9, 3.2 Hz, 2H), 4.93 (s, 2H), 3.99 (t, J=6.4 Hz, 2H), 3.49 (t, J=6.4 Hz, 2H)

HPLCMS (Method D): [m/z]: 397.1 [M+H]$^+$

2-{3-[(1H-1,3-Benzodiazol-2-yl)amino]propyl}-N-[(3-fluoropyridin-2-yl)methyl]-1,3-thiazole-4-carboxamide (Example Compound No. 135)

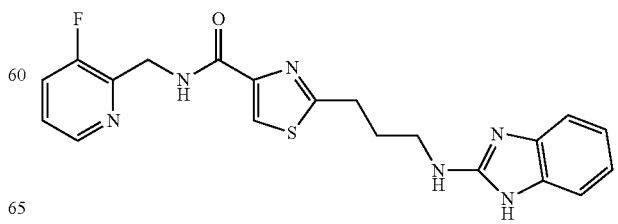

In a similar fashion to general procedure 9, 2-(3-amino-propyl)-N-[(3-fluoropyridin-2-yl)methyl]-1,3-thiazole-4-carboxamide dihydrochloride (115) (173 mg, 0.472 mmol), 2-chloro-1H-benzimidazole (60 mg, 0.393 mmol), DIPEA (0.21 ml, 1.18 mmol), n-BuOH (2 ml) and DMF (0.5 ml) at 150° C. in the microwave for 1 h, gave the title compound (26 mg, 16%) as an off-white solid after purification by basic prep-HPLC.

1H-NMR (DMSO-d6, 500 MHz): d[ppm]=10.74 (s, 1H), 8.68 (t, J=5.7 Hz, 1H), 8.37 (dt, J=4.7, 1.4 Hz, 1H), 8.15 (s, 1H), 7.70 (ddd, J=10.0, 8.3, 1.3 Hz, 1H), 7.40 (dt, J=8.6, 4.4 Hz, 1H), 7.11 (dd, J=14.8, 7.6 Hz, 2H), 6.96-6.75 (m, 2H), 6.67 (t, J=5.7 Hz, 1H), 4.65 (dd, J=5.7, 1.4 Hz, 2H), 3.39 (q, J=6.7 Hz, 2H), 3.18-3.07 (m, 2H), 2.07 (m, 2H)

HPLCMS (Method D): [m/z]: 411.2 [M+H]$^+$

General Scheme 7 Above:

Ethyl 2-({[2-(1H-1,3-benzodiazol-2-yl)ethyl]amino}methyl)-1,3-thiazole-4-carboxylate (120)

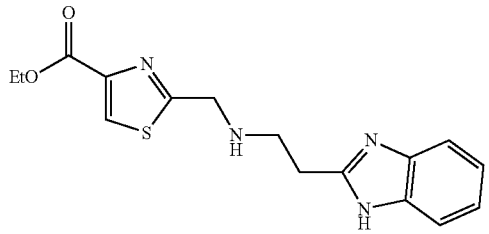 [SMILES: CCOC(=O)c1csc(CNCCc2nc3ccccc3[nH]2)n1]

In a similar fashion to general procedure 3, 2-(1H-benz-imidazol-2-yl)ethanamine dihydrochloride (379 mg, 1.62 mmol), ethyl 2-formyl-1,3-thiazole-4-carboxylate (300 mg, 1.62 mmol), DIPEA (1.13 ml, 6.48 mmol) and MgSO$_4$ (100 mg) in DCM (10 ml) at room temperature for 24 h, followed by addition of NaBH$_4$ (92 mg, 2.43 mmol) gave the title compound (201 mg, 35%) as a white solid after purification by flash column chromatography (kp-NH, eluting with a gradient of 0-15% MeOH/EtOAc).

1H-NMR (DMSO-d6, 500 MHz): d[ppm]=12.17 (s, 1H), 8.40 (s, 1H), 7.51 (d, J=7.8 Hz, 1H), 7.40 (d, J=7.1 Hz, 1H), 7.16-7.07 (m, 2H), 4.28 (q, J=7.1 Hz, 2H), 4.05 (m, 2H), 3.04 (m, 2H), 2.99 (t, J=5.8 Hz, 2H), 2.52 (s, 2H), 1.29 (t, J=7.1 Hz, 3H)

HPLCMS (Method A): [m/z]: 331.0 [M+H]$^+$

Ethyl 2-({[3-(1H-1,3-benzodiazol-2-yl)propyl]amino}methyl)-1,3-thiazole-4-carboxylate (121)

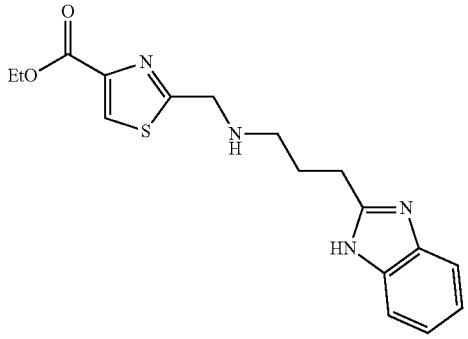 [SMILES: CCOC(=O)c1csc(CNCCCc2nc3ccccc3[nH]2)n1]

In a similar fashion to general procedure 3, 3-(1H-benz-imidazol-2-yl)propan-1-amine (568 mg, 3.24 mmol), ethyl 2-formyl-1,3-thiazole-4-carboxylate (600 mg, 3.24 mmol), DIPEA (2.26 ml, 12.96 mmol) and MgSO$_4$ (300 mg) in DCM (20 ml) at room temperature for 24 h, followed by addition of NaBH$_4$ (184 mg, 4.86 mmol) afforded the title compound (570 mg, 31%, 62% purity) as a white solid after purification by flash column chromatography (kp-NH, eluting with a gradient of 0-10% MeOH/EtOAc).

1H-NMR (DMSO-d6, 500 MHz): d[ppm]=12.14 (s, 1H), 8.39 (s, 1H), 7.50 (d, J=6.9 Hz, 1H), 7.39 (d, J=7.0 Hz, 1H), 7.14-7.05 (m, 2H), 4.28 (q, J=7.1 Hz, 2H), 3.99 (m, 2H), 2.87 (t, J=7.6 Hz, 2H), 1.94 (q, J=7.3 Hz, 2H), 1.29 (t, J=7.1 Hz, 3H)

HPLCMS (Method A): [m/z]: 345.00 [M+H]$^+$

Tert-butyl 2-(2-{[(tert-butoxy)carbonyl]({[4-(ethoxycarbonyl)-1,3-thiazol-2-yl]methyl})amino}ethyl)-1H-1,3-benzodiazole-1-carboxylate (122)

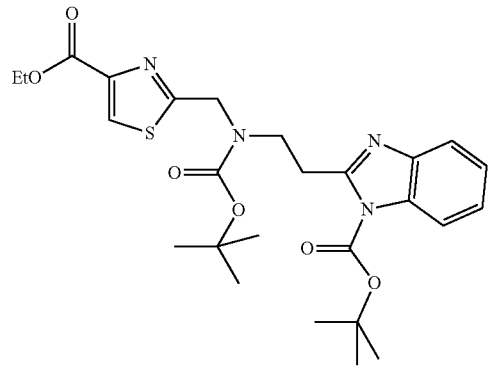 [SMILES: CCOC(=O)c1csc(CN(CCc2nc3ccccc3n2C(=O)OC(C)(C)C)C(=O)OC(C)(C)C)n1]

In a similar fashion to general procedure 4, ethyl 2-({[2-(1H-1,3-benzodiazol-2-yl)ethyl]amino}methyl)-1,3-thiazole-4-carboxylate (120) (201 mg, 0.608 mmol), Boc$_2$O (146 mg, 0.669 mmol) and TEA (0.08 ml, 0.608 mmol) in THF (10 ml) at room temperature for 20 h, gave the afforded the title compound (345 mg, 94%) as a colourless oil after purification by flash column chromatography (eluting with a gradient of 40-100% EtOAc/heptane).

HPLCMS (Method A): [m/z]: 531.15 [M+H]$^+$

Tert-butyl 2-(3-{[(tert-butoxy)carbonyl]({[4-(ethoxycarbonyl)-1,3-thiazol-2-yl]methyl})amino}propyl)-1H-1,3-benzodiazole-1-carboxylate (123)

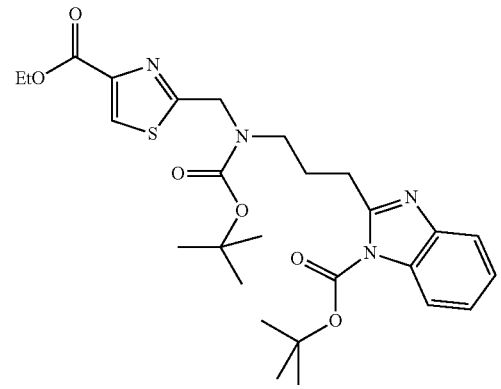 [SMILES: CCOC(=O)c1csc(CN(CCCc2nc3ccccc3n2C(=O)OC(C)(C)C)C(=O)OC(C)(C)C)n1]

In a similar fashion to general procedure 4, ethyl 2-({[3-(1H-1,3-benzodiazol-2-yl)propyl]amino}methyl)-1,3-thiazole-4-carboxylate (121) (0.570 g, 1.018 mmol, 62% purity), Boc₂O (1.56 g, 7.124 mmol) and TEA (0.671 ml, 5.089 mmol) in THF (40 ml) at room temperature for 72 h, following further Boc₂O (0.444 g, 2.036 mmol) for 4 h and further addition of Boc₂O (0.444 g, 2.036 mmol) for more 16 h, gave the title compound (1.162 g, 48% purity, quant.) as a yellow oil after purification by flash column chromatography (eluting with a gradient of 0-60% EtOAc/heptane).

HPLCMS (Method A): [m/z]: 545.15 [M+H]⁺

2-({[2-(1H-1,3-Benzodiazol-2-yl)ethyl][(tert-butoxy)carbonyl]amino}methyl)-1,3-thiazole-4-carboxylic Acid (124)

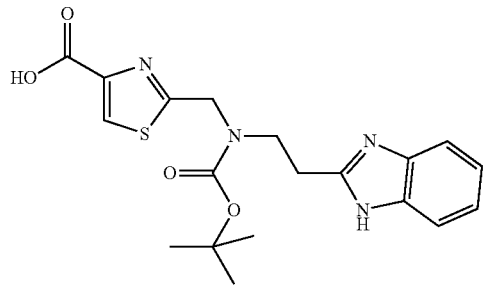 [SMILES: CC(C)(C)OC(=O)N(CCc1nc2ccccc2[nH]1)Cc1nc(C(=O)O)cs1]

In a similar fashion to general procedure 5, tert-butyl 2-(2-{[(tert-butoxy)carbonyl]({[4-(ethoxycarbonyl)-1,3-thiazol-2-yl]methyl})amino}ethyl)-1H-1,3-benzodiazole-1-carboxylate (122) (385 mg, 0.73 mmol) and LiOH (87 mg, 3.63 mmol) in THF/water (25 ml/5 ml) afforded the title compound (350 mg, 99%, 83% purity) as a white solid.

HPLCMS (Method A): [m/z]: 403.00 [M+H]⁺

2-({[3-(1H-1,3-Benzodiazol-2-yl)propyl][(tert-butoxy)carbonyl]amino}methyl)-1,3-thiazole-4-carboxylic Acid (125)

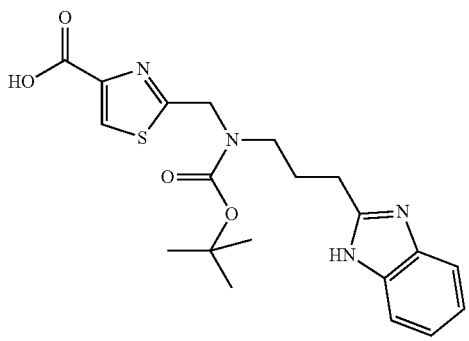 [SMILES: CC(C)(C)OC(=O)N(CCCc1nc2ccccc2[nH]1)Cc1nc(C(=O)O)cs1]

In a similar fashion to general procedure 5, tert-butyl 2-(3-{[(tert-butoxy)carbonyl]({[4-(ethoxycarbonyl)-1,3-thiazol-2-yl]methyl})amino}propyl)-1H-1,3-benzodiazole-1-carboxylate (123) (1.16 g, 1.02 mmol, 48% purity) and LiOH (122 mg, 5.09 mmol) in THF/water (20 ml/5 ml) afforded the crude title compound (811 mg, 52% purity) as an off-white solid.

1H-NMR (DMSO-d6, 500 MHz): d[ppm]=8.39 (s, 1H), 7.65 (br s, 2H), 7.37 (br s, 2H), 4.68 (br s, 2H), 3.38 (br s, 2H), 3.00 (br s, 2H), 2.08 (br s, 2H), 1.34 (s, 9H)

HPLCMS (Method A): [m/z]: 417.05 [M+H]⁺

Tert-butyl N-[2-(1H-1,3-benzodiazol-2-yl)ethyl]-N-[(4-{[(3-fluoropyridin-2-yl)methyl]carbamoyl}-1,3-thiazol-2-yl)methyl]carbamate (126)

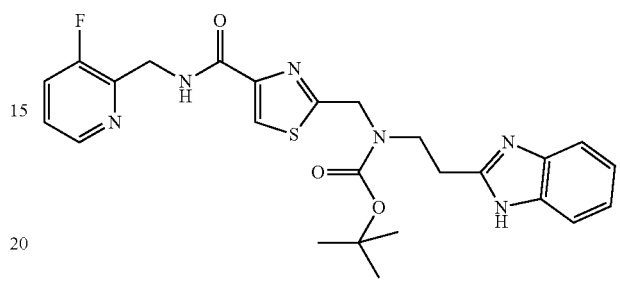

In a similar fashion to general procedure 6, 2-({[2-(1H-1,3-benzodiazol-2-yl)ethyl][(tert-butoxy)carbonyl]amino}methyl)-1,3-thiazole-4-carboxylic acid (124) (175 mg, 0.36 mmol, 83% purity), (3-fluoropyridin-2-yl)methanamine dihydrochloride (A2) (108 mg, 0.54 mmol), DIPEA (0.25 ml, 1.44 mmol) and HATU (206 mg, 0.54 mmol) in DMF (4 ml) afforded the title compound (81 mg, 44%) as a colourless solid after purification by basic prep-HPLC.

1H-NMR (DMSO-d6, 500 MHz): d[ppm]=12.24 (s, 1H), 8.75 (s, 1H), 8.36 (s, 1H), 8.22 (s, 1H), 7.73-7.66 (m, 1H), 7.50 (s, 1H), 7.46-7.37 (m, 2H), 7.11 (s, 2H), 4.72 (s, 2H), 4.66 (d, J=4.4 Hz, 2H), 3.76 (m, 2H), 3.20-3.05 (m, 2H), 1.30 (s, 9H)

HPLCMS (Method A): [m/z]: 511.10 [M+H]⁺

Tert-butyl N-[3-(1H-1,3-benzodiazol-2-yl)propyl]-N-[(4-{[(3-fluoropyridin-2-yl)methyl]carbamoyl}-1,3-thiazol-2-yl)methyl]carbamate (127)

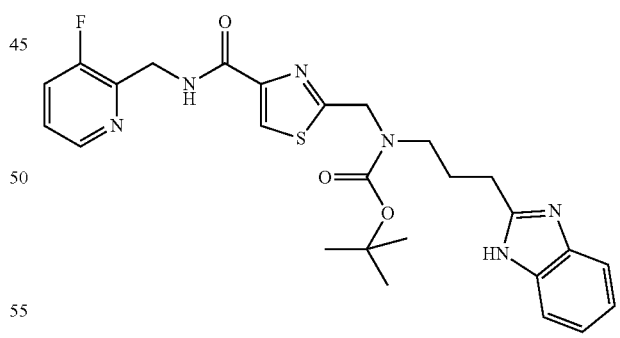

In a similar fashion to general procedure 6, 2-({[3-(1H-1,3-benzodiazol-2-yl)propyl][(tert-butoxy)carbonyl]amino}methyl)-1,3-thiazole-4-carboxylic acid (125) (406 mg, 0.51 mmol, 52% purity), (3-fluoropyridin-2-yl)methanamine dihydrochloride (A2) (152 mg, 0.76 mmol), DIPEA (0.36 ml, 2.04 mmol) and HATU (291 mg, 0.76 mmol) in DMF (4 ml) afforded the title compound (215 mg, 75%) as a white solid after purification by flash column chromatography (kp-NH, eluting with a gradient of 70-100% EtOAc/heptane).

1H-NMR (DMSO-d6, 500 MHz): d[ppm]=12.15 (s, 1H), 8.68 (t, J=5.5 Hz, 1H), 8.36 (s, 1H), 8.22 (s, 1H), 7.69 (t, J=9.3 Hz, 1H), 7.52-7.45 (m, 1H), 7.42-7.34 (m, 2H), 7.09 (s, 2H), 4.71 (s, 2H), 4.65 (d, J=5.5 Hz, 2H), 3.41 (s, 2H), 2.81 (t, J=7.3 Hz, 2H), 2.04 (m, 2H), 1.34 (s, 9H)

HPLCMS (Method A): [m/z]: 525.15 [M+H]$^+$

Tert-butyl N-[3-(1H-1,3-benzodiazol-2-yl)propyl]-N-[(4-{[(3,5-difluoropyridin-2-yl)methyl]carbamoyl}-1,3-thiazol-2-yl)methyl]carbamate (128)

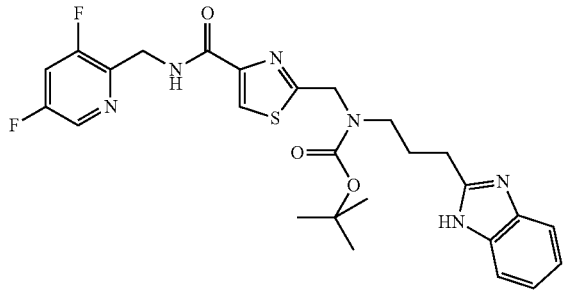 [SMILES: CC(C)(C)OC(=O)N(CCCc1nc2ccccc2[nH]1)Cc1nc(C(=O)NCc2ncc(F)cc2F)cs1]

In a similar fashion to general procedure 6, 2-({[3-(1H-1,3-benzodiazol-2-yl)propyl][(tert-butoxy)carbonyl]amino}methyl)-1,3-thiazole-4-carboxylic acid (125) (0.146 g, 0.351 mmol), (3,5-difluoropyridin-2-yl)methanamine dihydrochloride (0.114 g, 0.526 mmol), DIPEA (0.305 ml, 1.753 mmol) and HATU (0.227 g, 0.526 mmol) in DMF (3 ml) at room temperature for 2 h afforded the title compound (0.071 g, 37%) as a glassy solid after purification by basic prep-HPLC.

1H NMR (DMSO-d6, 500 MHz): d[ppm]=12.14 (s, 1H), 8.73-8.66 (m, 1H), 8.47-8.41 (m, 1H), 8.24-8.18 (m, 1H), 7.95-7.87 (m, 1H), 7.52-7.45 (m, 1H), 7.41-7.35 (m, 1H), 7.15-7.05 (m, 2H), 4.70 (s, 2H), 4.61 (d, J=5.7 Hz, 2H), 3.45-3.38 (m, 2H), 2.85-2.77 (m, 2H), 2.07-1.99 (m, 2H), 1.34 (s, 9H)

HPLCMS (Method A): [m/z]: 543.15 [M+H]$^+$ 2-({[2-(1H-1,3-Benzodiazol-2-yl)ethyl]amino}methyl)-N-[(3-fluoropyridin-2-yl)methyl]-1,3-thiazole-4-carboxamide Trihydrochloride (Example Compound No. 118)

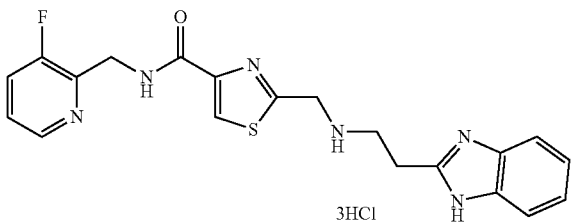 [SMILES: O=C(NCc1ncccc1F)c1csc(CNCCc2nc3ccccc3[nH]2)n1]

In a similar fashion to general procedure 2, tert-butyl N-[2-(1H-1,3-benzodiazol-2-yl)ethyl]-N-[(4-{[(3-fluoropyridin-2-yl)methyl]carbamoyl}-1,3-thiazol-2-yl)methyl]carbamate (126) (81 mg, 0.159 mmol) and 12M HCl (0.53 ml) in MeOH (5 ml) at room temperature for 4 d and then at 40° C. for 4 h afforded the title compound (49 mg, 58%) as a white solid.

1H-NMR (DMSO-d6, 500 MHz): d[ppm]=8.81 (s, 1H), 8.41 (s, 1H), 8.36 (dt, J=4.7, 1.4 Hz, 1H), 7.78 (dd, J=6.1, 3.1 Hz, 2H), 7.72 (ddd, J=10.0, 8.4, 1.2 Hz, 1H), 7.53 (dd, J=6.0, 3.1 Hz, 2H), 7.40 (dd, J=8.4, 4.3 Hz, 1H), 4.73 (s, 2H), 4.69 (d, J=5.1 Hz, 2H), 3.79 (br s, 2H), 3.73 (br s, 2H)

HPLCMS (Method D): [m/z]: 411.1 [M+H]$^+$ 2-({[3-(1H-1,3-Benzodiazol-2-yl)propyl]amino}methyl)-N-[(3-fluoropyridin-2-yl)methyl]-1,3-thiazole-4-carboxamide Trihydrochloride (Example Compound No. 119)

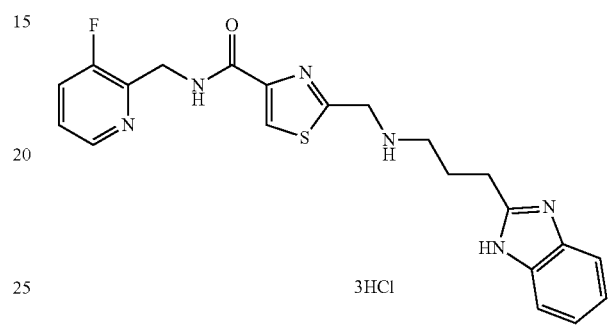

In a similar fashion to general procedure 2, 12M HCl (0.635 ml) was added to a solution of tertbutyl N-[3-(1H-1,3-benzodiazol-2-yl)propyl]-N-[(4-{[(3-fluoropyridin-2-yl)methyl]carbamoyl}-1,3-thiazol-2-yl)methyl]carbamate (127) (215 mg, 0.381 mmol) in MeOH (5 ml) and the mixture stirred for 16 h. Further 12M HCl (0.635 ml, 7.623 mmol) was added and the mixture stirred for a further 20 h. The reaction mixture was evaporated in vacuo to afford the title compound (139 mg, 68%) as a white solid.

1H-NMR (DMSO-d6, 500 MHz): d[ppm]=9.96 (br s, 1H), 8.78 (br s, 1H), 8.40 (s, 1H), 8.38 (d, J=4.4 Hz, 1H), 7.80-7.76 (m, 2H), 7.73 (t, J=8.1 Hz, 1H), 7.55-7.51 (m, 2H), 7.44-7.39 (m, 1H), 4.70 (d, J=4.6 Hz, 2H), 4.64 (s, 2H), 3.35 (t, J=7.2 Hz, 2H), 3.23 (t, J=7.4 Hz, 2H), 2.39-2.33 (m, 2H)

HPLCMS (Method D): [m/z]: 425.2 [M+H]$^+$ 2-({[3-(1H-1,3-Benzodiazol-2-yl)propyl]amino}methyl)-N-[(3,5-difluoropyridin-2-yl)methyl]-1,3-thiazole-4-carboxamide Dihydrochloride (Example Compound No. 124)

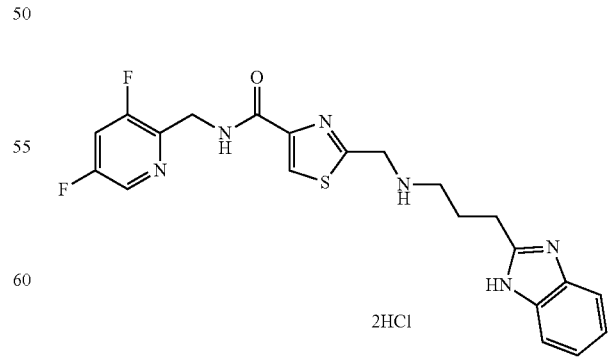

In a similar fashion to general procedure 2, 12M HCl (0.524 ml, 6.28 mmol) was added to a solution tert butyl tert-butyl N-[3-(1H-1,3-benzodiazol-2-yl)propyl]-N-[(4-{

[(3,5-difluoropyridin-2-yl)methyl]carbamoyl}-1,3-thiazol-2-yl)methyl]carbamate (128) (0.071 g, 0.131 mmol) in MeOH (3 ml) at 45° C. for 4 h, to give the title compound (0.036 g, 53%) as a white solid.

1H NMR (Methanol-d4, 500 MHz): d[ppm]=8.37 (s, 1H), 8.35-8.30 (m, 1H), 7.81-7.76 (m, 2H), 7.66-7.57 (m, 3H), 4.79 (s, 2H), 4.74 (s, 2H), 3.45-3.36 (m, 4H), 2.51-2.41 (m, 2H)

HPLCMS (Method D): [m/z]: 443.2 [M+H]+

General Scheme 8 Above:

General Procedure 10:
3-Bromo-N-(2-nitrophenyl)propanamide (129)

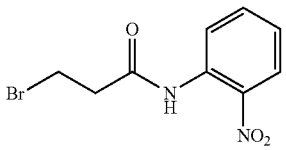 [SMILES: O=C(CCBr)Nc1ccccc1[N+](=O)[O-]]

3-Bromopropanoyl chloride (1.59 ml, 15.75 mmol) was added dropwise to an ice-cold solution of 2-nitroaniline (2.18 g, 15.75 mmol) and TEA (2.63 ml, 18.9 mmol) in toluene (50 ml) and the mixture stirred for 2 h. The reaction mixture was concentrated in vacuo and the residue triturated with water (10 ml) to give a brown precipitate which was collected by filtration. Purification by flash column chromatography (eluting with a gradient of 0-10% EtOAc/heptane) afforded the title compound (0.988 g, 23%) as a yellow crystalline solid.

1H-NMR (CDCl$_3$, 250 MHz): d[ppm]=10.45 (s, 1H), 8.81 (dd, J=8.5, 1.2 Hz, 1H), 8.25 (dd, J=8.5, 1.6 Hz, 1H), 7.78-7.61 (m, 1H), 7.24 (ddd, J=8.5, 7.3, 1.3 Hz, 1H), 3.74 (t, J=6.5 Hz, 2H), 3.11 (t, J=6.5 Hz, 2H)

HPLCMS (Method A): [m/z]: 272.95/274.90 [M+H]$^+$

3-Bromo-N-(4-fluoro-2-nitrophenyl)propanamide (130)

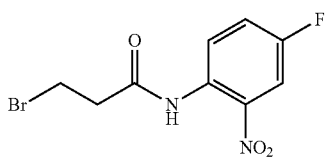 [SMILES: O=C(CCBr)Nc1ccc(F)cc1[N+](=O)[O-]]

In a similar fashion to general procedure 10, 3-bromopropanoyl chloride (2.29 ml, 23.06 mmol), 4-fluoro-2-nitroaniline (3 g, 19.22 mmol) and TEA (3.124 ml, 23.06 mmol) in toluene (35 ml) at room temperature for 40 h afforded the title compound (3.04 g, 42%) as a yellow solid after purification by flash column chromatography (eluting with a gradient of 0-40% EtOAc/heptane).

1H-NMR (DMSO-d6, 500 MHz): d[ppm]=10.38 (s, 1H), 7.91 (dd, J=8.6, 2.5 Hz, 1H), 7.65-7.60 (m, 2H), 3.68 (t, J=6.4 Hz, 2H), 2.97 (t, J=6.4 Hz, 2H)

HPLCMS (Method A): [m/z]: 290.75/292.75 [M+H]$^+$

4-Bromo-N-(2-nitrophenyl)butanamide (131)

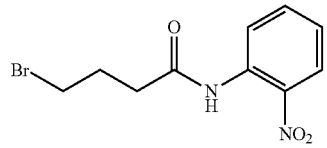

In a similar fashion to general procedure 10, 4-bromobutanoyl chloride (1.56 ml, 13.48 mmol), 2-nitroaniline (1.55 g, 11.24 mmol) and TEA (1.566 ml, 11.2 mmol) in toluene (25 ml) at room temperature for 16 h, gave the title compound (2.35 g, 41%) as a yellow oil after purification by flash column chromatography (eluting with a gradient of 0-40% EtOAc/heptane).

1H NMR (DMSO-d6, 500 MHz): d[ppm]=10.33 (s, 1H), 7.93 (dd, J=8.2, 1.4 Hz, 1H), 7.72-7.65 (m, 1H), 7.58 (dd, J=8.1, 1.2 Hz, 1H), 7.38-7.34 (m, 1H), 3.58 (t, J=6.6 Hz, 2H), 2.51 (t, J=6.6 Hz, 2H, obscured by DMSO), 2.13-2.06 (m, 2H)

HPLCMS (Method A): [m/z]: 288.75 [M+H]$^+$

General Procedure 11: Ethyl 2-[2-({2-[(2-nitrophenyl)carbamoyl]ethyl}amino)ethyl]-1,3-thiazole-4-carboxylate (132)

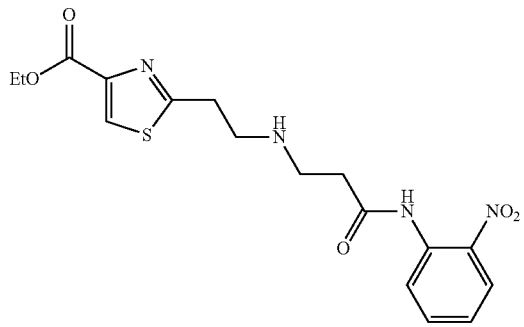 [SMILES: CCOC(=O)c1csc(CCNCCC(=O)Nc2ccccc2[N+](=O)[O-])n1]

To a solution of 3-Bromo-N-(2-nitrophenyl)propanamide (129) (1.04 g, 3.8 mmol) in DMF (10 ml) was added dropwise over 20 min to a mixture of ethyl 2-(2-aminoethyl)-1,3-thiazole-4-carboxylate hydrochloride (1 g, 3.8 mmol, 90% purity) and Na$_2$CO$_3$ (0.48 g, 4.56 mmol) in DMF (30 ml). The reaction mixture was stirred for 16 h at room temperature. Water (10 ml) was added and the mixture extracted with EtOAc (3×20 ml). The combined organic extracts were washed with brine (10 ml), dried (MgSO$_4$), filtered and evaporated in vacuo to give the crude title compound (1.5 g, 70%, 70% purity) which was used without purification.

HPLCMS (Method A): [m/z]: 393.1 [M+H]$^+$

Ethyl 2-[2-({2-[(4-fluoro-2-nitrophenyl)carbamoyl]ethyl}amino)ethyl]-1,3-thiazole-4-carboxylate (133)

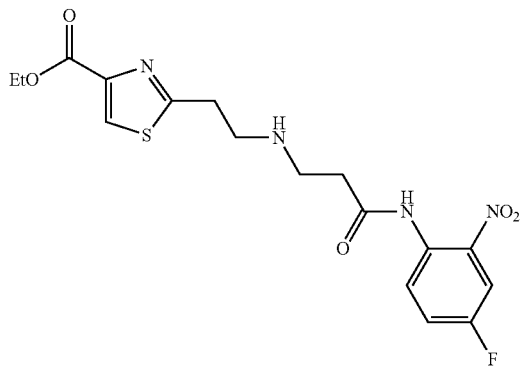 [SMILES: CCOC(=O)c1csc(CCNCCC(=O)Nc2ccc(F)cc2[N+](=O)[O-])n1]

In a similar fashion to general procedure 11, 3-bromo-N-(4-fluoro-2-nitrophenyl)propanamide (130) (1 g, 2.68 mmol), ethyl 2-(2-aminoethyl)-1,3-thiazole-4-carboxylate hydrochloride (0.634 g, 2.68 mmol) and Na$_2$CO$_3$ (0.426 g, 4.02 mmol) in DMF (10 ml) at room temperature for 24 h gave the crude title compound (2.26 g, 80%, 39% purity) which was used without purification.

HPLCMS (Method A): [m/z]: 411 [M+H]$^+$

Ethyl 2-[2-({3-[(2-nitrophenyl)carbamoyl]propyl}amino)ethyl]-1,3-thiazole-4-carboxylate (134)

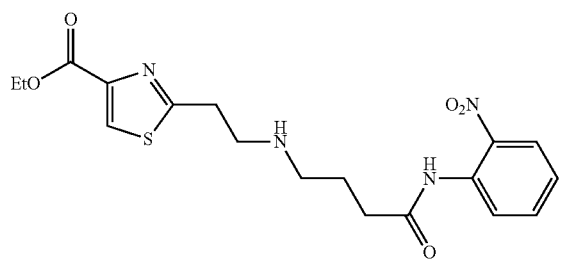 [SMILES: CCOC(=O)c1csc(CCNCCCC(=O)Nc2ccccc2[N+](=O)[O-])n1]

In a similar fashion to general procedure 11, 4-Bromo-N-(2-nitrophenyl)butanamide (131) (2.35 g, 4.65 mmol), ethyl 2-(2-aminoethyl)-1,3-thiazole-4-carboxylate hydrochloride (1.10 g, 4.66 mmol), Na$_2$CO$_3$ (0.74 g, 6.98 mmol) and DMF (25 ml) at room temperature for 16 h gave the crude title compound (3.0 g, quant.) as yellow oil, which was used in the next step without purification.

HPLCMS (Method A): [m/z]: 407 [M+H]$^+$

Ethyl 2-(2-{[(tert-butoxy)carbonyl]({2-[(2-nitrophenyl)carbamoyl]ethyl})amino}ethyl)-1,3-thiazole-4-carboxylate (135)

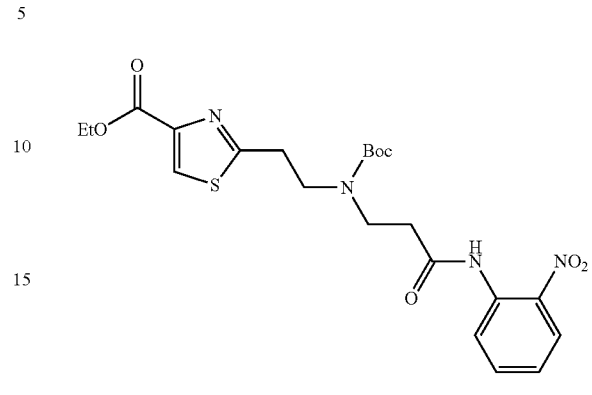

In a similar fashion to general procedure 4, ethyl 2-[2-({2-[(2-nitrophenyl)carbamoyl]ethyl}amino)ethyl]-1,3-thiazole-4-carboxylate (132) (1.3 g, 1.99 mmol, 60% purity), Boc$_2$O (477 mg, 2.19 mmol) and TEA (413 µl, 2.9 mmol) in THF (50 ml) were stirred at room temperature for 16 h. Additional Boc$_2$O (477 mg, 2.19 mmol) and TEA (413 µl, 2.98 mmol) were added and the mixture was stirred for a further 4 h. The reaction mixture was evaporated in vacuo, the residue was dissolved in EtOAc (10 ml) and washed with water (3×5 ml). The organic layer was dried (MgSO$_4$), filtered and evaporated in vacuo. Purification by flash column chromatography (eluting with a gradient of 10-100% EtOAc/heptane) afforded the title compound (132 mg, 12%) as a yellow oil.

HPLCMS (Method A): [m/z]: 493.15 [M+H]$^+$

Ethyl 2-(2-{[(tert-butoxy)carbonyl]({2-[(4-fluoro-2-nitrophenyl)carbamoyl]ethyl})amino}ethyl)-1,3-thiazole-4-carboxylate (136)

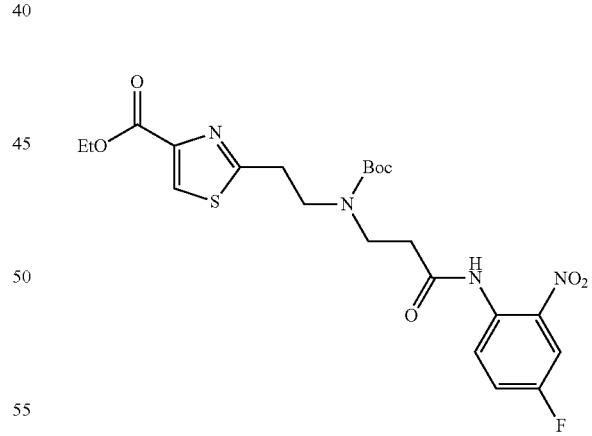

In a similar fashion to general procedure 4, 2-[2-({2-[(4-fluoro-2-nitrophenyl)carbamoyl]ethyl}amino)ethyl]-1,3-thiazole-4-carboxylate (133) (2.26 g, 2.145 mmol), Boc$_2$O (1.87 g, 8.58 mmol) and TEA (0.848 ml, 6.43 mmol) in THF (60 ml at room temperature for 16 h gave the title compound (0.43 g, 38%) as a yellow oil after purification by flash column chromatography (eluting with a gradient of 10-100% EtOAc/heptane).

1H-NMR (DMSO-d6, 500 MHz): d[ppm]=10.30 (s, 1H), 8.41 (s, 1H), 7.89 (d, J=8.5 Hz, 1H), 7.62 (m, 2H), 4.29 (q, J=7.1 Hz, 2H), 3.54 (m, 2H), 3.41 (t, J=7.1 Hz, 2H), 3.22 (t, J=7.0 Hz, 2H), 2.58 (m 2H), 1.35-1.27 (m, 12H)

HPLCMS (Method A): [m/z]: 511.1 [M+H]+

Ethyl 2-(2-{[(tert-butoxy)carbonyl]({3-[(2-nitrophenyl)carbamoyl]propyl})amino}ethyl)-1,3-thiazole-4-carboxylate (137)

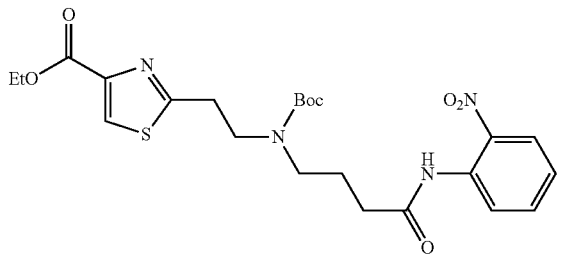 [SMILES: CCOC(=O)c1csc(CCN(CCCC(=O)Nc2ccccc2[N+](=O)[O-])C(=O)OC(C)(C)C)n1]

In a similar fashion to general procedure 4, ethyl 2-[2-({3-[(2-nitrophenyl)carbamoyl]propyl}amino)ethyl]-1,3-thiazole-4-carboxylate (134) (3.0 g, 5.32 mmol, 72% purity), Boc$_2$O (2.44 g, 11.17 mmol) and TEA (2.10 ml, 15.96 mmol) in THF (50 ml) were stirred at room temperature for 24 h. additional Boc$_2$O (2.32 g, 10.64 mmol) and TEA (0.7 ml, 5.32 mmol) were added and the reaction stirred at room temperature for 96 h, to give the title compound (0.287 g, 10%) as a yellow oil after purification by reverse-phase column chromatography (eluting with a gradient of 0-100% MeCN/water) gave 1H NMR (DMSO-d6, 500 MHz): d[ppm]=10.23 (s, 1H), 8.40 (s, 1H), 7.93 (dd, J=8.2, 1.4 Hz, 1H), 7.71-7.66 (m, 1H), 7.62 (dd, J=8.1, 1.4 Hz, 1H), 7.37-7.32 (m, 1H), 4.28 (q, J=7.1 Hz, 2H), 3.53 (t, J=6.9 Hz, 2H), 3.25-3.15 (m, 4H), 2.32 (t, J=7.4 Hz, 2H), 1.81-1.72 (m, 2H), 1.40-1.29 (br m, 9H), 1.28 (t, J=7.1 Hz, 3H)

HPLCMS (Method A): [m/z]: 507.1 [M+H]+

Ethyl 2-(2-{[2-(1H-1,3-benzodiazol-2-yl)ethyl][(tert-butoxy)carbonyl]amino}ethyl)-1,3-thiazole-4-carboxylate (138)

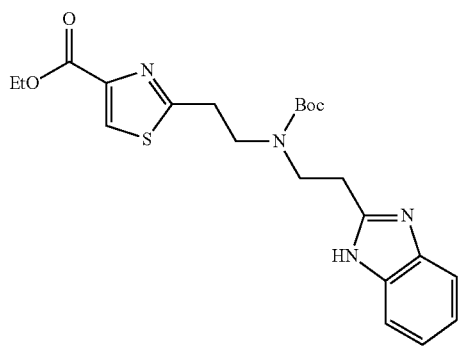 [SMILES: CCOC(=O)c1csc(CCN(CCc2nc3ccccc3[nH]2)C(=O)OC(C)(C)C)n1]

A suspension of ethyl 2-(2-{[(tert-butoxy)carbonyl]({2-[(2-nitrophenyl)carbamoyl]ethyl})amino}ethyl)-1,3-thiazole-4-carboxylate (135) (175 mg, 0.36 mmol) and iron powder (238 mg, 4.26 mmol) in AcOH was heated at 80° C. for 1 h. The reaction mixture was cooled to room temperature, diluted with DCM (10 ml) and neutralised with sat. NaHCO$_3$. The aqueous phase was extracted with DCM (3×10 ml), dried (Na$_2$SO$_4$), filtered and evaporated in vacuo to afford the title compound (121 mg, 76%) as a pale yellow oil.

HPLCMS (Method A): [m/z]: 445.15 [M+H]+

Ethyl 2-(2-{[(tert-butoxy)carbonyl][2-(5-fluoro-1H-1,3-benzodiazol-2-yl)ethyl]amino}ethyl)-1,3-thiazole-4-carboxylate (139)

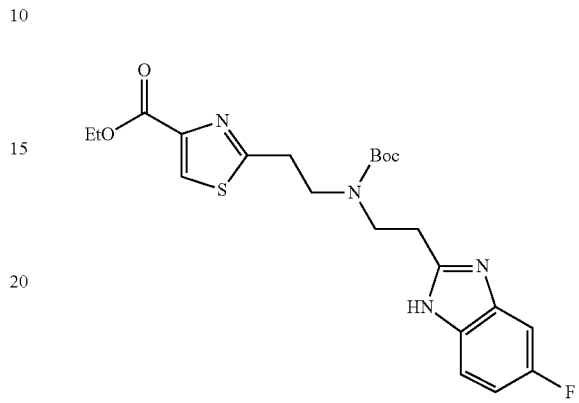

A suspension of ethyl 2-(2-{[(tert-butoxy)carbonyl]({2-[(4-fluoro-2-nitrophenyl)carbamoyl]ethyl})amino}ethyl)-1,3-thiazole-4-carboxylate (136) (0.43 g, 0.825 mmol) and iron powder (0.533 g, 9.905 mmol) in AcOH (40 ml) was heated at 80° C. for 2 h. The reaction mixture was cooled to room temperature and neutralised by slow addition sat. Na$_2$CO$_3$. The mixture was extracted with DCM (4×40 ml) and the combined organic extracts were dried (MgSO$_4$), filtered and evaporated in vacuo to afford the title compound as an off-white glassy solid (0.445 g, quant).

1H-NMR (DMSO-d6, 500 MHz): d[ppm]=12.34 (s, 1H), 8.40 (s, 1H), 7.27 (s, 2H), 696 (s, 1H), 4.28 (q, J=7.1 Hz, 2H), 3.59 (t, J=7.1 Hz, 2H), 3.55 (br s, 2H), 3.22 (br s, 2H), 3.00 (br s, 2H), 1.34-1.20 (m, 12H)

HPLCMS (Method A): [m/z]: 463.1 [M+H]+

Ethyl 2-(2-{[3-(1H-1,3-benzodiazol-2-yl)propyl][(tert-butoxy)carbonyl]amino}ethyl)-1,3-thiazole-4-carboxylate (140)

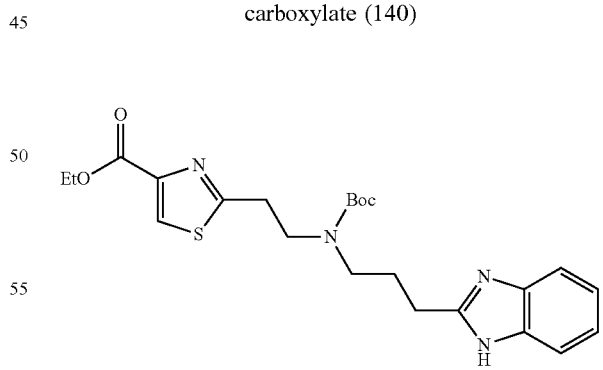

Iron powder (0.368 g, 6.595 mmol) was added to ethyl 2-(2-{[(tert-butoxy)carbonyl]({3-[(2-nitrophenyl)carbamoyl]propyl})amino}ethyl)-1,3-thiazole-4-carboxylate (137) (0.287 g, 0.55 mmol, 97% purity) in AcOH (10 ml). The reaction was stirred at 80° C. for 1 h. The reaction was allowed to cool to room temperature. Water (50 ml) was added followed by Na$_2$CO$_3$ until pH ~9. The aqueous layer was extracted with DCM (4×50 ml). The combined organic layers were dried (MgSO$_4$), filtered and the solvent evaporated to give the title compound (0.291 g, quant) as a pale orange oil.

1H-NMR (DMSO-d6, 500 MHz): d[ppm]=12.15 (s, 1H), 8.39 (s, 1H), 7.53-7.47 (m, 1H), 7.43-7.35 (m, 1H), 7.14-7.06 (m, 2H), 4.28 (q, J=7.1 Hz, 2H), 3.58-3.51 (m, 2H), 3.26-3.21 (m, 4H), 2.77 (t, J=7.6 Hz, 2H), 2.01-1.91 (m, 2H), 1.30 (s, 9H), 1.28 (t, J=7.1 Hz, 3H)

HPLCMS (Method A): [m/z]: 459.1 [M+H]$^+$ 2-(2-{[2-(1H-1,3-Benzodiazol-2-yl)ethyl][(tert-butoxy)carbonyl]amino}ethyl)-1,3-thiazole-4-carboxylic Acid (141)

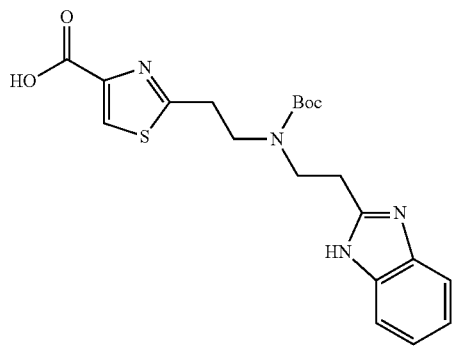 [SMILES: CC(C)(C)OC(=O)N(CCc1nc2ccccc2[nH]1)CCc1nc(C(=O)O)cs1]

In a similar fashion to general procedure 5, ethyl 2-(2-{[2-(1H-1,3-benzodiazol-2-yl)ethyl][(tert-butoxy)carbonyl]amino}ethyl)-1,3-thiazole-4-carboxylate (138) (156 mg, 0.35 mmol) and LiOH (33 mg, 1.35 mmol) in THF/water (5 ml/1 ml) gave the title compound (100 mg, 68%) as a tan solid after acidification with AcOH, extraction with 3:1 THF/EtOAc (3×10 ml), drying (MgSO$_4$), filtration and evaporation in vacuo.

HPLCMS (Method A): [m/z]: 417.1 [M+H]$^+$ 2-(2-{[(Tert-butoxy)carbonyl][2-(5-fluoro-1H-1,3-benzodiazol-2-yl)ethyl]amino}ethyl)-1,3-thiazole-4-carboxylic Acid (142)

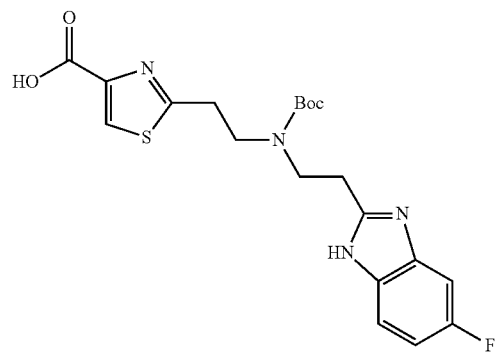 [SMILES: CC(C)(C)OC(=O)N(CCc1nc2cc(F)ccc2[nH]1)CCc1nc(C(=O)O)cs1]

In a similar fashion to general procedure 5, ethyl 2-(2-{[(tert-butoxy)carbonyl][2-(5-fluoro-1H-1,3-benzodiazol-2-yl)ethyl]amino}ethyl)-1,3-thiazole-4-carboxylate (139) (380 mg, 0.83 mmol) and LiOH (59 mg, 2.48 mmol) in THF/water (45 ml/15 ml) afforded the title compound (319 mg, 82%, 92% purity) as a white solid.

HPLCMS (Method A): [m/z]: 435.05 [M+H]$^+$ 2-(2-{[3-(1H-1,3-Benzodiazol-2-yl)propyl][(tert-butoxy)carbonyl]amino}ethyl)-1,3-thiazole-4-carboxylic Acid (143)

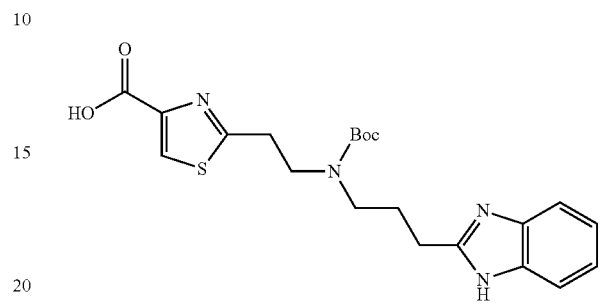

In a similar fashion to general procedure 5, ethyl 2-(2-{[3-(1H-1,3-benzodiazol-2-yl)propyl][(tert-butoxy)carbonyl]amino}ethyl)-1,3-thiazole-4-carboxylate (140) (291 mg, 0.550 mmol, 87% purity) and LiOH (39 mg, 1.649 mmol) in THF/water (25 ml/10 ml) at room temperature for 24 h, gave the title compound (219 mg, 72%) as a glassy solid.

1H-NMR (Acetone-d$_6$, 500 MHz): d[ppm]=7.87 (s, 1H), 7.06-6.96 (m, 2H), 6.70-6.63 (m, 2H), 3.90-3.85 (m, 2H), 3.10 (t, J=6.8 Hz, 2H), 2.76 (t, J=7.0 Hz, 2H), 2.34 (t, J=7.4 Hz, 2H), 1.57-1.49 (m, 2H), 0.85 (s, 9H)

HPLCMS (Method A): [m/z]: 431.1 [M+H]$^+$

Tert-butyl N-[2-(1H-1,3-benzodiazol-2-yl)ethyl]-N-[2-(4-{[(3,5-difluoropyridin-2-yl)methyl]carbamoyl}-1,3-thiazol-2-yl)ethyl]carbamate (144)

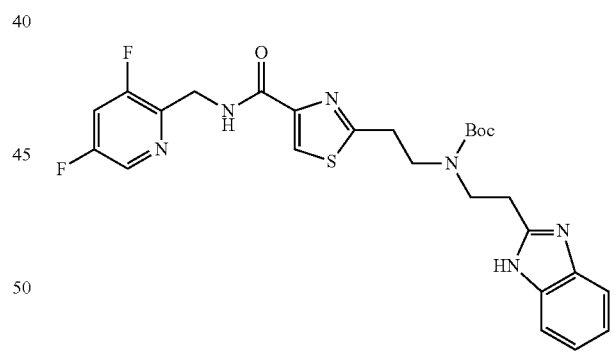

In a similar manner to general procedure 6, 2-(2-{[2-(1H-1,3-benzodiazol-2-yl)ethyl][(tert-butoxy)carbonyl]amino}ethyl)-1,3-thiazole-4-carboxylic acid (141) (100 mg, 0.24 mmol), (3,5-difluoropyridin-2-yl)methanamine dihydrochloride (78 mg, 0.36 mmol), DIPEA (0.21 ml, 1.2 mmol) and HATU (137 mg, 0.36 mmol) in DMF (3 ml) afforded the title compound (77 mg, 59%) as a white solid after purification by basic prep-HPLC.

1H-NMR (Methanol-d4, 500 MHz): d[ppm]=8.30 (br s, 1H), 8.09 (s, 1H), 7.55 (br s, 1H), 7.48 (s, 2H), 7.20 (d, J=3.3 Hz, 2H), 4.82 (s, 2H), 4.73 (s, 2H), 3.70 (m, 4H), 3.08 (m, 2H), 1.16 (s, 9H)

HPLCMS (Method A): [m/z]: 543.15 [M+H]$^+$

Tert-butyl N-[2-(5-fluoro-1H-1,3-benzodiazol-2-yl)ethyl]-N-[2-(4-{[(3-fluoropyridin-2-yl)methyl]carbamoyl}-1,3-thiazol-2-yl)ethyl]carbamate (145)

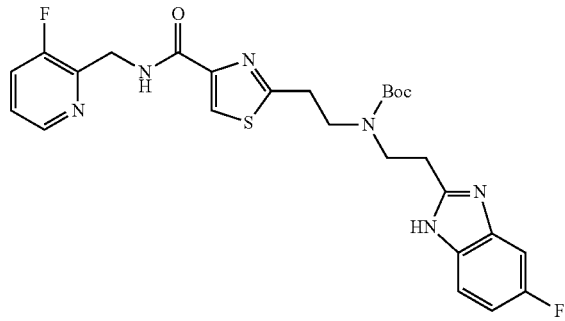 [SMILES: CC(C)(C)OC(=O)N(CCc1nc2cc(F)ccc2[nH]1)CCc1nc(C(=O)NCc2ncccc2F)cs1]

In a similar fashion to general procedure 6, 2-(2-{[(tert-butoxy)carbonyl][2-(5-fluoro-1H-1,3-benzodiazol-2-yl)ethyl]amino}ethyl)-1,3-thiazole-4-carboxylic acid (142) (160 mg, 0.34 mmol, 92% purity), (3-fluoropyridin-2-yl)methanamine dihydrochloride (A2) (101 mg, 0.51 mmol), DIPEA (0.18 ml, 1.01 mmol) and HATU (192 mg, 0.51 mmol) in DMF (4 ml) afforded the title compound (112 mg, 61%) as a white solid after purification by flash column chromatography (eluting with a gradient of 0-50% MeOH/EtOAc).

1H-NMR (DMSO-d6, 500 MHz): d[ppm]=12.33 (br s, 1H), 8.66 (br s, 1H), 8.36 (br s, 1H), 8.17 (br s, 1H), 7.72-7.66 (m, 1H), 7.53-7.36 (m, 2H), 7.33-7.21 (m, 1H), 7.00-6.91 (m, 1H), 4.66 (d, J=4.5 Hz, 2H), 3.63 (t, J=7.0 Hz, 2H), 3.58 (t, J=6.9 Hz, 2H), 3.24 (t, J=6.9 Hz, 2H), 3.02 (m, 2H), 1.35-1.18 (m, 9H)

HPLCMS (Method A): [m/z]: 543.1 [M+H]+

Tert-butyl N-[2-(4-{[(3,5-difluoropyridin-2-yl)methyl]carbamoyl}-1,3-thiazol-2-yl)ethyl]-N-[2-(5-fluoro-1H-1,3-benzodiazol-2-yl)ethyl]carbamate (146)

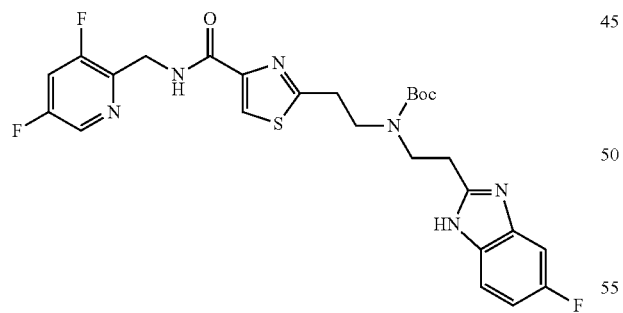

In a similar fashion to general procedure 6, 2-(2-{[(tert-butoxy)carbonyl][2-(5-fluoro-1H-1,3-benzodiazol-2-yl)ethyl]amino}ethyl)-1,3-thiazole-4-carboxylic acid (142) (12 mg, 0.28 mmol), (3,5-difluoropyridin-2-yl)methanamine dihydrochloride (90 mg, 0.41 mmol), DIPEA (0.24 ml, 1.38 mmol) and HATU (158 mg, 0.41 mmol) in DMF (3 ml) afforded the title compound (72 mg, 47%) as a colourless glassy solid after purification by basic prep-HPLC.

1H-NMR (DMSO-d6, 500 MHz): d[ppm]=12.33 (br s, 1H), 8.68 (br s, 1H), 8.44 (br s, 1H), 8.16 (br s, 1H), 7.90 (d, J=11.0 Hz, 1H), 7.27 (br s, 2H), 6.96 (br s, 1H), 4.62 (d, J=5.7 Hz, 2H), 3.65-3.57 (m, 4H), 3.22 (m, 2H), 3.01 (br s, 2H), 1.24 (m, 9H)

HPLCMS (Method A): [m/z]: 561.15 [M+H]+

Tert-butyl N-[3-(1H-1,3-benzodiazol-2-yl)propyl]-N-[2-(4-{[(3-fluoropyridin-2-yl)methyl]carbamoyl}-1,3-thiazol-2-yl)ethyl]carbamate (147)

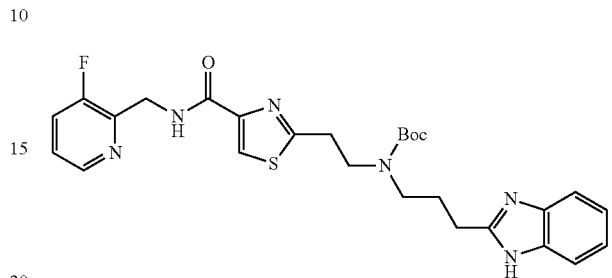

In a similar fashion to general procedure 6, 2-(2-{[3-(1H-1,3-benzodiazol-2-yl)propyl][(tert-butoxy)carbonyl]amino}ethyl)-1,3-thiazole-4-carboxylic acid (143) (219 mg, 0.39 mmol, 78% purity), (3-fluoropyridin-2-yl)methanamine dihydrochloride (A2) (118 mg, 0.59 mmol), DIPEA (0.346 ml, 1.98 mmol) and HATU (226 mg, 0.59 mmol) in DMF (3 ml) at room temperature for 2 h gave the title compound (111 mg, 52%) as a colourless oil after purification by basic prep-HPLC.

1H-NMR (DMSO-d6, 500 MHz): d[ppm]=12.15 (s, 1H), 8.66 (br s, 1H), 8.36 (d, J=4.3 Hz, 1H), 8.16 (s, 1H), 7.73-7.63 (m, 1H), 7.52-7.45 (m, 1H), 7.45-7.34 (m, 2H), 7.18-7.01 (m, 2H), 4.65 (d, J=5.5 Hz, 2H), 3.59 (t, J=7.0 Hz, 2H), 3.29-3.23 (m, 4H), 2.78 (t, J=7.5 Hz, 2H), 2.05-1.92 (m, 2H), 1.30 (s, 9H)

HPLCMS (Method A): [m/z]: 539.15 [M+H]+

2-(2-{[2-(1H-1,3-Benzodiazol-2-yl)ethyl]amino}ethyl)-N-[(3,5-difluoropyridin-2-yl)methyl]-1,3-thiazole-4-carboxamide trihydrochloride (Example Compound No. 116)

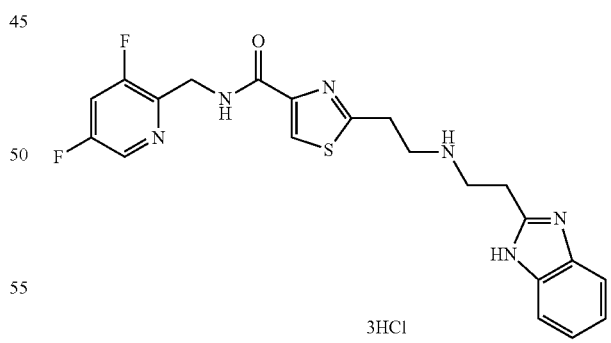

In a similar fashion to general procedure 2, 12M HCl (0.378 ml, 4.541 mmol) and tertbutyl N-[2-(1H-1,3-benzodiazol-2-yl)ethyl]-N-[2-(4-{[(3,5-difluoropyridin-2-yl)methyl]carbamoyl}-1,3-thiazol-2-yl)ethyl]carbamate (144) (77 mg, 0.142 mmol) in MeOH (3 ml) at room temperature for 5 h and at 40° C. for 20 h gave the title compound (60 mg, 73%) as a yellow solid.

1H-NMR (Methanol-d4, 500 MHz): d[ppm]=8.29 (d, J=2.3 Hz, 1H), 8.23 (s, 1H), 7.79 (dd, J=6.1, 3.2 Hz, 2H), 7.64-7.59 (m, 3H), 4.77 (s, 2H), 3.78 (s, 4H), 3.72 (t, J=6.4 Hz, 2H), 3.59 (d, J=5.9 Hz, 2H)

HPLCMS (Method D): [m/z]: 443.1 [M+H]+

2-(2-{[2-(5-Fluoro-1H-1,3-benzodiazol-2-yl)ethyl]amino}ethyl)-N-[(3-fluoropyridin-2-yl)methyl]-1,3-thiazole-4-carboxamide Trihydrochloride (Example Compound No. 120)

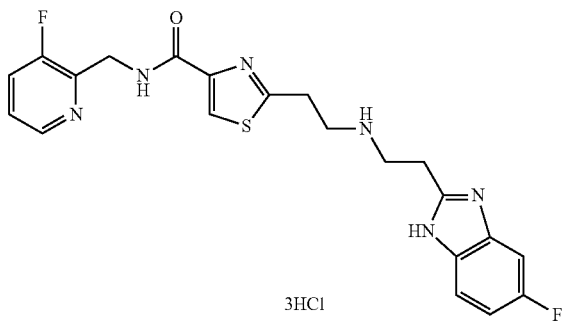 [SMILES: O=C(NCc1ncccc1F)c1csc(CCNCCc2nc3cc(F)ccc3[nH]2)n1]

In a similar fashion to general procedure 2, 12 M HCl (0.344 ml, 4.128 mmol) and N-[2-(5-fluoro-1H-1,3-benzodiazol-2-yl)ethyl]-N-[2-(4-{[(3-fluoropyridin-2-yl)methyl]carbamoyl}-1,3-thiazol-2-yl)ethyl]carbamate (145) (112 mg, 0.206 mmol) in MeOH (4 ml) at room temperature for 16 h, following the addition of 12M HCl (0.344 ml, 4.128 mmol) at room temperature for further 20 h and at 40° C. for 3 h, gave the title compound (80 mg, 67%) as a white solid.

1H-NMR (Methanol-d4, 500 MHz): d[ppm]=8.57 (d, J=5.4 Hz, 1H), 8.28 (t, J=8.8 Hz, 1H), 8.25 (s, 1H), 7.89 (dt, J=9.5, 5.0 Hz, 1H), 7.81 (dd, J=9.0, 4.3 Hz, 1H), 7.58 (dd, J=8.1, 2.3 Hz, 1H), 7.42 (td, J=9.3, 2.4 Hz, 1H), 4.97 (s, 2H), 3.85-3.79 (m, 4H), 3.75 (t, J=6.3 Hz, 2H), 3.62 (t, J=6.3 Hz, 2H)

HPLCMS (Method D): [m/z]: 443.2 [M+H]+

N-[(3,5-Difluoropyridin-2-yl)methyl]-2-(2-{[2-(5-fluoro-1H-1,3-benzodiazol-2-yl)ethyl]amino}ethyl)-1,3-thiazole-4-carboxamide Trihydrochloride (Example Compound No. 123)

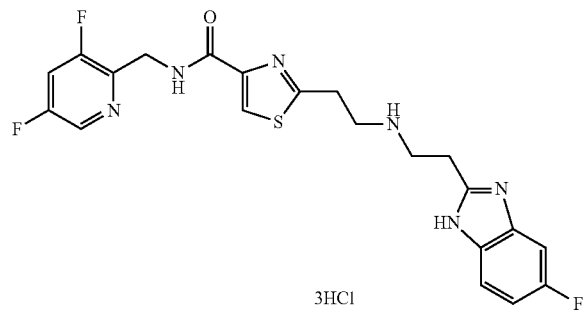 [SMILES: O=C(NCc1ncc(F)cc1F)c1csc(CCNCCc2nc3cc(F)ccc3[nH]2)n1]

In a similar fashion to general procedure 2, 12 M HCl (0.257 ml, 3.08 mmol) and tertbutyl N-[2-(4-{[(3,5-difluoropyridin-2-yl)methyl]carbamoyl}-1,3-thiazol-2-yl)ethyl]-N-[2-(5-fluoro-1H-1,3-benzodiazol-2-yl)ethyl]carbamate (146) (72 mg, 0.128 mmol) in MeOH (3 ml) at room temperature for 16 h, following additional 12M HCl (0.257 ml, 3.08 mmol) and the mixture stirred at 45° C. for 4 h, gave the title compound (28 mg, 38%) as a white solid.

1H-NMR (Methanol-d4, 500 MHz): d[ppm]=8.28 (d, J=2.3 Hz, 1H), 8.23 (s, 1H), 7.79 (dd, J=9.0, 4.3 Hz, 1H), 7.60 (m, 1H), 7.56 (dd, J=8.1, 2.3 Hz, 1H), 7.40 (td, J=9.3, 2.4 Hz, 1H), 4.76 (s, 2H), 3.77 (m, 4H), 3.73 (t, J=6.4 Hz, 2H), 3.60 (t, J=6.4 Hz, 2H)

HPLCMS (Method D): [m/z]: 461.2 [M+H]+

2-(2-{[3-(1H-1,3-Benzodiazol-2-yl)propyl]amino}ethyl)-N-[(3-fluoropyridin-2-yl)methyl]-1,3-thiazole-4-carboxamide Trihydrochloride (Example Compound No. 125)

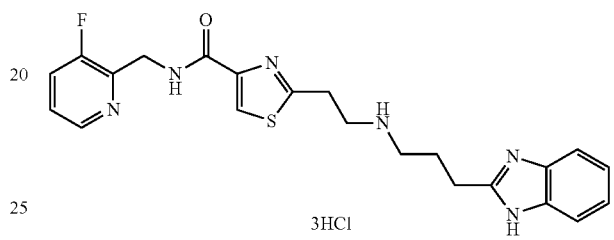

In a similar fashion to general procedure 2, 12M HCl (0.405 ml, 4.864 mmol) and tertbutyl N-[3-(1H-1,3-benzodiazol-2-yl)propyl]-N-[2-(4-{[(3-fluoropyridin-2-yl)methyl]carbamoyl}-1,3-thiazol-2-yl)ethyl]carbamate (147) (131 mg, 0.243 mmol) in MeOH (3 ml) at 40° C. for 16 h, gave the title compound (48 mg, 35%) as a white solid.

1H-NMR (Methanol-d4, 500 MHz): d[ppm]=8.48 (d, J=5.1 Hz, 1H), 8.23 (s, 1H), 8.07-8.00 (m, 1H), 7.80-7.76 (m, 2H), 7.74-7.66 (m, 1H), 7.63-7.58 (m, 2H), 4.91 (s, 2H), 3.65 (t, J=6.4 Hz, 2H), 3.57 (t, J=6.6 Hz, 2H), 3.41-3.32 (m, 4H), 2.49-2.40 (m, 2H)

HPLCMS (Method D): [m/z]: 439.2 [M+H]+

General Procedure 11: Tert-butyl 3-carbamothioylpyrrolidine-1-carboxylate (148)

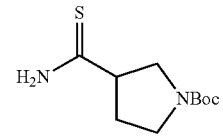

Lawesson reagent (0.42 g, 1.03 mmol) was added in one portion to tert-butyl 3-carbamoylpyrrolidine-1-carboxylate (0.4 g, 1.87 mmol) in DCM (5 ml) and the reaction was stirred at room temperature for 2 h. The reaction mixture was directly loaded onto silica and purified by flash column chromatography (eluting with a gradient of 0-100% EtOAc/heptane) to give the title compound (0.36 g, 79%) as an off-white solid.

1H-NMR (CDCl3, 500 MHz): d[ppm]=7.46 (d, J=8.6 Hz, 1H), 7.01 (br s, 1H), 3.75-3.66 (m, 1H), 3.65-3.54 (m, 1H), 3.59 (dd, 11 and 8.1 Hz, 1H), 3.37 (q, J=8.7 Hz, 1H), 3.27 (p, J=7.8 Hz, 1H), 2.24-2.12 (m, 3H), 1.46 (s, 9H)

HPLCMS (Method A): [m/z]: 252.95 [M+Na]+

Ethyl 2-{1-[(tert-butoxy)carbonyl]pyrrolidin-3-yl}-1,3-thiazole-4-carboxylate (149)

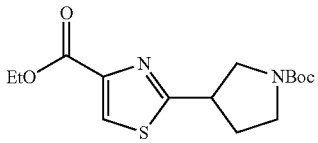 [SMILES: CCOC(=O)c1csc(C2CCN(C(=O)OC(C)(C)C)C2)n1]

In a similar fashion to general procedure 1, ethyl 3-bromo-2-oxopropanoate (2.5 ml, 19.75 mmol), tert-butyl 3-carbamothioylpyrrolidine-1-carboxylate (148) (3.96 g, 17.19 mmol) and CaCO$_3$ (0.87 g, 8.73 mmol) in EtOH (50 ml) at room temperature for 21 h, gave the title compound (2.81 g, 51.9%) as a yellow oil which solidified on standing, after purification by flash column chromatography (eluting with a gradient of 0-70% EtOAc/heptane).

1H-NMR (CDCl$_3$, 250 MHz): d[ppm]=8.08 (s, 1H), 4.41 (q, J=7.1 Hz, 2H), 3.96-3.76 (m, 2H), 3.73-3.51 (m, 2H), 3.51-3.35 (m, 1H), 2.35-2.44 (m, 1H), 2.28-2.14 (m, 1H), 1.46 (s, 9H), 1.39 (t, J=7.1 Hz, 3H)

HPLCMS (Method A): [m/z]: 349.05 [M+Na]$^+$

2-{1-[(Tert-butoxy)carbonyl]pyrrolidin-3-yl}-1,3-thiazole-4-carboxylic Acid (150)

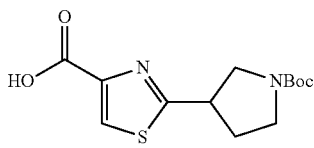

In a similar fashion to general procedure 5, LiOH (1.04 g, 43.5 mmol) and ethyl 2-{1-[(tert-butoxy)carbonyl]pyrrolidin-3-yl}-1,3-thiazole-4-carboxylate (149) (2.84 g, 8.7 mmol) in THF (30 ml)/water (30 ml) gave the title compound (2.48 g, 93.6%) as a yellow solid Compound was used in the next step without further purification.

1H-NMR (DMSO-d6, 250 MHz): d[ppm]=12.94 (s, 1H), 8.37 (s, 1H), 3.94-3.78 (m, 1H), 3.78-3.68 (m, 1H), 3.49-3.39 (m, 2H), 2.44-2.24 (m, 1H), 2.19-1.98 (m, 1H), 1.41 (s, 9H). A CH signal was obscured by the H$_2$O peak HPLCMS (Method A): [m/z]: 321.05 [M+Na]$^+$ and 297.1 [M+H]$^+$

Tert-butyl 3-(4-{[(3-fluoropyridin-2-yl)methyl]carbamoyl}-1,3-thiazol-2-yl)pyrrolidine-1-carboxylate (151)

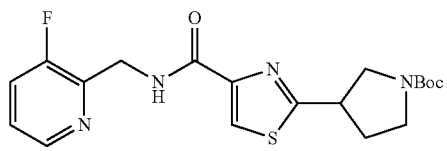 [SMILES: CC(C)(C)OC(=O)N1CCC(c2nc(C(=O)NCc3ncccc3F)cs2)C1]

In a similar fashion using general procedure 6, 2-{1-[(tert-butoxy)carbonyl]pyrrolidin-3-yl}-1,3-thiazole-4-carboxylic acid (150) (1 g, 3.35 mmol), (3-fluoropyridin-2-yl)methanamine dihydrochloride (A2) (1 g, 5.03 mmol), DIPEA (1.93 ml, 11.06 mmol), HATU (1.9 g, 5.03 mmol) in DMF (14 ml) gave the title compound (1.27 g, 86%) as a yellow oil after purification by flash column chromatography (eluting with a gradient of 0-100% EtOAc/heptane) followed by re-purification by flash column chromatography (eluting with a gradient of 0-10% MeOH/DCM).

1H-NMR (DMSO-d6, 250 MHz): d[ppm]=8.71 (t, J=5.6 Hz, 1H), 8.38 (dt, J=4.7, 1.4 Hz, 1H), 8.20 (s, 1H), 7.70 (ddd, J=10.2, 8.3, 1.3 Hz, 1H), 7.40 (dt, J=8.5, 4.4 Hz, 1H), 4.66 (dd, J=5.7, 1.5 Hz, 2H), 3.94-3.81 (m, 1H), 3.82-3.66 (m, 1H), 3.58-3.40 (m, 2H), 2.43-2.26 (m, 1H), 2.25-2.04 (m, 1H), 1.40 (s, 9H). A CH signal was obscured by the H$_2$O peak HPLCMS (Method A): [m/z]: 407.1 [M+H]$^+$

Tert-butyl 3-{4-[(pyridin-2-ylmethyl)carbamoyl]-1,3-thiazol-2-yl}pyrrolidine-1-carboxylate (152)

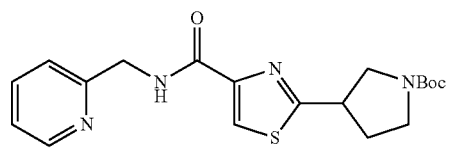 [SMILES: CC(C)(C)OC(=O)N1CCC(c2nc(C(=O)NCc3ccccn3)cs2)C1]

In a similar fashion using general procedure 6, 2-{1-[(tert-butoxy)carbonyl]pyrrolidin-3-yl}-1,3-thiazole-4-carboxylic acid (150) (1 g, 3.35 mmol), pyridin-2-ylmethanamine (0.52 ml, 5.03 mmol), DIPEA (1.17 ml, 6.7 mmol) and HATU (1.9 g, 5.03 mmol) in DMF (14 ml) gave the title compound (1.54 g, 100%) as a yellow solid after purification by flash column chromatography (eluting with a gradient of (100% EtOAc/heptane).

1H-NMR (DMSO-d6, 250 MHz): d[ppm]=8.90 (s, 1H), 8.52 (d, J=4.0 Hz, 1H), 8.22 (s, 1H), 7.76 (td, J=7.7, 1.8 Hz, 1H), 7.36-7.21 (m, 2H), 4.58 (d, J=6.0 Hz, 2H), 3.92-3.82 (m, 1H), 3.84-3.71 (m, 1H), 3.68-3.42 (m, 3H), 2.34-2.25 (m, 1H), 2.27-2.11 (m, 1H)

HPLCMS (Method A): [m/z]: 389.15 [M+H]$^+$

N-[(3-Fluoropyridin-2-yl)methyl]-2-(pyrrolidin-3-yl)-1,3-thiazole-4-carboxamide Dihydrochloride (153)

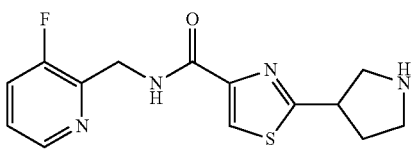

In a similar fashion using general procedure 2, 12M HCl (6 ml) and tert-butyl 3-(4-{[(3-fluoropyridin-2-yl)methyl]carbamoyl}-1,3-thiazol-2-yl)pyrrolidine-1-carboxylate (151) (1.27 g, 2.87 mmol) in MeOH (25 ml) at 40° C. for 4 h gave the title compound (1.11 g, 96.7%) as a cream foam. Compound was used in the next step without further purification.

1H-NMR (Methanol-d4, 250 MHz): d[ppm]=8.58 (dd, J=5.4, 1.2 Hz, 1H), 8.28-8.18 (m, 2H), 7.87 (dt, J=8.6, 4.8

Hz, 1H), 4.94 (d, J=1.3 Hz, 2H), 4.25-4.11 (m, 1H), 3.82 (dd, J=11.8, 4.6 Hz, 1H), 3.72-3.43 (m, 3H), 2.67-2.46 (m, 1H), 2.39-2.23 (m, 1H)

HPLCMS (Method A): [m/z]: 307.05 [M+H]+

N-(Pyridin-2-ylmethyl)-2-(pyrrolidin-3-yl)-1,3-thiazole-4-carboxamide Dihydrochloride (154)

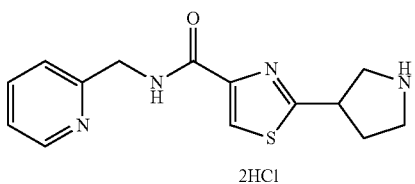 [SMILES: O=C(NCc1ccccn1)c1csc(C2CCNC2)n1]

In a similar fashion using general procedure 2, 12M HCl (7 ml) and and tert-butyl 3-{4-[(pyridin-2-ylmethyl)carbamoyl]-1,3-thiazol-2-yl}pyrrolidine-1-carboxylate (152) (1.54 g, 3.35 mmol) in MeOH (30 ml) at 40° C. for 4 h gave the title compound (1.42 g, 99%) as a pale brown foam. Compound was used in the next step without further purification.

1H-NMR (Methanol-d4, 250 MHz): d[ppm]=8.77 (d, J=5.9 Hz, 1H), 8.65-8.54 (m, 1H), 8.25 (s, 1H), 8.12 (d, J=8.1 Hz, 1H), 7.99 (t, J=6.8 Hz, 1H), 4.96 (s, 2H), 4.17 (ddd, J=11.5, 7.3, 4.3 Hz, 1H), 3.86 (dd, J=11.9, 4.2 Hz, 1H), 3.79-3.41 (m, 3H), 2.56 (dq, J=13.4, 8.3 Hz, 1H), 2.41-2.21 (m, 1H)

HPLCMS (Method A): [m/z]: 289.05 [M−H]+

N-[(3-Fluoropyridin-2-yl)methyl]-2-(1-{2-[(2-nitrophenyl)carbamoyl]ethyl}pyrrolidin-3-yl)-1,3-thiazole-4-carboxamide (155)

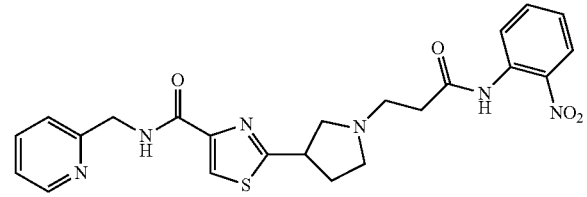

In a similar fashion to general procedure 8, N-[(3-fluoropyridin-2-yl)methyl]-2-(pyrrolidin-3-yl)-1,3-thiazole-4-carboxamide dihydrochloride (153) (1.11 g, 2.78 mmol), N-(2-nitrophenyl)prop-2-enamide (D) (0.59 g, 3.06 mmol), DBU (1.41 ml, 9.45 mmol) in MeCN (20 ml) at room temperature for 19 h, gave the title compound (1.53 g, 99%) as a yellow oil after work up.

1H-NMR (DMSO-d6, 500 MHz): d[ppm]=10.69 (s, 1H), 8.67 (t, J=5.7 Hz, 1H), 8.38 (dt, J=4.6, 1.4 Hz, 1H), 8.11 (s, 1H), 7.96 (dd, J=8.2, 1.5 Hz, 1H), 7.79 (dd, J=8.2, 1.2 Hz, 1H), 7.73-7.67 (m, 2H), 7.40 (dt, J=8.6, 4.4 Hz, 1H), 7.33 (ddd, J=8.5, 7.4, 1.4 Hz, 1H), 4.63 (d, J=4.6 Hz, 2H), 3.87-3.77 (m, 1H), 2.99 (dd, J=9.2, 7.4 Hz, 1H), 2.88-2.74 (m, 4H), 2.70-2.62 (m, 1H), 2.57 (td, J=6.7, 1.9 Hz, 2H), 2.43-2.34 (m, 1H), 2.08-1.99 (m, 1H)

HPLCMS (Method A): [m/z]: 499.1 [M+H]+

Tert-butyl 3-{4-[(pyridin-2-ylmethyl)carbamoyl]-1,3-thiazol-2-yl}pyrrolidine-1-carboxylate (Example Compound No. 214)

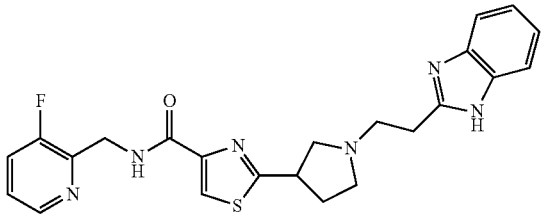 [SMILES: O=C(NCc1ncccc1F)c1csc(C2CCN(CCc3nc4ccccc4[nH]3)C2)n1]

In a similar fashion to general procedure 8, N-[(3-fluoropyridin-2-yl)methyl]-2-(1-{2-[(2-nitrophenyl)carbamoyl]ethyl}pyrrolidin-3-yl)-1,3-thiazole-4-carboxamide (155) (1.53 g, 2.78 mmol), AcOH (15 ml) and iron powder (0.62 g, 11.11 mmol) at 80° C. for 2 h, gave the title compound (94 mg, 8%) as a pale brown solid after purification by flash column chromatography (KP—NH, eluting with a grading of 0-25% MeOH/DCM) gave a residue (207 mg) which was re-purified by flash column chromatography (KP—NH, eluting with a gradient of 0-3% MeOH/DCM).

1H-NMR (Methanol-d4, 500 MHz): d[ppm]=8.33 (d, J=4.7 Hz, 1H), 7.94 (s, 1H), 7.58 (app t, J=9.1 Hz, 1H), 7.47 (br s, 2H), 7.40-7.32 (m, 1H), 7.24-7.16 (m, 2H), 4.75 (d, J=1.4 Hz, 2H), 3.87-3.80 (m, 1H), 3.17-3.11 (m, 2H), 3.11-2.96 (m, 5H), 2.78-2.69 (m, 1H), 2.48-2.38 (m, 1H), 2.18-2.04 (m, 1H)

HPLCMS (Method C): [m/z]: 451.1 [M+H]+

2-(1-{2-[(2-Nitrophenyl)carbamoyl]ethyl}pyrrolidin-3-yl)-N-(pyridin-2-ylmethyl)-1,3-thiazole-4-carboxamide (156)

In a similar fashion to general procedure 8, DBU (1.52 ml, 10.19 mmol), N-(pyridin-2-ylmethyl)-2-(pyrrolidin-3-yl)-1,3-thiazole-4-carboxamide dihydrochloride (154) (84.6%, 1.28 g, 3.0 mmol) and N-(2-nitrophenyl)prop-2-enamide (D) (0.63 g, 3.3 mmol) in MeCN (25 ml) room temperature for 19 h gave the title compound (1.43 g, 99%) as a yellow oil after purification by flash column chromatography (eluting with a gradient of 0-12% MeOH/DCM).

1H NMR (DMSO-d6, 500 MHz): d[ppm]=10.67 (s, 1H), 8.83 (t, J=6.0 Hz, 1H), 8.51 (d, J=4.2 Hz, 1H), 8.12 (s, 1H), 7.96 (dd, J=8.2, 1.4 Hz, 1H), 7.82 (d, J=8.2 Hz, 1H), 7.74 (td, J=7.7, 1.8 Hz, 1H), 7.69 (td, J=8.5, 8.0, 1.5 Hz, 1H), 7.36-7.24 (m, 3H), 4.55 (d, J=6.1 Hz, 2H), 3.87-3.78 (m, 1H), 3.04-2.98 (m, 1H), 2.89-2.74 (m, 4H), 2.71-2.65 (m, 1H), 2.57 (td, J=6.7, 1.7 Hz, 2H), 2.44-2.33 (m, 1H), 2.09-2.01 (m, 1H)

HPLCMS (Method A): [m/z]: 481.35 [M+H]+

2-{1-[2-(1H-1,3-Benzodiazol-2-yl)ethyl]pyrrolidin-3-yl}-N-(pyridin-2-ylmethyl)-1,3-thiazole-4-carboxamide (Example Compound No. 215)

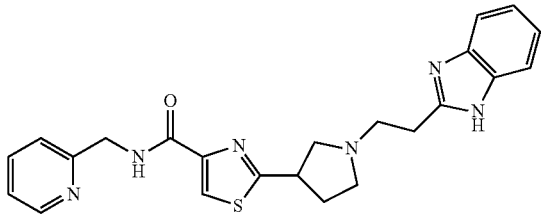 [SMILES: O=C(NCc1ccccn1)c1csc(C2CCN(CCc3nc4ccccc4[nH]3)C2)n1]

In a similar fashion to general procedure 8, 2-(1-{2-[(2-nitrophenyl)carbamoyl]ethyl}pyrrolidin-3-yl)-N-(pyridin-2-ylmethyl)-1,3-thiazole-4-carboxamide (156) (1.43 g, 2.77 mmol) and iron powder (0.62 g, 11.07 mmol) in AcOH (15 ml) at 80° C. for 2 h, gave the title compound (116 mg, 10%) as an off-white solid after purification by flash column chromatography (×3) (eluting with a gradient of 0-40% MeOH/DCM followed gradient of 0-3% MeOH/DCM and then a gradient of 0-10% MeOH/DCM).

1H-NMR (Methanol-d4, 500 MHz) d[ppm]=8.48 (d, J=4.4 Hz, 1H), 7.95 (s, 1H), 7.79 (app t, J=7.1 Hz, 1H), 7.48 (s, 2H), 7.39 (d, J=7.8 Hz, 1H), 7.36-7.26 (m, 1H), 7.25-7.12 (m, 2H), 4.67 (s, 2H), 3.89-3.78 (m, 1H), 3.18-3.11 (m, 2H), 3.11-2.96 (m, 5H), 2.73 (q, J=8.6 Hz, 1H), 2.49-2.39 (m, 1H), 2.19-2.06 (m, 1H)

HPLCMS (Method C): [m/z]: 433.1 [M+H]$^+$

General Scheme 9 Above:

General Procedure 12: Tert-butyl 3-carbamoylazetidine-1-carboxylate (157)

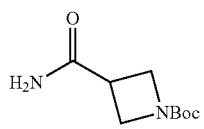

1-[(tert-butoxy)carbonyl]azetidine-3-carboxylic acid (4.96 g, 24.65 mmol) and TEA (5.84 ml, 42.0 mmol) were dissolved in THF (60 ml) and cooled to −20° C. Isobutyl chloroformate (4.8 ml, 37.0 mmol) was added slowly and the reaction mixture stirred at <−10° C. for 15 min. 28% aqueous ammonia (7.46 ml, 394 mmol) was added and the mixture allowed to warm to room temperature and stirred for 1 h. The reaction mixture was quenched with sat. NaHCO$_3$ (aq) and extracted with DCM (3×100 ml). The combined organic extracts were dried (Na$_2$SO$_4$), filtered and evaporated in vacuo. Purification by flash chromatography using a gradient elution of 20-100% EtOAc/heptane followed by 1-4% MeOH/EtOAc afforded the title compound (3.99 g, 81%) as a white solid.

1H-NMR (CDCl$_3$, 250 MHz): d[ppm]=5.47 (s, 2H), 4.22-4.01 (m, 4H), 3.34-3.15 (m, 1H), 1.46 (s, 9H)

HPLCMS (Method A): [m/z]: 222.95 [M+Na]$^+$

Tert-butyl 3-carbamoyl-3-methylazetidine-1-carboxylate (158)

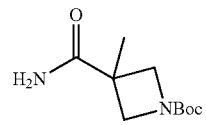

In a similar fashion to general procedure 12, 1-[(tert-butoxy)carbonyl]-3-methylazetidine-3-carboxylic acid (110 mg, 0.51 mmol), TEA (90 mg, 0.87 mmol), isobutyl chloroformate (0.1 ml, 0.77 mmol) and NH$_3$ (28% aqueous solution, 0.15 ml, 10 mmol) in THF (10 ml) gave the title compound (102 mg, 93%) as a white solid.

1H-NMR (CDCl$_3$, 500 MHz): d[ppm]=5.63 (s, 1H), 5.37 (s, 1H), 4.21 (d, J=8.4 Hz, 2H), 3.72 (d, J=8.4 Hz, 2H), 1.58 (s, 3H), 1.47 (s, 9H)

HPLCMS (Method A): [m/z]: 237 [M+Na]$^+$

Tert-butyl 3-carbamothioylazetidine-1-carboxylate (159)

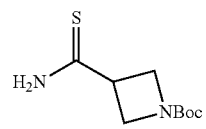

In a similar fashion to general procedure 11, Lawesson reagent (4.43 g, 11.0 mmol), tert-butyl 3-carbamoylazetidine-1-carboxylate (157) (3.99 g, 19.9 mmol) in DCM (60 ml) at room temperature for 30 min gave the title compound (4.47 g) as a pale yellow residue after being flushed through a plug of silica using a gradient elution of 10-80% EtOAc/heptane.

HPLCMS (Method A): [m/z]: 238.9 [M+Na]$^+$

Tert-butyl 3-carbamothioyl-3-methylazetidine-1-carboxylate (160)

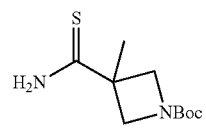

In a similar fashion to general procedure 11, tert-butyl 3-carbamoyl-3-methylazetidine-1-carboxylate (158) (1.0 g, 4.67 mmol) and Lawesson reagent (1.04 g, 3.0 mmol) in DCM (30 ml) gave the title compound (1.07 g) as a white solid.

1H-NMR (CDCl$_3$, 250 MHz): d[ppm]=7.47 (s, 1H), 6.88 (s, 1H), 4.33 (d, J=8.3 Hz, 2H), 3.81 (d, J=8.3 Hz, 2H), 1.72 (s, 3H), 1.47 (s, 9H)

HPLCMS (Method A): [m/z]: 253.05 [M+Na]$^+$

Ethyl 2-{1-[(tert-butoxy)carbonyl]azetidin-3-yl}-1,3-thiazole-4-carboxylate (161)

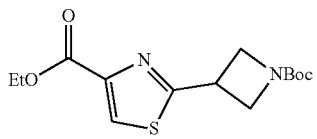 [SMILES: CCOC(=O)c1csc(C2CN(C(=O)OC(C)(C)C)C2)n1]

In a similar fashion to general procedure 1, tert-butyl 3-carbamothioylazetidine-1-carboxylate (159) (4.47 g, 20.67 mmol), ethyl 3-bromo-2-oxopropanoate (2.85 ml, 22.73 mmol) and calcium carbonate (1.12 g, 11.0 mmol) in EtOH (40 ml) afforded the title compound (3.54 g, 54%) as a yellow oil after purification by flash chromatography using a gradient elution from 10-50% EtOAc/heptane.

1H-NMR (DMSO-d6, 250 MHz): d[ppm]=8.49 (s, 1H), 4.37-4.23 (m, 5H), 4.00 (m, 2H), 1.41 (s, 9H), 1.31 (t, J=7.1 Hz, 3H)

HPLCMS (Method A): [m/z]: 335 [M+Na]+

Ethyl 2-{1-[(tert-butoxy)carbonyl]-3-methylazetidin-3-yl}-1,3-thiazole-4-carboxylate (162)

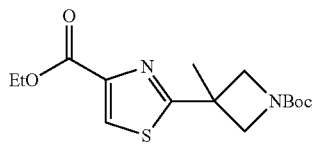

In a similar fashion to general procedure 1, tert-butyl 3-carbamothioyl-3-methylazetidine-1-carboxylate (160) (0.82 g, 3.56 mmol), ethyl 3-bromo-2-oxopropanoate (0.49 ml, 4.0 mmol) and calcium carbonate (0.2 g, 2.0 mmol) in EtOH (20 ml) gave the title compound (1.0 g) as a pale yellow oil.

1H-NMR (CDCl3, 500 MHz): d[ppm]=8.14 (s, 1H), 4.44 (q, J=7.1 Hz, 2H), 4.39 (d, J=8.0 Hz, 2H), 3.98 (d, J=8.0 Hz, 2H), 1.83 (s, 3H), 1.48 (s, 9H), 1.43 (t, J=7.1 Hz, 3H)

HPLCMS (Method A): [m/z]: 349.15 [M+Na]+

2-{1-[(Tert-butoxy)carbonyl]azetidin-3-yl}-1,3-thiazole-4-carboxylic Acid (163)

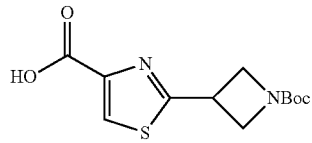 [SMILES: CC(C)(C)OC(=O)N1CC(c2nc(C(=O)O)cs2)C1]

In a similar fashion to general procedure 5, ethyl 2-{1-[(tert-butoxy)carbonyl]azetidin-3-yl}-1,3-thiazole-4-carboxylate (161) (2.52 g, 7.91 mmol) and LiOH (0.57 g, 23.72 mmol) in THF (40 ml) and water (40 ml) afforded the title compound (2.23 g, 87% purity, 86%) as an orange solid.

1H-NMR (DMSO-d6, 500 MHz): d[ppm]=13.03 (s, 1H), 8.40 (s, 1H), 4.31-4.23 (m, 2H), 4.23-4.17 (m, 1H), 4.05-3.93 (m, 2H), 1.40 (s, 9H)

HPLCMS (Method A): [m/z]: 306.85 [M+Na]+

2-{1-[(Tert-butoxy)carbonyl]-3-methylazetidin-3-yl}-1,3-thiazole-4-carboxylic Acid (164)

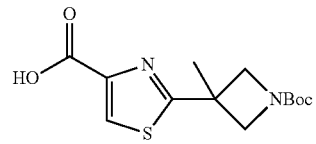 [SMILES: CC(C)(C)OC(=O)N1CC(C)(c2nc(C(=O)O)cs2)C1]

In a similar fashion to general procedure 5, ethyl 2-{1-[(tert-butoxy)carbonyl]-3-methylazetidin-3-yl}-1,3-thiazole-4-carboxylate (162) (1.0 g, 3.06 mmol) and LiOH (0.22 g, 10.0 mmol) in THF (30 ml) and water (15 ml) gave the title compound (853 mg, 93%) as a pale yellow foam.

1H-NMR (DMSO-d6, 250 MHz): d[ppm]=8.44 (s, 1H), 4.16 (d, J=8.2 Hz, 2H), 3.90 (d, J=8.2 Hz, 2H), 1.72 (s, 3H), 1.41 (s, 9H)

HPLCMS (Method A): [m/z]: 321.05 [M+Na]+

Tert-butyl 3-(4-{[(3-fluoropyridin-2-yl)methyl]carbamoyl}-1,3-thiazol-2-yl)azetidine-1-carboxylate (165)

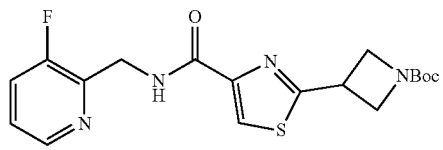

In a similar fashion to general procedure 6, 2-{1-[(tert-butoxy)carbonyl]azetidin-3-yl}-1,3-thiazole-4-carboxylic acid (163) (87%, 2.23 g, 6.69 mmol), (3-fluoropyridin-2-yl)methanamine dihydrochloride (A2) (1.6 g, 8.03 mmol), DIPEA (4.66 ml, 26.77 mmol) and HATU (3.05 g, 8.03 mmol) in DCM (40 ml) afforded the title compound (2.51 g, 82% purity, 79%) as an orange oil after purification by flash column chromatography using an elution gradient 20-100% EtOAc/heptane.

1H-NMR (DMSO-d6, 250 MHz): d[ppm]=8.79 (t, J=5.7 Hz, 1H), 8.38 (dt, J=4.6, 1.4 Hz, 1H), 8.24 (s, 1H), 7.76-7.62 (m, 1H), 7.46-7.35 (m, 1H), 4.66 (dd, J=5.7, 1.5 Hz, 2H), 4.34-4.17 (m, 3H), 4.16-4.05 (m, 2H), 1.39 (s, 9H)

HPLCMS (Method A): [m/z]: 393 [M+H]+

Tert-butyl 3-[4-({5H,6H,7H-cyclopenta[b]pyridin-7-yl}carbamoyl)-1,3-thiazol-2-yl]azetidine-1-carboxylate (166)

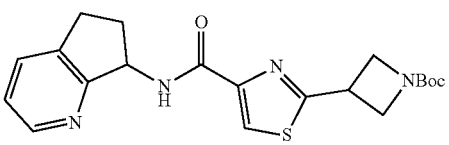 [SMILES: CC(C)(C)OC(=O)N1CC(c2nc(C(=O)NC3CCc4cccnc43)cs2)C1]

In a similar fashion to general procedure 6, 2-{1-[(tert-butoxy)carbonyl]azetidin-3-yl}-1,3-thiazole-4-carboxylic acid (163) (300 mg, 1.06 mmol), 5H,6H,7H-cyclopenta[b]

pyridin-7-amine dihydrochloride (284 mg, 1.37 mmol), DIPEA (0.61 ml, 3.5 mmol) and HATU (0.52 g, 1.4 mmol) in DCM (20 ml) afforded the crude title compound (1.32 g, 30% purity, 94%) which was used into the next step without purification.

HPLCMS (Method A): [m/z]: 401.1 [M+H]⁺

Tert-butyl 3-(4-{[(3-chloropyridin-2-yl)methyl]carbamoyl}-1,3-thiazol-2-yl)azetidine-1-carboxylate (167)

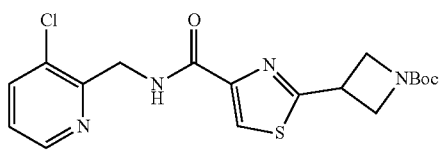 [SMILES: CC(C)(C)OC(=O)N1CC(c2nc(C(=O)NCc3ncccc3Cl)cs2)C1]

In a similar fashion to general procedure 6, 2-{1-[(tert-butoxy)carbonyl]azetidin-3-yl}-1,3-thiazole-4-carboxylic acid (163) (364 mg, 1.28 mmol), (3-chloropyridin-2-yl)methanamine dihydrochloride (359 mg, 1.66 mmol), DIPEA (0.74 ml, 4.2 mmol) and HATU (0.63 g, 1.7 mmol) in DCM (20 ml) afforded the title compound (493 mg, 94%) as a pale yellow oil after purification by flash column chromatography (eluting with a gradient of 0-100% EtOAc/heptane).

1H-NMR (DMSO-d6, 250 MHz): d[ppm]=8.79 (t, J=5.5 Hz, 1H), 8.51 (dd, J=4.7, 1.4 Hz, 1H), 8.27 (s, 1H), 7.96 (dd, J=8.1, 1.4 Hz, 1H), 7.39 (dd, J=8.1, 4.7 Hz, 1H), 4.70 (d, J=5.5 Hz, 2H), 4.38-4.18 (m, 3H), 4.09 (q, J=3.9 Hz, 2H), 1.41 (s, 9H)

HPLCMS (Method A): [m/z]: 409.05 [M+H]⁺

Tert-butyl 3-(4-{[(3-fluoropyridin-2-yl)methyl]carbamoyl}-1,3-thiazol-2-yl)-3-methylazetidine-1-carboxylate (168)

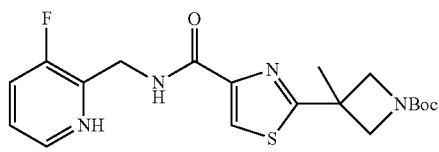 [SMILES: CC(C)(C)OC(=O)N1CC(C)(c2nc(C(=O)NCc3ncccc3F)cs2)C1]

In a similar fashion to general procedure 6, 2-{1-[(tert-butoxy)carbonyl]-3-methylazetidin-3-yl}-1,3-thiazole-4-carboxylic acid (164) (546 mg, 1.83 mmol), (3-fluoropyridin-2-yl)methanamine dihydrochloride (A2) (400 mg, 2.01 mmol), DIPEA (1.05 ml, 6.0 mmol) and HATU (830 mg, 2.0 mmol) in DCM (20 ml) gave the crude title compound (824 mg) as a pale yellow oil. The crude material was used in the next step without further purification.

1H-NMR (CDCl₃, 500 MHz): d[ppm]=8.38-8.33 (m, 1H), 8.28 (s, 1H), 8.02 (s, 1H), 7.37-7.31 (m, 1H), 7.23-7.17 (m, 1H), 4.81-4.76 (m, 2H), 4.30 (d, J=7.5 Hz, 2H), 3.88 (d, J=7.5 Hz, 2H), 1.52 (s, 3H), 1.40 (s, 9H)

HPLCMS (Method A): [m/z]: 407.2 [M+H]⁺

2-(Azetidin-3-yl)-N-[(3-fluoropyridin-2-yl)methyl]-1,3-thiazole-4-carboxamide dihydrochloride (169)

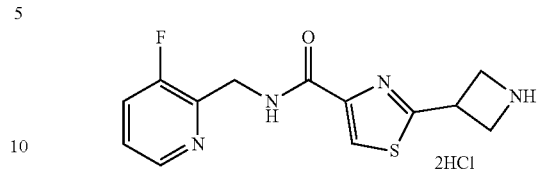

In a similar fashion to general procedure 4, tert-butyl 3-(4-{[(3-fluoropyridin-2-yl)methyl]carbamoyl}-1,3-thiazol-2-yl)azetidine-1-carboxylate (165) (82%, 2.51 g, 5.26 mmol) and 12 M HCl (8.8 ml) in MeOH (25 ml) afforded the title compound (2.26 g, 85% purity, quant.) as a light brown solid.

1H-NMR (Methanol-d4, 250 MHz): d[ppm]=8.56 (d, J=5.2 Hz, 1H), 8.27 (s, 1H), 8.24-8.07 (m, 1H), 7.87-7.73 (m, 1H), 4.96-4.91 (m, 2H), 4.57-4.41 (m, 5H)

HPLCMS (Method A): [m/z]: 292.95 [M+H]⁺

2-(Azetidin-3-yl)-N-{5H,6H,7H-cyclopenta[b]pyridin-7-yl}-1,3-thiazole-4-carboxamide (170)

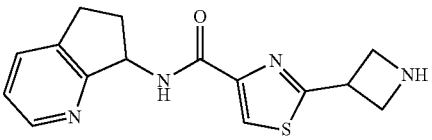 [SMILES: O=C(NC1CCc2cccnc21)c1csc(C2CNC2)n1]

In a similar fashion to general procedure 4, crude tert-butyl 3-[4-({5H,6H,7H-cyclopenta[b]pyridin-7-yl}carbamoyl)-1,3-thiazol-2-yl]azetidine-1-carboxylate (166) (1.32 g, 30% purity, 1.06 mmol) and 12 M HCl (1 ml) in MeOH (10 ml) afforded the title compound (322 mg, quant.) as a white solid after purification using an SCX-2 cartridge, rinsing with DCM and MeOH, then elution with 7 N ammonia in MeOH.

HPLCMS (Method A): [m/z]: 300.95 [M+H]⁺

2-(Azetidin-3-yl)-N-[(3-chloropyridin-2-yl)methyl]-1,3-thiazole-4-carboxamide (171)

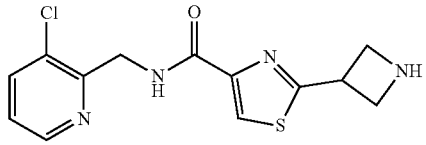 [SMILES: O=C(NCc1ncccc1Cl)c1csc(C2CNC2)n1]

In a similar fashion to general procedure 4, tert-butyl 3-(4-{[(3-chloropyridin-2-yl)methyl]carbamoyl}-1,3-thiazol-2-yl)azetidine-1-carboxylate (167) (423 mg, 1.03 mmol) and 12 M HCl (2 ml) in MeOH (30 ml) afforded the title compound (330 mg, 99%) as a white solid after purification using an SCX-2 cartridge, rinsing with DCM and MeOH, then elution with 7 N ammonia in MeOH.

1H-NMR (DMSO-d6, 500 MHz): d[ppm]=8.71 (t, J=5.5 Hz, 1H), 8.52 (dd, J=4.7, 1.4 Hz, 1H), 8.24 (s, 1H), 7.96 (dd, J=8.0, 1.4 Hz, 1H), 7.39 (dd, J=8.0, 4.7 Hz, 1H), 4.70 (d, J=5.5 Hz, 2H), 4.24 (m, 1H), 3.92-3.87 (m, 2H), 3.76-3.73 (m, 2H)

HPLCMS (Method A): [m/z]: 308.95 [M+H]+

N-[(3-Fluoropyridin-2-yl)methyl]-2-(3-methylazetidin-3-yl)-1,3-thiazole-4-carboxamide (172)

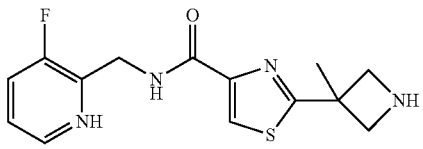 [SMILES: CC1(c2nc(C(=O)NCc3ncccc3F)cs2)CNC1]

In a similar fashion to general procedure 4, tert-butyl 3-(4-{[(3-fluoropyridin-2-yl)methyl]carbamoyl}-1,3-thiazol-2-yl)-3-methylazetidine-1-carboxylate (168) (824 mg, 2.03 mmol) and 12 M HCl (2 ml) in MeOH (20 ml) gave the title compound (476 mg, 74%) after purification using an SCX-2 cartridge, rinsing with DCM and MeOH, then elution with 7 N ammonia in MeOH.

1H-NMR (DMSO-d6, 250 MHz): d[ppm]=8.71 (t, J=5.7 Hz, 1H), 8.39 (dt, J=4.6, 1.3 Hz, 1H), 8.21 (s, 1H), 7.71 (ddd, J=10.0, 8.3, 1.3 Hz, 1H), 7.46-7.36 (m, 1H), 4.68 (m, 2H), 3.85 (d, J=7.5 Hz, 2H), 3.52 (d, J=7.5 Hz, 2H), 1.72 (s, 3H)

HPLCMS (Method A): [m/z]: 307.20 [M+H]+

2-{1-[2-(1H-1,3-Benzodiazol-2-yl)ethyl]azetidin-3-yl}-N-[(3-fluoropyridin-2-yl)methyl]-1,3-thiazole-4-carboxamide (Example Compound No. 193)

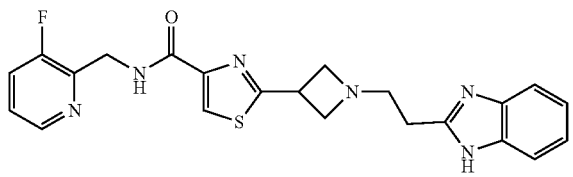 [SMILES: O=C(NCc1ncccc1Cl)c1csc(C2CN(CCc3nc4ccccc4[nH]3)C2)n1]

In a similar fashion to general procedure 8, 2-(azetidin-3-yl)-N-[(3-fluoropyridin-2-yl)methyl]-1,3-thiazole-4-carboxamide dihydrochloride (169) (85%, 2.26 g, 5.26 mmol), N-(2-nitrophenyl)prop-2-enamide (D) (1.21 g, 6.31 mmol) and DBU (2.35 ml, 15.77 mmol) in MeCN (30 ml) afforded a crude intermediate which was further reacted with iron powder (0.51 g, 9.0 mmol) and AcOH (5 ml) to afford the title compound (122 mg, 7%) as a cream solid after purification by basic prep-HPLC.

1H-NMR (Methanol-d4, 500 MHz): d[ppm]=8.33 (dt, J=4.7, 1.3 Hz, 1H), 8.12 (s, 1H), 7.62-7.56 (m, 1H), 7.53-7.47 (m, 2H), 7.39-7.34 (m, 1H), 7.22-7.17 (m, 2H), 4.79 (d, J=1.7 Hz, 2H), 4.11-4.03 (m, 1H), 3.80 (t, J=7.9 Hz, 2H), 3.55-3.50 (m, 2H), 3.07-3.02 (m, 2H), 3.01-2.96 (m, 2H)

HPLCMS (Method G): [m/z]: 437 [M+H]+

2-{1-[2-(1H-1,3-Benzodiazol-2-yl)ethyl]azetidin-3-yl}-N-{5H,6H,7H-cyclopenta[b]pyridin-7-yl}-1,3-thiazole-4-carboxamide (Example Compound No. 194)

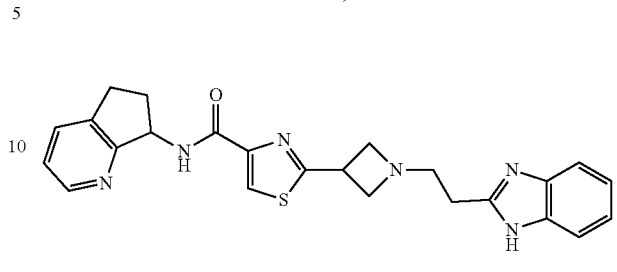

In a similar manner to general procedure 8, 2-(azetidin-3-yl)-N-{5H,6H,7H-cyclopenta[b]pyridin-7-yl}-1,3-thiazole-4-carboxamide (170) (322 mg, 1.07 mmol), N-(2-nitrophenyl)prop-2-enamide (D) (227 mg, 1.18 mmol) and DBU (0.21 ml, 1.4 mmol) in MeCN (10 ml) gave a crude intermediate which was further reacted with iron powder (0.15 g, 2.6 mmol) in AcOH (4 ml) to afford the title compound (139 mg, 48%) as a white solid after purification by basic prep-HPLC.

1H-NMR (Methanol-d4, 500 MHz): d[ppm]=8.35 (d, J=5.0 Hz, 1H), 8.15 (s, 1H), 7.78-7.74 (m, 1H), 7.50 (br s, 2H), 7.29 (dd, J=7.6, 5.0 Hz, 1H), 7.24-7.18 (m, 2H), 5.58 (t, J=8.3 Hz, 1H), 4.05 (tt, J=7.9, 6.4 Hz, 1H), 3.77 (t, J=7.9 Hz, 2H), 3.56-3.49 (m, 2H), 3.11 (ddd, J=16.3, 9.1, 2.8 Hz, 1H), 3.05-3.00 (m, 3H), 3.00-2.94 (m, 2H), 2.73 (m, 1H), 2.11 (m, 1H)

HPLCMS (Method C): [m/z]: 445.3 [M+H]+

2-{1-[2-(1H-1,3-Benzodiazol-2-yl)ethyl]azetidin-3-yl}-N-[(3-chloropyridin-2-yl)methyl]-1,3-thiazole-4-carboxamide (Example Compound No. 195)

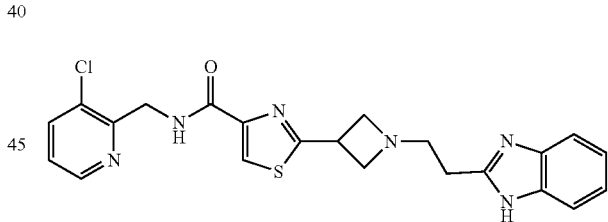

In a similar fashion to general procedure 8, 2-(azetidin-3-yl)-N-[(3-chloropyridin-2-yl)methyl]-1,3-thiazole-4-carboxamide (171) (330 mg, 1.07 mmol), N-(2-nitrophenyl)prop-2-enamide (D) (226 mg, 1.18 mmol) and DBU (0.21 ml, 1.4 mmol) in MeCN (10 ml) gave the required crude intermediate which was further reacted with iron powder (150 mg, 2.6 mmol) in AcOH (4 ml) to afford the title compound (80 mg, 27%) as a white solid after purification by basic prep-HPLC followed by flash column chromatography (eluting with a gradient of 0-12% MeOH/DCM).

1H-NMR (Methanol-d4, 500 MHz): d[ppm]=8.45 (dd, J=4.7, 1.4 Hz, 1H), 8.15 (s, 1H), 7.88 (dd, J=8.1, 1.4 Hz, 1H), 7.51 (br s, 2H), 7.32 (dd, J=8.1, 4.7 Hz, 1H), 7.24-7.19 (m, 2H), 4.85-4.82 (m, 2H), 4.11 (m, 1H), 3.84 (t, J=7.9 Hz, 2H), 3.59-3.53 (m, 2H), 3.10-3.05 (m, 2H), 3.03-2.98 (m, 2H)

HPLCMS (Method C): [m/z]: 453.2 [M+H]+

2-{1-[2-(1H-1,3-Benzodiazol-2-yl)ethyl]-3-methyl-azetidin-3-yl}-N-[(3-fluoropyridin-2-yl)methyl]-1,3-thiazole-4-carboxamide (Example Compound No. 212)

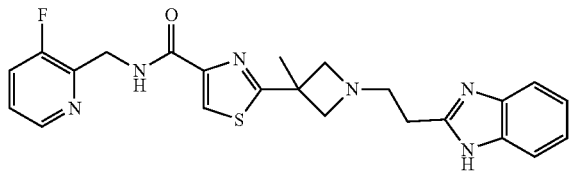 [SMILES: CC1(c2nc(C(=O)NCc3ncccc3F)cs2)CN(CCc2nc3ccccc3[nH]2)C1]

In a similar fashion to general procedure 8, N-[(3-fluoropyridin-2-yl)methyl]-2-(3-methylazetidin-3-yl)-1,3-thiazole-4-carboxamide (172) (476 mg, 1.55 mmol), N-(2-nitrophenyl)prop-2-enamide (D) (328 mg, 1.71 mmol) and DBU (0.26 ml, 2 mmol) in MeCN (15 ml) gave the required crude intermediate which was further reacted with iron powder (350 mg, 10.0 mmol) in AcOH (5 ml). Purification by basic prep-HPLC followed by flash column chromatography (eluting with a gradient of 0-30% MeOH/DCM) gave the title compound (162 mg, 23%) as a white solid.

1H-NMR (Methanol-d4, 500 MHz): d[ppm]=8.34-8.27 (m, 1H), 8.14 (s, 1H), 7.60 (ddd, J=9.7, 8.5, 1.2 Hz, 1H), 7.51 (s, 2H), 7.37-7.32 (m, 1H), 7.24-7.18 (m, 2H), 4.80 (d, J=1.3 Hz, 2H), 3.78 (d, J=7.7 Hz, 2H), 3.47 (d, J=7.7 Hz, 2H), 3.10 (t, J=7.2 Hz, 2H), 3.00 (t, J=7.2 Hz, 2H), 1.78 (s, 3H)

HPLCMS (Method C): [m/z]: 451.1 [M+H]$^+$

General Scheme 10 Above:

Methyl 2,2-dimethyl-3-oxopropanoate (173)

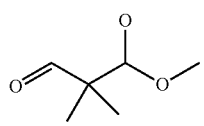

To an ice-cooled (0° C.) solution of methyl 3-hydroxy-2,2-dimethylpropanoate (1.45 ml, 11.35 mmol) and TEA (4.75 ml, 34.05 mmol) in DCM (45 ml) and DMSO (8 ml, 113.5 mmol) was added pyridine sulfur trioxide complex (5.42 g, 34.05 mmol). The resulting mixture was stirred at room temperature for 22 h. The reaction was quenched with saturated NH$_4$Cl (30 ml). The layers were separated and the aqueous layer was extracted with DCM (40 ml). The organic layer was washed sequentially with 2M HCl (2×20 ml) and brine (15 ml), dried (MgSO$_4$), filtered and evaporated to give the title compound (0.35 g, 99%) as an orange oil.

1H-NMR (CDCl$_3$, 250 MHz): d[ppm]=9.66 (s, 1H), 5.30 (s, 1H), 3.75 (s, 3H), 1.35 (s, 6H)

Methyl 3-{[2-(4-{[(3-fluoropyridin-2-yl)methyl]carbamoyl}-1,3-thiazol-2-yl)ethyl]amino}-2,2-dimethylpropanoate (174)

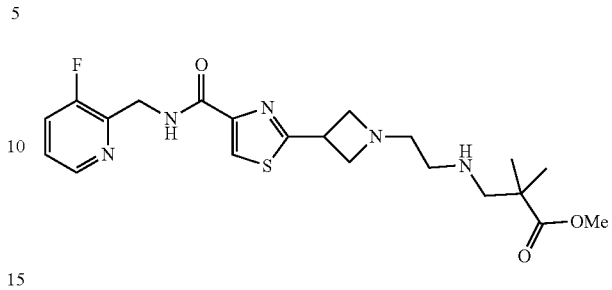

DIPEA (1.8 ml, 10.32 mmol) was added to 2-(2-aminoethyl)-N-[(3-fluoropyridin-2-yl)methyl]-1,3-thiazole-4-carboxamide dihydrochloride (103) (0.97 g, 2.58 mmol) and methyl 2,2-dimethyl-3-oxopropanoate (173) (0.52 g, 3.36 mmol) in MeOH (20 ml). The reaction was stirred at room temperature for 18 h. The reaction was cooled to 0° C. and NaBH$_4$ (146 mg, 3.87 mmol) was added portionwise. The reaction was allowed to warm to room temperature and stirred for 3.5 h. The solvent evaporated and water (10 ml) added. The aqueous layer extracted with EtOAc (3×20 ml). The combined organic layers were dried (MgSO4), filtered and evaporated to give an orange oil (1.1 g). Purification by flash column chromatography (eluting with a gradient of 0-15% MeOH/DCM) gave the title compound (0.95 g, 79%) as a pale yellow oil.

1H-NMR (CDCl$_3$, 250 MHz): d[ppm]=8.43-8.38 (m, 2H), 8.02 (s, 1H), 7.45-7.36 (m, 1H), 7.26-7.20 (m, 1H), 4.85 (dd, J=5.3, 1.7 Hz, 2H), 3.63 (s, 3H), 3.20 (t, J=5.6 Hz, 2H), 3.10 (t, J=5.8 Hz, 2H), 2.79 (s, 2H), 1.22 (s, 6H)

HPLCMS (Method A): [m/z]: 395.05 [M+H]$^+$

3-{[(Tert-butoxy)carbonyl][2-(4-{[(3-fluoropyridin-2-yl)methyl]carbamoyl}-1,3-thiazol-2-yl)ethyl]amino}-2,2-dimethylpropanoate (175)

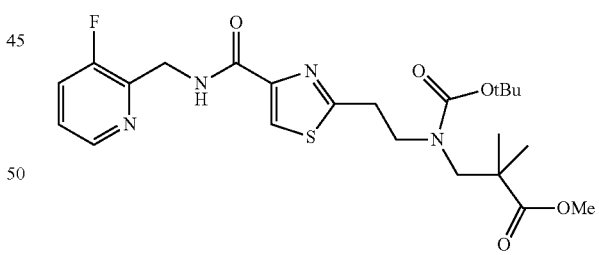

TEA (0.5 ml, 3.62 mmol) was added to methyl 3-{[2-(4-{[(3-fluoropyridin-2-yl)methyl]carbamoyl}-1,3-thiazol-2-yl)ethyl]amino}-2,2-dimethylpropanoate (174) (0.95 g, 2.41 mmol) in DCM (10 ml). The reaction was stirred for 5 min at room temperature, ditert-butyl dicarbonate (0.63 g, 2.9 mmol) in DCM (10 ml) was added dropwise and the reaction stirred at room temperature for 20 h. The solvent was evaporated and purification by flash column chromatography (eluting with a gradient of 0-100% EtOAc/heptane) to give the title compound (0.94 g, 90%) as a clear oil.

1H-NMR (CDCl$_3$, 500 MHz): d[ppm]=8.42 (d, J=4.3 Hz, 2H), 8.01 (s, 1H), 7.44-7.37 (m, 1H), 7.26 (m, 1H, obscured by solvent peak), 4.85 (dd, J=5.1, 1.7 Hz, 2H), 3.70 (s, 3H), 3.55 (t, J=7.0 Hz, 2H), 3.48-3.41 (br m, 2H), 3.31-3.14 (m, 2H), 1.45 (s, 9H), 1.19 (s, 6H)
HPLCMS (Method A): [m/z]: 495.15 [M+H]⁺

3-{[(Tert-butoxy)carbonyl][2-(4-{[(3-fluoropyridin-2-yl)methyl]carbamoyl}-1,3-thiazol-2-yl)ethyl]amino}-2,2-dimethylpropanoic Acid (176)

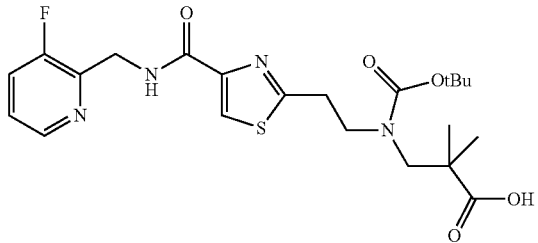 [SMILES: CC(C)(C)OC(=O)N(CCc1nc(C(=O)NCc2ncccc2F)cs1)CC(C)(C)C(=O)O]

In a similar fashion using general procedure 5, LiOH (0.27 g, 11.1 mmol) and 3{[(tert-butoxy)carbonyl][2-(4-{[(3-fluoropyridin-2-yl)methyl]carbamoyl}-1,3-thiazol-2-yl)ethyl]amino}-2,2-dimethylpropanoate (175) (0.94 g, 1.85 mmol) in THF (6 ml)/water (1.5 ml) gave the title compound (0.91 g, 96%) as an off-white solid.

1H-NMR (DMSO-d6, 500 MHz): d[ppm]=12.41 (s, 1H), 8.63 (s, 1H), 8.39 (s, 1H), 8.17 (s, 1H), 7.71 (ddd, J=10.0, 8.3, 1.2 Hz, 1H), 7.41 (dt, J=8.6, 4.4 Hz, 1H), 4.67 (dd, J=5.6, 1.3 Hz, 2H), 3.53 (t, J=7.1 Hz, 2H), 3.38 (s, 2H), 3.23 (t, J=7.1 Hz, 2H), 1.34 (s, 9H), 1.07 (s, 6H)
HPLCMS (Method A): [m/z]: 481.15 [M+H]⁺

Tert-butyl N-{2-[(2-aminophenyl)carbamoyl]-2,2-dimethylethyl}-N-[2-(4-{[(3-fluoropyridin-2-yl)methyl]carbamoyl}-1,3-thiazol-2-yl)ethyl]carbamate (177)

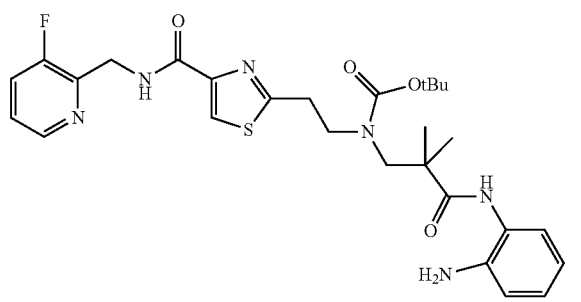 [SMILES: CC(C)(C)OC(=O)N(CCc1nc(C(=O)NCc2ncccc2F)cs1)CC(C)(C)C(=O)Nc1ccccc1N]

In a similar fashion using general procedure 6, 3-{[(tert-butoxy)carbonyl][2-(4-{[(3-fluoropyridin-2-yl)methyl]carbamoyl}-1,3-thiazol-2-yl)ethyl]amino}-2,2-dimethylpropanoic acid (176) (0.5 g, 0.98 mmol), benzene-1,2-diamine (0.14 g, 1.3 mmol), TEA (0.18 ml, 1.3 mmol) and HATU (0.49 g, 1.3 mmol) in DMF (10 ml) gave the title compound (0.51 g, 83%) as a yellow oil after purification by flash column chromatography using a gradient of 0-100% EtOAc/heptane.

1H-NMR (DMSO-d6, 250 MHz): d[ppm]=8.84 (s, 1H), 8.61 (s, 1H), 8.37 (d, J=4.5 Hz, 1H), 8.16 (s, 1H), 7.70 (ddd, J=10.1, 8.3, 1.2 Hz, 1H), 7.41 (dt, J=8.6, 4.4 Hz, 1H), 7.02-6.86 (m, 2H), 6.78-6.68 (m, 1H), 6.57-6.45 (m, 1H), 4.66 (d, J=4.4 Hz, 2H), 3.55 (t, J=6.9 Hz, 2H), 3.50 (s, 2H), 3.24 (t, J=6.9 Hz, 2H), 1.35 (s, 9H), 1.21 (s, 6H)
HPLCMS (Method A): [m/z]: 571.2 [M+H]⁺

Tert-butyl N-[2-(1H-1,3-benzodiazol-2-yl)-2-methylpropyl]-N-[2-(4-{[(3-fluoropyridin-2-yl)methyl]carbamoyl}-1,3-thiazol-2-yl)ethyl]carbamate (178)

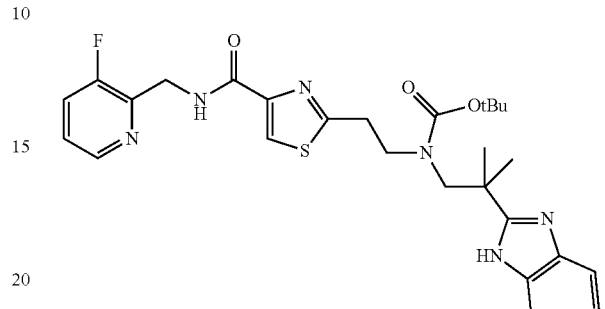

Tert-butyl N-{2-[(2-aminophenyl)carbamoyl]-2,2-dimethylethyl}-N-[2-(4-{[(3-fluoropyridin-2-yl)methyl]carbamoyl}-1,3-thiazol-2-yl)ethyl]carbamate (177) (260 mg, 0.415 mmol) in glacial AcOH (4 ml) was heated to 80° C. for 35 min. The reaction was cooled, concentrated in vacuo and the residue partitioned between EtOAc (10 ml) and saturated K₂CO₃ (10 ml). The layers were separated and the aqueous layer extracted with EtOAc (2×10 ml). The combined organic layers were dried (Na₂SO₄), filtered and evaporated to give a brown oil. Purification by flash column chromatography (KP—NH column eluting with a gradient of 0-100% DCM/heptane) gave the title compound (172 mg, 71%) as a pale brown oil.

¹H-NMR (CDCl₃, 500 MHz): d[ppm]=8.43 (br s, 1H), 8.42 (dt, J=4.6 and 1.2 Hz, 2H), 7.99 (s, 1H), 7.82-7.69 (m, 1H), 7.47-7.42 (m, 1H), 7.40-7.34 (m, 1H), 7.25-7.18 (m, 2H), 4.91 (d, J=4.5 Hz, 2H), 3.75-3.69 (br m, 2H), 3.59-3.39 (br m, 2H), 3.11 (t, J=6.3 Hz, 2H), 1.59 (s, 9H), 1.45 (s, 6H)
HPLCMS (Method A): [m/z]: 553.2 [M+H]⁺

2-(2-{[2-(1H-1,3-Benzodiazol-2-yl)-2-methylpropyl]amino}ethyl)-N-[(3-fluoropyridin-2-yl)methyl]-1,3-thiazole-4-carboxamide (Example Compound No. 199)

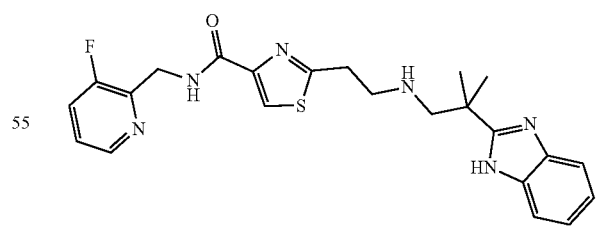

In a similar fashion to general procedure 2, TFA (2 ml) was added to tert-butyl N-{2-[(2-aminophenyl)carbamoyl]-2,2-dimethylethyl}-N-[2-(4-{[(3-fluoropyridin-2-yl)methyl]carbamoyl}-1,3-thiazol-2-yl)ethyl]carbamate (178) (172 mg, 0.25 mmol) in DCM (2 ml) and stirred at room temperature for 3 h, to give the title compound (79 mg, 70%) as a beige solid after purification by Isolute SCX-2 cartridge, eluted with DCM (2 CV), DCM/MeOH (1:1, 1 CV), MeOH (2 CV) and then 7M NH₃ in MeOH (2 CV).

1H-NMR (DMSO-d6, 500 MHz): d[ppm]=12.01 (s, 1H), 8.62 (t, J=5.7 Hz, 1H), 8.37 (dt, J=4.7 and 1.5 Hz, 1H), 8.02 (s, 1H), 7.74-7.63 (m, 1H), 7.53-7.35 (m, 2H), 7.42-7.38 (m, 1H), 7.14-7.06 (m, 2H), 4.64 (dd, J=5.6, 1.4 Hz, 2H), 3.11 (t, J=6.5 Hz, 2H), 2.91-2.87 (m, 4H), 1.39 (s, 6H)

HPLCMS (Method D): [m/z]: 453.2 [M+H]⁺

2-(1H-1,3-Benzodiazol-2-yl)acetic Acid (179)

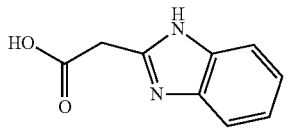 [SMILES: O=C(O)Cc1nc2ccccc2[nH]1]

2M NaOH (90.7 ml, 181 mmol) was added to 2-(1H-1,3-benzodiazol-2-yl)acetonitrile (9.5 g, 60.4 mmol). The reaction heated at 100° C. for 3 h. The reaction mixture was cooled to room temperature and acidified to pH 5-6 with 4 M HCl. The resulting precipitate was filtered, washed with water and dried in vacuo to give the title compound (9.7 g, 77%) as light brown solid.

1H-NMR (DMSO-d6, 500 MHz): d[ppm]=7.52-7.46 (m, 1H), 7.45-7.39 (m, 1H), 7.17-7.11 (m, 1H), 7.11-7.06 (m, 1H), 2.47 (s, 2H)

HPLCMS (Method F): [m/z]: 177.0 [M+H]⁺

Methyl 2-(1H-1,3-benzodiazol-2-yl)acetate (180)

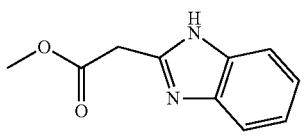

Thionyl dichloride (0.7 ml, 9.65 mmol) was added dropwise to an ice-cooled (0° C.) suspension of 2-(1H-1,3-benzodiazol-2-yl)acetic acid (179) (0.7 g, 3.97 mmol) in MeOH (30 ml). The reaction mixture was allowed to warm to room temperature and stirred for 18 h. The mixture was poured onto saturated NaHCO₃ (40 ml) and extracted with DCM (3×20 ml). The combined organic layers were washed with brine (30 ml), dried (NaSO₄), filtered and evaporated to give the title compound (0.65 g, 86%) as a cream solid.

1H-NMR (CDCl3, 500 MHz): d[ppm]=10.10 (br s, 1H), 7.72 (br s, 1H), 7.46 (br s, 1H), 7.29-7.23 (m, 2H), 4.09 (s, 2H), 3.82 (s, 3H)

HPLCMS (Method F): [m/z]: 191.2 [M+H]⁺

Tert-butyl 2-(2-methoxy-2-oxoethyl)-1H-1,3-benzodiazole-1-carboxylate (181)

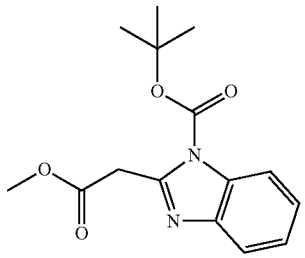 [SMILES: COC(=O)Cc1nc2ccccc2n1C(=O)OC(C)(C)C]

In a similar fashion to general procedure 4, methyl 2-(1H-1,3-benzodiazol-2-yl)acetate (180) (650 mg, 3.42 mmol), TEA (0.5 ml, 3.59 mmol), Boc₂O (890 mg, 4.11 mmol) and DMAP (84 mg, 0.68 mmol) in THF (30 ml) at room temperature for 18 h, gave the title compound (940 mg, 95%) as a cream solid after purification by flash column chromatography (eluting with a gradient of 0-100% EtOAc/heptane).

1H-NMR (CDCl₃, 500 MHz): d[ppm]=7.96-7.90 (m, 1H), 7.74-7.68 (m, 1H), 7.38-7.31 (m, 2H), 4.28 (s, 2H), 3.73 (s, 3H), 1.69 (s, 9H)

HPLCMS (Method A): [m/z]: 291 [M+H]⁺

Tert-butyl 2-(1,1-difluoro-2-methoxy-2-oxoethyl)-1H-1,3-benzodiazole-1-carboxylate (182)

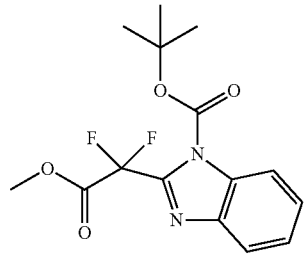 [SMILES: COC(=O)C(F)(F)c1nc2ccccc2n1C(=O)OC(C)(C)C]

KHMDS (1.5 g, 7.61 mmol) in THF (15 ml) was cooled to −78° C. tert-Butyl 2-(2-methoxy-2-oxoethyl)-1H-1,3-benzodiazole-1-carboxylate (181) (0.74 g, 2.54 mmol) was added and the mixture was stirred at −78° C. for 45 min. A combined mixture of 18-crown-6 (2.01 g, 7.61 mmol) and N-fluoro-N-(phenylsulfonyl)benzenesulfonamide (2.2 g, 7.1 mmol) was added. The mixture was stirred at −78° C. for 30 min. Additional KHMDS (0.75 g, 3.76 mmol) was added and stirred for 20 min. Additional N-fluoro-N-(phenylsulfonyl)benzenesulfonamide (1.1 g, 3.49 mmol) and 18-crown-6 (1 g, 3.78 mmol) were added. The reaction mixture was then allowed to slowly warm to room temperature and stirred for 18 h to give a ratio of 1.6:1 bis:mono fluorinated products. Saturated NH₄Cl (12 ml) was added followed by water (20 ml). The organic and aqueous layers were separated. The aqueous layer was extracted with EtOAc (3×50 ml). The combined organic layers were washed with brine (100 ml), dried (NaSO₄), filtered and evaporated to give a pink semi-solid (3 g). Purification by flash column chromatography (eluting with a gradient of (50% TBME/heptane followed by 100% TBME) gave the title compound (0.47 g, 48%) as a yellow oil which solidified on standing.

1H-NMR (CDCl₃, 250 MHz): d[ppm]=8.00-7.81 (m, 2H), 7.55-7.34 (m, 2H), 3.91 (s, 3H), 1.70 (s, 9H).
HPLCMS (Method A): [m/z]: 226.9 [M-BOC+H]⁺

Tert-butyl 2-(1,1-difluoro-2-hydroxy-2-methoxyethyl)-1H-1,3-benzodiazole-1-carboxylate (183)

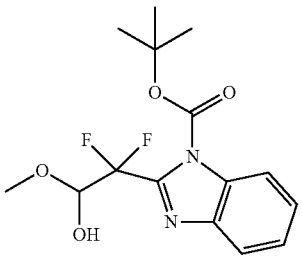 [SMILES: COC(O)C(F)(F)c1nc2ccccc2n1C(=O)OC(C)(C)C]

NaBH₄ (44 mg, 1.16 mmol) was added to an ice-cooled (0° C.) solution of tert-butyl 2-(1,1-difluoro-2-methoxy-2-oxoethyl)-1H-1,3-benzodiazole-1-carboxylate (182) (295 mg, 0.76 mmol) in EtOH (3.5 ml). The reaction was stirred at 0° C. for 1.5 h, quenched with dropwise addition of 1 M HCl (0.5 ml). Water (10 ml) was added and the aqueous layer extracted with EtOAc (3×10 ml). The combined organic layers dried (NaSO₄), filtered and evaporated to give a white solid (300 mg). Purification by flash column chromatography (eluting with a gradient of 0-40% EtOAc/heptane) gave the title compound (185 mg, 59%) as a white solid.
1H-NMR (CDCl₃, 250 MHz): d[ppm]=8.03-7.77 (m, 1H), 7.63-7.31 (m, 3H), 6.17 (dd, J=6.4, 4.9 Hz, 1H), 3.69 (s, 3H), 1.52 (s, 9H)
HPLCMS (Method A): [m/z]: 329.05 [M+H]⁺

4-(2-{[2-(1H-1,3-Benzodiazol-2-yl)-2,2-difluoroethyl]amino}ethyl)-N-[(3-fluoropyridin-2-yl)methyl]-1,3-thiazole-2-carboxamide (Example Compound No. 196)

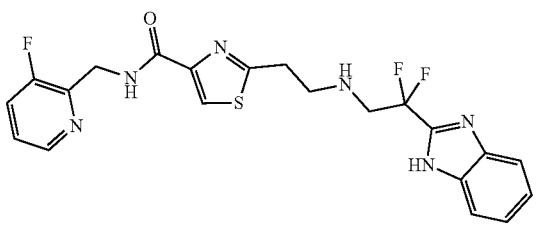 [SMILES: O=C(NCc1ncccc1F)c1csc(CCNCC(F)(F)c2nc3ccccc3[nH]2)n1]

Tert-Butyl 2-(1,1-difluoro-2-hydroxy-2-methoxyethyl)-1H-1,3-benzodiazole-1-carboxylate (183) (160 mg, 0.4 mmol), 2-(2-aminoethyl)-N-[(3-fluoropyridin-2-yl)methyl]-1,3-thiazole-4-carboxamide (103) (136 mg, 0.49 mmol) and activated molecular sieves in dry toluene (3 ml) was heated to 125° C. for 18 h. The reaction was cooled to room temperature and NaBH₄ (40 mg, 1.06 mmol) was added followed by EtOH (4 ml). The reaction mixture was stirred for 1 h. The reaction was quenched with dropwise addition of 1 M HCl (10 drops). Once effervescence ceased, water (10 ml) was added and using 2M K₂CO₃, the pH was adjusted to 10. The mixture was filtered and the aqueous layer extracted with EtOAc (3×20 ml). The combined organic layers dried (NaSO₄), filtered and evaporated to give a brown oily solid (176 mg). Purification by flash column chromatography (eluting with a gradient of 0-10% MeOH/DCM) gave a brown solid (40 mg). Further purification by basic prep HPLC gave a yellow oil (21 mg). Repurification by flash column chromatography (eluting with a gradient of 0-5% EtOH/DCM) gave the title compound (12 mg, 6%) as a pale yellow solid.
1H-NMR (Methanol-d4, 250 MHz): d[ppm]=8.38-8.32 (m, 1H), 7.90 (s, 1H), 7.65-7.55 (m, 3H), 7.42-7.36 (m, 1H), 7.36-7.30 (m, 2H), 4.73 (d, J=1.6 Hz, 2H), 3.60 (t, J=14.0 Hz, 2H), 3.20-3.08 (m, 4H)
HPLCMS (Method D): [m/z]: 461.2 [M+H]⁺
General Scheme 11 Above:

General Procedure 12: Ethyl 2-(2-{[(tert-butoxy)carbonyl]amino}ethyl)-5-chloro-1,3-thiazole-4-carboxylate (184)

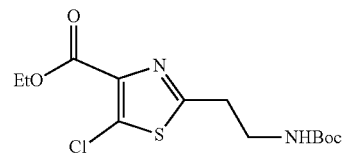 [SMILES: CCOC(=O)c1nc(CCNC(=O)OC(C)(C)C)sc1Cl]

A solution of ethyl 2-(2-{[(tert-butoxy)carbonyl]amino}ethyl)-1,3-thiazole-4-carboxylate (1) (2 g, 6.66 mmol) and hexachloroethane (1.49 g, 6.32 mmol) in THF (140 ml) was cooled to −78° C. 2 M NaHMDS (7.0 ml, 14.0 mmol) was added dropwise. The reaction mixture was stirred at −78° C. for 1 h, quenched with sat. NH₄Cl (aq) and allowed to warm to room temperature. The mixture was filtered and the residue was rinsed with THF (50 ml). The filtrates were evaporated in vacuo and the residue was partitioned between EtOAc and sat. NH₄Cl (aq). The organic layer was separated, dried (MgSO₄) and concentrated in vacuo. Purification by silica flash chromatography (eluting with a gradient of 0-30% EtOAc/DCM) gave the title compound (1.47 g, 65%) as a white solid.
1H-NMR (CDCl₃, 250 MHz): d[ppm]=4.91 (s, 1H), 4.45 (q, J=7.1 Hz, 2H), 3.55 (q, J=6.3 Hz, 2H), 3.18 (t, J=6.4 Hz, 2H), 1.49-1.39 (m, 12H)
HPLCMS (Method A): [m/z]: 356.95 [M+H]⁺

2-(2-{[(Tert-butoxy)carbonyl]amino}ethyl)-5-chloro-1,3-thiazole-4-carboxylic Acid (185)

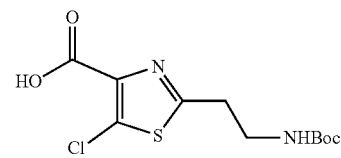

In a similar fashion using general procedure 5, LiOH (739 mg, 30.84 mmol) and ethyl 2-(2-{[(tert-butoxy)carbonyl]amino}ethyl)-5-chloro-1,3-thiazole-4-carboxylate (184) (1.47 g, 4.41 mmol) in THF (30 ml)/water (10 ml) gave the title compound (1.35 g, quant.) as a yellow oil. The compound was used in the next step without further purification.
1H-NMR (CDCl₃, 500 MHz): d[ppm]=4.92 (s, 1H), 3.58 (q, J=5.7 Hz, 2H), 3.18 (t, J=5.8 Hz, 2H), 1.46 (s, 9H)
HPLCMS (Method A): [m/z]: 328.9 [M+H]⁺

Tert-butyl N-[2-(5-chloro-4-{[(3-fluoropyridin-2-yl)methyl]carbamoyl}-1,3-thiazol-2-yl)ethyl]carbamate (186)

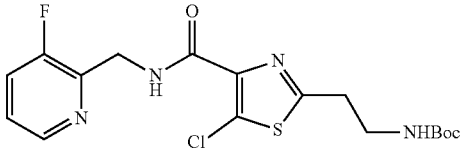 [SMILES: CC(C)(C)OC(=O)NCCc1nc(C(=O)NCc2ncccc2F)c(Cl)s1]

In a similar fashion using general procedure 6, 2-(2-{[(tert-butoxy)carbonyl]amino}ethyl)-5-chloro-1,3-thiazole-4-carboxylic acid (185) (800 mg, 2.61 mmol), (3-fluoropyridin-2-yl)methanamine dihydrochloride-(A2) (623 mg, 3.13 mmol), DIPEA (1.5 ml, 10.0 mmol), HATU (1.19 g, 3.0 mmol) in DCM (30 ml) gave the title compound (1.08 g, 80%) as a white solid after purification by flash column chromatography (eluting with a gradient of 0-60% EtOAc/heptane). Compound was used in the next step without further purification.

1H-NMR (CDCl$_3$, 250 MHz): d[ppm]=8.49-8.39 (m, 2H), 7.44 (ddd, J=9.4, 8.4, 1.3 Hz, 1H), 7.34-7.23 (m, 3H), 4.94 (s, 1H), 4.84 (dd, J=5.1, 1.7 Hz, 2H), 3.59 (q, J=6.3 Hz, 2H), 3.15 (t, J=6.4 Hz, 2H), 1.4 (s, 9H)

HPLCMS (Method A): [m/z]: 415 [M+H]$^+$

Tert-butyl N-[2-(5-chloro-4-{[(3-chloropyridin-2-yl)methyl]carbamoyl}-1,3-thiazol-2-yl)ethyl]carbamate (187)

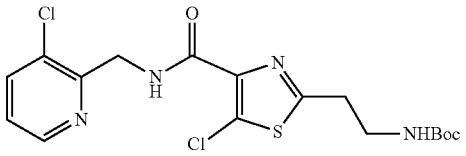 [SMILES: CC(C)(C)OC(=O)NCCc1nc(C(=O)NCc2ncccc2Cl)c(Cl)s1]

In a similar fashion using general procedure 6, 2-(2-{[(tert-butoxy)carbonyl]amino}ethyl)-5-chloro-1,3-thiazole-4-carboxylic acid (185) (220 mg, 0.72 mmol), (3-chloropyridin-2-yl)methanamine dihydrochloride (154.55 mg, 0.72 mmol), DIPEA (0.26 ml, 2 mmol), HATU (0.33 g, 0.85 mmol) in tetrahydrofuran (10 ml)/DMF (2 ml) gave the title compound (360 mg, quant.) as a white solid after purification by flash column chromatography (eluting with a gradient of 20-60% EtOAc/heptane). Compound was used in the next step without further purification.

1H-NMR (CDCl$_3$, 500 MHz): d[ppm]=8.66 (s, 1H), 8.56-8.52 (m, 1H), 7.74 (dd, J=8.0, 1.4 Hz, 1H), 7.24 (dd, J=8.0, 4.7 Hz, 1H), 4.98 (s, 1H), 4.85 (d, J=4.8 Hz, 2H), 3.61 (q, J=6.1 Hz, 2H), 3.17 (t, J=6.3 Hz, 2H), 1.46 (s, 9H).

HPLCMS (Method A): [m/z]: 431.1 [M+H]+

Tert-butyl N-(2-{5-chloro-4-[(pyridin-2-ylmethyl)carbamoyl]-1,3-thiazol-2-yl}ethyl)carbamate (188)

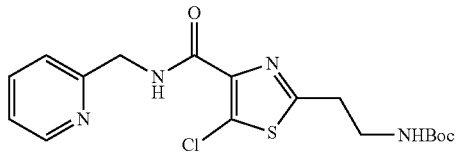 [SMILES: CC(C)(C)OC(=O)NCCc1nc(C(=O)NCc2ccccn2)c(Cl)s1]

In a similar fashion using general procedure 6, 2-(2-{[(tert-butoxy)carbonyl]amino}ethyl)-5-chloro-1,3-thiazole-4-carboxylic acid (185) (216 mg, 0.7 mmol), pyridin-2-ylmethanamine (0.09 ml, 0.84 mmol), DIPEA (0.26 ml, 1 mmol), HATU (0.32 g, 0.84 mmol) in tetrahydrofuran (10 ml) were stirred at room temperature. Further pyridin-2-ylmethanamine (0.09 ml, 0.84 mmol), DIPEA (0.26 ml, 0 mol) and HATU (0.32 g, 0 mol) were added and the reaction continued. The title compound (227 mg, 78%) was isolated as a brown oil after purification by flash column chromatography (eluting with a gradient of 5-100% EtOAc/heptane). Compound was used in the next step without further purification.

1H-NMR (Methanol-d4, 250 MHz): d[ppm]=8.50 (d, J=4.4 Hz, 1H), 7.81 (td, J=7.8, 1.5 Hz, 1H), 7.44 (d, J=7.9 Hz, 1H), 7.36-7.27 (m, 1H), 4.73 (s, 3H), 4.68 (s, 2H), 3.13 (t, J=6.4 Hz, 2H), 1.41 (s, 9H).

HPLCMS (Method A): [m/z]: 397.10 [M+H]$^+$

Tert-butyl N-(2-{5-chloro-4-[(pyridazin-3-ylmethyl)carbamoyl]-1,3-thiazol-2-yl}ethyl)carbamate (189)

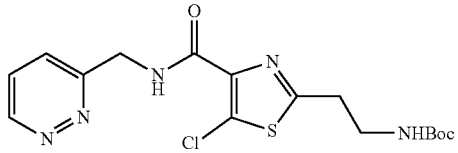 [SMILES: CC(C)(C)OC(=O)NCCc1nc(C(=O)NCc2cccnn2)c(Cl)s1]

In a similar fashion using general procedure 6, 2-(2-{[(tert-butoxy)carbonyl]amino}ethyl)-5-chloro-1,3-thiazole-4-carboxylic acid (185) (220 mg, 0.72 mmol), pyridazin-3-ylmethanamine (0.12 g, 1 mmol), DIPEA (0.31 ml, 2 mmol), HATU (0.41 g, 1 mmol) in DCM (20 ml) gave the title compound (278 mg, 91%) as a yellow residue after purification by flash column chromatography (eluting with a gradient of 50-100% EtOAc/heptane, then 2-6% methanol/ethyl acetate). Compound was used in the next step without further purification.

HPLCMS (Method A): [m/z]: 398.05 [M+H]$^+$

Tert-butyl N-(2-{5-chloro-4-[(pyrimidin-2-ylmethyl)carbamoyl]-1,3-thiazol-2-yl}ethyl)carbamate (190)

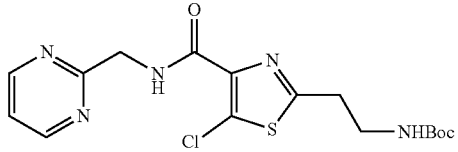 [SMILES: CC(C)(C)OC(=O)NCCc1nc(C(=O)NCc2ncccn2)c(Cl)s1]

In a similar fashion using general procedure 6, 2-(2-{[(tert-butoxy)carbonyl]amino}ethyl)-5-chloro-1,3-thiazole-4-carboxylic acid (185) (579 mg, 1.54 mmol), 1-(pyrimidin-2-yl)methanamine (0.14 g, 1.28 mmol), DIPEA (0.67 ml, 3.85 mmol), HATU (0.585 g, 1.54 mmol) in tetrahydrofuran (10 ml)/DMF (2 ml) gave the title compound (0.483 g, 73%) as a white solid after purification by flash column chromatography (eluting with a gradient of 50-100% EtOAc/heptane). Compound was used in the next step without further purification.

1H-NMR (DMSO-d6, 500 MHz): d[ppm]=8.83-8.79 (m, 1H), 8.78 (d, J=4.9 Hz, 2H), 7.41 (t, J=4.9 Hz, 1H), 7.11-7.05 (m, 1H), 4.64 (d, J=5.9 Hz, 2H), 3.09 (t, J=6.6 Hz, 2H), 1.37 (s, 9H).

HPLCMS (Method A): [m/z]: 398 [M+H]+

Tert-butyl N-[2-(5-chloro-4-{[(5-methylpyrimidin-2-yl)methyl]carbamoyl}-1,3-thiazol-2-yl)ethyl]carbamate (191)

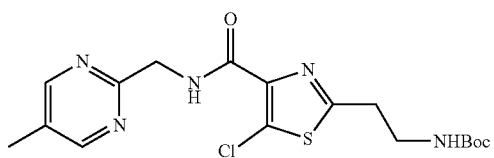 [SMILES: Cc1cnc(CNC(=O)c2nc(CCNC(=O)OC(C)(C)C)sc2Cl)nc1]

In a similar fashion using general procedure 6, 2-(2-{[(tert-butoxy)carbonyl]amino}ethyl)-5-chloro-1,3-thiazole-4-carboxylic acid (185) (556 mg, 1.48 mmol), (5-methylpyrimidin-2-yl)methanamine (0.14 g, 1.14 mmol), DIPEA (0.396 ml, 2.274 mmol), HATU (0.562 g, 1.478 mmol) in tetrahydrofuran (10 ml)/DMF (2 ml) gave the title compound (577 mg, 92%) as a colourless oil after purification by flash column chromatography (eluting with a gradient of 70-100% EtOAc/heptane). Compound was used in the next step without further purification.

1H-NMR (DMSO-d6, 500 MHz) δ 8.77 (t, J=5.8 Hz, 1H), 8.63 (s, 2H), 7.08 (s, 1H), 4.60 (d, J=5.9 Hz, 2H), 3.09 (t, J=6.6 Hz, 2H), 2.27 (s, 3H), 1.37 (s, 9H).

HPLCMS (Method A): [m/z]: 412.05 [M+H]+

2-(2-Aminoethyl)-5-chloro-N-[(3-fluoropyridin-2-yl)methyl]-1,3-thiazole-4-carboxamide (192)

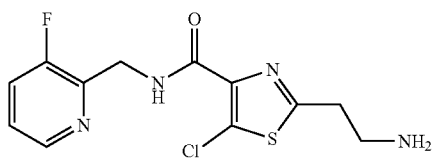 [SMILES: NCCc1nc(C(=O)NCc2ncccc2F)c(Cl)s1]

In a similar fashion using general procedure 2, 12M HCl (8 ml) and tertbutyl N-[2-(5-chloro-4-{[(3-fluoropyridin-2-yl)methyl]carbamoyl}-1,3-thiazol-2-yl)ethyl]carbamate (186) (1 g, 2.41 mmol) in MeOH (40 ml) at room temperature gave the title compound (703 mg, 93%) as a white solid after purification by SCX-2 cartridge (gradient elution 100% DCM, followed by 100% MeOH and then 7 N NH3/MeOH).

1H-NMR (DMSO-d6, 500 MHz): d[ppm]=8.73 (t, J=5.6 Hz, 1H), 8.40 (dt, J=4.6, 1.4 Hz, 1H), 7.71 (ddd, J=10.0, 8.3, 1.2 Hz, 1H), 7.42 (dt, J=8.6, 4.4 Hz, 1H), 4.63 (dd, J=5.7, 1.5 Hz, 2H), 3.02 (t, J=6.0 Hz, 2H), 2.93 (t, J=6.1 Hz, 2H)

HPLCMS (Method A): [m/z]: 314.95 [M+H]+

2-(2-Aminoethyl)-5-chloro-N-[(3-chloropyridin-2-yl)methyl]-1,3-thiazole-4-carboxamide (193)

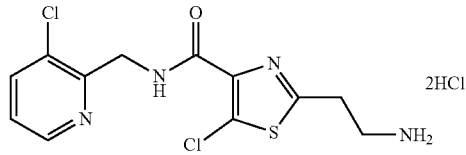 [SMILES: NCCc1nc(C(=O)NCc2ncccc2Cl)c(Cl)s1]

In a similar fashion using general procedure 2, 12M HCl (2 ml) and tertbutyl N-[2-(5-chloro-4-{[(3-chloropyridin-2-yl)methyl]carbamoyl}-1,3-thiazol-2-yl)ethyl]carbamate (187) (360 mg, 0.83 mmol) in MeOH (10 ml) at room temperature gave the title compound (320 mg, 95%) as a white solid.

1H-NMR (DMSO-d6, 250 MHz): d[ppm]=8.93 (t, J=6.0 Hz, 1H), 8.52 (dd, J=4.7, 1.3 Hz, 1H), 8.04 (s, 2H), 7.97 (dd, J=8.1, 1.4 Hz, 1H), 7.40 (dd, J=8.1, 4.7 Hz, 1H), 4.68 (d, J=5.8 Hz, 2H), 3.36-3.26 (m, 4H)

HPLCMS (Method A): [m/z]: 331.1 [M+H]+

2-(2-Aminoethyl)-5-chloro-N-(pyridin-2-ylmethyl)-1,3-thiazole-4-carboxamide Dihydrochloride (194)

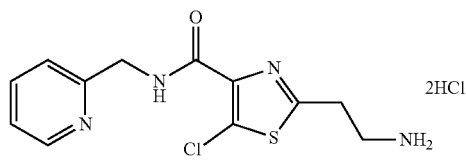 [SMILES: NCCc1nc(C(=O)NCc2ccccn2)c(Cl)s1]

In a similar fashion using general procedure 2, 12M HCl (2 ml) and tertbutyl N-(2-{5-chloro-4-[(pyridin-2-ylmethyl)carbamoyl]-1,3-thiazol-2-yl}ethyl)carbamate (188) (260 mg, 0.66 mmol) in MeOH (10 ml) at room temperature gave the title compound (198 mg, 82%) as a dark yellow gum. The crude product was used without further purification.

1H-NMR (Methanol-d4, 250 MHz): d[ppm]=8.80 (d, J=5.4 Hz, 1H), 8.64 (td, J=8.0, 1.3 Hz, 1H), 8.16 (d, J=8.1 Hz, 1H), 8.03 (t, J=6.7 Hz, 1H), 4.99 (s, 2H), 3.60-3.39 (m, 4H)

2-(2-Aminoethyl)-5-chloro-N-(pyridazin-3-ylmethyl)-1,3-thiazole-4-carboxamide Dihydrochloride (195)

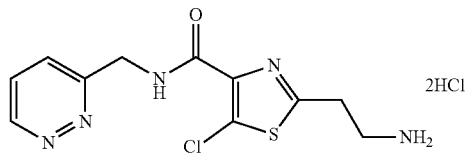 [SMILES: NCCc1nc(C(=O)NCc2cccnn2)c(Cl)s1]

In a similar fashion using general procedure 2, 12M HCl (1.86 ml) and tertbutyl N-(2-{5-chloro-4-[(pyridazin-3-yl-methyl)carbamoyl]-1,3-thiazol-2-yl}ethyl)carbamate (189) (278 mg, 0.65 mmol) in MeOH (10 ml) at 60° C. gave the crude title compound (296 mg) as a pale brown residue. Compound was taken to the next step without further purification.

HPLCMS (Method A): [m/z]: 298 [M+H]+

2-(2-Aminoethyl)-5-chloro-N-(pyrimidin-2-ylmethyl)-1,3-thiazole-4-carboxamide Dihydrochloride (196)

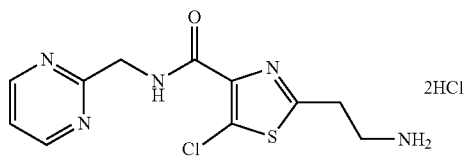 [SMILES: NCCc1nc(C(=O)NCc2ncccn2)c(Cl)s1]

In a similar fashion using general procedure 2, 12M HCl (1.56 ml) and tertbutyl N-(2-{5-chloro-4-[(pyrimidin-2-ylmethyl)carbamoyl]-1,3-thiazol-2-yl}ethyl)carbamate (190) (483 mg, 0.938 mmol) in MeOH (3 ml) at 40° C. gave the title compound (563 mg, 100%) as a beige solid.

1H-NMR (Methanol-d4, 500 MHz): d[ppm]=8.83 (d, J=5.0 Hz, 2H), 7.49 (t, J=5.0 Hz, 1H), 4.82 (s, 2H), 3.49 (t, J=6.2 Hz, 2H), 3.39 (t, J=6.2 Hz, 2H)

HPLCMS (Method A): [m/z]: 297.9 [M+H]+

2-(2-Aminoethyl)-5-chloro-N-[(5-methylpyrimidin-2-yl)methyl]-1,3-thiazole-4-carboxamide Dihydrochloride (197)

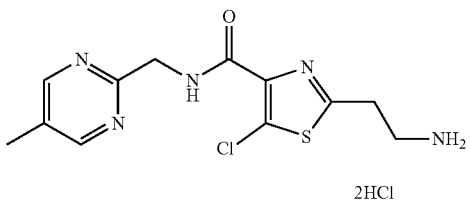 [SMILES: Cc1cnc(CNC(=O)c2nc(CCN)sc2Cl)nc1]

In a similar fashion using general procedure 2, 12M HCl (1.74 ml) and tert-butyl N-[2-(5-chloro-4-{[(5-methylpyrimidin-2-yl)methyl]carbamoyl}-1,3-thiazol-2-yl)ethyl]carbamate (191) (580 mg, 1.04 mmol) in MeOH (6 ml) at room temperature gave the title compound (447 mg, 100%) as a white solid.

1H-NMR (Methanol-d4, 500 MHz): d[ppm]=8.74 (s, 2H), 4.80 (s, 2H), 3.49 (t, J=6.2 Hz, 2H), 3.38 (t, J=6.2 Hz, 2H), 2.39 (s, 3H)

HPLCMS (Method A): [m/z]: 311.95 [M+H]+

2-{2-[(1H-1,3-Benzodiazol-2-ylmethyl)amino]ethyl}-5-chloro-N-[(3-fluoropyridin-2-yl)methyl]-1,3-thiazole-4-carboxamide (Example Compound No. 151)

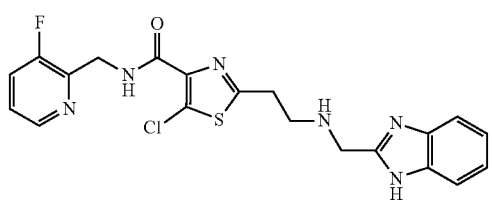 [SMILES: O=C(NCc1ncccc1F)c1nc(CCNCc2nc3ccccc3[nH]2)sc1Cl]

In a similar fashion to general procedure 3, 2-(2-aminoethyl)-5-chloro-N-[(3-fluoropyridin-2-yl)methyl]-1,3-thiazole-4-carboxamide dihydrochloride (192) (143 mg, 0.37 mmol), 1H-1,3-benzodiazole-2-carbaldehyde (70.1 mg, 0.48 mmol), MgSO4 (200 mg) in MeOH (10 ml) at room temperature for 3 d, followed by addition of NaBH4 (28 mg, 0.74 mmol) gave the title compound (94 mg, 56%) as a white solid after purification by prep-HPLC.

1H-NMR (DMSO-d6, 500 MHz): d[ppm]=12.19 (s, 1H), 8.71 (t, J=5.6 Hz, 1H), 8.37 (dt, J=4.6, 1.3 Hz, 1H), 7.70 (ddd, J=10.0, 8.4, 1.1 Hz, 1H), 7.54 (d, J=7.2 Hz, 1H), 7.45 (d, J=7.0 Hz, 1H), 7.40 (dt, J=8.6, 4.4 Hz, 1H), 7.14 (t, J=7.5 Hz, 2H), 4.66-4.58 (m, 2H), 3.97 (s, 2H), 3.12 (t, J=6.3 Hz, 2H), 2.94 (t, J=6.3 Hz, 2H)

HPLCMS (Method A): [m/z]: 445.1 [M+H]+

2-{2-[(1H-1,3-Benzodiazol-2-ylmethyl)amino]ethyl}-5-chloro-N-[(3-chloropyridin-2-yl)methyl]-1,3-thiazole-4-carboxamide (Example Compound No. 159)

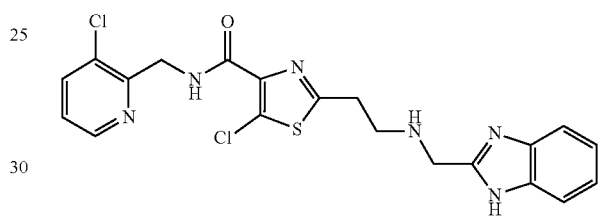

In a similar fashion to general procedure 3, 2-(2-aminoethyl)-5-chloro-N-[(3-chloropyridin-2-yl)methyl]-1,3-thiazole-4-carboxamide dihydrochloride (193) (320 mg, 0.79 mmol), 1H-1,3-benzodiazole-2-carbaldehyde (127.3 mg, 0.87 mmol), DIPEA (0.32 ml, 2.0 mmol) and MgSO4 (300 mg) in MeOH (20 ml) at room temperature for 16 h, followed by addition of NaBH4 (60 mg, 1.59 mmol) gave the title compound (191 mg, 52%) as a white solid after purification by prep-HPLC.

1H-NMR (DMSO-d6, 500 MHz): d[ppm]=12.18 (s, 1H), 8.72 (t, J=5.6 Hz, 1H), 8.49 (dd, J=4.7, 1.3 Hz, 1H), 7.95 (dd, J=8.1, 1.3 Hz, 1H), 7.54 (s, 1H), 7.46 (s, 1H), 7.38 (dd, J=8.1, 4.7 Hz, 1H), 7.17-7.09 (m, 2H), 4.65 (d, J=5.5 Hz, 2H), 3.98 (d, J=4.1 Hz, 2H), 3.13 (t, J=6.3 Hz, 2H), 2.95 (q, J=6.1, 5.3 Hz, 2H), 2.74 (s, 1H)

HPLCMS (Method C): [m/z]: 461 [M+H]+

2-{2-[(1H-1,3-Benzodiazol-2-ylmethyl)amino]ethyl}-5-chloro-N-(pyridin-2-ylmethyl)-1,3-thiazole-4-carboxamide (Example Compound No. 160)

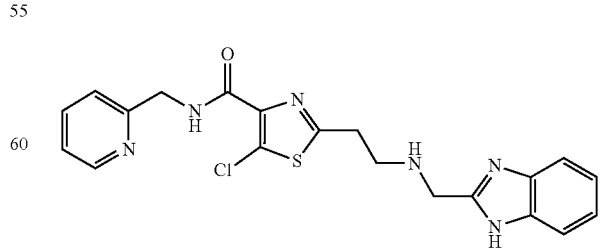

In a similar fashion to general procedure 3, 2-(2-aminoethyl)-5-chloro-N-(pyridin-2-ylmethyl)-1,3-thiazole-4-carboxamide dihydrochloride (194) (190 mg, 0.51 mmol), 1H-1,3-benzodiazole-2-carbaldehyde (113 mg, 0.77 mmol), DIPEA (0.3 ml, 2.0 mmol) and MgSO$_4$ (400 mg) in DCM (10 ml) and MeOH (10 ml) at room temperature for 16 h, followed by addition of NaBH$_4$ (39 mg, 1.03 mmol) gave the title compound (60 mg, 27%) as a pale yellow solid after purification by prep-HPLC.

1H-NMR (DMSO-d6, 500 MHz): d[ppm]=12.19 (s, 1H), 8.90 (t, J=6.0 Hz, 1H), 8.50 (d, J=5.5 Hz, 1H), 7.75 (td, J=7.7, 1.8 Hz, 1H), 7.58-7.42 (m, 2H), 7.31 (d, J=7.8 Hz, 1H), 7.27 (dd, J=7.0, 5.3 Hz, 1H), 7.17-7.10 (m, 2H), 4.54 (d, J=6.0 Hz, 2H), 3.98 (s, 2H), 3.12 (t, J=6.3 Hz, 2H), 2.95 (t, J=6.3 Hz, 2H), 2.76 (s, 1H)

HPLCMS (Method C): [m/z]: 427.1 [M+H]$^+$ 5-chloro-N-(pyridin-2-ylmethyl)-2-(2-{1,8,12-triaza-tricyclo[7.4.0.0$^2$,$^7$]trideca-2(7),3,5,8-tetraen-12-yl}ethyl)-1,3-thiazole-4-carboxamide (Example Compound No. 189)

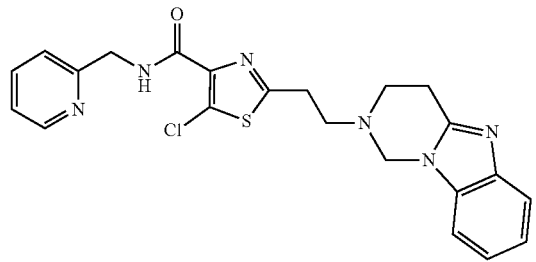 [SMILES: O=C(NCc1ccccn1)c1nc(CCN2CCc3nc4ccccc4n3C2)sc1Cl]

In a similar fashion to general procedure 8, 2-(2-Amino-ethyl)-5-chloro-N-(pyridin-2-ylmethyl)-1,3-thiazole-4-carboxamide dihydrochloride (194) (361.5 mg, 0.98 mmol), N-(2-nitrophenyl)prop-2-enamide (D) (187.9 mg, 0.98 mmol), DBU (219 μl, 1.47 mmol) in MeCN (5 ml) at room temperature for 3 h, give a mixture of mono and bis alkylated intermediates which were separated by flash column chromatography (eluting with a gradient of 0-10% MeOH/EtOAc followed by 0-10% MeOH/DCM). The mono alkylated intermediate (5-chloro-2-[2-({2-[(2-nitrophenyl)carbamoyl]ethyl}amino)ethyl]-N-(pyridin-2-ylmethyl)-1,3-thiazole-4-carboxamide) (66.0 mg, 0.135 mmol) was further reacted with iron powder (15.1 mg, 0.270 mmol) in AcOH (1 ml) at 80° C. for 1 h to give the title compound (61 mg, 25%) as a brown oil after purification by flash column chromatography (eluting with a gradient of 0-10% MeOH/DCM).

1H NMR (Acetone-d6, 500 MHz): d[ppm]=8.53 (d, J=4.2 Hz, 2H), 7.76 (td, J=7.7, 1.8 Hz, 1H), 7.61-7.53 (m, 1H), 7.45-7.37 (m, 2H), 7.26 (dd, J=7.0, 4.9 Hz, 1H), 7.22-7.14 (m, 2H), 5.14 (s, 2H), 4.66 (d, J=5.7 Hz, 2H), 3.39 (t, J=6.2 Hz, 2H), 3.36-3.28 (m, 2H), 3.20 (t, J=6.3 Hz, 2H), 3.14 (t, J=6.2 Hz, 2H)

HPLCMS (Method B): [m/z]: 453.1 [M+H]$^+$

2-{2-[(1H-1,3-Benzodiazol-2-ylmethyl)amino]ethyl}-5-chloro-N-(pyridazin-3-ylmethyl)-1,3-thiazole-4-carboxamide (Example Compound No. 161)

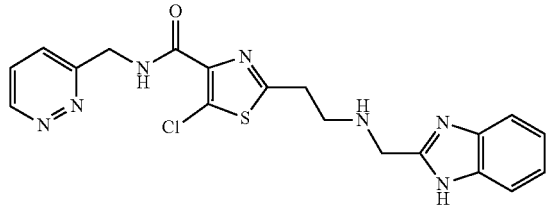 [SMILES: O=C(NCc1cccnn1)c1nc(CCNCc2nc3ccccc3[nH]2)sc1Cl]

In a similar fashion to general procedure 3, 2-(2-amino-ethyl)-5-chloro-N-(pyridazin-3-ylmethyl)-1,3-thiazole-4-carboxamide dihydrochloride (195) (296 mg, 0.8 mmol), 1H-1,3-benzodiazole-2-carbaldehyde (151.7 mg, 1.04 mmol), DIPEA (0.42 ml, 2.0 mmol) and MgSO$_4$ (400 mg) in DCM (10 ml) and MeOH (10 ml) at room temperature for 3 d, followed by addition of NaBH$_4$ (60 mg, 1.59 mmol) gave the title compound (96 mg, 28%) as a white solid after purification by prep-HPLC.

1H-NMR (DMSO-d6, 500 MHz): d[ppm]=12.18 (s, 1H), 9.14 (dd, J=4.8, 1.5 Hz, 1H), 9.07 (t, J=6.1 Hz, 1H), 7.66 (dd, J=8.5, 4.8 Hz, 1H), 7.60 (dd, J=8.5, 1.6 Hz, 1H), 7.54 (d, J=7.4 Hz, 1H), 7.45 (d, J=7.7 Hz, 1H), 7.13 (p, J=7.0, 6.6 Hz, 2H), 4.72 (d, J=6.1 Hz, 2H), 3.97 (s, 2H), 3.12 (t, J=6.3 Hz, 2H), 2.95 (t, J=6.2 Hz, 2H), 2.75 (s, 1H)

HPLCMS (Method C): [m/z]: 428 [M+H]$^+$

2-{2-[(1H-1,3-Benzodiazol-2-ylmethyl)amino]ethyl}-5-chloro-N-(pyrimidin-2-ylmethyl)-1,3-thiazole-4-carboxamide (Example Compound No. 175)

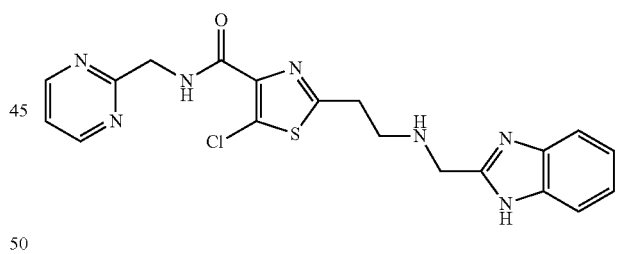

In a similar fashion to general procedure 3, 2-(2-amino-ethyl)-5-chloro-N-(pyrimidin-2-ylmethyl)-1,3-thiazole-4-carboxamide dihydrochloride (196) (563 mg, 0.94 mmol), 1H-benzimidazole-2-carbaldehyde (178 mg, 1.22 mmol), DIPEA (0.654 ml, 0.74 mmol) in MeOH (15 ml) at room temperature for 24 h, followed by addition of NaBH$_4$ (53 mg, 1.41 mmol) gave the title compound (224 mg, 54%) as a white solid after purification by basic prep-HPLC.

1H-NMR (DMSO-d6, 500 MHz): d[ppm]=12.20 (br s, 1H), 8.80-8.74 (m, 3H), 7.50 (br s, 2H), 7.40 (t, J=4.9 Hz, 1H), 7.21-7.07 (m, 2H), 4.64 (d, J=5.9 Hz, 2H), 3.98 (s, 2H), 3.13 (t, J=6.3 Hz, 2H), 2.96 (t, J=6.3 Hz, 2H), 2.76 (br s, 1H)

HPLCMS (Method G): [m/z]: 428.2 [M+H]$^+$

2-{2-[(1H-1,3-Benzodiazol-2-ylmethyl)amino]ethyl}-5-chloro-N-[(5-methylpyrimidin-2-yl)methyl]-1,3-thiazole-4-carboxamide (Example Compound No. 178)

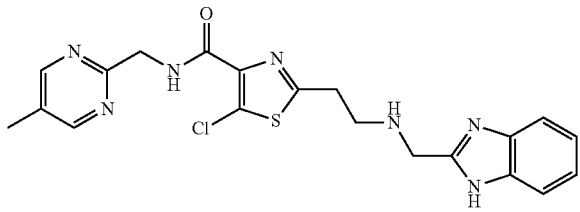 [SMILES: Cc1cnc(CNC(=O)c2nc(CCNCc3nc4ccccc4[nH]3)sc2Cl)nc1]

In a similar fashion to general procedure 3, 2-(2-aminoethyl)-5-chloro-N-[(5-methylpyrimidin-2-yl)methyl]-1,3-thiazole-4-carboxamide dihydrochloride (197) (223 mg, 0.52 mmol), 1H-benzimidazole-2-carbaldehyde (99 mg, 0.68 mmol), DIPEA (0.363 ml, 2.09 mmol) and MgSO$_4$ (400 mg) in MeOH (6 ml) at room temperature for 24 h, followed by addition of NaBH$_4$ (30 mg, 0.78 mmol) gave the title compound (120 mg, 52%) as a white solid after purification by basic prep-HPLC.

1H-NMR (DMSO-d6, 500 MHz): d[ppm]=12.21 (s, 1H), 8.72 (t, J=5.8 Hz, 1H), 8.63-8.57 (m, 2H), 7.50 (s, 1H), 7.14 (dd, J=6.0, 2.7 Hz, 2H), 4.61-4.56 (m, 2H), 3.98 (s, 2H), 3.13 (t, J=6.3 Hz, 2H), 2.95 (t, J=6.3 Hz, 2H), 2.75 (s, 1H), 2.26 (s, 3H)

HPLCMS (Method C): [m/z]: 442 [M+H]$^+$

5-Chloro-N-[(3-fluoropyridin-2-yl)methyl]-2-[2-({2-[(2-nitrophenyl)carbamoyl]ethyl}amino)ethyl]-1,3-thiazole-4-carboxamid (198)

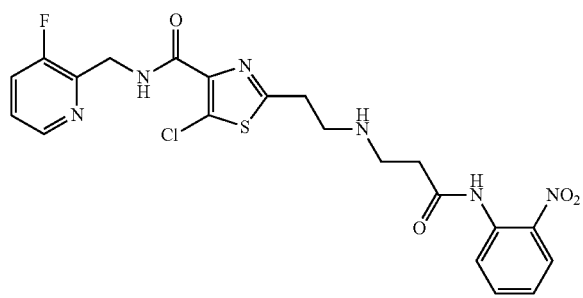 [SMILES: O=C(CCNCCc1nc(C(=O)NCc2ncccc2F)c(Cl)s1)Nc1ccccc1[N+](=O)[O-]]

In a similar fashion to general procedure 8, 2-(2-aminoethyl)-5-chloro-N-[(3-fluoropyridin-2-yl)methyl]-1,3-thiazole-4-carboxamide (192) (700 mg, 2.22 mmol) and N-(2-nitrophenyl)prop-2-enamide (D) (470 mg, 2.45 mmol) were combined in MeCN (40 ml) and DBU (0.37 ml, 2.0 mmol) was added. The mixture was stirred at room temperature for 3 d. The reaction mixture was evaporated directly onto silica. Purification by flash column chromatography (eluting with a gradient of 0-10% MeOH/DCM) gave the title compound (390 mg, 25%) as a yellow solid.

HPLCMS (Method A): [m/z]: 507 [M+H]$^+$

2-(2-{[2-(1H-1,3-Benzodiazol-2-yl)ethyl]amino}ethyl)-5-chloro-N-[(3-fluoropyridin-2-yl)methyl]-1,3-thiazole-4-carboxamide Trihydrochloride (Example Compound No. 154)

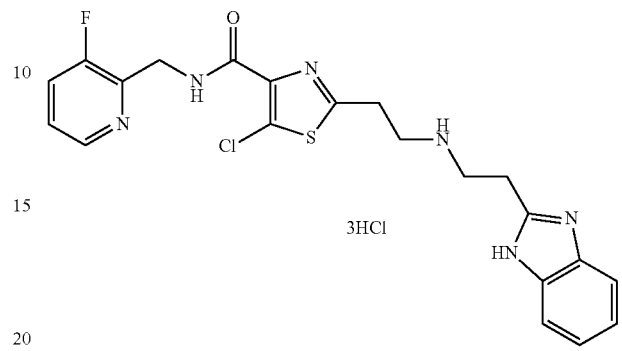 [SMILES: Cc1cnc(CNC(=O)c2nc(CCNCCc3nc4ccccc4[nH]3)sc2Cl)nc1]

In a similar fashion to general procedure 8, 5-chloro-N-[(3-fluoropyridin-2-yl)methyl]-2-[2-({2-[(2-nitrophenyl)carbamoyl]ethyl}amino)ethyl]-1,3-thiazole-4-carboxamide (198) (390 mg, 0.77 mmol) and iron powder (172 mg, 3 mmol) in AcOH (5 ml) at 90° C. for 30 min gave the crude product. The residue was flushed through a plug of silica, gradient elution 0.5-40% MeOH/DCM then 20% 7 M NH$_3$ in MeOH/DCM, followed by further purification by basic prep-HPLC to give the required product as the free base. The residue was re-dissolved in MeOH (10 ml) and treated with 12 M HCl (1 ml) for 1 h. The solvent was rigorously removed under vacuum to give the target compound as a pale yellow solid.

1H-NMR (D$_2$O, 500 MHz): d[ppm]=8.33-8.30 (m, 1H), 7.87 (ddd, J=9.6, 8.6, 1.2 Hz, 1H), 7.71 (dt, J=6.8, 3.4 Hz, 2H), 7.59 (dt, J=7.5, 4.2 Hz, 1H), 7.55 (dt, J=6.3, 3.4 Hz, 2H), 3.72-3.62 (m, 6H), 3.44 (t, J=6.6 Hz, 2H). Note that a benzylic CH$_2$ signal is obscured by D2O HPLCMS (Method A): [m/z]: 459.1 [M+H]$^+$

2-(2-{[2-(1H-1,3-Benzodiazol-2-yl)ethyl]amino}ethyl)-5-chloro-N-[(5-methylpyrimidin-2-yl)methyl]-1,3-thiazole-4-carboxamide (Example Compound No. 182)

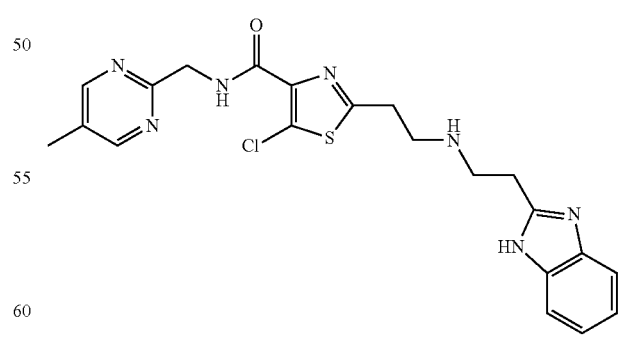

In a similar fashion using general procedure 8, 2-(2-aminoethyl)-5-chloro-N-[(5-methylpyrimidin-2-yl)methyl]-1,3-thiazole-4-carboxamide dihydrochloride (197) (0.223 g, 0.522 mmol), N-(2-nitrophenyl)prop-2-enamide (D) (0.090 g, 0.47 mmol) and DBU (0.171 ml, 1.148 mmol) in MeCN (10 ml) gave the intermediate (355 mg, 0.46 mmol) which was further reacted with iron powder (104 mg, 1.86 mmol) in AcOH (5 ml) at 80° C. for 2.5 h gave the title compound (6 mg, 3%) as an off-white solid after purification by basic prep-HPLC followed by flash column chromatography (eluting with a gradient of (05% MeOH/DCM).

1H-NMR (DMSO-d4, 500 MHz): d[ppm]=8.54 (s, 2H), 7.47-7.41 (m, 2H), 7.20-7.14 (m, 2H), 4.62 (s, 2H), 3.23-3.16 (m, 4H), 3.15-3.10 (m, 4H), 2.28 (s, 3H)

HPLCMS (Method D): [m/z]: 456.2 [M+H]$^+$ 2-(2-{[2-(1H-1,3-Benzodiazol-2-yl)ethyl]amino}ethyl)-5-chloro-N-(pyridazin-3-ylmethyl)-1,3-thiazole-4-carboxamide (Example Compound No. 183)

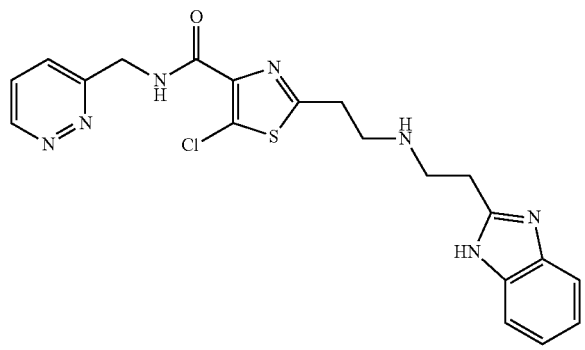 [SMILES: O=C(NCc1cccnn1)c1nc(CCNCCc2nc3ccccc3[nH]2)sc1Cl]

In a similar fashion using general procedure 8, 2-(2-aminoethyl)-5-chloro-N-(pyridazin-3-ylmethyl)-1,3-thiazole-4-carboxamide dihydrochloride (195) (255 mg, 0.689 mmol), N-(2-nitrophenyl)prop-2-enamide (D) (132 mg, 0.689) and DBU (0.154 mm, 1.03 mmol) in MeCN (5 mm) gave the intermediate (112 mg, 0.16 mmol) which was further reacted with iron powder (18 mg, 0.33 mmol) in AcOH (1 ml) at 80° C. for 2.5 h gave the title compound (6.4 mg, 8.5%) as a yellow oil after purification by flash column chromatography (eluting with a gradient of 0-20% MeOH/DCM) followed by basic prep HPLC.

1H-NMR (Methanol-d4, 500 MHz): d[ppm]=9.08 (dd, J=4.3, 2.3 Hz, 1H), 7.72-7.63 (m, 2H), 7.47 (dd, J=5.9, 3.2 Hz, 2H), 7.23-7.15 (m, 2H), 4.80 (s, 2H), 3.16-3.02 (m, 8H)

HPLCMS (Method B): [m/z]: 440.4 [M−H]$^-$ 2-(2-{[2-(1H-1,3-Benzodiazol-2-yl)ethyl]amino}ethyl)-5-chloro-N-(pyridazin-2-ylmethyl)-1,3-thiazole-4-carboxamide (Example Compound No. 184)

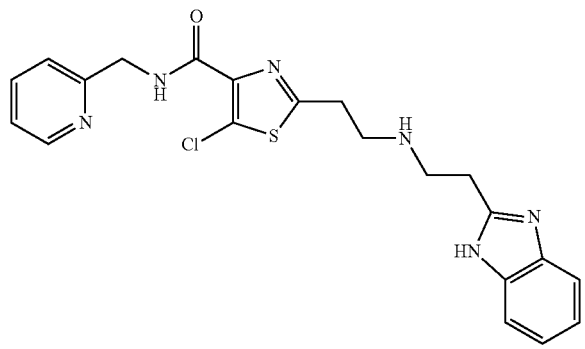 [SMILES: O=C(NCc1ccccn1)c1nc(CCNCCc2nc3ccccc3[nH]2)sc1Cl]

In a similar fashion using general procedure 8, 2-(2-aminoethyl)-5-chloro-N-(pyridin-2-ylmethyl)-1,3-thiazole-4-carboxamide dihydrochloride (194) (361.6 mg, 0.978 mmol), N-(2-nitrophenyl)prop-2-enamide (D) (187.9 mg, 0.978 mmol), DBU (0.219 ml, 1.467 mmol) in MeCN (5 ml) gave the intermediate (180 mg, 0.26 mmol) which was further reacted with iron powder (29 mg, 0.54 mmol) in AcOH (1 ml) at 80° C. for 2 h gave the title compound (8.8 mg, 7.5%) as a yellow oil after purification by basic prep HPLC.

1H-NMR (Methanol-d4, 500 MHz): d[ppm]=8.47 (ddd, J=5.0, 1.6, 0.9 Hz, 1H), 7.77 (td, J=7.7, 1.8 Hz, 1H), 7.47 (dd, J=5.9, 3.2 Hz, 2H), 7.37 (d, J=7.9 Hz, 1H), 7.33-7.25 (m, 1H), 7.20-7.16 (m, 2H), 4.61 (s, 2H), 3.16-3.01 (m, 8H)

HPLCMS (Method B): [m/z]: 439.3 [M−H]$^-$

Ethyl 5-bromo-2-(2-{[(tert-butoxy)carbonyl]amino}ethyl)-1,3-thiazole-4-carboxylate (199)

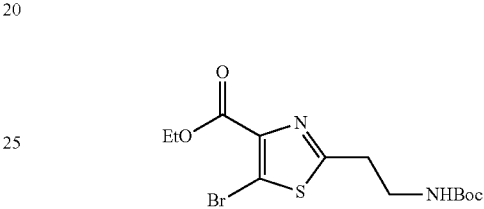

Ethyl 2-(2-{[(tert-butoxy)carbonyl]amino}ethyl)-1,3-thiazole-4-carboxylate (1) (1.56 g, 5.19 mmol) and 1,2-dibromo-1,1,2,2-tetrachloroethane (1.86 g, 10.0 mmol) were dissolved in THF (60 ml) and cooled to −78° C. 2 M NaHMDS (5.45 ml) was added dropwise and the mixture stirred at −78° C. for 2 h. The reaction was quenched with sat. NH$_4$Cl (aq) (30 ml) and allowed to warm to room temperature. The mixture was extracted with DCM (3×100 ml) and the combined organic extracts dried (Na$_2$SO$_4$), filtered and evaporated in vacuo. Purification by flash column chromatography using a gradient elution 10-50% EtOAc/heptane gave the title compound (1.62 g, 80%) as a colourless oil.

1H-NMR (CDCl$_3$, 250 MHz): d[ppm]=4.91 (s, 1H), 4.46 (q, J=7.1 Hz, 2H), 3.56 (q, J=6.3 Hz, 2H), 3.21 (t, J=6.3 Hz, 2H), 1.50-1.42 (m, 12H)

HPLCMS (Method A): [m/z]: 400.9/402.85 [M+H]$^+$ 2-(2-{[(Tert-butoxy)carbonyl]amino}ethyl)-5-(prop-1-en-2-yl)-1,3-thiazole-4-carboxylate (200)

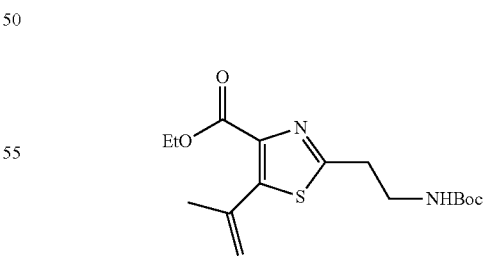

Ethyl 5-bromo-2-(2-{[(tert-butoxy)carbonyl]amino}ethyl)-1,3-thiazole-4-carboxylate (199) (626 mg, 1.65 mmol), PdCl$_2$(dppf) (120 mg, 0.17 mmol) and K$_2$CO$_3$ (460 mg, 3.0 mmol) were dissolved in MeCN (18 ml) and water (18 ml) under nitrogen and 4,4,5,5-tetramethyl-2-(prop-1-en-2-yl)-1,3,2-dioxaborolane (0.38 ml, 1.98 mmol) was added. The mixture was heated at 80° C. for 30 min, cooled to room temperature and diluted with water. The mixture was extracted with DCM (3×80 ml) and the combined organic extracts dried (Na$_2$SO$_4$), filtered and evaporated in vacuo. Purification by flash chromatography using a gradient elution 10-60% EtOAc/heptane gave the title compound (558 mg, 99%) as a yellow oil.

1H-NMR (CDCl$_3$, 250 MHz): d[ppm]=5.23 (s, 1H), 5.12 (s, 1H), 4.94 (s, 1H), 4.32 (q, J=7.2 Hz, 2H), 3.47 (q, J=6.5 Hz, 2H), 3.09 (t, J=6.5 Hz, 2H), 2.07 (s, 3H), 1.37 (s, 9H), 1.31 (t, J=7.2 Hz, 3H).

HPLCMS (Method A): [m/z]: 341.05 [M+H]$^+$

Ethyl 2-(2-{[(tert-butoxy)carbonyl]amino}ethyl)-5-(trifluoromethyl)-1,3-thiazole-4-carboxylate (201)

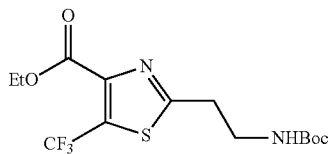

Ethyl 5-bromo-2-(2-{[(tert-butoxy)carbonyl]amino}ethyl)-1,3-thiazole-4-carboxylate (199) (0.54 g, 1.43 mmol) was dissolved in DMF (30 ml) under nitrogen and copper(I) iodide (1.36 g, 7.0 mmol), triphenylarsane (0.14 ml, 0.57 mmol), Pd$_2$dba$_3$ (0.065 g, 0.07 mmol) and methyl difluoro(fluorosulfonyl)acetate (0.23 ml, 1.85 mmol) were added. The mixture was heated at 100° C. for 3 h, then cooled to room temperature and concentrated in vacuo. The residue was partitioned between EtOAc and sat. NaHCO$_3$ (aq). The phases were separated and the aqueous phase was extracted with EtOAc (2×80 ml) and the combined organic extracts were washed with brine (2×50 ml), dried (Na$_2$SO$_4$), filtered and evaporated in vacuo. Purification by flash column chromatography (eluting with a gradient of 10-60% EtOAc/heptane) afforded the title compound (0.447 g, 84%) as a yellow oil.

1H-NMR (DMSO-d6, 500 MHz): d[ppm]=4.92 (s, 1H), 4.48 (q, J=7.1 Hz, 2H), 3.60 (q, J=6.2 Hz, 2H), 3.27 (t, J=6.2 Hz, 2H), 1.46 (s, 9H), 1.44 (t, J=7.1 Hz, 3H)

HPLCMS (Method A): [m/z]: 391 [M+Na]$^+$ 2-(2-{[(Tert-butoxy)carbonyl]amino}ethyl)-5-(prop-1-en-2-yl)-1,3-thiazole-4-carboxylic Acid (202)

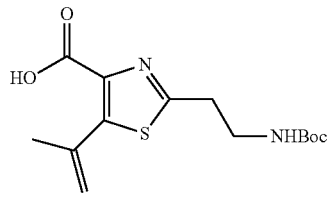 [SMILES: C=C(C)c1sc(CCNC(=O)OC(C)(C)C)nc1C(=O)O]

In a similar fashion to general procedure 5, ethyl 2-(2-{[(tert-butoxy)carbonyl]amino}ethyl)-5-(prop-1-en-2-yl)-1,3-thiazole-4-carboxylate (200) (550 mg, 1.62 mmol) and LiOH (390 mg, 16.0 mmol) in THF (20 ml) and water (20 ml) gave the crude title compound (569 mg, quant.) as a yellow oil.

1H-NMR (CDCl$_3$, 500 MHz): d[ppm]=5.41 (s, 1H), 5.38 (s, 1H), 4.84 (s, 1H), 3.59 (m, 2H), 3.16 (t, J=6.4 Hz, 2H), 2.23 (s, 3H), 1.47 (s, 9H)

HPLCMS (Method A): [m/z]: 312.9 [M+H]$^+$ 2-(2-{[(Tert-butoxy)carbonyl]amino}ethyl)-5-(trifluoromethyl)-1,3-thiazole-4-carboxylic Acid (203)

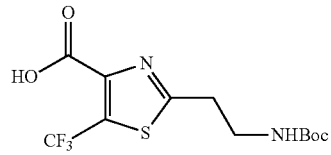

In a similar fashion to general procedure 5, ethyl 2-(2-{[(tert-butoxy)carbonyl]amino}ethyl)-5-(trifluoromethyl)-1,3-thiazole-4-carboxylate (201) (447 mg, 1.21 mmol) and LiOH (320 mg, 13.0 mmol) in THF (15 ml) and water (15 ml) afforded the title compound (365 mg, 88%) as a pale yellow solid.

1H-NMR (CDCl$_3$, 500 MHz): d[ppm]=4.81 (s, 1H), 3.53 (q, J=6.0 Hz, 2H), 3.18 (br s, 2H), 1.37 (s, 9H)

HPLCMS (Method A): [m/z]: 362.95 [M+Na]$^+$

Tert-butyl N-[2-(4-{[(3-fluoropyridin-2-yl)methyl]carbamoyl}-5-(prop-1-en-2-yl)-1,3-thiazol-2-yl)ethyl]carbamate (204)

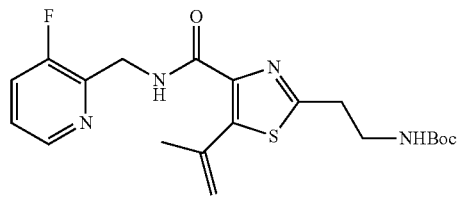 [SMILES: C=C(C)c1sc(CCNC(=O)OC(C)(C)C)nc1C(=O)NCc1ncccc1F]

In a similar fashion to general procedure 6, 2-(2-{[(tert-butoxy)carbonyl]amino}ethyl)-5-(prop-1-en-2-yl)-1,3-thiazole-4-carboxylic acid (202) (569 mg, 1.82 mmol), (3-fluoropyridin-2-yl)methanamine dihydrochloride (A2) (435 mg, 2.19 mmol), DIPEA (1.11 ml, 6.0 mmol) and HATU (830 mg, 2.0 mmol) in DCM (20 ml) gave the title compound (544 mg, 71%) as a colourless oil after purification by flash column chromatography (eluting with a gradient of 0-60% EtOAc/heptane).

1H-NMR (CDCl$_3$, 500 MHz): d[ppm]=8.51-8.43 (m, 2H), 7.45-7.38 (m, 1H), 7.30-7.24 (m, 1H), 5.34 (m, 1H), 5.27 (s, 1H), 4.83 (dd, J=5.1, 1.6 Hz, 2H), 3.61 (m, 2H), 3.15 (m, 2H), 2.25 (s, 3H), 1.46 (s, 9H).

HPLCMS (Method A): [m/z]: 421.05 [M+H]$^+$

Tert-butyl N-[2-(4-{[(3-fluoropyridin-2-yl)methyl]carbamoyl}-5-(trifluoromethyl)-1,3-thiazol-2-yl)ethyl]carbamate (205)

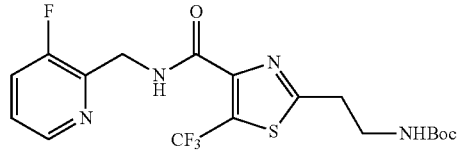

In a similar fashion to general procedure 6, 2-(2-{[(tert-butoxy)carbonyl]amino}ethyl)-5-(trifluoromethyl)-1,3-thiazole-4-carboxylic acid (203) (365 mg, 1.07 mmol), (3-fluoropyridin-2-yl)methanamine dihydrochloride (A2) (256.2 mg, 1.29 mmol), DIPEA (0.65 ml, 4 mmol) and HATU (490 mg, 1.3 mmol) in DCM (20 ml) gave the title compound (344 mg, 72%) after purification by flash column chromatography (eluting with a gradient of 20-30% EtOAc/heptane).

1H-NMR (CDCl$_3$, 250 MHz): d[ppm]=8.49 (s, 1H), 8.35 (dt, J=4.6, 1.3 Hz, 1H), 7.35 (ddd, J=9.4, 8.4, 1.3 Hz, 1H), 7.25-7.15 (m, 1H), 4.85 (s, 1H), 4.77 (dd, J=5.0, 1.6 Hz, 2H), 3.54 (q, J=6.3 Hz, 2H), 3.17 (t, J=6.3 Hz, 2H), 1.37 (s, 9H)

HPLCMS (Method A): [m/z]: 449.05 [M+H]$^+$ 2-(2-Aminoethyl)-N-[(3-fluoropyridin-2-yl)methyl]-5-(prop-1-en-2-yl)-1,3-thiazole-4-carboxamide Dihydrochloride (206)

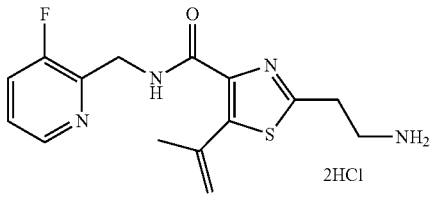 [SMILES: C=C(C)c1sc(CCN)nc1C(=O)NCc1ncccc1F]

In a similar fashion to general procedure 2, tert-butyl N-[2-(4-{[(3-fluoropyridin-2-yl)methyl]carbamoyl}-5-(prop-1-en-2-yl)-1,3-thiazol-2-yl)ethyl]carbamate (204) (544 mg, 1.29 mmol) and 12 M HCl (2 ml) in MeOH (10 ml) gave the title compound (486 mg, 94%) as a white solid.

HPLCMS (Method A): [m/z]: 321 [M+H]$^+$ 2-(2-Aminoethyl)-N-[(3-fluoropyridin-2-yl)methyl]-5-(trifluoromethyl)-1,3-thiazole-4-carboxamide Dihydrochloride (207)

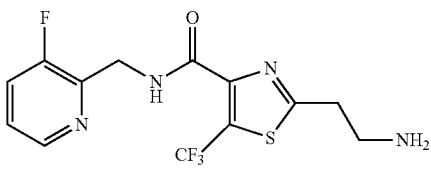

In a similar fashion to general procedure 2, tert-butyl N-[2-(4-{[(3-fluoropyridin-2-yl)methyl]carbamoyl}-5-(trifluoromethyl)-1,3-thiazol-2-yl)ethyl]carbamate (205) (347 mg, 0.77 mmol) and 12 M HCl (2 ml) in MeOH (10 ml) gave the title compound (330 mg, quant.) as a white solid.

1H-NMR (DMSO-d6, 250 MHz): d[ppm]=9.22 (t, J=5.6 Hz, 1H), 8.40 (dt, J=4.6, 1.4 Hz, 1H), 8.16 (s, 3H), 7.74 (ddd, J=10.1, 8.4, 1.4 Hz, 1H), 7.43 (dt, J=8.4, 4.4 Hz, 1H), 4.68 (dd, J=5.8, 1.5 Hz, 2H), 3.42-3.22 (m, 4H)

HPLCMS (Method A): [m/z]: 349 [M+H]$^+$

2-{2-[(1H-1,3-Benzodiazol-2-ylmethyl)amino]ethyl}-N-[(3-fluoropyridin-2-yl)methyl]-5-(prop-1-en-2-yl)-1,3-thiazole-4-carboxamide (Example Compound No. 177)

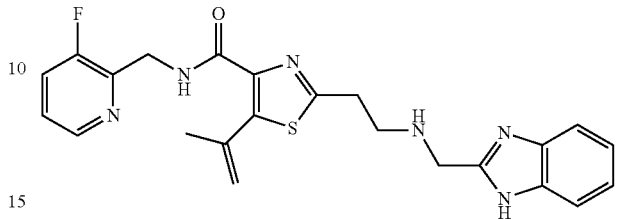

In a similar fashion using general procedure 3, 2-(2-aminoethyl)-N-[(3-fluoropyridin-2-yl)methyl]-5-(prop-1-en-2-yl)-1,3-thiazole-4-carboxamide dihydrochloride (206) (260 mg, 0.66 mmol), 1H-benzimidazole-2-carbaldehyde (96.6 mg, 0.66 mmol), DIPEA (0.36 ml, 2.0 mmol) and MgSO$_4$ (300 mg) in MeOH (20 ml) at room temperature for 18 h, followed by addition of NaBH$_4$ (500 mg, 1.3 mmol) afforded the title compound (148 mg, 50%) as pale yellow solid after purification by basic prep-HPLC.

1H-NMR (DMSO-d6, 500 MHz): d[ppm]=12.19 (s, 1H), 8.67 (t, J=5.5 Hz, 1H), 8.36 (d, J=4.6 Hz, 1H), 7.69 (t, J=8.8 Hz, 1H), 7.58-7.43 (m, 2H), 7.40 (m, 1H), 7.16-7.09 (m, 2H), 5.21 (s, 1H), 5.15 (s, 1H), 4.61 (d, J=5.5 Hz, 2H), 3.97 (s, 2H), 3.11 (t, J=6.7 Hz, 2H), 2.96 (t, J=6.7 Hz, 2H), 2.08 (s, 3H)

HPLCMS (Method C): [m/z]: 451.1 [M+H]$^+$

2-{2-[(1H-1,3-Benzodiazol-2-ylmethyl)amino]ethyl}-N-[(3-fluoropyridin-2-yl)methyl]-5-(trifluoromethyl)-1,3-thiazole-4-carboxamide (Example Compound No. 176)

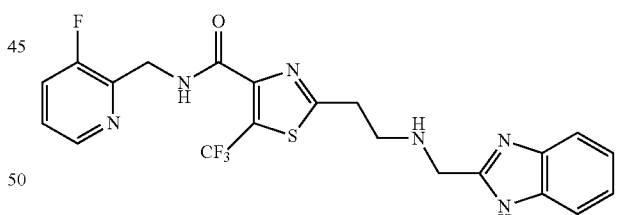

In a similar fashion using general procedure 3, 2-(2-aminoethyl)-N-[(3-fluoropyridin-2-yl)methyl]-5-(trifluoromethyl)-1,3-thiazole-4-carboxamide dihydrochloride (207) (130 mg, 0.31 mmol), 1H-benzimidazole-2-carbaldehyde (67.6 mg, 0.46 mmol), DIPEA (0.16 ml, 0.93 mmol) and MgSO$_4$ (300 mg) in MeOH (10 ml) at room temperature for 16 h, followed by addition of NaBH (23 mg, 0.62 mmol) gave the title compound (81 mg, 55%) as pale yellow solid ater purification by basic prep-HPLC.

1H-NMR (DMSO-d6, 500 MHz): d[ppm]=12.21 (s, 1H), 8.96 (t, J=5.7 Hz, 1H), 8.37 (dt, J=4.6, 1.3 Hz, 1H), 7.71 (ddd, J=10.0, 8.3, 1.3 Hz, 1H), 7.53 (s, 1H), 7.45 (s, 1H), 7.41 (dt, J=8.3, 4.4 Hz, 1H), 7.14 (s, 2H), 4.65 (dd, J=5.7, 1.4 Hz, 2H), 3.99 (s, 2H), 3.22 (t, J=6.3 Hz, 2H), 2.99 (t, J=6.3 Hz, 2H), 2.80 (s, 1H)

HPLCMS (Method C): [m/z]: 479.1 [M+H]+

2-{2-[(1H-1,3-Benzodiazol-2-ylmethyl)amino]ethyl}-N-[(3-fluoropyridin-2-yl)methyl]-5-(propan-2-yl)-1,3-thiazole-4-carboxamide (Example Compound No. 180)

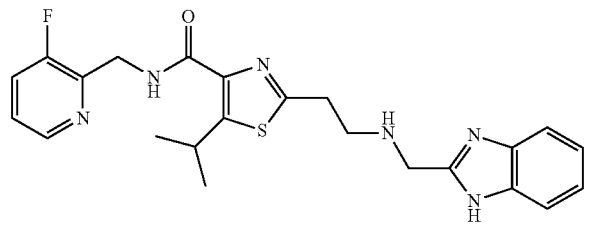 [SMILES: CC(C)c1sc(CCNCc2nc3ccccc3[nH]2)nc1C(=O)NCc1ncccc1F]

2-{2-[(1H-1,3-benzodiazol-2-ylmethyl)amino]ethyl}-N-[(3-fluoropyridin-2-yl)methyl]-5-(prop-1-en-2-yl)-1,3-thiazole-4-carboxamide (Example Compound No. 177) (120 mg, 0.27 mmol), and palladium on carbon (10%, 28 mg, 0.027 mmol) were combined in EtOH (10 ml) and the mixture stirred under an atmosphere of hydrogen for 1.5 h. The reaction mixture was filtered through a plug of Celite and the residue rinsed with MeOH. The combined filtrates were evaporated in vacuo and purified by basic prep-HPLC to afford the title compound (68 mg, 56%) as a white solid.

1H-NMR (DMSO-d6, 500 MHz): d[ppm]=12.20 (s, 1H), 8.60 (t, J=5.6 Hz, 1H), 8.38-8.34 (m, 1H), 7.70 (m, 1H), 7.58-7.43 (m, 2H), 7.40 (dt, J=8.6, 4.4 Hz, 1H), 7.16-7.09 (m, 2H), 4.63 (dd, J=5.6, 1.4 Hz, 2H), 4.24 (hept, J=6.8 Hz, 1H), 3.96 (s, 2H), 3.11 (t, J=6.8 Hz, 2H), 2.95 (t, J=6.8 Hz, 2H), 1.21 (d, J=6.8 Hz, 6H)

HPLCMS (Method C): [m/z]: 453.2 [M+H]+

2-(2-{[2-(1H-1,3-Benzodiazol-2-yl)ethyl]amino}ethyl)-N-[(3-fluoropyridin-2-yl)methyl]-5-(trifluoromethyl)-1,3-thiazole-4-carboxamide (Example Compound No. 186)

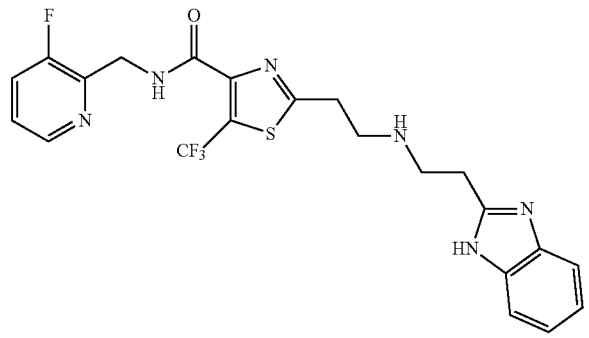 [SMILES: O=C(NCc1ncccc1F)c1nc(CCNCCc2nc3ccccc3[nH]2)sc1C(F)(F)F]

In a similar fashion using general procedure 8, 2-(2-aminoethyl)-N-[(3-fluoropyridin-2-yl)methyl]-5-(trifluoromethyl)-1,3-thiazole-4-carboxamide dihydrochloride (207) (242 mg, 0.57 mmol), N-(2-nitrophenyl)prop-2-enamide (110.4 mg, 0.57 mmol) and DBU (0.301 ml, 2 mmol) in MeCN (10 ml) gave a crude intermediate which was further reacted with iron powder (56 mg, 1 mmol) in AcOH (3 ml) to give the title compound (4 mg, 2%) after two purifications by basic prep-HPLC and a final purification by flash column chromatography (eluting with a gradient of 0-20% MeOH/DCM).

1H-NMR (DMSO-d6, 500 MHz): d[ppm]=12.14 (s, 1H), 8.94 (t, J=5.5 Hz, 1H), 8.39 (dt, J=4.5, 1.4 Hz, 1H), 7.71 (ddd, J=9.9, 8.3, 1.4 Hz, 1H), 7.41 (m, 2H), 7.10 (m, 2H), 4.64 (dd, J=5.7, 1.4 Hz, 2H), 3.18 (t, J=6.1 Hz, 2H), 3.06 (t, J=6.1 Hz, 2H), 3.02-2.92 (m, 4H)

HPLCMS (Method C): [m/z]: 493.1 [M+H]+

2-(Ethoxycarbonyl)-1,3-thiazole-4-carboxylic Acid (216)

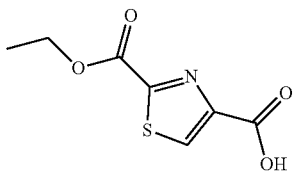

3-Bromo-2-oxopropanoic acid and ethyl amino(thioxo)acetate in THF (100 ml) were stirred at 60° C. for 16 h. The reaction mixture was reduced in vacuo to give an orange solid. The solid was triturated with Et2O, filtered and dried in vacuo to give the titled compound (4.54 g, 62.8%) as a colourless solid.

1H-NMR (DMSO-d6, 500 MHz): d[ppm]=13.40 (s, 1H), 8.77 (s, 1H), 4.40 (q, J=7.1 Hz, 2H), 1.35 (t, J=7.1 Hz, 3H)

HPLCMS (ESI+): [m/z]: 201.90 [M+H]+

Ethyl 4-(hydroxymethyl)-1,3-thiazole-2-carboxylate (217)

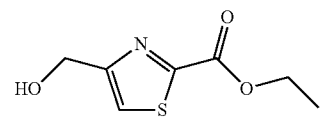

Isobutyl chloroformate (1.16 ml, 8.95 mmol) was added to an ice-cooled (0° C.) suspension of 2-(ethoxycarbonyl)-1,3-thiazole-4-carboxylic acid (216) (1.5 g, 7.46 mmol) and TEA (1.25 ml, 8.95 mmol) in THF (60 ml). The reaction was stirred at 0° C. for 1 h. The reaction was filtered through a plug of Celite and NaBH4 (0.705 g, 18.64 mmol) was added to the filtrate and stirred for 2 h. The reaction was diluted with sat. aq. Na2CO3 solution and stirred for 10 mins, then extracted with EtOAc. The combined organic layers were washed with brine, dried (Na2SO4), filtered and the solvent evaporated. Purification by flash column chromatography (eluting with a gradient of 40-50% EtOAc-Heptane) gave the titled compound (0.734 g, 52.6%) as a crystalline solid.

1H-NMR (DMSO-d6, 500 MHz) d[ppm]=7.85 (s, 1H), 5.50 (t, J=5.8 Hz, 1H), 4.63 (dd, J=5.8, 0.8 Hz, 2H), 4.37 (q, J=7.1 Hz, 2H), 1.33 (d, J=7.1 Hz, 3H)

HPLCMS (ESI+): [m/z]: 187.90 [M+H]+

Ethyl 4-{[(benzyloxy)methoxy]methyl}-1,3-thiazole-2-carboxylate (218)

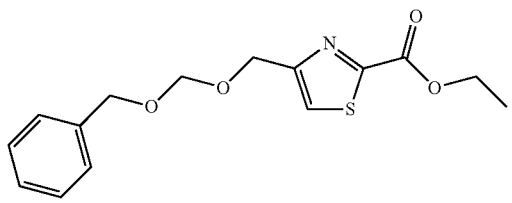 [SMILES: CCOC(=O)c1nc(COCOCc2ccccc2)cs1]

NaH (60%, 0.106 g, 2.66 mmol) was added to an ice-cooled (0° C.) solution of ethyl 4-(hydroxymethyl)-1,3-thiazole-2-carboxylate (217) (0.415 g, 2.22 mmol) in THF (20 ml) and the reaction stirred at 0° C. for 30 mins. [(Chloromethoxy)methyl]benzene (0.416 g, 2.66 mmol) was added and the reaction allowed to warm to room temperature over 3 h. The reaction was quenched by addition of sat. aq. NH$_4$Cl and extracted with EtOAc. The combined organic layers were combined, washed with brine, dried (Na$_2$SO$_4$), filtered and the solvent evaporated. Purification by flash column chromatography (eluting with 30-50% EtOAc-Heptane) gave the title compound (0.392 g, 48.9%) as a colourless oil.

1H-NMR (CDCl$_3$, 500 MHz) d[ppm]=7.52-7.50 (m, 1H), 7.36-7.33 (m, 5H), 4.90 (s, 2H), 4.86 (d, J=0.8 Hz, 2H), 4.66 (s, 2H), 4.48 (q, J=7.1 Hz, 2H), 1.44 (t, J=7.1, 3H).

HPLCMS (ESI+): [m/z]: 307.95 [M+H]$^+$

4-{[(Benzyloxy)methoxy]methyl}-1,3-thiazole-2-carboxylic Acid (219)

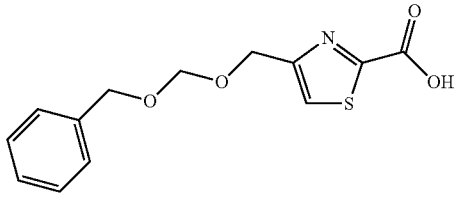 [SMILES: O=C(O)c1nc(COCOCc2ccccc2)cs1]

In a similar fashion to general procedure 5, LiOH (64 mg, 1.53 mmol) was added to a solution of ethyl 4 {[(benzyloxy)methoxy]methyl}-1,3-thiazole-2-carboxylate (218) (85%, 0.39 g, 1.28 mmol) in THF (5 ml), MeOH (5 ml) and water (5 ml) at room temperature for 4 h, gave the title compound (0.35 g, 88.4%) as a colourless oil.

1H-NMR (DMSO-d6, 500 MHz) d[ppm]=7.95 (s, 1H), 7.36-7.33 (m, 5H), 4.84 (s, 2H), 4.74 (s, 2H), 4.60 (s, 2H), 4.49 (s, 1H).

HPLCMS (ESI+): [m/z]: 279.95 [M+H]$^+$

4-{[(Benzyloxy)methoxy]methyl}-N-[(3-fluoropyridin-2-yl)methyl]-1,3-thiazole-2-carboxamide (220)

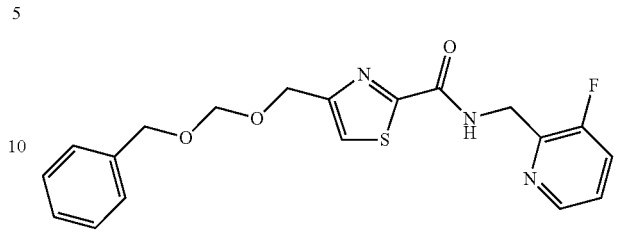

In a similar fashion to general procedure 6, 4-{[(benzyloxy)methoxy]methyl}-1,3-thiazole-2-carboxylic acid (219) (0.350 g, 1.25 mmol), (3-fluoropyridin-2-yl)methanamine dihydrochloride (A2) (0.374 g, 1.88 mmol), DIPEA (0.89 ml, 5.01 mmol) and HATU (0.714 g, 1.88 mmol) in DMF (10 ml) at room temperature for 16 h, gave the title compound (0.381 g, 76.1%) as a yellow oil after purification by flash column chromatography (eluting with a gradient of 0-5% MeOH-DCM).

1H-NMR (CDCl$_3$, 250 MHz) d[ppm]=8.42-8.38 (m, 1H), 7.40-7.27 (m, 7H), 4.90 (s, 2H), 4.86-4.82 (m, 2H), 4.80 (d, J=0.6 Hz, 2H), 4.68 (s, 2H)

HPLCMS (ESI+): [m/z]: 388.05 [M+H]$^+$

N-[(3-Fluoropyridin-2-yl)methyl]-4-(hydroxymethyl)-1,3-thiazole-2-carboxamide (221)

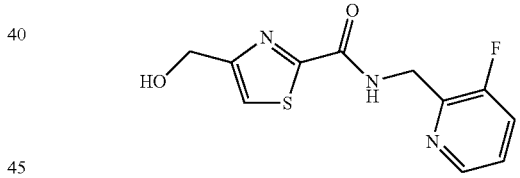

TFA (1 ml, 13.06 mmol) was added to an ice-cooled (0° C.) solution of 4-{[(benzyloxy)methoxy]methyl}-N-[(3-fluoropyridin-2-yl)methyl]-1,3-thiazole-2-carboxamide (220) (0.185 g, 0.48 mmol) in DCM (4 ml). The reaction allowed to warm to room temperature and stirred for 16 h. The solvent evaporated and the resulting residue dissolved in EtOAc (5 ml) and washed with sat. aq. NaHCO$_3$ (20 ml), brine (10 ml), dried (Na$_2$SO$_4$), filtered and the solvent evaporated. Purification by flash column chromatography (eluting with a gradient of 5% MeOH-DCM) gave the titled compound (0.085 g, 73.2%) as a colourless powder.

1H-NMR (CDCl$_3$, 500 MHz): d[ppm]=8.45-8.41 (m, 1H), 8.36 (br s, 1H), 7.45 (s, 1H), 7.44-7.40 (m, 1H), 7.31-7.26 (m, 1H), 4.85 (dd, J=5.1, 1.6 Hz, 2H), 4.83 (d, J=5.6 Hz, 2H), 2.20 (t, J=6.0 Hz, 1H)

HPLCMS (ESI+): [m/z]: 267.95 [M+H]$^+$

N-[(3-Fluoropyridin-2-yl)methyl]-4-formyl-1,3-thiazole-2-carboxamide (222)

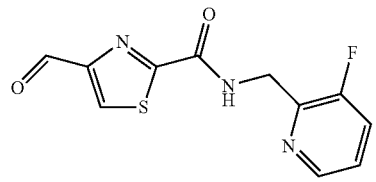 [SMILES: O=Cc1csc(C(=O)NCc2ncccc2F)n1]

IBX (189 mg, 0.70 mmol) was added to a solution of N-[(3-fluoropyridin-2-yl)methyl]-4-(hydroxymethyl)-1,3-thiazole-2-carboxamide (221) (60 mg, 0.22 mmol) in MeCN (5 ml) and the reaction heated at 80° C. for 3 h. The reaction was cooled to room temperature and filtered through Celite. The solution was directly absorbed onto silica and purified by flash column chromatography (eluting with a gradient of 5% MeOH DCM). The product was re-purified by flash column chromatography (eluting with a gradient of 30-50% EtOAc-Heptane) to give titled compound (56 mg, 94%) as a colourless solid.

1H-NMR (CDCl$_3$, 500 MHz): d[ppm]=10.10 (s, 1H), 8.46 (br s, 1H), 8.46-8.44 (m, 1H), 8.37 (s, 1H), 7.46-7.42 (m, 1H), 7.33-7.28 (m, 1H), 4.88 (dd, J=5.1, 1.7 Hz, 2H)

HPLCMS (ESI+): [m/z]: 265.95 [M+H]$^+$

4-({[2-(1H-1,3-Benzodiazol-2-yl)ethyl]amino}methyl)-N-[(3-fluoropyridin-2-yl)methyl]-1,3-thiazole-2-carboxamide (Example Compound No. 205)

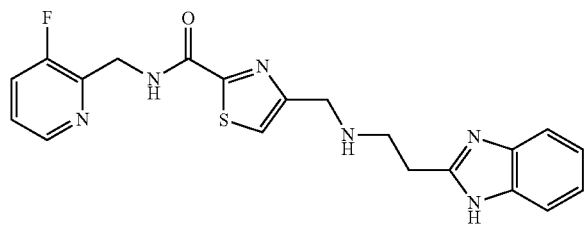 [SMILES: O=C(NCc1ncccc1F)c1nc(CNCCc2nc3ccccc3[nH]2)cs1]

A solution of N-[(3-fluoropyridin-2-yl)methyl]-4-formyl-1,3-thiazole-2-carboxamide (222) (56 mg, 0.21 mmol) in DCE (1 mL) was added to a suspension of 2-(1H-1,3-benzodiazol-2-yl)ethan-1-amine dihydrochloride (50 mg, 0.21 mmol) and DIPEA (147 µl, 0.84 mmol) in DCE (2 ml). 4 Å activated molecular sieves were added and the solution stirred at room temperature for 2 h, then filtered and the filtrate concentrated in vacuo. The residue was dissolved in MeOH (10 ml) and cooled to 0° C. NaBH$_4$ (12 mg, 0.32 mmol) was added, the mixture was warmed to room temperature and stirred for 1 h, then quenched with sat. Na$_2$CO$_3$ (aq) and extracted with EtOAc (2×10 ml). The combined organic extracts were dried (Na$_2$SO$_4$), filtered and evaporated in vacuo. Purification by basic prep-HPLC afforded the title compound (44 mg, 51%) as a colourless foam.

1H-NMR (Methanol-d4, 500 MHz): d[ppm]=8.31 (dt, J=4.5, 1.2 Hz, 1H), 7.62 (s, 1H), 7.57 (ddd, J=9.8, 8.5, 1.2 Hz, 1H), 7.46 (dt, J=6.6, 3.3 Hz, 2H), 7.36 (dt, J=8.5, 4.5 Hz, 1H), 7.18-7.14 (m, 2H), 4.75 (d, J=1.6 Hz, 2H), 3.96 (s, 2H), 3.13-3.07 (m, 4H).

HPLCMS (Method C): [m/z]: 411.1 [M+H]$^+$

General Scheme 12 Above

General Procedure 13: methyl 2-(3-{[(tert-butoxy)carbonyl]amino}propanamido)-3-hydroxypropanoate (223)

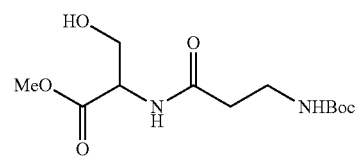

TEA (8.38 ml, 60.1 mmol) was added to a cooled (0° C.) solution of methyl serinate hydrochloride (1:1) (8.5 g, 54.6 mmol) in DCM (250 ml) under nitrogen. N-(tert-butoxycarbonyl)-beta-alanine (10.3 g, 54.6 mmol) and DCC (12.4 g, 60.1 mmol) were added portionwise. The reaction mixture was allowed to warm to room temperature and stirred for 19 h. The solvent was evaporated and EtOAc (250 ml) was added. The mixture was heated to 50° C. and stirred for 20 min, cooled to room temperature and filtered. The filtrate was evaporated to give a waxy off-white solid (21.7 g). The solid was dissolved in MeOH (200 ml) and silica (300 ml volume) was added. The solvent was evaporated under reduced pressure to give the compound dry loaded onto silica. Purification by flash column chromatography (eluting with a gradient of 20% EtOAc/heptane (2 L), 40% EtOAc/heptane (4 L), 80% EtOAc/heptane (2 L) followed by EtOAc 0 L) gave the title compound (10.4 g, 64.4%) as an off-white solid.

1H-NMR (CDCl$_3$, 250 MHz): d[ppm]=6.62 (s, 1H), 5.12 (s, 1H), 4.65 (dt, J=7.1, 3.4 Hz, 1H), 3.96 (t, J=3.2 Hz, 2H), 3.80 (s, 3H), 3.55-3.33 (m, 2H), 2.95 (s, 1H), 2.48 (td, J=5.8, 2.6 Hz, 2H), 1.43 (s, 9H)

HPLCMS (Method A): [m/z]: 291 [M+H]$^+$

Methyl 2-(2-{[(tert-butoxy)carbonyl]amino}acetamido)-3-hydroxypropanoate (224)

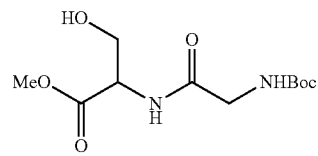 [SMILES: COC(=O)C(CO)NC(=O)CNC(=O)OC(C)(C)C]

In a similar fashion to general procedure 13, methyl serinate hydrochloride (3 g, 19.28 mmol), TEA (2.96 ml, 21.21 mmol), N-(tert-butoxycarbonyl)glycine (3.38 g, 19.28 mmol) and DCC (4.38 g, 21.21 mmol) in DCM (100 ml) afforded the title compound (4.5 g, 69%) as a pale yellow oil after purification by flash chromatography using an elution gradient 20-100% EtOAc/heptane.

1H-NMR (CDCl$_3$, 250 MHz): d[ppm]=7.07 (d, J=7.4 Hz, 1H), 5.32 (s, 1H), 4.77-4.60 (m, 1H), 3.99 (m, 2H), 3.87 (m, 2H), 3.81 (s, 3H), 3.04 (s, 1H), 1.48 (s, 9H)

HPLCMS (Method A): [m/z]: 298.95 [M+Na]$^+$

General Procedure 14: methyl 2-(2-{[(tert-butoxy)carbonyl]amino}ethyl)-4,5-dihydro-1,3-oxazole-4-carboxylate (225)

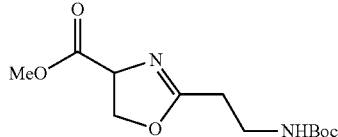 [SMILES: COC(=O)C1COC(CCNC(=O)OC(C)(C)C)=N1]

Methyl 2-(3-{[(tert-butoxy)carbonyl]amino}propanamido)-3-hydroxypropanoate (223) (98%, 10.42 g, 35.17 mmol) was dissolved in anhydrous DCM (280 ml) under nitrogen. The reaction mixture was cooled in a CO₂/MeCN bath (approx. −50° C.) and stirred for 30 min. DAST (5.58 ml, 42.21 mmol) was added dropwise and the mixture was stirred at −50° C. for 2.25 h. K₂CO₃ (4.86 g, 35.17 mmol) was added in one portion and the reaction mixture was allowed to stir for 20 min, before it was warmed up to room temperature. The reaction mixture was then immersed in a water bath and water (60 ml) was added cautiously (effervescence occurred) to the reaction followed by 2 M NaOH (5 ml). The reaction mixture was stirred for further 10 min and the layers were then separated. The aqueous layer was extracted with DCM (2×50 ml). The combined organic layers were dried (MgSO4), filtered and evaporated to give the title compound (10.3 g) as an orange oil. The crude product was carried through the next step without further purification.

1H-NMR (CDCl$_3$, 500 MHz): d[ppm]=5.14 (s, 1H), 4.72 (ddt, J=10.3, 7.6, 1.2 Hz, 1H), 4.47 (dd, J=8.7, 7.7 Hz, 1H), 4.39 (dd, J=10.6, 8.8 Hz, 1H), 3.78 (s, 3H), 3.49-3.36 (m, 2H), 2.48 (td, J=6.2, 1.2 Hz, 2H), 1.42 (s, 9H)

HPLCMS (Method A): [m/z]: 273 [M+H]$^+$

Methyl 2-({[(tert-butoxy)carbonyl]amino}methyl)-4,5-dihydro-1,3-oxazole-4-carboxylate (226)

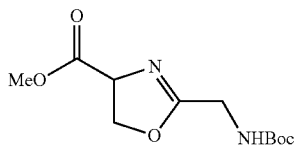 [SMILES: COC(=O)C1COC(CNC(=O)OC(C)(C)C)=N1]

In a similar fashion to general procedure 14, methyl 2-(2-{[(tert-butoxy)carbonyl]amino}acetamido)-3-hydroxypropanoate (224) (2.5 g, 7.42 mmol) and DAST (1.18 ml, 8.9 mmol) in DCM (70 ml) afforded the title compound (2.02 g, quant.) as a yellow oil.

1H-NMR (CDCl$_3$, 250 MHz): d[ppm]=5.12 (s, 1H), 4.86-4.68 (m, 1H), 4.62-4.42 (m, 2H), 4.11-3.89 (m, 2H), 3.82 (s, 3H), 1.44 (s, 9H)

HPLCMS (Method A): [m/z]: 258.95 [M+H]$^+$

General Procedure 15: methyl 2-(2-{[(tert-butoxy)carbonyl]amino}ethyl)-1,3-oxazole-4-carboxylate (227)

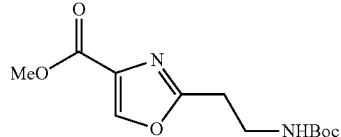 [SMILES: COC(=O)c1coc(CCNC(=O)OC(C)(C)C)n1]

Bromo(trichloro)methane (10.4 ml, 105.56 mmol) was added to a solution of methyl 2-(2-{[(tert-butoxy)carbonyl]amino}ethyl)-4,5-dihydro-1,3-oxazole-4-carboxylate (225) (93.2%, 10.28 g, 35.19 mmol) in anhydrous DCM (300 ml) under nitrogen cooled to 0° C. DBU (15.75 ml, 105.56 mmol) was added dropwise and the mixture was allowed to warm to room temperature and stirred for 2.5 h. Saturated aqueous citric acid (25 ml) was added followed by water (100 ml). The reaction mixture was stirred vigorously for 10 min. The layers were separated and the aqueous layer was extracted with DCM (3×100 ml). The organic layer was dried (MgSO4), filtered and evaporated to give a dark brown oil (14.6 g). The crude oil was dry loaded onto silica with MeOH (200 ml). The crude material was filtered through a silica plug [gradient elution with heptane (2×500 ml), 25% EtOAc/heptane (2×500 ml) and 50% EtOAc/heptane (11× 500 ml)] to give the title compound (8.63 g) as a yellow oil which solidified on standing.

1H-NMR (CDCl$_3$, 500 MHz): d[ppm]=8.16 (s, 1H), 4.99 (s, 1H), 3.90 (s, 3H), 3.57 (q, J=6.0 Hz, 2H), 2.99 (t, J=6.3 Hz, 2H), 1.40 (s, 9H)

HPLCMS (Method A): [m/z]: 293.0 [M+Na]$^+$

Methyl 2-({[(tert-butoxy)carbonyl]amino}methyl)-4,5-dihydro-1,3-oxazole-4-carboxylate (228)

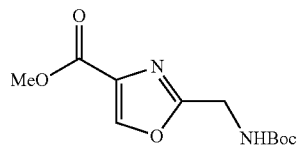 [SMILES: COC(=O)c1coc(CNC(=O)OC(C)(C)C)n1]

In a similar fashion to general procedure 15, methyl 2-({[(tert-butoxy)carbonyl]amino}methyl)-4,5-dihydro-1,3-oxazole-4-carboxylate (226) (2.02 g, 7.43 mmol), DBU (3.33 ml, 22.29 mmol) and bromo(trichloro)methane (2.2 ml, 22.29 mmol) in DCM (75 ml) afforded the title compound (1.04 g, 55%) as a colourless oil after purification by flash column chromatography using an elution gradient 0-100% TBME/heptane.

1H-NMR (CDCl$_3$, 500 MHz): d[ppm]=8.19 (s, 1H), 5.19 (br. s, 1H), 4.49 (d, J=5.5 Hz, 2H), 3.92 (s, 3H), 1.45 (s, 9H)

HPLCMS (Method A): [m/z]: 278.95 [M+Na]$^+$

2-(2-{[(Tert-butoxy)carbonyl]amino}ethyl)-1,3-oxazole-4-carboxylic Acid (229)

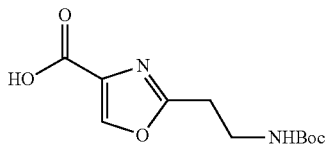

In a similar fashion using general procedure 5, LiOH (1.02 g, 42.76 mmol) and methyl 2-(2-{[(tert-butoxy)carbonyl]amino}ethyl)-1,3-oxazole-4-carboxylate (227) (97%, 6.62 g, 23.76 mmol) in THF (100 ml), and water (25 ml) gave the title compound (4.8 g, 79%) as an off white powder.

1H-NMR (DMSO-d6, 500 MHz): d[ppm]=8.62 (s, 1H), 6.94 (t, J=5.4 Hz, 1H), 3.31-3.26 (m, 2H, partially obscured by HOD peak), 2.87 (t, J=6.8 Hz, 2H), 1.35 (s, 9H)

HPLCMS (Method A): [m/z]: 278.9 [M+Na]$^+$

2-({[(Tert-butoxy)carbonyl]amino}methyl)-1,3-oxazole-4-carboxylic Acid (230)

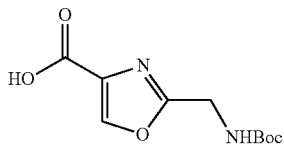 [SMILES: CC(C)(C)OC(=O)NCc1nc(C(=O)O)co1]

In a similar fashion to general procedure 5, methyl 2-({[(tert-butoxy)carbonyl]amino}methyl)-4,5-dihydro-1,3-oxazole-4-carboxylate (228) (1.04 g, 4.06 mmol) and LiOH (0.15 g, 6.09 mmol) in THF/water (20 ml/5 ml) afforded the title compound (1.07 g, quant.) as an off-white solid.

1H-NMR (CDCl$_3$, 500 MHz): d[ppm]=8.29 (s, 1H), 5.39 (br. s, 1H), 4.54 (d, J=4.9 Hz, 2H) 1.47 (s, 9H)

HPLCMS (Method A): [m/z]: 265 [M+Na]$^+$

Tert-butyl N-[2-(4-{[(3-fluoropyridin-2-yl)methyl]carbamoyl}-1,3-oxazol-2-yl)ethyl]carbamate (231)

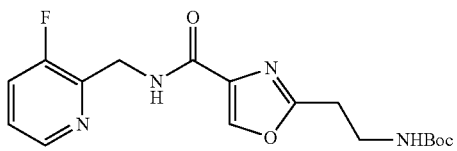 [SMILES: CC(C)(C)OC(=O)NCCc1nc(C(=O)NCc2ncccc2F)co1]

In a similar fashion using general procedure 6, 2-(2-{[(tert-butoxy)carbonyl]amino}ethyl)-1,3-oxazole-4-carboxylic acid (229) (3.78 g, 14.75 mmol), HATU (6.17 g, 16.23 mmol), (DIPEA) (8.48 ml, 48.68 mmol), (3-fluoropyridin-2-yl)methanamine dihydrochloride (A2) (2.94 g, 14.75 mmol) in THF/water (100 ml/40 ml) gave the title compound (4.83 g, 87%) as a yellow glassy solid after purification by flash column chromatography (eluting with a gradient 0-100% EtOAc/heptane).

1H-NMR (DMSO-d6, 500 MHz): d[ppm]=8.51 (s, 2H), 8.40 (d, J=4.4 Hz, 1H), 7.70 (t, J=9.3 Hz, 1H), 7.45-7.37 (m, 1H), 6.98 (t, J=5.5 Hz, 1H), 4.62 (d, J=5.5 Hz, 2H), 3.32-3.28 (m, 2H, signal partially obscured by HOD peak), 2.90 (t, J=6.7 Hz, 2H), 1.35 (s, 9H)

HPLCMS (Method A): [m/z]: 365.0 [M+H]$^+$

Tert-butyl N-(2-{4-[(pyridin-2-ylmethyl)carbamoyl]-1,3-oxazol-2-yl}ethyl)carbamate (232)

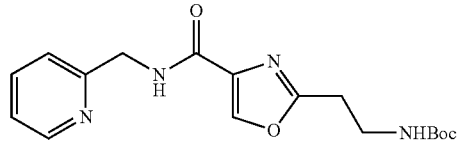

In a similar fashion using general procedure 6, 2-(2-{[(tert-butoxy)carbonyl]amino}ethyl)-1,3-oxazole-4-carboxylic acid (229) (4 g, 15.61 mmol), DIPEA (5.44 ml, 31.22 mmol), HATU (8.9 g, 23.41 mmol), pyridin-2-ylmethanamine (2.41 ml, 23.41 mmol) in DMF (65 ml) gave the title compound (6.03 g) as a yellow viscous oil after purification by flash column chromatography (eluting with a gradient (100% EtOAc/heptane).

1H-NMR (DMSO-d6, 250 MHz): d[ppm]=8.74 (t, J=5.9 Hz, 1H), 8.54-8.48 (m, 2H), 7.75 (td, J=7.7, 1.8 Hz, 1H), 7.32-7.22 (m, 2H), 6.98 (s, 1H), 4.52 (d, J=6.0 Hz, 2H), 3.29 (d, J=6.5 Hz, 2H), 2.90 (t, J=6.7 Hz, 2H), 1.34 (s, 9H)

HPLCMS (Method A): [m/z]: 347.1 [M+H]$^+$

Tert-butyl N-[2-(4-{[(3-chloropyridin-2-yl)methyl]carbamoyl}-1,3-oxazol-2-yl)ethyl]carbamate (233)

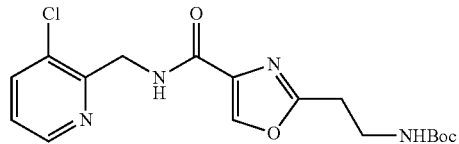

In a similar fashion to general procedure 6, 2-(2-{[(tert-butoxy)carbonyl]amino}ethyl)-1,3-oxazole-4-carboxylic acid (229) (295 mg, 0.76 mmol, 66%), (3-chloropyridin-2-yl)methanamine dihydrochloride (246 mg, 1.14 mmol), TEA (0.1 ml, 0.76 mmol) and HATU (0.43 g, 1.14 mmol) in DMF (10 ml) afforded the title compound (202 mg, 59%, 85% purity) as a yellow oil after purification by flash column chromatography (eluting with a gradient of 0-10% MeOH/DCM).

1H-NMR (DMSO-d6, 250 MHz): d[ppm]=8.58-8.45 (m, 2H), 7.96 (dd, J=8.1, 1.4 Hz, 1H), 7.40 (dd, J=8.1, 4.7 Hz, 1H), 7.00 (t, J=6.2 Hz, 1H), 4.65 (d, J=5.4 Hz, 2H), 2.97-2.86 (m, 4H), 1.35 (s, 9H)

HPLCMS (Method A): [m/z]: 381.05 [M+H]$^+$

Tert-butyl N-[(4-{[(3-fluoropyridin-2-yl)methyl]carbamoyl}-1,3-oxazol-2-yl)methyl]carbamate (234)

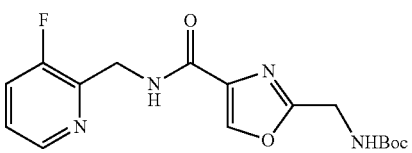 [SMILES: CC(C)(C)OC(=O)NCc1nc(C(=O)NCc2ncccc2F)co1]

In a similar fashion to general procedure 6, 2-({[(tert-butoxy)carbonyl]amino}methyl)-1,3-oxazole-4-carboxylic acid (230) (0.5 g, 2.06 mmol), (3-fluoropyridin-2-yl)methanamine dihydrochloride (A2) (0.41 g, 2.06 mmol), DIPEA (1.19 ml, 6.81 mmol) and HATU (0.86 g, 2.27 mmol) in THF (15 ml) and DMF (6 ml) gave the title compound (0.744 g, 98%) as a colourless oil after purification by flash chromatography using an elution gradient 0-100% EtOAc/heptane.

1H-NMR (DMSO-d6, 500 MHz): d[ppm]=8.56 (s, 1H), 8.51 (t, J=5.2 Hz, 1H), 8.38 (d, J=4.6 Hz, 1H), 7.73-7.65 (m, 1H), 7.55 (t, J=5.8 Hz, 1H), 7.44-7.37 (m, 1H), 4.65-4.59 (m, 2H), 4.29 (d, J=5.9 Hz, 2H), 1.39 (s, 9H)

HPLCMS (Method A): [m/z]: 351.0 [M+H]$^+$ 2-(2-Aminoethyl)-N-[(3-fluoropyridin-2-yl)methyl]-1,3-oxazole-4-carboxamide dihydrochloride (235)

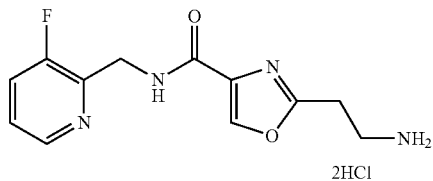 [SMILES: NCCc1nc(C(=O)NCc2ncccc2F)co1]

In a similar fashion using general procedure 2, tert-butyl N-[2-(4-{[(3-fluoropyridin-2-yl)methyl]carbamoyl}-1,3-oxazol-2-yl)ethyl]carbamate (231) (4.83 g, 12.86 mmol), 4 M HCl in 1,4-dioxane (50 ml) and DCM (80 ml) gave the title compound (4.61 g) as an off-white solid.

1H-NMR (DMSO-d6, 500 MHz): d[ppm]=8.71 (t, J=5.8 Hz, 1H), 8.59 (s, 1H), 8.42-8.36 (m, 1H), 8.13 (br. s, 3H), 7.76-7.68 (m, 1H), 7.46-7.39 (m, 1H), 4.64 (dd, J=5.8, 1.4 Hz, 2H), 3.25 (app. q, J=6.1 Hz, 2H), 3.20-3.14 (m, 2H)

HPLCMS (Method F): [m/z]: 265.1 [M+H]$^+$ 2-(2-Aminoethyl)-N-(pyridin-2-ylmethyl)-1,3-oxazole-4-carboxamide dihydrochloride (236)

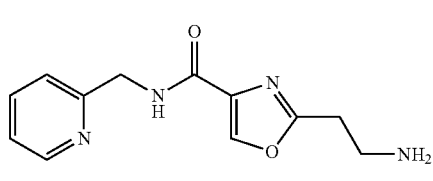

In a similar fashion using general procedure 2, tert-butyl N-(2-{4-[(pyridin-2-ylmethyl)carbamoyl]-1,3-oxazol-2-yl}ethyl)carbamate (232) (90%, 6.03 g, 15.68 mmol), 12 M HCl (26.13 ml) in MeOH gave the title compound (5.78 g) as a cream foam.

1H-NMR (Methanol-d4, 250 MHz): d[ppm]=8.80 (dd, J=5.9, 0.8 Hz, 1H), 8.62 (td, J=8.0, 1.6 Hz, 1H), 8.44 (s, 1H), 8.10 (d, J=7.8 Hz, 1H), 8.01 (t, J=6.3 Hz, 1H), 4.93 (s, 2H), 3.51-3.43 (m, 2H), 3.26 (t, J=6.4 Hz, 2H).

HPLCMS (Method A): [m/z]: 246.9 [M+H]$^+$ 2-(2-Aminoethyl)-N-[(3-chloropyridin-2-yl)methyl]-1,3-oxazole-4-carboxamide Dihydrochloride (237)

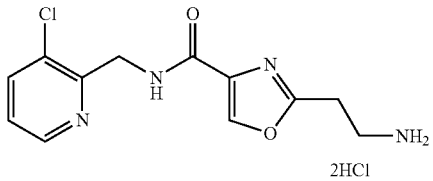 [SMILES: NCCc1nc(C(=O)NCc2ncccc2Cl)co1]

In a similar fashion using general procedure 2, tert-butyl N-[2-(4-{[(3-chloropyridin-2-yl)methyl]carbamoyl}-1,3-oxazol-2-yl)ethyl]carbamate (233) (85%, 202 mg, 0.45 mmol), MeOH (5 ml) and 4 M HCl in dioxane (1.65 ml) gave the title compound (125 mg, 62%) as a brown solid.

1H NMR (DMSO-d6, 500 MHz): d[ppm]=8.67 (t, J=5.6 Hz, 1H), 8.61 (s, 1H), 8.52 (dd, J=4.7, 1.4 Hz, 1H), 8.15 (s, 3H), 7.96 (dd, J=8.1, 1.4 Hz, 1H), 7.40 (dd, J=8.1, 4.7 Hz, 1H), 4.67 (d, J=5.6 Hz, 2H), 3.29-3.23 (m, 2H), 3.21-3.16 (m, 2H).

HPLCMS (Method A): [m/z]: 281.1 [M+H]$^+$ 2-(Aminomethyl)-N-[(3-fluoropyridin-2-yl)methyl]-1,3-oxazole-4-carboxamide Dihydrochloride (238)

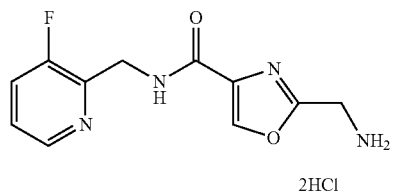 [SMILES: NCc1nc(C(=O)NCc2ncccc2F)co1]

In a similar fashion to general procedure 2, tert-butyl N-[(4-{[(3-fluoropyridin-2-yl)methyl]carbamoyl}-1,3-oxazol-2-yl)methyl]carbamate (234) (744 mg, 2.02 mmol) and 4 M HCl in 1,4-dioxane (15 ml) in DCM (20 ml) afforded the title compound (668 mg, quant.) as a white solid.

1H-NMR (DMSO-d6, 500 MHz): d[ppm]=8.79 (s, 1H), 8.73 (br. s, 3H), 8.54 (t, J=5.6 Hz, 1H), 8.39 (d, J=4.7 Hz, 1H), 7.80-7.68 (m, 1H), 7.49-7.38 (m, 1H), 4.66 (d, J=4.6 Hz, 2H), 4.32 (t, J=5.5 Hz, 2H)

HPLCMS (Method F): [m/z]: 251.1 [M+H]$^+$ 2-(2-{[2-(1H-1,3-Benzodiazol-2-yl)ethyl]amino}ethyl)-N-[(3-fluoropyridin-2-yl)methyl]-1,3-oxazole-4-carboxamide Trihydrochloride (Example Compound No. 127)

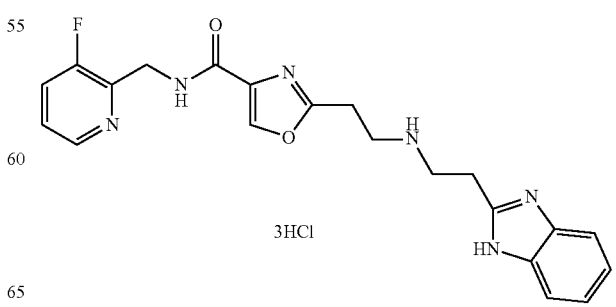

In a similar fashion to general procedure 8, 2-(2-amino-ethyl)-N-[(3-fluoropyridin-2-yl)methyl]-1,3-oxazole-4-carboxamide dihydrochloride (235) (1 g, 2.97 mmol), N-(2-nitrophenyl)prop-2-enamide (D) (0.63 g, 3.26 mmol) and DBU (1.5 ml, 10.08 mmol) in MeCN (30 ml) at room temperature overnight gave the crude intermediate which was further reacted with iron powder (0.5 g) in AcOH (10 ml) under nitrogen at 80° C. for 3 h. the crude material was purified by basic prep-HPLC followed by further purification by flash column chromatography (eluting with gradient 0-30% MeOH in DCM) gave 2-(2-{[2-(1H-1,3-benzodiazol-2-yl)ethyl]amino}ethyl)-N-[(3-fluoropyridin-2-yl)methyl]-1,3-oxazole-4-carboxamide. The free base was dissolved in MeOH (10 ml) and treated with 12 M hydrogen chloride (1.5 ml). The solvent was then rigorously evaporated under vacuum to give the title compound (333 mg, 22%) as a white solid.

1H-NMR (D$_2$O, 500 MHz): d[ppm]=8.34-8.30 (m, 2H), 7.86 (ddd, J=9.6, 8.7, 1.2 Hz, 1H), 7.74-7.69 (m, 2H), 7.62-7.57 (m, 1H), 7.57-7.52 (m, 2H), 3.74-3.66 (m, J=4.3 Hz, 4H), 3.64 (t, J=6.7 Hz, 2H), 3.33 (t, J=6.7 Hz, 2H)

HPLCMS (Method C): [m/z]: 409.1 [M+H]$^+$ 2-(2-{bis[2-(1H-1,3-Benzodiazol-2-yl)ethyl]amino}ethyl)-N-[(3-fluoropyridin-2-yl)methyl]-1,3-oxazole-4-carboxamide Tetrahydrochloride (Example Compound No. 128)

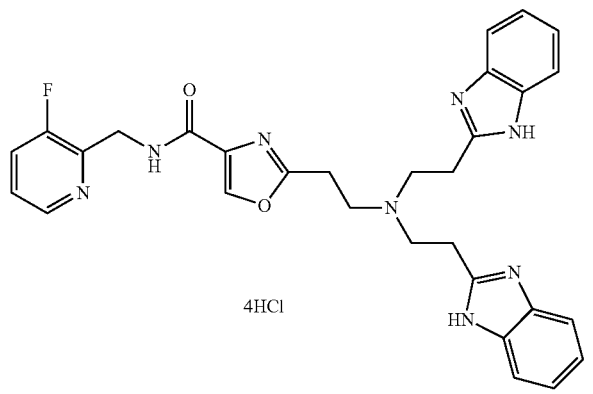 [SMILES: O=C(NCc1ncccc1F)c1coc(CCN(CCc2nc3ccccc3[nH]2)CCc2nc3ccccc3[nH]2)n1]

In a similar fashion to general procedure 7, 2-(2-amino-ethyl)-N-[(3-fluoropyridin-2-yl)methyl]-1,3-oxazole-4-carboxamide dihydrochloride (Example Compound No. 127) (305 mg, 0.9 mmol), 2-(2-chloroethyl)-1H-1,3-benzodiazole hydrochloride (216 mg, 1 mmol) and DIPEA (3.15 ml, 18 mmol) in DMF (5 ml) afforded the title compound freebase after purification by basic prep-HPLC. The freebase was treated with 12 M HCl (0.5 ml) in MeOH (5 ml) to afford the title compound as tetrahydrochloride salt (5 mg, 0.8%) as a brown residue.

1H-NMR (Methanol-d4, 500 MHz): d[ppm]=8.56-8.52 (m, 1H), 8.45 (s, 1H), 8.21-8.15 (m, 1H), 7.90-7.84 (m, 2H), 7.84-7.77 (m, 3H), 7.69-7.60 (m, 3H), 7.58 (ddd, J=8.2, 7.4, 0.6 Hz, 1H), 5.32-5.22 (m, 2H), 4.90 (s, 2H), 4.17-4.11 (m, 2H), 4.02-3.94 (m, 2H), 3.93-3.86 (m, 2H), 3.78 (t, J=6.3 Hz, 2H), 3.48 (t, J=6.3 Hz, 2H)

HPLCMS (Method C): [m/z]: 553.2 [M+H]$^+$ 2-(2-{[2-(1H-1,3-Benzodiazol-2-yl)ethyl]amino}ethyl)-N-(pyridin-2-ylmethyl)-1,3-oxazole-4-carboxamide Trihydrochloride (Example Compound No. 171)

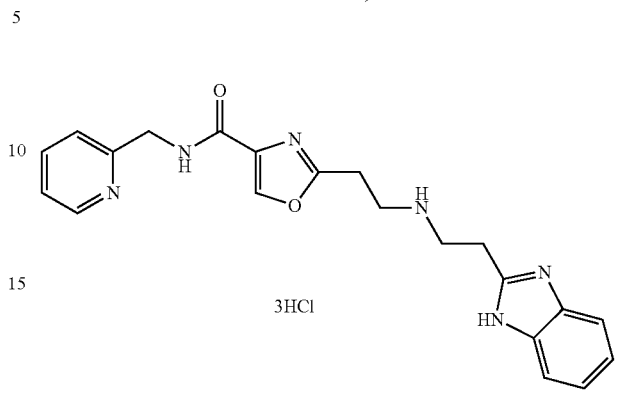

In a similar fashion using general procedure 8, 2-(2-aminoethyl)-N-(pyridin-2-ylmethyl)-1,3-oxazole-4-carboxamide dihydrochloride (236) (86%, 1.2 g, 3.25 mmol), DBU (1.46 ml, 9.76 mmol) and N-(2-nitrophenyl)prop-2-enamide (D) (0.69 g, 3.58 mmol) in MeCN (30 ml) gave the crude intermediate, which was further reacted with iron powder (0.52 g) in AcOH (10 ml) to give the title compound (0.22 g, 12%) as a pale brown solid.

1H-NMR (D$_2$O), 500 MHz): d[ppm]=8.72 (d, J=5.8 Hz, 1H), 8.54 (td, J=8.0, 1.5 Hz, 1H), 8.46 (s, 1H), 8.00-7.94 (m, 2H), 7.81 (dt, J=6.2, 3.2 Hz, 2H), 7.63 (dt, J=6.2, 3.3 Hz, 2H), 4.88 (s, 2H), 3.83-3.70 (m, 6H), 3.43 (t, J=6.9 Hz, 2H)

HPLCMS (Method C): [m/z]: 391.2 [M+H]$^+$ 2-(2-{[2-(1H-1,3-Benzodiazol-2-yl)ethyl]amino}ethyl)-N-[(3-chloropyridin-2-yl)methyl]-1,3-oxazole-4-carboxamide (Example Compound No. 173)

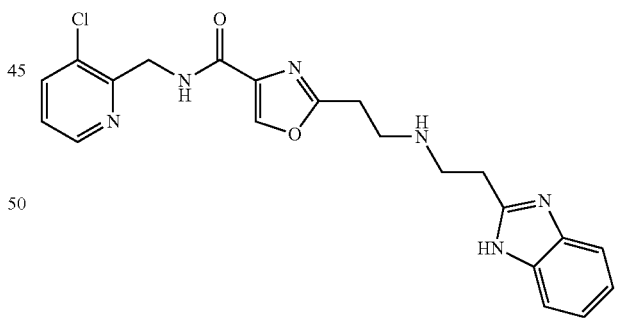

In a similar fashion using general procedure 8, 2-(2-aminoethyl)-N-[(3-chloropyridin-2-yl)methyl]-1,3-oxazole-4-carboxamide dihydrochloride (237) (75%, 120 mg, 0.25 mmol), DBU (76 µl, 0.51 mmol) and N-(2-nitrophenyl)prop-2-enamide (D) (48 mg, 0.25 mmol) in MeCN (5 ml) gave the crude intermediate, which was further reacted with iron powder (36.9 mg) in AcOH (2 ml) to give the title compound (4.6 mg, 3%) as a clear film after purification by basic prep-HPLC.

1H-NMR (Methanol-d4, 500 MHz): d[ppm]=8.44 (dd, J=4.7, 1.4 Hz, 1H), 8.28 (s, 1H), 7.86 (dd, J=8.1, 1.4 Hz, 1H), 7.47-7.41 (m, 2H), 7.33 (dd, J=8.1, 4.8 Hz, 1H), 7.19-7.14 (m, 2H), 4.70 (s, 2H), 3.18-3.04 (m, 8H)

HPLCMS (Method C): [m/z]: 425.2 [M+H]⁺

2-({[2-(1H-1,3-Benzodiazol-2-yl)ethyl]amino}methyl)-N-[(3-fluoropyridin-2-yl)methyl]-1,3-oxazole-4-carboxamide (Example Compound No. 206

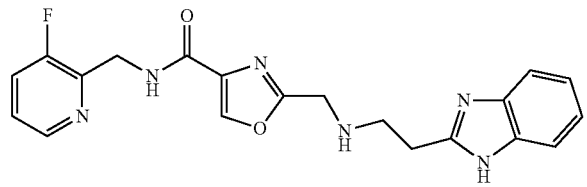 [SMILES: O=C(NCc1ncccc1F)c1coc(CNCCc2nc3ccccc3[nH]2)n1]

In a similar fashion to general procedure 8, 2-(aminomethyl)-N-[(3-fluoropyridin-2-yl)methyl]-1,3-oxazole-4-carboxamide dihydrochloride (238) (300 mg, 0.93 mmol), N-(2-nitrophenyl)prop-2-enamide (D) (196 mg, 1.02 mmol) and DBU (471.1 μl, 3.16 mmol) in MeCN (10 ml) gave a crude intermediate which was further reacted with iron powder (156 mg, 2.79 mmol) in AcOH (5 ml) to afford the title compound (20 mg, 27%) as a white solid after purification by basic prep-HPLC followed by flash chromatography using an elution gradient 2-20% MeOH/DCM.

1H-NMR (DMSO-d6, 500 MHz): d[ppm]=12.15 (s, 1H), 8.57 (s, 1H), 8.53 (t, J=5.6 Hz, 1H), 8.38 (dt, J=4.6, 1.3 Hz, 1H), 7.70 (m, 1H), 7.51 (d, J=6.9 Hz, 1H), 7.41 (m, 2H), 7.15-7.07 (m, 2H), 4.62 (dd, J=5.6, 1.3 Hz, 2H), 3.92 (s, 2H), 3.04-2.99 (m, 2H), 2.98-2.94 (m, 2H)

HPLCMS (Method C): [m/z]: 395.1 [M+H]⁺

2-{2-[(1H-1,3-Benzodiazol-2-ylmethyl)amino]ethyl}-N-[(3-fluoropyridin-2-)methyl)]-1,3-oxazole-4-carboxamide Trihydrochloride (Example Compound No. 126)

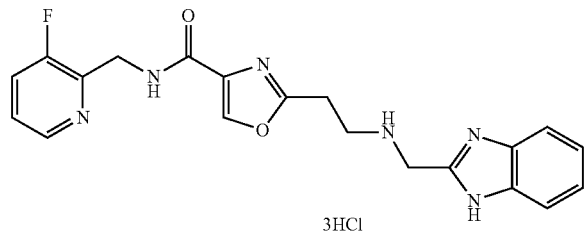 [SMILES: O=C(NCc1ncccc1F)c1coc(CCNCc2nc3ccccc3[nH]2)n1]

In a similar fashion using general procedure 3, 2-(2-aminoethyl)-N-[(3-fluoropyridin-2-yl)methyl]-1,3-oxazole-4-carboxamide dihydrochloride (235) (100 mg, 0.3 mmol), 1H-benzimidazole-2-carbaldehyde (43.3 mg, 0.3 mmol), DIPEA (0.207 ml, 1.19 mmol) and anhydrous MgSO₄ (200 mg) in DCM (10 ml) at room temperature for 16 h, followed by addition of NaBH₄ (17 mg, 0.45 mmol) afforded the free base compound after purification by basic prep-HPLC. The residue was re-dissolved in MeOH (5 ml) and treated with 12M HCl (1 ml) for 30 min to give the title compound (64 mg, 42%) a; a white hygroscopic solid.

1H-NMR (Methanol-d4, 500 MHz): d[ppm]=8.57 (dd, J=5.4, 0.9 Hz, 1H), 8.46 (s, 1H), 8.26-8.19 (m, 1H), 7.88 (ddt, J=13.4, 8.9, 4.1 Hz, 3H), 7.68 (td, J=6.3, 5.5, 2.1 Hz, 2H), 5.02 (s, 2H), 4.94 (s, 2H), 3.83 (t, J=6.3 Hz, 2H), 3.47 (t, J=6.3 Hz, 2H)

HPLCMS (Method C): [m/z]: 395.2 [M+H]⁺

2-{2-[(1H-1,3-Benzodiazol-2-ylmethyl)amino]ethyl}-N-(pyridine-2-ylmethyl)-1,3-oxazole-4-carboxamide (Example Compound No. 137)

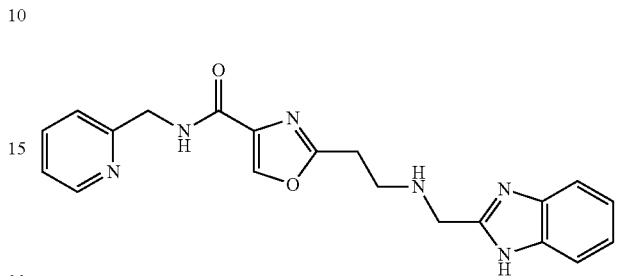

In a similar fashion using general procedure 3, 2-(2-aminoethyl)-N-(pyridine-2-ylmethyl)-1,3-oxazole-4-carboxamide dihydrochloride (236) (430 mg, 1.31 mmol), 1H-benzimidazole-2-carbaldehyde (229 mg, 1.57 mmol) and DIPEA (0.91 ml, 5.23 mmol) in MeOH (20 ml) at room temperature for 17 h, followed by addition of NaBH₄ (74 mg, 1.96 mmol) afforded the title compound (380 mg, 77%) as a yellow solid after purification by flash chromatography using a gradient elution of 0-20% MeOH/DCM.

1H-NMR (DMSO-d6, 500 MHz): d[ppm]=12.17 (s, 1H), 8.72 (t, J=5.9 Hz, 1H), 8.53-8.46 (m, 2H), 7.74 (td, J=7.7, 1.7 Hz, 1H), 7.48 (m, 2H), 7.31-7.22 (m, 2H), 7.12 (m, 2H), 4.52 (d, J=6.0 Hz, 2H), 3.95 (s, 2H), 3.03-2.93 (m, 4H)

HPLCMS (Method C): [m/z]: 377.2 [M+H]⁺

2-{2-[(1H-1,3-Benzodiazol-2-ylmethyl)amino]ethyl}-N-[(3-chloropyridin-2-yl)methyl]-1,3-oxazole-4-carboxamide (Example Compound No. 141)

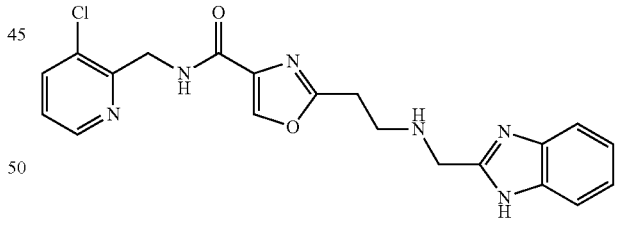

In a similar fashion using general procedure 3, 2-(2-aminoethyl)-N-[(3-chloropyridin-2-yl)methyl]-1,3-oxazole-4-carboxamide dihydrochloride (237) (118 mg, 0.31 mmol), 1H-benzimidazole-2-carbaldehyde (54 mg, 0.37 mmol) and DIPEA (0.216 ml, 1.24 mmol) in MeOH (4 ml) at room temperature for 24 h, followed by addition of NaBH₄ (18 mg, 0.46 mmol) gave the title compound (51 mg, 40%) as a brown solid after purification by basic prep-HPLC.

1H-NMR (Methanol-d4, 500 MHz): d[ppm]=8.41 (dd, J=4.8, 1.4 Hz, 1H), 8.29 (s, 1H), 7.86 (dd, J=8.1, 1.4 Hz, 1H), 7.53-7.49 (m, 2H), 7.34-7.30 (m, 1H), 7.21-7.18 (m, 2H), 4.76 (s, 2H), 4.08 (s, 2H), 3.14- 3.09 (m, 2H), 3.07-3.03 (m, 2H)

HPLCMS (Method D): [m/z]: 411.2 [M+H]⁺

2-(2-{[2-(4,5-Difluoro-1H-1,3-benzodiazol-2-yl)ethyl]amino}ethyl)-N-[(3-fluoropyridin-2-yl)methyl]-1,3-oxazole-4-carboxamide (Example Compound No. 257)

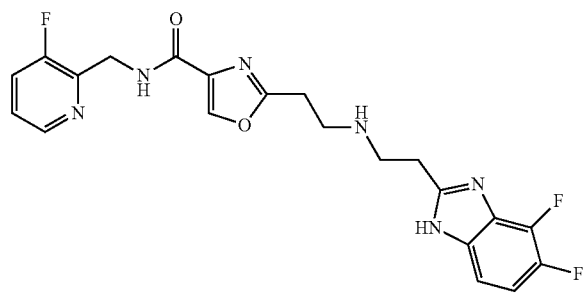 [SMILES: O=C(NCc1ncccc1F)c1coc(CCNCCc2nc3c(F)c(F)ccc3[nH]2)n1]

In a similar fashion to general procedure 8, 2-(2-aminoethyl)-N-[(3-fluoropyridin-2-yl)methyl]-1,3-oxazole-4-carboxamide dihydrochloride (235) (350 mg, 1.04 mmol), N-(2,3-difluoro-6-nitrophenyl)prop-2-enamide (K10) (250 mg, 1.10 mmol) and DBU (465 µl, 3.11 mmol) in MeCN (10 ml) gave an intermediate (193 mg) after purification by flash column chromatography (eluting with a gradient 0-20% MeOH/DCM). The intermediate was further reacted with iron powder (88 mg, 1.57 mmol) in AcOH (2 ml) to give the title compound (14 mg, 8%) as a pale yellow solid after purification by flash column chromatography (eluting with a gradient of 0-30% MeOH/DCM) followed by basic prep-HPLC.

1H-NMR (DMSO-d6, 500 MHz): d[ppm]=8.55-8.47 (m, 2H), 8.38 (d, J=4.6 Hz, 1H), 7.74-7.67 (m, 1H), 7.44-7.36 (m, 1H), 7.23 (dd, J=8.8, 3.6 Hz, 1H), 7.17-7.09 (m, 1H), 4.61 (d, J=4.8 Hz, 2H), 3.02-2.91 (m, 8H)

HPLCMS (Method G): [m/z]: 445.2 [M+H]$^+$

2-(2-{[2-(4-Chloro-1H-1,3-benzodiazol-2-yl)ethyl]amino}ethyl)-N-[(3-fluoropyridin-2-yl)methyl]-1,3-oxazole-4-carboxamide (Example Compound No. 226)

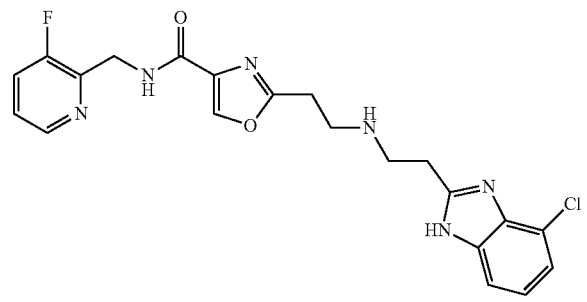 [SMILES: O=C(NCc1ncccc1F)c1coc(CCNCCc2nc3c(Cl)cccc3[nH]2)n1]

In a similar fashion to general procedure 8, 2-(2-aminoethyl)-N-[(3-fluoropyridin-2-yl)methyl]-1,3-oxazole-4-carboxamide dihydrochloride (235) (340 mg, 1.01 mmol), N-(3-chloro-2-nitrophenyl)prop-2-enamide (245 mg, 1.08 mmol) and DBU (147 µl, 0.98 mmol) in MeCN (10 ml) gave a crude intermediate which was further reacted with iron powder (81 mg, 1.45 mmol) in AcOH (4 ml) to give the title compound (31 mg, 19%) as a white solid after purification by basic prep-HPLC followed by flash column chromatography (eluting with a gradient of 0-40% MeOH/DCM).

1H-NMR (DMSO-d6, 500 MHz): d[ppm]=8.51 (m, 2H), 8.38 (dt, J=4.6, 1.2 Hz, 1H), 7.70 (ddd, J=10.0, 8.3, 1.2 Hz, 1H), 7.41 (m, 2H), 7.19 (dd, J=7.7, 0.8 Hz, 1H), 7.12 (t, J=7.7 Hz, 1H), 4.62 (dd, J=5.6, 1.3 Hz, 2H), 3.09-2.95 (m, 8H)

HPLCMS (Method C): [m/z]: 443.1 [M+H]$^+$

N-[(3-fluoropyridin-2-yl)methyl]-2-(2-{[2-(4-methoxy-1H-1,3-benzodiazol-2-yl)ethyl]amino}ethyl)-1,3-oxazole-4-carboxamide (Example Compound No. 227)

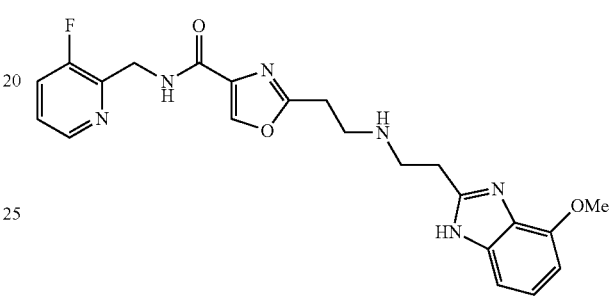

In a similar fashion to general procedure 8, 2-(2-aminoethyl)-N-[(3-fluoropyridin-2-yl)methyl]-1,3-oxazole-4-carboxamide dihydrochloride (235) (301 mg, 0.89 mmol), N-(2-methoxy-6-nitrophenyl)prop-2-enamide (I) (198 mg, 0.89 mmol) and DBU (0.4 ml, 2.68 mmol) in MeCN (10 ml) gave a crude intermediate which was partially purified by flash column chromatography using a gradient elution of 0-10% MeOH in DCM. The intermediate was further reacted with iron powder (86 mg) in AcOH (3 ml) to give the title compound (2 mg, 1%) as a white solid after purification by basic prep-HPLC followed by flash column chromatography (eluting with a gradient of 0-20% MeOH/DCM).

1H-NMR (MeOD, 500 MHz): d[ppm]=8.30 (d, J=4.7 Hz, 1H), 8.26 (s, 1H), 7.60-7.54 (m, 1H), 7.39-7.32 (m, 1H), 7.09 (t, J=8.0 Hz, 1H), 7.03 (d, 1H), 6.70 (d, J=7.8 Hz, 1H), 4.65 (d, J=1.4 Hz, 2H), 3.93 (s, 3H), 3.22-3.16 (m, 4H), 3.14-3.05 (m, 4H)

HPLCMS (Method G): [m/z]: 439.2 [M+H]$^+$

2-(2-{[2-(4-Fluoro-1H-1,3-benzodiazol-2-yl)ethyl]amino}ethyl)-N-[(3-fluoropyridin-2-yl)methyl]-1,3-oxazole-4-carboxamide (Example Compound No. 228)

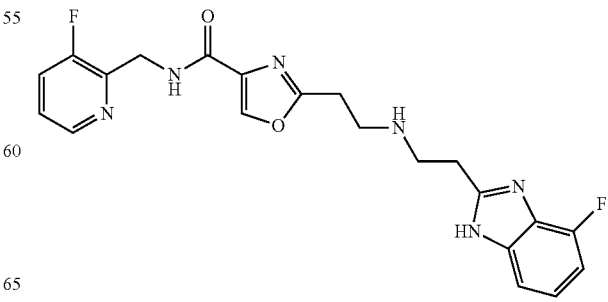

In a similar fashion to general procedure 8, 2-(2-aminoethyl)-N-[(3-fluoropyridin-2-yl)methyl]-1,3-oxazole-4-carboxamide dihydrochloride (235) (200 mg, 0.59 mmol), N-(3-fluoro-2-nitrophenyl)prop-2-enamide (G) (198 mg, 0.89 mmol) and DBU (266 µl, 1.78 mmol) in MeCN (10 ml) gave an intermediate which was partially purified by flash column chromatography with a gradient elution of 0-10% MeOH in DCM. The intermediate was further reacted with iron powder (114 mg) in AcOH (2 ml) to afford the title compound (10 mg, 5%) as an off-white solid after purification by basic prep-HPLC followed by flash column chromatography (eluting with a gradient of 0-30% MeOH/DCM) and kp-NH flash chromatography (eluting with a gradient of 0-4% MeOH/DCM).

1H-NMR (DMSO-d6, 500 MHz): d[ppm]=8.53-8.45 (m, 2H), 8.39-8.35 (m, 1H), 7.72-7.67 (m, 1H), 7.42-7.37 (m, 1H), 7.26 (d, J=8.0 Hz, 1H), 7.11-7.05 (m, 1H), 6.93-6.88 (m, 1H), 4.61 (d, J=4.4 Hz, 2H), 3.01-2.91 (m, 8H)

HPLCMS (Method G): [m/z]: 427.1 [M+H]+

2-(2-{[2-(7-Chloro-4-fluoro-1H-1,3-benzodiazol-2-yl)ethyl]amino}ethyl)-N-[(3-fluoropyridin-2-yl)methyl]-1,3-oxazole-4-carboxamide (Example Compound No. 247)

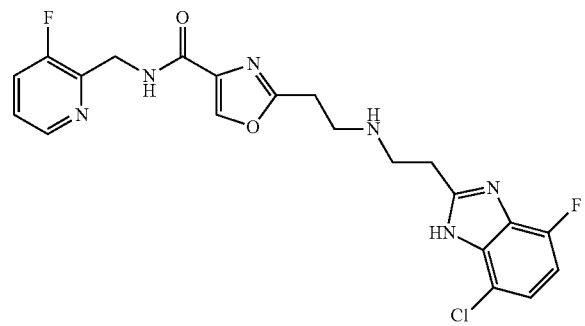 [SMILES: O=C(NCc1ncccc1F)c1coc(CCNCCc2nc3c(F)ccc(F)c3[nH]2)n1]

In a similar fashion to general procedure 8, 2-(2-aminoethyl)-N-[(3-fluoropyridin-2-yl)methyl]-1,3-oxazole-4-carboxamide dihydrochloride (235) (300 mg, 0.89 mmol), N-(6-chloro-3-fluoro-2-nitrophenyl)prop-2-enamide (K2) (272 mg, 0.89 mmol) and DBU (0.398 ml, 2.67 mmol) in MeCN (15 ml) gave a crude intermediate which was purified by flash column chromatography using an elution gradiant 0-15% MeOH in DCM. The intermediated was further reacted with iron powder (145 mg) in AcOH (3 ml) to give the title compound (7 mg, 2%) as a beige solid after purification by flash column chromatography (eluting with a gradient of 0-35% MeOH/DCM) followed by kp-NH column chromatography (eluting with a gradient of 0-15% MeOH/DCM) and basic prep-HPLC.

1H-NMR (MeOD, 500 MHz): d[ppm]=8.34 (d, J=4.7 Hz, 1H), 8.27 (s, 1H), 7.63-7.56 (m, 1H), 7.42-7.36 (m, 1H), 7.16 (dd, J=8.6, 3.9 Hz, 1H), 6.93 (dd, J=10.2, 8.6 Hz, 1H), 4.71 (d, J=1.6 Hz, 2H), 3.16-3.11 (m, 6H), 3.07-3.03 (m, 2H)

HPLCMS (Method D): [m/z]: 461.1 [M+H]+

2-(2-{[2-(4,6-Difluoro-1H-1,3-benzodiazol-2-yl)ethyl]amino}ethyl)-N-[(3-fluoropyridin-2-yl)methyl]-1,3-oxazole-4-carboxamide (Example Compound No. 249)

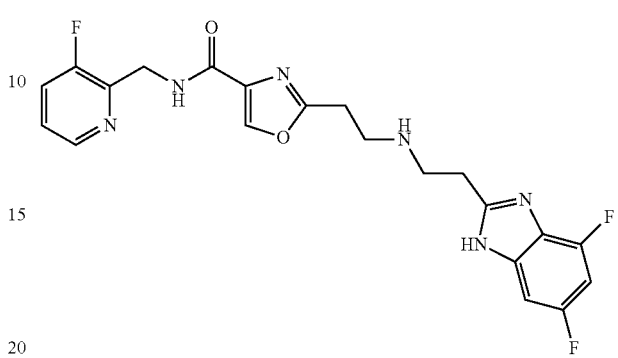

In a similar fashion to general procedure 8, 2-(2-aminoethyl)-N-[(3-fluoropyridin-2-yl)methyl]-1,3-oxazole-4-carboxamide dihydrochloride (235) (500 mg, 1.48 mmol), N-(2,4-difluoro-6-nitrophenyl)prop-2-enamide (K4) (338 mg, 1.48 mmol) and DBU (0.664 ml, 4.45 mmol) in MeCN (15 ml) gave a crude intermediate which was partially purified by flash column chromatography using a gradient of 0-20% MeOH in DCM. The intermediate was further reacted with iron powder (145 mg) in AcOH (4 ml) to give the title compound (23 mg, 8%) as an off-white solid after purification by flash column chromatography (eluting with a gradient of 0-40% MeOH/DCM) followed by kp-NH flash chromatography (eluting with a gradient of 0-5% MeOH/DCM).

1H-NMR (DMSO-d6, 500 MHz): d[ppm]=8.53-8.46 (m, 2H), 8.41-8.36 (m, 1H), 7.73-7.67 (m, 1H), 7.43-7.37 (m, 1H), 7.14 (dd, J=8.9, 2.2 Hz, 1H), 6.96 (td, J=10.7, 2.2 Hz, 1H), 4.62 (dd, J=5.7, 1.4 Hz, 2H), 3.02-2.90 (m, 8H)

HPLCMS (Method G): [m/z]: 445.2 [M+H]+

2-(2-{[2-(5-fluoro-1H-1,3-benzodiazol-2-yl)ethyl]amino}ethyl)-N-[(3-fluoropyridin-2-yl)methyl]-1,3-oxazole-4-carboxamide (Example Compound No. 250)

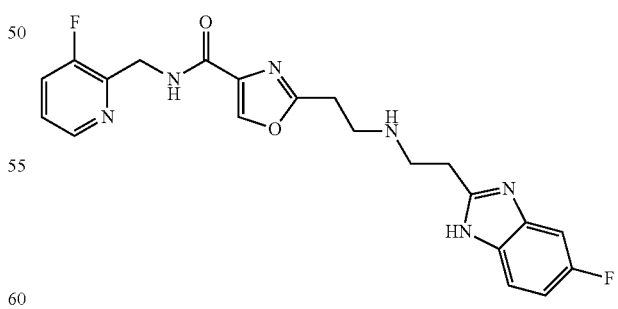

In a similar fashion to general procedure 8, 2-(2-aminoethyl)-N-[(3-fluoropyridin-2-yl)methyl]-1,3-oxazole-4-carboxamide dihydrochloride (235) (1.07 g, 2.59 mmol, 82% purity), N-(5-fluoro-2-nitrophenyl)prop-2-enamide (J) (0.54 g, 2.59 mmol) and DBU (1.28 ml, 8.54 mmol) in MeCN (30 ml) at room temperature for 20 h gave a crude mixture of mono:bis-alkylated (1:1.4) adducts (1.1 g) which was further reacted with iron powder (0.52 g) in AcOH (8 ml) to give the title compound (90 mg, 9%) as a brown solid after purification by flash column chromatography (eluting with a gradient of 0-30% MeOH/DCM), followed by kp-NH flash column chromatography (eluting with a gradient of 0-2% MeOH/DCM), then by flash column chromatography (eluting with a gradient of 0-20% MeOH/DCM) and basic prep-HPLC.

1H-NMR (DMSO-d6, 500 MHz): d[ppm]=8.52-8.47 (m, 2H), 8.39-8.36 (m, 1H), 7.72-7.66 (m, 1H), 7.46-7.36 (m, 2H), 7.24 (dd, J=9.6, 2.3 Hz, 1H), 6.99-6.89 (m, 1H), 4.61 (dd, J=5.7, 1.3 Hz, 2H), 3.02-2.89 (m, 8H)

HPLCMS (Method C): [m/z]: 427.2 [M+H]$^+$

2-(2-{[2-(4,7-Difluoro-1H-1,3-benzodiazol-2-yl)ethyl]amino}ethyl)-N-[(3-fluoropyridin-2-yl)methyl]-1,3-oxazole-4-carboxamide (Example Compound No. 251)

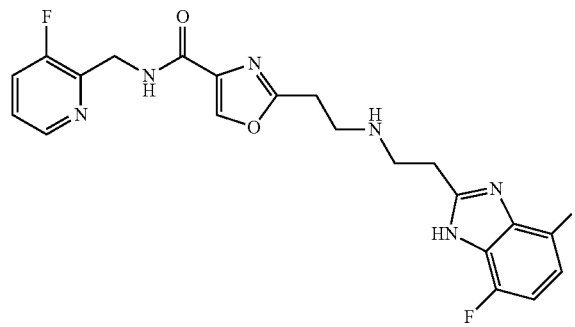

In a similar fashion to general procedure 8, 2-(2-aminoethyl)-N-[(3-fluoropyridin-2-yl)methyl]-1,3-oxazole-4-carboxamide dihydrochloride (235) (400 mg, 1.19 mmol), N-(3,6-difluoro-2-nitrophenyl)prop-2-enamide (K6) (316 mg, 1.20 mmol) and DBU (0.53 ml, 3.56 mmol) in MeCN (15 ml) gave a crude intermediate which was partially purified by flash column chromatography using a gradient elution of 0.20% MeOH in DCM. This intermediate was further reacted with iron powder (230 mg) in AcOH (4 ml) to give the title compound (63 mg, 14%) as an off-white solid after purification by flash column chromatography (eluting with a gradient of 0-40% MeOH/DCM) followed by kp-NH flash chromatography (eluting with a gradient of 0-5% MeOH/DCM).

1H-NMR (DMSO-d6, 500 MHz): d[ppm]=8.52-8.46 (m, 2H), 8.38 (m, 1H), 7.74-7.66 (m, 1H), 7.44-7.37 (m, 1H), 6.95-6.91 (m, 2H), 4.62 (dd, J=5.6, 1.4 Hz, 2H), 3.03-2.90 (m, 8H).

HPLCMS (Method G): [m/z]: 445.2 [M+H]$^+$

N-[(3-fluoropyridin-2-yl)methyl]-2-[2-({2-[4-(trifluoromethyl)-1H-1,3-benzodiazol-2-yl]ethyl}amino)ethyl]-1,3-oxazole-4-carboxamide (Example Compound No. 256)

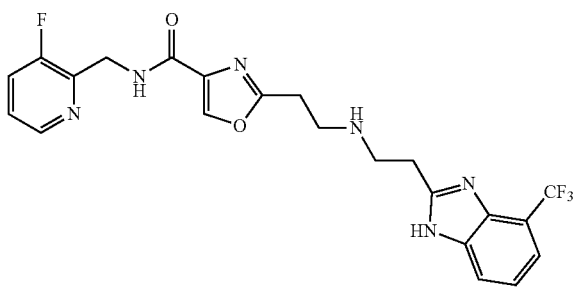 [SMILES: O=C(NCc1ncccc1F)c1coc(CCNCCc2nc3c(C(F)(F)F)cccc3[nH]2)n1]

In a similar fashion to general procedure 8, 2-(2-aminoethyl)-N-[(3-fluoropyridin-2-yl)methyl]-1,3-oxazole-4-carboxamide dihydrochloride (235) (300 mg, 0.89 mmol), N-[2-nitro-6-(trifluoromethyl)phenyl]prop-2-enamide (K8) (272 mg, 0.90 mmol) and DBU (398 µl, 2.67 mmol) in MeCN (10 ml) gave a crude intermediate which was partially purified by flash column chromatography using a gradient of 0-10% MeOH in DCM. The intermediate was further reacted with iron powder (177 mg) in AcOH (3 ml) to give the title compound (99 mg, 26%) as a yellow solid after purification by flash column chromatography (eluting with a gradient of 0-25% MeOH/DCM) followed by kp-NH flash chromatography (eluting with a gradient of 0-6% MeOH/DCM).

1H-NMR (DMSO-d6, 500 MHz): d[ppm]=8.53-8.47 (m, 2H), 8.40-8.37 (m, 1H), 7.75 (d, J=8.0 Hz, 1H), 7.73-7.67 (m, 1H), 7.45 (d, J=7.6 Hz, 1H), 7.43-7.38 (m, 1H), 7.28 (t, J=7.8 Hz, 1H), 4.62 (d, J=4.7 Hz, 2H), 3.01 (s, 4H), 3.00-2.93 (m, 4H)

HPLCMS (Method G): [m/z]: 477.4 [M+H]$^+$

2-(2-{[2-(4-fluoro-1H-1,3-benzodiazol-2-yl)ethyl]amino}ethyl)-N-(pyridin-2-ylmethyl)-1,3-oxazole-4-carboxamide (Example Compound No. 236)

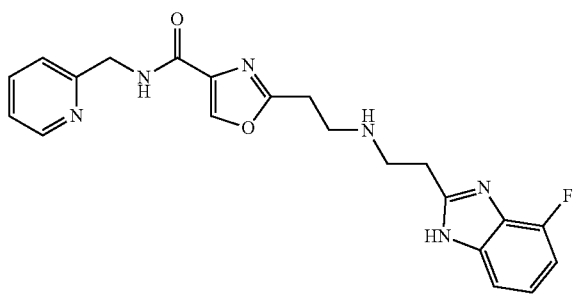 [SMILES: O=C(NCc1ccccn1)c1coc(CCNCCc2nc3c(F)cccc3[nH]2)n1]

In a similar fashion to general procedure 8, 2-(2-aminoethyl)-N-(pyridin-2-ylmethyl)-1,3-oxazole-4-carboxamide dihydrochloride (236) (350 mg, 0.95 mmol), N-(3-fluoro-2-nitrophenyl)prop-2-enamide (G) (206 mg, 0.95 mmol), DBU (1.0 ml, 2.85 mmol) in MeCN (15 ml) gave a crude mixture which was partially purified by flash column chromatography (eluting with a gradient of 0-15% MeOH/DCM). The mixture was further reacted with iron powder (136 mg) in AcOH (4 ml) to afford the title compound (9 mg, 4%) as a pale brown solid after purification by flash column chromatography (eluting with a gradient of 0-40% MeOH/DCM), kp-NH flash column chromatography (eluting with a gradient of 0-10% MeOH/DCM) and basic prep-HPLC.

1H-NMR (MeOD, 500 MHz): d[ppm]=8.52-8.47 (m, 1H), 8.28 (s, 1H), 7.80 (td, J=7.7, 1.8 Hz, 1H), 7.39 (d, J=7.9 Hz, 1H), 7.34-7.30 (m, 1H), 7.28 (d, J=8.0 Hz, 1H), 7.19-7.10 (m, 1H), 6.96-6.88 (m, 1H), 4.65 (s, 2H), 3.17-3.08 (m, 6H), 3.08-3.02 (m, 2H)

HPLCMS (Method D): [m/z]: 409.1 [M+H]+

Methyl 2-(3-{[(tert-butoxy)carbonyl]amino}propanamido)-3-hydroxybutanoate (315)

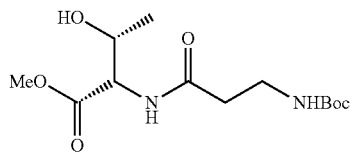

In a similar fashion to general procedure 13, methyl L-threoninate hydrochloride (1:1) (11 g, 64.9 mmol), N-(tert-butoxycarbonyl)-beta-alanine (12.3 g, 64.9 mmol), TEA (9.94 ml, 71.3 mmol) and DCC (14.7 g, 71.3 mmol) in DCM (250 ml) afforded the title compound (16.4 g, 72.4%, 87% purity) as a viscous yellow oil after purification by flash column chromatography (eluting with a gradient of 0-100% EtOAc/heptane).

1H-NMR (CDCl3, 500 MHz): d[ppm]=6.35 (s, 1H), 5.12 (s, 1H), 4.59 (dd, J=8.8, 2.5 Hz, 1H), 4.36 (qd, J=6.4, 2.5 Hz, 1H), 3.78 (s, 3H), 3.45 (q, J=5.9 Hz, 2H), 2.57-2.46 (m, 2H), 1.43 (s, 9H), 1.23 (d, J=6.4 Hz, 3H)

HPLCMS (Method A): [m/z]: 291.05 [M+H]+

Methyl 2-(2-{[(tert-butoxy)carbonyl]amino}ethyl)-5-methyl-4,5-dihydro-1,3-oxazole-4-carboxylate (316)

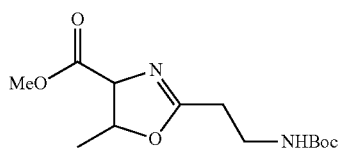 [SMILES: COC(=O)C1N=C(CCNC(=O)OC(C)(C)C)OC1C]

In a similar fashion to general procedure 14, methyl 2-(3-{[(tert-butoxy)carbonyl]amino}propanamido)-3-hydroxybutanoate (315) (1 g, 2.87 mmol, 87% purity), DAST (0.45 ml, 3.44 mmol) and K2CO3 (0.79 g, 5.73 mmol) in anhydrous DCM (25 ml) gave the title compound (0.61 g, 67%) as a pale yellow oil after purification by flash column chromatography (eluting with a gradient of 0-100% EtOAc/heptane).

1H-NMR (CDCl3, 250 MHz): d[ppm]=5.22 (br s, 1H), 4.87 (dq, J=9.9, 6.3 Hz, 1H), 4.76 (dt, J=10.1, 1.2 Hz, 1H), 3.76 (s, 3H), 3.52-3.37 (m, 2H), 2.53-2.44 (m, 2H), 1.44 (s, 9H), 1.29 (d, J=6.3 Hz, 3H)

Methyl 2-(2-{[(tert-butoxy)carbonyl]amino}ethyl)-5-methyl-1,3-oxazole-4-carboxylate (317)

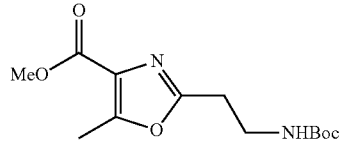

In a similar fashion to general procedure 15, methyl 2-(2-{[(tert-butoxy)carbonyl]amino}ethyl)-5-methyl-4,5-dihydro-1,3-oxazole-4-carboxylate (316) (0.61 g, 1.98 mmol), bromo(trichloro)methane (0.59 ml, 5.95 mmol) and DBU (0.89 ml, 5.95 mmol) in DCM (15 ml) gave the title compound (0.42 g, 71%) as a dark orange oil which solidified on standing after purification by flash column chromatography (eluting with a gradient of 0-100% EtOAc/heptane).

1H-NMR (CDCl3, 250 MHz): d[ppm]=4.94 (s, 1H), 3.90 (s, 3H), 3.55 (q, J=6.2 Hz, 2H), 2.93 (t, J=6.3 Hz, 2H), 2.59 (s, 3H), 1.42 (s, 9H)

HPLCMS (Method A): [m/z]: 284.95 [M+H]+

2-(2-{[(Tert-butoxy)carbonyl]amino}ethyl)-5-methyl-1,3-oxazole-4-carboxylic Acid (318)

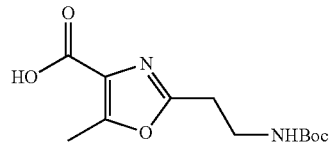

In a similar fashion to general procedure 5, methyl 2-(2-{[(tert-butoxy)carbonyl]amino}ethyl)-5-methyl-1,3-oxazole-4-carboxylate (317) (0.42 g, 1.42 mmol), LiOH (0.067 g, 2.84 mmol) in THF (8 ml) and water (2 ml) gave the title compound (0.4 g, 98%) as a pale orange oil which solidified on standing.

1H-NMR (DMSO-d6, 250 MHz): d[ppm]=12.72 (s, 1H), 6.90 (t, J=5.5 Hz, 1H), 3.25 (d, J=6.2 Hz, 2H), 2.79 (t, J=6.9 Hz, 2H), 1.34 (s, 9H) [CH3 peak obscured by DMSO peak]

HPLCMS (Method A): [m/z]: 293.00 [M+Na]+

Tert-butyl N-[2-(4-{[(3-fluoropyridin-2-yl)methyl]carbamoyl}-5-methyl-1,3-oxazol-2-yl)ethyl]carbamate (319)

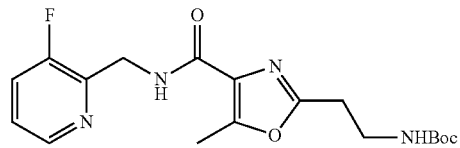 [SMILES: Cc1oc(CCNC(=O)OC(C)(C)C)nc1C(=O)NCc1ncccc1F]

In a similar fashion to general procedure 6, 2-(2-{[(tert-butoxy)carbonyl]amino}ethyl)-5-methyl-1,3-oxazole-4-carboxylic acid (318) (0.4 g, 1.39 mmol), (3-fluoropyridin-2-yl)methanamine dihydrochloride (A2) (0.415 g, 2.09 mmol), DIPEA (0.8 ml, 4.59 mmol) and HATU (0.79 g, 2.09 mmol)

in DMF (6 ml) gave the title compound (0.653 g, 79%, 64% purity) as a yellow oil after purification by flash column chromatography (eluting with a gradient of 0-100% EtOAc/heptane).

1H-NMR (DMSO-d6, 250 MHz): d[ppm]=8.44-8.30 (m, 2H), 7.75-7.64 (m, 1H), 7.46-7.34 (m, 1H), 6.97 (br s, 1H), 4.60 (d, J=4.2 Hz, 2H), 3.34-3.24 (m, 2H), 2.83 (t, J=6.8 Hz, 2H), 1.35 (s, 9H)

HPLCMS (Method A): [m/z]: 379.05 [M+H]$^+$

2-(2-Aminoethyl)-N-[(3-fluoropyridin-2-yl)methyl]-5-methyl-1,3-oxazole-4-carboxamide Dihydrochloride (320)

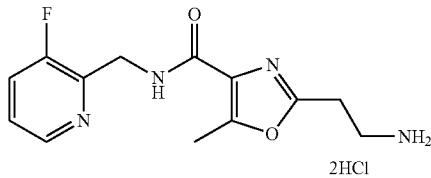 [SMILES: Cc1oc(CCN)nc1C(=O)NCc1ncccc1F]

In a similar fashion to general procedure 2, tert-butyl N-[2-(4-{[(3-fluoropyridin-2-yl)methyl]carbamoyl}-5-methyl-1,3-oxazol-2-yl)ethyl]carbamate (319) (0.65 g, 1.10 mmol, 64% purity) and 12M HCl (1.16 ml, 11.04 mmol) in MeOH (10 ml) gave the title compound (0.51 g, 76% purity) as a hygroscopic off-white solid. The compound was used in the next step without further purification.

1H-NMR (MeOD, 250 MHz): d[ppm]=8.55 (dd, J=5.3, 1.0 Hz, 1H), 8.22-8.10 (m, 1H), 7.86-7.75 (m, 1H), 3.70 (dd, J=11.2, 7.3 Hz, 3H), 3.43 (t, J=6.5 Hz, 2H), 3.17 (t, J=6.5 Hz, 2H), 2.58 (s, 3H) [CH$_2$ peak obscured by the H$_2$O]

HPLCMS (Method A): [m/z]: 279.2 [M+H]$^+$

N-[(3-fluoropyridin-2-yl)methyl]-5-methyl-2-[2-({2-[(2-nitrophenyl)carbamoyl]ethyl}amino)ethyl]-1,3-oxazole-4-carboxamide (Example Compound No. 230)

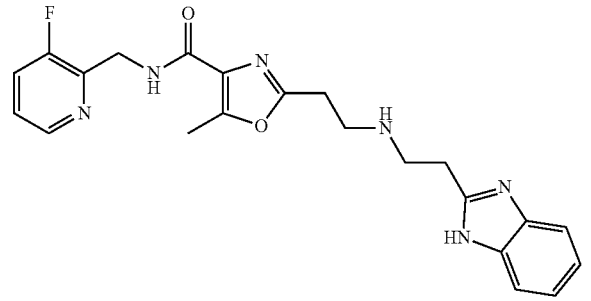 [SMILES: Cc1oc(CCNCCc2nc3ccccc3[nH]2)nc1C(=O)NCc1ncccc1F]

In a similar fashion to general procedure 8, 2-(2-aminoethyl)-N-[(3-fluoropyridin-2-yl)methyl]-5-methyl-1,3-oxazole-4-carboxamide dihydrochloride (320) (0.51 g, 1.11 mmol, 76% purity), N-(2-nitrophenyl)prop-2-enamide (D) (0.4 g, 2.09 mmol) and DBU (0.69 ml, 4.59 mmol) in MeCN (15 ml) at room temperature for 20 h gave a mixture of mono:bis-alkylated (1:3.6) adducts which was further reacted with iron powder (0.31 g) in AcOH (3.5 ml) to give the title compound (0.12 g, 20%) as a pale green solid after purification by flash column chromatography (eluting with a gradient of 0-30% MeOH/DCM), followed by flash column chromatography (KP—NH, eluting with a gradient of 0-5% MeOH/DCM) and a final purification by flash column chromatography (eluting with a slow gradient of 0-30% MeOH/DCM).

1H-NMR (MeOD, 250 MHz): d[ppm]=8.33-8.30 (d, J=4.7 Hz, 1H), 7.60-7.54 (m, 1H), 7.48-7.40 (m, 2H), 7.38-7.33 (m, 1H), 7.18-7.14 (m, 2H), 4.65 (d, J=1.6 Hz, 2H), 3.15-3.07 (m, 6H), 2.97 (t, J=6.6 Hz, 2H), 2.52 (s, 3H)

HPLCMS (Method C): [m/z]: 423.1 [M+H]$^+$

2-(2-{[2-(5-cyano-1H-1,3-benzodiazol-2-yl)ethyl]amino}ethyl)-N-[(3-fluoropyridin-2-yl)methyl]-1,3-oxazole-4-carboxamide (Example Compound No. 265)

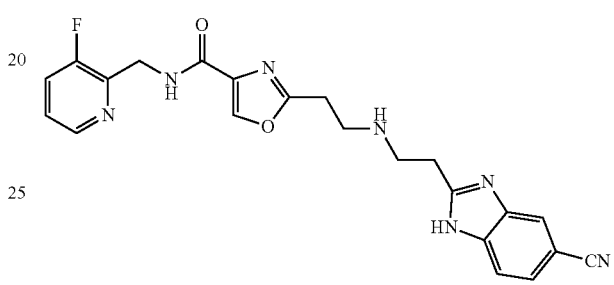

In a similar fashion to general procedure 8, 2-(2-aminoethyl)-N-[(3-fluoropyridin-2-yl)methyl]-1,3-oxazole-4-carboxamide dihydrochloride (235) (400 mg, 1.19 mmol) and N-(4-cyano-2-nitrophenyl)prop-2-enamide (K12) (325 mg, 1.49 mmol) and DBU (0.53 ml, 3.56 mmol) in MeCN (12 ml) gave a crude intermediate which was further reacted with iron powder (239 mg, 4.28 mmol) in AcOH (4 ml) to afford the title compound (24 mg, 5%) as a brown solid after purification by flash column chromatography (eluting with a gradient of 0-20% MeOH/DCM).

1H-NMR (DMSO-d6, 500 MHz): d[ppm]=8.51-8.46 (m, 2H), 8.39-8.36 (m, 1H), 8.01-7.95 (m, 1H), 7.72-7.67 (m, 1H), 7.63-7.59 (m, 1H), 7.50 (dd, J=8.3, 1.5 Hz, 1H), 7.42-7.38 (m, 1H), 4.63-4.59 (m, 2H), 3.02-2.91 (m, 8H)

HPLCMS (Method B): [m/z]: 434.2 [M+H]$^+$

General Scheme 13 Above:

Methyl 1-(cyanomethyl)-1H-1,2,4-triazole-3-carboxylate (239)

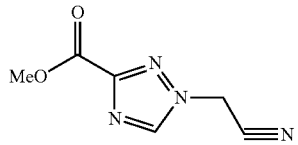

Methyl 1H-1,2,4-triazole-3-carboxylate (5 g, 39.34 mmol) and 2-bromoacetonitrile (2.7 ml, 39.34 mmol) in DMF (45 ml) were stirred for 5 min. K$_2$CO$_3$ (5.44 g, 39.34 mmol) was added and the reaction stirred at room temperature for 23 h. The solvent was evaporated under vacuum, water (20 ml) added and the aqueous layer extracted with EtOAc (8×50 ml). The combined organic layers were washed with 5% aqueous LiCl (2×20 ml), brine (2×20 ml), dried (MgSO4), filtered and evaporated to give a mixture of regioisomers (1.5:1) as a dark brown oil (5.27 g). The crude material was purified by flash column chromatography (eluting with a gradient of 10 to 100% EtOAc/heptane) to give the title compound (3.5 g, 45%) as a pale brown oil which solidified on standing.

1H-NMR (DMSO-d6, 250 MHz): d[ppm]=8.30 (s, 1H), 5.79 (s, 2H), 3.94 (s, 3H)

Methyl 1-(2-{[(tert-butoxy)carbonyl]amino}ethyl)-1H-1,2,4-triazole-3-carboxylate (240)

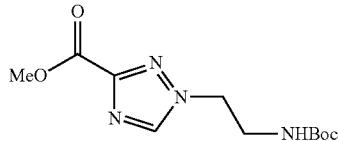

Methyl 1-(cyanomethyl)-1H-1,2,4-triazole-3-carboxylate (239) (1 g, 6.02 mmol), di-tert-butyl dicarbonate (2.63 g, 12.04 mmol) and TEA (1.7 ml, 12.04 mmol) in EtOH (30 ml) were stirred for 5 min before 10% palladium on carbon (128 mg, 0.602 mmol) was added. The reaction was stirred under a hydrogen atmosphere for 18 h. The reaction mixture was filtered through celite and the residue washed with EtOH (30 ml). The filtrate was evaporated to give a brown oil which began crystallising on standing (1.95 g). Purification by flash column chromatography (eluting with a gradient of 0 to 100% EtOAc/heptane) gave the title compound (1.35 g, 69.7%) as a pale brown solid.

1H-NMR (CDCl₃, 250 MHz): d[ppm]=8.13 (s, 1H), 4.69 (brs, 1H), 4.40 (t, J=5.6 Hz, 2H), 4.00 (s, 3H), 3.60 (app q, J=5.9 Hz, 2H), 1.42 (s, 9H)

HPLCMS (Method A): [m/z]: 271.1 [M+H]⁺

1-(2-{[(Tert-butoxy)carbonyl]amino}ethyl)-1H-1,2,4-triazole-3-carboxylic Acid (241)

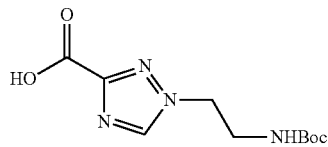

In a similar fashion using general procedure 5, LiOH (0.11 g, 4.72 mmol) and methyl 1-(2-{[(tert-butoxy)carbonyl]amino}ethyl)-1H-1,2,4-triazole-3-carboxylate (240) (0.87 g, 2.69 mmol) in THF (20 ml)/water (5 ml) gave the title compound (0.71 g, 100%) as a cream solid. The compound was used in the next step without further purification.

1H-NMR (DMSO-d6, 250 MHz): d[ppm]=8.54 (s, 1H), 6.97 (br s, 1H), 4.26 (t, J=5.9 Hz, 2H), 3.34 (app q, J=5.8 Hz, 2H) obscured by H₂O peak, 1.34 (s, 9H)

HPLCMS (Method A): [m/z]: 257.05 [M+H]⁺

Tert-butyl N-[2-(3-{[(3-fluoropyridin-2-yl)methyl]carbamoyl}-1H-1,2,4-triazol-1-yl)ethyl]carbamate (242)

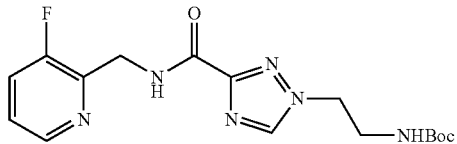

In a similar fashion using general procedure 6, 1-(2-{[(tert-butoxy)carbonyl]amino}ethyl)-1H-1,2,4-triazole-3-carboxylic acid (241) (0.5 g, 1.95 mmol), (3-fluoropyridin-2-yl)methanamine dihydrochloride (A2) (0.58 g, 2.93 mmol), DIPEA (1.7 ml, 9.76 mmol), HATU (1.11 g, 2.93 mmol) in DMF (10 ml) gave the title compound (0.55 g, 76%) as an off-white solid after purification by flash column chromatography (eluting with a gradient 0 to 10% MeOH/DCM) followed by a second flash column chromatography (eluting with a gradient 0 to 10% MeOH/EtOAc).

1H-NMR (DMSO-d6, 500 MHz): d[ppm]=8.74 (t, J=5.6 Hz, 1H), 8.57 (s, 1H), 8.39 (d, J=4.6 Hz, 1H), 7.78-7.63 (m, 1H), 7.42 (dt, J=8.6, 4.4 Hz, 1H), 7.00 (s, 1H), 4.64 (d, J=4.7 Hz, 2H), 4.28 (t, J=5.9 Hz, 2H), 3.36 (app q, J=5.9 Hz, 2H), 1.35 (s, 9H)

HPLCMS (Method A): [m/z]: 365.15 [M+H]⁺

Tert-butyl N-[2-(3-{[(3-chloropyridin-2-yl)methyl]carbamoyl}-1H-1,2,4-triazol-1-yl)ethyl]carbamate (243)

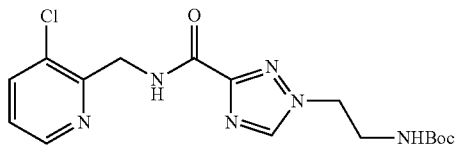

In a similar fashion using general procedure 6, 1-(2-{[(tert-butoxy)carbonyl]amino}ethyl)-1H-1,2,4-triazole-3-carboxylic acid (241) (0.58 g, 2.26 mmol), (3-chloropyridin-2-yl)methanamine dihydrochloride (0.732 g, 3.4 mmol), HATU (1.29 g, 3.4 mmol), DIPEA (1971 µl, 11.32 mmol) in DMF (11 ml) gave the title compound (0.87 g, 96%) as a brown foam after purification by flash column chromatography eluting with a gradient of 0 to 10% MeOH/DCM.

1H-NMR (DMSO-d6, 500 MHz): d[ppm]=8.73 (t, J=5.3 Hz, 1H), 8.57 (s, 1H), 8.52 (d, J=4.4 Hz, 1H), 7.96 (d, J=8.0 Hz, 1H), 7.39 (dd, J=8.0, 4.7 Hz, 1H), 7.00 (s, 1H), 4.67 (d, J=5.4 Hz, 2H), 4.28 (t, J=5.9 Hz, 2H), 3.36 (app q, J=6.1 Hz, 2H), 1.35 (s, 9H)

HPLCMS (Method A): [m/z]: 381.05 [M+H]⁺

1-(2-Aminoethyl)-N-[(3-fluoropyridin-2-yl)methyl]-1H-1,2,4-triazole-3-carboxamide dihydrochloride (244)

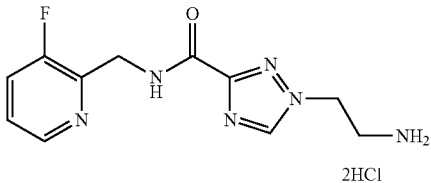

In a similar fashion using general procedure 2, 12 M HCl (2.48 ml) and tert-butyl N-[2-(3-{[(3-fluoropyridin-2-yl)methyl]carbamoyl}-1H-1,2,4-triazol-1-yl)ethyl]carbamate (242) (0.54 g, 1.49 mmol) in MeOH (10 ml) at 40° C. for 2 h gave the title compound (0.52 g, 100%) as an off-white foam. The compound was used in the next step without further purification.

1H-NMR (DMSO-d6, 250 MHz): d[ppm]=8.89 (t, J=5.6 Hz, 1H), 8.70 (s, 1H), 8.39 (d, J=4.7 Hz, 1H), 8.25 (s, 3H), 7.80-7.67 (m, 1H), 7.43 (dt, J=8.6, 4.5 Hz, 1H), 4.66 (d, J=4.4 Hz, 2H), 4.55 (t, J=5.9 Hz, 2H), 3.32 (q, J=5.6 Hz, 2H)

HPLCMS (Method A): [m/z]: 265.05 [M+H]$^+$

1-(2-Aminoethyl)-N-[(3-chloropyridin-2-yl)methyl]-1H-1,2,4-triazole-3-carboxamide Dihydrochloride (245)

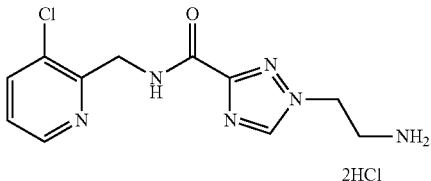

In a similar fashion using general procedure 2, 12 M HCl (3.6 ml) and tertbutyl N-[2-(3-{[(3-chloropyridin-2-yl)methyl]carbamoyl}-1H-1,2,4-triazol-1-yl)ethyl]carbamate (243) (0.87 g, 2.17 mmol) in MeOH (15 ml) at 40° C. for 3 h gave the title compound (0.84 g, 99%) as a pale orange foam.

1H-NMR (DMSO-d6, 250 MHz): d[ppm]=8.89 (t, J=5.5 Hz, 1H), 8.74 (s, 1H), 8.53 (dd, J=4.7, 1.3 Hz, 1H), 8.35 (s, 3H), 7.99 (dd, J=8.1, 1.4 Hz, 1H), 7.42 (dd, J=8.1, 4.7 Hz, 1H), 4.69 (d, J=5.5 Hz, 2H), 4.58 (t, J=5.9 Hz, 2H), 3.33 (q, J=5.8 Hz, 2H), 3.17 (s, 1H), 2.69 (s, 1H)

HPLCMS (Method A): [m/z]: 280.95 [M+H]$^+$

1-{2-[(1H-1,3-Benzodiazol-2-ylmethyl)amino]ethyl}-N-[(3-fluoropyridin-2-yl)methyl]-1H-1,2,4-triazole-3-carboxamide (Example Compound No. 169)

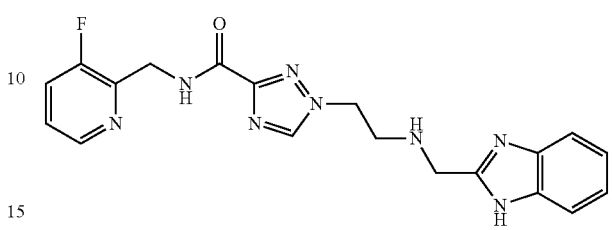

In a similar fashion using general procedure 3, 1H-1,3-Benzodiazole-2-carbaldehyde (104 mg, 0.71 mmol), 1-(2-aminoethyl)-N-[(3-fluoropyridin-2-yl)methyl]-1H-1,2,4-triazole-3-carboxamide dihydrochloride (244) (200 mg, 0.59 mmol) and DIPEA (0.41 ml, 2.37 mmol) in MeOH (8 ml) at room temperature for 17 h, followed by addition of NaBH$_4$ (32 mg, 0.86 mmol) gave the title compound (79 mg, 34%) as a beige solid after purification by basic prep-HPLC.

1H-NMR (DMSO-d6, 500 MHz): d[ppm]=12.16 (s, 1H), 8.76 (t, J=5.6 Hz, 1H), 8.65 (s, 1H), 8.38 (d, J=4.7 Hz, 1H), 7.70 (app t, J=9.3 Hz, 1H), 7.49 (br d, J=38.6 Hz, 2H), 7.40-7.43 (m, 1H), 7.12 (d, J=3.7 Hz, 2H), 4.64 (d, J=5.5 Hz, 2H), 4.34 (t, J=6.0 Hz, 2H), 3.92 (s, 2H), 3.02 (t, J=5.9 Hz, 2H)

HPLCMS (Method C): [m/z]: 395.2 [M+H]$^+$

1-(2-{[2-(1H-1,3-Benzodiazol-2-yl)ethyl]amino}ethyl)-N-[(3-fluoropyridin-2-yl)methyl]-1H-1,2,4-triazole-3-carboxamide (Example Compound No. 181)

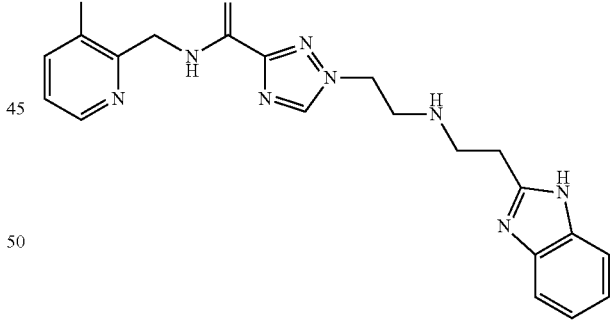

In a similar fashion using general procedure 8, DBU (0.39 ml, 2.58 mmol), 1-(2-aminoethyl)-N-[(3-fluoropyridin-2-yl)methyl]-1H-1,2,4-triazole-3-carboxamide dihydrochloride (244) (300 mg, 0.86 mmol) and N-(2-nitrophenyl)prop-2-enamide (D) (165 mg, 0.86 mmol) in MeCN (14 ml) at room temperature for 16 h, gave the crude intermediate (0.364 g) as a mixture of mono:bis-alkylated (2:1) adducts. The mixture was dissolved in AcOH (5 ml), iron (112 mg) was added and the reaction heated to 80° C. for 4 h to give the title compound (20 mg, 11%) as an off-white solid after purification by basic prep-HPLC followed by flash column chromatography (×2) (KP—NH, eluting with a gradient 0-30% MeOH/DCM and 5-20% MeOH/DCM).

1H-NMR (DMSO-d6, 500 MHz) d[ppm]=12.14 (s, 1H), 8.75 (t, J=5.6 Hz, 1H), 8.59 (s, 1H), 8.41-8.35 (m, 1H), 7.73-7.67 (m, 1H), 7.45 (br s, 2H), 7.43-7.38 (m, 1H), 7.13-7.07 (m, 2H), 4.64 (dd, J=5.6, 1.3 Hz, 2H), 4.31 (t, J=6.0 Hz, 2H), 2.99 (dt, J=12.3, 6.0 Hz, 4H), 2.94-2.89 (m, 2H)

HPLCMS (Method C): [m/z]: 409.3 [M+H]+

1-{2-[(1H-1,3-Benzodiazol-2-ylmethyl)amino]ethyl}-N-[(3-chloropyridin-2-yl)methyl]-1H-1,2,4-triazole-3-carboxamide (Example Compound No. 170)

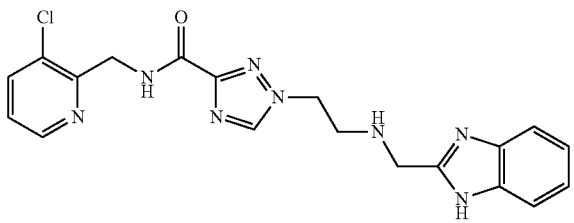

In a similar fashion using general procedure 3, 1H-1,3-Benzodiazole-2-carbaldehyde (156 mg, 1.07 mmol), 1-(2-aminoethyl)-N-[(3-chloropyridin-2-yl)methyl]-1H-1,2,4-triazole-3-carboxamide dihydrochloride (245) (350 mg, 0.89 mmol) and DIPEA (0.62 ml, 3.56 mmol) in MeOH (10 ml) at 40° C. for 2 h, followed by addition of NaBH4 (50.5 mg, 1.34 mmol) added gave the title compound (190 mg, 52%) as a cream solid after purification by basic prep-HPLC.

1H-NMR (DMSO-d6, 500 MHz): d[ppm]=12.16 (s, 1H), 8.75 (t, J=5.4 Hz, 1H), 8.66 (s, 1H), 8.51 (dd, J=4.7, 1.1 Hz, 1H), 7.95 (dd, J=8.1, 1.2 Hz, 1H), 7.49 (br d, J=37.6 Hz, 2H), 7.39 (dd, J=8.0, 4.7 Hz, 1H), 7.12 (s, 2H), 4.67 (d, J=5.4 Hz, 2H), 4.35 (t, J=6.0 Hz, 2H), 3.93 (s, 2H), 3.03 (t, J=5.9 Hz, 2H)

HPLCMS (Method C): [m/z]: 411.3 [M+H]+

General Scheme 14 Above

Methyl 1-(2-{[(tert-butoxy)carbonyl]amino}ethyl)-1H-pyrazole-4-carboxylate (246)

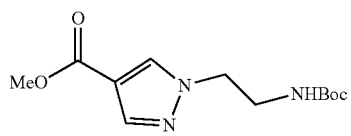 [SMILES: COC(=O)c1cnn(CCNC(=O)OC(C)(C)C)c1]

DIAD (9.39 ml, 43.61 mmol) was added dropwise to an ice-cooled solution of methyl 1H-pyrazole-4-carboxylate (5 g, 39.65 mmol), tert-butyl (2-hydroxyethyl)carbamate (6.13 ml, 39.65 mmol) and PPh3 (11.44 g, 43.61 mmol) in THF (300 ml). The reaction was then allowed to warm to room temperature and stirred for 1.5 h. The reaction mixture was quenched with water (150 ml) and the layers separated. The aqueous layer was extracted using EtOAc (3×150 ml). The combined organic layers were washed with brine, dried (MgSO4), filtered and the solvent evaporated to give the crude product. Purification by flash column chromatography (eluting with a gradient of 15-100% EtOAc/heptane) gave the title compound (11.3 g, 68%) as a white solid.

1H-NMR (CDCl3, 500 MHz): d[ppm]=7.93 (s, 1H), 7.87 (s, 1H), 4.25 (t, J=5.3 Hz, 2H), 3.83 (s, 3H), 3.61-3.54 (m, 2H), 1.44 (s, 9H)

HPLCMS (Method A): [m/z]: 270.1 [M+H]+

Ethyl 1-(cyanomethyl)-3,5-dimethyl-1H-pyrazole-4-carboxylate (247)

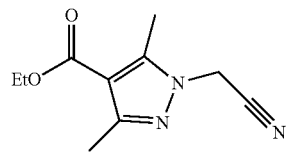

A mixture of ethyl 3,5-dimethyl-1H-pyrazole-4-carboxylate (2 g, 11.89 mmol), bromoacetonitrile (1.24 ml, 17.84 mmol), K2CO3 (3.29 g, 23.78 mmol) and acetone (6 ml) was heated at 100° C. under microwave irradiation for 1 h. Further bromoacetonitrile (0.828 ml, 11.89 mmol) was added and the mixture was heated at 100° C. under microwave irradiation for a further 1 h. The reaction mixture was concentrated in vacuo, the residue was taken up in water (100 ml) and extracted with EtOAc (5×50 ml). The combined organic extracts were dried (MgSO4), filtered and evaporated in vacuo. Purification by flash column chromatography using an elution gradient 0-20% MeOH/DCM afforded the title compound (2.22 g, 71%) as an orange solid.

1H-NMR (DMSO-d6, 500 MHz): d[ppm]=5.42 (s, 2H), 4.21 (q, J=7.1 Hz, 2H), 2.50 (s, 3H), 2.30 (s, 3H), 1.28 (t, J=7.1 Hz, 3H)

HPLCMS (Method A): [m/z]: 207.95 [M+H]+

Ethyl 1-(2-{[(tert-butoxy)carbonyl]amino}ethyl)-3,5-dimethyl-1H-pyrazole-4-carboxylate (248)

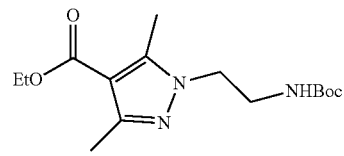

A suspension of ethyl 1-(cyanomethyl)-3,5-dimethyl-1H-pyrazole-4-carboxylate (247) (2.22 g, 9.64 mmol), BOC anhydride (4.21 g, 19.27 mmol), TEA (2.69 ml, 19.27 mmol) aid palladium on carbon (10% wt, 0.103 g, 0.964 mmol) in EtOH (100 ml) was stirred under an atmosphere of hydrogen for 28 h. The reaction mixture was filtered and the residue rinsed with MeOH. The combined filtrates were evaporated in vacuo and the residue partitioned between water (100 ml) and EtOAc (50 ml). The phases were separated and the aqueous phase extracted with EtOAc (3×50 ml). The combined organic layers were dried (MgSO4), filtered and evaporated in vacuo. Purification by flash column chromatography using an elution gradient 70-100% EtOAc/heptane afforded the title compound (1.52 g, 51%) as a yellow-brown solid.

1H-NMR (DMSO-d6, 500 MHz): d[ppm]=6.90 (s, 1H), 4.18 (q, J=7.1 Hz, 2H), 4.02 (t, J=6.1 Hz, 2H), 3.21 (q, J=6.1 Hz, 2H), 2.42 (s, 3H), 2.27 (s, 3H), 1.38-1.28 (s, 9H), 1.26 (t, J=7.1 Hz, 3H)

HPLCMS (Method A): [m/z]: 312.45 [M+H]+

Ethyl 1-(2-{[(tert-butoxy)carbonyl]amino}ethyl)-3-(trifluoromethyl)-1H-pyrazole-4-carboxylate (248)

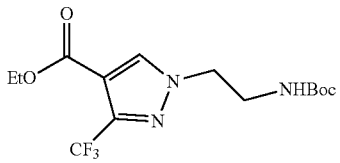

A solution of ethyl 3-(trifluoromethyl)-1H-pyrazole-4-carboxylate (3 g, 14.41 mmol), tert-butyl (2-hydroxyethyl) carbamate (2.45 ml, 15.85 mmol) and PPh$_3$ (4.16 g, 15.85 mmol) in THF (50 ml) was stirred at room temperature for 16 h. Additional (2-hydroxyethyl)carbamate (2.45 ml, 15.85 mmol) was added aid the reaction stirred at room temperature for a further 48 h. The reaction was quenched with water (30 ml) and extracted into EtOAc (3×50 ml). The combined organic layers were washed with brine (30 ml), dried (MgSO$_4$), filtered and evaporated gave a yellow oil. Purification by flash column chromatography (eluting with a gradient of 5-80% TBME/heptane) gave a residue which was re-purified by flash column chromatography (eluting with a gradient of 5-60% TBME/heptane) providing the title compound (1.19 g, 21%) as a white solid.

1H-NMR (CDCl$_3$, 500 MHz): d[ppm]=7.97 (s, 1H), 4.72 (br s, 1H), 4.32 (q, J=7.1 Hz, 2H), 4.32-4.27 (m, 2H), 3.59 (app q, J=5.9 Hz, 2H), 1.44 (s, 9H), 1.35 (t, J=7.1 Hz, 3H)
HPLCMS (Method A): [m/z]: 374 [M+Na]$^+$

1-(2-{[(Tert-butoxy)carbonyl]amino}ethyl)-1H-pyrazole-4-carboxylic Acid (249)

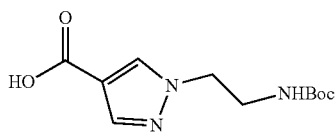 [SMILES: CC(C)(C)OC(=O)NCCn1cc(C(=O)O)cn1]

In a similar fashion to general procedure 5, LiOH (0.72 g, 30.08 mmol) and 1-(2-{[(tert-butoxy)carbonyl]amino}ethyl)-1H-pyrazole-4-carboxylate (246) (54%, 5 g, 10.03 mmol) in THF (80 ml) and water (30 ml) at room temperature for 24 h gave the title compound (2.6 g, 96.5%). Compound was used without purification.

1H-NMR (Methanol-d4, 500 MHz): d[ppm]=8.06 (s, 1H), 7.87 (s, 1H), 4.23 (t, J=5.8 Hz, 2H), 3.46 (app q, J=5.5 Hz, 2H), 1.42 (d, J=19.0 Hz, 9H)
HPLCMS (Method A): [m/z]: 255.95 [M+H]$^+$

1-(2-{[(Tert-butoxy)carbonyl]amino}ethyl)-3,5-dimethyl-1H-pyrazole-4-carboxylic Acid (250)

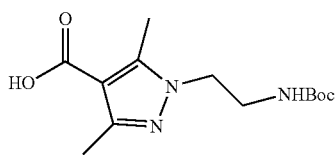 [SMILES: Cc1nn(CCNC(=O)OC(C)(C)C)c(C)c1C(=O)O]

In a similar fashion to general procedure 5, ethyl 1-(2-{[(tert-butoxy)carbonyl]amino}ethyl)-3,5-dimethyl-1H-pyrazole-4-carboxylate (247) (1 g, 2.58 mmol, 80% purity) and LiOH (0.37 g, 15.49 mmol) in THF (60 ml) and water (30 ml) at 70° C. afforded the title compound (0.417 g, 52%, 90% purity) as a yellow solid.

1H-NMR (DMSO-d6, 500 MHz): d[ppm]=12.02 (s, 1H), 6.91 (t, J=5.6 Hz, 1H), 4.00 (t, J=6.0 Hz, 2H), 3.21 (q, J=6.0 Hz, 2H), 2.40 (s, 3H), 2.26 (s, 3H), 1.37 (s, 9H)
HPLCMS (Method A): [m/z]: 284.05 [M+H]$^+$

1-(2-{[(Tert-butoxy)carbonyl]amino}ethyl)-3-(trifluoromethyl)-1H-pyrazole-4-carboxylic Acid (251)

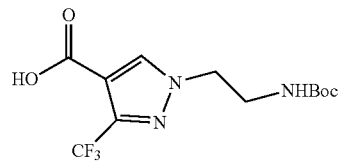

In a similar fashion to general procedure 5, LiOH (0.241 g, 10.08 mmol) and ethyl 1-(2-{[(tert-butoxy)carbonyl]amino}ethyl)-3-(trifluoromethyl)-1H-pyrazole-4-carboxylate (248) (89%, 1.18 g, 2.99 mmol) in THF/water (25 ml/8 ml) at room temperature for 16 h gave the title compound (0.54 g, 45%) as a white solid.

1H-NMR (CDCl$_3$, 250 MHz): d[ppm]=8.03 (s, 1H), 4.80 (br s, 1H), 4.36-4.18 (br m, 2H), 3.71-3.54 (m, 2H), 1.45 (s, 9H)
HPLCMS (Method A): [m/z]: 346.1 [M+Na]$^+$

Tert-butyl N-(2-{4-[(pyridin-2-ylmethyl)carbamoyl]-1H-pyrazol-1-yl}ethyl)carbamate (252)

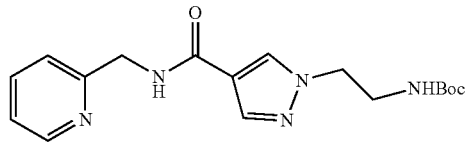 [SMILES: CC(C)(C)OC(=O)NCCn1cc(C(=O)NCc2ccccn2)cn1]

In a similar fashion using general procedure 6, 1-(2-{[(tert-butoxy)carbonyl]amino}ethyl)-1H-pyrazole-4-carboxylic acid (249) (0.50 g, 1.96 mmol), 1-(pyridin-2-yl)methanamine (0.30 ml, 2.94 mmol), DIPEA (1.0 ml, 5.88 mmol) and HATU (1.12 g, 2.94 mmol) in DCM (30 ml) gave the title compound (0.647 g, 56%, 59% purity) as a yellow oil after purification by flash column chromatography (eluting with a gradient of 3:2 EtOAc/heptane and 100% EtOAc). The compound was used in the next step without further purification.

1H-NMR (CDCl$_3$, 500 MHz): d[ppm]=8.56 (d, J=4.4 Hz, 1H), 7.87 (d, J=3.8 Hz, 2H), 7.68 (td, J=7.7, 1.8 Hz, 1H), 7.31 (d, J=7.8 Hz, 1H), 7.24-7.20 (m, 1H), 7.14 (s, 1H), 4.84 (s, 1H), 4.71 (d, J=4.8 Hz, 2H), 4.25 (t, J=5.4 Hz, 2H), 3.58 (q, J=5.4 Hz, 2H), 1.43 (s, 9H)
HPLCMS (Method A): [m/z]: 346.3 [M+H]$^+$

Tert-butyl N-{2-[4-({5H,6H,7H-cyclopenta[b]pyridin-7-yl}carbamoyl)-1H-pyrazol-1-yl]ethyl}carbamate (253)

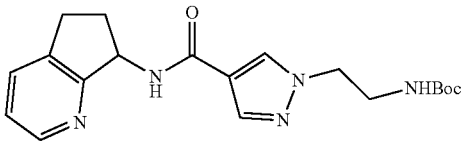 [SMILES: CC(C)(C)OC(=O)NCCn1cc(C(=O)NC2CCc3cccnc32)cn1]

In a similar fashion using general procedure 6, 1-(2-{[(tert-butoxy)carbonyl]amino}ethyl)-1H-pyrazole-4-carboxylic acid (249) (0.7 g, 2.74 mmol), 5H,6H,7H-cyclopenta[b]pyridin-7-amine hydrochloride (0.7 g, 4.11 mmol), DIPEA (1.4 ml, 8.23 mmol) and HATU (1.56 g, 4.11 mmol) in DMF (15 ml) gave the title compound (0.709 g, 70%) as an off-white solid after purification by flash column chromatography (eluting with a gradient of 80-100% EtOAc/heptane).

1H-NMR (MeOD-d6, 500 MHz): d[ppm]=8.35 (d, J=4.6 Hz, 1H), 8.07 (s, 1H), 7.94 (s, 1H), 7.73 (d, J=7.8 Hz, 1H), 7.28 (dd, J=7.6, 5.0 Hz, 1H), 5.53 (t, J=8.1 Hz, 1H), 4.23 (t, J=5.7 Hz, 2H), 3.49-3.43 (m, 2H), 3.13-3.03 (m, 1H), 2.95 (dt, J=16.8, 8.5 Hz, 1H), 2.66 (ddt, J=11.3, 8.1, 3.9 Hz, 1H), 2.07-1.95 (m, 1H), 1.40 (s, 9H)

HPLCMS (Method A): [m/z]: 372.1 [M+H]$^+$

Tert-butyl N-[2-(4-{[(3-fluoropyridin-2-yl)methyl]carbamoyl}-1H-pyrazol-1-yl)ethyl]carbamate (254)

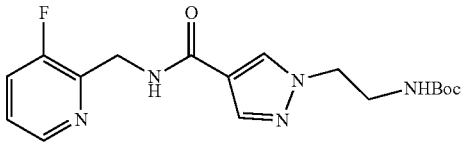 [SMILES: CC(C)(C)OC(=O)NCCn1cc(C(=O)NCc2ncccc2F)cn1]

In a similar fashion using general procedure 6, 1-(2-{[(tert-butoxy)carbonyl]amino}ethyl)-1H-pyrazole-4-carboxylic acid (249) (0.35 g, 1.3 mmol), (3-fluoropyridin-2-yl)methanamine dihydrochloride (A2) (0.46 g, 1.95 mmol), DIPEA (1.13 ml, 6.51 mmol) and HATU (0.74 g, 1.95 mmol) in DMF (7 ml) gave the title compound (0.4 g, 82%) as an orange foam after purification by flash column chromatography (eluting with a gradient of 0-50% MeOH/EtOAc).

1H-NMR (CDCl$_3$, 500 MHz): d[ppm]=8.40-8.37 (m, 1H), 7.89 (s, 2H), 7.46-7.38 (m, 1H), 7.30-7.24 (m, 1H), 4.86 (br s, 1H), 4.78 (dd, J=4.4 and 1.2 Hz 2H), 4.26 (t, J=5.3 Hz, 2H), 3.64-3.50 (m, 2H), 1.43 (s, 9H)

HPLCMS (Method A): [m/z]: 364.40 [M+H]$^+$

Tert-butyl N-[2-(4-{[(3-chloropyridin-2-yl)methyl]carbamoyl}-1H-pyrazol-1-yl)ethyl]carbamate (255)

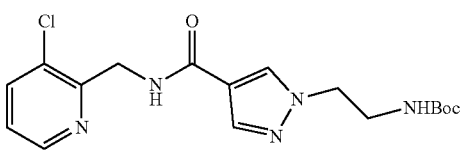 [SMILES: CC(C)(C)OC(=O)NCCn1cc(C(=O)NCc2ncccc2Cl)cn1]

In a similar fashion using general procedure 6, 1-(2-{[(tert-butoxy)carbonyl]amino}ethyl)-1H-pyrazole-4-carboxylic acid (249) (0.7 g, 2.74 mmol), (3-chloropyridin-2-yl)methanamine dihydrochloride (0.89 g, 4.11 mmol), DIPEA (2.39 ml, 13.71 mmol) and HATU (1.56 g, 4.11 mmol) in DMF (15 ml) at room temperature for 24 h, gave the title compound (0.79 g, 76%) as a viscous brown oil after purification by flash column chromatography (eluting with a gradient of 0-50% MeOH/EtOAc). The oil solidified on standing.

1H-NMR (CDCl$_3$, 500 MHz): d[ppm]=8.48 (dd, J=4.7, 1.0 Hz, 1H), 7.91 (s, 1H), 7.91 (s, 1H), 7.72 (dd, J=8.0, 1.2 Hz, 1H), 7.50 (br s, 1H), 7.23 (dd, J=8.0, 4.8 Hz, 1H), 4.87 (br s, 1H), 4.78 (d, J=4.2 Hz, 2H), 4.26 (t, J=5.3 Hz, 2H), 3.59 (app q, J=5.6 Hz, 2H), 1.44 (s, 9H)

HPLCMS (Method A): [m/z]: 380.4 [M+H]$^+$

Tert-butyl N-[2-(4-{[(3-fluoropyridin-2-yl)methyl]carbamoyl}-3,5-dimethyl-1H-pyrazol-1-yl)ethyl]carbamate (256)

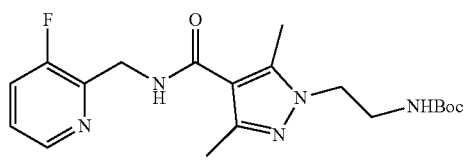 [SMILES: Cc1nn(CCNC(=O)OC(C)(C)C)c(C)c1C(=O)NCc1ncccc1F]

In a similar fashion to general procedure 6, 1-(2-{[(tert-butoxy)carbonyl]amino}ethyl)-3,5-dimethyl-1H-pyrazole-4-carboxylic acid (250) (0.42 g, 1.33 mmol, 90% purity), (3-fluoropyridin-2-yl)methanamine dihydrochloride (A2) (0.47 g, 2.0 mmol), DIPEA (1.16 ml, 6.67 mmol) and HATU (0.76 g, 2.0 mmol) in THF (15 ml) and DMF (3 ml) afforded the title compound (0.40 g, 77%) as a colourless glassy solid after purification by flash column chromatography (kp-NH, eluting with a gradient of 60-100% EtOAc/heptane).

1H-NMR (DMSO-d6, 500 MHz): d[ppm]=8.38 (d, J=4.7 Hz, 1H), 7.81-7.77 (m, 1H), 7.71-7.65 (m, 1H), 7.39 (dt, J=8.6, 4.4 Hz, 1H), 6.94-6.89 (m, 1H), 4.59 (d, J=4.3 Hz, 2H), 3.99 (t, J=6.5 Hz, 2H), 3.20 (q, J=6.5 Hz, 2H), 2.34 (s, 3H), 2.25 (s, 3H), 1.37 (s, 9H)

HPLCMS (Method A): [m/z]: 392.1 [M+H]$^+$

Tert-butyl N-[2-(4-{[(3-fluoropyridin-2-yl)methyl]carbamoyl}-3-(trifluoromethyl)-1H-pyrazol-1-yl)ethyl]carbamate (257)

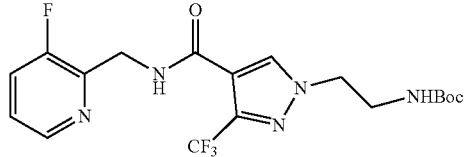 [SMILES: CC(C)(C)OC(=O)NCCn1cc(C(=O)NCc2ncccc2F)c(C(F)(F)F)n1]

In a similar fashion using general procedure 6, 1-(2-{[(tert-butoxy)carbonyl]amino}ethyl)-3-(trifluoromethyl)-1H-pyrazole-4-carboxylic acid (251) (90%, 0.54 g, 1.53 mmol), (3-fluoropyridin-2-yl)methanamine dihydrochloride (A2) (0.23 g, 1.8 mmol), DIPEA (0.87 ml, 5.01 mmol) and HATU (0.57 g, 1.5 mmol) in DMF (3 ml) and THF (15 ml) at room temperature for 72 h, gave the gave the title compound (0.646 g, 65%) after purification by flash column chromatography (eluting with a gradient of 5-100% EtOAc/heptane).

1H-NMR (CDCl$_3$, 250 MHz): d[ppm]=8.40-8.35 (m, 1H), 7.98 (s, 1H), 7.56 (s, 1H), 7.46-7.37 (m, 1H), 7.31-7.23 (m, 4H), 4.80 (dd, J=4.3, 1.2 Hz, 2H), 4.30 (t, J=5.4 Hz, 2H), 3.60 (app q, J=6.0 Hz, 2H), 1.44 (s, 9H)

HPLCMS (Method A): [m/z]: 432.1 [M+H]$^+$ 1-(2-Aminoethyl)-N-(pyridin-2-ylmethyl)-1H-pyrazole-4-carboxamide Dihydrochloride (258)

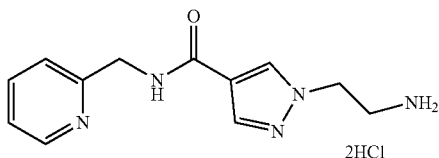 [SMILES: NCCn1cc(C(=O)NCc2ccccn2)cn1]

In a similar fashion using general procedure 2, 12 M HCl (6.5 ml) and tert-butyl N-(2-{4-[(pyridin-2-ylmethyl)carbamoyl]-1H-pyrazol-1-yl}ethyl)carbamate (252) (0.647 g, 1.11 mmol, 59% pure) in MeOH (6.5 ml) at room temperature for 2.5 h, gave the title compound (0.513 g, quant.) as a pale yellow oil. The compound was used in the next step without further purification.

1H-NMR (DMSO-d6, 500 MHz): d[ppm]=9.16 (s, 1H), 8.77 (s, 1H), 8.33 (s, 1H), 8.13 (s, 2H), 8.05 (s, 1H), 7.80 (s, 2H), 4.72 (s, 2H), 4.42 (s, 2H), 3.27 (d, J=5.9 Hz, 2H), 3.05-2.78 (m, 3H)

HPLCMS (Method A): [m/z]: 246 [M+H]$^+$ 1-(2-Aminoethyl)-N-{5H,6H,7H-cyclopenta[b]pyridin-7-yl}-1H-pyrazole-4-carboxamide Dihydrochloride (259)

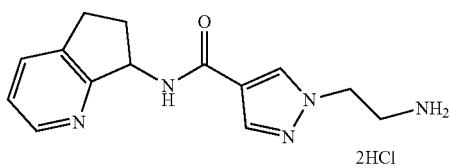 [SMILES: NCCn1cc(C(=O)NC2CCc3cccnc32)cn1]

In a similar fashion using general procedure 2, 12 M HCl (3.2 ml) and tert-butyl N-{2-[4-({5H,6H,7H-cyclopenta[b]pyridin-7-yl}carbamoyl)-1H-pyrazol-1-yl]ethyl}carbamate (253) (0.709 g, 1.909 mmol) in MeOH (20 ml) at room temperature for 20 h, gave the title compound (0.745 g, quant.) as a grey solid. 1H NMR (500 MHz, Methanol-d4): d[ppm]=8.60 (d, J=5.8 Hz, 1H), 8.51 (d, J=7.8 Hz, 1H), 8.29 (s, 1H), 8.05 (s, 1H), 7.93 (dd, J=7.7, 6.0 Hz, 1H), 5.80 (t, J=8.4 Hz, 1H), 4.53-4.49 (m, 2H), 3.46 (t, J=5.7 Hz, 2H), 3.39-3.35 (m, 1H), 3.18 (dt, J=17.0, 8.5 Hz, 1H), 2.83-2.74 (m, 1H), 2.41-2.31 (m, 1H)

HPLCMS (Method A): [m/z]: 272.05 [M+H]$^+$ 1-(2-Aminoethyl)-N-[(3-fluoropyridin-2-yl)methyl]-1H-pyrazole-4-carboxamide Dihydrochloride (260)

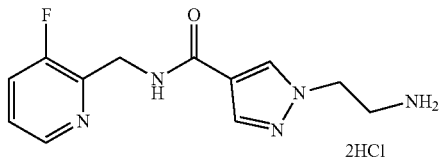 [SMILES: NCCn1cc(C(=O)NCc2ncccc2F)cn1]

In a similar fashion using general procedure 2, 12 M HCl (3.67 ml) and tertbutyl N-[2-(4-{[(3-fluoropyridin-2-yl)methyl]carbamoyl}-1H-pyrazol-1-yl)ethyl]carbamate (254) (0.4 g, 1.1 mmol) in MeOH (5 ml) at room temperature for 16 h, gave the title compound (0.38 g, quant.) as a cream foam. The compound was used in the next step without further purification.

1H-NMR (DMSO-d6, 500 MHz): d[ppm]=8.65 (t, J=5.7 Hz, 1H), 8.38 (dt, J=4.6, 1.4 Hz, 1H), 8.25 (s, 1H), 8.12 (br s, 3H), 8.00-7.97 (m, 1H), 7.73-7.68 (m, 1H), 7.43-7.39 (m, 1H), 4.59 (dd, J=5.6, 1.5 Hz, 2H), 4.40 (t, J=6.1 Hz, 2H), 3.25 (app h, J=5.7 Hz, 2H)

HPLCMS (Method A): [m/z]: 264.05 [M+H]$^+$ 1-(2-Aminoethyl)-N-[(3-chloropyridin-2-yl)methyl]-1H-pyrazole-4-carboxamide Dihydrochloride (261)

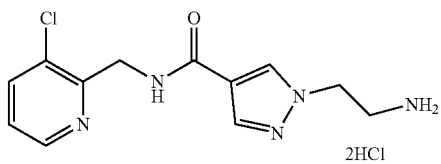

In a similar fashion using general procedure 2, 12 M HCl (6.5 ml) and tertbutyl N-[2-(4-{[(3-chloropyridin-2-yl)methyl]carbamoyl}-1H-pyrazol-1-yl)ethyl]carbamate (255) (0.79 g, 1.97 mmol) in MeOH (10 ml) at room temperature for 25 h, gave the title compound (0.7 g, 95%) as a beige solid. The compound was used in the next step without further purification.

1H-NMR (Methanol-d4, 500 MHz): d[ppm]=8.69 (dd, J=5.5, 1.2 Hz, 1H), 8.51 (dd, J=8.3, 1.2 Hz, 1H), 8.26 (s, 1H), 8.05 (s, 1H), 7.86 (dd, J=8.3, 5.5 Hz, 1H), 4.88 (s, 2H), 4.51 (t, J=5.6 Hz, 2H), 3.46 (t, J=5.6 Hz, 2H)

HPLCMS (Method A): [m/z]: 279.9 [M+H]$^+$ 1-(2-Aminoethyl)-N-[(3-fluoropyridin-2-yl)methyl]-3,5-dimethyl-1H-pyrazole-4-carboxamide Dihydrochloride (262)

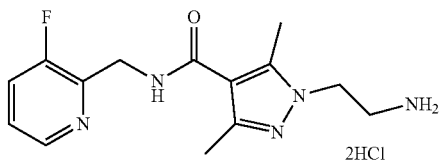 [SMILES: Cc1nn(CCN)c(C)c1C(=O)NCc1ncccc1F]

In a similar fashion to general procedure 2, tert-butyl N-[2-(4-{[(3-fluoropyridin-2-yl)methyl]carbamoyl}-3,5-dimethyl-1H-pyrazol-1-yl)ethyl]carbamate (256) (0.4 g, 1.02 mmol) and 12 M HCl (1.7 ml) in MeOH (5 ml) afforded the title compound (0.399 g, 93% purity) as a white solid.

1H-NMR (Methanol-d4, 500 MHz): d[ppm]=8.64 (dd, J=5.5, 1.2 Hz, 1H), 8.33 (t, J=8.9 Hz, 1H), 7.97-7.92 (m, 1H), 4.86-4.85 (m, 2H), 4.34-4.29 (m, 2H), 3.40 (t, J=5.8 Hz, 2H), 2.46 (s, 3H), 2.38 (s, 3H)

HPLCMS (Method A): [m/z]: 292 [M+H]$^+$ 1-(2-Aminoethyl)-N-[(3-fluoropyridin-2-yl)methyl]-3-(trifluoromethyl)-1H-pyrazole-4-carboxamide Dihydrochloride (263)

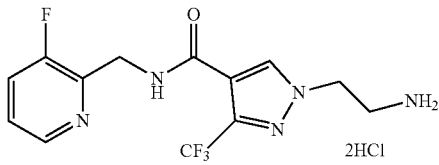 [SMILES: NCCn1cc(C(=O)NCc2ncccc2F)c(C(F)(F)F)n1]

In a similar fashion using general procedure 2, 12 M HCl (2.1 ml) and tert-butyl N-[2-(4-{[(3-fluoropyridin-2-yl)methyl]carbamoyl}-3-(trifluoromethyl)-1H-pyrazol-1-yl)ethyl]carbamate (257) (80%, 0.68 g, 1.26 mmol) in MeOH (10 ml) at room temperature for 17 h, gave the title compound (0.588 g, 93.4%) as a pink solid. The compound was used in the next step without further purification.

1H-NMR (DMSO-d6, 250 MHz): d[ppm]=8.80 (t, J=5.7 Hz, 1H), 8.52 (s, 1H), 8.42-8.36 (m, 1H), 8.23 (s, 3H), 7.78-7.68 (m, 1H), 7.48-7.39 (m, 1H), 4.59 (dd, J=5.5, 1.3 Hz, 2H), 4.50 (t, J=6.0 Hz, 2H), 3.29 (q, J=5.7 Hz, 2H), 2.89 (s, 1H), 2.69 (s, 7H)

HPLCMS (Method A): [m/z]: 332.2 [M+H]$^+$

1-{2-[(1H-1,3-Benzodiazol-2-ylmethyl)amino]ethyl}-N-(pyridin-2-ylmethyl)-1H-pyrazole-4-carboxamide (Example Compound No. 92)

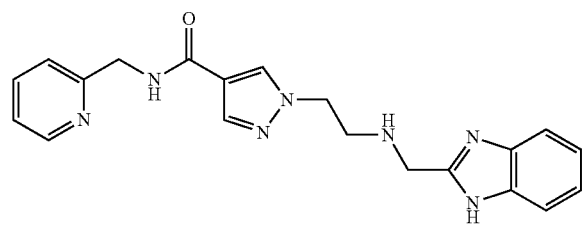 [SMILES: O=C(NCc1ccccn1)c1cnn(CCNCc2nc3ccccc3[nH]2)c1]

In a similar fashion using general procedure 3, 1-(2-aminoethyl)-N-(pyridin-2-ylmethyl)-1H-pyrazole-4-carboxamide dihydrochloride (258) (256 mg, 0.805 mmol), 1H-benzimidazole-2-carbaldehyde (129 mg, 0.885 mmol) and DIPEA (0.70 ml, 4.02 mmol) in MeOH (7 ml) at room temperature for 65 h, followed by addition of NaBH$_4$ (46 mg, 1.21 mmol) gave the title compound (58 mg, 19%) as a pale yellow solid after purification by prep-HPLC.

1H-NMR (DMSO-d6, 500 MHz): d[ppm]=12.17 (s, 1H), 8.68 (t, J=6.0 Hz, 1H), 8.49 (d, J=4.2 Hz, 1H), 8.23 (s, 1H), 7.91 (s, 1H), 7.74 (td, J=7.7, 1.8 Hz, 1H), 7.51 (s, 1H), 7.45 (s, 1H), 7.29 (d, J=7.8 Hz, 1H), 7.25 (dd, J=7.1, 5.1 Hz, 1H), 7.18-7.05 (m, 2H), 4.49 (d, J=6.0 Hz, 2H), 4.22 (t, J=6.2 Hz, 2H), 3.91 (s, 2H), 2.97 (t, J=6.1 Hz, 2H), 2.45 (s, 1H)

HPLCMS (Method B): [m/z]: 376.2 [M+H]$^+$

1-{2-[(1H-1,3-Benzodiazol-2-ylmethyl)amino]ethyl}-N-{5H,6H,7H-cyclopenta[b]pyridin-7-yl}-1H-pyrazole-4-carboxamide (Example Compound No. 132)

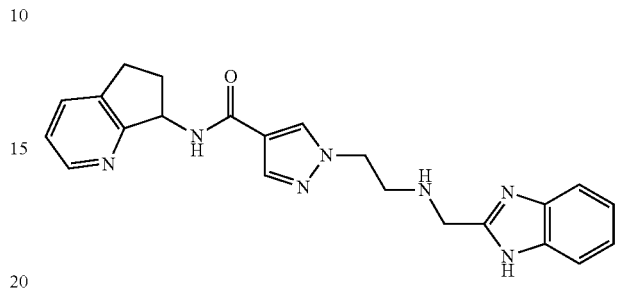

In a similar fashion using general procedure 3, 1-(2-aminoethyl)-N-{5H,6H,7H-cyclopenta[b]pyridin-7-yl}-1H-pyrazole-4-carboxamide dihydrochloride (259) (150 mg, 0.38 mmol), 1H-benzimidazole-2-carbaldehyde (67 mg, 0.46 mmol) and DIPEA (0.267 ml, 1.53 mmol) in MeOH (6 ml) at room temperature for 24 h, followed by addition of NaBH$_4$ (22 mg, 0.57 mmol) gave the title compound (23 mg, 15%) as a yellow solid after purification by basic prep-HPLC followed by flash column chromatography (kp-NH, eluting with a gradient of 0-20% MeOH/EtOAc).

1H-NMR (Methanol-d4, 500 MHz): d[ppm]=8.35 (d, J=4.9 Hz, 1H), 8.17 (s, 1H), 7.93 (s, 1H), 7.74 (d, J=7.6 Hz, 1H), 7.51 (s, 2H), 7.28 (dd, J=7.6, 4.9 Hz, 1H), 7.20 (dd, J=6.0, 3.2 Hz, 2H), 5.54 (t, J=8.2 Hz, 1H), 4.29 (t, J=5.9 Hz, 2H), 4.01 (s, 2H), 3.09 (t, J=5.9 Hz, 2H), 3.08-3.04 (m, 1H), 2.99-2.91 (m, 1H), 2.71-2.63 (m, 1H), 2.06-1.97 (m, 1H)

HPLCMS (Method B): [m/z]: 402.1 [M+H]$^+$

1-{2-[(1H-1,3-Benzodiazol-2-ylmethyl)amino]ethyl}-N-[(3-fluoropyridin-2-yl)methyl]-1H-pyrazole-4-carboxamide (Example Compound No. 145)

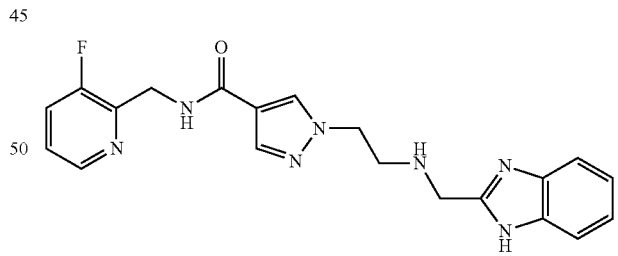

In a similar fashion using general procedure 3, 1-(2-aminoethyl)-N-[(3-fluoropyridin-2-yl)methyl]-1H-pyrazole-4-carboxamide dihydrochloride (260) (200 mg, 0.59 mmol), 1H-benzimidazole-2-carbaldehyde (104 mg, 0.71 mmol) and DIPEA (0.41 ml, 2.38 mmol) in MeOH (8 ml) at room temperature for 18 h, followed by addition of NaBH$_4$ (32.7 mg, 0.87 mmol) gave the title compound (91 mg, 40%) as a colourless film after purification by flash column chromatography (kp-NH, eluting with a gradient of 0-10% MeOH/DCM) followed by basic prep-HPLC.

1H-NMR (DMSO-d6, 500 MHz): d[ppm]=12.15 (br s, 1H), 8.53 (t, J=5.7 Hz, 1H), 8.37 (dt, J=4.6, 1.4 Hz, 1H), 8.21 (s, 1H), 7.88 (s, 1H), 7.70-7.65 (m, 1H), 7.59-7.41 (m, 2H), 7.41-7.37 (m, 1H), 7.12 (d, J=4.7 Hz, 2H), 4.57 (dd, J=5.7, 1.6 Hz, 2H), 4.21 (t, J=6.2 Hz, 2H), 3.90 (br s, 2H), 2.96 (app br s, 2H)

HPLCMS (Method C): [m/z]: 394.1 [M+H]+

1-{2-[(1H-1,3-Benzodiazol-2-ylmethyl)amino]ethyl}-N-[(3-chloropyridin-2-yl)methyl]-1H-pyrazole-4-carboxamide (Example Compound No. 138)

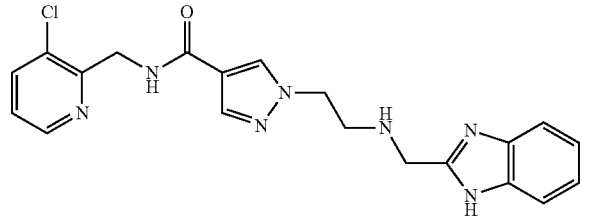 [SMILES: O=C(NCc1ncccc1Cl)c1cnn(CCNCc2nc3ccccc3[nH]2)c1]

In a similar fashion using general procedure 3, 1-(2-aminoethyl)-N-[(3-chloropyridin-2-yl)methyl]-1H-pyrazole-4-carboxamide dihydrochloride (261) (200 mg, 0.54 mmol), 1H-benzimidazole-2-carbaldehyde (94.5 mg, 0.65 mmol) and DIPEA (0.38 ml, 2.16 mmol) in MeOH (8 ml) at room temperature for 16 h, followed by addition of NaBH4 (30.6 mg, 0.81 mmol) gave the title compound (127 mg, 56%) as a pale green foam after purification by basic prep-HPLC.

1H-NMR (DMSO-d6, 500 MHz): d[ppm]=12.17 (s, 1H), 8.51-8.46 (m, 2H), 8.23 (s, 1H), 7.92 (dd, J=8.1, 1.4 Hz, 1H), 7.90 (s, 1H), 7.58-7.41 (br m, 2H), 7.37 (dd, J=8.1, 4.7 Hz, 1H), 7.17-7.08 (m, 2H), 4.62 (d, J=5.6 Hz, 2H), 4.23 (t, J=6.2 Hz, 2H), 3.92 (br s, 2H), 2.98 (br s, 2H)

HPLCMS (Method C): [m/z]: 410.2 [M+H]+

1-{2-[(1H-1,3-Benzodiazol-2-ylmethyl)amino]ethyl}-N-[(3-fluoropyridin-2-yl)methyl]-3,5-dimethyl-1H-pyrazole-4-carboxamide (Example Compound No. 142)

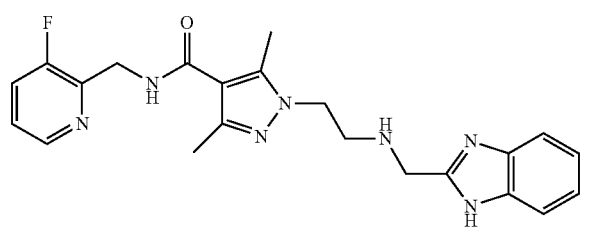 [SMILES: Cc1nn(CCNCc2nc3ccccc3[nH]2)c(C)c1C(=O)NCc1ncccc1F]

In a similar fashion using general procedure 3, 1-(2-aminoethyl)-N-[(3-fluoropyridin-2-yl)methyl]-3,5-dimethyl-1H-pyrazole-4-carboxamide dihydrochloride (262) (150 mg, 0.384 mmol), 1H-benzimidazole-2-carbaldehyde (73 mg, 0.499 mmol), DIPEA (0.268 ml, 1.537 mmol) and MgSO4 (100 mg) in MeOH (7 ml) at room temperature for 16 h, followed by addition of NaBH4 (22 mg, 0.576 mmol) gave the title compound (14 mg, 9%) as a yellow solid after purification by basic prep-HPLC.

1H-NMR (DMSO-d6, 500 MHz): d[ppm]=12.16 (s, 1H), 8.40-8.37 (m, 1H), 7.84 (t, J=5.6 Hz, 1H), 7.72-7.66 (m, 1H), 7.56-7.50 (m, 1H), 7.46-7.42 (m, 1H), 7.40 (dt, J=8.4, 4.4 Hz, 1H), 7.17-7.09 (m, 2H), 4.59 (d, J=4.3 Hz, 2H), 4.05 (t, J=6.4 Hz, 2H), 3.92 (s, 2H), 2.90 (t, J=6.4 Hz, 2H), 2.38 (s, 3H), 2.24 (s, 3H)

HPLCMS (Method D): [m/z]: 422.3 [M+H]+

1-{2-[(1H-1,3-Benzodiazol-2-ylmethyl)amino]ethyl}-N-[(3-fluoropyridin-2-yl)methyl]-3-(trifluoromethyl)-1H-pyrazole-4-carboxamide (Example Compound No. 156)

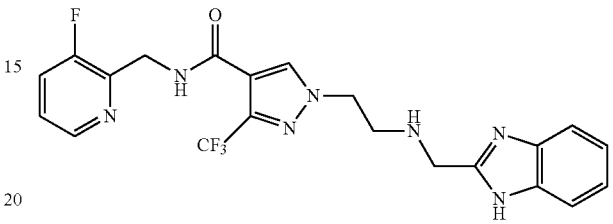

In a similar fashion using general procedure 3, 1-(2-aminoethyl)-N-[(3-fluoropyridin-2-yl)methyl]-3-(trifluoromethyl)-1H-pyrazole-4-carboxamide dihydrochloride (263) (81%, 100 mg, 0.20 mmol), 1H-benzimidazole-2-carbaldehyde (35 mg, 0.24 mmol) and DIPEA (0.14 ml, 0.8 mmol) in MeOH (5 ml) at room temperature for 16 h, followed by addition of NaBH4 (22 mg, 0.6 mmol) gave the title compound (12 mg, 13%) as a white solid after purification by basic prep-HPLC followed by flash column chromatography (eluting with a gradient of 0-10% MeOH/DCM).

1H-NMR (DMSO-d6, 500 MHz): d[ppm]=12.15 (s, 1H), 8.69 (t, 1H), 8.45 (s, 1H), 8.37 (d, 1H), 7.72-7.66 (m, 1H), 7.53 (d, 1H), 7.45-7.38 (m, 2H), 7.12 (t, 2H), 4.71-4.45 (m, 2H), 4.29 (t, 2H), 3.92 (s, 2H), 2.99 (s, 2H)

HPLCMS (Method C): [m/z]: 462.1 [M+H]+

1-(2-{[2-(1H-1,3-Benzodiazol-2-yl)ethyl]amino}ethyl)-N-(pyridin-2-ylmethyl)-1H-pyrazole-4-carboxamide (Example Compound No. 109)

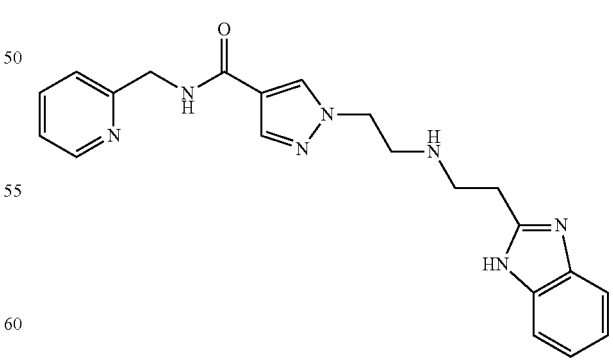

In a similar fashion using general procedure 7, 1-(2-aminoethyl)-N-(pyridin-2-ylmethyl)-1H-pyrazole-4-carboxamide dihydrochloride (258) (250 mg, 0.79 mmol), 2-(2-chloroethyl)-1H-benzimidazole hydrochloride (340 mg, 1.58 mmol) and DIPEA (2.1 ml, 11.8 mmol) in DMF (7.5 ml) at room temperature for 6 d to give the title compound (17 mg, 5%) as a pale yellow solid after purification by prep-HPLC, followed by (KP—NH) flash column chromatography using 4:6 EtOAc/heptane to 100% EtOAc then 20% MeOH: 80% DCM followed by prep-HPLC (MeCN/Water, 2 mM NH₄HCO₃).

1H-NMR (DMSO-d6, 500 MHz): d[ppm]=12.10 (s, 1H), 8.68 (t, J=6.0 Hz, 1H), 8.50 (d, J=4.1 Hz, 1H), 8.21 (s, 1H), 7.90 (s, 1H), 7.74 (td, J=7.7, 1.8 Hz, 1H), 7.58-7.33 (m, 2H), 7.29 (d, J=7.9 Hz, 1H), 7.25 (dd, J=7.4, 4.9 Hz, 1H), 7.09 (dd, J=6.0, 2.8 Hz, 2H), 4.49 (d, J=6.0 Hz, 2H), 4.19 (t, J=6.2 Hz, 2H), 3.00-2.93 (m, 4H), 2.91 (t, J=6.2 Hz, 2H), 2.05 (s, 1H)

HPLCMS (Method B): [m/z]: 390.2 [M+H]⁺

1-(2-{[2-(1H-1,3-Benzodiazol-2-yl)ethyl]amino}ethyl)-N-[(3-fluoropyridin-2-yl)methyl]-1H-pyrazole-4-carboxamide Tetrahydrochloride (Example Compound No. 111)

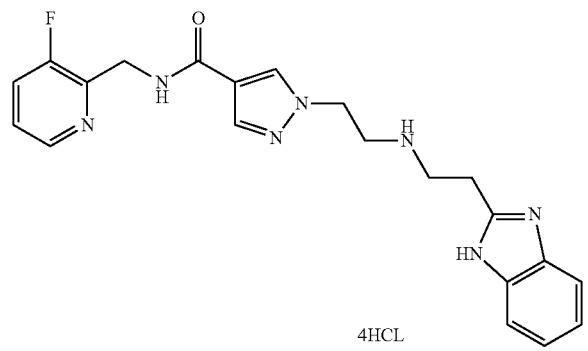 [SMILES: O=C(NCc1ncccc1F)c1cnn(CCNCCc2nc3ccccc3[nH]2)c1]

4HCL

In a similar fashion using general procedure 7, 1-(2-aminoethyl)-N-[(3-fluoropyridin-2-yl)methyl]-1H-pyrazole-4-carboxamide dihydrochloride (260) (0.7 g, 2.08 mmol), 2-(2-chloroethyl)-1H-benzimidazole (0.451 g, 2.499 mmol) and DIPEA (5.4 ml, 31.23 mmol) in DMF (15 ml) at 30° C. for 6 d gave the product as the free base (63 mg) after purification by silica column chromatography (kp-NH, eluting with a gradient of 0-40% MeOH/EtOAc) followed by basic prep-HPLC. The freebase product was dissolved in MeOH (3 ml) and 12 M HCl (2 ml) at room temperature for 2 h to give the title compound (65 mg, 5.6%) as a brown solid.

1H-NMR (Methanol-d4, 500 MHz): d[ppm]=8.46 (s, 1H), 8.25 (s, 1H), 8.01 (s, 1H), 7.81 (dd, J=6.2, 3.2 Hz, 3H), 7.63 (dd, J=6.2, 3.1 Hz, 3H), 4.78 (s, 2H), 4.64 (s, 2H), 3.72 (t, J=7.6 Hz, 6H)

HPLCMS (Method B): [m/z]: 408.2 [M+H]⁺

1-(2-{[2-(1H-1,3-Benzodiazol-2-yl)ethyl]amino}ethyl)-N-{5H,6H,7H-cyclopenta[b]pyridin-7-yl}-1H-pyrazole-4-carboxamide Trihydrochloride (Example Compound No. 131)

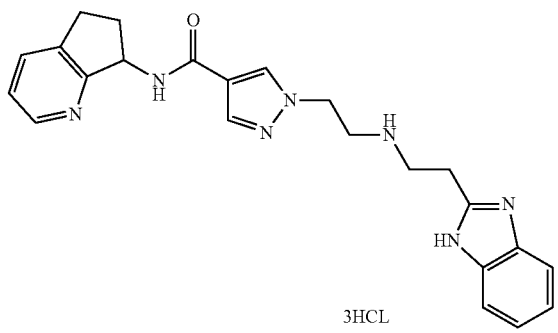 [SMILES: O=C(NC1CCc2cccnc21)c1cnn(CCNCCc2nc3ccccc3[nH]2)c1]

3HCL

In a similar fashion using general procedure 7, 1-(2-aminoethyl)-N-{5H,6H,7H-cyclopenta[b]pyridin-7-yl}-1H-pyrazole-4-carboxamide dihydrochloride (259) (0.2 g, 0.51 mmol), 2-(2-chloroethyl)-1H-benzimidazole hydrochloride (0.13 g, 0.61 mmol) and DIPEA (0.44 ml, 2.55 mmol) in DMF (3 ml) at room temperature for 72 h then heated to 40° C. for 21 h gave the free base product (55 mg) after purification basic prep-HPLC. The free base product was then dissolved in MeOH (3 ml) and 12 M HCl (0.5 ml) at room temperature for 2 h to give the title compound (0.049 g, 18%) as a brown solid.

1H-NMR (Methanol-d4, 500 MHz): d[ppm]=8.60 (d, J=5.2 Hz, 1H), 8.51 (d, J=6.8 Hz, 1H), 8.31 (s, 1H), 8.03 (s, 1H), 7.95-7.91 (m, 1H), 7.83-7.79 (m, 2H), 7.65-7.62 (m, 2H), 5.80 (t, J=8.5 Hz, 1H), 4.68-4.64 (m, 2H), 3.77-3.70 (m, 6H), 3.34 (d, J=3.3 Hz, 1H), 3.23-3.17 (m, 1H), 2.83-2.75 (m, 1H), 2.39-2.30 (m, 1H)

HPLCMS (Method B): [m/z]: 416.1 [M+H]⁺

1-(2-{[2-(1H-1,3-Benzodiazol-2-yl)ethyl]amino}ethyl)-N-[(3-chloropyridin-2-yl)methyl]-1H-pyrazole-4-carboxamide (Example Compound No. 144)

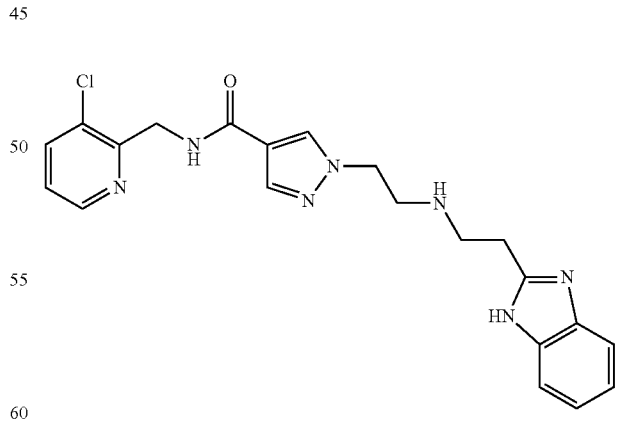

In a similar fashion using general procedure 7, 1-(2-aminoethyl)-N-[(3-chloropyridin-2-yl)methyl]-1H-pyrazole-4-carboxamide dihydrochloride (261) (0.45 g, 1.28 mmol), 2-(2-chloroethyl)-1H-benzimidazole (0.28 g, 1.53 mmol) and DIPEA (3.3 ml, 19.14 mmol) in DMF (7 ml) at room temperature for 66 h, then heated to 40° C. for 90 h, gave the title compound (112 mg, 21%) as a colourless film after purification by flash column chromatography (kp-NH, eluting with a gradient of 0-10% MeOH/DCM) followed by basic prep-HPLC.

1H-NMR (DMSO-d6, 500 MHz): d[ppm]=12.10 (s, 1H), 8.52-8.44 (m, 2H), 8.22 (s, 1H), 7.92 (dd, J=8.1, 1.4 Hz, 1H), 7.90 (s, 1H), 7.55-7.38 (br m, 2H), 7.37 (dd, J=8.1, 4.7 Hz, 1H), 7.13-7.07 (m, 2H), 4.63 (d, J=5.7 Hz, 2H), 4.20 (t, J=6.2 Hz, 2H), 2.99-2.93 (m, 4H), 2.93-2.89 (m, 2H)

HPLCMS (Method C): [m/z]: 424.1 [M+H]+

1-(2-{[2-(1H-1,3-Benzodiazol-2-yl)ethyl]amino}ethyl)-N-[(3-fluoropyridin-2-yl)methyl]-3-(trifluoromethyl)-1H-pyrazole-4-carboxamide (Example Compound No. 162)

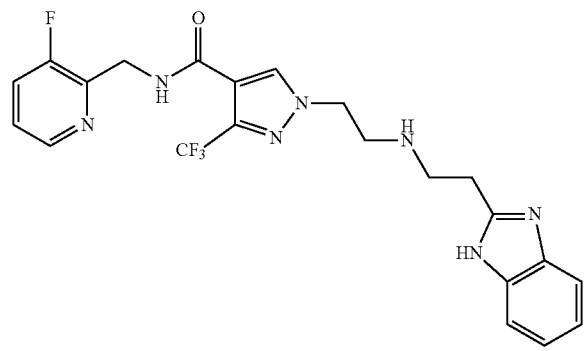 [SMILES: O=C(NCc1ncccc1F)c1cn(CCNCCc2nc3ccccc3[nH]2)nc1C(F)(F)F]

In a similar fashion using general procedure 8, DBU (62.94 µl, 0.42 mmol), 1-(2-aminoethyl)-N-[(3-fluoropyridin-2-yl)methyl]-3-(trifluoromethyl)-1H-pyrazole-4-carboxamide dihydrochloride (263) (81%, 140 mg, 0.28 mmol) and N-(2-nitrophenyl)prop-2-enamide (D) (52.84 mg, 0.27 mmol) in MeCN (5 ml) at room temperature for 16 h gave a residue (0.160 g) as a mixture of mono:bis-alkylated (1:1) adducts.

The residue was dissolved in AcOH (4 ml). Iron (0.03 g) was added and the reaction heated to 80° C. for 1 h. The reaction was cooled and diluted with water (5 ml). The mixture was cooled in an ice-bath and basified to pH 12 using 10 M NaOH. Water (10 ml) was added and the mixture extracted with CHCl3:IPA (4:1, 4×30 ml). The combined organic layers were dried (Na2SO4), filtered and evaporated. Purification by flash column chromatography (eluting with a gradient 5-10% MeOH/DCM followed by 0-10% 7 N NH3 in MeOH/DCM) followed by purification by basic prep-HPLC gave the title compound (19 mg, 13.9%) as a colourless oil.

1H-NMR (DMSO-d6, 500 MHz): d[ppm]=12.11 (br s, 1H), 8.69 (t, J=5.6 Hz, 1H), 8.43 (s, 1H), 8.42-8.35 (m, 1H), 7.74-7.65 (m, 1H), 7.52-7.36 (br m, 2H), 7.43-7.37 (m, 1H), 7.15-7.06 (br m, 2H), 4.59-4.55 (m, 2H), 4.26 (t, J=6.1 Hz, 2H), 3.02-2.94 (m, 4H), 2.94-2.89 (m, 2H)

HPLCMS (Method C): [m/z]: 476.2 [M+H]+

Ethyl 1-[2-(benzyloxy)-2-oxoethyl]-1H-pyrazole-4-carboxylate (268)

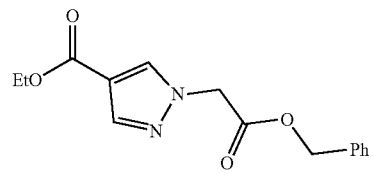 [SMILES: CCOC(=O)c1cnn(CC(=O)OCc2ccccc2)c1]

Benzyl bromoacetate (2.82 ml, 18 mmol) was added dropwise to an ice-cold suspension of ethyl 1H-pyrazole-4-carboxylate (2.3 g, 16 mmol) and K2CO3 (3.4 g, 25 mmol) in DMF (20 ml). The mixture was warmed to room temperature and stirred for 2 h. The mixture was diluted with diethyl ether (100 ml) and washed with water (2×40 ml) and brine (5×20 ml). The organic phase was dried (Na2SO4), filtered and evaporated in vacuo. Purification by flash chromatography using an elution gradient 0-100% DCM/heptane afforded the title compound (1.57 g, 33%) as a colourless oil.

1H-NMR (CDCl3, 500 MHz): d[ppm]=8.01 (s, 1H), 7.98 (s, 1H), 7.44-7.32 (m, 5H), 5.24 (s, 2H), 4.98 (s, 2H), 4.32 (q, J=7.1 Hz, 2H), 1.37 (t, J=7.1 Hz, 3H)

HPLCMS (Method A): [m/z]: 288.95 [M+H]+

2-[4-(Ethoxycarbonyl)-1H-pyrazol-1-yl]acetic Acid (269)

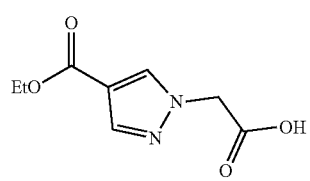 [SMILES: CCOC(=O)c1cnn(CC(=O)O)c1]

A suspension of ethyl 1-[2-(benzyloxy)-2-oxoethyl]-1H-pyrazole-4-carboxylate (268) (1.57 g, 5.44 mmol) and palladium on carbon (10% wt, 0.590 g, 0.55 mol) in EtOH (50 ml) was stirred under an atmosphere of hydrogen for 2.5 h. The mixture was filtered through a plug of Celite and the residue rinsed with MeOH. The combined filtrates were evaporated in vacuo to give the title compound (0.99 mg, 92%) as a yellow solid.

1H-NMR (CDCl3, 500 MHz): d[ppm]=8.07 (s, 1H), 8.03 (s, 1H), 5.07 (s, 2H), 4.34 (q, J=7.1 Hz, 2H), 1.37 (t, J=7.1 Hz, 3H)

HPLCMS (Method A): [m/z]: 198.9 [M+H]+

Ethyl 1-({[2-(1H-1,3-benzodiazol-2-yl)ethyl]carbamoyl}methyl)-1H-pyrazole-4-carboxylate (270)

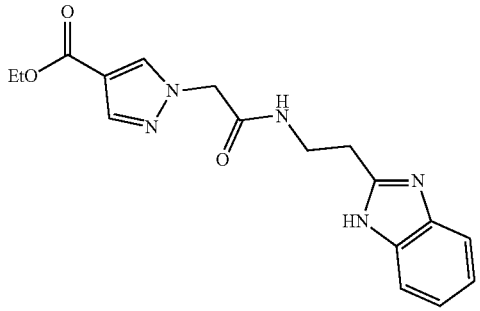 [SMILES: CCOC(=O)c1cnn(CC(=O)NCCc2nc3ccccc3[nH]2)c1]

In a similar fashion to general procedure 6, HATU (1.1 g, 2.88 mmol), 2-[4-(ethoxycarbonyl)-1H-pyrazol-1-yl]acetic acid (269) (0.476 g, 2.4 mmol), 2-(1H-1,3-benzodiazol-2-yl)ethan-1-amine dihydrochloride (0.62 g, 2.64 mmol) and DIPEA (1.67 ml, 9.61 mmol) in THF (30 ml) at room temperature for 2 h afforded the title compound (0.676 g, 82%) as a white solid after purification by flash chromatography (eluting with a gradient elution 0-8% MeOH/DCM).

1H-NMR (CDCl$_3$, 500 MHz): d[ppm]=8.01 (s, 1H), 7.87 (s, 1H), 7.62 (m, 2H), 7.36 (m, 3H), 4.90 (s, 2H), 4.28 (q, J=7.1 Hz, 2H), 3.80 (q, J=5.9 Hz, 3H), 3.39 (t, J=5.9 Hz, 2H), 1.34 (t, J=7.1 Hz, 3H)

HPLCMS (Method A): [m/z]: 342.1 [M+H]$^+$

1-({[2-(1H-1,3-Benzodiazol-2-yl)ethyl]carbamoyl}methyl)-1H-pyrazole-4-carboxylic Acid (271)

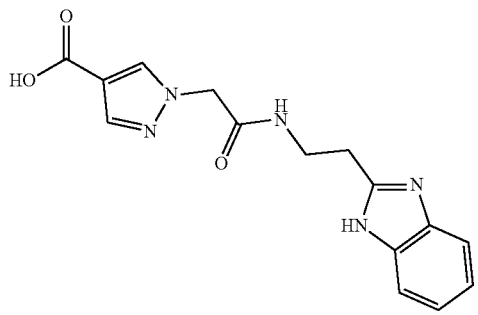 [SMILES: O=C(Cn1cc(C(=O)O)cn1)NCCc1nc2ccccc2[nH]1]

In a similar fashion to general procedure 5, ethyl 1-({[2-(1H-1,3-benzodiazol-2-yl)ethyl]carbamoyl}methyl)-1H-pyrazole-4-carboxylate (270) (667 mg, 1.95 mmol) and LiOH (140 mg, 5.85 mmol) in THF/water (30 ml/4 ml) at room temperature for 16 h, gave the crude title compound (420 mg) as a white residue.

HPLCMS (Method A): [m/z]: 314 [M+H]$^+$

1-({[2-(1H-1,3-Benzodiazol-2-yl)ethyl]carbamoyl}methyl)-N-[(3-fluoropyridin-2-yl)methyl]-1H-pyrazole-4-carboxamide Dihydrochloride (Example Compound No. 117)

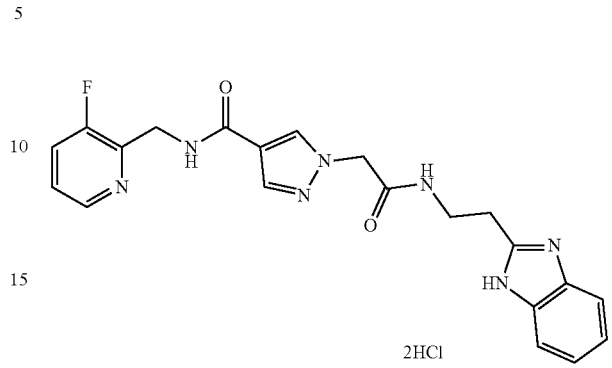

In a similar fashion to general procedure 6, crude 1-({[2-(1H-1,3-benzodiazol-2-yl)ethyl]carbamoyl}methyl)-1H-pyrazole-4-carboxylic acid (271) (200 mg), (3-fluoropyridin-2-yl)methanamine dihydrochloride (A2) (140 mg, 0.7 mmol), DIPEA (0.44 ml, 2.55 mmol) and HATU (290 mg, 0.76 mmol) in THF (10 ml) and DMF (2 ml) afforded the title compound as the freebase after purification by flash column chromatography (eluting with a gradient of 0-20% MeOH/DCM) followed by basic prep-HPLC. The freebase was converted to the di HCl salt (28 mg, 9%) after treatment with 12M HCl (1 ml) in MeOH (5 ml).

1H-NMR (Methanol-d4, 500 MHz): d[ppm]=8.49 (d, J=5.2 Hz, 1H), 8.13 (s, 1H), 8.00-7.92 (m, 2H), 7.76 (dt, J=6.7, 3.4 Hz, 2H), 7.67 (dt, J=8.8, 4.8 Hz, 1H), 7.59 (dt, J=6.2, 3.4 Hz, 2H), 4.88 (s, 2H), 4.79 (d, J=1.4 Hz, 2H), 3.77 (t, J=6.4 Hz, 2H), 3.39 (t, J=6.4 Hz, 2H)

HPLCMS (Method C): [m/z]: 422.2 [M+H]$^+$

General Scheme 15 Above:

1-{1-[(Tert-butoxy)carbonyl]piperidin-4-yl}-1H-pyrazole-4-carboxylic Acid (272)

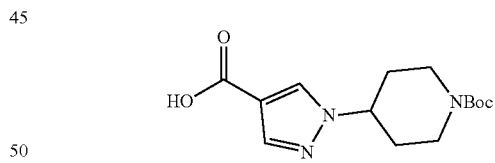

Ethyl 1H-pyrazole-4-carboxylate (0.2 g, 1.427 mmol), tert-butyl 4-[(methylsulfonyl)oxy]piperidine-1-carboxylate (0.362 g, 1.296 mmol) in DMF (5 ml) were stirred for 5 min. The reaction was cooled to 0° C. and NaH (0.234 g, 5.85 mmol) added portion wise. Once gas evolution ceased, the reaction was heated to 50° C. for 26 h. The reaction was cooled, quenched with water (15 ml) and evaporated to dryness. Water (40 ml) was added and the aqueous layer extracted with EtOAc (3×15 ml). The aqueous layer was acidified with saturated KHSO$_4$ to pH 3 and extracted with EtOAc (4×20 ml). The combined organic layers were dried (MgSO$_4$), filtered and evaporated to give the title compound (0.331 g, 79%) as a pale yellow solid.

1H-NMR (DMSO-d6, 500 MHz): d[ppm]=8.29 (s, 1H), 7.81 (s, 1H), 4.44-4.36 (m, 1H), 4.08-3.97 (m, 2H), 2.89 (s, 2H), 2.01-1.95 (m, 2H), 1.79 (qd, J=12.4, 4.4 Hz, 2H), 1.41 (s, 9H)

HPLCMS (Method A): [m/z]: 318.0 [M+Na]+

Tert-butyl 4-(4-{[(3-fluoropyridin-2-yl)methyl]carbamoyl}-1H-pyrazol-1-yl)piperidine-1-carboxylate (273)

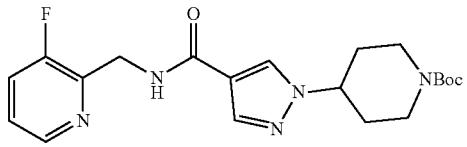 [SMILES: CC(C)(C)OC(=O)N1CCC(n2cc(C(=O)NCc3ncccc3F)cn2)CC1]

In a similar fashion using general procedure 6, 1-{1-[(tert-butoxy)carbonyl]piperidin-4-yl}-1H-pyrazole-4-carboxylic acid (272) (301 mg, 1.02 mmol), 3-fluoropyridin-2-yl)methanamine dihydrochloride (A2) (358 mg, 1.53 mmol), DIPEA (0.8 ml), HATU (581 mg, 1.53 mmol) in THF (15 ml) and DMF (3 ml) gave the title compounds (315 mg, 65%) as a glassy solid after purification by flash column chromatography (eluting with a gradient of 20-100% EtOAc/heptane).

1H-NMR (DMSO-d6, 500 MHz): d[ppm]=8.51 (t, J=5.7 Hz, 1H), 8.37 (dt, J=4.6 and 1.5 Hz, 1H), 8.25 (s, 1H), 7.89 (s, 1H), 7.71-7.64 (m, 1H), 7.42-7.36 (m, 1H), 4.57 (dd, J=5.7, 1.5 Hz, 2H), 4.44-4.32 (m, 1H), 4.04-3.96 (m, 2H), 2.89 (br s, 2H), 2.01 (s, 2H), 1.74 (qd, J=12.4, 4.4 Hz, 2H), 1.41 (s, 9H)

HPLCMS (Method A): [m/z]: 404.1 [M+H]+

N-[(3-Fluoropyridin-2-yl)methyl]-1-(piperidin-4-yl)-1H-pyrazole-4-carboxamide Dihydrochloride (274)

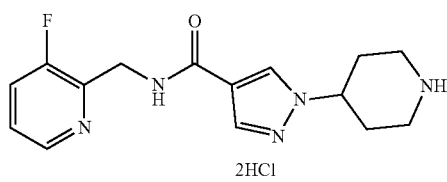 [SMILES: O=C(NCc1ncccc1F)c1cnn(C2CCNCC2)c1]

In a similar fashion using general procedure 2, 12M HCl (1.1 ml) and tert-butyl 4-(4-{[(3-fluoropyridin-2-yl)methyl]carbamoyl}-1H-pyrazol-1-yl)piperidine-1-carboxylate (273) (315 mg, 0.664 mmol) in MeOH (4 ml) at 35° C. for 16 h gave the title compound (277 mg) as an off-white solid. The compound was used in the next step without further purification.

1H-NMR (Methanol-d4, 500 MHz): d[ppm]=8.54-8.47 (m, 1H), 8.22 (d, J=2.4 Hz, 1H), 8.00-8.11 (m, 1H), 7.98 (s, 1H), 7.69-7.78 (m, 1H), 4.80 (s, 2H), 4.66-4.56 (m, 1H), 3.56 (dt, J=13.1, 3.4 Hz, 2H), 3.22 (td, J=12.8, 3.4 Hz, 2H), 2.38-2.19 (m, 4H)

HPLCMS (Method A): [m/z]: 304 [M+H]+

1-[1-(1H-1,3-Benzodiazol-2-ylmethyl)piperidin-4-yl]-N-[(3-fluoropyridin-2-yl)methyl]-1H-pyrazole-4-carboxamide (Example Compound No. 150)

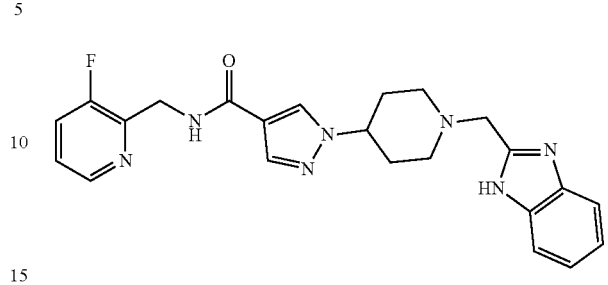

In a similar fashion to general procedure 7, 2-(Chloromethyl)-1H-benzimidazole (71 mg, 0.424 mmol), N-[(3-fluoropyridin-2-yl)methyl]-1-(piperidin-4-yl)-1H-pyrazole-4-carboxamide (274) (99 mg, 0.326 mmol) and DIPEA (0.171 ml, 0.98 mmol) in DMF (2 ml) at 30° C. for 16 h, gave the title compound (21 mg, 15%) as a white solid after purification by basic prep-HPLC followed by further purification by flash column chromatography (kp-NH, eluting with a gradient of 0-20% MeOH/EtOAc).

1H-NMR (DMSO-d6, 500 MHz): d[ppm]=12.28 (s, 1H), 8.52 (t, J=5.7 Hz, 1H), 8.37 (dt, J=4.6, 1.5 Hz, 1H), 8.22 (s, 1H), 7.89 (s, 1H), 7.71-7.65 (m, 1H), 7.54 (br s, 1H), 7.44 (br s, 1H), 7.42-7.36 (m, 1H), 7.14 (br s, 2H), 4.58 (dd, J=5.7, 1.6 Hz, 2H), 4.26-4.12 (m, 1H), 3.77 (s, 2H), 2.95 (d, J=12.0 Hz, 2H), 2.32-2.23 (m, 2H), 2.05-1.94 (m, 4H)

HPLCMS (Method D): [m/z]: 434.3 [M+H]+

1-{1-[2-(1H-1,3-Benzodiazol-2-yl)ethyl]piperidin-4-yl}-N-[(3-fluoropyridin-2-yl)methyl]-1H-pyrazole-4-carboxamide (Example Compound No. 198)

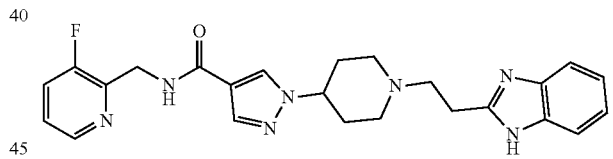

In a similar fashion to general procedure 8, DBU (0.28 ml, 1.89 mmol), N-[(3-fluoropyridin-2-yl)methyl]-1-(piperidin-4-yl)-1H-pyrazole-4-carboxamide dihydrochloride (274) (248 mg, 0.47 mmol) and N-(2-nitrophenyl)prop-2-enamide (D) (154 mg, 0.8 mmol) in MeCN (10 ml) at room temperature for 17 h gave the required intermediate (200 mg, 82%) after purified by flash column chromatography (eluting with a gradient of 0-25% MeOH/EtOAc) to give the title compound as a yellow solid.

HPLCMS (Method A): [m/z]: 496.1 [M+H]+

The intermediate was further treated with iron powder (87 mg, 1.56 mmol) in AcOH (3 ml) at 80° C. for 1.5 h, to give the title compound (72 mg, 33%) as an off-white solid after purification by flash column chromatography eluting with 0 to 20% MeOH/DCM.

1H-NMR (DMSO-d6, 500 MHz): d[ppm]=12.14 (s, 1H), 8.51 (t, J=5.7 Hz, 1H), 8.38 (dt, J=4.6, 1.5 Hz, 1H), 8.24 (s, 1H), 7.89 (s, 1H), 7.72-7.65 (m, 1H), 7.51 (s, 1H), 7.46-7.37 (m, 2H), 7.11 (d, J=5.1 Hz, 2H), 4.58 (dd, J=5.7, 1.6 Hz, 2H), 4.22-4.12 (m, 1H), 3.07-2.96 (m, 4H), 2.82 (t, J=7.5

Hz, 2H), 2.23-2.14 (m, 2H), 2.05-1.97 (m, 2H), 1.95-1.86 (m, 2H)

HPLCMS (Method C): [m/z]: 448.3 [M+H]+

Tert-butyl 3-{[4-(ethoxycarbonyl)-1H-pyrazol-1-yl]methyl}piperidine-1-carboxylate (275)

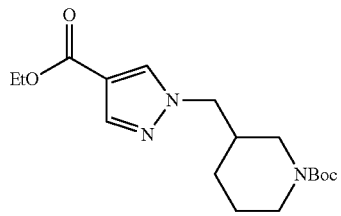 [SMILES: CC(C)(C)OC(=O)N1CCCC(Cn2cc(C(=O)O)cn2)C1]

Ethyl 1H-pyrazole-4-carboxylate (334 mg, 2.38 mmol), tert-butyl 3-(hydroxymethyl)piperidine-1-carboxylate (667 mg, 3.1 mmol) and triphenylphosphine (1.25 g, 4.8 mmol) were dissolved in THF (30 ml) and cooled in an ice-water bath. DIAD (0.94 ml, 4.8 mmol) was added dropwise. The mixture was stirred whilst warming to room temperature for 18 h. The reaction mixture was diluted with ethyl acetate (80 ml) and washed with sat.NaHCO$_3$(aq) (50 ml) and brine (50 ml). The organic phase was dried (Na$_2$SO$_4$), filtered and evaporated in vacuo. Purification by flash chromatography using a gradient elution of 0-40% EtOAc/heptane gave the crude title compound (2.23 g) as a colourless oil. The crude product was used in the next step without further purification.

HPLCMS (Method A): [m/z]: 338.15 [M+H]+

1-({1-[(Tert-butoxy)carbonyl]piperidin-3-yl}methyl)-1H-pyrazole-4-carboxylic Acid (276)

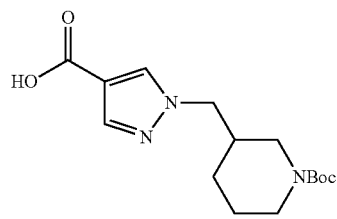

In a similar fashion using general procedure 5, tert-butyl 3-{[4-(ethoxycarbonyl)-1H-pyrazol-1-yl]methyl}piperidine-1-carboxylate (275) (2.23 g, 4.69 mmol, 71% purity) and LiOH (1.12 g, 0.05 mol) in THF/water (20 ml/20 ml) gave the crude product (638 mg, 16%, 38% purity) as a colourless oil.

HPLCMS (Method A): [m/z]: 310.05 [M+H]+

Tert-butyl 3-[(4-{[(3-fluoropyridin-2-yl)methyl]carbamoyl}-1H-pyrazol-1-yl)methyl]piperidine-1-carboxylate (277)

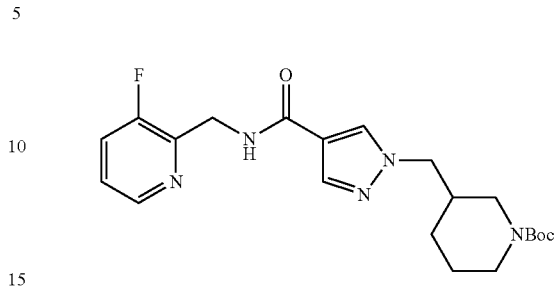

In a similar fashion using general procedure 6, 1-({1-[(tert-butoxy)carbonyl]piperidin-3-yl}methyl)-1H-pyrazole-4-carboxylic acid (276) (0.638 g, 2.06 mmol), (3-fluoropyridin-2-yl)methanamine dihydrochloride (A2) (0.451 g, 2.27 mmol), DIPEA (1.26 ml, 7.2 mmol) and HATU (1.18 g, 3.1 mmol) in THF (40 ml) and DMF (5 ml) gave the crude title compound (0.348 g, 32%, 79% purity) as a hygroscopic yellow solid after purification by flash column chromatography (eluting with a gradient of 0-100% EtOAc/heptane followed by 4-8% MeOH/EtOAc).

HPLCMS (Method A): [m/z]: 418.15 [M+H]+

N-[(3-Fluoropyridin-2-yl)methyl]-1-(piperidin-3-ylmethyl)-1H-pyrazole-4-carboxamide (278)

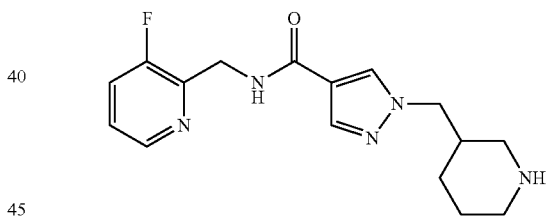

In a similar fashion using general procedure 2, tert-butyl 3-[(4-{[(3-fluoropyridin-2-yl)methyl]carbamoyl}-1H-pyrazol-1-yl)methyl]piperidine-1-carboxylate (277) (348 mg, 0.83 mmol) and 12 M HCl (0.69 ml) gave the title compound (182 mg, 64%) as the free base after purification using an SCX-2 cartridge, rinsing with DCM and MeOH, then elution with 7 N ammonia in MeOH.

1H-NMR (Methanol-d4, 500 MHz): d[ppm]=8.36 (dt, J=4.7, 1.1 Hz, 1H), 8.18 (s, 1H), 7.97 (s, 1H), 7.60 (ddd, J=9.8, 8.4, 1.2 Hz, 1H), 7.39 (dt, J=8.6, 4.4 Hz, 1H), 4.73 (d, J=1.5 Hz, 2H), 4.18 (td, J=7.1, 2.6 Hz, 2H), 3.29-3.22 (m, 1H), 3.19-3.13 (m, 1H), 2.81 (td, J=12.5, 3.1 Hz, 1H), 2.70 (t, J=12.1 Hz, 1H), 2.42-2.30 (m, 1H), 1.94-1.85 (m, 1H), 1.83-1.66 (m, 2H), 1.35-1.22 (m, 1H)

HPLCMS (Method A): [m/z]: 318.10 [M+H]+

1-{[1-(1H-1,3-Benzodiazol-2-ylmethyl)piperidin-3-yl]methyl}-N-[(3-fluoropyridin-2-yl)methyl]-1H-pyrazole-4-carboxamide (Example Compound No. 153)

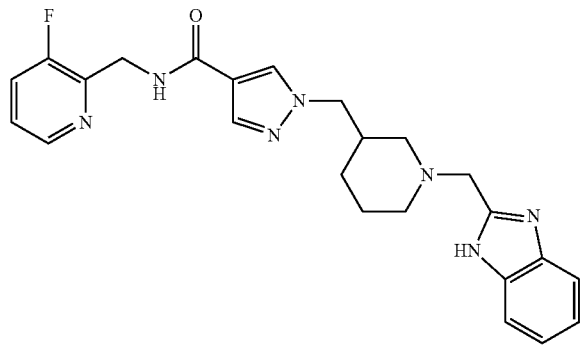 [SMILES: O=C(NCc1ncccc1F)c1cnn(CC2CCCN(Cc3nc4ccccc4[nH]3)C2)c1]

In a similar fashion using general procedure 7, N-[(3-fluoropyridin-2-yl)methyl]-1-(piperidin-3-ylmethyl)-1H-pyrazole-4-carboxamide (278) (180 mg, 0.57 mmol), 2-(chloromethyl)-1H-1,3-benzodiazole (189 mg, 1.13 mmol) and DIPEA (180 mg, 1.4 mmol) in DMF (8 ml) gave the title compound (66 mg, 25%) after purification by basic prep-HPLC.

1H-NMR (DMSO-d6, 500 MHz): d[ppm]=12.20 (s, 1H), 8.54 (t, J=5.7 Hz, 1H), 8.37 (dt, J=4.6, 1.2 Hz, 1H), 8.16 (s, 1H), 7.88 (s, 1H), 7.71-7.65 (m, 1H), 7.53 (d, J=7.4 Hz, 1H), 7.45-7.36 (m, 2H), 7.18-7.07 (m, 2H), 5.75 (s, 0H), 4.60-4.54 (m, 2H), 4.12-3.99 (m, 2H), 3.67 (q, J=14.0 Hz, 2H), 2.71-2.62 (m, 3H), 2.17-2.04 (m, 2H), 1.96 (t, J=10.4 Hz, 1H), 1.67-1.58 (m, 1H), 1.54-1.38 (m, 2H), 1.05-0.91 (m, 1H)

HPLCMS (Method C): [m/z]: 448.3 [M+H]$^+$

Ethyl 1-({1-[(tert-butoxy)carbonyl]azetidin-3-yl}methyl)-1H-pyrazole-4-carboxylate (279)

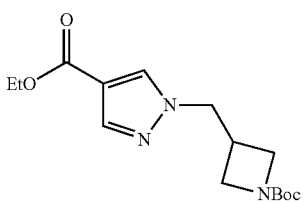 [SMILES: CCOC(=O)c1cnn(CC2CN(C(=O)OC(C)(C)C)C2)c1]

Ethyl 1H-pyrazole-4-carboxylate (0.55 g, 3.92 mmol), tert-butyl 3-(bromomethyl)azetidine-1-carboxylate (0.982 g, 3.92 mmol) and potassium carbonate (1.08 g, 8 mmol) in DMF (10 ml) were stirred at room temperature for 16 h. The mixture was diluted with water and extracted with EtOAc (3×50 ml). The combined organic extracts were washed with brine (4×50 ml), dried (Na$_2$SO$_4$), filtered and evaporated in vacuo to yield the title compound (1.33 g) as a pale yellow oil.

1H-NMR (CDCl$_3$, 500 MHz): d[ppm]=7.92 (s, 1H), 7.90 (s, 1H), 4.38-4.26 (m, 4H), 4.06 (t, J=9.0 Hz, 2H), 3.74 (dd, J=9.0, 5.1 Hz, 2H), 3.17-3.01 (m, 1H), 1.46 (s, 9H), 1.37 (t, J=7.1 Hz, 3H)

HPLCMS (Method A): [m/z]: 310.15 [M+H]$^+$

1-({1-[(Tert-butoxy)carbonyl]azetidin-3-yl}methyl)-1H-pyrazole-4-carboxylic Acid (280)

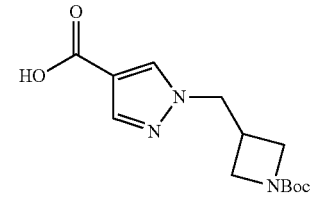 [SMILES: CC(C)(C)OC(=O)N1CC(Cn2cc(C(=O)O)cn2)C1]

In a similar fashion using general procedure 5, LiOH (2.06 g, 86 mmol) and ethyl 1-({1-[(tert-butoxy)carbonyl]azetidin-3-yl}methyl)-1H-pyrazole-4-carboxylate (279) (1.33 g, 4.3 mmol) in THF (30 ml) and water (30 ml) gave the title compound (1.02 g, 83%) as a white solid.

1H-NMR (CDCl$_3$, 500 MHz): d[ppm]=12.31 (s, 1H), 8.31 (s, 1H), 7.81 (s, 1H), 4.36 (d, J=7.3 Hz, 2H), 3.94-3.81 (m, 2H), 3.72-3.61 (m, 2H), 3.07-2.89 (m, 1H), 1.37 (s, 9H)

HPLCMS (Method A): [m/z]: 304.05 [M+Na]$^+$

Tert-butyl 3-[(4-{[(3-fluoropyridin-2-yl)methyl]carbamoyl}-1H-pyrazol-1-yl)methyl]azetidine-1-carboxylate (281)

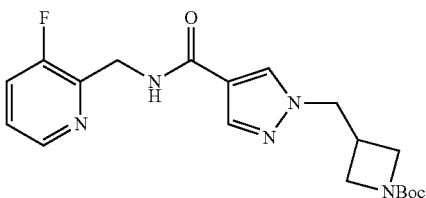 [SMILES: CC(C)(C)OC(=O)N1CC(Cn2cc(C(=O)NCc3ncccc3F)cn2)C1]

In a similar fashion using general procedure 6, 1-({1-[(tert-butoxy)carbonyl]azetidin-3-yl}methyl)-1H-pyrazole-4-carboxylic acid (280) (500 mg, 1.78 mmol), (3-fluoropyridin-2-yl)methanamine dihydrochloride (A2) (389 mg, 1.96 mmol), DIPEA (1.1 ml, 6 mmol) and HATU (740 mg, 2 mmol) in DCM (30 ml) gave the title compound (624 mg, 89%) as a colourless oil after purification by flash column chromatography using a gradient elution of 50 to 100% EtOAc/heptane followed by 0 to 10% MeOH/EtOAc.

1H-NMR (CDCl$_3$, 500 MHz): d[ppm]=8.32 (dt, J=4.7, 1.1 Hz, 1H), 7.84 (s, 1H), 7.79 (s, 1H), 7.35 (m, 1H), 7.24-7.20 (m, 1H), 4.71 (dd, J=4.5, 1.3 Hz, 2H), 4.27 (d, J=7.6 Hz, 2H), 3.97 (t, J=8.6 Hz, 2H), 3.66 (dt, J=7.6, 3.9 Hz, 2H), 3.02-2.98 (m, 1H), 1.36 (s, 9H)

HPLCMS (Method A): [m/z]: 390.1 [M+H]$^+$

1-(Azetidin-3-ylmethyl)-N-[(3-fluoropyridin-2-yl)methyl]-1H-pyrazole-4-carboxamide (282)

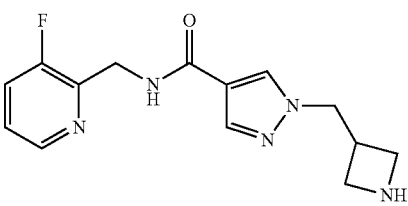 [SMILES: O=C(NCc1ncccc1F)c1cnn(CC2CNC2)c1]

In a similar fashion using general procedure 2, tert-butyl 3-[(4-{[(3-fluoropyridin-2-yl)methyl]carbamoyl}-1H-pyrazol-1-yl)methyl]azetidine-1-carboxylate (281) (624 mg, 1.6 mmol) and 12 M HCl (2 ml) in MeOH (20 ml) gave the free base title compound (248 mg, 54%) as a white solid after purification using an SCX-2 cartridge, rinsing with DCM and MeOH, then elution with 7 N ammonia in MeOH.

1H-NMR (CDCl$_3$, 500 MHz): d[ppm]=8.42 (d, J=4.6 Hz, 1H), 7.94 (s, 1H), 7.88 (s, 1H), 7.44 (t, J=9.3 Hz, 1H), 7.34-7.25 (m, 1H), 4.81 (d, J=4.2 Hz, 2H), 4.42 (d, J=7.4 Hz, 2H), 3.82 (t, J=8.2 Hz, 2H), 3.55-3.47 (m, 2H), 3.28 (m, 1H)

HPLCMS (Method A): [m/z]: 290 [M+H]$^+$

1-{[1-(1H-1,3-Benzodiazol-2-ylmethyl)azetidin-3-yl]methyl}-N-[(3-fluoropyridin-2-yl)methyl]-1H-pyrazole-4-carboxamide (Example Compound No. 187)

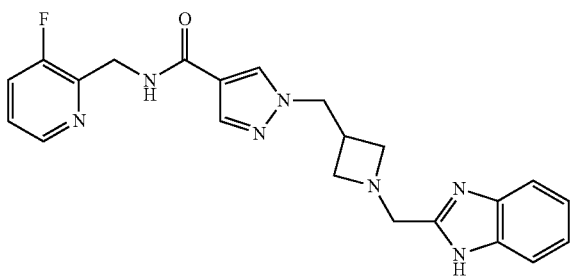 [SMILES: O=C(NCc1ncccc1F)c1cnn(CC2CN(Cc3nc4ccccc4[nH]3)C2)c1]

In a similar fashion using general procedure 3, 1-(azetidin-3-ylmethyl)-N-[(3-fluoropyridin-2-yl)methyl]-1H-pyrazole-4-carboxamide (281) (50 mg, 0.17 mmol), 1H-benzimidazole-2-carbaldehyde (37.9 mg, 0.26 mmol), DIPEA (0.06 ml, 0.34 mmol) and MgSO$_4$ (300 mg) in MeOH (5 ml) at room temperature for 18 h, followed by addition of NaBH$_4$ (7 mg, 0.17 mmol) afforded the title compound (32 mg, 43%) as pale yellow solid after purification by basic prep-HPLC.

1H-NMR (DMSO-d6, 500 MHz): d[ppm]=12.08 (s, 1H), 8.54 (t, J=5.7 Hz, 1H), 8.37 (dt, J=4.6, 1.4 Hz, 1H), 8.18 (s, 1H), 7.87 (s, 1H), 7.68 (ddd, J=10.1, 8.3, 1.3 Hz, 1H) 7.47 (s, 2H), 7.40 (dt, J=8.6, 4.4 Hz, 1H), 7.15-7.10 (m, 2H), 4.57 (dd, J=5.6, 1.5 Hz, 2H), 4.35 (d, J=7.5 Hz, 2H), 3.77 (s, 2H), 3.38 (t, J=7.5 Hz, 2H), 3.12-3.05 (m, 2H), 2.89-2.79 (m, 1H)

HPLCMS (Method C): [m/z]: 420.1 [M+H]$^+$ 1-({1-[2-(1H-1,3-Benzodiazol-2-yl)ethyl]azetidin-3-yl}methyl)-N-[(3-fluoropyridin-2-yl)methyl]-1H-pyrazole-4-carboxamide [Example Compound No. 192]

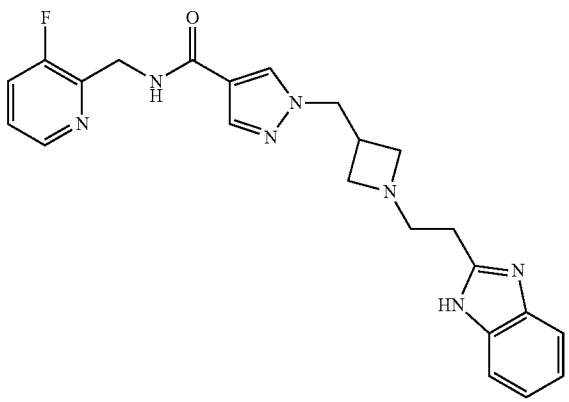 [SMILES: O=C(NCc1ncccc1F)c1cnn(CC2CN(CCc3nc4ccccc4[nH]3)C2)c1]

In a similar fashion using general procedure 8, 1-(azetidin-3-ylmethyl)-N-[(3-fluoropyridin-2-yl)methyl]-1H-pyrazole-4-carboxamide (281) (200 mg, 0.69 mmol), N-(2-nitrophenyl)prop-2-enamide (D) (139.5 mg, 0.73 mmol) and DBU (0.12 ml, 0.83 mmol) in MeCN (10 ml) gave the crude intermediate which was further reacted with iron powder (130 mg) in AcOH (3 ml). Purification by basic prep-HPLC followed by flash column chromatography (eluting with a gradient of 0-20% MeOH/DCM) gave the title compound (67 mg, 25%) as a white solid.

1H-NMR (Methanol-d4, 500 MHz): d[ppm]=8.36 (dt, J=4.5, 1.3 Hz, 1H), 8.12 (s, 1H), 7.93 (s, 1H) 7.61 (ddd, J=9.8, 8.5, 1.3 Hz, 1H), 7.52 (td, J=6.1, 3.1 Hz, 2H), 7.40 (dt, J=8.5, 4.5 Hz, 1H), 7.24-7.17 (m, 2H), 4.73 (d, J=1.6 Hz, 2H), 4.37 (d, J=7.2 Hz, 2H), 3.45 (t, J=7.9 Hz, 2H), 3.14-3.07 (m, 2H), 3.00 (dq, J=13.8, 7.0 Hz, 1H), 2.94 (s, 4H)

HPLCMS (Method C): [m/z]: 434.2 [M+H]$^+$

General Scheme 16 Above

Methyl 1H-pyrazole-4-carboxylate (282)

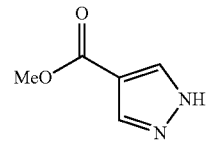

1H-pyrazole-4-carboxylic acid (20 g, 178.4 mmol) and sulfuric acid (39.65 ml) in MeOH (200 ml) were heated at 70° C. for 20 h. The reaction mixture was cooled to room temperature and concentrated in vacuo. Aqueous NaOH solution was added to adjust the pH to ~6. The aqueous layer was extracted with EtOAc (3×200 ml) and the combined organic extracts were dried (MgSO$_4$), filtered and evaporated in vacuo to afford the title compound (18.5 g, 78%) as a white solid.

1H-NMR (CDCl$_3$, 500 MHz): d[ppm]=8.10 (s, 2H), 3.87 (s, 3H)

HPLCMS (Method A): [m/z]: 126.85 [M+H]$^+$

467

Methyl 1-[1-(diphenylmethyl)azetidin-3-yl]-1H-pyrazole-4-carboxylate (283)

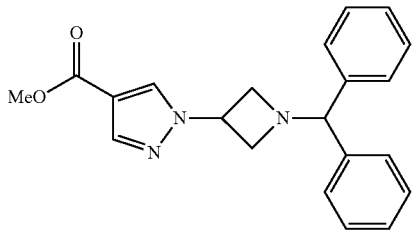 [SMILES: COC(=O)c1cnn(C2CN(C(c3ccccc3)c3ccccc3)C2)c1]

A suspension of methyl 1H-pyrazole-4-carboxylate (282) (3.34 g, 26.48 mmol), 1-(diphenylmethyl)azetidin-3-yl methanesulfonate (10.93 g, 34.43 mmol) and potassium carbonate (10.98 g, 79 mmol) in DMF (70 ml) was heated at 100° C. for 3 h. The reaction mixture was cooled to room temperature and diluted with water (150 ml). The mixture was extracted with EtOAc (3×150 ml), the combined organic extracts were washed with brine (5×100 ml), dried (Na₂SO₄), filtered and evaporated in vacuo. The residue was flushed through a plug of silica (~15 g) (eluting with 10-20% EtOAc/heptane), the eluent was evaporated in vacuo and the title compound (4.03 g, 44%) obtained as a white solid after precipitation from EtOAc/heptane.

1H-NMR (CDCl₃, 250 MHz): d[ppm]=8.14 (s, 1H), 7.96 (s, 1H), 7.49-7.42 (m, 4H), 7.36-7.17 (m, 6H), 4.98 (m, 1H), 4.54 (s, 1H), 3.86 (s, 3H), 3.75-3.69 (td, J=7.2, 1.5 Hz, 2H), 3.54-3.45 (m, 2H)

HPLCMS (Method A): [m/z]: 348.10 [M+H]⁺

1-[1-(Diphenylmethyl)azetidin-3-yl]-1H-pyrazole-4-carboxylic Acid (284)

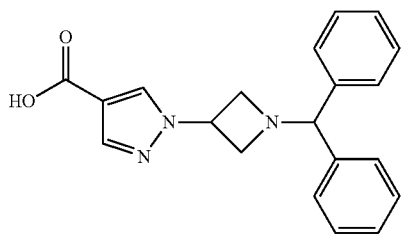 [SMILES: O=C(O)c1cnn(C2CN(C(c3ccccc3)c3ccccc3)C2)c1]

In a similar fashion to general procedure 5, methyl 1-[1-(diphenylmethyl)azetidin-3-yl]-1H-pyrazole-4-carboxylate (283) (2.1 g, 6.04 mmol) and LiOH (1.45 g, 60 mmol) in THF/water (20 ml/20 ml) afforded the title compound (1.95 g, 93%) as a white solid.

1H-NMR (CDCl₃, 250 MHz): d[ppm]=8.15 (s, 1H), 8.04 (s, 1H), 7.82-7.70 (m, 4H), 7.51-7.37 (m, 6H), 5.65-5.55 (m, 1H), 5.55-5.42 (m, 1H), 4.84-4.69 (m, 2H), 4.39-4.25 (m, 2H)

HPLCMS (Method A): [m/z]: 334.1 [M+H]⁺

468

1-[1-(Diphenylmethyl)azetidin-3-yl]-N-[(3-fluoropyridin-2-yl)methyl]-1H-pyrazole-4-carboxamide (285)

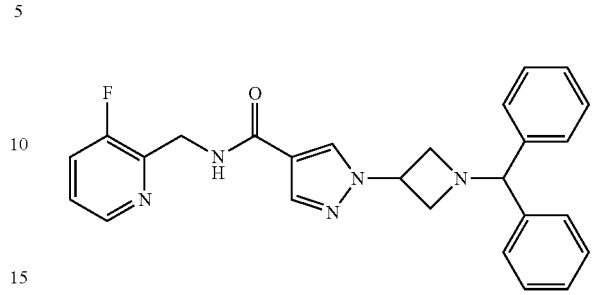

In a similar fashion to general procedure 6, 1-[1-(diphenylmethyl)azetidin-3-yl]-1H-pyrazole-4-carboxylic acid (284) (1.18 g, 2.46 mmol), (3-fluoropyridin-2-yl)methanamine dihydrochloride (A2) (0.587 g, 2.95 mmol), DIPEA (1.71 ml, 9.82 mmol) and HATU (1.21 g, 3.19 mmol) in THF (50 ml) and DMF (10 ml) afforded the title compound (1.06 g, 82%) as a yellow solid after purification by flash column chromatography (eluting with a gradient of 60-100% EtOAc/heptane).

1H-NMR (DMSO-d6, 500 MHz): d[ppm]=8.59 (t, J=5.7 Hz, 1H), 8.40 (s, 1H), 8.37 (d, J=4.6 Hz, 1H), 7.93 (s, 1H), 7.68 (t, J=9.3 Hz, 1H), 7.47 (m, 4H), 7.39 (m, 1H), 7.29 (t, J=7.6 Hz, 4H), 7.19 (t, J=7.3 Hz, 2H), 5.04 (p, J=6.8 Hz, 1H), 4.62-4.56 (m, 3H), 3.59 (t, J=7.7 Hz, 2H), 3.35 (s, 2H)

HPLCMS (Method A): [m/z]: 442.15 [M+H]⁺

N-{5H,6H,7H-Cyclopenta[b]pyridin-7-yl}-1-[1-(diphenylmethyl)azetidin-3-yl]-1H-pyrazole-4-carboxamide (286)

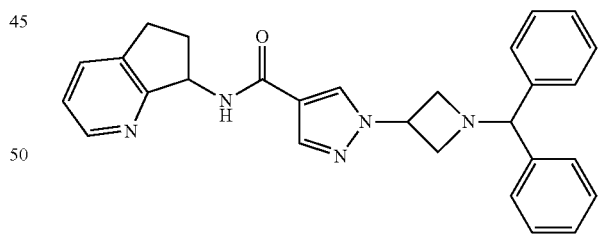

In a similar fashion to general procedure 6 1-[1-(diphenylmethyl)azetidin-3-yl]-1H-pyrazole-4-carboxylic acid (284) (500 mg, 1.5 mmol), 5H,6H,7H-cyclopenta[b]pyridin-7-amine dihydrochloride (404 mg, 1.95 mmol), DIPEA (0.86 ml, 5 mmol) and HATU (0.74 g, 2 mmol) in DCM (20 ml) afforded the crude title compound (949 mg) as a white residue which was used in the next step without further purification.

HPLCMS (Method A): [m/z]: 450.15 [M+H]⁺

1-(Azetidin-3-yl)-N-[(3-fluoropyridin-2-yl)methyl]-1H-pyrazole-4-carboxamide (287)

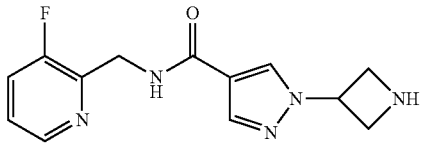 [SMILES: O=C(NCc1ncccc1F)c1cnn(C2CNC2)c1]

1-[1-(diphenylmethyl)azetidin-3-yl]-N-[(3-fluoropyridin-2-yl)methyl]-1H-pyrazole-4-carboxamide (285) (1.06 g, 2.01 mmol) and Pd/C (10%) (0.20 g, 0.201 mmol) were suspended in EtOH (11 ml). A solution of TEA (0.849 ml, 6.04 mmol) and formic acid (0.228 ml 6.04 mmol) in EtOH (11 ml) was added and the reaction mixture was stirred at reflux for 2 h. The mixture was cooled to room temperature, filtered through a plug of Celite and the residue rinsed with MeOH (10 ml). The filtrate was evaporated in vacuo to afford the crude material. Purification using a SCX-2 cartridge, washing with DCM and MeOH and eluting with 7 N ammonia/MeOH gave the title compound (0.354 g, 56%) as a colourless oil.

1H-NMR (DMSO-d6, 500 MHz): d[ppm]=8.57 (t, J=5.6 Hz, 1H), 8.37 (d, J=4.6 Hz, 1H), 8.34 (s, 1H), 7.93 (s, 1H), 7.72-7.65 (m, 1H), 7.40 (dd, J=8.5, 4.3 Hz, 1H), 5.18 (p, J=7.3 Hz, 1H), 4.58 (dd, J=5.6, 1.4 Hz, 2H), 3.84 (t, J=7.7 Hz, 2H), 3.73 (t, J=8.1 Hz, 2H)

HPLCMS (Method A): [m/z]: 276.1 [M+H]$^+$

1-(Azetidin-3-yl)-N-{5H,6H,7H-cyclopenta[b]pyridin-7-yl}-1H-pyrazole-4-carboxamide (288)

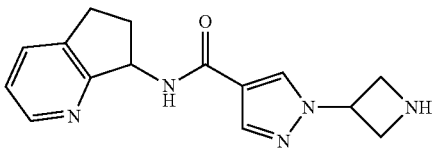 [SMILES: O=C(NC1CCc2cccnc21)c1cnn(C2CNC2)c1]

Crude N-{5H,6H,7H-cyclopenta[b]pyridin-7-yl}-1-[1-(diphenylmethyl)azetidin-3-yl]-1H-pyrazole-4-carboxamide (286) (949 mg) and palladium (10% wt. on carbon, 0.12 g, 0.11 mmol) were suspended in EtOH (20 ml). TEA (454 µL, 3 mmol) and formic acid (125 µL, 3 mmol) in EtOH (20 ml) were added and the mixture heated at reflux for 1 h. The reaction mixture was cooled to room temperature and filtered through a plug of Celite. The residue was rinsed with MeOH and the combined filtrates evaporated in vacuo. The residue was dissolved in a minimum amount of MeOH and purified by passage through an SCX-2 cartridge, rinsing with DCM and MeOH and elution with 7 N ammonia in MeOH. Evaporation d the basic eluent afforded the title compound (342 mg, quant) as a white solid.

1H-NMR (DMSO-d6, 500 MHz): d[ppm]=8.40-8.34 (m, 3H), 7.94 (s, 1H), 7.68 (d, J=7.6 Hz, 1H), 7.22 (dd, J=7.6, 4.9 Hz, 1H), 5.48-5.40 (m, 1H), 5.18 (m, 1H), 3.88-3.81 (m, 2H), 3.78-3.71 (m, 2H), 2.98 (ddd, J=16.0, 8.9, 3.0 Hz, 1H), 2.86 (dt, J=16.0, 8.3 Hz, 2H), 2.47 (dd, J=6.5, 4.8 Hz, 1H), 1.95-1.84 (m, 1H)

HPLCMS (Method A): [m/z]: 284.05 [M+H]$^+$

1-[1-(1H-1,3-Benzodiazol-2-ylmethyl)azetidin-3-yl]-N-[(3-fluoropyridin-2-yl)methyl]-1H-pyrazole-4-carboxamide (Example Compound No. 136)

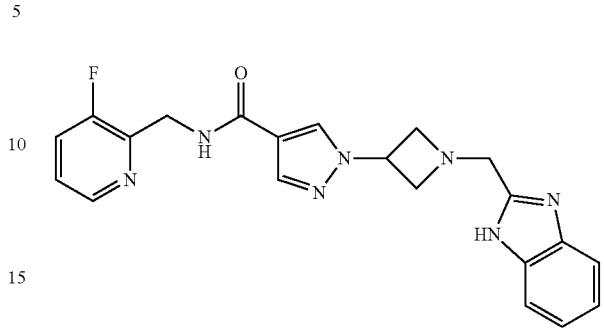

In a similar fashion using general procedure 3, 1-(azetidin-3-yl)-N-[(3-fluoropyridin-2-yl)methyl]-1H-pyrazole-4-carboxamide (287) (196 mg, 0.71 mmol), 1H-1,3-benzodiazole-2-carbaldehyde (125 mg, 0.85 mmol) and MgSO$_4$ (100 mg) in MeOH (8 ml) at room temperature for 3 d, followed by addition of NaBH$_4$ (81 mg, 2.1 mmol) afforded the title compound (82 mg, 28%) as a white solid after purification by basic prep-HPLC.

1H-NMR (DMSO-d6, 500 MHz): d[ppm]=12.32 (s, 1H), 8.58 (t, J=5.7 Hz, 1H), 8.43 (s, 1H), 8.39-8.37 (m, 1H), 7.96 (s, 1H), 7.69 (ddd, J=10.0, 8.3, 1.2 Hz, 1H), 7.61-7.45 (m, 2H), 7.40 (dt, J=8.6, 4.4 Hz, 1H), 7.17-7.10 (m, 2H), 5.06 (m, 1H), 4.59 (dd, J=5.7, 1.5 Hz, 2H), 3.92 (s, 2H), 3.85-3.81 (m, 2H), 3.61-3.57 (m, 2H)

HPLCMS (Method C): [m/z]: 406.2 [M+H]$^+$

1-{1-[2-(1H-1,3-Benzodiazol-2-yl)ethyl]azetidin-3-yl}-N-[(3-fluoropyridin-2-yl)methyl]-1H-pyrazole-4-carboxamide (Example Compound No. 167)

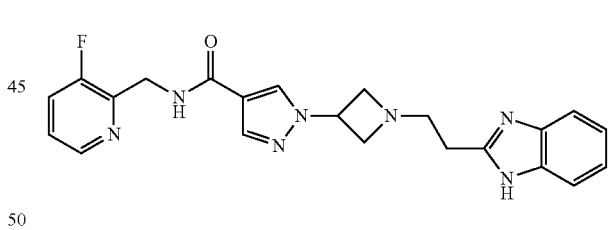

In a similar fashion to general procedure 8, 1-(azetidin-3-yl)-N-[(3-fluoropyridin-2-yl)methyl]-1H-pyrazole-4-carboxamide (287) (364 mg, 1.32 mmol), N-(2-nitrophenyl)prop-2-enamide (D) (254 mg, 1.32 mmol) and DBU (0.197 ml, 1.32 mmol) in MeCN (12 ml) gave the crude intermediate which was following treatment with AcOH (8 ml) and iron powder (62 mg) gave the title compound (104 mg, 43%) as a white solid after purification by basic prep-HPLC.

1H-NMR (DMSO-d6, 500 MHz): d[ppm]=12.15 (s, 1H), 8.56 (t, J=5.7 Hz, 1H), 8.37 (d, J=4.6 Hz, 1H), 8.34 (s, 1H), 7.93 (s, 1H), 7.71-7.65 (m, 1H), 7.49 (br s, 1H), 7.45-7.37 (m, 2H), 7.14-7.07 (m, 2H), 4.98 (p, J=6.8 Hz, 1H), 4.59-4.56 (m, 2H), 3.69 (t, J=7.6 Hz, 2H), 3.38 (t, J=7.3 Hz, 2H), 2.94 (t, J=7.1 Hz, 2H), 2.85 (t, J=7.0 Hz, 2H)

HPLCMS (Method D): [m/z]: 420.3 [M+H]$^+$

1-{1-[2-(1H-1,3-Benzodiazol-2-yl)ethyl]azetidin-3-yl}-N-{5H,6H,7H-cyclopenta[b]pyridin-7-yl}-1H-pyrazole-4-carboxamide (Example Compound No. 191)

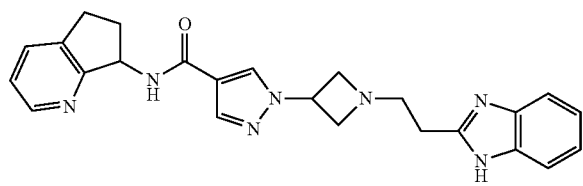 [SMILES: O=C(NC1CCc2cccnc21)c1cnn(C2CN(CCc3nc4ccccc4[nH]3)C2)c1]

In a similar fashion to general procedure 8, 1-(azetidin-3-yl)-N-{5H,6H,7H-cyclopenta[b]pyridin-7-yl}-1H-pyrazole-4-carboxamide (288) (342 mg, 1.21 mmol), N-(2-nitrophenyl)prop-2-enamide (D) (244 mg, 1.27 mmol) and DBU (0.22 ml, 1.5 mmol) in MeCN (10 ml) afforded a crude intermediate which was further reacted with iron powder (170 mg, 3 mmol) in AcOH (4 ml) to afford the title compound (145 mg, 44%) as a white solid after purification by basic prep-HPLC followed by flash column chromatography (eluting with a gradient of 0-20% MeOH/DCM).

1H-NMR (Methanol-d4, 500 MHz): d[ppm]=8.37 (d, J=5.0 Hz, 1H), 8.26 (s, 1H), 8.01 (s, 1H), 7.78-7.73 (m, 1H), 7.52 (dd, J=5.4, 3.0 Hz, 2H), 7.30 (dd, J=7.6, 5.0 Hz, 1H), 7.24-7.18 (m, 2H), 5.56 (t, J=8.2 Hz, 1H), 5.06 (m, 1H), 3.86 (td, J=7.3, 1.6 Hz, 2H), 3.64-3.58 (m, 2H), 3.11-3.07 (m, 3H), 3.03-2.92 (m, 3H), 2.69 (m, 1H), 2.02 (m, 1H)

HPLCMS (Method C): [m/z]: 428.2 [M+H]$^+$

General Scheme 18 Above:

Tert-butyl 2-(cyanomethyl)-1H-1,3-benzodiazole-1-carboxylate (296)

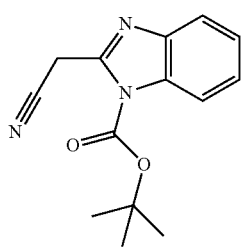 [SMILES: CC(C)(C)OC(=O)n1c(CC#N)nc2ccccc21]

2-(1H-1,3-benzodiazol-2-yl)acetonitrile (1 g, 6.36 mmol) and TEA (887 µl, 6.36 mmol) were dissolved in THF (20 ml) and BOC anhydride (1.64 g, 7.51 mmol) was added. The mixture was stirred at room temperature for 16 h. The reaction mixture was concentrated in vacuo. The residue was dissolved in chloroform and washed with 1 M HCl (aq) (50 ml), sat. NaHCO$_3$ (aq) (50 ml) and brine (50 ml). The organic phase was dried (Na$_2$SO$_4$), filtered and evaporated in vacuo. Purification by flash chromatography using an elution gradient 10-30% EtOAc/heptane afforded the title compound (923 mg, 56%) as an orange solid following trituration with DCM/heptane.

1H-NMR (CDCl$_3$, 250 MHz): d[ppm]=8.00-7.91 (m, 1H), 7.84-7.74 (m, 1H), 7.48-7.36 (m, 2H), 4.37 (s, 2H), 1.77 (s, 9H)

HPLCMS (Method A): [m/z]: 158.35 [M+H-Boc]$^+$

Tert-butyl 2-(2-{[(tert-butoxy)carbonyl]amino}ethyl)-1H-1,3-benzodiazole-1-carboxylate (297)

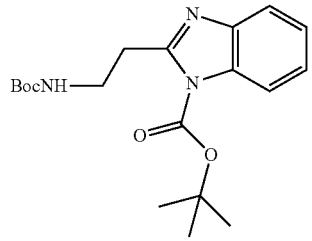 [SMILES: CC(C)(C)OC(=O)NCCc1nc2ccccc2n1C(=O)OC(C)(C)C]

A suspension of tert-butyl 2-(cyanomethyl)-1H-1,3-benzodiazole-1-carboxylate (296) (597 mg, 2.32 mmol), TEA (258 mg, 2.55 mmol), Boc$_2$O (557 mg, 2.55 mmol) and Pd (10% wt on carbon, 247 mg, 0.23 mmol) in EtOH (20 ml) was stirred under an atmosphere of hydrogen for 16 h. The reaction mixture was filtered through a plug of Celite and the residue rinsed with MeOH and 7 N ammonia in MeOH. The combined filtrates were evaporated in vacuo. Purification by flash chromatography using an elution gradient 0-60% EtOAc/heptane afforded the title compound (748 mg, 89%) as a white solid.

1H-NMR (CDCl$_3$, 250 MHz): d[ppm]=7.99-7.90 (m, 1H), 7.75-7.67 (m, 1H), 7.39-7.31 (m, 2H), 5.50 (s, 1H), 3.76 (q, J=5.7 Hz, 2H), 3.36 (t, J=5.7 Hz, 2H), 1.73 (s, 9H), 1.43 (s, 9H)

HPLCMS (Method A): [m/z]: 362.1 [M+H]$^+$

Ethyl 3-(bromomethyl)-1-methyl-1H-pyrazole-5-carboxylate (298)

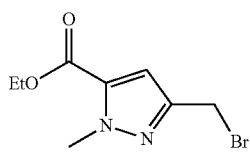

Ethyl 1,3-dimethyl-1H-pyrazole-5-carboxylate (433 mg, 2.57 mmol), NBS (0.623 g, 3.5 mmol) and AIBN (40 mg) in DCE (10 ml) was heated at 80° C. for 1.5 h. The reaction mixture was cooled to room temperature and evaporated in vacuo. Purification by flash chromatography using an edition gradient 0-10% Et$_2$O/heptane afforded the title compound (419 mg, 66%) as a white waxy solid.

1H-NMR (CDCl$_3$, 250 MHz): d[ppm]=6.90 (s, 1H), 4.48 (s, 2H), 4.36 (q, J=7.1 Hz, 3H), 4.18 (s, 3H), 1.40 (t, J=7.1 Hz, 3H)

HPLCMS (Method A): [m/z]: 246.75/248.75 [M+H]$^+$

Tert-butyl 2-(2-{[(tert-butoxy)carbonyl]({[5-(ethoxycarbonyl)-1-methyl-1H-pyrazol-3-yl]methyl})amino}ethyl)-1H-1,3-benzodiazale-1-carboxylate (299)

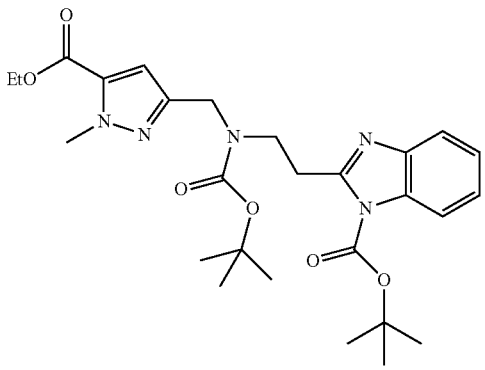 [SMILES: Cn1nc(CN(CCc2nc3ccccc3n2C(=O)OC(C)(C)C)C(=O)OC(C)(C)C)cc1C(=O)O]

Tert-butyl 2-(2-{[(tert-butoxy)carbonyl]amino}ethyl)-1H-1,3-benzodiazole-1-carboxylate (298) (263 mg, 0.73 mmol) in THF (5 ml) was cooled in an ice/water bath. NaBH$_4$ (60% in mineral oil, 60 mg, 1.5 mmol) was added and the mixture stirred for 5 min. Ethyl 3-(bromomethyl)-1-methyl-1H-pyrazole-5-carboxylate (297) (90 mg, 0.36 mmol) in THF (2 ml) was added, the mixture allowed to warm to room temperature and stirred for 10 min. The reaction mixture was quenched by dropwise addition of water, then further diluted with water and extracted with DCM (3×20 ml). The combined organic extracts were dried (Na$_2$SO$_4$), filtered and evaporated in vacuo. Purification by flash chromatography using an elution gradient 0-80% EtOAc/heptane afforded the title compound (126 mg, 66%) as a colourless oil.

1H-NMR (CDCl$_3$, 500 MHz): d[ppm]=7.68-7.62 (m, 1H), 7.32-7.27 (m, 1H), 7.18-7.13 (m, 2H), 6.43 (s, 1H), 5.26 (s, 2H), 4.19 (q, J=7.1 Hz, 2H), 4.09-4.06 (m, 2H), 4.05 (s, 3H), 3.18 (dd, J=8.4, 6.8 Hz, 2H), 1.39 (s, 18H), 1.23 (t, J=7.1 Hz, 3H)

HPLCMS (Method A): [m/z]: 528.2 [M+H]$^+$

3-({[(Tert-butoxy)carbonyl](2-{1-[(tert-butoxy)carbonyl]-1H-1,3-benzodiazol-2-yl}ethyl)amino}methyl)-1-methyl-1H-pyrazole-5-carboxylic Acid (300)

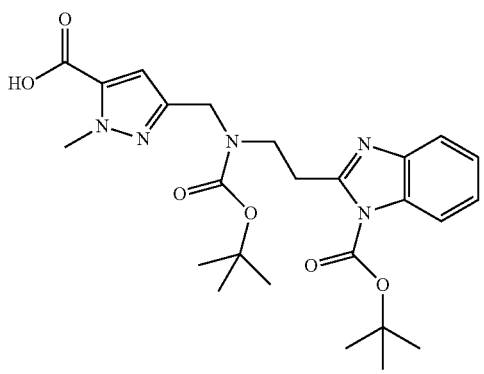

In a similar fashion to general procedure 5, tert-butyl 2-(2-{[(tert-butoxy)carbonyl]({[5-(ethoxycarbonyl)-1-methyl-1H-pyrazol-3-yl]methyl})amino}ethyl)-1H-1,3-benzodiazale-1-carboxylate (299) (126 mg, 0.24 mmol) and LiOH (17 mg, 0.72 mmol) in THF (5 ml) and water (5 ml) afforded the title compound (152 mg) as a pale yellow oil.

HPLCMS (Method A): [m/z]: 500.15 [M+H]$^+$

Tert-butyl 2-(2-{[(tert-butoxy)carbonyl][(5-{[(3-fluoropyridin-2-yl)methyl]carbamoyl}-1-methyl-1H-pyrazol-3-yl)methyl]amino}ethyl)-1H-1,3-benzodiazole-1-carboxylate (301)

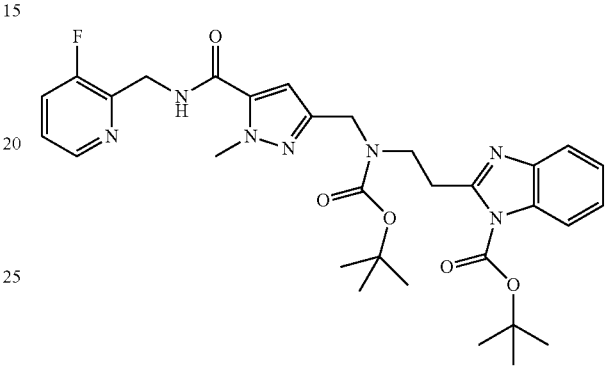

In a similar fashion to general procedure 6, tert-butyl 2-(2-{[(tert-butoxy)carbonyl]({[5-(ethoxycarbonyl)-1-methyl-1H-pyrazol-3-yl]methyl})amino}ethyl)-1H-1,3-benzodiazale-1-carboxylate (300) (130 mg, 0.26 mmol), (3-fluoropyridin-2-yl)methanamine dihydrochloride (A2) (57 mg, 0.29 mmol), DIPEA (150 µl, 0.86 mmol) and HATU (119 mg, 0.31 mmol) in DCM (10 ml) afforded the crude title compound (317 mg, 30% purity) as a white solid which was used in the next step without purification.

HPLCMS (Method A): [m/z]: 608.2 [M+H]$^+$

3-({[2-(1H-1,3-Benzodiazol-2-yl)ethyl]amino}methyl)-N-[(3-fluoropyridin-2-yl)methyl]-1-methyl-1H-pyrazole-5-carboxamide (Example Compound No. 220)

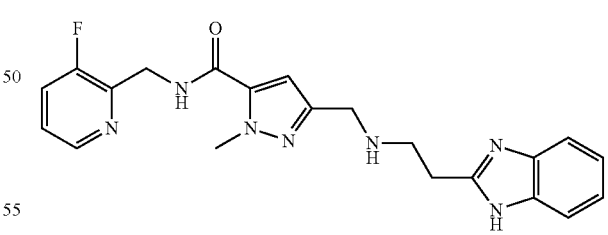

In a similar fashion to general procedure 2, tert-butyl 2-(2-{[(tert-butoxy)carbonyl][(5-{[(3-fluoropyridin-2-yl)methyl]carbamoyl}-1-methyl-1H-pyrazol-3-yl)methyl]amino}ethyl)-1H-1,3-benzodiazole-1-carboxylate (301) (30%, 317 mg, 0.16 mmol) and 12 M HCl (0.63 ml) in MeOH (5 ml) at 60° C. for 15 min afforded the title compound (44 mg, 69%) as a white solid after purification by basic prep-HPLC 1H-NMR (DMSO-d6, 500 MHz): d[ppm]=8.93 (m, 1H), 8.34 (dt, J=4.6, 1.4 Hz, 1H), 7.72-7.63 (m, 1H), 7.56 (m, 1H), 7.52 (dd, J=7.0, 1.4 Hz, 1H), 7.43-7.33 (m, 1H), 7.21-7.11 (m, 2H), 6.71 (s, 1H), 5.41 (s, 2H), 4.57-4.49 (m, 2H), 4.00 (s, 3H), 3.05-2.96 (m, 4H)

HPLCMS (Method C): [m/z]: 408.1 [M+H]+

General Scheme 19 Above

Methyl 2-bromo-1-methyl-1H-imidazole-4-carboxylate (302)

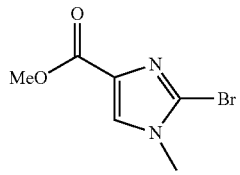

To a stirring solution of methyl 1-methyl-1H-imidazole-4-carboxylate (5 g, 46.38 mmol) in THF (100 ml) was added NBS (8.25 g, 46.38 mmol). The reaction mixture was allowed to stir at room temperature for 72 h. The mixture was concentrated and the crude residue was dissolved in EtOAc (80 ml), washed with sat.Na$_2$S$_2$O$_3$ (100 ml) and a ~pH 12 solution of NaOH (50 ml). The NaOH solution was extracted using 1:4 IPA:CHCl3 (5×10 ml) and the organic layers were combined, dried over MgSO$_4$, filtered and concentrated to give the crude product. Purification by column chromatography with a gradient of 0-100% EtOAc/heptane gave the purified product which was dissolved in a pH~12 solution of NaOH (50 ml) and extracted using DCM. The organic layers were combined, dried over MgSO$_4$, filtered and concentrated to give the title compound (5.58 g, 71%) as a white solid.

1H-NMR (DMSO-d6, 250 MHz): d[ppm]=8.08 (s, 1H), 3.74 (s, 3H), 3.63 (s, 3H)

HPLCMS (Method A): [m/z]: 218.8, 220.75 [M+H]+

Methyl 2-formyl-1-methyl-1H-imidazole-4-carboxylate (303)

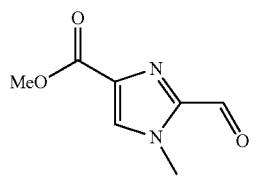

To an N$_2$ purged stirring solution of methyl 2-bromo-1-methyl-1H-imidazole-4-carboxylate (302) (200 mg, 0.91 mmol) in THF (1 ml) at −40° C. was added dropwise 2 M iPrMgCl in THF (3.31 ml, 6.62 mmol). After 20 min, the reaction was cooled to −78° C. and DMF (1.08 ml, 13.96 mmol) added dropwise. The reaction was allowed to warm to room temperature, after 40 min, the reaction was quenched with sat NaHCO$_3$ (10 ml) which gave a thick white emulsion. The product was extracted with EtOAc (5×10 ml). The combined organic layers were dried over MgSO$_4$, filtered and concentrated to give the crude product. Purification by silica flash column chromatography with a gradient of 0-70% EtOAc/heptane gave the title compound (128 mg, 66%) as a white solid.

1H-NMR (DMSO-d6, 250 MHz): d[ppm]=9.74 (d, J=0.7 Hz, 1H), 8.26 (s, 1H), 3.96 (s, 3H), 3.80 (s, 3H)

HPLCMS (Method A): [m/z]: 168.9 [M+H]+

Methyl 2-(1-hydroxy-2-nitroethyl)-1-methyl-1H-imidazole-4-carboxylate (304)

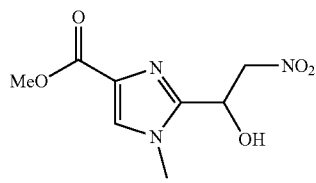 [SMILES: COC(=O)c1cn(C)c(C(O)C[N+](=O)[O-])n1]

To a stirring solution of methyl 2-formyl-1-methyl-1H-imidazole-4-carboxylate (303) (523 mg, 1.47 mmol), MeOH (12 ml) and nitromethane (78.9 μl, 1.47 mmol) followed by dropwise addition of 1 M NaOH solution (12 ml), the reaction was allowed to warm to room temperature over the duration of the experiment. After 1 h, the solution was acidified using 2 M HCl to ~pH 4 and concentrated to remove methanol. The aqueous layer was extracted with 1:4 IPA/CHCl$_3$ (4×10 ml) and the combined organic layers were dried over MgSO$_4$, filtered and concentrated to give the crude product, which was purified by silica flash column chromatography with a gradient of 0-80% EtOAc/heptane to give the final product (165 mg, 36%) as an off-white oil.

1H-NMR (DMSO-d6, 500 MHz): d[ppm]=7.94 (s, 1H), 6.35 (d, J=7.7 Hz, 1H), 5.40 (m, 1H), 5.13 (dd, J=13.3, 4.0 Hz, 1H), 4.90 (dd, J=13.3, 9.4 Hz, 1H), 3.75 (s, 3H), 3.73 (s, 3H)

HPLCMS (Method A): [m/z]: 229.9 [M+H]+

Methyl 1-methyl-2-[(E)-2-nitroethenyl]-1H-imidazole-4-carboxylate (305)

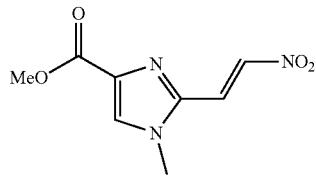

A stirring solution of methyl 2-(1-hydroxy-2-nitroethyl)-1-methyl-1H-imidazole-4-carboxylate (304) (197 mg, 0.64 mmol) and acetic anhydride (3.5 ml) was heated to 45° C. After 4 h, the reaction was concentrated to give a yellow residue which was partitioned between sat.NaHCO$_3$ (20 ml) and EtOAc (20 ml). The organic layer was separated and the aqueous extracted using EtOAc (4×5 ml). The combined organic layers were dried over MgSO$_4$, filtered and concentrated to give the crude product, purified by silica flash column chromatography with a gradient of 20-100% EtOAc/heptane to give the required product (97 mg, 60%) as a yellow solid.

1H-NMR (DMSO-d6, 500 MHz): d[ppm]=8.19 (s, 1H), 8.02-7.93 (m, 2H), 3.89 (s, 3H), 3.78 (s, 3H)

HPLCMS (Method A): [m/z]: 211.9 [M+H]+

Methyl 2-(2-{[(tert-butoxy)carbonyl]amino}ethyl)-1-methyl-1H-imidazole-4-carboxylate (306)

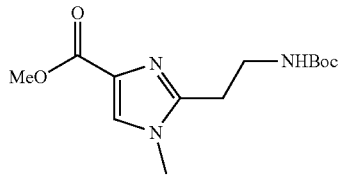 [SMILES: COC(=O)c1cn(C)c(CCNC(=O)OC(C)(C)C)n1]

To an $N_2$ purged stirring solution of methyl 1-methyl-2-[(E)-2-nitroethenyl]-1H-imidazole-4-carboxylate (305) (110 mg, 0.44 mmol), di-tert-butyl dicarbonate (386.5 mg, 1.77 mmol) and EtOH (5 ml) was added Pd/C (10%) (47.1 mg, 0.04 mmol). The reaction was purged (×3) with $N_2$ followed by $H_2$. After 48 h, the reaction was filtered under vacuum through glass fibre paper using methanol (20 ml) to wash the filter cake and the filtrate was concentrated to give the crude product. The crude was purified by flash column chromatography (eluting with a gradient of 0-8% MeOH/DCM) to give the purified product (75 mg, 26%) as a yellow solid.

HPLCMS (Method A): [m/z]: 284 [M+H]$^+$

2-(2-{[(Tert-butoxy)carbonyl]amino}ethyl)-1-methyl-1H-imidazole-4-carboxylic Acid (307)

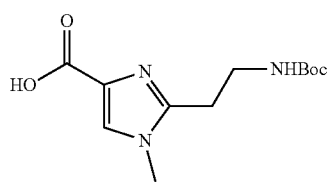 [SMILES: Cn1cc(C(=O)O)nc1CCNC(=O)OC(C)(C)C]

In a similar fashion to general procedure 5, methyl 2-(2-{[(tert-butoxy)carbonyl]amino}ethyl)-1-methyl-1H-imidazole-4-carboxylate (306) (0.5 g, 0.79 mmol) and LiOH (0.19 g, 7.94 mmol) in THF (20 ml) and water (10 ml) gave the crude product as a yellow solid (0.703 g, quant.)

HPLCMS (Method A): [m/z]: 270.05 [M+H]$^+$

Tert-butyl N-[2-(4-{[(3-fluoropyridin-2-yl)methyl]carbamoyl}-1-methyl-1H-imidazol-2-yl)ethyl]carbamate (308)

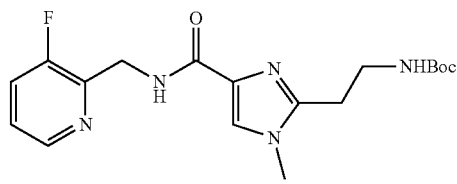 [SMILES: Cn1cc(C(=O)NCc2ncccc2F)nc1CCNC(=O)OC(C)(C)C]

In a similar fashion to general procedure 6, 2-(2-{[(tert-butoxy)carbonyl]amino}ethyl)-1-methyl-1H-imidazole-4-carboxylic acid (307) (0.703 g, 0.79 mmol), HATU (0.604 g, 1.59 mmol), (3-fluoropyridin-2-yl)methanamine dihydrochloride (A2) (0.316 g, 1.58 mmol) and DIPEA (0.968 ml, 5.56 mmol) in THF (20 ml) and DMF (5 ml) at room temperature for 3 h gave the title compound (0.092 g, 30%) as a yellow solid after purification by flash column chromatography (eluting with a gradient of (9% MeOH/DCM)

HPLCMS (Method A): [m/z]: 378.15 [M+H]$^+$

2-(2-Aminoethyl)-N-[(3-fluoropyridin-2-yl)methyl]-1-methyl-1H-imidazole-4-carboxamide (309)

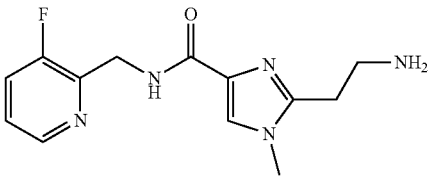 [SMILES: Cn1cc(C(=O)NCc2ncccc2F)nc1CCN]

In a similar fashion to general procedure 2, tert-butyl N-[2-(4-{[(3-fluoropyridin-2-yl)methyl]carbamoyl}-1-methyl-1H-imidazol-2-yl)ethyl]carbamate (308) (94 mg, 0.25 mmol) and 12M HCl (0.415 ml, 4.98 mmol) in MeOH (4 ml) at 40° C. for 2 h gave the product (9 mg, 13%) as a brown solid after flushing through a the column with 7 M $NH_3$/MeOH (×3).

HPLCMS (Method D): [m/z]: 278.05 [M+H]$^+$

2-{2-[(1H-1,3-Benzodiazol-2-ylmethyl)amino]ethyl}-N-[(3-fluoropyridin-2-yl)]-1-methyl-1H-imidazole-4-carboxamide (Example Compound No. 210)

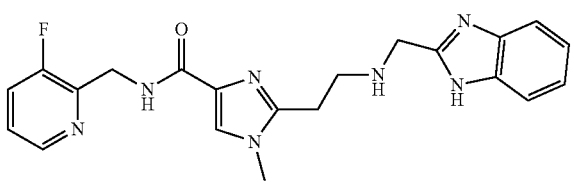 [SMILES: Cn1cc(C(=O)NCc2ncccc2F)nc1CCNCc1nc2ccccc2[nH]1]

In a similar fashion to general procedure 3, 2-(2-aminoethyl)-N-[(3-fluoropyridin-2-yl)methyl]-1-methyl-1H-imidazole-4-carboxamide (309) (9 mg, 0.032 mmol), anhydrous $MgSO_4$ (150 mg), 1H-benzimidazole-2-carbaldehyde (6.2 mg, 0.042 mmol) and DIPEA (11.3 µl, 0.065 mmol) in MeOH (2 ml) for 72 h, followed by the addition of $NaBH_4$ (1.8 mg, 0.049 mmol) gave the title compound (4.1 mg, 30%) as a brown solid after purification by flash column chromatography with a gradient of 0-50% MeOH/DCM.

1H-NMR (MeOD, 500 MHz): d[ppm]=8.18 (d, J=4.7 Hz, 1H), 7.49-7.44 (m, 1H), 7.44 (s, 1H), 7.42-7.37 (m, 2H), 7.28-7.22 (m, 1H), 7.11-7.06 (m, 2H), 4.63 (s, 2H), 3.97 (s, 2H), 3.53 (s, 3H), 2.97 (t, J=6.6 Hz, 2H), 2.81 (t, J=6.6 Hz, 2H)

HPLCMS (Method A): [m/z]: 408.1 [M+H]$^+$

General Scheme 20 Above:

Ethyl 1-(cyanomethyl)-5-methyl-1H-imidazole-4-carboxylate (310)

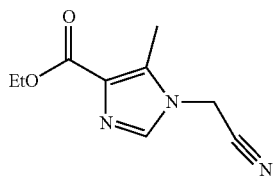

To a N$_2$ purged, stirring solution of NaH (60% in oil) (0.856 g, 21.41 mmol) in DMF (10 ml) at 00° C. was added a solution of ethyl 4-methyl-1H-imidazole-5-carboxylate (3 g, 19.46 mmol) in DMF (25 ml) dropwise. After 10 min, bromoacetonitrile (1.63 ml, 23.35 mmol) was added dropwise to the solution giving a red mixture. The reaction was allowed to warm to room temperature. Ater 16 h, the reaction was concentrated and the residue diluted with sat.NaHCO$_3$ (40 ml). The solution was extracted with EtOAc (6×20 ml) and the combined organic layers were washed with brine (4×15 ml), dried over MgSO$_4$, filtered and concentrated to give the crude product. Purification by flash column chromatography with a gradient of 0-6% MeOH/DCM gave the title compound (1.3 g, 35%) as an orange solid.

1H-NMR (DMSO-d6, 500 MHz): d[ppm]=7.76 (s, 1H), 5.38 (s, 2H), 4.22 (q, J=7.1 Hz, 2H), 2.52 (s, 3H), 1.27 (t, J=7.1 Hz, 3H)

HPLCMS (Method A): [m/z]: 194 [M+H]$^+$

Ethyl 1-(2-{[(tert-butoxy)carbonyl]amino}ethyl)-4-methyl-1H-imidazole-4-carboxylate (311)

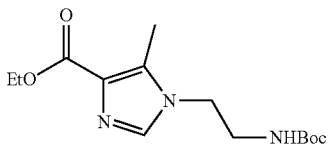 [SMILES: CCOC(=O)c1ncn(CCNC(=O)OC(C)(C)C)c1C]

To a N$_2$ purged stirring solution of ethyl 1-(cyanomethyl)-5-methyl-1H-imidazole-4-carboxylate (310) (0.72 g, 3.73 mmol), EtOH (20 ml), TEA (0.675 ml, 4.85 mmol) and ditert-butyl dicarbonate (1.06 g, 4.85 mmol) at room temperature was added Pd/C (10%) (0.397 g, 0.37 mmol). The reaction was purged with N$_2$ (×3) followed by H$_2$. After 16 h, the reaction was filtered through glass fibre paper and the filter cake washed with 7 M NH$_3$/MeOH (40 ml). The filtrate was concentrated to give the crude product which was further purified by flash column chromatography using a gradient of 0-10% MeOH/DCM yielding the required product (1.07 g, 84%) as an off-white solid.

1H-NMR (DMSO-d6, 500 MHz): d[ppm]=7.53 (s, 1H), 7.01-6.93 (m, 1H), 4.19 (q, J=7.1 Hz, 2H), 3.97 (t, J=5.9 Hz, 2H), 3.19 (q, J=6.0 Hz, 2H), 2.43 (s, 3H), 1.37-1.32 (m, 9H), 1.28-1.23 (m, 3H)

HPLCMS (Method A): [m/z]: 298.1 [M+H]$^+$

Lithium 1-(2-{[(tert-butoxy)carbonyl]amino}ethyl)-5-methyl-1H-imidazole-4-carboxylate (312)

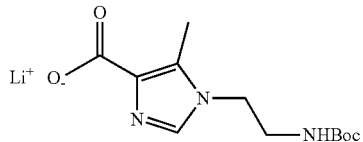

To a stirring solution of ethyl 1-(2-{[(tert-butoxy)carbonyl]amino}ethyl)-5-methyl-1H-imidazole-4-carboxylate (311) (1.07 g, 3.12 mmol), THF (35 ml) and water (10 ml) was added LiOH (0.224 g, 9.36 mmol), the reaction was heated to 50° C. After 24 h, the reaction was concentrated to give the lithium salt of the product (0.670 g) as a yellow solid.

HPLCMS (Method A): [m/z]: 270.05 [M+H]$^+$

Tert-butyl N-[2-(4-{[(3-fluoropyridin-2-yl)methyl]carbamoyl}-5-methyl-1H-imidazol-1-yl)ethyl]carbamate (313)

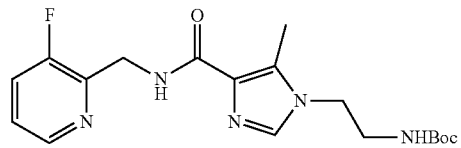 [SMILES: Cc1c(C(=O)NCc2ncccc2F)ncn1CCNC(=O)OC(C)(C)C]

In a similar fashion to general procedure 6, lithium 1-(2-{[(tert-butoxy)carbonyl]amino}ethyl)-5-methyl-1H-imidazole-4-carboxylate (312) (0.670 g, 2.488 mmol), THF (30 ml), DMF (10 ml) and DIPEA (1.733 ml, 9.952 mmol) at room temperature was added HATU (1.419 g, 3.732 mmol) and (3-fluoropyridin-2-yl)methanamine dihydrochloride (0.743 g, 3.732 mmol). After 2 h, the reaction mixture was concentrated and the residue dissolved in sat.NaHCO$_3$ (100 ml) which was extracted with EtOAc (6×20 ml). The combined organic layers were washed with brine (3×20 ml), dried over MgSO$_4$, filtered and concentrated to give the crude product which was further purified by silica column chromatography with a gradient of 0-10% MeOH in DCM to give an orange oil, further purified using a kp-NH silica column chromatography with a gradient of 0-100% EtOAc in heptane to give the final product (0.320 g, 31%) as a yellow oil.

1H-NMR (DMSO-d6, 500 MHz) d[ppm]=8.39 (d, J=4.6 Hz, 1H), 8.22 (t, J=5.4 Hz, 1H), 7.70 (t, J=9.3 Hz, 1H), 7.54 (s, 1H), 7.45-7.37 (m, 1H), 6.98 (t, J=5.6 Hz, 1H), 4.60 (d, J=4.4 Hz, 2H), 3.96 (t, J=6.0 Hz, 2H), 3.19 (q, J=5.9 Hz, 2H), 2.44 (s, 3H), 1.39-1.20 (m, 9H)

HPLCMS (Method A): [m/z]: 378.05 [M+H]$^+$

1-(2-Aminoethyl)-N-[(3-fluoropyridin-2-yl)methyl]-5-methyl-1H-imidazole-4-carboxamide Dihydrochloride (314)

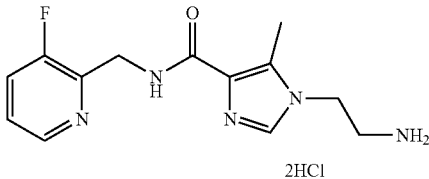 [SMILES: Cc1c(C(=O)NCc2ncccc2F)ncn1CCN]

In a similar fashion to general procedure 2, To a stirred solution of tert-butyl N-[2-(4-{[(3-fluoropyridin-2-yl)methyl]carbamoyl}-5-methyl-1H-imidazol-1-yl)ethyl]carbamate (313) (0.320 g, 0.776 mmol) in MeOH (10 ml) at room temperature was added conc. HCl (1.293 ml, 15.52 mmol), the reaction was heated to 50° C. After 2 h, the reaction was concentrated to give the required product (0.294 g, quant) as a yellow solid.

1H-NMR (Methanol-d4, 500 MHz): d[ppm]=9.03 (s, 1H), 8.54 (s, 1H), 8.06 (s, 1H), 7.75 (s, 1H), 4.89 (s, 2H), 4.58 (t, J=6.5 Hz, 2H), 3.48 (t, J=6.4 Hz 2H), 2.67 (s, 3H)

HPLCMS (Method A): [m/z]: 277.95 [M+H]$^+$

1-(2-{[2-(1H-1,3-Benzodiazol-2-yl)ethyl]amino}ethyl)-N-[(3-fluoropyridin-2-yl)methyl]-5-methyl-1H-imidazole-4-carboxamide (Example Compound No. 219)

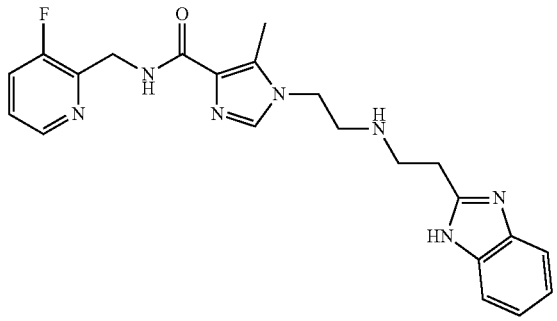 [SMILES: Cc1c(C(=O)NCc2ncccc2F)ncn1CCNCCc1nc2ccccc2[nH]1]

In a similar fashion to general procedure 8, 1-(2-aminoethyl)-N-[(3-fluoropyridin-2-yl)methyl]-5-methyl-1H-imidazole-4-carboxamide dihydrochloride (314) (0.294 g, 0.77 mmol), DBU (0.347 ml, 2.33 mmol) and N-(2-nitrophenyl)prop-2-enamide (D) (0.332 g, 1.73 mmol) in MeCN (20 ml) followed by silica column chromatography (0-3% MeOH in DCM) followed by reaction with AcOH (2 ml) and iron powder (0.041 g) gave the title compound (0.030 g, 30%) as an off-white solid after purification by basic prep-HPLC followed by flash column chromatography (kp-NH, eluting with a gradient 0-5% MeOH/DCM).

1H-NMR (DMSO-d6, 500 MHz): d[ppm]=12.09 (br s, 1H), 8.39 (d, J=4.7 Hz, 1H), 8.22 (t, J=5.5 Hz, 1H), 7.75-7.66 (m, 1H), 7.61 (s, 1H), 7.53-7.35 (m, 3H), 7.13-7.06 (m, 2H), 4.60 (d, J=4.3 Hz, 2H), 3.97 (t, J=6.3 Hz, 2H), 3.00-2.93 (m, 2H), 2.94-2.88 (m, 2H), 2.84 (t, J=6.3 Hz, 2H), 2.47 (s, 3H)

HPLCMS (Method G): [m/z]: 422.1 [M+H]$^+$

General Scheme 21 Above:

Ethyl 2-{1-[(tert-butoxy)carbonyl]-3-chloroazetidin-3-yl}-5-chloro-1,3-thiazole-4-carboxylate (321)

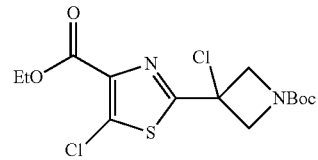 [SMILES: CCOC(=O)c1nc(C2(Cl)CN(C(=O)OC(C)(C)C)C2)sc1Cl]

Ethyl 2-{1-[(tert-butoxy)carbonyl]azetidin-3-yl}-1,3-thiazole-4-carboxylate (161) (1.15 g, 3.68 mmol) and hexachloroethane (0.83 g, 3 mmol) were dissolved in THF (40 ml) and cooled to −78° C. 2 M NaHMDS (1.75 ml) was added dropwise and the reaction mixture was left stirring at −78° C. for 30 min. Further 2M NaHMDS (0.6 ml) were added and the reaction mixture and left stirred at −78° C. for further 30 min. The reaction was quenched with sat. NH$_4$Cl (aq), warmed to room temperature, diluted with water and extracted with DCM (3×80 ml). The combined organic extracts were dried (Na$_2$SO$_4$), filtered and evaporated in vacuo. Two major components were identified in the crude mixture. Purification by flash column chromatography (eluting with a gradient of 2-15% EtOAc/heptane) gave the title compound (456 mg, 32%) as a pale yellow oil.

1H-NMR (CDCl$_3$, 500 MHz): d[ppm]=4.72 (d, J=9.2 Hz, 2H), 4.37 (q, J=7.1 Hz, 2H), 4.32 (m, 2H), 1.40 (s, 9H), 1.35 (t, J=7.1 Hz, 3H)

HPLCMS (Method A): [m/z]: 402.9 [M+Na]$^+$

2-{1-[(Tert-butoxy)carbonyl]-3-chloroazetidin-3-yl}-5-chloro-1,3-thiazole-4-carboxylic Acid (322)

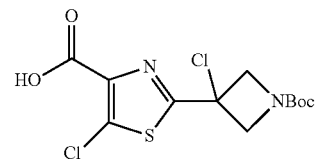 [SMILES: CC(C)(C)OC(=O)N1CC(Cl)(c2nc(C(=O)O)c(Cl)s2)C1]

In a similar fashion to general procedure 5, ethyl 2-{1-[(tert-butoxy)carbonyl]-3-chloroazetidin-3-yl}-5-chloro-1,3-thiazole-4-carboxylate (321) (450 mg, 1.18 mmol) and LiOH (0.08 g, 4 mmol) in THF (5 ml) and water (5 ml) gave the crude title compound (461 mg) as a colourless oil which crystallised on standing.

1H-NMR (CDCl$_3$, 250 MHz): d[ppm]=4.76 (dd, J=9.6, 1.0 Hz, 2H), 4.45 (dd, J=9.6, 1.0 Hz, 2H), 1.50 (s, 9H)

HPLCMS (Method A): [m/z]: 378.85 [M+Na]$^+$

Tert-butyl 3-chloro-3-(5-chloro-4-{[(3-fluoropyridin-2-yl)methyl]carbamoyl}-1,3-thiazol-2-yl)azetidine-1-carboxylate (323)

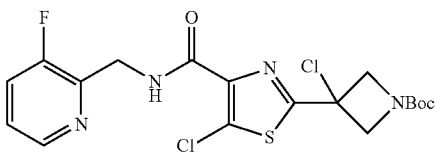 [SMILES: CC(C)(C)OC(=O)N1CC(Cl)(c2nc(C(=O)NCc3ncccc3F)c(Cl)s2)C1]

In a similar fashion to general procedure 6, 2-{1-[(tert-butoxy)carbonyl]-3-chloroazetidin-3-yl}-5-chloro-1,3-thiazole-4-carboxylic acid (322) (460 mg, 1.3 mmol), (3-fluoropyridin-2-yl)methanamine dihydrochloride—(A2) (311 mg, 1.56 mmol), DIPEA (0.75 ml, 4 mmol) and HATU (0.59 g, 2 mmol) in DCM (10 ml) afforded the title compound (479 mg, 80%) after purification by flash column chromatography (eluting with a gradient of 10-50% EtOAc/heptane).

1H-NMR (CDCl₃, 500 MHz): d[ppm]=8.34 (dt, J=4.7, 1.1 Hz, 1H), 8.26-8.20 (m, 1H), 7.38-7.31 (m, 1H), 7.23-7.16 (m, 1H), 4.75 (m, 2H), 4.70 (m, 2H), 4.35 (m, 2H), 1.40 (s, 9H)

HPLCMS (Method A): [m/z]: 460.95 [M+H]⁺

5-Chloro-2-(3-chloroazetidin-3-yl)-N-[(3-fluoropyridin-2-yl)methyl]-1,3-thiazole-4-carboxamide (324)

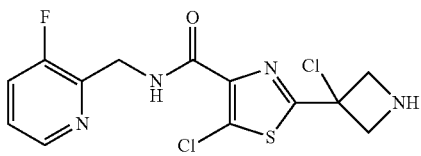 [SMILES: O=C(NCc1ncccc1F)c1nc(C2(Cl)CNC2)sc1Cl]

In a similar fashion to general procedure 2, tert-butyl 3-chloro-3-(5-chloro-4-{[(3-fluoropyridin-2-yl)methyl]carbamoyl}-1,3-thiazol-2-yl)azetidine-1-carboxylate (323) (479 mg, 1.04 mmol) and 12 M HCl (2 ml) in MeOH (20 ml) gave the title compound (375 mg, quant.) as a white solid following purification using an SCX-2 cartridge, rinsing with DCM and MeOH, then eluting with 7 N ammonia in MeOH.

1H-NMR (DMSO-d6, 250 MHz): d[ppm]=9.05-8.96 (m, 1H), 8.40 (dt, J=4.6, 1.4 Hz, 1H), 7.78-7.66 (m, 1H), 7.48-7.37 (m, 1H), 4.66 (dd, J=5.8, 1.6 Hz, 2H), 4.41 (d, J=10.5 Hz, 2H), 4.07 (d, J=10.5 Hz, 2H)

HPLCMS (Method A): [m/z]: 360.8 [M+H]⁺

2-{1-[2-(1H-1,3-benzodiazol-2-yl)ethyl]azetidin-3-yl}-5-chloro-N-[(3-fluoropyridin-2-yl)methyl]-1,3-thiazole-4-carboxamide (Example Compound No. 209) and 2-{1-[2-(1H-1,3-benzodiazol-2-yl)ethyl]-3-hydroxyazetidin-3-yl}-5-chloro-N-[(3-fluoropyridin-2-yl)methyl]-1,3-thiazole-4-carboxamide (Example Compound No. 211)

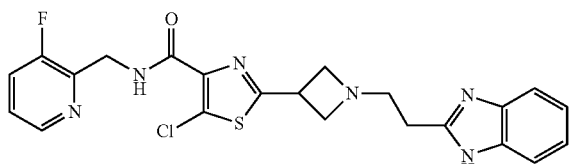

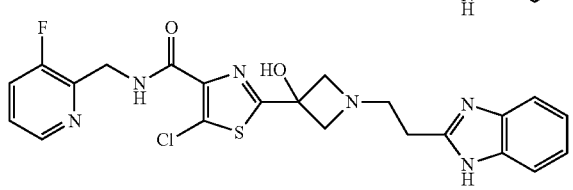

In a similar fashion to general procedure 8, 5-chloro-2-(3-chloroazetidin-3-yl)-N-[(3-fluoropyridin-2-yl)methyl]-1,3-thiazole-4-carboxamide (324) (375 mg, 1.04 mmol), N-(2-nitrophenyl)prop-2-enamide (D) (219 mg, 1.14 mmol) and DBU (0.17 ml, 1.14 mmol) in MeCN (20 ml) gave a crude mixture which was further reacted with iron powder (0.2 g) in AcOH (5 ml). Purification by basic pep-HPLC followed by flash column chromatography (eluting with a gradient of 0-20% MeOH/DCM) gave the title compound (Example Compound No. 209) (60 mg, 14%) as a white solid.

1H-NMR (DMSO-d6, 500 MHz): d[ppm]=12.14 (s, 1H), 8.77 (t, J=5.6 Hz, 1H), 8.38 (dt, J=4.6, 1.3 Hz, 1H), 7.75-7.67 (m, 1H), 7.56-7.37 (m, 3H), 7.12 (dd, J=5.9, 2.6 Hz, 2H), 4.66-4.60 (m, 2H), 3.89 (ddd, J=13.1, 7.4, 5.6 Hz, 1H), 3.61 (t, J=7.2 Hz, 2H), 2.94-2.88 (m, 2H), 2.87-2.81 (m, 2H). One CH₂ signal is obscured by the water peak.

HPLCMS (Method C): [m/z]: 471.1 [M+H]⁺

A byproduct was also isolated by basic prep-HPLC to give 2-{1-[2-(1H-1,3-benzodiazol-2-yl)ethyl]-3-hydroxyazetidin-3-yl}-5-chloro-N-[(3-fluoropyridin-2-yl)methyl]-1,3-thiazole-4-carboxamide (Example Compound No. 211) (2 mg) as a white solid.

1H-NMR (DMSO-d6, 500 MHz): d[ppm]=12.16 (s, 1H), 8.86 (t, J=5.5 Hz, 1H), 8.35 (dt, J=4.6, 1.4 Hz, 1H), 7.74-7.67 (m, 1H), 7.54-7.48 (m, 1H), 7.44-7.34 (m, 2H), 7.15-7.07 (m, 2H), 4.65 (d, J=5.5 Hz, 2H), 3.70 (d, J=8.3 Hz, 2H), 3.43 (d, J=8.3 Hz, 2H), 3.01 (t, J=7.2 Hz, 2H), 2.87 (t, J=7.2 Hz, 2H)

HPLCMS (Method C): [m/z]: 487.1 [M+H]⁺
General Scheme 22 Above:

Tert-butyl (1R,5S,6S)-6-carbamoyl-3-azabicyclo[3.1.0]hexane-3-carboxylate (325)

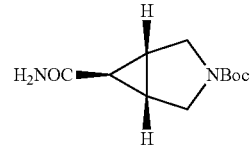 [SMILES: CC(C)(C)OC(=O)N1C[C@@H]2[C@H](C1)[C@H]2C(N)=O]

In a similar fashion to general procedure 12, (1R,5S,6S)-3-[(tert-butoxy)carbonyl]-3-azabicyclo[3.1.0]hexane-6-carboxylic acid (1 g, 4.4 mmol), TEA (1.04 ml, 0.01 mol), isobutyl chloroformate (0.86 ml, 0.01 mol) and NH₃ 28% aqueous (1.33 ml, 0.07 mol) in THF (15 ml) gave the crude title product (1.20 g) as a pale yellow solid. The material was used directly in the next step.

HPLCMS (Method A): [m/z]: 249.05 [M+Na]⁺

Tert-butyl (1R,5S,6S)-6-carbamothioyl-3-azabicyclo[3.1.0]hexane-3-carboxylate (326)

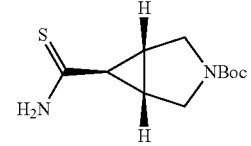 [SMILES: CC(C)(C)OC(=O)N1C[C@@H]2[C@H](C1)[C@H]2C(N)=S]

In a similar fashion to general procedure 11, tert-butyl (1R,5S,6S)-6-carbamoyl-3-azabicyclo[3.1.0]hexane-3-carboxylate (325) (1.2 g, 5.3 mmol) and Lawesson reagent (1.18 g, 2.9 mmol) in DCM (40 ml) gave the title compound (939 mg, 73%) as a white foam after purification by flash column chromatography using a gradient elution of 0-10% EtOAc/heptane.
HPLCMS (Method A): [m/z]: 242.95 [M+H]⁺

Tert-butyl (1R,5S,6R)-6-[4-(ethoxycarbonyl)-1,3-thiazol-2-yl]-3-azabicyclo[3.1.0]hexane-3-carboxylate (327)

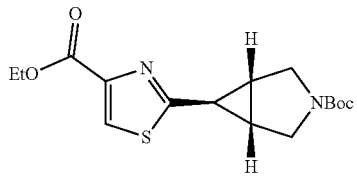 [SMILES: CCOC(=O)c1csc([C@H]2[C@@H]3CN(C(=O)OC(C)(C)C)C[C@@H]32)n1]

In a similar fashion to general procedure 1, tert-butyl (1R,5S,6R)-6-carbamothioyl-3-azabicyclo[3.1.0]hexane-3-carboxylate (326) (939 mg, 3.87 mmol), ethyl 3-bromo-2-oxopropanoate (0.53 ml, 4 mmol) and CaCO₃ (0.21 g, 2 mmol) in EtOH (20 ml) afforded the title compound (546 mg, 42%) as a colourless residue after purification by flash column chromatography using a isocratic elution of 30% EtOAc/heptane followed by a second flash column chromatography using a gradient elution of 0-40% EtOAc/heptane.
HPLCMS (Method A): [m/z]: 339.1 [M+H]⁺

2-[(1R,5S,6R)-3-[(Tert-butoxy)carbonyl]-3-azabicyclo[3.1.0]hexan-6-yl]-1,3-thiazole-4-carboxylic Acid (328)

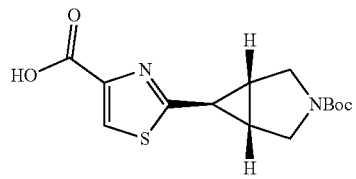 [SMILES: CC(C)(C)OC(=O)N1C[C@@H]2[C@H](C1)[C@H]2c1nc(C(=O)O)cs1]

In a similar fashion to general procedure 5, tert-butyl (1R,5S,6R)-6-[4-(ethoxycarbonyl)-1,3-thiazol-2-yl]-3-azabicyclo[3.1.0]hexane-3-carboxylate (327) (546 mg, 1.61 mmol) and LiOH (0.12 g, 5 mmol) in THF (20 ml) and water (10 ml) afforded the crude title compound (500 mg, 1.61 mmol) as a pale yellow oil which was used in the next step without purification.
HPLCMS (Method A): [m/z]: 311.1 [M+H]⁺

Tert-butyl (1R,5S,6S)-6-(4-{[(3-fluoropyridin-2-yl)methyl]carbamoyl}-1,3-thiazol-2-yl)-3-azabicyclo[3.1.0]hexane-3-carboxylate (329)

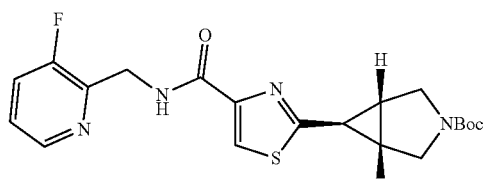

In a similar fashion to general procedure 6, 2-[(1R,5S,6R)-3-[(tert-butoxy)carbonyl]-3-azabicyclo[3.1.0]hexan-6-yl]-1,3-thiazole-4-carboxylic acid (328) (500 mg, 1.61 mmol), (3-fluoropyridin-2-yl)methanamine dihydrochloride (A2) (352.7 mg, 1.77 mmol), DIPEA (0.93 ml, 5.31 mmol) and HATU (0.74 g, 1.93 mmol) in DCM (30 ml) afforded the title compound (650 mg, 96%) as a colourless foam after purification by flash column chromatography eluting with a gradient of 20-100% EtOAc/heptane.
HPLCMS (Method A): [m/z]: 419.1 [M+H]⁺

2-[(1R,5S,6S)-3-Azabicyclo[3.1.0]hexan-6-yl]-N-[(3-fluoropyridin-2-yl)methyl]-1,3-thiazole-4-carboxamide (330)

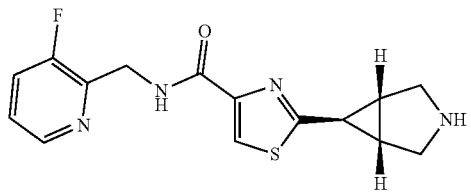 [SMILES: O=C(NCc1ncccc1F)c1csc([C@H]2[C@@H]3CNC[C@@H]32)n1]

In a similar fashion to general procedure 4, tert-butyl (1R,5S,6S)-6-(4-{[(3-fluoropyridin-2-yl)methyl]carbamoyl}-1,3-thiazol-2-yl)-3-azabicyclo[3.1.0]hexane-3-carboxylate (329) (624 mg, 1.49 mmol) and 12 M HCl (2 ml) in MeOH (20 ml) afforded the title compound (475 mg, 83%) after purification using an SCX-2 cartridge, rinsing with DCM and MeOH, then elution with 7 N ammonia in MeOH.
1H-NMR (DMSO-d6, 500 MHz): d[ppm]=8.65 (t, J=5.6 Hz, 1H), 8.39 (dt, J=4.6, 1.3 Hz, 1H), 8.03 (s, 1H), 7.75-7.69 (m, 1H), 7.45-7.39 (m, 1H), 4.67-4.63 (m, 2H), 3.05 (m, 3H), 2.78 (d, J=11.4 Hz, 2H), 2.38 (t, J=3.3 Hz, 1H), 2.03-2.00 (m, 2H)
HPLCMS (Method A): [m/z]: 319.05 [M+H]⁺

2-[(1R,5S,6S)-3-(1H-1,3-Benzodiazol-2-ylmethyl)-3-azabicyclo[3.1.0]hexan-6-yl]-N-[(3-fluoropyridin-2-yl)methyl]-1,3-thiazole-4-carboxamide (331)

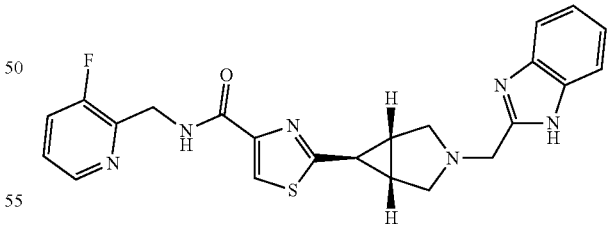

In a similar fashion to general procedure 3, 2-[(1R,5S,6S)-3-azabicyclo[3.1.0]hexan-6-yl]-N-[(3-fluoropyridin-2-yl)methyl]-1,3-thiazole-4-carboxamide (330) (200 mg, 0.63 mmol), 1H-1,3-benzodiazole-2-carbaldehyde (110.17 mg, 0.75 mmol), DIPEA (0.33 ml, 2 mmol) and MgSO₄ (300 mg) in MeOH (10 ml) at room temperature for 18 h, followed by addition of NaBH₄ (48 mg, 1.3 mmol) gave the title compound (62 mg, 22%) as a pale yellow solid after trituration of the residue in 1:1 DMSO/MeCN followed by rinsing with MeOH.

1H-NMR (DMSO-d6, 500 MHz): d[ppm]=12.17 (s, 1H), 8.63 (t, J=5.7 Hz, 1H), 8.40 (d, J=4.6 Hz, 1H), 8.04 (s, 1H), 7.76-7.67 (m, 1H), 7.55 (d, J=7.8 Hz, 1H), 7.46 (d, J=7.8 Hz, 1H), 7.44-7.39 (m, 1H), 7.20-7.09 (m, 2H), 4.66 (d, J=4.9 Hz, 2H), 3.91 (s, 2H), 3.15 (d, J=9.1 Hz, 2H), 2.96 (t, J=2.8 Hz, 1H), 2.66-2.60 (m, 2H), 2.14-2.10 (m, 2H)

HPLCMS (Method C): [m/z]: 449.1 [M+H]+

2-[(1R,5S,6S)-3-(1H-1,3-Benzodiazol-2-ylmethyl)-3-azabicyclo[3.1.0]hexan-6-yl]-N-[(3-fluoropyridin-2-yl)methyl]-1,3-thiazole-4-carboxamide Trihydrochloride (Example Compound No. 213)

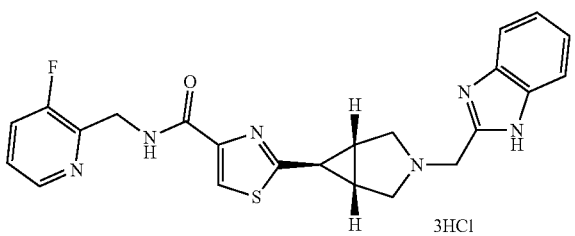 [SMILES: O=C(NCc1ncccc1F)c1csc([C@H]2[C@@H]3CN(Cc4nc5ccccc5[nH]4)C[C@@H]32)n1]

2-[(1R,5S,6S)-3-(1H-1,3-benzodiazol-2-ylmethyl)-3-azabicyclo[3.1.0]hexan-6-yl]-N-[(3-fluoropyridin-2-yl)methyl]-1,3-thiazole-4-carboxamide (331) (20 mg, 0.44 mmol) was suspended in MeOH (3 ml) and treated with 12 M HCl (0.5 ml), causing dissolution. The mixture was stirred for 1 h, evaporated under vacuum to give the title compound (25 mg, quant.) as a yellow solid.

1H-NMR (MeOD, 500 MHz): d[ppm]=8.58-8.55 (m, 1H), 8.19-8.13 (m, 1H), 8.05 (s, 1H), 7.86-7.78 (m, 3H), 7.66-7.61 (m, 2H), 4.90 (s, 2H), 4.52 (s, 2H), 3.60-3.52 (m, 2H), 3.22-3.13 (m, 2H), 3.11 (t, J=3.1 Hz, 1H), 2.43 (s, 2H)

HPLCMS (Method C): [m/z]: 449.1 [M+H]+

2-[(1R,5S,6S)-3-[2-(1H-1,3-Benzodiazol-2-yl)ethyl]-3-azabicyclo[3.1.0]hexan-6-yl]-N-[(3-fluoropyridin-2-yl)methyl]-1,3-thiazole-4-carboxamide (Example Compound No. 218)

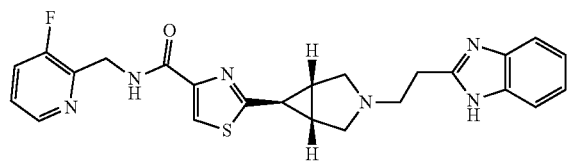 [SMILES: O=C(NCc1ncccc1F)c1csc([C@H]2[C@@H]3CN(CCc4nc5ccccc5[nH]4)C[C@@H]32)n1]

In a similar fashion to general procedure 8, 2-[(1R,5S,6S)-3-azabicyclo[3.1.0]hexan-6-yl]-N-[(3-fluoropyridin-2-yl)methyl]-1,3-thiazole-4-carboxamide (330) (264 mg, 0.83 mmol), N-(2-nitrophenyl)prop-2-enamide (D) (175 mg, 0.91 mmol) and DBU (0.14 ml, 0.91 mmol) in MeCN (15 ml) gave a crude intermediate which was further reacted with iron powder (180 mg, 3.2 mmol) in AcOH (5 ml) to give the title compound (4 mg, 1%) as a colourless residue after purification by sequential flash chromatography (eluting with a gradient of 0-40% MeOH/DCM), basic prep-HPLC and flash column chromatography (eluting with a gradient of 0-5% MeOH/DCM).

1H-NMR (MeOD, 500 MHz): d[ppm]=8.38 (d, J=4.7 Hz, 1H), 7.94 (s, 1H), 7.61 (ddd, J=9.7, 8.4, 1.2 Hz, 1H), 7.53 (m, 2H), 7.43-7.38 (m, 1H), 7.22 (m, 2H), 4.77 (d, J=1.5 Hz, 2H), 3.30 (m, 2H), 3.09 (m, 2H), 3.01 (m, 2H), 2.66 (m, 1H), 2.58 (m, 2H), 2.15 (s, 2H)

HPLCMS (Method C): [m/z]: 463.1 [M+H]+

General Scheme 23

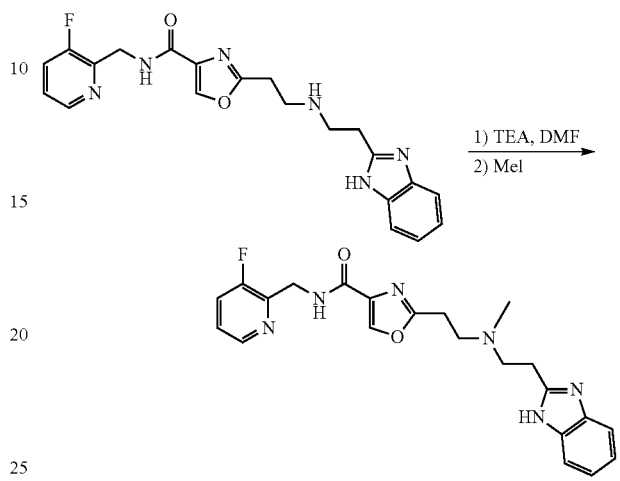

2-(2-{[2-(1H-1,3-Benzodiazol-2-yl)ethyl](methyl)amino}ethyl)-N-[(3-fluoropyridin-2-yl)methyl]-1,3-oxazole-4-carboxamide (Example Compound No. 223)

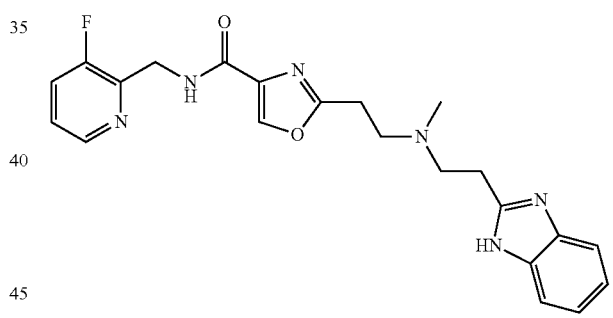

2-(2-{[2-(1H-1,3-benzodiazol-2-yl)ethyl]amino}ethyl)-N-[(3-fluoropyridin-2-yl)methyl]-1,3-oxazole-4-carboxamide (Example Compound No. 127) (59 mg, 0.14 mmol), TEA (60 µl, 0.43 mmol) in DMF (1 ml were stirred at room temperature for 1 h. MeI (8.9 µl, 0.14 mmol) was added and stirred at room temperature for 24 h. The reaction mixture was re-treated with MeI (62.9 µl, 0.79 mmol) and TEA (80 µl, 0.58 mmol) and left stirring at room temperature for 2 d. The mixture was vigorously reduced in vacuo to give a yellow oil (200 mg) which was purification by basic prep-HPLC, followed by kp-NH column chromatography (eluting with a gradient of 0-10% MeOH/DCM) and flash column chromatography (eluting with a gradient of 0-20% MeOH/DCM) to give the title compound (13 mg, 21%) as an off-white solid.

1H-NMR (MeOD, 500 MHz): d[ppm]=8.34-8.29 (m, 1H), 8.15 (s, 1H), 7.61-7.54 (m, 1H), 7.44 (br s, 2H), 7.38-7.33 (m, 1H), 7.19-7.13 (m, 2H), 4.69 (d, J=1.6 Hz, 2H), 3.09-3.04 (m, 2H), 3.04-2.99 (m, 2H), 2.98-2.91 (m, 4H), 2.39 (s, 3H)

HPLCMS (Method G): [m/z]: 423.1 [M+H]+

General Scheme 25 Above:

Tert-butyl 3-[(3-hydroxy-1-methoxy-1-oxopropan-2-yl)carbamoyl]azetidine-1-carboxylate (339)

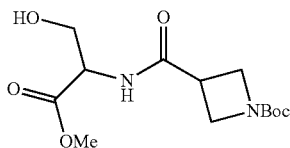 [SMILES: COC(=O)C(CO)NC(=O)C1CN(C(=O)OC(C)(C)C)C1]

A stirring solution of methyl serinate hydrochloride (1:1) (2.3 g, 14.78 mmol) and TEA (2.27 ml, 16.26 mmol) in DCM (150 ml) was cooled to 0° C. 1-[(tert-butoxy)carbonyl]azetidine-3-carboxylic acid (2.97 g, 14.78 mmol) was added followed by addition of DCC (3.36 g, 16.26 mmol) portion wise, the reaction was then allowed to warm to room temperature. After 24 h the mixture was concentrated and dissolved in EtOAc (~250 ml). The reaction mixture was left stirring at 50° C. for 45 min. The precipitate was then filtered off and the filtrate was concentrated to give the crude product as a white solid. Purification by flash column chromatography using a gradient elution of 100% TBME followed by DCM/MeOH afforded the title compound (4.5 g, 91%) as a yellow solid.

1H-NMR (CDCl$_3$, 500 MHz): d[ppm]=6.75 (d, 1H), 4.66 (dt, 1H), 4.14-4.02 (m, 4H), 3.99 (dd, 1H), 3.88 (d, 1H), 3.77 (s, 3H), 3.29 (ddd, 1H), 1.42 (s, 9H)

HPLCMS (Method A): [m/z]: 246.95 [M-$^t$Bu]$^+$

Methyl 2-{1-[(tert-butoxy)carbonyl]azetidin-3-yl}-4,5-dihydro-1,3-oxazole-4-carboxylate (340)

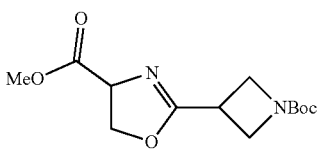 [SMILES: COC(=O)C1COC(C2CN(C(=O)OC(C)(C)C)C2)=N1]

In a similar fashion to general procedure 14, tert-butyl 3-[(3-hydroxy-1-methoxy-1-oxopropan-2-yl)carbamoyl]azetidine-1-carboxylate (339) (4.5 g, 13.4 mmol) and DAST (2.3 ml, 17.42 mmol) in DCM (120 ml) afforded the title compound (3.3 g, 78%) as a pale yellow oil. Compound was used into the next step without further purification.

1H-NMR (CDCl$_3$, 500 MHz): d[ppm]=4.78 (m, 1H), 4.60-4.53 (m, 1H), 4.47 (m, 1H), 4.12 (m, 4H), 3.80 (s, 3H), 3.48-3.36 (m, 1H), 1.43 (s, 9H)

Methyl 2-{1-[(tert-butoxy)carbonyl]azetidin-3-yl}-1,3-oxazole-4-carboxylate (341)

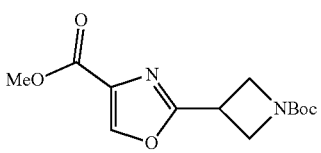 [SMILES: COC(=O)c1coc(C2CN(C(=O)OC(C)(C)C)C2)n1]

In a similar fashion to general procedure 15, methyl 2-{1-[(tert-butoxy)carbonyl]azetidin-3-yl}-4,5-dihydro-1,3-oxazole-4-carboxylate (340) (3.3 g, 10.45 mmol), DBU (2.21 ml, 14.77 mmol) and bromo(trichloro)methane (2.57 ml, 26.12 mmol) in DCM (25 ml) afforded the title compound (2.3 g, 70%) as an yellow oil after purification by flash column chromatography using a gradient of 0-10% MeOH in DCM.

1H-NMR (CDCl$_3$, 500 MHz): d[ppm]=8.21 (s, 1H), 4.30-4.24 (m, 4H), 3.96-3.89 (m, 4H), 1.44 (s, 9H)

HPLCMS (Method A): [m/z]: 305.00 [M+Na]$^+$

2-{1-[(Tert-butoxy)carbonyl]azetidin-3-yl}-1,3-oxazole-4-carboxylic Acid (342)

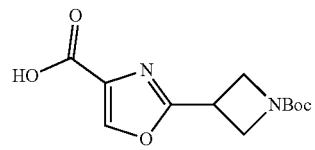

In a similar fashion to general procedure 5, methyl 2-{1-[(tert-butoxy)carbonyl]azetidin-3-yl}-1,3-oxazole-4-carboxylate (341) (2.3 g, 7.33 mmol) and LiOH (0.26 g, 0.01 mol) in THF (35 ml) and water (8.5 ml) at room temperature for 4 h afforded the title compound (2.0 g, 86%) as a pale yellow oil. The crude material was used in the next step without further purification.

HPLCMS (Method A): [m/z]: 290.95 [M+Na]$^+$

2-{1-[(tert-butoxy)carbonyl]azetidin-3-yl}-1,3-oxazole-4-carboxylic Acid (343)

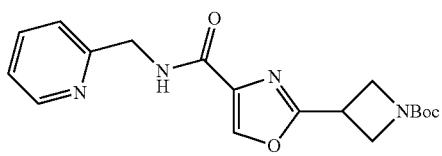 [SMILES: CC(C)(C)OC(=O)N1CC(c2nc(C(=O)NCc3ccccn3)co2)C1]

In a similar fashion to general procedure 6, tert-butyl 3-{4-[(pyridin-2-ylmethyl)carbamoyl]-1,3-oxazol-2-yl}azetidine-1-carboxylate (342) (1 g, 3.17 mmol), pyridin-2-ylmethanamine (0.343 g, 3.17 mmol), TEA (0.42 ml, 3.17 mmol) and HATU (1.81 g, 4.75 mmol) in DMF (10 ml) at room temperature for 48 h afforded the title compound (1.07 g, 32%) as a brown oil after purification by flash column chromatography (eluting with a gradient of 40-80% EtOAc/heptane).

1H-NMR (CDCl$_3$, 500 MHz): d[ppm]=8.55-8.51 (m, 1H), 8.11 (s, 1H), 7.84 (s, 1H), 7.61 (td, J=7.7, 1.8 Hz, 1H), 7.25 (d, J=7.8 Hz, 1H), 7.15 (dd, J=7.4, 4.9 Hz, 1H), 4.67 (d, J=5.5 Hz, 2H), 4.22 (t, J=8.8 Hz, 2H), 4.16 (dd, J=8.6, 6.2 Hz, 2H), 3.86-3.78 (m, 1H), 1.39 (s, 9H)

HPLCMS (Method A): [m/z]: 359.10 [M+H]$^+$

Tert-butyl 3-(4-{[(3-fluoropyridin-2-yl)methyl]carbamoyl}-1,3-oxazol-2-yl)azetidine-1-carboxylate (344)

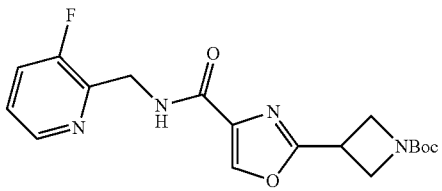 [SMILES: CC(C)(C)OC(=O)N1CC(c2nc(C(=O)NCc3ncccc3F)co2)C1]

In a similar fashion to general procedure 6, 2-{1-[(tert-butoxy)carbonyl]azetidin-3-yl}-1,3-oxazole-4-carboxylic acid (342) (1.0 g, 3.48 mmol), (3-fluoropyridin-2-yl)methanamine dihydrochloride (A2) (0.83 g, 4.17 mmol), DIPEA (2.42 ml, 13.91 mmol) and HATU (1.59 g, 4.17 mmol) in THF (50 ml) and DMF (10 ml) afforded the title compound (1.56 g, 90%) as a yellow oil after purification by flash column chromatography (eluting with a gradient of 20-100% EtOAc/heptane).

1H-NMR (DMSO-d6, 250 MHz): d[ppm]=8.68-8.54 (m, 2H), 8.38 (d, J=4.6 Hz, 1H), 7.75-7.63 (m, 1H), 7.40 (m, 1H), 4.66-4.57 (m, 2H), 4.31-4.15 (m, 2H), 4.11-3.95 (m, 3H), 1.39 (s, 9H)

HPLCMS (Method A): [m/z]: 377.15 [M+H]+

Tert-butyl 3-{4-[(pyridazin-3-ylmethyl)carbamoyl]-1,3-oxazol-2-yl}azetidine-1-carboxylate (345)

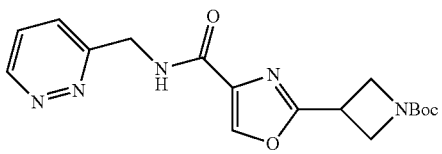 [SMILES: CC(C)(C)OC(=O)N1CC(c2nc(C(=O)NCc3cccnn3)co2)C1]

In a similar fashion to general procedure 6, 2-{1-[(tert-butoxy)carbonyl]azetidin-3-yl}-1,3-oxazole-4-carboxylic acid (342) (0.8 g, 2.98 mmol), 1-(pyridazin-3-yl)methanamine (0.42 g, 3.28 mmol, 85% purity), DIPEA (779 μl, 4.47 mmol) and HATU (1.36 g, 3.58 mmol) in DCM (20 ml) afforded the title compound (0.90 g, 84%) as a brown residue after purification by flash column chromatography (eluting with a gradient of 50-100% EtOAc/heptane followed by 0-20% MeOH/EtOAc).

HPLCMS (Method M): [m/z]: 360.00 [M+H]+

2-(Azetidin-3-yl)-N-(pyridin-2-ylmethyl)-1,3-oxazole-4-carboxamide (346)

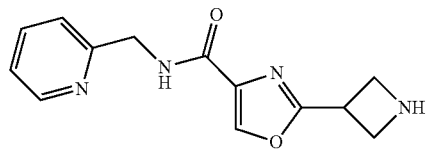 [SMILES: O=C(NCc1ccccn1)c1coc(C2CNC2)n1]

In a similar fashion to general procedure 2, tert-butyl 3-{4-[(pyridin-2-ylmethyl)carbamoyl]-1,3-oxazol-2-yl}azetidine-1-carboxylate (343) (1.07 g, 2.99 mmol) and 12M HCl (2 ml) in MeOH (20 ml) at 50° C. for 30 min afforded the title compound (0.457 g, 59%) as a yellow solid after purification using an SCX-2 cartridge (10 g), rinsing with DCM and MeOH and then eluting with 7N NH3/MeOH. The basic eluent was then concentrated to give the title compound as the free base.

HPLCMS (Method A): [m/z]: 259.00 [M+H]+

2-(Azetidin-3-yl)-N-[(3-fluoropyridin-2-yl)methyl]-1,3-oxazole-4-carboxamide Dihydrochloride (347)

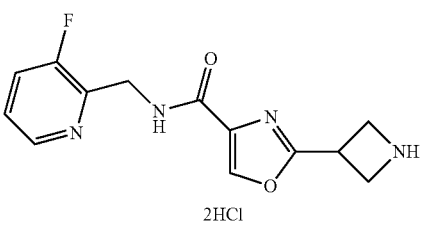 [SMILES: O=C(NCc1ncccc1F)c1coc(C2CNC2)n1]

In a similar fashion to general procedure 2, tert-butyl 3-(4-{[(3-fluoropyridin-2-yl)methyl]carbamoyl}-1,3-oxazol-2-yl)azetidine-1-carboxylate (344) (1.56 g, 3.12 mmol) and concentrated HCl (5.2 ml, 62.51 mmol) in MeOH (25 ml) at room temperature for 16 h afford the title compound (1.31 g, quant.) as an off-white solid. The crude material was used in the next step without purification.

HPLCMS (Method A): [m/z]: 277.05 [M+H]+

2-(Azetidin-3-yl)-N-(pyridazin-3-ylmethyl)-1,3-oxazole-4-carboxamide (348)

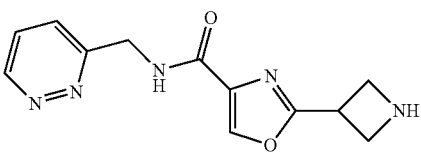 [SMILES: O=C(NCc1cccnn1)c1coc(C2CNC2)n1]

In a similar fashion to general procedure 2, tert-butyl 3-{4-[(pyridazin-3-ylmethyl)carbamoyl]-1,3-oxazol-2-yl}azetidine-1-carboxylate (345) (900 mg, 2.5 mmol) and TFA (10 ml, 130.6 mmol) in DCM (10 ml) at room temperature for 40 min afforded the title compound (447 mg, 69%) as a beige solid after purification using an SCX-2 cartridge (10 g), rinsing with DCM and MeOH and then eluting with 7N NH3/MeOH. The basic eluent was then concentrated to give the title compound as the free base.

1H-NMR (DMSO-d6, 250 MHz): d[ppm]=9.14 (dd, J=4.7, 1.7 Hz, 1H), 8.95 (t, J=6.0 Hz, 1H), 8.60 (s, 1H), 7.67 (dd, J=8.5, 4.7 Hz, 1H), 7.59 (dd, J=8.5, 1.8 Hz, 1H), 4.73 (d, J=6.2 Hz, 2H), 4.13-3.99 (m, 1H), 3.89-3.70 (m, 4H)

HPLCMS (Method M): [m/z]: 260.00 [M+H]+

2-{1-[2-(1H-1,3-benzodiazol-2-yl)ethyl]azetidin-3-yl}-N-(pyridin-2-ylmethyl)-1,3-oxazole-4-carboxamide (Example Compound No. 207)

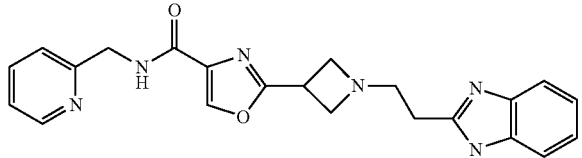

In a similar fashion to general procedure 8, 2-(azetidin-3-yl)-N-(pyridin-2-ylmethyl)-1,3-oxazole-4-carboxamide (346) (457 mg, 1.769 mmol), N-(2-nitrophenyl)prop-2-enamide (D) (408 mg, 2.123 mmol) and DBU (0.32 ml, 2.123 mmol) in MeCN (20 ml) gave the crude intermediate which was purified by flash column chromatography (eluting with a gradient of 0-5% MeOH/DCM). The intermediate was further reacted with iron powder (134 mg) in AcOH (3 ml) to give the title compound (26 mg, 8%) as a white solid after purification by basic prep-HPLC.

1H-NMR (DMSO-d6, 500 MHz): d[ppm]=8.50 (d, J=4.3 Hz, 1H), 8.33 (s, 1H), 7.80 (m, 1H), 7.50 (s, 2H), 7.40 (d, J=7.9 Hz, 1H), 7.34-7.29 (m, 1H), 7.22-7.16 (m, 2H), 4.67 (s, 2H), 3.88 (p, J=7.3 Hz, 1H), 3.75 (t, J=8.0 Hz, 2H), 3.54 (t, J=7.5 Hz, 2H), 3.05-2.99 (m, 2H), 2.99-2.93 (m, 2H)
HPLCMS (Method G): [m/z]: 403.2 [M+H]$^+$

2-{1-[2-(1H-1,3-benzodiazol-2-yl)ethyl]azetidin-3-yl}-N-[(3-fluoropyridin-2-yl)methyl]-1,3-oxazole-4-carboxamide (Example Compound No. 208)

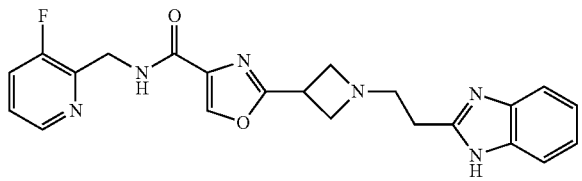 [SMILES: O=C(NCc1ncccc1F)c1coc(C2CN(CCc3nc4ccccc4[nH]3)C2)n1]

In a similar fashion to general procedure 8, 2-(azetidin-3-yl)-N-[(3-fluoropyridin-2-yl)methyl]-1,3-oxazole-4-carboxamide dihydrochloride (347) (0.657 g, 1.571 mmol), DBU (0.703 ml, 4.713 mmol) and N-(2-nitrophenyl)prop-2-enamide (D) (0.332 g, 1.728 mmol) in MeCN (30 ml) at room temperature for 4 h gave the crude intermediate which was purified by flash column chromatography (eluting with a gradient of 0-3% MeOH/DCM) to give a yellow oil (0.778 g). This was further reacted with iron powder (0.191 g) in AcOH (4 ml) at 80° C. for 2 h to give the title compound (0.072 g, 15%) as a white solid after purification by flash column chromatography (kp-NH, eluting with a gradient of 0-3% MeOH/DCM) followed by another flash column chromatography (eluting with a gradient of 0-20% MeOH/DCM).

1H-NMR (MeOD, 500 MHz): d[ppm]=8.36 (d, J=4.7 Hz, 1H), 8.32 (s, 1H), 7.62-7.56 (m, 1H), 7.50 (br s, 2H), 7.41-7.36 (m, 1H), 7.22-7.17 (m, 2H), 4.75 (d, J=1.5 Hz, 2H), 3.88 (p, J=7.3 Hz, 1H), 3.75 (t, J=8.0 Hz, 2H), 3.53 (t, J=7.5 Hz, 2H), 3.04-2.99 (m, 2H), 2.99-2.93 (m, 2H)
HPLCMS (Method C): [m/z]: 421.1 [M+H]$^+$

2-{1-[2-(1H-1,3-benzodiazol-2-yl)ethyl]azetidin-3-yl}-N-(pyridazin-3-ylmethyl)-1,3-oxazole-4-carboxamide (Example Compound No. 244)

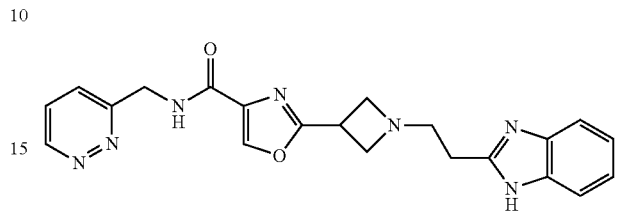

In a similar fashion to general procedure 8, 2-(azetidin-3-yl)-N-(pyridazin-3-ylmethyl)-1,3-oxazole-4-carboxamide (348) (440 mg, 1.7 mmol), N-(2-nitrophenyl)prop-2-enamide (D) (326 mg, 1.7 mmol) and DBU (279 µl, 1.87 mmol) in MeCN (20 ml) gave a crude intermediate which was further reacted with iron powder (302 mg, 5.41 mmol) in AcOH (5 ml) to afforded the title compound (82 mg, 15%) as a white solid after purification by basic prep-HPLC.

1H-NMR (MeOD, 500 MHz): d[ppm]=9.12 (dd, J=4.5, 2.1 Hz, 1H), 8.36 (s, 1H), 7.76-7.69 (m, 2H), 7.51 (s, 2H), 7.24-7.19 (m, 2H), 4.88 (s, 2H), 3.93-3.85 (m, 1H), 3.78-3.74 (m, 2H), 3.58-3.53 (m, 2H), 3.07-3.01 (m, 2H), 3.01-2.95 (m, 2H)
HPLCMS (Method B): [m/z]: 404.2 [M+H]$^+$

2-{1-[2-(4-Fluoro-1H-1,3-benzodiazol-2-yl)ethyl]azetidin-3-yl}-N-[(3-fluoropyridin-2-yl)methyl]-1,3-oxazole-4-carboxamide (Example Compound No. 239)

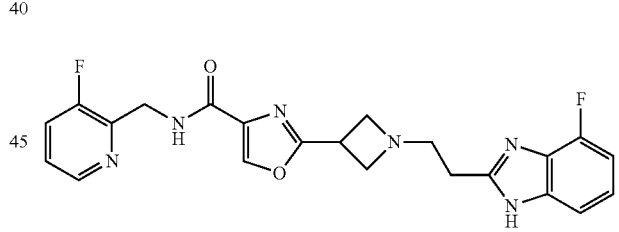

In a similar fashion to general procedure 8, 2-(azetidin-3-yl)-N-[(3-fluoropyridin-2-yl)methyl]-1,3-oxazole-4-carboxamide; bis(trifluoroacetic acid)(347) (700 mg, 1.39 mmol), DBU (1.04 ml, 6.94 mmol) and N-(3-fluoro-2-nitrophenyl)prop-2-enamide (G) (292 mg, 1.39 mmol) in MeCN (30 ml) gave a crude intermediate which was further reacted with iron powder (173 mg, 3.1 mmol) in AcOH (5 ml) to afford the title compound (98 mg, 29%) as a pale pink solid after purification by flash column chromatography (eluting with a gradient of 0-8% MeOH/DCM).

1H-NMR (MeOD, 500 MHz): d[ppm]=8.38 (dt, J=4.6, 1.1 Hz, 1H), 8.35 (s, 1H), 7.62 (ddd, J=9.8, 8.4, 1.2 Hz, 1H), 7.41 (dt, J=8.6, 4.5 Hz, 1H), 7.31 (d, J=8.1 Hz, 1H), 7.18 (td, J=8.1, 4.8 Hz, 1H), 6.95 (dd, J=10.8, 8.0 Hz, 1H), 4.77 (d, J=1.5 Hz, 2H), 3.94-3.86 (m, 1H), 3.78 (t, J=7.9 Hz, 2H), 3.57 (t, J=7.5 Hz, 2H), 3.08-3.03 (m, 2H), 3.02-2.97 (m, 2H)
HPLCMS (Method B): [m/z]: 439.2 [M+H]$^+$

2-{1-[2-(4-Fluoro-1H-1,3-benzodiazol-2-yl)ethyl]azetidin-3-yl}-N-(pyridin-2-ylmethyl)-1,3-oxazole-4-carboxamide (Example Compound No. 258)

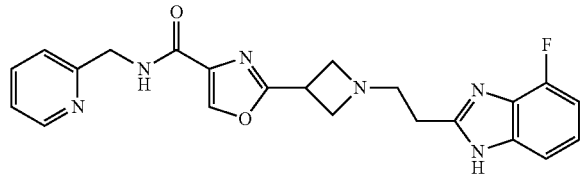 [SMILES: O=C(NCc1ccccn1)c1coc(C2CN(CCc3nc4c(F)cccc4[nH]3)C2)n1]

In a similar fashion to general procedure 8, 2-(azetidin-3-yl)-N-(pyridin-2-ylmethyl)-1,3-oxazole-4-carboxamide (346) (0.88 g, 3.21 mmol), N-(3-fluoro-2-nitrophenyl)prop-2-enamide (G) (0.80 g, 3.53 mmol) and DBU (580 µl, 3.86 mmol) in MeCN (30 ml) gave a crude intermediate which was further reacted with iron powder (0.57 g, 10.24 mmol) in AcOH (16 ml) to afford the title compound (0.59 g, 55%) as an off white solid after purification by flash column chromatography (eluting with a gradient of 0-15% MeOH/DCM) followed by basic prep-HPLC.

1H-NMR (MeOD, 500 MHz): d[ppm]=8.51-8.48 (m, 1H), 8.33 (s, 1H), 7.80 (td, J=7.7, 1.8 Hz, 1H), 7.40 (d, J=7.9 Hz, 1H), 7.34-7.27 (m, 2H), 7.16 (td, J=8.1, 4.8 Hz, 1H), 6.92 (dd, J=10.8, 8.1 Hz, 1H), 4.67 (s, 2H), 3.93-3.83 (m, 1H), 3.75 (t, J=7.9 Hz, 2H), 3.54 (t, J=7.5 Hz, 2H), 3.05-3.00 (m, 2H), 2.99-2.95 (m, 2H)

HPLCMS (Method C): [m/z]: 421.3 [M+H]$^+$

2-{1-[2-(4-Fluoro-1H-1,3-benzodiazol-2-yl)ethyl]azetidin-3-yl}-N-(pyridazin-3-ylmethyl)-1,3-oxazole-4-carboxamide (Example Compound No. 261)

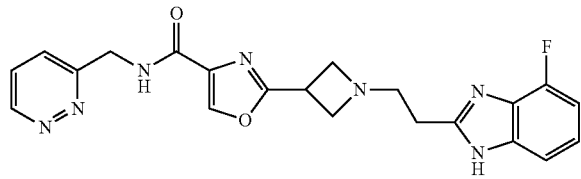 [SMILES: O=C(NCc1cccnn1)c1coc(C2CN(CCc3nc4c(F)cccc4[nH]3)C2)n1]

In a similar fashion to general procedure 8, 2-(azetidin-3-yl)-N-(pyridazin-3-ylmethyl)-1,3-oxazole-4-carboxamide (348) (417 mg, 1.61 mmol), N-(3-fluoro-2-nitrophenyl)prop-2-enamide (G) (372 mg, 1.77 mmol) and DBU (264 µl, 1.77 mmol) in MeCN (50 ml) gave a crude intermediate which was further reacted with iron powder (261 mg, 4.67 mmol) in AcOH (10 ml) to afford the title compound (268 mg, 54%) as a white solid after purification by basic prep-HPLC.

1H-NMR (MeOD, 500 MHz): d[ppm]=9.12 (dd, J=4.5, 2.1 Hz, 1H), 8.36 (s, 1H), 7.76-7.70 (m, 2H), 7.31 (d, J=8.1 Hz, 1H), 7.18 (td, J=8.1, 4.8 Hz, 1H), 6.97-6.91 (m, 1H), 4.88 (s, 2H), 3.89 (p, J=7.3 Hz, 1H), 3.79-3.74 (m, 2H), 3.58-3.53 (m, 2H), 3.06-3.02 (m, 2H), 3.02-2.96 (m, 2H)

HPLCMS (Method B): [m/z]: 422.2 [M+H]$^+$

N-[(3-Fluoropyridin-2-yl)methyl]-2-(1-{2-[7-(trifluoromethyl)-1H-1,3-benzodiazol-2-yl]ethyl}azetidin-3-yl)-1,3-oxazole-4-carboxamide (Example Compound No. 273)

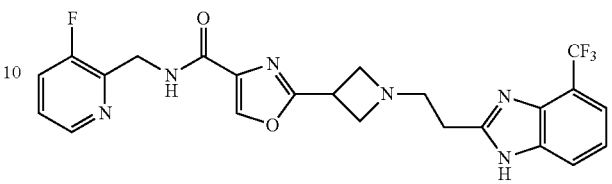

In a similar fashion to general procedure 8, 2-(azetidin-3-yl)-N-[(3-fluoropyridin-2-yl)methyl]-1,3-oxazole-4-carboxamide (347) (393 mg, 1.42 mmol), N-[2-nitro-6-(trifluoromethyl)phenyl]prop-2-enamide (K8) (474 mg, 1.42 mmol, 78% purity) and DBU (0.23 ml, 1.56 mmol) in MeCN (18 ml) gave a crude intermediate which was further reacted with iron powder (280 mg, 5.01 mmol) in AcOH (8 ml) to afford the title compound (197 mg, 32%) as a light brown foam after purification by flash column chromatography (eluting with a gradient of 0-20% MeOH/DCM).

1H-NMR (DMSO-d6, 500 MHz): d[ppm]=12.64 (s, 1H), 8.55 (s, 1H), 8.52 (t, J=5.7 Hz, 1H), 8.39-8.35 (m, 1H), 7.76 (s, 1H), 7.71-7.65 (m, 1H), 7.48-7.43 (m, 1H), 7.43-7.37 (m, 1H), 7.30-7.26 (m, 1H), 4.66-4.58 (m, 2H), 3.81 (p, J=7.4 Hz, 1H), 3.63 (t, J=7.5 Hz, 2H), 3.35 (t, J=7.2 Hz, 2H), 2.90 (s, 4H)

HPLCMS (Method D): [m/z]: 489.1 [M+H]$^+$

General Scheme 26 Above:

2-(3-Chloropropyl)-1-{[2-(trimethylsilyl)ethoxy]methyl}-1H-1,3-benzodiazole (349)

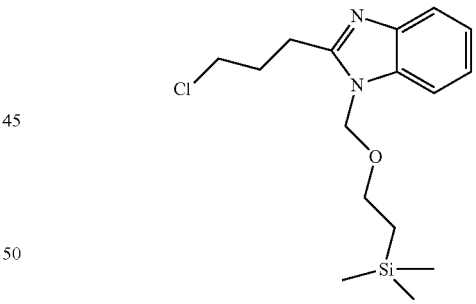

[2-(chloromethoxy)ethyl](trimethyl)silane (553 µl, 3.12 mmol) was added to a solution of 2-(3-chloropropyl)-1H-1,3-benzodiazole hydrochloride (555 mg, 2.4 mmol) and DIPEA (962 µl, 5.52 mmol) in THF (25 ml). The reaction mixture was stirred at room temperature for 18 h, then quenched with saturated NaHCO$_3$ (aq) and extracted with EtOAc (3×80 ml). The combined organic extracts were washed with brine (50 ml), dried (Na$_2$SO$_4$) and evaporated in vacuo. Purification by flash column chromatography (eluting with a gradient of 0-50% EtOAc/heptane) afforded the title compound (571 mg, 73%) as a pale yellow oil.

1H-NMR (CDCl$_3$, 250 MHz): d[ppm]=7.85-7.75 (m, 1H), 7.53-7.44 (m, 1H), 7.38-7.31 (m, 2H), 5.57 (s, 2H), 3.78 (t, J=6.1 Hz, 2H), 3.60 (dd, J=8.6, 7.7 Hz, 2H), 3.21 (t, J=7.3 Hz, 2H), 2.59-2.44 (m, 2H), 0.96 (dd, J=8.6, 7.7 Hz, 2H), 0.00 (s, 9H)

HPLCMS (Method M): [m/z]: 325.50 [M+H]$^+$

Methyl 2-(azetidin-3-yl)-1,3-oxazole-4-carboxylate Hydrochloride (350)

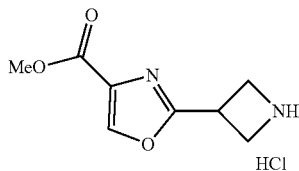 [SMILES: COC(=O)c1coc(C2CNC2)n1 ; Cl]

In a similar fashion to general procedure 4, methyl 2-{1-[(tert-butoxy)carbonyl]azetidin-3-yl}-1,3-oxazole-4-carboxylate (341) (634 mg, 2.25 mmol) and 12M HCl (0.89 ml) in MeOH (20 ml) at 60° C. afforded the title compound (201 mg, 41%) as a white solid after trituration in DCM/Et$_2$O.

1H-NMR (DMSO-d6, 250 MHz): d[ppm]=8.91 (s, 1H), 4.36-4.15 (m, 5H), 3.83 (s, 3H)

HPLCMS (Method M): [m/z]: 183.20 [M+H]$^+$

Methyl 2-{1-[3-(1-{[2-(trimethylsilyl)ethoxy]methyl}-1H-1,3-benzodiazol-2-yl)propyl]azetidin-3-yl}-1,3-oxazole-4-carboxylate (351)

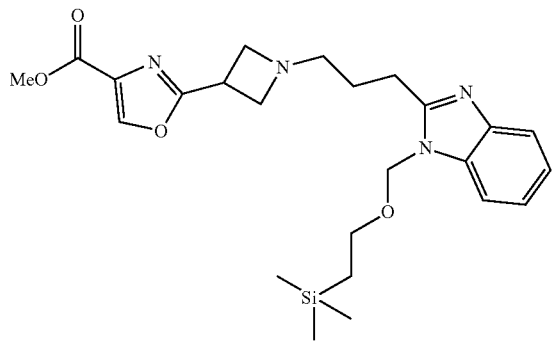 [SMILES: COC(=O)c1coc(C2CN(CCCc3nc4ccccc4n3COCC[Si](C)(C)C)C2)n1]

A suspension of methyl 2-(azetidin-3-yl)-1,3-oxazole-4-carboxylate hydrochloride (350) (300 mg, 1.37 mmol), 2-(3-chloropropyl)-1-{[2-(trimethylsilyl)ethoxy]methyl}-1H-1,3-benzodiazole (349) (758 mg, 2.33 mmol), DIPEA (837 μl, 4.8 mmol) and KI (228 mg, 1.37 mmol) in DMF (10 ml) was stirred at room temperature for 7 d. The reaction was quenched with saturated NaHCO$_3$ (aq) and extracted with EtOAc (3×50 ml). The combined organic extracts were washed with brine (4×50 ml), dried (Na$_2$SO$_4$), filtered and evaporated in vacuo. Purification by flash column chromatography (eluting with a gradient of 40-100% EtOAc/heptane followed by 2-40% MeOH/EtOAc) afforded the title compound (329 mg, 46%, 91% purity) as a yellow residue.

HPLCMS (Method M): [m/z]: 471.15 [M+H]$^+$

2-{1-[3-(1-{[2-(Trimethylsilyl)ethoxy]methyl}-1H-1,3-benzodiazol-2-yl)propyl]azetidin-3-yl}-1,3-oxazole-4-carboxylic Acid (352)

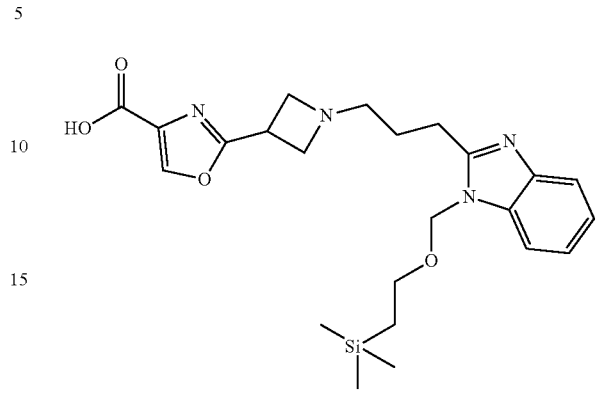

In a similar fashion to general procedure 5, 2-{1-[3-(1-{[2-(trimethylsilyl)ethoxy]methyl}-1H-1,3-benzodiazol-2-yl)propyl]azetidin-3-yl}-1,3-oxazole-4-carboxylate (351) (329 mg, 0.7 mmol) and LiOH (50 mg, 2.1 mmol) in THF (10 ml) and water (10 ml) afforded the title compound (363 mg, 91%, 80% purity) as a yellow residue. The compound was used in the next step without purification.

HPLCMS (Method M): [m/z]: 457.10 [M+H]$^+$

N-[(3-fluoropyridin-2-yl)methyl]-2-{1-[3-(1-{[2-(trimethylsilyl)ethoxy]methyl}-1H-1,3-benzodiazol-2-yl)propyl]azetidin-3-yl}-1,3-oxazole-4-carboxamide (353)

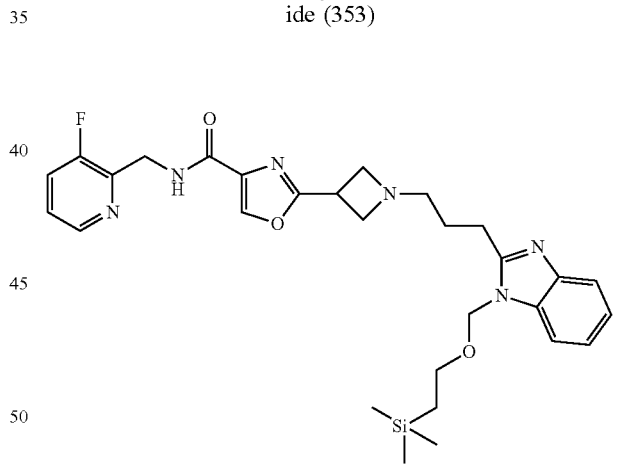

In a similar manner to general procedure 6, 2-{1-[3-(1-{[2-(trimethylsilyl)ethoxy]methyl}-1H-1,3-benzodiazol-2-yl)propyl]azetidin-3-yl}-1,3-oxazole-4-carboxylic acid (352) (363 mg, 0.64 mmol, 80% purity), (3-fluoropyridin-2-yl)methanamine dihydrochloride (A2) (152 mg, 0.76 mmol), DIPEA (388 μl, 2.23 mmol) and HATU (290 mg, 0.76 mmol) in DCM (20 ml) afforded the title compound (302 mg, 84%) as a pale yellow residue after purification by flash column chromatography (eluting with a gradient of 0-40% MeOH/DCM).

HPLCMS (Method M): [m/z]: 565.15 [M+H]$^+$

2-{1-[3-(1H-1,3-Benzodiazol-2-yl)propyl]azetidin-3-yl}-N-[(3-fluoropyridin-2-yl)methyl]-1,3-oxazole-4-carboxamide (Example Compound No. 233)

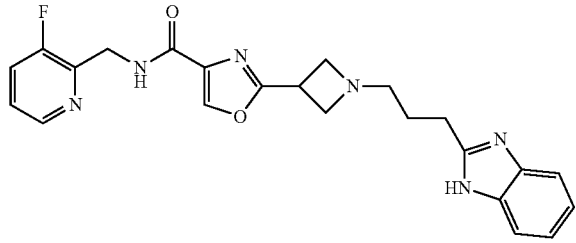 [SMILES: O=C(NCc1ncccc1F)c1coc(C2CN(CCCc3nc4ccccc4[nH]3)C2)n1]

TFA (4 ml, 52.23 mmol) was added to a solution of N-[(3-fluoropyridin-2-yl)methyl]-2-{1-[3-(1-{[2-(trimethylsilyl)ethoxy]methyl}-1H-1,3-benzodiazol-2-yl)propyl]azetidin-3-yl}-1,3-oxazole-4-carboxamide (353) (300 mg, 0.53 mmol) in DCM (4 ml). The reaction mixture was stirred at room temperature for 3 h. The reaction mixture was concentrated in vacuo and the residue was dissolved in water basified by the addition of 2M NaOH (aq). The mixture was then extracted with 4:1 CHCl$_3$/IPA (4×50 ml). The combined organic extracts were dried (Na$_2$SO$_4$), filtered and evaporated in vacuo. The residue was dissolved in a minimum volume of MeOH and loaded onto an SCX-2 cartridge (10 g). The cartridge was rinsed with DCM, followed by MeOH, and eluted with 7N NH$_3$/MeOH. The basic eluent was evaporated under vacuum. Purification of the residue by basic prep-HPLC afforded the title compound (75 mg, 33%) as a white solid.

1H-NMR (MeOD, 500 MHz): d[ppm]=8.37 (dt, J=4.6, 1.1 Hz, 1H), 8.33 (s, 1H), 7.61 (ddd, J=9.8, 8.4, 1.2 Hz, 1H), 7.50 (s, 2H), 7.41 (dt, J=8.7, 4.4 Hz, 1H), 7.23-7.17 (m, 2H), 4.77 (d, J=1.5 Hz, 2H), 3.93-3.84 (m, 1H), 3.75 (t, J=8.0 Hz, 2H), 3.53 (t, J=7.5 Hz, 2H), 2.94 (t, J=7.6 Hz, 2H), 2.66-2.60 (m, 2H), 1.97-1.88 (m, 2H)

HPLCMS (Method B): [m/z]: 435.1 [M+H]$^+$

General Scheme 28 Above:

3-{[(Tert-butoxy)carbonyl]amino}-3-methylbutanoic Acid (360)

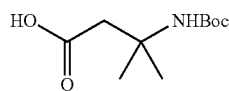

1M KOH (15.19 ml) was added to a mixture of 3-amino-3-methylbutanoic acid (1.78 g, 15.19 mmol) and Boc$_2$O (3.48 g, 15.95 mmol) in 1,4-dioxane (30 ml) and stirred at room temperature for 40 h. The solvent was concentrated and diluted with water (60 ml). 1M LiOH was added until pH 13. The aqueous phase was extracted with Et$_2$O (3×30 ml), then the pH adjusted to 3 using 2M HCl and extracted with EtOAc (4×60 ml). The combined organic layers were washed with brine (30 ml), dried (Na$_2$SO$_4$), filtered and evaporated to give the title compound (2.13 g, 65%) as an off-white solid. Compound will be used in the next step without further purification.

1H-NMR (CDCl$_3$, 250 MHz): d[ppm]=5.07 (s, 1H), 2.75 (s, 2H), 1.44 (s, 9H) 1.40 (s, 6H)

3-{[(Tert-butoxy)carbonyl]amino}-2,2-dimethylpropanoic Acid (361)

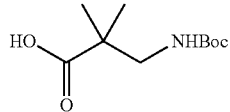

1M KOH (52.08 ml, 52.08 mmol) was added to a mixture of 3-amino-2,2-dimethylpropanoic acid hydrochloride (4 g, 26.04 mmol) and Boc$_2$O (5.97 g, 27.34 mmol) in 1,4-dioxane (80 ml) and stirred at room temperature for 20 h. The solvent was concentrated and diluted with water (50 ml). 1M LiOH was added until pH 13. The aqueous phase was extracted with Et$_2$O (3×50 ml), then the pH adjusted to 3 using 2M HCl and extracted with EtOAc (4×50 ml). The combined organic layers were washed with brine (50 ml), dried (Na$_2$SO$_4$), filtered and evaporated to give the title compound (5.38 g, 95%) as a white solid. Compound will be used in the next step without further purification.

1H-NMR (CDCl$_3$, 250 MHz): d[ppm]=5.01 (s, 1H), 3.29-3.18 (m, 2H), 1.45 (d, 9H), 1.23 (s, 6H)

Tert-butyl N-(1-carbamoyl-2-methylpropan-2-yl)carbamate (362)

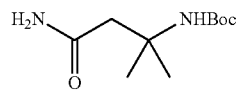

TEA (2.82 ml, 20.27 mmol) was added to an ice-cooled (0° C.) solution of 3-{[(tert-butoxy)carbonyl]amino}-3-methylbutanoic acid (360) (2.59 g, 11.92 mmol) in THF (30 ml). The reaction mixture was stirred for 20 min before the addition of 2-methylpropyl carbonochloridate (2.78 ml, 17.88 mmol) dropwise at 0° C. The reaction was stirred for 1 h before the addition of 35% NH$_3$ (aqueous solution) (3.09 ml, 66.76 mmol) dropwise and the reaction warmed to room temperature and stirred for 18 h. Saturated NaHCO$_3$ (50 ml) was added and the aqueous layer extracted with DCM (3×50 ml). The combined organic layers were dried (MgSO$_4$), filtered and evaporated to give a pale yellow oil (4.11 g). Purification by flash column chromatography (eluting with a gradient of 0-10% MeOH-DCM) gave the title compound (1.7 g, 55%, 84% purity) as a clear oil which solidified on standing.

1H-NMR (CDCl$_3$, 250 MHz): d[ppm]=5.85 (br s, 1H), 5.39 (br s, 1H), 4.89 (br s, 1H), 2.64 (s, 2H), 1.42 (s, 9H), 1.39 (s, 6H)

HPLCMS (Method A): [m/z]: 238.95 [M+Na]$^+$

Tert-butyl N-(2-carbamoyl-2,2-dimethylethyl)carbamate (363)

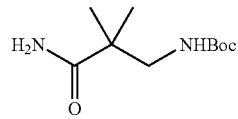

TEA (5.73 ml, 41.08 mmol) was added to an ice-cooled (0° C.) solution of 3-{[(tert-butoxy)carbonyl]amino}-2,2-dimethylpropanoic acid (361) (5.25 g, 24.16 mmol) in THF (50 ml). The reaction was stirred for 20 min, before the addition of 2-methylpropyl carbonochloridate (4.7 ml, 36.3 mmol) dropwise at 0° C. The reaction was stirred for 1 h before the dropwise addition of 35% NH$_3$ (aqueous solution) (7.48 ml, 135.31 mmol). The reaction mixture was warmed to room temperature and stirred for 22 h. Saturated NaHCO$_3$ (100 ml) was added and the aqueous layer extracted with DCM (3×150 ml). The combined organic layers were dried (MgSO$_4$), filtered and evaporated to give an off-white semi-solid (6.61 g). Purification by flash column chromatography (eluting with a gradient of 0-10% MeOH/DCM) gave the title compound (3.7 g, 71%) as a white solid.

1H-NMR (CDCl$_3$, 250 MHz): d[ppm]=5.95 (s, 1H), 5.30 (s, 1H), 5.08 (s, 1H), 3.25 (d, J=6.6 Hz, 2H), 1.43 (s, 9H), 1.21 (s, 6H)

HPLCMS (Method A): [m/z]: 239.10 [M+Na]$^+$

Tert-butyl N-(1-carbamothioyl-2-methylpropan-2-yl)carbamate (364)

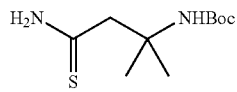

In a similar fashion to general procedure 11, Lawesson reagent (1.65 g, 4.08 mmol) and tertbutyl N-(1-carbamoyl-2-methylpropan-2-yl)carbamate (362) (1.7 g, 6.6 mmol, 84% purity) in DCM (50 ml) at room temperature for 19 h gave the title compound (0.914 g, 60%) as a yellow oil after purification by flash column chromatography (eluting with a gradient of 0-50% EtOAc/Heptane) which solidified on standing.

1H-NMR (MeOD, 250 MHz): d[ppm]=2.91 (s, 2H), 1.43 (s, 9H), 1.38 (s, 6H)

HPLCMS (Method A): [m/z]: 232.95 [M+H]$^+$

Tert-butyl N-(2-carbamothioyl-2,2-dimethylethyl)carbamate (365)

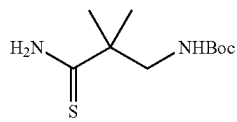

In a similar fashion to general procedure 11, Lawesson reagent (3.29 g, 8.14 mmol) and tertbutyl N-(2-carbamoyl-2,2-dimethylethyl)carbamate (363) (3.2 g, 14.8 mmol) in DCM (65 ml) at room temperature for 24 h gave the title compound (1.67 g, 49%) as a white solid after purification by flash column chromatography (eluting with a gradient of 0-50% EtOAc-Heptane).

1H-NMR (MeOD, 250 MHz): d[ppm]=3.35 (s, 2H), 1.44 (s, 9H), 1.25 (s, 6H)

HPLCMS (Method A): [m/z]: 254.95 [M+Na]$^+$

Ethyl 2-(2-{[(tert-butoxy)carbonyl]amino}-2-methylpropyl)-1,3-thiazole-4-carboxylate (366)

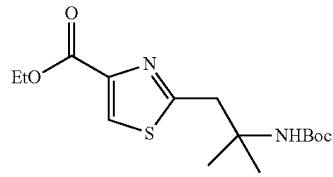 [SMILES: CCOC(=O)c1csc(CC(C)(C)NC(=O)OC(C)(C)C)n1]

In a similar fashion to general procedure 1, tert-butyl N-(1-carbamothioyl-2-methylpropan-2-yl)carbamate (364) (0.91 g, 3.93 mmol), ethyl 3-bromo-2-oxopropanoate (0.64 ml, 4.33 mmol) and CaCO$_3$ (0.22 g, 2.16 mmol) in EtOH (10 ml) gave the title compound (0.285 g, 19%) as an orange oil after purification by flash column chromatography (eluting with a gradient of 0-100% EtOAc/heptane).

1H-NMR (DMSO-d6, 250 MHz): d[ppm]=8.42 (s, 1H), 4.29 (q, J=7.2 Hz, 2H), 3.39 (s, 2H), 1.36 (s, 9H), 1.30 (d, J=7.0 Hz, 3H), 1.20 (s, 6H)

HPLCMS (Method A): [m/z]: 329.00 [M+H]$^+$

Ethyl 2-(1-{[(tert-butoxy)carbonyl]amino}-2-methylpropan-2-yl)-1,3-thiazole-4-carboxylate (367)

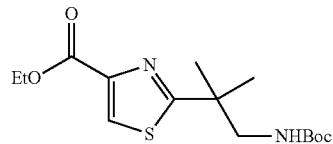 [SMILES: CCOC(=O)c1csc(C(C)(C)CNC(=O)OC(C)(C)C)n1]

In a similar fashion to general procedure 1, tert-butyl N-(2-carbamothioyl-2,2-dimethylethyl)carbamate (365) (1.67 g, 7.9 mmol), ethyl 3-bromo-2-oxopropanoate (1.2 ml, 7.9 mmol) and CaCO$_3$ (0.4 g, 3.95 mmol) in EtOH (20 ml) was stirred at room temperature for 72 h. The reaction was further treated with MgSO$_4$ (0.8 g) and CaCO$_3$ (0.4 g, 3.95 mmol) and heated at 80° C. for 7 h. The reaction was cooled and the solvent evaporated to give a residue which was partitioned taken up in EtOAc (50 ml) and washed with saturated NaHCO$_3$ (7 ml). The aqueous layer was extracted with EtOAc (3×15 ml) and the combined organic layers were dried (MgSO$_4$), filtered and evaporated to give a brown oil (2.61 g). The oil was dissolved in DCM (50 ml) and TEA (2.9 ml, 20.58 mmol) was added followed by dropwise addition of di-tert-butyl dicarbonate (3.74 g, 17.15 mmol) in DCM (20 ml). The reaction was stirred at room temperature for 22 h. The reaction mixture was diluted with DCM (10 ml) and the organic layer was washed with water (20 ml), brine (20 ml), dried (MgSO$_4$), filtered and evaporated to give a brown oil (4.82 g). Purification by flash column chromatography (eluting with 0-50% EtOAc-heptane) gave the title compound (1.4 g, 36%) as a yellow oil.

1H-NMR (DMSO-d6, 250 MHz): d[ppm]=8.06 (s, 1H), 5.19 (br s, 1H), 4.40 (q, J=7.1 Hz, 2H), 3.50 (br s, 2H), 1.44 (s, 6H), 1.42 (s, 9H)

HPLCMS (Method A): [m/z]: 329.00 [M+H]$^+$

2-(2-{[(Tert-butoxy)carbonyl]amino}-2-methylpropyl)-1,3-thiazole-4-carboxylic Acid (368)

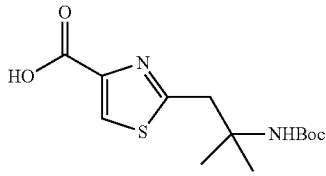

In a similar fashion to general procedure 5, ethyl 2-(2-{[(tert-butoxy)carbonyl]amino}-2-methylpropyl)-1,3-thiazole-4-carboxylate (366) (0.285 g, 0.867 mmol, 85% purity) and LiOH (88 mg, 3.67 mmol) in THF (4 ml) and H$_2$O (2 ml) at room temperature for 5 h gave the title compound (0.215 g, 66%, 68% purity) as a dark yellow oil. Compound was used in the next step without further purification.

1H-NMR (DMSO-d6, 250 MHz): d[ppm]=8.35 (s, 1H), 3.38 (s, 2H), 1.43 (s, 9H), 1.21 (s, 6H)
HPLCMS (Method A): [m/z]: 301.00 [M+H]$^+$

2-(1-{[(Tert-butoxy)carbonyl]amino}-2-methylpropan-2-yl)-1,3-thiazole-4-carboxylic Acid (369)

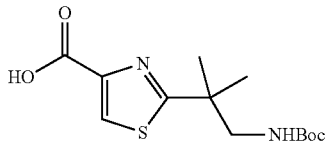 [SMILES: CC(C)(C)OC(=O)NCC(C)(C)c1nc(C(=O)O)cs1]

In a similar fashion to general procedure 5, ethyl 2-(1-{[(tert-butoxy)carbonyl]amino}-2-methylpropan-2-yl)-1,3-thiazole-4-carboxylate (367) (1.4 g, 4.12 mmol) and LiOH (0.49 g, 20.6 mmol) in THF (20 ml) and water (10 ml) at room temperature for 3 h gave the title compound (1.5 g, 98%, 83% purity) as a yellow oil which solidified on standing. To be used without purification.

1H-NMR (DMSO-d6, 250 MHz): d[ppm]=8.32 (s, 1H), 6.98-6.88 (m, 1H), 3.18 (d, J=6.5 Hz, 2H), 1.34 (s, 9H), 1.32 (s, 6H)
HPLCMS (Method A): [m/z]: 301.05 [M+H]$^+$

Tert-butyl N-[1-(4-{[(3-fluoropyridin-2-yl)methyl]carbamoyl}-1,3-thiazol-2-yl)-2-methylpropan-2-yl]carbamate (370)

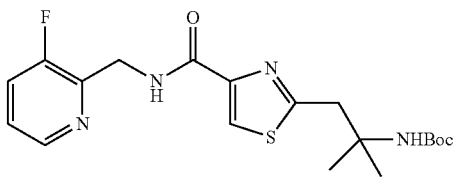 [SMILES: CC(C)(Cc1nc(C(=O)NCc2ncccc2F)cs1)NC(=O)OC(C)(C)C]

In a similar fashion to general procedure 6, 2-(2-{[(tert-butoxy)carbonyl]amino}-2-methylpropyl)-1,3-thiazole-4-carboxylic acid (368) (0.28 g, 0.63 mmol, 68% purity), (3-fluoropyridin-2-yl)methanamine dihydrochloride (A2) (0.20 g, 1.01 mmol), HATU (0.4 g, 1.04 mmol) and DIPEA (0.4 ml, 2.29 mmol) in DMF (6 ml) were stirred at room temperature for 2 h, gave the title compound (0.33 g, 84%, 72% purity) as a dark yellow oil after purification by flash column chromatography (eluting with a gradient of 0-100% EtOAc/heptane). To be used without further purification.

1H-NMR (DMSO-d6, 250 MHz): d[ppm]=8.58 (t, J=5.6 Hz, 1H), 8.39 (dt, J=4.7, 1.5 Hz, 1H), 8.19 (s, 1H), 7.78-7.63 (m, 1H), 7.47-7.35 (m, 1H), 6.68 (s, 1H), 4.67 (dd, J=5.6, 1.3 Hz, 2H), 3.41 (s, 2H), 1.41 (s, 9H), 1.23 (s, 6H)
HPLCMS (Method A): [m/z]: 409.05 [M+H]$^+$

Tert-butyl N-[2-(4-{[(3-fluoropyridin-2-yl)methyl]carbamoyl}-1,3-thiazol-2-yl)-2-methylpropyl]carbamate (371)

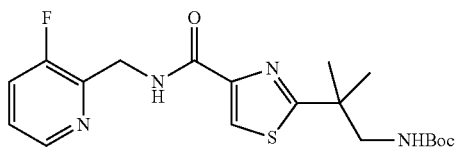 [SMILES: CC(C)(C)OC(=O)NCC(C)(C)c1nc(C(=O)NCc2ncccc2F)cs1]

In a similar fashion to general procedure 6, 2-(1-{[(tert-butoxy)carbonyl]amino}-2-methylpropan-2-yl)-1,3-thiazole-4-carboxylic acid (369) (0.64 g, 1.73 mmol, 83% purity), (3-fluoropyridin-2-yl)methanamine dihydrochloride (A2) (0.41 g, 2.08 mmol), HATU (0.79 g, 2.08 mmol) and DIPEA (0.99 ml, 5.71 mmol) in DCM (8 ml) at room temperature for 17 h gave the title compound (1.78 g, 90% purity) after purification by flash column chromatography (eluting with a gradient of 0-100% EtOAc/heptane) as a yellow oil which solidified on standing.

1H-NMR (DMSO-d6, 250 MHz): d[ppm]=8.71 (t, J=5.8 Hz, 1H), 8.43-8.33 (m, 1H), 8.15 (s, 1H), 7.76-7.65 (m, 1H), 7.47-7.34 (m, 1H), 6.97 (t, J=6.3 Hz, 1H), 4.67 (dd, J=5.8, 1.5 Hz, 2H), 3.25 (d, J=6.5 Hz, 2H), 1.34 (s, 6H), 1.34 (s, 9H)
HPLCMS (Method A): [m/z]: 409.45 [M+H]$^+$

2-(2-Amino-2-methylpropyl)-N-[(3-fluoropyridin-2-yl)methyl]-1,3-thiazole-4-carboxamide Dihydrochloride (372)

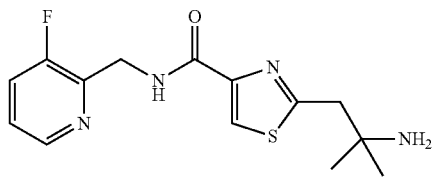

In a similar fashion to general procedure 2, tert-butyl N-[1-(4-{[(3-fluoropyridin-2-yl)methyl]carbamoyl}-1,3-thiazol-2-yl)-2-methylpropan-2-yl]carbamate (370) (0.33 g, 0.58 mmol, 72% purity) and 12M HCl (0.73 ml, 8.78 mmol) in MeOH (5 ml) at 50° C. for 2 h gave the title compound (0.26 g, 90%, 76% purity) as a beige residue which was used in the next step without purification.

1H-NMR (MeOD, 250 MHz): d[ppm]=8.53 (dd, J=5.3, 1.0 Hz, 1H), 8.24 (s, 1H), 8.16-8.06 (m, 1H), 7.82-7.73 (m, 1H), 4.91 (d, J=1.4 Hz, 2H), 3.42 (s, 2H), 1.46 (s, 6H)

HPLCMS (Method A): [m/z]: 308.95 as the freebase [M+H]⁺

2-(1-Amino-2-methylpropan-2-yl)-N-[(3-fluoropyridin-2-yl)methyl]-1,3-thiazole-4-carboxamide Dihydrochloride (373)

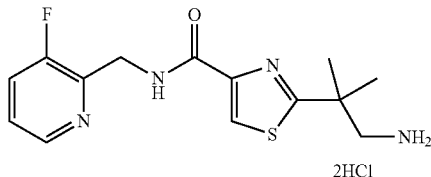 [SMILES: CC(C)(CN)c1nc(C(=O)NCc2ncccc2F)cs1]

2HCl

In a similar fashion to general procedure 2, tert-butyl N-[2-(4-{[(3-fluoropyridin-2-yl)methyl]carbamoyl}-1,3-thiazol-2-yl)-2-methylpropyl]carbamate (371) (1.78 g, 3.93 mmol, 90% purity) and 12M HCl (6.61 ml, 79.3 mmol) in MeOH (30 ml) at room temperature for 70 h gave the title compound (1.54 g, 98%) as a brown foam. To be used without purification.

1H-NMR (MeOD, 250 MHz): d[ppm]=8.49-8.44 (m, 1H), 8.24 (s, 1H), 7.98-7.88 (m, 1H), 7.68-7.59 (m, 1H), 4.88 (d, J=1.5 Hz, 2H), 3.37 (s, 2H), 1.58 (s, 6H)

HPLCMS (Method A): [m/z]: 309.00 as the freebase [M+H]⁺

2-{2-[(1H-1,3-Benzodiazol-2-ylmethyl)amino]-2-methylpropyl}-N-[(3-fluoropyridin-2-yl)methyl]-1,3-thiazole-4-carboxamide (Example Compound No. 231)

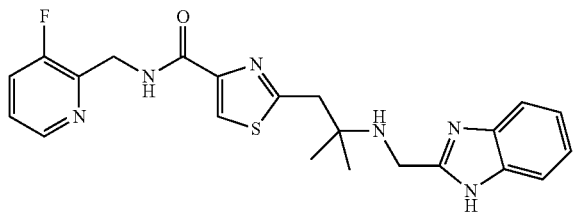 [SMILES: CC(C)(Cc1nc(C(=O)NCc2ncccc2F)cs1)NCc1nc2ccccc2[nH]1]

In a similar fashion to general procedure 3, 2-(2-amino-2-methylpropyl)-N-[(3-fluoropyridin-2-yl)methyl]-1,3-thiazole-4-carboxamide dihydrochloride (372) (0.26 g, 0.52 mmol, 77% purity) 1H-1,3-benzodiazole-2-carbaldehyde (0.106 g, 0.73 mmol), DIPEA (0.36 ml, 2.09 mmol) in MeOH (5 ml) at 50° C. for 3.5 h, followed by the addition of NaBH₄ (35 mg, 0.93 mmol) at 0° C., gave the title compound (0.054 g, 24%) as a cream solid after purification by kp-NH flash column chromatography (eluting with a gradient of 0-6% MeOH/DCM) followed by flash column chromatography (eluting with a gradient of 0-20% MeOH/DCM).

1H-NMR (MeOD, 500 MHz): d[ppm]=8.14-8.12 (m, 1H), 8.11 (s, 1H), 7.52-7.46 (m, 1H), 7.46-7.41 (m, 2H), 7.27-7.22 (m, 1H), 7.17-7.12 (m, 2H), 4.70 (d, J=1.5 Hz, 2H), 4.21 (s, 2H), 3.27 (s, 2H), 1.25 (s, 6H)

HPLCMS (Method C): [m/z]: 439.1 [M+H]⁺

2-(1-{[2-(1H-1,3-benzodiazol-2-yl)ethyl]amino}-2-methylpropan-2-yl)-N-[(3-fluoropyridin-2-yl)methyl]-1,3-thiazole-4-carboxamide (Example Compound No. 242)

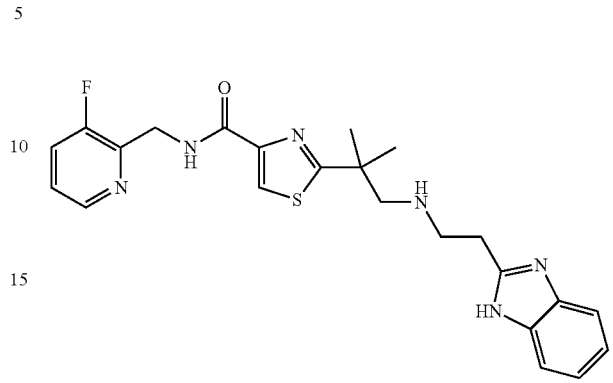

In a similar fashion to general procedure 8, 2-(1-amino-2-methylpropan-2-yl)-N-[(3-fluoropyridin-2-yl)methyl]-1,3-thiazole-4-carboxamide dihydrochloride (373) (1.54 g, 3.85 mmol), N-(2-nitrophenyl)prop-2-enamide (D) (0.81 g, 4.24 mmol) and DBU (1.73 ml, 11.56 mmol) in MeCN (35 ml) at room temperature for 18 h gave a mixture of mono: bis-alkylated adducts (3.7:1) (2.23 g) as an orange oil. This was further reacted with iron powder (0.86 g) in AcOH (10 ml) at 75° C. for 0.5 h to give the title compound (0.29 g, 17%) as an off-white solid after purification by flash column chromatography (eluting with a gradient of 0-40% MeOH/DCM) followed by kp-NH column chromatography (eluting with a gradient of 0-5% MeOH/DCM) and basic prep-HPLC.

1H-NMR (MeOD, 500 MHz): d[ppm]=8.30-8.25 (m, 1H), 7.97 (s, 1H), 7.57-7.52 (m, 1H), 7.43-7.35 (m, 2H), 7.34-7.29 (m, 1H), 7.18-7.13 (m, 2H), 4.65 (d, J=1.5 Hz, 2H), 3.09-3.05 (m, 2H), 3.05-3.01 (m, 2H), 2.98 (s, 2H), 1.46 (s, 6H)

HPLCMS (Method C): [m/z]: 453.1 [M+H]⁺

General Scheme 29 Above:

Methyl 3-(2-aminoethyl)benzoate (374)

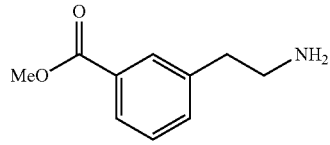 [SMILES: COC(=O)c1cccc(CCN)c1]

H₂SO₄ (conc., 0.28 ml) was added to 3-(2-aminoethyl)benzoic acid hydrochloride (0.350 g, 1.736 mmol) in MeOH (12 ml) and the reaction heated to 65° C. for 22 h. Water (20 ml) was added. The aqueous layer extracted with EtOAc (3×20 ml) and CHCl₃:IPA (4:1, 3×20 ml). The combined organic layers were dried (MgSO₄), filtered and the solvent evaporated reduced in vacuo to give the title compound (0.250 g, 80%, 85% purity) as a yellow solid.

1H-NMR (MeOD, 500 MHz): d[ppm]=7.91-7.90 (m, 1H), 7.90-7.87 (m, 1H), 7.51-7.48 (m, 1H), 7.45-7.41 (m, 1H), 3.90 (s, 3H), 3.00-2.94 (m, 2H), 2.90-2.85 (m, 2H)

HPLCMS (Method A): [m/z]: 180.1 [M+H]⁺

Methyl 3-(2-{[(tert-butoxy)carbonyl]amino}ethyl) benzoate (375)

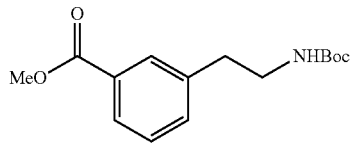 [SMILES: COC(=O)c1cccc(CCNC(=O)OC(C)(C)C)c1]

In a similar fashion to general procedure 4, methyl 3-(2-aminoethyl)benzoate (374) (0.25 g, 1.19 mmol, 85% purity), Boc₂O (0.29 mg, 1.3 mmol) and Et₃N (0.165 ml, 1.19 mmol) in THF (20 ml) at room temperature for 72 h, gave the title compound (0.25 mg, 75%) as a colourless oil after purification by flash column chromatography (eluting with a gradient 5-70% EtOAc/heptane).

1H-NMR (MeOD, 500 MHz): d[ppm]=7.89-7.87 (m, 1H), 7.87-7.84 (m, 1H), 7.47 (d, J=7.6 Hz, 1H), 7.40 (t, J=7.6 Hz, 1H), 3.90 (s, 3H), 3.28 (t, J=7.2 Hz, 2H), 2.82 (t, J=7.2 Hz, 2H), 1.40 (s, 9H)

HPLCMS (Method E): [m/z]: 278.4 [M−H]⁺

3-(2-{[(Tert-butoxy)carbonyl]amino}ethyl)benzoic Acid (376)

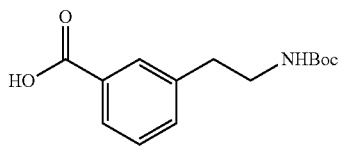 [SMILES: CC(C)(C)OC(=O)NCCc1cccc(C(=O)O)c1]

In a similar fashion to general procedure 5, methyl 3-(2-{[(tert-butoxy)carbonyl]amino}ethyl)benzoate (375) (0.249 g, 0.891 mmol) and LiOH (64 mg, 2.674 mmol) in THF (15 ml) and water (5 ml) at room temperature for 16 h gave the title compound (0.236 g, quant.) as a colourless oil. Compound was used in the next step without further purification.

1H-NMR (DMSO-d6, 500 MHz): d[ppm]=7.79-7.74 (m, 2H), 7.46-7.37 (m, 2H), 6.90-6.83 (m, 1H), 3.17-3.12 (m, 2H), 2.74 (t, J=7.2 Hz, 2H), 1.34 (s, 9H)

HPLCMS (Method E): [m/z]: 264.4 [M−H]⁺

Tert-butyl N-{2-[3-(benzylcarbamoyl)phenyl]ethyl}carbamate (377)

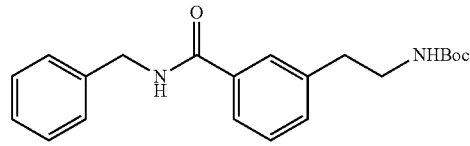 [SMILES: CC(C)(C)OC(=O)NCCc1cccc(C(=O)NCc2ccccc2)c1]

In a similar fashion to general procedure 6, 3-(2-{[(tert-butoxy)carbonyl]amino}ethyl)benzoic acid (376) (0.24 g, 0.89 mmol), 1-phenylmethanamine (97 µl, 0.89 mmol), DIPEA (0.46 ml, 2.66 mmol) and HATU (0.51 g, 1.334 mmol) in DCM (15 ml) at room temperature for 18 h gave the title compound (0.19 g, 60%) as a colourless oil after purification by flash column chromatography (eluting with a gradient of 10-90% EtOAc/heptane).

1H-NMR (MeOD, 500 MHz): d[ppm]=7.74-7.65 (m, 2H), 7.43-7.27 (m, 6H), 7.24 (t, J=7.2 Hz, 1H), 4.57 (s, 2H), 3.30-3.26 (m, 2H), 2.81 (t, J=7.2 Hz, 2H), 1.39 (s, 9H).

HPLCMS (Method A): [m/z]: 355.3 [M+H]⁺

Tert-butyl N-[2-(3-{[(3-fluoropyridin-2-yl)methyl]carbamoyl}phenyl)ethyl]carbamate (378)

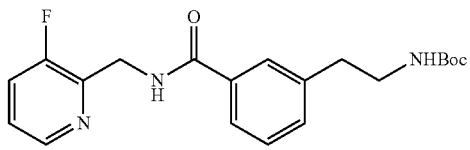 [SMILES: CC(C)(C)OC(=O)NCCc1cccc(C(=O)NCc2ncccc2F)c1]

In a similar fashion to general procedure 6, 3-(2-{[(tert-butoxy)carbonyl]amino}ethyl)benzoic acid (376) (1.16 g, 2.62 mmol), (3-fluoropyridin-2-yl)methanamine dihydrochloride (A2) (0.57 g, 2.89 mmol), DIPEA (1.6 ml, 9.18 mmol) and HATU (1.2 g, 3.15 mmol) in DCM (30 ml) afforded the title compound (1.63 g, 60% purity) as a colourless oil after flash column chromatography (eluting with a gradient of (100% EtOAc/heptane followed by 0-5% MeOH/EtOAc).

HPLCMS (Method M): [m/z]: 374.45 [M+H]⁺

Tert-butyl N-{2-[4-(benzylcarbamoyl)phenyl]ethyl}carbamate (379)

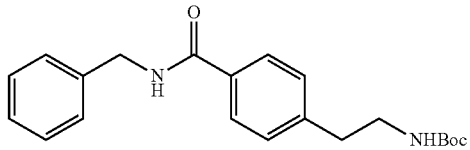 [SMILES: CC(C)(C)OC(=O)NCCc1ccc(C(=O)NCc2ccccc2)cc1]

In a similar fashion to general procedure 6, 4-(2-{[(tert-butoxy)carbonyl]amino}ethyl)benzoic acid (0.5 g, 1.885 mmol), 1-phenylmethanamine (0.2 ml, 1.88 mmol), DIPEA (1.313 ml, 7.449 mmol) and HATU (1.29 g, 3.39 mmol) in DCM (20 ml) at room temperature for 5 h gave the title compound (0.68 g, 87%, 85% purity) as a white solid after purification by flash column chromatography (eluting with a gradient of 6-70% EtOAc/heptane).

1H-NMR (MeOD, 500 MHz): d[ppm]=7.79 (d, J=8.0 Hz, 2H), 7.37-7.28 (m, 6H), 7.27-7.22 (m, 1H), 4.57 (s, 2H), 3.29-3.26 (m, 2H), 2.84-2.80 (m, 2H), 1.41 (s, 9H)

HPLCMS (Method A): [m/z]: 377.10 [M+Na]⁺

3-(2-Aminoethyl)-N-benzylbenzamide Hydrochloride (380)

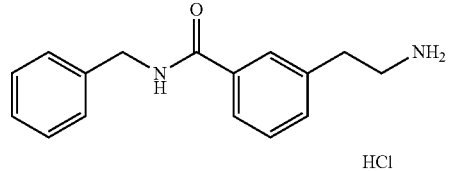 [SMILES: NCCc1cccc(C(=O)NCc2ccccc2)c1 ; Cl]

In a similar fashion to general procedure 2, tert-butyl N-{2-[3-(benzylcarbamoyl)phenyl]ethyl}carbamate (377) (190 mg, 0.54 mmol) and 12M HCl (1.0 ml, 12.5 mmol) in MeOH (5 ml) at room temperature for 20 h gave the title compound (171 mg, quant.) as a beige solid.

1H-NMR (MeOD, 500 MHz): d[ppm]=7.79-7.74 (m, 2H), 7.49-7.45 (m, 2H), 7.37-7.30 (m, 4H), 7.27-7.23 (m, 1H), 4.58 (s, 2H), 3.21 (t, J=7.7 Hz, 2H), 3.05-3.00 (m, 2H)

HPLCMS (Method A): [m/z]: 255.1 [M+H]$^+$

3-(2-aminoethyl)-N-[(3-fluoropyridin-2-yl)methyl]benzamide (381)

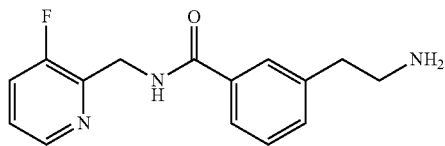

In a similar fashion to general procedure 2, tert-butyl N-[2-(3-{[(3-fluoropyridin-2-yl)methyl]carbamoyl}phenyl)ethyl]carbamate (378) (1.63 g, 2.62 mmol, 60% purity) and 12M HCl (1 ml) in MeOH (20 ml) at 60° C. afforded the title compound (640 mg, 89%) as a sticky white residue after purification using an SCX-2 cartridge (10 g), rinsing with DCM and MeOH, then eluting with 7N ammonia in MeOH.

1H-NMR (DMSO-d6, 250 MHz): d[ppm]=8.94 (t, J=5.2 Hz, 1H), 8.38 (dt, J=4.5, 1.5 Hz, 1H), 7.76-7.64 (m, 3H), 7.45-7.34 (m, 3H), 4.65 (dd, J=5.7, 1.6 Hz, 2H), 2.89-2.66 (m, 4H)

HPLCMS (Method M): [m/z]: 274.05 [M+H]$^+$

4-(2-Aminoethyl)-N-benzylbenzamide Hydrochloride (382)

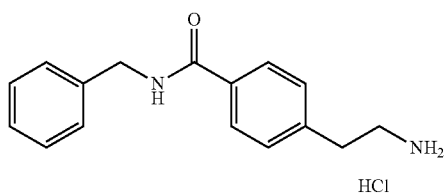 [SMILES: NCCc1ccc(C(=O)NCc2ccccc2)cc1 ; Cl]

In a similar fashion to general procedure 2, tert-butyl N-{2-[4-(benzylcarbamoyl)phenyl]ethyl}carbamate (379) (0.68 g, 1.63 mmol, 85% purity) and 12M HCl (3.7 ml, 44.8 mmol) in MeOH (10 ml) at room temperature for 19 h gave the title compound (0.55 g, 95%) as a white solid.

1H-NMR (MeOD, 500 MHz): d[ppm]=7.86 (d, J=8.2 Hz, 2H), 7.39 (d, J=8.2 Hz, 2H), 7.38-7.28 (m, 4H), 7.27-7.22 (m, 1H), 4.58 (s, 2H), 3.21 (t, J=7.7 Hz, 2H), 3.05-2.99 (m, 2H)

HPLCMS (Method A): [m/z]: 255.05 [M+H]$^+$

3-{2-[(1H-1,3-Benzodiazol-2-ylmethyl)amino]ethyl}-N-benzylbenzamide (Example Compound No. 67)

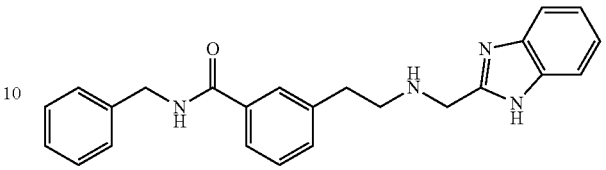

In a similar fashion using general procedure 3, 3-(2-aminoethyl)-N-benzylbenzamide hydrochloride (380) (171 mg, 0.59 mmol), 1H-1,3-benzodiazole-5-carbaldehyde (129 mg, 0.88 mmol) and DIPEA (102 μl, 0.59 mmol) in MeOH (5 ml) at room temperature for 72 h, followed by the addition NaBH$_4$ (33 mg, 0.88 mmol) gave the title compound (75 mg, 33%) as a beige solid after purification by basic prep-HPLC followed by trituration with DCM.

1H-NMR (DMSO-d6, 500 MHz): d[ppm]=12.16 (s, 1H), 8.98 (t, J=5.9 Hz, 1H), 7.75 (s, 1H), 7.73-7.69 (m, 1H), 7.54-7.39 (m, 2H), 7.39-7.34 (m, 2H), 7.32-7.29 (m, 4H), 7.26-7.20 (m, 1H), 7.15-7.07 (m, 2H), 4.47 (d, J=6.0 Hz, 2H), 3.93 (s, 2H), 2.86-2.77 (m, 4H)

HPLCMS (Method B): [m/z]: 384.5 [M+H]$^+$

4-{2-[(1H-1,3-Benzodiazol-2-yl)amino]ethyl}-N-benzylbenzamide (Example Compound No. 66)

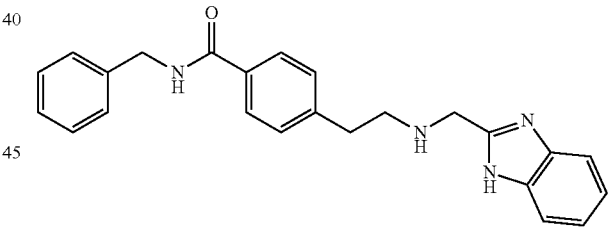

In a similar fashion using general procedure 3, 4-(2-Aminoethyl)-N-benzylbenzamide hydrochloride (382) (200 mg, 0.786 mmol), 1H-1,3-benzodiazole-5-carbaldehyde (172 mg, 1.18 mmol) and DIPEA (0.137 ml, 0.786 mmol) in MeOH (10 ml) at room temperature for 16 h, followed by the addition of NaBH$_4$ (45 mg, 1.18 mmol) gave the title compound (45 mg, 15%) as a whit solid after purification by basic prep-HPLC.

1H-NMR (DMSO-d6, 500 MHz): d[ppm]=8.95 (t, J=6.1 Hz, 1H), 7.80 (d, J=8.2 Hz, 2H), 7.57-7.38 (m, 2H), 7.32-7.28 (m, 5H), 7.26-7.20 (m, 1H), 7.15-7.07 (m, 2H), 4.46 (d, J=6.0 Hz, 2H), 3.92 (s, 2H), 2.81 (s, 4H)

HPLCMS (Method B): [m/z]: 385.2 [M+H]$^+$

3-(2-{[2-(1H-1,3-benzodiazol-2-yl)ethyl]amino}ethyl)-N-[(3-fluoropyridin-2-yl)methyl]benzamide (Example Compound No. 235)

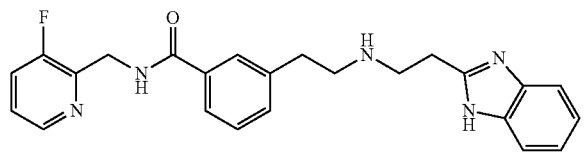 [SMILES: O=C(NCc1ncccc1F)c1cccc(CCNCCc2nc3ccccc3[nH]2)c1]

In a similar fashion to general procedure 8, 3-(2-aminoethyl)-N-[(3-fluoropyridin-2-yl)methyl]benzamide (381) (300 mg, 1.1 mmol), N-(2-nitrophenyl)prop-2-enamide (D) (169 mg, 0.88 mmol) and DBU (180 μl, 1.21 mmol) in MeCN (10 ml) gave a crude intermediate which was further reacted with iron powder (133 mg, 2.39 mmol) in AcOH (4 ml) to afford the title compound (85 mg, 34%) as a white solid after purification by basic prep-HPLC followed by flash column chromatography (eluting with a gradient of 0-40% MeOH/DCM).

1H-NMR (DMSO-d6, 500 MHz): d[ppm]=8.92 (t, J=5.5 Hz, 1H), 8.40-8.33 (m, 1H), 7.76 (s, 1H), 7.73-7.66 (m, 2H), 7.48-7.43 (m, 2H), 7.42-7.31 (m, 3H), 7.14-7.08 (m, 2H), 4.67-4.61 (m, 2H), 3.01 (t, J=6.5 Hz, 2H), 2.95 (t, J=6.4 Hz, 2H), 2.87-2.81 (m, 2H), 2.81-2.74 (m, 2H)

HPLCMS (Method B): [m/z]: 418.2 [M+H]$^+$

3-(2-{[2-(4-fluoro-1H-1,3-benzodiazol-2-yl)ethyl]amino}ethyl)-N-[(3-fluoropyridin-2-yl)methyl]benzamide (Example Compound No. 241)

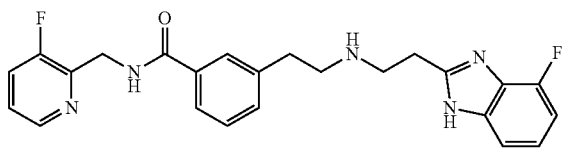 [SMILES: O=C(NCc1ncccc1F)c1cccc(CCNCCc2nc3c(F)cccc3[nH]2)c1]

In a similar fashion to general procedure 8, 3-(2-aminoethyl)-N-[(3-fluoropyridin-2-yl)methyl]benzamide (381) (372 mg, 1.36 mmol), N-(3-fluoro-2-nitrophenyl)prop-2-enamide (G) (229 mg, 1.09 mmol) and DBU (224 μl, 1.5 mmol) in MeCN (10 ml) gave a crude intermediate which was further reacted with iron powder (204 mg, 3.65 mmol) in AcOH (4 ml) to afford the title compound (5B mg, 20%) as a white solid after purification by basic prep-HPLC followed by flash column chromatography (eluting with a gradient of 0-40% MeOH/DCM).

1H-NMR (DMSO-d6, 500 MHz): d[ppm]=8.92 (t, J=5.6 Hz, 1H), 8.37 (dt, J=4.5, 1.3 Hz, 1H), 7.76 (s, 1H), 7.72-7.66 (m, 2H), 7.42-7.31 (m, 3H), 7.27 (d, J=8.0 Hz, 1H), 7.13-7.06 (m, 1H), 6.92 (dd, J=10.9, 7.9 Hz, 1H), 4.67-4.61 (m, 2H), 3.05-3.00 (m, 2H), 2.99-2.94 (m, 2H), 2.88-2.82 (m, 2H), 2.80-2.74 (m, 2H)

HPLCMS (Method B): [m/z]: 436.2 [M+H]$^+$

General Scheme 30 Above:

Tert-butyl 2-(2-{[(tert-butoxy)carbonyl]({[3-(methoxycarbonyl)phenyl]methyl})amino}ethyl)-1H-1,3-benzodiazole-1-carboxylate (383)

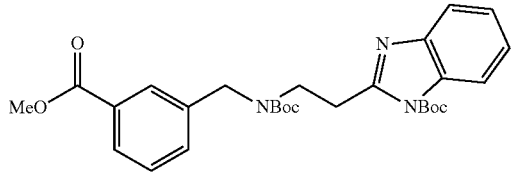 [SMILES: COC(=O)c1cccc(CN(CCc2nc3ccccc3n2C(=O)OC(C)(C)C)C(=O)OC(C)(C)C)c1]

NaH (60% in mineral oil, 144 mg, 3.6 mmol) was added to an ice-cold solution of tert-butyl 2-(2-{[(tert-butoxy)carbonyl]amino}ethyl)-1H-1,3-benzodiazole-1-carboxylate (297) (260 mg, 0.72 mmol) in THF (20 ml) and the mixture was stirred for 10 min. Methyl 3-(bromomethyl)benzoate (214 mg, 0.94 mmol) was then added and the mixture stirred for a further 30 min. The reaction mixture was quenched with water and extracted with DCM (3×50 ml). The combined organic extracts were dried (Na$_2$SO$_4$), filtered and evaporated in vacuo. Purification by flash column chromatography using an eluting gradient 0-60% EtOAc/heptane afforded the title compound (363 mg, 99%) as a colourless oil.

1H-NMR (CDCl$_3$, 250 MHz): d[ppm]=7.98 (d, J=7.8 Hz, 1H), 7.90 (s, 1H), 7.79 (d, J=6.9 Hz, 1H), 7.38 (t, J=7.7 Hz, 1H), 7.27-7.09 (m, 4H), 5.48 (s, 2H), 4.12 (dd, J=8.4, 6.6 Hz, 2H), 3.91 (s, 3H), 3.26-3.13 (m, 2H), 1.45 (s, 18H)

HPLCMS (Method M): [m/z]: 510.10 [M+H]$^+$

3-({[(Tert-butoxy)carbonyl](2-{1-[(tert-butoxy)carbonyl]-1H-1,3-benzodiazol-2-yl}ethyl)amino}methyl)benzoic Acid (384)

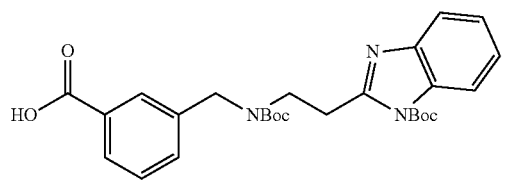 [SMILES: CC(C)(C)OC(=O)N(CCc1nc2ccccc2n1C(=O)OC(C)(C)C)Cc1cccc(C(=O)O)c1]

In a similar fashion to general procedure 5, tert-butyl 2-(2-{[(tert-butoxy)carbonyl]({[3-(methoxycarbonyl)phenyl]methyl})amino}ethyl)-1H-1,3-benzodiazole-1-carboxylate (383) (363 mg, 0.71 mmol) and LiOH (34 mg, 1.42 mmol) in THF (10 ml) and water (10 ml) afforded the title compound (391 mg, 78% purity) as a white solid.

HPLCMS (Method M): [m/z]: 496.15 [M+H]$^+$

Tert-butyl 2-(2-{[(tert-butoxy)carbonyl][(3-{[(3-fluoropyridin-2-yl)methyl]carbamoyl}phenyl)methyl]amino}ethyl)-1H-1,3-benzodiazole-1-carboxylate (385)

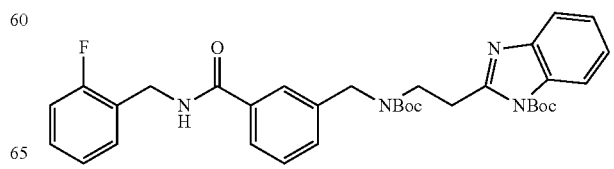

In a similar fashion to general procedure 6, crude 3-({[(tert-butoxy)carbonyl](2-{1-[(tert-butoxy)carbonyl]-1H-1,3-benzodiazol-2-yl}ethyl)amino}methyl)benzoic acid (384) (391 mg, 0.79 mmol), (3-fluoropyridin-2-yl)methanamine dihydrochloride (A2) (173 mg, 0.87 mmol), DIPEA (454 µl, 2.6 mmol) and HATU (360 mg, 0.95 mmol) in DCM (15 ml) afforded the crude title compound (523 mg, 50% purity) as a colourless oil.

HPLCMS (Method M): [m/z]: 604.35 [M+H]$^+$ 3-({[2-(1H-1,3-Benzodiazol-2-yl)ethyl]amino}methyl)-N-[(3-fluoropyridin-2-yl)methyl]benzamide (Example Compound No. 224)

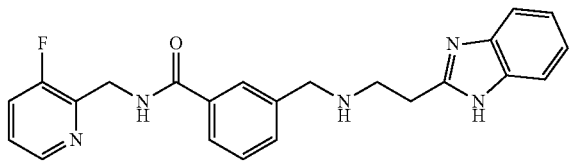 [SMILES: O=C(NCc1ncccc1F)c1cccc(CNCCc2nc3ccccc3[nH]2)c1]

In a similar fashion to general procedure 2, tert-butyl 2-(2-{[(tert-butoxy)carbonyl][(3-{[(3-fluoropyridin-2-yl)methyl]carbamoyl}phenyl)methyl]amino}ethyl)-1H-1,3-benzodiazole-1-carboxylate (385) (523 mg, 0.87 mmol) and 12M HCl (1 ml) in MeOH (10 ml) at 60° C. for 30 min gave the title compound (142 mg, 41%) as a white solid after purification by SCX-2 cartridge (10 g), rinsing with DCM and MeOH, then eluted with 7N ammonia in MeOH, followed by trituration with DCM/Et$_2$O.

1H-NMR (DMSO-d6, 500 MHz): d[ppm]=9.01 (t, J=5.6 Hz, 1H), 8.36 (dt, J=4.6, 1.4 Hz, 1H), 7.82 (d, J=7.8 Hz, 1H), 7.73 (s, 1H), 7.71-7.66 (m, 1H), 7.65-7.61 (m, 1H), 7.53-7.48 (m, 1H), 7.43 (t, J=7.7 Hz, 1H), 7.41-7.37 (m, 1H), 7.25-7.17 (m, 3H), 5.56 (s, 2H), 4.64-4.60 (m, 2H), 3.21 (t, J=6.8 Hz, 2H), 3.09 (t, J=6.8 Hz, 2H)

HPLCMS (Method B): [m/z]: 404.2 [M+H]$^+$
General Scheme 31 Above:

6-(Cyanomethyl)pyridine-2-carboxylic Acid (386)

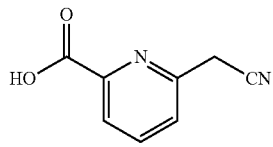 [SMILES: N#CCc1cccc(C(=O)O)n1]

n-BuLi (2.5 M in hexane, 79.21 mmol, 31.68 ml) was slowly added to anhydrous THF (84 ml) at −78° C. Anhydrous MeCN (4.14 ml, 79.21 mmol) was added dropwise and the mixture stirred for 30 min. A solution of 6-bromopyridine-2-carboxylic acid (2 g, 9.90 mmol) in anhydrous THF (80 ml) at 0° C. was added dropwise and the mixture stirred at −78° C. for 2 h. The reaction mixture was concentrated in vacuo, the residue was dissolved in DCM and extracted with NaHCO$_3$ (3×100 ml). The aqueous layer was acidified with solid citric acid to pH 1 and extracted with DCM (4×100 ml). The combined organic layers were dried (MgSO$_4$), filtered and concentrated in vacuo to give the title compound (1.45 g, 90%) as a light brown solid.

1H-NMR (CDCl$_3$, 500 MHz): d[ppm]=8.24 (d, J=7.7 Hz, 1H), 8.05 (t, J=7.8 Hz, 1H), 7.72 (d, J=7.8 Hz, 1H), 4.05 (s, 2H)

Methyl 6-(cyanomethyl)pyridine-2-carboxylate (387)

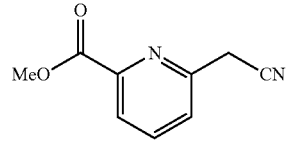 [SMILES: COC(=O)c1cccc(CC#N)n1]

(diazomethyl)(trimethyl)silane (2M in Et$_2$O, 14.76 ml, 29.51 mmol) was added dropwise to a solution of 6-(cyanomethyl)pyridine-2-carboxylic acid (386) (1.45 g, 8.94 mmol) in anhydrous MeOH (30 ml) at 0° C. The mixture was warmed to room temperature and stirred for 2.5 h, then quenched with sat. NaHCO$_3$ (20 ml). The precipitate was filtered and rinsed with DCM. The combined filtrates were then extracted with DCM (3×50 ml), the combined organic layers were dried (MgSO$_4$), filtered and evaporated in vacuo. Purification by flash column chromatography (eluting with a gradient of 0-70% EtOAc/heptane) afforded the title compound (0.738 g, 47%) as a brown oil.

1H-NMR (CDCl$_3$, 500 MHz): d[ppm]=8.11 (d, J=7.8 Hz, 1H), 7.93 (dd, J=7.8, 7.8 Hz, 1H), 7.71 (d, J=7.8 Hz, 1H), 4.07 (s, 2H), 4.01 (s, 3H)

Methyl 6-(2-{[(tert-butoxy)carbonyl]amino}ethyl)pyridine-2-carboxylate (388)

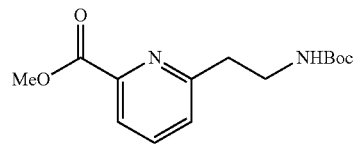 [SMILES: COC(=O)c1cccc(CCNC(=O)OC(C)(C)C)n1]

A suspension of methyl 6-(cyanomethyl)pyridine-2-carboxylate (387) (0.838 g, 4.76 mmol), Boc$_2$O (2.76 g, 9.51 mmol) and Raney nickel (50% w/w slurry in water, 4 ml) in EtOH (60 ml) was stirred under an atmosphere of hydrogen for 16 h. The reaction mixture was filtered through a plug of Celite and the residue rinsed with EtOH. The combined filtrates were concentrated in vacuo. Purification by flash column chromatography (eluting with a gradient of 0-50% EtOAc/DCM) afforded the title compound (0.793 g, 58%) as a colourless oil.

1H-NMR (CDCl$_3$, 250 MHz): d[ppm]=7.99 (d, J=7.7 Hz, 1H), 7.76 (dd, J=7.7, 7.7 Hz, 1H), 7.37 (d, J=7.7 Hz, 1H), 5.16 (s, 1H), 4.00 (s, 3H), 3.56 (q, J=6.5 Hz, 2H), 3.08 (t, J=6.5 Hz, 2H), 1.43 (s, 9H)

HPLCMS (Method A): [m/z]: 281 [M+H]$^+$

6-(2-{[(Tert-butoxy)carbonyl]amino}ethyl)pyridine-2-carboxylic Acid (389)

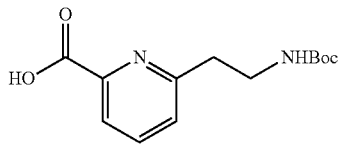

In a similar fashion to general procedure 5, methyl 6-(2-{[(tert-butoxy)carbonyl]amino}ethyl)pyridine-2-carboxylate (388) (864 mg, 3.08 mmol) and LiOH (221 mg, 9.25 mmol) in THF (15 ml) and water (5 ml) at room temperature for 16 h gave the title compound (654 mg, 79%) as a white solid.

1H-NMR (DMSO-d6, 500 MHz): d[ppm]=7.78 (m, 2H), 7.25 (d, J=6.9 Hz, 1H), 6.88 (s, 1H), 3.30-3.15 (m, 2H), 2.85 (t, J=7.1 Hz, 2H), 1.34 (s, 9H)

HPLCMS (Method A): [m/z]: 267 [M+H]$^+$

Tert-butyl N-[2-(6-{[(3-fluoropyridin-2-yl)methyl]carbamoyl}pyridin-2-yl)ethyl]carbamate (390)

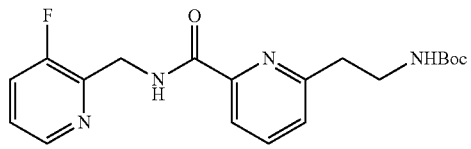 [SMILES: CC(C)(C)OC(=O)NCCc1cccc(C(=O)NCc2ncccc2F)n1]

In a similar fashion to general procedure 6, 6-(2-{[(tert-butoxy)carbonyl]amino}ethyl)pyridine-2-carboxylic acid (389) (369 mg, 1.39 mmol), (3-fluoropyridin-2-yl)methanamine dihydrochloride (A2) (414 mg, 2.08 mmol), DIPEA (1.45 ml, 8.31 mmol) and HATU (632 mg, 1.66 mmol) in THF (4 ml) and DMF (4 ml) afforded the title compound (536 mg, 90%, 87% purity) as a pale yellow oil after flash column chromatography (eluting with a gradient of 0-100% EtOAc/heptane).

HPLCMS (Method A): [m/z]: 375.45 [M+H]$^+$

6-(2-Aminoethyl)-N-[(3-fluoropyridin-2-yl)methyl]pyridine-2-carboxamide Dihydrochloride (391)

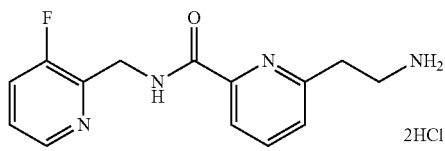 [SMILES: NCCc1cccc(C(=O)NCc2ncccc2F)n1]

In a similar fashion to general procedure 2, tert-butyl N-[2-(6-{[(3-fluoropyridin-2-yl)methyl]carbamoyl}pyridin-2-yl)ethyl]carbamate (390) (519 mg, 1.39 mmol) and 4M HCl/1,4-dioxane (1.73 ml) in 1,4-dioxane (6 ml) and MeOH (2 ml) afforded the crude title compound (610 mg) as a yellow oil which was used on the next step without purification.

HPLCMS (Method F): [m/z]: 275.1 [M+H]$^+$

6-(2-{[2-(1H-1,3-benzodiazol-2-yl)ethyl]amino}ethyl)-N-[(3-fluoropyridin-2-yl)methyl]pyridine-2-carboxamide (Example Compound No. 146) and 6-(2-{bis[2-(1H-1,3-benzodiazol-2-yl)ethyl]amino}ethyl)-N-[(3-fluoropyridin-2-yl)methyl]pyridine-2-carboxamide (Example Compound No. 147)

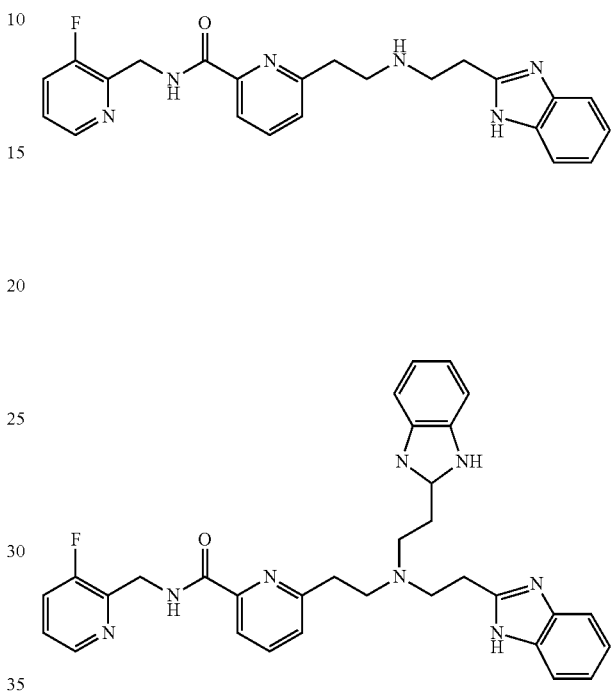

In a similar fashion to general procedure 7, crude 6-(2-aminoethyl)-N-[(3-fluoropyridin-2-yl)methyl]pyridine-2-carboxamide dihydrochloride (391) (460 mg, 1.32 mmol), 2-(2-chloroethyl)-1H-1,3-benzodiazole hydrochloride (345 mg, 1.59 mmol) and DIPEA (3.55 ml, 19.87 mmol) in DMF (5 ml) afforded the title compound (Example Compound No. 146) (95 mg, 17%) as a yellow oil after purification by basic prep-HPLC and flash column chromatography (eluting with a gradient of 0-10% MeOH/DCM followed by 0-10% 7 N ammonia in MeOH/DCM).

1H-NMR (DMSO-d6, 500 MHz): d[ppm]=9.14 (t, J=5.6 Hz, 1H), 8.37 (dt, J=4.6, 1.3 Hz, 1H), 7.93-7.79 (m, 2H), 7.70 (ddd, J=10.0, 8.3, 1.2 Hz, 1H), 7.48 (dd, J=6.2, 2.7 Hz, 1H), 7.46-7.35 (m, 3H), 7.17-7.02 (m, 2H), 4.69 (dd, J=5.6, 1.3 Hz, 2H), 3.08-2.87 (m, 8H)

HPLCMS (Method D): [m/z]: 419.2 [M+H]$^+$

Also isolated after purification by basic prep-HPLC and flash column chromatography (eluting with a gradient of 0-10% MeOH/DCM followed by 0-10% 7 N ammonia in MeOH/DCM) was the title compound (Example Compound No. 147) (9 mg, 1%) as a yellow oil.

1H-NMR (Acetone-d6, 500 MHz): d[ppm]=9.17 (s, 1H), 8.39 (d, J=4.7 Hz, 1H), 7.95 (d, J=7.3 Hz, 1H), 7.81 (t, J=7.7 Hz, 1H), 7.55 (ddd, J=9.9, 8.3, 1.3 Hz, 1H), 7.52-7.41 (m, 5H), 7.34 (dt, J=8.7, 4.4 Hz, 1H), 7.17-7.08 (m, 4H), 4.81-4.63 (m, 4H), 3.37 (t, J=7.2 Hz, 2H), 3.10 (m, 5H), 3.05-2.99 (m, 3H)

HPLCMS (Method B): [m/z]: 563.7 [M+H]$^+$

6-{2-[(1H-1,3-Benzodiazol-2-ylmethyl)amino]ethyl}-N-[(3-fluoropyridin-2-yl)methyl]pyridine-2-carboxamide (392)

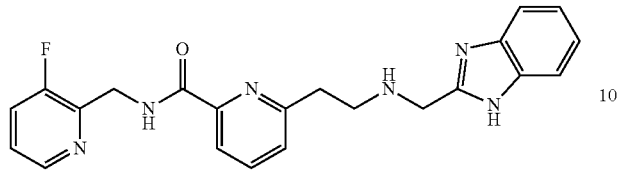

In a similar fashion using general procedure 3, 6-(2-aminoethyl)-N-[(3-fluoropyridin-2-yl)methyl]pyridine-2-carboxamide hydrochloride (391) (100 mg, 0.322 mmol), 1H-benzimidazole-2-carbaldehyde (56 mg, 0.39 mmol), DIPEA (0.22 ml, 1.29 mmol) in MeOH (2 ml) at room temperature for 2.5 h, followed by addition of NaBH$_4$ (18 mg, 0.48 mmol) afforded the title compound (35 mg, 27%) as a colourless oil after purification by basic prep-HPLC.

1H-NMR (DMSO-d6, 500 MHz): d[ppm]=12.16 (s, 1H), 9.16 (t, J=5.6 Hz, 1H), 8.33 (dt, J=4.6, 1.4 Hz, 1H), 7.96-7.82 (m, 2H), 7.70 (ddd, J=10.0, 8.3, 1.2 Hz, 1H), 7.60-7.30 (m, 4H), 7.11 (d, J=4.9 Hz, 2H), 4.71 (dd, J=5.6, 1.3 Hz, 2H), 3.96 (s, 2H), 3.02 (s, 4H)

HPLCMS (Method D): [m/z]: 405.2 [M+H]$^+$

6-{2-[(1H-1,3-benzodiazol-2-ylmethyl)amino]ethyl}-N-[(3-fluoropyridin-2-yl)methyl]pyridine-2-carboxamide Trihydrochloride (Example Compound No. 133)

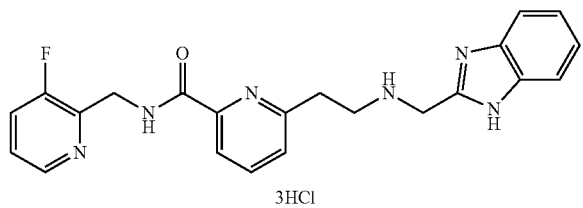 [SMILES: O=C(NCc1ncccc1F)c1cccc(CCNCc2nc3ccccc3[nH]2)n1]

In a similar fashion to general procedure 2, 6-{2-[(1H-1,3-benzodiazol-2-ylmethyl)amino]ethyl}-N-[(3-fluoropyridin-2-yl)methyl]pyridine-2-carboxamide (392) (10 mg, 0.024 mmol) and 12 M HCl (10 µl, 0.12 mmol) in MeOH (2 ml) afforded the title compound (14 mg) as an off-white solid.

1H-NMR (D$_2$O, 500 MHz): d[ppm]=8.41 (dd, J=5.4, 1.1 Hz, 1H), 8.11-8.05 (m, 1H), 8.02 (t, J=7.8 Hz, 1H), 7.96 (d, J=6.9 Hz, 1H), 7.79 (m, 3H), 7.68-7.60 (m, 3H), 4.93 (s, 2H), 4.88 (d, J=1.1 Hz, 2H), 3.88 (t, J=6.7 Hz, 2H), 3.43 (t, J=6.7 Hz, 2H)

HPLCMS (Method D): [m/z]: 405.2 [M+H]$^+$

General Scheme 32 Above:

General Procedure 17: Tert-butyl 5-bromopyridine-3-carboxylate (393)

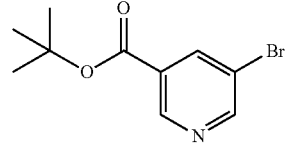

Boc$_2$O (4.28 g, 19.6 mmol) in THF (40 ml) was added to an ice-cold solution of 5-bromonicotinic acid (3.6 g, 17.82 mmol) and DMAP (1.09 g, 8.91 mmol) in THF (70 ml). The reaction mixture was stirred and allowed to warm to room temperature over 1.5 h then concentrated in vacuo. The residue was dissolved in saturated NaHCO$_3$(aq) and extracted with DCM (3×100 ml). The combined organic extracts were dried (Na$_2$SO$_4$), filtered and evaporated in vacuo. Purification by flash column chromatography (eluting with a gradient of 0-10% EtOAc/heptane) afforded the title compound (3.79 g, 82%) as a colourless oil which solidified over time.

1H-NMR (CDCl$_3$, 250 MHz): d[ppm]=9.09 (m, 1H), 8.83 (d, J=2.2 Hz, 1H), 8.38 (t, J=2.2 Hz, 1H), 1.63 (s, 9H)

HPLCMS (Method M): [m/z]: 259.85/261.85 [M+H]$^+$

Tert-butyl 2-bromopyridine-4-carboxylate (394)

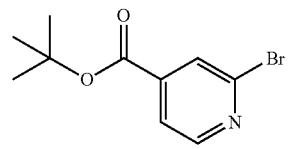

In a similar fashion to general procedure 17, 2-bromoisonicotinic acid (541 mg, 2.68 mmol), Boc$_2$O (643 mg, 2.95 mmol) and DMAP (164 mg, 1.34 mmol) in THF (30 ml) at room temperature for 18 h gave the title compound (423 mg, 61%) as a colourless oil after purification by flash column chromatography (eluting with a gradient of 0-20% EtOAc/heptane).

1H-NMR (CDCl$_3$, 250 MHz): d[ppm]=8.51 (dd, J=5.0, 0.6 Hz, 1H), 8.02-7.95 (m, 1H), 7.77 (dd, J=5.0, 1.4 Hz, 1H), 1.62 (s, 9H)

HPLCMS (Method M): [m/z]: 259.85/261.85 [M+H]$^+$

Tert-butyl 4-bromopyridine-2-carboxylate (395)

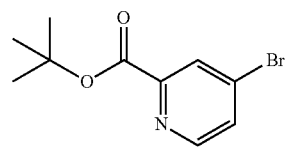

In a similar fashion to general procedure 17, 4-bromopyridine-2-carboxylic acid (2 g, 9.9 mmol), Boc$_2$O (2.38 g, 10.89 mmol) and DMAP (0.6 g, 4.95 mmol) in THF (40 ml) at room temperature for 18 have the title compound (1.75 g, 68%) as a pale yellow oil after purification by flash column chromatography (eluting with a gradient of 0-60% EtOAc/heptane).

1H-NMR (CDCl₃, 250 MHz): d[ppm]=8.58 (d, J=5.2 Hz, 1H), 8.22 (d, J=1.9 Hz, 1H), 7.63 (dd, J=5.2, 1.9 Hz, 1H), 1.66 (s, 9H)

HPLCMS (Method M): [m/z]: 257.95/259.75 [M+H]⁺

General Procedure 18: Tert-butyl 5-[2-(tert-butoxy)-1-cyano-2-oxoethyl]pyridine-3-carboxylate (396)

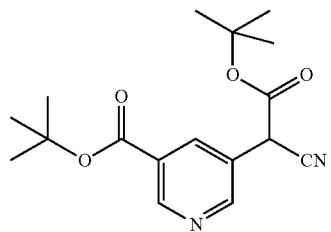 [SMILES: CC(C)(C)OC(=O)c1cncc(C(C#N)C(=O)OC(C)(C)C)c1]

KOᵗBu (638 mg, 5.69 mmol) was suspended in 1,4-dioxane (5 ml) and tert-butyl cyanoacetate (357 µl, 2.5 mmol), tert-butyl 5-bromopyridine-3-carboxylate (393) (587 mg, 2.27 mmol) and PdCl₂dppf (166 mg, 0.23 mmol) were added. The reaction mixture was heated at 70° C. for 1 h, then cooled to room temperature and quenched with saturated NH₄Cl (aq). The mixture was then extracted with EtOAc (3×50 ml) and the combined organic extracts were washed with brine (50 ml), dried (Na₂SO₄), filtered and evaporated in vacuo. Purification by flash column chromatography using an eluting gradient 0-30% EtOAc/heptane afforded the title compound (478 mg, 66%) as a white solid.

1H-NMR (CDCl₃, 250 MHz): d[ppm]=9.22 (s, 1H), 8.84 (s, 1H), 8.40 (s, 1H), 4.75 (s, 1H), 1.65 (s, 9H), 1.51 (s, 9H)

HPLCMS (Method M): [m/z]: 319.00 [M+H]⁺

Tert-butyl 2-[2-(tert-butoxy)-1-cyano-2-oxoethylidene]-1,2-dihydropyridine-4-carboxylate (397)

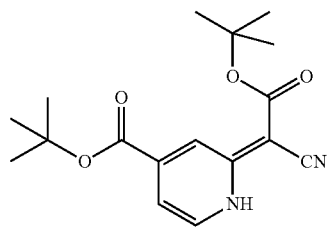 [SMILES: CC(C)(C)OC(=O)C1=C/C(=C(/C#N)C(=O)OC(C)(C)C)NC=C1]

In a similar fashion to general procedure 18, tert-butyl cyanoacetate (256 µl, 1.79 mmol), tert-butyl 2-bromopyridine-4-carboxylate (394) (420 mg, 1.63 mmol), PdCl₂dppf (8 mg, 0.01 mmol) and KOtBu (153 mg, 1.36 mmol) in 1,4-dioxane (5 ml) at 70° C. for 1 h gave the title compound (436 mg, 85%) as a yellow solid after purification by flash column chromatography (eluting with a gradient of (30% EtOAc/heptane).

1H-NMR (CDCl₃, 250 MHz): d[ppm]=14.10 (s, 1H), 7.86-7.79 (m, 1H), 7.58 (t, J=6.5 Hz, 1H), 7.01 (dt, J=6.5, 1.5 Hz, 1H), 1.62 (s, 9H), 1.57 (s, 9H)

HPLCMS (Method M): [m/z]: 319.10 [M+H]⁺

Tert-butyl 4-[2-(tert-butoxy)-1-cyano-2-oxoethyl]pyridine-2-carboxylate (398)

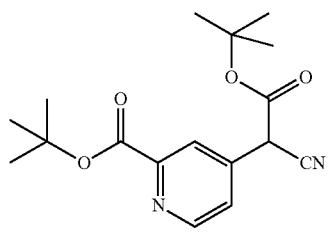 [SMILES: CC(C)(C)OC(=O)c1cc(C(C#N)C(=O)OC(C)(C)C)ccn1]

In a similar fashion to general procedure 18, tert-butyl cyanoacetate (1.07 ml, 7.46 mmol), tert-butyl 4-bromopyridine-2-carboxylate (395) (1.75 g, 6.78 mmol), PdCl₂dppf (0.5 g, 0.68 mmol) and KOtBu (1.9 g, 16.95 mmol) in 1,4-dioxane (50 ml) at 70° C. for 1 h gave the title compound (1.37 g, 63%) as a yellow solid after purification by flash column chromatography (eluting with a gradient of 0-60% EtOAc/heptane) followed by trituration with DCM/heptane.

HPLCMS (Method M): [m/z]: 319.00 [M+H]⁺

General Procedure 19:
5-(Cyanomethyl)pyridine-3-carboxylic Acid (399)

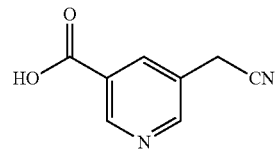 [SMILES: N#CCc1cncc(C(=O)O)c1]

Tert-butyl 5-[2-(tert-butoxy)-1-cyano-2-oxoethyl]pyridine-3-carboxylate (396) (420 mg, 1.32 mmol) and PTSA (454 mg, 2.64 mmol) in MeCN (20 ml) were heated at reflux for 1.5 h. The reaction mixture was cooled to room temperature and concentrated in vacuo. Purification using an SCX-2 cartridge (10 g), rinsing with DCM and MeOH, then eluting with 7N ammonia in MeOH afforded the title compound (205 mg, 96%) as a white solid upon evaporation of the basic eluent.

1H-NMR (CDCl₃, 250 MHz): d[ppm]=8.89 (m, 1H), 8.47 (d, J=2.2 Hz, 1H), 8.13 (t, J=2.2 Hz, 1H), 4.11 (s, 2H)

HPLCMS (Method M): [m/z]: 162.90 [M+H]⁺

2-Cyanomethyl)pyridine-4-carboxylic Acid (400)

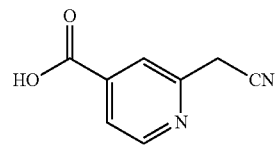 [SMILES: N#CCc1cc(C(=O)O)ccn1]

In a similar fashion to general procedure 19, tert-butyl 2-[2-(tert-butoxy)-1-cyano-2-oxoethyl]pyridine-4-carboxylate (397) (430 mg, 1.35 mmol) and PTSA (465 mg, 2.70 mmol) in MeCN (20 ml) at reflux for 1.5 h gave the title compound (201 mg, 92%) as a pale pink solid after purification using an SCX-2 cartridge (10 g), rinsing with DCM and MeOH, then eluting with 7N ammonia in MeOH.

1H-NMR (DMSO-d6, 250 MHz): d[ppm]=8.49 (dd, J=4.9, 0.7 Hz, 1H), 7.73 (s, 1H), 7.62 (dd, J=4.9, 1.4 Hz, 1H), 4.19 (s, 2H)

HPLCMS (Method M): [m/z]: 162.90 [M+H]$^+$ 4-(Cyanomethyl)pyridine-2-carboxylic Acid (401)

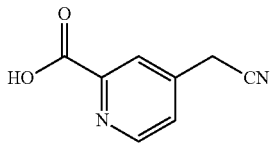 [SMILES: N#CCc1ccnc(C(=O)O)c1]

In a similar fashion to general procedure 19, tert-butyl 4-[2-(tert-butoxy)-1-cyano-2-oxoethyl]pyridine-2-carboxylate (398) (1.37 g, 4.3 mmol) and PTSA (1.64 g, 8.61 mmol) in MeCN (30 ml) at reflux for 2 h gale the title compound (0.532 g, 76%) as a pale brown solid after purification using an SCX-2 cartridge (10 g), rinsing with DCM and MeOH, then eluting with 7N ammonia in MeOH.

1H-NMR (DMSO-d6, 250 MHz): d[ppm]=8.53 (d, J=4.9 Hz, 1H), 7.89 (s, 1H), 7.32 (d, J=4.9 Hz, 1H), 4.16 (s, 2H)

HPLCMS (Method M): [m/z]: 163.30 [M+H]$^+$ 5-(Cyanomethyl)-N-[(3-fluoropyridin-2-yl)methyl]pyridine-3-carboxamide (402)

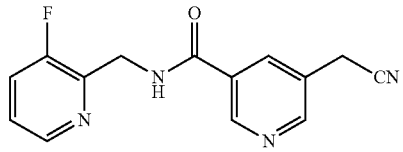 [SMILES: N#CCc1cncc(C(=O)NCc2ncccc2F)c1]

In a similar fashion to general procedure 6, 5-(cyanomethyl)pyridine-3-carboxylic acid (399) (200 mg, 1.23 mmol), (3-fluoropyridin-2-yl)methanamine dihydrochloride (A2) (270 mg, 1.36 mmol), DIPEA (709 μl, 4.07 mmol) and HATU (563 mg, 1.48 mmol) in DCM (20 ml) afforded the crude title compound (539 mg) as a white solid which was used in the next step without purification.

HPLCMS (Method M): [m/z]: 270.95 [M+H]$^+$ 2-(Cyanomethyl)-N-[(3-fluoropyridin-2-yl)methyl]pyridine-4-carboxamide (403)

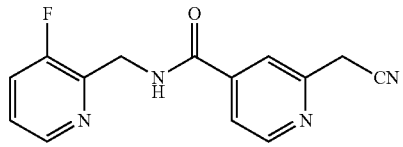 [SMILES: N#CCc1cc(C(=O)NCc2ncccc2F)ccn1]

In a similar fashion to general procedure 6, 2-(cyanomethyl)pyridine-4-carboxylic acid (400) (200 mg, 1.23 mmol), (3-fluoropyridin-2-yl)methanamine dihydrochloride (A2) (270 mg, 1.36 mmol), DIPEA (709 μl, 4.07 mmol) and HATU (563 mg, 1.48 mmol) in DCM (20 ml) afforded the crude title compound (573 mg) as a yellow residue which was used in the next step without purification.

HPLCMS (Method M): [m/z]: 270.95 [M+H]$^+$ 4-(Cyanomethyl)-N-[(3-fluoropyridin-2-yl)methyl]pyridine-2-carboxamide (404)

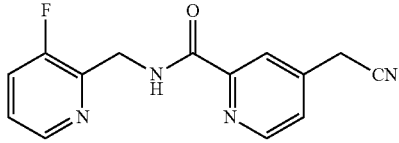 [SMILES: N#CCc1ccnc(C(=O)NCc2ncccc2F)c1]

In a similar fashion to general procedure 6, 4-(cyanomethyl)pyridine-2-carboxylic acid (401) (0.53 g, 3.28 mmol), (3-fluoropyridin-2-yl)methanamine dihydrochloride (A2) (0.72 g, 3.61 mmol), DIPEA (1.89 ml, 10.83 mmol) and HATU (1.5 g, 3.94 mmol) in DCM (40 ml) afforded the title compound (0.48 g, 51%) as a white solid after purification by flash column chromatography (eluting with a gradient of 50-100% EtOAc/heptane followed by 2-20% MeOH/EtOAc).

1H-NMR (DMSO-d6, 250 MHz): d[ppm]=9.26 (t, J=5.7 Hz, 1H), 8.71 (d, J=5.3 Hz, 1H), 8.41 (m, 1H), 8.10-8.04 (m, 1H), 7.73 (m, 1H), 7.62 (dd, J=5.0, 1.8 Hz, 1H), 7.43 (dt, J=8.6, 4.5 Hz, 1H), 4.73 (dd, J=5.7, 1.5 Hz, 2H), 4.29 (s, 2H)

HPLCMS (Method M): [m/z]: 271.05 [M+H]$^+$

Tert-butyl N-[2-(5-{[(3-fluoropyridin-2-yl)methyl]carbamoyl}pyridin-3-yl)ethyl]carbamate (405)

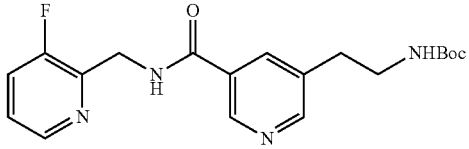 [SMILES: CC(C)(C)OC(=O)NCCc1cncc(C(=O)NCc2ncccc2F)c1]

A suspension of crude 5-(cyanomethyl)-N-[(3-fluoropyridin-2-yl)methyl]pyridine-3-carboxamide (402) (539 mg), Boc$_2$O (320 mg, 1.47 mmol), TEA (221 μl, 1.59 mmol) and palladium on carbon (10% wt, 130 mg, 0.12 mmol) in EtOH (10 ml) was stirred under an atmosphere of hydrogen for 24 h. The reaction mixture was filtered through a plug of Celite and the residue rinsed with MeOH. The combined filtrates were evaporated in vacuo. The residue was flushed through a plug of silica (eluting with a gradient 10-100% EtOAc/heptane followed by 2-30% MeOH/EtOAc) to afford the crude title compound (344 mg) as a yellow residue which was used in the next step without further purification.

HPLCMS (Method M): [m/z]: 375.05 [M+H]$^+$

Tert-butyl N-[2-(4-{[(3-fluoropyridin-2-yl)methyl]carbamoyl}pyridin-2-yl)ethyl]carbamate (406)

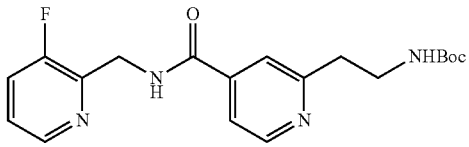 [SMILES: CC(C)(C)OC(=O)NCCc1cc(C(=O)NCc2ncccc2F)ccn1]

A suspension of crude 2-(cyanomethyl)-N-[(3-fluoropyridin-2-yl)methyl]pyridine-4-carboxamide (403) (573 mg), Boc₂O (320 mg, 1.47 mmol), TEA (221 µl, 1.59 mmol) and palladium on carbon (10% wt, 130 mg, 0.12 mmol) in EtOH (10 ml) was stirred under an atmosphere of hydrogen for 24 h. The reaction mixture was filtered through a plug of Celite and the residue rinsed with MeOH. The combined organic filtrates were evaporated in vacuo. The residue was flushed through a plug of silica (eluting with a gradient of 10-100% EtOAc/heptane followed by 2-30% MeOH/EtOAc) to afford the crude title compound (319 mg) as a yellow residue which was used in the next step without further purification.

HPLCMS (Method M): [m/z]: 375.05 [M+H]⁺

Tert-butyl N-[2-(2-{[(3-fluoropyridin-2-yl)methyl]carbamoyl}pyridin-4-yl)ethyl]carbamate (407)

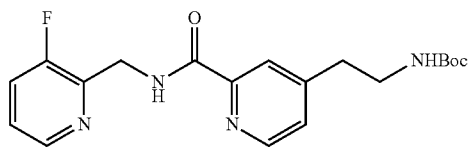 [SMILES: CC(C)(C)OC(=O)NCCc1ccnc(C(=O)NCc2ncccc2F)c1]

A suspension of 4-(cyanomethyl)-N-[(3-fluoropyridin-2-yl)methyl]pyridine-2-carboxamide (404) (470 mg, 1.74 mmol), Boc₂O (418 mg, 1.91 mmol), TEA (267 µl, 1.91 mmol) and palladium on carbon (10% wt, 185 mg, 0.17 mmol) in EtOH (50 ml) was stirred under an atmosphere of hydrogen for 18 h. The reaction mixture was filtered through a plug of Celite and the residue rinsed with MeOH and 7N NH3/MeOH. The combined filtrates were evaporated in vacuo. Purification by flash column chromatography (eluting with a gradient of 0-100% EtOAc/heptane) afforded the title compound (436 mg, 71%) as a white solid.

1H-NMR (CDCl₃, 250 MHz): d[ppm]=9.05 (s, 1H), 8.52 (d, J=4.9 Hz, 1H), 8.44 (dt, J=4.6, 1.2 Hz, 1H), 8.12-8.01 (m, 1H), 7.48-7.35 (m, 1H), 7.33-7.24 (m, 2H), 4.88 (dd, J=5.2, 1.7 Hz, 2H), 4.56 (s, 1H), 3.43 (dt, J=6.7, 6.7 Hz, 2H), 2.90 (t, J=6.7 Hz, 2H), 1.42 (s, 9H)

HPLCMS (Method M): [m/z]: 375.10 [M+H]⁺

5-(2-Aminoethyl)-N-[(3-fluoropyridin-2-yl)methyl]pyridine-3-carboxamide (408)

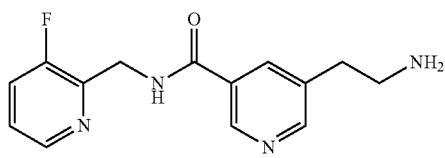 [SMILES: NCCc1cncc(C(=O)NCc2ncccc2F)c1]

In a similar fashion to general procedure 2, tert-butyl N-[2-(5-{[(3-fluoropyridin-2-yl)methyl]carbamoyl}pyridin-3-yl)ethyl]carbamate (405) (340 mg) and 12M HCl (1 ml) in MeOH (5 ml) afforded the crude title compound (280 mg) as a yellow residue after freebasing using an SCX-2 cartridge (10 g), rinsing with DCM/MeOH, then eluting with 7N ammonia in MeOH.

HPLCMS (Method M): [m/z]: 274.95 [M+H]⁺

2-(2-Aminoethyl)-N-[(3-fluoropyridin-2-yl)methyl]pyridine-4-carboxamide (409)

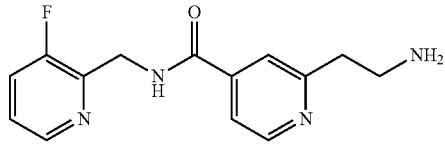 [SMILES: NCCc1cc(C(=O)NCc2ncccc2F)ccn1]

In a similar fashion to general procedure 2, crude tert-butyl N-[2-(4-{[(3-fluoropyridin-2-yl)methyl]carbamoyl}pyridin-2-yl)ethyl]carbamate (406) (320 mg) and 12M HCl (1 ml) in MeOH (5 ml) afforded the crude title compound (200 mg) as a yellow residue ater freebasing using an SCX-2 cartridge (10 g), rinsing with DCM/MeOH, then eluting with 7N ammonia in MeOH.

HPLCMS (Method M): [m/z]: 274.95 [M+H]⁺

4-(2-Aminoethyl)-N-[(3-fluoropyridin-2-yl)methyl]pyridine-2-carboxamide (410)

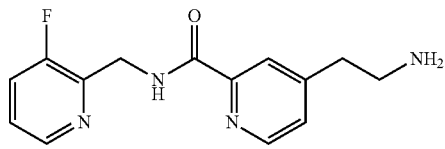 [SMILES: NCCc1ccnc(C(=O)NCc2ncccc2F)c1]

In a similar fashion to general procedure 2, tert-butyl N-[2-(2-{[(3-fluoropyridin-2-yl)methyl]carbamoyl}pyridin-4-yl)ethyl]carbamate (407) (430 mg, 1.15 mmol) and 12M HCl (1 ml) in MeOH (20 ml) afforded the title compound (258 mg, 82%) as a white solid after freebasing using an SCX-2 cartridge (10 g), rinsing with DCM and MeOH, then eluting with 7N ammonia in MeOH.

1H-NMR (DMSO-d6, 250 MHz): d[ppm]=9.19 (t, J=6.1 Hz, 1H), 8.56 (m, 1H), 8.41 (dt, J=4.7, 1.4 Hz, 1H), 7.95-7.90 (m, 1H), 7.73 (m, 1H), 7.51-7.38 (m, 2H), 4.72 (dd, J=5.6, 1.6 Hz, 2H), 2.90-2.71 (m, 4H)

HPLCMS (Method M): [m/z]: 274.95 [M+H]⁺

5-{2-[(1H-1,3-Benzodiazol-2-ylmethyl)amino]ethyl}-N-[(3-fluoropyridin-2-yl)methyl]pyridine-3-carboxamide (Example Compound No. 221)

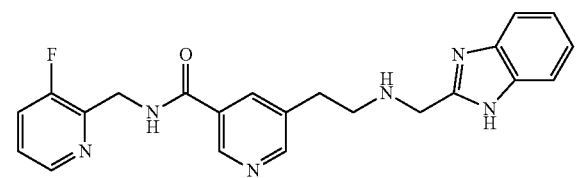 [SMILES: O=C(NCc1ncccc1F)c1cncc(CCNCc2nc3ccccc3[nH]2)c1]

In a similar fashion to general procedure 3, 5-(2-aminoethyl)-N-[(3-fluoropyridin-2-yl)methyl]pyridine-3-carboxamide (408) (280 mg, 1.02 mmol), 1H-benzimidazole-2-carbaldehyde (179 mg, 1.22 mmol) and DIPEA (533 µl, 3.06 mmol) in MeOH (10 ml) at room temperature for 3 d, followed by addition of NaBH₄ (77 mg, 2.04 mml) gave the title compound (76 mg, 18%) as a white solid after purification by basic prep-HPLC followed by flash column chromatography (eluting with a gradient of 0-30% MeOH/DCM).

1H-NMR (DMSO-d6, 500 MHz): d[ppm]=12.16 (s, 1H), 9.16 (t, J=5.6 Hz, 1H), 8.87 (d, J=2.1 Hz, 1H), 8.59 (d, J=2.1 Hz, 1H), 8.38 (m, 1H), 8.10 (t, J=2.1 Hz, 1H), 7.71 (m, 1H), 7.57-7.37 (m, 3H), 7.17-7.07 (m, 2H), 4.67 (dd, J=5.6, 1.5 Hz, 2H), 3.94 (s, 2H), 2.90-2.80 (m, 4H)

HPLCMS (Method C): [m/z]: 405.2 [M+H]+

2-{2-[(1H-1,3-benzodiazol-2-ylmethyl)amino]ethyl}-N-[(3-fluoropyridin-2-yl)methyl]pyridine-4-carboxamide (Example Compound No. 222)

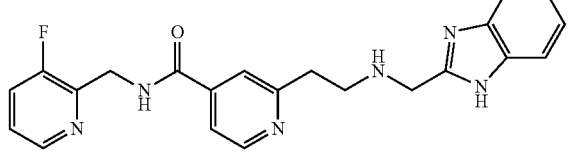

In a similar fashion to general procedure 3, crude 2-(2-aminoethyl)-N-[(3-fluoropyridin-2-yl)methyl]pyridine-4-carboxamide (409) (200 mg), 1H-benzimidazole-2-carbaldehyde (128 mg, 0.87 mmol), DIPEA (381 µl, 2.19 mmol) and MgSO4 (300 mg) in MeOH (10 ml) at room temperature for 3 d, followed by addition of NaBH4 (55 mg, 1.46 mmol) afforded the title compound (55 mg, 19%) as a white solid after purification by basic prep-HPLC followed by flash column chromatography (eluting with a gradient of (30% MeOH/DCM).

1H-NMR (DMSO-d6, 500 MHz): d[ppm]=9.23 (t, J=5.6 Hz, 1H), 8.63-8.60 (m, 1H), 8.40-8.36 (m, 1H), 7.73-7.66 (m, 2H), 7.61 (dd, J=5.1, 1.6 Hz, 1H), 7.49 (s, 2H), 7.44-7.38 (m, 1H), 7.16-7.09 (m, 2H), 4.66 (dd, J=5.6, 1.5 Hz, 2H), 3.96 (s, 2H), 3.04-2.94 (m, 4H)

HPLCMS (Method C): [m/z]: 405.2 [M+H]+

5-(2-{[2-(1H-1,3-Benzodiazol-2-yl)ethyl]amino}ethyl)-N-[(3-fluoropyridin-2-yl)methyl]pyridine-3-carboxamide (Example Compound No. 229)

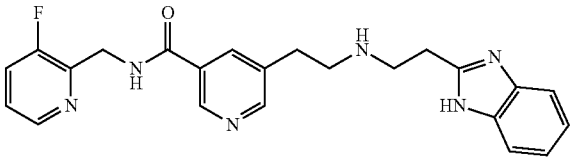

In a similar fashion to general procedure 8, N-[(3-fluoropyridin-2-yl)methyl]-5-[2-({2-[(2-nitrophenyl)carbamoyl]ethyl}amino)ethyl]pyridine-3-carboxamide (408) (448 mg, 1.63 mmol), N-(2-nitrophenyl)prop-2-enamide (D) (314 mg, 1.63 mmol) and DBU (268 µl, 1.8 mmol) in MeCN (10 ml) gave a crude intermediate which was further reacted with iron powder (142 mg, 2.54 mmol) and AcOH (4 ml) to afford the title compound (53 mg, 20%) as a white solid after purification by basic prep-HPLC followed by flash column chromatography (eluting with a gradient of 0-30% MeOH/DCM).

1H-NMR (DMSO-d6, 500 MHz): d[ppm]=9.16 (t, J=5.5 Hz, 1H), 8.87 (d, J=2.1 Hz, 1H), 8.59 (d, J=2.0 Hz, 1H), 8.39 (dt, J=4.6, 1.4 Hz, 1H), 8.10 (t, J=2.0 Hz, 1H), 7.74-7.66 (m, 1H), 7.49-7.38 (m, 3H), 7.12-7.07 (m, 2H), 4.69-4.64 (m, 2H), 3.02-2.96 (m, 2H), 2.96-2.90 (m, 2H), 2.87-2.82 (m, 2H), 2.82- 2.77 (m, 2H)

HPLCMS (Method C): [m/z]: 419.1 [M+H]+

5-(2-{[2-(5-Fluoro-1H-1,3-benzodiazol-2-yl)ethyl]amino}ethyl)-N-[(3-fluoropyridin-2 yl)methyl]pyridine-3-carboxamide (Example Compound No. 245)

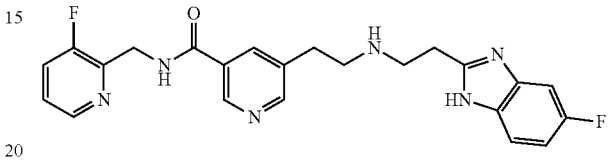

In a similar fashion to general procedure 8, 5-(2-aminoethyl)-N-[(3-fluoropyridin-2-yl)methyl]pyridine-3-carboxamide (408) (200 mg, 0.73 mmol), N-(5-fluoro-2-nitrophenyl)prop-2-enamide (J) (184 mg, 0.87 mmol) and DBU (131 µl, 0.87 mmol) in MeCN (8 ml) afforded a crude intermediate which was further reacted with iron powder (68 mg, 1.21 mmol) in AcOH (5 ml) to afford the title compound (7 mg, 5%) as a white solid after purification by flash column chromatography (eluting with a gradient of 0-30% MeOH/DCM) followed by basic prep-HPLC.

1H-NMR (MeOD, 500 MHz): d[ppm]=8.86 (d, J=2.1 Hz, 1H), 8.59 (d, J=2.1 Hz, 1H), 8.38 (dt, J=4.7, 1.2 Hz, 1H), 8.18 (t, J=2.1 Hz, 1H), 7.63 (ddd, J=9.8, 8.4, 1.3 Hz, 1H), 7.43 (ddd, J=18.1, 8.7, 4.6 Hz, 2H), 7.19 (dd, J=9.1, 2.4 Hz, 1H), 6.98 (ddd, J=9.7, 8.9, 2.5 Hz, 1H), 4.81 (d, J=1.7 Hz, 2H), 3.12 (dd, J=7.9, 4.9 Hz, 2H), 3.07 (dd, J=8.0, 4.9 Hz, 2H), 2.98 (dd, J=8.2, 4.5 Hz, 2H), 2.94 (dd, J=8.1, 4.4 Hz, 2H)

HPLCMS (Method C): [m/z]: 437.2 [M+H]+

5-(2-{[2-(4-Fluoro-1H-1,3-benzodiazol-2-yl)ethyl]amino}ethyl)-N-[(3-fluoropyridin-2-yl)methyl]pyridine-3-carboxamide (Example Compound No. 246)

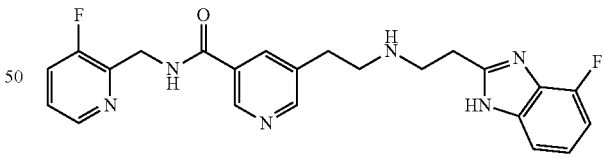

In a similar fashion to general procedure 8, 5-(2-aminoethyl)-N-[(3-fluoropyridin-2-yl)methyl]pyridine-3-carboxamide (408) (340 mg, 1.24 mmol), N-(3-fluoro-2-nitrophenyl)prop-2-enamide (G) (547 mg, 2.6 mmol) and DBU (204 µl, 1.36 mmol) in MeCN (20 ml) gave a crude intermediate which was further reacted with iron powder (125 mg, 2.24 mmol) in AcOH (5 ml) to afford the title compound (107 mg, 44%) as a white solid after purification by basic prep-HPLC followed by flash column chromatography (eluting with a gradient of 0-25% MeOH/DCM then 10% 7N ammonia in MeOH/DCM).

1H-NMR (DMSO-d6, 500M Hz): d[ppm]=9.15 (t, J=5.6 Hz, 1H), 8.87 (d, J=2.1 Hz, 1H), 8.58 (d, J=2.1 Hz, 1H), 8.39

(dt, J=4.6, 1.4 Hz, 1H), 8.10 (t, J=2.1 Hz, 1H), 7.71 (ddd, J=10.0, 8.3, 1.2 Hz, 1H), 7.41 (dt, J=8.6, 4.4 Hz, 1H), 7.29-7.24 (m, 1H), 7.09 (td, J=8.0, 4.9 Hz, 1H), 6.92 (dd, J=11.2, 7.8 Hz, 1H), 4.67 (dd, J=5.6, 1.5 Hz, 2H), 3.00 (dd, J=7.7, 5.0 Hz, 2H), 2.95 (dd, J=7.8, 4.9 Hz, 2H), 2.87-2.83 (m, 2H), 2.81-2.77 (m, 2H)
HPLCMS (Method B): [m/z]: 437.3 [M+H]+

4-{2-[(1H-1,3-Benzodiazol-2-ylmethyl)amino]ethyl}-N-[(3-fluoropyridin-2-yl)methyl]pyridine-2-carboxamide (Example Compound No. 232)

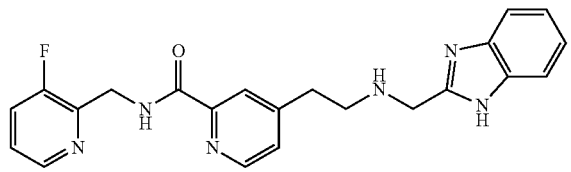 [SMILES: O=C(NCc1ncccc1F)c1ccnc(CCNCc2nc3ccccc3[nH]2)c1]

In a similar fashion to general procedure 3, 4-(2-aminoethyl)-N-[(3-fluoropyridin-2-yl)methyl]pyridine-2-carboxamide (410) (258 mg, 0.94 mmol), 1H-benzimidazole-2-carbaldehyde (151 mg, 1.03 mmol), DIPEA (492 µl, 2.82 mmol) and MgSO4 (200 mg) in MeOH (10 ml) at room temperature for 3 d, followed by addition of NaBH4 (71 mg, 1.88 mmol) gave the title compound (192 mg, 50%) as a white solid after purification by basic prep-HPLC followed by flash column chromatography (eluting with a gradient of 0-30% MeOH/DCM).
1H-NMR (DMSO-d6, 500 MHz): d[ppm]=12.15 (s, 1H), 9.19 (t, J=5.5 Hz, 1H), 8.55 (d, J=4.9 Hz, 1H), 8.41 (dt, J=4.6, 1.3 Hz, 1H), 7.94 (m, 1H), 7.73 (m, 1H), 7.50 (m, 2H), 7.43 (dt, J=8.7, 4.4 Hz, 2H), 7.12 (d, J=4.9 Hz, 2H), 4.75-4.69 (m, 2H), 3.93 (s, 2H), 2.88 (s, 4H)
HPLCMS (Method B): [m/z]: 405.1 [M+H]+
General Scheme 33 Above:

Ethyl 5-{1-[(tert-butoxy)carbonyl]azetidin-3-yl}pyridine-3-carboxylate (411)

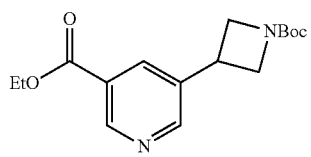 [SMILES: CCOC(=O)c1cncc(C2CN(C(=O)OC(C)(C)C)C2)c1]

1.3M iPrMgCl.LiCl in THF (6.69 ml, 8.69 mmol) was added dropwise to tert-butyl 3-iodoazetidine-1-carboxylate (1.85 g, 6.52 mmol) in THF (20 ml) at 0° C. The reaction mixture was stirred at 0° C. for 20 min and the resultant solution was added dropwise to a solution of ethyl 5-bromopyridine-3-carboxylate (0.5 g, 2.17 mmol) and FeCl2 (anhydrous) (0.22 g, 1.74 mmol) at 0° C. The mixture was stirred at 0° C. for 25 min. The reaction mixture was quenched with saturated NH4Cl (aq), further diluted with water and DCM and stirred vigorously for 10 min. The mixture was extracted with DCM (3×80 ml) aid the combined organic extracts were dried (Na2SO4), filtered and evaporated under vacuum. Purification by flash column chromatography (eluting with a gradient of 0-80% EtOAc/heptane) afforded the title compound (0.652 g, 94%) as a yellow oil.
1H-NMR (CDCl3, 250 MHz): d[ppm]=9.15 (d, J=1.9 Hz, 1H), 8.72 (d, J=2.2 Hz, 1H), 8.35 (t, J=2.1 Hz, 1H), 4.52-4.37 (m, 4H), 4.02 (dd, J=8.6, 5.8 Hz, 2H), 3.91-3.78 (m, 1H), 1.50 (s, 9H), 1.45 (t, J=7.1 Hz, 3H)
HPLCMS (Method M): [m/z]: 307.40 [M+H]+

5-{1-[(Tert-butoxy)carbonyl]azetidin-3-yl}pyridine-3-carboxylic Acid (412)

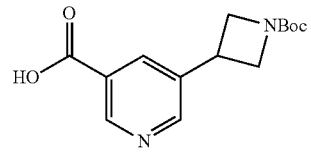 [SMILES: CC(C)(C)OC(=O)N1CC(c2cncc(C(=O)O)c2)C1]

In a similar fashion to general procedure 5, ethyl 5-{1-[(tert-butoxy)carbonyl]azetidin-3-yl}pyridine-3-carboxylate (411) (650 mg, 2.12 mmol) and LiOH (152 mg, 6.36 mmol) in THF (10 ml) and water (10 ml) at room temperature for 18 h gave the title compound (340 mg, 58%) as a pale yellow solid.
1H-NMR (DMSO-d6, 250 MHz): d[ppm]=8.96 (d, J=2.0 Hz, 1H), 8.75 (d, J=2.2 Hz, 1H), 8.24 (t, J=2.1 Hz, 1H), 4.34-4.22 (m, 2H), 3.99-3.83 (m, 3H), 1.41 (s, 9H)
HPLCMS (Method M): [m/z]: 279.05 [M+H]+

Tert-butyl 3-(5-{[(3-fluoropyridin-2-yl)methyl]carbamoyl}pyridin-3-yl)azetidine-1-carboxylate (413)

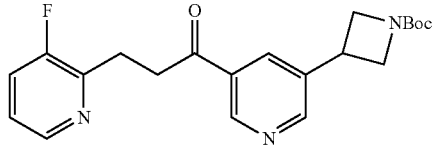 [SMILES: CC(C)(C)OC(=O)N1CC(c2cncc(C(=O)CCc3ncccc3F)c2)C1]

In a similar fashion to general procedure 6, 5-{1-[(tert-butoxy)carbonyl]azetidin-3-yl}pyridine-3-carboxylic acid (412) (340 mg, 1.22 mmol), (3-fluoropyridin-2-yl)methanamine dihydrochloride (A2) (268 mg, 1.34 mmol), DIPEA (745 µl, 4.28 mmol) and HATU (557 mg, 1.47 mmol) in DCM (20 ml) afforded the title compound (518 mg) as a pale yellow foam after purification by flash column chromatography (eluting with a gradient of 0-100% EtOAc/heptane followed by 0-20% MeOH/EtOAc).
HPLCMS (Method M): [m/z]: 387.45 [M+H]+

5-(Azetidin-3-yl)-N-[(3-fluoropyridin-2-yl)methyl]pyridine-3-carboxamide (414)

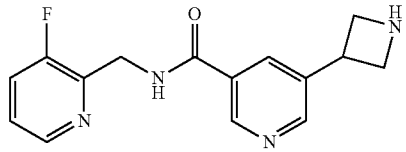 [SMILES: O=C(NCc1ncccc1F)c1cncc(C2CNC2)c1]

A solution of tert-butyl 3-(5-{[(3-fluoropyridin-2-yl)methyl]carbamoyl}pyridin-3-yl)azetidine-1-carboxylate (413) (518 mg, 1.34 mmol) and TFA (2 ml, 26.1 mmol) in DCM (5 ml) was stirred at room temperature for 3 h. The reaction mixture was concentrated under vacuum and free-based using an SCX-2 cartridge (10 g), rinsing with DCM and MeOH, then eluted with 7N ammonia in MeOH to afford the title compound (265 mg, 69%) as a white solid.

1H-NMR (DMSO-d6, 250 MHz): d[ppm]=9.23 (t, J=5.4 Hz, 1H), 8.91 (d, J=2.1 Hz, 1H), 8.66 (d, J=2.1 Hz, 1H), 8.39 (dt, J=4.7, 1.5 Hz, 1H), 8.30 (t, J=2.2 Hz, 1H), 7.72 (ddd, J=10.1, 8.3, 1.2 Hz, 1H), 7.42 (dt, J=8.4, 4.4 Hz, 1H), 4.69 (dd, J=5.6, 1.6 Hz, 2H), 3.94-3.83 (m, 2H), 3.69 (t, J=7.0 Hz, 2H)

HPLCMS (Method M): [m/z]: 287.00 [M+H]+

5-{1-[2-(1H-1,3-Benzodiazol-2-yl)ethyl]azetidin-3-yl}-N-[(3-fluoropyridin-2-yl)methyl]pyridine-3-carboxamide (Example Compound No. 237)

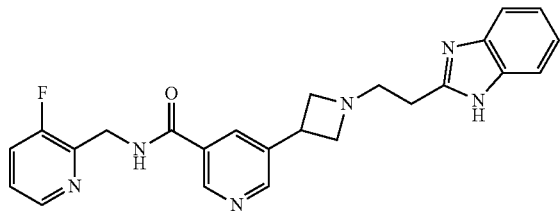 [SMILES: O=C(NCc1ncccc1F)c1cncc(C2CN(CCc3nc4ccccc4[nH]3)C2)c1]

In a similar fashion to general procedure 8, 5-(azetidin-3-yl)-N-[(3-fluoropyridin-2-yl)methyl]pyridine-3-carboxamide (414) (260 mg, 0.91 mmol), N-(2-nitrophenyl)prop-2-enamide (D) (175 mg, 0.91 mmol) and DBU (149 µl, 1 mmol) in MeCN (10 ml) gave a crude intermediate which was further reacted with iron powder (154 mg, 2.75 mmol) in AcOH (4 ml) to afford the title compound (120 mg, 41%) as a white solid after purification by flash column chromatography (eluting with a gradient of 0-40% MeOH/DCM).

1H-NMR (DMSO-d6, 500 MHz): d[ppm]=12.14 (s, 1H), 9.24 (t, J=5.6 Hz, 1H), 8.90 (d, J=2.1 Hz, 1H), 8.66 (d, J=2.1 Hz, 1H), 8.39 (dt, J=4.6, 1.4 Hz, 1H), 8.24 (t, J=2.1 Hz, 1H), 7.71 (ddd, J=10.0, 8.3, 1.3 Hz, 1H), 7.56-7.38 (m, 3H), 7.14-7.08 (m, 2H), 4.68 (dd, J=5.6, 1.5 Hz, 2H), 3.75-3.68 (m, 1H), 3.66 (t, J=7.1 Hz, 2H), 3.19 (t, J=6.4 Hz, 2H), 2.94-2.89 (m, 2H), 2.87-2.82 (m, 2H)

HPLCMS (Method B): [m/z]: 431.2 [M+H]+

5-{1-[2-(4-fluoro-1H-1,3-benzodiazol-2-yl)ethyl]azetidin-3-yl}-N-[(3-fluoropyridin-2-yl)methyl]pyridine-3-carboxamide (Example Compound No. 248)

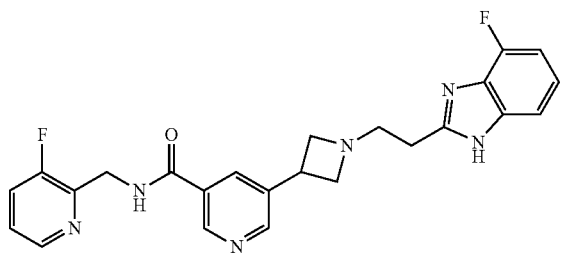 [SMILES: O=C(NCc1ncccc1F)c1cncc(C2CN(CCc3nc4c(F)cccc4[nH]3)C2)c1]

In a similar fashion to general procedure 8, 5-(azetidin-3-yl)-N-[(3-fluoropyridin-2-yl)methyl]pyridine-3-carboxamide (414) (0.50 g, 1.75 mmol), DBU (313 µl, 2.10 mmol) and N-(3-fluoro-2-nitrophenyl)prop-2-enamide (G) (0.48 g, 2.10 mmol) in MeCN (15 ml) gave a crude mixture which was partially purified by flash column chromatography (eluting with a gradient of 0-40% MeOH/DCM followed by 10% 7M NH3/MeOH/DCM). The mixture was further reacted with iron powder (0.292 g) in AcOH (4 ml) to give the title compound (0.08 g, 13%) as a white solid after purification by flash chromatography (eluting with a gradient of 0-40% MeOH/DCM) followed by kp-NH flash chromatography (eluting with a gradient of 0-10% MeOH/DCM).

1H-NMR (DMSO-d6, 500 MHz): d[ppm]=12.51 (s, 1H), 9.23 (t, J=5.6 Hz, 1H), 8.90 (d, J=2.1 Hz, 1H), 8.66 (d, J=2.1 Hz, 1H), 8.41-8.36 (m, 1H), 8.24 (t, J=2.1 Hz, 1H), 7.75-7.68 (m, 1H), 7.45-7.38 (m, 1H), 7.29 (d, J=8.0 Hz, 1H), 7.14-7.07 (m, 1H), 6.96-6.87 (m, 1H), 4.68 (dd, J=5.6, 1.4 Hz, 2H), 3.75-3.69 (m, 1H), 3.67 (m, 2H), 3.19 (t, J=6.4 Hz, 2H), 2.97-2.89 (m, 2H), 2.89-2.82 (m, 2H)

HPLCMS (Method D): [m/z]: 449.2 [M+H]+

General Scheme 34 Above:

Ethyl 2-[(2-{[(benzyloxy)carbonyl]amino}ethyl)carbamoyl]acetate (415)

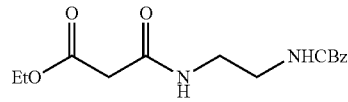

Ethyl 3-chloro-3-oxopropanoate (480 mg, 3.17 mmol) was added dropwise over 5 min to an ice-cold mixture of benzyl N-(2-aminoethyl)carbamate hydrochloride (665 mg, 2.88 mmol) and DIPEA (1 ml, 6 mmol) in DCM (10 ml) and DMF (1 ml). The reaction mixture was stirred for 30 min, then quenched with saturated NaHCO3 (aq) and extracted with DCM (3×50 ml). The combined organic extracts were dried (Na2SO4), filtered and evaporated in vacuo. Purification by flash column chromatography (eluting with a gradient of 5-100% EtOAc/heptane followed by 5-20% MeOH/EtOAc) afforded the title compound (451 mg, 42%) as a yellow-orange solid.

1H-NMR (CDCl3, 500 MHz): d[ppm]=7.41-7.30 (m, 6H), 5.23 (s, 1H), 5.12 (s, 2H), 4.22 (q, J=7.1 Hz, 2H), 3.45 (q, J=5.5 Hz, 2H), 3.38 (q, J=5.5 Hz, 2H), 3.30 (s, 2H), 1.30 (t, J=7.1 Hz, 3H)

HPLCMS (Method A): [m/z]: 309.05 [M+H]+

2-[(2-{[(Benzyloxy)carbonyl]amino}ethyl)carbamoyl]acetic Acid (416)

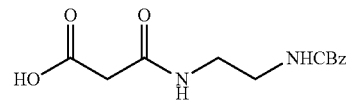

In a similar fashion to general procedure 5, ethyl 2-[(2{[(benzyloxy)carbonyl]amino}ethyl)carbamoyl]acetate (415) (451 mg, 1.46 mmol) and LiOH (110 mg, 4.3 mmol) in THF (5 ml) and water (5 ml) afforded the title compound (302 mg, 72%) as a white solid.

1H-NMR (MeOD, 500 MHz): d[ppm]=7.41-7.26 (m, 5H), 5.09 (s, 2H), 3.26 (q, J=5.0 Hz, 4H)

HPLCMS (Method A): [m/z]: 280.95 [M+H]+

Benzyl N-[2-(2-{[(3-fluoropyridin-2-yl)methyl]carbamoyl}acetamido)ethyl]carbamate (417)

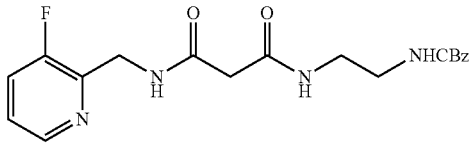

In a similar fashion to general procedure 6, 2-[(2-{[(benzyloxy)carbonyl]amino}ethyl)carbamoyl]acetic acid (416) (300 mg, 1.07 mmol), (3-fluoropyridin-2-yl)methanamine dihydrochloride (A2) (234 mg, 1.18 mmol), DIPEA (410 µl, 2.4 mmol) and HATU (450 mg, 1.17 mmol) in DCM (10 ml) and DMF (2 ml) afforded the title compound (324 mg, 75%) as a white solid after purification by flash column chromatography (eluting with a gradient of 50-100% EtOAc/heptane followed by 2-15% MeOH/EtOAc).

1H-NMR (DMSO-d6, 250 MHz): d[ppm]=8.57 (t, J=5.3 Hz, 1H), 8.40 (d, J=4.7 Hz, 1H), 8.12 (t, J=5.3 Hz, 1H), 7.70 (m, 1H), 7.47-7.21 (m, 7H), 5.01 (s, 2H), 4.48 (dd, J=5.4, 1.6 Hz, 2H), 3.20-3.00 (m, 6H)

HPLCMS (Method A): [m/z]: 389.40 [M+H]+

N-2-aminoethyl)-N'-[(3-fluoropyridin-2-yl)methyl]propanediamide (418)

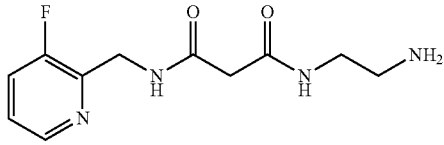 [SMILES: NCCNC(=O)CC(=O)NCc1ncccc1F]

Benzyl N-[2-(2-{[(3-fluoropyridin-2-yl)methyl]carbamoyl}acetamido)ethyl]carbamate (417) (320 mg, 0.82 mmol) and Pd/C (10%) (90 mg) were suspended in EtOH (10 ml). The reaction mixture was stirred under an atmosphere of hydrogen for 3 h. The mixture was filtered through a plug of Celite and the residue rinsed with MeOH and 7N ammonia in MeOH. The combined filtrates were evaporated in vacuo to afford the title compound (198 mg, 95%) as a hygroscopic colourless residue.

HPLCMS (Method A): [m/z]: 255.05 [M+H]+

N-{2-[(1H-1,3-benzodiazol-2-ylmethyl)amino]ethyl}-N'-[(3-fluoropyridin-2-yl)methyl]propanediamide (Example Compound No. 149)

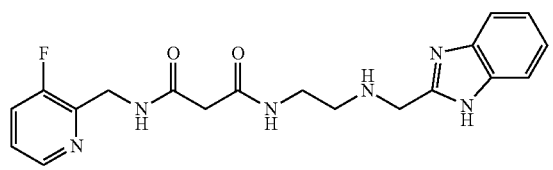 [SMILES: O=C(CC(=O)NCc1ncccc1F)NCCNCc1nc2ccccc2[nH]1]

In a similar fashion to general procedure 3, N-(2-aminoethyl)-N'-[(3-fluoropyridin-2-yl)methyl]propanediamide (418) (190 mg, 0.75 mmol), 1H-1,3-benzodiazole-2-carbaldehyde (120 mg, 0.82 mmol) and MgSO4 (100 mg) in DCM (10 ml) and MeOH (5 ml) at room temperature for 16 h, followed by addition of NaBH4 (57 mg, 1.51 mmol) gave the title compound (87 mg, 28%) as a pale yellow solid after purification by basic prep-HPLC.

1H-NMR (DMSO-d6, 500 MHz): d[ppm]=12.14 (s, 1H), 8.59 (t, J=5.5 Hz, 1H), 8.40-8.35 (m, 1H), 8.06 (t, J=5.5 Hz, 1H), 7.69 (m, 1H), 7.57-7.47 (m, 1H), 7.47-7.36 (m, 2H), 7.16-7.08 (m, 2H), 4.48 (dd, J=5.5, 1.7 Hz, 2H), 3.91 (s, 2H), 3.20 (dt, J=6.5, 6.5 Hz, 2H), 3.13 (s, 2H), 2.63 (t, J=6.5 Hz, 2H)

HPLCMS (Method C): [m/z]: 385.2 [M+H]+

N-(2-{[2-(1H-1,3-benzodiazol-2-yl)ethyl]amino}ethyl)-N'-[(3-fluoropyridin-2-yl)methyl]propanediamide (Example Compound No. 168)

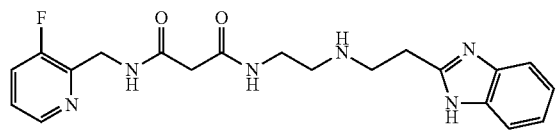 [SMILES: O=C(CC(=O)NCc1ncccc1F)NCCNCCc1nc2ccccc2[nH]1]

In a similar fashion to general procedure 8, N-(2-aminoethyl)-N'-[(3-fluoropyridin-2-yl)methyl]propanediamide (418) (300 mg, 1.18 mmol), DBU (176 µl, 1.18 mmol) and N-(2-nitrophenyl)prop-2-enamide (D) (220 mg, 1.14 mmol) in MeCN (10 ml) gave a crude intermediate which was further reacted with iron powder (76 mg) in AcOH (7 ml) to give the title compound (36 mg, 23%) as a yellow solid after purification by prep-HPLC followed by flash column chromatography (kp-NH, eluting with a gradient of 0-30% MeOH/EtOAc).

1H-NMR (DMSO-d6, 500 MHz): d[ppm]=12.09 (br s, 1H), 8.57 (t, J=5.3 Hz, 1H), 8.38 (d, J=4.7 Hz, 1H), 8.04 (t, J=5.4 Hz, 1H), 7.72-7.66 (m, 1H), 7.45 (br s, 2H), 7.42-7.37 (m, 1H), 7.12-7.07 (m, 2H), 4.47 (dd, J=5.4, 1.6 Hz, 2H), 3.16 (m, 2H), 3.11 (s, 2H), 2.97-2.88 (m, J=3.9 Hz, 4H), 2.62 (t, J=6.4 Hz, 2H)

HPLCMS (Method B): [m/z]: 399.2 [M+H]+

General Scheme 35 Above

Tert-butyl N-({[(3-fluoropyridin-2-yl)methyl]carbamoyl}methyl)carbamate (419)

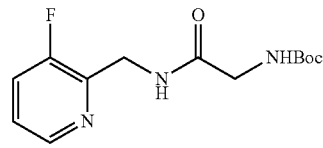 [SMILES: CC(C)(C)OC(=O)NCC(=O)NCc1ncccc1F]

In a similar fashion to general procedure 6, N-(tert-butoxycarbonyl)glycine (2.0 g, 11.4 mmol), (3-fluoropyridin-2-yl)methanamine dihydrochloride (A2) (2.3 g, 13.7 mmol), DIPEA (7.9 ml, 45.7 mmol) and HATU (5.2 g, 13.7 mmol) in THF (50 ml) and DMF (10 ml) at room temperature for 2 h gave the title compound (4.54 g) as an orange oil after purification by flash column chromatography (eluting with a gradient of 60-100% EtOAc/heptane).

1H-NMR (DMSO-d6, 500 MHz): d[ppm]=8.38 (d, J=4.4 Hz, 1H), 8.24-8.18 (m, 1H), 7.69 (t, J=9.3 Hz, 1H), 7.43-7.38 (m, 1H), 7.00-6.94 (m, 1H), 4.46 (d, J=5.3 Hz, 2H), 3.57 (d, J=6.0 Hz, 2H), 1.38 (s, 9H)

HPLCMS (Method A): [m/z]: 284.00 [M+H]+

2-Amino-N-[(3-fluoropyridin-2-yl)methyl]acetamide Dihydrochloride (420)

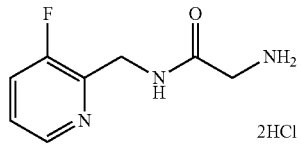 [SMILES: NCC(=O)NCc1ncccc1F]

In a similar fashion to general procedure 2, tert-butyl N-({[(3-fluoropyridin-2-yl)methyl]carbamoyl}methyl)carbamate (419) (4.5 g, 11.4 mmol) and 12M HCl (19.0 ml, 228.4 mmol) in MeOH (80 ml) at room temperature for 16 h gave the title compound (4.1 g) as a light pink solid.

1H-NMR (MeOD, 500 MHz): d[ppm]=8.70-8.66 (m, 1H), 8.44 (t, J=8.8 Hz, 1H), 8.03 (m, 1H), 4.84 (s, 2H), 3.84 (s, 2H)

HPLCMS (Method A): [m/z]: 183.90 [M+H]$^+$

Benzyl N-{2-[({[(3-fluoropyridin-2-yl)methyl]carbamoyl}methyl)carbamoyl]ethyl}carbamate (421)

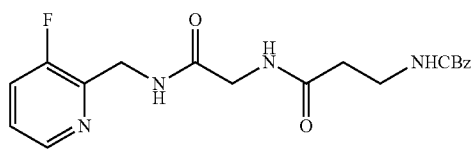

In a similar fashion to general procedure 6, 2-amino-N-[(3-fluoropyridin-2-yl)methyl]acetamide dihydrochloride (420) (4.5 g, 12.54 mmol), 3-{[(benzyloxy)carbonyl]amino}propanoic acid (2.3 g, 10.45 mmol), DIPEA (7.3 ml, 41.81 mmol) and HATU (4.8 g, 12.54 mmol) in DMF (15 ml) and THF (80 ml) at room temperature for 2 h gave the title compound (2.97 g, 63%) as a grey solid after purification by flash column chromatography (eluting with a gradient of 0-25% MeOH/EtOAc).

1H-NMR (DMSO-d6, 500 MHz): d[ppm]=8.37 (d, J=4.7 Hz, 1H), 8.31 (t, J=5.5 Hz, 1H), 8.15 (t, J=5.8 Hz, 1H), 7.68 (t, J=9.3 Hz, 1H), 7.40 (m, 1H), 7.35 (m, 5H), 7.21 (m, 1H), 5.00 (s, 2H), 4.45 (dd, J=5.5, 1.7 Hz, 2H), 4.09 (q, J=5.3 Hz, 2H), 3.72 (d, J=5.8 Hz, 2H), 2.33 (t, J=7.2 Hz, 2H)

HPLCMS (Method A): [m/z]: 389.05 [M+H]$^+$

3-Amino-N-({[(3-fluoropyridin-2-yl)methyl]carbamoyl}methyl)propanamide (422)

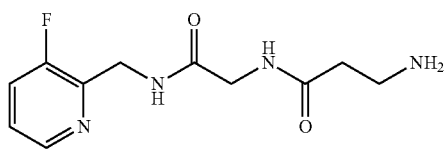 [SMILES: NCCC(=O)NCC(=O)NCc1ncccc1F]

To an N2 purged stirring solution of benzyl N-{2-[({[(3-fluoropyridin-2-yl)methyl]carbamoyl}methyl)carbamoyl]ethyl}carbamate (421) (1.49 g, 3.32 mmol) in EtOH (40 ml) was added Pd/C (10%, 0.35 g, 0.33 mmol). The reaction mixture was then purged three times with H2 and stirred at room temperature for 16 h. The reaction was filtered through glass fibre paper and the residue was washed with 7M NH3/MeOH (40 ml). The filtrate was then concentrated to give the product (0.88 g) as a colourless viscous oil.

1H-NMR (DMSO-d6, 500 MHz): d[ppm]=8.46 (t, J=5.4 Hz, 1H), 8.37 (m, 1H), 8.25 (t, J=5.6 Hz, 1H), 7.71-7.65 (m, 1H), 7.40 (m, 1H), 4.48-4.42 (m, 2H), 3.75 (d, J=5.7 Hz, 2H), 2.85 (t, J=6.6 Hz, 2H), 2.32 (t, J=6.6 Hz, 2H)

HPLCMS (Method A): [m/z]: 255.00 [M+H]$^+$

3-[(1H-1,3-Benzodiazol-2-ylmethyl)amino]-N-({[(3-fluoropyridin-2-yl)methyl]carbamoyl}methyl)propanamide (Example Compound No. 172)

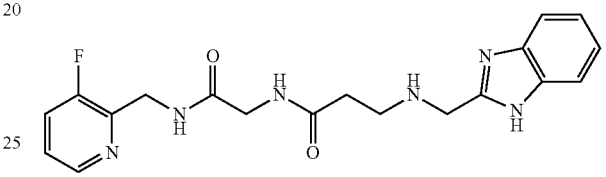

In a similar fashion to general procedure 3, 3-amino-N-({[(3-fluoropyridin-2-yl)methyl]carbamoyl}methyl)propanamide (422) (300 mg, 1.13 mmol), 1H-benzimidazole-2-carbaldehyde (214 mg, 1.47 mmol) and DIPEA (393 µl, 2.26 mmol) in MeOH (15 ml) at room temperature for 16 h, followed by addition of NaBH$_4$ (64 mg, 1.69 mmol) gave the title compound (167 mg, 37%) as a yellow solid after purification by basic prep-HPLC.

1H-NMR (DMSO-d6, 500 MHz): d[ppm]=12.14 (br s, 1H), 8.44 (t, J=5.5 Hz, 1H), 8.36-8.34 (m, 1H), 8.32 (t, J=5.8 Hz, 1H), 7.69-7.63 (m, 1H), 7.54-7.39 (br m, 2H), 7.39-7.35 (m, 1H), 7.14-7.08 (m, 2H), 4.46 (dd, J=5.6, 1.6 Hz, 2H), 3.90 (s, 2H), 3.77 (d, J=5.8 Hz, 2H), 2.78 (t, J=6.6 Hz, 2H), 2.33 (t, J=6.6 Hz, 2H)

HPLCMS (Method G): [m/z]: 385.2 [M+H]$^+$

3-{[2-(1H-1,3-Benzodiazol-2-yl)ethyl]amino}-N-({[(3-fluoropyridin-2-yl)methyl]carbamoyl}methyl)propanamide (Example Compound No. 190)

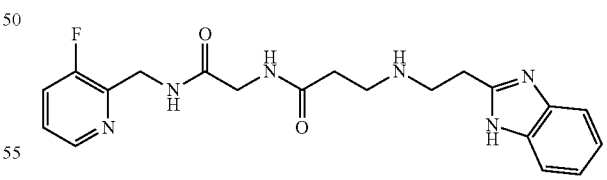

In a similar fashion to general procedure 8, 3-amino-N-({[(3-fluoropyridin-2-yl)methyl]carbamoyl}methyl)propanamide (422) (588 mg, 2.21 mmol), N-(2-nitrophenyl)prop-2-enamide (404 mg, 2.10 mmol) (D), DBU (660 µl, 4.42 mmol) in MeCN (20 ml) gave an intermediate which was further reacted with iron powder (54 mg) in AcOH (3 ml) to give the title compound (43 mg, 22%) as a white solid after purification by prep-HPLC followed by flash column chromatography (kp-NH, eluting with a gradient of 0-50% MeOH/EtOAc).

1H-NMR (DMSO-d6, 500 MHz): d[ppm]=8.40-8.35 (m, 2H), 8.27 (t, J=5.8 Hz, 1H), 7.70-7.64 (m, 1H), 7.45 (br s, 2H), 7.39 (m, 1H), 7.13-7.07 (m, 2H), 4.45 (dd, J=5.5, 1.6 Hz, 2H), 3.73 (d, J=5.9 Hz, 2H), 2.98-2.89 (m, J=3.9 Hz, 4H), 2.79 (t, J=6.6 Hz, 2H), 2.30 (t, J=6.6 Hz, 2H)

HPLCMS (Method D): [m/z]: 399.2 [M+H]+

General Scheme 36 Above

Tert-butyl 3-[({[(3-fluoropyridin-2-yl)methyl]carbamoyl}methyl)carbamoyl]azetidine-1-carboxylate (423)

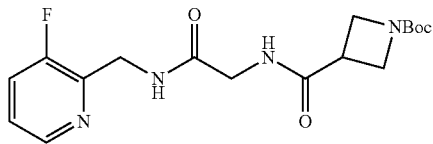 [SMILES: CC(C)(C)OC(=O)N1CC(C(=O)NCC(=O)NCc2ncccc2F)C1]

In a similar fashion to general procedure 6, 2-amino-N-[(3-fluoropyridin-2-yl)methyl]acetamide dihydrochloride (420) (5.8 g, 9.76 mmol), 1-(tert-butoxycarbonyl)azetidine-3-carboxylic acid (2.1 g, 10.73 mmol), DIPEA (8.5 ml, 48.77 mmol) and HATU (4.1 g, 10.73 mmol) in THF (70 ml) and DMF (20 ml) at room temperature for 2 h, gave the title compound (1.2 g, 32%) as a yellow oil after purification by kp-NH flash column chromatography (eluting with a gradient of 20-100% of EtOAc/heptane).

1H-NMR (DMSO-d6, 500 MHz): d[ppm]=8.38 (m, 1H), 8.35 (t, J=5.5 Hz, 1H), 8.26 (t, J=5.8 Hz, 1H), 7.69 (m, 1H), 7.41 (m, 1H), 4.45 (m, 2H), 3.88 (br d, 4H), 3.76 (d, J=5.9 Hz, 2H), 1.37 (s, 9H) HPLCMS (Method A): [m/z]: 367.05 [M+H]+

2-(Azetidin-3-ylformamido)-N-[(3-fluoropyridin-2-yl)methyl]acetamide Dihydrochloride (424)

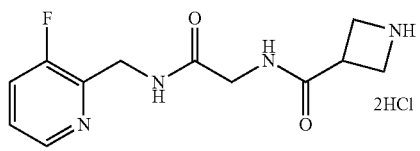 [SMILES: O=C(CNC(=O)C1CNC1)NCc1ncccc1F]

In a similar fashion to general procedure 2, tert-butyl 3-[({[(3-fluoropyridin-2-yl)methyl]carbamoyl}methyl)carbamoyl]azetidine-1-carboxylate (423) (1.2 g, 3.1 mmol) and 12M HCl (5.2 ml, 62.1 mmol) in MeOH (40 ml) at room temperature for 16 h, gave the title compound (1.1 g) as a pink solid.

HPLCMS (Method A): [m/z]: 266.95 [M+H]+

2-({1-[2-(1H-1,3-benzodiazol-2-yl)ethyl]azetidin-3-yl}formamido)-N-[(3-fluoropyridin-2-yl)methyl]acetamide (Example Compound No. 201)

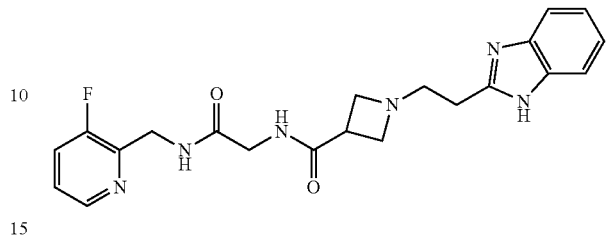

In a similar fashion to general procedure 8, 2-(azetidin-3-ylformamido)-N-[(3-fluoropyridin-2-yl)methyl]acetamide dihydrochloride (424) (550 mg, 1.55 mmol), N-(2-nitrophenyl)prop-2-enamide (D) (298 mg, 1.55 mmol), DBU (695 µl, 4.66 mmol) in MeCN (25 ml) gave a intermediate which was purified by flash column chromatography (eluting with a gradient of 0-5% MeOH/DCM). This intermediate was further reacted with iron powder (60 mg) in AcOH (3 ml) to give the title compound (24 mg, 11%) as a white solid after purification by basic prep-HPLC followed by a kp-NH flash column chromatography (eluting with a gradient of 0-10% MeOH/DCM) and a flash column chromatography (eluting with a gradient of 0-40% MeOH/DCM).

1H-NMR (DMSO-d6, 500 MHz): d[ppm]=12.12 (s, 1H), 8.37 (d, J=4.6 Hz, 1H), 8.31 (t, J=5.5 Hz, 1H), 8.08 (t, J=5.8 Hz, 1H), 7.71-7.65 (m, 1H), 7.53-7.37 (m, 3H), 7.10 (d, J=4.7 Hz, 2H), 4.44 (dd, J=5.5, 1.6 Hz, 2H), 3.73 (d, J=5.9 Hz, 2H), 3.21-3.13 (m, 2H), 3.08 (m, 2H), 2.77 (s, 4H) HPLCMS (Method D): [m/z]: 411.2 [M+H]+

General Scheme 37 Above

Tert-butyl N-{4-[(1H-1,3-benzodiazol-2-ylmethyl)amino]butyl}carbamate (425)

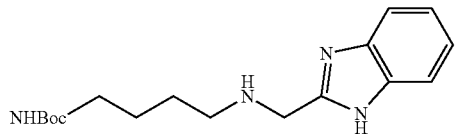 [SMILES: CC(C)(C)OC(=O)NCCCCNCc1nc2ccccc2[nH]1]

In a similar fashion to general procedure 3, tert-butyl N-(4-aminobutyl)carbamate (1 g, 5.31 mmol), 1H-1,3-benzodiazole-2-carbaldehyde (0.93 g, 6.37 mmol) and DIPEA (1.85 mL, 10.62 mmol) in MeOH (40 ml) at room temperature for 16 h, followed by addition of NaBH4 (0.3 g, 7.97 mmol) gave the title compound (1.15 g, 61%) as a pale yellow oil which solidified upon standing. The product was used in the next step without further purification.

1H-NMR (MeOD, 500 MHz): d[ppm]=7.56-7.51 (m, 2H), 7.25-7.19 (m, 2H), 4.01 (s, 2H), 3.04 (t, J=6.7 Hz, 2H), 2.65 (t, J=7.1 Hz, 2H), 1.59-1.47 (m, 4H), 1.42 (s, 9H)

HPLCMS (Method A): [m/z]: 319.3 [M+H]+

Benzyl 2-({[(benzyloxy)carbonyl](4-{[(tert-butoxy)carbonyl]amino}butyl)amino}methyl)-1H-1,3-benzodiazole-1-carboxylate (426)

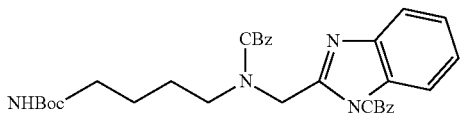

Benzyl chloroformate (0.27 ml, 1.88 mmol) was added dropwise to an ice-cooled (0° C.) suspension of tert-butyl N-{4-[(1H-1,3-benzodiazol-2-ylmethyl)amino]butyl}carbamate (425) (250 mg, 0.79 mmol) and K$_2$CO$_3$ (220 mg, 1.57 mmol) in MeCN (2 ml) and the reaction mixture was stirred for 2 h. The reaction was quenched with water and extracted with DCM (3×100 ml). The combined organic layers were dried (Na$_2$SO$_4$), filtered and evaporated to give the title compound (563 mg, 82%) as a yellow oil which solidified upon cooling. The product was used in the next step without purification.

HPLCMS (Method A): [m/z]: 587.2 [M+H]$^+$

Benzyl N-(4-aminobutyl)-N-(1H-1,3-benzodiazol-2-ylmethyl)carbamate (427)

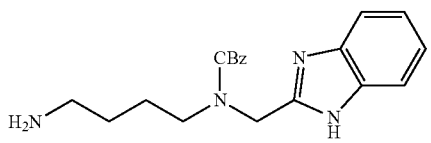

In a similar fashion to general procedure 2, benzyl 2-({[(benzyloxy)carbonyl](4-{[(tert-butoxy)carbonyl]amino}butyl)amino}methyl)-1H-1,3-benzodiazole-1-carboxylate (426) (437 mg, 0.49 mmol, 66% purity) and 4M HCl/dioxane (1.8 ml) in MeOH (10 ml) at room temperature for 72 h, gave the title compound (250 mg) as a yellow oil after purification by flash column chromatography (eluting with a gradient of 0-10% 7N NH$_3$ in MeOH/DCM).

1H-NMR (MeOD 500 MHz): d[ppm]=7.53 (s, 2H), 7.44-7.29 (m, 3H), 7.27-7.21 (m, 2H), 7.20-7.04 (m, 2H), 5.26-5.07 (br m, 2H), 4.75 (s, 2H), 3.54-3.36 (br m, 2H), 2.70-2.46 (br m, 2H), 1.69-1.50 (br m, 2H), 1.50-1.31 (br m, 2H)

HPLCMS (Method A): [m/z]: 353.15 [M+H]$^+$

Benzyl N-(1H-1,3-benzodiazol-2-ylmethyl)-N-[4-({[(3-fluoropyridin-2-yl)methyl]carbamoyl}amino)butyl]carbamate (428)

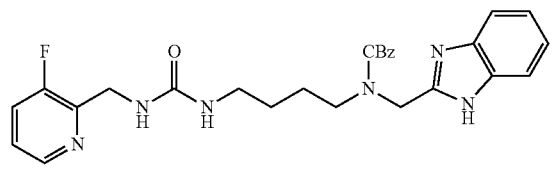

To a stirring solution of (3-fluoropyridin-2-yl)methanamine (A2) (85 mg, 0.67 mmol) in THF at 0° C. was added CDI (131 mg, 0.81 mmol) and the reaction mixture stirred for 1 h. Benzyl N-(4-aminobutyl)-N-(1H-1, 3-benzodiazol-2-ylmethyl)carbamate (427) (130 mg, 0.37 mmol) was added and the reaction was stirred for 2 h. TEA (190 µl, 1.36 mmol) and DMAP (catalytic) was added and the reaction stirred for further 72 h. The reaction was filtered and the filtrate evaporated to give a residue which was purified by flash column chromatography (eluting with a gradient 0-10% MeOH/DCM) followed by acidic prep-HPLC to give the title compound (72 mg, 18%). The product was used in the next step without further purification.

HPLCMS (Method A): [m/z]: 505.15 [M+H]$^+$

3-{4-[(1H-1,3-Venzodiazol-2-ylmethyl)amino]butyl}-1-[(3-fluoropyridin-2-yl)methyl]urea (Example Compound No. 197)

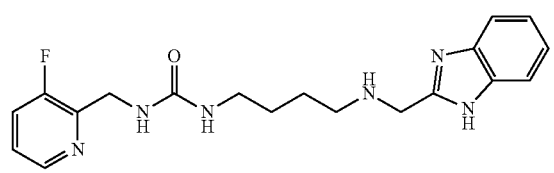 [SMILES: O=C(NCCCCNCc1nc2ccccc2[nH]1)NCc1ncccc1F]

Benzyl N-(1H-1,3-benzodiazol-2-ylmethyl)-N-[4-({[(3-fluoropyridin-2-yl)methyl]carbamoyl}amino)butyl]carbamate (428) (72 mg, 0.14 mmol) and Pd/C (10%, 21 mg, 20.3 µmol) in EtOH (5 ml) was stirred under a hydrogen atmosphere for 24 h. The reaction was filtered through Celite and the solvent evaporated to give a residue. Purification by basic prep-HPLC gave the title compound (38 mg, 51%) as a colourless film.

1H-NMR (MeOD, 500 MHz): d[ppm]=8.34-8.29 (m, 1H), 7.56-7.49 (m, 3H), 7.36-7.31 (m, 1H), 7.24-7.18 (m, 2H), 4.50 (d, J=1.6 Hz, 2H), 4.00 (s, 2H), 3.14 (t, J=6.6 Hz, 2H), 2.65 (t, J=7.0 Hz, 2H), 1.61- 1.49 (m, 4H)

HPLCMS (Method C): [m/z]: 371.4 [M+H]$^+$

General Scheme 38 Above

Tert-butyl N-{2-[1-(1H-imidazole-1-carbonyl)piperidin-3-yl]ethyl}carbamate (429)

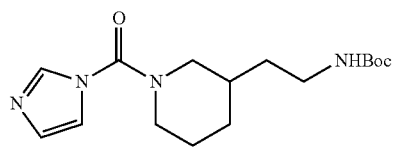 [SMILES: CC(C)(C)OC(=O)NCCC1CCCN(C(=O)n2ccnc2)C1]

Tert-butyl [2-(piperidin-3-yl)ethyl]carbamate (0.45 g, 1.97 mmol) was added to an ice-cooled (0° C.) solution of CDI (0.383 g, 2.36 mmol) in DCM (4 ml). The reaction was allowed to warm to room temperature and stirred for 6 h. The reaction mixture was poured onto 10% citric acid solution (20 ml), the layers separated and the aqueous layer extracted with DCM (3×20 ml). The combined organic layers were dried (Na$_2$SO$_4$), filtered and evaporated to give the title compound (0.61 g, 83%) as a yellow oil.

1H-NMR (CDCl$_3$, 500 MHz): d[ppm]=7.86 (br s, 1H), 7.19 (br s, 1H), 7.09 (br s, 1H), 4.54 (br s, 1H), 4.06-3.89 (m, 2H), 3.24-3.10 (m, 2H), 3.10-2.98 (m, 1H), 2.75 (dd, J=13.1, 10.6 Hz, 1H), 2.09-1.91 (m, 1H), 1.82-1.75 (m, 1H), 1.75-1.62 9 (m, 2H), 1.61-1.51 (m, 1H), 1.50-1.38 (m, 1H), 1.44 (s, 9H), 1.31-1.17 (m, 1H)

HPLCMS (Method A): [m/z]: 323.10 [M+H]⁺

Tert-butyl N-[2-(1-{[(3-fluoropyridin-2-yl)methyl]carbamoyl}piperidin-3-yl)ethyl]carbamate (430)

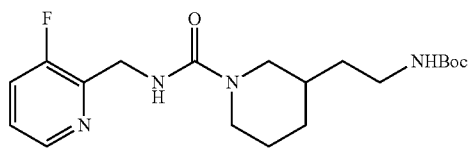 [SMILES: CC(C)(C)OC(=O)NCCC1CCCN(C(=O)NCc2ncccc2F)C1]

Iodomethane (3.0 ml, 49 mmol) was added to tert-butyl N-{2-[1-(1H-imidazole-1-carbonyl)piperidin-3-yl]ethyl}carbamate (429) (0.61 g, 1.63 mmol, 86% purity) in THF (6 ml). The reaction mixture was stirred at room temperature for 16 h. The solvent was evaporated to give a yellow foam (0.78 g) which was dissolved in CHCl₃ (10 ml) and cooled to 0° C. DIPEA (1 ml, 5.74 mmol) was then added followed by (3-fluoropyridin-2-yl)methanamine dihydrochloride (A2) (0.389 g, 1.96 mmol). The reaction mixture was allowed to warm to room temperature and stirred for 20 h. The reaction was poured onto water (20 ml) and the layers separated. The aqueous layer extracted with DCM (2×20 ml) and the combined organic layers were dried (Na₂SO₄), filtered and evaporated to give a yellow oil. Purification by flash column chromatography (eluting with a gradient of 20-100% EtOAc/heptane) gave the title compound (0.561 g, 84%) as a yellow oil.

1H-NMR (CDCl₃, 500 MHz) d[ppm]=8.37-8.34 (m, 1H), 7.39-7.34 (m, 1H), 7.24-7.19 (m, 1H), 5.99 (br s, 1H), 4.69-4.56 (m, 3H), 4.00-3.93 (m, 1H), 3.93-3.86 (m, 1H), 3.29-3.19 (m, 1H), 3.19-3.11 (m, 1H), 2.91-2.83 (m, 1H), 2.57 (dd, J=13.1, 10.2 Hz, 1H), 1.90-1.83 (m, 1H), 1.72-1.65 (m, 1H), 1.58-1.53 (m, 1H), 1.52-1.35 (m, 3H), 1.42 (s, 9H), 1.19-1.09 (m, 1H)

HPLCMS (Method A): [m/z]: 381.15 [M+H]⁺

3-(2-aminoethyl)-N-[(3-fluoropyridin-2-yl)methyl]piperidine-1-carboxamide Dihydrochloride (431)

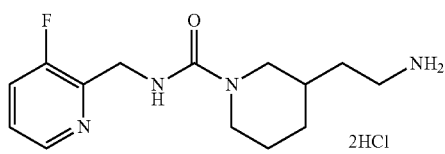 [SMILES: NCCC1CCCN(C(=O)NCc2ncccc2F)C1]

In a similar fashion to general procedure 2, tert-butyl N-[2-(1-{[(3-fluoropyridin-2-yl)methyl]carbamoyl}piperidin-3-yl)ethyl]carbamate (430) (0.561 g, 1.37 mmol) and 4M HCl/1,4-dioxane (15 ml) in DCM (15 ml) was stirred at room temperature for 20 h to give the title compound (0.664 g) as a yellow solid. Product will be used in the next step without purification.

HPLCMS (Method F): [m/z]: 281.3 [M+H]⁺

3-(2-{[2-(1H-1,3-Benzodiazol-2-yl)ethyl]amino}ethyl)-N-[(3-fluoropyridin-2-yl)methyl]piperidine-1-carboxamide (Example Compound No. 200)

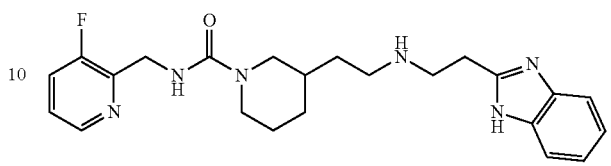

In a similar fashion to general procedure 8, 3-(2-aminoethyl)-N-[(3-fluoropyridin-2-yl)methyl]piperidine-1-carboxamide dihydrochloride (431) (200 mg, 0.42 mmol, 74% purity), N-(2-nitrophenyl)prop-2-enamide (D) (161 mg, 0.84 mmol) and DBU (187 µl, 1.26 mmol) in MeCN (6 ml) at room temperature for 6 h, gave an intermediate which was further reacted with iron powder (170 mg) in AcOH (3 ml) at 70° C. for 4 h to give the title compound (34 mg, 19%) as a colourless oil after purification by SCX-2 column (eluting with a gradient of 100% DCM, MeOH/DCM (50:50), 100% MeOH and 7N NH₃/MeOH) followed by basic prep-HPLC and a final purification by flash column chromatography (eluting with a gradient of 10-50% MeOH/DCM).

1H-NMR (DMSO-d6, 500 MHz): d[ppm]=8.41-8.30 (m, 1H), 7.67-7.56 (m, 1H), 7.50-7.39 (m, 2H), 7.38-7.29 (m, 1H), 7.14-7.05 (m, 2H), 6.90 (t, J=5.5 Hz, 1H), 4.46-4.29 (m, 2H), 3.91-3.73 (m, 2H), 2.99-2.87 (m, 4H), 2.72-2.64 (m, 1H), 2.59 (t, J=7.2 Hz, 2H), 2.42-2.35 (m, 1H), 1.82-1.69 (m, 1H), 1.59-1.47 (m, 1H), 1.47-1.38 (m, 1H), 1.39-1.20 (m, 3H), 1.11-0.98 (m, 1H)

HPLCMS (Method D): [m/z]: 425.2 [M+H]⁺

General Scheme 39 Above

Tert-butyl(S)-3-{[(3-fluoropyridin-2-yl)methyl]carbamoyl}pyrrolidine-1-carboxylate (432)

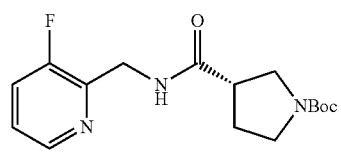 [SMILES: CC(C)(C)OC(=O)N1CC[C@H](C(=O)NCc2ncccc2F)C1]

In a similar fashion to general procedure 6, (3S)-1-[(tert-butoxy)carbonyl]pyrrolidine-3-carboxylic (1 g, 4.69 mmol), (3-fluoropyridin-2-yl)methanamine dihydrochloride (A2) (1.4 g, 7.03 mmol), HATU (2.7 g, 7.03 mmol) and DIPEA (3.3 ml, 18.76 mmol in DMF (25 ml) at room temperature for 16 h, gave title compound (1.5 g, 99%) as a yellow oil after purification by flash column chromatography (eluting with a gradient of 2-6% MeOH/DCM).

1H-NMR (CDCl₃, 250 MHz): d[ppm]=8.39-8.31 (m, 1H), 7.44-7.35 (m, 1H), 7.31-7.21 (m, 1H), 7.01 (s, 1H), 4.64 (dd, J=4.5, 1.5 Hz, 2H), 3.70-3.47 (m, 2H), 3.53 (dd, J=10.9, 8.0 Hz, 1H), 3.35 (app q, J=9.4, 8.6 Hz, 1H), 3.05-2.92 (m, 1H), 2.29-2.07 (m, 2H), 1.45 (s, 9H)

HPLCMS (Method A): [m/z]: 324.05 [M+H]⁺

Tert-butyl (3R)-3-{[(3-fluoropyridin-2-yl)methyl]carbamoyl}pyrrolidine-1-carboxylate (433)

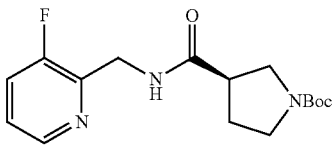 [SMILES: CC(C)(C)OC(=O)N1CC[C@@H](C(=O)NCc2ncccc2F)C1]

In a similar fashion to general procedure 6, (3R)-1-[(tert-butoxy)carbonyl]pyrrolidine-3-carboxylic acid (1 g, 4.69 mmol), (3-fluoropyridin-2-yl)methanamine dihydrochloride (A2) (1.4 g, 7.03 mmol), HATU (2.7 g, 7.03 mmol) and DIPEA (3.3 ml, 18.76 mmol) in DMF (25 ml) at room temperature for 3 h gave the title compound (1.5 g, 96%) as a yellow oil after purification by flash column chromatography (eluting with a gradient of 0-5% MeOH/DCM).

1H-NMR (CDCl$_3$, 250 MHz): d[ppm]=8.38-8.31 (m, 1H), 7.44-7.34 (m, 1H), 7.33-7.22 (m, 1H), 7.06 (s, 1H), 4.63 (dd, J=4.5, 1.5 Hz, 2H), 3.79-3.57 (m, 2H), 3.52 (dd, J=10.9, 7.9 Hz, 1H), 3.45-3.27 (m, 1H), 3.25-3.11 (m, 1H), 2.27-2.09 (m, 2H), 1.45 (s, 9H)

HPLCMS (Method A): [m/z]: 324.10 [M+H]$^+$

(3S)—N-[(3-Fluoropyridin-2-yl)methyl]pyrrolidine-3-carboxamide Dihydrochloride (434)

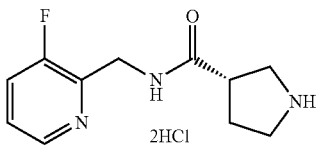 [SMILES: O=C(NCc1ncccc1F)[C@H]1CCNC1]

In a similar fashion to general procedure 2, tert-butyl (3S)-3-{[(3-fluoropyridin-2-yl)methyl]carbamoyl}pyrrolidine-1-carboxylate (432) (1.5 g, 4.64 mmol) and 4M HCl/dioxane (17 ml) in MeOH (5 ml) at room temperature for 2 h gave the title compound (1.38 g) as a yellow foam.

1H-NMR (DMSO-d6, 250 MHz): d[ppm]=9.58 (br s, 1H), 9.26 (br s, 1H), 8.78 (t, J=5.4 Hz, 1H), 8.45-8.37 (m, 1H), 7.86-7.69 (m, 1H), 7.54-7.36 (m, 1H), 4.51-4.47 (m, 2H), 3.39-3.26 (m, 1H), 3.25-3.07 (m, 4H), 2.27-2.04 (m, 1H), 2.04-1.84 (m, 1H)

HPLCMS (Method A): [m/z]: 224.0 [M+H]$^+$

(3R)—N-[(3-fluoropyridin-2-yl)methyl]pyrrolidine-3-carboxamide Dihydrochloride (435)

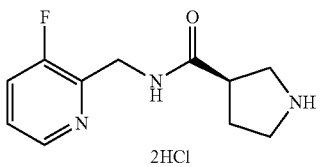 [SMILES: O=C(NCc1ncccc1F)[C@@H]1CCNC1]

In a similar fashion to general procedure 2, tert-butyl (3R)-3-{[(3-fluoropyridin-2-yl)methyl]carbamoyl}pyrrolidine-1-carboxylate (433) (1.5 g, 4.64 mmol) and 4M HCl/dioxane (17 ml) in MeOH (5 ml) at room temperature for 2 h gave the title compound (1.4 g, 92%) as a yellow foam.

1H-NMR (DMSO-d6, 500 MHz): d[ppm]=9.44 (br s, 1H), 9.16 (br s, 1H), 8.78-8.70 (m, 1H), 8.41-8.38 (m, 1H), 7.76-7.71 (m, 1H), 7.47-7.42 (m, 1H), 4.58 (dd, J=5.9, 1.5 Hz, 2H), 3.34-3.28 (m, 1H), 3.17-3.08 (m, 4H), 2.18-2.09 (m, 1H), 2.01-1.85 (m, 1H)

HPLCMS (Method A): [m/z]: 223.95 [M+H]$^+$

(3S)-1-(Cyanomethyl)-N-[(3-fluoropyridin-2-yl)methyl]pyrrolidine-3-carboxamide (436)

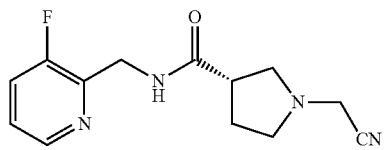 [SMILES: N#CCN1CC[C@H](C(=O)NCc2ncccc2F)C1]

Bromoacetonitrile (322 μl, 4.63 mmol) was added to a solution of (3S)—N-[(3-fluoropyridin-2-yl)methyl]pyrrolidine-3-carboxamide dihydrochloride (434) (1.37 g, 4.63 mmol) and K$_2$CO$_3$ (1.92 g, 13.9 mmol) in DMF (40 ml) and the reaction mixture heated at 60° C. for 2 h. The reaction was cooled to room temperature and the solvent evaporated to dryness. The residue was dissolved in EtOAc (50 ml) and washed with saturated K$_2$CO$_3$ (aq) (20 ml), brine (20 ml), dried (Na$_2$SO$_4$), filtered and the solvent evaporated to give a residue which was purified by flash column chromatography (eluting with a gradient of 2-6% MeOH/DCM) to give the title compound (0.76 g, 63%) as pale yellow solid.

1H-NMR (CDCl$_3$, 500 MHz): d[ppm]=8.37-8.33 (m, 1H), 7.41-7.37 (m, 1H), 7.28-7.23 (m, 1H), 4.67-4.58 (m, 2H), 3.70 (s, 2H), 3.08-3.00 (m, 2H), 2.97-2.90 (m, 1H), 2.90-2.83 (m, 1H), 2.71 (app q, J=8.3 Hz, 1H), 2.28-2.14 (m, 2H)

HPLCMS (Method A): [m/z]: 263.05 [M+H]$^+$

(3R)-1-(cyanomethyl)-N-[(3-fluoropyridin-2-yl)methyl]pyrrolidine-3-carboxamide (437)

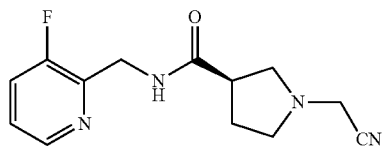 [SMILES: N#CCN1CC[C@@H](C(=O)NCc2ncccc2F)C1]

Bromoacetonitrile (322 μl, 4.63 mmol) was added to a solution of (3S)—N-[(3-fluoropyridin-2-yl)methyl]pyrrolidine-3-carboxamide dihydrochloride (435) (1.37 g, 4.63 mmol, 90% purity) and K$_2$CO$_3$ (1.92 g, 13.9 mmol) in DMF (40 ml) and the reaction mixture heated at 60° C. for 2 h. The reaction was cooled to room temperature and the solvent evaporated to dryness. The residue was dissolved in EtOAc (50 ml) and washed with saturated K$_2$CO$_3$ (aq) (20 ml), brine (20 ml), dried (Na$_2$SO$_4$), filtered and the solvent evaporated to give a residue which was purified by flash column chromatography (eluting with a gradient of 2-6% MeOH/DCM) to give the title compound (0.49 g, 41%) as pale yellow solid.

1H-NMR (CDCl₃, 500 MHz): d[ppm]=8.38-8.31 (m, 1H), 7.42-7.36 (m, 1H), 7.28-7.22 (m, 3H), 4.68-4.58 (m, 2H), 3.70 (s, 2H), 3.07-3.01 (m, 2H), 2.94 (td, J=8.6, 5.0 Hz, 1H), 2.89-2.83 (m, 1H), 2.75-2.68 (m, 1H), 2.29-2.14 (m, 2H)

HPLCMS (Method A): [m/z]: 263.00 [M+H]⁺

(3S)-1-(2-Aminoethyl)-N-[(3-fluoropyridin-2-yl)methyl]pyrrolidine-3-carboxamide (438)

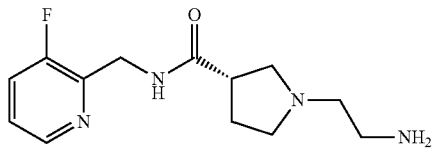 [SMILES: NCCN1CC[C@H](C(=O)NCc2ncccc2F)C1]

In a round bottomed flask Raney Nickel (1.7 g, 14.5 mmol, 50% purity) was washed twice with EtOH (2×5 ml) and decanted to remove excess water. EtOH (10 ml) was added under a nitrogen atmosphere followed by a solution of (3S)-1-(cyanomethyl)-N-[(3-fluoropyridin-2-yl)methyl]pyrrolidine-3-carboxamide (436) (0.38 g, 1.45 mmol) in EtOH (10 ml). The reaction mixture was left stirring at room temperature for 3 h. The mixture was filtered through Celite and the residue washed with MeOH (20 ml). The filtrate was concentrated under reduced pressure to give the title compound (0.31 g, 72%) as a colourless solid. The product was used in the next step without purification.

1H-NMR (MeOD, 500 MHz): d[ppm]=8.40-8.29 (m, 1H), 7.58 (t, J=9.1 Hz, 1H), 7.45-7.29 (m, 1H), 4.57 (s, 2H), 3.14-2.80 (m, 3H), 2.81-2.46 (m, 5H), 2.19-1.96 (m, 2H)

HPLCMS (Method A): [m/z]: 267.05 [M+H]⁺

(3R)-1-(2-aminoethyl)-N-[(3-fluoropyridin-2-yl)methyl]pyrrolidine-3-carboxamide (439)

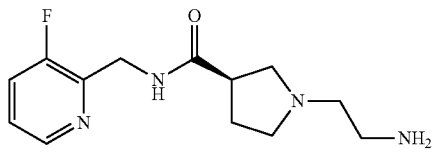 [SMILES: NCCN1CC[C@@H](C(=O)NCc2ncccc2F)C1]

In a round bottomed flask, Raney Nickel (2.21 g, 18.8 mmol, 50% purity) was washed twice with EtOH (2×5 ml) and decanted to remove excess water. EtOH (10 ml) was added and under a nitrogen atmosphere followed by a solution of ((3R)-1-(cyanomethyl)-N-[(3-fluoropyridin-2-yl)methyl]pyrrolidine-3-carboxamide (437) (0.49 g, 1.88 mmol) in EtOH (20 ml). The reaction mixture was left stirring at room temperature for 3 h. The mixture was filtered through Celite and the residue washed with MeOH (30 ml) The filtrate was concentrated under reduced pressure to give the title compound (0.4 g, 72%) as a colourless oil. The product was used in the next step without purification.

HPLCMS (Method A): [m/z]: 267.05 [M+H]⁺

(3S)-1-{2-[(1H-1,3-benzodiazol-2-ylmethyl)amino]ethyl}-N-[(3-fluoropyridin-2-yl)methyl]pyrrolidine-3-carboxamide (Example Compound No. 202)

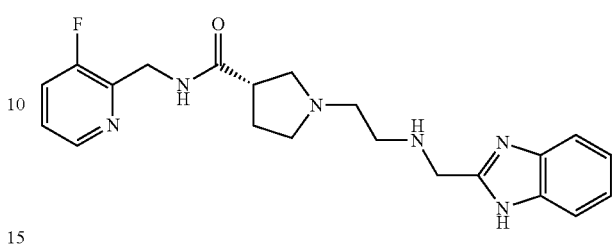

In a similar fashion using general procedure 3, (3S)-1-(2-aminoethyl)-N-[(3-fluoropyridin-2-yl)methyl]pyrrolidine-3-carboxamide (438) (150 mg, 0.56 mmol), 1H-1,3-benzodiazole-2-carbaldehyde (82 mg, 0.56 mmol) and DIPEA (196 µl, 1.13 mmol) in MeCN (10 ml) at room temperature for 16 h, followed by the addition NaBH₄ (31 mg, 0.81 mmol) gave the title compound (47 mg, 21%) as a pale yellow film after purification by basic prep-HPLC.

1H-NMR (MeOD, 500 MHz): d[ppm]=8.31-8.26 (m, 1H), 7.54-7.48 (m, 3H), 7.32-7.27 (m, 1H), 7.23-7.17 (m, 2H), 4.55 (d, J=1.5 Hz, 2H), 4.03 (s, 2H), 3.05-2.97 (m, 1H), 2.83-2.76 (m, 3H), 2.75-2.60 (m, 5H), 2.15-2.06 (m, 1H), 2.06-1.97 (m, 1H)

HPLCMS (Method C): [m/z]: 397.2 [M+H]+

(3R)-1-{2-[(1H-1,3-benzodiazol-2-ylmethyl)amino]ethyl}-N-[(3-fluoropyridin-2-yl)methyl]pyrrolidine-3-carboxamide (Example Compound No. 204)

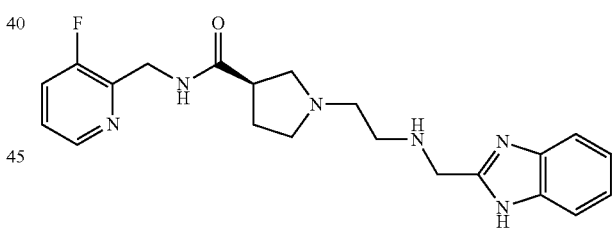

In a similar fashion using general procedure 3, (3R)-1-(2-aminoethyl)-N-[(3-fluoropyridin-2-yl)methyl]pyrrolidine-3-carboxamide (439) (200 mg, 0.75 mmol), 1H-1,3-benzodiazole-2-carbaldehyde (110 mg, 0.75 mmol) and DIPEA (262 µl, 1.50 mmol) in MeCN (10 ml) at room temperature 16 h, followed by the addition NaBH₄ (42 mg, 1.13 mmol) gave the title compound (69 mg, 23%) as a pale yellow film after purification by basic prep-HPLC.

1H-NMR (MeOD, 500 MHz): d[ppm]=8.29-8.27 (m, 1H), 7.55-7.48 (m, 3H), 7.32-7.28 (m, 1H), 7.23-7.17 (m, 2H), 4.55 (d, J=1.6 Hz, 2H), 4.03 (s, 2H), 3.07-2.95 (m, 1H), 2.84-2.76 (m, 3H), 2.74 (dd, J=9.5, 6.4 Hz, 1H), 2.71-2.60 (m, 4H), 2.15-2.06 (m, 1H), 2.06-1.97 (m, 1H)

HPLCMS (Method C): [m/z]: 397.2 [M+H]⁺

General Scheme 1 Above:

Tert-butyl N-(1H-1,3-benzodiazol-2-ylmethyl)-N-[2-(4-carbamoyl-1,3-thiazol-2-yl)ethyl]carbamate (440)

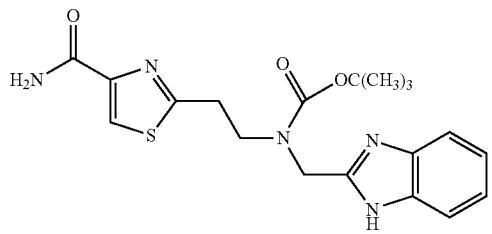

7M ammonia (10 ml) was added to a solution of ethyl 2-{2-[(1H-1,3-benzodiazol-2-ylmethyl)[(tert-butoxy)carbonyl]amino]ethyl}-1,3-thiazole-4-carboxylate (250 mg, 0.58 mmol) in MeOH (5 ml) and the reaction mixture stirred at 80° C. for 16 h. The solvent was removed under reduced pressure to give the title compound (190 mg, 58% purity. The compound was used in the next step without further purification.

HPLCMS (Method H): [m/z]: 402.4 [M+H]$^+$

N-(1H-1,3-Benzodiazol-2-ylmethyl)-N-[2-(4-{[(3-methylpyridin-2-yl)methyl]carbamoyl}-1,3-thiazol-2-yl)ethyl]carbamate (441)

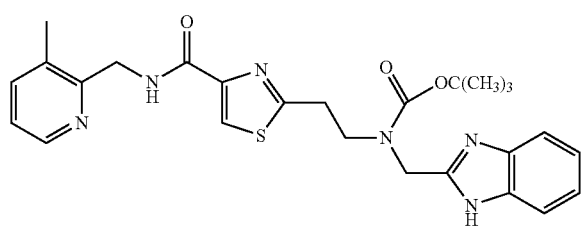

In a similar fashion to general procedure 6, 2-{2-[(1H-1,3-benzodiazol-2-ylmethyl)[(tert-butoxy)carbonyl]amino]ethyl}-1,3-thiazole-4-carboxylic acid (8) (2.75 g, 6.49 mmol), 1-(3-methylpyridin-2-yl)methanamine (1.19 g, 9.74 mmol), DIPEA (3.39 ml, 19.47 mmol) and HATU (4.94 g, 12.98 mmol) in DMF (50 ml) for 16 h, gave the title compound (1.7 g, 51%) as an yellow foam after purification by flash column chromatography (Kp-NH, eluting with a gradient of 20-100% EtOAc/heptane) followed by azeotroping with heptane.

1H-NMR (MeOD, 250 MHz): d[ppm]=8.32 (d, J=4.4 Hz, 1H), 8.09 (s, 1H), 7.63 (d, J=7.6 Hz, 1H), 7.53 (s, 2H), 7.30-7.14 (m, 3H), 4.74 (s, 2H), 4.69 (s, 2H), 3.86 (s, 2H), 3.34 (s, 3H), 2.40 (s, 3H), 1.40 (s, 10H)

HPLCMS (Method C): [m/z]: 507.1 [M+H]$^+$

2-{2-[(1H-1,3-Benzodiazol-2-ylmethyl)amino]ethyl}-1,3-thiazole-4-carboxamide (Example Compound No. 23)

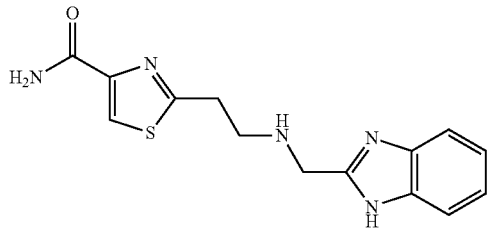 [SMILES: NC(=O)c1csc(CCNCc2nc3ccccc3[nH]2)n1]

In a similar fashion to general procedure 2, tert-butyl N-(1H-1,3-benzodiazol-2-ylmethyl)-N-[2-(4-carbamoyl-1,3-thiazol-2-yl)ethyl]carbamate (440) (190 mg, 0.473 mmol) and HCl/dioxane (5 ml) at room temperature for 3 h gave the title compound (70 mg, 45%) as an yellow oil after purification by flash column chromatography.

1H-NMR (MeOD, 300 MHz): d[ppm]=7.92 (s, 1H), 7.40-7.36 (m, 2H), 7.08-7.04 (m, 2H), 3.93 (s, 2H), 3.19-3.15 (m, 1H), 3.07 (t, J=6.4 Hz, 2H), 2.94 (t, J=6.4 Hz, 2H)

2-{2-[(1H-1,3-Benzodiazol-2-ylmethyl)amino]ethyl}-N-[(3-methylpyridin-2-yl)methyl]-1,3-thiazole-4-carboxamide Trihydrochloride (Example Compound No. 55)

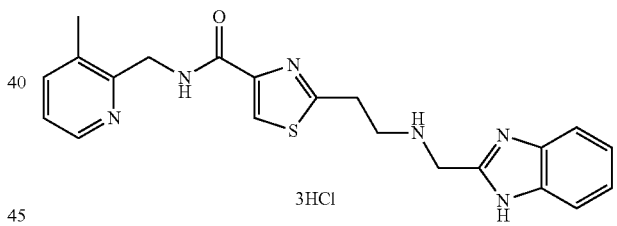

In a similar fashion to general procedure 2, tert-butyl N-(1H-1,3-benzodiazol-2-ylmethyl)-N-[2-(4-{[(3-methylpyridin-2-yl)methyl]carbamoyl}-1,3-thiazol-2-yl)ethyl]carbamate (441) (1.7 g, 3.36 mmol) and 4M HCl/dioxane (8.4 ml) in dioxane (30 ml) at room temperature for 16 h gave the title compound (1.09 g, 63%) as a white solid after trituration from Et$_2$O (2×30 ml), DCM (2×20 ml) and Et$_2$O (2×30 ml) followed by recrystalisation from DCM/MeOH and Heptane.

1H-NMR (DMSO-d6, 500 MHz): d[ppm]=10.29 (s, 1H), 9.56 (t, J=5.6 Hz, 1H), 8.64-8.57 (m, 1H), 8.37 (d, J=7.7 Hz, 1H), 8.29 (s, 1H), 7.85 (dd, J=7.8, 5.8 Hz, 1H), 7.73 (dt, J=6.6, 3.3 Hz, 2H), 7.41 (dt, J=6.1, 3.3 Hz, 2H), 4.85 (d, J=5.7 Hz, 3H), 4.74 (s, 2H), 3.64 (dt, J=35.5, 7.0 Hz, 5H), 2.50 (s, 3H)

HPLCMS (Method C): [m/z]: 407.05 [M+H]$^+$

547

Tert-butyl N-{2-[4-(piperidine-1-carbonyl)-1,3-thiazol-2-yl]ethyl}carbamate (442)

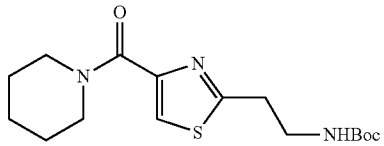 [SMILES: CC(C)(C)OC(=O)NCCc1nc(C(=O)N2CCCCC2)cs1]

T3P (1.75 g, 2.75 mmol, 50% purity) was added to a solution of 2-(2-{[(tert-butoxy)carbonyl]amino}ethyl)-1,3-thiazole-4-carboxylic acid (87) (0.50 g, 1.84 mmol) in DCM (7 ml) at room temperature under argon. DIPEA (0.48 g, 3.67 mmol) and piperidine (0.16 g, 1.84 mmol) were then added dropwise. The reaction mixture was left stirring overnight. The solvent was then removed in vacuum and the residue diluted with saturated sodium bicarbonate (5 ml) and EtOAc (10 ml). The organic layer was separated, wash with saturated $KHSO_4$ (5 ml), water (5 ml) and dried ($Na_2SO_4$). The solvent was evaporated to afford the crude product. Purification by flash column chromatography (eluting with a gradient of MeOH/DCM) afforded the title compound (610 mg, 98%) as a white solid.

HPLCMS (Method H): [m/z]: 240.4 [M-Boc+H]$^+$

2-[4-(Piperidine-1-carbonyl)-1,3-thiazol-2-yl]ethan-1-amine (443)

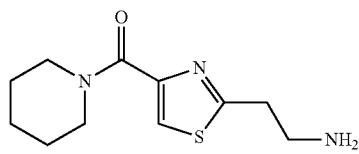 [SMILES: NCCc1nc(C(=O)N2CCCCC2)cs1]

Tert-butyl N-{2-[4-(piperidine-1-carbonyl)-1,3-thiazol-2-yl]ethyl}carbamate (442) (418 mg, 1.42 mmol) was dissolved in a solution of TFA:DCM (1:1) (10 ml). The reaction mixture was stirred at room temperature overnight. The solvent was evaporated to dryness to afford a sticky solid. Saturated $NaHCO_3$ (5 ml) was added and the mixture was extracted with 15% of IPA/EtOAc (3×10 ml). The combined organic layers were separated, dried ($Na_2SO_4$) and concentrated under reduced pressure until dryness to afford the title compound (328 mg, 97%) as a pale yellow oil. The crude product was used in the next step without purification.

1H-NMR (CDCl$_3$, 400 MHz): d[ppm]=8.61 (s, 2H), 7.55 (s, 1H), 3.61 (d, J=47.7 Hz, 3H), 3.46 (dd, J=9.3, 4.3 Hz, 3H), 1.69 (s, 8H)

HPLCMS (Method H): [m/z]: 240.4 [M+H]$^+$

548

Tert-butyl 2-[({2-[4-(piperidine-1-carbonyl)-1,3-thiazol-2-yl]ethyl}amino)methyl]-1H-1,3-benzodiazole-1-carboxylate (444)

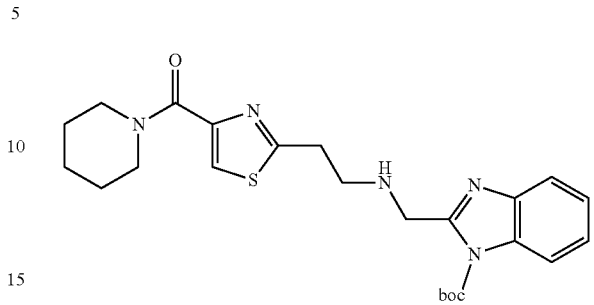

To a solution of 2-[4-(piperidine-1-carbonyl)-1,3-thiazol-2-yl]ethan-1-amine (443) (100 mg, 0.428 mmol) in DMF (2 ml) was added $Et_3N$ (58 µl, 0.418 mmol) under argon at room temperature. Tert-butyl 2-(chloromethyl)-1H-1,3-benzodiazole-1-carboxylate (L) (56 mg, 0.209 mmol) in DMF (1 ml) was added dropwise and the reaction mixture was stirred for 4 h. The solvent was removed under vacuum and the crude mixture diluted with EtOAc (5 ml) and water (5 ml). The organic layer was separated, dried ($Na_2SO_4$) and evaporated under reduced pressure to give the crude title compound (190 mg, 28% purity) as a off white oil.

HPLCMS (Method H): [m/z]: 470.6 [M+H]$^+$, 370.5 [M-Boc+H]$^+$ (1H-1,3-Benzodiazol-2-ylmethyl)({2-[4-(piperidine-1-carbonyl)-1,3-thiazol-2-yl]ethyl})amine (Example Compound No. 14)

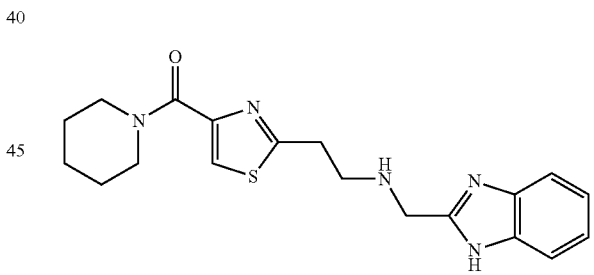

A solution of tert-butyl 2-[({2-[4-(piperidine-1-carbonyl)-1,3-thiazol-2-yl]ethyl}amino)methyl]-1H-1,3-benzodiazole-1-carboxylate (444) (190 mg) in TFA/DCM (1:1) (6 ml) was stirred at 0° C. to room temperature overnight. The solvent was evaporated under reduced pressure and basified with saturated ethanolic ammonia (5 ml). Purification by flash column chromatography (eluting with a gradient of 5-7% MeOH/DCM) afforded the title compound (14 mg, 9%) as an off white oil.

1H-NMR (CDCl$_3$, 400 MHz): d[ppm]=7.59-7.57 (m, 2H), 7.56 (s, 1H), 7.24-7.17 (m, 2H), 4.15 (s, 2H), 3.80-3.51 (m, 4H), 3.22-3.20 (m, 2H), 3.14-3.12 (m, 2H), 1.60 (m, 6H)

HPLCMS (Method H): [m/z]: 370.5 [M+H]$^+$

General Scheme 41 Above:

Tert-butyl 3-[(pyridin-2-ylmethyl)carbamoyl]-4H,
5H,6H,7H-thieno[2,3-c]pyridine-6-carboxylate
(449)

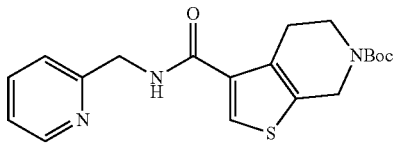 [SMILES: CC(C)(C)OC(=O)N1CCc2c(C(=O)NCc3ccccn3)csc2C1]

In a similar fashion to general procedure 6, 6-(tert-butoxycarbonyl)-4,5,6,7-tetrahydrothieno[2,3-c]pyridine-3-carboxylic acid (220 mg, 0.77 mmol), 1-(pyridin-2-yl)methanamine (88 μl, 0.85 mmol), DIPEA (407 μl, 2.33 mmol) and HATU (443 mg, 1.17 mmol) in DCM (12 ml) at room temperature for 1 h gave the title compound (466 mg) as a yellow oil after purification by flash column chromatography (eluting with a gradient 50-100% EtOAc/heptane).

1H-NMR (CDCl$_3$, 500 MHz): d[ppm]=8.55 (d, J=4.8 Hz, 1H), 7.68 (td, J=7.7, 1.8 Hz, 1H), 7.64 (s, 1H), 7.31 (d, J=7.8 Hz, 1H), 7.22 (dd, J=7.2, 5.2 Hz, 1H), 4.70 (d, J=4.8 Hz, 2H), 4.62 (s, 2H), 3.76-3.61 (m, 2H), 2.99 (s, 2H), 1.48 (s, 9H), 1.44 (d, J=6.6 Hz, 1H)

HPLCMS (Method E): [m/z]: 374.05 [M+H]$^+$

N-(pyridin-2-ylmethyl)-4H,5H,6H,7H-thieno[2,3-c]
pyridine-3-carboxamide (450)

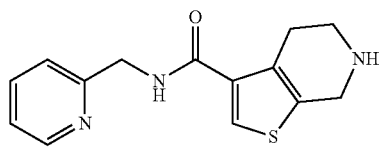 [SMILES: O=C(NCc1ccccn1)c1csc2c1CCNC2]

In a similar fashion to general procedure 2, tert-butyl 3-[(pyridin-2-ylmethyl)carbamoyl]-4H,5H,6H,7H-thieno[2,3-c]pyridine-6-carboxylate (449) (466 mg, 1.09 mmol) and TFA (940 μl) in DCM (5 ml) at room temperature for 16 h gave the title compound (130 mg, 44%) as an yellow oil. The compound was used in the next step without purification.

1H-NMR (MeOD, 500 MHz): d[ppm]=8.49 (d, J=4.3 Hz, 1H), 7.92 (s, 1H), 7.82 (td, J=7.7, 1.8 Hz, 1H), 7.43 (d, J=7.9 Hz, 1H), 7.37-7.27 (m, 1H), 4.59 (s, 2H), 4.16 (s, 2H), 3.21 (t, J=6.0 Hz, 2H), 3.01 (t, J=6.0 Hz, 2H)

HPLCMS (Method E): [m/z]: 273.95 [M+H]$^+$ 6-(1H-1,3-Benzodiazol-2-ylmethyl)-N-(pyridin-2-ylmethyl)-4H,5H,6H,7H-thieno[2,3-c]pyridine-3-carboxamide (Example Compound No. 48)

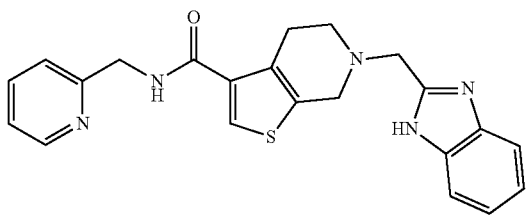 [SMILES: O=C(NCc1ccccn1)c1csc2c1CCN(Cc1nc3ccccc3[nH]1)C2]

In a similar fashion to general procedure 7, N-(pyridin-2-ylmethyl)-4H,5H,6H,7H-thieno[2,3-c]pyridine-3-carboxamide (450) (65 mg, 0.24 mmol), K$_2$CO$_3$ (49 mg, 0.36 mmol) and 2-(chloromethyl)-1H-benzimidazole (44 mg, 0.26 mmol) in acetone (3 ml) at room temperature for 72 h, gave the title compound (25 mg, 26%) as a pale yellow solid after purification flash column chromatography (kp-NH, eluting with a gradient of 0-10% MeOH/DCM) followed by basic prep-HPLC.

1H-NMR (DMSO-d6, 500 MHz): d[ppm]=12.36 (s, 1H), 8.78 (t, J=6.0 Hz, 1H), 8.50 (d, J=4.7 Hz, 1H), 7.95 (s, 1H), 7.76 (td, J=7.7, 1.7 Hz, 1H), 7.49 (s, 2H), 7.31 (d, J=7.8 Hz, 1H), 7.29-7.23 (m, 1H), 7.14 (dd, J=5.9, 3.1 Hz, 2H), 4.49 (d, J=6.0 Hz, 2H), 3.93 (s, 2H), 3.73 (s, 2H), 2.89 (d, J=5.5 Hz, 2H), 2.79 (t, J=5.7 Hz, 2H)

HPLCMS (Method D): [m/z]: 404.2 [M+H]$^+$

6-[2-(1H-1,3-Benzodiazol-2-yl)ethyl]-N-(pyridin-2-ylmethyl)-4H,5H,6H,7H-thieno[2,3-c]pyridine-3-carboxamide (Example Compound No. 49)

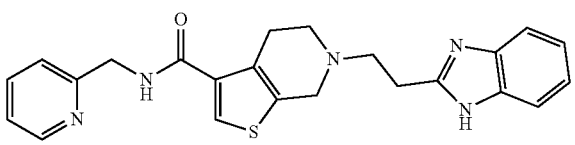 [SMILES: O=C(NCc1ccccn1)c1csc2c1CCN(CCc1nc3ccccc3[nH]1)C2]

In a similar fashion to general procedure 7, N-(pyridin-2-ylmethyl)-4H,5H,6H,7H-thieno[2,3-c]pyridine-3-carboxamide (450) (65 mg, 0.24 mmol), K$_2$CO$_3$ (49 mg, 0.36 mmol) and 2-(2-chloroethyl)-1H-benzimidazole (47 mg, 0.26 mmol) in acetone (3 ml) at room temperature for 24 h, followed by the addition of DMF (5 ml), NaI (39 mg, 0.26 mmol), DIPEA (0.16 ml, 0.95 mmol) and 2-(2-chloroethyl)-1H-benzimidazole (94 mg, 0.52 mmol) at room temperature for 72 h, gave the title compound (9 mg, 9%) as an orange solid after purification by basic prep-HPLC.

1H-NMR (DMSO-d6, 500 MHz): d[ppm]=12.17 (s, 1H), 8.75 (t, J=6.0 Hz, 1H), 8.50 (d, J=4.2 Hz, 1H), 7.94 (s, 1H), 7.75 (td, J=7.7, 1.8 Hz, 1H), 7.46 (s, 2H), 7.31 (d, J=7.8 Hz, 1H), 7.28-7.23 (m, 1H), 7.10 (dd, J=6.0, 3.1 Hz, 2H), 4.48 (d, J=6.0 Hz, 2H), 3.71 (s, 2H), 3.05 (t, J=7.2 Hz, 2H), 2.96 (t, J=7.2 Hz, 2H), 2.82 (d, J=5.3 Hz, 2H), 2.75 (t, J=5.7 Hz, 2H)

HPLCMS (Method B): [m/z]: 418.2 [M+H]$^+$

General Scheme 42 Above:

2-{2-[N-(1H-1,3-benzodiazol-2-ylmethyl)-2-bromoacetamido]ethyl}-N-[(3-fluoropyridin-2-yl)methyl]-1,3-thiazole-4-carboxamide (451)

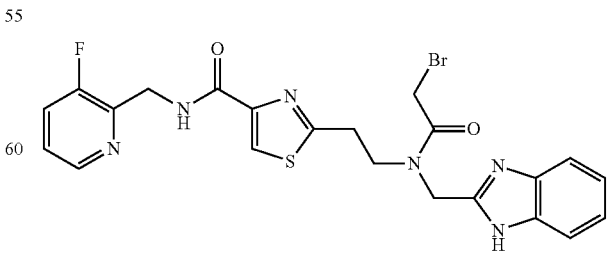

2-{2-[(1H-1,3-benzodiazol-2-ylmethyl)amino]ethyl}-N-[(3-fluoropyridin-2-yl)methyl]-1,3-thiazole-4-carboxamide (Example Compound No. 40) (150 mg, 0.37 mmol) and TEA (127 µl, 0.91 mmol) were dissolved in DCM (10 ml) and bromoacetyl chloride (61 µl, 0.73 mmol) was added dropwise. The mixture was stirred at room temperature for 15 mins, then quenched with saturated NaHCO$_3$ (aq) (20 ml) and extracted with DCM (3×30 ml) and 4:1 chloroform/IPA (30 ml). The combined organic extracts were dried (Na$_2$SO$_4$) and evaporated in vacuo. Purification by flash column chromatography (eluting with a gradient of 0-5% MeOH/DCM) afforded the title compound (224 mg, 82% purity) as a brown residue. Compound was used in the next step without further purification.

HPLCMS (Method M): [m/z]: 530.85/532.85 [M+H]$^+$

N-[(3-fluoropyridin-2-yl)methyl]-2-(2-{12-oxo-1,8,11-triazatricyclo[7.4.0.0$^{2,7}$]trideca-2(7),3,5,8-tetraen-11-yl}ethyl)-1,3-thiazole-4-carboxamide (Example Compound No. 275)

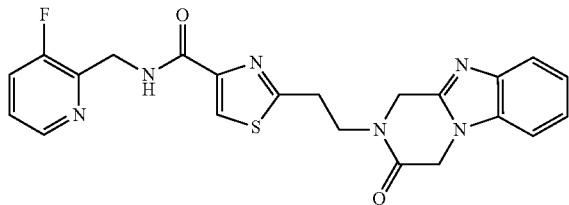 [SMILES: O=C(NCc1ncccc1F)c1csc(CCN2Cc3nc4ccccc4n3CC2=O)n1]

2-{2-[N-(1H-1,3-benzodiazol-2-ylmethyl)-2-bromoacetamido]ethyl}-N-[(3-fluoropyridin-2-yl)methyl]-1,3-thiazole-4-carboxamide (451) (220 mg, 0.41 mmol, 82% purity) was dissolved in THF (10 ml) and NaH (60%, 50 mg, 1.24 mmol) was added. The mixture was stirred at room temperature for 10 mins. The reaction was quenched with saturated NaHCO$_3$ (aq) (20 ml) and extracted with DCM (3×20 ml) and 4:1 chloroform/IPA (20 ml). The combined organic extracts were dried (Na$_2$SO$_4$) and evaporated in vacuo. Purification by basic prep-HPLC afforded the title compound (15 mg, 8%) as an off-white solid.

1H-NMR (DMSO-d6, 500 MHz): d[ppm]=8.65 (t, J=5.6 Hz, 1H), 8.36-8.32 (m, 1H), 8.18 (s, 1H), 7.71-7.64 (m, 1H), 7.61 (dt, J=5.4, 3.4 Hz, 1H), 7.56-7.51 (m, 1H), 7.40-7.34 (m, 1H), 7.26-7.21 (m, 2H), 4.91 (s, 2H), 4.88 (s, 2H), 4.63-4.57 (m, 2H), 3.93 (t, J=7.2 Hz, 2H), 3.42 (t, J=7.2 Hz, 2H)

HPLCMS (Method B): [m/z]: 451.2 [M+H]$^+$

N-[(3-fluoropyridin-2-yl)methyl]-2-(2-{1,8,11-triazatricyclo[7.4.0.0$^{2,7}$]trideca-2(7),3,5,8-tetraen-11-yl}ethyl)-1,3-thiazole-4-carboxamide (Example Compound No. 276)

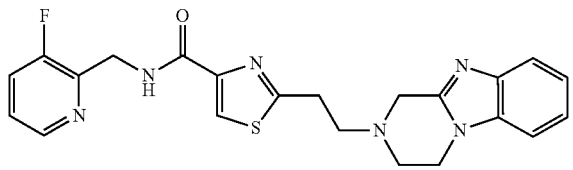 [SMILES: O=C(NCc1ncccc1F)c1csc(CCN2CCn3c(nc4ccccc43)C2)n1]

2-{2-[(1H-1,3-Benzodiazol-2-ylmethyl)amino]ethyl}-N-[(3-fluoropyridin-2-yl)methyl]-1,3-thiazole-4-carboxamide (Example Compound No. 40) (150 mg, 0.37 mmol) and TEA (509 µl, 3.65 mmol) were combined in DMF (4 ml) and 1,2-dibromoethane (315 µl, 3.65 mmol) was added. The mixture was heated at 100° C. for 40 mins, then cooled to room temperature and quenched with saturated NaHCO$_3$ (aq). The mixture was extracted with DCM (3×50 ml) and the combined organic extracts were washed with aqueous LiCl (2M, 50 ml), dried (Na$_2$SO$_4$) and evaporated in vacuo. Purification by basic prep-HPLC followed by flash column chromatography (eluting with a gradient 0-4% MeOH/DCM) afforded the title compound (45 mg, 28%) as a pale yellow solid.

1H-NMR (MeOD, 500 MHz): d[ppm]=8.37 (dt, J=4.7, 1.2 Hz, 1H), 8.09 (s, 1H), 7.64-7.57 (m, 2H), 7.51-7.46 (m, 1H), 7.42-7.37 (m, 1H), 7.32-7.26 (m, 2H), 4.80 (d, J=1.6 Hz, 2H), 4.23 (t, J=5.5 Hz, 2H), 4.04 (s, 2H), 3.41 (t, J=6.8 Hz, 2H), 3.25-3.20 (m, 2H), 3.16 (t, J=6.8 Hz, 2H)

HPLCMS (Method B): [m/z]: 437.1 [M+H]$^+$ tert-butyl (2-(4-(((3-fluoropyridin-2-yl)methyl)carbamoyl)-1H-1,2,3-triazol-1-yl)ethyl)carbamate (452)

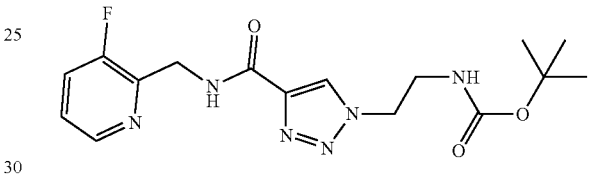

1-(2-((tert-butoxycarbonyl)amino)ethyl)-1H-1,2,3-triazole-4-carboxylic acid (commercial available) (2.0 g, 7.8 mmol) in 50 ml DCM was cooled to −5° C. and N-methylmorpholine (0.94 ml, 8.6 mmol) and ethylchlorofomate were added to the mixture. During the addition temperature was kept below 0° C. and after addition the mixture was stirred at 0° C. for one hour. A second portion of N-methylmorpholine (2.7 ml, 24.2 mmol) and (3-Fluoropyridin-2-yl)methanamine dihydrochloride (A2) were added. The reaction was allowed to warm to room temperature and stirred overnight. 50 ml of water were added to the reaction and extracted with DCM. The organic phase was dried (Na2SO4), filtered and concentrated in vacuo to the crude product which was purified by flash column chromatography to give the title compound (2.1 g, 74%).

1H-NMR (DMSO, 400 MHz): d[ppm]=8.82 (t, 1H), 8.50 (s, 1H), 8.38 (d, 1H), 7.70 (m, 1H), 7.40 (m, 1H), 7.01 (s, 1H), 4.65 (d, 2H), 4.46 (m, 2H), 3.39 (m, 2H), 1.40-1.24 (m, 9H)

1-(2-aminoethyl)-N-((3-fluoropyridin-2-yl)methyl)-1H-1,2,3-triazole-4-carboxamide Hydrochloride (453)

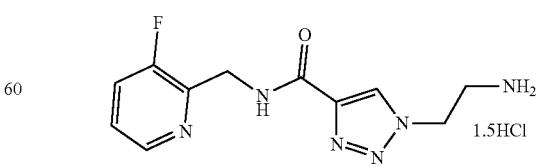

16 ml conc. HCl was added to a solution of tert-butyl (2-(4-(((3-fluoropyridin-2-yl)methyl)carbamoyl)-1H-1,2,3-triazol-1-yl)ethyl)carbamate (452) (2.00 g, 5.49 mmol) in 100 ml methanol and stirred at room temperature for 2 h. The mixture was evaporated in vacuo to afford the title compound (1.74 g, 99%) as a white solid.

1H-NMR (DMSO, 400 MHz): d[ppm]=8.99 (t, 1H), 8.73 (s, 1H), 8.51 (s, 3H), 8.45 (d, 1H), 7.87 (m, 1H), 7.53 (m, 1H), 4.78 (m, 2H), 4.71 (d, 2H), 3.37 (m, 2H)

N-((3-fluoropyridin-2-yl)methyl)-1-(2-((3-((2-nitrophenyl)amino)-3-oxopropyl)amino)ethyl)-1H-1,2,3-triazole-4-carboxamide (454)

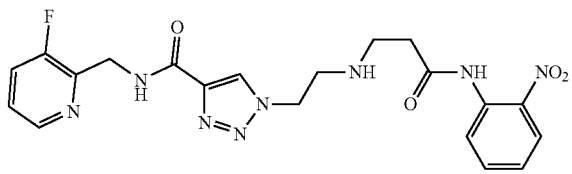 [SMILES: O=C(CCNCCn1cc(C(=O)NCc2ncccc2F)nn1)Nc1ccccc1[N+](=O)[O-]]

1-(2-aminoethyl)-N-((3-fluoropyridin-2-yl)methyl)-1H-1,2,3-triazole-4-carboxamide hydrochloride (453) (4.46 g, 13.2 mmol) and DBU (10.1 g, 66.1 mmol) were suspended in 120 ml acetonitrile. N-(2-Nitrophenyl)prop-2-enamide (D) (2.54 g, 13.2 mmol) in 10 ml acetonitrile was added dropwise to the reaction mixture within 1 h and stirred at room temperature overnight. The reaction was evaporated to dryness and redissolved in 100 ml DCM. 50 ml water were added and extracted with DCM. The organic phases was dried (Na₂SO₄), filtered and concentrated in vacuo to the crude product which was purified by flash column chromatography to give the title compound (2.1 g, 35%).

1H-NMR (DMSO, 400 MHz): d[ppm]=10.55 (s, 1H), 8.78 (t, 1H), 8.57 (s, 1H), 8.38 (d, 1H), 7.93 (m, 1H), 7.76-7.62 (m, 3H), 7.40 (m, 1H), 7.32 (m, 1H), 4.65 (d, 2H), 4.50 (m, 2H), 3.02 (t, 2H), 2.81 (t, 2H), 2.51 (m, 2H)

1-(2-((2-(1H-benzo[d]imidazol-2-yl)ethyl)amino)ethyl)-N-((3-fluoropyridin-2-yl)methyl)-1H-1,2,3-triazole-4-carboxamide (Example Compound No. 277)

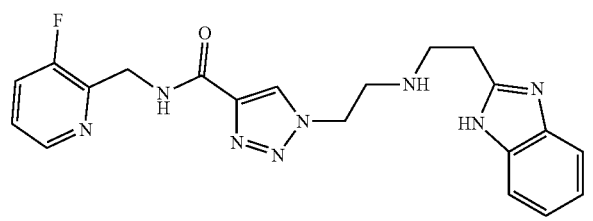 [SMILES: O=C(NCc1ncccc1F)c1cn(CCNCCc2nc3ccccc3[nH]2)nn1]

N-((3-fluoropyridin-2-yl)methyl)-1-(2-((3-((2-nitrophenyl)amino)-3-oxopropyl)amino)ethyl)-1H-1,2,3-triazole-4-carboxamide (454) (900 mg, 1.97 mmol) and iron powder (335 mg, 5.92 mmol) were suspended in 10 ml acetic acid and stirred under nitrogen at 80° C. for 2 h. The reaction mixture was evaporated to dryness and the residue treated with 60 ml chloroform/isopropanol (1:4). The pH was adjusted to 11 by addition of 1N NaOH and the phases were separated. After extraction of the aqueous phase with chloroform the combined organic phases were dried (Na₂SO₄), filtered and concentrated in vacuo to the crude product which was purified by flash column chromatography to give the title compound (430 mg, 53%).

1H-NMR (d4-methanol, 400 MHz): d[ppm]=8.40 (s, 1H), 8.38 (m, 1H), 7.63-7.58 (m, 1H), 7.50-7.45 (m, 2H), 7.41-7.36 (m, 1H), 7.18-12 (m, 2H), 4.78 (d, 2H), 4.56 (m, 2H), 3.16 (t, 2H), 3.10-3.0 (m, 4H)

5-(2-((tert-butoxycarbonyl)amino)ethyl)-1,2,4-oxadiazole-3-carboxylic Acid

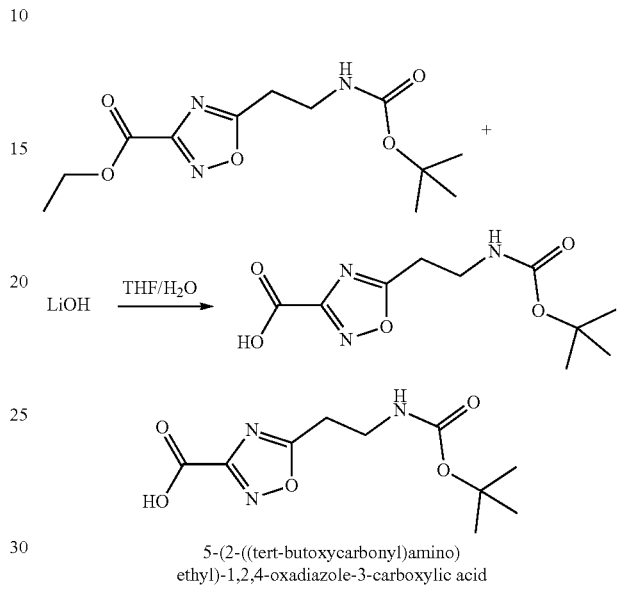

5-(2-((tert-butoxycarbonyl)amino)ethyl)-1,2,4-oxadiazole-3-carboxylic acid

To a round bottomed flask was added ethyl 5-(2-((tert-butoxycarbonyl)amino)ethyl)-1,2,4-oxadiazole-3-carboxylate (4 g, 14.06 mmol), THF (80 ml) and water (20 ml) with stirring at room temperature. Lithium hydroxide (1 g, 41.75 mmol) was then added to the solution and the reaction mixture stirred at room temperature for 2 hr. The reaction mixture was then acidified to pH2.8 (using aq. 32% HCl), extracted with ethyl acetate (3×80 ml), dried (Na2SO4), filtered and evaporated to afford the title compound as a brown oil (2.95 g), which was used without purification.

tert-butyl (2-(3-((pyridin-2-ylmethyl)carbamoyl)-1,3,4-oxadiazol-5-yl)ethyl)carbamate

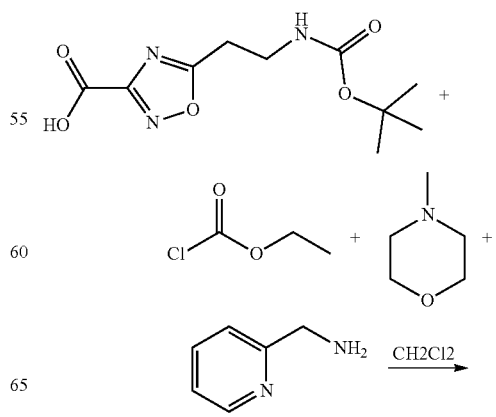

-continued

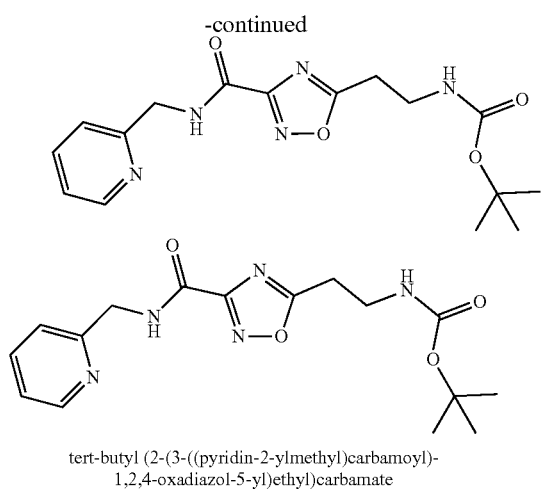

tert-butyl (2-(3-((pyridin-2-ylmethyl)carbamoyl)-1,2,4-oxadiazol-5-yl)ethyl)carbamate To a solution of 5-(2-(((tert-butoxycarbonyl)amino)ethyl)-1,2,4-oxadiazole-3-carboxylic acid (2.95 g, 11.47 mmol) in 100 ml dichloromethane at 0° C. was added 4-methylmorpholine (2.8 ml, 25.47 mmol) and ethylchloroformate (1 ml, 10.46 mmol). After 60 min stirring at 0° C., 2-picolylamine (1.7 ml, 16.82) was added and the reaction mixture was stirred 2 h at RT. The reaction mixture washed with water (100 ml), dried (Na2SO4), filtered and evaporated. The crude product was purified using a 100 g SNAP Ultra column (eluted with a gradient of 0 to 100% ethylacetate in petrolether) to give a pale brown oil (2.29 g, 6.6 mmol, 58%).

$^1$H NMR (400 MHz, CDCl3): δ 8.5 (s, 1H), 8.1 (m, 2H), 7.7 (m, 1H), 7.3 (m, 2H), 6.8 (s, 1H), 4.6 (s, 2H), 3.4 (m, 2H), 2.5 (m, 2H), 1.4 (s, 9H).

5-(2-aminoethyl)-N-(pyridine-2-ylmethyl)-1,2,4-oxadiazole-3-carboxamide Dihydrochloride

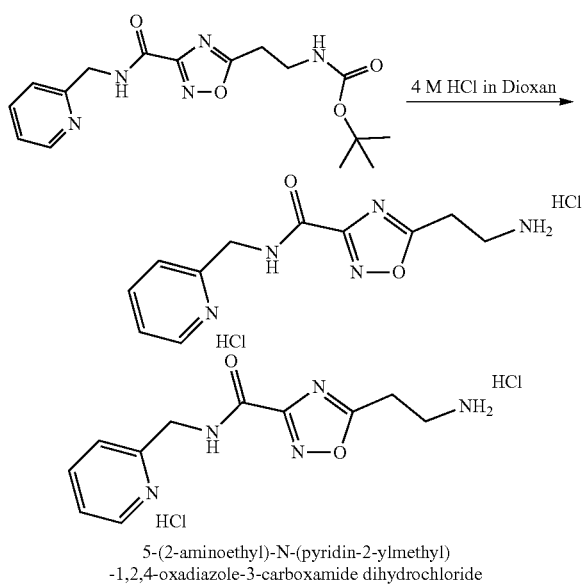

5-(2-aminoethyl)-N-(pyridin-2-ylmethyl)-1,2,4-oxadiazole-3-carboxamide dihydrochloride To a solution of tert-butyl (2-(3-((pyridin-2-ylmethyl)carbamoyl)-1,2,4-oxadiazol-5-yl)ethyl)carbamate (2.41 g, 6.94 mmol) in dioxane (25 ml) and was added 4 M HCl in dioxane (25 ml). After stirring at RT for 2 hours the reaction mixture was evaporated to afford the title compound as a brown oil (2.83 g), which was used without purification.

5-(2-((3-((2-nitrophenyl)amino)-3-oxopropyl)amino)ethyl)-N-(pyridin-2-ylmethyl)-1,2,4-oxadiazole-3-carboxamide

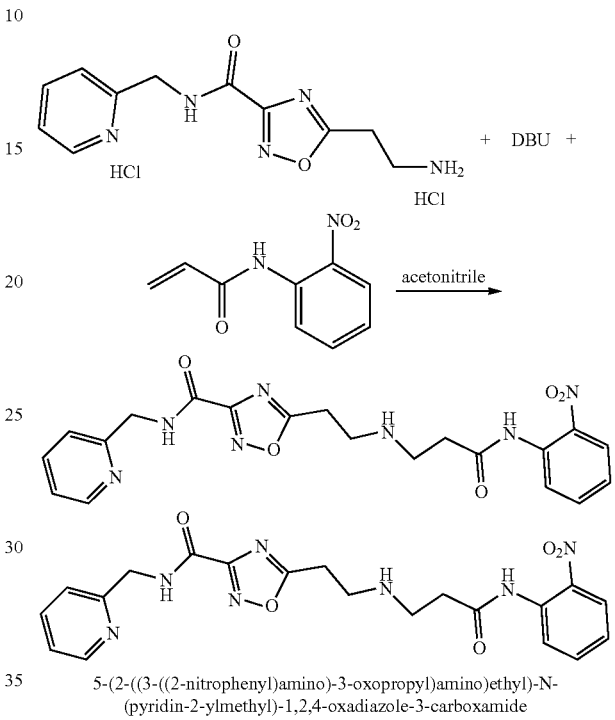

5-(2-((3-((2-nitrophenyl)amino)-3-oxopropyl)amino)ethyl)-N-(pyridin-2-ylmethyl)-1,2,4-oxadiazole-3-carboxamide In a round bottomed flask, 5-(2-aminoethyl)-N-(pyridin-2-ylmethyl)-1,2,4-oxadiazole-3-carboxamide dihydrochloride (3.48 g, 9.76 mmol) was suspended in acetonitrile (100 ml) under nitrogen and 1,8-diazabicycloundec-7-ene (DBU) (7.1 ml, 47.48 mmol, 4.9 eq) was added dropwise followed by N-(2-nitrophenyl)prop-2-enamide (1.9 g, 9.89). The reaction was stirred at room temperature overnight, then evaporated, diluted with 100 ml dichloromethane, washed with 50 ml water, dried (Na$_2$SO$_4$), filtered and evaporated. The crude product was purified using a 100 g SNAP Ultra column (eluted each time with a gradient of 0 to 25% methanol in dichloromethane) to give a pale brown oil (0.74 g, 1.7 mmol, 17%).

$^1$H NMR (400 MHz, CDCl3): δ 8.5 (s, 1H), 8.1 (m, 2H), 7.8 (m, 1H), 7.6 (m, 1H), 7.3 (m, 3H), 4.4 (s, 2H), 3.1 (m, 4H), 2.7 (m, 2H), 2.5 (m, 2H).

5-(2-((2-(1H-benzo[d]imidazol-2-yl)ethyl)amino)ethyl)-N-(pyridin-2-ylmethyl)-1,2,4-oxadiazole-3-carboxamide (Example Compound No. 278)

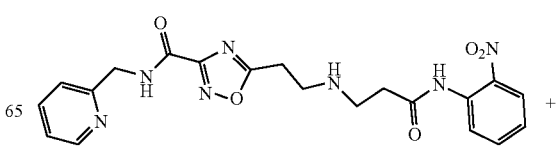

-continued

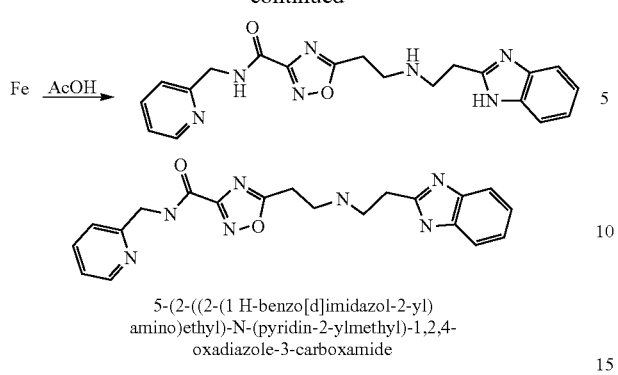

5-(2-((2-(1H-benzo[d]imidazol-2-yl)amino)ethyl)-N-(pyridin-2-ylmethyl)-1,2,4-oxadiazole-3-carboxamide 5-(2-((3-((2-nitrophenyl)amino)-3-oxopropyl)amino)ethyl)-N-(pyridin-2-ylmethyl)-1,2,4-oxadiazole-3-carboxamide (0.74 g, 1.68 mmol) was dissolved in acetic acid (5 ml) under nitrogen and iron powder (0.3 g) was added. The reaction mixture was heated to 80° C. for 3 hours. After cooling at RT, toluene (50 ml) was added and the mixture evaporated. A mixture of chloroform:IPA (4:1, 40 ml) was added, the reaction mixture cooled to 0° C., basified using 6M NaOH solution to pH 10-12, filtered, dried ($Na_2SO_4$), filtered and evaporated. The crude product was purified using a 50 g SNAP KP-Sil column (eluted with a gradient of 0 to 25% methanol in dichloromethane) to give a pale brown oil (0.31 g, 0.8 mmol, 47).

$^1$H NMR (400 MHz, MeOD): δ 8.4 (s, 1H), 7.9 (s, 1H), 7.7 (m, 2H), 7.3 (m, 1H), 7.2 (m, 1H), 7.1 (m, 2H), 4.4 (s, 2H), 3.1 (m, 4H), 2.9 (m, 2H), 2.5 (m, 2H).

tert-butyl (2-(3-(((3-fluoropyridin-2-yl)methyl)carbamoyl)-1,2,4-oxadiazol-5-yl)ethyl)carbamate

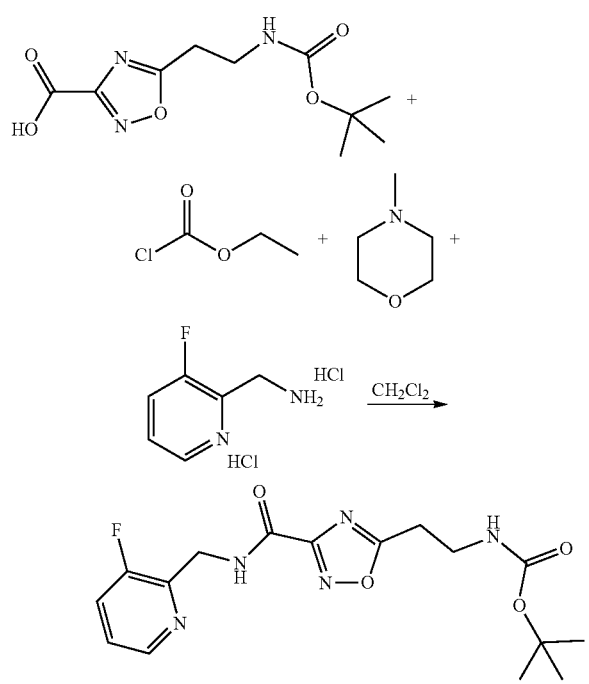

tert-butyl (2-(3-(((3-fluoropyridin-2-yl)methyl)carbamoyl)-1,2,4-oxadiazol-5-yl)ethyl)carbamate To a solution of 5-(2-((tert-butoxycarbonyl)amino)ethyl)-1,2,4-oxadiazole-3-carboxylic acid (8.16 g, 31.72 mmol) in 400 ml dichloromethane at −5° C. was added 4-methylmorpholine (20 ml, 182 mmol) and ethylchloroformate (2.7 ml, 28.24 mmol). After 60 min stirring at −5° C., (3-fluoropyridin-2-yl)methanamine dihydrochloride (9.50, 47.73) was added and the reaction mixture was stirred 2 h at RT. The reaction mixture washed with water (400 ml), dried ($Na_2SO_4$), filtered and evaporated. The crude product was purified using a 100 g SNAP Ultra column (eluted with a gradient of 0 to 100% ethylacetate in petrolether) to give a pale brown oil (4.15 g, 11.4 mmol, 36%).

$^1$H NMR (400 MHz, CDCl3): δ 8.3 (s, 1H), 7.4 (m, 1H), 7.3 (m, 1H), 6.9 (s, 1H), 4.6 (s, 2H), 3.4 (m, 2H), 2.5 (m, 2H), 1.4 (s, 9H).

5-(2-aminoethyl)-N-((3-fluoropyridin-2-yl)methyl)-1,2,4-oxadiazole-3-carboxamide dihydrochloride

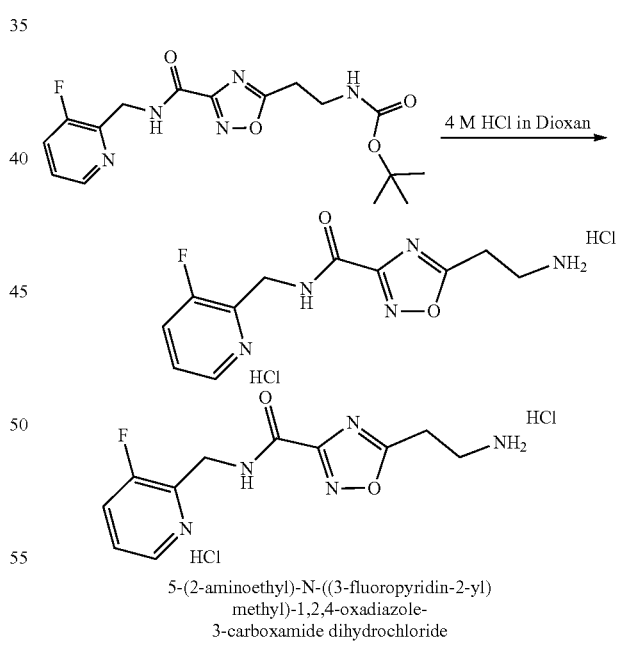

5-(2-aminoethyl)-N-((3-fluoropyridin-2-yl)methyl)-1,2,4-oxadiazole-3-carboxamide dihydrochloride To a solution of tert-butyl (2-(3-(((3-fluoropyridin-2-yl)methyl)carbamoyl)-1,2,4-oxadiazol-5-yl)ethyl)carbamate (4.23 g, 11.58 mmol) in dioxane (50 ml) and was added 4 M HCl in dioxane (50 ml). After stirring at RT for 3 hours the reaction mixture was evaporated to afford the title compound as a brown oil (3.78 g), which was used without purification.

559

N-((3-fluoropyridin-2-yl)methyl)-5-(2-((3-((2-nitrophenyl)amino)-3-oxopropyl)amino)ethyl)-1,2,4-oxadiazole-3-carboxamide

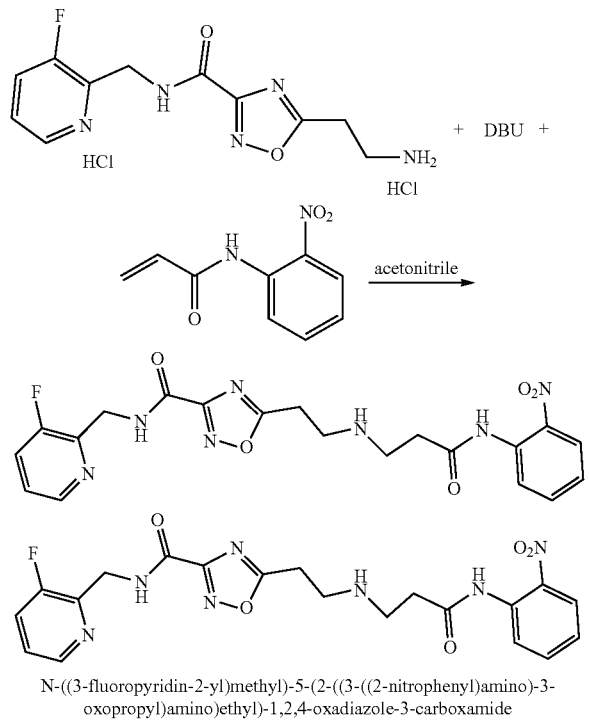

N-((3-fluoropyridin-2-yl)methyl)-5-(2-((3-((2-nitrophenyl)amino)-3-oxopropyl)amino)ethyl)-1,2,4-oxadiazole-3-carboxamide In a round bottomed flask, 5-(2-aminoethyl)-N-((3-fluoropyridin-2-yl)methyl)-1,2,4-oxadiazole-3-carboxamide dihydrochloride (3.72 g, 9.93 mmol) was suspended in acetonitrile (100 ml) under nitrogen and 1,8-diazabicycloundec-7-ene (DBU) (7.42 ml, 49.65 mmol, 5 eq) was added dropwise followed by N-(2-nitrophenyl)prop-2-enamide (1.91 g, 9.93). The reaction was stirred at room temperature overnight, then evaporated, diluted with 100 ml dichloromethane, washed with 50 ml water, dried (Na₂SO₄), filtered and evaporated. The crude product was purified using a 100 g SNAP KP-Sil column (eluted with a gradient of 0 to 25% methanol in dichloromethane) to give a pale brown oil (1.7 g, 3.7 mmol, 37%).

¹H NMR (400 MHz, MeOD): δ 8.3 (s, 1H), 8.1 (m, 2H), 7.6 (m, 1H), 7.5 (m, 1H), 7.3 (m, 2H), 4.5 (s, 2H), 3.0 (m, 4H), 2.7 (m, 2H), 2.5 (m, 2H).

5-(2-((2-(1H-benzo[d]imidazol-2-yl)ethyl)amino)ethyl)-N-((3-fluoropyridin-2-yl)methyl)-1,2,4-oxadiazole-3-carboxamide (Example Compound No. 279)

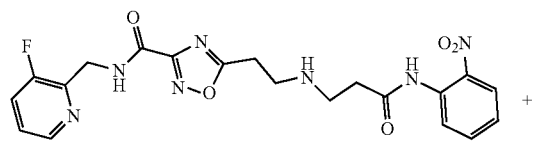 +

560

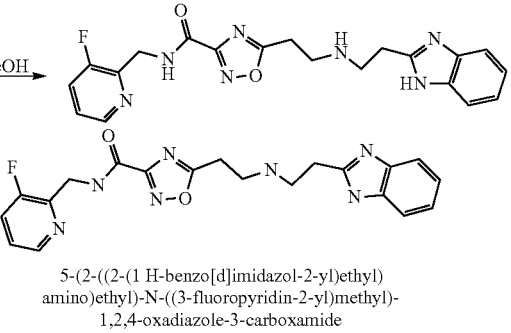

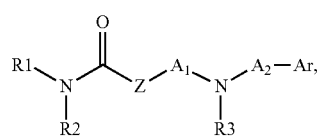

5-(2-((2-(1H-benzo[d]imidazol-2-yl)ethyl)amino)ethyl)-N-((3-fluoropyridin-2-yl)methyl)-1,2,4-oxadiazole-3-carboxamide N-((3-fluoropyridin-2-yl)methyl)-5-(2-((3-((2-nitrophenyl)amino)-3-oxopropyl)amino)ethyl)-1,2,4-oxadiazole-3-carboxamide (2.3 g, 5.03 mmol) was dissolved in acetic acid (20 ml) under nitrogen and iron powder (1.4 g) was added. The reaction mixture was heated to 80° C. for 3 hours. After cooling at RT, toluene (200 ml) was added and the mixture evaporated. A mixture of chloroform:IPA (4:1, 100 ml) was added, the reaction mixture cooled to 0° C., basified using 6M NaOH solution to pH 10-12, filtered, dried (Na₂SO₄), filtered and evaporated. The crude product was purified using a 100 g SNAP KP-Sil column (eluted with a gradient of 0 to 25% methanol in dichloromethane) to give a pale brown oil (1.51 g, 3.7 mmol, 74%).

¹H NMR (400 MHz, MeOD): δ 8.2 (s, 1H), 7.5 (m, 3H), 7.3 (m, 1H), 7.1 (m, 2H), 4.5 (s, 2H), 3.1 (m, 4H), 2.9 (m, 2H), 2.4 (m, 2H).

Further Embodiments of the Invention

1. Compounds according to formula (I)

$$R_1 \underset{R_2}{\overset{}{N}} \underset{}{\overset{O}{\|}} Z \underset{}{A_1} \underset{R_3}{\overset{}{N}} A_2 - Ar, \quad (I)$$

or pharmaceutically acceptable salts thereof, for the use as ferroportin inhibitors, wherein
R¹ and R² are the same or different and are independently selected from the group consisting of
  hydrogen,
  optionally substituted alkyl,
  optionally substituted aryl,
  optionally substituted heteroaryl, or
  R¹ and R² together with the nitrogen atom to which they are bonded form an optionally substituted 3 to 6-membered ring, which may optionally contain further heteroatoms, or
  one of R¹ and R² is an alkanoyl-group, which together with Z being an amino group (—NH—) forms a 5- or 6-membered heterocyclic diketone containing two nitrogen atoms;
Z is a cyclic group or a linear group and is selected from
  optionally substituted 5- or 6-membered heteroaryl
  optionally substituted aryl,
  optionally substituted aliphatic 5- or 6-membered heterocyclyl,
  amino (—NH—), an alkylaminocarbonyl group [—(CH₂)—NH—(C=O)—], or an alkylcarbonylamino group [—(CH₂)—(C=O)—NH—];

A¹ is optionally substituted alkanediyl;

A² is
optionally substituted alkanediyl,
a direct bond, or
a sulfonyl group;

R³ is
hydrogen, or
optionally substituted alkyl; or

A¹ and R³ together with the nitrogen atom to which they are bonded form an optionally substituted 4- to 6-membered aliphatic mono- or bicyclic ring; or R³ and A² together with the nitrogen atom to which they are bonded form an optionally substituted 4- to 7-membered aliphatic ring; and Ar is
optionally substituted aryl,
optionally substituted monocyclic heteroaryl, or
optionally substituted bicyclic heteroaryl, which may be fused with a ring formed by R³ and A² together with the nitrogen atom to which they are bonded.

2. Compounds for the use according to embodiment 1, wherein

R¹ and R² are the same or different and are independently selected from the group consisting of
hydrogen,
optionally substituted alkyl, or
R¹ and R² together with the nitrogen atom to which they are bonded form an optionally substituted 3 to 6-membered ring, which may optionally contain further heteroatoms;

Z is a cyclic group or a linear group and is selected from
optionally substituted 5- or 6-membered heteroaryl
optionally substituted aryl,
optionally substituted aliphatic 5- or 6-membered heterocyclyl,
amino (—NH—),
an alkylaminocarbonyl group [—(CH₂)—NH—(C=O)—], or
an alkylcarbonylamino group [—(CH₂)—(C=O)—NH—];

A¹ is optionally substituted alkanediyl;

A² is
optionally substituted alkanediyl, or
a direct bond;

R³ is
hydrogen, or
$C_1$-$C_3$-alkyl; or

A¹ and R³ together with the nitrogen atom to which they are bonded form an optionally substituted 4-membered aliphatic monocyclic ring; or R³ and A² together with the nitrogen atom to which they are bonded form an optionally substituted 4- to 7-membered aliphatic ring; and Ar is optionally substituted bicyclic heteroaryl.

3. Compounds for the use according to embodiment 1 or 2, wherein

Z is an optionally substituted cyclic group Z-Cycl, forming compounds according to formula (II),

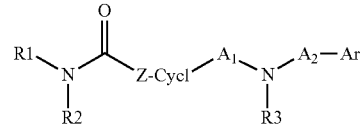

(II)

with Z-Cycl being selected from
an optionally substituted 5- or 6-membered heteroaryl,
an optionally substituted aryl, and
an optionally substituted aliphatic 5- or 6-membered heterocyclyl; and wherein R¹, R², R³, A¹, A² and Ar have the meaning as defined in embodiment 1 or 2.

4. Compounds for the use according to any one of embodiments 1 to 3, wherein

Z is an optionally substituted cyclic group Z-Cycl, selected from an optionally substituted aromatic group, comprising
an optionally substituted heteroaryl and
an optionally substituted aryl.

5. Compounds for the use according to any one of the preceding embodiments, wherein Z is an optionally substituted cyclic group Z-Cycl, selected from an optionally substituted 5- or 6-membered heteroaryl, forming
a compound of the formula (IIa)

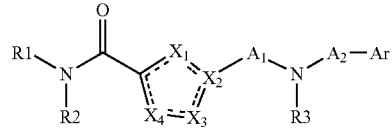

(IIa)

wherein 1 to 3 heteroatoms X are present, wherein X¹ to X⁴ may be the same or different and are independently selected from the group consisting of C, N, S and O, preferably in formula (IIa) 1 to 3 heteroatoms X are present, wherein X¹ is C, N, S or O;
X² is C or N;
X³ is C, N, S or O; and
X⁴ is C, N, S or O, and wherein X¹, X³ and X⁴ with the meaning of C or N may carry a further substituent;

or
a compound of the formula (IIb)

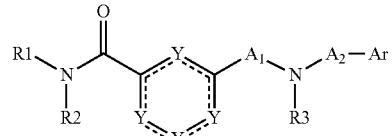

(IIb)

wherein Y is N or C, with at least one Y being N, preferably with one Y being N;

and wherein in formula (IIa) and (IIb) R¹, R², R³, A¹, A² and Ar have the meaning as defined in the preceding embodiments.

6. Compounds for the use according to any one of the preceding embodiments, wherein the compounds are defined by
formula (IIa-b)

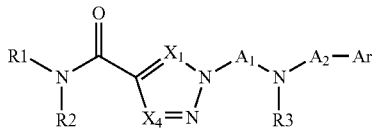

(IIa-b)

with $X^1$ and $X^4$ being C and wherein $X^1$ and/or $X^4$ may carry a further substituent; as well as by
formula (IIa-c)

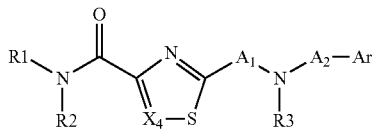

(IIa-c)

with $X^4$ being C, which may carry a further substituent, and
formula (IIa-d)

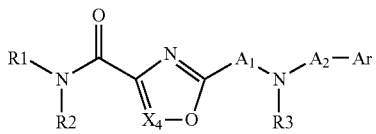

(IIa-d)

with $X^4$ being C, which may carry a further substituent; and wherein in in each case $R^1$, $R^2$, $R^3$, $A^1$, $A^2$ and Ar have the meaning as defined in the preceding embodiments.

7. Compounds for the use according to any one of the preceding embodiments, wherein the compounds are defined by
formula (IIb-a)

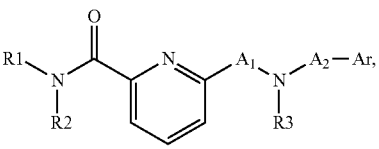

(IIb-a)

formula (Ib-b)

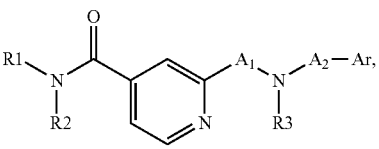

(IIb-b)

formula (Ib-c)

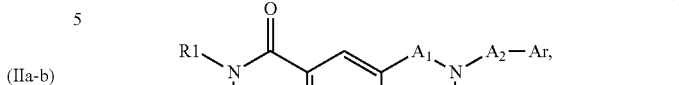

(IIb-c)

formula (Ib-d)

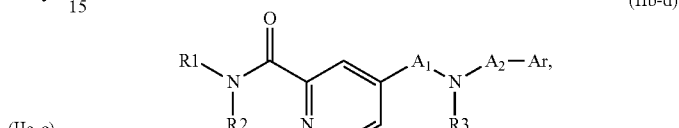

(IIb-d)

wherein in in each case $R^1$, $R^2$, $R^3$, $A^1$, $A^2$ and Ar have the meaning as defined in the preceding embodiments.

8. Compounds for the use according to any one of the preceding embodiments, wherein at least one of $R^1$ and $R^2$ is a linear, branched or cyclic alkyl group, which is substituted with a cyclic group "Cycl", designated as $R^{2*}$, forming compounds according to formula (III)

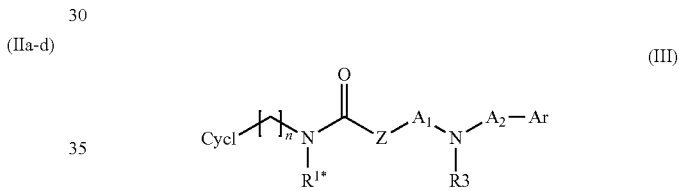

(III)

wherein
Cycl is selected from
  optionally substituted aryl, and
  optionally substituted heteroaryl; preferably forming compounds such as of
  formula (IIIa)

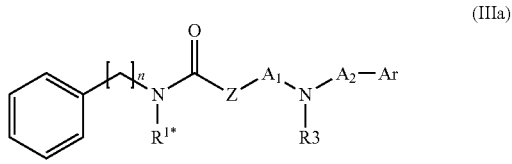

(IIIa)

formula (IIIb)

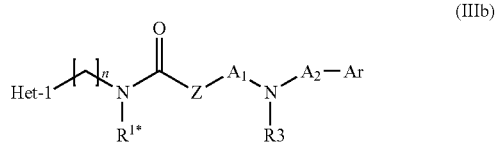

(IIIb)

with Het-1 being
  an optionally substituted, optionally fused 5- to 6-membered heteroaryl, or an optionally substituted 5- or 6-membered aliphatic heterocyclyl, such as preferably a 6-membered aliphatic heterocyclyl, which contain 1 or 2 identical or different heteroatoms selected from the group consisting of N, O and S, preferably N;

and wherein in each case n is an integer of 1 to 3;

the remaining of $R^1$ or $R^2$, designated as $R^{1*}$, is selected from hydrogen, and optionally substituted alkyl; and Z, $R^3$, $A^1$, $A^2$ and Ar have the meaning as defined in the preceding embodiments.

9. Compounds for the use according to any one of the preceding claims, wherein the compounds are defined by formula (IIIb-c)

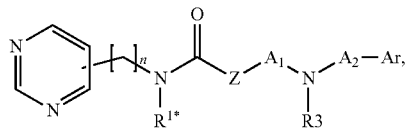
(IIIb-c)

formula (IIIb-d)

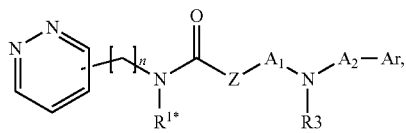
(IIIb-d)

and formula (IIIb-e)

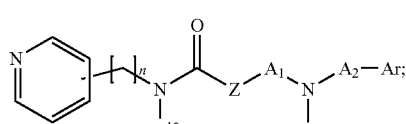
(IIIb-e)

wherein the pyrimidinyl, pyridazinyl and pyridinyl ring each may carry 1 to 3, preferably 1 or 2 further substituents, and wherein in each case n is an integer of 1 to 3;

the remaining of $R^1$ or $R^2$, designated as $R^{1*}$, is selected from hydrogen, and optionally substituted alkyl; and Z, $R^3$, $A^1$, $A^2$ and Ar have the meaning as defined in the preceding embodiments.

10. Compounds for the use according to any one of the preceding embodiments, wherein the compounds are defined by formula (IIIb-f)

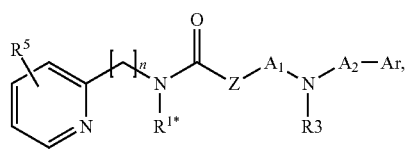
(IIIb-f)

wherein $R^5$ indicates 1 to 3, preferably 1 or 2 optional substituents, which may be selected from $C_1$-$C_3$-alkyl and halogen, such as in particular compounds of formula (IIb-g)

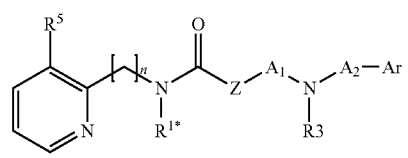
(IIIb-g)

wherein $R^5$ is preferably selected from $C_1$-$C_3$-alkyl and halogen, such as preferably F;

and wherein in each case n is an integer of 1 to 3;

the remaining of $R^1$ or $R^2$, designated as $R^{1*}$, is selected from hydrogen, and optionally substituted alkyl; and Z, $R^3$, $A^1$, $A^2$ and Ar have the meaning as defined in the preceding embodiments.

11. Compounds for the use according to any one of the preceding embodiments, wherein Ar is an optionally substituted mono- or bicyclic heteroaryl, forming compounds according to formula (IV)

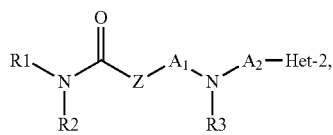
(IV)

with Het-2 being an optionally substituted, 5- or 6-membered monocyclic heteroaryl, or an optionally substituted bicyclic heteroaryl, which may be fused with a ring formed by $R^3$ and $A^2$ together with the nitrogen atom to which they are bonded; such as preferably compounds according to formula (IVc)

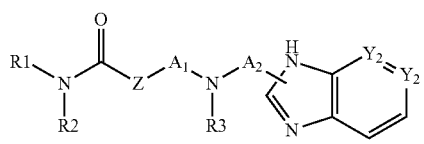
(IVc)

with both $Y^2$ being C or one $Y^2$ being N and one $Y^2$ being C, such as in particular compounds according to formula (IVd)

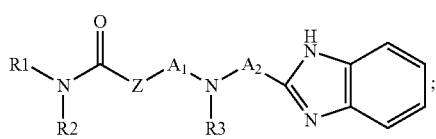

(IVd)

wherein in each case the bicyclic heteroaryl ring of Het-2 may carry 1 to 3 substituents, preferably 1 or 2 substituents; and wherein the bicyclic heteroaryl ring of Het-2 of formula (IVc) or (IVd), may be fused with a ring formed by $R^3$ and $A^2$ together with the nitrogen atom to which they are bonded, and
wherein in each case $R^1$, $R^2$, Z, $R^3$, $A^1$ and $A^2$ have the meaning as defined in the preceding embodiments.

12. Compounds for the use according to any one of the preceding embodiments, wherein
$A^1$ and $A^2$ are optionally substituted alkanediyl and are the same or different and are independently selected from optionally substituted
  methylene and
  ethane-1,2-diyl, or wherein
  $A^1$ and $R^3$ together with the nitrogen atom to which they are bonded form an optionally substituted 4-membered aliphatic monocyclic ring.

13. Compounds as defined in any one of the preceding embodiments for the use in the inhibition of iron transport mediated by ferroportin or for the use in the prophylaxis and/or treatment of iron metabolism disorders leading to increased iron levels, iron overload, diseases related to or caused by increased iron levels or tissue iron overload-diseases associated with ineffective erythropoiesis, diseases caused by reduced levels of hepcidin, or to limit the amount of iron available to pathogenic microorganisms, such as the bacterium *Vibrio vulnificus*, and thereby for the use as adjunctive therapy to treat infections 14. Compounds as defined in any one of the preceding embodiments, for the use according to embodiment 13 wherein the diseases related to or caused by increased iron levels or iron overload comprise thalassemia (beta-thalassemia), haemochromatosis, neurodegenerative diseases such as Alzheimer's disease and Parkinson's disease, formation of radicals, reactive oxygen species (ROS) and oxidative stress, cardiac, liver and endocrine damage caused by iron overload, and inflammation triggered by excess iron; and wherein the diseases associated with ineffective erythropoiesis comprise myelodysplastic syndromes (MDS, myelodysplasia), polycythemia vera.

15. A medicament containing one or more of the compounds as defined in any one of the preceding embodiments, the medicament being preferably for the use as defined in embodiments 13 and 14, and which may further contain one or more pharmaceutical carriers and/or auxiliaries and/or solvents and/or at least one further pharmaceutically active compound, in particular a compound for the prophylaxis and treatment of iron overload, thalassemia, haemochromatosis, neurodegenerative diseases (such as Alzheimer's disease or Parkinson's disease) and the associated symptoms, preferably an iron-chelating compound; and wherein the medicament is preferably for oral or parenteral administration.

The invention claimed is:
1. A method for inhibiting ferroportin; the method comprising administering, to a patient in need thereof, a therapeutic composition, said therapeutic composition comprising at least one compound according to formula (IVd)

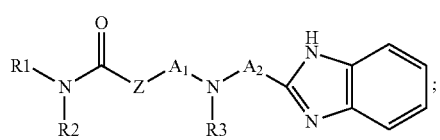

(IVd)

wherein
(a)
(i) $R^1$ and $R^2$ are the same or different and are independently selected from the group consisting of
  hydrogen,
  linear or branched, unsubstituted or substituted $C_1$-$C_8$-alkyl, wherein substituents of alkyl are selected from optionally substituted heteroaryl, optionally substituted heterocyclyl and an alkylene group,
  optionally substituted heteroaryl,
or
(ii) $R^1$ and $R^2$ together with the nitrogen atom to which they are bonded form an optionally substituted 3- to 6-membered ring, which may optionally contain further heteroatoms,
or
(iii) one of $R^1$ and $R^2$ is an alkanoyl-group, which together with Z being an amino group (—NH—) forms a 5- or 6-membered heterocyclic diketone containing two nitrogen atoms;
(b) Z is a cyclic group or a linear group and is selected from
  optionally substituted 5- or 6-membered heteroaryl
  optionally substituted aryl,
  optionally substituted 5- or 6-membered heterocyclyl,
  amino (—NH—),
  an alkylaminocarbonyl group [—(CH$_2$)—NH—(C=O)—], or
  an alkylcarbonylamino group [—(CH$_2$)—(C=O)—NH—];
(c) $A^1$ is optionally substituted alkanediyl;
(d) $A^2$ is
  optionally substituted alkanediyl,
  a direct bond, or
  a sulfonyl group;
(e) $R^3$ is
(i) hydrogen, or
(ii) optionally substituted alkyl; or
(iii) $A^1$ and $R^3$ together with the nitrogen atom to which they are bonded form an optionally substituted 4- to 6-membered mono- or bicyclic ring; or
(iv) $R^3$ and $A^2$ together with the nitrogen atom to which they are bonded form an optionally substituted 4- to 7-membered ring; and
wherein the bicyclic heteroaryl ring may carry 1 to 3 substituents, and wherein the bicyclic heteroaryl ring may be fused with a ring formed by $R^3$ and $A^2$ together with the nitrogen atom to which they are bonded.

2. The method of claim 1 wherein
(a) $R^1$ and $R^2$ are the same or different and are independently selected from the group consisting of
  hydrogen,
  linear or branched, unsubstituted or substituted $C_1$-$C_8$-alkyl, wherein possible substituents of alkyl are selected from optionally substituted heteroaryl, optionally substituted heterocyclyl and an alkylene group; or R¹ and R² together with the nitrogen atom to which they are bonded form an optionally substituted 3- to 6-membered ring, which may optionally contain further heteroatoms;

(b) Z is a cyclic group or a linear group and is selected from
optionally substituted 5- or 6-membered heteroaryl
optionally substituted aryl,
optionally substituted 5- or 6-membered heterocyclyl,
amino (—NH—),
an alkylaminocarbonyl group [—(CH₂)—NH—(C=O)—], or
an alkylcarbonylamino group [—(CH₂)—(C=O)—NH—];

(c) A¹ is optionally substituted alkanediyl;
(d) A² is
optionally substituted alkanediyl, or
a direct bond;
(e) R³ is
hydrogen, or
$C_1$-$C_3$-alkyl; or
(f) A¹ and R³ together with the nitrogen atom to which they are bonded form an optionally substituted 4-membered monocyclic ring; or
(g) R³ and A² together with the nitrogen atom to which they are bonded form an optionally substituted 4- to 7-membered aliphatic ring.

3. The method of claim 1, wherein
Z is selected from
an optionally substituted 5- or 6-membered heteroaryl,
an optionally substituted aryl, and
an optionally substituted 5- or 6-membered heterocyclyl.

4. The method of claim 1 wherein
Z is an optionally substituted 5-membered heteroaryl, forming a compound of the formula (IIa)

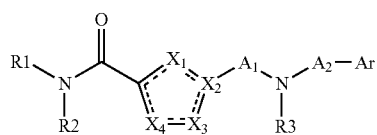
(IIa)

wherein $X^1$ to $X^4$ may be the same or different and are independently selected from the group consisting of C, N, S and O, wherein 1 to 3 of $X_1$-$X_4$ are heteroatoms
or wherein
Z is an optionally substituted 5-membered heteroaryl forming a compound of the formula (IIa-a)

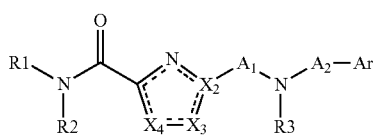
(IIa-a)

wherein one or two further heteroatoms X ($X^2$, $X^3$, $X^4$) are present, and wherein
$X^2$ is C or N;
$X^3$ is C, N, S or O; and
$X^4$ is C or N;
with the proviso that in case of two further heteroatoms both are selected to be N or one is N and one (except $X^2$) is O; and wherein $X^3$ and $X^4$ with the meaning of C or N may carry a further substituent;
and wherein R¹, R², R³, A¹, A² and Ar have the meaning as defined in the preceding claims;
or compounds defined by formula (IIa-d)

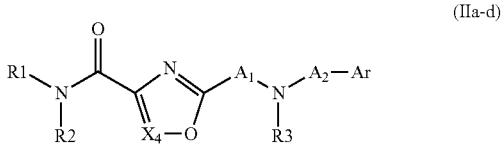
(IIa-d)

with $X^4$ being C, which may carry a further substituent
or defined by formula (IIa-c)

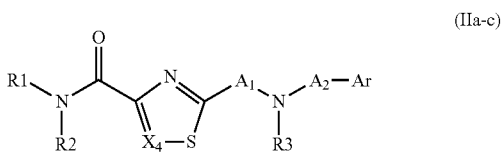
(IIa-c)

with $X^4$ being C, which may carry a further substituent,
or defined by formula (IIa-b)

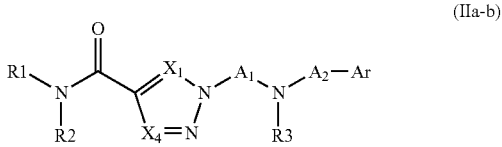
(IIa-b)

with $X^1$ and $X^4$ being C and wherein X' and/or $X^4$ may carry a further substituent;
or defined by formula (IIa-e)

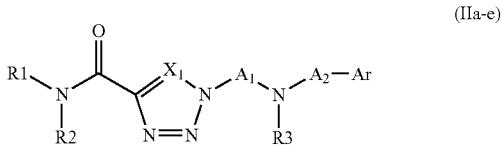
(IIa-e)

with $X^1$ being C, which may carry a further substituent.

5. The method of claim 1, wherein
Z is an optionally substituted 6-membered heteroaryl, forming a compound of the formula (IIb)

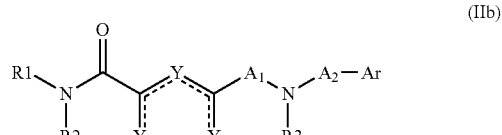
(IIb)

wherein Y is N or C, with at least one Y being N;
and wherein any Y with the meaning of C may carry a further substituent;

or compounds defined by
formula (IIb-a)

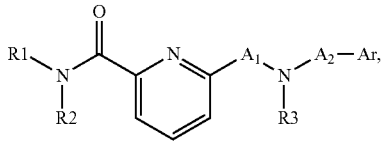
(IIb-a)

formula (Ib-b)

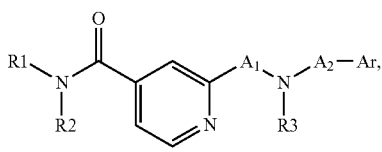
(IIb-b)

formula (Ib-c)

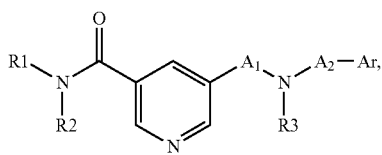
(IIb-c)

or
formula (Ib-d)

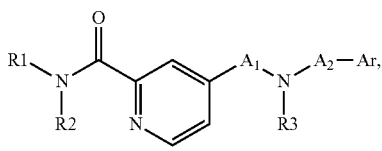
(IIb-d)

wherein in each case the pyridinyl-ring may optionally carry one or more further substituents.

6. The method of claim 1, wherein
Z is an optionally substituted 6-membered aryl, forming a compound of the formula (IIc)

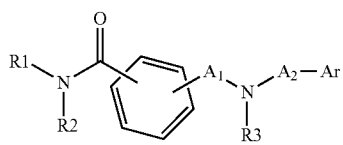
(IIc)

wherein $R^1$, $R^2$, $R^3$, $A^1$, $A^2$ and Ar have the meaning as defined in the preceding claims and wherein the phenyl-ring may be substituted with 1 to 3 substituents or Z is a nitrogen containing 5- or 6-membered heterocyclyl forming compounds according to formula (IId-a) or (IId-b)

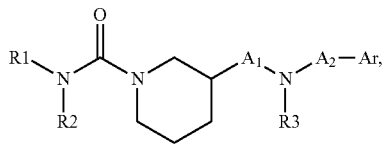
(IId-a)

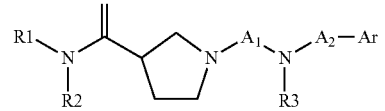
(IId-b)

wherein the heterocyclyl-ring may be substituted with 1 to 3 substituents.

7. The method of claim 1 wherein
at least one of $R^1$ and $R^2$ is a linear or branched alkyl group $[CQ]_n$- with Q=H or $C_1$-$C_4$-alkyl and n=1, 2 or 3, which is substituted with a cyclic group "Cycl", designated as $R^{2*}$, wherein Cycl is selected from
optionally substituted heteroaryl,
and wherein n is an integer of 1 to 3;
the remaining of $R^1$ or $R^2$, designated as $R^{1*}$, is selected from
hydrogen, and
optionally substituted alkyl; and
forming
compounds defined by formula (A-IIIb-f)

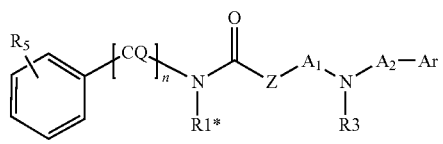
(A-IIIb-f)

wherein $R^5$ indicates 1 to 3, preferably 1 or 2 optional substituents, which may be selected from $C_1$-$C_3$-alkyl and halogen, preferably fluorine;
or compounds defined by formula (A-IIIb-g)

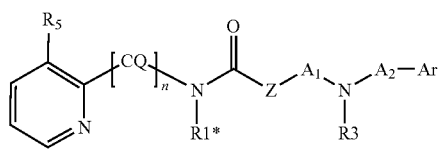
(A-IIIb-g)

wherein $R^5$ is preferably selected from $C_1$-$C_3$-alkyl and halogen, preferably fluorine;
and wherein n is an integer of 1 to 3;
the remaining of $R^1$ or $R^2$, designated as $R^{1*}$, is selected from
hydrogen, and
optionally substituted alkyl;

or compounds defined by formula (A-IIIb-c)

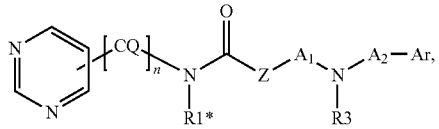
(A-IIIb-c)

or
formula (A-IIIb-d)

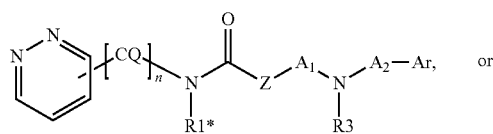
(A-III-b-d)

-continued

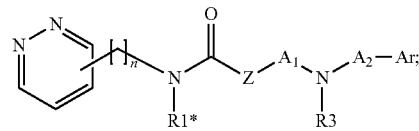
(IIIb-d)

wherein the pyrimidinyl and pyridazinyl ring each may carry 1 to 3 further substituents, and wherein in each case n is an integer of 1 to 3;
the remaining of $R^1$ or $R^2$, designated as $R^{1*}$, is selected from
   hydrogen, and
   optionally substituted alkyl.

8. The method of claim 1 wherein
$A^1$ and $A^2$ are optionally substituted alkanediyl and are the same or different and are independently selected from optionally substituted
   methylene and
   ethane-1,2-diyl, or wherein
   $A^1$ and $R^3$ together with the nitrogen atom to which they are bonded form an optionally substituted 4-membered aliphatic monocyclic ring.

9. The method of claim 1, wherein the compound to be administered is selected from the group consisting of:

| Exp No. | Compound |
|---|---|
| 1 | |
| 7 | |
| 12 | 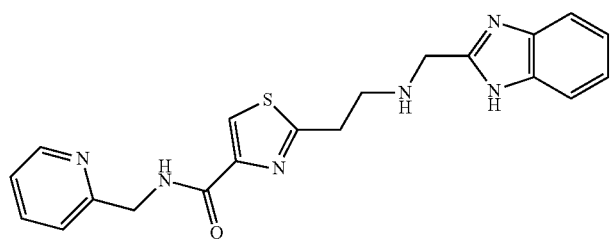 [SMILES: O=C(NCc1ccccn1)c1csc(CCNCc2nc3ccccc3[nH]2)n1] |
| 13 | 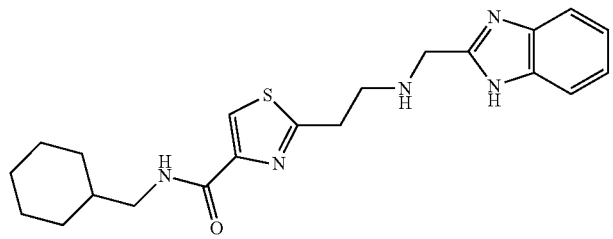 [SMILES: O=C(NCC1CCCCC1)c1csc(CCNCc2nc3ccccc3[nH]2)n1] |
| 14 | 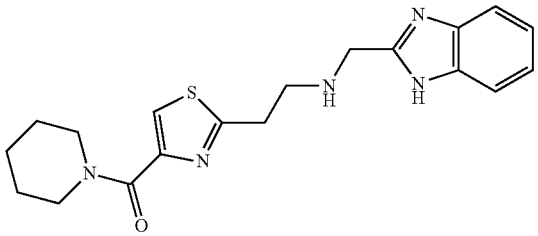 [SMILES: O=C(c1csc(CCNCc2nc3ccccc3[nH]2)n1)N1CCCCC1] |

| Exp No. | Compound |
|---|---|
| 15 | 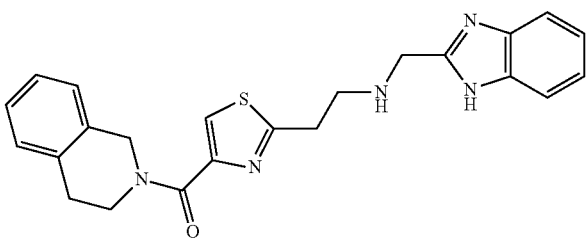 [SMILES: O=C(c1csc(CCNCc2nc3ccccc3[nH]2)n1)N1CCc2ccccc2C1] |
| 16 | 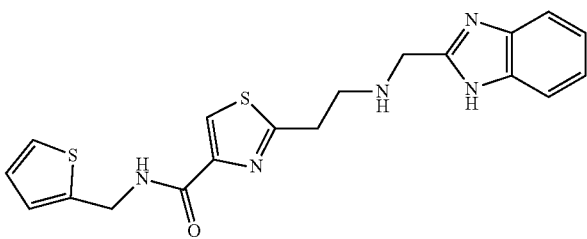 [SMILES: O=C(NCc1cccs1)c1csc(CCNCc2nc3ccccc3[nH]2)n1] |
| 17 | |
| 18 | 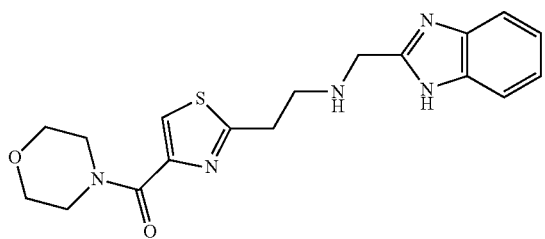 [SMILES: O=C(c1csc(CCNCc2nc3ccccc3[nH]2)n1)N1CCOCC1] |
| 19 | 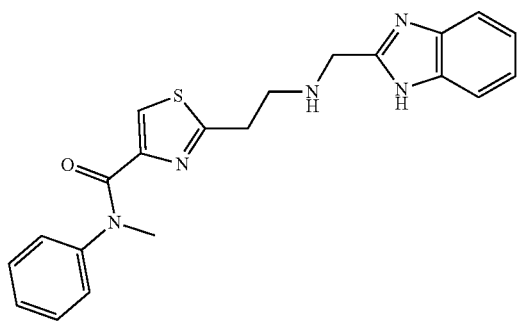 [SMILES: CN(C(=O)c1csc(CCNCc2nc3ccccc3[nH]2)n1)c1ccccc1] |
| 21 | |
| 22 | 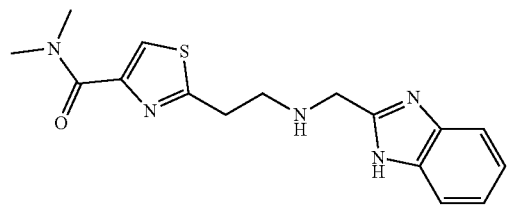 [SMILES: CN(C)C(=O)c1csc(CCNCc2nc3ccccc3[nH]2)n1] |
| 23 | 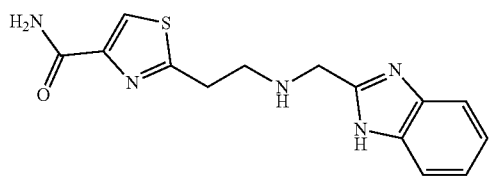 [SMILES: NC(=O)c1csc(CCNCc2nc3ccccc3[nH]2)n1] |

| Exp No. | Compound |
|---|---|
| 25 | |
| 26 | |
| 28 | |
| 29 | |
| 30 | |
| 31 | |
| 32 | |
| 35 | |
| 36 | |
| 37 | |

-continued
| Exp No. | Compound |
|---|---|
| 38 | 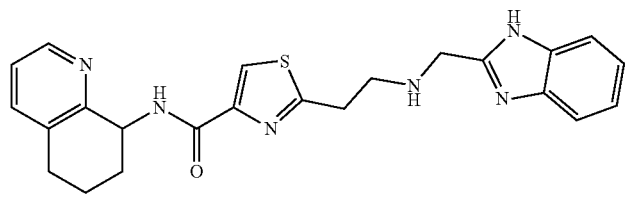 [SMILES: O=C(NC1CCCc2cccnc21)c1csc(CCNCc2nc3ccccc3[nH]2)n1] |
| 39 | 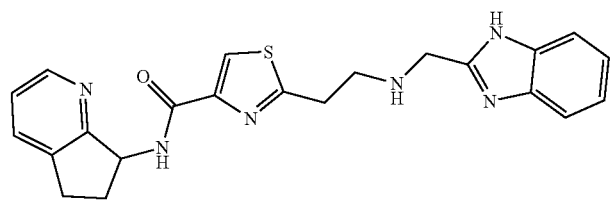 [SMILES: O=C(NC1CCc2cccnc21)c1csc(CCNCc2nc3ccccc3[nH]2)n1] |
| 40 | 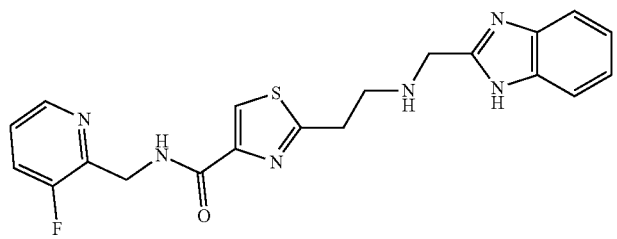 [SMILES: O=C(NCc1ncccc1F)c1csc(CCNCc2nc3ccccc3[nH]2)n1] |
| 41 | 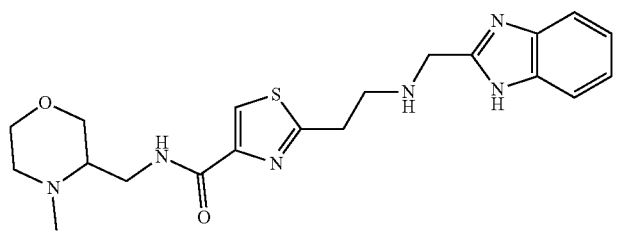 [SMILES: CN1CCOCC1CNC(=O)c1csc(CCNCc2nc3ccccc3[nH]2)n1] |
| 42 | 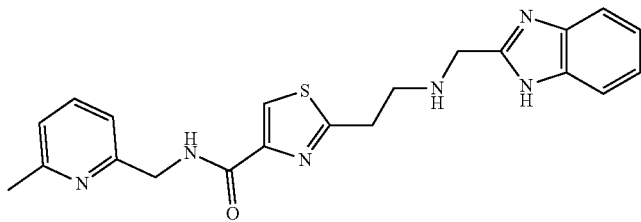 [SMILES: Cc1cccc(CNC(=O)c2csc(CCNCc3nc4ccccc4[nH]3)n2)n1] |
| 43 | 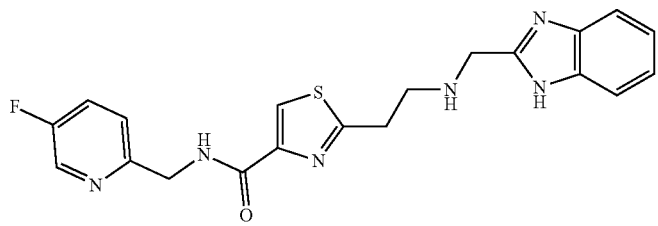 [SMILES: O=C(NCc1ccc(F)cn1)c1csc(CCNCc2nc3ccccc3[nH]2)n1] |

-continued

| Exp No. | Compound |
|---|---|
| 44 | (structure) |
| 45 | (structure) |
| 46 | (structure) |
| 47 | (structure) |
| 48 | (structure) |
| 49 | (structure) |
| 50 | |
| 51 | |
| 52 | |

-continued
| Exp No. | Compound |
|---|---|
| 54 | 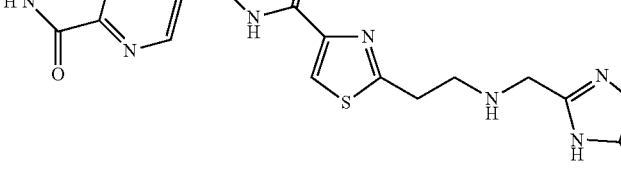 |
| 55 | 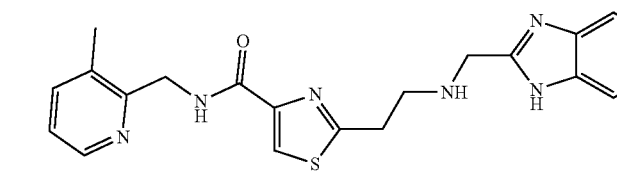 |
| 56 | 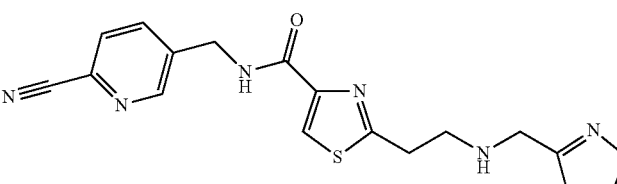 |
| 57 | 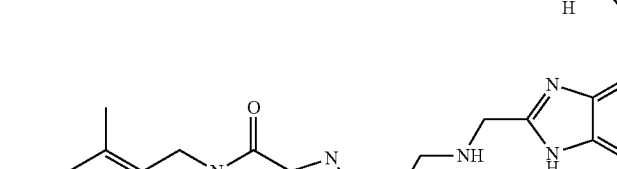 |
| 58 | 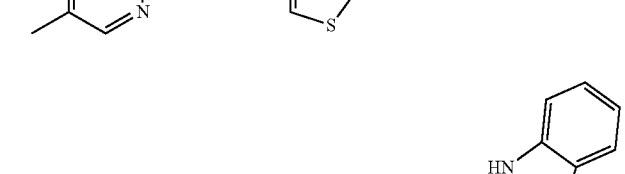 |
| 59 | 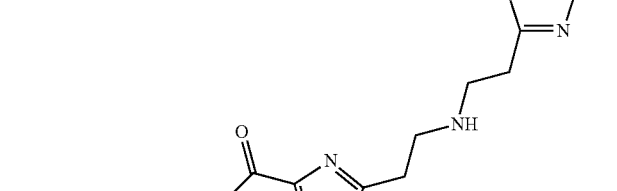 |

| Exp No. | Compound |
|---|---|
| 60 | 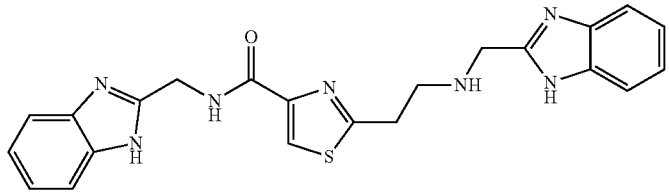 [SMILES: O=C(NCc1nc2ccccc2[nH]1)c1csc(CCNCc2nc3ccccc3[nH]2)n1] |
| 61 | 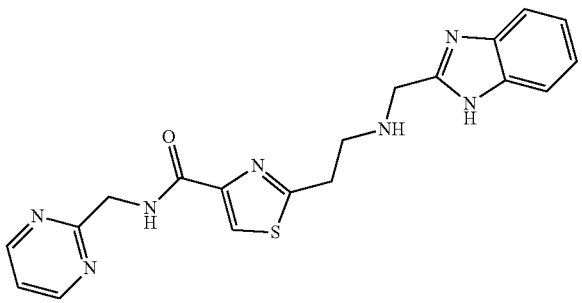 [SMILES: O=C(NCc1ncccn1)c1csc(CCNCc2nc3ccccc3[nH]2)n1] |
| 62 | |
| 63 | |
| 64 | 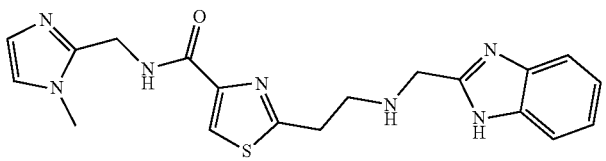 [SMILES: Cn1ccnc1CNC(=O)c1csc(CCNCc2nc3ccccc3[nH]2)n1] |
| 65 | |
| 66 | |
| 67 | |
| 68 | |
| 69 | |
| 70 | |
| 71 | |
| 72 | |
| 73 | |
| 74 | |
| 75 | |
| 76 | 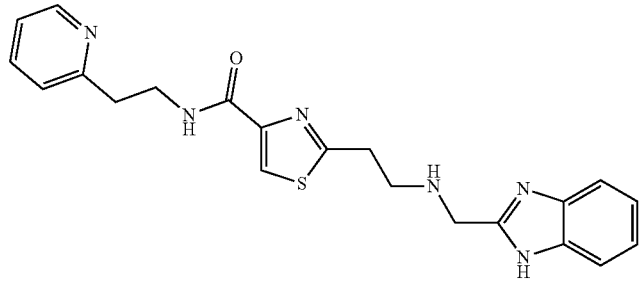 [SMILES: O=C(NCCc1ccccn1)c1csc(CCNCc2nc3ccccc3[nH]2)n1] |
| 77 | 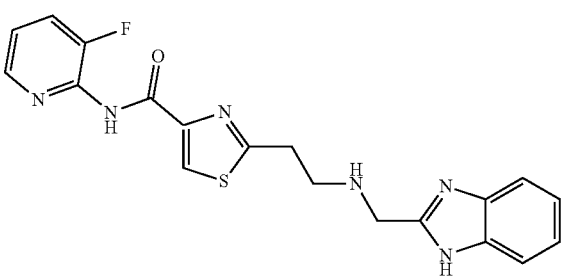 [SMILES: O=C(Nc1ncccc1F)c1csc(CCNCc2nc3ccccc3[nH]2)n1] |

-continued

| Exp No. | Compound |
|---|---|
| 78 | |
| 79 | |
| 80 | |
| 81 | |
| 82 | |
| 83 | |
| 84 | |

-continued

| Exp No. | Compound |
|---|---|
| 85 | *(chemical structure: oxazol-2-ylmethyl-NH-C(O)-thiazole-CH2CH2-NH-CH2-benzimidazole)* |
| 86 | *(chemical structure: (1-methyl-1H-pyrazol-3-yl)methyl-NH-C(O)-thiazole-CH2CH2-NH-CH2-benzimidazole)* |
| 87 | *(chemical structure: pyridazin-3-ylmethyl-NH-C(O)-thiazole-CH2CH2-NH-CH2-benzimidazole)* |
| 88 | *(chemical structure: (1-methyl-1H-pyrazol-5-yl)methyl-NH-C(O)-thiazole-CH2CH2-NH-CH2-benzimidazole)* |
| 89 | *(chemical structure: (3-fluoropyridin-4-yl)methyl-NH-C(O)-thiazole-CH2CH2-NH-CH2-benzimidazole)* |
| 90 | *(chemical structure: (3-methylpyridin-4-yl)methyl-NH-C(O)-thiazole-CH2CH2-NH-CH2-benzimidazole)* |
| 91 | *(chemical structure: (1-methyl-1H-pyrazol-4-yl)methyl-NH-C(O)-thiazole-CH2CH2-NH-CH2-benzimidazole)* |

-continued
| Exp No. | Compound |
|---|---|
| 92 | 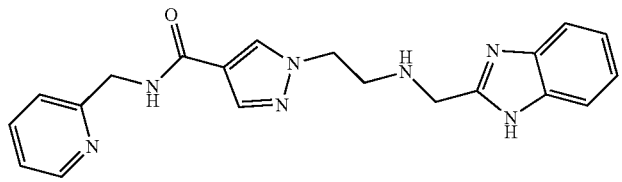 [SMILES: O=C(NCc1ccccn1)c1cnn(CCNCc2nc3ccccc3[nH]2)c1] |
| 93 | 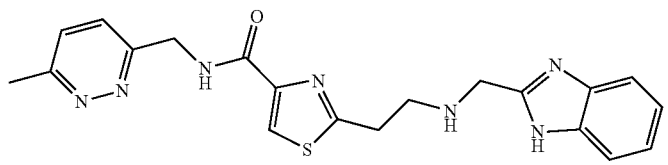 [SMILES: Cc1ccc(CNC(=O)c2csc(CCNCc3nc4ccccc4[nH]3)n2)nn1] |
| 94 | 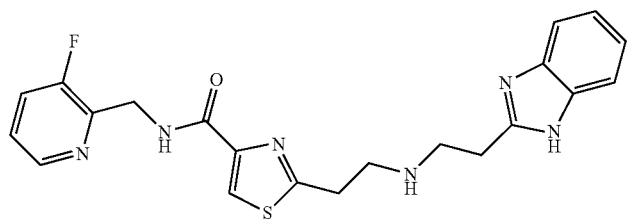 [SMILES: O=C(NCc1ncccc1F)c1csc(CCNCCc2nc3ccccc3[nH]2)n1] |
| 95 | 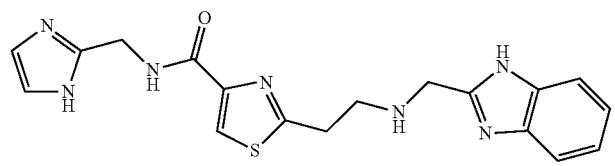 [SMILES: O=C(NCc1ncc[nH]1)c1csc(CCNCc2nc3ccccc3[nH]2)n1] |
| 96 | 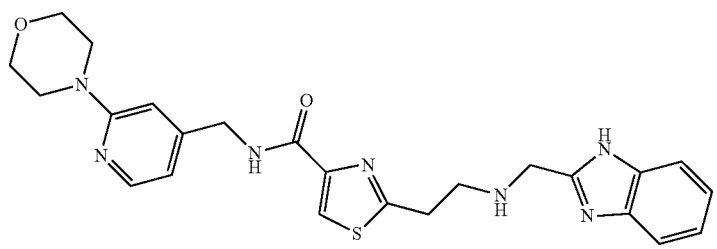 [SMILES: O=C(NCc1ccnc(N2CCOCC2)c1)c1csc(CCNCc2nc3ccccc3[nH]2)n1] |
| 97 | 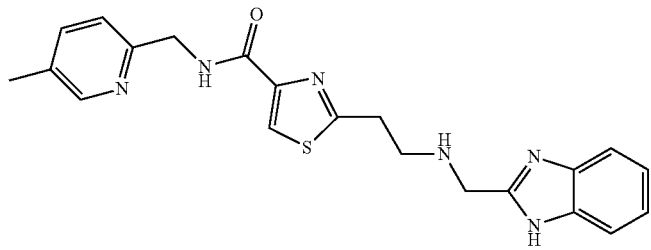 [SMILES: Cc1ccc(CNC(=O)c2csc(CCNCc3nc4ccccc4[nH]3)n2)nc1] |
| 98 | 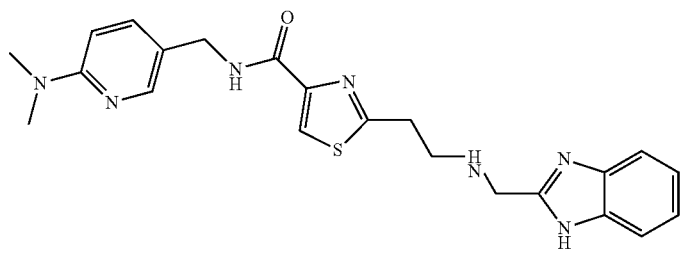 [SMILES: CN(C)c1ccc(CNC(=O)c2csc(CCNCc3nc4ccccc4[nH]3)n2)cn1] |

-continued
| Exp No. | Compound |
|---|---|
| 99 | 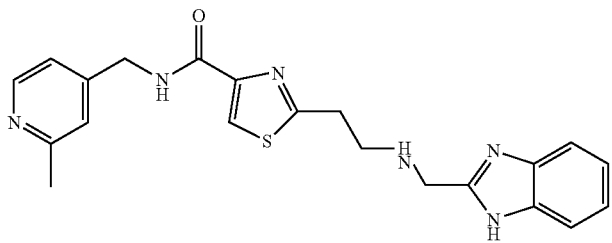 [SMILES: Cc1cc(CNC(=O)c2csc(CCNCc3nc4ccccc4[nH]3)n2)ccn1] |
| 100 | 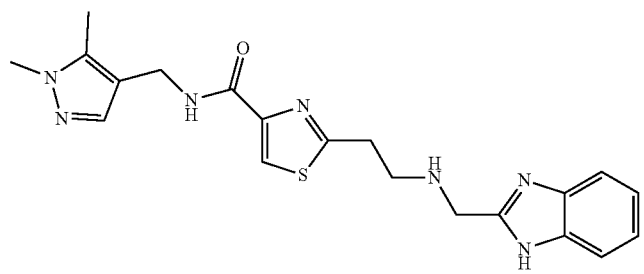 [SMILES: Cc1c(CNC(=O)c2csc(CCNCc3nc4ccccc4[nH]3)n2)cnn1C] |
| 101 | 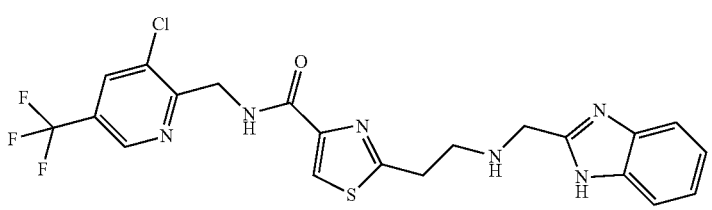 [SMILES: O=C(NCc1ncc(C(F)(F)F)cc1Cl)c1csc(CCNCc2nc3ccccc3[nH]2)n1] |
| 102 | 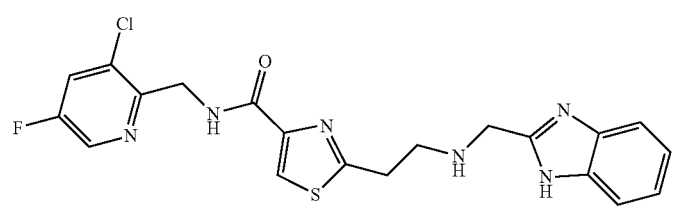 [SMILES: O=C(NCc1ncc(F)cc1Cl)c1csc(CCNCc2nc3ccccc3[nH]2)n1] |
| 103 | 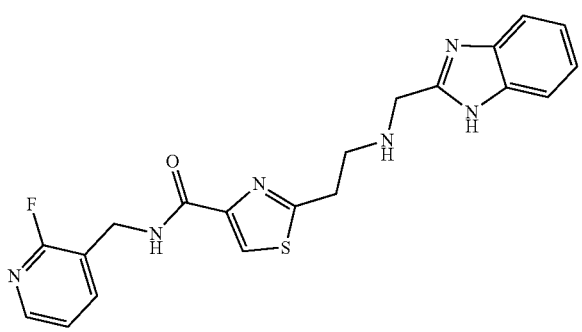 [SMILES: O=C(NCc1cccnc1F)c1csc(CCNCc2nc3ccccc3[nH]2)n1] |
| 104 | 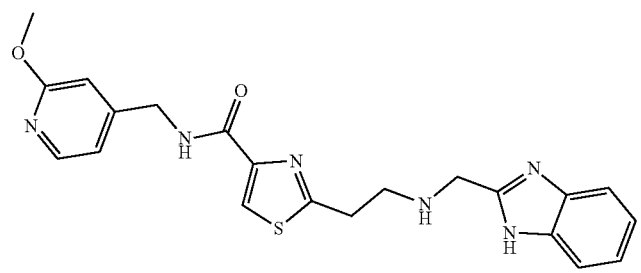 [SMILES: COc1cc(CNC(=O)c2csc(CCNCc3nc4ccccc4[nH]3)n2)ccn1] |

-continued
| Exp No. | Compound |
|---|---|
| 105 | 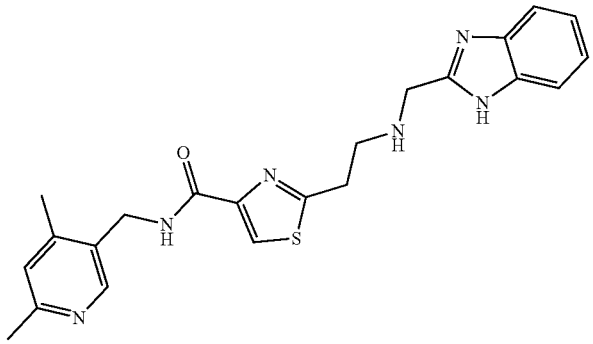 [SMILES: Cc1cc(C)c(CNC(=O)c2csc(CCNCc3nc4ccccc4[nH]3)n2)cn1] |
| 106 | 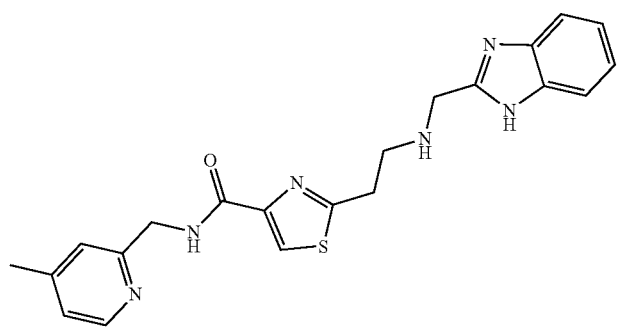 [SMILES: Cc1ccnc(CNC(=O)c2csc(CCNCc3nc4ccccc4[nH]3)n2)c1] |
| 107 | 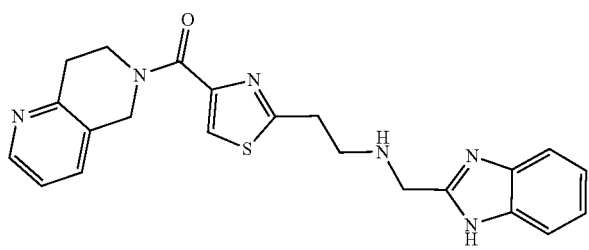 [SMILES: O=C(c1csc(CCNCc2nc3ccccc3[nH]2)n1)N1CCc2ncccc2C1] |
| 108 | 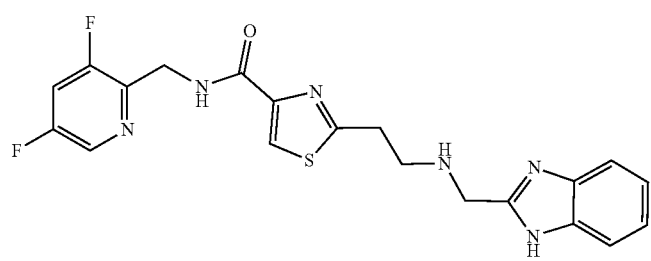 [SMILES: O=C(NCc1ncc(F)cc1F)c1csc(CCNCc2nc3ccccc3[nH]2)n1] |
| 109 | 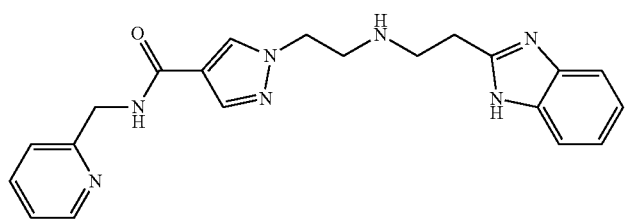 [SMILES: O=C(NCc1ccccn1)c1cnn(CCNCCc2nc3ccccc3[nH]2)c1] |

| Exp No. | Compound |
|---|---|
| 110 | 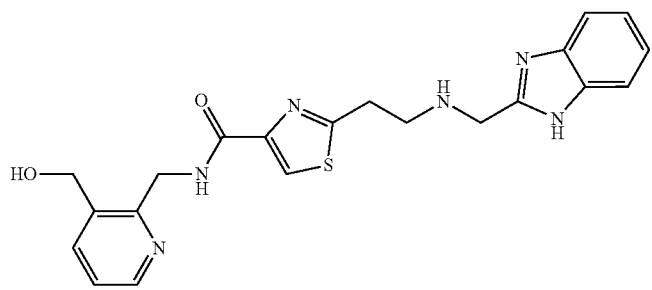 [SMILES: O=C(NCc1ncccc1CO)c1csc(CCNCc2nc3ccccc3[nH]2)n1] |
| 111 | 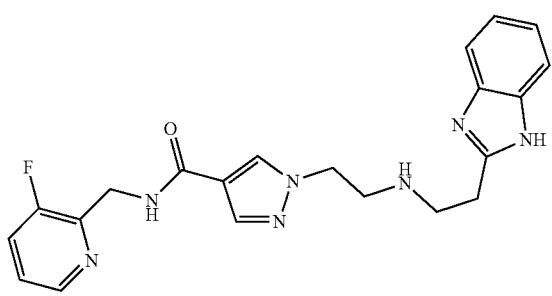 [SMILES: O=C(NCc1ncccc1F)c1cnn(CCNCCc2nc3ccccc3[nH]2)c1] |
| 112 | 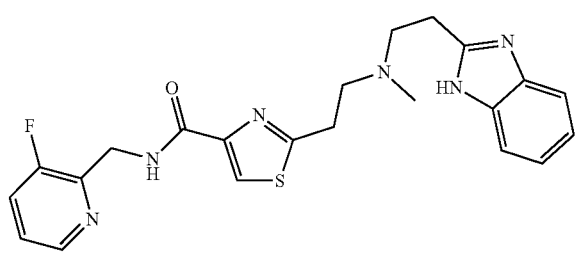 [SMILES: CN(CCc1nc2ccccc2[nH]1)CCc1nc(C(=O)NCc2ncccc2F)cs1] |
| 113 | 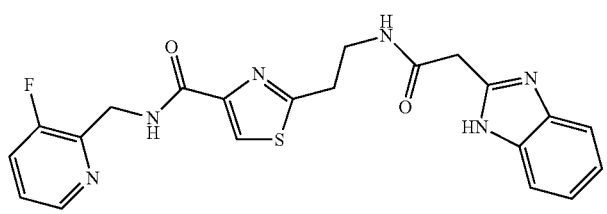 [SMILES: O=C(Cc1nc2ccccc2[nH]1)NCCc1nc(C(=O)NCc2ncccc2F)cs1] |
| 114 | 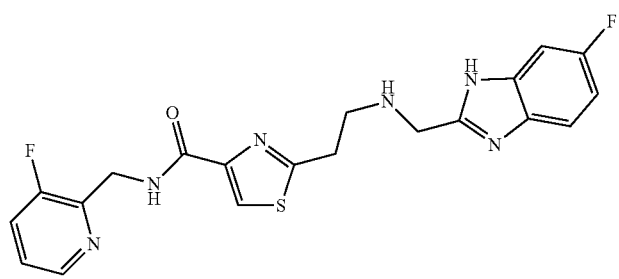 [SMILES: O=C(NCc1ncccc1F)c1csc(CCNCc2nc3ccc(F)cc3[nH]2)n1] |

-continued

| Exp No. | Compound |
|---|---|
| 116 | |
| 117 | |
| 118 | |
| 119 | |
| 120 | |
| 121 | |

| Exp No. | Compound |
|---|---|
| 122 | 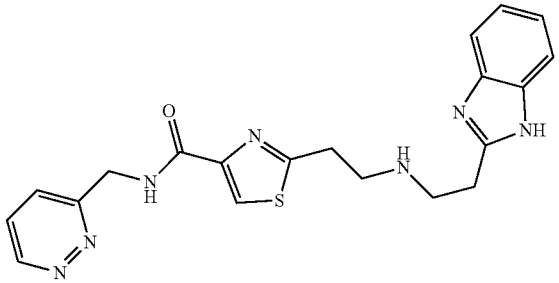 [SMILES: O=C(NCc1cccnn1)c1csc(CCNCCc2nc3ccccc3[nH]2)n1] |
| 123 | 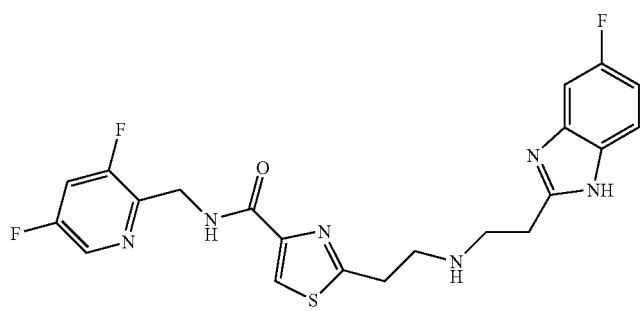 [SMILES: O=C(NCc1ncc(F)cc1F)c1csc(CCNCCc2nc3cc(F)ccc3[nH]2)n1] |
| 124 | 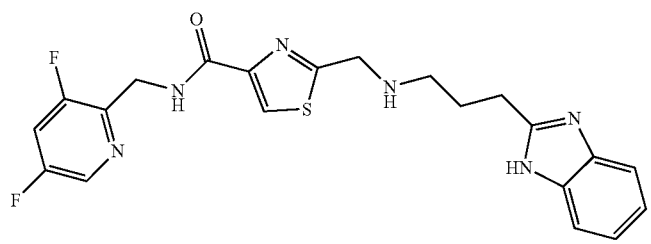 [SMILES: O=C(NCc1ncc(F)cc1F)c1csc(CNCCCc2nc3ccccc3[nH]2)n1] |
| 125 | 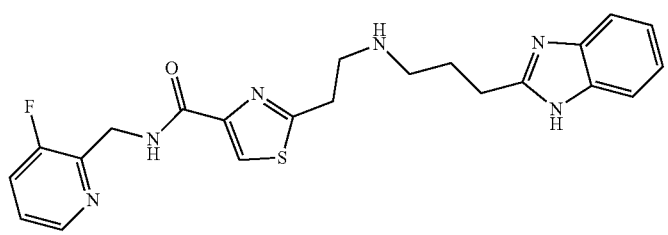 [SMILES: O=C(NCc1ncccc1F)c1csc(CCNCCCc2nc3ccccc3[nH]2)n1] |
| 126 | 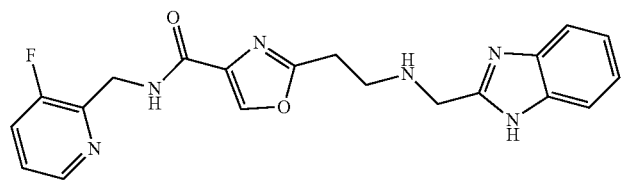 [SMILES: O=C(NCc1ncccc1F)c1coc(CCNCc2nc3ccccc3[nH]2)n1] |
| 127 | 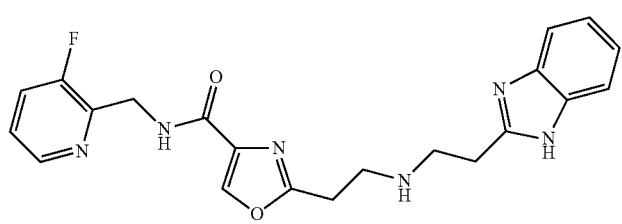 [SMILES: O=C(NCc1ncccc1F)c1coc(CCNCCc2nc3ccccc3[nH]2)n1] |

-continued
| Exp No. | Compound |
|---|---|
| 128 | 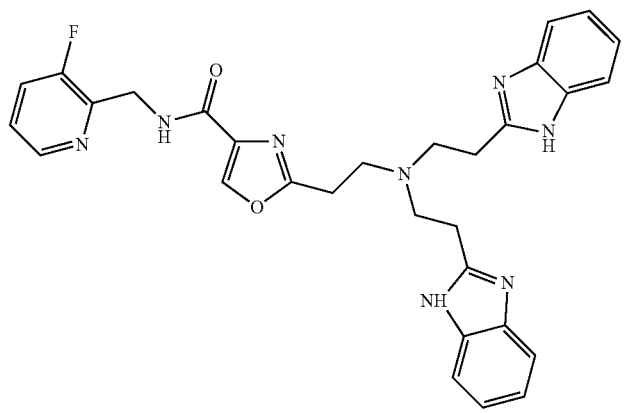 [SMILES: O=C(NCc1ncccc1F)c1coc(CCN(CCc2nc3ccccc3[nH]2)CCc2nc3ccccc3[nH]2)n1] |
| 129 | 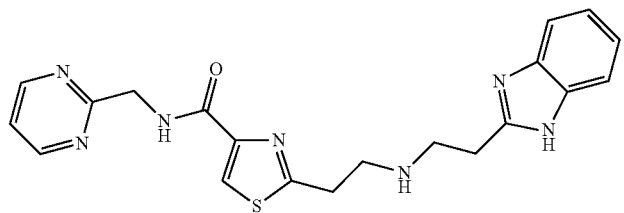 [SMILES: O=C(NCc1ncccn1)c1csc(CCNCCc2nc3ccccc3[nH]2)n1] |
| 131 | 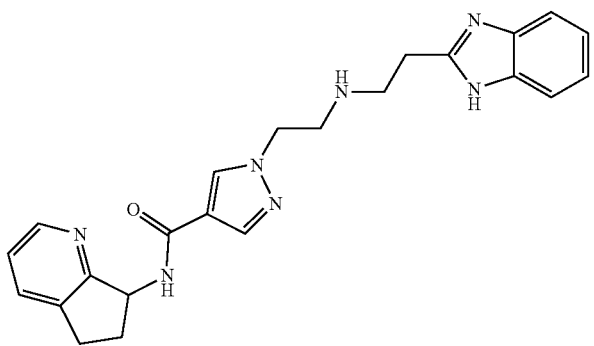 [SMILES: O=C(NC1CCc2cccnc21)c1cnn(CCNCCc2nc3ccccc3[nH]2)c1] |
| 132 | 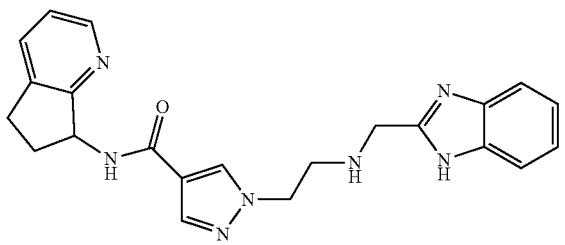 [SMILES: O=C(NC1CCc2cccnc21)c1cnn(CCNCc2nc3ccccc3[nH]2)c1] |

| Exp No. | Compound |
|---|---|
| 133 | 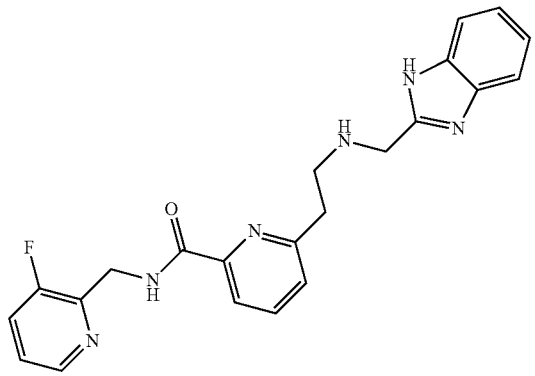 [SMILES: O=C(NCc1ncccc1F)c1cccc(CCNCc2nc3ccccc3[nH]2)n1] |
| 134 | 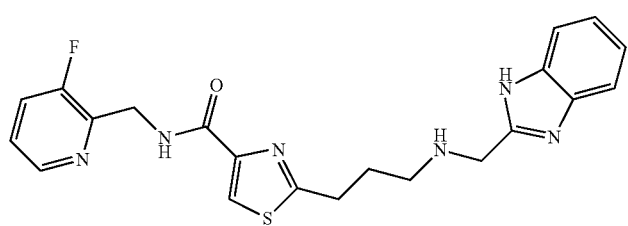 [SMILES: O=C(NCc1ncccc1F)c1csc(CCCNCc2nc3ccccc3[nH]2)n1] |
| 135 | 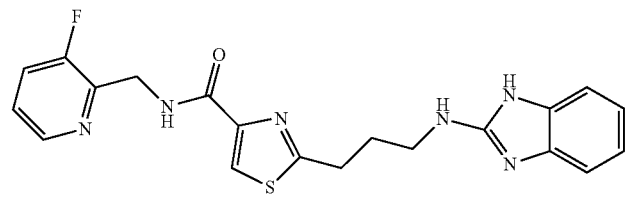 [SMILES: O=C(NCc1ncccc1F)c1csc(CCCNc2nc3ccccc3[nH]2)n1] |
| 136 | 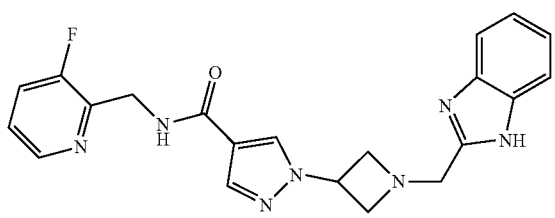 [SMILES: O=C(NCc1ncccc1F)c1cnn(C2CN(Cc3nc4ccccc4[nH]3)C2)c1] |
| 137 | 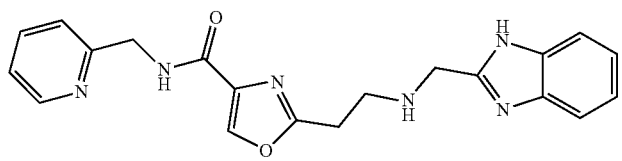 [SMILES: O=C(NCc1ccccn1)c1coc(CCNCc2nc3ccccc3[nH]2)n1] |
| 138 | 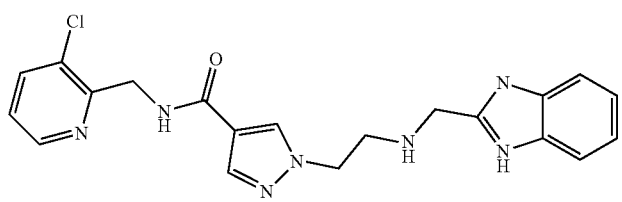 [SMILES: O=C(NCc1ncccc1Cl)c1cnn(CCNCc2nc3ccccc3[nH]2)c1] |

| Exp No. | Compound |
|---|---|
| 141 | 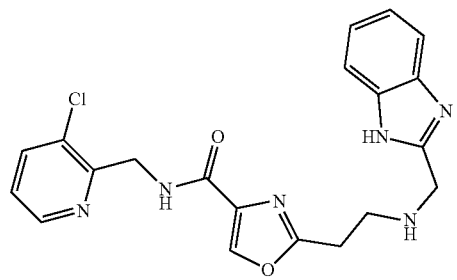 [SMILES: O=C(NCc1ncccc1Cl)c1coc(CCNCc2nc3ccccc3[nH]2)n1] |
| 142 | 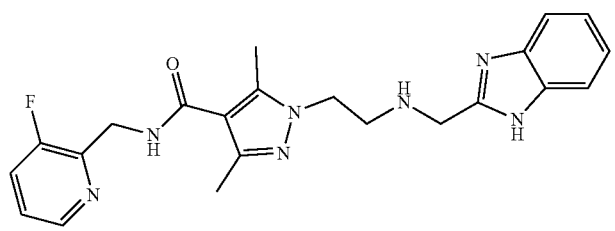 [SMILES: Cc1nn(CCNCc2nc3ccccc3[nH]2)c(C)c1C(=O)NCc1ncccc1F] |
| 144 | 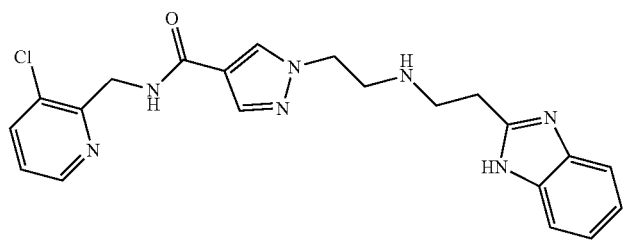 [SMILES: O=C(NCc1ncccc1Cl)c1cnn(CCNCCc2nc3ccccc3[nH]2)c1] |
| 145 | 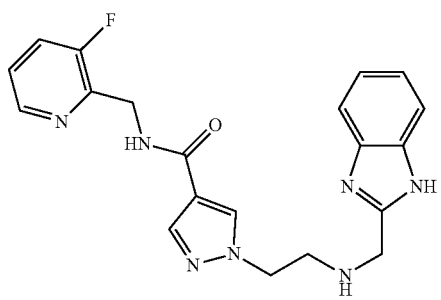 [SMILES: O=C(NCc1ncccc1F)c1cnn(CCNCc2nc3ccccc3[nH]2)c1] |
| 146 | 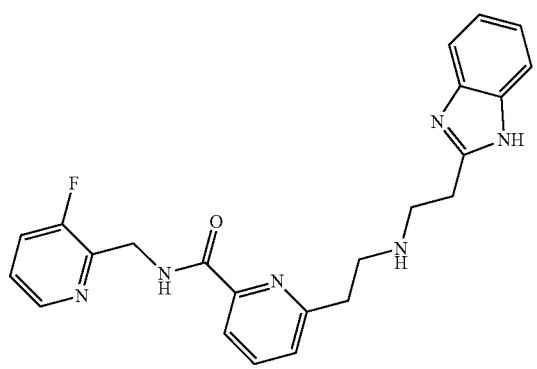 [SMILES: O=C(NCc1ncccc1F)c1cccc(CCNCCc2nc3ccccc3[nH]2)n1] |

| Exp No. | Compound |
|---|---|
| 147 | 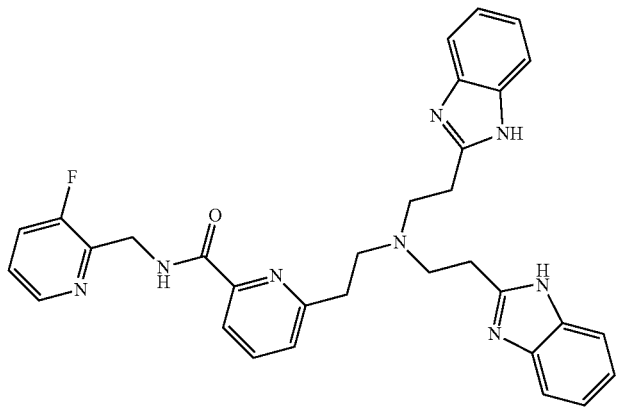 [SMILES: O=C(NCc1ncccc1F)c1cccc(CCN(CCc2nc3ccccc3[nH]2)CCc2nc3ccccc3[nH]2)n1] |
| 148 | 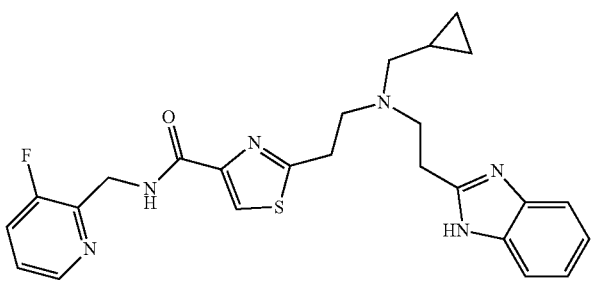 [SMILES: O=C(NCc1ncccc1F)c1csc(CCN(CCc2nc3ccccc3[nH]2)CC2CC2)n1] |
| 149 | 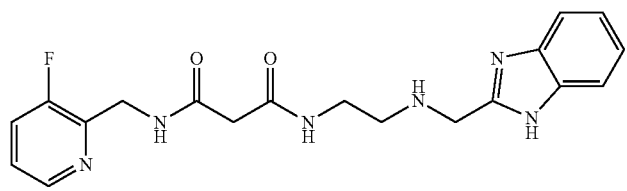 [SMILES: O=C(CC(=O)NCc1ncccc1F)NCCNCc1nc2ccccc2[nH]1] |
| 150 | 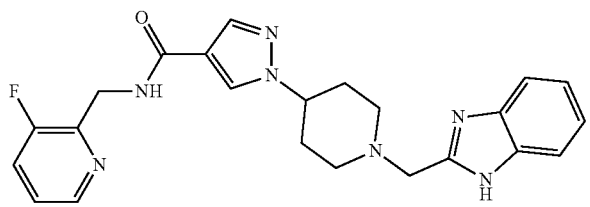 [SMILES: O=C(NCc1ncccc1F)c1cnn(C2CCN(Cc3nc4ccccc4[nH]3)CC2)c1] |
| 151 | 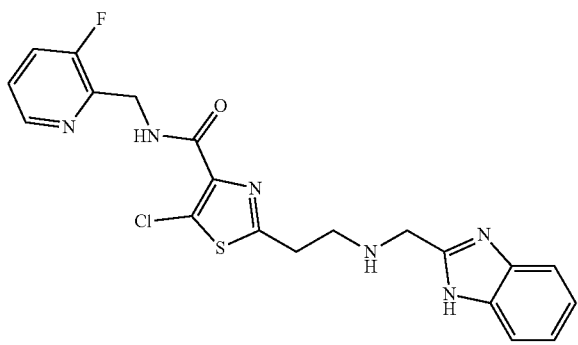 [SMILES: O=C(NCc1ncccc1F)c1nc(CCNCc2nc3ccccc3[nH]2)sc1Cl] |

-continued
| Exp No. | Compound |
|---|---|
| 152 | 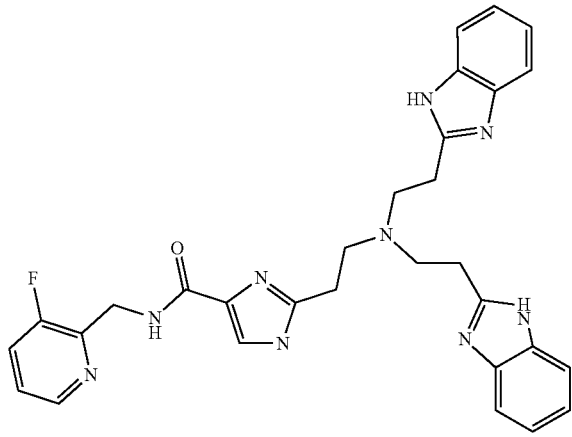 [SMILES: O=C(NCc1ncccc1F)c1c[nH]c(CCN(CCc2nc3ccccc3[nH]2)CCc2nc3ccccc3[nH]2)n1] |
| 153 | 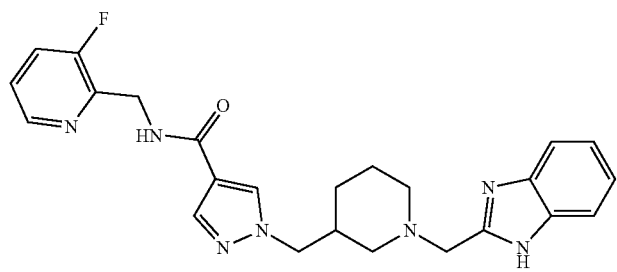 [SMILES: O=C(NCc1ncccc1F)c1cnn(CC2CCCN(Cc3nc4ccccc4[nH]3)C2)c1] |
| 154 | 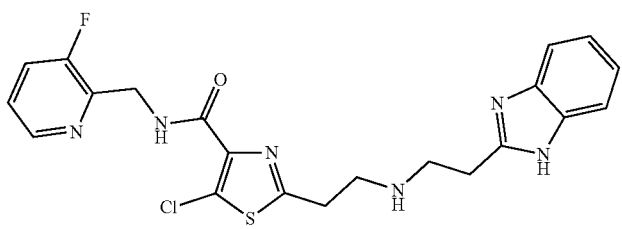 [SMILES: O=C(NCc1ncccc1F)c1nc(CCNCCc2nc3ccccc3[nH]2)sc1Cl] |
| 155 | 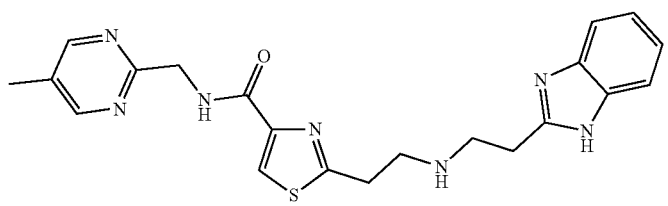 [SMILES: Cc1cnc(CNC(=O)c2csc(CCNCCc3nc4ccccc4[nH]3)n2)nc1] |
| 156 | 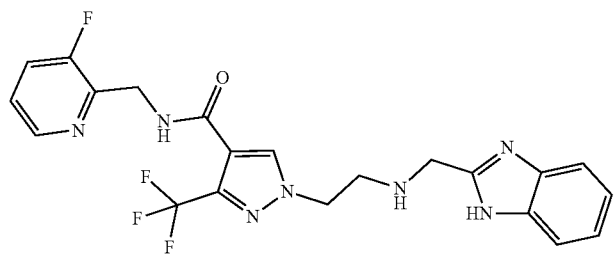 [SMILES: O=C(NCc1ncccc1F)c1cn(CCNCc2nc3ccccc3[nH]2)nc1C(F)(F)F] |

-continued
| Exp No. | Compound |
|---|---|
| 157 | 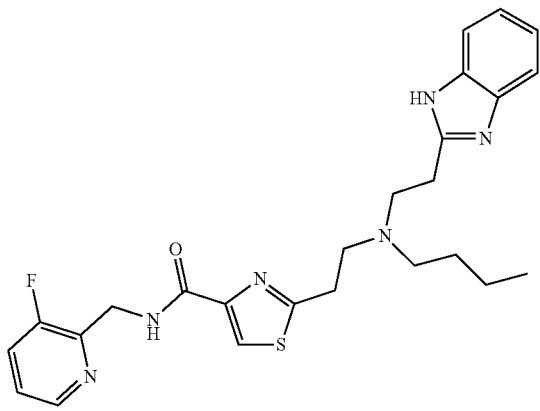 [SMILES: CCCCN(CCc1nc2ccccc2[nH]1)CCc1nc(C(=O)NCc2ncccc2F)cs1] |
| 158 | 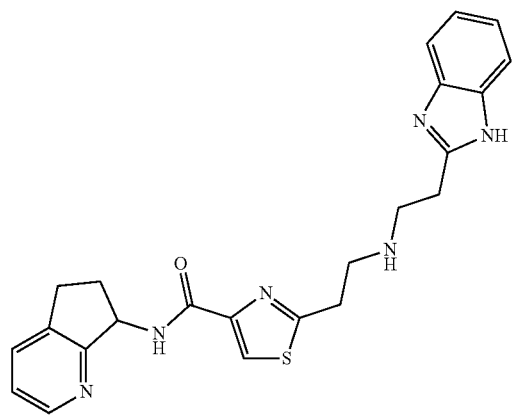 [SMILES: O=C(NC1CCc2cccnc21)c1csc(CCNCCc2nc3ccccc3[nH]2)n1] |
| 159 | 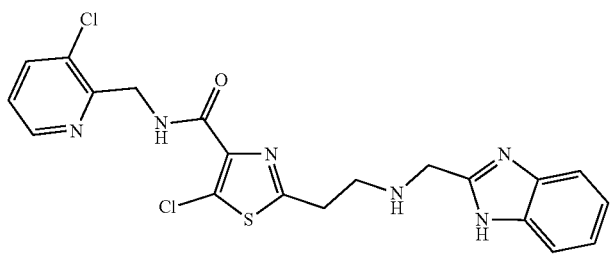 [SMILES: O=C(NCc1ncccc1Cl)c1nc(CCNCc2nc3ccccc3[nH]2)sc1Cl] |
| 160 | 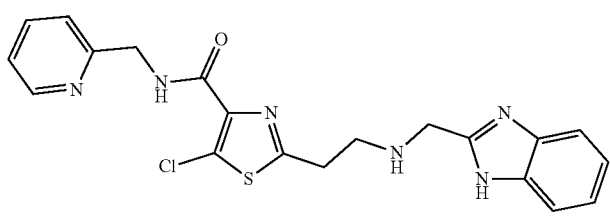 [SMILES: O=C(NCc1ccccn1)c1nc(CCNCc2nc3ccccc3[nH]2)sc1Cl] |
| 161 | 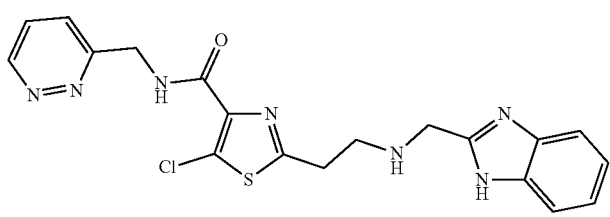 [SMILES: O=C(NCc1cccnn1)c1nc(CCNCc2nc3ccccc3[nH]2)sc1Cl] |

-continued
| Exp No. | Compound |
|---|---|
| 162 | 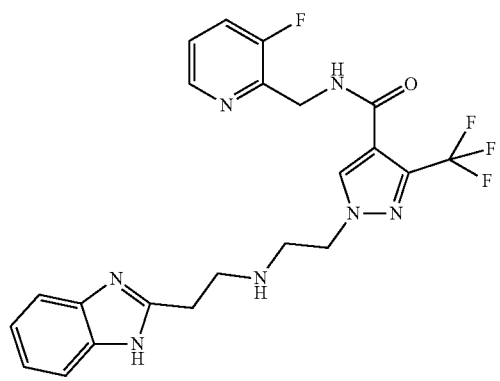 [SMILES: O=C(NCc1ncccc1F)c1cn(CCNCCc2nc3ccccc3[nH]2)nc1C(F)(F)F] |
| 163 | 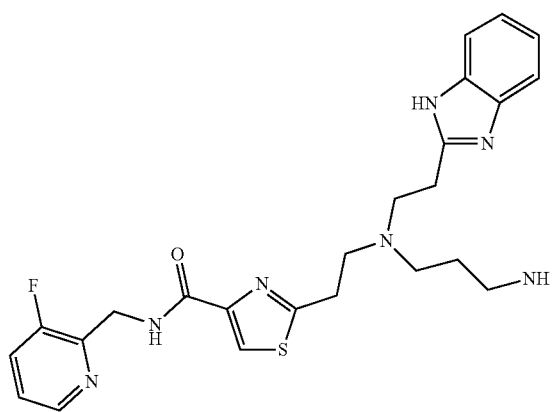 [SMILES: NCCCN(CCc1nc2ccccc2[nH]1)CCc1nc(C(=O)NCc2ncccc2F)cs1] |
| 164 | 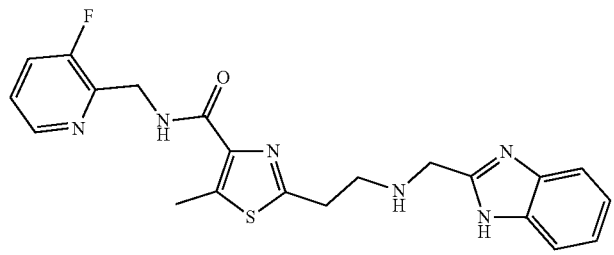 [SMILES: Cc1sc(CCNCc2nc3ccccc3[nH]2)nc1C(=O)NCc1ncccc1F] |
| 165 | 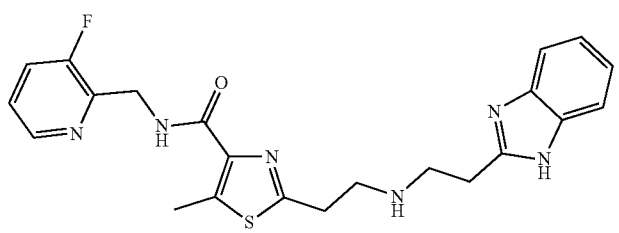 [SMILES: Cc1sc(CCNCCc2nc3ccccc3[nH]2)nc1C(=O)NCc1ncccc1F] |

-continued
| Exp No. | Compound |
|---|---|
| 166 | 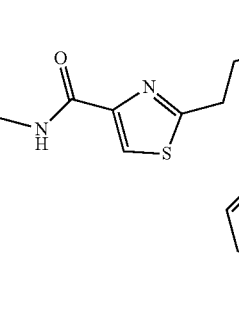 |
| 167 | 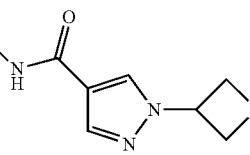 |
| 168 | 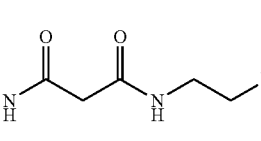 |
| 169 |  |
| 170 | 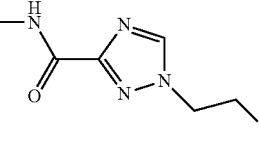 |

-continued
| Exp No. | Compound |
|---|---|
| 171 | 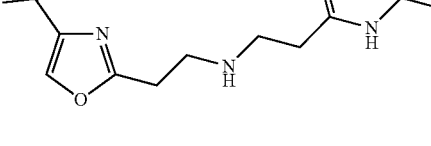 |
| 172 | 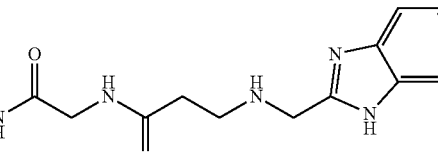 |
| 173 |  |
| 174 | 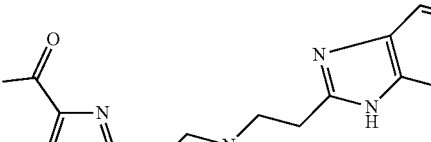 |
| 175 | 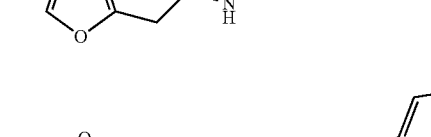 |
| 176 | 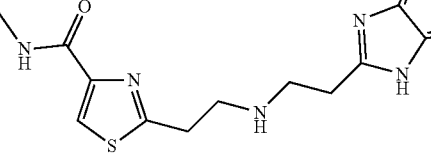 |

| Exp No. | Compound |
|---|---|
| 177 | |
| 178 | |
| 179 | |
| 180 | |
| 181 | |

| Exp No. | Compound |
|---|---|
| 182 | 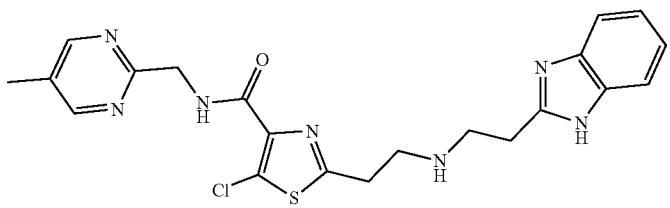 [SMILES: Cc1cnc(CNC(=O)c2nc(CCNCCc3nc4ccccc4[nH]3)sc2Cl)nc1] |
| 183 | 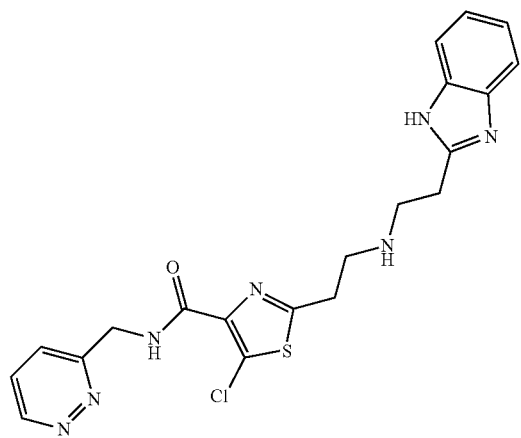 [SMILES: O=C(NCc1cccnn1)c1nc(CCNCCc2nc3ccccc3[nH]2)sc1Cl] |
| 184 | 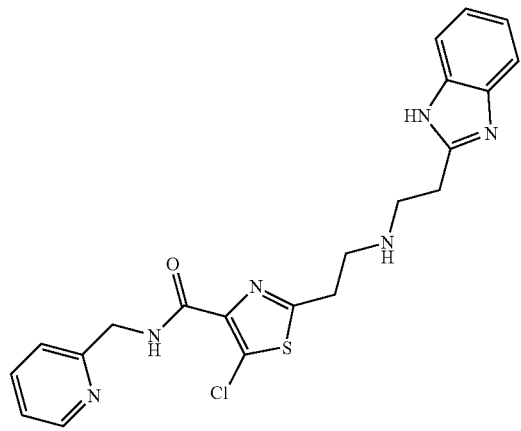 [SMILES: O=C(NCc1ccccn1)c1nc(CCNCCc2nc3ccccc3[nH]2)sc1Cl] |
| 185 | 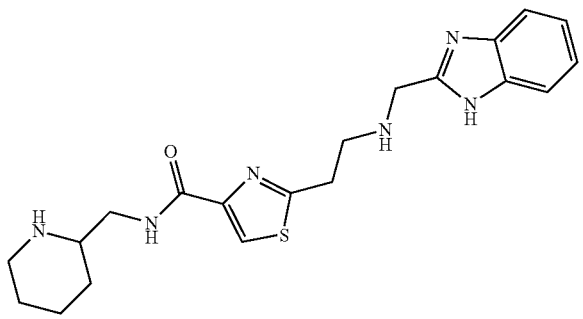 [SMILES: O=C(NCC1CCCCN1)c1csc(CCNCc2nc3ccccc3[nH]2)n1] |

-continued
| Exp No. | Compound |
|---|---|
| 186 | 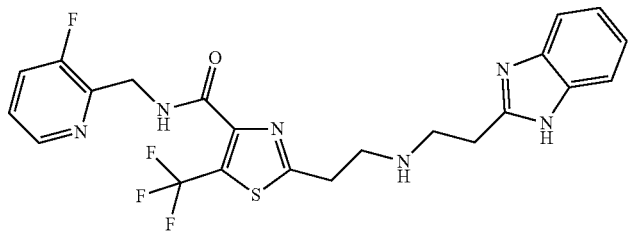 [SMILES: O=C(NCc1ncccc1F)c1nc(CCNCCc2nc3ccccc3[nH]2)sc1C(F)(F)F] |
| 187 | 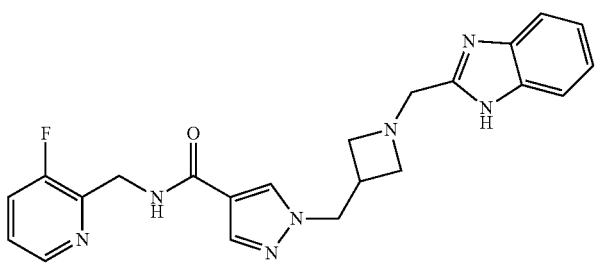 [SMILES: O=C(NCc1ncccc1F)c1cnn(CC2CN(Cc3nc4ccccc4[nH]3)C2)c1] |
| 188 | 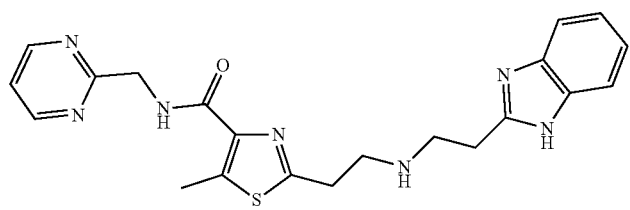 [SMILES: Cc1sc(CCNCCc2nc3ccccc3[nH]2)nc1C(=O)NCc1ncccn1] |
| 189 | 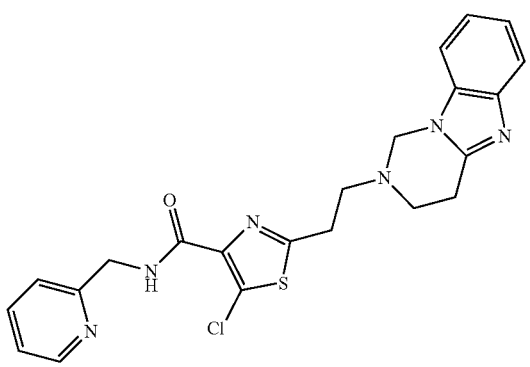 [SMILES: O=C(NCc1ccccn1)c1nc(CCN2CCc3nc4ccccc4n3C2)sc1Cl] |
| 190 | 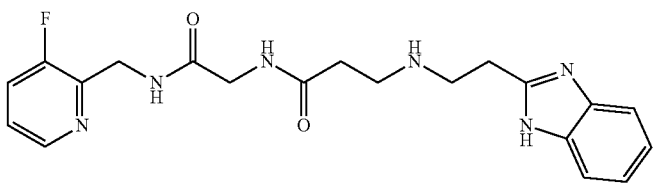 [SMILES: O=C(CCNCCc1nc2ccccc2[nH]1)NCC(=O)NCc1ncccc1F] |
| 191 | 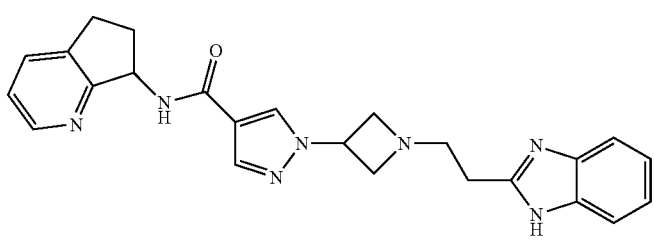 [SMILES: O=C(NC1CCc2cccnc21)c1cnn(C2CN(CCc3nc4ccccc4[nH]3)C2)c1] |

| Exp No. | Compound |
|---|---|
| 192 | 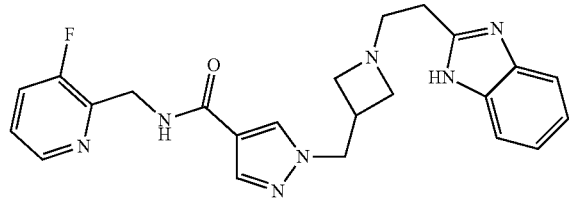 [SMILES: O=C(NCc1ncccc1F)c1cnn(CC2CN(CCc3nc4ccccc4[nH]3)C2)c1] |
| 193 | 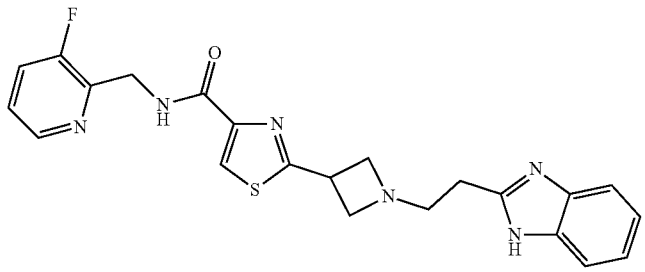 [SMILES: O=C(NCc1ncccc1F)c1csc(C2CN(CCc3nc4ccccc4[nH]3)C2)n1] |
| 194 | 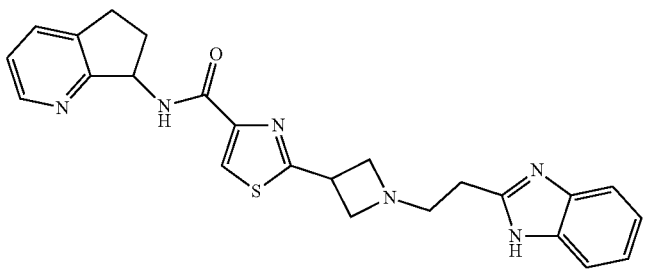 [SMILES: O=C(NC1CCc2cccnc21)c1csc(C2CN(CCc3nc4ccccc4[nH]3)C2)n1] |
| 195 | 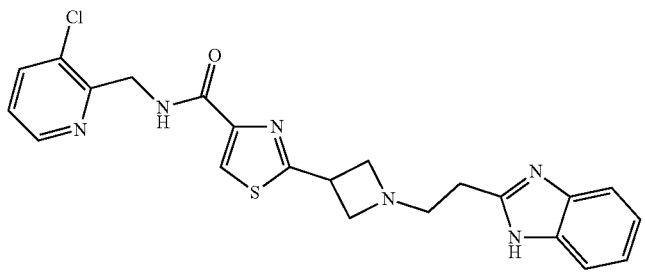 [SMILES: O=C(NCc1ncccc1Cl)c1csc(C2CN(CCc3nc4ccccc4[nH]3)C2)n1] |
| 196 | 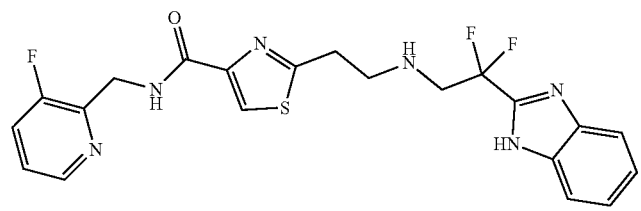 [SMILES: O=C(NCc1ncccc1F)c1csc(CCNCC(F)(F)c2nc3ccccc3[nH]2)n1] |
| 197 | 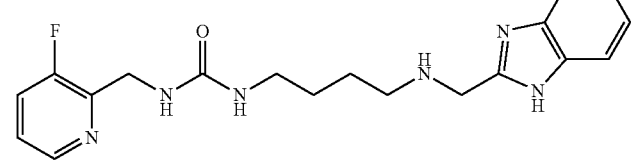 |

| Exp No. | Compound |
|---|---|
| 198 | 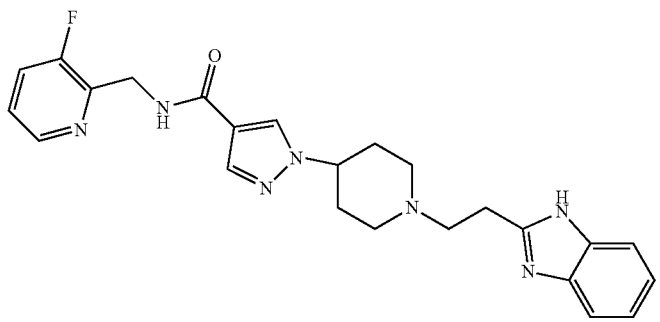 [SMILES: O=C(NCc1ncccc1F)c1cnn(C2CCN(CCc3nc4ccccc4[nH]3)CC2)c1] |
| 199 | 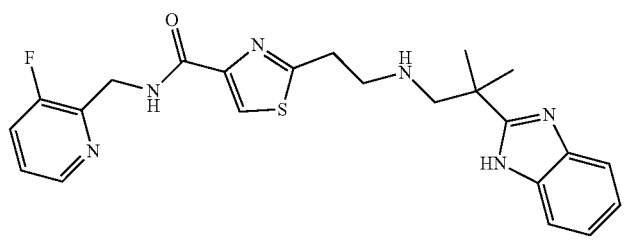 [SMILES: CC(C)(CNCCc1nc(C(=O)NCc2ncccc2F)cs1)c1nc2ccccc2[nH]1] |
| 200 | 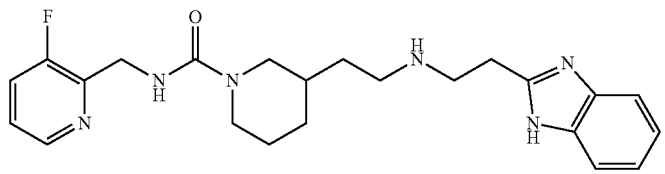 [SMILES: O=C(NCc1ncccc1F)N1CCCC(CCNCCc2nc3ccccc3[nH]2)C1] |
| 201 | 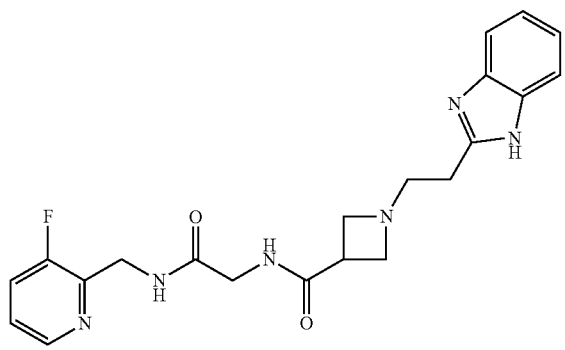 [SMILES: O=C(CNC(=O)C1CN(CCc2nc3ccccc3[nH]2)C1)NCc1ncccc1F] |
| 202 | 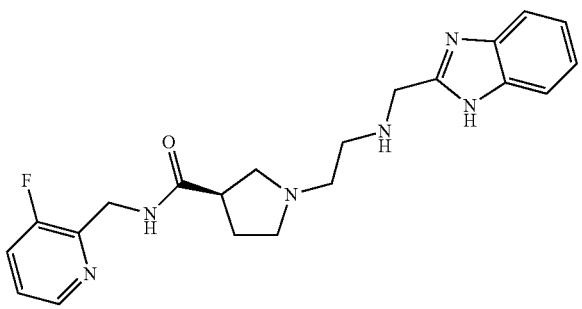 [SMILES: O=C(NCc1ncccc1F)[C@@H]1CCN(CCNCc2nc3ccccc3[nH]2)C1] |

| Exp No. | Compound |
|---|---|
| 204 | 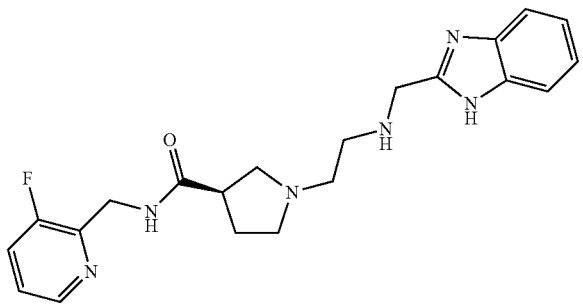 [SMILES: O=C(NCc1ncccc1F)[C@@H]1CCN(CCNCc2nc3ccccc3[nH]2)C1] |
| 205 | 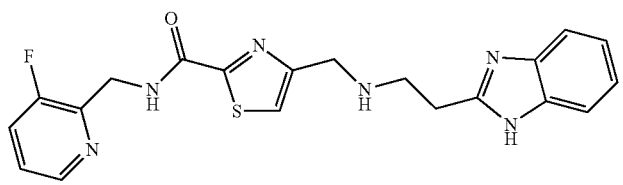 [SMILES: O=C(NCc1ncccc1F)c1nc(CNCCc2nc3ccccc3[nH]2)cs1] |
| 206 | 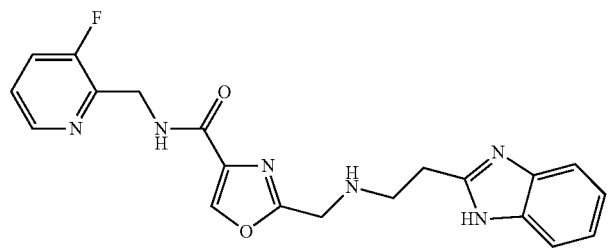 [SMILES: O=C(NCc1ncccc1F)c1coc(CNCCc2nc3ccccc3[nH]2)n1] |
| 207 | 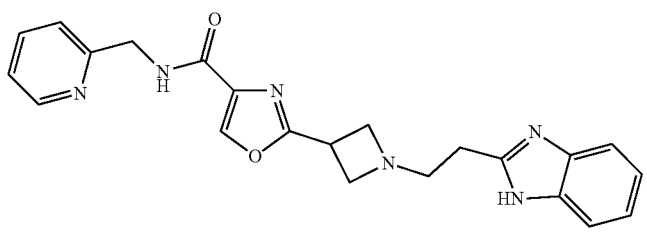 [SMILES: O=C(NCc1ccccn1)c1coc(C2CN(CCc3nc4ccccc4[nH]3)C2)n1] |
| 208 | 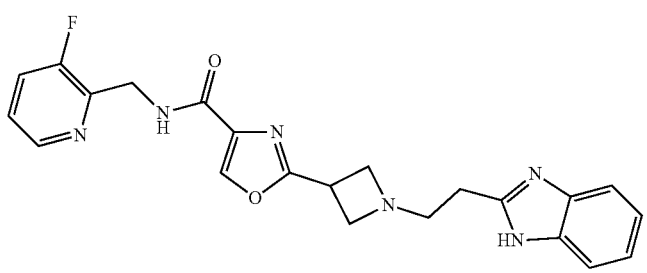 [SMILES: O=C(NCc1ncccc1F)c1coc(C2CN(CCc3nc4ccccc4[nH]3)C2)n1] |
| 209 | 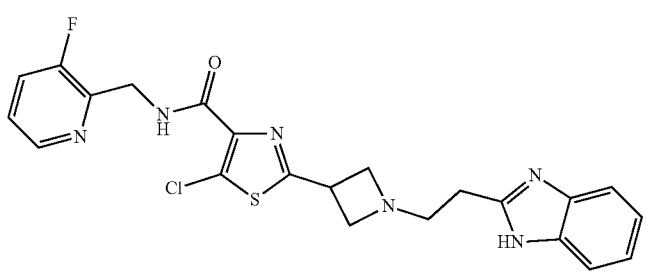 [SMILES: O=C(NCc1ncccc1F)c1nc(C2CN(CCc3nc4ccccc4[nH]3)C2)sc1Cl] |

| Exp No. | Compound |
|---|---|
| 210 | |
| 211 | |
| 212 | |
| 213 | |
| 214 | |

-continued
| Exp No. | Compound |
|---|---|
| 215 | 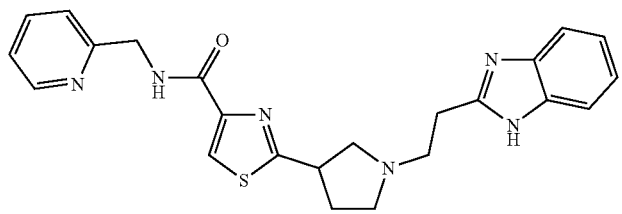 [SMILES: O=C(NCc1ccccn1)c1csc(C2CCN(CCc3nc4ccccc4[nH]3)C2)n1] |
| 218 | 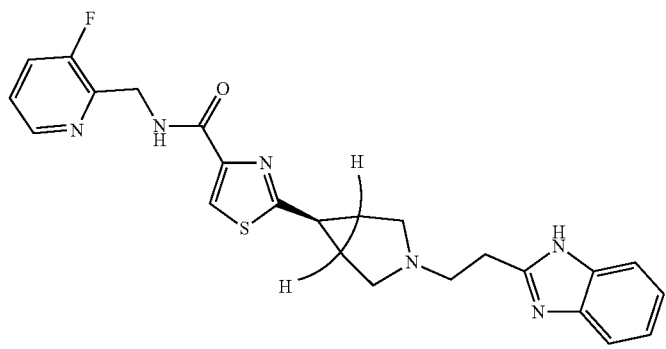 |
| 219 | 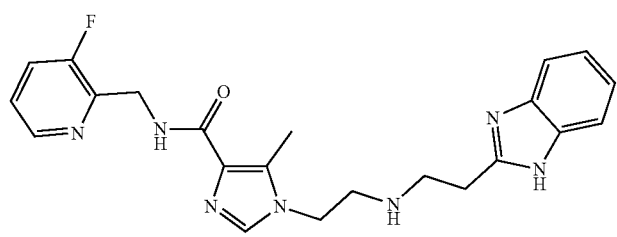 [SMILES: Cc1c(C(=O)NCc2ncccc2F)ncn1CCNCCc1nc2ccccc2[nH]1] |
| 220 | 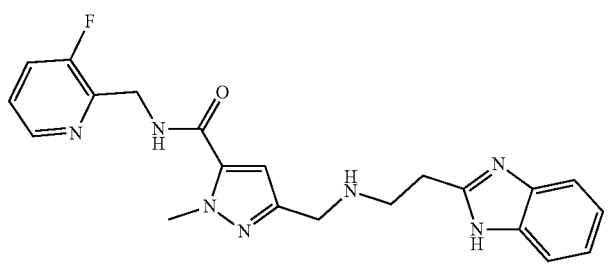 [SMILES: Cn1nc(CNCCc2nc3ccccc3[nH]2)cc1C(=O)NCc1ncccc1F] |
| 221 | 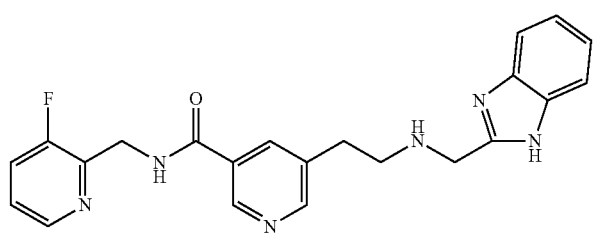 [SMILES: O=C(NCc1ncccc1F)c1cncc(CCNCc2nc3ccccc3[nH]2)c1] |
| 222 | 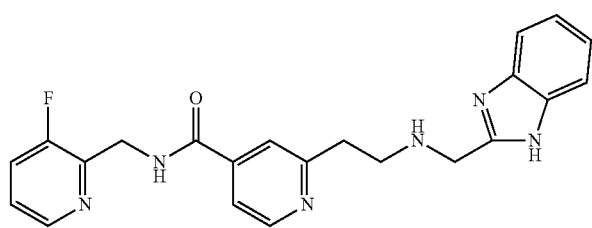 [SMILES: O=C(NCc1ncccc1F)c1ccnc(CCNCc2nc3ccccc3[nH]2)c1] |

-continued
| Exp No. | Compound |
|---|---|
| 223 | 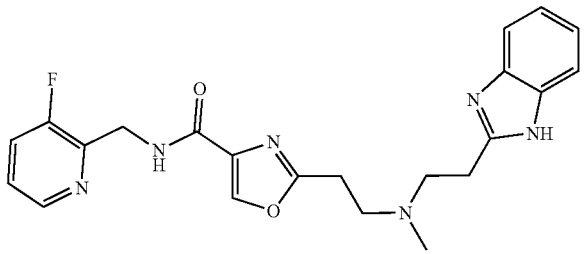 [SMILES: CN(CCc1nc2ccccc2[nH]1)CCc1nc(C(=O)NCc2ncccc2F)co1] |
| 224 | 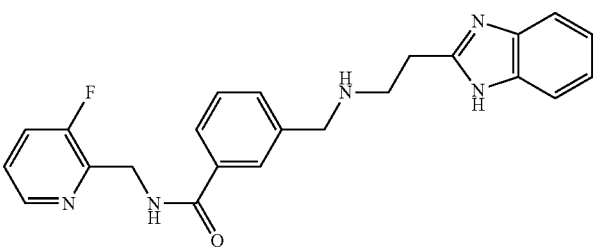 [SMILES: O=C(NCc1ncccc1F)c1cccc(CNCCc2nc3ccccc3[nH]2)c1] |
| 226 | 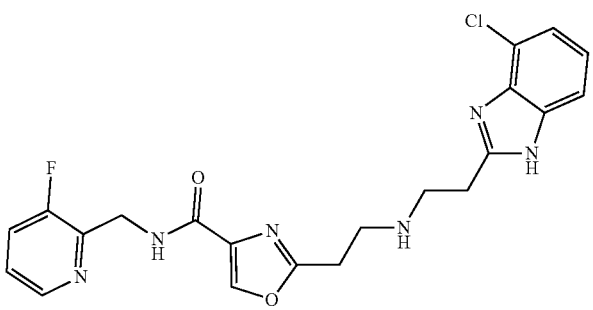 [SMILES: O=C(NCc1ncccc1F)c1coc(CCNCCc2nc3c(Cl)cccc3[nH]2)n1] |
| 227 | 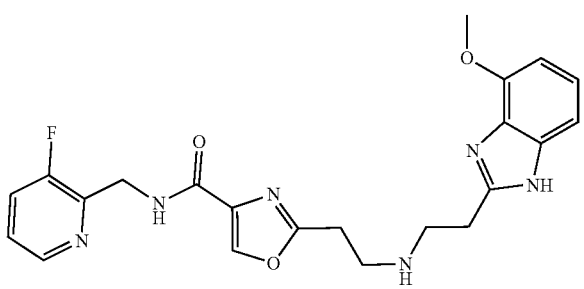 [SMILES: COc1cccc2[nH]c(CCNCCc3nc(C(=O)NCc4ncccc4F)co3)nc12] |
| 228 | 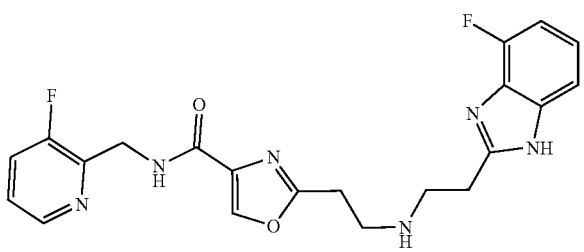 [SMILES: O=C(NCc1ncccc1F)c1coc(CCNCCc2nc3c(F)cccc3[nH]2)n1] |
| 229 | 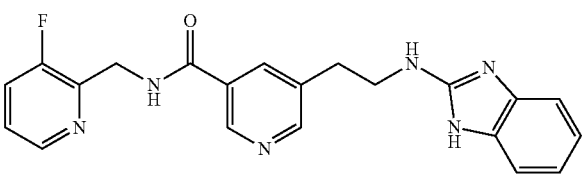 [SMILES: O=C(NCc1ncccc1F)c1cncc(CCNc2nc3ccccc3[nH]2)c1] |

-continued
| Exp No. | Compound |
|---|---|
| 230 | 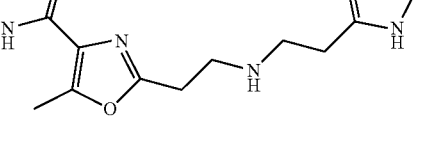 |
| 231 | 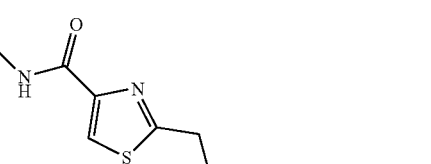 |
| 232 | 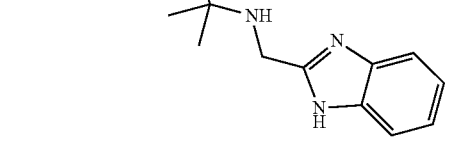 |
| 233 | 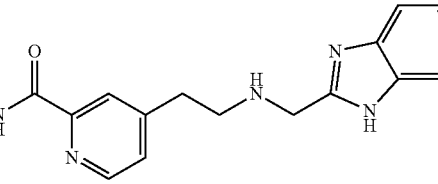 |
| 235 |  |
| 236 |  |

| Exp No. | Compound |
|---|---|
| 237 | 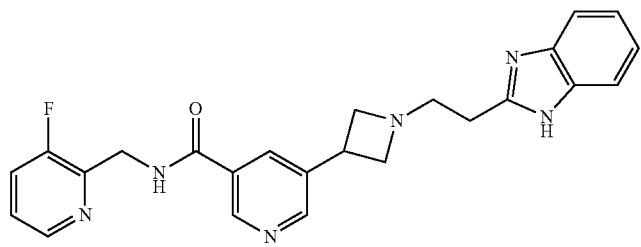 [SMILES: O=C(NCc1ncccc1F)c1cncc(C2CN(CCc3nc4ccccc4[nH]3)C2)c1] |
| 239 | 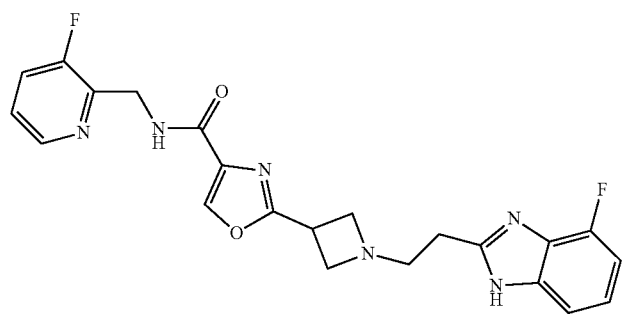 [SMILES: O=C(NCc1ncccc1F)c1coc(C2CN(CCc3nc4c(F)cccc4[nH]3)C2)n1] |
| 240 | 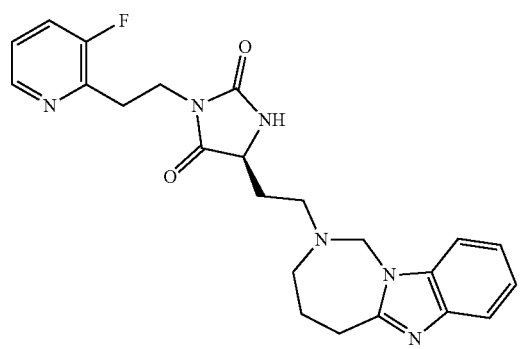 [SMILES: O=C1N[C@@H](CCN2CCCc3nc4ccccc4n3C2)C(=O)N1CCc1ncccc1F] |
| 241 | 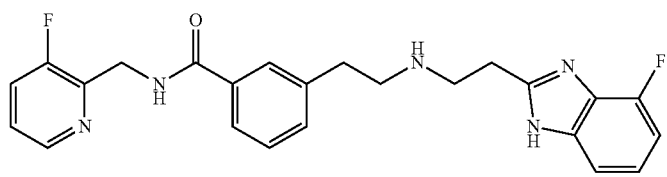 [SMILES: O=C(NCc1ncccc1F)c1cccc(CCNCCc2nc3c(F)cccc3[nH]2)c1] |
| 242 | 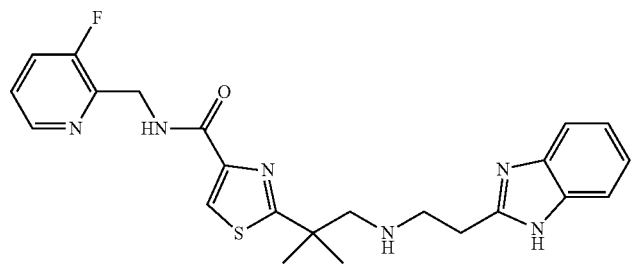 [SMILES: CC(C)(CNCCc1nc2ccccc2[nH]1)c1nc(C(=O)NCc2ncccc2F)cs1] |

-continued
| Exp No. | Compound |
|---|---|
| 243 | 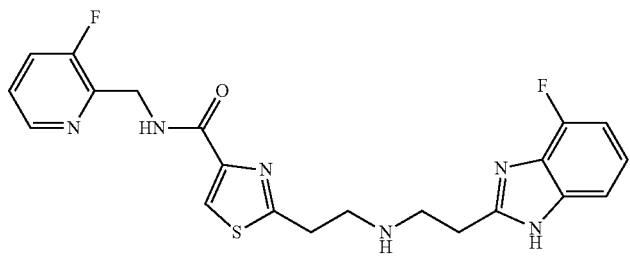 [SMILES: O=C(NCc1ncccc1F)c1csc(CCNCCc2nc3c(F)cccc3[nH]2)n1] |
| 244 | 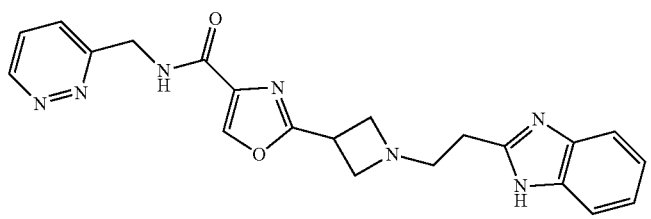 [SMILES: O=C(NCc1cccnn1)c1coc(C2CN(CCc3nc4ccccc4[nH]3)C2)n1] |
| 245 | 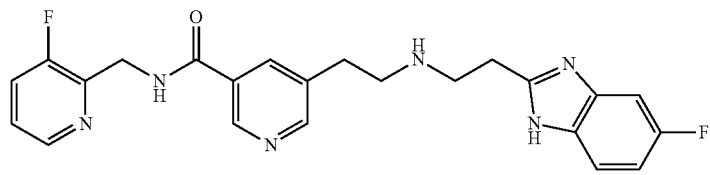 [SMILES: O=C(NCc1ncccc1F)c1cncc(CCNCCc2nc3cc(F)ccc3[nH]2)c1] |
| 246 | 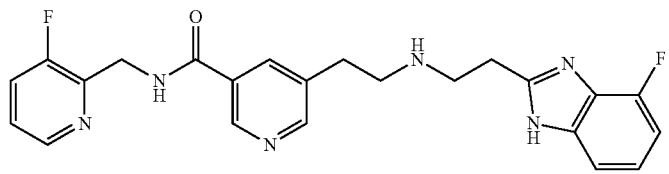 [SMILES: O=C(NCc1ncccc1F)c1cncc(CCNCCc2nc3c(F)cccc3[nH]2)c1] |
| 247 | 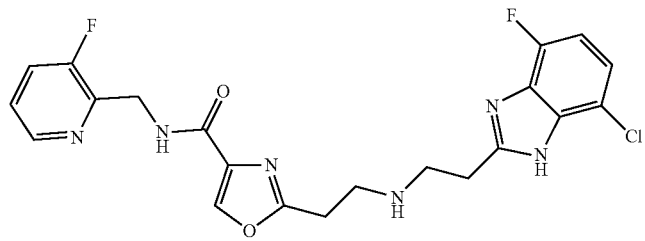 [SMILES: O=C(NCc1ncccc1F)c1coc(CCNCCc2nc3c(F)ccc(Cl)c3[nH]2)n1] |
| 248 | 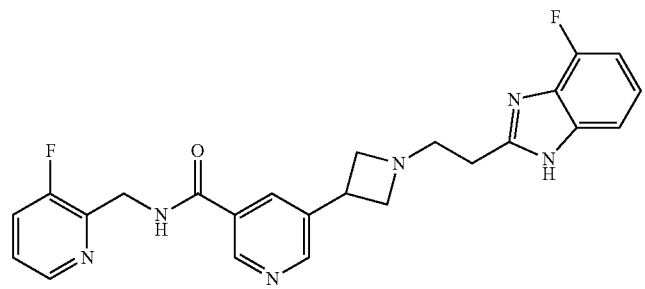 [SMILES: O=C(NCc1ncccc1F)c1cncc(C2CN(CCc3nc4c(F)cccc4[nH]3)C2)c1] |

-continued

| Exp No. | Compound |
|---|---|
| 249 | (structure) |
| 250 | (structure) |
| 251 | (structure) |
| 252 | (structure) |
| 253 | (structure) |
| 255 | (structure) |

-continued
| Exp No. | Compound |
|---|---|
| 256 | 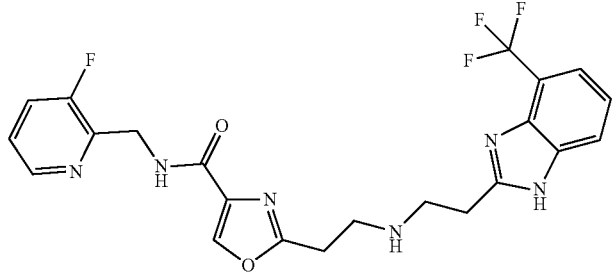 [SMILES: O=C(NCc1ncccc1F)c1coc(CCNCCc2nc3c(C(F)(F)F)cccc3[nH]2)n1] |
| 257 | 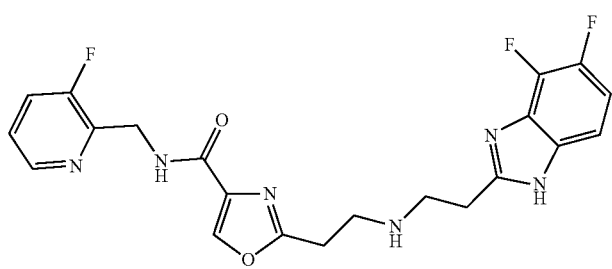 [SMILES: O=C(NCc1ncccc1F)c1coc(CCNCCc2nc3c(F)c(F)ccc3[nH]2)n1] |
| 258 | 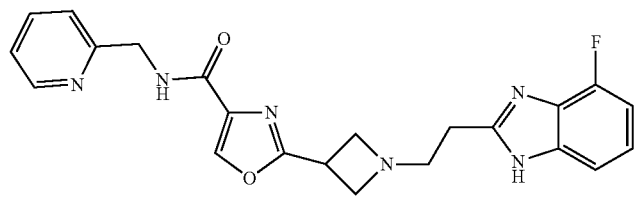 [SMILES: O=C(NCc1ccccn1)c1coc(C2CN(CCc3nc4c(F)cccc4[nH]3)C2)n1] |
| 261 | 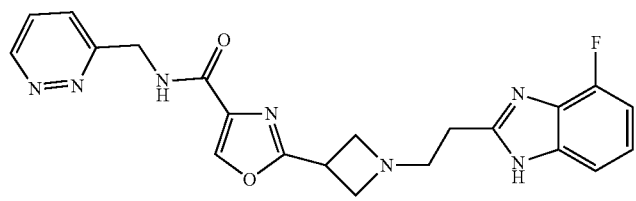 [SMILES: O=C(NCc1cccnn1)c1coc(C2CN(CCc3nc4c(F)cccc4[nH]3)C2)n1] |
| 262 | 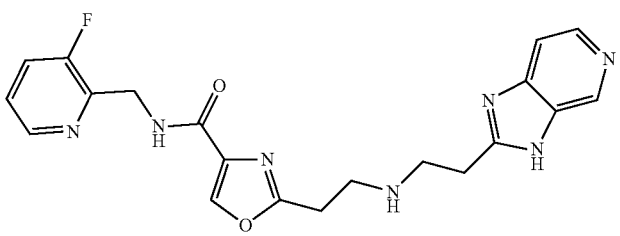 [SMILES: O=C(NCc1ncccc1F)c1coc(CCNCCc2nc3ccncc3[nH]2)n1] |
| 263 | 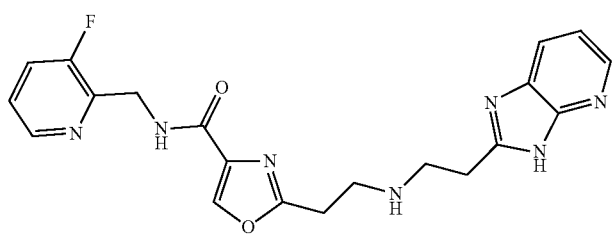 [SMILES: O=C(NCc1ncccc1F)c1coc(CCNCCc2nc3cccnc3[nH]2)n1] |

-continued
| Exp No. | Compound |
|---|---|
| 264 | 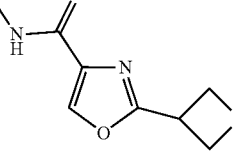 |
| 265 | 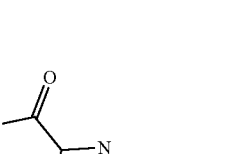 |
| 266 | 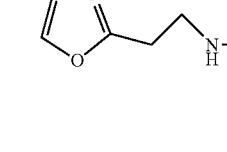 |
| 267 | 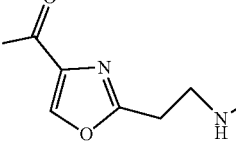 |
| 268 |  |
| 269 | 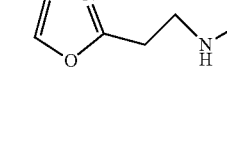 |

-continued
| Exp No. | Compound |
|---|---|
| 270 | 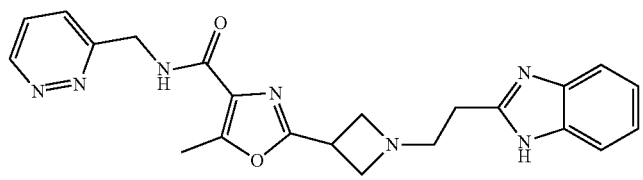 [SMILES: Cc1oc(C2CN(CCc3nc4ccccc4[nH]3)C2)nc1C(=O)NCc1cccnn1] |
| 271 | 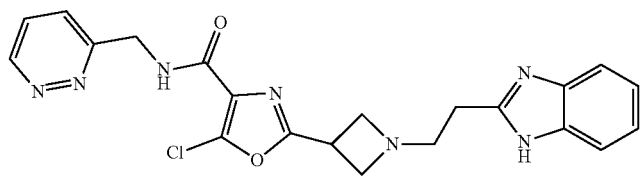 [SMILES: O=C(NCc1cccnn1)c1nc(C2CN(CCc3nc4ccccc4[nH]3)C2)oc1Cl] |
| 272 | 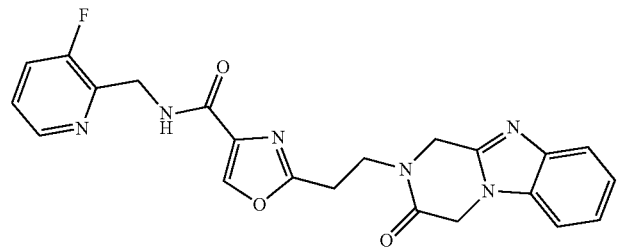 [SMILES: O=C(NCc1ncccc1F)c1coc(CCN2Cc3nc4ccccc4n3CC2=O)n1] |
| 273 | 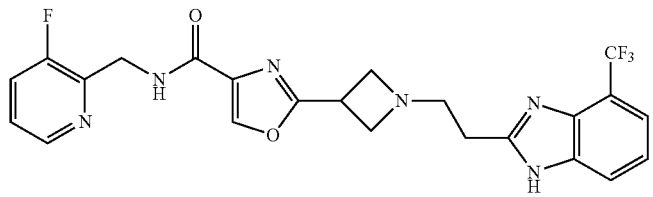 [SMILES: O=C(NCc1ncccc1F)c1coc(C2CN(CCc3nc4c(C(F)(F)F)cccc4[nH]3)C2)n1] |
| 274 | 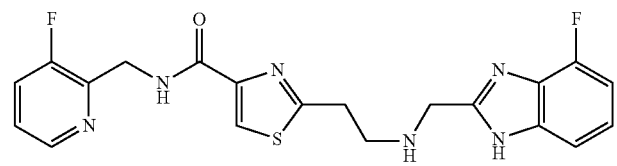 [SMILES: O=C(NCc1ncccc1F)c1csc(CCNCc2nc3c(F)cccc3[nH]2)n1] |
| 275 | 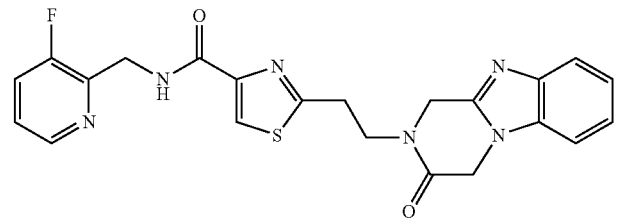 [SMILES: O=C(NCc1ncccc1F)c1csc(CCN2Cc3nc4ccccc4n3CC2=O)n1] |
| 276 | 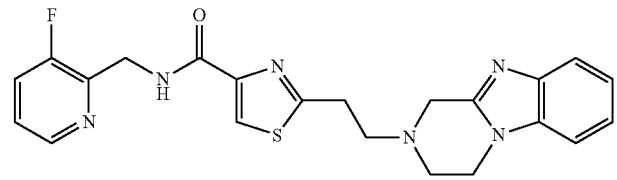 [SMILES: O=C(NCc1ncccc1F)c1csc(CCN2CCn3c(nc4ccccc43)C2)n1] |

-continued

| Exp No. | Compound |
|---|---|
| 277 | |
| 278 | |
| 279 | | or pharmaceutically acceptable salts thereof.

10. The method of claim 1, wherein the compound to be administered has the formula

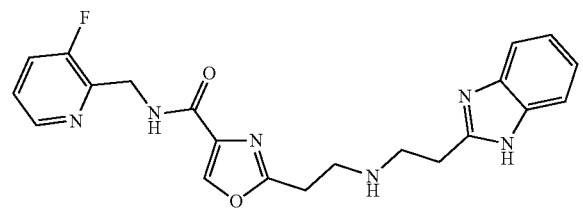 [SMILES: O=C(NCc1ncccc1F)c1coc(CCNCCc2nc3ccccc3[nH]2)n1]

or pharmaceutically acceptable salts thereof.

11. The method of claim 1, wherein the compounds according to formula (IVd) to be administered inhibit iron transport mediated by ferroportin.

12. The method of claim 1, wherein the ferroportin inhibition allows the treatment of diseases selected from the group consisting of increased iron levels, increased iron absorption, iron overload, or diseases associated with ineffective erythropoiesis selected from myelodysplastic syndromes (MDS, myelodysplasia), polycythemia vera and congenital dyserythropoietic anemia.

13. The method of claim 1, wherein the ferroportin inhibition allows the treatment of diseases selected from thalassemia, alpha-thalassemia, beta-thalassemia, delta-thalassemia, hemoglobinopathy, hemoglobin E disease, hemoglobin H disease, haemochromatosis, hemolytic anemia, including in particular sickle cell anemia and congenital dyserythropoietic anemia.

14. The method of claim 1, wherein the ferroportin inhibition allows the treatment of diseases selected from neurodegenerative diseases, Alzheimer's disease, Parkinson's disease, and wherein the therapeutic composition limits the deposition or increase of iron in tissue or cells.

15. The method of claim 1, wherein the ferroportin inhibition allows the treatment of diseases selected from the group consisting of cardiac, liver and endocrine damage caused by iron overload and/or inflammation triggered by excess iron.

16. The method of claim 1 wherein the ferroportin inhibition allows the treatment of infections caused by pathogenic microorganisms in an adjunctive therapy, the method comprising administering, to a patient in need thereof, a therapeutic composition comprising the at least one compound as defined in claim 1, thereby limiting the amount of iron available to the pathogenic microorganisms.

17. The method of claim 1 wherein the ferroportin inhibition allows the prevention of the formation of at least one of radicals, reactive oxygen species (ROS) and oxidative stress, the method comprising administering, to a patient in need thereof, a therapeutic composition comprising the at least one compound as defined in claim 1.

18. The method of claim 1 wherein the method further comprises administration of at least one additional pharmaceutically active compound, wherein said co-administration of the combination therapy may be carried out in a fixed dose combination therapy by co-administration of the compounds as defined in any of the preceding claims with at least one additional pharmaceutically active compound in a fixed-dose formulation; or said co-administration of the combination therapy may be carried out in a free dose combination therapy by co-administration of the compounds as defined in any of the preceding claims and the at least one additional pharmaceutically active compound in free doses of the respective compounds, either by simultaneous administration of the individual compounds or by sequential use of the individual compounds distributed over a time period; and wherein the one or more other pharmaceutically active compounds are preferably active compounds for reducing iron overload, which are selected from Tmprss6-

ASO, iron chelators, curcumin, SSP-004184, Deferitrin, deferasirox, deferoxamine and/or deferiprone;
and/or
pharmaceutically active compounds which are selected from antioxidants, such as n-acetyl cysteine; anti-diabetics, such as GLP-1 receptor agonists; antibiotics, such as vancomycin (Van) or tobramycin; drugs for the treatment of malaria; anticancer agents; antifungal drugs; drugs for the treatment of neurodegenerative diseases such as Alzheimer's disease and Parkinson's disease, comprising dopamine agonists such as Levodopa; anti-viral drugs, such as interferon-a or ribavirin; immunosuppressents, such as cyclosporine A or cyclosporine A derivatives; iron supplements; vitamin supplements; red cell production stimulators; anti-inflammatory biologies; anti-thrombolytics; statins; vasopressors; and inotropic compounds.

* * * * *